US012753171B2

(12) United States Patent
Liao et al.

(10) Patent No.: US 12,753,171 B2
(45) Date of Patent: Oct. 6, 2026

(54) 5-MEMBERED HETEROARYLAMINOSULFONAMIDES FOR TREATING CONDITIONS MEDIATED BY DEFICIENT CFTR ACTIVITY

(71) Applicant: Genzyme Corporation, Cambridge, MA (US)

(72) Inventors: Junkai Liao, Bridgewater, NJ (US); Mark Munson, Bridgewater, NJ (US); Zhongli Gao, Bridgewater, NJ (US); Gregory Donald Hurlbut, Bridgewater, NJ (US); Sylvie Baltzer, Bridgewater, NJ (US); Bertrand Vivet, Bridgewater, NJ (US); Brian Freed, Bridgewater, NJ (US); Hans Peter Nestler, Bridgewater, NJ (US); Helen Yeoman, Bridgewater, NJ (US); Ingrid Mechin, Bridgewater, NJ (US); Martin Smrcina, Bridgewater, NJ (US); Nina Ma, Bridgewater, NJ (US); Sylvain Lebreton, Bridgewater, NJ (US); Ryan Hartung, Bridgewater, NJ (US); William Wire, Bridgewater, NJ (US); Sukanthini Thurairatnam, Bridgewater, NJ (US)

(73) Assignee: Genzyme Corporation, Cambridge, MA (US)

( * ) Notice: Subject to any disclaimer, the term of this patent is extended or adjusted under 35 U.S.C. 154(b) by 863 days.

(21) Appl. No.: 17/742,169

(22) Filed: May 11, 2022

(65) Prior Publication Data

US 2024/0002374 A1 Jan. 4, 2024

Related U.S. Application Data

(63) Continuation of application No. PCT/US2020/060180, filed on Nov. 12, 2020.

(60) Provisional application No. 62/934,293, filed on Nov. 12, 2019.

(51) Int. Cl.

| | |
|---|---|
| ***C07D 417/12*** | (2006.01) |
| ***C07D 277/52*** | (2006.01) |
| ***C07D 417/04*** | (2006.01) |
| ***C07D 417/14*** | (2006.01) |
| ***C07D 498/10*** | (2006.01) |
| ***C07F 9/22*** | (2006.01) |

(52) U.S. Cl.

CPC ......... *C07D 417/12* (2013.01); *C07D 277/52* (2013.01); *C07D 417/04* (2013.01); *C07D 417/14* (2013.01); *C07D 498/10* (2013.01); *C07F 9/222* (2013.01)

(58) Field of Classification Search

CPC .. C07D 417/12; C07D 277/52; C07D 417/04; C07D 417/14; C07D 498/10

See application file for complete search history.

(56) References Cited

U.S. PATENT DOCUMENTS

| | | | |
|---|---|---|---|
| 4,172,896 | A | 10/1979 | Uno et al. |
| 5,358,970 | A | 10/1994 | Ruff et al. |
| 5,427,798 | A | 6/1995 | Ludwig et al. |
| 5,449,783 | A | 9/1995 | Saita et al. |
| 5,541,231 | A | 7/1996 | Ruff et al. |
| 5,731,000 | A | 3/1998 | Ruff et al. |
| 5,763,493 | A | 6/1998 | Ruff et al. |
| 5,856,347 | A | 1/1999 | Hashiguchi et al. |
| 6,110,973 | A | 8/2000 | Young |
| 8,999,976 | B2 | 4/2015 | Binch et al. |
| 9,790,219 | B2 | 10/2017 | Bastos et al. |
| 2007/0022507 | P1 | 1/2007 | Scully |
| 2009/0233975 | A1 | 9/2009 | Suetsugu et al. |
| 2010/0184739 | A1 | 7/2010 | Sheth et al. |
| 2011/0184177 | A1 | 7/2011 | Hachtel et al. |
| 2013/0186801 | A1 | 7/2013 | Verwijs |
| 2015/0005275 | A1 | 1/2015 | Plas et al. |
| 2015/0045327 | A1 | 2/2015 | Van Der Plas et al. |
| 2016/0095858 | A1 | 4/2016 | Miller et al. |
| 2016/0120841 | A1 | 5/2016 | Kym et al. |
| 2016/0122331 | A1 | 5/2016 | Kym et al. |
| 2016/0355480 | A1 | 12/2016 | Altenbach et al. |
| 2019/0248809 | A1 | 8/2019 | Clemens et al. |
| 2023/0137585 | A1 | 5/2023 | Gao et al. |
| 2023/0147360 | A1 | 5/2023 | Liao et al. |
| 2023/0159438 | A1 | 5/2023 | Liao et al. |
| 2023/0159439 | A1 | 5/2023 | Liao et al. |
| 2025/0197420 | A1 | 6/2025 | Liao et al. |
| 2025/0197422 | A1 | 6/2025 | Liao et al. |

(Continued)

FOREIGN PATENT DOCUMENTS

| | | | |
|---|---|---|---|
| EP | 0699438 | A2 | 3/1996 |
| EP | 0790057 | A1 | 8/1997 |

(Continued)

OTHER PUBLICATIONS

Ivacaftor Prescribing Information, 17 pages, Vertex Pharmaceuticals, Feb. 2017. (Year: 2017).*

(Continued)

*Primary Examiner* — Golam M Shameem

(74) *Attorney, Agent, or Firm* — Goodwin Procter LLP

(57) ABSTRACT

The invention relates to heteroaryl compounds, pharmaceutically acceptable salts thereof, and pharmaceutical preparations thereof. Also described herein are compositions and the use of such compounds in methods of treating diseases and conditions mediated by deficient CFTR activity, in particular cystic fibrosis.

49 Claims, No Drawings

(56) References Cited

U.S. PATENT DOCUMENTS

| | | | |
|---|---|---|---|
| 2025/0248975 | A1 | 8/2025 | Liao et al. |
| 2025/0255859 | A1 | 8/2025 | Hurlbut |

FOREIGN PATENT DOCUMENTS

| | | | | |
|---|---|---|---|---|
| EP | 3464282 | A1 | 4/2019 | |
| JP | H07149745 | A | 6/1995 | |
| JP | 2007504255 | A | 3/2007 | |
| JP | 2017074057 | A | 4/2017 | |
| WO | WO-9616650 | A1 | 6/1996 | |
| WO | WO-98024782 | A2 | 6/1998 | |
| WO | WO-03039451 | A2 | 5/2003 | |
| WO | WO-2005075435 | A1 | 8/2005 | |
| WO | WO-2005120497 | A2 | 12/2005 | |
| WO | WO-2006002421 | | 1/2006 | |
| WO | WO-2006069656 | A1 | 7/2006 | |
| WO | WO-2006113704 | A2 | 10/2006 | |
| WO | WO-2007056341 | A1 | 5/2007 | |
| WO | WO-2007087066 | A2 | 8/2007 | |
| WO | WO-2008000408 | A1 | 1/2008 | |
| WO | WO-2008121877 | A2 | 10/2008 | |
| WO | WO-2008147952 | A1 | 12/2008 | |
| WO | WO-2009074575 | A2 | 6/2009 | |
| WO | WO-2009076593 | A1 | 6/2009 | |
| WO | WO-2010048526 | A2 | 4/2010 | |
| WO | WO-2010048564 | A1 | 4/2010 | |
| WO | WO-2010048573 | A1 | 4/2010 | |
| WO | WO-2010151747 | A1 | 12/2010 | |
| WO | WO-2011072241 | A1 | 6/2011 | |
| WO | WO-2011113894 | A1 | 9/2011 | |
| WO | WO-2012170889 | A1 | 12/2012 | |
| WO | WO-2013003837 | A1 | 1/2013 | |
| WO | WO-2013038373 | A1 | 3/2013 | |
| WO | WO-2013038378 | A1 | 3/2013 | |
| WO | WO-2013038381 | A1 | 3/2013 | |
| WO | WO-2013038386 | A1 | 3/2013 | |
| WO | WO-2013038390 | A1 | 3/2013 | |
| WO | WO-2013043720 | A1 | 3/2013 | |
| WO | WO-2014180562 | A1 | 11/2014 | |
| WO | WO-2014186704 | A2 | 11/2014 | |
| WO | WO-2015018823 | A1 | 2/2015 | |
| WO | WO-2015138909 | A1 | 9/2015 | |
| WO | WO-2015138934 | A1 | 9/2015 | |
| WO | WO-2016130929 | A1 | 8/2016 | |
| WO | WO-2016130943 | A1 | 8/2016 | |
| WO | WO-2016183173 | A1 | 11/2016 | |
| WO | WO-2017062581 | A1 | 4/2017 | |
| WO | WO-2017173274 | A1 | 10/2017 | |
| WO | WO-2017208115 | A1 | 12/2017 | |
| WO | WO-2018042316 | A1 | 3/2018 | |
| WO | WO-2018167690 | A1 | 9/2018 | |
| WO | WO-2019161078 | A1 | 8/2019 | |
| WO | WO-2020206080 | A1 | 10/2020 | |
| WO | WO-2021097054 | A1 | 5/2021 | |
| WO | WO-2021097057 | A1 | 5/2021 | |
| WO | WO-2021113808 | A1 | 6/2021 | |
| WO | WO-2021113809 | A1 | 6/2021 | |
| WO | WO-20210113806 | A1 | 6/2021 | |
| WO | WO-2022032068 | | 2/2022 | |
| WO | WO-2022076622 | | 4/2022 | |
| WO | WO-2022109573 | A1 | 5/2022 | |
| WO | WO-2023034946 | A1 | 3/2023 | |
| WO | WO-2023034992 | | 3/2023 | |
| WO | WO-2024054840 | A1 | 3/2024 | |
| WO | WO-2024054845 | A1 | 3/2024 | |
| WO | WO-2024054851 | A1 | 3/2024 | |
| WO | WO-2024097227 | A1 * | 5/2024 | ........... A61K 31/357 |
| WO | WO-2025189008 | A1 | 9/2025 | |

OTHER PUBLICATIONS

Jenkins et al., A 3D similarity method for scaffold hopping from the known drugs or natural ligands to new chemotypes, J. Medical Chemistry, 47(25): 6144-6159 (2004).

Hitchin, et al., Development and evaluation of selective, reversible LSD1 inhibitors derived from fragments, MEDCHEMCOMM, 4(11): 1513 (2013).

Wang, et al., Synthesis and biological evaluation of diarylthiazole derivatives as antimitotic and antivascular agents with potent antitumor activity, Bioorganic & Medicinal Chemistry, 23: 3337-3350 (2015).

PCT/US2020/060180 International Search Report and Written Opinion mailed Feb. 24, 2021, 13 pages.

PCT/US2020/060180 International Preliminary Report on Patentability mailed Mar. 27, 2022, 9 pages.

PCT/US2020/060176 International Preliminary Report on Patentability mailed May 27, 2022, 9 pages.

PCT/US2020/060176 International Search Report and Written Opinion mailed Jan. 29, 2021, 12 pages.

Saikachi et al., "Synthesis of the Furan Derivatives. XLVII. Synthesis of 5, 6-Bis (5-nitro-2-furyl)-2-aminopyrazine and Its Related Compound", Yakugaku Zasshi. 89(8):1071-1077 (1969).

Yoshii et al., "Antiviral and Antibacterial Activities of 3-(Substituted benzenesulfonylamino)-5, 6-di(p-substituted phenyl)-1, 2, 4-triazines", Yakugaku Zasshi. 108(1):50-57 (1988).

Azam S., et al., The Ageing Brain: Molecular and Cellular Basis of Neurodegeneration, Front Cell Dev Biol, 9:683459 (2021).

Chiba, T., Emerging Therapeutic Strategies in Alzheimer's Disease, Intech, 181-225 (2013).

Damia, G., et al., Contemporary pre-clinical development of anticancer agents—What are the optimal preclinical models?, Eur J Cancer, 45(16):2768-2781 (2009).

Derichs, Targeting a genetic defect: cystic fibrosis transmembrane conductance regulator modulators in cystic fibrosis, European Respiratory Review, 22:127, 58-65 (2013).

Felis, A., et al., Current and Investigational Therapeutics for Fabry Disease, Kidney Int Rep, 5(4):407-413 (2020).

Ghelani, D.P., et al., Emerging Cystic Fibrosis Transmembrane Conductance Regulator Modulators as New Drugs for Cystic Fibrosis: A Portrait of in VitroÂ Pharmacology and Clinical Translation, ACS Pharmacol Transl Sci., 3(1):4-10 (2019).

Gregory, R. J. et al., Expression and charaterization of the cystic fibrosis transmembrane conductance regulator, Nature, 347:382-386 (1990).

Guan, X., et al., Dysregulated Chemokine Signaling in Cystic Fibrosis Lung Disease: A Potential Therapeutic Target, Curr Drug Targets, 17(13): 1535-1544 (2016).

Johnson, J.I., et al., Relationships between drug activity in NCI preclinical in vitro and in vivo models and early clinical trials, Br J Cancer, 84(10):1424-1431 (2001).

Ledford, H., US cancer institute overhauls cell lines, Nature, 530(7591):391 (2016).

Lopes-Pacheco, M., CFTR Modulators: The Changing Face of Cystic Fibrosis in the Era of Precision Medicine, Front Pharmacol., 10:1662 (2020).

Makrilakis, K., Pathophysiology of Type 2 diabetes, Chapter 3 in Diabetes in Clinical Practice: Questions and Answers from Case Studies, Nicholas Katsilambros et al. eds. John Wiley & Sons: 2006, pp. 43-58.

Ocana, A., et al., Preclinical development of molecular targeted agents for cancer, Nat Rev Clin Oneal, 8(4):200-209 (2011).

PCT/US2020/063586 International Preliminary Report on Patentability mailed Jun. 16, 2022.

PCT/US2020/063586 International Search Report and Written Opinion mailed Feb. 15, 2021.

PCT/US2020/063589 International Preliminary Report on Patentability mailed Jun. 16, 2022.

PCT/US2020/063589 International Search Report and Written Opinion mailed Feb. 11, 2021.

PCT/US2020/063590 International Preliminary Report on Patentability mailed Jun. 16, 2022.

PCT/US2020/063590 International Search Report and Written Opinion mailed Feb. 15, 2021.

PCT/US2024/060181 International Search Report and Written Opinion mailed Mar. 25, 2025.

(56) References Cited

OTHER PUBLICATIONS

Rich, D. P. et al., Expression of cystic fibrosis transmembrane conductance regulator corrects defective chloride channel regulation in cystic fibrosis airway epithelial cells, Nature, 347:358-362 (1990).

Riordan, J. R. et al., Identification of the Cystic Fibrosis Gene: Cloning and Characterization of Complementary DNA, Science, 245:1066-1073 (1989).

Sharma, S.V., et al., Cell line-based platforms to evaluate the therapeutic efficacy of candidate anticancer agents, Nat Rev Cancer, 10(4):241-53 (2010).

Stavrou, M., et al., Genetic mechanisms of peripheral nerve disease, Neurosci Lett, 742:135357 (2021).

Types of CFTR Mutations, Online: "https://www.cff.org/research-clinical-trials/types-cftr-mutations", accessed Jun. 2, 2025.

University of Cambridge John van Geest Centre for Brain Repair School of Clinical Medicine "Alzheimer's disease and tauopathy" Online "http://www.brc.cam.ac.uk/research/alzheimers-disease-and-tauopathy/" accessed Sep. 10, 2015.

Van Goor, F., et al., Correction of the F508del-CFTR protein processing defect in vitro by the investigational drug VX-809, Proc Natl Acad Sci USA, 108(46):18843-8 (2011).

Weijlard et al., Some New Aminopyrazines and their Sulfanilamide Derivatives, J. Am. Chem. Soc., 67:802-806 (1945).

Bartlett, P.A., Exploiting Chemical Diversity for Drug Discovery, Edited by Paul A Bartlett and Michael Entzeroth, The Royal Society of Chemistry: 113-118 (2006).

Find ETDs Home > Thesis Resources > Find ETDs, retrieved Jan. 31, 2023 from https://ndltd.org/thesis-resources/find-etds/.

He, et al., Restoration of NBD1 thermal stability is necessary and sufficient to correct F508 CFTR folding and assembly, J Mol Biol., 427(1): 106-120 (2015).

Irwin, J.J., et al., Zinc—A Free Database of Commercially Available Compounds for Virtual Screening, J. Chem. Inf. Model., 45: 177-182 (2005).

Kim, S. et al. PubChem in 2021: new data content and improved web interfaces, Nucleic Acids Research, 49 (2021).

Patani, G.A., et al., Bioisosterism: a rational approach in drug design, Chem Rev, 96(): 3147-3176 (1996).

PCT/US2023/073543 International Preliminary Report on Patentability mailed Mar. 20, 2025.

PCT/US2023/073543 International Search Report and Written Opinion mailed Nov. 21, 2023.

PCT/US2023/073551 International Preliminary Report on Patentability mailed Mar. 20, 2025.

PCT/US2023/073551 International Search Report and Written Opinion mailed Nov. 21, 2023.

PCT/US2023/073558 International Preliminary Report on Patentability mailed Mar. 20, 2025.

PCT/US2023/073558 International Search Report and Written Opinion mailed Oct. 26, 2023.

Silverman, R. B., The Organic Chemistry of Drug Design and Drug Action (2nd ed.), Elsevier, 29, Table 2.3 (2004).

* cited by examiner

5-MEMBERED HETEROARYLAMINOSULFONAMIDES FOR TREATING CONDITIONS MEDIATED BY DEFICIENT CFTR ACTIVITY

RELATED APPLICATIONS

This application is a continuation of International Patent Application No. PCT/2020/060180, filed Nov. 12, 2020, which claims priority to and the benefit of U.S. Provisional Patent Application No. 62/934,293, filed on Nov. 12, 2019, each of which are incorporated herein by reference in their entirety.

BACKGROUND

Cystic fibrosis (CF), an autosomal recessive disorder, is caused by functional deficiency of the cAMP-activated plasma membrane chloride channel, cystic fibrosis transmembrane conductance regulator (CFTR), which can result in damage to the lung, pancreas and other organs. The gene encoding CFTR has been identified and sequenced (See Gregory, R. J. et al. (1990) Nature 347:382-386; Rich, D. P. et al. (1990) Nature 347:358-362; Riordan, J. R. et al. (1989) Science 245:1066-1073). CFTR, a member of the ATP binding cassette (ABC) superfamily is composed of two six membrane-spanning domains (MSD1 and MSD2), two nucleotide binding domains (NBD1 and NBD2), a regulatory region (R) and four cytosolic loops (CL1-4). Normally, CFTR protein is located primarily in the apical membrane of epithelial cells where it functions to conduct anions, including chloride, bicarbonate and thiocyanate into and out of the cell. CFTR may have a regulatory role over other electrolyte channels, including the epithelial sodium channel ENaC.

In cystic fibrosis patients, the absence or dysfunction of CFTR leads to exocrine gland dysfunction and a multisystem disease, characterized by pancreatic insufficiency and malabsorption, as well as abnormal mucociliary clearance in the lung, mucostasis, chronic lung infection and inflammation, decreased lung function and ultimately respiratory failure.

While more than 1,900 mutations have been identified in the CFTR gene, a detailed understanding of how each CFTR mutation may impact channel function is known for only a subset. (Derichs, European Respiratory Review, 22:127, 58-65 (2013)). The most frequent CFTR mutation is the in-frame deletion of phenylalanine at residue 508 (ΔF508) in the first nucleotide binding domain (NBD1). Over 80% of cystic fibrosis patients have the deletion at residue 508 in at least one allele. The loss of this key phenylalanine renders the CFTR NBD1 domain conformationally unstable at physiological temperature and compromises the integrity of the interdomain interface between NBD1 and CFTR's second transmembrane domain (ICL4). The ΔF508 mutation causes production of misfolded CFTR protein which, rather than traffic to the plasma membrane, is instead retained in the endoplasmic reticulum and targeted for degradation by the ubiquitin-proteasome system.

The loss of a functional CFTR channel at the plasma membrane disrupts ionic homeostasis and airway surface hydration leading to reduced lung function. Reduced periciliary liquid volume and increased mucus viscosity impede mucociliary clearance resulting in chronic infection and inflammation. In the lung, the loss of CFTR-function leads to numerous physiological effects downstream of altered anion conductance that result in the dysfunction of additional organs such as the pancreas, intestine and gall bladder.

Guided, in part, by studies of the mechanistic aspects of CFTR misfolding and dysfunction, small molecule CFTR modulators have been identified, that can increase CFTR channel function. Despite the identification of compounds that modulate CFTR, there is no cure for this fatal disease and identification of new compounds and new methods of therapy are needed as well as new methods for treating or lessening the severity of cystic fibrosis and other CFTR mediated conditions and diseases in a patient.

SUMMARY

In certain aspects, the present application is directed to a compound of Formula (I):

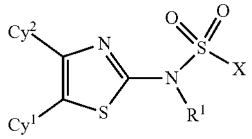

(I)

or a pharmaceutically acceptable salt thereof, wherein:

$R^1$ is hydrogen or $C_{1-6}$ alkyl;

X is $C_{1-6}$ alkyl, 5-6 membered aryl, 4-10 membered heterocycloalkyl, or 5-6 membered heteroaryl, each of which is substituted with 0-3 occurrences of $R^2$;

$Cy^1$ is $C_{3-9}$ cycloalkyl, 5-6 membered aryl, 4-10 membered heterocycloalkyl or 5-6 membered heteroaryl, each of which is substituted with 0-3 occurrences of $R^3$;

$Cy^2$ is $C_{3-9}$ cycloalkyl, 5-6 membered aryl, 4-10 membered heterocycloalkyl, or 5-6 membered heteroaryl, each of which is substituted with 1-3 occurrences of $R^4$;

each $R^2$ is independently hydroxyl, halo, —$NH_2$, nitro, $C_{1-6}$ alkyl, $C_{1-6}$ alkoxy, $C_{1-6}$ haloalkyl, $C_{1-6}$ haloalkoxy, 4-10 membered heterocycloalkyl, 5-6 membered heteroaryl, $C_{3-9}$ cycloalkyl, $C_{3-9}$ cycloalkoxy, —C(O)$NH_2$, —N($R^a$)($R^5$), —N($R^a$)C(O)—$R^5$, —N($R^a$)$SO_2$—$R^5$, —$SO_2$—$R^5$, —C(O)N($R^a$)($R^5$), —S(O)—$R^5$, —N($R^a$)S(O)(NH)—$R^5$ or —P(O)$(R^5)_2$, wherein each $C_{1-6}$ alkyl, $C_{1-6}$ alkoxy, $C_{1-6}$ haloalkyl, $C_{3-9}$ cycloalkyl or 4-10 membered heterocycloalkyl is further substituted by 0-3 occurrences of $R^5$;

each $R^3$ is independently halo, $C_{1-6}$ alkyl, $C_{1-6}$ alkenyl, $C_{1-6}$ alkoxy, $C_{1-6}$ haloalkyl, $C_{1-6}$ haloalkoxy, $C_{3-9}$ cycloalkyl, $C_{1-4}$ alkyl-$C_{3-9}$ cycloalkyl, $C_{1-4}$ alkoxy-$C_{3-9}$ cycloalkyl, $C_{3-9}$ cycloalkoxy, $C_{3-9}$ cycloalkenyl, 5-6 membered aryl, aralkyl, aralkoxy, 5-6 membered heteroaryl, 4-10 membered heterocycloalkyl, —C(O)—$R^7$, —C(O)N($R^a$)($R^7$) or —N($R^a$)($R^8$), wherein each $C_{3-9}$ cycloalkyl, $C_{3-9}$ cycloalkoxy, $C_{1-8}$ haloalkoxy, $C_{1-8}$ alkoxy, 4-10 membered heterocycloalkyl, 5-6 membered aryl, 5-6 membered heteroaryl, cycloalkenyl, $C_{1-4}$ alkyl-$C_{3-9}$ cycloalkyl or $C_{1-4}$ alkoxy-$C_{3-9}$ cycloalkyl is further substituted with 0-3 occurrences of $R^7$;

each $R^4$ is independently halo, $C_{1-6}$ alkyl, $C_{1-6}$ alkoxy, $C_{1-6}$ haloalkyl, $C_{1-6}$ haloalkoxy, $C_{3-6}$ cycloalkyl, $N(R^a)_2$ or 4-10 membered heterocycloalkyl, wherein each 4-10 membered heterocycloalkyl may be further substituted with 0-3 $R^b$;

each $R^5$ is independently $C_{1-6}$ alkyl, $C_{1-6}$ haloalkyl, $C_{3-9}$ cycloalkyl, hydroxyl, —$SO_2$—$R^6$, —$CO_2H$, —$NH_2$, —$CO_2$—$C_{1-4}$ alkyl or 4-10 membered heterocycloalkyl, wherein each $C_{1-6}$ alkyl, $C_{3-9}$ cycloalkyl or 4-10 membered heterocycloalkyl is further substituted by 0-3 occurrences of $R^6$;

each $R^6$ is independently hydroxyl, —$NH_2$, halo, $C_{1-4}$ alkyl, $C_{1-4}$ haloalkyl, —$CO_2H$ or —$CO_2$—($C_{1-4}$ alkyl);

each $R^7$ is independently halo, $C_{1-5}$ alkyl, $C_{1-5}$ alkoxy, $C_{1-5}$ haloalkyl, $C_{1-5}$ haloalkoxy, $C_{1-5}$ haloalkenyl, $C_{3-7}$ cycloalkyl, hydroxyl, 5-6 membered aryl, aralkyl, aralkoxy, —C(O)—O—$C_{1-4}$alkyl, —C(O)N($R^a$)($C_{1-4}$ alkyl), 5-6 membered heteroaryl or 4-10 membered heterocycloalkyl, wherein each $C_{3-7}$ cycloalkyl, 5-6 membered aryl or 4-10 membered heterocycloalkyl is further substituted by 0-3 occurrences of $R^8$;

each $R^8$ is independently halo, $C_{1-4}$ alkyl, $C_{1-4}$ haloalkoxy, C(O)—$C_{1-4}$ alkyl or C(O)N($R^a$)($C_{1-4}$ alkyl);

each $R^a$ is independently H or $C_{1-6}$ alkyl; and each $R^b$ is $C_{1-4}$ alkyl;

wherein a) if $Cy^1$ is phenyl and has 3 occurrences of $R^3$, then each $R^3$ is not methoxy;

b) when X and $Cy^2$ are each phenyl, then $R^2$ and $R^4$ are not each methyl;

c) $R^3$ and $R^4$ are not simultaneously tert-butyl or simultaneously methoxy;

d) when $Cy^1$ and $Cy^2$ are mono-substituted phenyl, then X is not thienyl; and e) when $Cy^1$ and $Cy^2$ are mono-substituted phenyl, then $R^2$ is not OH, $R^3$ is not Cl and $R^4$ is not OMe.

Disclosed herein are methods of treating deficient CFTR activity, thereby treating a disease or condition mediated by deficient CFTR activity. Such diseases and conditions include, but are not limited to, cystic fibrosis, congenital bilateral absence of vas deferens (CBAVD), acute, recurrent, or chronic pancreatitis, disseminated bronchiectasis, asthma, allergic pulmonary aspergillosis, congenital pneumonia, intestinal malabsorption, celiac disease, nasal polyposis, non-tuberculous mycobacterial infection, pancreatic steatorrhea, intestinal atresia, chronic obstructive pulmonary disease (COPD), chronic sinusitis, dry eye disease, protein C deficiency, abetalipoproteinemia, lysosomal storage disease, type 1 chylomicronemia, mild pulmonary disease, lipid processing deficiencies, type 1 hereditary angioedema, coagulation-fibrinolyis, hereditary hemochromatosis, CFTR-related metabolic syndrome, chronic bronchitis, constipation, pancreatic insufficiency, hereditary emphysema, and Sjogren's syndrome. In some embodiments, the disease is cystic fibrosis.

In certain embodiments, the present invention provides a pharmaceutical composition suitable for use in a subject in the treatment or prevention of disease and conditions associate with deficient CFTR activity, comprising an effective amount of any of the compounds described herein (e.g., a compound of the invention, such as a compound of formula (I)), and one or more pharmaceutically acceptable excipients. In certain embodiments, the pharmaceutical preparations may be for use in treating or preventing a condition or disease as described herein.

Provided herein are combination therapies of compounds of formula (I) with CFTR-active agents that can enhance the therapeutic benefit beyond the ability of the primary therapy alone.

DETAILED DESCRIPTION

In certain aspects, the present application is directed to a compound of Formula (I):

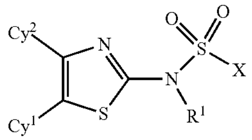

(I)

or a pharmaceutically acceptable salt thereof, wherein:

$R^1$ is hydrogen or $C_{1-6}$ alkyl;

X is $C_{1-6}$ alkyl, 5-6 membered aryl, 4-10 membered heterocycloalkyl, or 5-6 membered heteroaryl, each of which is substituted with 0-3 occurrences of $R^2$;

$Cy^1$ is $C_{3-9}$ cycloalkyl, 5-6 membered aryl, 4-10 membered heterocycloalkyl or 5-6 membered heteroaryl, each of which is substituted with 0-3 occurrences of $R^3$;

$Cy^2$ is $C_{3-9}$ cycloalkyl, 5-6 membered aryl, 4-10 membered heterocycloalkyl, or 5-6 membered heteroaryl, each of which is substituted with 1-3 occurrences of $R^4$;

each $R^2$ is independently hydroxyl, halo, —$NH_2$, nitro, $C_{1-6}$ alkyl, $C_{1-6}$ alkoxy, $C_{1-6}$ haloalkyl, $C_{1-6}$ haloalkoxy, 4-10 membered heterocycloalkyl, 5-6 membered heteroaryl, $C_{3-9}$ cycloalkyl, $C_{3-9}$ cycloalkoxy, —C(O)$NH_2$, —N($R^a$)($R^5$), —N($R^a$)C(O)—$R^5$, —N($R^a$)$SO_2$—$R^5$, —$SO_2$—$R^5$, —C(O)N($R^a$)($R^5$), —S(O)—$R^5$, —N($R^a$)S(O)(NH)—$R^5$ or —P(O)($R^5$)$_2$, wherein each $C_{1-6}$ alkyl, $C_{1-6}$ alkoxy, $C_{1-6}$ haloalkyl, $C_{3-9}$ cycloalkyl or 4-10 membered heterocycloalkyl is further substituted by 0-3 occurrences of $R^5$;

each $R^3$ is independently halo, $C_{1-6}$ alkyl, $C_{1-6}$ alkenyl, $C_{1-6}$ alkoxy, $C_{1-6}$ haloalkyl, $C_{1-6}$ haloalkoxy, $C_{3-9}$ cycloalkyl, $C_{1-4}$ alkyl-$C_{3-9}$ cycloalkyl, $C_{1-4}$ alkoxy-$C_{3-9}$ cycloalkyl, $C_{3-9}$ cycloalkoxy, $C_{3-9}$ cycloalkenyl, 5-6 membered aryl, aralkyl, aralkoxy, 5-6 membered heteroaryl, 4-10 membered heterocycloalkyl, —C(O)—$R^7$, —C(O)N($R^a$)($R^7$) or —N($R^a$)($R^8$), wherein each $C_{3-9}$ cycloalkyl, $C_{3-9}$ cycloalkoxy, $C_{1-8}$ haloalkoxy, $C_{1-8}$ alkoxy, 4-10 membered heterocycloalkyl, 5-6 membered aryl, 5-6 membered heteroaryl, cycloalkenyl, $C_{1-4}$ alkyl-$C_{3-9}$ cycloalkyl or $C_{1-4}$ alkoxy-$C_{3-9}$ cycloalkyl is further substituted with 0-3 occurrences of $R^7$;

each $R^4$ is independently halo, $C_{1-6}$ alkyl, $C_{1-6}$ alkoxy, $C_{1-6}$ haloalkyl, $C_{1-6}$ haloalkoxy, $C_{3-6}$ cycloalkyl, N($R^a$)$_2$ or 4-10 membered heterocycloalkyl, wherein each 4-10 membered heterocycloalkyl may be further substituted with 0-3 $R^b$;

each $R^5$ is independently $C_{1-6}$ alkyl, $C_{1-6}$ haloalkyl, $C_{3-9}$ cycloalkyl, hydroxyl, —$SO_2$—$R^6$, —$CO_2H$, —$NH_2$, —$CO_2$—$C_{1-4}$ alkyl or 4-10 membered heterocycloalkyl, wherein each $C_{1-6}$ alkyl, $C_{3-9}$ cycloalkyl or 4-10 membered heterocycloalkyl is further substituted by 0-3 occurrences of $R^6$;

each $R^6$ is independently hydroxyl, —$NH_2$, halo, $C_{1-4}$ alkyl, $C_{1-4}$ haloalkyl, —$CO_2H$ or —$CO_2$—($C_{1-4}$ alkyl);

each $R^7$ is independently halo, $C_{1-5}$ alkyl, $C_{1-5}$ alkoxy, $C_{1-5}$ haloalkyl, $C_{1-5}$ haloalkoxy, $C_{1-5}$ haloalkenyl, $C_{3-7}$ cycloalkyl, hydroxyl, 5-6 membered aryl, aralkyl, aralkoxy, —C(O)—O—$C_{1-4}$alkyl, —C(O)N($R^a$)($C_{1-4}$ alkyl), 5-6 membered heteroaryl or 4-10 membered heterocycloalkyl, wherein each $C_{3-7}$ cycloalkyl, 5-6 membered aryl or 4-10 membered heterocycloalkyl is further substituted by 0-3 occurrences of $R^8$;

each $R^8$ is independently halo, $C_{1-4}$ alkyl, $C_{1-4}$ haloalkoxy, C(O)—$C_{1-4}$ alkyl or C(O)N($R^a$)($C_{1-4}$ alkyl);

each $R^a$ is independently H or $C_{1-6}$ alkyl; and each $R^b$ is $C_{1-4}$ alkyl;

wherein a) if $Cy^1$ is phenyl and has 3 occurrences of $R^3$, then each $R^3$ is not methoxy;

b) when X and $Cy^2$ are each phenyl, then $R^2$ and $R^4$ are not each methyl;

c) $R^3$ and $R^4$ are not simultaneously tert-butyl or simultaneously methoxy;

d) when $Cy^1$ and $Cy^2$ are mono-substituted phenyl, then X is not thienyl; and e) when $Cy^1$ and $Cy^2$ are mono-substituted phenyl, then $R^2$ is not OH, $R^3$ is not Cl and $R^4$ is not OMe.

Disclosed herein are compounds of Formula (I):

(I)

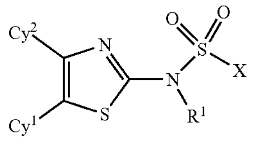

or a pharmaceutically acceptable salt thereof, wherein:

$R^1$ is hydrogen;

X is 5-6 membered aryl or 5-6 membered heteroaryl, each of which is substituted with 0-3 occurrences of $R^2$;

$Cy^1$ is 5-6 membered aryl, 4-10 membered heterocycloalkyl or 5-6 membered heteroaryl, each of which is substituted with 0-3 occurrences of $R^3$;

$Cy^2$ is 5-6 membered aryl, which is substituted with 1-3 occurrences of $R^4$;

each $R^2$ is independently halo, —$NH_2$, $C_{1-6}$ alkyl, $C_{1-8}$ haloalkoxy, 5-6 membered heteroaryl, —N($R^a$)($R^5$), —N($R^a$)C(O)—$R^5$, —SO—$R^5$ or —$SO_2$—$R^5$;

each $R^3$ is independently halo, $C_{1-8}$ alkyl, $C_{1-8}$ alkoxy, $C_{1-8}$ haloalkoxy, $C_{3-9}$ cycloalkyl, $C_{3-9}$ cycloalkoxy, or 4-10 membered heterocycloalkyl, wherein each $C_{3-9}$ cycloalkyl, $C_{3-9}$ cycloalkoxy, $C_{1-8}$ haloalkoxy, $C_{1-8}$ alkoxy, and 4-10 membered heterocycloalkyl is further substituted with 0-3 occurrences of $R^7$;

each $R^4$ is independently halo, $C_{1-6}$ alkyl, $C_{1-6}$ alkoxy, or $C_{1-6}$ haloalkyl;

each $R^5$ is independently $C_{1-6}$ alkyl, $C_{1-6}$ haloalkyl, $C_{3-9}$ cycloalkyl, hydroxyl, or —$CO_2$H, wherein each $C_{1-6}$ alkyl, or $C_{3-9}$ cycloalkyl is further substituted by 0-3 occurrences of $R^6$;

each $R^6$ is independently halo, hydroxyl, $C_{1-6}$ alkyl, —$CO_2$H or —$CO_2$—($C_{1-4}$ alkyl);

each $R^7$ is independently halo, $C_{1-5}$ alkyl, $C_{1-5}$ haloalkoxy, $C_{3-7}$ cycloalkyl, and hydroxyl; and each $R^a$ is independently H or $C_{1-6}$ alkyl.

In some embodiments, $R^1$ is H. In some embodiments, $R^1$ is $C_{1-6}$ alkyl (e.g., methyl or ethyl).

In some embodiments, X is aryl substituted with 0-3 occurrences of $R^2$. In some embodiments, X is phenyl substituted with 0-3 occurrences of $R^2$. In some embodiments, X is phenyl substituted with 0 occurrences of $R^2$.

In some embodiments, X is phenyl substituted with 1 occurrence of $R^2$. In some embodiments, $R^2$ is —$NH_2$. In some embodiments, $R^2$ is hydroxyl. In some embodiments, $R^2$ is halo (e.g., fluoro, chloro or bromo). In some embodiments, $R^2$ is nitro. In some embodiments, $R^2$ is $C_{1-6}$ alkoxy (e.g., methoxy, ethoxy or isopropoxy). In some embodiments, $R^2$ is $C_{1-6}$ haloalkyl (e.g., trifluoromethyl, difluoromethyl or 2,2,2-trifluoroethyl) substituted with 0-3 occurrences of $R^5$. In some embodiments, $R^2$ is $C_{1-6}$ haloalkyl (e.g., trifluormethyl, difluoromethyl or 2,2,2-trifluoroethyl) substituted with 0 occurrences of $R^5$. In some embodiments, $R^2$ is $C_{1-6}$ haloalkyl (e.g., trifluormethyl, difluoromethyl or 2,2,2-trifluoroethyl) substituted with 1 occurrence of $R^5$. In further embodiments, $R^5$ is hydroxyl.

In some embodiments, X is phenyl substituted with 1 occurrence of $R^2$. In some embodiments, $R^2$ is —C(O)$NH_2$. In some embodiments, $R^2$ is $C_{1-6}$ haloalkoxy (e.g., trifluoromethoxy or difluoromethoxy) substituted with 0-3 occurrences of $R^5$. In some embodiments, $R^2$ is $C_{1-6}$ haloalkoxy (e.g., trifluoromethoxy or difluoromethoxy) substituted with 0 occurrences of $R^5$. In some embodiments, $R^2$ is $C_{1-6}$ alkyl (e.g., methyl or isopropyl) substituted with 0-3 occurrences of $R^5$. In some embodiments, $R^2$ is $C_{1-6}$ alkyl (e.g., methyl or isopropyl) substituted with 0 occurrences of $R^5$. In some embodiments, $R^2$ is $C_{1-6}$ alkyl (e.g., methyl or isopropyl) substituted with 1 occurrence of $R^5$. In some embodiments, $R^5$ is hydroxyl. In some embodiments, $R^5$ is —$SO_2$—$R^6$. In some embodiments, $R^6$ is $C_{1-4}$ alkyl (e.g., methyl). In some embodiments, $R^2$ is —S(O)—$R^5$. In some embodiments, $R^5$ is $C_{1-6}$ alkyl (e.g., methyl). In some embodiments, $R^2$ is —P(O)($R^5$)$_2$. In some embodiments, both $R^5$ are $C_{1-6}$ alkyl (e.g., methyl). In some embodiments, $R^2$ is —N($R^a$)$SO_2$—$R^5$. In some embodiments, $R^a$ is H and $R^5$ is $C_{1-6}$ alkyl (e.g., methyl). In some embodiments, $R^a$ is H and $R^5$ is $C_{1-6}$ haloalkyl (e.g., trifluoromethyl). In some embodiments, $R^a$ is $C_{1-6}$ alkyl (e.g., methyl) and $R^5$ is $C_{1-6}$ alkyl (e.g., methyl). In some embodiments, $R^a$ is $C_{1-6}$ alkyl (e.g., methyl) and $R^5$ is $C_{1-6}$ haloalkyl (e.g., trifluoromethyl). In some embodiments, $R^2$ is —$SO_2R^5$. In some embodiments, $R^5$ is —$NH_2$.

In some embodiments, X is phenyl substituted with 1 occurrence of $R^2$. In some embodiments, wherein $R^2$ is heteroaryl (e.g., 1-pyrazolyl or 5-pyrazolyl) substituted with 0-3 occurrences of $R^5$. In some embodiments, $R^2$ is heteroaryl (e.g., 1-pyrazolyl or 5-pyrazolyl) substituted with 0 occurrences of $R^5$. In some embodiments, $R^2$ is —N($R^a$)($R^5$). In some embodiments, $R^a$ is H and $R^5$ is $C_{1-6}$ alkyl (e.g., methyl). In some embodiments, $R^a$ is $C_{1-6}$ alkyl (e.g., methyl) and $R^5$ is $C_{1-6}$ alkyl (e.g., methyl). In some embodiments, $R^a$ is H and $R^5$ is $C_{1-6}$ haloalkyl (e.g., trifluoromethyl or 1,1,1-trifluoroisopropyl). In some embodiments, $R^a$ is H and $R^5$ is heterocycloalkyl (e.g., 3-tetrahydrofuranyl) substituted with 0-3 occurrences of $R^6$. In some embodiments, $R^a$ is H and $R^5$ is heterocycloalkyl (e.g., 3-tetrahydrofuranyl) substituted with 0 occurrences of $R^6$. In some embodiments, $R^a$ is H and $R^5$ is $C_{3-9}$ cycloalkyl (e.g., cyclobutyl or cyclopentyl) further substituted with 0-3 occurrences of $R^6$. In some embodiments, $R^a$ is H and $R^5$ is $C_{3-9}$ cycloalkyl (e.g., cyclobutyl or cyclopentyl) further substituted with 0 occurrences of $R^6$. In some embodiments, $R^a$ is H and $R^5$ is $C_{3-9}$ cycloalkyl (e.g., cyclobutyl or cyclopentyl) further substituted with 1 occurrence of $R^6$. In some embodiments, $R^6$ is —$CO_2$H. In some embodiments, $R^6$ is —C(O)$_2$—$C_{1-4}$ alkyl (e.g., —$CO_2$Me or —$CO_2$Et). In some embodiments, $R^a$ is H and $R^5$ is $C_{3-9}$ cycloalkyl (e.g., cyclobutyl or cyclopentyl) further substituted with 2 occurrences of $R^6$. In some embodiments, 1 occurrence of $R^6$ is hydroxyl and the other occurrence is $C_{1-4}$ alkyl (e.g., methyl).

In some embodiments, X is phenyl substituted with 1 occurrence of $R^2$. In some embodiments, $R^2$ is —N($R^a$)C(O)—$R^5$. In some embodiments, $R^a$ is H and $R^5$ is $C_{1-6}$ alkyl (e.g., methyl, ethyl or isopropyl) substituted with 0-3 occurrences of $R^6$. In some embodiments, $R^a$ is H and $R^5$ is $C_{1-6}$ alkyl (e.g., methyl, ethyl or isopropyl) substituted with 0 occurrences of $R^6$. In some embodiments, $R^a$ is H and $R^5$ is $C_{1-6}$ alkyl (e.g., methyl, ethyl or isopropyl) substituted with 1 occurrence of $R^6$. In some embodiments, $R^6$ is —$NH_2$. In some embodiments, $R^6$ is hydroxyl. In some embodiments, $R^a$ is H and $R^5$ is $C_{1-6}$ haloalkyl (e.g., trifluoromethyl). In some embodiments, $R^a$ is H and $R^5$ is $C_{3-9}$ cycloalkyl (e.g., cyclopropyl) substituted with 0-3 occurrences of $R^6$. In some embodiments, $R^a$ is H and $R^5$ is $C_{3-9}$ cycloalkyl (e.g., cyclopropyl) substituted with 0 occurrences of $R^6$. In some embodiments, $R^a$ is H and $R^5$ is $C_{3-9}$ cycloalkyl (e.g., cyclopropyl) substituted with 1 occurrence of $R^6$. In some embodiments, $R^6$ is halo (e.g., fluoro). In some embodiments, $R^6$ is $C_{1-4}$ haloalkyl (e.g., trifluoromethyl).

In some embodiments, $R^2$ is heterocycloalkyl (e.g., N-pyrrolidinyl) substituted with 0-3 occurrences of $R^5$. In some embodiments, $R^2$ is heterocycloalkyl (e.g., N-pyrrolidinyl) substituted with 0 occurrences of $R^5$. In some embodiments, $R^2$ is heterocycloalkyl (e.g., N-pyrrollidinyl) substituted with 1 occurrence of $R^5$. In some embodiments, $R^5$ is $C_{1-6}$ alkyl (e.g., methyl) substituted with 0-3 occurrences of $R^6$. In some embodiments, $R^5$ is $C_{1-6}$ alkyl (e.g., methyl) substituted with 0 occurrences of $R^6$. In some embodiments, $R^2$ is —C(O)—N($R^a$)($R^5$). In some embodiments, $R^a$ is H and $R^5$ is $C_{1-6}$ alkyl (e.g., methyl or ethyl) substituted with 0-3 occurrences of $R^6$. In some embodiments, $R^a$ is H and $R^5$ is $C_{1-6}$ alkyl (e.g., methyl or ethyl) substituted with 0 occurrences of $R^6$. In some embodiments, $R^a$ is H and $R^5$ is $C_{1-6}$ alkyl (e.g., methyl or ethyl) substituted with 1 occurrence of $R^6$. In some embodiments, $R^6$ is hydroxyl. In some embodiments, $R^2$ is —N($R^a$)S(O)(NH)—$R^5$. In some embodiments, $R^a$ is H and $R^5$ is $C_{1-6}$ alkyl (e.g., methyl) substituted with 0-3 occurrences of $R^6$. In some embodiments, $R^a$ is H and $R^5$ is $C_{1-6}$ alkyl (e.g., methyl) substituted with 0 occurrences of $R^6$.

In some embodiments, wherein X is

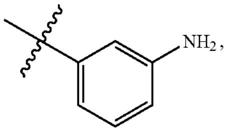
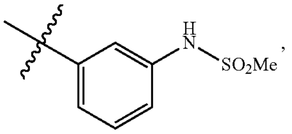
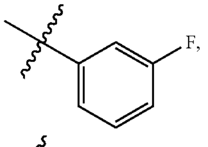
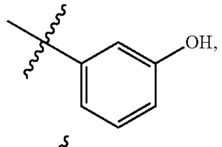
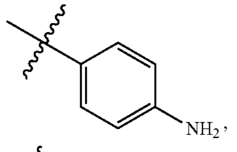
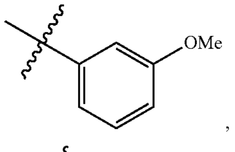
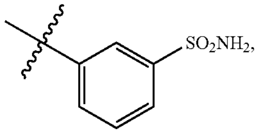
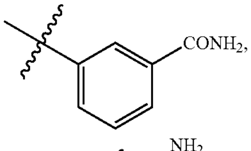
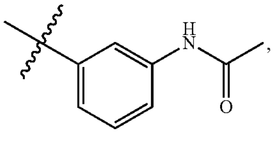
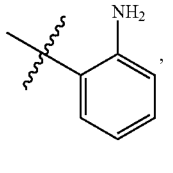

-continued

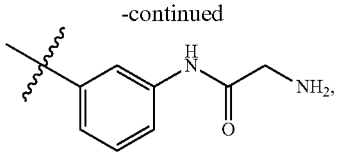
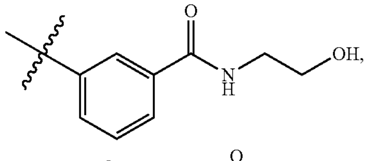
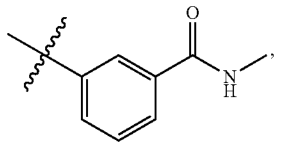
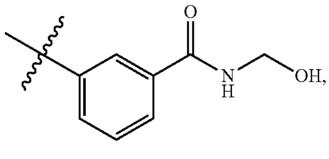
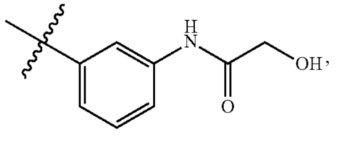
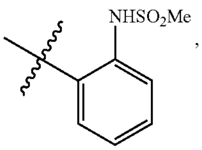
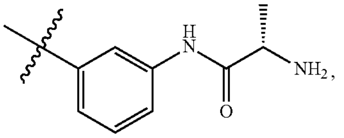
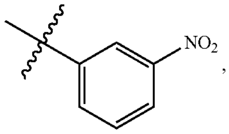
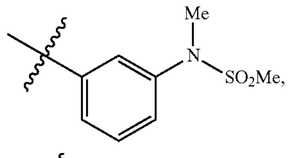
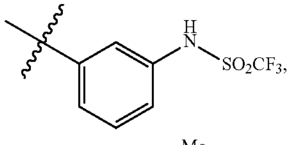
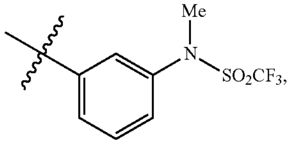
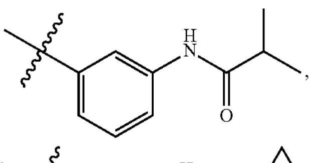
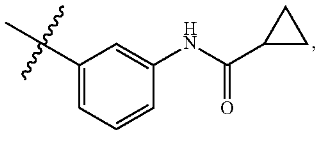
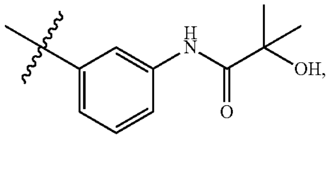

-continued

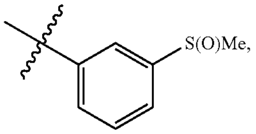
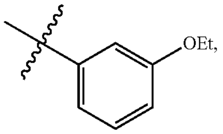
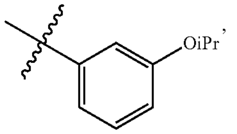
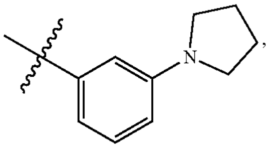
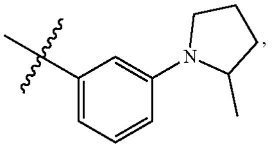
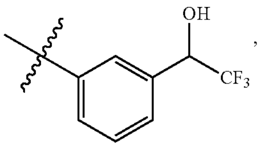
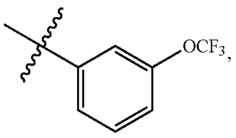
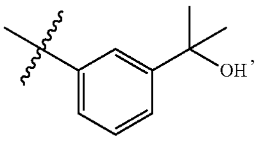
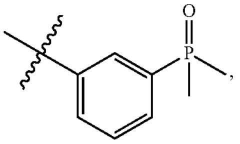
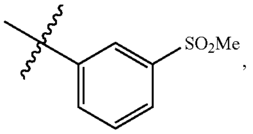
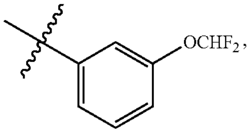
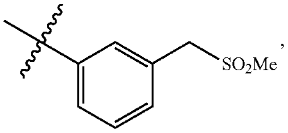
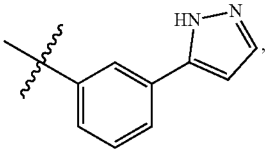
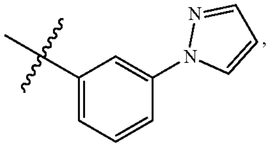
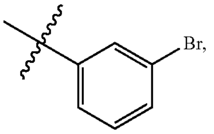
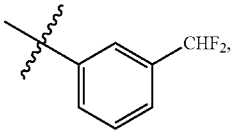
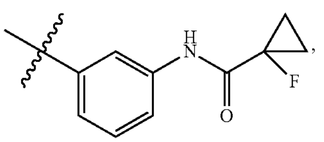
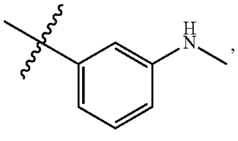
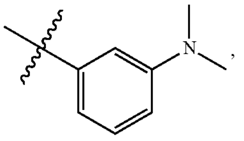
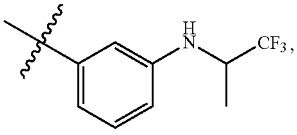
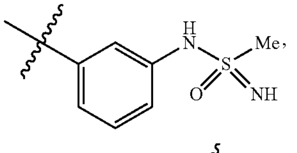
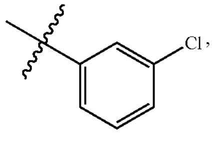
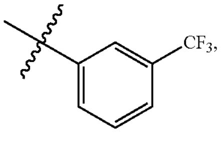

-continued

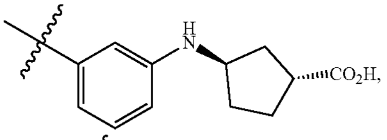
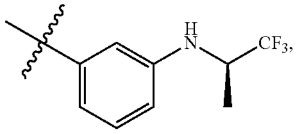
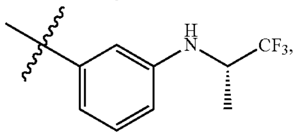
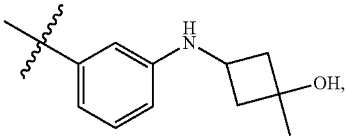
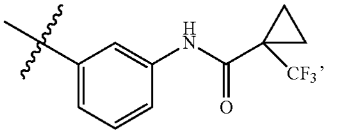
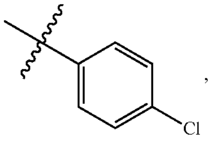
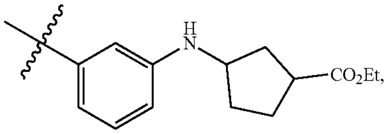
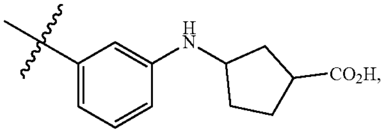
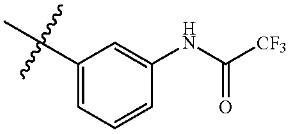
or
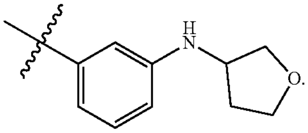

In some embodiments, X is phenyl substituted with 2 occurrences of $R^2$. In some embodiments, each $R^2$ is halo (e.g., fluoro or chloro). In some embodiments, each $R^2$ is fluoro. In some embodiments, each $R^2$ is chloro. In some embodiments, one $R^2$ is —$NH_2$ and one $R^2$ is halo (e.g., fluoro). In some embodiments, one $R^2$ is $C_{1-6}$ alkyl (e.g., methyl) and the other $R^2$ is $C_{1-6}$ haloalkyl (e.g., difluoromethyl). In some embodiments, one $R^2$ is halo (e.g., fluoro) and the other $R^2$ is —$N(R^a)(R^5)$ (e.g., —NHMe). In some embodiments, $R^a$ is H and $R^5$ is $C_{1-6}$ alkyl (e.g., methyl). In some embodiments, $R^a$ is H and $R^5$ is $C_{3-9}$ cycloalkyl (e.g., cyclopentyl) further substituted with 0-3 occurrences of $R^6$. In some embodiments, $R^a$ is H and $R^5$ is $C_{3-9}$ cycloalkyl (e.g., cyclopentyl) further substituted with 1 occurrence of $R^6$. In some embodiments, $R^6$ is $C_{1-6}$ alkyl (e.g., methyl). In some embodiments, $R^a$ is H and $R^5$ is heterocycloalkyl (e.g., 3-pyrrolidinyl) further substituted with 0-3 occurrences of $R^6$. In some embodiments, $R^a$ is H and $R^5$ is heterocycloalkyl (e.g., 3-pyrrolidinyl) further substituted with 1 occurrence of $R^6$. In some embodiments, $R^6$ is $C_{1-4}$ alkyl (e.g., methyl).

In some embodiments, X is

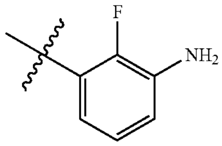
,
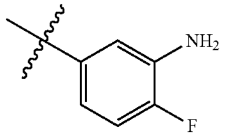
,
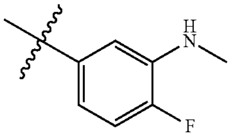
,
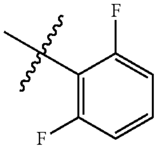
,
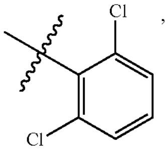
,
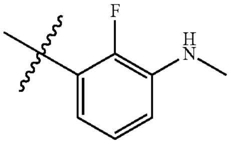
,
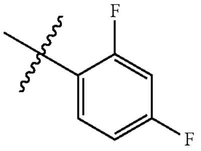
,
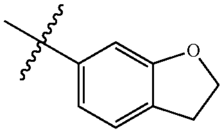
,
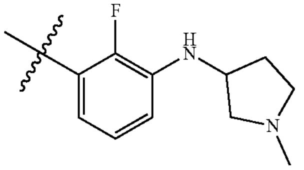
or
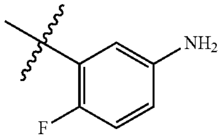
.

In some embodiments, X is phenyl substituted with 3 occurrences of $R^2$. In some embodiments, two $R^2$ are halo (e.g., fluoro) and the remaining $R^2$ is —$NH_2$. In some embodiments, X is

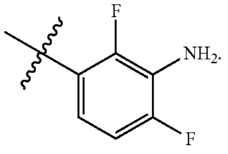 [SMILES: *c1ccc(F)c(N)c1F]

In some embodiments, X is 5-6 membered heteroaryl substituted 0-3 occurrences of $R^2$. In some embodiments, X is selected from pyridinyl, pyrazolyl, isoxazolyl, pyrazolyl, indolyl, thiazolyl, thiophenyl or furanyl substituted with 0-3 occurrences of $R^2$.

In some embodiments, X is 2-pyridinyl substituted with 0-3 occurrences of $R^2$. In some embodiments, X is 2-pyridinyl substituted with 0 occurrences of $R^2$.

In some embodiments, X is 2-pyridinyl substituted with 1 occurrence of $R^2$. In some embodiments, wherein $R^2$ is —$NH_2$. In some embodiments, $R^2$ is halo (e.g., fluoro or chloro). In some embodiments, $R^2$ is $C_{1-6}$ alkoxy (e.g., methoxy or isopropoxy) substituted with 0-3 occurrences of $R^5$. In some embodiments, $R^2$ is $C_{1-6}$ alkoxy (e.g., methoxy, ethoxy or isopropoxy) substituted with 0 occurrences of $R^5$. In some embodiments, $R^2$ is $C_{1-6}$ alkoxy (e.g., methoxy, ethoxy or isopropoxy) substituted with 1 occurrence of $R^5$. In some embodiments, $R^5$ is $C_{3-9}$ cycloalkyl (e.g., cyclopropyl or cyclobutyl) substituted with 0-3 occurrences of $R^6$. In some embodiments, $R^5$ is $C_{3-9}$ cycloalkyl (e.g., cyclopropyl or cyclobutyl) substituted with 1 occurrence of $R^6$. In some embodiments, $R^6$ is $C_{1-4}$ haloalkyl (e.g., trifluoromethyl). In some embodiments, $R^5$ is $C_{3-9}$ cycloalkyl (e.g., cyclopropyl or cyclobutyl) substituted with 2 occurrences of $R^6$. In some embodiments, both $R^6$ are halo (e.g., fluoro).

In some embodiments, $R^2$ is —$N(R^a)SO_2$—$R^5$. In some embodiments, $R^a$ is H and $R^5$ is $C_{1-6}$ alkyl (e.g., methyl) substituted with 0-3 occurrences of $R^6$. In some embodiments, $R^a$ is H and $R^5$ is $C_{1-6}$ alkyl (e.g., methyl) substituted with 0 occurrences of $R^6$. In some embodiments, $R^2$ is —$N(R^a)C(O)$—$R^5$. In some embodiments, $R^a$ is H and $R^5$ is $C_{1-6}$ alkyl (e.g., methyl or isopropyl) substituted with 0-3 occurrences of $R^6$. In some embodiments, $R^a$ is H and $R^5$ is $C_{1-6}$ alkyl (e.g., methyl or isopropyl) substituted with 0 occurrences of $R^6$.

In some embodiments, $R^2$ is —$N(R^a)(R^5)$. In some embodiments, $R^a$ is H and $R^5$ is $C_{1-6}$ alkyl (e.g., methyl or neopentyl) substituted with 0-3 occurrences of $R^6$. In some embodiments, $R^a$ is H and $R^5$ is $C_{1-6}$ alkyl (e.g., methyl or neopentyl) substituted with 0 occurrences of $R^6$. In some embodiments, $R^a$ is H and $R^5$ is $C_{1-6}$ alkyl (e.g., methyl or neopentyl) substituted with 1 occurrence of $R^6$. In some embodiments, $R^6$ is —$CO_2H$. In some embodiments, $R^6$ is —$CO_2$—$C_{1-4}$ alkyl (e.g., —$CO_2Me$ or —$CO_2Et$). In some embodiments, $R^a$ is $C_{1-6}$ alkyl (e.g., methyl or ethyl) and $R^5$ is $C_{1-6}$ alkyl (e.g., methyl or isopropyl) substituted with 0-3 occurrences of $R^6$. In some embodiments, $R^a$ is $C_{1-6}$ alkyl (e.g., methyl or ethyl) and $R^5$ is $C_{1-6}$ alkyl (e.g., methyl or isopropyl) substituted with 0 occurrences of $R^6$. In some embodiments, $R^a$ is H and $R^5$ is $C_{3-9}$ cycloalkyl (e.g., cyclopropyl or cyclopentyl) substituted with 0-3 occurrences of $R^6$. In some embodiments, $R^a$ is H and $R^5$ is $C_3$-9 cycloalkyl (e.g., cyclopropyl or cyclopentyl) substituted with 0 occurrences of $R^6$. In some embodiments, $R^a$ is H and $R^5$ is $C_{3-9}$ cycloalkyl (e.g., cyclopropyl, cyclohexyl or cyclopentyl) substituted with 1 occurrence of $R^6$. In some embodiments, $R^6$ is —$CO_2H$. In some embodiments, $R^6$ is —$CO_2$—$C_{1-4}$ alkyl (e.g., —$CO_2Me$ or —$CO_2Et$). In some embodiments, $R^a$ is H and $R^5$ is $C_{1-6}$ haloalkyl (e.g., 1,1,1-trifluoroisopropyl) substituted with 0-3 occurrences of $R^6$. In some embodiments, $R^a$ is H and $R^5$ is $C_{1-6}$ haloalkyl (e.g., 1,1,1-trifluoroisopropyl) substituted with 0 occurrences of $R^6$. In some embodiments, $R^a$ is $C_{1-6}$ alkyl (e.g., methyl) and $R^5$ is $C_{1-6}$ haloalkyl (e.g., 2,2,2-trifluoroethyl) substituted with 0-3 occurrences of $R^6$. In some embodiments, $R^a$ is $C_1$-6 alkyl (e.g., methyl) and $R^5$ is $C_{1-6}$ haloalkyl (e.g., 2,2,2-trifluoroethyl) substituted with 0 occurrences of $R^6$. In some embodiments, $R^2$ is $C_{3-9}$ cycloalkoxy (e.g., cyclopropoxy) substituted with 0 occurrences of $R^5$. In some embodiments, $R^2$ is $C_{1-6}$ haloalkoxy (e.g., trifluoromethyl, 2,2-difluoroethyl, 1,1,1-trifluoroisopropyl, 1,1,1-trifluoro-tert-butyl or 1,3-difluoroisopropyl). In some embodiments, $R^2$ is $C_{3-9}$ cycloalkyl (e.g., cyclopentyl or cyclohexyl) substituted with 0-3 occurrences of $R^5$. In some embodiments, $R^2$ is $C_{3-9}$ cycloalkyl (e.g., cyclopentyl or cyclohexyl) substituted with 1 occurrence of $R^5$. In some embodiments, $R^5$ is —$CO_2H$. In some embodiments, $R^5$ is —$CO_2$—$R^6$. In some embodiments, $R^6$ is $C_{1-4}$ alkyl (e.g., methyl).

In some embodiments, $R^2$ is heterocycloalkyl (e.g., azetidinyl, pyrrolidinyl, piperidinyl or morpholinyl) substituted with 0-3 occurrences of $R^5$. In some embodiments, $R^2$ is heterocycloalkyl (e.g., azetidinyl, pyrrolidinyl, piperidinyl or morpholinyl) substituted with 0 occurrences of $R^5$. In some embodiments, $R^2$ is heterocycloalkyl (e.g., azetidinyl, pyrrolidinyl, piperidinyl or morpholinyl) substituted with 2 occurrences of $R^5$. In some embodiments, both occurrences of $R^5$ are halo (e.g., fluoro). In some embodiments, both occurrences of $R^5$ are $C_{1-6}$ alkyl (e.g., methyl) substituted with 0-3 occurrences of $R^6$. In some embodiments, both occurrences of $R^5$ are $C_{1-6}$ alkyl (e.g., methyl) substituted with 0 occurrences of $R^6$. In some embodiments, one occurrence of $R^5$ is —$CO_2H$ and the other occurrence of $R^5$ is $C_{1-6}$ alkyl (e.g., methyl) further substituted with 0-3 occurrences of $R^6$. In some embodiments, one occurrence of $R^5$ is —$CO_2H$ and the other occurrence of $R^5$ is $C_{1-6}$ alkyl (e.g., methyl) further substituted with 0 occurrences of $R^6$. In some embodiments, one occurrence of $R^5$ is —$CO_2$—$C_{1-4}$ alkyl (e.g., —$CO_2Me$) and the other occurrence of $R^5$ is $C_{1-6}$ alkyl (e.g., methyl) further substituted with 0-3 occurrences of $R^6$. In some embodiments, one occurrence of $R^5$ is —$CO_2$—$C_{1-4}$ alkyl (e.g., —$CO_2Me$) and the other occurrence of $R^5$ is $C_{1-6}$ alkyl (e.g., methyl) further substituted with 0 occurrences of $R^6$.

In some embodiments, X is

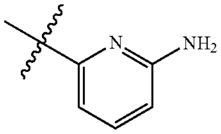,
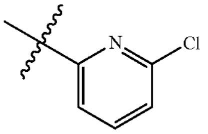,
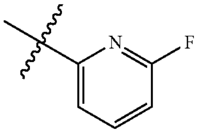,
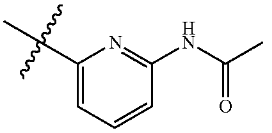,
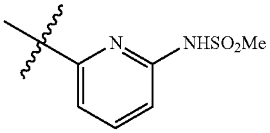,
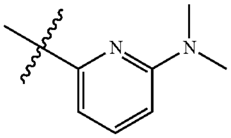,
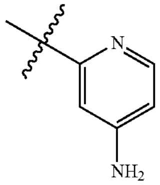,
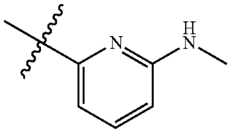,
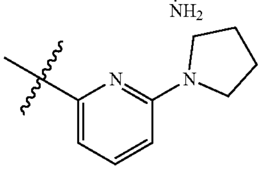,
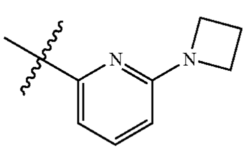,
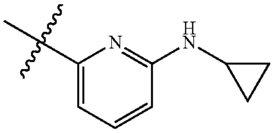,
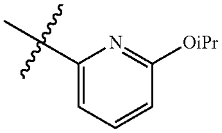,
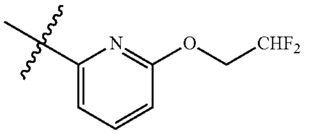, -continued

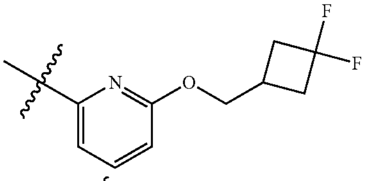,
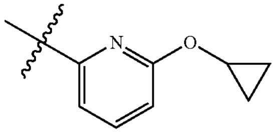,
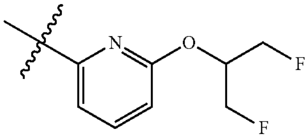,
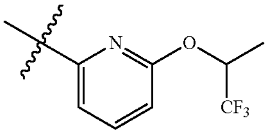,
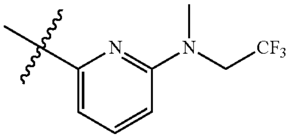,
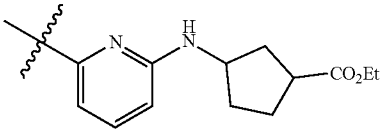,
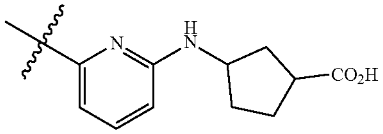,
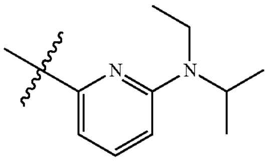,
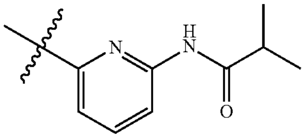,
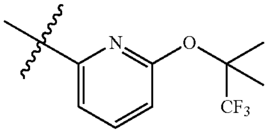,
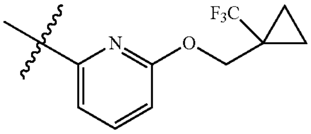,
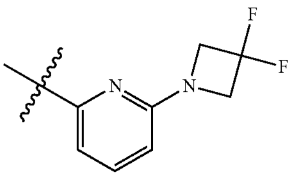, -continued

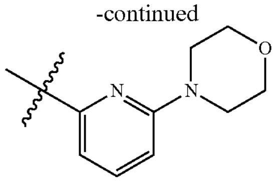

,

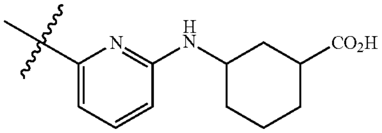

,

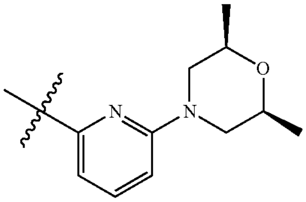

,

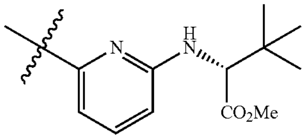

,

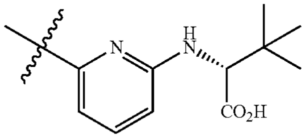

,

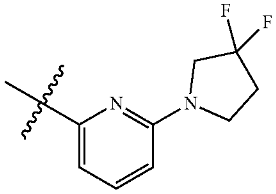

,

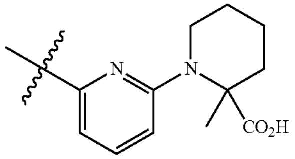

or

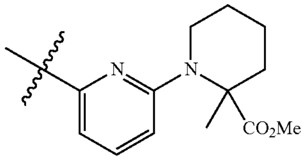

.

In some embodiments, X is 2-pyridinyl substituted with 2 occurrences of $R^2$. In some embodiments, one $R^2$ is —$NH_2$ and the other is halo (e.g., fluoro). In some embodiments, one $R^2$ is hydroxyl and the other is halo (e.g., fluoro).

In some embodiments, X is

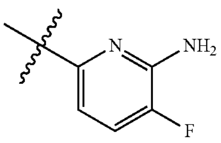

or

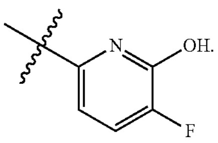

In some embodiments, X is 3-pyrazolyl substituted with 0-3 occurrences of $R^2$. In some embodiments, X is 3-pyrazolyl substituted with 0 occurrences of $R^2$. In some embodiments, X is 3-pyrazolyl substituted with 1 occurrence of $R^2$. In some embodiments, $R^2$ is $C_{1-6}$ alkyl (e.g., methyl). In some embodiments, X is

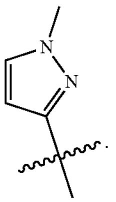 [SMILES: *c1ccn(C)n1]

In some embodiments, X is 4-isoxazolyl substituted with 0-3 occurrences of $R^2$. In some embodiments, X is 4-isoxazolyl substituted with 0 occurrences of $R^2$.

In some embodiments, X is 4-isoxazolyl substituted with 2 occurrences of $R^2$. In some embodiments, each $R^2$ is independently $C_{1-6}$ alkyl (e.g., methyl). In some embodiments, X is

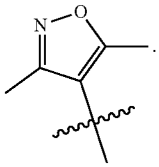

In some embodiments, X is 3-pyridinyl substituted with 0-3 occurrences of $R^2$. In some embodiments, X is 3-pyridinyl substituted with 0 occurrences of $R^2$.

In some embodiments, X is 3-pyridinyl substituted with 1 occurrence of $R^2$. In some embodiments, $R^2$ is —$NH_2$. In some embodiments, $R^2$ is $C_{1-6}$ alkoxy (e.g., methoxy). In some embodiments, $R^2$ is —$N(R^a)SO_2$—$R^5$. In some embodiments, $R^a$ is H and $R^5$ is $C_{1-6}$ alkyl (e.g., methyl) substituted with 0-3 occurrences of $R^6$. In some embodiments, $R^a$ is H and $R^5$ is $C_{1-6}$ alkyl (e.g., methyl) substituted with 0 occurrences of $R^6$. In some embodiments, $R^2$ is heterocycloalkyl (e.g., N-oxetanyl) substituted with 0-3 occurrences of $R^5$. In some embodiments, $R^2$ is heterocycloalkyl (e.g., N-oxetanyl) substituted with 0 occurrences of $R^5$. In some embodiments, $R^2$ is N-oxetanyl substituted with 0 occurrences of $R^1$.

In some embodiments, X is

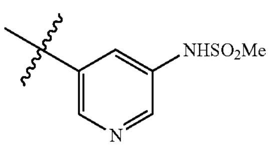

,

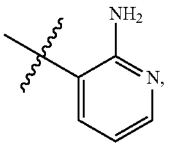

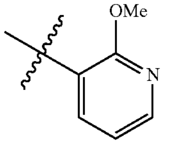

or

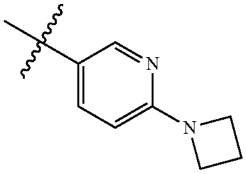

.

In some embodiments, X is 5-thiazolyl substituted with 0-3 occurrences of $R^2$. In some embodiments, X is 5-thiazolyl substituted with 0 occurrences of $R^2$. In some embodiments, X is 5-thiazolyl substituted with 1 occurrence of $R^2$.

In some embodiments, $R^2$ is —$NH_2$. In some embodiments, $R^2$ is halo (e.g., chloro). In some embodiments, $R^2$ is —$N(R^a)(R^5)$. In some embodiments, $R^a$ is H and $R^5$ is $C_{1-6}$ alkyl substituted with 0 occurrences of $R^6$. In some embodiments, $R^2$ is —NHEt. In some embodiments, $R^a$ is H and $R^5$ is $C_{1-6}$ alkyl substituted with 1 occurrence of $R^6$ (e.g., methyl or ethyl). In some embodiments, $R^6$ is hydroxyl. In some embodiments, $R^2$ is

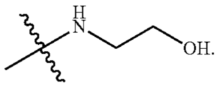 [SMILES: *NCCO]

In some embodiments, X is

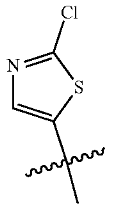

,

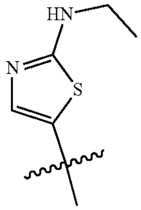

or

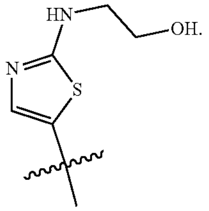

In some embodiments, X is 4-pyrazolyl substituted with 0-3 occurrences of $R^2$. In some embodiments, X is 4-pyrazolyl substituted with 0 occurrences of $R^2$. In some embodiments, X is 4-pyrazolyl substituted with 1 occurrence of $R^2$. In some embodiments, $R^2$ is $C_{1-6}$ haloalkyl (e.g., difluoromethyl). In some embodiments, $R^2$ is heterocycloalkyl (e.g., 3-tetrahydrofuranyl) substituted with 0-3 occurrences of $R^5$. In some embodiments, $R^2$ is heterocycloalkyl (e.g., 3-tetrahydrofuranyl) substituted with 0 occurrences of $R^5$.

In some embodiments, X is

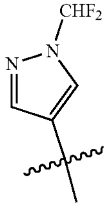

or

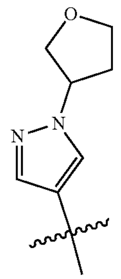

.

In some embodiments, X is 4-pyrazolyl substituted with 2 occurrences of $R^2$. In some embodiments, each $R^2$ is independently $C_{1-6}$ alkyl (e.g., methyl). In some embodiments, one $R^2$ is $C_{1-6}$ alkyl (e.g., methyl) and the other $R^2$ is $C_{1-6}$ haloalkyl (e.g., 1,1,1-trifluoroisopropyl).

In some embodiments, X is

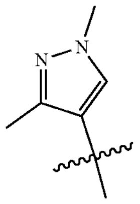

or

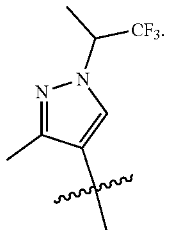

In some embodiments, X is 6-indolyl substituted with 0-3 occurrences of $R^2$. In some embodiments, X is 6-indolyl substituted with 0 occurrences of $R^2$.

In some embodiments, X is 4-pyridinyl substituted with 0-3 occurrences of $R^2$. In some embodiments, X is 4-pyridinyl substituted with 0 occurrences of $R^2$.

In some embodiments, X is 4-pyridinyl substituted with 1 occurrence of $R^2$. In some embodiments, $R^2$ is —$NH_2$. In some embodiments, $R^2$ is —$N(R^a)(R^5)$. In some embodiments, $R^a$ is $C_{1-6}$ alkyl (e.g., methyl) and $R^5$ is $C_{1-6}$ alkyl (e.g., methyl) substituted with 0-3 occurrences of $R^6$. In some embodiments, $R^a$ is $C_{1-6}$ alkyl (e.g., methyl) and $R^5$ is $C_{1-6}$ alkyl (e.g., methyl) substituted with 0 occurrences of $R^6$. In some embodiments, $R^2$ is —$N(R^a)C(O)$—$R^5$. In some embodiments, $R^a$ is H and $R^5$ is $C_{1-6}$ alkyl (e.g., methyl) substituted with 0-3 occurrences of $R^6$. In some embodiments, $R^a$ is H and $R^5$ is $C_{1-6}$ alkyl (e.g., methyl) substituted with 0 occurrences of $R^6$. In some embodiments, $R^2$ is heterocycloalkyl (e.g., N-pyrrolidinyl) substituted with 0-3 occurrences of $R^5$. In some embodiments, $R^2$ is heterocycloalkyl (e.g., N-pyrrolidinyl) substituted with 0 occurrences of $R^5$.

In some embodiments, X is

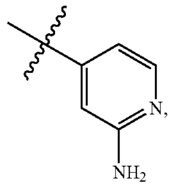

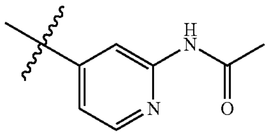

,

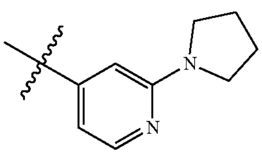

or

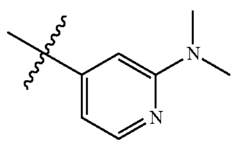

In some embodiments, X is 4-pyridinyl substituted with 2 occurrences of $R^2$. In some embodiments, one $R^2$ is —$NH_2$ and the other $R^2$ is hydroxyl.

In some embodiments, X is 4-thiazolyl substituted with 0-3 occurrences of $R^2$. In some embodiments, X is 4-thiazolyl substituted with 0 occurrences of $R^2$.

In some embodiments, X is 4-thiazolyl substituted with 1 occurrence of $R^2$. In some embodiments, $R^2$ is —$NH_2$. In some embodiments, X is

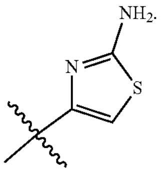 [SMILES: *c1csc(N)n1]

In some embodiments, X is 3-thiazolyl substituted with 0-3 occurrences of $R^2$.

In some embodiments, X is 3-thiophenyl substituted with 0-3 occurrences of $R^2$. In some embodiments, X is 3-thiophenyl substituted with 0 occurrences of $R^2$.

In some embodiments, X is 3-thiophenyl substituted with 1 occurrence of $R^2$. In some embodiments, $R^2$ is nitro. In some embodiments, $R^2$ is —$NH_2$. In some embodiments, X is

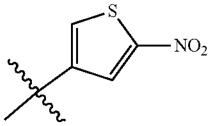 or 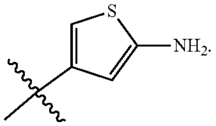

In some embodiments, $Cy^2$ is

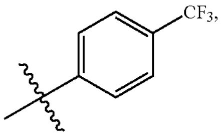 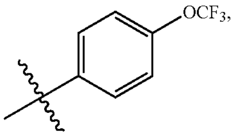

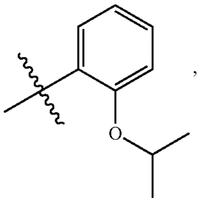, 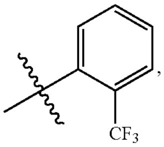,

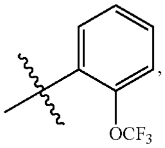, 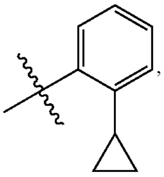, 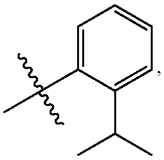,

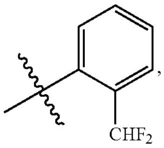, 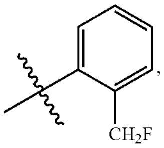,

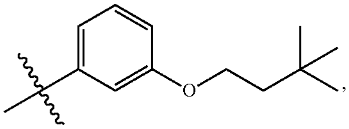, 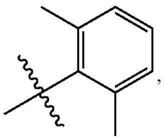,

-continued

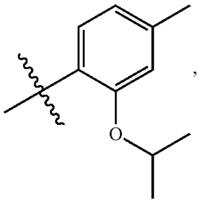, 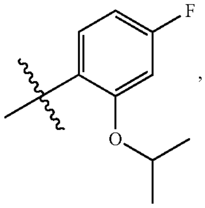,

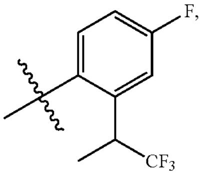 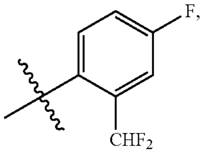

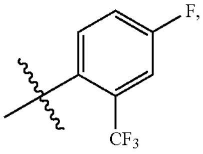 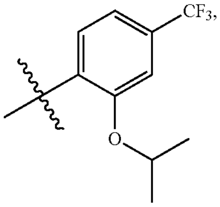

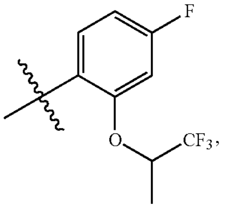 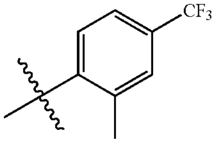,

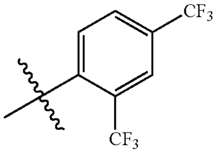,

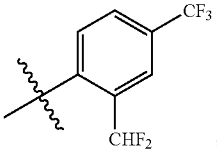, 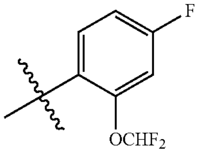,

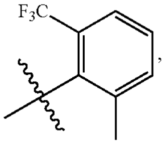, 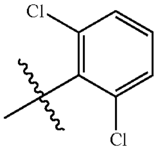,

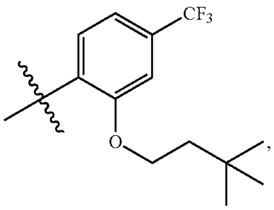, 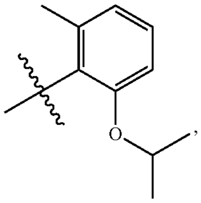,

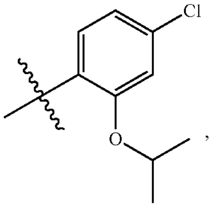, 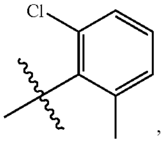,

-continued

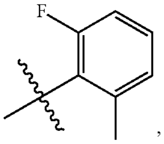
,
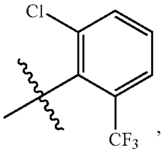
,
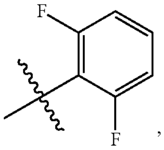
,
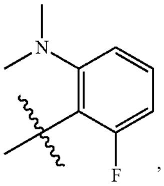
,
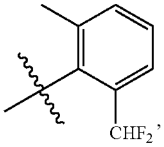
,
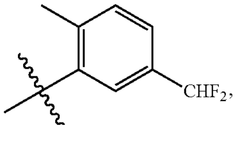
,
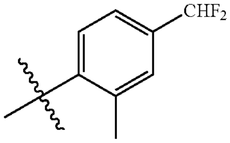
,
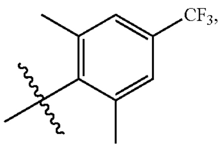
,
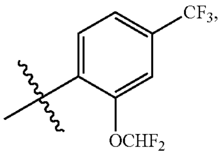
,
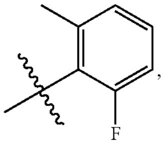
,
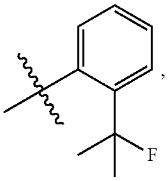
,
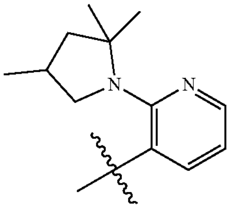
,
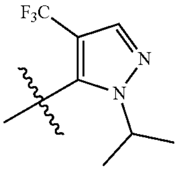
or
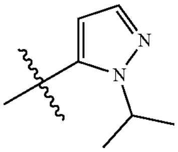
.

In some embodiments, $Cy^2$ is aryl substituted with 1-3 occurrences of $R^4$. In some embodiments, $Cy^2$ is phenyl substituted with 1-3 occurrences of $R^4$. In some embodiments, $Cy^2$ is phenyl substituted with 1 occurrence of $R^4$. In some embodiments, $R^4$ is $C_{1-6}$ alkyl (e.g., methyl or isopropyl), $C_{1-6}$ haloalkyl (e.g., trifluoromethyl, difluoromethyl, 2-fluoroisopropyl or fluoromethyl), $C_{1-6}$ alkoxy (e.g., methoxy, isopropoxy or 3,3-dimethylbutoxy), $C_{1-6}$ haloalkoxy (e.g., trifluoromethoxy) or $C_{3-6}$ cycloalkyl (e.g., cyclopropyl). In some embodiments, $Cy^2$ is

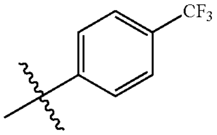
,
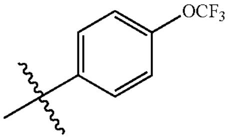
,

-continued

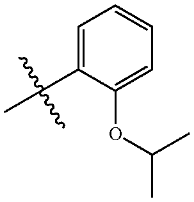
,
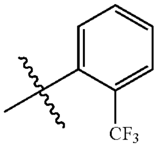
,
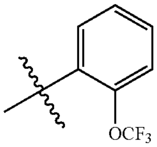
,
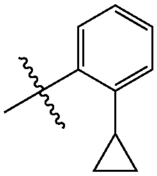
,
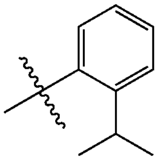
,
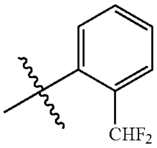
,
or
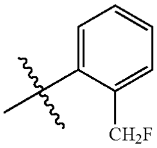
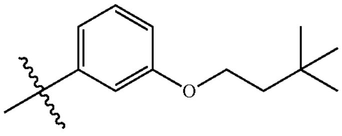
.

In some embodiments, $Cy^2$ is phenyl substituted with 2 occurrences of $R^4$. In some embodiments, both $R^4$ are $C_{1-6}$ alkyl (e.g., methyl). In some embodiments, both $R^4$ are halo (e.g., fluoro or chloro). In some embodiments, both $R^4$ are $C_{1-6}$ haloalkyl (e.g., trifluoromethyl or difluoromethyl). In some embodiments, one $R^4$ is $C_{1-6}$ alkyl (e.g., methyl) and one $R^4$ is $C_{1-6}$ alkoxy (e.g., isopropoxy). In some embodiments, one $R^4$ is $C_{1-6}$ alkoxy (e.g., isopropoxy) and one $R^4$ is halo (e.g., fluoro or chloro). In some embodiments, one $R^4$ is $C_{1-6}$ haloalkoxy (e.g., trifluoromethoxy, 1,1,1-trifluoroisopropoxy or difluoromethoxy) and one $R^4$ is halo (e.g., fluoro or chloro). In some embodiments, one $R^4$ is $C_{1-6}$ alkyl (e.g., methyl) and one $R^4$ is halo (e.g., fluoro or chloro). In some embodiments, one $R^4$ is $C_{1-6}$ alkoxy (e.g., isopropoxy) and one $R^4$ is $C_{1-6}$ alkyl (e.g., methyl). In some embodiments, one $R^4$ is $C_{1-6}$ haloalkyl (e.g., trifluoromethyl, difluoromethyl or 1,1,1-trifluoropropan-2-yl) and one $R^4$ is halo (e.g., fluoro or chloro). In some embodiments, one $R^4$ is $C_{1-6}$ alkoxy (e.g., isopropoxy or 3,3-dimethylbutoxy) and one $R^4$ is $C_{1-6}$ haloalkyl (e.g., trifluoromethyl). In some embodiments, one $R^4$ is $C_{1-6}$ alkyl (e.g., methyl) and one $R^4$ is $C_{1-6}$ haloalkyl (e.g., trifluoromethyl or difluoromethyl). In some embodiments, one $R^4$ is $—N(R^a)_2$ (e.g., $—N(CH_3)_2$) and one $R^4$ is halo (e.g., fluoro). In some embodiments, $Cy^2$ is

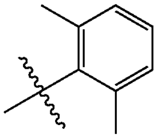
,
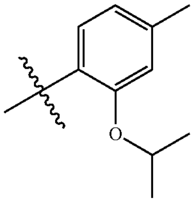
,

-continued

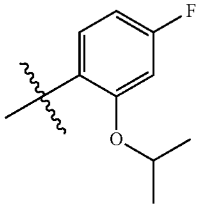,
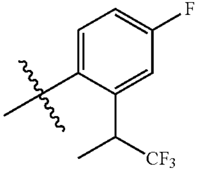,
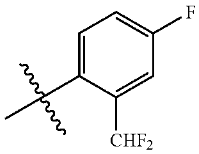,
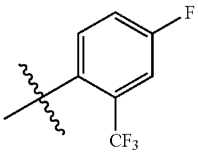,
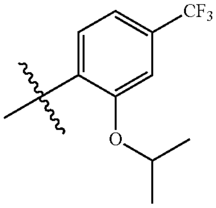,
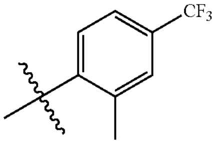,
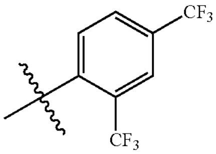,
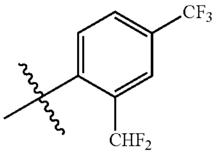,
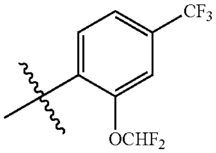,
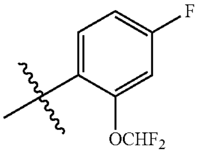,
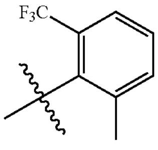,
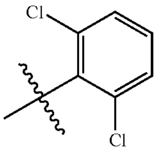,
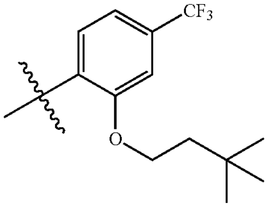,
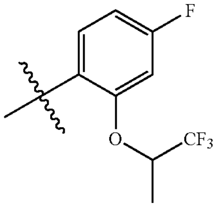,
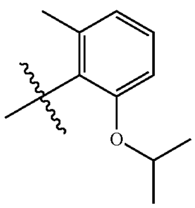,
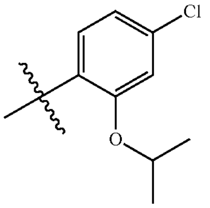,
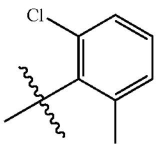,
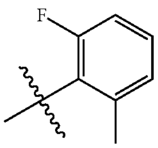,
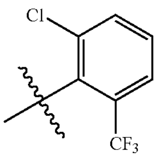, -continued

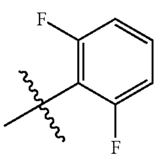,
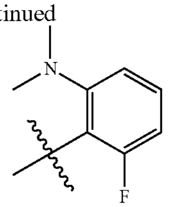,
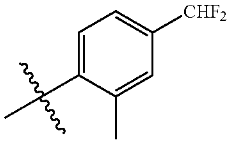,
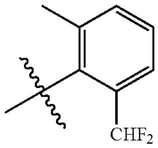
or
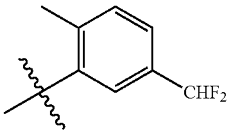.

In some embodiments, $Cy^2$ is phenyl substituted with 3 occurrences of $R^4$. In some embodiments, two $R^4$ are $C_{1-6}$ alkyl (e.g., methyl) and one $R^4$ is $C_{1-6}$ haloalkyl (e.g., trifluoromethyl). In some embodiments, $Cy^2$ is

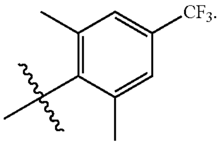 [SMILES: *c1c(C)cc(C(F)(F)F)cc1C].

In some embodiments, $Cy^2$ is 5-6 membered heteroaryl substituted with 1-3 occurrences of $R^4$. In some embodiments, $Cy^2$ is 3-pyridinyl substituted with 1-3 occurrences of $R^4$. In some embodiments, $Cy^2$ is 3-pyridinyl substituted with 1 occurrence of $R^4$. In some embodiments, $R^4$ is 4-10 membered heterocycloalkyl substituted with 0-3 occurrences of $R^b$. In some embodiments, $R^4$ is N-pyrrolidinyl substituted with 0-3 occurrences of $R^b$. In some embodiments, $R^4$ is N-pyrrolidinyl substituted with 3 occurrences of $R^b$ (e.g., methyl). In some embodiments, $Cy^2$ is

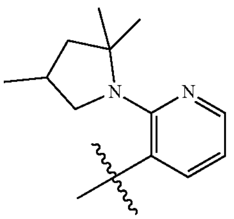.

In some embodiments, $Cy^2$ is 3-pyrazolyl substituted with 1-3 occurrences of $R^4$. In some embodiments, $Cy^2$ is 3-pyrazolyl substituted with 1 occurrence of $R^4$. In some embodiments, $R^4$ is $C_{1-6}$ alkyl (e.g., isopropyl). In some embodiments, $Cy^2$ is 3-pyrazolyl substituted with 2 occurrences of $R^4$. In some embodiments, one $R^4$ is $C_{1-6}$ alkyl (e.g., isopropyl) and one $R^4$ is $C_{1-6}$ haloalkyl (e.g., trifluoroalkyl). In some embodiments, $Cy^2$ is

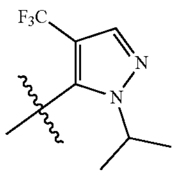
or
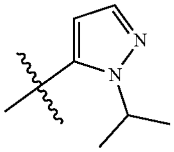
.

In some embodiments, $Cy^1$ is aryl substituted with 0-3 occurrences of $R^3$. In some embodiments, $Cy^1$ is phenyl substituted with 0-3 occurrences of $R^3$. In some embodiments, $Cy^1$ is phenyl substituted with 0 occurrences of $R^3$. In some embodiments, $Cy^1$ is phenyl substituted with 1 occurrence of $R^3$. In some embodiments, $R^3$ is $C_{1-8}$ alkyl (e.g., o-isopropyl) substituted with 0 occurrences of $R^7$. In some embodiments, $R^3$ is $C_{1-8}$ haloalkyl (e.g., m-trifluoromethyl, m-1,1-difluoro-3,3-dimethylbutyl or m-1,1-difluoro-4,4-dimethylpentyl) substituted with 0 occurrences of $R^7$. In some embodiments, $R^3$ is $C_{1-8}$ alkoxy (e.g., m-methoxy, m-3,3-dimethylbutoxy, p-3,3-dimethylbutoxy, m-neopentyloxy, m-2-ethylbutoxy, m-(4,4-dimethylpentan-2-yl)oxy or m-(3,3-dimethylpentyl)oxy) substituted with 0 occurrences of $R^7$. In some embodiments, $Cy^1$ is

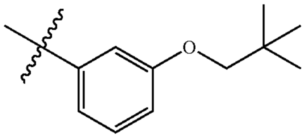
,
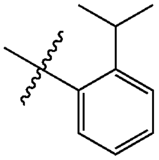
,
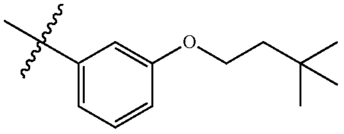
,
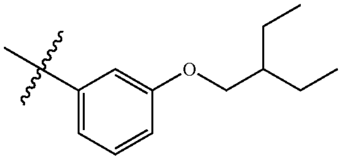
,
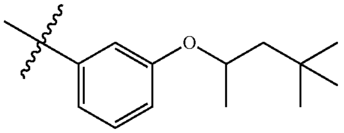
,
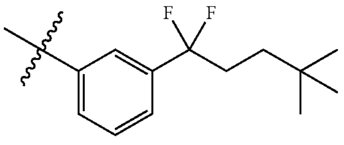
,
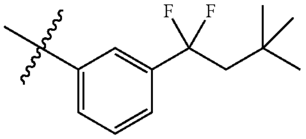
,
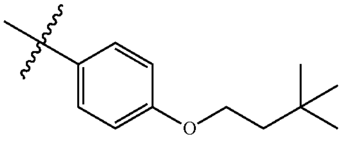
or -continued

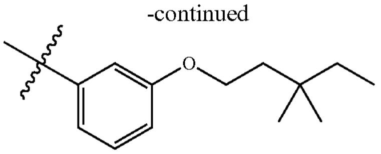
.

In some embodiments, $R^3$ is $C_{1-8}$ alkoxy (e.g., methoxy or ethoxy) substituted with 1 occurrence of $R^7$. In some embodiments, $R^3$ is methoxy substituted with 1 occurrence of $R^7$. In some embodiments, $R^7$ is 5-6 membered heteroaryl (e.g., 5-thiazolyl) further substituted with 0 occurrences of $R^5$. In some embodiments, $R^7$ is 4-10 membered heterocycloalkyl (e.g., 2-azetidinyl) substituted with 1 occurrence of $R^5$. In some embodiments, $R^5$ is $C_{1-4}$ alkyl (e.g., isopropyl), $C(O)(C_{1-4}$ alkyl) (e.g., C(O)-t-butyl) or $C(O)N(R^a)(C_{1-4}$ alkyl) (e.g., C(O)—NH-t-butyl). In some embodiments, $R^3$ is ethoxy substituted with 1 occurrence of $R^7$. In some embodiments, $R^7$ is heterocycloalkyl (e.g., N-morpholinyl) substituted with 0 occurrences of $R^5$. In some embodiments, $Cy^1$ is

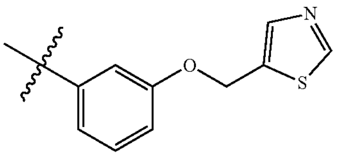
,
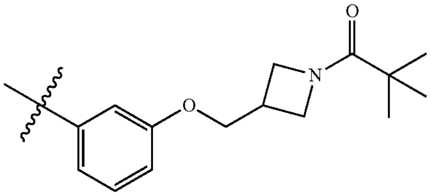
,
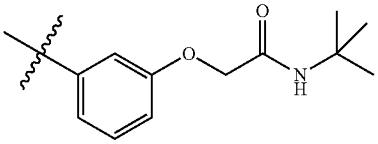
,
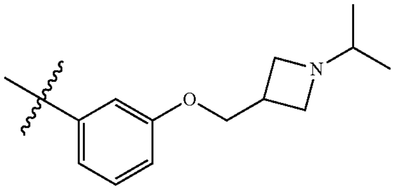
or
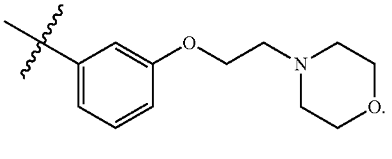

In some embodiments, $R^3$ is $C_{1-6}$ haloalkoxy (e.g., m-trifluoromethoxy, m-2,2,2-trifluoroethoxy, m-3,3,3-trifluoropropoxy, m-3,3,3-trifluoro-2-methylpropoxy, m-4,4,4-trifluoro-3-methylbutoxy, m-3,3,3-trifluoro-2,2-dimethylpropoxy, m-2-fluoro-3,3-dimethylbutoxy, m-1,1-difluoro-3,3-dimethylbutoxy or m-2,2-difluoro-3,3-dimethylbutoxy) substituted with 0 occurrences of $R^7$. In some embodiments, $R^3$ is $C_{3-9}$ cycloalkyl (e.g., cyclopentyl) further substituted with 0-3 occurrences of $R^7$. In some embodiments, $Cy^1$ is

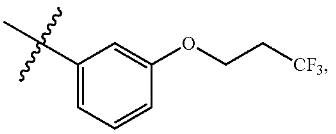

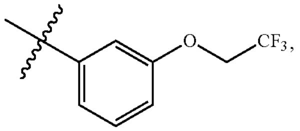

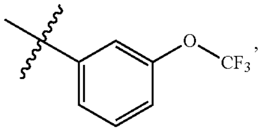

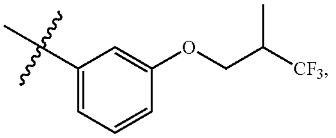

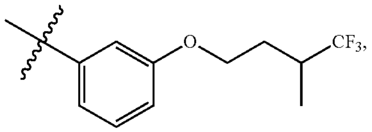

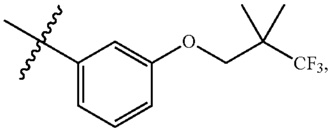

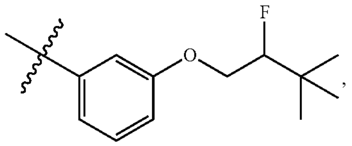

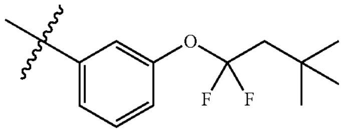

or

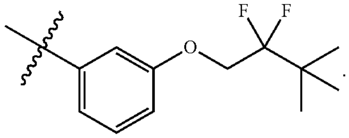

In some embodiments, $R^3$ is m-cyclopentyl or p-cyclopentyl substituted with 1 occurrence of $R^7$. In some embodiments, $R^7$ is $C_{1-4}$ haloalkoxy (e.g., trifluoromethoxy). In some embodiments, $R^7$ is $C_{1-4}$ haloalkyl (e.g., 1,1-difluoroethyl or 2-2-difluoropropyl). In some embodiments, $R^3$ is m-cyclopentyl substituted with 2 occurrences of $R^7$. In some embodiments, both $R^7$ is $C_{1-4}$ alkyl (e.g., methyl). In some embodiments, $Cy^1$ is

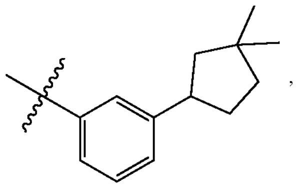

-continued

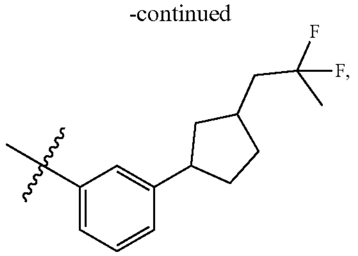

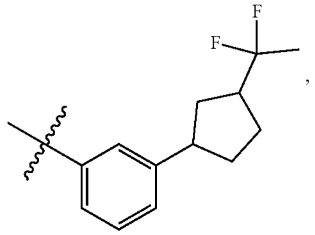

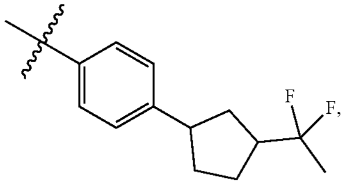

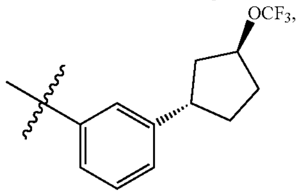

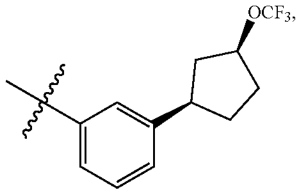

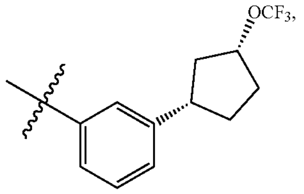

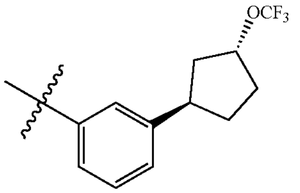

or

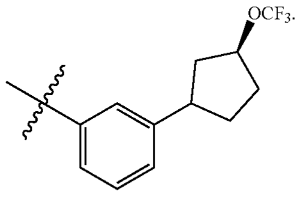

In some embodiments, $R^3$ is $C_{3-9}$ cycloalkoxy (e.g., cyclopentoxy) further substituted with 0-3 occurrences of $R^7$. In some embodiments, $R^3$ is m-cyclopentoxy substituted with 1 occurrence of $R^7$. In some embodiments, $R^7$ is $C_{1-4}$ alkyl (e.g., methyl). In some embodiments, $R^3$ is m-cyclopentoxy substituted with 2 occurrences of $R^7$. In some embodiments, both $R^7$ is $C_{1-4}$ alkyl (e.g., methyl). In some embodiments, $Cy^1$ is

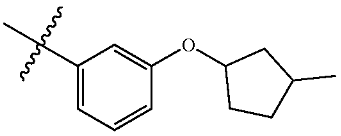

or

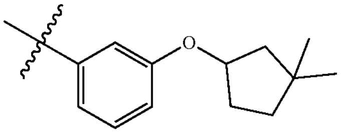

.

In some embodiments, $R^3$ is $C_{1-4}$ alkyl-$C_{3-9}$ cycloalkyl (e.g., cyclopentylmethyl) substituted with 0-3 occurrences of $R^7$. In some embodiments, $R^3$ is cyclopentylmethyl substituted with 3 occurrences of $R^7$. In some embodiments, two $R^7$ are halo (e.g., fluoro) and the other $R^7$ is hydroxy. In some embodiments, $R^3$ is $C_{1-4}$ alkoxy-$C_{3-9}$ cycloalkyl (e.g., cyclohexylmethoxy, cyclopropylmethoxy or 2-cyclopropylethoxy) substituted with 0-3 occurrences of $R^7$. In some embodiments, $R^3$ is cyclopropylmethoxy substituted with 1 occurrence of $R^7$. In some embodiments, $R^7$ is $C_{1-4}$ alkyl (e.g., methyl). In some embodiments, $R^7$ is $C_{1-4}$ haloalkyl (e.g., trifluoromethyl). In some embodiments, $R^3$ is 2-cyclopropylethoxy substituted with 1 occurrence of $R^7$. In some embodiments, $R^7$ is $C_{1-4}$ haloalkyl (e.g., trifluoromethyl). In some embodiments, $R^3$ is cyclohexylmethoxy substituted with 2 occurrences of $R^7$. In some embodiments, both $R^7$ are halo (e.g., fluoro). In some embodiments, $Cy^1$ is

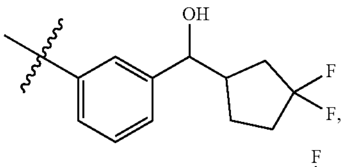

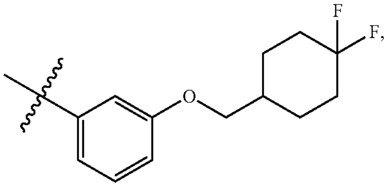

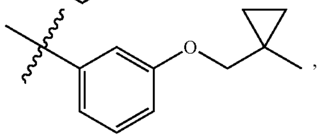

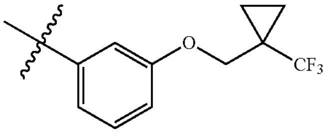

or

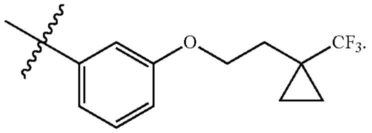

In some embodiments, $R^3$ is heteroaryl (e.g., 3-isoxazolyl) substituted with 0-3 occurrences of $R^7$. In some embodiments, $R^3$ is heteroaryl (e.g., 3-isoxazolyl) substituted with 0 occurrences of $R^7$. In some embodiments, $R^3$ is heteroaryl (e.g., 3-isoxazolyl) substituted with 1 occurrence of $R^7$. In some embodiments, $R^7$ is $C_{1-4}$ haloalkyl (e.g., trifluoromethyl). In some embodiments, $R^3$ is —C(O)—$R^7$. In some embodiments, $R^7$ is heterocycloalkyl (e.g., N-pyrrolidinyl) substituted with 0-3 occurrences of $R^8$. In some embodiments, $R^7$ is heterocycloalkyl (e.g., N-pyrrolidinyl) substituted with 0 occurrences of $R^8$. In some embodiments, $R^7$ is heterocycloalkyl (e.g., N-pyrrolidinyl) substituted with 1 occurrence of $R^8$. In some embodiments, $R^8$ is $C_{1-4}$ haloalkoxy (e.g., trifluoromethoxy). In some embodiments, $R^7$ is heterocycloalkyl (e.g., N-pyrrolidinyl) substituted with 2 occurrences of $R^8$. In some embodiments, each $R^8$ is halo (e.g., fluoro). In some embodiments, $Cy^1$ is

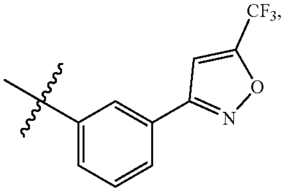

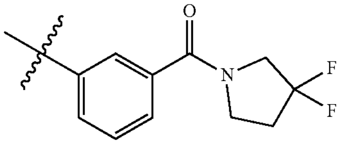

or

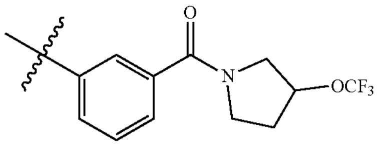

In some embodiments, $Cy^1$ is phenyl substituted with 2 occurrences of $R^3$. In some embodiments, one $R^3$ is halo (e.g., fluoro or chloro) and the other $R^3$ is $C_{1-8}$ alkoxy (e.g., methoxy, ethoxy, 3,3-dimethylbutoxy, 2,3-dimethylbutoxy, neopentyloxy, (3-methylbutanyl-2-yl)oxy, 2,3,3-trimethylbutoxy or (4,4-dimethylpentan-2-yl)oxy) further substituted with 0 occurrences of $R^7$. In some embodiments, $Cy^1$ is

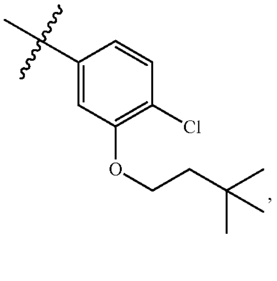

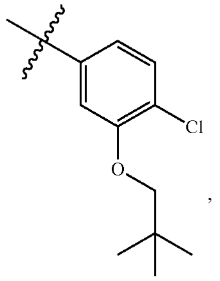

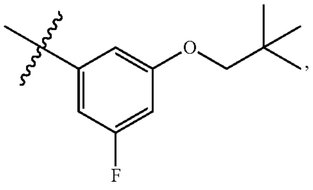

-continued

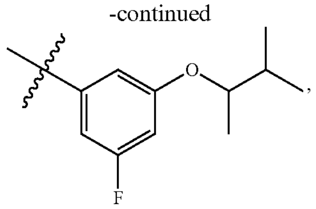

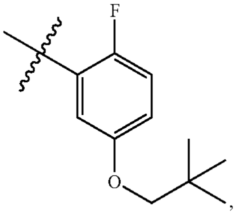

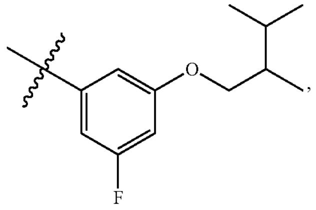

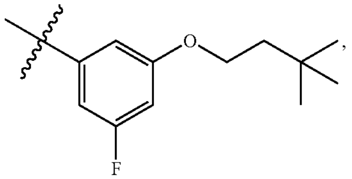

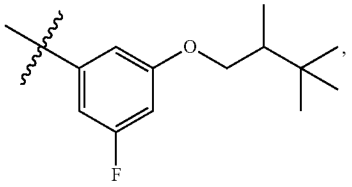

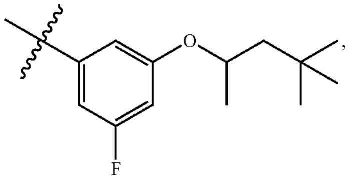

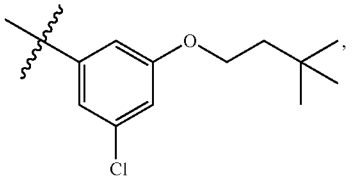

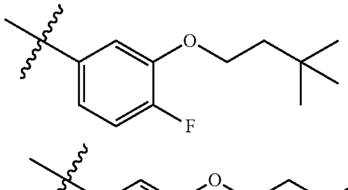

or

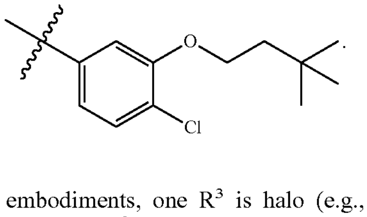

In some embodiments, one $R^3$ is halo (e.g., fluoro or chloro) and the other $R^3$ is $C_{1-8}$ alkoxy (e.g., isopentyoxy, 2,3,3,-trimethylbutoxy or 2,3-dimethylbutoxy) substituted with 1 occurrence of $R^7$. In some embodiments, $R^7$ is hydroxyl. In some embodiments, $Cy^1$ is

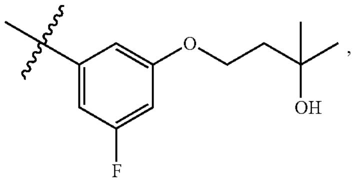

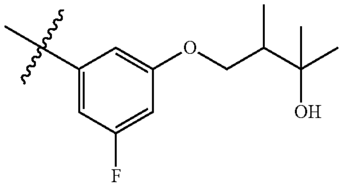

or

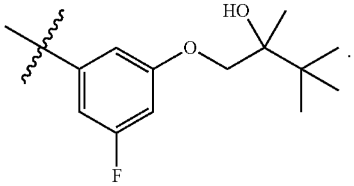

In some embodiments, one $R^3$ is halo (e.g., fluoro or chloro) and the other $R^8$ is $C_{1-8}$ alkoxy (e.g., propoxy or 2,3-dimethylbutoxy) substituted with 2 occurrences of $R^7$. In some embodiments, both $R^7$ are hydroxyl. In some embodiments, one $R^7$ is hydroxyl and the other $R^7$ is —C(O)—O—$C_{1-4}$ alkyl (e.g., —$CO_2Me$). In some embodiments, $Cy^1$ is

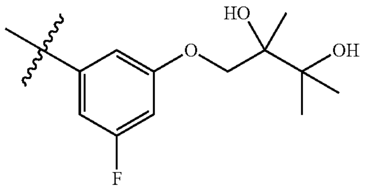

or

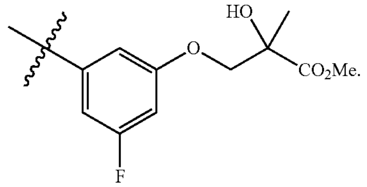

In some embodiments, one $R^3$ is halo (e.g., fluoro or chloro) and the other $R^3$ is $C_{1-8}$ alkyl (e.g., methyl, ethyl, isobutyl or neopentyl) substituted with 0 occurrences of $R^7$. In some embodiments, $Cy^1$ is

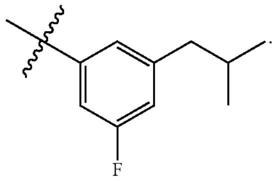 [SMILES: *c1cc(F)cc(CC(C)C)c1]

In some embodiments, one $R^3$ is halo (e.g., fluoro or chloro) and the other $R^3$ is $C_{1-8}$ haloalkoxy (e.g., trifluoromethoxy, 2,2,2-trifluoroethoxy, 3,3,3-trifluoropropoxy, 2,2-difluoro-3,3-dimethylbutoxy or 3,3,3-trifluoro-2-methylpropoxy) substituted with 0 occurrences of $R^7$. In some embodiments, $Cy^1$ is

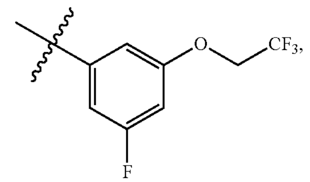

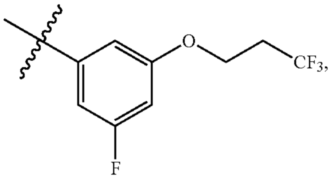

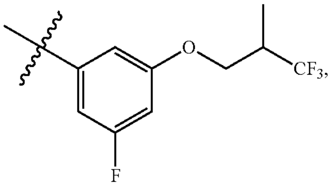

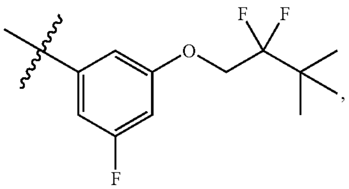

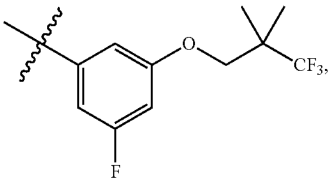

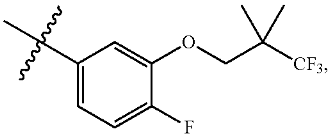

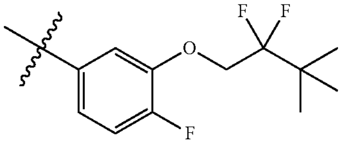

or

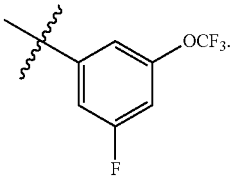

In some embodiments, one $R^3$ is halo (e.g., fluoro or chloro) and the other $R^3$ is $C_{1-8}$ haloalkoxy (e.g., 3,3,3-trifluoropropoxy, (1,1,1-trifluoropropan-2-yl)oxy or 4,4,4-trifluoro-3-methylbutoxy) substituted with 1 occurrence of $R^7$. In some embodiments, $R^7$ is hydroxyl. In some embodiments, $R^7$ is $C_{1-4}$ alkoxy (e.g., methoxy). In some embodiments, $R^7$ is aralkoxy (e.g., benzoxy). In some embodiments, $Cy^1$ is

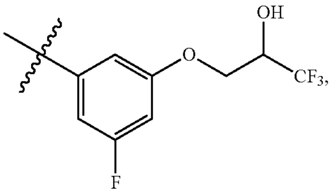

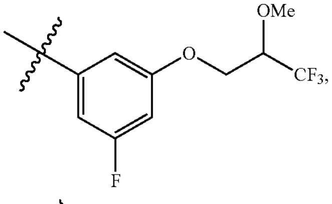

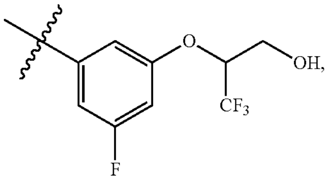

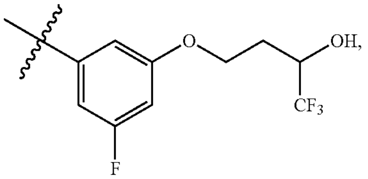

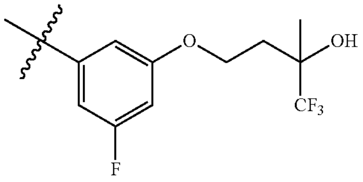

or

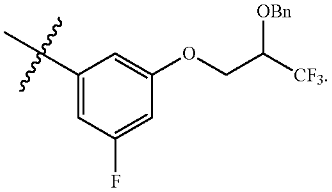

In some embodiments, one $R^3$ is halo (e.g., fluoro or chloro) and the other $R^3$ is $C_{3-9}$ alkoxy (e.g., cyclopentoxy or cyclohexyloxy) substituted with 1 occurrence of $R^7$. In some embodiments, $R^7$ is $C_{1-4}$ haloalkoxy (e.g., trifluoromethoxy). In some embodiments, $R^7$ is $C_{1-4}$ alkyl (e.g., t-butyl). In some embodiments, one $R^3$ is halo (e.g., fluoro or chloro) and the other $R^3$ is $C_{3-9}$ alkoxy (e.g., cyclopentoxy or cyclohexyloxy) substituted with 2 occurrences of $R^7$. In some embodiments, both $R^7$ are $C_{1-4}$ alkyl (e.g., methyl). In some embodiments, one $R^3$ is $C_{1-8}$ haloalkyl (e.g., difluoromethyl) substituted with 0 occurrences of $R^7$ and the other $R^3$ is $C_{1-8}$ alkoxy (e.g., 3,3-dimethylbutoxy) substituted with 0 occurrences of $R^7$. In some embodiments, one $R^3$ is halo (e.g., fluoro or chloro) and the other $R^3$ is $C_{3-9}$ cycloalkyl (e.g., cyclohexyl) substituted with 2 occurrences of $R^7$. In some embodiments, both $R^7$ are $C_{1-4}$ alkyl (e.g., methyl). In some embodiments, $Cy^1$ is

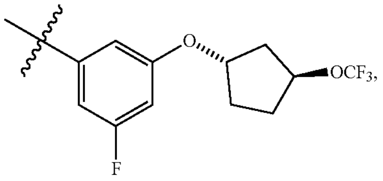

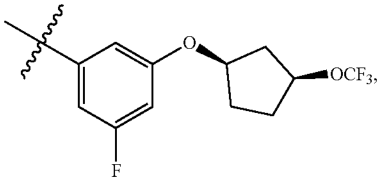

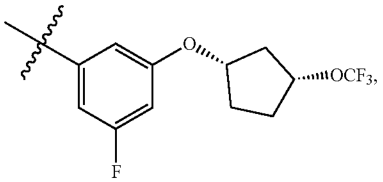

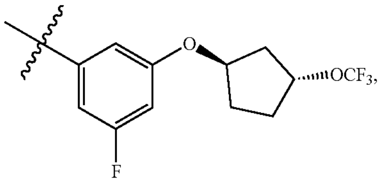

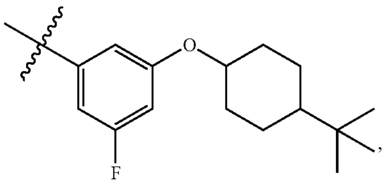

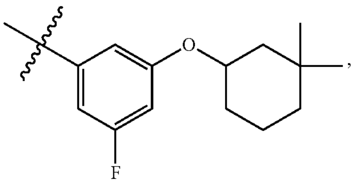

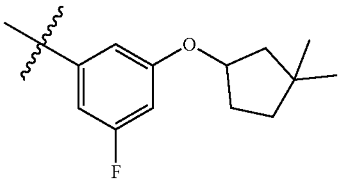

or

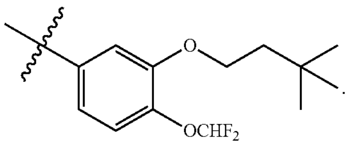

In some embodiments, one $R^3$ is halo (e.g., fluoro) and the other $R^3$ is aryl (e.g., phenyl) substituted with 1 occurrence of $R^7$. In some embodiments, $R^7$ is $C_{1-4}$ alkyl (e.g., isopropyl). In some embodiments, $R^7$ is $C_{1-4}$ haloalkyl (e.g., trifluoromethyl). In some embodiments, $Cy^1$ is

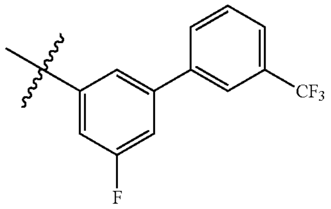

or

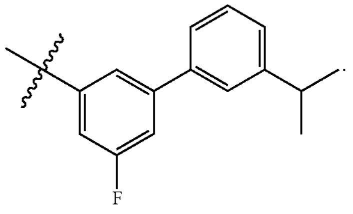

In some embodiments, one $R^3$ is halo (e.g., fluoro) and the other $R^3$ is —C(O)$R^7$. In some embodiments, $R^7$ is heterocycloalkyl (e.g., morpholinyl) substituted with 0 occurrences of $R^8$. In some embodiments, one $R^3$ is halo (e.g., fluoro) and the other $R^3$ is —C(O)N($R^a$)($R^7$). In some embodiments, $R^a$ is H and $R^7$ is $C_{1-5}$ alkyl (e.g., tert-butyl or neopentyl). In some embodiments, one $R^3$ is halo (e.g., fluoro) and the other $R^3$ is aralkoxy (e.g., benzyloxy). In some embodiments, $Cy^1$ is

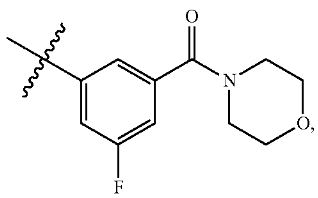

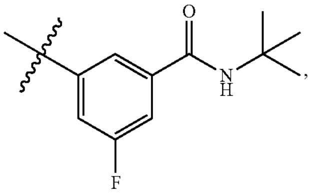

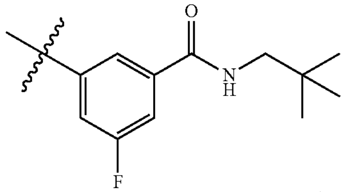

or

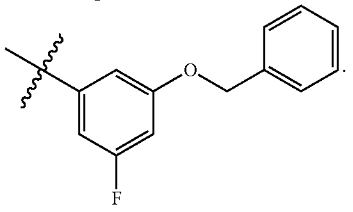

In some embodiments, one $R^3$ is halo (e.g., fluoro) and the other $R^3$ is $C_{3-9}$ cycloalkyl substituted with 2 occurrences of $R^7$. In some embodiments, both $R^7$ are $C_{1-5}$ alkyl (e.g., methyl). In some embodiments, one $R^3$ is halo (e.g., fluoro) and the other $R^3$ is $C_{1-4}$ alkoxy-$C_{3-9}$ cycloalkyl substituted with 1 occurrence of $R^7$. In some embodiments, $R^7$ is $C_{1-5}$ haloalkyl (e.g., trifluoromethyl). In some embodiments, one $R^3$ is halo (e.g., fluoro) and the other $R^3$ is $C_{1-4}$ alkoxy-$C_{3-9}$ cycloalkyl (methoxycyclobutyl or methoxycyclohexyl) substituted with 2 occurrences of $R^7$. In some embodiments, both $R^7$ are halo (e.g., fluoro). In some embodiments, one $R^3$ is halo (e.g., chloro) and other $R^3$ is $C_{3-9}$ cycloalkenyl (e.g., cyclohexenyl) substituted with 2 occurrences of $R^7$. In some embodiments, both $R^7$ are $C_{1-5}$ alkyl (e.g., methyl). In some embodiments, one $R^3$ is halo (e.g., fluoro) and the other $R^3$ is $C_{1-8}$ alkenyl (e.g., 2-methylprop-1-en-1-yl). In some embodiments, one $R^3$ is halo (e.g., fluoro) and the other $R^3$ is heterocycloalkyl (e.g., pyrrolidinyl) substituted with 1 occurrence of $R^7$. In some embodiments, $R^7$ is $C_{1-5}$ alkyl (e.g., tert-butyl). In some embodiments, $Cy^1$ is

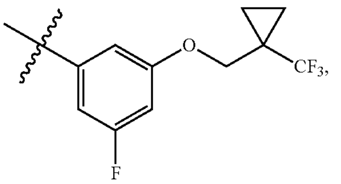

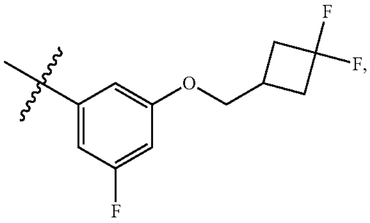

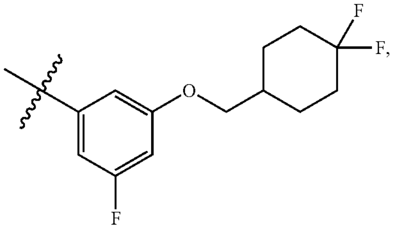

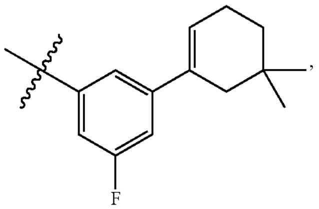

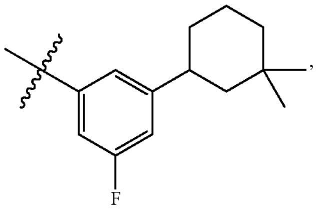

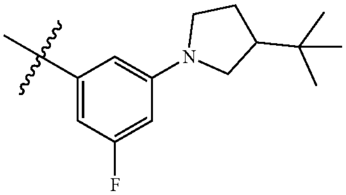

or

-continued

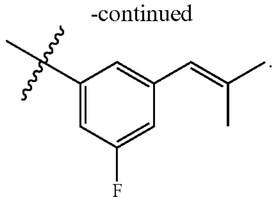

In some embodiments, $Cy^1$ is phenyl substituted with 3 occurrences of $R^3$. In some embodiments, two $R^3$ are halo (e.g., fluoro) and the other $R^3$ is $C_{1-8}$ alkoxy (e.g., neopentyloxy or 3,3-dimethylbutoxy) substituted with 0 occurrences of $R^7$. In some embodiments, two $R^3$ are halo (e.g., fluoro) and the other $R^3$ is $C_{3-9}$ cycloalkoxy (e.g., cyclopentoxy) substituted with 2 occurrences of $R^7$. In some embodiments, both $R^7$ are $C_{1-5}$ alkyl (e.g., methyl). In some embodiments, $Cy^1$ is

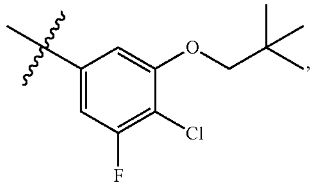

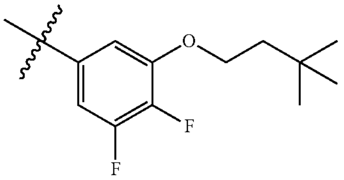

or

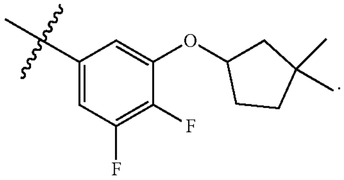

In some embodiments, $Cy^1$ is heterocycloalkyl substituted with 0-3 occurrences of $R^3$. In some embodiments, $Cy^1$ is heterocycloalkyl substituted with 0 occurrences of $R^3$. In some embodiments, $Cy^1$ is heterocycloalkyl substituted with 1 occurrence of $R^3$. In some embodiments, $Cy^1$ is heterocycloalkyl (e.g., N-azetidinyl, N-pyrrolidinyl, N-morpholinyl, N-piperidinyl, N-piperidin-2-only, N-pyrrolidin-2-only, 3-tetrahydropyranyl, 3-(3,6-dihydro-2H-pyranyl), 2N-6-oxa-9-azaspiro[4.5]decanyl or 2N-6-oxa-2,9-diazaspiro[4.5] decanyl) substituted with 1 occurrence of $R^3$. In some embodiments, $R^3$ is $C_{1-8}$ alkyl (e.g., neopentyl, 4,4-dimethylpentyl, 3-methylbutyl or 3,3-dimethylbutyl) substituted with 0 occurrences of $R^7$. In some embodiments, $R^3$ is $C_{1-8}$ alkyl (e.g., 3,3-dimethylbutyl) substituted with 1 occurrence of $R^7$. In some embodiments, $R^7$ is hydroxyl. In some embodiments, $R^3$ is $C_{1-8}$ alkoxy (e.g., 3,3-dimethylbutoxy, neopentyloxy or tert-butoxy) substituted with 0 occurrences of $R^7$. In some embodiments, $R^3$ is $C_{1-8}$ haloalkoxy (e.g., trifluoromethoxy). In some embodiments, $R^3$ is —C(O)—$R^7$. In some embodiments, $R^7$ is $C_{1-5}$ alkoxy (e.g., tert-butoxy). In some embodiments, $Cy^1$ is

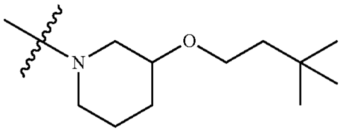
,

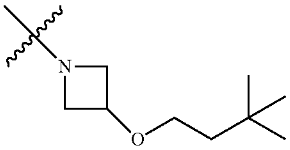
,

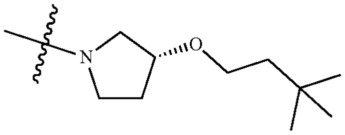
,

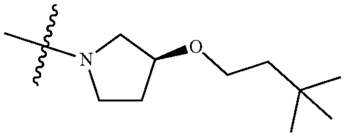
,

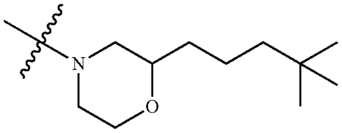
,

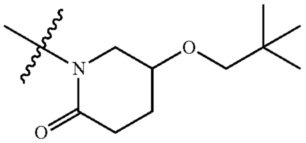
,

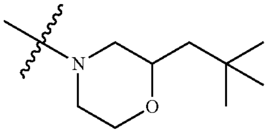
,
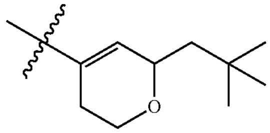
,

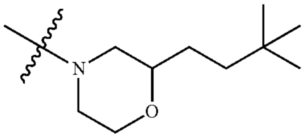
,

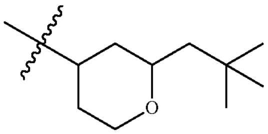
,

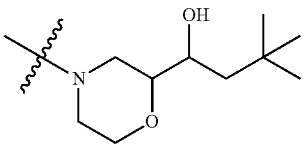
,

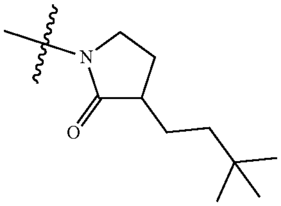
,

-continued

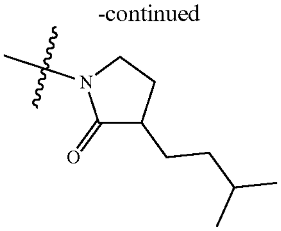
,

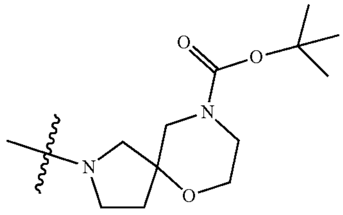
or

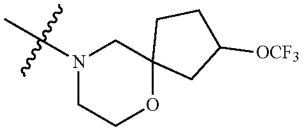
.

In some embodiments, $Cy^1$ is heterocycloalkyl (e.g., N-piperidinyl, 9-(oxa-9-azaspiro[4.5]decanyl) or 2-(3-oxa-1-azaspiro[4.4]non-1-enyl)) substituted with 2 occurrences of $R^3$ substituted. In some embodiments, one $R^3$ is $C_{1-8}$ alkyl (e.g., methyl) and the other $R^3$ is $C_{1-8}$ alkoxy (e.g., tert-butoxy). In some embodiments, both $R^3$ are $C_{1-8}$ alkyl (e.g., methyl). In some embodiments, $Cy^1$ is

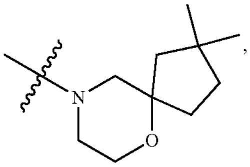
,
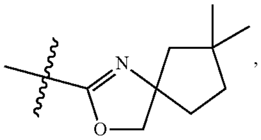
,

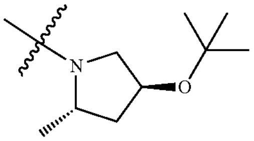
or
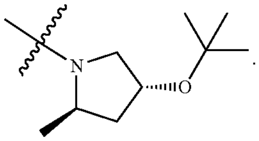
.

In some embodiments, $Cy^1$ is heterocycloalkyl (e.g., 9-(oxa-9-azaspiro[4.5]decanyl)) substituted with 3 occurrences of $R^3$ substituted. In some embodiments, three $R^3$ are $C_{1-8}$ alkyl (e.g., methyl). In some embodiments, $Cy^1$ is

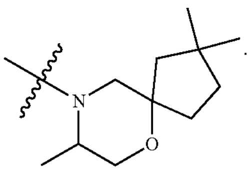 [SMILES: *N1CC2(CCC(C)(C)C2)OCC1C]
.

In some embodiments, $Cy^1$ is heteroaryl substituted with 0-3 occurrences of $R^3$. In some embodiments, $Cy^1$ is heteroaryl substituted with 0 occurrences of $R^3$. In some embodiments, $Cy^1$ is heteroaryl substituted with 1 occurrence of $R^3$. In some embodiments, $Cy^1$ is heteroaryl (e.g., 4-thiazolyl, 2-pyridinyl, 4-pyridinyl, 1-pyrazolyl, 3-pyrazolyl, 2-thiophenyl, 4-pyrazolyl or 2-(1,3,4-thiadiazolyl))

substituted with 1 occurrence of $R^3$ substituted. In some embodiments, $R^3$ is $C_{1-6}$ alkyl (e.g., 3,3-dimethylbutyl) substituted with 0 occurrences of $R^7$. In some embodiments, $R^3$ is $C_{1-8}$ alkoxy (e.g., 3,3-dimethylbutoxy, neopentyloxy or 4,4-dimethylpentyloxy) substituted with 0 occurrences of $R^7$. In some embodiments, $R^3$ is $C_{1-8}$ haloalkoxy (e.g., 2,2,2-trifluoroethoxy, 3,3,3-trifluoro-2,2-dimethylpropoxy and 2,2-difluoro-3,3-dimethylbutoxy) substituted with 0 occurrences of $R^7$. In some embodiments, $R^3$ is $C_{1-8}$ haloalkyl (e.g., 4,4,4-trifluoro-3,3-dimethylbutyl or 5,5,5-trifluoro-4,4-dimethylpentan-2-yl) substituted with 1 occurrence of $R^7$. In some embodiments, $R^7$ is hydroxyl. In some embodiments, $R^3$ is heterocycloalkyl (e.g., N-pyrrolidinyl) substituted with 1 occurrence of $R^7$. In some embodiments, $R^7$ is $C_{1-5}$ haloalkoxy (e.g., trifluoromethoxy). In some embodiments, $R^3$ is $C_{1-4}$ alkoxy-$C_{3-9}$ cycloalkyl substituted with 0 occurrences of $R^7$. In some embodiments, $R^3$ is

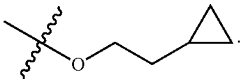 [SMILES: *OCCC1CC1]

In some embodiments, $R^3$ is $C_{1-4}$ alkyl-$C_{3-9}$ cycloalkyl substituted with 3 occurrences of $R^7$. In some embodiments, two $R^7$ are halo (e.g., fluoro) and one $R^7$ is hydroxyl. In some embodiments, $R^3$ is

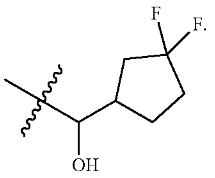 [SMILES: *C(O)C1CCC(F)(F)C1]

In some embodiments, $R^3$ is $C_{3-9}$ cycloalkyl (e.g., cyclohexyl) substituted with 1 occurrence of $R^7$. In some embodiments, $R^7$ is $C_{1-5}$ haloalkyl (e.g., 1,1-difluoroethyl). In some embodiments, $R^7$ is $C_{1-5}$ haloalkenyl (e.g., 1-fluoroethylidenyl). In some embodiments, $R^3$ is —C(O)$R^7$. In some embodiments, $R^7$ is 3,3,3-trifluoro-2,2-dimethylpropyl. In some embodiments, $R^7$ is $C_{3-7}$ cycloalkyl (e.g., cyclopentyl) substituted with 2 occurrences of $R^8$. In some embodiments, both $R^8$ are halo (e.g., fluoro). In some embodiments, $Cy^1$ is

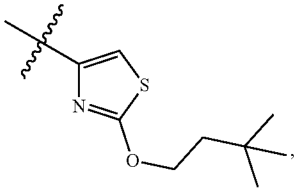

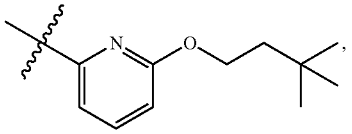

-continued

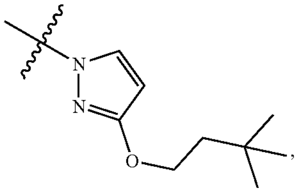

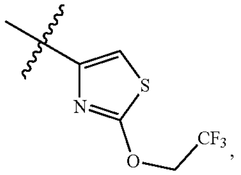

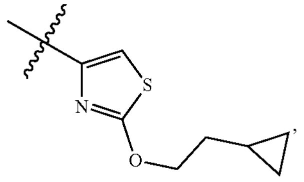

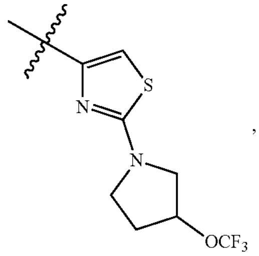

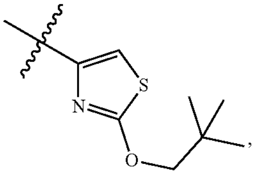

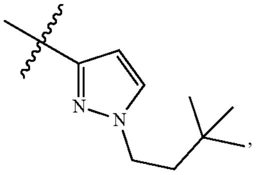

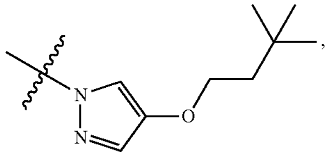

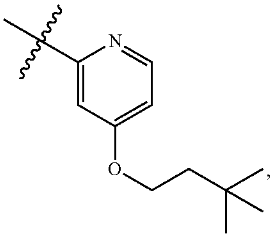

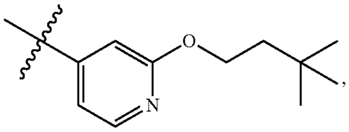

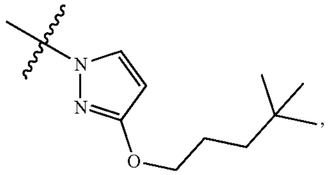

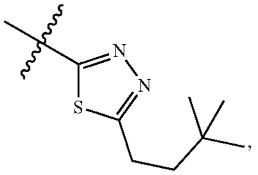

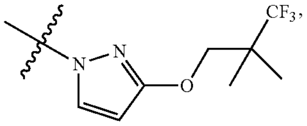

-continued

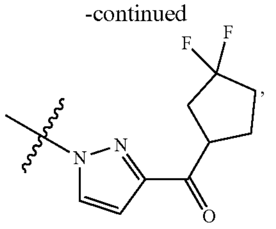

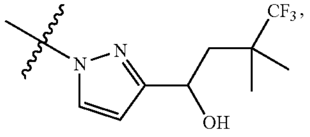

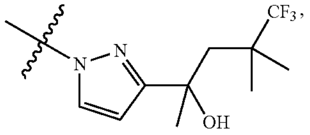

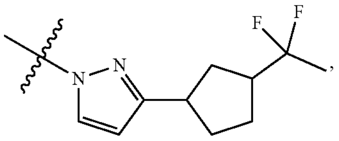

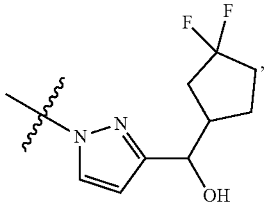

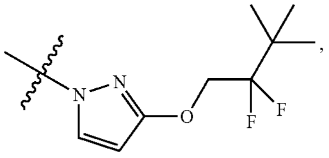

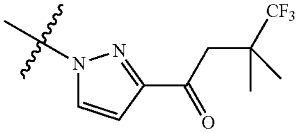

or

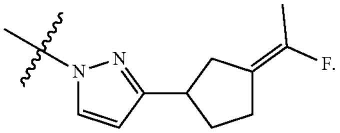

In some embodiments, $Cy^1$ is heteroaryl substituted with 2 occurrences of $R^3$. In some embodiments, $Cy^1$ is 2-pyridinyl substituted with 2 occurrences of $R^3$. In some embodiments, one $R^3$ is halo (e.g., fluoro) and the other $R^3$ is $C_{1-8}$ alkoxy (e.g., 3,3-dimethylbutoxy) substituted with 0 occurrences of $R^7$. In some embodiments, one $R^3$ is $C_{1-8}$ haloalkyl (e.g., trifluoromethyl) substituted with 0 occurrences of $R^7$ and the other $R^3$ is $C_{1-8}$ alkoxy (e.g., 3,3-dimethylbutoxy) substituted with 0 occurrences of $R^7$. In some embodiments, $Cy^1$ is 2-thiophenyl substituted with 2 occurrences of $R^3$. In some embodiments, one $R^3$ is halo (e.g., chloro) and the other $R^3$ is $C_{1-8}$ alkoxy (e.g., 3,3-dimethylbutoxy) substituted with 0 occurrences of $R^7$. In some embodiments, $Cy^1$ is

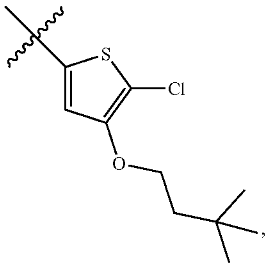

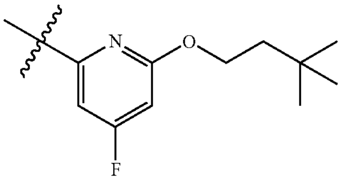

or

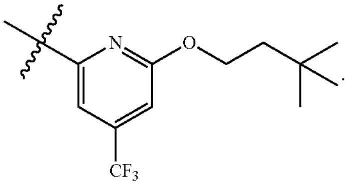

In some embodiments, $Cy^1$ is $C_{3-9}$ cycloalkyl substituted with 0-3 occurrences of $R^3$. In some embodiments, $Cy^1$ is $C_{3-9}$ cycloalkyl (e.g., cyclohexyl) substituted with 0 occurrences of $R^3$. In some embodiments, $Cy^1$ is $C_{3-9}$ cycloalkyl (e.g., cyclohexyl or cyclopentyl) substituted with 1 occurrence of $R^3$. In some embodiments, $R^3$ is $C_{1-8}$ alkoxy (e.g., 3,3-dimethybutoxy). In some embodiments, $Cy^1$ is

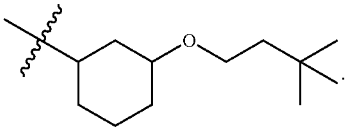 [SMILES: *C1CCCC(OCCC(C)(C)C)C1]

In some embodiments, the compound of formula (I) is selected from the following compounds represented in Table 1 below:

TABLE 1
| Compound Number | Compound Structural Formula | Compound Name |
|---|---|---|
| 186 | 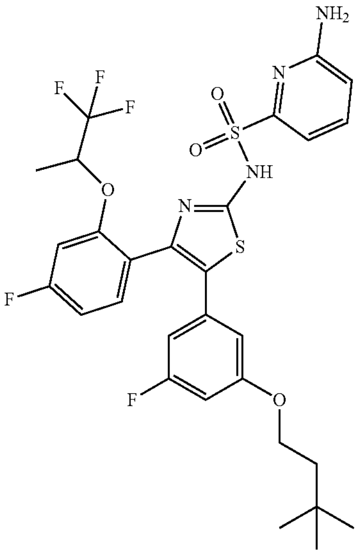 [SMILES: CC(Oc1cc(F)ccc1-c1nc(NS(=O)(=O)c2cccc(N)n2)sc1-c1cc(F)cc(OCCC(C)(C)C)c1)C(F)(F)F] | 6-amino-N-(5-(3-(3,3-dimethylbutoxy)-5-fluorophenyl)-4-(4-fluoro-2-((1,1,1-trifluoropropan-2-yl)oxy)phenyl)thiazol-2-yl)pyridine-2-sulfonamide |
| 97 | 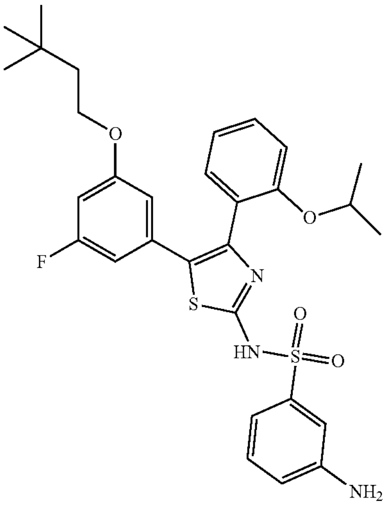 | 3-amino-N-(5-(3-(3,3-dimethylbutoxy)-5-fluorophenyl)-4-(2-isopropoxyphenyl)thiazol-2-yl)benzenesulfonamide |
| 510 | 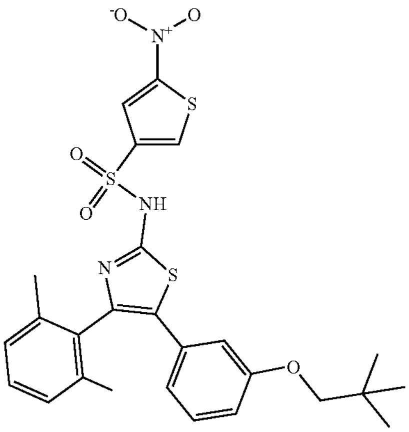 | N-(4-(2,6-dimethylphenyl)-5-(3-(neopentyloxy)phenyl)thiazol-2-yl)-5-nitrothiophene-3-sulfonamide |

TABLE 1-continued
| Compound Number | Compound Structural Formula | Compound Name |
|---|---|---|
| 81 | 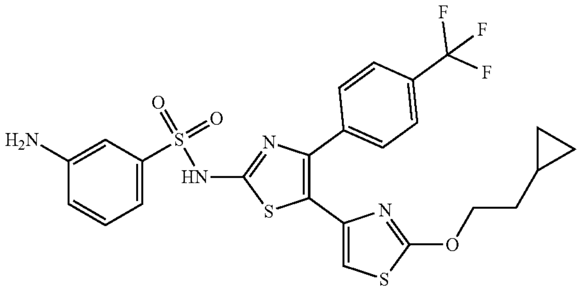 [SMILES: Nc1cccc(S(=O)(=O)Nc2nc(-c3ccc(C(F)(F)F)cc3)c(-c3csc(OCCC4CC4)n3)s2)c1] | 3-amino-N-(2-(2-cyclopropylethoxy)-4'-(4-(trifluoromethyl)phenyl)-[4,5'-bithiazol]-2'-yl)benzenesulfonamide |
| 80 | 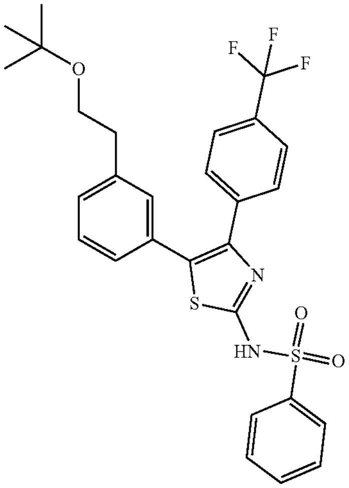 [SMILES: CC(C)(C)OCCc1cccc(-c2sc(NS(=O)(=O)c3ccccc3)nc2-c2ccc(C(F)(F)F)cc2)c1] | N-[5-[3-[2-[(2-methylpropan-2-yl)oxy]ethyl]phenyl]-4-[4-(trifluoromethyl)phenyl]-1,3-thiazol-2-yl]benzenesulfonamide |
| 167 | 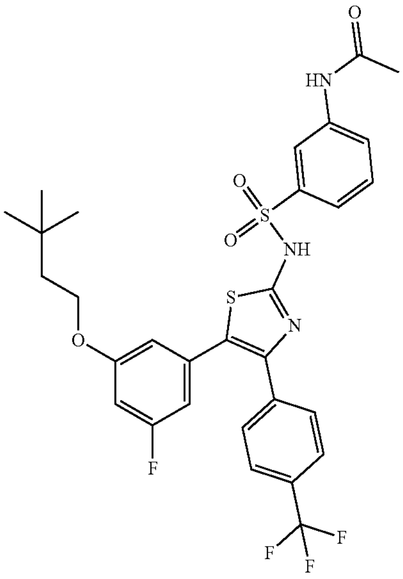 [SMILES: CC(=O)Nc1cccc(S(=O)(=O)Nc2nc(-c3ccc(C(F)(F)F)cc3)c(-c3cc(F)cc(OCCC(C)(C)C)c3)s2)c1] | N-[3-[[5-[3-(3,3-dimethylbutoxy)-5-fluorophenyl]-4-[4-(trifluoromethyl)phenyl]-1,3-thiazol-2-yl]sulfamoyl]phenyl]acetamide |

TABLE 1-continued

| Compound Number | Compound Structural Formula | Compound Name |
|---|---|---|
| 363 | 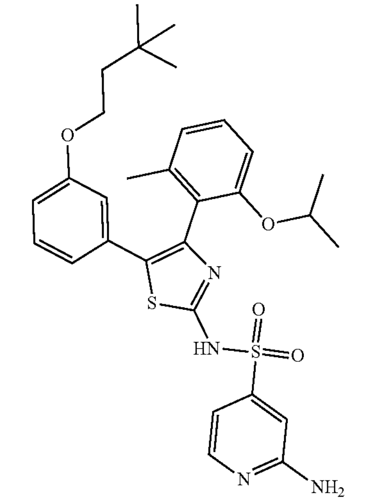 [SMILES: Cc1cccc(OC(C)C)c1-c1nc(NS(=O)(=O)c2ccnc(N)c2)sc1-c1cccc(OCCC(C)(C)C)c1] | 2-amino-N-[5-[3-(3,3-dimethylbutoxy)phenyl]-4-(2-methyl-6-propan-2-yloxyphenyl)-1,3-thiazol-2-yl]pyridine-4-sulfonamide |
| 348 | 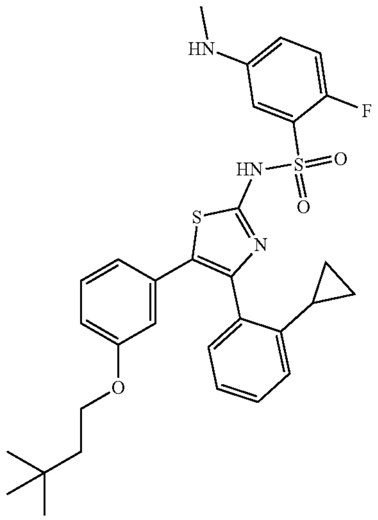 [SMILES: CNc1ccc(F)c(S(=O)(=O)Nc2nc(-c3ccccc3C3CC3)c(-c3cccc(OCCC(C)(C)C)c3)s2)c1] | N-[4-(2-cyclopropylphenyl)-5-[3-(3,3-dimethylbutoxy)phenyl]-1,3-thiazol-2-yl]-2-fluoro-5-(methylamino)benzenesulfonamide |
| 262 | 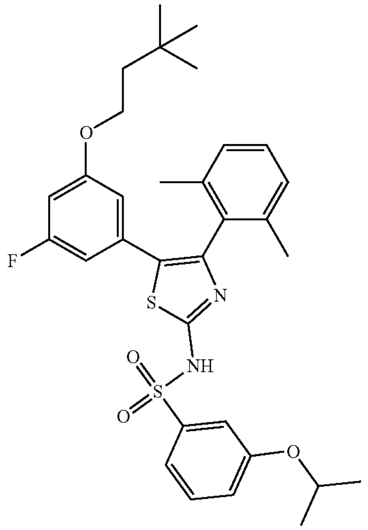 [SMILES: Cc1cccc(C)c1-c1nc(NS(=O)(=O)c2cccc(OC(C)C)c2)sc1-c1cc(F)cc(OCCC(C)(C)C)c1] | N-[5-[3-(3,3-dimethylbutoxy)-5-fluorophenyl]-4-(2,6-dimethylphenyl)-1,3-thiazol-2-yl]-3-propan-2-yloxybenzenesulfonamide |

TABLE 1-continued

| Compound Number | Compound Structural Formula | Compound Name |
|---|---|---|
| 48A2 | 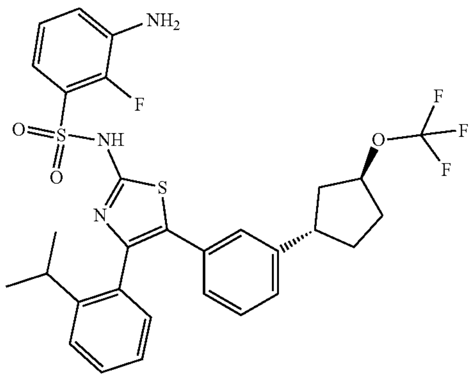 [SMILES: CC(C)c1ccccc1-c1nc(NS(=O)(=O)c2cccc(N)c2F)sc1-c1cccc([C@H]2CC[C@H](OC(F)(F)F)C2)c1] | 3-amino-2-fluoro-N-[4-(2-propan-2-ylphenyl)-5-[3-[(1S,3S)-3-(trifluoromethoxy)cyclopentyl]phenyl]-1,3-thiazol-2-yl]benzenesulfonamide |
| 511 | 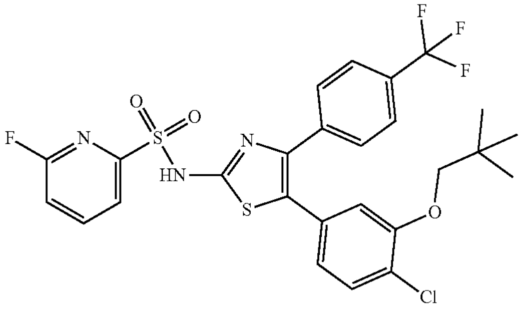 [SMILES: CC(C)(C)COc1cc(-c2sc(NS(=O)(=O)c3cccc(F)n3)nc2-c2ccc(C(F)(F)F)cc2)ccc1Cl] | N-(5-(4-chloro-3-(neopentyloxy)phenyl)-4-(4-(trifluoromethyl)phenyl)thiazol-2-yl)-6-fluoropyridine-2-sulfonamide |
| 496 | 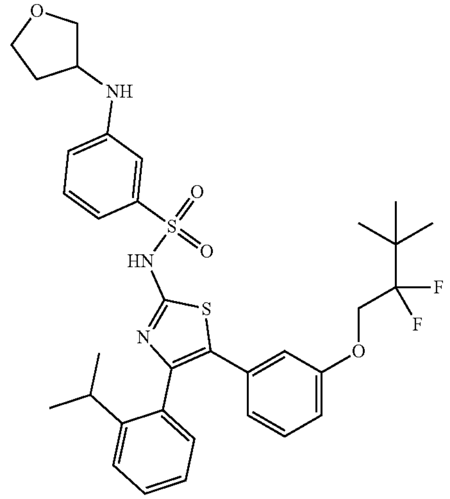 [SMILES: CC(C)c1ccccc1-c1nc(NS(=O)(=O)c2cccc(NC3CCOC3)c2)sc1-c1cccc(OCC(F)(F)C(C)(C)C)c1] | N-[5-[3-(2,2-difluoro-3,3-dimethylbutoxy)phenyl]-4-(2-propan-2-ylphenyl)-1,3-thiazol-2-yl]-3-(oxolan-3-ylamino)benzenesulfonamide |
| 512 | 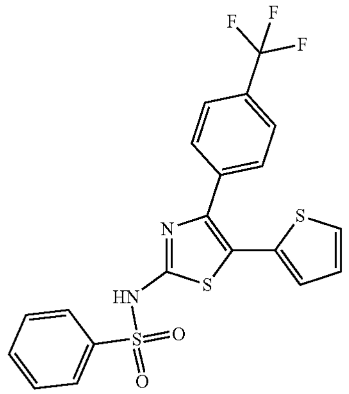 [SMILES: O=S(=O)(Nc1nc(-c2ccc(C(F)(F)F)cc2)c(-c2cccs2)s1)c1ccccc1] | N-(5-(thiophen-2-yl)-4-(4-(trifluoromethyl)phenyl)thiazol-2-yl)benzenesulfonamide |

TABLE 1-continued

| Compound Number | Compound Structural Formula | Compound Name |
|---|---|---|
| 379 | 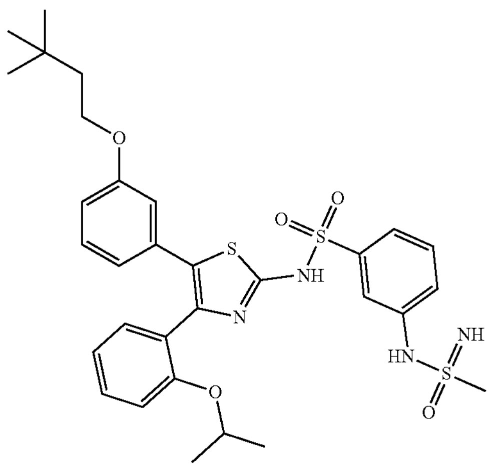 [SMILES: CC(C)Oc1ccccc1-c1nc(NS(=O)(=O)c2cccc(NS(C)(=N)=O)c2)sc1-c1cccc(OCCC(C)(C)C)c1] | N-[5-[3-(3,3-dimethylbutoxy)phenyl]-4-(2-propan-2-yloxyphenyl)-1,3-thiazol-2-yl]-3-[(methylsulfonimidoyl)amino] benzenesulfonamide |
| 47B1 | 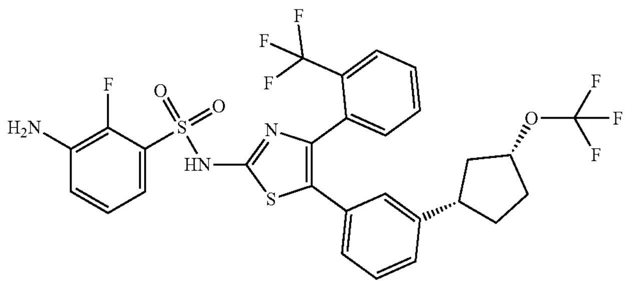 [SMILES: Nc1cccc(S(=O)(=O)Nc2nc(-c3ccccc3C(F)(F)F)c(-c3cccc([C@H]4CC[C@@H](OC(F)(F)F)C4)c3)s2)c1F] | 3-amino-2-fluoro-N-[5-[3-[(1S,3R)-3-(trifluoromethoxy)cyclopentyl]phenyl]-4-[2-(trifluoromethyl)phenyl]-1,3-thiazol-2-yl]benzenesulfonamide |
| 513 | 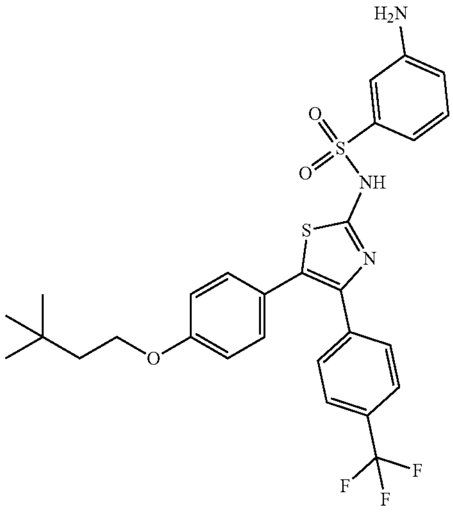 [SMILES: CC(C)(C)CCOc1ccc(-c2sc(NS(=O)(=O)c3cccc(N)c3)nc2-c2ccc(C(F)(F)F)cc2)cc1] | 3-amino-N-(5-(4-(3,3-dimethylbutoxy)phenyl)-4-(4-(trifluoromethyl)phenyl)thiazol-2-yl)benzenesulfonamide |

TABLE 1-continued

| Compound Number | Compound Structural Formula | Compound Name |
|---|---|---|
| 145 | 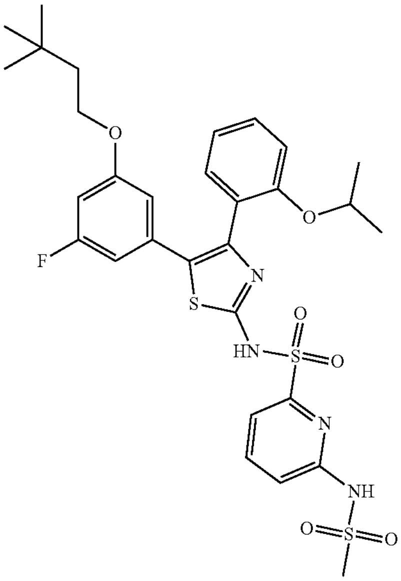 [SMILES: CC(C)Oc1ccccc1-c1nc(NS(=O)(=O)c2cccc(NS(C)(=O)=O)n2)sc1-c1cc(F)cc(OCCC(C)(C)C)c1] | N-[5-[3-(3,3-dimethylbutoxy)-5-fluorophenyl]-4-(2-propan-2-yloxyphenyl)-1,3-thiazol-2-yl]-6-(methanesulfonamido)pyridine-2-sulfonamide |
| 96 | 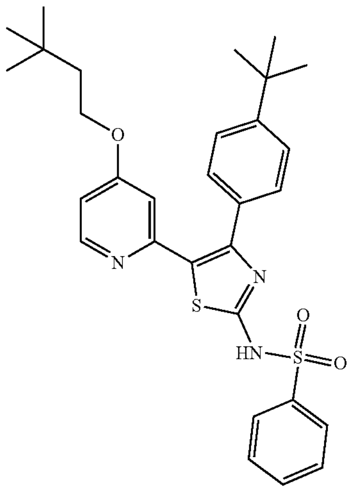 [SMILES: CC(C)(C)CCOc1ccnc(-c2sc(NS(=O)(=O)c3ccccc3)nc2-c2ccc(C(C)(C)C)cc2)c1] | N-[5-[4-(3,3-dimethylbutoxy)pyridin-2-yl]-4-[4-(trifluoromethyl)phenyl]-1,3-thiazol-2-yl]benzenesulfonamide |
| 381 | 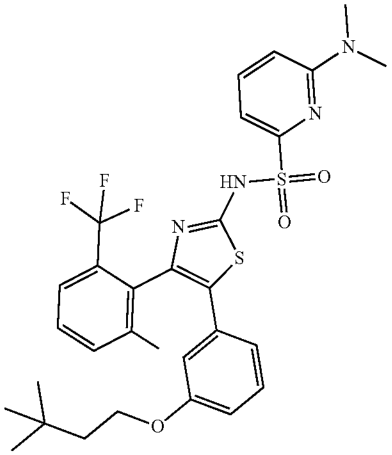 [SMILES: Cc1cccc(C(F)(F)F)c1-c1nc(NS(=O)(=O)c2cccc(N(C)C)n2)sc1-c1cccc(OCCC(C)(C)C)c1] | 6-(dimethylamino)-N-[5-[3-(3,3-dimethylbutoxy)phenyl]-4-[2-methyl-6-(trifluoromethyl)phenyl]-1,3-thiazol-2-yl]pyridine-2-sulfonamide |

TABLE 1-continued

| Compound Number | Compound Structural Formula | Compound Name |
|---|---|---|
| 305 | 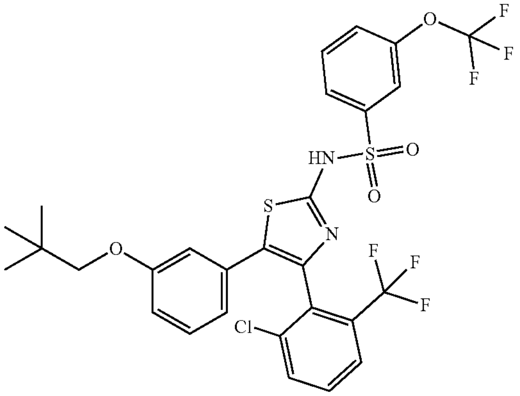 [SMILES: CC(C)(C)COc1cccc(-c2sc(NS(=O)(=O)c3cccc(OC(F)(F)F)c3)nc2-c2c(Cl)cccc2C(F)(F)F)c1] | N-[4-[2-chloro-6-(trifluoromethyl)phenyl]-5-[3-(2,2-dimethylpropoxy)phenyl]-1,3-thiazol-2-yl]-3-(trifluoromethoxy)benzenesulfonamide |
| 268 | 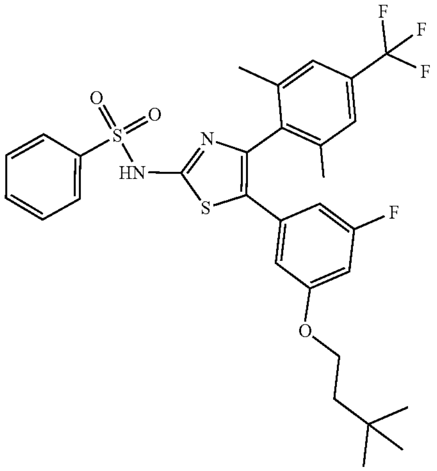 [SMILES: Cc1cc(C(F)(F)F)cc(C)c1-c1nc(NS(=O)(=O)c2ccccc2)sc1-c1cc(F)cc(OCCC(C)(C)C)c1] | N-[5-[3-(3,3-dimethylbutoxy)-5-fluorophenyl]-4-[2,6-dimethyl-4-(trifluoromethyl)phenyl]-1,3-thiazol-2-yl]benzenesulfonamide |
| 100 | 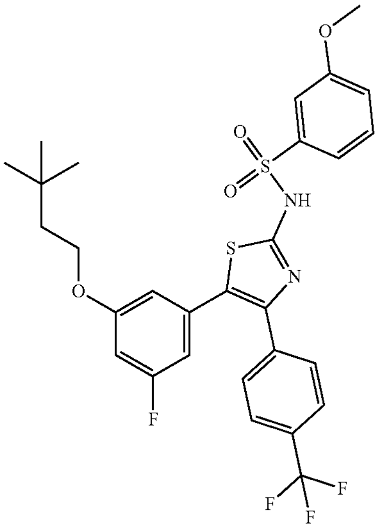 [SMILES: COc1cccc(S(=O)(=O)Nc2nc(-c3ccc(C(F)(F)F)cc3)c(-c3cc(F)cc(OCCC(C)(C)C)c3)s2)c1] | N-[5-[3-(3,3-dimethylbutoxy)-5-fluorophenyl]-4-[4-(trifluoromethyl)phenyl]-1,3-thiazol-2-yl]-3-methoxybenzenesulfonamide |

TABLE 1-continued

| Compound Number | Compound Structural Formula | Compound Name |
|---|---|---|
| 83 | 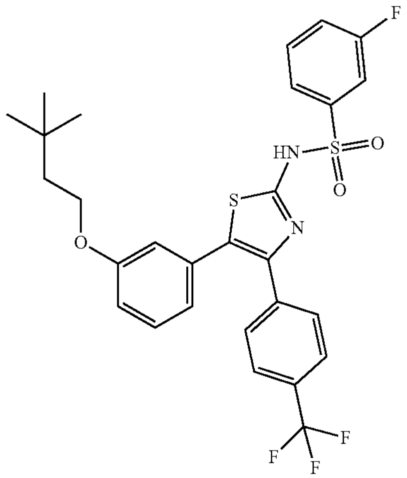 [SMILES: CC(C)(C)CCOc1cccc(-c2sc(NS(=O)(=O)c3cccc(F)c3)nc2-c2ccc(C(F)(F)F)cc2)c1] | N-[5-[3-(3,3-dimethylbutoxy)phenyl]-4-[4-(trifluoromethyl)phenyl]-1,3-thiazol-2-yl]-3-fluorobenzenesulfonamide |
| 514 | 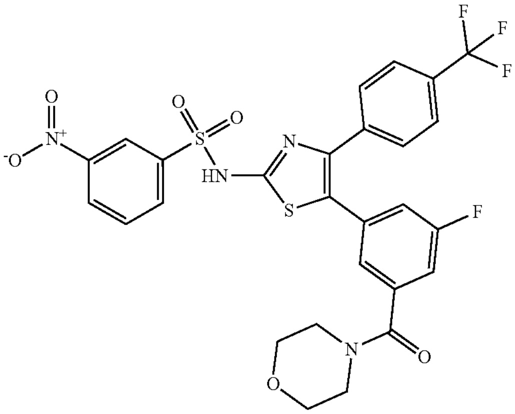 | N-(5-(3-fluoro-5-(morpholine-4-carbonyl)phenyl)-4-(4-(trifluoromethyl)phenyl)thiazol-2-yl)-3-nitrobenzenesulfonamide |
| 233 | 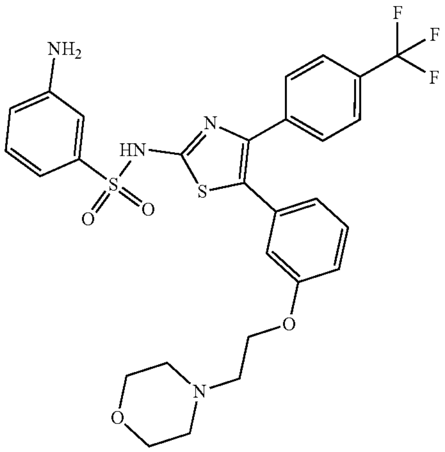 [SMILES: Nc1cccc(S(=O)(=O)Nc2nc(-c3ccc(C(F)(F)F)cc3)c(-c3cccc(OCCN4CCOCC4)c3)s2)c1] | 3-amino-N-[5-[3-(2-morpholin-4-ylethoxy)phenyl]-4-[4-(trifluoromethyl)phenyl]-1,3-thiazol-2-yl]benzenesulfonamide |

TABLE 1-continued

| Compound Number | Compound Structural Formula | Compound Name |
|---|---|---|
| 174 | 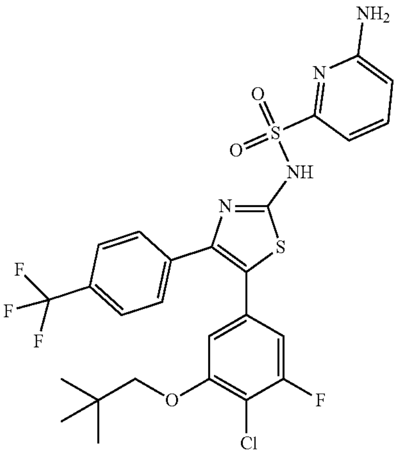 [SMILES: CC(C)(C)COc1cc(-c2sc(NS(=O)(=O)c3cccc(N)n3)nc2-c2ccc(C(F)(F)F)cc2)cc(F)c1Cl] | 6-amino-N-[5-[4-chloro-3-(2,2-dimethylpropoxy)-5-fluorophenyl]-4-[4-(trifluoromethyl)phenyl]-1,3-thiazol-2-yl]pyridine-2-sulfonamide |
| 196 | 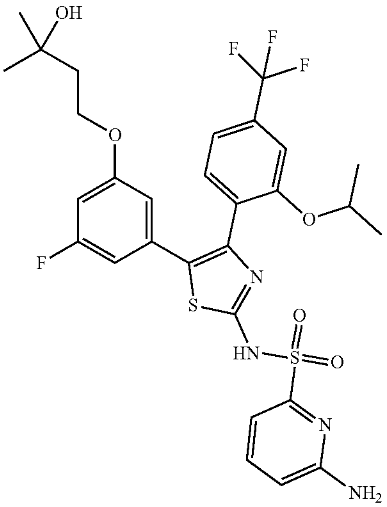 [SMILES: CC(C)Oc1cc(C(F)(F)F)ccc1-c1nc(NS(=O)(=O)c2cccc(N)n2)sc1-c1cc(F)cc(OCCC(C)(C)O)c1] | 6-amino-N-[5-[3-fluoro-5-(3-hydroxy-3-methylbutoxy)phenyl]-4-[2-propan-2-yloxy-4-(trifluoromethyl)phenyl]-1,3-thiazol-2-yl]pyridine-2-sulfonamide |
| 239 | 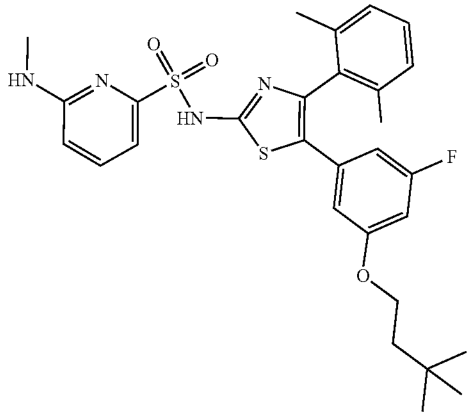 [SMILES: CNc1cccc(S(=O)(=O)Nc2nc(-c3c(C)cccc3C)c(-c3cc(F)cc(OCCC(C)(C)C)c3)s2)n1] | N-[5-[3-(3,3-dimethylbutoxy)-5-fluorophenyl]-4-(2,6-dimethylphenyl)-1,3-thiazol-2-yl]-6-(methylamino)pyridine-2-sulfonamide |

TABLE 1-continued

| Compound Number | Compound Structural Formula | Compound Name |
|---|---|---|
| 290 | 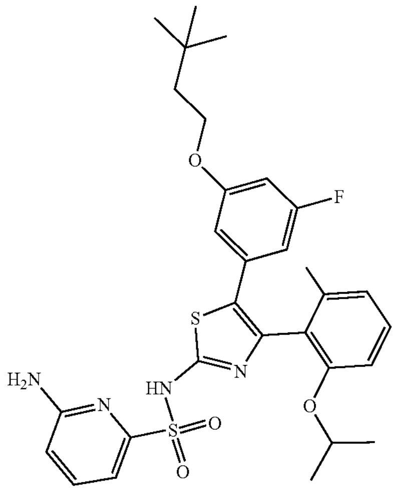 [SMILES: Cc1cccc(OC(C)C)c1-c1nc(NS(=O)(=O)c2cccc(N)n2)sc1-c1cc(F)cc(OCCC(C)(C)C)c1] | 6-amino-N-[5-[3-(3,3-dimethylbutoxy)-5-fluorophenyl]-4-(2-methyl-6-propan-2-yloxyphenyl)-1,3-thiazol-2-yl]pyridine-2-sulfonamide |
| 211 | 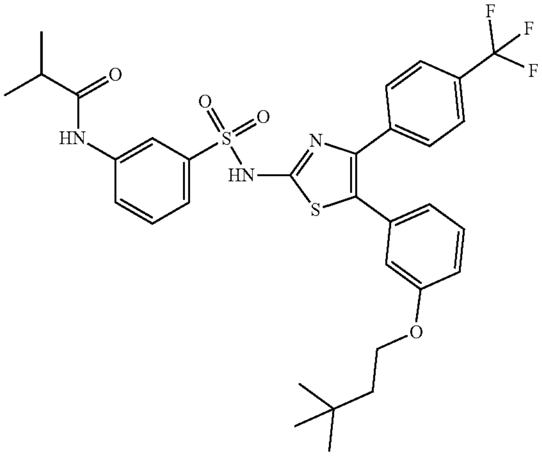 [SMILES: CC(C)C(=O)Nc1cccc(S(=O)(=O)Nc2nc(-c3ccc(C(F)(F)F)cc3)c(-c3cccc(OCCC(C)(C)C)c3)s2)c1] | N-[3-[5-[3-(3,3-dimethylbutoxy)phenyl]-4-[4-(trifluoromethyl)phenyl]-1,3-thiazol-2-yl]sulfamoyl]phenyl]-2-methylpropanamide |
| 183 | 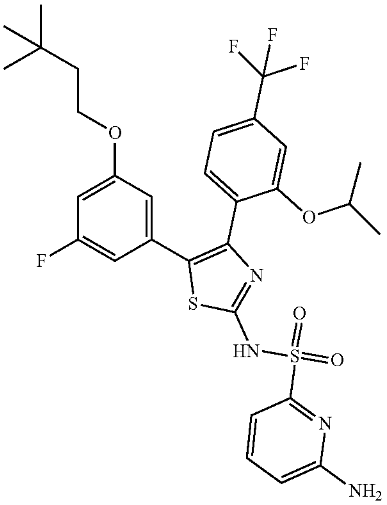 [SMILES: CC(C)Oc1cc(C(F)(F)F)ccc1-c1nc(NS(=O)(=O)c2cccc(N)n2)sc1-c1cc(F)cc(OCCC(C)(C)C)c1] | 6-amino-N-[5-[3-(3,3-dimethylbutoxy)-5-fluorophenyl]-4-[2-propan-2-yloxy-4-(trifluoromethyl)phenyl]-1,3-thiazol-2-yl]pyridine-2-sulfonamide |

TABLE 1-continued

| Compound Number | Compound Structural Formula | Compound Name |
| --- | --- | --- |
| 251 | 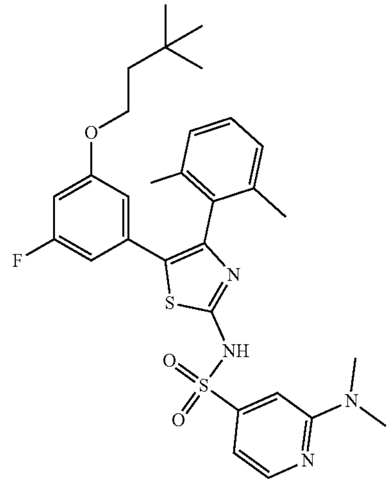 [SMILES: Cc1cccc(C)c1-c1nc(NS(=O)(=O)c2ccnc(N(C)C)c2)sc1-c1cc(F)cc(OCCC(C)(C)C)c1] | 2-(dimethylamino)-N-[5-[3-(3,3-dimethylbutoxy)-5-fluorophenyl]-4-(2,6-dimethylphenyl)-1,3-thiazol-2-yl]pyridine-4-sulfonamide |
| 218 | 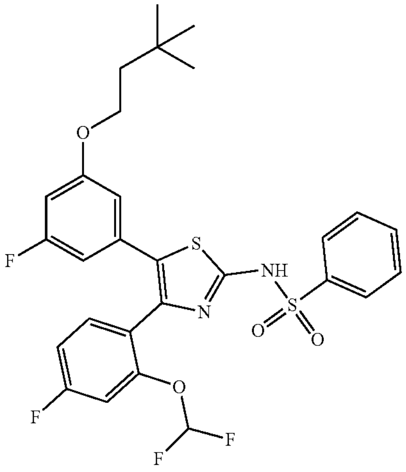 [SMILES: CC(C)(C)CCOc1cc(F)cc(-c2sc(NS(=O)(=O)c3ccccc3)nc2-c2ccc(F)cc2OC(F)F)c1] | N-[4-[2-(difluoromethoxy)-4-fluorophenyl]-5-[3-(3,3-dimethylbutoxy)-5-fluorophenyl]-1,3-thiazol-2-yl]benzenesulfonamide |
| 160 | 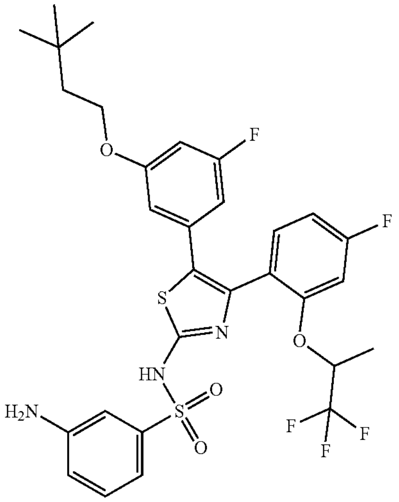 [SMILES: CC(Oc1cc(F)ccc1-c1nc(NS(=O)(=O)c2cccc(N)c2)sc1-c1cc(F)cc(OCCC(C)(C)C)c1)C(F)(F)F] | 3-amino-N-[5-[3-(3,3-dimethylbutoxy)-5-fluorophenyl]-4-[4-fluoro-2-(1,1,1-trifluoropropan-2-yloxy)phenyl]-1,3-thiazol-2-yl]benzenesulfonamide |
| 410 | | 6-amino-N-[4-(4-chloro-2-propan-2-yloxyphenyl)-5-[3-[(4,4-difluorocyclohexyl)methoxy]-5-fluorophenyl]-1,3-thiazol-2-yl]pyridine-2-sulfonamide |

TABLE 1-continued

| Compound Number | Compound Structural Formula | Compound Name |
|---|---|---|
| 416 | 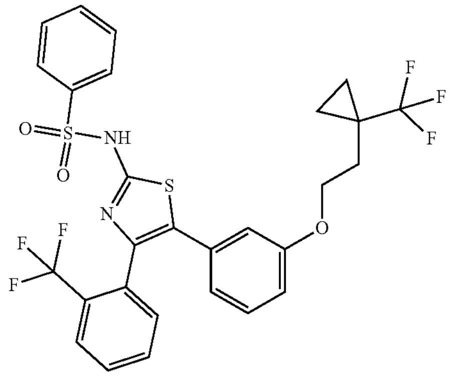 [SMILES: O=S(=O)(Nc1nc(-c2ccccc2C(F)(F)F)c(-c2cccc(OCCC3(C(F)(F)F)CC3)c2)s1)c1ccccc1] | N-[5-[3-[2-[1-(trifluoromethyl)cyclopropyl]ethoxylphenyl]-4-[2-(trifluoromethyl)phenyl]-1,3-thiazol-2-yl]benzenesulfonamide |
| 199 | 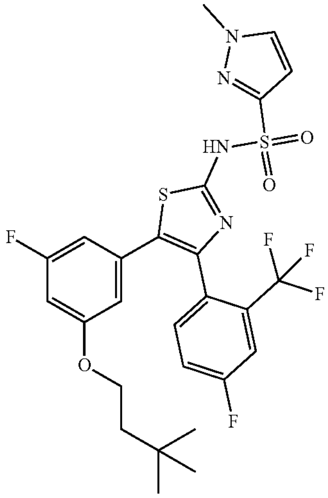 [SMILES: Cn1ccc(S(=O)(=O)Nc2nc(-c3ccc(F)cc3C(F)(F)F)c(-c3cc(F)cc(OCCC(C)(C)C)c3)s2)n1] | N-[5-[3-(3,3-dimethylbutoxy)-5-fluorophenyl]-4-[4-fluoro-2-(trifluoromethyl)phenyl]-1,3-thiazol-2-yl]-1-methylpyrazole-3-sulfonamide |
| 515 | 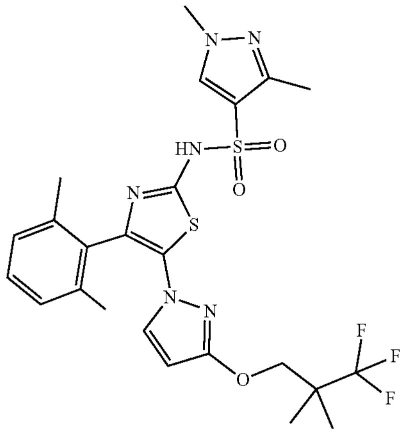 [SMILES: Cc1cccc(C)c1-c1nc(NS(=O)(=O)c2cn(C)nc2C)sc1-n1ccc(OCC(C)(C)C(F)(F)F)n1] | N-(4-(2,6-dimethylphenyl)-5-(3-(3,3,3-trifluoro-2,2-dimethylpropoxy)-1H-pyrazol-1-yl)thiazol-2-yl)-1,3-dimethyl-1H-pyrazole-4-sulfonamide |

TABLE 1-continued

| Compound Number | Compound Structural Formula | Compound Name |
|---|---|---|
| 191 | 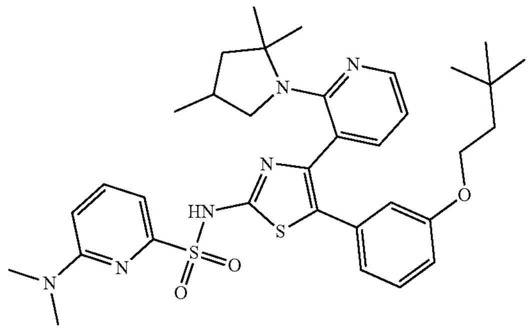 [SMILES: CC1CN(c2ncccc2-c2nc(NS(=O)(=O)c3cccc(N(C)C)n3)sc2-c2cccc(OCCC(C)(C)C)c2)C(C)(C)C1] | 6-(dimethylamino)-N-[5-[3-(3,3-dimethylbutoxy)phenyl]-4-[2-(2,2,4-trimethylpyrrolidin-1-yl)pyridin-3-yl]-1,3-thiazol-2-yl]pyridine-2-sulfonamide |
| 102 | 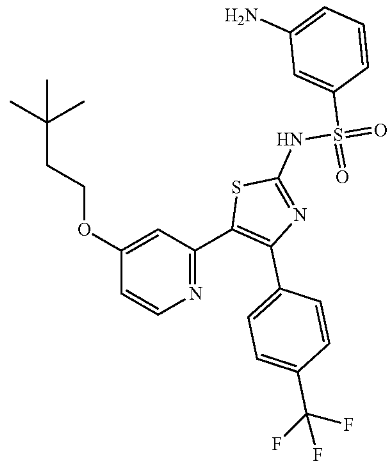 [SMILES: CC(C)(C)CCOc1ccnc(-c2sc(NS(=O)(=O)c3cccc(N)c3)nc2-c2ccc(C(F)(F)F)cc2)c1] | 3-amino-N-[5-[4-(3,3-dimethylbutoxy)pyridin-2-yl]-4-[4-(trifluoromethyl)phenyl]-1,3-thiazol-2-yl]benzenesulfonamide |
| 458 | 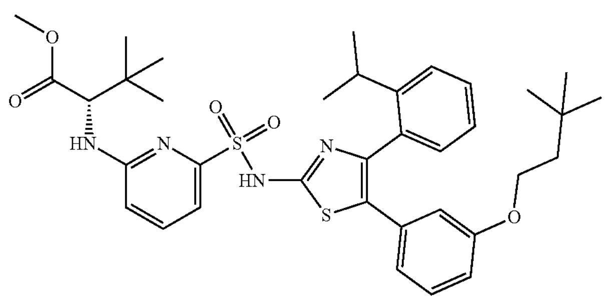 [SMILES: COC(=O)[C@@H](Nc1cccc(S(=O)(=O)Nc2nc(-c3ccccc3C(C)C)c(-c3cccc(OCCC(C)(C)C)c3)s2)n1)C(C)(C)C] | Methyl-(2S)-2-[6-[5-[3-(3,3-dimethylbutoxy)phenyl]-4-(2-propan-2-ylphenyl)-1,3-thiazol-2-yl]sulfamoyl]pyridin-2-yl]amino]-3,3-dimethylbutanoate |

TABLE 1-continued

| Compound Number | Compound Structural Formula | Compound Name |
|---|---|---|
| 353 | 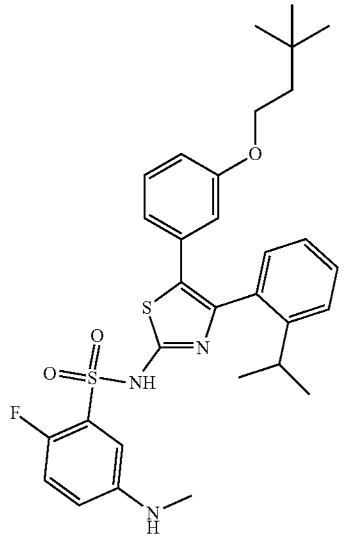 [SMILES: CNc1ccc(F)c(S(=O)(=O)Nc2nc(-c3ccccc3C(C)C)c(-c3cccc(OCCC(C)(C)C)c3)s2)c1] | N-[5-[3-(3,3-dimethylbutoxy)phenyl]-4-(2-propan-2-ylphenyl)-1,3-thiazol-2-yl]-2-fluoro-5-(methylamino)benzenesulfonamide |
| 203 | 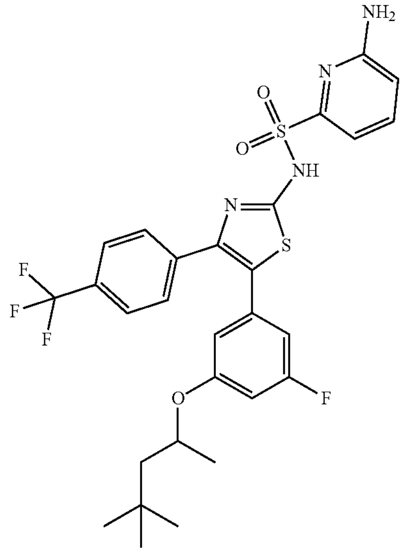 [SMILES: CC(CC(C)(C)C)Oc1cc(F)cc(-c2sc(NS(=O)(=O)c3cccc(N)n3)nc2-c2ccc(C(F)(F)F)cc2)c1] | 6-amino-N-[5-[3-(4,4-dimethylpentan-2-yloxy)-5-fluorophenyl]-4-[4-(trifluoromethyl)phenyl]-1,3-thiazol-2-yl]pyridine-2-sulfonamide |
| 488 | 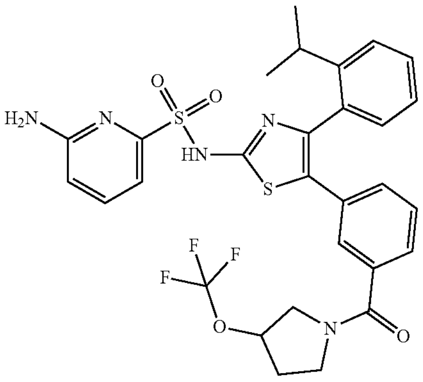 [SMILES: CC(C)c1ccccc1-c1nc(NS(=O)(=O)c2cccc(N)n2)sc1-c1cccc(C(=O)N2CCC(OC(F)(F)F)C2)c1] | 6-amino-N-[4-(2-propan-2-ylphenyl)-5-[3-[3-(trifluoromethoxy)pyrrolidine-1-carbonyl]phenyl]-1,3-thiazol-2-yl]pyridine-2-sulfonamide |

TABLE 1-continued

| Compound Number | Compound Structural Formula | Compound Name |
|---|---|---|
| 299 | 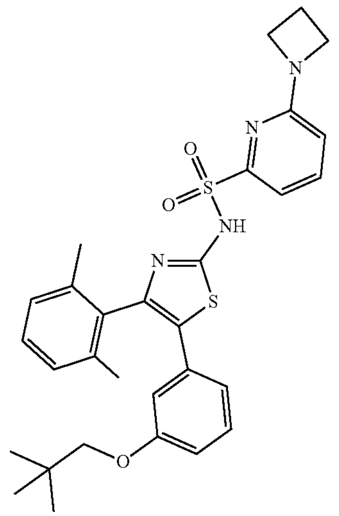 [SMILES: Cc1cccc(C)c1-c1nc(NS(=O)(=O)c2cccc(N3CCC3)n2)sc1-c1cccc(OCC(C)(C)C)c1] | 6-(azetidin-1-yl)-N-[4-(2,6-dimethylphenyl)-5-[3-(2,2-dimethylpropoxy)phenyl]-1,3-thiazol-2-yl]pyridine-2-sulfonamide |
| 16 | 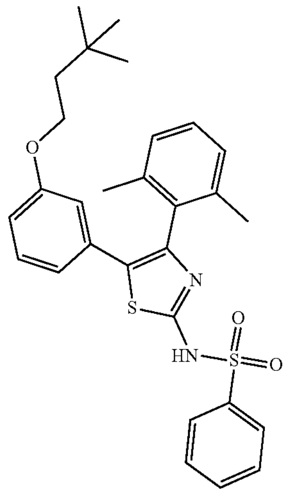 [SMILES: Cc1cccc(C)c1-c1nc(NS(=O)(=O)c2ccccc2)sc1-c1cccc(OCCC(C)(C)C)c1] | N-[5-[3-(3,3-dimethylbutoxy)phenyl]-4-(2,6-dimethylphenyl)-1,3-thiazol-2-yl]benzenesulfonamide |
| 136 | 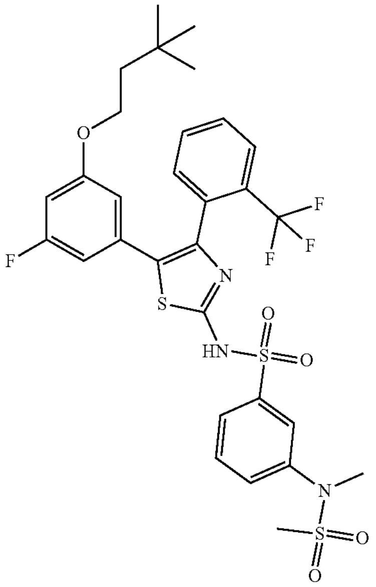 [SMILES: CN(c1cccc(S(=O)(=O)Nc2nc(-c3ccccc3C(F)(F)F)c(-c3cc(F)cc(OCCC(C)(C)C)c3)s2)c1)S(C)(=O)=O] | N-[5-[3-(3,3-dimethylbutoxy)-5-fluorophenyl]-4-[2-(trifluoromethyl)phenyl]-1,3-thiazol-2-yl]-3-[methyl(methylsulfonyl)amino]benzenesulfonamide |

TABLE 1-continued

| Compound Number | Compound Structural Formula | Compound Name |
|---|---|---|
| 328 | 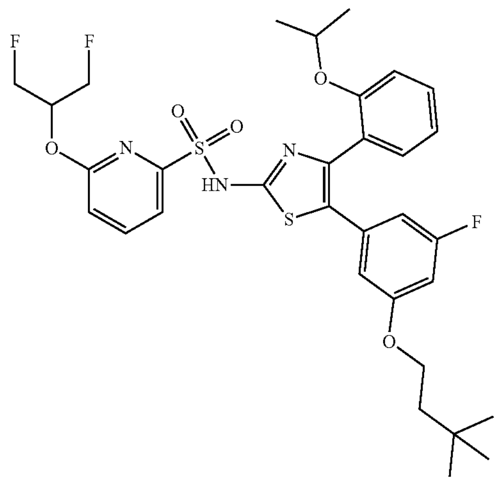 [SMILES: CC(C)Oc1ccccc1-c1nc(NS(=O)(=O)c2cccc(OC(CF)CF)n2)sc1-c1cc(F)cc(OCCC(C)(C)C)c1] | 6-(1,3-difluoropropan-2-yloxy)-N-[5-[3-(3,3-dimethylbutoxy)-5-fluorophenyl]-4-(2-propan-2-yloxyphenyl)-1,3-thiazol-2-yl]pyridine-2-sulfonamide |
| 200 | 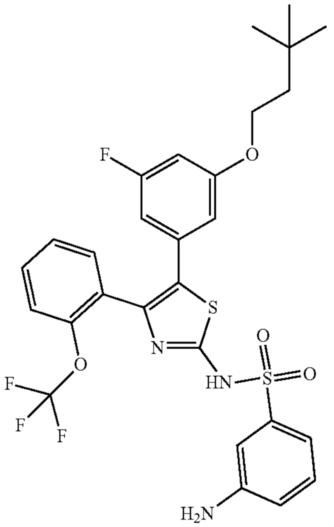 [SMILES: CC(C)(C)CCOc1cc(F)cc(-c2sc(NS(=O)(=O)c3cccc(N)c3)nc2-c2ccccc2OC(F)(F)F)c1] | 3-amino-N-[5-[3-(3,3-dimethylbutoxy)-5-fluorophenyl]-4-[2-(trifluoromethoxy)phenyl]-1,3-thiazol-2-yl]benzenesulfonamide |
| 139 | 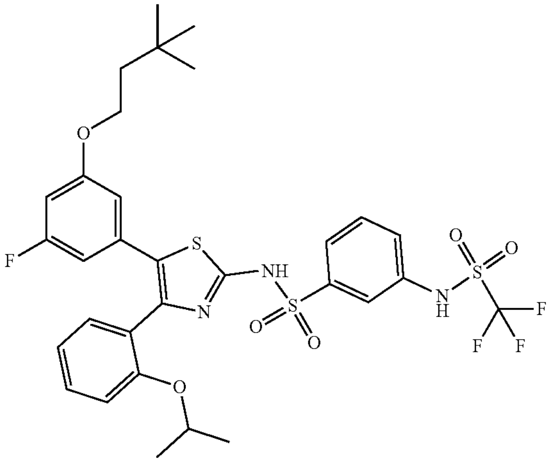 [SMILES: CC(C)Oc1ccccc1-c1nc(NS(=O)(=O)c2cccc(NS(=O)(=O)C(F)(F)F)c2)sc1-c1cc(F)cc(OCCC(C)(C)C)c1] | N-[5-[3-(3,3-dimethylbutoxy)-5-fluorophenyl]-4-(2-propan-2-yloxyphenyl)-1,3-thiazol-2-yl]-3-(trifluoromethylsulfonylamino) benzenesulfonamide |

TABLE 1-continued
| Compound Number | Compound Structural Formula | Compound Name |
| --- | --- | --- |
| 30 | 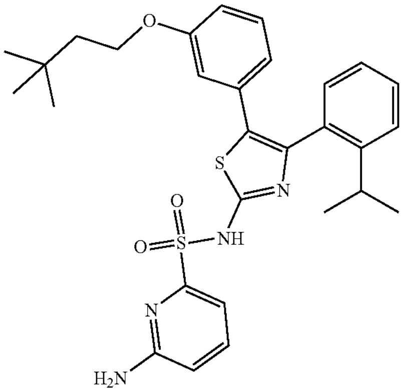 [SMILES: CC(C)c1ccccc1-c1nc(NS(=O)(=O)c2cccc(N)n2)sc1-c1cccc(OCCC(C)(C)C)c1] | 6-amino-N-[5-[3-(3,3-dimethylbutoxy)phenyl]-4-(2-propan-2-ylphenyl)-1,3-thiazol-2-yl]pyridine-2-sulfonamide |
| 452 | 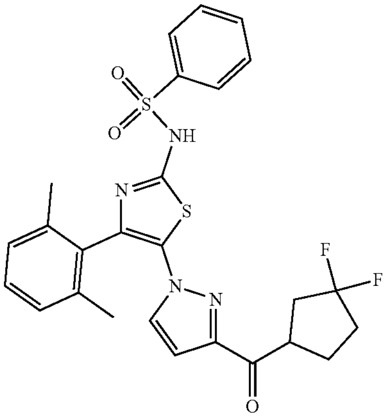 [SMILES: Cc1cccc(C)c1-c1nc(NS(=O)(=O)c2ccccc2)sc1-n1ccc(C(=O)C2CCC(F)(F)C2)n1] | N-[5-[3-(3,3-difluorocyclopentanecarbonyl)pyrazol-1-yl]-4-(2,6-dimethylphenyl)-1,3-thiazol-2-yl]benzenesulfonamide |
| 73 | 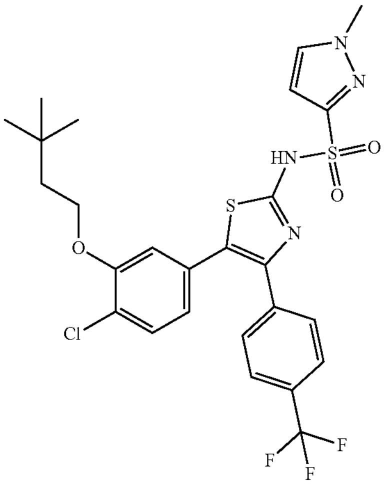 [SMILES: Cn1ccc(S(=O)(=O)Nc2nc(-c3ccc(C(F)(F)F)cc3)c(-c3ccc(Cl)c(OCCC(C)(C)C)c3)s2)n1] | N-[5-[4-chloro-3-(3,3-dimethylbutoxy)phenyl]-4-[4-(trifluoromethyl)phenyl]-1,3-thiazol-2-yl]-1-methylpyrazole-3-sulfonamide |

TABLE 1-continued

| Compound Number | Compound Structural Formula | Compound Name |
|---|---|---|
| 252 | 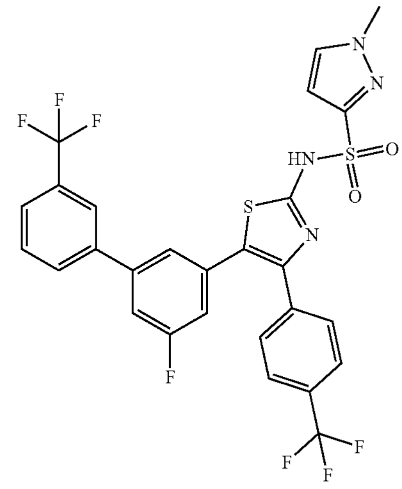 [SMILES: Cn1ccc(S(=O)(=O)Nc2nc(-c3ccc(C(F)(F)F)cc3)c(-c3cc(F)cc(-c4cccc(C(F)(F)F)c4)c3)s2)n1] | N-[5-[3-fluoro-5-[3-(trifluoromethyl)phenyl]phenyl]-4-[4-(trifluoromethyl)phenyl]-1,3-thiazol-2-yl]-1-methylpyrazole-3-sulfonamide |
| 242 | 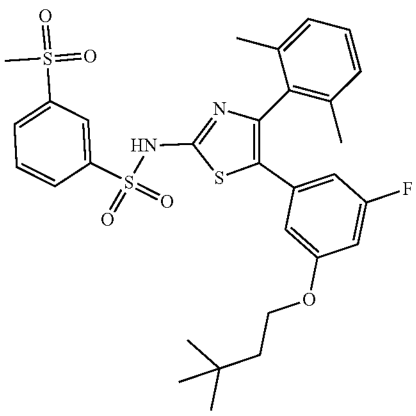 [SMILES: Cc1cccc(C)c1-c1nc(NS(=O)(=O)c2cccc(S(C)(=O)=O)c2)sc1-c1cc(F)cc(OCCC(C)(C)C)c1] | N-[5-[3-(3,3-dimethylbutoxy)-5-fluorophenyl]-4-(2,6-dimethylphenyl)-1,3-thiazol-2-yl]-3-methylsulfonylbenzenesulfonamide |
| 261 | 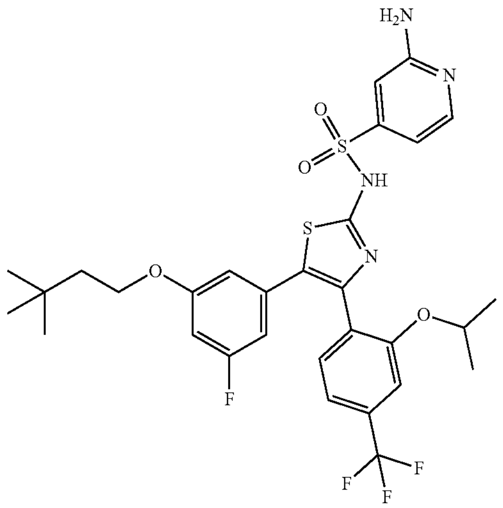 [SMILES: CC(C)Oc1cc(C(F)(F)F)ccc1-c1nc(NS(=O)(=O)c2ccnc(N)c2)sc1-c1cc(F)cc(OCCC(C)(C)C)c1] | 2-amino-N-[5-[3-(3,3-dimethylbutoxy)-5-fluorophenyl]-4-[2-propan-2-yloxy-4-(trifluoromethyl)phenyl]-1,3-thiazol-2-yl]pyridine-4-sulfonamide |

TABLE 1-continued
| Compound Number | Compound Structural Formula | Compound Name |
|---|---|---|
| 516 | 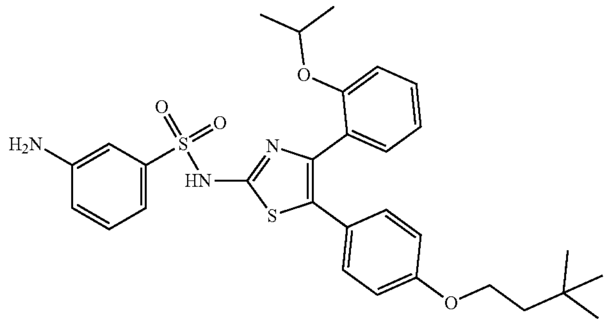 [SMILES: CC(C)Oc1ccccc1-c1nc(NS(=O)(=O)c2cccc(N)c2)sc1-c1ccc(OCCC(C)(C)C)cc1] | 3-amino-N-(5-(4-(3,3-dimethylbutoxy)phenyl)-4-(2-isopropoxyphenyl)thiazol-2-yl)benzenesulfonamide |
| 517 | 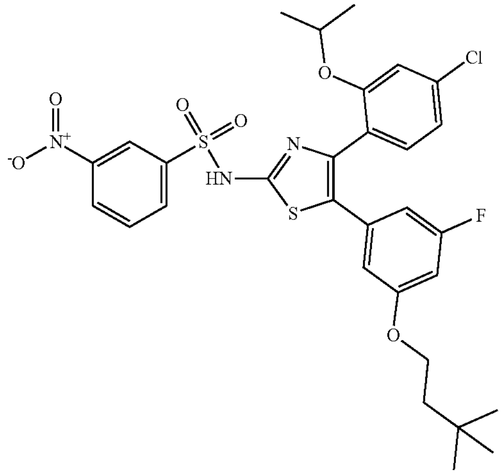 | N-(4-(4-chloro-2-isopropoxyphenyl)-5-(3-(3,3-dimethylbutoxy)-5-fluorophenyl)thiazol-2-yl)-3-nitrobenzenesulfonamide |
| 518 | 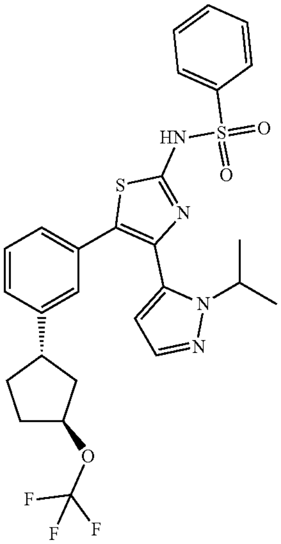 [SMILES: CC(C)n1nccc1-c1nc(NS(=O)(=O)c2ccccc2)sc1-c1cccc([C@H]2CC[C@H](OC(F)(F)F)C2)c1] | N-(4-(1-isopropyl-1H-pyrazol-5-yl)-5-(3-((1S,3S)-3-(trifluoromethoxy)cyclopentyl)phenyl)thiazol-2-yl)benzenesulfonamide |

TABLE 1-continued

| Compound Number | Compound Structural Formula | Compound Name |
|---|---|---|
| 117 | 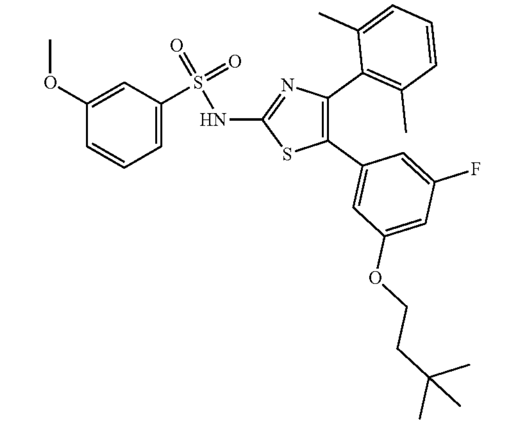 [SMILES: COc1cccc(S(=O)(=O)Nc2nc(-c3c(C)cccc3C)c(-c3cc(F)cc(OCCC(C)(C)C)c3)s2)c1] | N-[5-[3-(3,3-dimethylbutoxy)-5-fluorophenyl]-4-(2,6-dimethylphenyl)-1,3-thiazol-2-yl]-3-methoxybenzenesulfonamide |
| 519 | 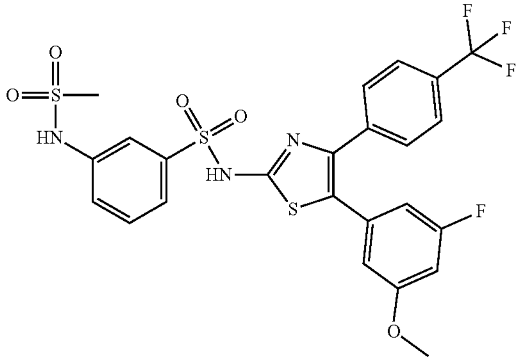 [SMILES: COc1cc(F)cc(-c2sc(NS(=O)(=O)c3cccc(NS(C)(=O)=O)c3)nc2-c2ccc(C(F)(F)F)cc2)c1] | N-(5-(3-fluoro-5-methoxyphenyl)-4-(4-(trifluoromethyl)phenyl)thiazol-2-yl)-3-(methylsulfonamido)benzenesulfonamide |
| 164 | 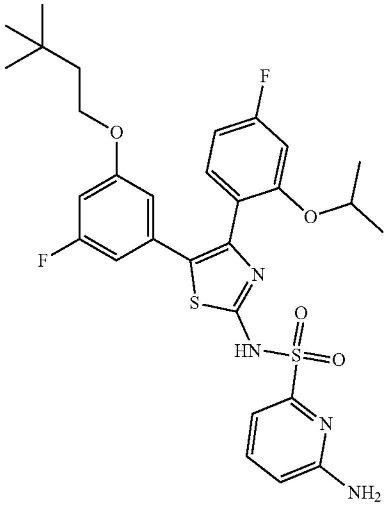 [SMILES: CC(C)Oc1cc(F)ccc1-c1nc(NS(=O)(=O)c2cccc(N)n2)sc1-c1cc(F)cc(OCCC(C)(C)C)c1] | 6-amino-N-[5-[3-(3,3-dimethylbutoxy)-5-fluorophenyl]-4-(4-fluoro-2-propan-2-yloxyphenyl)-1,3-thiazol-2-yl]pyridine-2-sulfonamide |

TABLE 1-continued

| Compound Number | Compound Structural Formula | Compound Name |
|---|---|---|
| 520 | 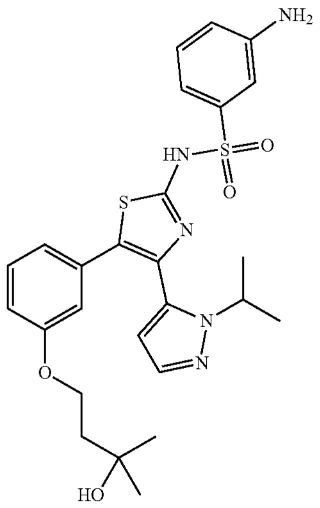 [SMILES: CC(C)n1nccc1-c1nc(NS(=O)(=O)c2cccc(N)c2)sc1-c1cccc(OCCC(C)(C)O)c1] | 3-amino-N-(5-(3-(3-hydroxy-3-methylbutoxy)phenyl)-4-(1-isopropyl-1H-pyrazol-5-yl)thiazol-2-yl)benzenesulfonamide |
| 321 | 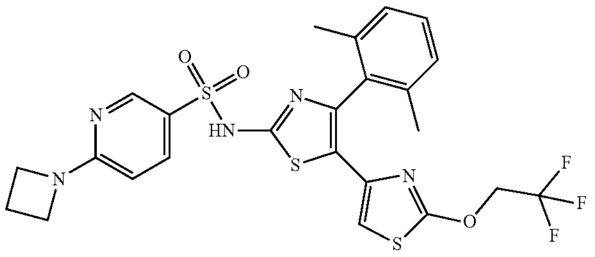 [SMILES: Cc1cccc(C)c1-c1nc(NS(=O)(=O)c2ccc(N3CCC3)nc2)sc1-c1csc(OCC(F)(F)F)n1] | 6-(azetidin-1-yl)-N-[4-(2,6-dimethylphenyl)-5-[2-(2,2,2-trifluoroethoxy)-1,3-thiazol-4-yl]-1,3-thiazol-2-yl]pyridine-3-sulfonamide |
| 221 | 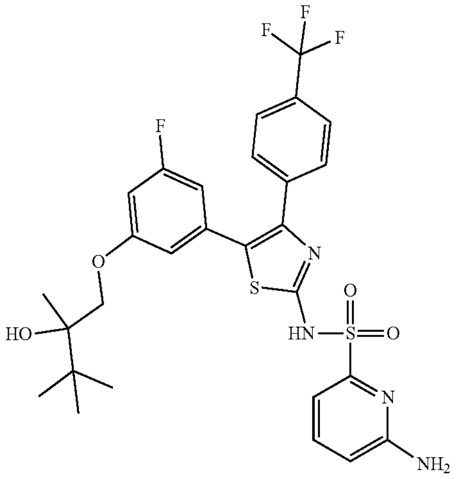 [SMILES: CC(C)(C)C(C)(O)COc1cc(F)cc(-c2sc(NS(=O)(=O)c3cccc(N)n3)nc2-c2ccc(C(F)(F)F)cc2)c1] | 6-amino-N-[5-[3-fluoro-5-(2-hydroxy-2,3,3-trimethylbutoxy)phenyl]-4-[4-(trifluoromethyl)phenyl]-1,3-thiazol-2-yl]pyridine-2-sulfonamide |

TABLE 1-continued

| Compound Number | Compound Structural Formula | Compound Name |
|---|---|---|
| 85 | 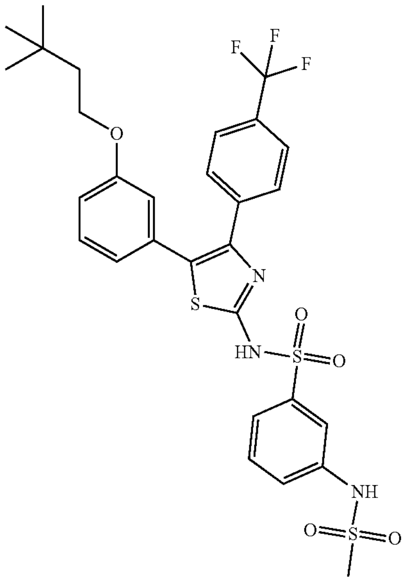 [SMILES: CC(C)(C)CCOc1cccc(-c2sc(NS(=O)(=O)c3cccc(NS(C)(=O)=O)c3)nc2-c2ccc(C(F)(F)F)cc2)c1] | N-[5-[3-(3,3-dimethylbutoxy)phenyl]-4-[4-(trifluoromethyl)phenyl]-1,3-thiazol-2-yl]-3-(methanesulfonamido)benzenesulfonamide |
| 64 | 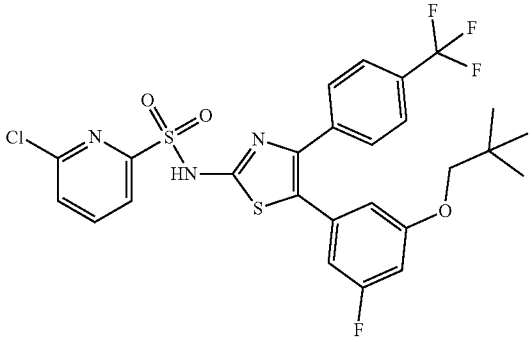 [SMILES: CC(C)(C)COc1cc(F)cc(-c2sc(NS(=O)(=O)c3cccc(Cl)n3)nc2-c2ccc(C(F)(F)F)cc2)c1] | 6-chloro-N-[5-[3-(2,2-dimethylpropoxy)-5-fluorophenyl]-4-[4-(trifluoromethyl)phenyl]-1,3-thiazol-2-yl]pyridine-2-sulfonamide |
| 48B1 | 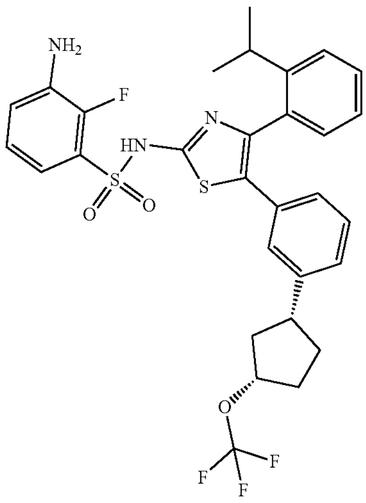 [SMILES: CC(C)c1ccccc1-c1nc(NS(=O)(=O)c2cccc(N)c2F)sc1-c1cccc([C@@H]2CC[C@H](OC(F)(F)F)C2)c1] | 3-amino-2-fluoro-N-[4-(2-propan-2-ylphenyl)-5-[3-[(1R,3S)-3-(trifluoromethoxy)cyclopentyl]phenyl]-1,3-thiazol-2-yl]benzenesulfonamide |

TABLE 1-continued

| Compound Number | Compound Structural Formula | Compound Name |
|---|---|---|
| 253 | 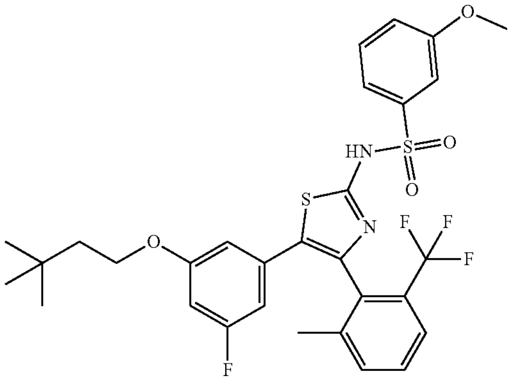 [SMILES: COc1cccc(S(=O)(=O)Nc2nc(-c3c(C)cccc3C(F)(F)F)c(-c3cc(F)cc(OCCC(C)(C)C)c3)s2)c1] | N-[5-[3-(3,3-dimethylbutoxy)-5-fluorophenyl]-4-[2-methyl-6-(trifluoromethyl)phenyl]-1,3-thiazol-2-yl]-3-methoxybenzenesulfonamide |
| 497 | 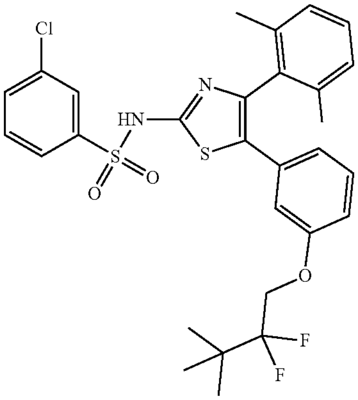 [SMILES: Cc1cccc(C)c1-c1nc(NS(=O)(=O)c2cccc(Cl)c2)sc1-c1cccc(OCC(F)(F)C(C)(C)C)c1] | 3-chloro-N-[5-[3-(2,2-difluoro-3,3-dimethylbutoxy)phenyl]-4-(2,6-dimethylphenyl)-1,3-thiazol-2-yl]benzenesulfonamide |
| 40 | 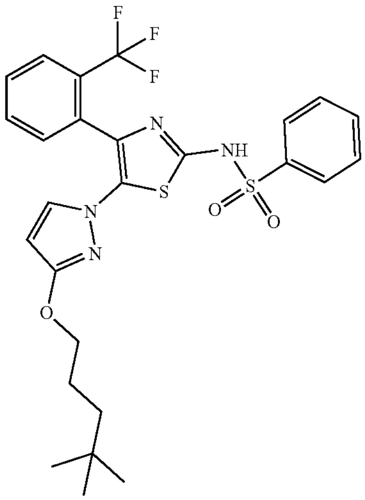 [SMILES: CC(C)(C)CCCOc1ccn(-c2sc(NS(=O)(=O)c3ccccc3)nc2-c2ccccc2C(F)(F)F)n1] | N-[5-[3-(4,4-dimethylpentoxy)pyrazol-1-yl]-4-[2-(trifluoromethyl)phenyl]-1,3-thiazol-2-yl]benzenesulfonamide |

TABLE 1-continued

| Compound Number | Compound Structural Formula | Compound Name |
|---|---|---|
| 521 | 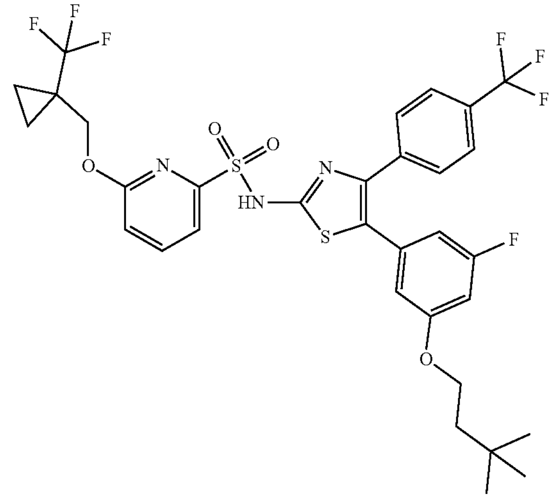 [SMILES: CC(C)(C)CCOc1cc(F)cc(-c2sc(NS(=O)(=O)c3cccc(OCC4(C(F)(F)F)CC4)n3)nc2-c2ccc(C(F)(F)F)cc2)c1] | N-(5-(3-(3,3-dimethylbutoxy)-5-fluorophenyl)-4-(4-(trifluoromethyl)phenyl)thiazol-2-yl)-6-((1-(trifluoromethyl)cyclopropyl)methoxy)pyridine-2-sulfonamide |
| 437 | 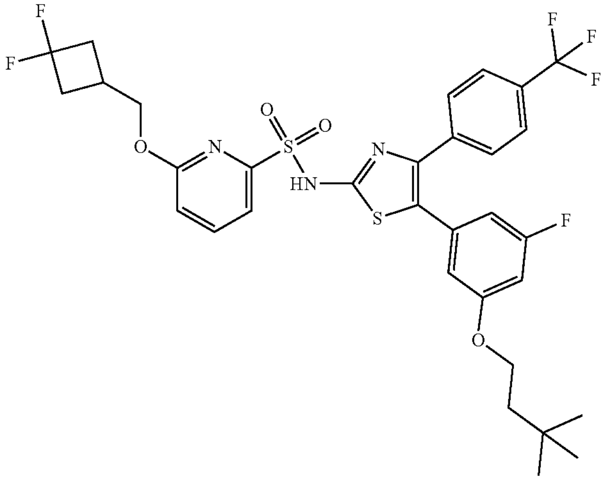 [SMILES: CC(C)(C)CCOc1cc(F)cc(-c2sc(NS(=O)(=O)c3cccc(OCC4CC(F)(F)C4)n3)nc2-c2ccc(C(F)(F)F)cc2)c1] | 6-[(3,3-difluorocyclobutyl)methoxy]-N-[5-[3-(3,3-dimethylbutoxy)-5-fluorophenyl]-4-[4-(trifluoromethyl)phenyl]-1,3-thiazol-2-yl]pyridine-2-sulfonamide |
| 505 | 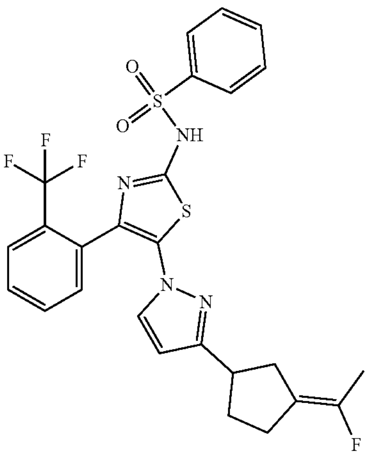 [SMILES: C/C(F)=C1/CCC(c2ccn(-c3sc(NS(=O)(=O)c4ccccc4)nc3-c3ccccc3C(F)(F)F)n2)C1] | N-[5-[3-[(3E)-3-(1-fluoroethylidene)cyclopentyl]pyrazol-1-yl]-4-[2-(trifluoromethyl)phenyl]-1,3-thiazol-2-yl]benzenesulfonamide |

TABLE 1-continued

| Compound Number | Compound Structural Formula | Compound Name |
|---|---|---|
| 55 | 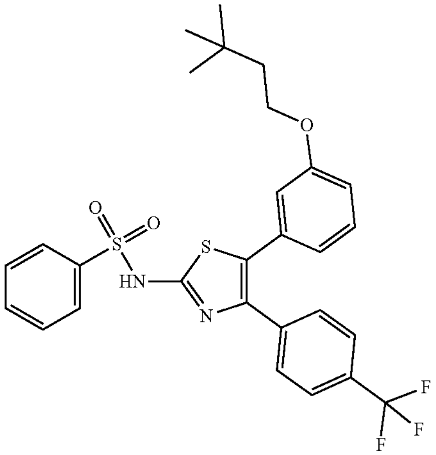 [SMILES: CC(C)(C)CCOc1cccc(-c2sc(NS(=O)(=O)c3ccccc3)nc2-c2ccc(C(F)(F)F)cc2)c1] | N-[5-[3-(3,3-dimethylbutoxy)phenyl]-4-[4-(trifluoromethyl)phenyl]-1,3-thiazol-2-yl]benzenesulfonamide |
| 82 | 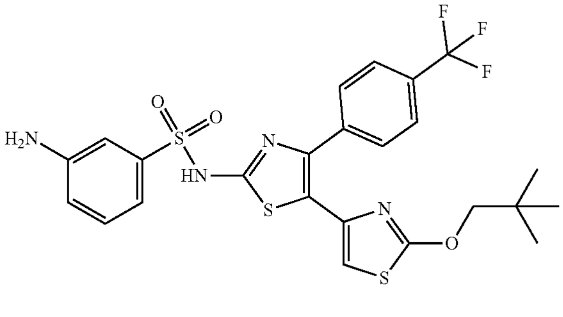 [SMILES: CC(C)(C)COc1nc(-c2sc(NS(=O)(=O)c3cccc(N)c3)nc2-c2ccc(C(F)(F)F)cc2)cs1] | 3-amino-N-[5-[2-(2,2-dimethylpropoxy)-1,3-thiazol-4-yl]-4-[4-(trifluoromethyl)phenyl]-1,3-thiazol-2-yl]benzenesulfonamide |
| 270 | 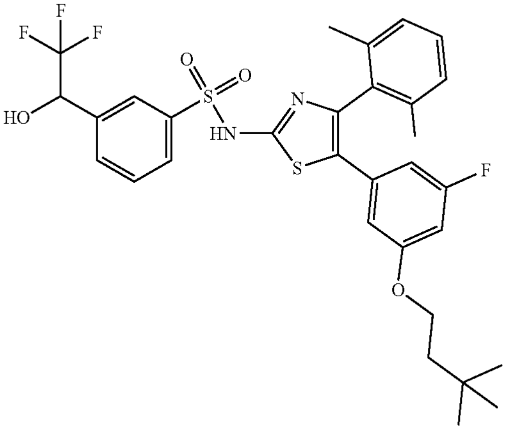 [SMILES: Cc1cccc(C)c1-c1nc(NS(=O)(=O)c2cccc(C(O)C(F)(F)F)c2)sc1-c1cc(F)cc(OCCC(C)(C)C)c1] | N-[5-[3-(3,3-dimethylbutoxy)-5-fluorophenyl]-4-(2,6-dimethylphenyl)-1,3-thiazol-2-yl]-3-(2,2,2-trifluoro-1-hydroxyethyl)benzenesulfonamide |

TABLE 1-continued

| Compound Number | Compound Structural Formula | Compound Name |
|---|---|---|
| 152 | 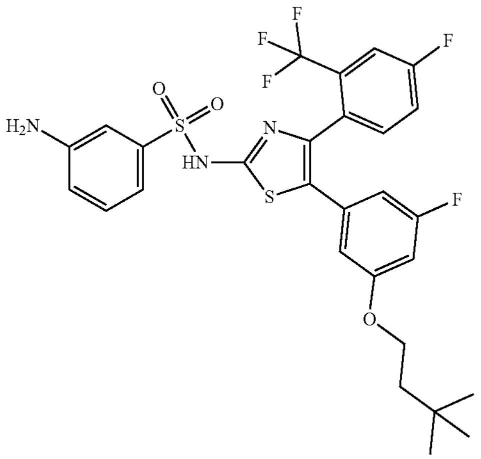 [SMILES: CC(C)(C)CCOc1cc(F)cc(-c2sc(NS(=O)(=O)c3cccc(N)c3)nc2-c2ccc(F)cc2C(F)(F)F)c1] | 3-amino-N-[5-[3-(3,3-dimethylbutoxy)-5-fluorophenyl]-4-[4-fluoro-2-(trifluoromethyl)phenyl]-1,3-thiazol-2-yl]benzenesulfonamide |
| 99 | 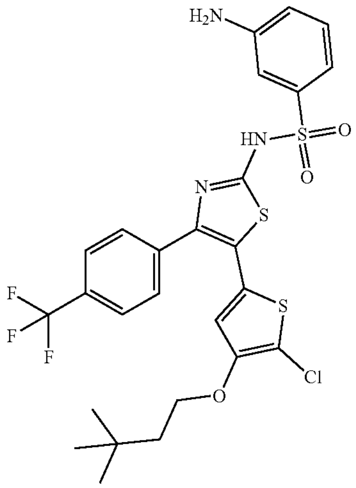 [SMILES: CC(C)(C)CCOc1cc(-c2sc(NS(=O)(=O)c3cccc(N)c3)nc2-c2ccc(C(F)(F)F)cc2)sc1Cl] | 3-amino-N-[5-[5-chloro-4-(3,3-dimethylbutoxy)thiophen-2-yl]-4-[4-(trifluoromethyl)phenyl]-1,3-thiazol-2-yl]benzenesulfonamide |
| 217 | 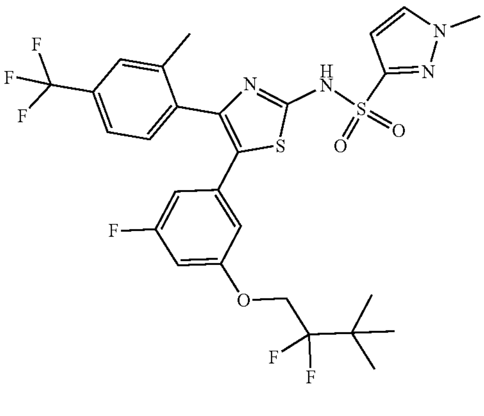 [SMILES: Cc1cc(C(F)(F)F)ccc1-c1nc(NS(=O)(=O)c2ccn(C)n2)sc1-c1cc(F)cc(OCC(F)(F)C(C)(C)C)c1] | N-[5-[3-(2,2-difluoro-3,3-dimethylbutoxy)-5-fluorophenyl]-4-[2-methyl-4-(trifluoromethyl)phenyl]-1,3-thiazol-2-yl]-1-methylpyrazole-3-sulfonamide |

TABLE 1-continued

| Compound Number | Compound Structural Formula | Compound Name |
|---|---|---|
| 219 | 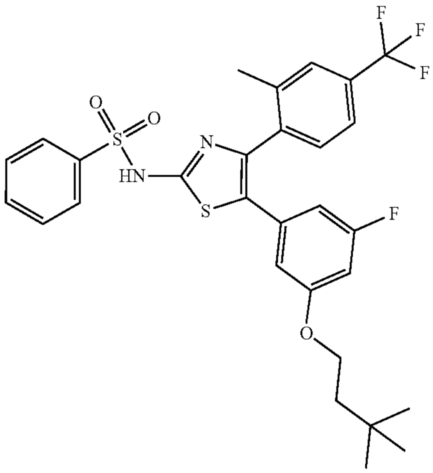 [SMILES: Cc1cc(C(F)(F)F)ccc1-c1nc(NS(=O)(=O)c2ccccc2)sc1-c1cc(F)cc(OCCC(C)(C)C)c1] | N-[5-[3-(3,3-dimethylbutoxy)-5-fluorophenyl]-4-[2-methyl-4-(trifluoromethyl)phenyl]-1,3-thiazol-2-yl]benzenesulfonamide |
| 522 | 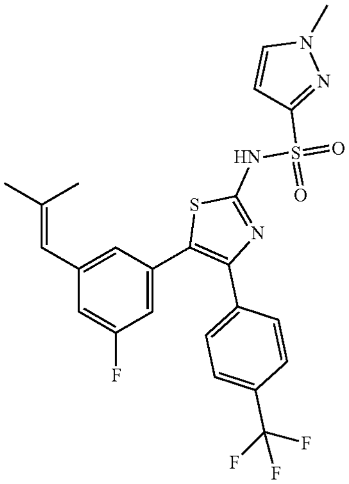 [SMILES: CC(C)=Cc1cc(F)cc(-c2sc(NS(=O)(=O)c3ccn(C)n3)nc2-c2ccc(C(F)(F)F)cc2)c1] | N-(5-(3-fluoro-5-(2-methylprop-1-en-1-yl)phenyl)-4-(4-(trifluoromethyl)phenyl)thiazol-2-yl)-1-methyl-1H-pyrazole-3-sulfonamide |
| 156 | 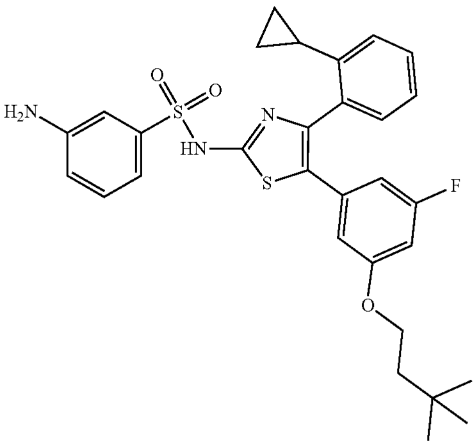 [SMILES: CC(C)(C)CCOc1cc(F)cc(-c2sc(NS(=O)(=O)c3cccc(N)c3)nc2-c2ccccc2C2CC2)c1] | 3-amino-N-[4-(2-cyclopropylphenyl)-5-[3-(3,3-dimethylbutoxy)-5-fluorophenyl]-1,3-thiazol-2-yl]benzenesulfonamide |

TABLE 1-continued

| Compound Number | Compound Structural Formula | Compound Name |
|---|---|---|
| 401 | 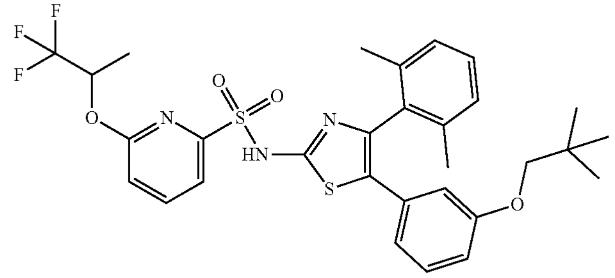 [SMILES: Cc1cccc(C)c1-c1nc(NS(=O)(=O)c2cccc(OC(C)C(F)(F)F)n2)sc1-c1cccc(OCC(C)(C)C)c1] | N-[4-(2,6-dimethylphenyl)-5-[3-(2,2-dimethylpropoxy)phenyl]-1,3-thiazol-2-yl]-6-(1,1,1-trifluoropropan-2-yloxy)pyridine-2-sulfonamide |
| 407 | 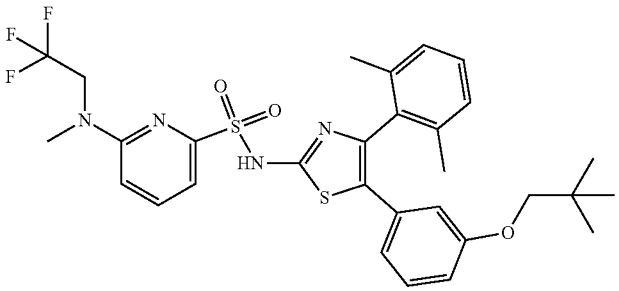 [SMILES: Cc1cccc(C)c1-c1nc(NS(=O)(=O)c2cccc(N(C)CC(F)(F)F)n2)sc1-c1cccc(OCC(C)(C)C)c1] | N-[4-(2,6-dimethylphenyl)-5-[3-(2,2-dimethylpropoxy)phenyl]-1,3-thiazol-2-yl]-6-[methyl(2,2,2-trifluoroethyl)amino]pyridine-2-sulfonamide |
| 155 | 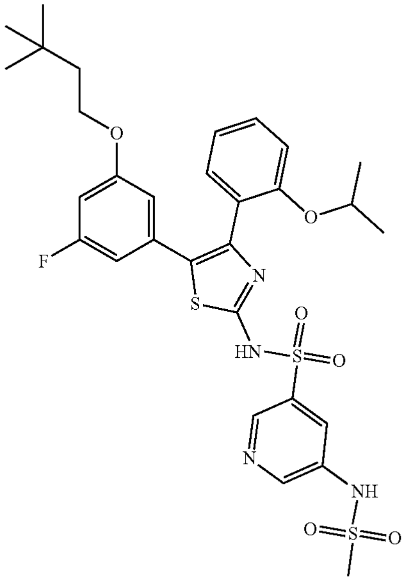 [SMILES: CC(C)Oc1ccccc1-c1nc(NS(=O)(=O)c2cncc(NS(C)(=O)=O)c2)sc1-c1cc(F)cc(OCCC(C)(C)C)c1] | N-[5-[3-(3,3-dimethylbutoxy)-5-fluorophenyl]-4-(2-propan-2-yloxyphenyl)-1,3-thiazol-2-yl]-5-(methanesulfonamido)pyridine-3-sulfonamide |

TABLE 1-continued

| Compound Number | Compound Structural Formula | Compound Name |
|---|---|---|
| 215 | 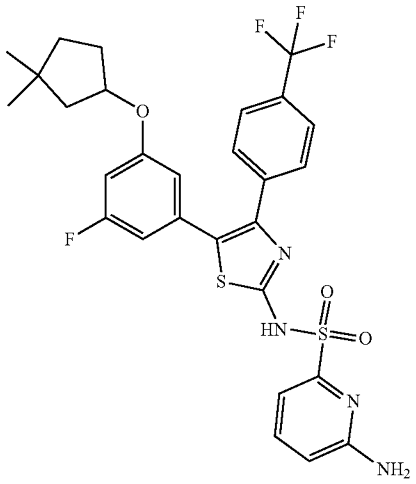 [SMILES: CC1(C)CCC(Oc2cc(F)cc(-c3sc(NS(=O)(=O)c4cccc(N)n4)nc3-c3ccc(C(F)(F)F)cc3)c2)C1] | 6-amino-N-[5-[3-(3,3-dimethylcyclopentyl)oxy-5-fluorophenyl]-4-[4-(trifluoromethyl)phenyl]-1,3-thiazol-2-yl]pyridine-2-sulfonamide |
| 122 | 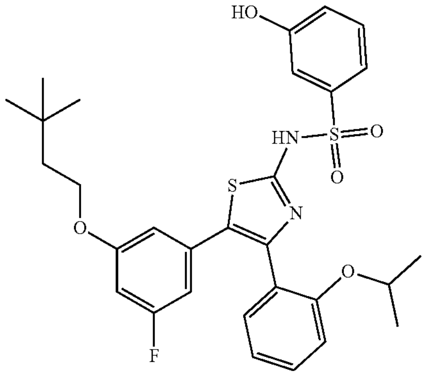 [SMILES: CC(C)Oc1ccccc1-c1nc(NS(=O)(=O)c2cccc(O)c2)sc1-c1cc(F)cc(OCCC(C)(C)C)c1] | N-[5-[3-(3,3-dimethylbutoxy)-5-fluorophenyl]-4-(2-propan-2-yloxyphenyl)-1,3-thiazol-2-yl]-3-hydroxybenzenesulfonamide |
| 256 | 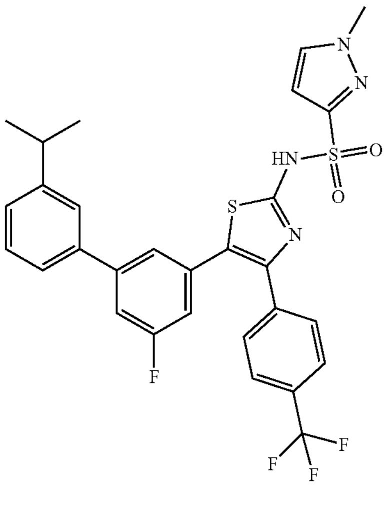 [SMILES: CC(C)c1cccc(-c2cc(F)cc(-c3sc(NS(=O)(=O)c4ccn(C)n4)nc3-c3ccc(C(F)(F)F)cc3)c2)c1] | N-[5-[3-fluoro-5-(3-propan-2-ylphenyl)phenyl]-4-[4-(trifluoromethyl)phenyl]-1,3-thiazol-2-yl]-1-methylpyrazole-3-sulfonamide |

TABLE 1-continued

| Compound Number | Compound Structural Formula | Compound Name |
|---|---|---|
| 440 | 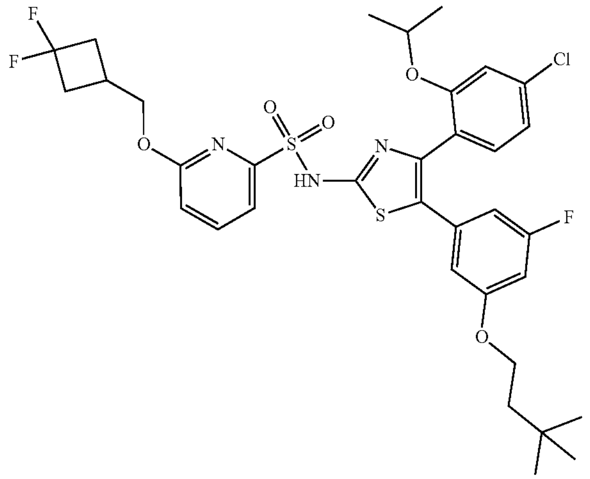 [SMILES: CC(C)Oc1cc(Cl)ccc1-c1nc(NS(=O)(=O)c2cccc(OCC3CC(F)(F)C3)n2)sc1-c1cc(F)cc(OCCC(C)(C)C)c1] | N-[4-(4-chloro-2-propan-2-yloxyphenyl)-5-[3-(3,3-dimethylbutoxy)-5-fluorophenyl]-1,3-thiazol-2-yl]-6-[(3,3-difluorocyclobutyl)methoxy]pyridine-2-sulfonamide |
| 418 | 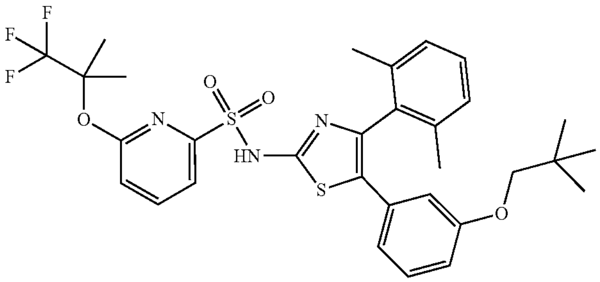 [SMILES: Cc1cccc(C)c1-c1nc(NS(=O)(=O)c2cccc(OC(C)(C)C(F)(F)F)n2)sc1-c1cccc(OCC(C)(C)C)c1] | N-[4-(2,6-dimethylphenyl)-5-[3-(2,2-dimethylpropoxy)phenyl]-1,3-thiazol-2-yl]-6-(1,1,1-trifluoro-2-methylpropan-2-yl)oxypyridine-2-sulfonamide |
| 523 | 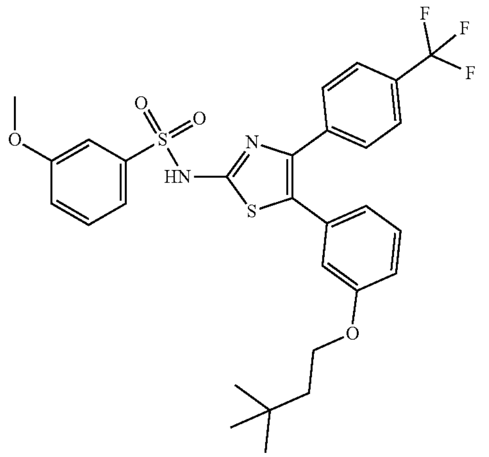 [SMILES: COc1cccc(S(=O)(=O)Nc2nc(-c3ccc(C(F)(F)F)cc3)c(-c3cccc(OCCC(C)(C)C)c3)s2)c1] | N-(5-(3-(3,3-dimethylbutoxy)phenyl)-4-(4-(trifluoromethyl)phenyl)thiazol-2-yl)-3-methoxybenzenesulfonamide |

TABLE 1-continued

| Compound Number | Compound Structural Formula | Compound Name |
|---|---|---|
| 524 | 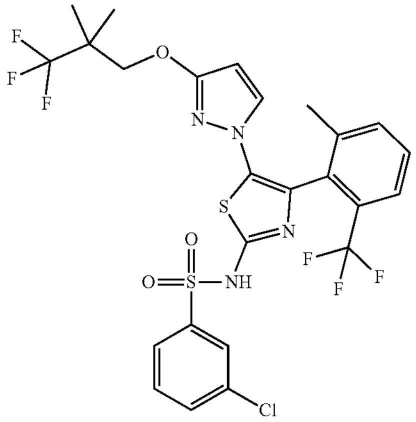 [SMILES: Cc1cccc(C(F)(F)F)c1-c1nc(NS(=O)(=O)c2cccc(Cl)c2)sc1-n1ccc(OCC(C)(C)C(F)(F)F)n1] | 3-chloro-N-(4-(2-methyl-6-(trifluoromethyl)phenyl)-5-(3-(3,3,3-trifluoro-2,2-dimethylpropoxy)-1H-pyrazol-1-yl)thiazol-2-yl)benzenesulfonamide |
| 185 | 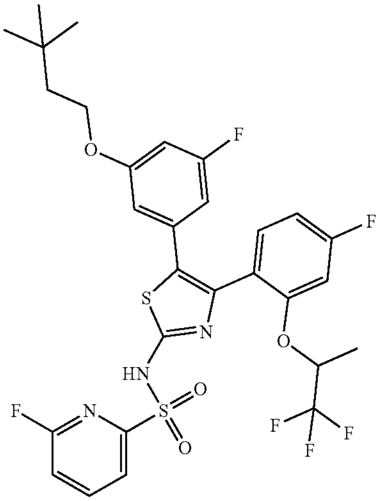 [SMILES: CC(Oc1cc(F)ccc1-c1nc(NS(=O)(=O)c2cccc(F)n2)sc1-c1cc(F)cc(OCCC(C)(C)C)c1)C(F)(F)F] | N-[5-[3-(3,3-dimethylbutoxy)-5-fluorophenyl]-4-[4-fluoro-2-(1,1,1-trifluoropropan-2-yloxy)phenyl]-1,3-thiazol-2-yl]-6-fluoropyridine-2-sulfonamide |
| 357 | 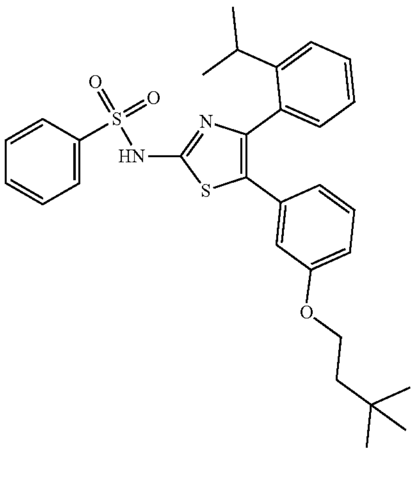 [SMILES: CC(C)c1ccccc1-c1nc(NS(=O)(=O)c2ccccc2)sc1-c1cccc(OCCC(C)(C)C)c1] | N-[5-[3-(3,3-dimethylbutoxy)phenyl]-4-(2-propan-2-ylphenyl)-1,3-thiazol-2-yl]benzenesulfonamide |

TABLE 1-continued

| Compound Number | Compound Structural Formula | Compound Name |
|---|---|---|
| 79 | 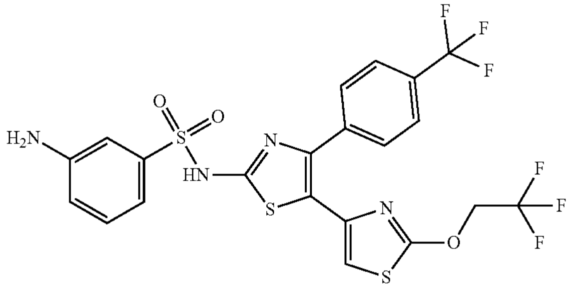 [SMILES: Nc1cccc(S(=O)(=O)Nc2nc(-c3ccc(C(F)(F)F)cc3)c(-c3csc(OCC(F)(F)F)n3)s2)c1] | 3-amino-N-[5-[2-(2,2,2-trifluoroethoxy)-1,3-thiazol-4-yl]-4-[4-(trifluoromethyl)phenyl]-1,3-thiazol-2-yl]benzenesulfonamide |
| 128 | 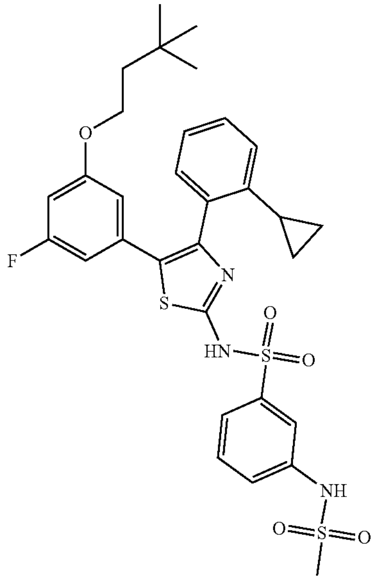 [SMILES: CC(C)(C)CCOc1cc(F)cc(-c2sc(NS(=O)(=O)c3cccc(NS(C)(=O)=O)c3)nc2-c2ccccc2C2CC2)c1] | N-[4-(2-cyclopropylphenyl)-5-[3-(3,3-dimethylbutoxy)-5-fluorophenyl]-1,3-thiazol-2-yl]-3-(methanesulfonamido)benzenesulfonamide |
| 63 | 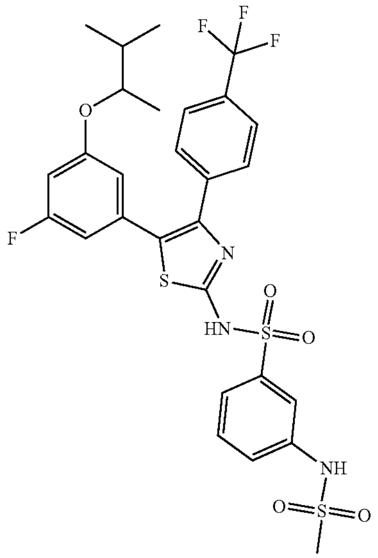 [SMILES: CC(C)C(C)Oc1cc(F)cc(-c2sc(NS(=O)(=O)c3cccc(NS(C)(=O)=O)c3)nc2-c2ccc(C(F)(F)F)cc2)c1] | N-[5-[3-fluoro-5-(3-methylbutan-2-yloxy)phenyl]-4-[4-(trifluoromethyl)phenyl]-1,3-thiazol-2-yl]-3-(methanesulfonamido)benzenesulfonamide |

TABLE 1-continued

| Compound Number | Compound Structural Formula | Compound Name |
| --- | --- | --- |
| 525 | 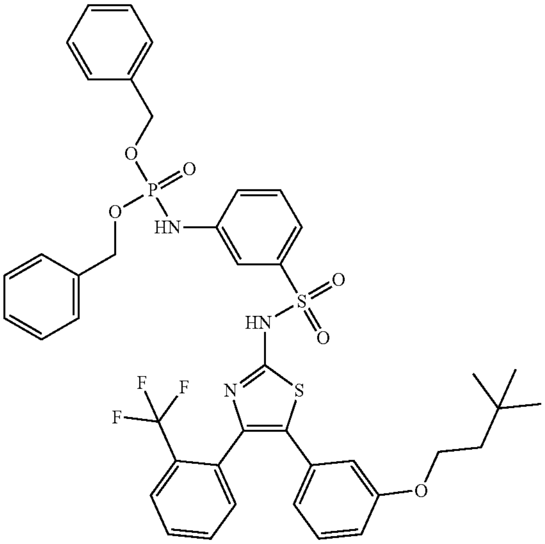 [SMILES: CC(C)(C)CCOc1cccc(-c2sc(NS(=O)(=O)c3cccc(NP(=O)(OCc4ccccc4)OCc4ccccc4)c3)nc2-c2ccccc2C(F)(F)F)c1] | dibenzyl (3-(N-(5-(3-(3,3-dimethylbutoxy)phenyl)-4-(2-(trifluoromethyl)phenyl)thiazol-2-yl)sulfamoyl)phenyl)phosphoramidate |
| 368 | 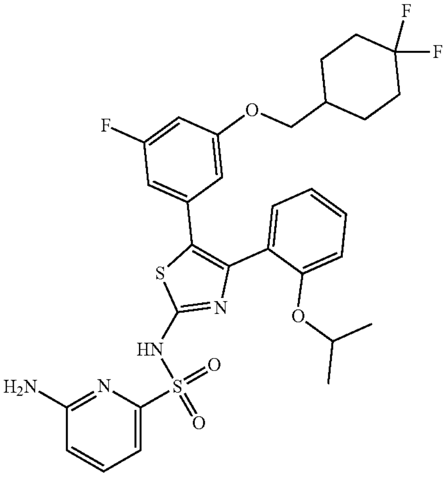 [SMILES: CC(C)Oc1ccccc1-c1nc(NS(=O)(=O)c2cccc(N)n2)sc1-c1cc(F)cc(OCC2CCC(F)(F)CC2)c1] | 6-amino-N-[5-[3-[(4,4-difluorocyclohexyl)methoxy]-5-fluorophenyl]-4-(2-propan-2-yloxyphenyl)-1,3-thiazol-2-yl]pyridine-2-sulfonamide |
| 250 | 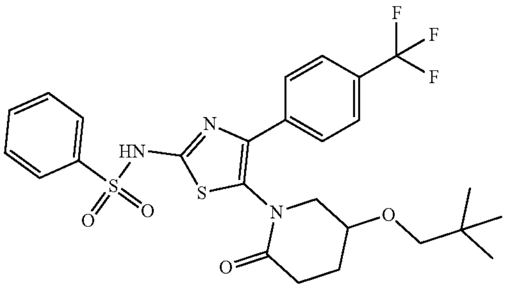 [SMILES: CC(C)(C)COC1CCC(=O)N(c2sc(NS(=O)(=O)c3ccccc3)nc2-c2ccc(C(F)(F)F)cc2)C1] | N-[5-[5-(2,2-dimethylpropoxy)-2-oxopiperidin-1-yl]-4-[4-(trifluoromethyl)phenyl]-1,3-thiazol-2-yl]benzenesulfonamide |

TABLE 1-continued

| Compound Number | Compound Structural Formula | Compound Name |
|---|---|---|
| 351 | 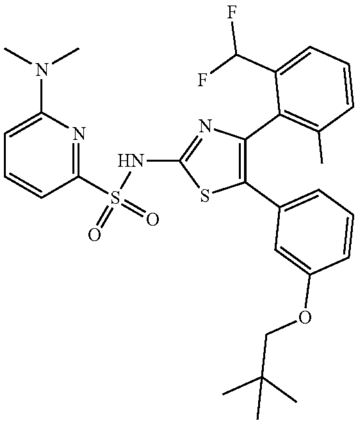 [SMILES: Cc1cccc(C(F)F)c1-c1nc(NS(=O)(=O)c2cccc(N(C)C)n2)sc1-c1cccc(OCC(C)(C)C)c1] | N-[4-[2-(difluoromethyl)-6-methylphenyl]-5-[3-(2,2-dimethylpropoxy)phenyl]-1,3-thiazol-2-yl]-6-(dimethylamino)pyridine-2-sulfonamide |
| 205 | 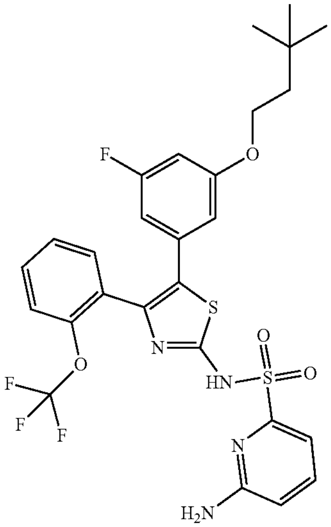 [SMILES: CC(C)(C)CCOc1cc(F)cc(-c2sc(NS(=O)(=O)c3cccc(N)n3)nc2-c2ccccc2OC(F)(F)F)c1] | 6-amino-N-[5-[3-(3,3-dimethylbutoxy)-5-fluorophenyl]-4-[2-(trifluoromethoxy)phenyl]-1,3-thiazol-2-yl]pyridine-2-sulfonamide |
| 482 | 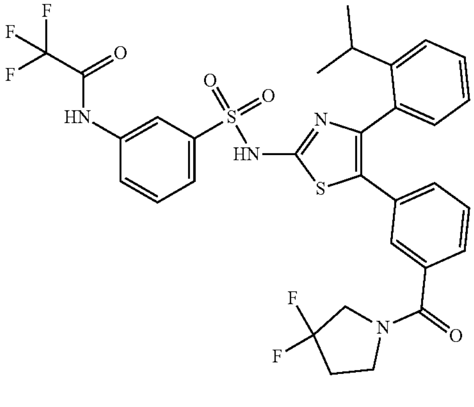 [SMILES: CC(C)c1ccccc1-c1nc(NS(=O)(=O)c2cccc(NC(=O)C(F)(F)F)c2)sc1-c1cccc(C(=O)N2CCC(F)(F)C2)c1] | N-[3-[[5-[3-(3,3-difluoropyrrolidine-1-carbonyl)phenyl]-4-(2-propan-2-ylphenyl)-1,3-thiazol-2-yl]sulfamoyl]phenyl]-2,2,2-trifluoroacetamide |

TABLE 1-continued

| Compound Number | Compound Structural Formula | Compound Name |
|---|---|---|
| 430 | 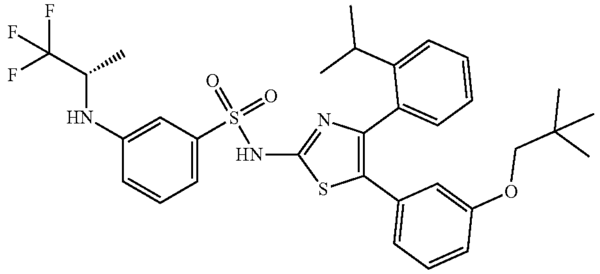 [SMILES: CC(C)c1ccccc1-c1nc(NS(=O)(=O)c2cccc(N[C@@H](C)C(F)(F)F)c2)sc1-c1cccc(OCC(C)(C)C)c1] | N-[5-[3-(2,2-dimethylpropoxy)phenyl]-4-(2-propan-2-ylphenyl)-1,3-thiazol-2-yl]-3-[(2S)-1,1,1-trifluoropropan-2-yl]amino]benzenesulfonamide |
| 526 | 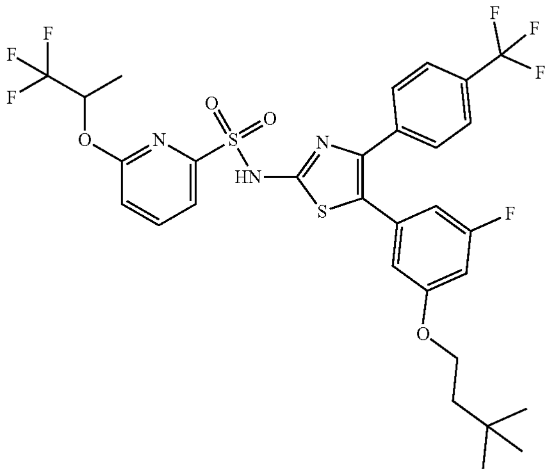 [SMILES: CC(Oc1cccc(S(=O)(=O)Nc2nc(-c3ccc(C(F)(F)F)cc3)c(-c3cc(F)cc(OCCC(C)(C)C)c3)s2)n1)C(F)(F)F] | N-(5-(3-(3,3-dimethylbutoxy)-5-fluorophenyl)-4-(4-(trifluoromethyl)phenyl)thiazol-2-yl)-6-((1,1,1-trifluoropropan-2-yl)oxy)pyridine-2-sulfonamide |
| 527 | 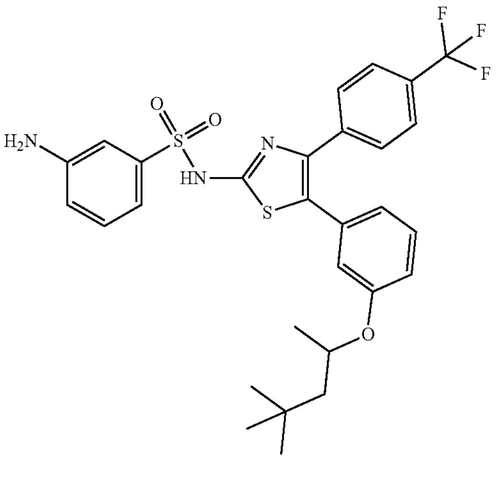 [SMILES: CC(CC(C)(C)C)Oc1cccc(-c2sc(NS(=O)(=O)c3cccc(N)c3)nc2-c2ccc(C(F)(F)F)cc2)c1] | 3-amino-N-(5-(3-((4,4-dimethylpentan-2-yl)oxy)phenyl)-4-(4-(trifluoromethyl)phenyl)thiazol-2-yl)benzenesulfonamide |

TABLE 1-continued

| Compound Number | Compound Structural Formula | Compound Name |
|---|---|---|
| 154 | 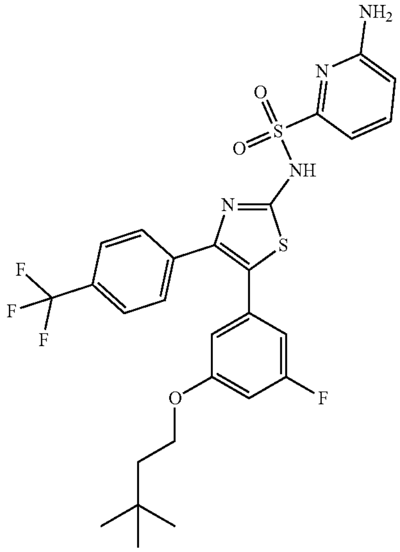 [SMILES: CC(C)(C)CCOc1cc(F)cc(-c2sc(NS(=O)(=O)c3cccc(N)n3)nc2-c2ccc(C(F)(F)F)cc2)c1] | 6-amino-N-[5-[3-(3,3-dimethylbutoxy)-5-fluorophenyl]-4-[4-(trifluoromethyl)phenyl]-1,3-thiazol-2-yl]pyridine-2-sulfonamide |
| 25 | 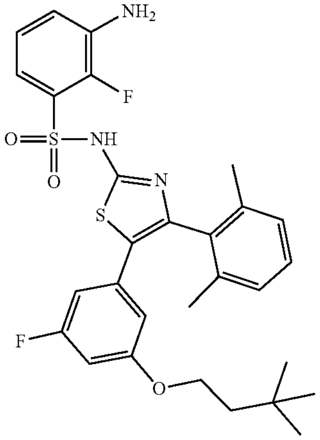 [SMILES: Cc1cccc(C)c1-c1nc(NS(=O)(=O)c2cccc(N)c2F)sc1-c1cc(F)cc(OCCC(C)(C)C)c1] | 3-amino-N-[5-[3-(3,3-dimethylbutoxy)-5-fluorophenyl]-4-(2,6-dimethylphenyl)-1,3-thiazol-2-yl]-2-fluorobenzenesulfonamide |
| 187 | 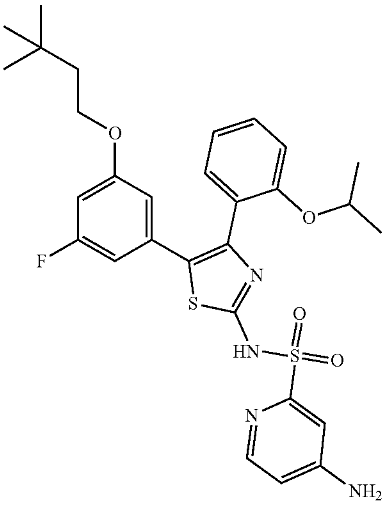 [SMILES: CC(C)Oc1ccccc1-c1nc(NS(=O)(=O)c2cc(N)ccn2)sc1-c1cc(F)cc(OCCC(C)(C)C)c1] | 4-amino-N-[5-[3-(3,3-dimethylbutoxy)-5-fluorophenyl]-4-(2-propan-2-yloxyphenyl)-1,3-thiazol-2-yl]pyridine-2-sulfonamide |

TABLE 1-continued

| Compound Number | Compound Structural Formula | Compound Name |
|---|---|---|
| 528 | 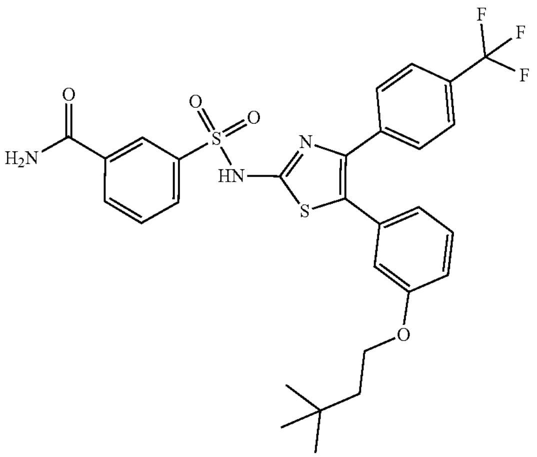 [SMILES: CC(C)(C)CCOc1cccc(-c2sc(NS(=O)(=O)c3cccc(C(N)=O)c3)nc2-c2ccc(C(F)(F)F)cc2)c1] | 3-(N-(5-(3-(3,3-dimethylbutoxy)phenyl)-4-(4-(trifluoromethyl)phenyl)thiazol-2-yl)sulfamoyl)benzamide |
| 275 | 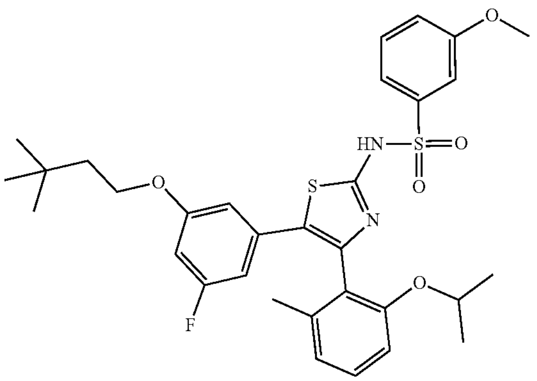 [SMILES: COc1cccc(S(=O)(=O)Nc2nc(-c3c(C)cccc3OC(C)C)c(-c3cc(F)cc(OCCC(C)(C)C)c3)s2)c1] | N-[5-[3-(3,3-dimethylbutoxy)-5-fluorophenyl]-4-(2-methyl-6-propan-2-yloxyphenyl)-1,3-thiazol-2-yl]-3-methoxybenzenesulfonamide |
| 131 | 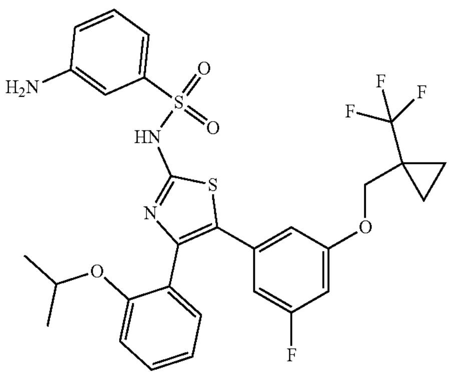 [SMILES: CC(C)Oc1ccccc1-c1nc(NS(=O)(=O)c2cccc(N)c2)sc1-c1cc(F)cc(OCC2(C(F)(F)F)CC2)c1] | 3-amino-N-[5-[3-fluoro-5-[1-(trifluoromethyl)cyclopropyl]methoxy]phenyl]-4-(2-propan-2-yloxyphenyl)-1,3-thiazol-2-yl]benzenesulfonamide |

TABLE 1-continued

| Compound Number | Compound Structural Formula | Compound Name |
|---|---|---|
| 257 | 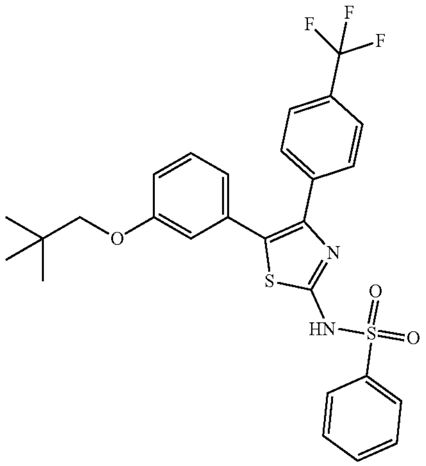 [SMILES: CC(C)(C)COc1cccc(-c2sc(NS(=O)(=O)c3ccccc3)nc2-c2ccc(C(F)(F)F)cc2)c1] | N-[5-[3-(2,2-dimethylpropoxy)phenyl]-4-[4-(trifluoromethyl)phenyl]-1,3-thiazol-2-yl]benzenesulfonamide |
| 529 | 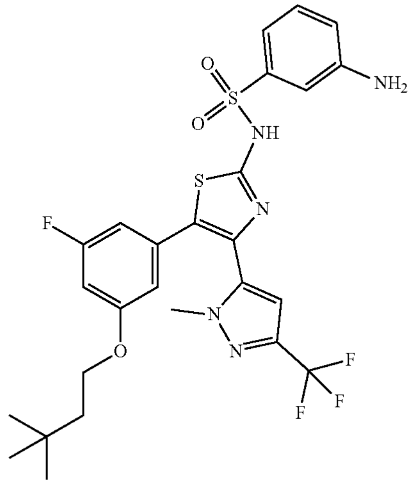 [SMILES: Cn1nc(C(F)(F)F)cc1-c1nc(NS(=O)(=O)c2cccc(N)c2)sc1-c1cc(F)cc(OCCC(C)(C)C)c1] | 3-amino-N-(5-(3-(3,3-dimethylbutoxy)-5-fluorophenyl)-4-(1-methyl-3-(trifluoromethyl)-1H-pyrazol-5-yl)thiazol-2-yl)benzenesulfonamide |
| 228 | 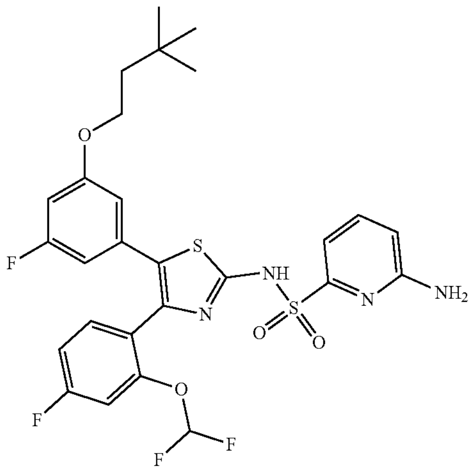 [SMILES: CC(C)(C)CCOc1cc(F)cc(-c2sc(NS(=O)(=O)c3cccc(N)n3)nc2-c2ccc(F)cc2OC(F)F)c1] | 6-amino-N-[4-[2-(difluoromethoxy)-4-fluorophenyl]-5-[3-(3,3-dimethylbutoxy)-5-fluorophenyl]-1,3-thiazol-2-yl]pyridine-2-sulfonamide |

TABLE 1-continued

| Compound Number | Compound Structural Formula | Compound Name |
|---|---|---|
| 43B | 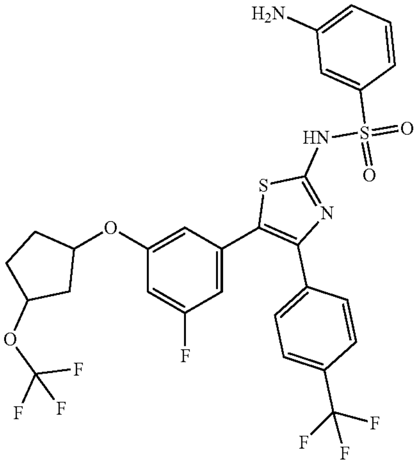 [SMILES: Nc1cccc(S(=O)(=O)Nc2nc(-c3ccc(C(F)(F)F)cc3)c(-c3cc(F)cc(OC4CCC(OC(F)(F)F)C4)c3)s2)c1] | 3-amino-N-[5-[3-fluoro-5-[3-(trifluoromethoxy)cyclopentyl]oxyphenyl 1-4-[4-(trifluoromethyl)phenyl]-1,3-thiazol-2-yl]benzenesulfonamide |
| 342 | 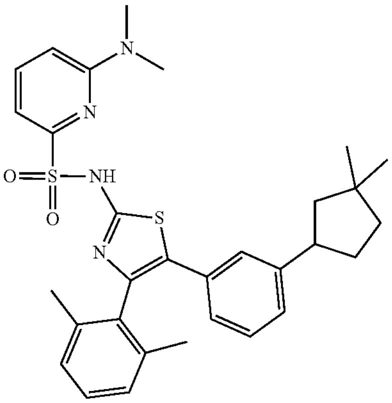 [SMILES: Cc1cccc(C)c1-c1nc(NS(=O)(=O)c2cccc(N(C)C)n2)sc1-c1cccc(C2CCC(C)(C)C2)c1] | 6-(dimethylamino)-N-[5-[3-(3,3-dimethylcyclopentyl)phenyl]-4-(2,6-dimethylphenyl)-1,3-thiazol-2-yl]pyridine-2-sulfonamide |
| 163 | 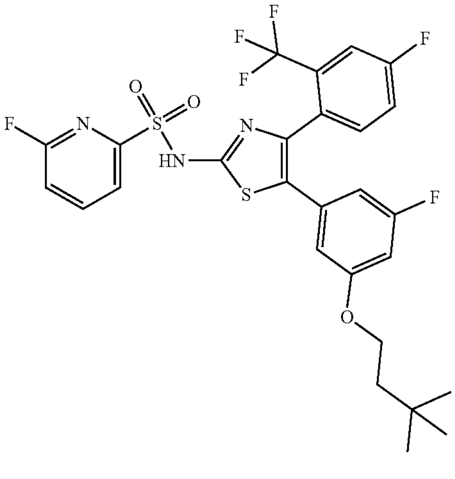 [SMILES: CC(C)(C)CCOc1cc(F)cc(-c2sc(NS(=O)(=O)c3cccc(F)n3)nc2-c2ccc(F)cc2C(F)(F)F)c1] | N-[5-[3-(3,3-dimethylbutoxy)-5-fluorophenyl]-4-[4-fluoro-2-(trifluoromethyl)phenyl]-1,3-thiazol-2-yl]-6-fluoropyridine-2-sulfonamide |

TABLE 1-continued

| Compound Number | Compound Structural Formula | Compound Name |
| --- | --- | --- |
| 295 | 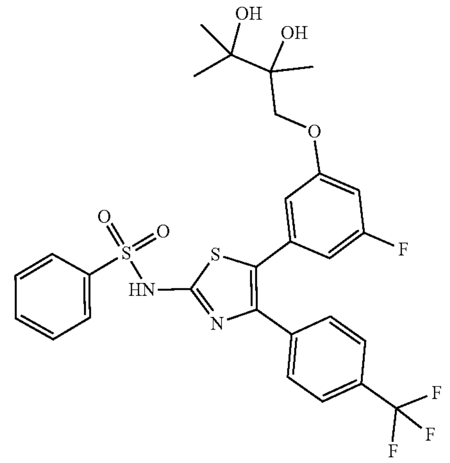 [SMILES: CC(C)(O)C(C)(O)COc1cc(F)cc(-c2sc(NS(=O)(=O)c3ccccc3)nc2-c2ccc(C(F)(F)F)cc2)c1] | N-[5-[3-(2,3-dihydroxy-2,3-dimethylbutoxy)-5-fluorophenyl]-4-[4-(trifluoromethyl)phenyl]-1,3-thiazol-2-yl]benzenesulfonamide |
| 530 | 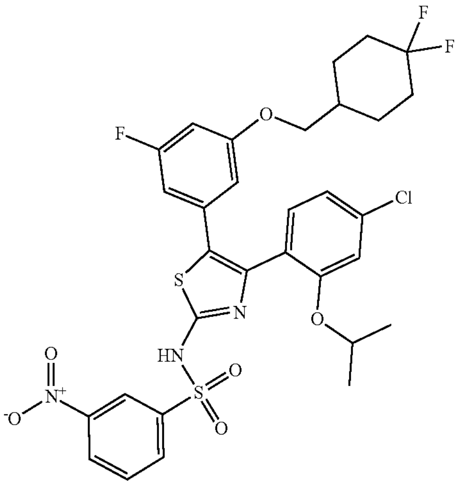 | N-(4-(4-chloro-2-isopropoxyphenyl)-5-(3-((4,4-difluorocyclohexyl)methoxy)-5-fluorophenyl)thiazol-2-yl)-3-nitrobenzenesulfonamide |
| 442 | 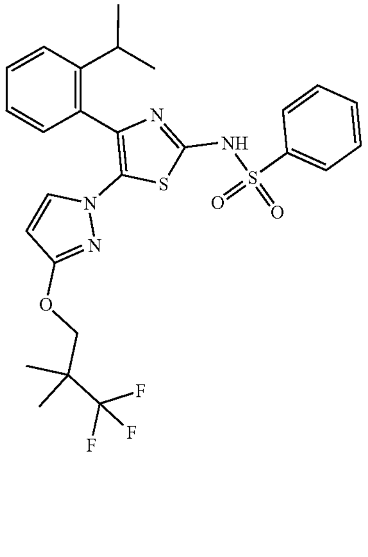 [SMILES: CC(C)c1ccccc1-c1nc(NS(=O)(=O)c2ccccc2)sc1-n1ccc(OCC(C)(C)C(F)(F)F)n1] | N-[4-(2-propan-2-ylphenyl)-5-[3-(3,3,3-trifluoro-2,2-dimethylpropoxy)pyrazol-1-yl]-1,3-thiazol-2-yl]benzenesulfonamide |

TABLE 1-continued
| Compound Number | Compound Structural Formula | Compound Name |
|---|---|---|
| 2 | 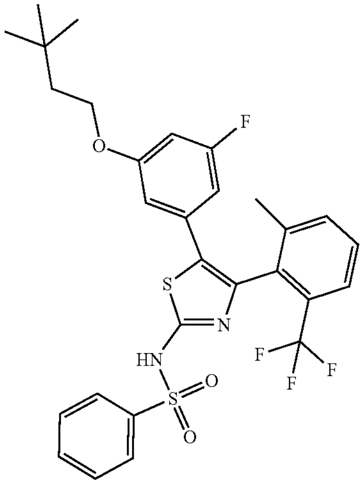 [SMILES: Cc1cccc(C(F)(F)F)c1-c1nc(NS(=O)(=O)c2ccccc2)sc1-c1cc(F)cc(OCCC(C)(C)C)c1] | N-(5-(3-(3,3-dimethylbutoxy)-5-fluorophenyl)-4-(2-methyl-6-(trifluoromethyl)phenyl)thiazol-2-yl)benzenesulfonamide |
| 126 | 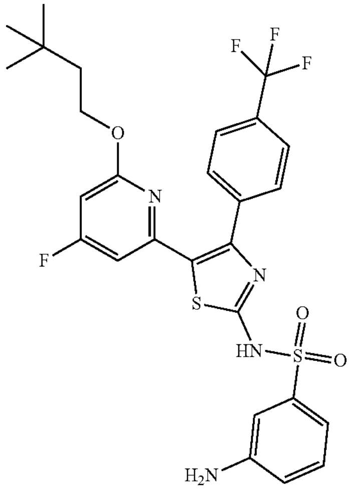 [SMILES: CC(C)(C)CCOc1cc(F)cc(-c2sc(NS(=O)(=O)c3cccc(N)c3)nc2-c2ccc(C(F)(F)F)cc2)n1] | 3-amino-N-[5-[6-(3,3-dimethylbutoxy)-4-fluoropyridin-2-yl]-4-[4-(trifluoromethyl)phenyl]-1,3-thiazol-2-yl]benzenesulfonamide |
| 531 | 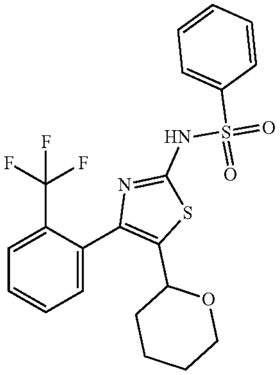 [SMILES: O=S(=O)(Nc1nc(-c2ccccc2C(F)(F)F)c(C2CCCCO2)s1)c1ccccc1] | N-(5-(tetrahydro-2H-pyran-2-yl)-4-(2-(trifluoromethyl)phenyl)thiazol-2-yl)benzenesulfonamide |

TABLE 1-continued

| Compound Number | Compound Structural Formula | Compound Name |
| --- | --- | --- |
| 266 | 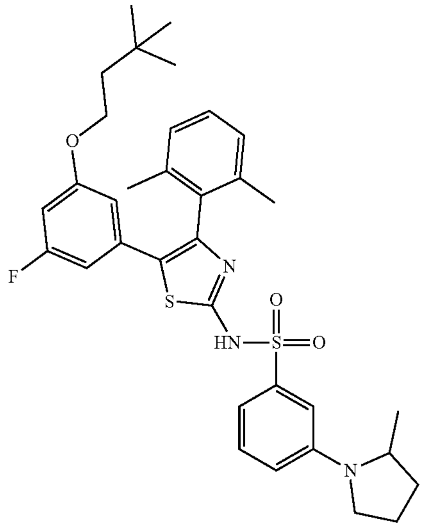 [SMILES: Cc1cccc(C)c1-c1nc(NS(=O)(=O)c2cccc(N3CCCC3C)c2)sc1-c1cc(F)cc(OCCC(C)(C)C)c1] | N-[5-[3-(3,3-dimethylbutoxy)-5-fluorophenyl]-4-(2,6-dimethylphenyl)-1,3-thiazol-2-yl]-3-(2-methylpyrrolidin-1-yl)benzenesulfonamide |
| 532 | 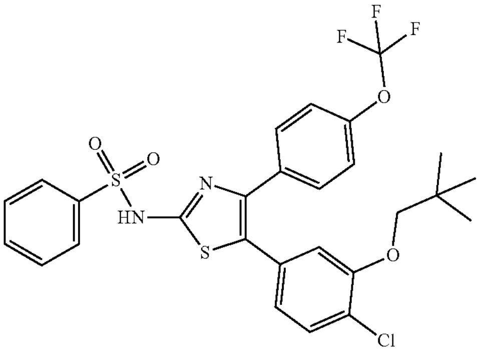 [SMILES: CC(C)(C)COc1cc(-c2sc(NS(=O)(=O)c3ccccc3)nc2-c2ccc(OC(F)(F)F)cc2)ccc1Cl] | N-(5-(4-chloro-3-(neopentyloxy)phenyl)-4-(4-(trifluoromethoxy)phenyl)thiazol-2-yl)benzenesulfonamide |
| 46A1 | 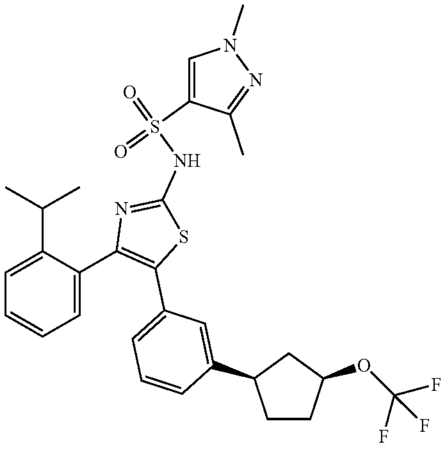 [SMILES: Cc1nn(C)cc1S(=O)(=O)Nc1nc(-c2ccccc2C(C)C)c(-c2cccc([C@@H]3CC[C@H](OC(F)(F)F)C3)c2)s1] | 1,3-dimethyl-N-[4-(2-propan-2-ylphenyl)-5-[3-[(1R,3S)-3-(trifluoromethoxy)cyclopentyl]phenyl]-1,3-thiazol-2-yl]pyrazole-4-sulfonamide |

TABLE 1-continued

| Compound Number | Compound Structural Formula | Compound Name |
|---|---|---|
| 533 | 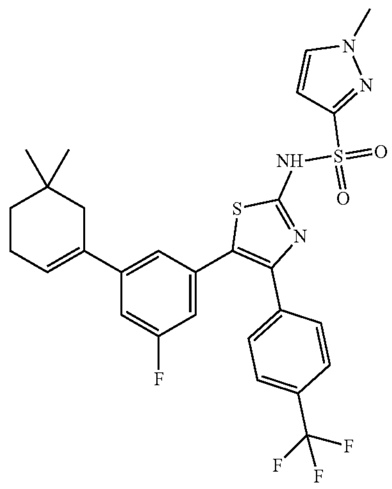 [SMILES: Cn1ccc(S(=O)(=O)Nc2nc(-c3ccc(C(F)(F)F)cc3)c(-c3cc(F)cc(C4=CCCC(C)(C)C4)c3)s2)n1] | N-(5-(5-fluoro-3',3'-dimethyl-2',3',4',5'-tetrahydro-[1,1'-biphenyl]-3-yl)-4-(4-(trifluoromethyl)phenyl)thiazol-2-yl)-1-methyl-1H-pyrazole-3-sulfonamide |
| 534 | 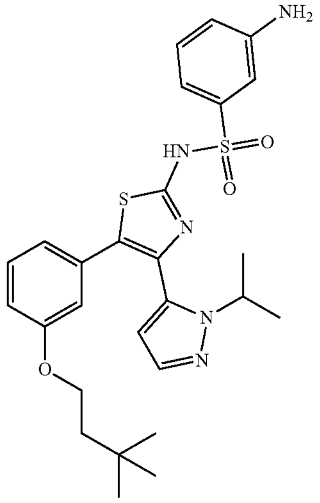 [SMILES: CC(C)n1nccc1-c1nc(NS(=O)(=O)c2cccc(N)c2)sc1-c1cccc(OCCC(C)(C)C)c1] | 3-amino-N-(5-(3-(3,3-dimethylbutoxy)phenyl)-4-(1-isopropyl-1H-pyrazol-5-yl)thiazol-2-yl)benzenesulfonamide |
| 89 | 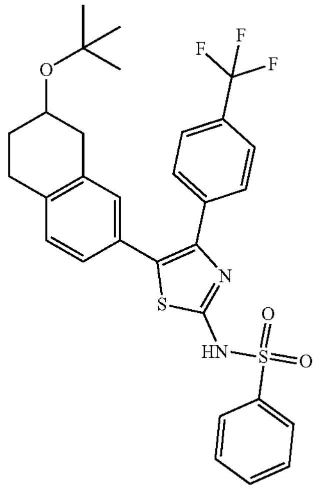 [SMILES: CC(C)(C)OC1CCc2ccc(-c3sc(NS(=O)(=O)c4ccccc4)nc3-c3ccc(C(F)(F)F)cc3)cc2C1] | N-[5-[7-[(2-methylpropan-2-yl)oxy]-5,6,7,8-tetrahydronaphthalen-2-yl]-4-[4-(trifluoromethyl)phenyl]-1,3-thiazol-2-yl]benzenesulfonamide |

TABLE 1-continued

| Compound Number | Compound Structural Formula | Compound Name |
|---|---|---|
| 62 | 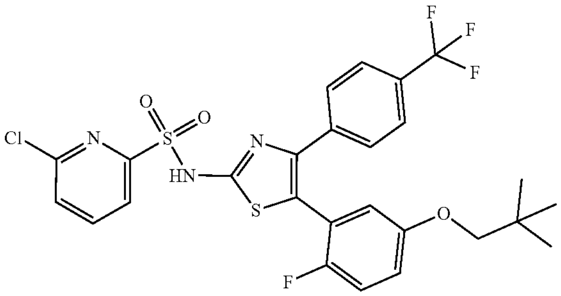 [SMILES: CC(C)(C)COc1ccc(F)c(-c2sc(NS(=O)(=O)c3cccc(Cl)n3)nc2-c2ccc(C(F)(F)F)cc2)c1] | 6-chloro-N-[5-[5-(2,2-dimethylpropoxy)-2-fluorophenyl]-4-[4-(trifluoromethyl)phenyl]-1,3-thiazol-2-yl]pyridine-2-sulfonamide |
| 535 | 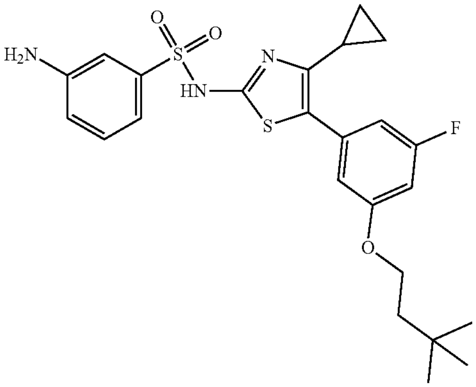 [SMILES: CC(C)(C)CCOc1cc(F)cc(-c2sc(NS(=O)(=O)c3cccc(N)c3)nc2C2CC2)c1] | 3-amino-N-(4-cyclopropyl-5-(3-(3,3-dimethylbutoxy)-5-fluorophenyl)thiazol-2-yl)benzenesulfonamide |
| 132 | 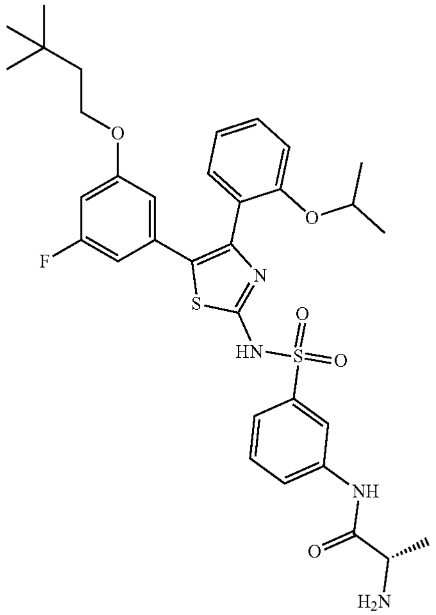 [SMILES: CC(C)Oc1ccccc1-c1nc(NS(=O)(=O)c2cccc(NC(=O)[C@H](C)N)c2)sc1-c1cc(F)cc(OCCC(C)(C)C)c1] | (2S)-2-amino-N-[3-[[5-[3-(3,3-dimethylbutoxy)-5-fluorophenyl]-4-(2-propan-2-yloxyphenyl)-1,3-thiazol-2-yl]sulfamoyl]phenyl]propanamide |

TABLE 1-continued
| Compound Number | Compound Structural Formula | Compound Name |
|---|---|---|
| 371 | 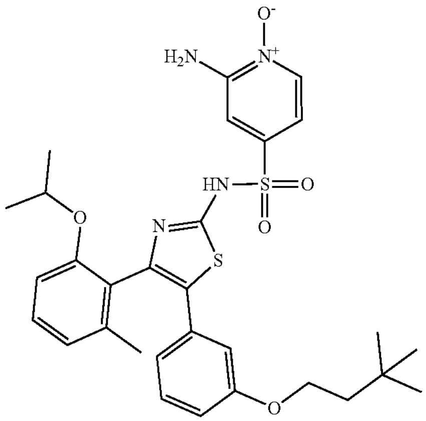 [SMILES: Cc1cccc(OC(C)C)c1-c1nc(NS(=O)(=O)c2cc[n+]([O-])c(N)c2)sc1-c1cccc(OCCC(C)(C)C)c1] | 2-amino-N-[5-[3-(3,3-dimethylbutoxy)phenyl]-4-(2-methyl-6-propan-2-yloxyphenyl)-1,3-thiazol-2-yl]-1-oxidopyridin-1-ium-4-sulfonamide |
| 37 | 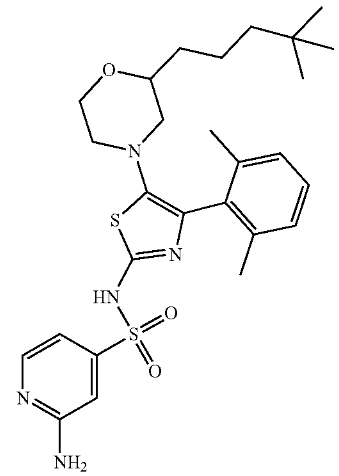 [SMILES: Cc1cccc(C)c1-c1nc(NS(=O)(=O)c2ccnc(N)c2)sc1N1CCOC(CCCC(C)(C)C)C1] | 2-amino-N-[5-[2-(4,4-dimethylpentyl)morpholin-4-yl]-4-(2,6-dimethylphenyl)-1,3-thiazol-2-yl]pyridine-4-sulfonamide |
| 278 | 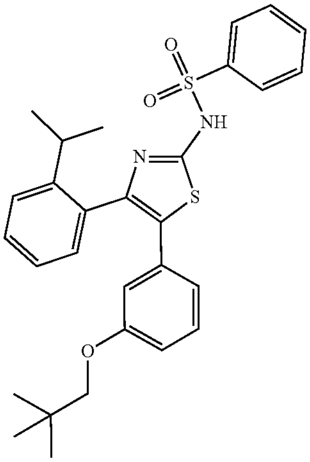 [SMILES: CC(C)c1ccccc1-c1nc(NS(=O)(=O)c2ccccc2)sc1-c1cccc(OCC(C)(C)C)c1] | N-[5-[3-(2,2-dimethylpropoxy)phenyl]-4-(2-propan-2-ylphenyl)-1,3-thiazol-2-yl]benzenesulfonamide |

TABLE 1-continued

| Compound Number | Compound Structural Formula | Compound Name |
|---|---|---|
| 293 | 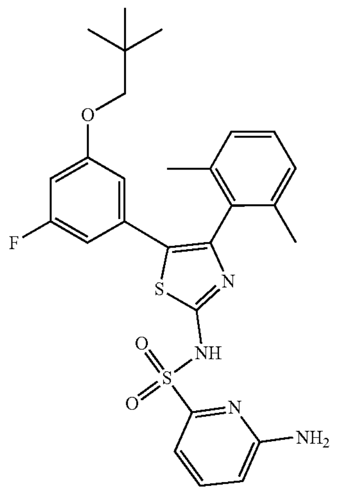 [SMILES: Cc1cccc(C)c1-c1nc(NS(=O)(=O)c2cccc(N)n2)sc1-c1cc(F)cc(OCC(C)(C)C)c1] | 6-amino-N-[4-(2,6-dimethylphenyl)-5-[3-(2,2-dimethylpropoxy)-5-fluorophenyl]-1,3-thiazol-2-yl]pyridine-2-sulfonamide |
| 44B2 | 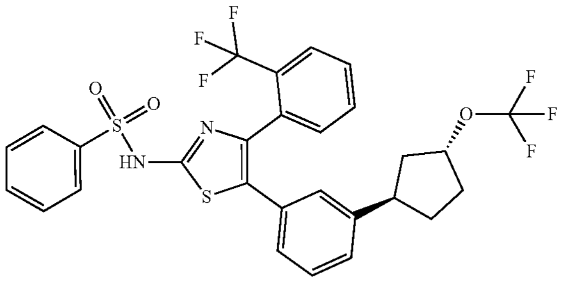 [SMILES: O=S(=O)(Nc1nc(-c2ccccc2C(F)(F)F)c(-c2cccc([C@@H]3CC[C@@H](OC(F)(F)F)C3)c2)s1)c1ccccc1] | N-[5-[3-[(1S,3S)-3-(trifluoromethoxy)cyclopentyl]phenyl]-4-[2-(trifluoromethyl)phenyl]-1,3-thiazol-2-yl]benzenesulfonamide |
| 84 | 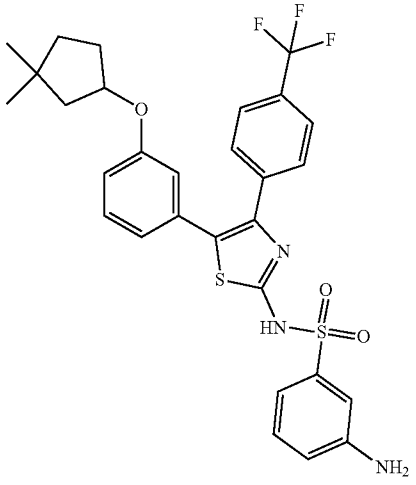 [SMILES: CC1(C)CCC(Oc2cccc(-c3sc(NS(=O)(=O)c4cccc(N)c4)nc3-c3ccc(C(F)(F)F)cc3)c2)C1] | 3-amino-N-[5-[3-(3,3-dimethylcyclopentyl)oxyphenyl]-4-[4-(trifluoromethyl)phenyl]-1,3-thiazol-2-yl]benzenesulfonamide |

TABLE 1-continued

| Compound Number | Compound Structural Formula | Compound Name |
|---|---|---|
| 277 | 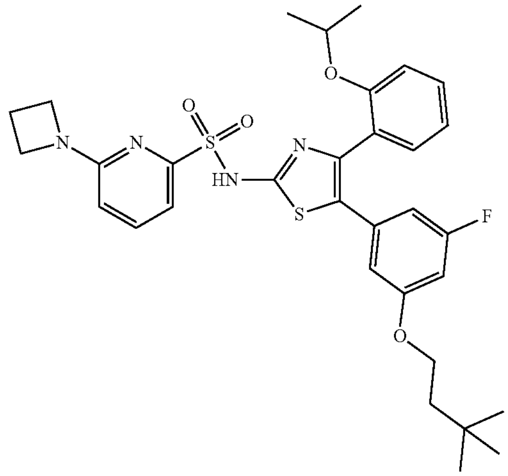 [SMILES: CC(C)Oc1ccccc1-c1nc(NS(=O)(=O)c2cccc(N3CCC3)n2)sc1-c1cc(F)cc(OCCC(C)(C)C)c1] | 6-(azetidin-1-yl)-N-[5-[3-(3,3-dimethylbutoxy)-5-fluorophenyl]-4-(2-propan-2-yloxyphenyl)-1,3-thiazol-2-yl]pyridine-2-sulfonamide |
| 395 | 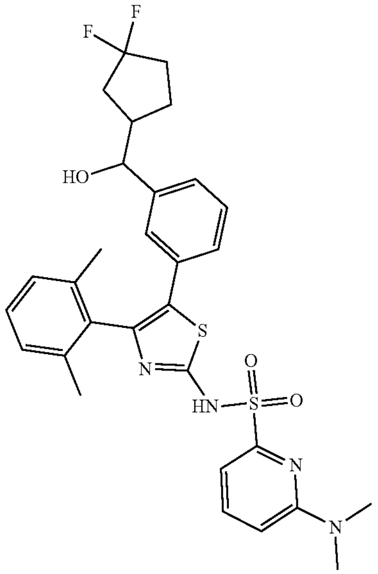 [SMILES: Cc1cccc(C)c1-c1nc(NS(=O)(=O)c2cccc(N(C)C)n2)sc1-c1cccc(C(O)C2CCC(F)(F)C2)c1] | N-[5-[3-[(3,3-difluorocyclopentyl)-hydroxymethyl]phenyl]-4-(2,6-dimethylphenyl)-1,3-thiazol-2-yl]-6-(dimethylamino)pyridine-2-sulfonamide |
| 6 | 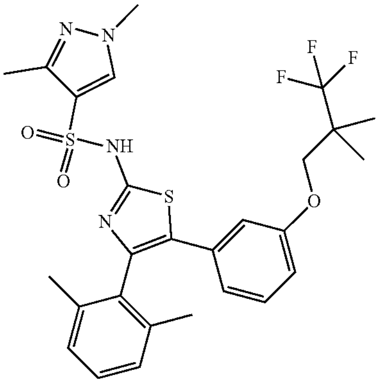 [SMILES: Cc1cccc(C)c1-c1nc(NS(=O)(=O)c2cn(C)nc2C)sc1-c1cccc(OCC(C)(C)C(F)(F)F)c1] | N-(4-(2,6-dimethylphenyl)-5-(3-(3,3,3-trifluoro-2,2-dimethylpropoxy)phenyl)thiazol-2-yl)-1,3-dimethyl-1H-pyrazole-4-sulfonamide |

TABLE 1-continued

| Compound Number | Compound Structural Formula | Compound Name |
| --- | --- | --- |
| 389 | 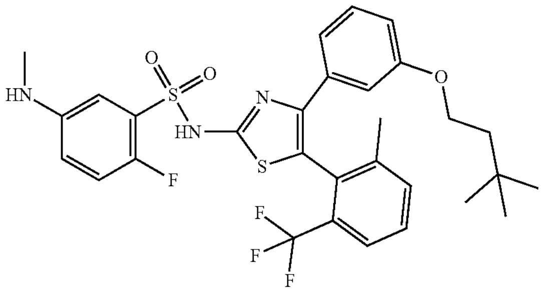 [SMILES: CNc1ccc(F)c(S(=O)(=O)Nc2nc(-c3cccc(OCCC(C)(C)C)c3)c(-c3c(C)cccc3C(F)(F)F)s2)c1] | N-[5-[3-(3,3-dimethylbutoxy)phenyl]-4-[2-methyl-6-(trifluoromethyl)phenyl]-1,3-thiazol-2-yl]-2-fluoro-5-(methylamino)benzenesulfonamide |
| 27 | 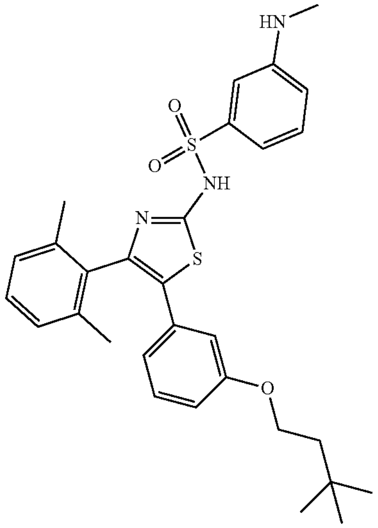 [SMILES: CNc1cccc(S(=O)(=O)Nc2nc(-c3c(C)cccc3C)c(-c3cccc(OCCC(C)(C)C)c3)s2)c1] | N-[5-[3-(3,3-dimethylbutoxy)phenyl]-4-(2,6-dimethylphenyl)-1,3-thiazol-2-yl]-3-(methylamino)benzenesulfonamide |
| 507 | 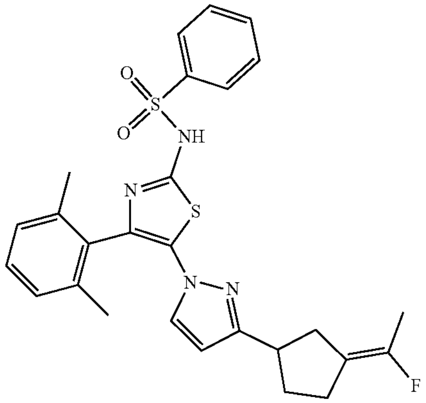 [SMILES: C/C(F)=C1/CCC(c2ccn(-c3sc(NS(=O)(=O)c4ccccc4)nc3-c3c(C)cccc3C)n2)C1] | N-[4-(2,6-dimethylphenyl)-5-[3-[(3E)-3-(1-fluoroethylidene)cyclopentyl]pyrazol-1-yl]-1,3-thiazol-2-yl]benzenesulfonamide |

TABLE 1-continued

| Compound Number | Compound Structural Formula | Compound Name |
|---|---|---|
| 225 | 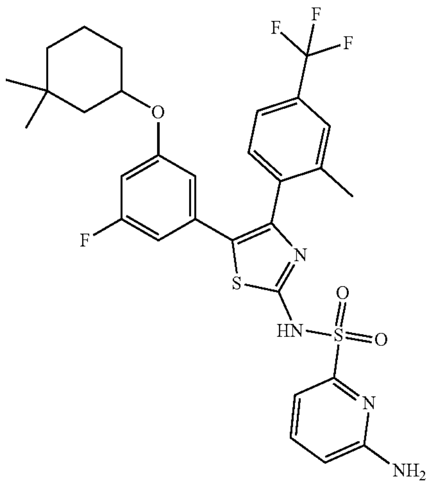 [SMILES: Cc1cc(C(F)(F)F)ccc1-c1nc(NS(=O)(=O)c2cccc(N)n2)sc1-c1cc(F)cc(OC2CCCC(C)(C)C2)c1] | 6-amino-N-[5-[3-(3,3-dimethylcyclohexyl)oxy-5-fluorophenyl]-4-[2-methyl-4-(trifluoromethyl)phenyl]-1,3-thiazol-2-yl]pyridine-2-sulfonamide |
| 450 | 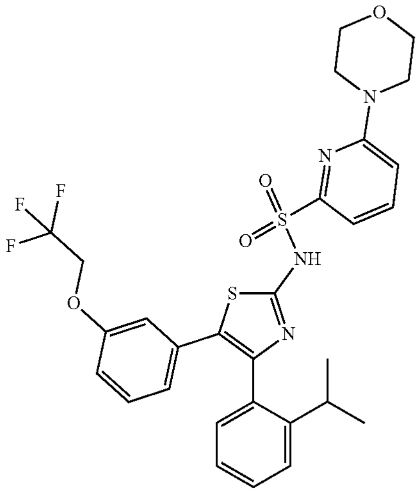 [SMILES: CC(C)c1ccccc1-c1nc(NS(=O)(=O)c2cccc(N3CCOCC3)n2)sc1-c1cccc(OCC(F)(F)F)c1] | 6-morpholin-4-yl-N-[4-(2-propan-2-ylphenyl)-5-[3-(2,2,2-trifluoroethoxy)phenyl]-1,3-thiazol-2-yl]pyridine-2-sulfonamide |
| 424 | 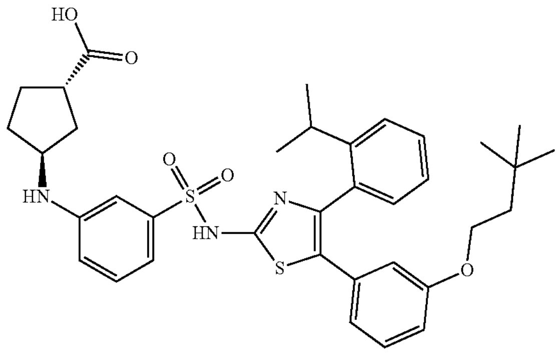 [SMILES: CC(C)c1ccccc1-c1nc(NS(=O)(=O)c2cccc(N[C@H]3CC[C@H](C(=O)O)C3)c2)sc1-c1cccc(OCCC(C)(C)C)c1] | (1S,3S)-3-[3-[[5-[3-(3,3-dimethylbutoxy)phenyl]-4-(2-propan-2-ylphenyl)-1,3-thiazol-2-yl]sulfamoyl]anilino]cyclopentane-1-carboxylic acid |

TABLE 1-continued

| Compound Number | Compound Structural Formula | Compound Name |
|---|---|---|
| 384 | 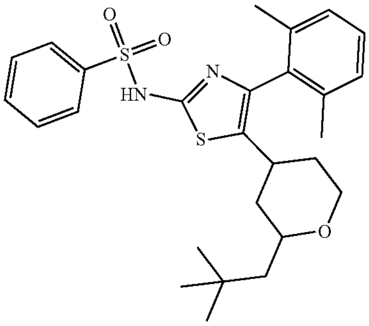 [SMILES: Cc1cccc(C)c1-c1nc(NS(=O)(=O)c2ccccc2)sc1C1CCOC(CC(C)(C)C)C1] | N-[4-(2,6-dimethylphenyl)-5-[2-(2,2-dimethylpropyl)oxan-4-yl]-1,3-thiazol-2-yl]benzenesulfonamide |
| 272 | 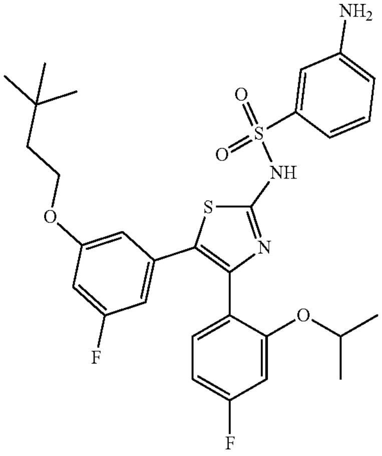 [SMILES: CC(C)Oc1cc(F)ccc1-c1nc(NS(=O)(=O)c2cccc(N)c2)sc1-c1cc(F)cc(OCCC(C)(C)C)c1] | 3-amino-N-[5-[3-(3,3-dimethylbutoxy)-5-fluorophenyl]-4-(4-fluoro-2-propan-2-yloxyphenyl)-1,3-thiazol-2-yl]benzenesulfonamide |
| 58 | 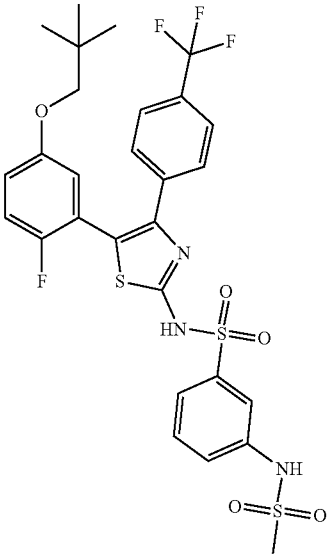 [SMILES: CC(C)(C)COc1ccc(F)c(-c2sc(NS(=O)(=O)c3cccc(NS(C)(=O)=O)c3)nc2-c2ccc(C(F)(F)F)cc2)c1] | N-[5-[5-(2,2-dimethylpropoxy)-2-fluorophenyl]-4-[4-(trifluoromethyl)phenyl]-1,3-thiazol-2-yl]-3-(methanesulfonamido)benzenesulfonamide |

TABLE 1-continued
| Compound Number | Compound Structural Formula | Compound Name |
| --- | --- | --- |
| 536 | 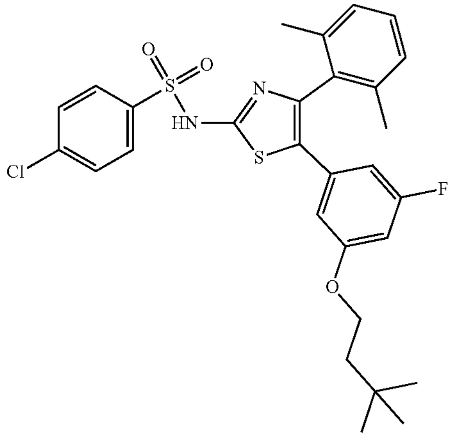 [SMILES: Cc1cccc(C)c1-c1nc(NS(=O)(=O)c2ccc(Cl)cc2)sc1-c1cc(F)cc(OCCC(C)(C)C)c1] | 4-chloro-N-(5-(3-(3,3-dimethylbutoxy)-5-fluorophenyl)-4-(2,6-dimethylphenyl)thiazol-2-yl)benzenesulfonamide |
| 537 | 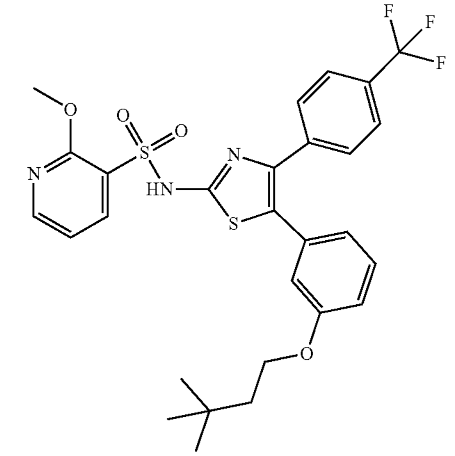 [SMILES: COc1ncccc1S(=O)(=O)Nc1nc(-c2ccc(C(F)(F)F)cc2)c(-c2cccc(OCCC(C)(C)C)c2)s1] | N-(5-(3-(3,3-dimethylbutoxy)phenyl)-4-(4-(trifluoromethyl)phenyl)thiazol-2-yl)-2-methoxypyridine-3-sulfonamide |
| 74 | 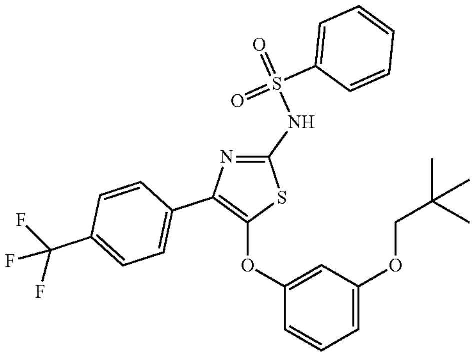 [SMILES: CC(C)(C)COc1cccc(Oc2sc(NS(=O)(=O)c3ccccc3)nc2-c2ccc(C(F)(F)F)cc2)c1] | N-[5-[3-(2,2-dimethylpropoxy)phenoxy]-4-[4-(trifluoromethyl)phenyl]-1,3-thiazol-2-yl]benzenesulfonamide |

TABLE 1-continued

| Compound Number | Compound Structural Formula | Compound Name |
|---|---|---|
| 238 | 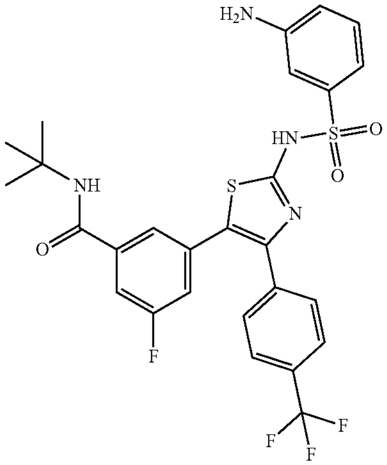 [SMILES: CC(C)(C)NC(=O)c1cc(F)cc(-c2sc(NS(=O)(=O)c3cccc(N)c3)nc2-c2ccc(C(F)(F)F)cc2)c1] | 3-[2-[(3-aminophenyl)sulfonylamino]-4-[4-(trifluoromethyl)phenyl]-1,3-thiazol-5-yl]-N-(tert-butyl-5-fluorobenzamide |
| 282 | 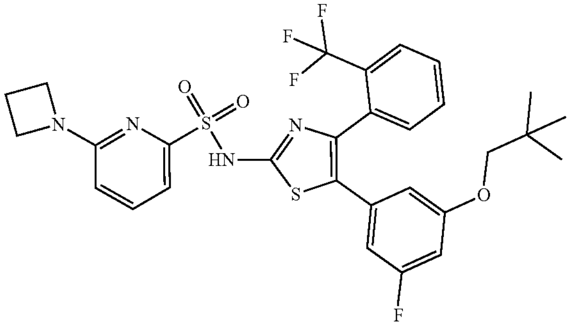 [SMILES: CC(C)(C)COc1cc(F)cc(-c2sc(NS(=O)(=O)c3cccc(N4CCC4)n3)nc2-c2ccccc2C(F)(F)F)c1] | 6-(azetidin-1-yl)-N-[5-[3-(2,2-dimethylpropoxy)-5-fluorophenyl]-4-[2-(trifluoromethyl)phenyl]-1,3-thiazol-2-yl]pyridine-2-sulfonamide |
| 94 | 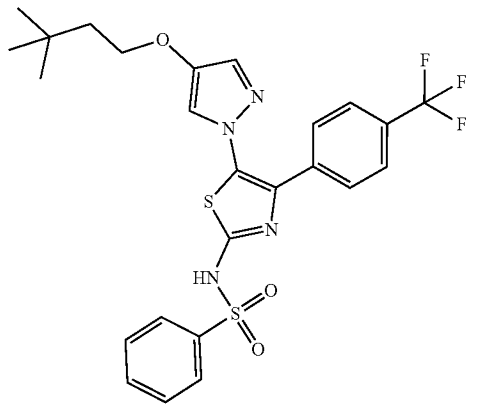 [SMILES: CC(C)(C)CCOc1cnn(-c2sc(NS(=O)(=O)c3ccccc3)nc2-c2ccc(C(F)(F)F)cc2)c1] | N-[5-[4-(3,3-dimethylbutoxy)pyrazol-1-yl]-4-[4-(trifluoromethyl)phenyl]-1,3-thiazol-2-yl]benzenesulfonamide |

TABLE 1-continued

| Compound Number | Compound Structural Formula | Compound Name |
|---|---|---|
| 493 | 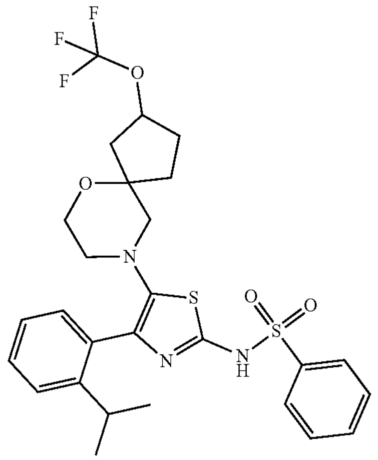 [SMILES: CC(C)c1ccccc1-c1nc(NS(=O)(=O)c2ccccc2)sc1N1CCOC2(CCC(OC(F)(F)F)C2)C1] | N-[4-(2-propan-2-ylphenyl)-5-[3-(trifluoromethoxy)-6-oxa-9-azaspiro[4.5]decan-9-yl]-1,3-thiazol-2-yl]benzenesulfonamide |
| 148 | 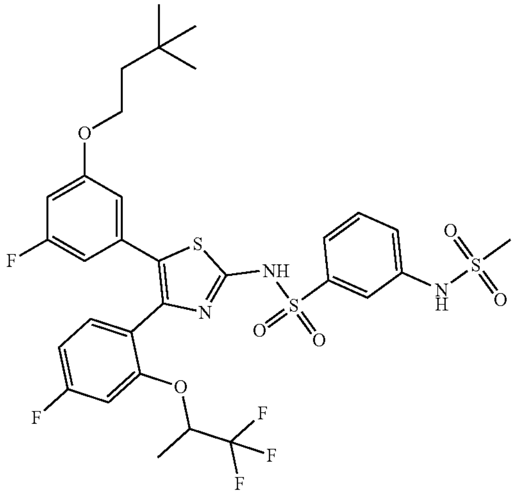 [SMILES: CC(Oc1cc(F)ccc1-c1nc(NS(=O)(=O)c2cccc(NS(C)(=O)=O)c2)sc1-c1cc(F)cc(OCCC(C)(C)C)c1)C(F)(F)F] | N-[5-[3-(3,3-dimethylbutoxy)-5-fluorophenyl]-4-[4-fluoro-2-(1,1,1-trifluoropropan-2-yloxy)phenyl]-1,3-thiazol-2-yl]-3-(methanesulfonamido)benzenesulfonamide |
| 11 | 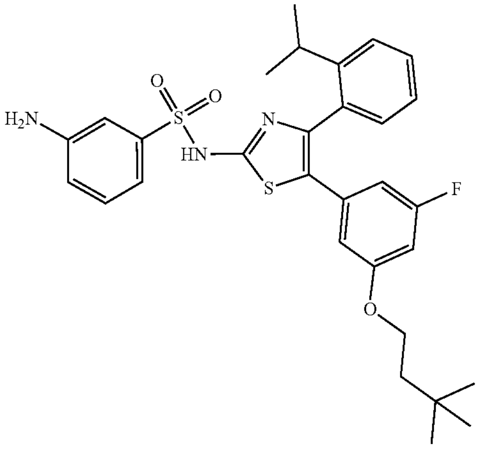 [SMILES: CC(C)c1ccccc1-c1nc(NS(=O)(=O)c2cccc(N)c2)sc1-c1cc(F)cc(OCCC(C)(C)C)c1] | 3-amino-N-[5-[3-(3,3-dimethylbutoxy)-5-fluorophenyl]-4-(2-propan-2-ylphenyl)-1,3-thiazol-2-yl]benzenesulfonamide |

TABLE 1-continued

| Compound Number | Compound Structural Formula | Compound Name |
|---|---|---|
| 538 | 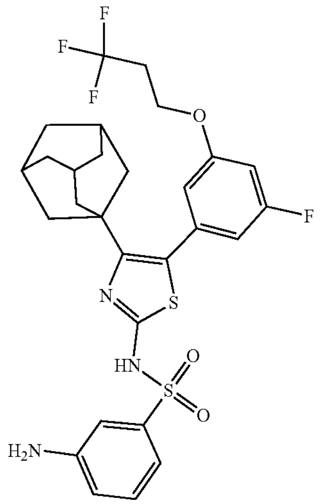 [SMILES: Nc1cccc(S(=O)(=O)Nc2nc(C34CC5CC(CC(C5)C3)C4)c(-c3cc(F)cc(OCCC(F)(F)F)c3)s2)c1] | N-(4-(adamantan-1-yl)-5-(3-fluoro-5-(3,3,3-trifluoropropoxy)phenyl)thiazol-2-yl)-3-aminobenzenesulfonamide |
| 264 | 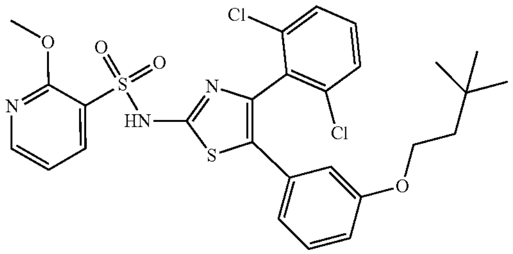 [SMILES: COc1ncccc1S(=O)(=O)Nc1nc(-c2c(Cl)cccc2Cl)c(-c2cccc(OCCC(C)(C)C)c2)s1] | N-[4-(2,6-dichlorophenyl)-5-[3-(3,3-dimethylbutoxy)phenyl]-1,3-thiazol-2-yl]-2-methoxypyridine-3-sulfonamide |
| 494 | 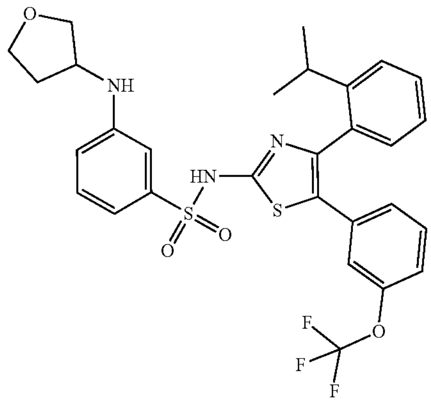 [SMILES: CC(C)c1ccccc1-c1nc(NS(=O)(=O)c2cccc(NC3CCOC3)c2)sc1-c1cccc(OC(F)(F)F)c1] | 3-(oxolan-3-ylamino)-N-[4-(2-propan-2-ylphenyl)-5-[3-(trifluoromethoxy)phenyl]-1,3-thiazol-2-yl]benzenesulfonamide |
| 314 | 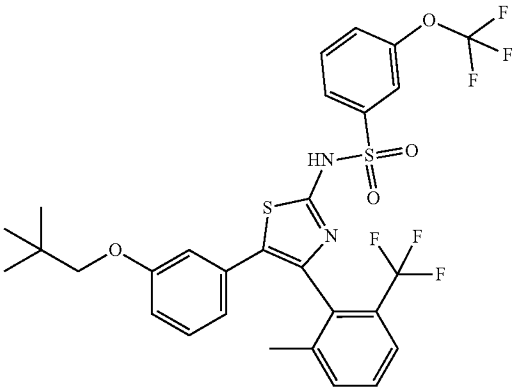 [SMILES: Cc1cccc(C(F)(F)F)c1-c1nc(NS(=O)(=O)c2cccc(OC(F)(F)F)c2)sc1-c1cccc(OCC(C)(C)C)c1] | N-[5-[3-(2,2-dimethylpropoxy)phenyl]-4-[2-methyl-6-(trifluoromethyl)phenyl]-1,3-thiazol-2-yl]-3-(trifluoromethoxy)benzenesulfonamide |

TABLE 1-continued

| Compound Number | Compound Structural Formula | Compound Name |
|---|---|---|
| 539 | 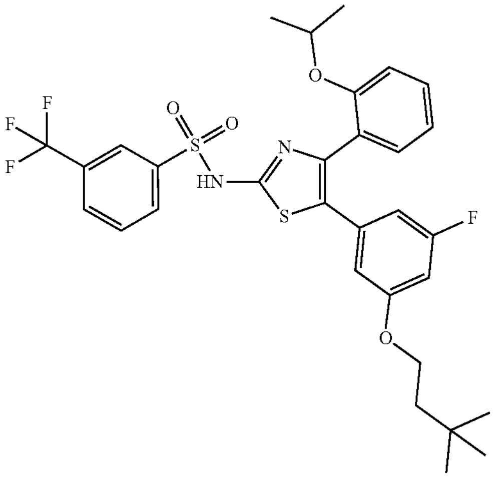 [SMILES: CC(C)Oc1ccccc1-c1nc(NS(=O)(=O)c2cccc(C(F)(F)F)c2)sc1-c1cc(F)cc(OCCC(C)(C)C)c1] | N-(5-(3-(3,3-dimethylbutoxy)-5-fluorophenyl)-4-(2-isopropoxyphenyl)thiazol-2-yl)-3-(trifluoromethyl)benzenesulfonamide |
| 180 | 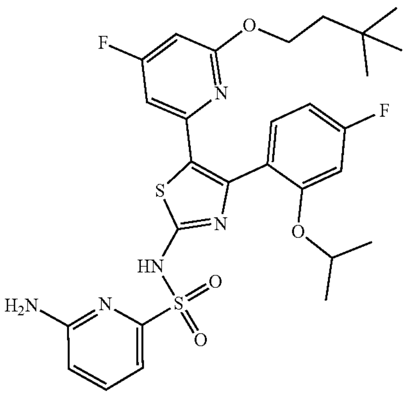 [SMILES: CC(C)Oc1cc(F)ccc1-c1nc(NS(=O)(=O)c2cccc(N)n2)sc1-c1cc(F)cc(OCCC(C)(C)C)n1] | 6-amino-N-[5-[6-(3,3-dimethylbutoxy)-4-fluoropyridin-2-yl]-4-(4-fluoro-2-propan-2-yloxyphenyl)-1,3-thiazol-2-yl]pyridine-2-sulfonamide |
| 222 | 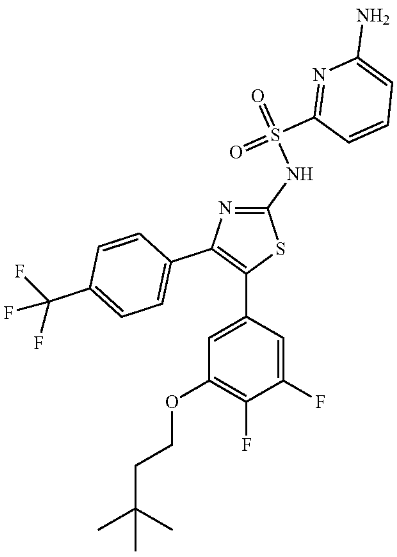 [SMILES: CC(C)(C)CCOc1cc(-c2sc(NS(=O)(=O)c3cccc(N)n3)nc2-c2ccc(C(F)(F)F)cc2)cc(F)c1F] | 6-amino-N-[5-[3-(3,3-dimethylbutoxy)-4,5-difluorophenyl]-4-[4-(trifluoromethyl)phenyl]-1,3-thiazol-2-yl]pyridine-2-sulfonamide |

TABLE 1-continued

| Compound Number | Compound Structural Formula | Compound Name |
|---|---|---|
| 202 | 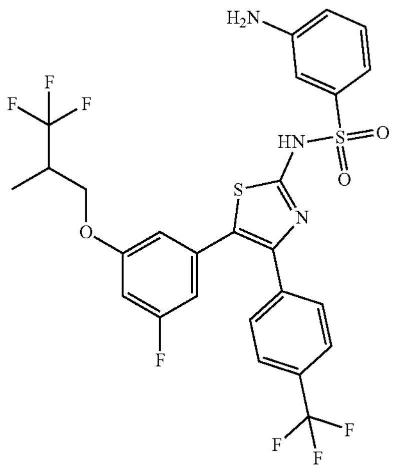 [SMILES: CC(COc1cc(F)cc(-c2sc(NS(=O)(=O)c3cccc(N)c3)nc2-c2ccc(C(F)(F)F)cc2)c1)C(F)(F)F] | 3-amino-N-[5-[3-fluoro-5-(3,3,3-trifluoro-2-methylpropoxy)phenyl]-4-[4-(trifluoromethyl)phenyl]-1,3-thiazol-2-yl]benzenesulfonamide |
| 540 | 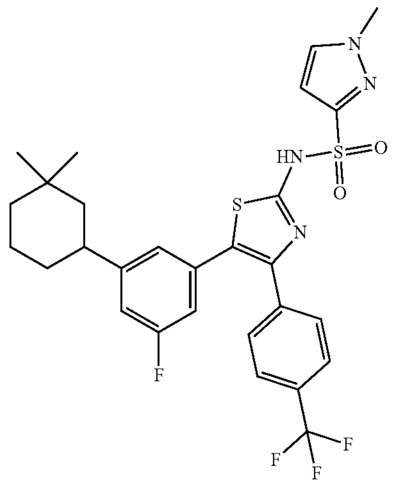 [SMILES: Cn1ccc(S(=O)(=O)Nc2nc(-c3ccc(C(F)(F)F)cc3)c(-c3cc(F)cc(C4CCCC(C)(C)C4)c3)s2)n1] | N-(5-(3-(3,3-dimethylcyclohexyl)-5-fluorophenyl)-4-(4-(trifluoromethyl)phenyl)thiazol-2-yl)-1-methyl-1H-pyrazole-3-sulfonamide |
| 112 | 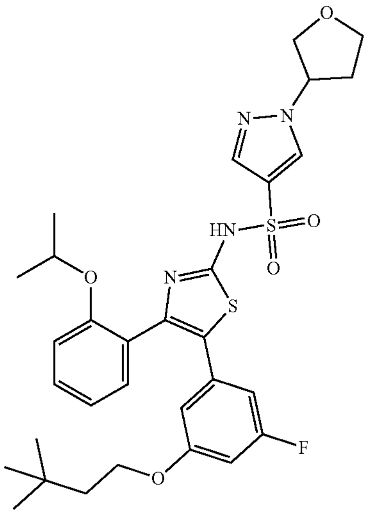 [SMILES: CC(C)Oc1ccccc1-c1nc(NS(=O)(=O)c2cnn(C3CCOC3)c2)sc1-c1cc(F)cc(OCCC(C)(C)C)c1] | N-[5-[3-(3,3-dimethylbutoxy)-5-fluorophenyl]-4-(2-propan-2-yloxyphenyl)-1,3-thiazol-2-yl]-1-(oxolan-3-yl)pyrazole-4-sulfonamide |

TABLE 1-continued
| Compound Number | Compound Structural Formula | Compound Name |
|---|---|---|
| 490 | 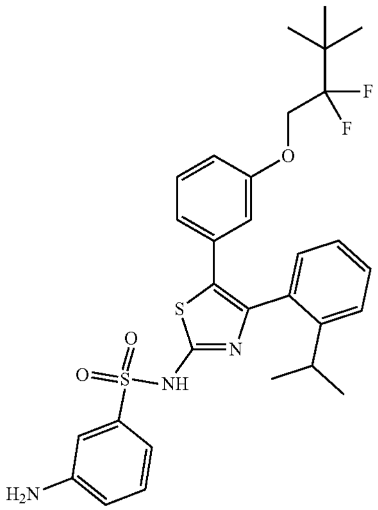 [SMILES: CC(C)c1ccccc1-c1nc(NS(=O)(=O)c2cccc(N)c2)sc1-c1cccc(OCC(F)(F)C(C)(C)C)c1] | 3-amino-N-[5-[3-(2,2-difluoro-3,3-dimethylbutoxy)phenyl]-4-(2-propan-2-ylphenyl)-1,3-thiazol-2-yl]benzenesulfonamide |
| 541 | 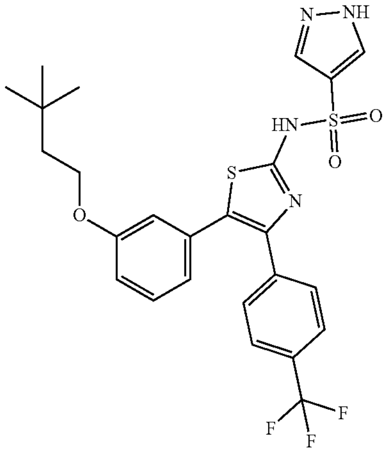 [SMILES: CC(C)(C)CCOc1cccc(-c2sc(NS(=O)(=O)c3cn[nH]c3)nc2-c2ccc(C(F)(F)F)cc2)c1] | N-(5-(3-(3,3-dimethylbutoxy)phenyl)-4-(4-(trifluoromethyl)phenyl)thiazol-2-yl)-1H-pyrazole-4-sulfonamide |
| 336 | 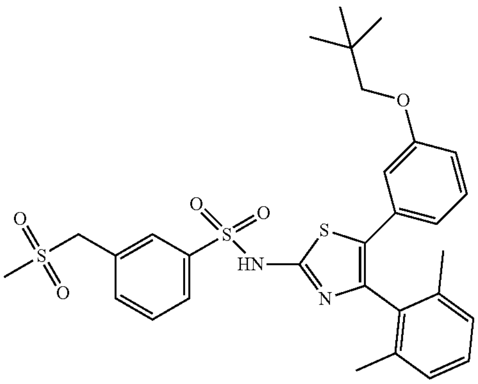 [SMILES: Cc1cccc(C)c1-c1nc(NS(=O)(=O)c2cccc(CS(C)(=O)=O)c2)sc1-c1cccc(OCC(C)(C)C)c1] | N-[4-(2,6-dimethylphenyl)-5-[3-(2,2-dimethylpropoxy)phenyl]-1,3-thiazol-2-yl]-3-(methylsulfonylmethyl)benzenesulfonamide |

TABLE 1-continued
| Compound Number | Compound Structural Formula | Compound Name |
|---|---|---|
| 364 | 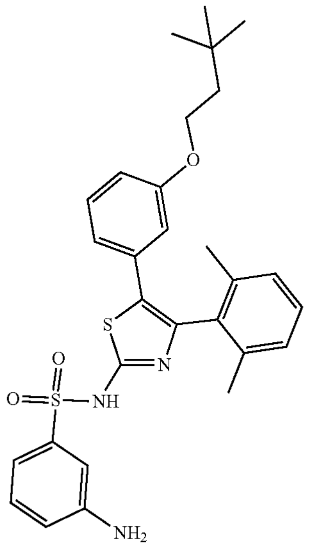 [SMILES: Cc1cccc(C)c1-c1nc(NS(=O)(=O)c2cccc(N)c2)sc1-c1cccc(OCCC(C)(C)C)c1] | 3-amino-N-[5-[3-(3,3-dimethylbutoxy)phenyl]-4-(2,6-dimethylphenyl)-1,3-thiazol-2-yl]benzenesulfonamide |
| 504 | 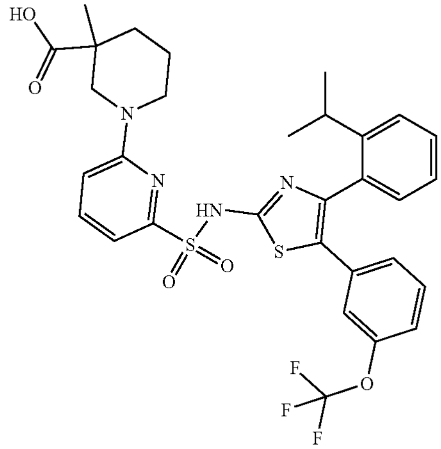 [SMILES: CC(C)c1ccccc1-c1nc(NS(=O)(=O)c2cccc(N3CCCC(C)(C(=O)O)C3)n2)sc1-c1cccc(OC(F)(F)F)c1] | 3-methyl-1-[6-[[4-(2-propan-2-ylphenyl)-5-[3-(trifluoromethoxy)phenyl]-1,3-thiazol-2-yl]sulfamoyl]pyridin-2-yl]piperidine-3-carboxylic acid |
| 542 | 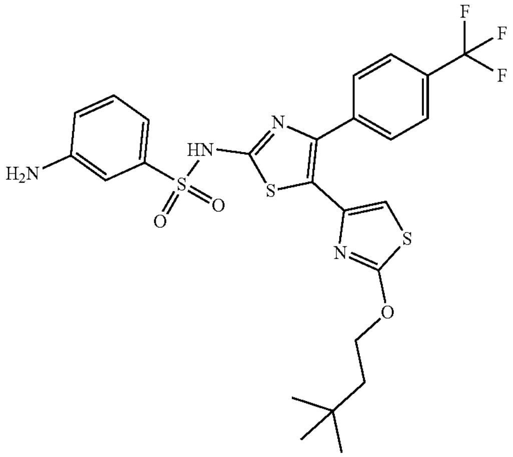 [SMILES: CC(C)(C)CCOc1nc(-c2sc(NS(=O)(=O)c3cccc(N)c3)nc2-c2ccc(C(F)(F)F)cc2)cs1] | 3-amino-N-(2-(3,3-dimethylbutoxy)-4'-(4-(trifluoromethyl)phenyl)-[4,5'-bithiazol]-2'-yl)benzenesulfonamide |

TABLE 1-continued

| Compound Number | Compound Structural Formula | Compound Name |
|---|---|---|
| 543 | 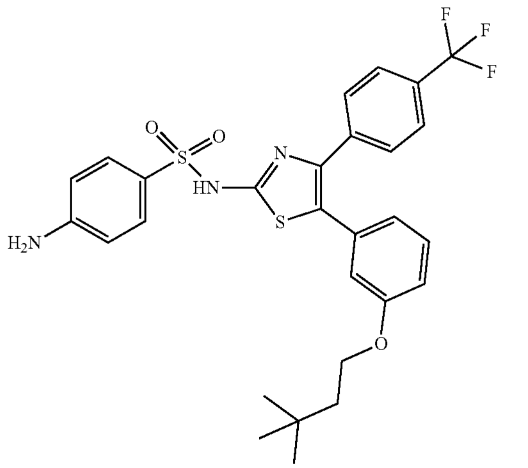 [SMILES: CC(C)(C)CCOc1cccc(-c2sc(NS(=O)(=O)c3ccc(N)cc3)nc2-c2ccc(C(F)(F)F)cc2)c1] | 4-amino-N-(5-(3-(3,3-dimethylbutoxy)phenyl)-4-(4-(trifluoromethyl)phenyl)thiazol-2-yl)benzenesulfonamide |
| 44A2 | 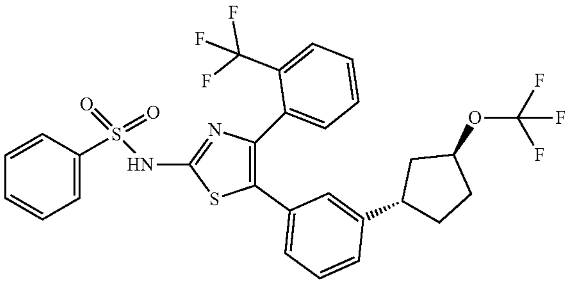 [SMILES: O=S(=O)(Nc1nc(-c2ccccc2C(F)(F)F)c(-c2cccc([C@H]3CC[C@H](OC(F)(F)F)C3)c2)s1)c1ccccc1] | N-[5-[3-[(1R,3R)-3-(trifluoromethoxy)cyclopentyl]phenyl]-4-[2-(trifluoromethyl)phenyl]-1,3-thiazol-2-yl]benzenesulfonamide |
| 133 | 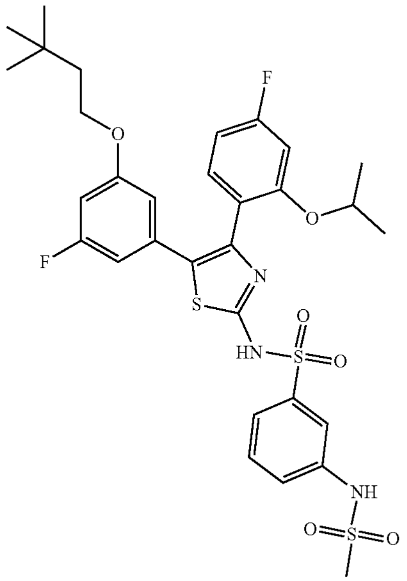 [SMILES: CC(C)Oc1cc(F)ccc1-c1nc(NS(=O)(=O)c2cccc(NS(C)(=O)=O)c2)sc1-c1cc(F)cc(OCCC(C)(C)C)c1] | N-[5-[3-(3,3-dimethylbutoxy)-5-fluorophenyl]-4-(4-fluoro-2-propan-2-yloxyphenyl)-1,3-thiazol-2-yl]-3-(methanesulfonamido)benzenesulfonamide |

TABLE 1-continued

| Compound Number | Compound Structural Formula | Compound Name |
|---|---|---|
| 57 | 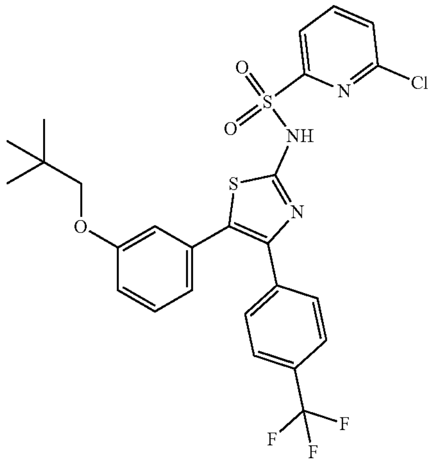 [SMILES: CC(C)(C)COc1cccc(-c2sc(NS(=O)(=O)c3cccc(Cl)n3)nc2-c2ccc(C(F)(F)F)cc2)c1] | 6-chloro-N-[5-[3-(2,2-dimethylpropoxy)phenyl]-4-[4-(trifluoromethyl)phenyl]-1,3-thiazol-2-yl]pyridine-2-sulfonamide |
| 19 | 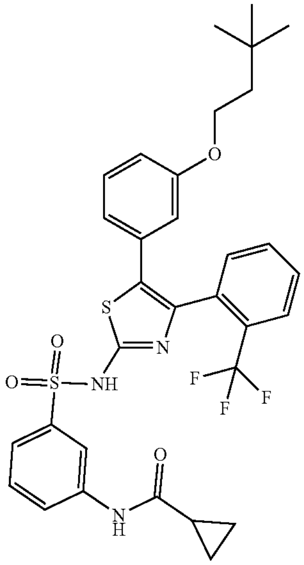 [SMILES: CC(C)(C)CCOc1cccc(-c2sc(NS(=O)(=O)c3cccc(NC(=O)C4CC4)c3)nc2-c2ccccc2C(F)(F)F)c1] | N-[3-[5-[3-(3,3-dimethylbutoxy)phenyl]-4-[2-(trifluoromethyl)phenyl]-1,3-thiazol-2-yl]sulfamoyl]phenyl] cyclopropanecarboxamide |
| 259 | 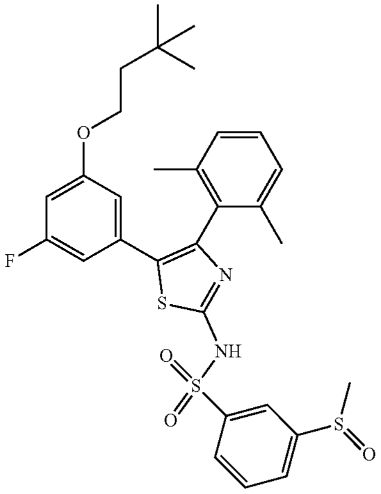 [SMILES: Cc1cccc(C)c1-c1nc(NS(=O)(=O)c2cccc(S(C)=O)c2)sc1-c1cc(F)cc(OCCC(C)(C)C)c1] | N-[5-[3-(3,3-dimethylbutoxy)-5-fluorophenyl]-4-(2,6-dimethylphenyl)-1,3-thiazol-2-yl]-3-methylsulfinylbenzenesulfonamide |

TABLE 1-continued

| Compound Number | Compound Structural Formula | Compound Name |
|---|---|---|
| 75 | 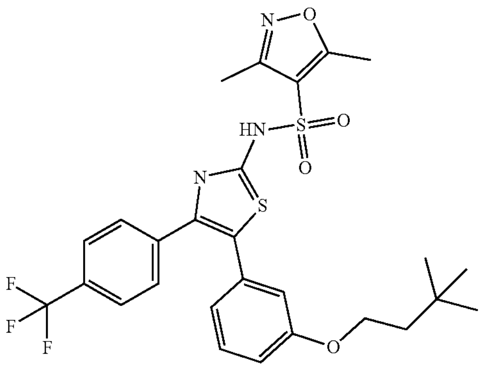 | N-[5-[3-(3,3-dimethylbutoxy)phenyl]-4-[4-(trifluoromethyl)phenyl]-1,3-thiazol-2-yl]-3,5-dimethyl-1,2-oxazole-4-sulfonamide |
| 544 | 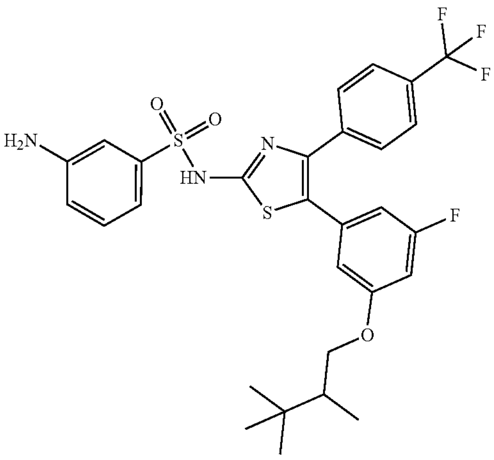 [SMILES: CC(COc1cc(F)cc(-c2sc(NS(=O)(=O)c3cccc(N)c3)nc2-c2ccc(C(F)(F)F)cc2)c1)C(C)(C)C] | 3-amino-N-(5-(3-fluoro-5-(2,3,3-trimethylbutoxy)phenyl)-4-(4-(trifluoromethyl)phenyl)thiazol-2-yl)benzenesulfonamide |
| 212 | 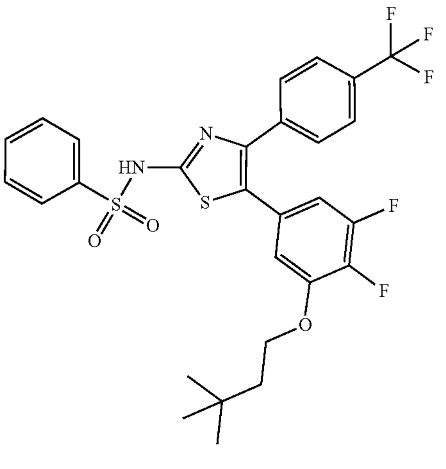 [SMILES: CC(C)(C)CCOc1cc(-c2sc(NS(=O)(=O)c3ccccc3)nc2-c2ccc(C(F)(F)F)cc2)cc(F)c1F] | N-[5-[3-(3,3-dimethylbutoxy)-4,5-difluorophenyl]-4-[4-(trifluoromethyl)phenyl]-1,3-thiazol-2-yl]benzenesulfonamide |

TABLE 1-continued

| Compound Number | Compound Structural Formula | Compound Name |
|---|---|---|
| 201 | 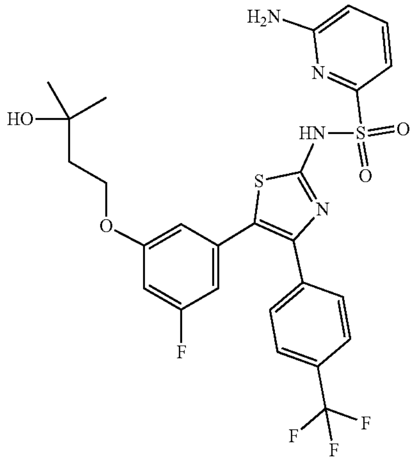 [SMILES: CC(C)(O)CCOc1cc(F)cc(-c2sc(NS(=O)(=O)c3cccc(N)n3)nc2-c2ccc(C(F)(F)F)cc2)c1] | 6-amino-N-[5-[3-fluoro-5-(3-hydroxy-3-methylbutoxy)phenyl]-4-[4-(trifluoromethyl)phenyl]-1,3-thiazol-2-yl]pyridine-2-sulfonamide |
| 470 | 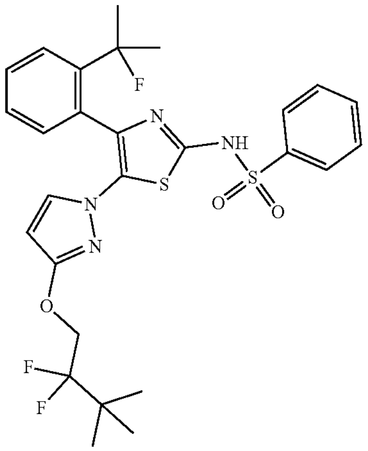 [SMILES: CC(C)(F)c1ccccc1-c1nc(NS(=O)(=O)c2ccccc2)sc1-n1ccc(OCC(F)(F)C(C)(C)C)n1] | N-[5-[3-(2,2-difluoro-3,3-dimethylbutoxy)pyrazol-1-yl]-4-[2-(2-fluoropropan-2-yl)phenyl]-1,3-thiazol-2-yl]benzenesulfonamide |
| 545 | 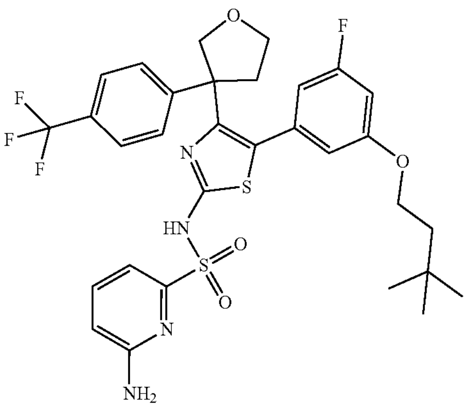 [SMILES: CC(C)(C)CCOc1cc(F)cc(-c2sc(NS(=O)(=O)c3cccc(N)n3)nc2C2(c3ccc(C(F)(F)F)cc3)CCOC2)c1] | 6-amino-N-(5-(3-(3,3-dimethylbutoxy)-5-fluorophenyl)-4-(3-(4-(trifluoromethyl)phenyl)tetrahydrofuran-3-yl)thiazol-2-yl)pyridine-2-sulfonamide |

TABLE 1-continued
| Compound Number | Compound Structural Formula | Compound Name |
|---|---|---|
| 303 | 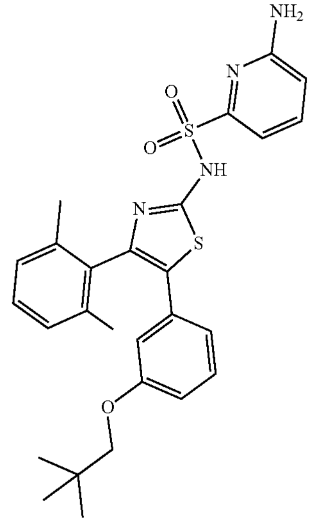 [SMILES: Cc1cccc(C)c1-c1nc(NS(=O)(=O)c2cccc(N)n2)sc1-c1cccc(OCC(C)(C)C)c1] | 6-amino-N-[4-(2,6-dimethylphenyl)-5-[3-(2,2-dimethylpropoxy)phenyl]-1,3-thiazol-2-yl]pyridine-2-sulfonamide |
| 332 | 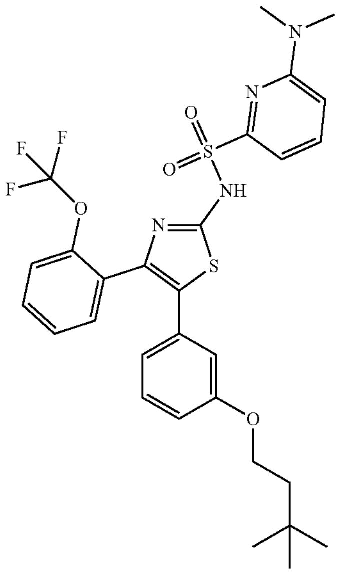 [SMILES: CN(C)c1cccc(S(=O)(=O)Nc2nc(-c3ccccc3OC(F)(F)F)c(-c3cccc(OCCC(C)(C)C)c3)s2)n1] | 6-(dimethylamino)-N-[5-[3-(3,3-dimethylbutoxy)phenyl]-4-[2-(trifluoromethoxy)phenyl]-1,3-thiazol-2-yl]pyridine-2-sulfonamide |
| 546 | 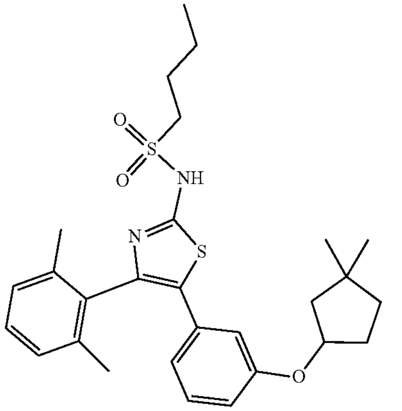 [SMILES: CCCCS(=O)(=O)Nc1nc(-c2c(C)cccc2C)c(-c2cccc(OC3CCC(C)(C)C3)c2)s1] | N-(5-(3-((3,3-dimethylcyclopentyl)oxy)phenyl)-4-(2,6-dimethylphenyl)thiazol-2-yl)butane-1-sulfonamide |

TABLE 1-continued

| Compound Number | Compound Structural Formula | Compound Name |
|---|---|---|
| 323 | 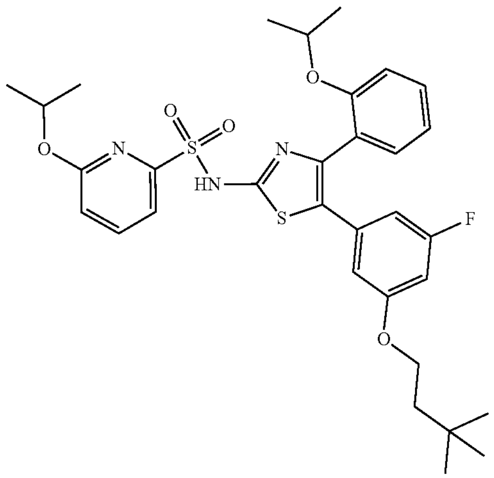 [SMILES: CC(C)Oc1cccc(S(=O)(=O)Nc2nc(-c3ccccc3OC(C)C)c(-c3cc(F)cc(OCCC(C)(C)C)c3)s2)n1] | N-[5-[3-(3,3-dimethylbutoxy)-5-fluorophenyl]-4-(2-propan-2-yloxyphenyl)-1,3-thiazol-2-yl]-6-propan-2-yloxypyridine-2-sulfonamide |
| 484 | 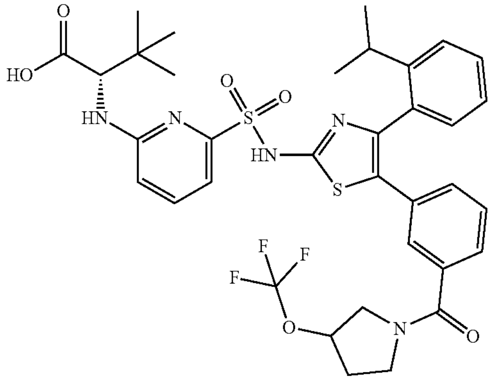 [SMILES: CC(C)c1ccccc1-c1nc(NS(=O)(=O)c2cccc(N[C@H](C(=O)O)C(C)(C)C)n2)sc1-c1cccc(C(=O)N2CCC(OC(F)(F)F)C2)c1] | (2S)-3,3-dimethyl-2-[6-[4-(2-propan-2-ylphenyl)-5-[3-[3-(trifluoromethoxy)pyrrolidine-1-carbonyl]phenyl]-1,3-thiazol-2-yl]sulfamoyl]pyridin-2-yl]amino]butanoic acid |
| 291 | 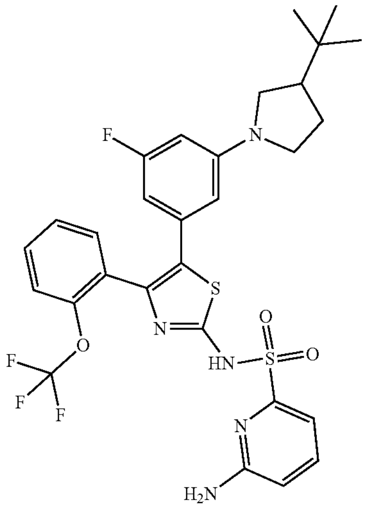 [SMILES: CC(C)(C)C1CCN(c2cc(F)cc(-c3sc(NS(=O)(=O)c4cccc(N)n4)nc3-c3ccccc3OC(F)(F)F)c2)C1] | 6-amino-N-[5-[3-(3-tert-butylpyrrolidin-1-yl)-5-fluorophenyl]-4-[2-(trifluoromethoxy)phenyl]-1,3-thiazol-2-yl]pyridine-2-sulfonamide |

TABLE 1-continued

| Compound Number | Compound Structural Formula | Compound Name |
|---|---|---|
| 209 | 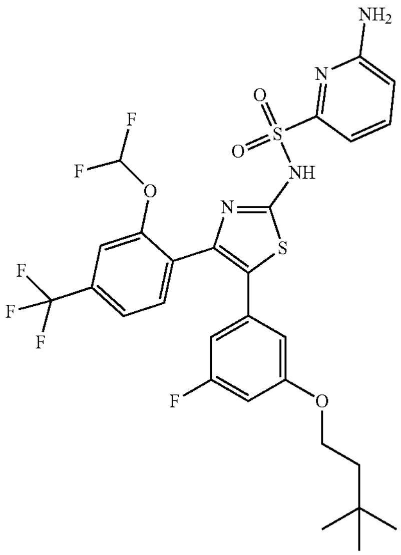 [SMILES: CC(C)(C)CCOc1cc(F)cc(-c2sc(NS(=O)(=O)c3cccc(N)n3)nc2-c2ccc(C(F)(F)F)cc2OC(F)F)c1] | 6-amino-N-[4-[2-(difluoromethoxy)-4-(trifluoromethyl)phenyl]-5-[3-(3,3-dimethylbutoxy)-5-fluorophenyl]-1,3-thiazol-2-yl]pyridine-2-sulfonamide |
| 298 | 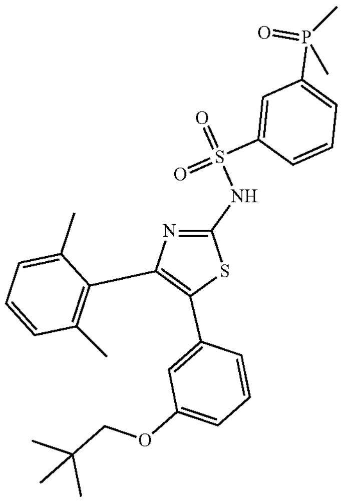 [SMILES: Cc1cccc(C)c1-c1nc(NS(=O)(=O)c2cccc(P(C)(C)=O)c2)sc1-c1cccc(OCC(C)(C)C)c1] | N-[4-(2,6-dimethylphenyl)-5-[3-(2,2-dimethylpropoxy)phenyl]-1,3-thiazol-2-yl]-3-dimethylphosphorylbenzenesulfonamide |
| 230 | 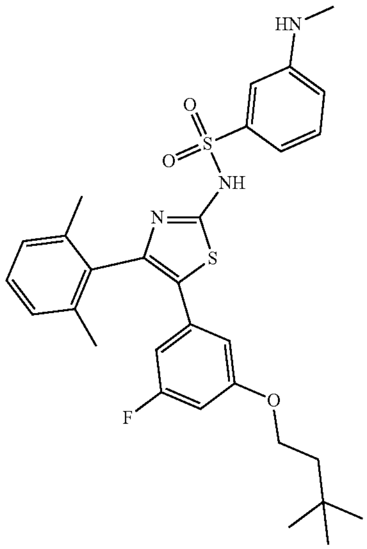 [SMILES: CNc1cccc(S(=O)(=O)Nc2nc(-c3c(C)cccc3C)c(-c3cc(F)cc(OCCC(C)(C)C)c3)s2)c1] | N-[5-[3-(3,3-dimethylbutoxy)-5-fluorophenyl]-4-(2,6-dimethylphenyl)-1,3-thiazol-2-yl]-3-(methylamino)benzenesulfonamide |

TABLE 1-continued

| Compound Number | Compound Structural Formula | Compound Name |
|---|---|---|
| 279 | 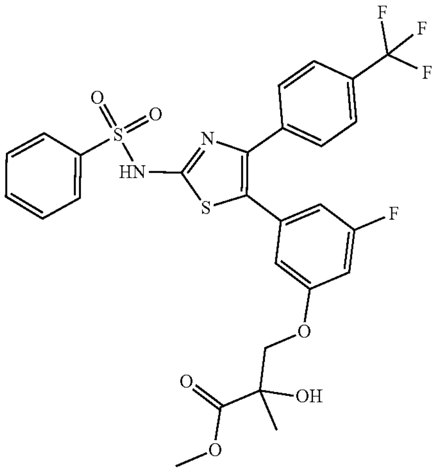 [SMILES: COC(=O)C(C)(O)COc1cc(F)cc(-c2sc(NS(=O)(=O)c3ccccc3)nc2-c2ccc(C(F)(F)F)cc2)c1] | methyl 3-[3-[2-(benzenesulfonamido)-4-[4-(trifluoromethyl)phenyl]-1,3-thiazol-5-yl]-5-fluorophenoxy]-2-hydroxy-2-methylpropanoate |
| 22 | 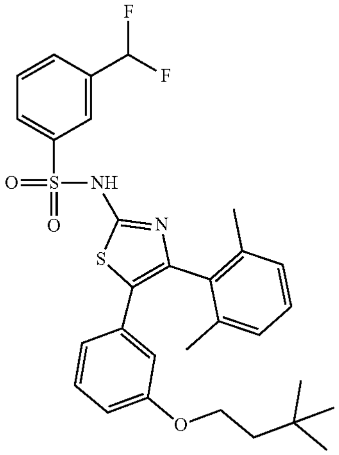 [SMILES: Cc1cccc(C)c1-c1nc(NS(=O)(=O)c2cccc(C(F)F)c2)sc1-c1cccc(OCCC(C)(C)C)c1] | 3-(difluoromethyl)-N-[5-[3-(3,3-dimethylbutoxy)phenyl]-4-(2,6-dimethylphenyl)-1,3-thiazol-2-yl]benzenesulfonamide |
| 116 | 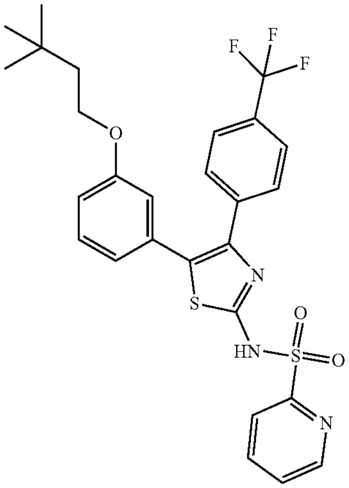 [SMILES: CC(C)(C)CCOc1cccc(-c2sc(NS(=O)(=O)c3ccccn3)nc2-c2ccc(C(F)(F)F)cc2)c1] | N-[5-[3-(3,3-dimethylbutoxy)phenyl]-4-[4-(trifluoromethyl)phenyl]-1,3-thiazol-2-yl]pyridine-2-sulfonamide |

TABLE 1-continued

| Compound Number | Compound Structural Formula | Compound Name |
|---|---|---|
| 263 | 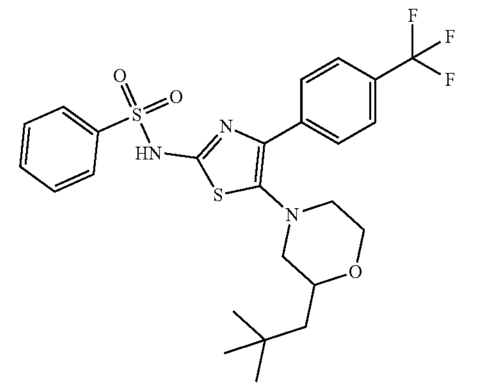 [SMILES: CC(C)(C)CC1CN(c2sc(NS(=O)(=O)c3ccccc3)nc2-c2ccc(C(F)(F)F)cc2)CCO1] | N-[5-[2-(2,2-dimethylpropyl)morpholin-4-yl]-4-[4-(trifluoromethyl)phenyl]-1,3-thiazol-2-yl]benzenesulfonamide |
| 377 | 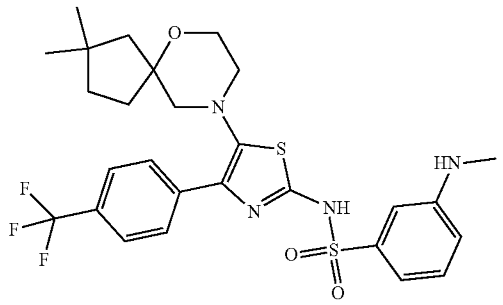 [SMILES: CNc1cccc(S(=O)(=O)Nc2nc(-c3ccc(C(F)(F)F)cc3)c(N3CCOC4(CCC(C)(C)C4)C3)s2)c1] | N-[5-(3,3-dimethyl-6-oxa-9-azaspiro[4.5]decan-9-yl)-4-[4-(trifluoromethyl)phenyl]-1,3-thiazol-2-yl]-3-(methylamino)benzenesulfonamide |
| 60 | 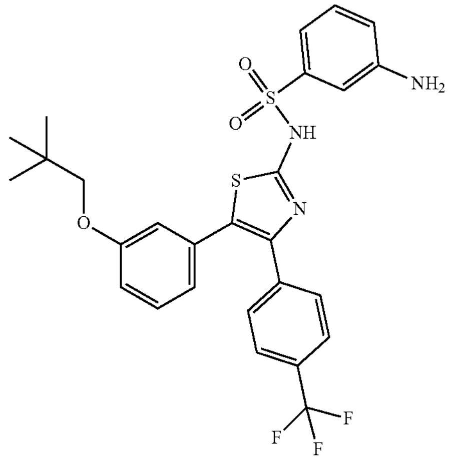 [SMILES: CC(C)(C)COc1cccc(-c2sc(NS(=O)(=O)c3cccc(N)c3)nc2-c2ccc(C(F)(F)F)cc2)c1] | 3-amino-N-[5-[3-(2,2-dimethylpropoxy)phenyl]-4-[4-(trifluoromethyl)phenyl]-1,3-thiazol-2-yl]benzenesulfonamide |
| 396 | 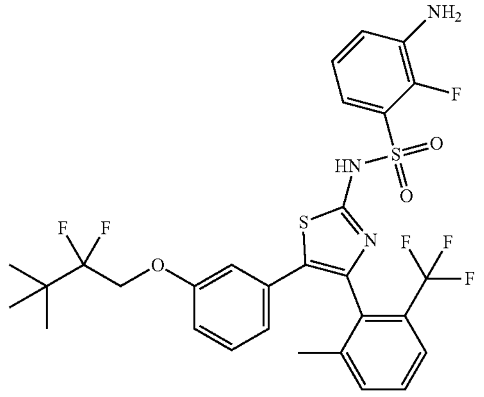 [SMILES: Cc1cccc(C(F)(F)F)c1-c1nc(NS(=O)(=O)c2cccc(N)c2F)sc1-c1cccc(OCC(F)(F)C(C)(C)C)c1] | 3-amino-N-[5-[3-(2,2-difluoro-3,3-dimethylbutoxy)phenyl]-4-[2-methyl-6-(trifluoromethyl)phenyl]-1,3-thiazol-2-yl]-2-fluorobenzenesulfonamide |

TABLE 1-continued

| Compound Number | Compound Structural Formula | Compound Name |
|---|---|---|
| 547 | 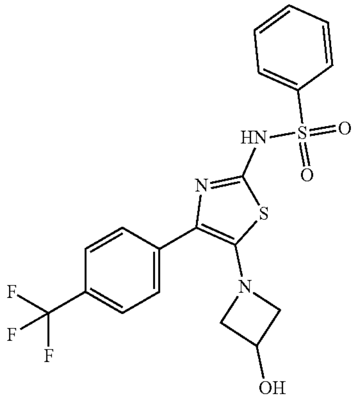 [SMILES: O=S(=O)(Nc1nc(-c2ccc(C(F)(F)F)cc2)c(N2CC(O)C2)s1)c1ccccc1] | N-(5-(3-hydroxyazetidin-1-yl)-4-(4-(trifluoromethyl)phenyl)thiazol-2-yl)benzenesulfonamide |
| 443 | 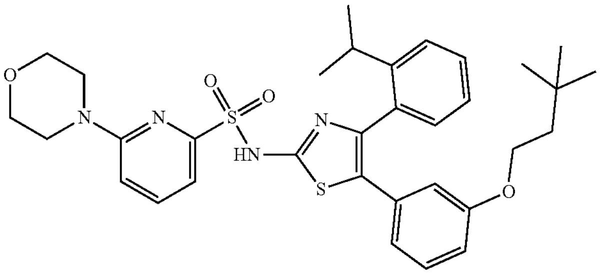 [SMILES: CC(C)c1ccccc1-c1nc(NS(=O)(=O)c2cccc(N3CCOCC3)n2)sc1-c1cccc(OCCC(C)(C)C)c1] | N-[5-[3-(3,3-dimethylbutoxy)phenyl]-4-(2-propan-2-ylphenyl)-1,3-thiazol-2-yl]-6-morpholin-4-ylpyridine-2-sulfonamide |
| 53 | 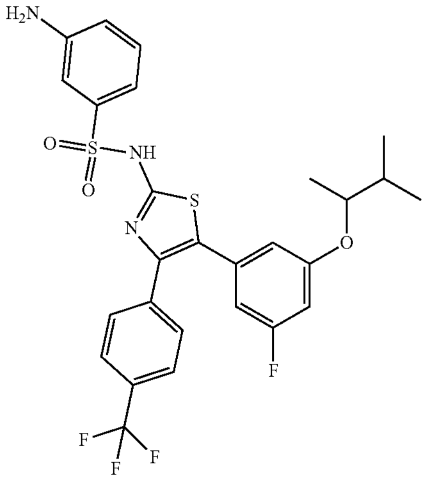 [SMILES: CC(C)C(C)Oc1cc(F)cc(-c2sc(NS(=O)(=O)c3cccc(N)c3)nc2-c2ccc(C(F)(F)F)cc2)c1] | 3-amino-N-[5-[3-fluoro-5-(3-methylbutan-2-yloxy)phenyl]-4-[4-(trifluoromethyl)phenyl]-1,3-thiazol-2-yl]benzenesulfonamide |
| 454 | 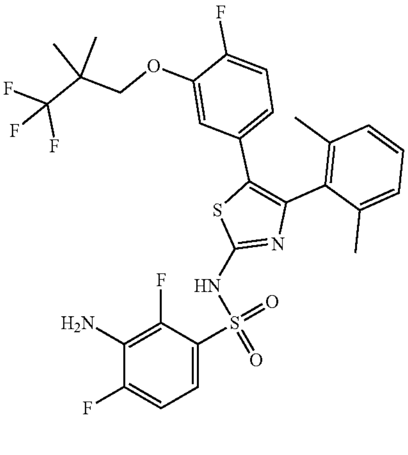 [SMILES: Cc1cccc(C)c1-c1nc(NS(=O)(=O)c2ccc(F)c(N)c2F)sc1-c1ccc(F)c(OCC(C)(C)C(F)(F)F)c1] | 3-amino-N-[4-(2,6-dimethylphenyl)-5-[4-fluoro-3-(3,3,3-trifluoro-2,2-dimethylpropoxy)phenyl]-1,3-thiazol-2-yl]-2,4-difluorobenzenesulfonamide |

TABLE 1-continued

| Compound Number | Compound Structural Formula | Compound Name |
|---|---|---|
| 548 | 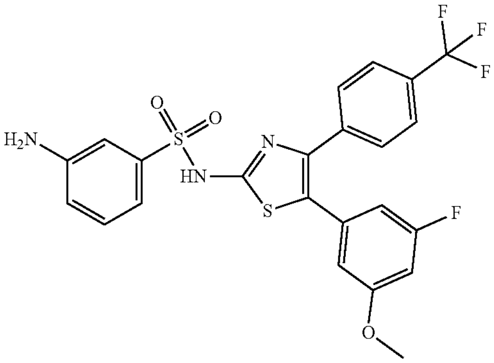 [SMILES: COc1cc(F)cc(-c2sc(NS(=O)(=O)c3cccc(N)c3)nc2-c2ccc(C(F)(F)F)cc2)c1] | 3-amino-N-(5-(3-fluoro-5-methoxyphenyl)-4-(4-(trifluoromethyl)phenyl)thiazol-2-yl)benzenesulfonamide |
| 207 | 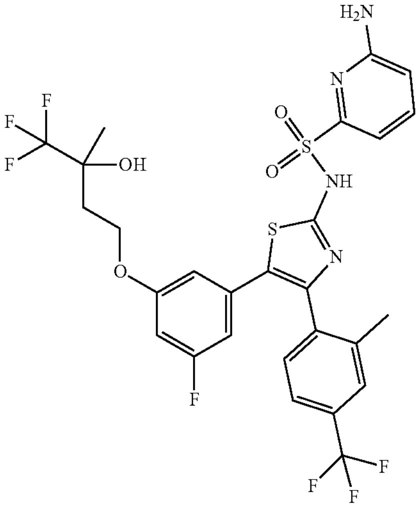 [SMILES: Cc1cc(C(F)(F)F)ccc1-c1nc(NS(=O)(=O)c2cccc(N)n2)sc1-c1cc(F)cc(OCCC(C)(O)C(F)(F)F)c1] | 6-amino-N-[5-[3-fluoro-5-(4,4,4-trifluoro-3-hydroxy-3-methylbutoxy)phenyl]-4-[2-methyl-4-(trifluoromethyl)phenyl]-1,3-thiazol-2-yl]pyridine-2-sulfonamide |
| 226 | 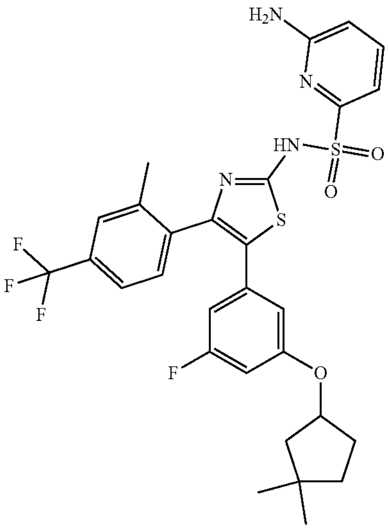 [SMILES: Cc1cc(C(F)(F)F)ccc1-c1nc(NS(=O)(=O)c2cccc(N)n2)sc1-c1cc(F)cc(OC2CCC(C)(C)C2)c1] | 6-amino-N-[5-[3-(3,3-dimethylcyclopentyl)oxy-5-fluorophenyl]-4-[2-methyl-4-(trifluoromethyl)phenyl]-1,3-thiazol-2-yl]pyridine-2-sulfonamide |

TABLE 1-continued

| Compound Number | Compound Structural Formula | Compound Name |
|---|---|---|
| 449 | 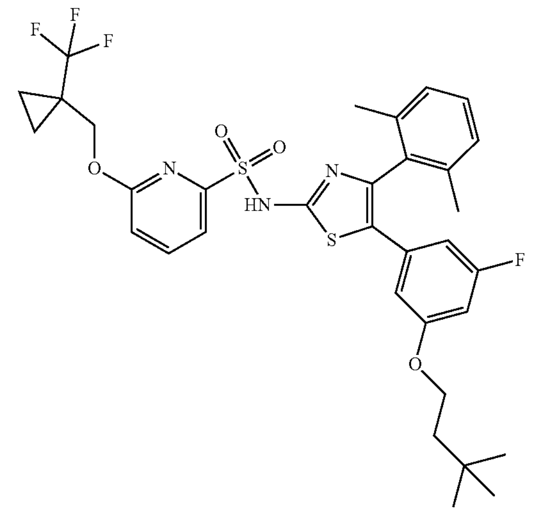 [SMILES: Cc1cccc(C)c1-c1nc(NS(=O)(=O)c2cccc(OCC3(C(F)(F)F)CC3)n2)sc1-c1cc(F)cc(OCCC(C)(C)C)c1] | N-[5-[3-(3,3-dimethylbutoxy)-5-fluorophenyl]-4-(2,6-dimethylphenyl)-1,3-thiazol-2-yl]-6-[[1-(trifluoromethyl)cyclopropyl]methoxy]pyridine-2-sulfonamide |
| 457 | 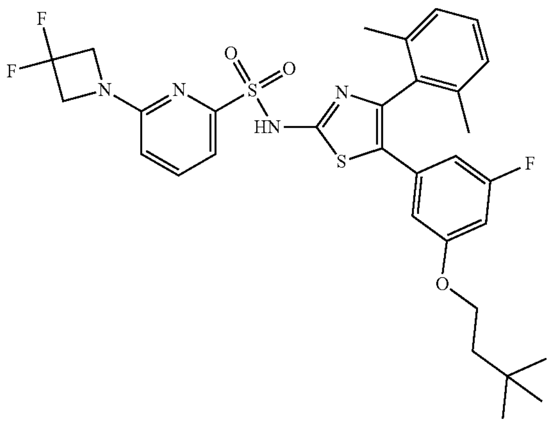 [SMILES: Cc1cccc(C)c1-c1nc(NS(=O)(=O)c2cccc(N3CC(F)(F)C3)n2)sc1-c1cc(F)cc(OCCC(C)(C)C)c1] | 6-(3,3-difluoroazetidin-1-yl)-N-[5-[3-(3,3-dimethylbutoxy)-5-fluorophenyl]-4-(2,6-dimethylphenyl)-1,3-thiazol-2-yl]pyridine-2-sulfonamide |
| 91 | 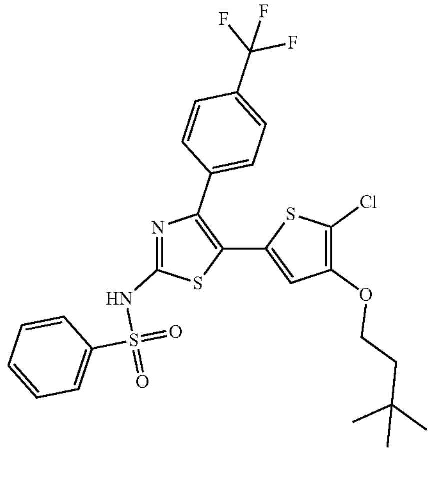 [SMILES: CC(C)(C)CCOc1cc(-c2sc(NS(=O)(=O)c3ccccc3)nc2-c2ccc(C(F)(F)F)cc2)sc1Cl] | N-[5-[5-chloro-4-(3,3-dimethylbutoxy)thiophen-2-yl]-4-[4-(trifluoromethyl)phenyl]-1,3-thiazol-2-yl]benzenesulfonamide |

TABLE 1-continued
| Compound Number | Compound Structural Formula | Compound Name |
|---|---|---|
| 144 | 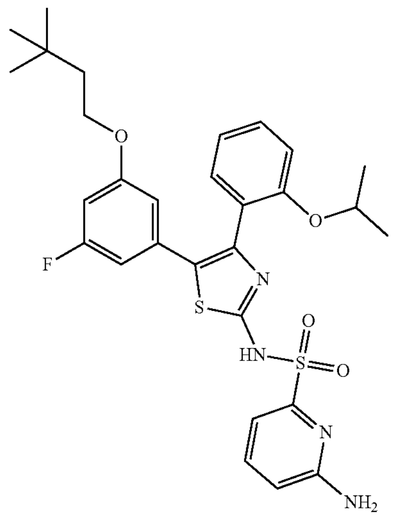 [SMILES: CC(C)Oc1ccccc1-c1nc(NS(=O)(=O)c2cccc(N)n2)sc1-c1cc(F)cc(OCCC(C)(C)C)c1] | 6-amino-N-[5-[3-(3,3-dimethylbutoxy)-5-fluorophenyl]-4-(2-propan-2-yloxyphenyl)-1,3-thiazol-2-yl]pyridine-2-sulfonamide |
| 316 | 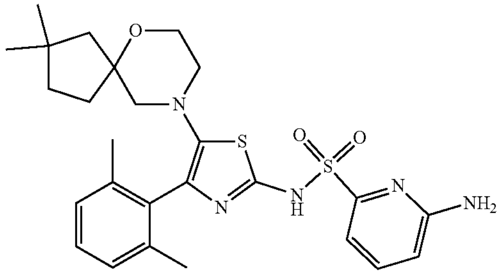 [SMILES: Cc1cccc(C)c1-c1nc(NS(=O)(=O)c2cccc(N)n2)sc1N1CCOC2(CCC(C)(C)C2)C1] | 6-amino-N-[5-(3,3-dimethyl-6-oxa-9-azaspiro[4.5]decan-9-yl)-4-(2,6-dimethylphenyl)-1,3-thiazol-2-yl]pyridine-2-sulfonamide |
| 70 | 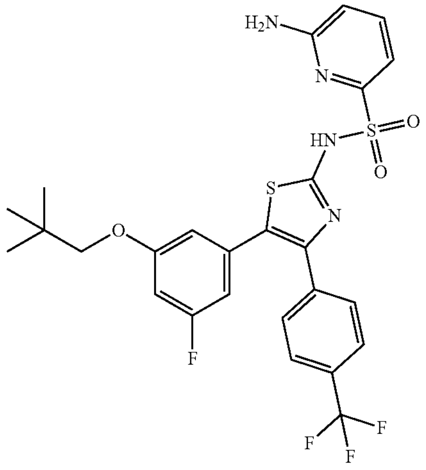 [SMILES: CC(C)(C)COc1cc(F)cc(-c2sc(NS(=O)(=O)c3cccc(N)n3)nc2-c2ccc(C(F)(F)F)cc2)c1] | 6-amino-N-[5-[3-(2,2-dimethylpropoxy)-5-fluorophenyl]-4-[4-(trifluoromethyl)phenyl]-1,3-thiazol-2-yl]pyridine-2-sulfonamide |

TABLE 1-continued

| Compound Number | Compound Structural Formula | Compound Name |
| --- | --- | --- |
| 119 | 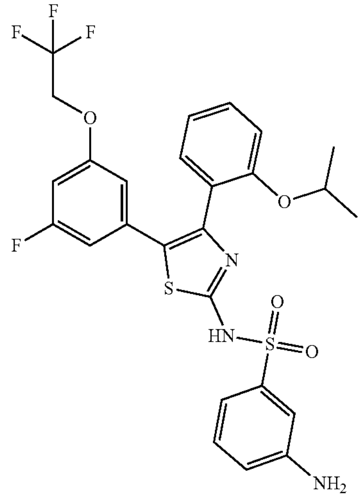 [SMILES: CC(C)Oc1ccccc1-c1nc(NS(=O)(=O)c2cccc(N)c2)sc1-c1cc(F)cc(OCC(F)(F)F)c1] | 3-amino-N-[5-[3-fluoro-5-(2,2,2-trifluoroethoxy)phenyl]-4-(2-propan-2-yloxyphenyl)-1,3-thiazol-2-yl]benzenesulfonamide |
| 276 | 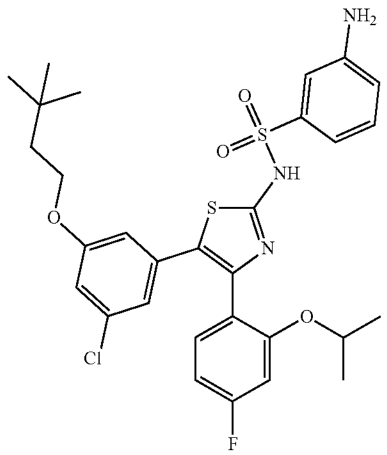 [SMILES: CC(C)Oc1cc(F)ccc1-c1nc(NS(=O)(=O)c2cccc(N)c2)sc1-c1cc(Cl)cc(OCCC(C)(C)C)c1] | 3-amino-N-[5-[3-chloro-5-(3,3-dimethylbutoxy)phenyl]-4-(4-fluoro-2-propan-2-yloxyphenyl)-1,3-thiazol-2-yl]benzenesulfonamide |
| 61 | 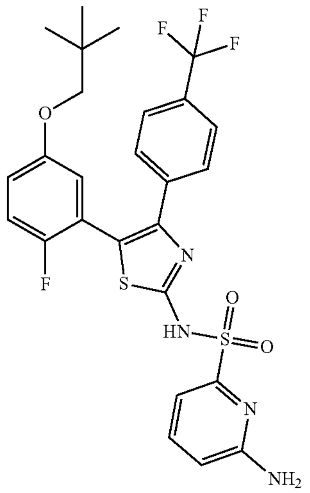 [SMILES: CC(C)(C)COc1ccc(F)c(-c2sc(NS(=O)(=O)c3cccc(N)n3)nc2-c2ccc(C(F)(F)F)cc2)c1] | 6-amino-N-[5-[5-(2,2-dimethylpropoxy)-2-fluorophenyl]-4-[4-(trifluoromethyl)phenyl]-1,3-thiazol-2-yl]pyridine-2-sulfonamide |

TABLE 1-continued

| Compound Number | Compound Structural Formula | Compound Name |
| --- | --- | --- |
| 549 | 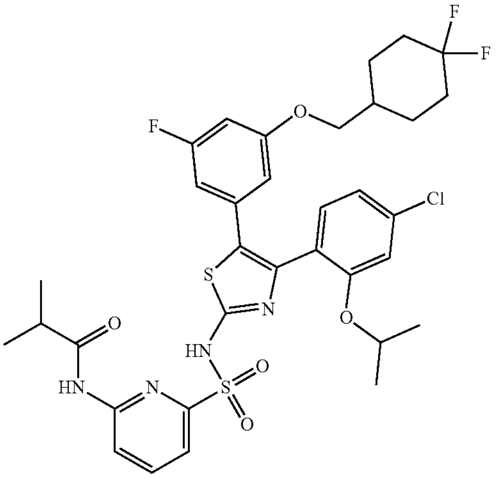 [SMILES: CC(C)Oc1cc(Cl)ccc1-c1nc(NS(=O)(=O)c2cccc(NC(=O)C(C)C)n2)sc1-c1cc(F)cc(OCC2CCC(F)(F)CC2)c1] | N-(6-(N-(4-(4-chloro-2-isopropoxyphenyl)-5-(3-((4,4-difluorocyclohexyl)methoxy)-5-fluorophenyl)thiazol-2-yl)sulfamoyl)pyridin-2-yl)isobutyramide |
| 503 | 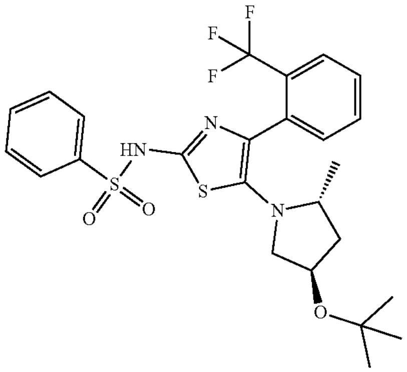 [SMILES: C[C@@H]1C[C@@H](OC(C)(C)C)CN1c1sc(NS(=O)(=O)c2ccccc2)nc1-c1ccccc1C(F)(F)F] | N-[5-[(2R,4R)-2-methyl-4-[(2-methylpropan-2-yl)oxy]pyrrolidin-1-yl]-4-[2-(trifluoromethyl)phenyl]-1,3-thiazol-2-yl]benzenesulfonamide |
| 508 | 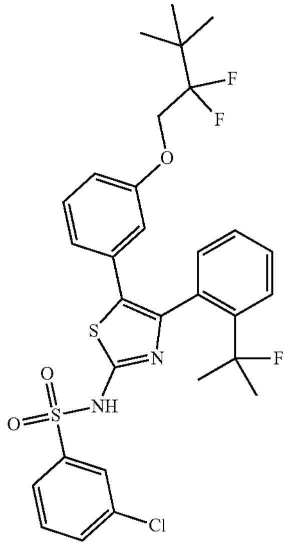 [SMILES: CC(C)(F)c1ccccc1-c1nc(NS(=O)(=O)c2cccc(Cl)c2)sc1-c1cccc(OCC(F)(F)C(C)(C)C)c1] | 3-chloro-N-[5-[3-(2,2-difluoro-3,3-dimethylbutoxy)phenyl]-4-[2-(2-fluoropropan-2-yl)phenyl]-1,3-thiazol-2-yl]benzenesulfonamide |

TABLE 1-continued

| Compound Number | Compound Structural Formula | Compound Name |
| --- | --- | --- |
| 46B1 | 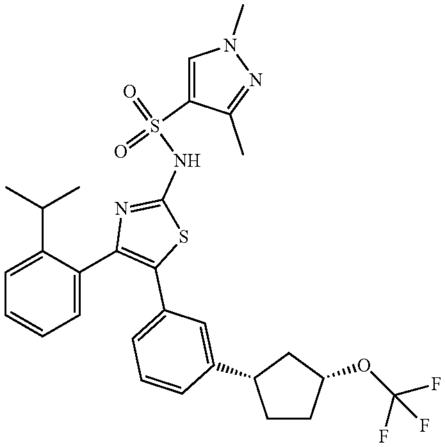 [SMILES: Cc1nn(C)cc1S(=O)(=O)Nc1nc(-c2ccccc2C(C)C)c(-c2cccc([C@H]3CC[C@@H](OC(F)(F)F)C3)c2)s1] | 1,3-dimethyl-N-[4-(2-propan-2-ylphenyl)-5-[3-[(1S,3R)-3-(trifluoromethoxy)cyclopentyl]phenyl]-1,3-thiazol-2-yl]pyrazole-4-sulfonamide |
| 138 | 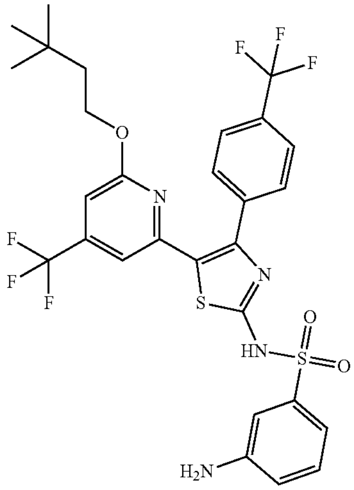 [SMILES: CC(C)(C)CCOc1cc(C(F)(F)F)cc(-c2sc(NS(=O)(=O)c3cccc(N)c3)nc2-c2ccc(C(F)(F)F)cc2)n1] | 3-amino-N-[5-[6-(3,3-dimethylbutoxy)-4-(trifluoromethyl)pyridin-2-yl]-4-[4-(trifluoromethyl)phenyl]-1,3-thiazol-2-yl]benzenesulfonamide |
| 7 | 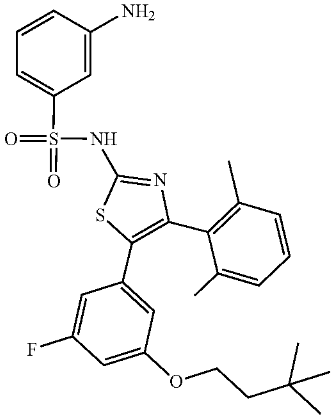 [SMILES: Cc1cccc(C)c1-c1nc(NS(=O)(=O)c2cccc(N)c2)sc1-c1cc(F)cc(OCCC(C)(C)C)c1] | 3-amino-N-(5-(3-(3,3-dimethylbutoxy)-5-fluorophenyl)-4-(2,6-dimethylphenyl)thiazol-2-yl)benzenesulfonamide |

TABLE 1-continued
| Compound Number | Compound Structural Formula | Compound Name |
| --- | --- | --- |
| 413 | 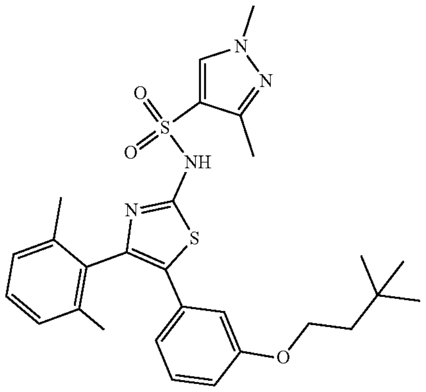 [SMILES: Cc1cccc(C)c1-c1nc(NS(=O)(=O)c2cn(C)nc2C)sc1-c1cccc(OCCC(C)(C)C)c1] | N-[5-[3-(3,3-dimethylbutoxy)phenyl]-4-(2,6-dimethylphenyl)-1,3-thiazol-2-yl]-1,3-dimethylpyrazole-4-sulfonamide |
| 213 | 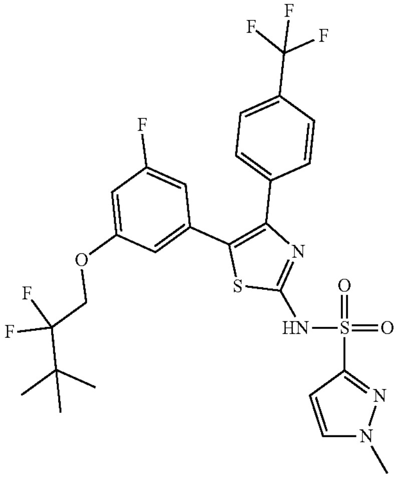 [SMILES: Cn1ccc(S(=O)(=O)Nc2nc(-c3ccc(C(F)(F)F)cc3)c(-c3cc(F)cc(OCC(F)(F)C(C)(C)C)c3)s2)n1] | N-[5-[3-(2,2-difluoro-3,3-dimethylbutoxy)-5-fluorophenyl]-4-[4-(trifluoromethyl)phenyl]-1,3-thiazol-2-yl]-1-methylpyrazole-3-sulfonamide |
| 403 | 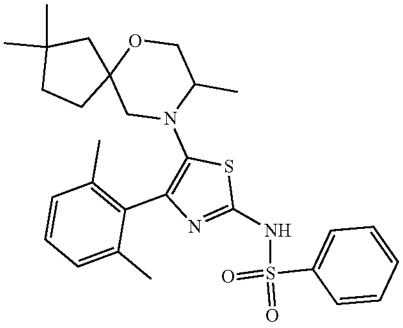 [SMILES: Cc1cccc(C)c1-c1nc(NS(=O)(=O)c2ccccc2)sc1N1CC2(CCC(C)(C)C2)OCC1C] | N-[4-(2,6-dimethylphenyl)-5-(3,3,8-trimethyl-6-oxa-9-azaspiro[4.5]decan-9-yl)-1,3-thiazol-2-yl]benzenesulfonamide |

TABLE 1-continued

| Compound Number | Compound Structural Formula | Compound Name |
|---|---|---|
| 206 | 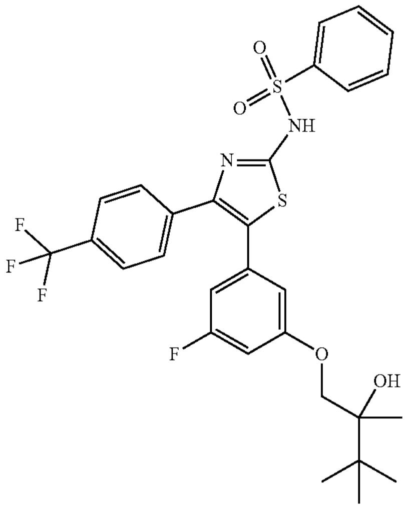 [SMILES: CC(C)(C)C(C)(O)COc1cc(F)cc(-c2sc(NS(=O)(=O)c3ccccc3)nc2-c2ccc(C(F)(F)F)cc2)c1] | N-[5-[3-fluoro-5-(2-hydroxy-2,3,3-trimethylbutoxy)phenyl]-4-[4-(trifluoromethyl)phenyl]-1,3-thiazol-2-yl]benzenesulfonamide |
| 246 | 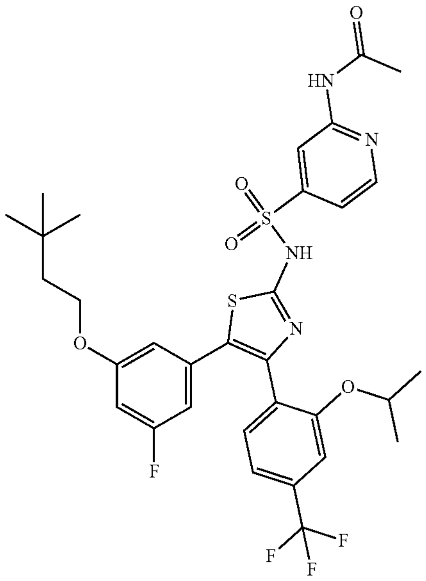 [SMILES: CC(=O)Nc1cc(S(=O)(=O)Nc2nc(-c3ccc(C(F)(F)F)cc3OC(C)C)c(-c3cc(F)cc(OCCC(C)(C)C)c3)s2)ccn1] | N-[4-[5-[3-(3,3-dimethylbutoxy)-5-fluorophenyl]-4-[2-propan-2-yloxy-4-(trifluoromethyl)phenyl]-1,3-thiazol-2-yl]sulfamoyl]pyridin-2-yl]acetamide |
| 178 | 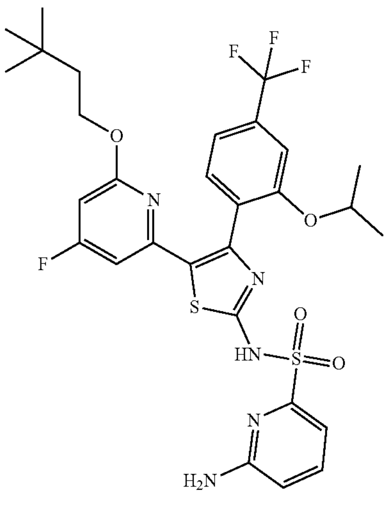 [SMILES: CC(C)Oc1cc(C(F)(F)F)ccc1-c1nc(NS(=O)(=O)c2cccc(N)n2)sc1-c1cc(F)cc(OCCC(C)(C)C)n1] | 6-amino-N-[5-[6-(3,3-dimethylbutoxy)-4-fluoropyridin-2-yl]-4-[2-propan-2-yloxy-4-(trifluoromethyl)phenyl]-1,3-thiazol-2-yl]pyridine-2-sulfonamide |

TABLE 1-continued

| Compound Number | Compound Structural Formula | Compound Name |
|---|---|---|
| 115 | 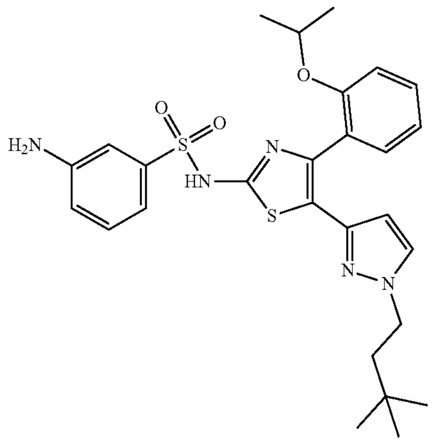 [SMILES: CC(C)Oc1ccccc1-c1nc(NS(=O)(=O)c2cccc(N)c2)sc1-c1ccn(CCC(C)(C)C)n1] | 3-amino-N-[5-[1-(3,3-dimethylbutyl)pyrazol-3-yl]-4-(2-propan-2-yloxyphenyl)-1,3-thiazol-2-yl]benzenesulfonamide |
| 172 | 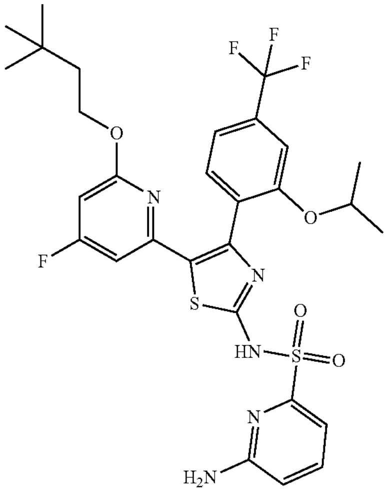 [SMILES: CC(C)Oc1cc(C(F)(F)F)ccc1-c1nc(NS(=O)(=O)c2cccc(N)n2)sc1-c1cc(F)cc(OCCC(C)(C)C)n1] | 6-amino-N-[5-[6-(3,3-dimethylbutoxy)-4-fluoropyridin-2-yl]-4-[4-(trifluoromethyl)phenyl]-1,3-thiazol-2-yl]pyridine-2-sulfonamide |
| 550 | 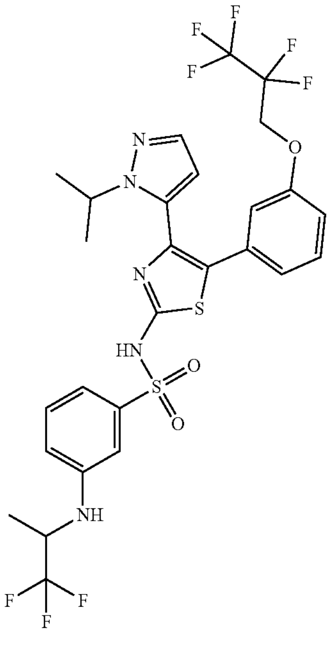 [SMILES: CC(C)n1nccc1-c1nc(NS(=O)(=O)c2cccc(NC(C)C(F)(F)F)c2)sc1-c1cccc(OCC(F)(F)C(F)(F)F)c1] | N-(5-(3-(2,2-difluoro-3,3-dimethylbutoxy)phenyl)-4-(1-isopropyl-1H-pyrazol-5-yl)thiazol-2-yl)-3-((1,1,1-trifluoropropan-2-yl)amino)benzenesulfonamide |

TABLE 1-continued

| Compound Number | Compound Structural Formula | Compound Name |
|---|---|---|
| 296 | 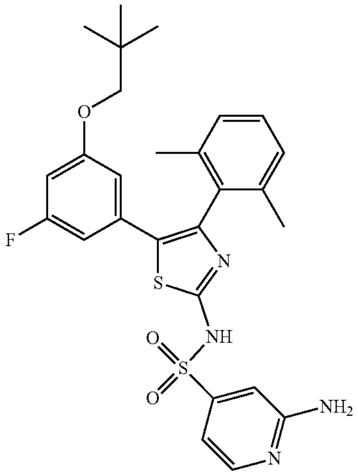 [SMILES: Cc1cccc(C)c1-c1nc(NS(=O)(=O)c2ccnc(N)c2)sc1-c1cc(F)cc(OCC(C)(C)C)c1] | 2-amino-N-[4-(2,6-dimethylphenyl)-5-[3-(2,2-dimethylpropoxy)-5-fluorophenyl]-1,3-thiazol-2-yl]pyridine-4-sulfonamide |
| 243 | 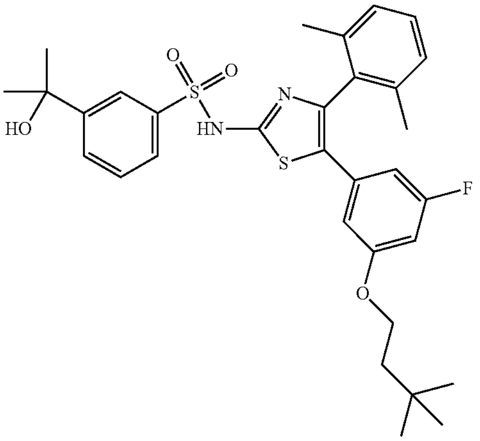 [SMILES: Cc1cccc(C)c1-c1nc(NS(=O)(=O)c2cccc(C(C)(C)O)c2)sc1-c1cc(F)cc(OCCC(C)(C)C)c1] | N-[5-[3-(3,3-dimethylbutoxy)-5-fluorophenyl]-4-(2,6-dimethylphenyl)-1,3-thiazol-2-yl]-3-(2-hydroxypropan-2-yl)benzenesulfonamide |
| 472 | 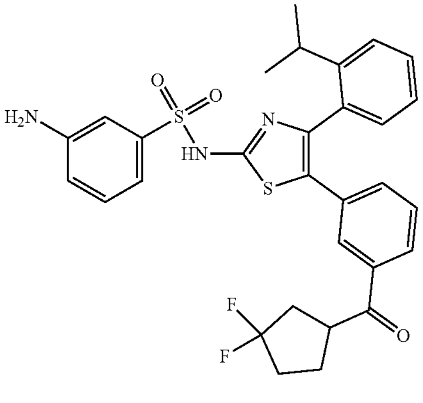 [SMILES: CC(C)c1ccccc1-c1nc(NS(=O)(=O)c2cccc(N)c2)sc1-c1cccc(C(=O)C2CCC(F)(F)C2)c1] | 3-amino-N-[5-[3-(3,3-difluoropyrrolidine-1-carbonyl)phenyl]-4-(2-propan-2-ylphenyl)-1,3-thiazol-2-yl]benzenesulfonamide |

TABLE 1-continued

| Compound Number | Compound Structural Formula | Compound Name |
|---|---|---|
| 421 | 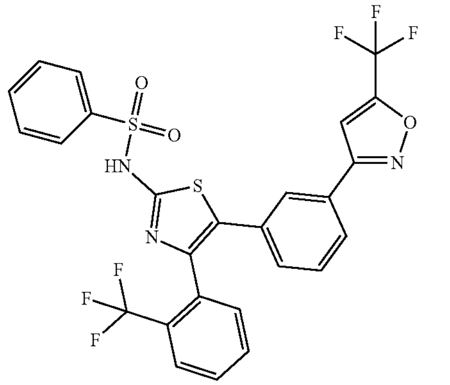 [SMILES: O=S(=O)(Nc1nc(-c2ccccc2C(F)(F)F)c(-c2cccc(-c3cc(C(F)(F)F)on3)c2)s1)c1ccccc1] | N-[5-[3-[5-(trifluoromethyl)-1,2-oxazol-3-yl]phenyl]-4-[2-(trifluoromethyl)phenyl]-1,3-thiazol-2-yl]benzenesulfonamide |
| 383 | 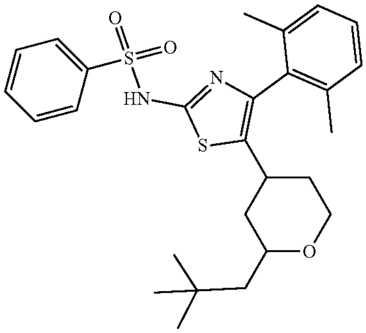 [SMILES: Cc1cccc(C)c1-c1nc(NS(=O)(=O)c2ccccc2)sc1C1CCOC(CC(C)(C)C)C1] | N-[4-(2,6-dimethylphenyl)-5-[2-(2,2-dimethylpropyl)oxan-4-yl]-1,3-thiazol-2-yl]benzenesulfonamide |
| 463 | 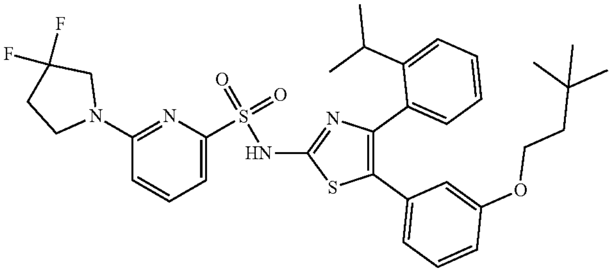 [SMILES: CC(C)c1ccccc1-c1nc(NS(=O)(=O)c2cccc(N3CCC(F)(F)C3)n2)sc1-c1cccc(OCCC(C)(C)C)c1] | 6-(3,3-difluoropyrrolidin-1-yl)-N-[5-[3-(3,3-dimethylbutoxy)phenyl]-4-(2-propan-2-ylphenyl)-1,3-thiazol-2-yl]pyridine-2-sulfonamide |
| 333 | 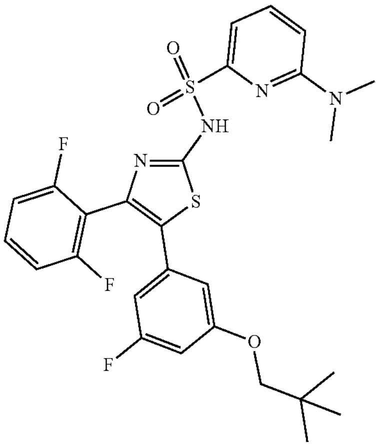 [SMILES: CN(C)c1cccc(S(=O)(=O)Nc2nc(-c3c(F)cccc3F)c(-c3cc(F)cc(OCC(C)(C)C)c3)s2)n1] | N-[4-(2,6-difluorophenyl)-5-[3-(2,2-dimethylpropoxy)-5-fluorophenyl]-1,3-thiazol-2-yl]-6-(dimethylamino)pyridine-2-sulfonamide |

TABLE 1-continued

| Compound Number | Compound Structural Formula | Compound Name |
|---|---|---|
| 204 | 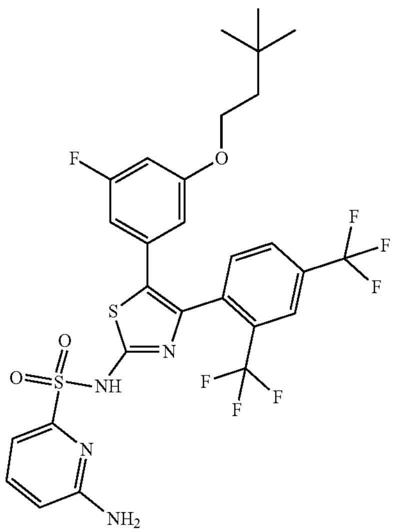 [SMILES: CC(C)(C)CCOc1cc(F)cc(-c2sc(NS(=O)(=O)c3cccc(N)n3)nc2-c2ccc(C(F)(F)F)cc2C(F)(F)F)c1] | 6-amino-N-[4-[2,4-bis(trifluoromethyl)phenyl]-5-[3-(3,3-dimethylbutoxy)-5-fluorophenyl]-1,3-thiazol-2-yl]pyridine-2-sulfonamide |
| 280 | 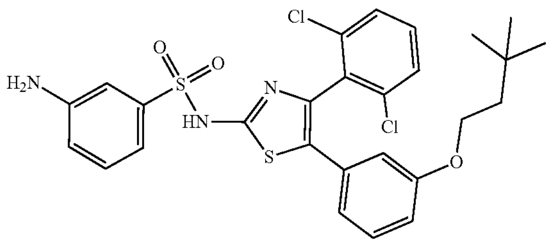 [SMILES: CC(C)(C)CCOc1cccc(-c2sc(NS(=O)(=O)c3cccc(N)c3)nc2-c2c(Cl)cccc2Cl)c1] | 3-amino-N-[4-(2,6-dichlorophenyl)-5-[3-(3,3-dimethylbutoxy)phenyl]-1,3-thiazol-2-yl]benzenesulfonamide |
| 13 | 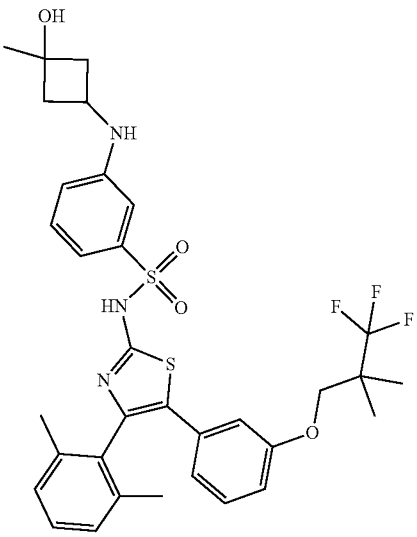 [SMILES: Cc1cccc(C)c1-c1nc(NS(=O)(=O)c2cccc(NC3CC(C)(O)C3)c2)sc1-c1cccc(OCC(C)(C)C(F)(F)F)c1] | N-[4-(2,6-dimethylphenyl)-5-[3-(3,3,3-trifluoro-2,2-dimethylpropoxy)phenyl]-1,3-thiazol-2-yl]-3-[(3-hydroxy-3-methylcyclobutyl)amino] benzenesulfonamide |

TABLE 1-continued

| Compound Number | Compound Structural Formula | Compound Name |
|---|---|---|
| 17 | 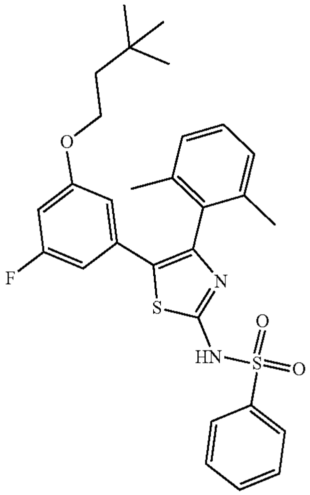 [SMILES: Cc1cccc(C)c1-c1nc(NS(=O)(=O)c2ccccc2)sc1-c1cc(F)cc(OCCC(C)(C)C)c1] | N-[5-[3-(3,3-dimethylbutoxy)-5-fluorophenyl]-4-(2,6-dimethylphenyl)-1,3-thiazol-2-yl]benzenesulfonamide |
| 382 | 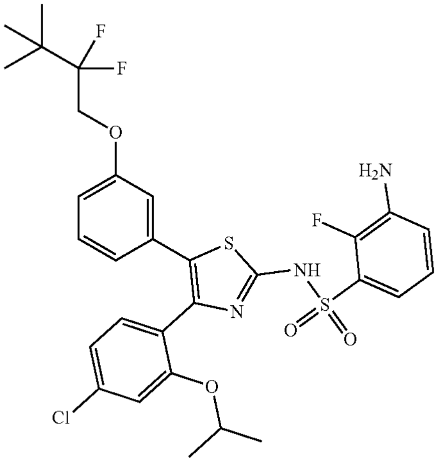 [SMILES: CC(C)Oc1cc(Cl)ccc1-c1nc(NS(=O)(=O)c2cccc(N)c2F)sc1-c1cccc(OCC(F)(F)C(C)(C)C)c1] | 6-amino-N-[5-[1-(3,3-dimethylbutyl)pyrazol-3-yl]-4-(2-propan-2-yloxyphenyl)-1,3-thiazol-2-yl]pyridine-2-sulfonamide |
| 47A2 | 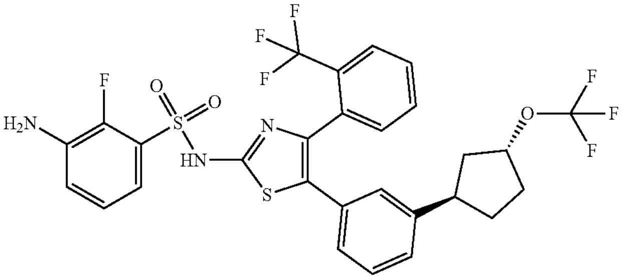 [SMILES: Nc1cccc(S(=O)(=O)Nc2nc(-c3ccccc3C(F)(F)F)c(-c3cccc([C@@H]4CC[C@@H](OC(F)(F)F)C4)c3)s2)c1F] | 3-amino-2-fluoro-N-[5-[3-[(1R,3R)-3-(trifluoromethoxy)cyclopentyl]phenyl]-4-[2-(trifluoromethyl)phenyl]-1,3-thiazol-2-yl]benzenesulfonamide |

TABLE 1-continued

| Compound Number | Compound Structural Formula | Compound Name |
|---|---|---|
| 4 | 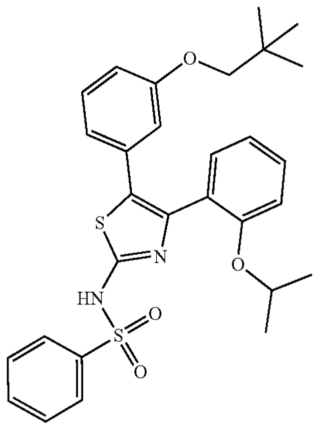 [SMILES: CC(C)Oc1ccccc1-c1nc(NS(=O)(=O)c2ccccc2)sc1-c1cccc(OCC(C)(C)C)c1] | N-(4-(2-isopropoxyphenyl)-5-(3-(neopentyloxy)phenyl)thiazol-2-yl)benzenesulfonamide |
| 414 | 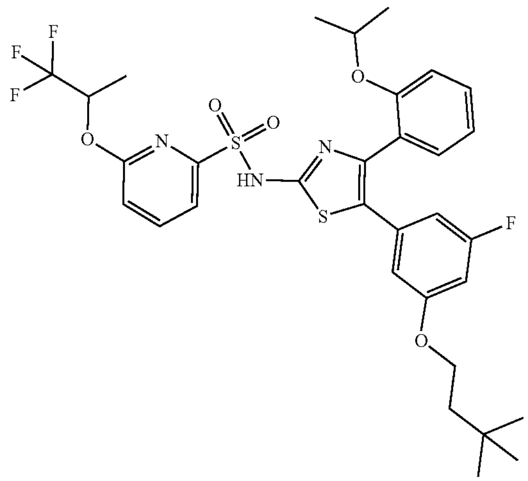 [SMILES: CC(C)Oc1ccccc1-c1nc(NS(=O)(=O)c2cccc(OC(C)C(F)(F)F)n2)sc1-c1cc(F)cc(OCCC(C)(C)C)c1] | N-[5-[3-(3,3-dimethylbutoxy)-5-fluorophenyl]-4-(2-propan-2-yloxyphenyl)-1,3-thiazol-2-yl]-6-(1,1,1-trifluoropropan-2-yloxy)pyridine-2-sulfonamide |
| 432 | 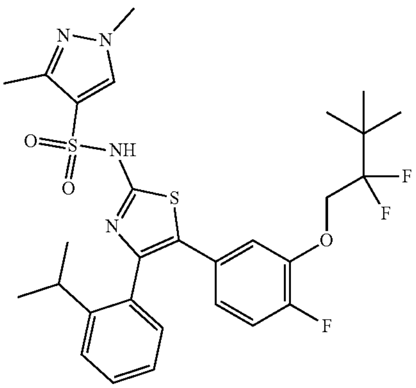 [SMILES: Cc1nn(C)cc1S(=O)(=O)Nc1nc(-c2ccccc2C(C)C)c(-c2ccc(F)c(OCC(F)(F)C(C)(C)C)c2)s1] | N-[5-[3-(2,2-difluoro-3,3-dimethylbutoxy)-4-fluorophenyl]-4-(2-propan-2-ylphenyl)-1,3-thiazol-2-yl]-1,3-dimethylpyrazole-4-sulfonamide |

TABLE 1-continued

| Compound Number | Compound Structural Formula | Compound Name |
|---|---|---|
| 283 | 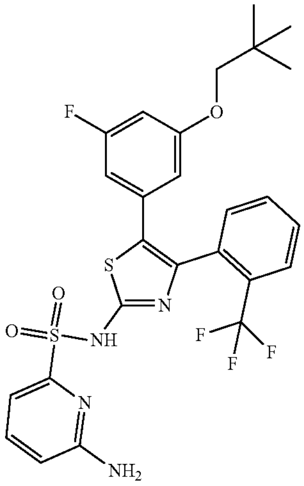 [SMILES: CC(C)(C)COc1cc(F)cc(-c2sc(NS(=O)(=O)c3cccc(N)n3)nc2-c2ccccc2C(F)(F)F)c1] | 6-amino-N-[5-[3-(2,2-dimethylpropoxy)-5-fluorophenyl]-4-[2-(trifluoromethyl)phenyl]-1,3-thiazol-2-yl]pyridine-2-sulfonamide |
| 48B2 | 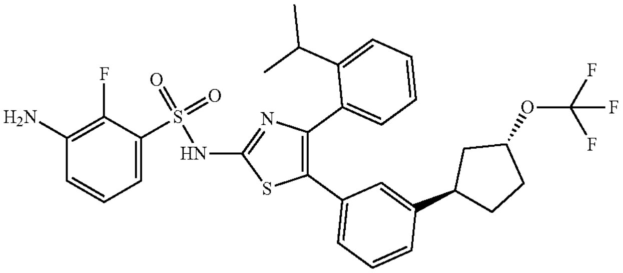 [SMILES: CC(C)c1ccccc1-c1nc(NS(=O)(=O)c2cccc(N)c2F)sc1-c1cccc([C@@H]2CC[C@@H](OC(F)(F)F)C2)c1] | 3-amino-2-fluoro-N-[4-(2-propan-2-ylphenyl)-5-[3-[(1R,3R)-3-(trifluoromethoxy)cyclopentyl]phenyl]-1,3-thiazol-2-yl]benzenesulfonamide |
| 340 | 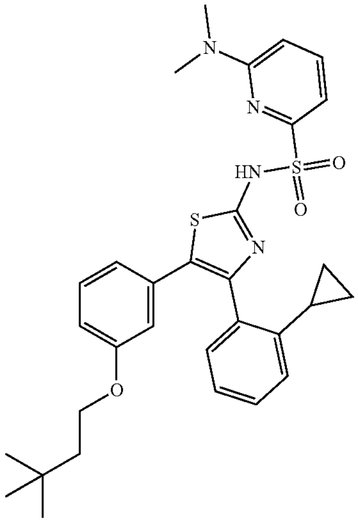 [SMILES: CN(C)c1cccc(S(=O)(=O)Nc2nc(-c3ccccc3C3CC3)c(-c3cccc(OCCC(C)(C)C)c3)s2)n1] | N-[4-(2-cyclopropylphenyl)-5-[3-(3,3-dimethylbutoxy)phenyl]-1,3-thiazol-2-yl]-6-(dimethylamino)pyridine-2-sulfonamide |

TABLE 1-continued

| Compound Number | Compound Structural Formula | Compound Name |
|---|---|---|
| 365 | 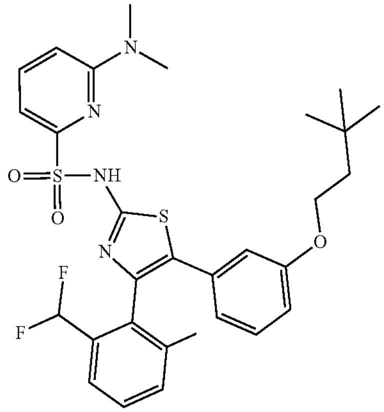 [SMILES: Cc1cccc(C(F)F)c1-c1nc(NS(=O)(=O)c2cccc(N(C)C)n2)sc1-c1cccc(OCCC(C)(C)C)c1] | N-[4-[2-(difluoromethyl)-6-methylphenyl]-5-[3-(3,3-dimethylbutoxy)phenyl]-1,3-thiazol-2-yl]-6-(dimethylamino)pyridine-2-sulfonamide |
| 551 | 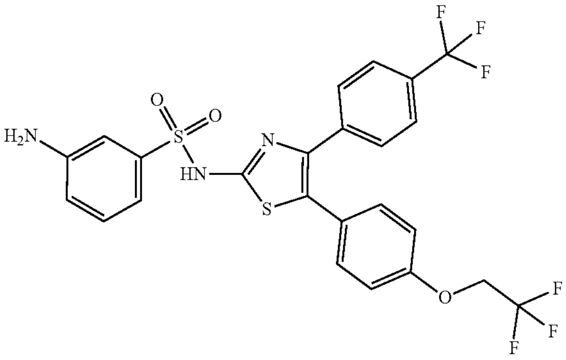 [SMILES: Nc1cccc(S(=O)(=O)Nc2nc(-c3ccc(C(F)(F)F)cc3)c(-c3ccc(OCC(F)(F)F)cc3)s2)c1] | 3-amino-N-(5-(4-(2,2,2-trifluoroethoxy)phenyl)-4-(4-(trifluoromethyl)phenyl)thiazol-2-yl)benzenesulfonamide |
| 552 | 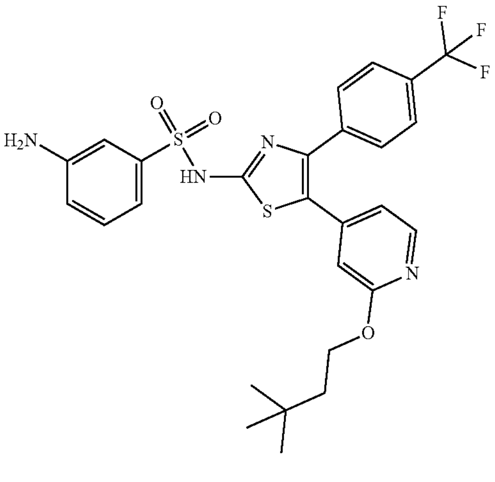 [SMILES: CC(C)(C)CCOc1cc(-c2sc(NS(=O)(=O)c3cccc(N)c3)nc2-c2ccc(C(F)(F)F)cc2)ccn1] | 3-amino-N-(5-(2-(3,3-dimethylbutoxy)pyridin-4-yl)-4-(4-(trifluoromethyl)phenyl)thiazol-2-yl)benzenesulfonamide |

TABLE 1-continued

| Compound Number | Compound Structural Formula | Compound Name |
|---|---|---|
| 101 | 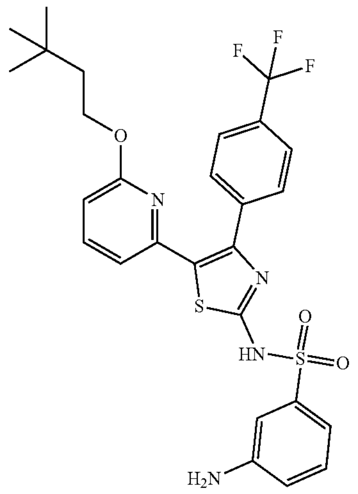 [SMILES: CC(C)(C)CCOc1cccc(-c2sc(NS(=O)(=O)c3cccc(N)c3)nc2-c2ccc(C(F)(F)F)cc2)n1] | 3-amino-N-[5-[6-(3,3-dimethylbutoxy)pyridin-2-yl]-4-[4-(trifluoromethyl)phenyl]-1,3-thiazol-2-yl]benzenesulfonamide |
| 173 | 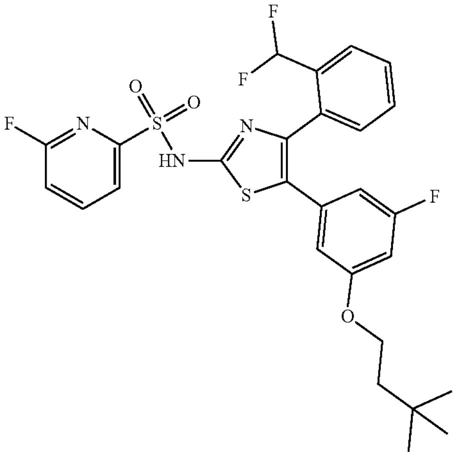 [SMILES: CC(C)(C)CCOc1cc(F)cc(-c2sc(NS(=O)(=O)c3cccc(F)n3)nc2-c2ccccc2C(F)F)c1] | N-[4-[2-(difluoromethyl)phenyl]-5-[3-(3,3-dimethylbutoxy)-5-fluorophenyl]-1,3-thiazol-2-yl]-6-fluoropyridine-2-sulfonamide |
| 447 | 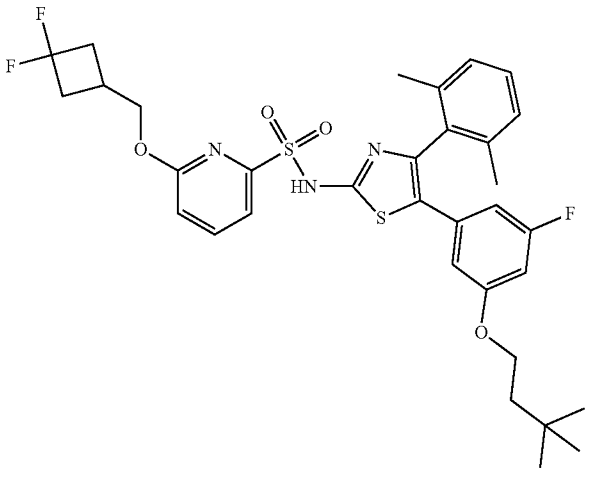 [SMILES: Cc1cccc(C)c1-c1nc(NS(=O)(=O)c2cccc(OCC3CC(F)(F)C3)n2)sc1-c1cc(F)cc(OCCC(C)(C)C)c1] | 6-[(3,3-difluorocyclobutyl)methoxy]-N-[5-[3-(3,3-dimethylbutoxy)-5-fluorophenyl]-4-(2,6-dimethylphenyl)-1,3-thiazol-2-yl]pyridine-2-sulfonamide |

TABLE 1-continued

| Compound Number | Compound Structural Formula | Compound Name |
|---|---|---|
| 462 | 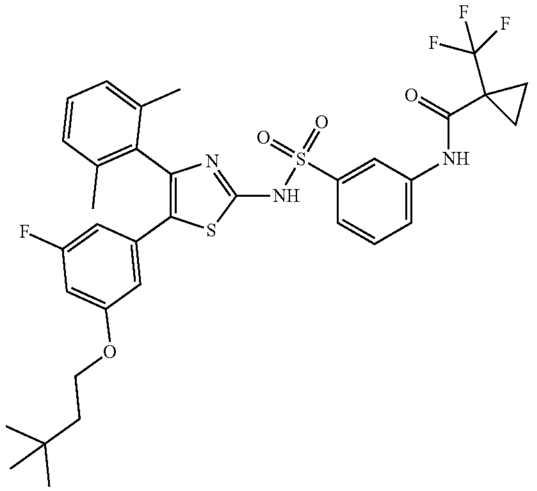 [SMILES: Cc1cccc(C)c1-c1nc(NS(=O)(=O)c2cccc(NC(=O)C3(C(F)(F)F)CC3)c2)sc1-c1cc(F)cc(OCCC(C)(C)C)c1] | N-[3-[5-[3-(3,3-dimethylbutoxy)-5-fluorophenyl]-4-(2,6-dimethylphenyl)-1,3-thiazol-2-yl]sulfamoyl]phenyl]-1-(trifluoromethyl)cyclopropane-1-carboxamide |
| 553 | 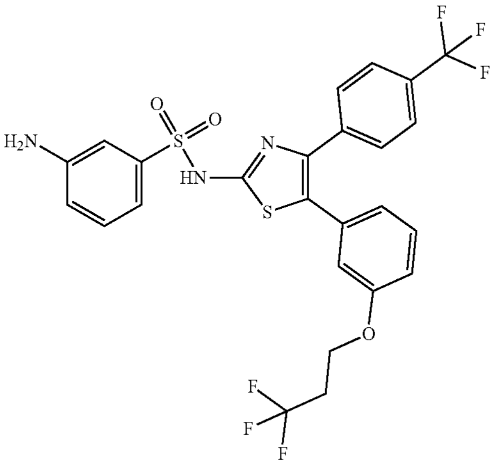 [SMILES: Nc1cccc(S(=O)(=O)Nc2nc(-c3ccc(C(F)(F)F)cc3)c(-c3cccc(OCCC(F)(F)F)c3)s2)c1] | 3-amino-N-(4-(4-(trifluoromethyl)phenyl)-5-(3-(3,3,3-trifluoropropoxy)phenyl)thiazol-2-yl)benzenesulfonamide |
| 425 | 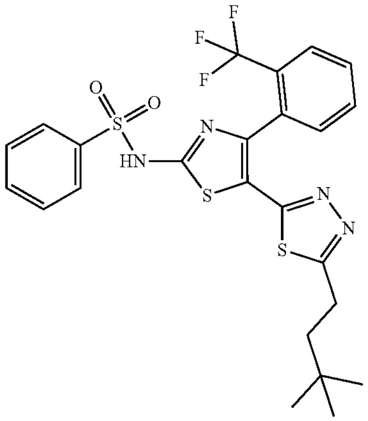 [SMILES: CC(C)(C)CCc1nnc(-c2sc(NS(=O)(=O)c3ccccc3)nc2-c2ccccc2C(F)(F)F)s1] | N-[5-[5-(3,3-dimethylbutyl)-1,3,4-thiadiazol-2-yl]-4-[2-(trifluoromethyl)phenyl]-1,3-thiazol-2-yl]benzenesulfonamide |

TABLE 1-continued

| Compound Number | Compound Structural Formula | Compound Name |
|---|---|---|
| 182 | 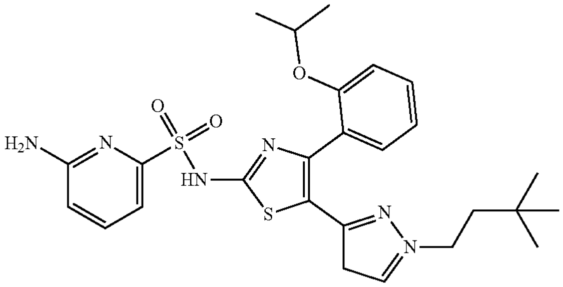 | 6-amino-N-[5-[1-(3,3-dimethylbutyl)pyrazol-3-yl]-4-(2-propan-2-yloxyphenyl)-1,3-thiazol-2-yl]pyridine-2-sulfonamide |
| 320 | 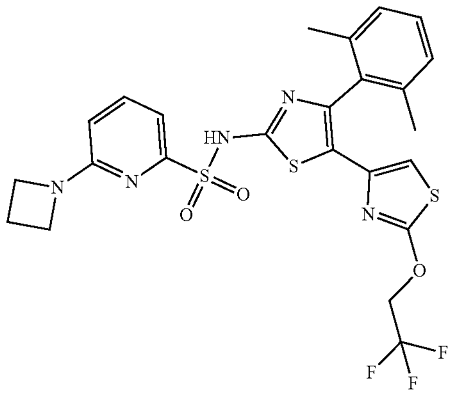 [SMILES: Cc1cccc(C)c1-c1nc(NS(=O)(=O)c2cccc(N3CCC3)n2)sc1-c1csc(OCC(F)(F)F)n1] | 6-(azetidin-1-yl)-N-[4-(2,6-dimethylphenyl)-5-[2-(2,2,2-trifluoroethoxy)-1,3-thiazol-4-yl]-1,3-thiazol-2-yl]pyridine-2-sulfonamide |
| 400 | 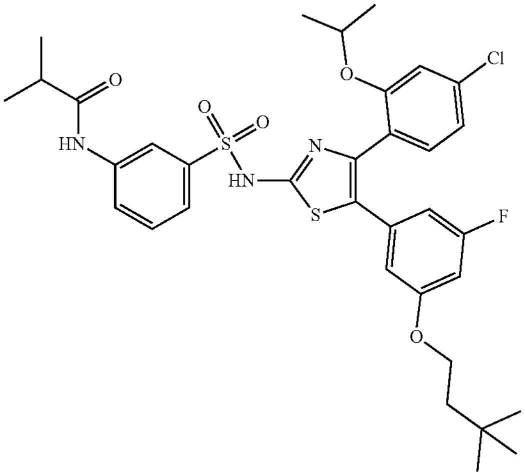 [SMILES: CC(C)Oc1cc(Cl)ccc1-c1nc(NS(=O)(=O)c2cccc(NC(=O)C(C)C)c2)sc1-c1cc(F)cc(OCCC(C)(C)C)c1] | N-[3-[4-(4-chloro-2-propan-2-yloxyphenyl)-5-[3-(3,3-dimethylbutoxy)-5-fluorophenyl]-1,3-thiazol-2-yl]sulfamoyl]phenyl]-2-methylpropanamide |
| 394 | 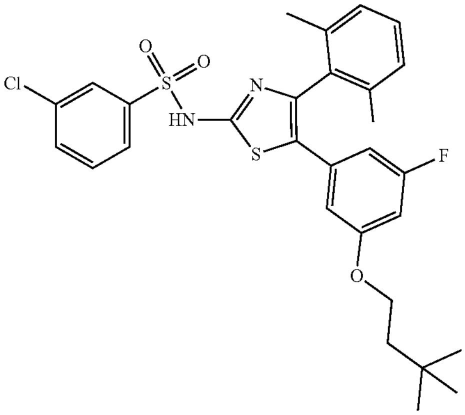 [SMILES: Cc1cccc(C)c1-c1nc(NS(=O)(=O)c2cccc(Cl)c2)sc1-c1cc(F)cc(OCCC(C)(C)C)c1] | 3-chloro-N-[5-[3-(3,3-dimethylbutoxy)-5-fluorophenyl]-4-(2,6-dimethylphenyl)-1,3-thiazol-2-yl]benzenesulfonamide |

TABLE 1-continued

| Compound Number | Compound Structural Formula | Compound Name |
|---|---|---|
| 289 | 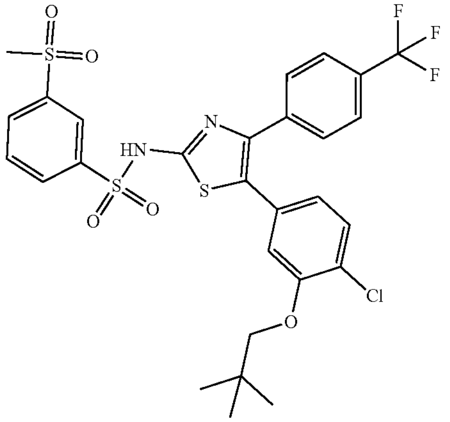 [SMILES: CC(C)(C)COc1cc(-c2sc(NS(=O)(=O)c3cccc(S(C)(=O)=O)c3)nc2-c2ccc(C(F)(F)F)cc2)ccc1Cl] | N-[5-[4-chloro-3-(2,2-dimethylpropoxy)phenyl]-4-[4-(trifluoromethyl)phenyl]-1,3-thiazol-2-yl]-3-methylsulfonylbenzenesulfonamide |
| 554 | 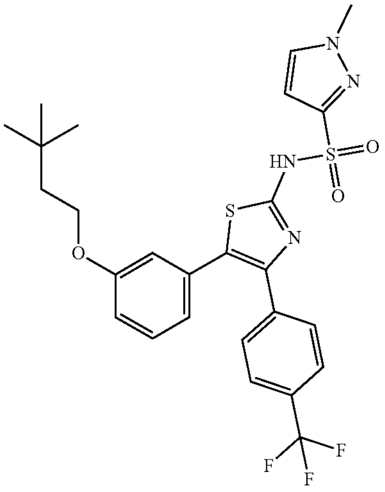 [SMILES: Cn1ccc(S(=O)(=O)Nc2nc(-c3ccc(C(F)(F)F)cc3)c(-c3cccc(OCCC(C)(C)C)c3)s2)n1] | N-(5-(3-(3,3-dimethylbutoxy)phenyl)-4-(4-(trifluoromethyl)phenyl)thiazol-2-yl)-1-methyl-1H-pyrazole-3-sulfonamide |
| 104 | 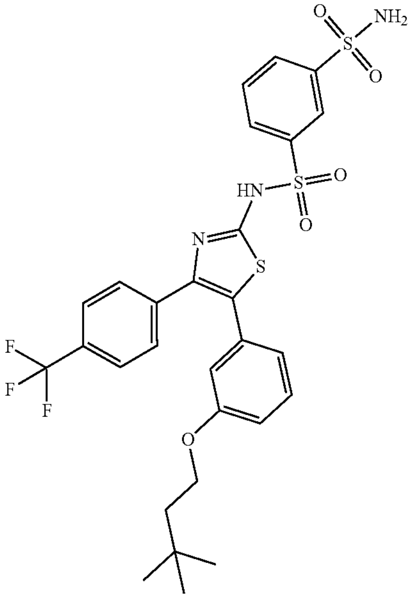 [SMILES: CC(C)(C)CCOc1cccc(-c2sc(NS(=O)(=O)c3cccc(S(N)(=O)=O)c3)nc2-c2ccc(C(F)(F)F)cc2)c1] | 3-N-[5-[3-(3,3-dimethylbutoxy)phenyl]-4-[4-(trifluoromethyl)phenyl]-1,3-thiazol-2-yl]benzene-1,3-disulfonamide |

TABLE 1-continued

| Compound Number | Compound Structural Formula | Compound Name |
|---|---|---|
| 555 | 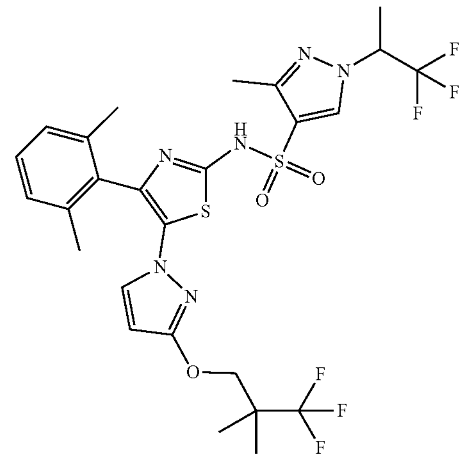 [SMILES: Cc1cccc(C)c1-c1nc(NS(=O)(=O)c2cn(C(C)C(F)(F)F)nc2C)sc1-n1ccc(OCC(C)(C)C(F)(F)F)n1] | N-(4-(2,6-dimethylphenyl)-5-(3-(3,3,3-trifluoro-2,2-dimethylpropoxy)-1H-pyrazol-1-yl)thiazol-2-yl)-3-methyl-1-(1,1,1-trifluoropropan-2-yl)-1H-pyrazole-4-sulfonamide |
| 426 | 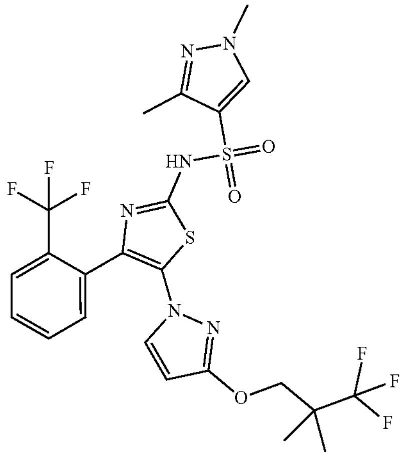 [SMILES: Cc1nn(C)cc1S(=O)(=O)Nc1nc(-c2ccccc2C(F)(F)F)c(-n2ccc(OCC(C)(C)C(F)(F)F)n2)s1] | 1,3-dimethyl-N-[5-[3-(3,3,3-trifluoro-2,2-dimethylpropoxy)pyrazol-1-yl]-4-[2-(trifluoromethyl)phenyl]-1,3-thiazol-2-yl]pyrazole-4-sulfonamide |
| 483 | 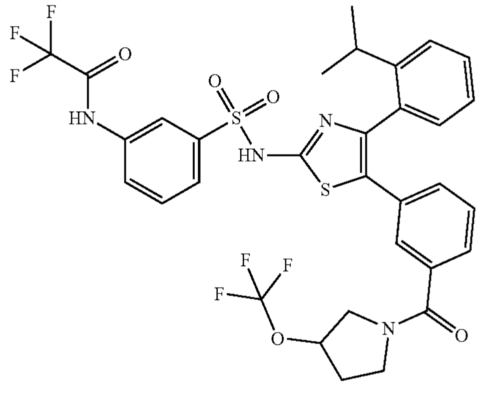 [SMILES: CC(C)c1ccccc1-c1nc(NS(=O)(=O)c2cccc(NC(=O)C(F)(F)F)c2)sc1-c1cccc(C(=O)N2CCC(OC(F)(F)F)C2)c1] | 2,2,2-trifluoro-N-[3-[[4-(2-propan-2-ylphenyl)-5-[3-[3-(trifluoromethoxy)pyrrolidine-1-carbonyl]phenyl]-1,3-thiazol-2-yl]sulfamoyl]phenyl]acetamide |

TABLE 1-continued

| Compound Number | Compound Structural Formula | Compound Name |
|---|---|---|
| 485 | 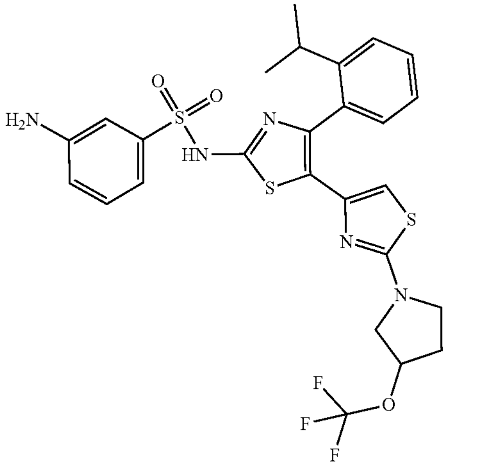 [SMILES: CC(C)c1ccccc1-c1nc(NS(=O)(=O)c2cccc(N)c2)sc1-c1csc(N2CCC(OC(F)(F)F)C2)n1] | 3-amino-N-[4-(2-propan-2-ylphenyl)-5-[2-[3-(trifluoromethoxy)pyrrolidin-1-yl]-1,3-thiazol-4-yl]-1,3-thiazol-2-yl]benzenesulfonamide |
| 556 | 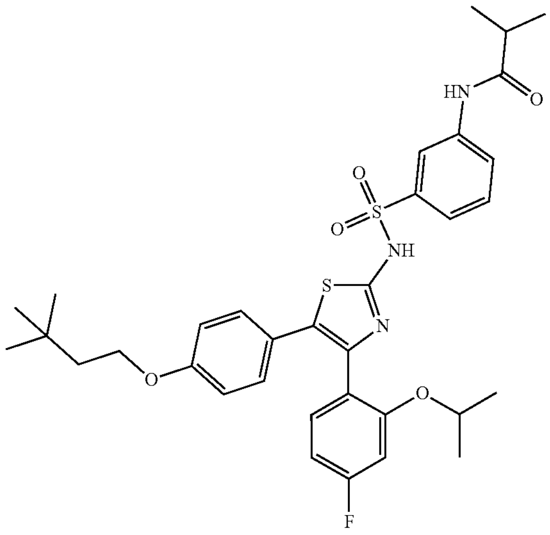 [SMILES: CC(C)Oc1cc(F)ccc1-c1nc(NS(=O)(=O)c2cccc(NC(=O)C(C)C)c2)sc1-c1ccc(OCCC(C)(C)C)cc1] | N-(3-(N-(5-(4-(3,3-dimethylbutoxy)phenyl)-4-(4-fluoro-2-isopropoxyphenyl)thiazol-2-yl)sulfamoyl)phenyl)isobutyramide |
| 287 | 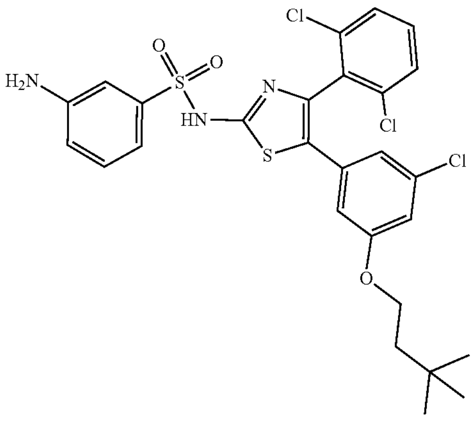 [SMILES: CC(C)(C)CCOc1cc(Cl)cc(-c2sc(NS(=O)(=O)c3cccc(N)c3)nc2-c2c(Cl)cccc2Cl)c1] | 3-amino-N-[5-[3-chloro-5-(3,3-dimethylbutoxy)phenyl]-4-(2,6-dichlorophenyl)-1,3-thiazol-2-yl]benzenesulfonamide |

TABLE 1-continued

| Compound Number | Compound Structural Formula | Compound Name |
| --- | --- | --- |
| 557 | 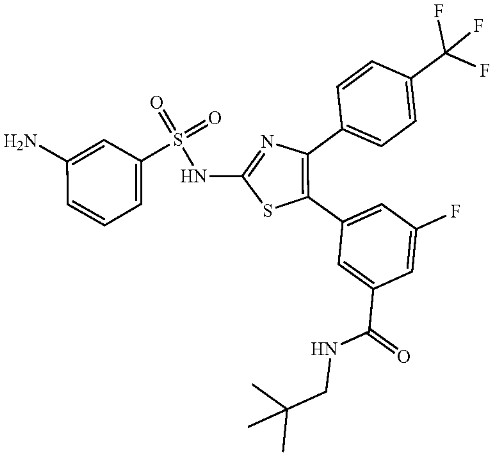 [SMILES: CC(C)(C)CNC(=O)c1cc(F)cc(-c2sc(NS(=O)(=O)c3cccc(N)c3)nc2-c2ccc(C(F)(F)F)cc2)c1] | 3-(2-((3-aminophenyl)sulfonamido)-4-(4-(trifluoromethyl)phenyl)thiazol-5-yl)-5-fluoro-N-neopentylbenzamide |
| 334 | 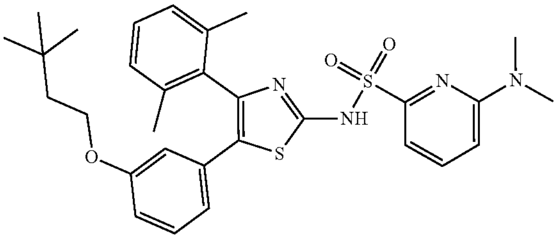 [SMILES: Cc1cccc(C)c1-c1nc(NS(=O)(=O)c2cccc(N(C)C)n2)sc1-c1cccc(OCCC(C)(C)C)c1] | 6-(dimethylamino)-N-[5-[3-(3,3-dimethylbutoxy)phenyl]-4-(2,6-dimethylphenyl)-1,3-thiazol-2-yl]pyridine-2-sulfonamide |
| 558 | 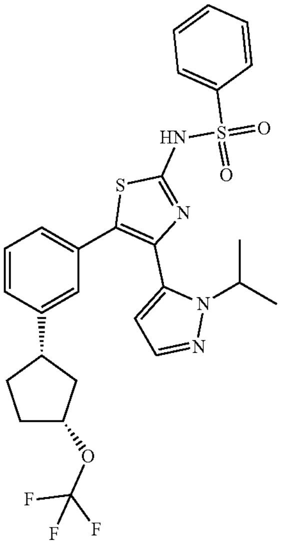 [SMILES: CC(C)n1nccc1-c1nc(NS(=O)(=O)c2ccccc2)sc1-c1cccc([C@H]2CC[C@@H](OC(F)(F)F)C2)c1] | N-(4-(1-isopropyl-1H-pyrazol-5-yl)-5-(3-((1S,3R)-3-(trifluoromethoxy)cyclopentyl)phenyl)thiazol-2-yl)benzenesulfonamide |

TABLE 1-continued

| Compound Number | Compound Structural Formula | Compound Name |
|---|---|---|
| 338 | 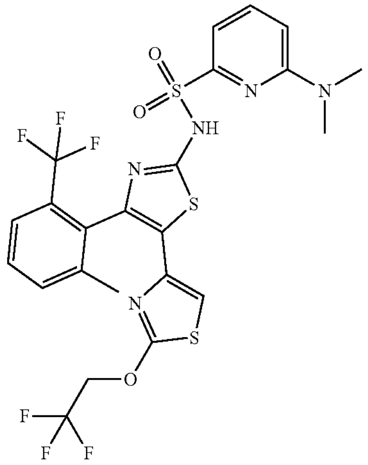 [SMILES: Cc1cccc(C(F)(F)F)c1-c1nc(NS(=O)(=O)c2cccc(N(C)C)n2)sc1-c1csc(OCC(F)(F)F)n1] | 6-(dimethylamino)-N-[4-[2-methyl-6-(trifluoromethyl)phenyl]-5-[2-(2,2,2-trifluoroethoxy)-1,3-thiazol-4-yl]-1,3-thiazol-2-yl]pyridine-2-sulfonamide |
| 339 | 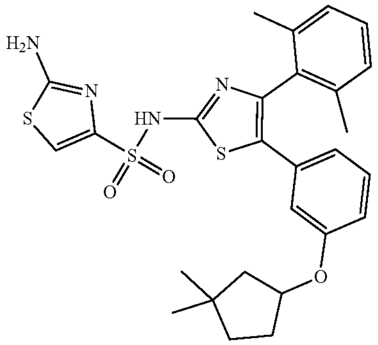 [SMILES: Cc1cccc(C)c1-c1nc(NS(=O)(=O)c2csc(N)n2)sc1-c1cccc(OC2CCC(C)(C)C2)c1] | 2-amino-N-[5-[3-(3,3-dimethylcyclopentyl)oxyphenyl]-4-(2,6-dimethylphenyl)-1,3-thiazol-2-yl]-1,3-thiazole-4-sulfonamide |
| 108 | 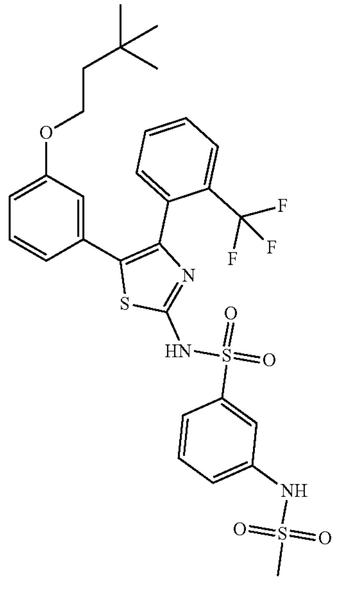 [SMILES: CC(C)(C)CCOc1cccc(-c2sc(NS(=O)(=O)c3cccc(NS(C)(=O)=O)c3)nc2-c2ccccc2C(F)(F)F)c1] | N-[5-[3-(3,3-dimethylbutoxy)phenyl]-4-[2-(trifluoromethyl)phenyl]-1,3-thiazol-2-yl]-3-(methanesulfonamido)benzenesulfonamide |

TABLE 1-continued

| Compound Number | Compound Structural Formula | Compound Name |
|---|---|---|
| 559 | 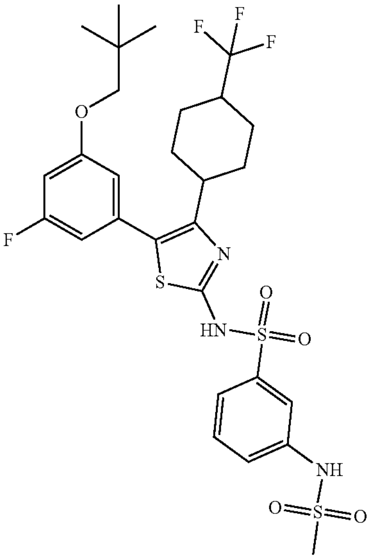 [SMILES: CC(C)(C)COc1cc(F)cc(-c2sc(NS(=O)(=O)c3cccc(NS(C)(=O)=O)c3)nc2C2CCC(C(F)(F)F)CC2)c1] | N-(5-(3-fluoro-5-(neopentyloxy)phenyl)-4-(4-(trifluoromethyl)cyclohexyl)thiazol-2-yl)-3-(methylsulfonamido)benzenesulfonamide |
| 423 | 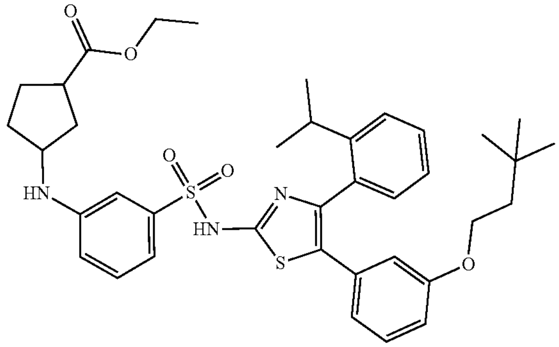 [SMILES: CCOC(=O)C1CCC(Nc2cccc(S(=O)(=O)Nc3nc(-c4ccccc4C(C)C)c(-c4cccc(OCCC(C)(C)C)c4)s3)c2)C1] | ethyl 3-[3-[[5-[3-(3,3-dimethylbutoxy)phenyl]-4-(2-propan-2-ylphenyl)-1,3-thiazol-2-yl]sulfamoyl]anilino]cyclopentane-1-carboxylate |
| 45A2 | 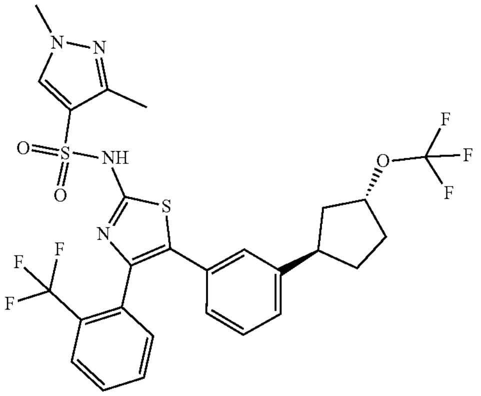 [SMILES: Cc1nn(C)cc1S(=O)(=O)Nc1nc(-c2ccccc2C(F)(F)F)c(-c2cccc([C@@H]3CC[C@@H](OC(F)(F)F)C3)c2)s1] | 1,3-dimethyl-N-[5-[3-[(1R,3R)-3-(trifluoromethoxy)cyclopentyl]phenyl]-4-[2-(trifluoromethyl)phenyl]-1,3-thiazol-2-yl]pyrazole-4-sulfonamide |

TABLE 1-continued

| Compound Number | Compound Structural Formula | Compound Name |
|---|---|---|
| 45B2 | 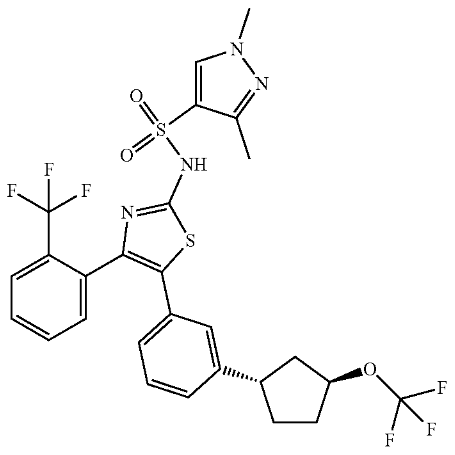 [SMILES: Cc1nn(C)cc1S(=O)(=O)Nc1nc(-c2ccccc2C(F)(F)F)c(-c2cccc([C@H]3CC[C@H](OC(F)(F)F)C3)c2)s1] | 1,3-dimethyl-N-[5-[3-[(1S,3S)-3-(trifluoromethoxy)cyclopentyl]phenyl]-4-[2-(trifluoromethyl)phenyl]-1,3-thiazol-2-yl]pyrazole-4-sulfonamide |
| 560 | 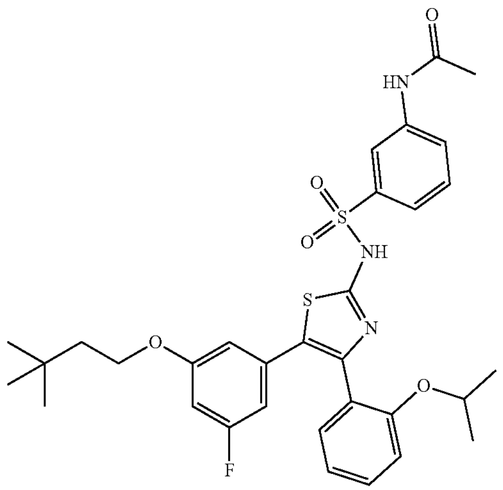 [SMILES: CC(=O)Nc1cccc(S(=O)(=O)Nc2nc(-c3ccccc3OC(C)C)c(-c3cc(F)cc(OCCC(C)(C)C)c3)s2)c1] | N-(3-(N-(5-(3-(3,3-dimethylbutoxy)-5-fluorophenyl)-4-(2-isopropoxyphenyl)thiazol-2-yl)sulfamoyl)phenyl)acetamide |
| 71 | 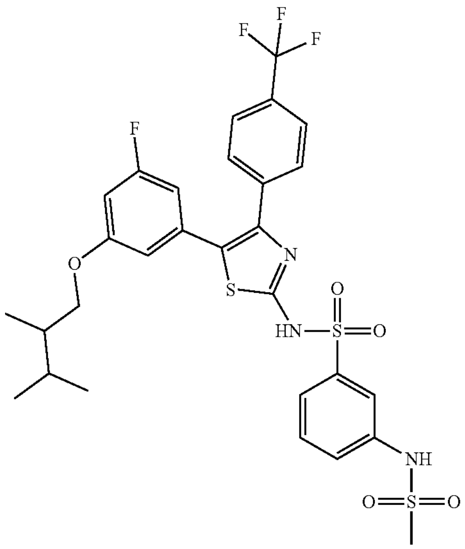 [SMILES: CC(C)C(C)COc1cc(F)cc(-c2sc(NS(=O)(=O)c3cccc(NS(C)(=O)=O)c3)nc2-c2ccc(C(F)(F)F)cc2)c1] | N-[5-[3-(2,3-dimethylbutoxy)-5-fluorophenyl]-4-[4-(trifluoromethyl)phenyl]-1,3-thiazol-2-yl]-3-(methanesulfonamido)benzenesulfonamide |

TABLE 1-continued

| Compound Number | Compound Structural Formula | Compound Name |
|---|---|---|
| 236 | 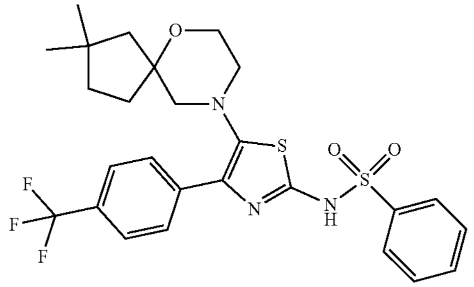 [SMILES: CC1(C)CCC2(CN(c3sc(NS(=O)(=O)c4ccccc4)nc3-c3ccc(C(F)(F)F)cc3)CCO2)C1] | N-[5-(3,3-dimethyl-6-oxa-9-azaspiro[4.5]decan-9-yl)-4-[4-(trifluoromethyl)phenyl]-1,3-thiazol-2-yl]benzenesulfonamide |
| 388 | 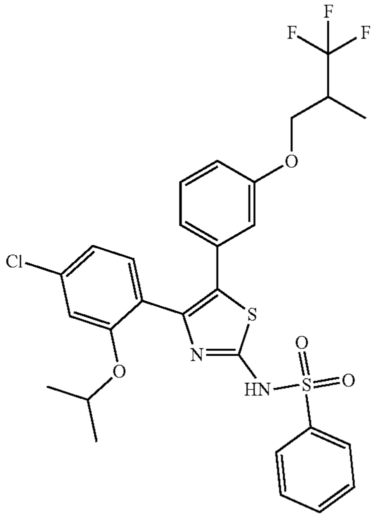 [SMILES: CC(C)Oc1cc(Cl)ccc1-c1nc(NS(=O)(=O)c2ccccc2)sc1-c1cccc(OCC(C)C(F)(F)F)c1] | N-[4-(4-chloro-2-propan-2-yloxyphenyl)-5-[3-(3,3,3-trifluoro-2-methylpropoxy)phenyl]-1,3-thiazol-2-yl]benzenesulfonamide |
| 169 | 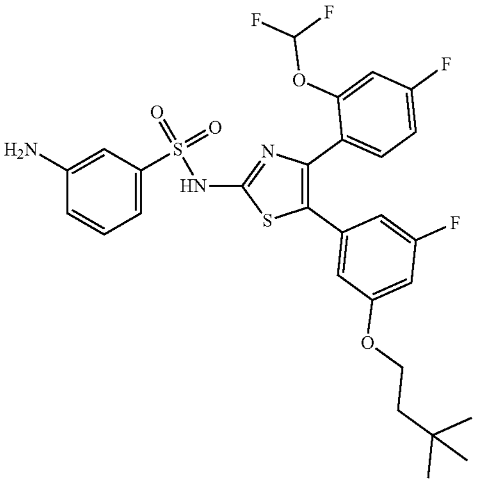 [SMILES: CC(C)(C)CCOc1cc(F)cc(-c2sc(NS(=O)(=O)c3cccc(N)c3)nc2-c2ccc(F)cc2OC(F)F)c1] | 3-amino-N-[4-[2-(difluoromethoxy)-4-fluorophenyl]-5-[3-(3,3-dimethylbutoxy)-5-fluorophenyl]-1,3-thiazol-2-yl]benzenesulfonamide |

TABLE 1-continued
| Compound Number | Compound Structural Formula | Compound Name |
|---|---|---|
| 107 | 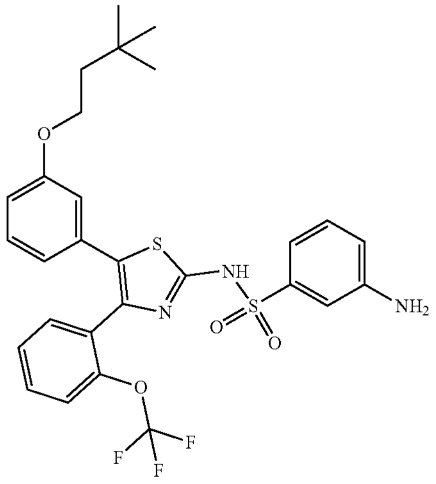 [SMILES: CC(C)(C)CCOc1cccc(-c2sc(NS(=O)(=O)c3cccc(N)c3)nc2-c2ccccc2OC(F)(F)F)c1] | 3-amino-N-[5-[3-(3,3-dimethylbutoxy)phenyl]-4-[2-(trifluoromethoxy)phenyl]-1,3-thiazol-2-yl]benzenesulfonamide |
| 125 | 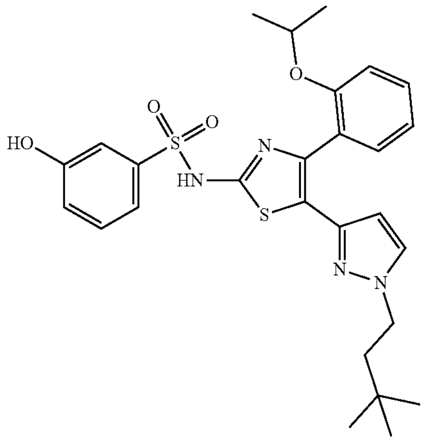 [SMILES: CC(C)Oc1ccccc1-c1nc(NS(=O)(=O)c2cccc(O)c2)sc1-c1ccn(CCC(C)(C)C)n1] | N-[5-[1-(3,3-dimethylbutyl)pyrazol-3-yl]-4-(2-propan-2-yloxyphenyl)-1,3-thiazol-2-yl]-3-hydroxybenzenesulfonamide |
| 67 | 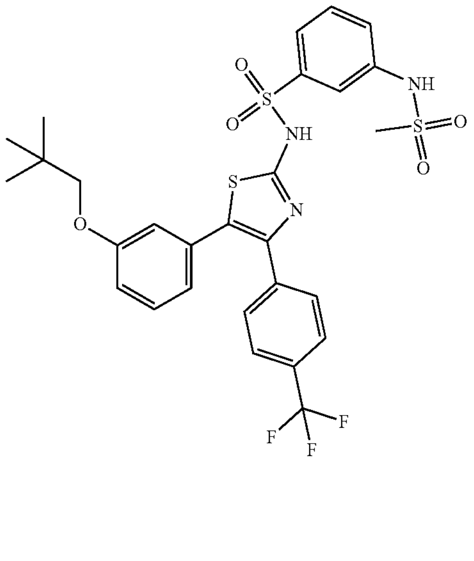 [SMILES: CC(C)(C)COc1cccc(-c2sc(NS(=O)(=O)c3cccc(NS(C)(=O)=O)c3)nc2-c2ccc(C(F)(F)F)cc2)c1] | N-[3-[5-[3-(3,3-dimethylbutoxy)-5-fluorophenyl]-4-[4-(trifluoromethyl)phenyl]-1,3-thiazol-2-yl]sulfamoyl]phenyl]acetamide |

TABLE 1-continued

| Compound Number | Compound Structural Formula | Compound Name |
| --- | --- | --- |
| 439 | 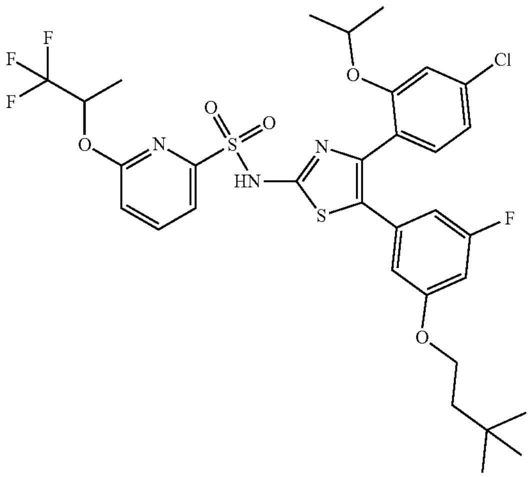 [SMILES: CC(C)Oc1cc(Cl)ccc1-c1nc(NS(=O)(=O)c2cccc(OC(C)C(F)(F)F)n2)sc1-c1cc(F)cc(OCCC(C)(C)C)c1] | N-[4-(4-chloro-2-propan-2-yloxyphenyl)-5-[3-(3,3-dimethylbutoxy)-5-fluorophenyl]-1,3-thiazol-2-yl]-6-(1,1,1-trifluoropropan-2-yloxy)pyridine-2-sulfonamide |
| 561 | 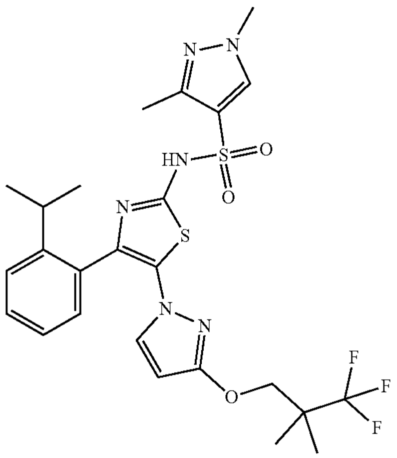 [SMILES: Cc1nn(C)cc1S(=O)(=O)Nc1nc(-c2ccccc2C(C)C)c(-n2ccc(OCC(C)(C)C(F)(F)F)n2)s1] | N-(4-(2-isopropylphenyl)-5-(3-(3,3,3-trifluoro-2,2-dimethylpropoxy)-1H-pyrazol-1-yl)thiazol-2-yl)-1,3-dimethyl-1H-pyrazole-4-sulfonamide |
| 562 | 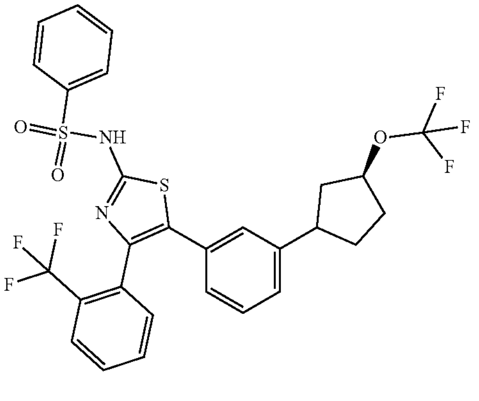 [SMILES: O=S(=O)(Nc1nc(-c2ccccc2C(F)(F)F)c(-c2cccc(C3CC[C@H](OC(F)(F)F)C3)c2)s1)c1ccccc1] | N-(5-(3-((3S)-3-(trifluoromethoxy)cyclopentyl)phenyl)-4-(2-(trifluoromethyl)phenyl)thiazol-2-yl)benzenesulfonamide |

TABLE 1-continued

| Compound Number | Compound Structural Formula | Compound Name |
|---|---|---|
| 149 | 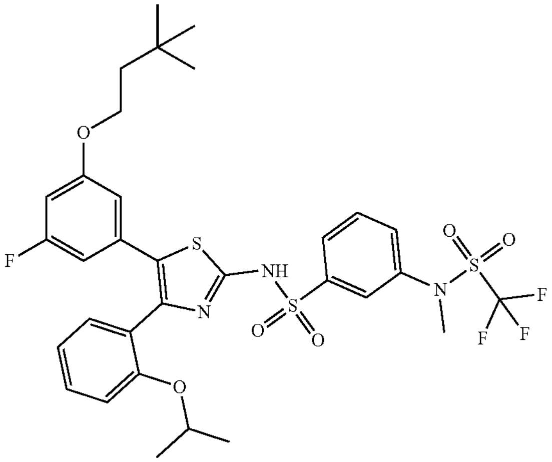 [SMILES: CC(C)Oc1ccccc1-c1nc(NS(=O)(=O)c2cccc(N(C)S(=O)(=O)C(F)(F)F)c2)sc1-c1cc(F)cc(OCCC(C)(C)C)c1] | N-[5-[3-(3,3-dimethylbutoxy)-5-fluorophenyl]-4-(2-propan-2-yloxyphenyl)-1,3-thiazol-2-yl]-3-[methyl(trifluoromethylsulfonyl)amino] benzenesulfonamide |
| 563 | 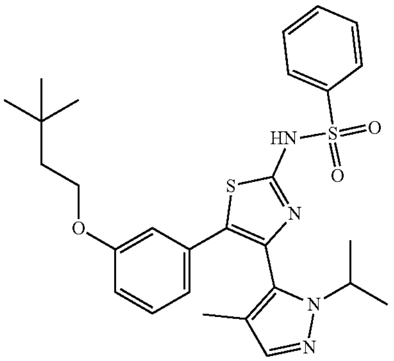 [SMILES: Cc1cnn(C(C)C)c1-c1nc(NS(=O)(=O)c2ccccc2)sc1-c1cccc(OCCC(C)(C)C)c1] | N-(5-(3-(3,3-dimethylbutoxy)phenyl)-4-(1-isopropyl-4-methyl-1H-pyrazol-5-yl)thiazol-2-yl)benzenesulfonamide |
| 448 | 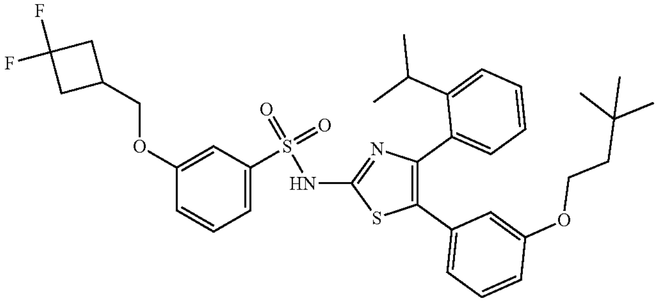 [SMILES: CC(C)c1ccccc1-c1nc(NS(=O)(=O)c2cccc(OCC3CC(F)(F)C3)c2)sc1-c1cccc(OCCC(C)(C)C)c1] | 6-[(3,3-difluorocyclobutyl)methoxy]-N-[5-[3-(3,3-dimethylbutoxy)phenyl]-4-(2-propan-2-ylphenyl)-1,3-thiazol-2-yl]pyridine-2-sulfonamide |

TABLE 1-continued

| Compound Number | Compound Structural Formula | Compound Name |
|---|---|---|
| 229 | 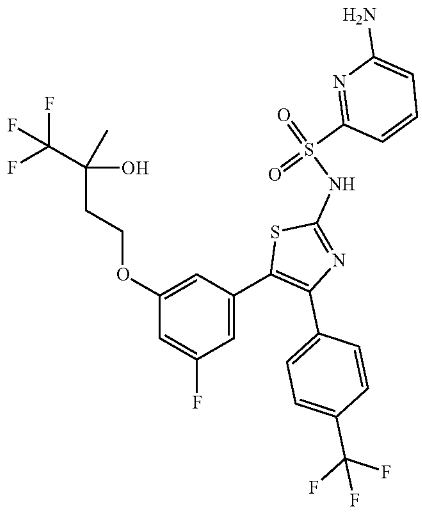 [SMILES: CC(O)(CCOc1cc(F)cc(-c2sc(NS(=O)(=O)c3cccc(N)n3)nc2-c2ccc(C(F)(F)F)cc2)c1)C(F)(F)F] | 6-amino-N-[5-[3-fluoro-5-(4,4,4-trifluoro-3-hydroxy-3-methylbutoxy)phenyl]-4-[4-(trifluoromethyl)phenyl]-1,3-thiazol-2-yl]pyridine-2-sulfonamide |
| 265 | 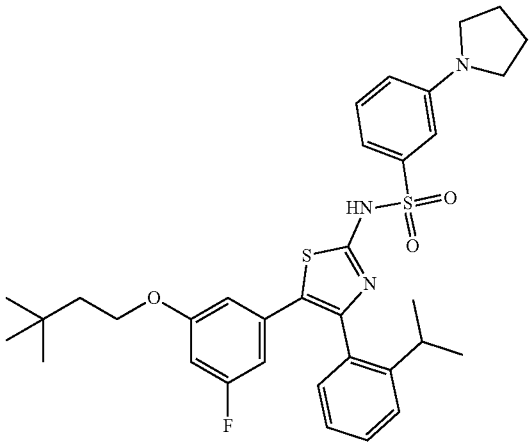 [SMILES: CC(C)c1ccccc1-c1nc(NS(=O)(=O)c2cccc(N3CCCC3)c2)sc1-c1cc(F)cc(OCCC(C)(C)C)c1] | N-[5-[3-(3,3-dimethylbutoxy)-5-fluorophenyl]-4-(2-propan-2-ylphenyl)-1,3-thiazol-2-yl]-3-pyrrolidin-1-ylbenzenesulfonamide |
| 331 | 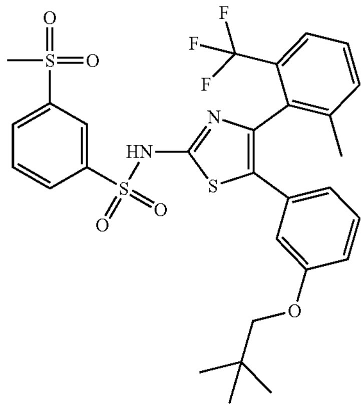 [SMILES: Cc1cccc(C(F)(F)F)c1-c1nc(NS(=O)(=O)c2cccc(S(C)(=O)=O)c2)sc1-c1cccc(OCC(C)(C)C)c1] | N-[5-[3-(2,2-dimethylpropoxy)phenyl]-4-[2-methyl-6-(trifluoromethyl)phenyl]-1,3-thiazol-2-yl]-3-methylsulfonylbenzenesulfonamide |

TABLE 1-continued

| Compound Number | Compound Structural Formula | Compound Name |
|---|---|---|
| 465 | 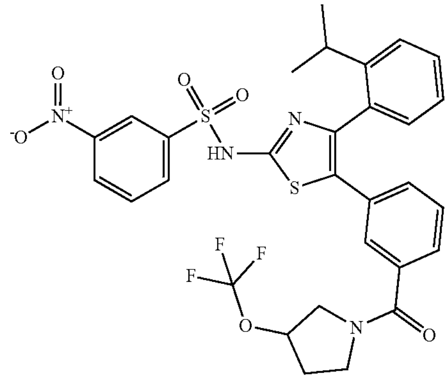 | 3-nitro-N-[4-(2-propan-2-ylphenyl)-5-[3-[3-(trifluoromethoxy)pyrrolidine-1-carbonyl]phenyl]-1,3-thiazol-2-yl]benzenesulfonamide |
| 564 | 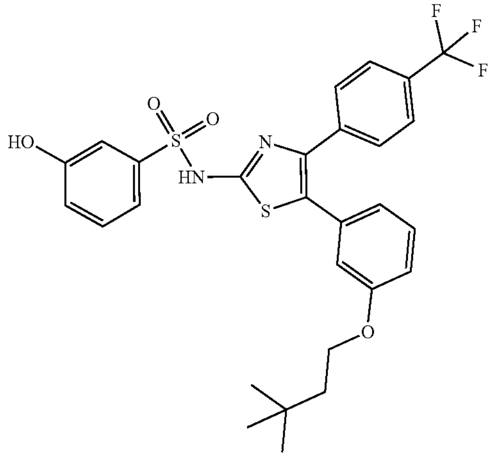 [SMILES: CC(C)(C)CCOc1cccc(-c2sc(NS(=O)(=O)c3cccc(O)c3)nc2-c2ccc(C(F)(F)F)cc2)c1] | N-(5-(3-(3,3-dimethylbutoxy)phenyl)-4-(4-(trifluoromethyl)phenyl)thiazol-2-yl)-3-hydroxybenzenesulfonamide |
| 47B2 | 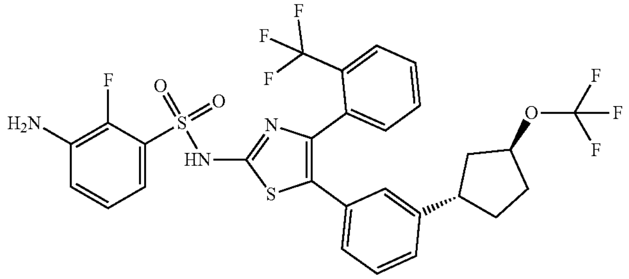 [SMILES: Nc1cccc(S(=O)(=O)Nc2nc(-c3ccccc3C(F)(F)F)c(-c3cccc([C@H]4CC[C@H](OC(F)(F)F)C4)c3)s2)c1F] | 3-amino-2-fluoro-N-[5-[3-[(1S,3S)-3-(trifluoromethoxy)cyclopentyl]phenyl]-4-[2-(trifluoromethyl)phenyl]-1,3-thiazol-2-yl]benzenesulfonamide |

TABLE 1-continued

| Compound Number | Compound Structural Formula | Compound Name |
| --- | --- | --- |
| 325 | 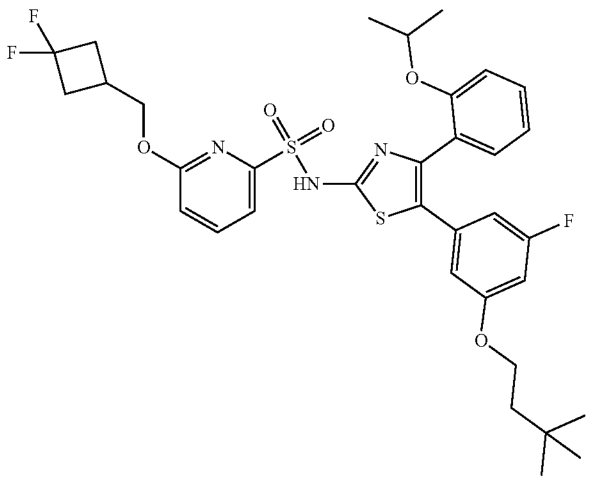 [SMILES: CC(C)Oc1ccccc1-c1nc(NS(=O)(=O)c2cccc(OCC3CC(F)(F)C3)n2)sc1-c1cc(F)cc(OCCC(C)(C)C)c1] | 6-[(3,3-difluorocyclobutyl)methoxy]-N-[5-[3-(3,3-dimethylbutoxy)-5-fluorophenyl]-4-(2-propan-2-yloxyphenyl)-1,3-thiazol-2-yl]pyridine-2-sulfonamide |
| 358 | 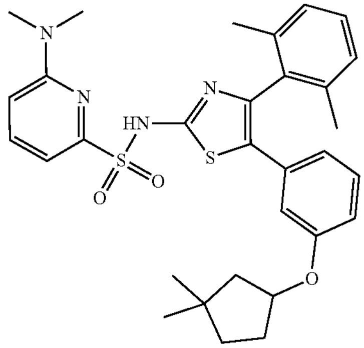 [SMILES: Cc1cccc(C)c1-c1nc(NS(=O)(=O)c2cccc(N(C)C)n2)sc1-c1cccc(OC2CCC(C)(C)C2)c1] | 6-(dimethylamino)-N-[5-[3-(3,3-dimethylcyclopentyl)oxyphenyl]-4-(2,6-dimethylphenyl)-1,3-thiazol-2-yl]pyridine-2-sulfonamide |
| 428 | 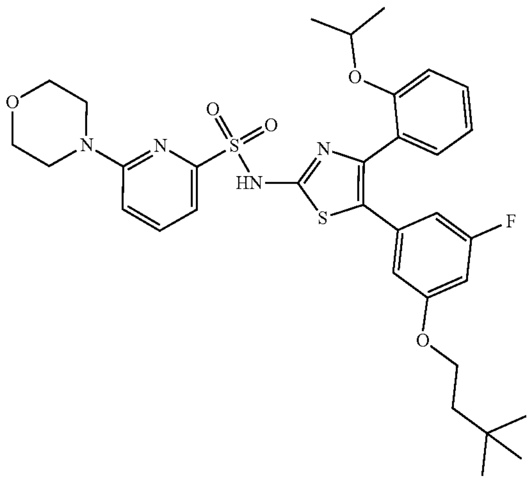 [SMILES: CC(C)Oc1ccccc1-c1nc(NS(=O)(=O)c2cccc(N3CCOCC3)n2)sc1-c1cc(F)cc(OCCC(C)(C)C)c1] | N-[5-[3-(3,3-dimethylbutoxy)-5-fluorophenyl]-4-(2-propan-2-yloxyphenyl)-1,3-thiazol-2-yl]-6-morpholin-4-ylpyridine-2-sulfonamide |

TABLE 1-continued
| Compound Number | Compound Structural Formula | Compound Name |
|---|---|---|
| 8 | 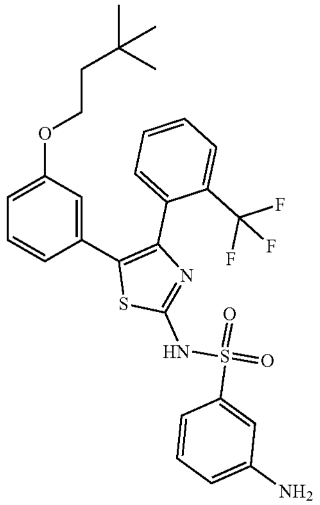 [SMILES: CC(C)(C)CCOc1cccc(-c2sc(NS(=O)(=O)c3cccc(N)c3)nc2-c2ccccc2C(F)(F)F)c1] | 3-amino-N-(5-(3-(3,3-dimethylbutoxy)phenyl)-4-(2-(trifluoromethyl)phenyl)thiazol-2-yl)benzenesulfonamide |
| 501 | 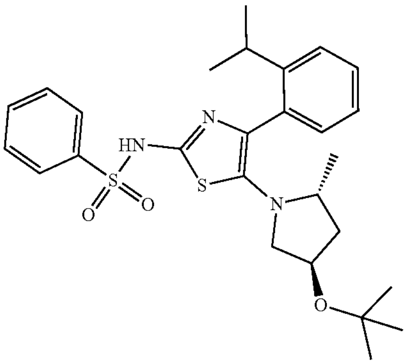 [SMILES: CC(C)c1ccccc1-c1nc(NS(=O)(=O)c2ccccc2)sc1N1C[C@H](OC(C)(C)C)C[C@H]1C] | N-[5-[(2R,4R)-2-methyl-4-[(2-methylpropan-2-yl)oxy]pyrrolidin-1-yl]-4-(2-propan-2-ylphenyl)-1,3-thiazol-2-yl]benzenesulfonamide |
| 565 | 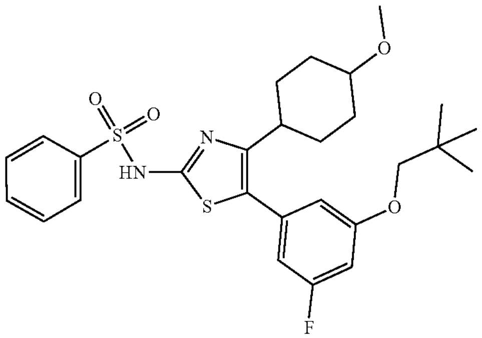 [SMILES: COC1CCC(c2nc(NS(=O)(=O)c3ccccc3)sc2-c2cc(F)cc(OCC(C)(C)C)c2)CC1] | N-(5-(3-fluoro-5-(neopentyloxy)phenyl)-4-(4-methoxycyclohexyl)thiazol-2-yl)benzenesulfonamide |

TABLE 1-continued

| Compound Number | Compound Structural Formula | Compound Name |
|---|---|---|
| 134 | 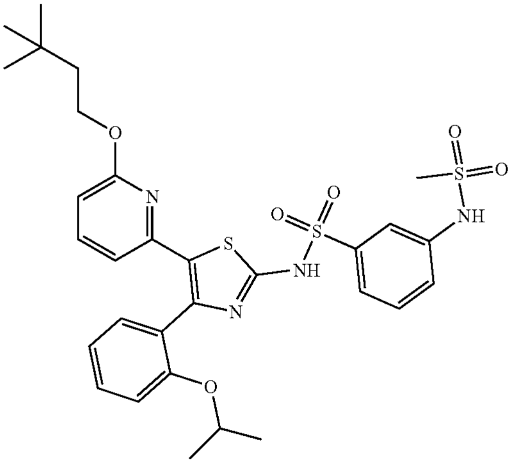 [SMILES: CC(C)Oc1ccccc1-c1nc(NS(=O)(=O)c2cccc(NS(C)(=O)=O)c2)sc1-c1cccc(OCCC(C)(C)C)n1] | N-[5-[6-(3,3-dimethylbutoxy)pyridin-2-yl]-4-(2-propan-2-yloxyphenyl)-1,3-thiazol-2-yl]-3-(methanesulfonamido)benzenesulfonamide |
| 142 | 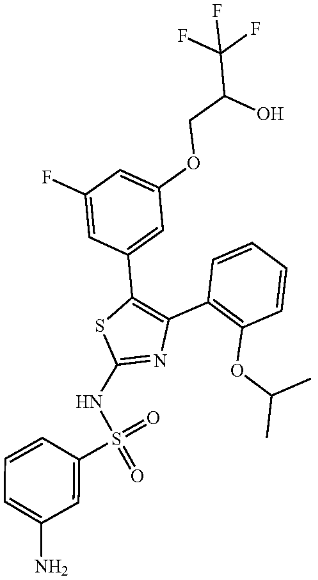 [SMILES: CC(C)Oc1ccccc1-c1nc(NS(=O)(=O)c2cccc(N)c2)sc1-c1cc(F)cc(OCC(O)C(F)(F)F)c1] | 3-amino-N-[5-[3-fluoro-5-(3,3,3-trifluoro-2-hydroxypropoxy)phenyl]-4-(2-propan-2-yloxyphenyl)-1,3-thiazol-2-yl]benzenesulfonamide |
| 451 | 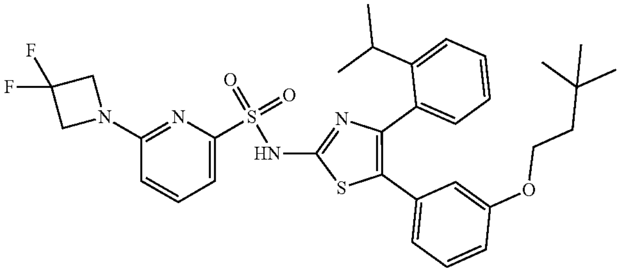 [SMILES: CC(C)c1ccccc1-c1nc(NS(=O)(=O)c2cccc(N3CC(F)(F)C3)n2)sc1-c1cccc(OCCC(C)(C)C)c1] | 6-(3,3-difluoroazetidin-1-yl)-N-[5-[3-(3,3-dimethylbutoxy)phenyl]-4-(2-propan-2-ylphenyl)-1,3-thiazol-2-yl]pyridine-2-sulfonamide |

TABLE 1-continued

| Compound Number | Compound Structural Formula | Compound Name |
|---|---|---|
| 245 | 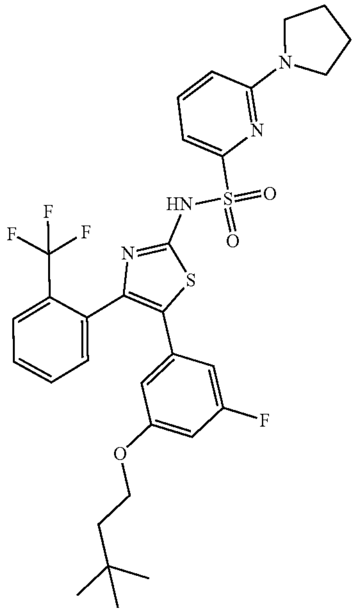 [SMILES: CC(C)(C)CCOc1cc(F)cc(-c2sc(NS(=O)(=O)c3cccc(N4CCCC4)n3)nc2-c2ccccc2C(F)(F)F)c1] | N-[5-[3-(3,3-dimethylbutoxy)-5-fluorophenyl]-4-[2-(trifluoromethyl)phenyl]-1,3-thiazol-2-yl]-6-pyrrolidin-1-ylpyridine-2-sulfonamide |
| 241 | 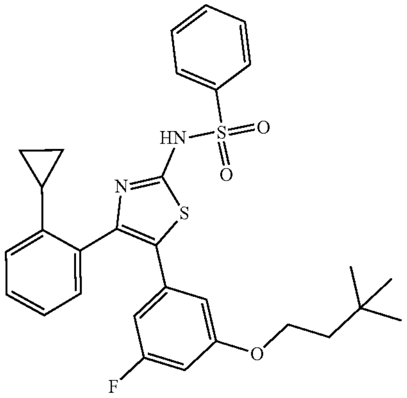 [SMILES: CC(C)(C)CCOc1cc(F)cc(-c2sc(NS(=O)(=O)c3ccccc3)nc2-c2ccccc2C2CC2)c1] | N-[4-(2-cyclopropylphenyl)-5-[3-(3,3-dimethylbutoxy)-5-fluorophenyl]-1,3-thiazol-2-yl]benzenesulfonamide |
| 220 | 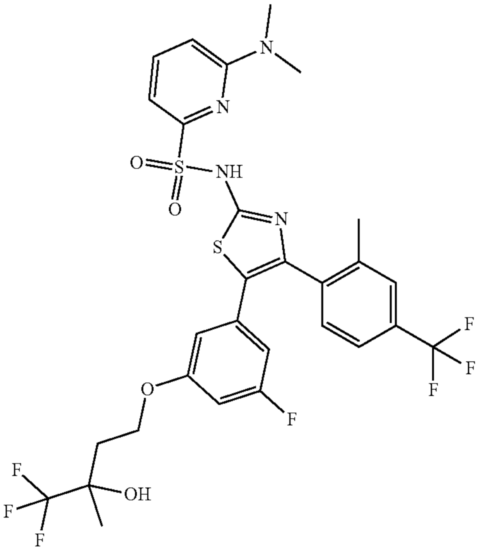 [SMILES: Cc1cc(C(F)(F)F)ccc1-c1nc(NS(=O)(=O)c2cccc(N(C)C)n2)sc1-c1cc(F)cc(OCCC(C)(O)C(F)(F)F)c1] | 6-(dimethylamino)-N-[5-[3-fluoro-5-(4,4,4-trifluoro-3-hydroxy-3-methylbutoxy)phenyl]-4-[2-methyl-4-(trifluoromethyl)phenyl]-1,3-thiazol-2-yl]pyridine-2-sulfonamide |

TABLE 1-continued
| Compound Number | Compound Structural Formula | Compound Name |
|---|---|---|
| 456 | 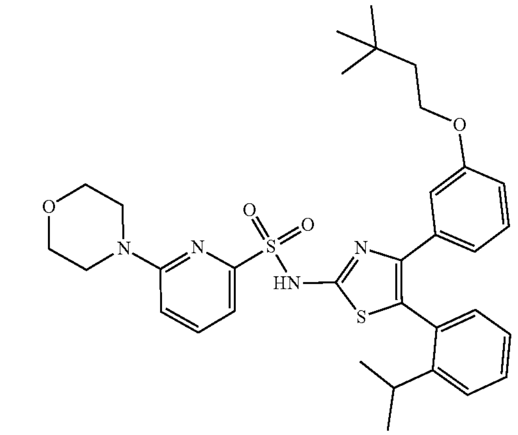 [SMILES: CC(C)c1ccccc1-c1sc(NS(=O)(=O)c2cccc(N3CCOCC3)n2)nc1-c1cccc(OCCC(C)(C)C)c1] | N-[4-[3-(3,3-dimethylbutoxy)phenyl]-5-(2-propan-2-ylphenyl)-1,3-thiazol-2-yl]-6-morpholin-4-ylpyridine-2-sulfonamide |
| 231 | 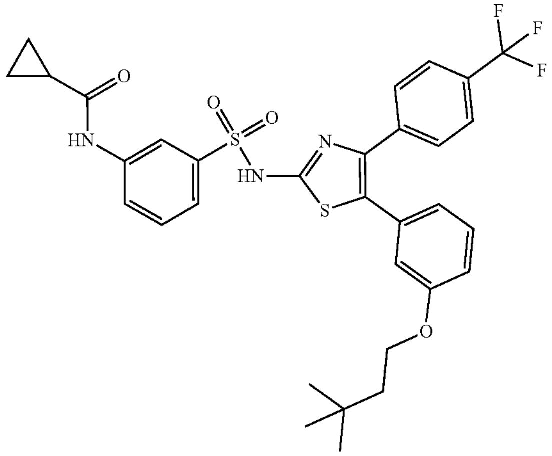 [SMILES: CC(C)(C)CCOc1cccc(-c2sc(NS(=O)(=O)c3cccc(NC(=O)C4CC4)c3)nc2-c2ccc(C(F)(F)F)cc2)c1] | N-[3-[[5-[3-(3,3-dimethylbutoxy)phenyl]-4-[4-(trifluoromethyl)phenyl]-1,3-thiazol-2-yl]sulfamoyl]phenyl] cyclopropanecarboxamide |
| 346 | 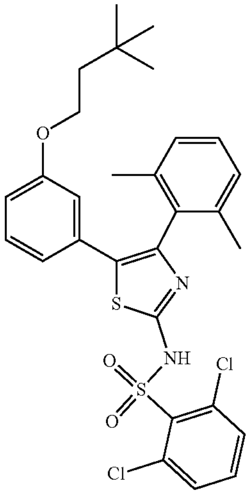 [SMILES: Cc1cccc(C)c1-c1nc(NS(=O)(=O)c2c(Cl)cccc2Cl)sc1-c1cccc(OCCC(C)(C)C)c1] | 2,6-dichloro-N-[5-[3-(3,3-dimethylbutoxy)phenyl]-4-(2,6-dimethylphenyl)-1,3-thiazol-2-yl]benzenesulfonamide |

TABLE 1-continued

| Compound Number | Compound Structural Formula | Compound Name |
|---|---|---|
| 468 | 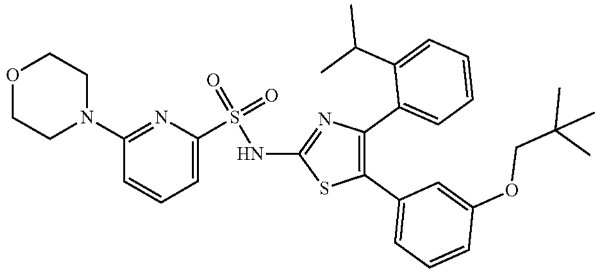 [SMILES: CC(C)c1ccccc1-c1nc(NS(=O)(=O)c2cccc(N3CCOCC3)n2)sc1-c1cccc(OCC(C)(C)C)c1] | N-[5-[3-(2,2-dimethylpropoxy)phenyl]-4-(2-propan-2-ylphenyl)-1,3-thiazol-2-yl]-6-morpholin-4-ylpyridine-2-sulfonamide |
| 111 | 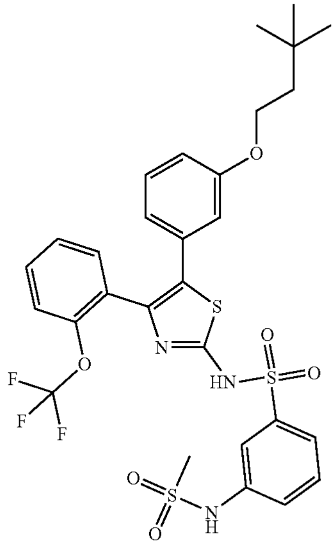 [SMILES: CC(C)(C)CCOc1cccc(-c2sc(NS(=O)(=O)c3cccc(NS(C)(=O)=O)c3)nc2-c2ccccc2OC(F)(F)F)c1] | N-[5-[3-(3,3-dimethylbutoxy)phenyl]-4-[2-(trifluoromethoxy)phenyl]-1,3-thiazol-2-yl]-3-(methanesulfonamido)benzenesulfonamide |
| 267 | 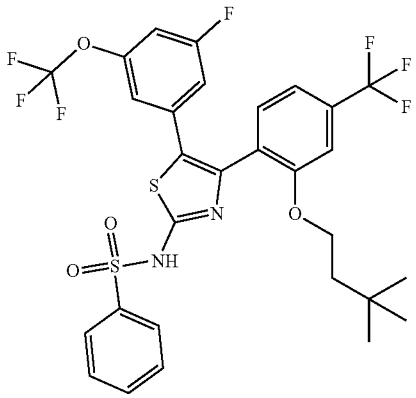 [SMILES: CC(C)(C)CCOc1cc(C(F)(F)F)ccc1-c1nc(NS(=O)(=O)c2ccccc2)sc1-c1cc(F)cc(OC(F)(F)F)c1] | N-[4-[2-(3,3-dimethylbutoxy)-4-(trifluoromethyl)phenyl]-5-[3-fluoro-5-(trifluoromethoxy)phenyl]-1,3-thiazol-2-yl]benzenesulfonamide |

TABLE 1-continued
| Compound Number | Compound Structural Formula | Compound Name |
|---|---|---|
| 566 | 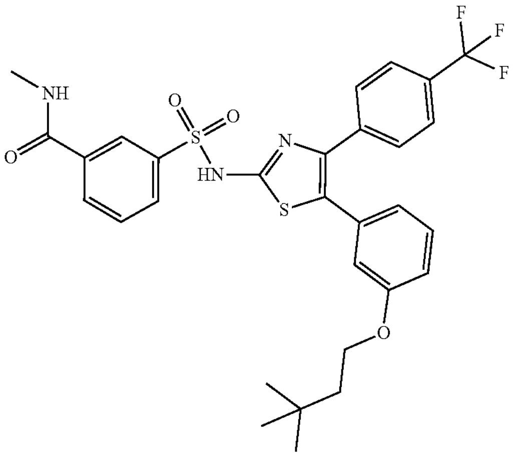 [SMILES: CNC(=O)c1cccc(S(=O)(=O)Nc2nc(-c3ccc(C(F)(F)F)cc3)c(-c3cccc(OCCC(C)(C)C)c3)s2)c1] | 3-(N-(5-(3-(3,3-dimethylbutoxy)phenyl)-4-(4-(trifluoromethyl)phenyl)thiazol-2-yl)sulfamoyl)-N-methylbenzamide |
| 50 | 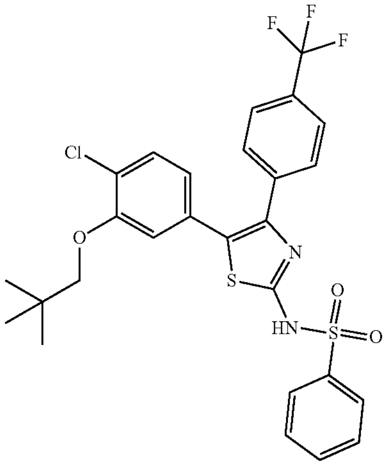 [SMILES: CC(C)(C)COc1cc(-c2sc(NS(=O)(=O)c3ccccc3)nc2-c2ccc(C(F)(F)F)cc2)ccc1Cl] | N-[5-[4-chloro-3-(2,2-dimethylpropoxy)phenyl]-4-[4-(trifluoromethyl)phenyl]-1,3-thiazol-2-yl]benzenesulfonamide |
| 237 | 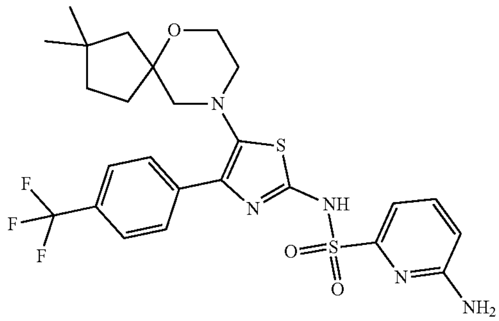 [SMILES: CC1(C)CCC2(CN(c3sc(NS(=O)(=O)c4cccc(N)n4)nc3-c3ccc(C(F)(F)F)cc3)CCO2)C1] | 6-amino-N-[5-(3,3-dimethyl-6-oxa-9-azaspiro[4.5]decan-9-yl)-4-[4-(trifluoromethyl)phenyl]-1,3-thiazol-2-yl]pyridine-2-sulfonamide |

TABLE 1-continued

| Compound Number | Compound Structural Formula | Compound Name |
| --- | --- | --- |
| 567 | 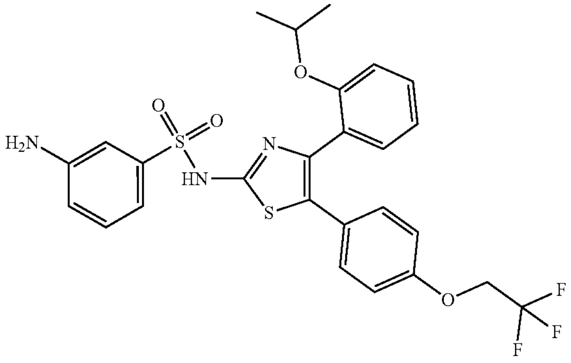 [SMILES: CC(C)Oc1ccccc1-c1nc(NS(=O)(=O)c2cccc(N)c2)sc1-c1ccc(OCC(F)(F)F)cc1] | 3-amino-N-(4-(2-isopropoxyphenyl)-5-(4-(2,2,2-trifluoroethoxy)phenyl)thiazol-2-yl)benzenesulfonamide |
| 192 | 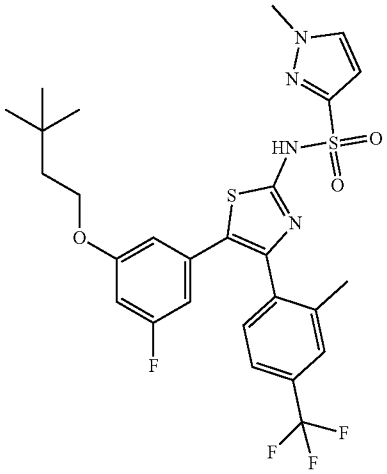 [SMILES: Cc1cc(C(F)(F)F)ccc1-c1nc(NS(=O)(=O)c2ccn(C)n2)sc1-c1cc(F)cc(OCCC(C)(C)C)c1] | N-[5-[3-(3,3-dimethylbutoxy)-5-fluorophenyl]-4-[2-methyl-4-(trifluoromethyl)phenyl]-1,3-thiazol-2-yl]-1-methylpyrazole-3-sulfonamide |
| 146 | 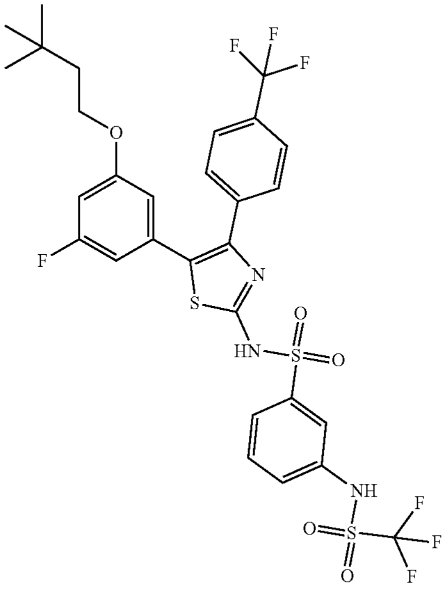 [SMILES: CC(C)(C)CCOc1cc(F)cc(-c2sc(NS(=O)(=O)c3cccc(NS(=O)(=O)C(F)(F)F)c3)nc2-c2ccc(C(F)(F)F)cc2)c1] | N-[5-[3-(3,3-dimethylbutoxy)-5-fluorophenyl]-4-[4-(trifluoromethyl)phenyl]-1,3-thiazol-2-yl]-3-(trifluoromethylsulfonylamino)benzenesulfonamide |

TABLE 1-continued
| Compound Number | Compound Structural Formula | Compound Name |
|---|---|---|
| 249 | 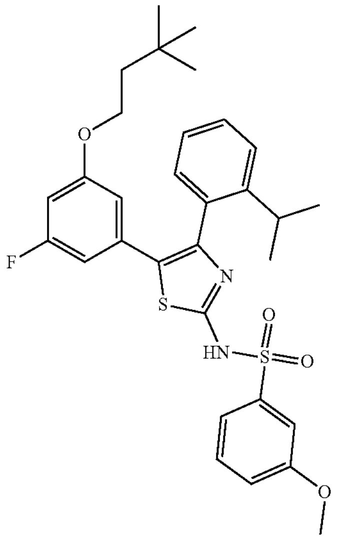 [SMILES: COc1cccc(S(=O)(=O)Nc2nc(-c3ccccc3C(C)C)c(-c3cc(F)cc(OCCC(C)(C)C)c3)s2)c1] | N-[5-[3-(3,3-dimethylbutoxy)-5-fluorophenyl]-4-(2-propan-2-ylphenyl)-1,3-thiazol-2-yl]-3-methoxybenzenesulfonamide |
| 31 | 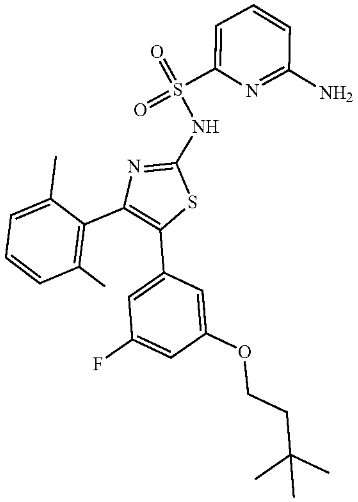 [SMILES: Cc1cccc(C)c1-c1nc(NS(=O)(=O)c2cccc(N)n2)sc1-c1cc(F)cc(OCCC(C)(C)C)c1] | 6-amino-N-[5-[3-(3,3-dimethylbutoxy)-5-fluorophenyl]-4-(2,6-dimethylphenyl)-1,3-thiazol-2-yl]pyridine-2-sulfonamide |
| 302 | 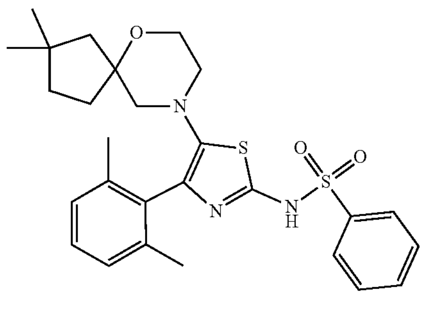 [SMILES: Cc1cccc(C)c1-c1nc(NS(=O)(=O)c2ccccc2)sc1N1CCOC2(CCC(C)(C)C2)C1] | N-[5-(3,3-dimethyl-6-oxa-9-azaspiro[4.5]decan-9-yl)-4-(2,6-dimethylphenyl)-1,3-thiazol-2-yl]benzenesulfonamide |

TABLE 1-continued

| Compound Number | Compound Structural Formula | Compound Name |
|---|---|---|
| 158 | 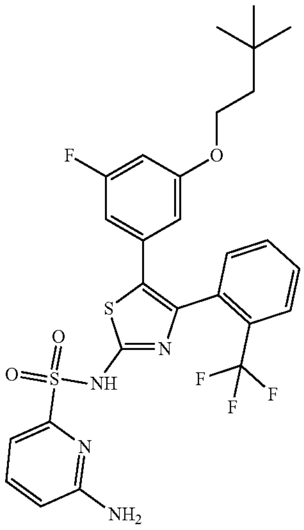 [SMILES: CC(C)(C)CCOc1cc(F)cc(-c2sc(NS(=O)(=O)c3cccc(N)n3)nc2-c2ccccc2C(F)(F)F)c1] | 6-amino-N-[5-[3-(3,3-dimethylbutoxy)-5-fluorophenyl]-4-[2-(trifluoromethyl)phenyl]-1,3-thiazol-2-yl]pyridine-2-sulfonamide |
| 281 | 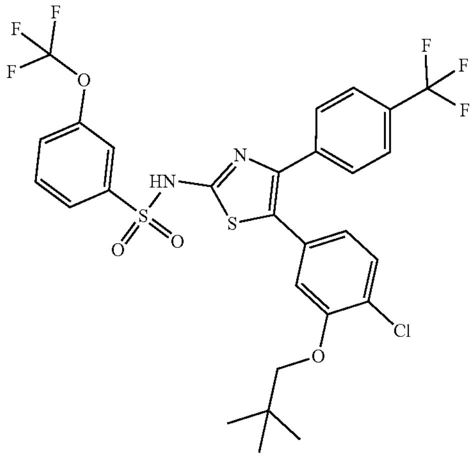 [SMILES: CC(C)(C)COc1cc(-c2sc(NS(=O)(=O)c3cccc(OC(F)(F)F)c3)nc2-c2ccc(C(F)(F)F)cc2)ccc1Cl] | N-[5-[4-chloro-3-(2,2-dimethylpropoxy)phenyl]-4-[4-(trifluoromethyl)phenyl]-1,3-thiazol-2-yl]-3-(trifluoromethoxy)benzenesulfonamide |
| 135 | 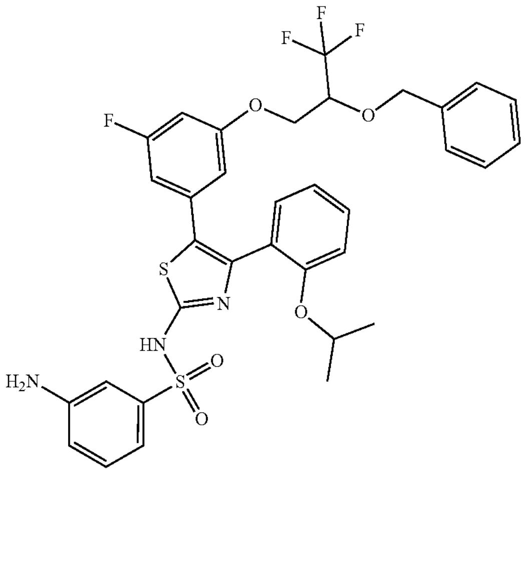 [SMILES: CC(C)Oc1ccccc1-c1nc(NS(=O)(=O)c2cccc(N)c2)sc1-c1cc(F)cc(OCC(OCc2ccccc2)C(F)(F)F)c1] | 3-amino-N-[5-[3-fluoro-5-(3,3,3-trifluoro-2-phenylmethoxypropoxy)phenyl]-4-(2-propan-2-yloxyphenyl)-1,3-thiazol-2-yl]benzenesulfonamide |

TABLE 1-continued

| Compound Number | Compound Structural Formula | Compound Name |
|---|---|---|
| 459 | 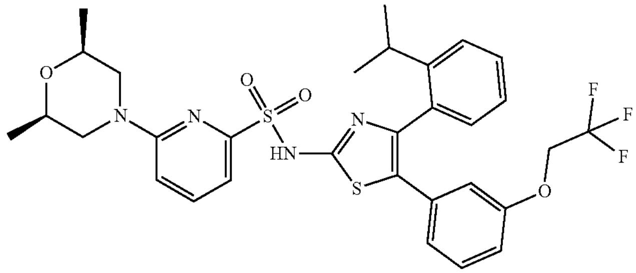 [SMILES: CC(C)c1ccccc1-c1nc(NS(=O)(=O)c2cccc(N3C[C@@H](C)O[C@@H](C)C3)n2)sc1-c1cccc(OCC(F)(F)F)c1] | 6-[(2S,6R)-2,6-dimethylmorpholin-4-yl]-N-[4-(2-propan-2-ylphenyl)-5-[3-(2,2,2-trifluoroethoxy)phenyl]-1,3-thiazol-2-yl]pyridine-2-sulfonamide |
| 327 | 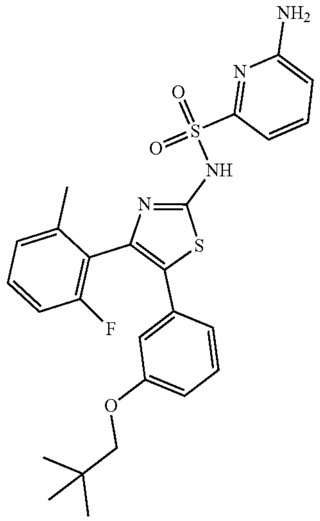 [SMILES: Cc1cccc(F)c1-c1nc(NS(=O)(=O)c2cccc(N)n2)sc1-c1cccc(OCC(C)(C)C)c1] | 6-amino-N-[5-[3-(2,2-dimethylpropoxy)phenyl]-4-(2-fluoro-6-methylphenyl)-1,3-thiazol-2-yl]pyridine-2-sulfonamide |
| 87 | 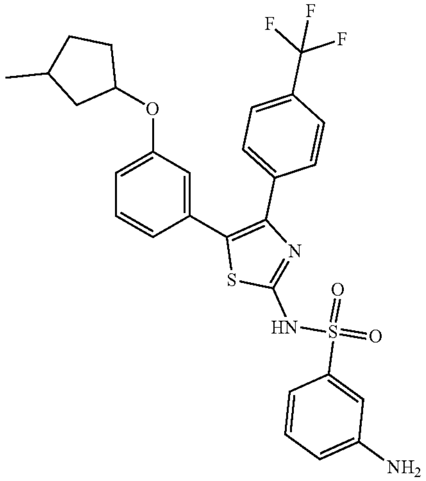 [SMILES: CC1CCC(Oc2cccc(-c3sc(NS(=O)(=O)c4cccc(N)c4)nc3-c3ccc(C(F)(F)F)cc3)c2)C1] | 3-amino-N-[5-[3-(3-methylcyclopentyl)oxyphenyl]-4-[4-(trifluoromethyl)phenyl]-1,3-thiazol-2-yl]benzenesulfonamide |

TABLE 1-continued

| Compound Number | Compound Structural Formula | Compound Name |
|---|---|---|
| 313 | 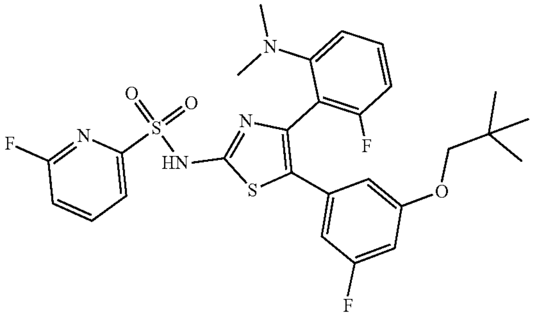 [SMILES: CN(C)c1cccc(F)c1-c1nc(NS(=O)(=O)c2cccc(F)n2)sc1-c1cc(F)cc(OCC(C)(C)C)c1] | N-[4-[2-(dimethylamino)-6-fluorophenyl]-5-[3-(2,2-dimethylpropoxy)-5-fluorophenyl]-1,3-thiazol-2-yl]-6-fluoropyridine-2-sulfonamide |
| 568 | 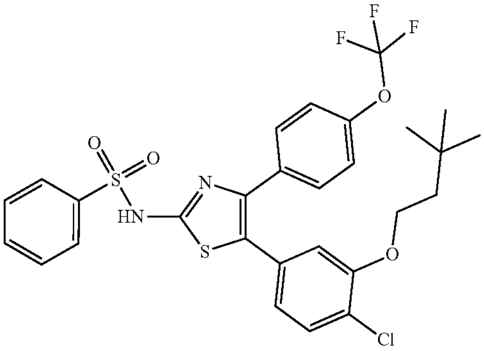 [SMILES: CC(C)(C)CCOc1cc(-c2sc(NS(=O)(=O)c3ccccc3)nc2-c2ccc(OC(F)(F)F)cc2)ccc1Cl] | N-(5-(4-chloro-3-(3,3-dimethylbutoxy)phenyl)-4-(4-(trifluoromethoxy)phenyl)thiazol-2-yl)benzenesulfonamide |
| 308 | 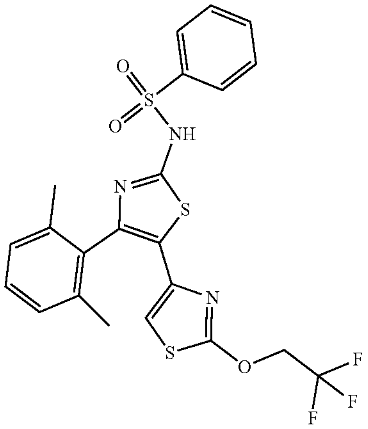 [SMILES: Cc1cccc(C)c1-c1nc(NS(=O)(=O)c2ccccc2)sc1-c1csc(OCC(F)(F)F)n1] | N-[4-(2,6-dimethylphenyl)-5-[2-(2,2,2-trifluoroethoxy)-1,3-thiazol-4-yl]-1,3-thiazol-2-yl]benzenesulfonamide |
| 402 | 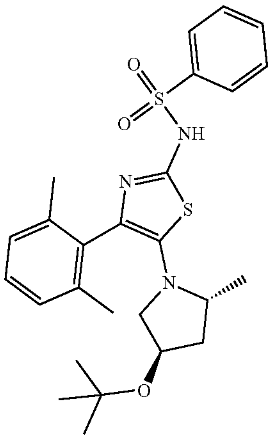 [SMILES: Cc1cccc(C)c1-c1nc(NS(=O)(=O)c2ccccc2)sc1N1C[C@H](OC(C)(C)C)C[C@H]1C] | N-[4-(2,6-dimethylphenyl)-5-[(2R,4R)-2-methyl-4-[(2-methylpropan-2-yl)oxy]pyrrolidin-1-yl]-1,3-thiazol-2-yl]benzenesulfonamide |

TABLE 1-continued

| Compound Number | Compound Structural Formula | Compound Name |
|---|---|---|
| 569 | 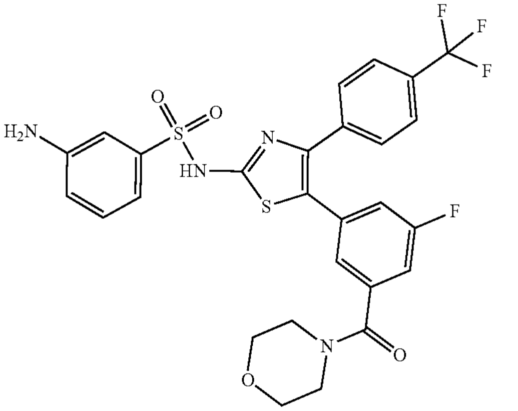 [SMILES: Nc1cccc(S(=O)(=O)Nc2nc(-c3ccc(C(F)(F)F)cc3)c(-c3cc(F)cc(C(=O)N4CCOCC4)c3)s2)c1] | 3-amino-N-(5-(3-fluoro-5-(morpholine-4-carbonyl)phenyl)-4-(4-(trifluoromethyl)phenyl)thiazol-2-yl)benzenesulfonamide |
| 391 | 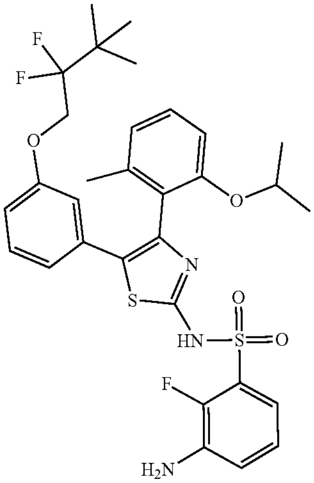 [SMILES: Cc1cccc(OC(C)C)c1-c1nc(NS(=O)(=O)c2cccc(N)c2F)sc1-c1cccc(OCC(F)(F)C(C)(C)C)c1] | 3-amino-N-[5-[3-(2,2-difluoro-3,3-dimethylbutoxy)phenyl]-4-(2-methyl-6-propan-2-yloxyphenyl)-1,3-thiazol-2-yl]-2-fluorobenzenesulfonamide |
| 570 | 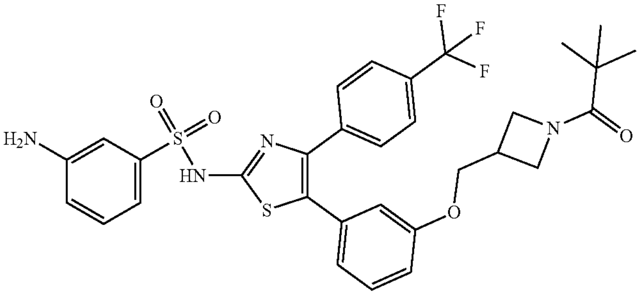 [SMILES: CC(C)(C)C(=O)N1CC(COc2cccc(-c3sc(NS(=O)(=O)c4cccc(N)c4)nc3-c3ccc(C(F)(F)F)cc3)c2)C1] | 3-amino-N-(5-(3-((1-pivaloylazetidin-3-yl)methoxy)phenyl)-4-(4-(trifluoromethyl)phenyl)thiazol-2-yl)benzenesulfonamide |

TABLE 1-continued

| Compound Number | Compound Structural Formula | Compound Name |
|---|---|---|
| 441 | 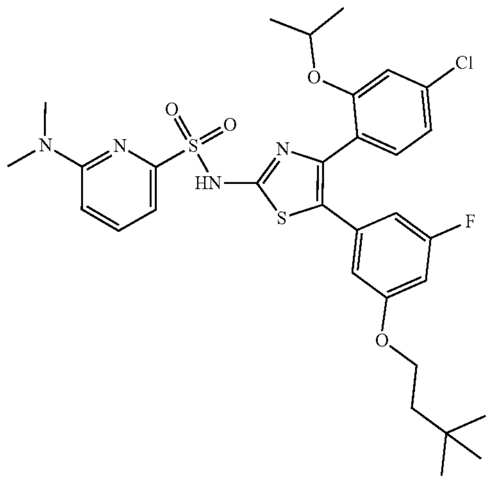 [SMILES: CC(C)Oc1cc(Cl)ccc1-c1nc(NS(=O)(=O)c2cccc(N(C)C)n2)sc1-c1cc(F)cc(OCCC(C)(C)C)c1] | N-[4-(4-chloro-2-propan-2-yloxyphenyl)-5-[3-(3,3-dimethylbutoxy)-5-fluorophenyl]-1,3-thiazol-2-yl]-6-(dimethylamino)pyridine-2-sulfonamide |
| 59 | 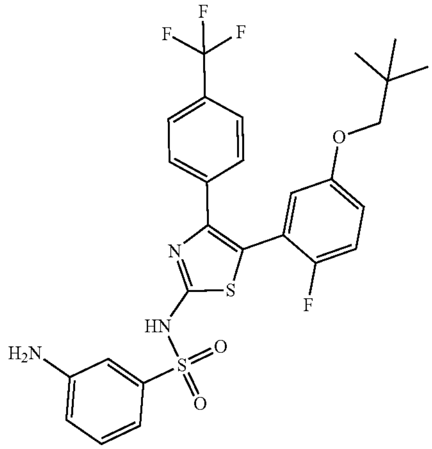 [SMILES: CC(C)(C)COc1ccc(F)c(-c2sc(NS(=O)(=O)c3cccc(N)c3)nc2-c2ccc(C(F)(F)F)cc2)c1] | 3-amino-N-[5-[5-(2,2-dimethylpropoxy)-2-fluorophenyl]-4-[4-(trifluoromethyl)phenyl]-1,3-thiazol-2-yl]benzenesulfonamide |
| 194 | 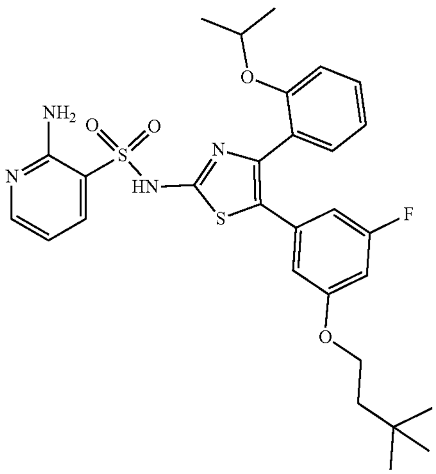 [SMILES: CC(C)Oc1ccccc1-c1nc(NS(=O)(=O)c2cccnc2N)sc1-c1cc(F)cc(OCCC(C)(C)C)c1] | 2-amino-N-[5-[3-(3,3-dimethylbutoxy)-5-fluorophenyl]-4-(2-propan-2-yloxyphenyl)-1,3-thiazol-2-yl]pyridine-3-sulfonamide |

TABLE 1-continued

| Compound Number | Compound Structural Formula | Compound Name |
|---|---|---|
| 72 | 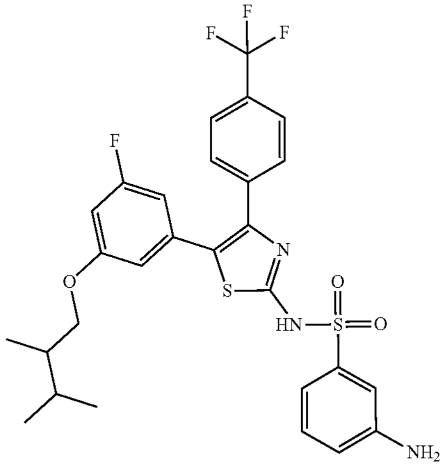 [SMILES: CC(C)C(C)COc1cc(F)cc(-c2sc(NS(=O)(=O)c3cccc(N)c3)nc2-c2ccc(C(F)(F)F)cc2)c1] | 3-amino-N-[5-[3-(2,3-dimethylbutoxy)-5-fluorophenyl]-4-[4-(trifluoromethyl)phenyl]-1,3-thiazol-2-yl]benzenesulfonamide |
| 110 | 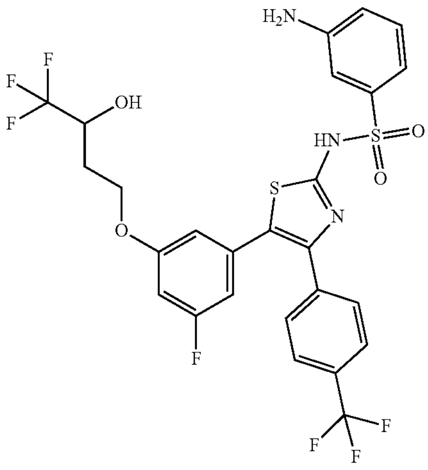 [SMILES: Nc1cccc(S(=O)(=O)Nc2nc(-c3ccc(C(F)(F)F)cc3)c(-c3cc(F)cc(OCCC(O)C(F)(F)F)c3)s2)c1] | 3-amino-N-[5-[3-fluoro-5-(4,4,4-trifluoro-3-hydroxybutoxy)phenyl]-4-[4-(trifluoromethyl)phenyl]-1,3-thiazol-2-yl]benzenesulfonamide |
| 461 | 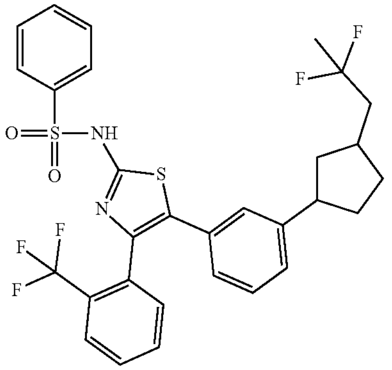 [SMILES: CC(F)(F)CC1CCC(c2cccc(-c3sc(NS(=O)(=O)c4ccccc4)nc3-c3ccccc3C(F)(F)F)c2)C1] | N-[5-[3-[3-(2,2-difluoropropyl)cyclopentyl]phenyl]-4-[2-(trifluoromethyl)phenyl]-1,3-thiazol-2-yl]benzenesulfonamide |

TABLE 1-continued

| Compound Number | Compound Structural Formula | Compound Name |
| --- | --- | --- |
| 46A2 | 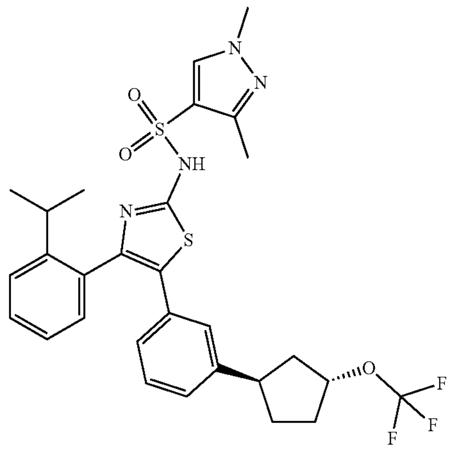 [SMILES: Cc1nn(C)cc1S(=O)(=O)Nc1nc(-c2ccccc2C(C)C)c(-c2cccc([C@@H]3CC[C@@H](OC(F)(F)F)C3)c2)s1] | 1,3-dimethyl-N-[4-(2-propan-2-ylphenyl)-5-[3-[(1R, 3R)-3-(trifluoromethoxy)cyclopentyl]phenyl]-1,3-thiazol-2-yl]pyrazole-4-sulfonamide |
| 571 | 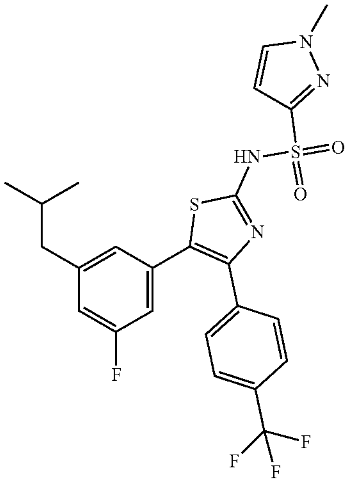 [SMILES: CC(C)Cc1cc(F)cc(-c2sc(NS(=O)(=O)c3ccn(C)n3)nc2-c2ccc(C(F)(F)F)cc2)c1] | N-(5-(3-fluoro-5-isobutylphenyl)-4-(4-(trifluoromethyl)phenyl)thiazol-2-yl)-1-methyl-1H-pyrazole-3-sulfonamide |
| 572 | 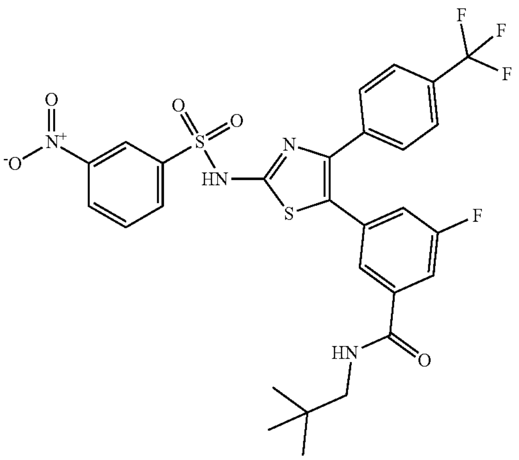 | 3-fluoro-N-neopentyl-5-(2-((3-nitrophenyl)sulfonamido)-4-(4-(trifluoromethyl)phenyl)thiazol-5-yl)benzamide |

TABLE 1-continued

| Compound Number | Compound Structural Formula | Compound Name |
|---|---|---|
| 45A1 | 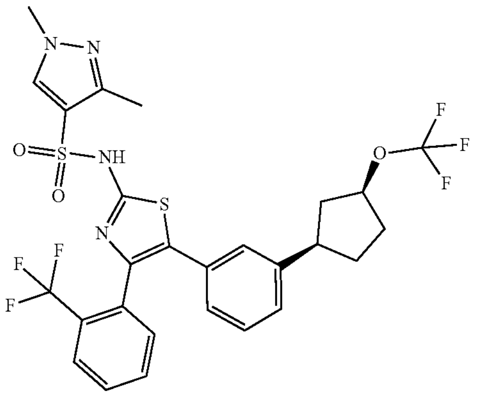 [SMILES: Cc1nn(C)cc1S(=O)(=O)Nc1nc(-c2ccccc2C(F)(F)F)c(-c2cccc([C@@H]3CC[C@H](OC(F)(F)F)C3)c2)s1] | 1,3-dimethyl-N-[5-[3-[(1R, 3S)-3-(trifluoromethoxy)cyclopentyl]phenyl]-4-[2-(trifluoromethyl)phenyl]-1,3-thiazol-2-yl]pyrazole-4-sulfonamide |
| 380 | 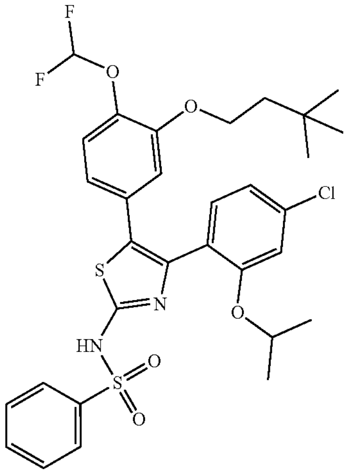 [SMILES: CC(C)Oc1cc(Cl)ccc1-c1nc(NS(=O)(=O)c2ccccc2)sc1-c1ccc(OC(F)F)c(OCCC(C)(C)C)c1] | N-[4-(4-chloro-2-propan-2-yloxyphenyl)-5-[4-(difluoromethoxy)-3-(3,3-dimethylbutoxy)phenyl]-1,3-thiazol-2-yl]benzenesulfonamide |
| 44B1 | 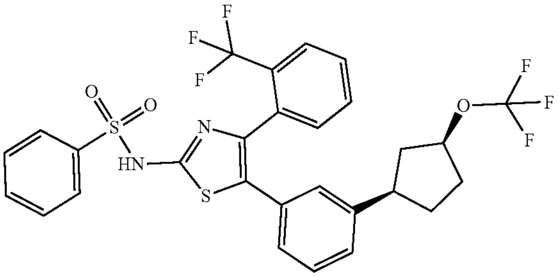 [SMILES: O=S(=O)(Nc1nc(-c2ccccc2C(F)(F)F)c(-c2cccc([C@@H]3CC[C@H](OC(F)(F)F)C3)c2)s1)c1ccccc1] | N-[5-[3-[(1S, 3R)-3-(trifluoromethoxy)cyclopentyl]phenyl]-4-[2-(trifluoromethyl)phenyl]-1,3-thiazol-2-yl]benzenesulfonamide |
| 52 | 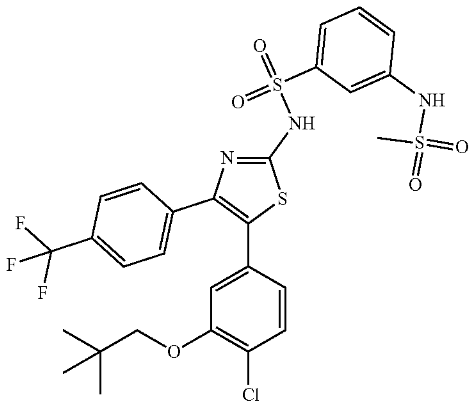 [SMILES: CC(C)(C)COc1cc(-c2sc(NS(=O)(=O)c3cccc(NS(C)(=O)=O)c3)nc2-c2ccc(C(F)(F)F)cc2)ccc1Cl] | N-[5-[4-chloro-3-(2,2-dimethylpropoxy)phenyl]-4-[4-(trifluoromethyl)phenyl]-1,3-thiazol-2-yl]-3-(methanesulfonamido)benzenesulfonamide |

TABLE 1-continued

| Compound Number | Compound Structural Formula | Compound Name |
|---|---|---|
| 573 | 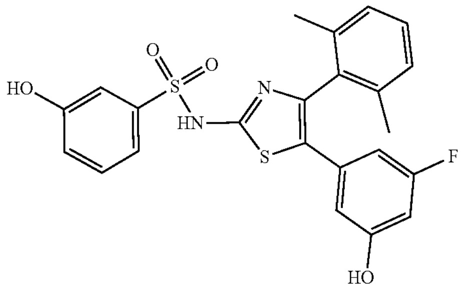 [SMILES: Cc1cccc(C)c1-c1nc(NS(=O)(=O)c2cccc(O)c2)sc1-c1cc(O)cc(F)c1] | N-(4-(2,6-dimethylphenyl)-5-(3-fluoro-5-hydroxyphenyl)thiazol-2-yl)-3-hydroxybenzenesulfonamide |
| 341 | 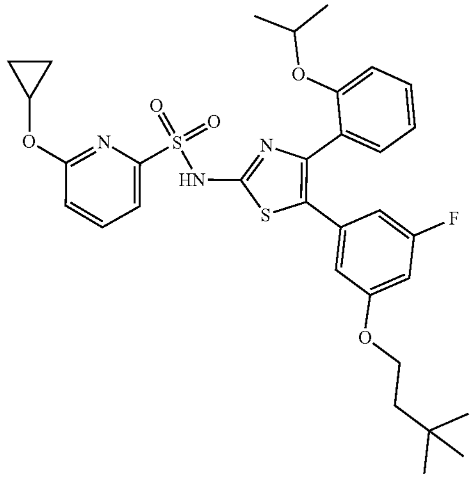 [SMILES: CC(C)Oc1ccccc1-c1nc(NS(=O)(=O)c2cccc(OC3CC3)n2)sc1-c1cc(F)cc(OCCC(C)(C)C)c1] | 6-cyclopropyloxy-N-[5-[3-(3,3-dimethylbutoxy)-5-fluorophenyl]-4-(2-propan-2-yloxyphenyl)-1,3-thiazol-2-yl]pyridine-2-sulfonamide |
| 433 | 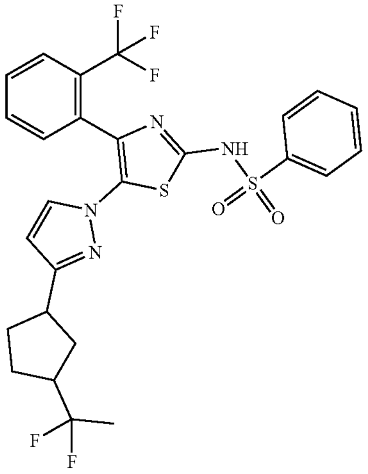 [SMILES: CC(F)(F)C1CCC(c2ccn(-c3sc(NS(=O)(=O)c4ccccc4)nc3-c3ccccc3C(F)(F)F)n2)C1] | N-[5-[3-[3-(1,1-difluoroethyl)cyclopentyl]pyrazol-1-yl]-4-[2-(trifluoromethyl)phenyl]-1,3-thiazol-2-yl]benzenesulfonamide |

TABLE 1-continued

| Compound Number | Compound Structural Formula | Compound Name |
|---|---|---|
| 469 | 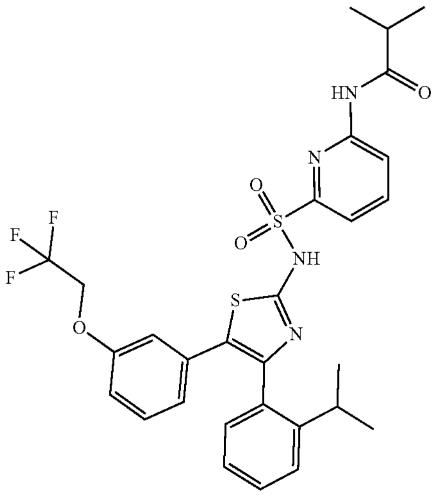 [SMILES: CC(C)C(=O)Nc1cccc(S(=O)(=O)Nc2nc(-c3ccccc3C(C)C)c(-c3cccc(OCC(F)(F)F)c3)s2)n1] | 2-methyl-N-[6-[4-(2-propan-2-ylphenyl)-5-[3-(2,2,2-trifluoroethoxy)phenyl]-1,3-thiazol-2-yl]sulfamoyl]pyridin-2-yl]propanamide |
| 475 | 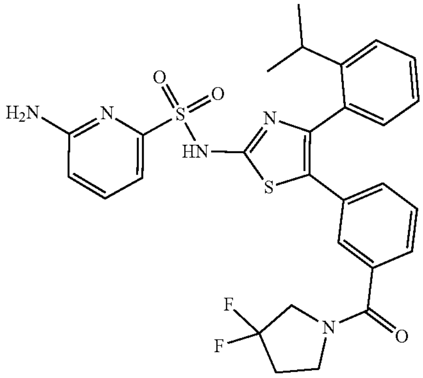 [SMILES: CC(C)c1ccccc1-c1nc(NS(=O)(=O)c2cccc(N)n2)sc1-c1cccc(C(=O)N2CCC(F)(F)C2)c1] | 6-amino-N-[5-[3-(3,3-difluoropyrrolidine-1-carbonyl)phenyl]-4-(2-propan-2-ylphenyl)-1,3-thiazol-2-yl]pyridine-2-sulfonamide |
| 427 | 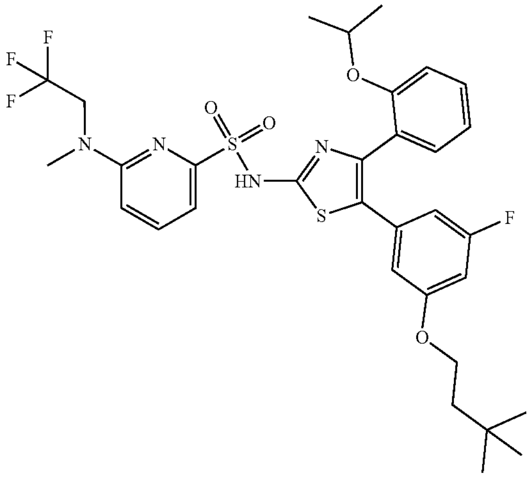 [SMILES: CC(C)Oc1ccccc1-c1nc(NS(=O)(=O)c2cccc(N(C)CC(F)(F)F)n2)sc1-c1cc(F)cc(OCCC(C)(C)C)c1] | N-[5-[3-(3,3-dimethylbutoxy)-5-fluorophenyl]-4-(2-propan-2-yloxyphenyl)-1,3-thiazol-2-yl]-6-[methyl(2,2,2-trifluoroethyl)amino]pyridine-2-sulfonamide |

TABLE 1-continued

| Compound Number | Compound Structural Formula | Compound Name |
|---|---|---|
| 118 | 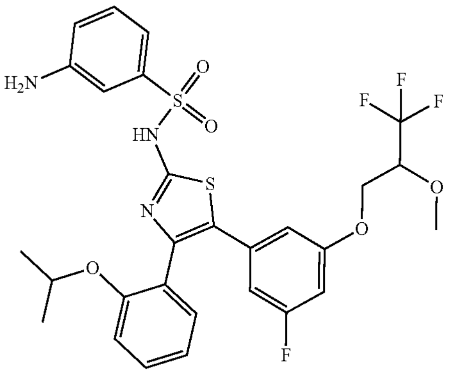 [SMILES: COC(COc1cc(F)cc(-c2sc(NS(=O)(=O)c3cccc(N)c3)nc2-c2ccccc2OC(C)C)c1)C(F)(F)F] | 3-amino-N-[5-[3-fluoro-5-(3,3,3-trifluoro-2-methoxypropoxy)phenyl]-4-(2-propan-2-yloxyphenyl)-1,3-thiazol-2-yl]benzenesulfonamide |
| 43A | 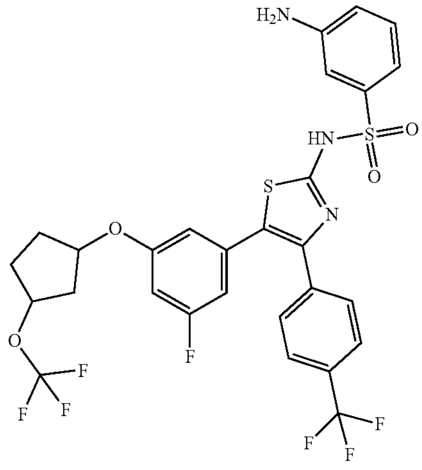 [SMILES: Nc1cccc(S(=O)(=O)Nc2nc(-c3ccc(C(F)(F)F)cc3)c(-c3cc(F)cc(OC4CCC(OC(F)(F)F)C4)c3)s2)c1] | 3-amino-N-[5-[3-fluoro-5-[3-(trifluoromethoxy)cyclopentyl]oxyphenyl]-4-[4-(trifluoromethyl)phenyl]-1,3-thiazol-2-yl]benzenesulfonamide |
| 444 | 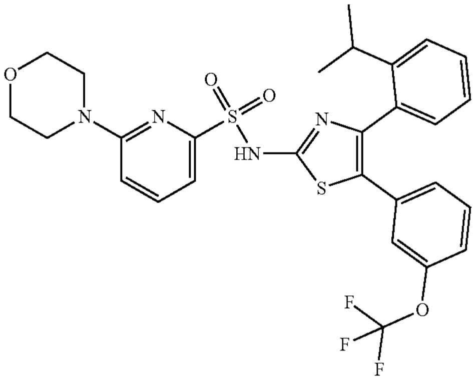 [SMILES: CC(C)c1ccccc1-c1nc(NS(=O)(=O)c2cccc(N3CCOCC3)n2)sc1-c1cccc(OC(F)(F)F)c1] | 6-morpholin-4-yl-N-[4-(2-propan-2-ylphenyl)-5-[3-(trifluoromethoxy)phenyl]-1,3-thiazol-2-yl]pyridine-2-sulfonamide |

TABLE 1-continued
| Compound Number | Compound Structural Formula | Compound Name |
|---|---|---|
| 255 | 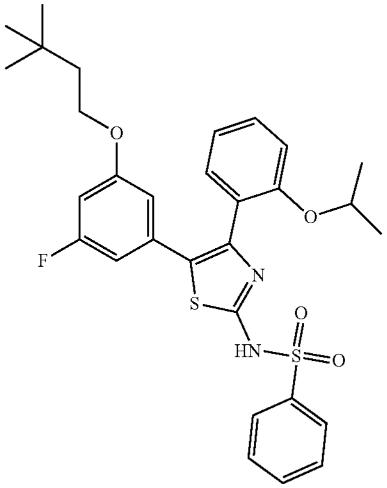 [SMILES: CC(C)Oc1ccccc1-c1nc(NS(=O)(=O)c2ccccc2)sc1-c1cc(F)cc(OCCC(C)(C)C)c1] | N-[5-[3-(3,3-dimethylbutoxy)-5-fluorophenyl]-4-(2-propan-2-yloxyphenyl)-1,3-thiazol-2-yl]benzenesulfonamide |
| 29 | 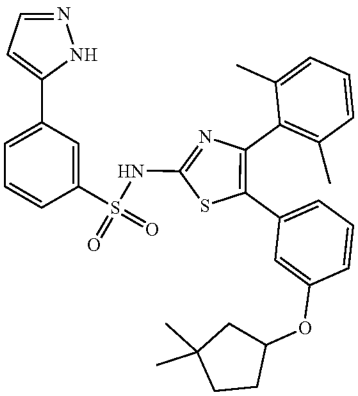 [SMILES: Cc1cccc(C)c1-c1nc(NS(=O)(=O)c2cccc(-c3ccn[nH]3)c2)sc1-c1cccc(OC2CCC(C)(C)C2)c1] | N-[5-[3-(3,3-dimethylcyclopentyl)oxyphenyl]-4-(2,6-dimethylphenyl)-1,3-thiazol-2-yl]-3-(1H-pyrazol-5-yl)benzenesulfonamide |
| 467 | 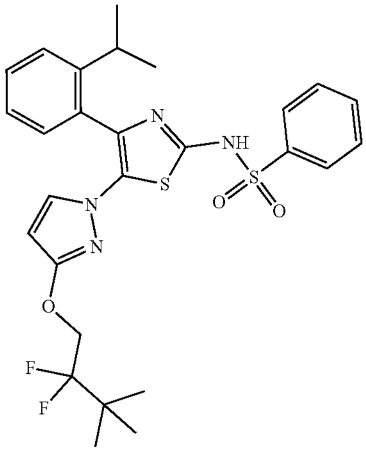 [SMILES: CC(C)c1ccccc1-c1nc(NS(=O)(=O)c2ccccc2)sc1-n1ccc(OCC(F)(F)C(C)(C)C)n1] | N-[5-[3-(2,2-difluoro-3,3-dimethylbutoxy)pyrazol-1-yl]-4-(2-propan-2-ylphenyl)-1,3-thiazol-2-yl]benzenesulfonamide |

TABLE 1-continued

| Compound Number | Compound Structural Formula | Compound Name |
| --- | --- | --- |
| 420 | 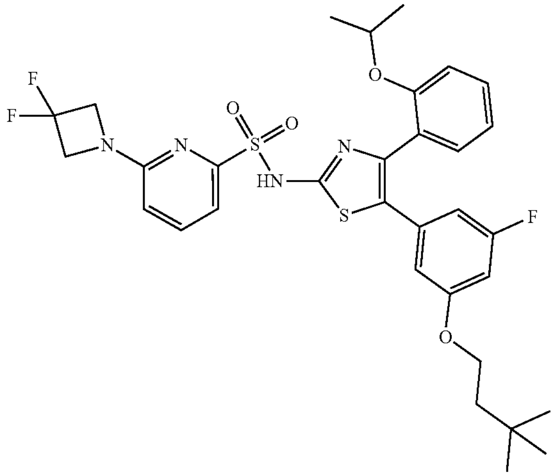 [SMILES: CC(C)Oc1ccccc1-c1nc(NS(=O)(=O)c2cccc(N3CC(F)(F)C3)n2)sc1-c1cc(F)cc(OCCC(C)(C)C)c1] | 6-(3,3-difluoroazetidin-1-yl)-N-[5-[3-(3,3-dimethylbutoxy)-5-fluorophenyl]-4-(2-propan-2-yloxyphenyl)-1,3-thiazol-2-yl]pyridine-2-sulfonamide |
| 258 | 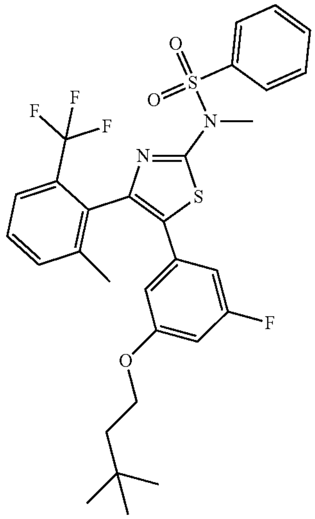 [SMILES: Cc1cccc(C(F)(F)F)c1-c1nc(N(C)S(=O)(=O)c2ccccc2)sc1-c1cc(F)cc(OCCC(C)(C)C)c1] | N-[5-[3-(3,3-dimethylbutoxy)-5-fluorophenyl]-4-[2-methyl-6-(trifluoromethyl)phenyl]-1,3-thiazol-2-yl]-N-methylbenzenesulfonamide |
| 574 | 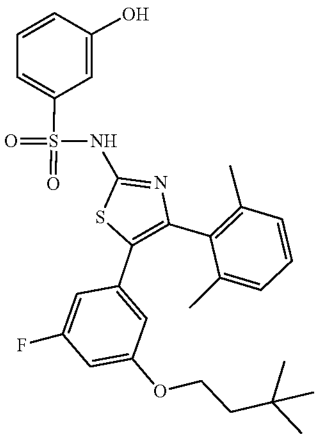 [SMILES: Cc1cccc(C)c1-c1nc(NS(=O)(=O)c2cccc(O)c2)sc1-c1cc(F)cc(OCCC(C)(C)C)c1] | N-(5-(3-(3,3-dimethylbutoxy)-5-fluorophenyl)-4-(2,6-dimethylphenyl)thiazol-2-yl)-3-hydroxybenzenesulfonamide |

TABLE 1-continued

| Compound Number | Compound Structural Formula | Compound Name |
| --- | --- | --- |
| 575 | 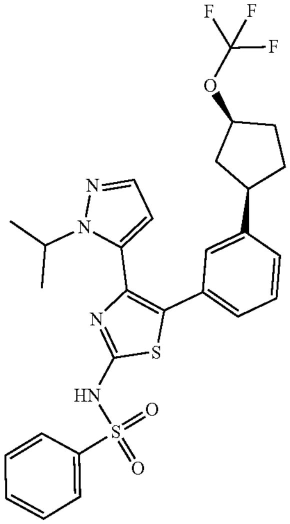 [SMILES: CC(C)n1nccc1-c1nc(NS(=O)(=O)c2ccccc2)sc1-c1cccc([C@@H]2CC[C@H](OC(F)(F)F)C2)c1] | N-(4-(1-isopropyl-1H-pyrazol-5-yl)-5-(3-((1R,3S)-3-(trifluoromethoxy)cyclopentyl)phenyl) thiazol-2-yl)benzenesulfonamide |
| 24 | 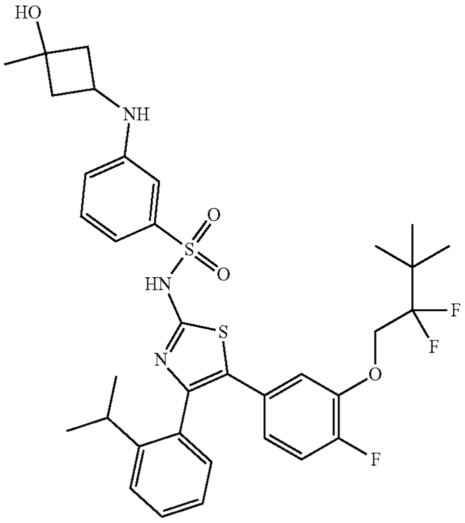 [SMILES: CC(C)c1ccccc1-c1nc(NS(=O)(=O)c2cccc(NC3CC(C)(O)C3)c2)sc1-c1ccc(F)c(OCC(F)(F)C(C)(C)C)c1] | N-[5-[3-(2,2-difluoro-3,3-dimethylbutoxy)-4-fluorophenyl]-4-(2-propan-2-ylphenyl)-1,3-thiazol-2-yl]-3-[(3-hydroxy-3-methylcyclobutyl)amino] benzenesulfonamide |
| 88 | 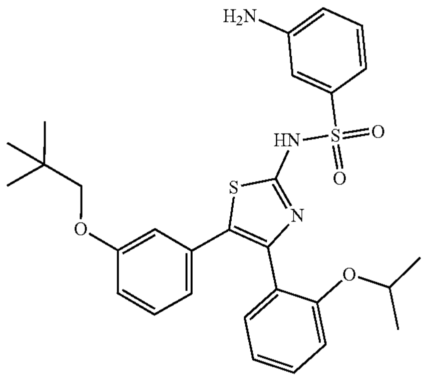 [SMILES: CC(C)Oc1ccccc1-c1nc(NS(=O)(=O)c2cccc(N)c2)sc1-c1cccc(OCC(C)(C)C)c1] | 3-amino-N-[5-[3-(2,2-dimethylpropoxy)phenyl]-4-(2-propan-2-yloxyphenyl)-1,3-thiazol-2-yl]benzenesulfonamide |

TABLE 1-continued

| Compound Number | Compound Structural Formula | Compound Name |
|---|---|---|
| 576 | 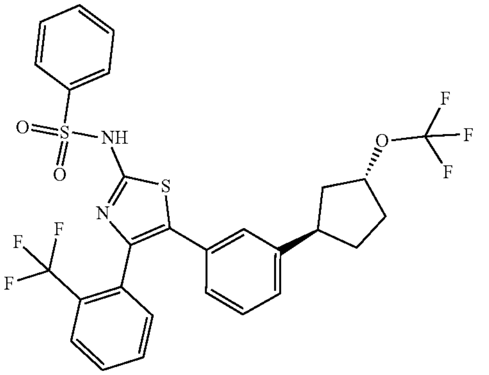 [SMILES: O=S(=O)(Nc1nc(-c2ccccc2C(F)(F)F)c(-c2cccc([C@@H]3CC[C@@H](OC(F)(F)F)C3)c2)s1)c1ccccc1] | N-(5-(3-((1R,3R)-3-(trifluoromethoxy)cyclopentyl)phenyl)-4-(2-(trifluoromethyl)phenyl)thiazol-2-yl)benzenesulfonamide |
| 48A1 | 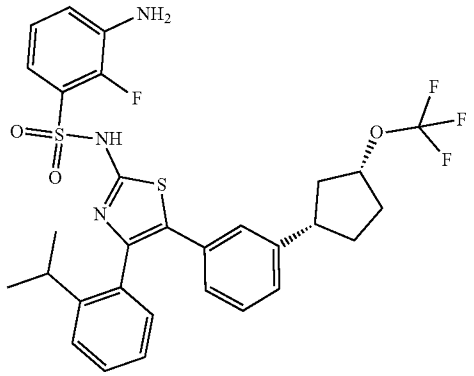 [SMILES: CC(C)c1ccccc1-c1nc(NS(=O)(=O)c2cccc(N)c2F)sc1-c1cccc([C@H]2CC[C@@H](OC(F)(F)F)C2)c1] | 3-amino-2-fluoro-N-[4-(2-propan-2-ylphenyl)-5-[3-[(1S, 3R)-3-(trifluoromethoxy)cyclopentyl]phenyl]-1,3-thiazol-2-yl]benzenesulfonamide |
| 306 | 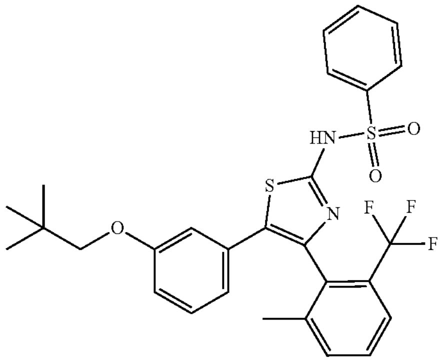 [SMILES: Cc1cccc(C(F)(F)F)c1-c1nc(NS(=O)(=O)c2ccccc2)sc1-c1cccc(OCC(C)(C)C)c1] | N-[5-[3-(2,2-dimethylpropoxy)phenyl]-4-[2-methyl-6-(trifluoromethyl)phenyl]-1,3-thiazol-2-yl]benzenesulfonamide |
| 577 | 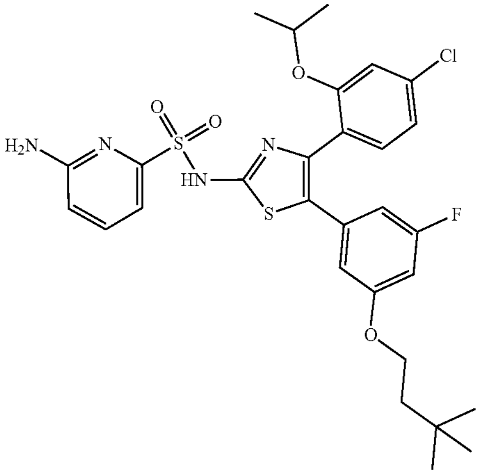 [SMILES: CC(C)Oc1cc(Cl)ccc1-c1nc(NS(=O)(=O)c2cccc(N)n2)sc1-c1cc(F)cc(OCCC(C)(C)C)c1] | 6-amino-N-(4-(4-chloro-2-isopropoxyphenyl)-5-(3-(3,3-dimethylbutoxy)-5-fluorophenyl)thiazol-2-yl)pyridine-2-sulfonamide |

TABLE 1-continued

| Compound Number | Compound Structural Formula | Compound Name |
|---|---|---|
| 129 | 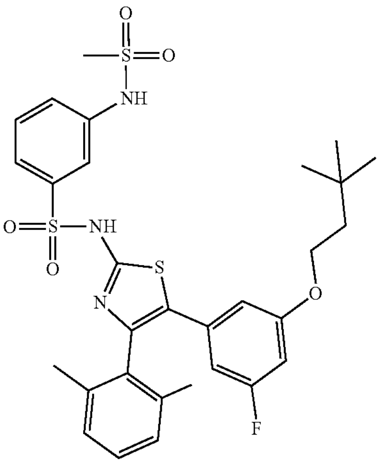 [SMILES: Cc1cccc(C)c1-c1nc(NS(=O)(=O)c2cccc(NS(C)(=O)=O)c2)sc1-c1cc(F)cc(OCCC(C)(C)C)c1] | N-[5-[3-(3,3-dimethylbutoxy)-5-fluorophenyl]-4-(2,6-dimethylphenyl)-1,3-thiazol-2-yl]-3-(methanesulfonamido) benzenesulfonamide |
| 386 | 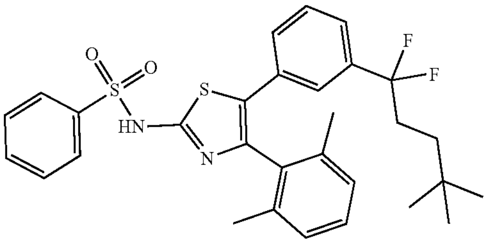 [SMILES: Cc1cccc(C)c1-c1nc(NS(=O)(=O)c2ccccc2)sc1-c1cccc(C(F)(F)CCC(C)(C)C)c1] | N-[5-[3-(1,1-difluoro-4,4-dimethylpentyl)phenyl]-4-(2,6-dimethylphenyl)-1,3-thiazol-2-yl]benzenesulfonamide |
| 124 | 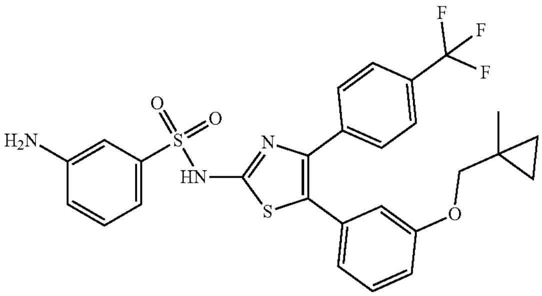 [SMILES: CC1(COc2cccc(-c3sc(NS(=O)(=O)c4cccc(N)c4)nc3-c3ccc(C(F)(F)F)cc3)c2)CC1] | 3-amino-N-[5-[3-[(1-methylcyclopropyl)methoxy]phenyl]-4-[4-(trifluoromethyl)phenyl]-1,3-thiazol-2-yl]benzenesulfonamide |
| 292 | 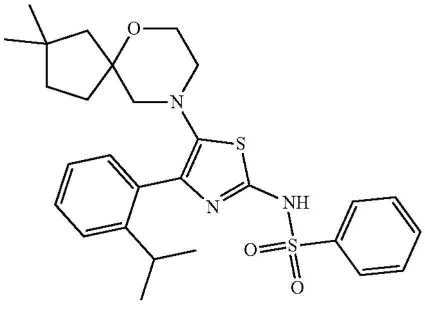 [SMILES: CC(C)c1ccccc1-c1nc(NS(=O)(=O)c2ccccc2)sc1N1CCOC2(CCC(C)(C)C2)C1] | N-[5-(3,3-dimethyl-6-oxa-9-azaspiro[4.5]decan-9-yl)-4-(2-propan-2-ylphenyl)-1,3-thiazol-2-yl]benzenesulfonamide |

TABLE 1-continued
| Compound Number | Compound Structural Formula | Compound Name |
|---|---|---|
| 578 | 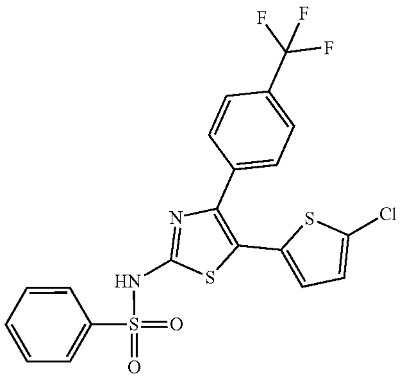 [SMILES: O=S(=O)(Nc1nc(-c2ccc(C(F)(F)F)cc2)c(-c2ccc(Cl)s2)s1)c1ccccc1] | N-(5-(5-chlorothiophen-2-yl)-4-(4-(trifluoromethyl)phenyl)thiazol-2-yl)benzenesulfonamide |
| 579 | 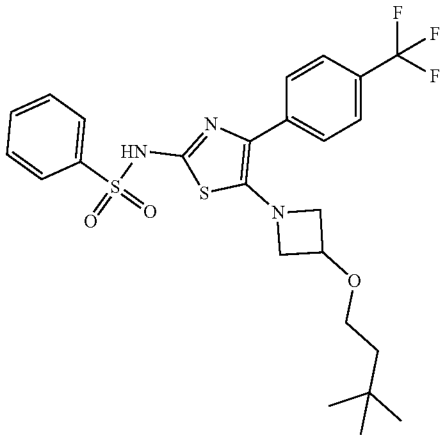 [SMILES: CC(C)(C)CCOC1CN(c2sc(NS(=O)(=O)c3ccccc3)nc2-c2ccc(C(F)(F)F)cc2)C1] | N-(5-(3-(3,3-dimethylbutoxy)azetidin-1-yl)-4-(4-(trifluoromethyl)phenyl)thiazol-2-yl)benzenesulfonamide |
| 438 | 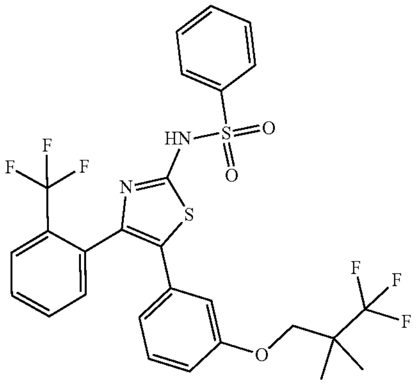 [SMILES: CC(C)(COc1cccc(-c2sc(NS(=O)(=O)c3ccccc3)nc2-c2ccccc2C(F)(F)F)c1)C(F)(F)F] | N-[5-[3-(3,3,3-trifluoro-2,2-dimethylpropoxy)phenyl]-4-[2-(trifluoromethyl)phenyl]-1,3-thiazol-2-yl]benzenesulfonamide |

TABLE 1-continued

| Compound Number | Compound Structural Formula | Compound Name |
|---|---|---|
| 355 | 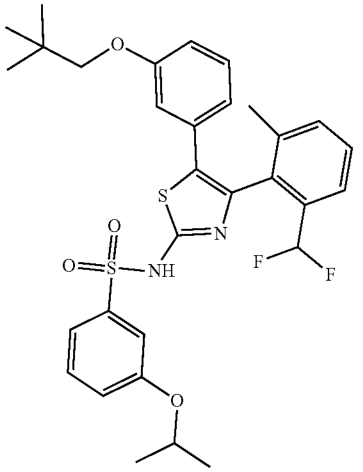 [SMILES: Cc1cccc(C(F)F)c1-c1nc(NS(=O)(=O)c2cccc(OC(C)C)c2)sc1-c1cccc(OCC(C)(C)C)c1] | N-[4-[2-(difluoromethyl)-6-methylphenyl]-5-[3-(2,2-dimethylpropoxy)phenyl]-1,3-thiazol-2-yl]-3-propan-2-yloxybenzenesulfonamide |
| 349 | 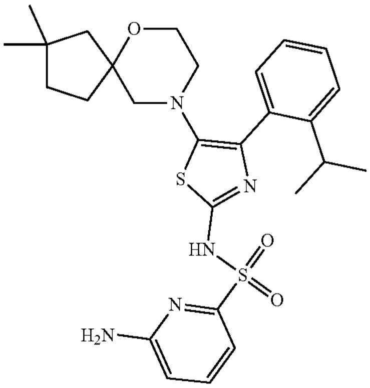 [SMILES: CC(C)c1ccccc1-c1nc(NS(=O)(=O)c2cccc(N)n2)sc1N1CCOC2(CCC(C)(C)C2)C1] | 6-amino-N-[5-(3,3-dimethyl-6-oxa-9-azaspiro[4.5]decan-9-yl)-4-(2-propan-2-ylphenyl)-1,3-thiazol-2-yl]pyridine-2-sulfonamide |
| 398 | 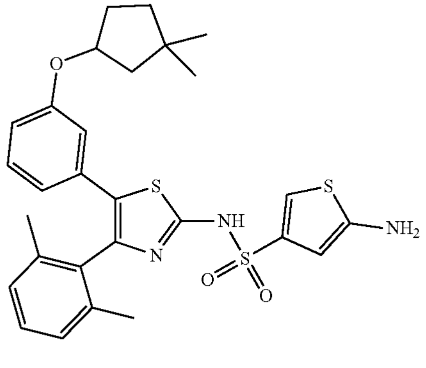 [SMILES: Cc1cccc(C)c1-c1nc(NS(=O)(=O)c2csc(N)c2)sc1-c1cccc(OC2CCC(C)(C)C2)c1] | 5-amino-N-[5-[3-(3,3-dimethylcyclopentyl)oxyphenyl]-4-(2,6-dimethylphenyl)-1,3-thiazol-2-yl]thiophene-3-sulfonamide |

TABLE 1-continued
| Compound Number | Compound Structural Formula | Compound Name |
|---|---|---|
| 189 | 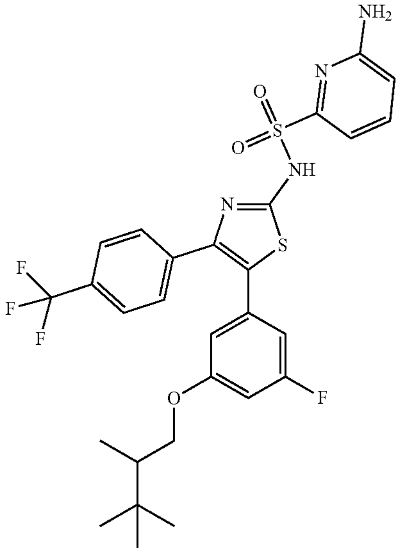 [SMILES: CC(COc1cc(F)cc(-c2sc(NS(=O)(=O)c3cccc(N)n3)nc2-c2ccc(C(F)(F)F)cc2)c1)C(C)(C)C] | 6-amino-N-[5-[3-fluoro-5-(2,3,3-trimethylbutoxy)phenyl]-4-[4-(trifluoromethyl)phenyl]-1,3-thiazol-2-yl]pyridine-2-sulfonamide |
| 502 | 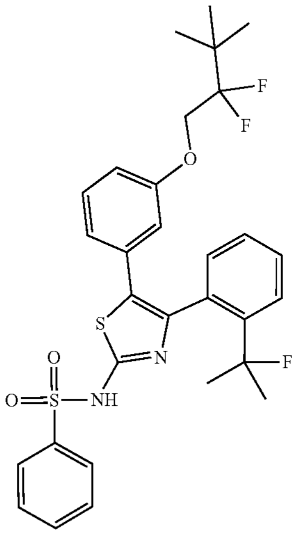 [SMILES: CC(C)(F)c1ccccc1-c1nc(NS(=O)(=O)c2ccccc2)sc1-c1cccc(OCC(F)(F)C(C)(C)C)c1] | N-[5-[3-(2,2-difluoro-3,3-dimethylbutoxy)phenyl]-4-[2-(2-fluoropropan-2-yl)phenyl]-1,3-thiazol-2-yl]benzenesulfonamide |

TABLE 1-continued

| Compound Number | Compound Structural Formula | Compound Name |
|---|---|---|
| 65 | 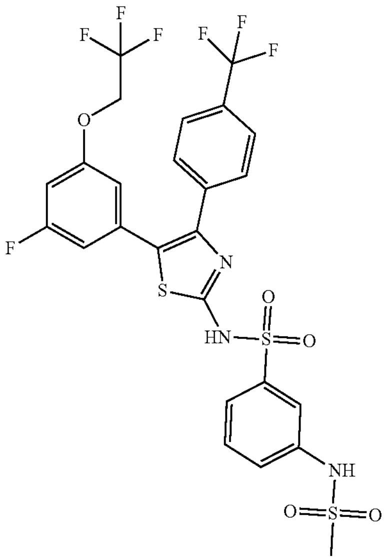 [SMILES: CS(=O)(=O)Nc1cccc(S(=O)(=O)Nc2nc(-c3ccc(C(F)(F)F)cc3)c(-c3cc(F)cc(OCC(F)(F)F)c3)s2)c1] | N-[5-[3-fluoro-5-(2,2,2-trifluoroethoxy)phenyl]-4-[4-(trifluoromethyl)phenyl]-1,3-thiazol-2-yl]-3-(methanesulfonamido)benzenesulfonamide |
| 491 | 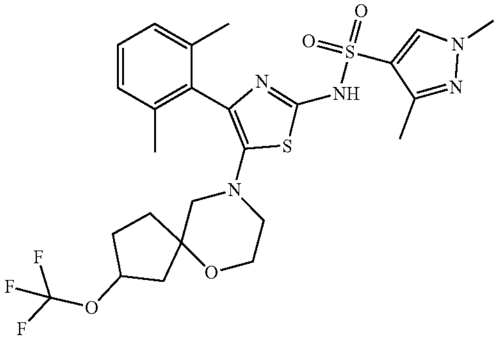 [SMILES: Cc1cccc(C)c1-c1nc(NS(=O)(=O)c2cn(C)nc2C)sc1N1CCOC2(CCC(OC(F)(F)F)C2)C1] | N-[4-(2,6-dimethylphenyl)-5-[3-(trifluoromethoxy)-6-oxa-9-azaspiro[4.5]decan-9-yl]-1,3-thiazol-2-yl]-1,3-dimethylpyrazole-4-sulfonamide |
| 352 | 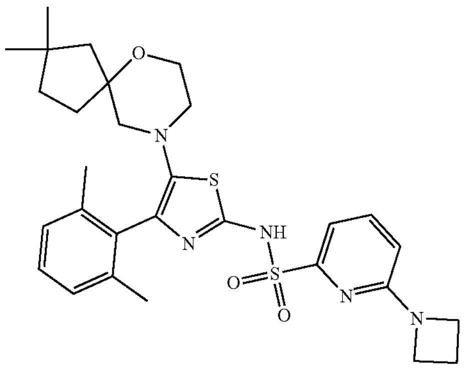 [SMILES: Cc1cccc(C)c1-c1nc(NS(=O)(=O)c2cccc(N3CCC3)n2)sc1N1CCOC2(CCC(C)(C)C2)C1] | 6-(azetidin-1-yl)-N-[5-(3,3-dimethyl-6-oxa-9-azaspiro[4.5]decan-9-yl)-4-(2,6-dimethylphenyl)-1,3-thiazol-2-yl]pyridine-2-sulfonamide |

TABLE 1-continued

| Compound Number | Compound Structural Formula | Compound Name |
|---|---|---|
| 214 | 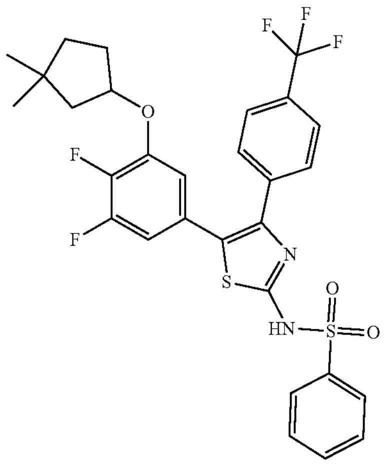 [SMILES: CC1(C)CCC(Oc2cc(-c3sc(NS(=O)(=O)c4ccccc4)nc3-c3ccc(C(F)(F)F)cc3)cc(F)c2F)C1] | N-[5-[3-(3,3-dimethylcyclopentyl)oxy-4,5-difluorophenyl]-4-[4-(trifluoromethyl)phenyl]-1,3-thiazol-2-yl]benzenesulfonamide |
| 76 | 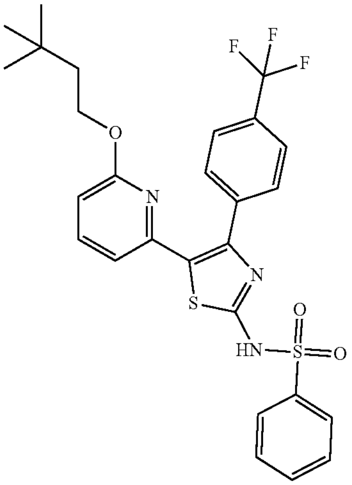 [SMILES: CC(C)(C)CCOc1cccc(-c2sc(NS(=O)(=O)c3ccccc3)nc2-c2ccc(C(F)(F)F)cc2)n1] | N-[5-[6-(3,3-dimethylbutoxy)pyridin-2-yl]-4-[4-(trifluoromethyl)phenyl]-1,3-thiazol-2-yl]benzenesulfonamide |
| 23 | 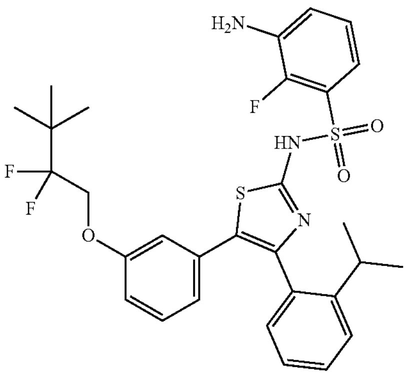 [SMILES: CC(C)c1ccccc1-c1nc(NS(=O)(=O)c2cccc(N)c2F)sc1-c1cccc(OCC(F)(F)C(C)(C)C)c1] | 3-amino-N-[5-[3-(2,2-difluoro-3,3-dimethylbutoxy)phenyl]-4-(2-propan-2-ylphenyl)-1,3-thiazol-2-yl]-2-fluorobenzenesulfonamide |

TABLE 1-continued

| Compound Number | Compound Structural Formula | Compound Name |
|---|---|---|
| 404 | 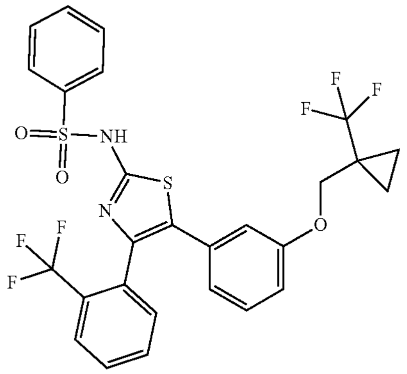 [SMILES: O=S(=O)(Nc1nc(-c2ccccc2C(F)(F)F)c(-c2cccc(OCC3(C(F)(F)F)CC3)c2)s1)c1ccccc1] | N-[5-[3-[1-(trifluoromethyl)cyclopropyl]methoxy]phenyl]-4-[2-(trifluoromethyl)phenyl]-1,3-thiazol-2-yl]benzenesulfonamide |
| 580 | 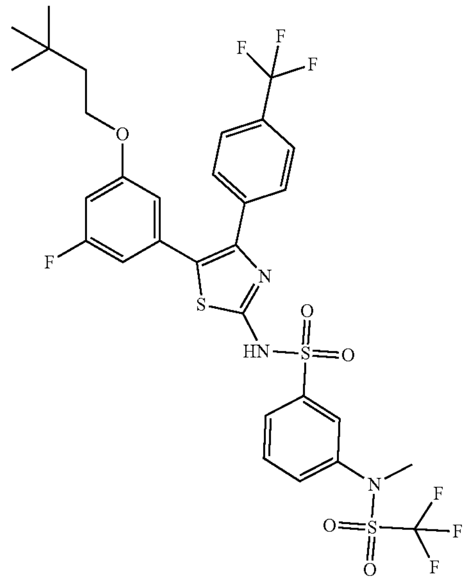 [SMILES: CN(c1cccc(S(=O)(=O)Nc2nc(-c3ccc(C(F)(F)F)cc3)c(-c3cc(F)cc(OCCC(C)(C)C)c3)s2)c1)S(=O)(=O)C(F)(F)F] | N-(5-(3-(3,3-dimethylbutoxy)-5-fluorophenyl)-4-(4-(trifluoromethyl)phenyl)thiazol-2-yl)-3-((1,1,1-trifluoro-N-methylmethyl)sulfonamido) benzenesulfonamide |
| 509 | 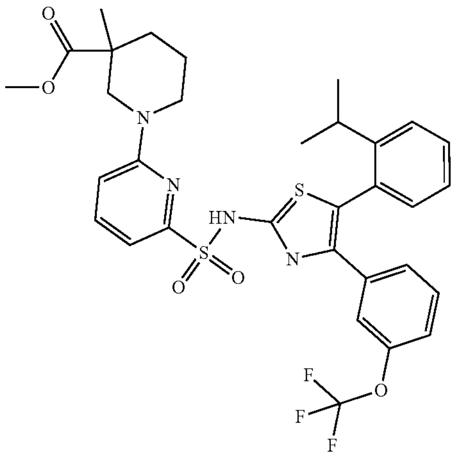 | methyl 3-methyl-1-[6-[[4-(2-propan-2-ylphenyl)-5-[3-(trifluoromethoxy)phenyl]-1,3-thiazol-2-yl]sulfamoyl]pyridin-2-yl]piperidine-3-carboxylate |

TABLE 1-continued

| Compound Number | Compound Structural Formula | Compound Name |
| --- | --- | --- |
| 480 | 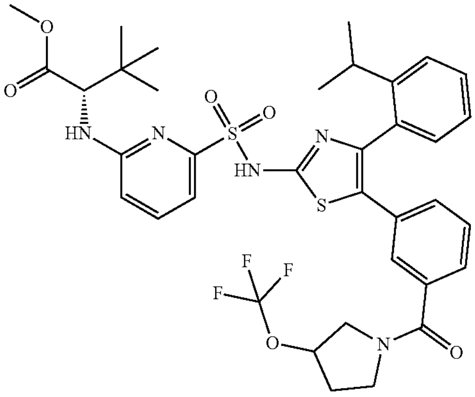 [SMILES: COC(=O)[C@@H](Nc1cccc(S(=O)(=O)Nc2nc(-c3ccccc3C(C)C)c(-c3cccc(C(=O)N4CCC(OC(F)(F)F)C4)c3)s2)n1)C(C)(C)C] | methyl (2S)-3,3-dimethyl-2-[[6-[4-(2-propan-2-ylphenyl)-5-[3-[3-(trifluoromethoxy)pyrrolidine-1-carbonyl]phenyl]-1,3-thiazol-2-yl]sulfamoyl]pyridin-2-yl]amino]butanoate |
| 581 | 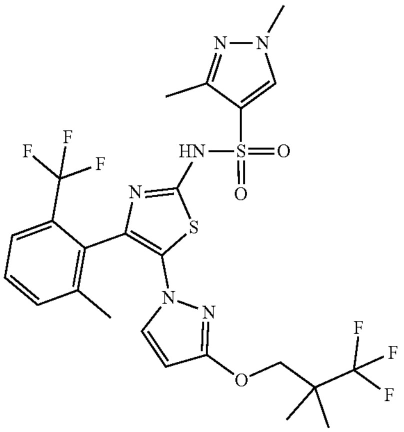 [SMILES: Cc1cccc(C(F)(F)F)c1-c1nc(NS(=O)(=O)c2cn(C)nc2C)sc1-n1ccc(OCC(C)(C)C(F)(F)F)n1] | 1,3-dimethyl-N-(4-(2-methyl-6-(trifluoromethyl)phenyl)-5-(3-(3,3,3-trifluoro-2,2-dimethylpropoxy)-1H-pyrazol-1-yl)thiazol-2-yl)-1H-pyrazole-4-sulfonamide |
| 269 | 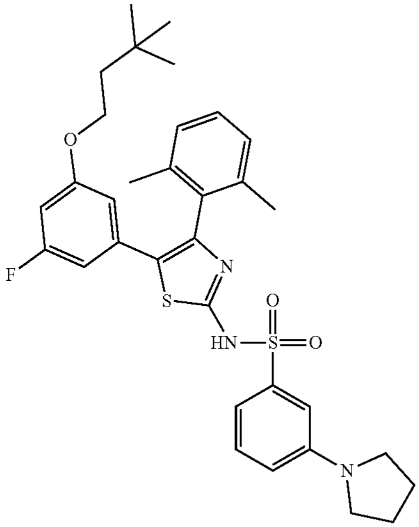 [SMILES: Cc1cccc(C)c1-c1nc(NS(=O)(=O)c2cccc(N3CCCC3)c2)sc1-c1cc(F)cc(OCCC(C)(C)C)c1] | N-[5-[3-(3,3-dimethylbutoxy)-5-fluorophenyl]-4-(2,6-dimethylphenyl)-1,3-thiazol-2-yl]-3-pyrrolidin-1-ylbenzenesulfonamide |

TABLE 1-continued

| Compound Number | Compound Structural Formula | Compound Name |
| --- | --- | --- |
| 66 | 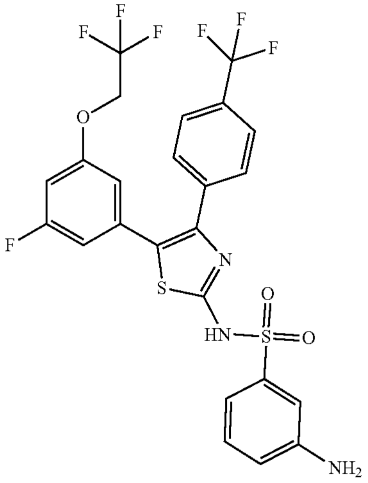 [SMILES: Nc1cccc(S(=O)(=O)Nc2nc(-c3ccc(C(F)(F)F)cc3)c(-c3cc(F)cc(OCC(F)(F)F)c3)s2)c1] | 3-amino-N-[5-[3-fluoro-5-(2,2,2-trifluoroethoxy)phenyl]-4-[4-(trifluoromethyl)phenyl]-1,3-thiazol-2-yl]benzenesulfonamide |
| 15 | 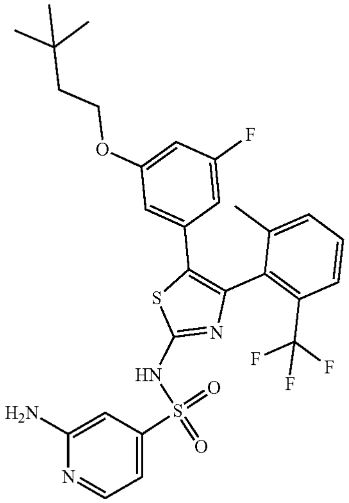 [SMILES: Cc1cccc(C(F)(F)F)c1-c1nc(NS(=O)(=O)c2ccnc(N)c2)sc1-c1cc(F)cc(OCCC(C)(C)C)c1] | 2-amino-N-[5-[3-(3,3-dimethylbutoxy)-5-fluorophenyl]-4-[2-methyl-6-(trifluoromethyl)phenyl]-1,3-thiazol-2-yl]pyridine-4-sulfonamide |
| 582 | 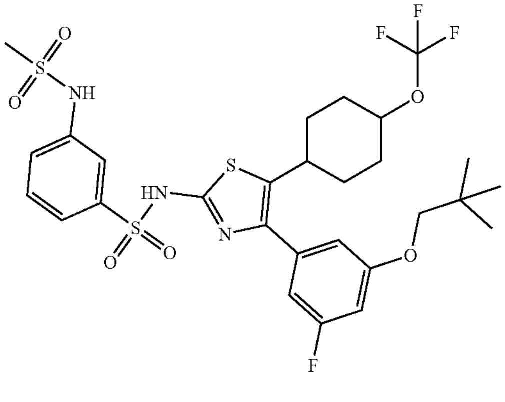 [SMILES: CC(C)(C)COc1cc(F)cc(-c2nc(NS(=O)(=O)c3cccc(NS(C)(=O)=O)c3)sc2C2CCC(OC(F)(F)F)CC2)c1] | N-(5-(3-fluoro-5-(neopentyloxy)phenyl)-4-(4-(trifluoromethoxy)cyclohexyl)thiazol-2-yl)-3-(methylsulfonamido)benzenesulfonamide |

TABLE 1-continued
| Compound Number | Compound Structural Formula | Compound Name |
|---|---|---|
| 445 | 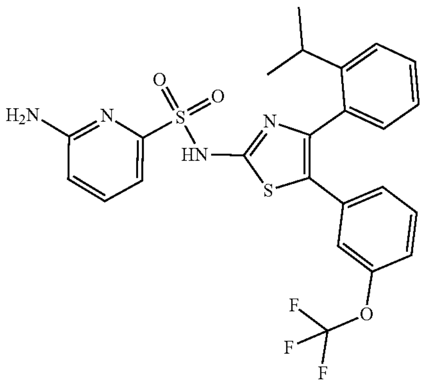 [SMILES: CC(C)c1ccccc1-c1nc(NS(=O)(=O)c2cccc(N)n2)sc1-c1cccc(OC(F)(F)F)c1] | 6-amino-N-[4-(2-propan-2-ylphenyl)-5-[3-(trifluoromethoxy)phenyl]-1,3-thiazol-2-yl]pyridine-2-sulfonamide |
| 297 | 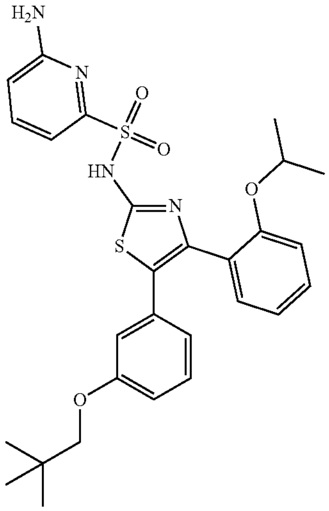 [SMILES: CC(C)Oc1ccccc1-c1nc(NS(=O)(=O)c2cccc(N)n2)sc1-c1cccc(OCC(C)(C)C)c1] | 6-amino-N-[5-[3-(2,2-dimethylpropoxy)phenyl]-4-(2-propan-2-yloxyphenyl)-1,3-thiazol-2-yl]pyridine-2-sulfonamide |
| 583 | 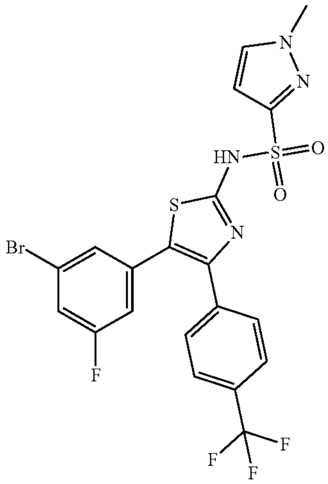 [SMILES: Cn1ccc(S(=O)(=O)Nc2nc(-c3ccc(C(F)(F)F)cc3)c(-c3cc(F)cc(Br)c3)s2)n1] | N-(5-(3-bromo-5-fluorophenyl)-4-(4-(trifluoromethyl)phenyl)thiazol-2-yl)-1-methyl-1H-pyrazole-3-sulfonamide |

TABLE 1-continued

| Compound Number | Compound Structural Formula | Compound Name |
|---|---|---|
| 106 | 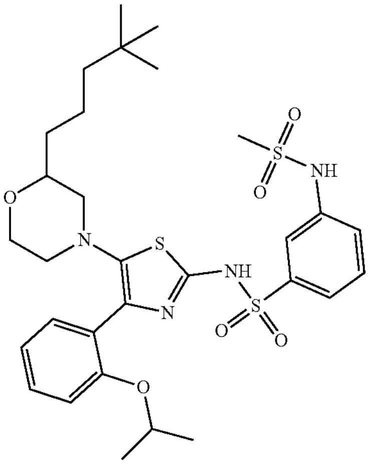 [SMILES: CC(C)Oc1ccccc1-c1nc(NS(=O)(=O)c2cccc(NS(C)(=O)=O)c2)sc1N1CCOC(CCCC(C)(C)C)C1] | N-[5-[2-(4,4-dimethylpentyl)morpholin-4-yl]-4-(2-propan-2-yloxyphenyl)-1,3-thiazol-2-yl]-3-(methanesulfonamido)benzenesulfonamide |
| 9 | 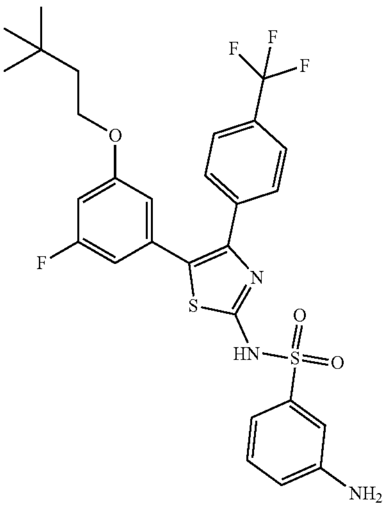 [SMILES: CC(C)(C)CCOc1cc(F)cc(-c2sc(NS(=O)(=O)c3cccc(N)c3)nc2-c2ccc(C(F)(F)F)cc2)c1] | 3-amino-N-(5-(3-(3,3-dimethylbutoxy)-5-fluorophenyl)-4-(4-(trifluoromethyl)phenyl)thiazol-2-yl)benzenesulfonamide |
| 408 | 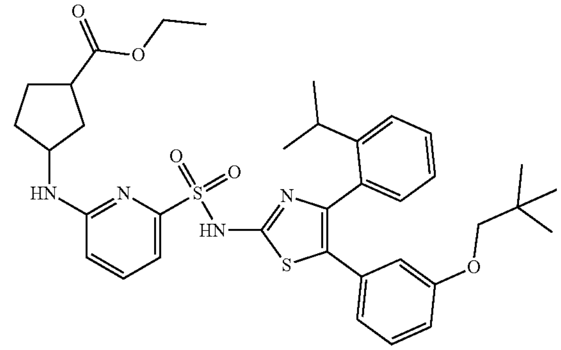 [SMILES: CCOC(=O)C1CCC(Nc2cccc(S(=O)(=O)Nc3nc(-c4ccccc4C(C)C)c(-c4cccc(OCC(C)(C)C)c4)s3)n2)C1] | ethyl 3-[[6-[5-[3-(2,2-dimethylpropoxy)phenyl]-4-(2-propan-2-ylphenyl)-1,3-thiazol-2-yl]sulfamoyl]pyridin-2-yl]amino]cyclopentane-1-carboxylate |

TABLE 1-continued

| Compound Number | Compound Structural Formula | Compound Name |
| --- | --- | --- |
| 171 | 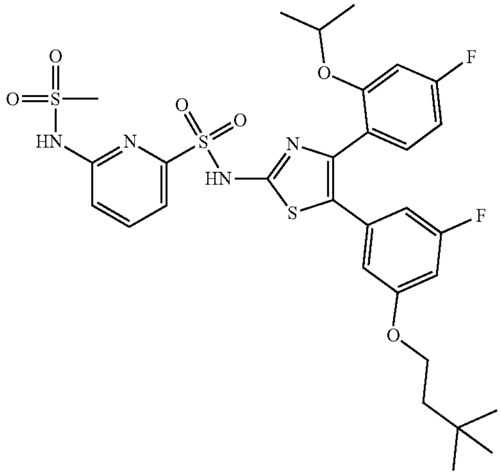 [SMILES: CC(C)Oc1cc(F)ccc1-c1nc(NS(=O)(=O)c2cccc(NS(C)(=O)=O)n2)sc1-c1cc(F)cc(OCCC(C)(C)C)c1] | N-[5-[3-(3,3-dimethylbutoxy)-5-fluorophenyl]-4-(4-fluoro-2-propan-2-yloxyphenyl)-1,3-thiazol-2-yl]-6-(methanesulfonamido)pyridine-2-sulfonamide |
| 317 | 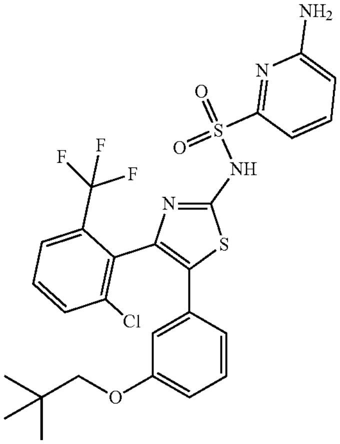 [SMILES: CC(C)(C)COc1cccc(-c2sc(NS(=O)(=O)c3cccc(N)n3)nc2-c2c(Cl)cccc2C(F)(F)F)c1] | 6-amino-N-[4-[2-chloro-6-(trifluoromethyl)phenyl]-5-[3-(2,2-dimethylpropoxy)phenyl]-1,3-thiazol-2-yl]pyridine-2-sulfonamide |
| 113 | 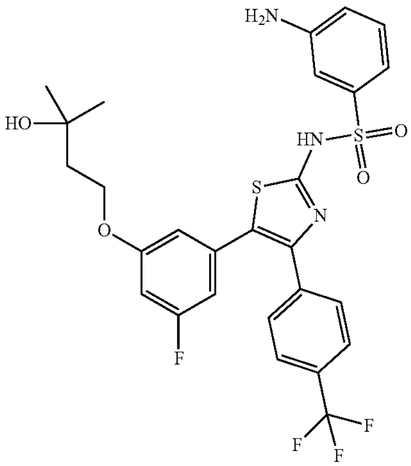 | 3-amino-N-[5-[3-fluoro-5-(3-hydroxy-3-methylbutoxy)phenyl]-4-[4-(trifluoromethyl)phenyl]-1,3-thiazol-2-yl]benzenesulfonamide |

TABLE 1-continued
| Compound Number | Compound Structural Formula | Compound Name |
|---|---|---|
| 375 | 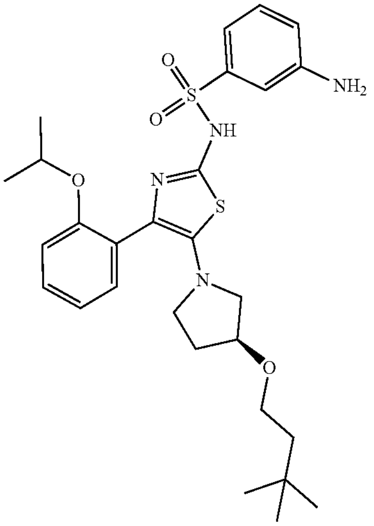 [SMILES: CC(C)Oc1ccccc1-c1nc(NS(=O)(=O)c2cccc(N)c2)sc1N1CC[C@H](OCCC(C)(C)C)C1] | 3-amino-N-[5-[(3S)-3-(3,3-dimethylbutoxy)pyrrolidin-1-yl]-4-(2-propan-2-yloxyphenyl)-1,3-thiazol-2-yl]benzenesulfonamide |
| 3 | 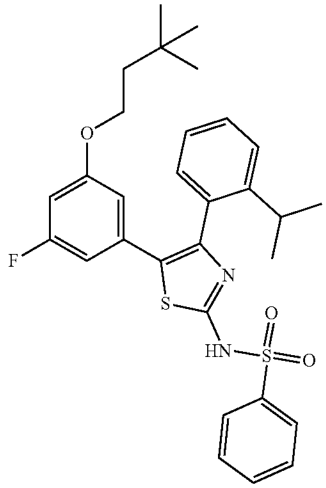 [SMILES: CC(C)c1ccccc1-c1nc(NS(=O)(=O)c2ccccc2)sc1-c1cc(F)cc(OCCC(C)(C)C)c1] | N-(5-(3-(3,3-dimethylbutoxy)-5-fluorophenyl)-4-(2-isopropylphenyl)thiazol-2-yl)benzenesulfonamide |
| 294 | 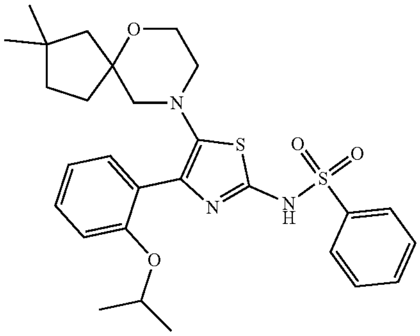 [SMILES: CC(C)Oc1ccccc1-c1nc(NS(=O)(=O)c2ccccc2)sc1N1CCOC2(CCC(C)(C)C2)C1] | N-[5-(3,3-dimethyl-6-oxa-9-azaspiro[4.5]decan-9-yl)-4-(2-propan-2-yloxyphenyl)-1,3-thiazol-2-yl]benzenesulfonamide |

TABLE 1-continued

| Compound Number | Compound Structural Formula | Compound Name |
|---|---|---|
| 359 | 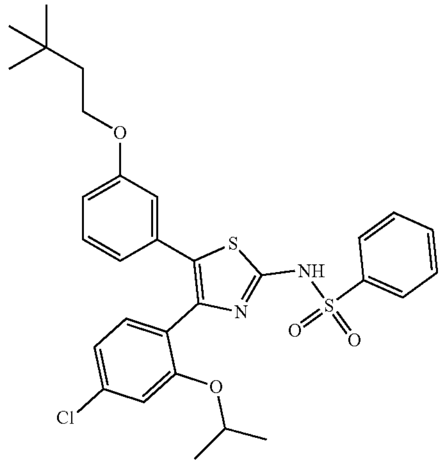 [SMILES: CC(C)Oc1cc(Cl)ccc1-c1nc(NS(=O)(=O)c2ccccc2)sc1-c1cccc(OCCC(C)(C)C)c1] | N-[4-(4-chloro-2-propan-2-yloxyphenyl)-5-[3-(3,3-dimethylbutoxy)phenyl]-1,3-thiazol-2-yl]benzenesulfonamide |
| 584 | 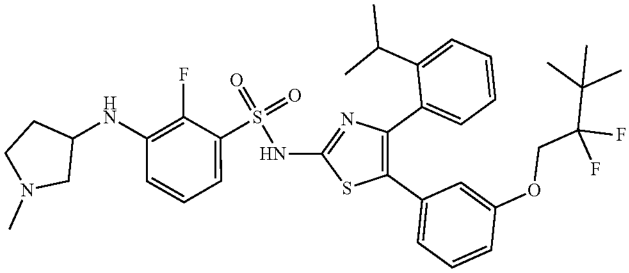 [SMILES: CC(C)c1ccccc1-c1nc(NS(=O)(=O)c2cccc(NC3CCN(C)C3)c2F)sc1-c1cccc(OCC(F)(F)C(C)(C)C)c1] | N-(5-(3-(2,2-difluoro-3,3-dimethylbutoxy)phenyl)-4-(2-isopropylphenyl)thiazol-2-yl)-2-fluoro-3-((1-methylpyrrolidin-3-yl)amino)benzenesulfonamide |
| 244 | 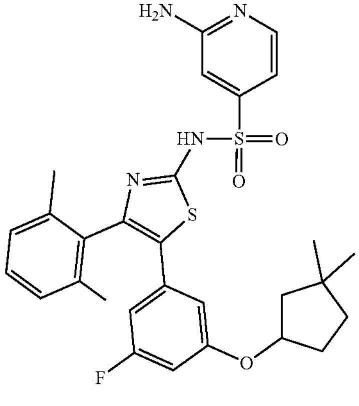 [SMILES: Cc1cccc(C)c1-c1nc(NS(=O)(=O)c2ccnc(N)c2)sc1-c1cc(F)cc(OC2CCC(C)(C)C2)c1] | 2-amino-N-[5-[3-(3,3-dimethylcyclopentyl)oxy-5-fluorophenyl]-4-(2,6-dimethylphenyl)-1,3-thiazol-2-yl]pyridine-4-sulfonamide |

TABLE 1-continued

| Compound Number | Compound Structural Formula | Compound Name |
|---|---|---|
| 274 | 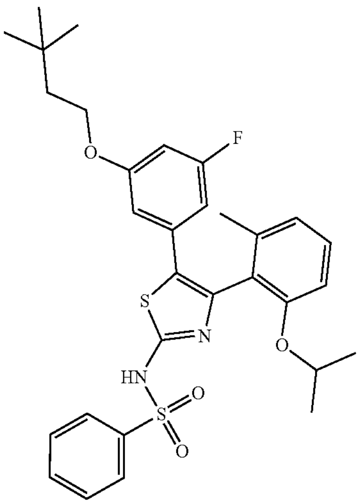 [SMILES: Cc1cccc(OC(C)C)c1-c1nc(NS(=O)(=O)c2ccccc2)sc1-c1cc(F)cc(OCCC(C)(C)C)c1] | N-[5-[3-(3,3-dimethylbutoxy)-5-fluorophenyl]-4-(2-methyl-6-propan-2-yloxyphenyl)-1,3-thiazol-2-yl]benzenesulfonamide |
| 434 | 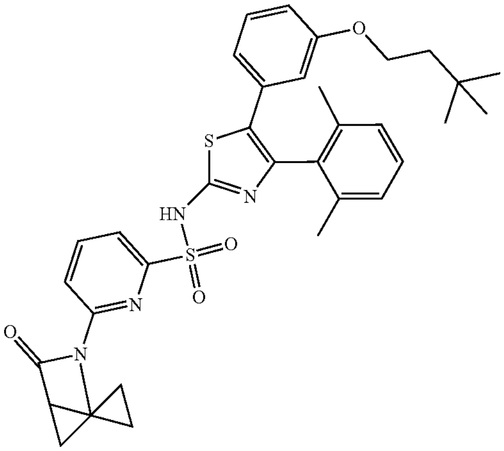 | N-[5-[3-(3,3-dimethylbutoxy)phenyl]-4-(2,6-dimethylphenyl)-1,3-thiazol-2-yl]-6-(7-oxo-6-azabicyclo[3.2.1]octan-6-yl)pyridine-2-sulfonamide |
| 360 | 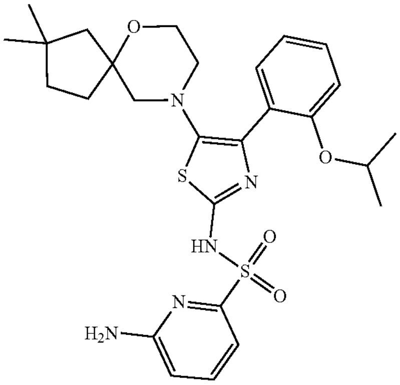 [SMILES: CC(C)Oc1ccccc1-c1nc(NS(=O)(=O)c2cccc(N)n2)sc1N1CCOC2(CCC(C)(C)C2)C1] | 6-amino-N-[5-(3,3-dimethyl-6-oxa-9-azaspiro[4.5]decan-9-yl)-4-(2-propan-2-yloxyphenyl)-1,3-thiazol-2-yl]pyridine-2-sulfonamide |

TABLE 1-continued

| Compound Number | Compound Structural Formula | Compound Name |
|---|---|---|
| 310 | 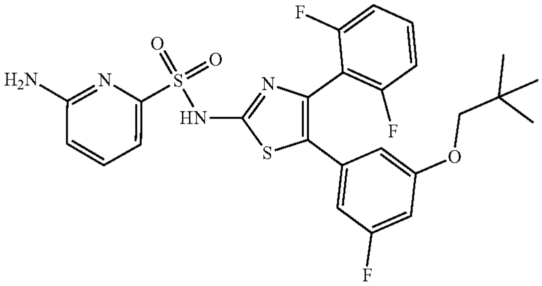 [SMILES: CC(C)(C)COc1cc(F)cc(-c2sc(NS(=O)(=O)c3cccc(N)n3)nc2-c2c(F)cccc2F)c1] | 6-amino-N-[4-(2,6-difluorophenyl)-5-[3-(2,2-dimethylpropoxy)-5-fluorophenyl]-1,3-thiazol-2-yl]pyridine-2-sulfonamide |
| 234 | 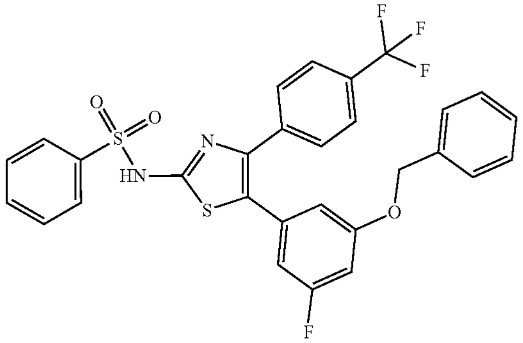 [SMILES: O=S(=O)(Nc1nc(-c2ccc(C(F)(F)F)cc2)c(-c2cc(F)cc(OCc3ccccc3)c2)s1)c1ccccc1] | N-[5-(3-fluoro-5-phenylmethoxyphenyl)-4-[4-(trifluoromethyl)phenyl]-1,3-thiazol-2-yl]benzenesulfonamide |
| 33 | 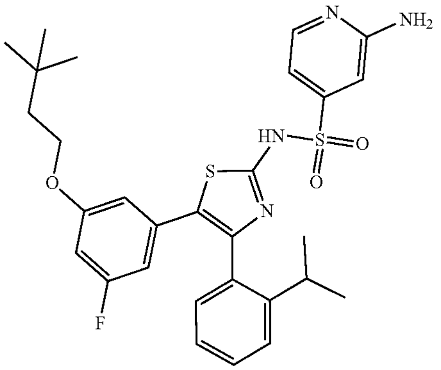 [SMILES: CC(C)c1ccccc1-c1nc(NS(=O)(=O)c2ccnc(N)c2)sc1-c1cc(F)cc(OCCC(C)(C)C)c1] | 2-amino-N-[5-[3-(3,3-dimethylbutoxy)-5-fluorophenyl]-4-(2-propan-2-ylphenyl)-1,3-thiazol-2-yl]pyridine-4-sulfonamide |
| 98 | 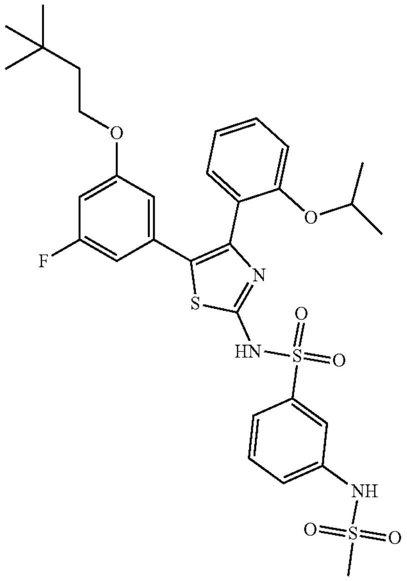 [SMILES: CC(C)Oc1ccccc1-c1nc(NS(=O)(=O)c2cccc(NS(C)(=O)=O)c2)sc1-c1cc(F)cc(OCCC(C)(C)C)c1] | N-[5-[3-(3,3-dimethylbutoxy)-5-fluorophenyl]-4-(2-propan-2-yloxyphenyl)-1,3-thiazol-2-yl]-3-(methanesulfonamido) benzenesulfonamide |

TABLE 1-continued
| Compound Number | Compound Structural Formula | Compound Name |
|---|---|---|
| 318 | 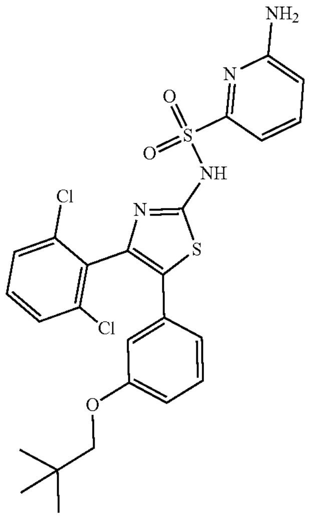 [SMILES: CC(C)(C)COc1cccc(-c2sc(NS(=O)(=O)c3cccc(N)n3)nc2-c2c(Cl)cccc2Cl)c1] | 6-amino-N-[4-(2,6-dichlorophenyl)-5-[3-(2,2-dimethylpropoxy)phenyl]-1,3-thiazol-2-yl]pyridine-2-sulfonamide |
| 405 | 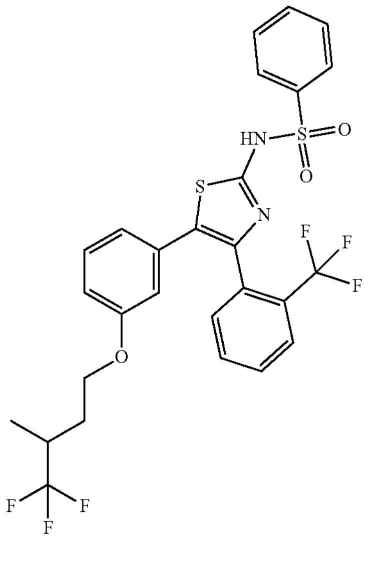 [SMILES: CC(CCOc1cccc(-c2sc(NS(=O)(=O)c3ccccc3)nc2-c2ccccc2C(F)(F)F)c1)C(F)(F)F] | N-[5-[3-(4,4,4-trifluoro-3-methylbutoxy)phenyl]-4-[2-(trifluoromethyl)phenyl]-1,3-thiazol-2-yl]benzenesulfonamide |

TABLE 1-continued

| Compound Number | Compound Structural Formula | Compound Name |
|---|---|---|
| 162 | 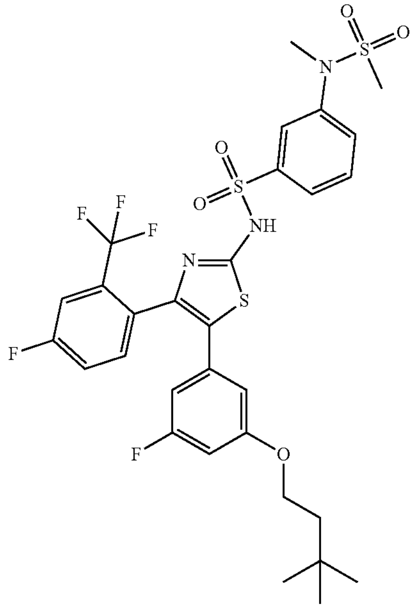 [SMILES: CN(c1cccc(S(=O)(=O)Nc2nc(-c3ccc(F)cc3C(F)(F)F)c(-c3cc(F)cc(OCCC(C)(C)C)c3)s2)c1)S(C)(=O)=O] | N-[5-[3-(3,3-dimethylbutoxy)-5-fluorophenyl]-4-[4-fluoro-2-(trifluoromethyl)phenyl]-1,3-thiazol-2-yl]-3-[methyl(methylsulfonyl)amino] benzenesulfonamide |
| 184 | 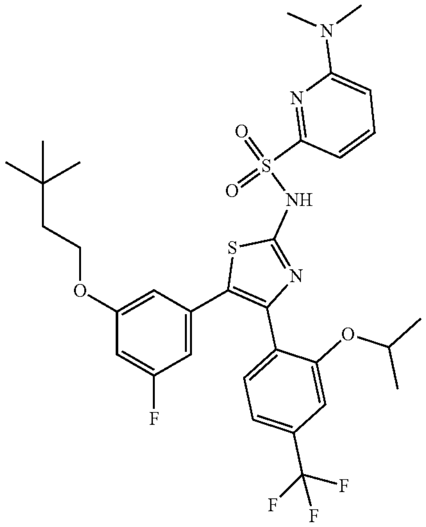 [SMILES: CC(C)Oc1cc(C(F)(F)F)ccc1-c1nc(NS(=O)(=O)c2cccc(N(C)C)n2)sc1-c1cc(F)cc(OCCC(C)(C)C)c1] | 6-(dimethylamino)-N-[5-[3-(3,3-dimethylbutoxy)-5-fluorophenyl]-4-[2-propan-2-yloxy-4-(trifluoromethyl)phenyl]-1,3-thiazol-2-yl]pyridine-2-sulfonamide |
| 315 | 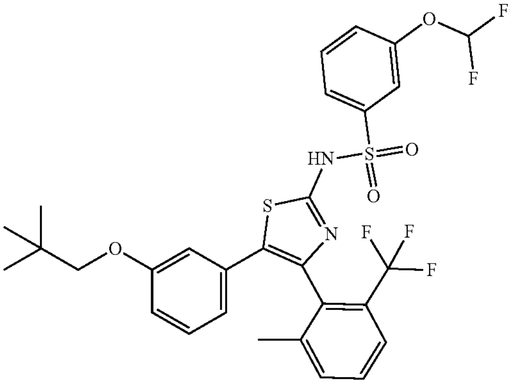 [SMILES: Cc1cccc(C(F)(F)F)c1-c1nc(NS(=O)(=O)c2cccc(OC(F)F)c2)sc1-c1cccc(OCC(C)(C)C)c1] | 3-(difluoromethoxy)-N-[5-[3-(2,2-dimethylpropoxy)phenyl]-4-[2-methyl-6-(trifluoromethyl)phenyl]-1,3-thiazol-2-yl]benzenesulfonamide |

TABLE 1-continued

| Compound Number | Compound Structural Formula | Compound Name |
|---|---|---|
| 585 | 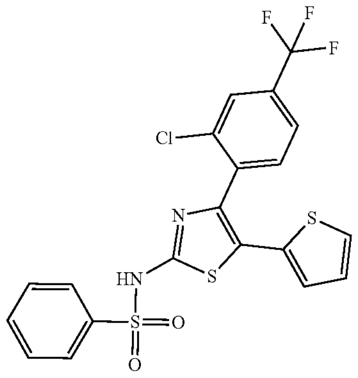 [SMILES: O=S(=O)(Nc1nc(-c2ccc(C(F)(F)F)cc2Cl)c(-c2cccs2)s1)c1ccccc1] | N-(4-(2-chloro-4-(trifluoromethyl)phenyl)-5-(thiophen-2-yl)thiazol-2-yl)benzenesulfonamide |
| 506 | 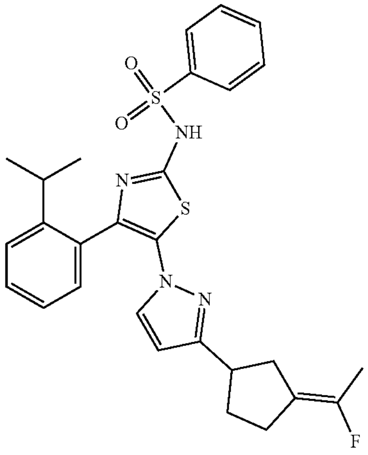 [SMILES: C/C(F)=C1/CCC(c2ccn(-c3sc(NS(=O)(=O)c4ccccc4)nc3-c3ccccc3C(C)C)n2)C1] | N-[5-[3-[(3E)-3-(1-fluoroethylidene)cyclopentyl]pyrazol-1-yl]-4-(2-propan-2-ylphenyl)-1,3-thiazol-2-yl]benzenesulfonamide |
| 285 | 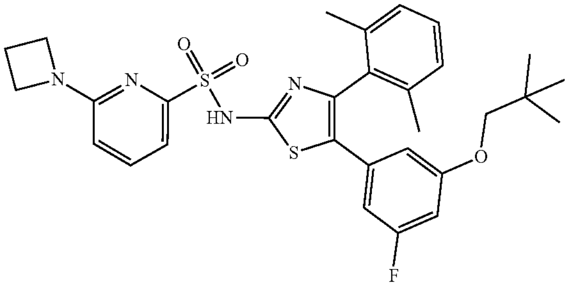 [SMILES: Cc1cccc(C)c1-c1nc(NS(=O)(=O)c2cccc(N3CCC3)n2)sc1-c1cc(F)cc(OCC(C)(C)C)c1] | 6-(azetidin-1-yl)-N-[4-(2,6-dimethylphenyl)-5-[3-(2,2-dimethylpropoxy)-5-fluorophenyl]-1,3-thiazol-2-yl]pyridine-2-sulfonamide |
| 586 | 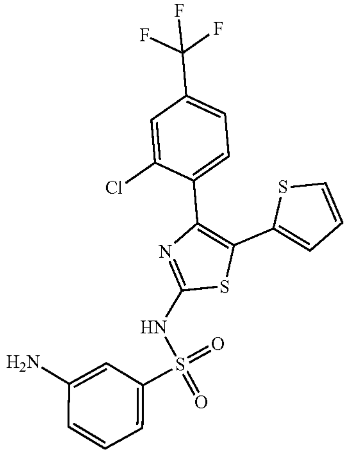 [SMILES: Nc1cccc(S(=O)(=O)Nc2nc(-c3ccc(C(F)(F)F)cc3Cl)c(-c3cccs3)s2)c1] | 3-amino-N-(4-(2-chloro-4-(trifluoromethyl)phenyl)-5-(thiophen-2-yl)thiazol-2-yl)benzenesulfonamide |

TABLE 1-continued

| Compound Number | Compound Structural Formula | Compound Name |
|---|---|---|
| 69 | 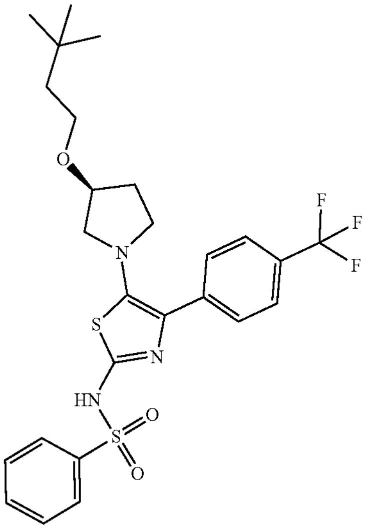 [SMILES: CC(C)(C)CCO[C@H]1CCN(c2sc(NS(=O)(=O)c3ccccc3)nc2-c2ccc(C(F)(F)F)cc2)C1] | N-[5-[(3S)-3-(3,3-dimethylbutoxy)pyrrolidin-1-yl]-4-[4-(trifluoromethyl)phenyl]-1,3-thiazol-2-yl]benzenesulfonamide |
| 47A1 | 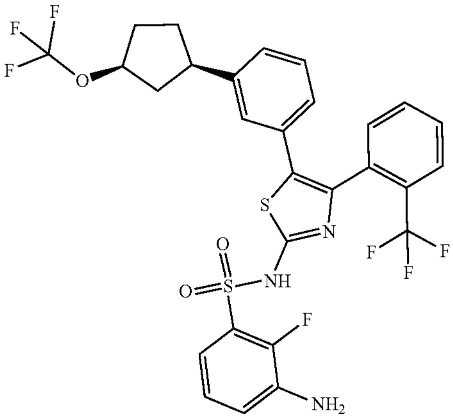 [SMILES: Nc1cccc(S(=O)(=O)Nc2nc(-c3ccccc3C(F)(F)F)c(-c3cccc([C@@H]4CC[C@H](OC(F)(F)F)C4)c3)s2)c1F] | 3-amino-2-fluoro-N-[5-[3-[(1R, 3S)-3-(trifluoromethoxy)cyclopentyl]phenyl]-4-[2-(trifluoromethyl)phenyl]-1,3-thiazol-2-yl]benzenesulfonamide |
| 446 | 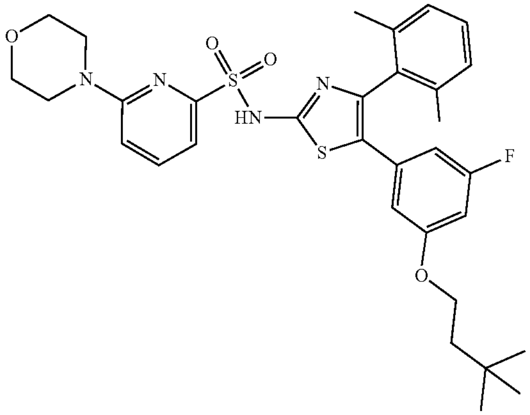 [SMILES: Cc1cccc(C)c1-c1nc(NS(=O)(=O)c2cccc(N3CCOCC3)n2)sc1-c1cc(F)cc(OCCC(C)(C)C)c1] | N-[5-[3-(3,3-dimethylbutoxy)-5-fluorophenyl]-4-(2,6-dimethylphenyl)-1,3-thiazol-2-yl]-6-morpholin-4-ylpyridine-2-sulfonamide |

TABLE 1-continued
| Compound Number | Compound Structural Formula | Compound Name |
|---|---|---|
| 34 | 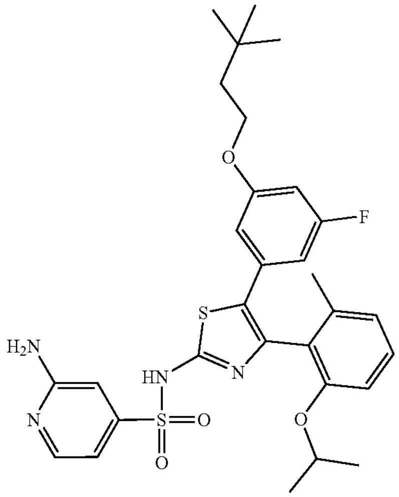 [SMILES: Cc1cccc(OC(C)C)c1-c1nc(NS(=O)(=O)c2ccnc(N)c2)sc1-c1cc(F)cc(OCCC(C)(C)C)c1] | 2-amino-N-[5-[3-(3,3-dimethylbutoxy)-5-fluorophenyl]-4-(2-methyl-6-propan-2-yloxyphenyl)-1,3-thiazol-2-yl]pyridine-4-sulfonamide |
| 68 | 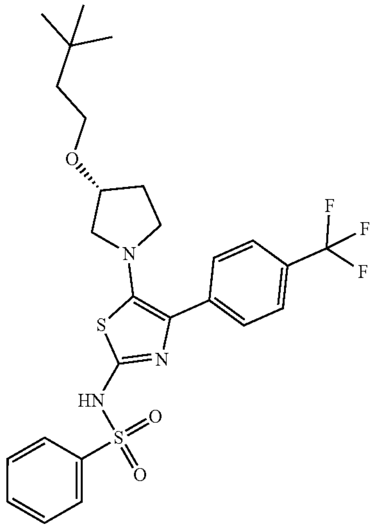 [SMILES: CC(C)(C)CCO[C@@H]1CCN(c2sc(NS(=O)(=O)c3ccccc3)nc2-c2ccc(C(F)(F)F)cc2)C1] | N-[5-[(3R)-3-(3,3-dimethylbutoxy)pyrrolidin-1-yl]-4-[4-(trifluoromethyl)phenyl]-1,3-thiazol-2-yl]benzenesulfonamide |
| 159 | 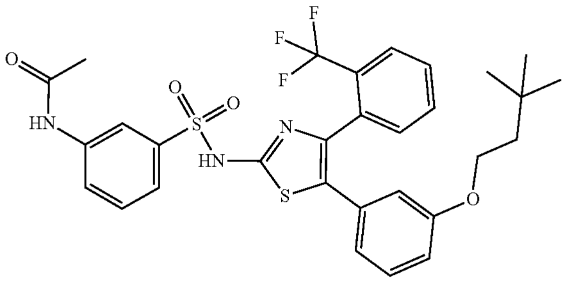 [SMILES: CC(=O)Nc1cccc(S(=O)(=O)Nc2nc(-c3ccccc3C(F)(F)F)c(-c3cccc(OCCC(C)(C)C)c3)s2)c1] | N-[3-[[5-[3-(3,3-dimethylbutoxy)phenyl]-4-[2-(trifluoromethyl)phenyl]-1,3-thiazol-2-yl]sulfamoyl]phenyl]acetamide |

TABLE 1-continued

| Compound Number | Compound Structural Formula | Compound Name |
|---|---|---|
| 147 | 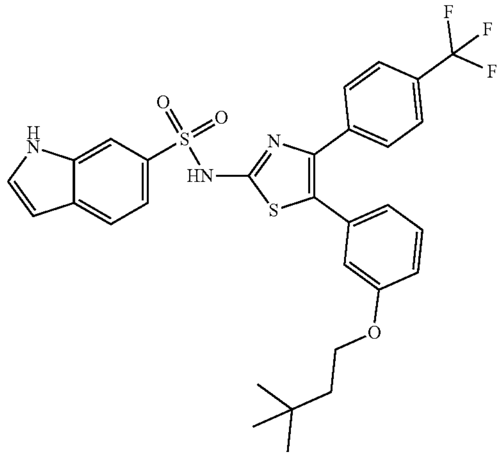 [SMILES: CC(C)(C)CCOc1cccc(-c2sc(NS(=O)(=O)c3ccc4cc[nH]c4c3)nc2-c2ccc(C(F)(F)F)cc2)c1] | N-[5-[3-(3,3-dimethylbutoxy)phenyl]-4-[4-(trifluoromethyl)phenyl]-1,3-thiazol-2-yl]-1H-indole-6-sulfonamide |
| 5 | 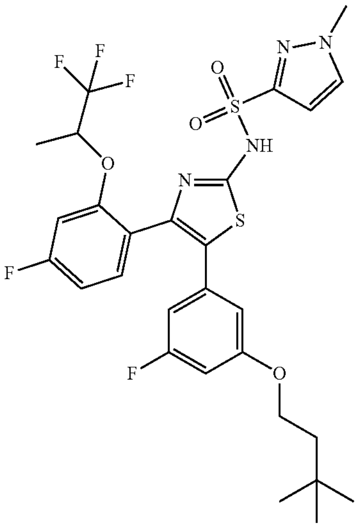 [SMILES: CC(Oc1cc(F)ccc1-c1nc(NS(=O)(=O)c2ccn(C)n2)sc1-c1cc(F)cc(OCCC(C)(C)C)c1)C(F)(F)F] | N-(5-(3-(3,3-dimethylbutoxy)-5-fluorophenyl)-4-(4-fluoro-2-((1,1,1-trifluoropropan-2-yl)oxy)phenyl)thiazol-2-yl)-1-methyl-1H-pyrazole-3-sulfonamide |
| 587 | 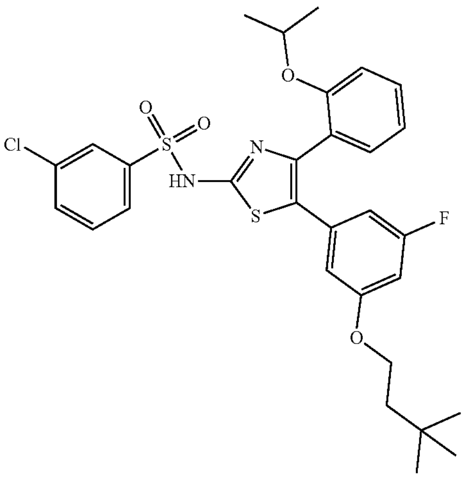 [SMILES: CC(C)Oc1ccccc1-c1nc(NS(=O)(=O)c2cccc(Cl)c2)sc1-c1cc(F)cc(OCCC(C)(C)C)c1] | 3-chloro-N-(5-(3-(3,3-dimethylbutoxy)-5-fluorophenyl)-4-(2-isopropoxyphenyl)thiazol-2-yl)benzenesulfonamide |

TABLE 1-continued

| Compound Number | Compound Structural Formula | Compound Name |
|---|---|---|
| 123 | 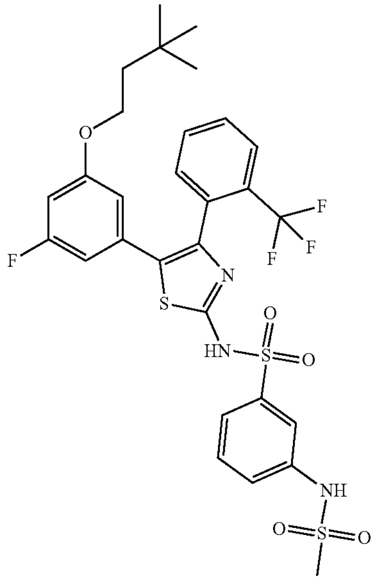 [SMILES: CC(C)(C)CCOc1cc(F)cc(-c2sc(NS(=O)(=O)c3cccc(NS(C)(=O)=O)c3)nc2-c2ccccc2C(F)(F)F)c1] | N-[5-[3-(3,3-dimethylbutoxy)-5-fluorophenyl]-4-[2-(trifluoromethyl)phenyl]-1,3-thiazol-2-yl]-3-(methanesulfonamido) benzenesulfonamide |
| 137 | 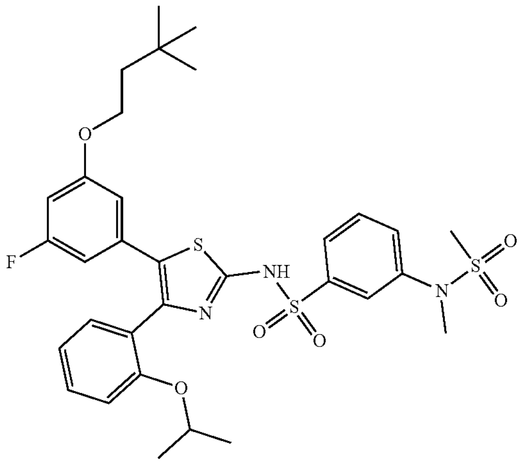 [SMILES: CC(C)Oc1ccccc1-c1nc(NS(=O)(=O)c2cccc(N(C)S(C)(=O)=O)c2)sc1-c1cc(F)cc(OCCC(C)(C)C)c1] | N-[5-[3-(3,3-dimethylbutoxy)-5-fluorophenyl]-4-(2-propan-2-yloxyphenyl)-1,3-thiazol-2-yl]-3-[methyl(methylsulfonyl)amino] benzenesulfonamide |
| 487 | 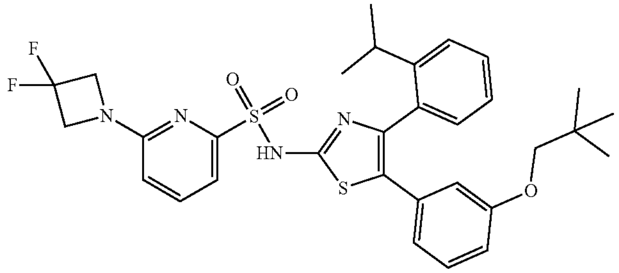 [SMILES: CC(C)c1ccccc1-c1nc(NS(=O)(=O)c2cccc(N3CC(F)(F)C3)n2)sc1-c1cccc(OCC(C)(C)C)c1] | 6-(3,3-difluoroazetidin-1-yl)-N-[5-[3-(2,2-dimethylpropoxy)phenyl]-4-(2-propan-2-ylphenyl)-1,3-thiazol-2-yl]pyridine-2-sulfonamide |

TABLE 1-continued

| Compound Number | Compound Structural Formula | Compound Name |
|---|---|---|
| 588 | 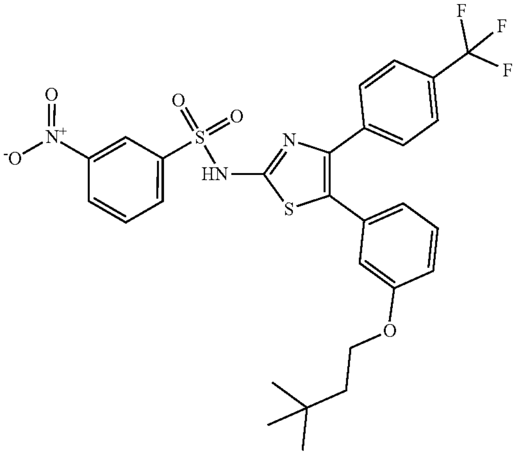 | N-(5-(3-(3,3-dimethylbutoxy)phenyl)-4-(4-(trifluoromethyl)phenyl)thiazol-2-yl)-3-nitrobenzenesulfonamide |
| 188 | 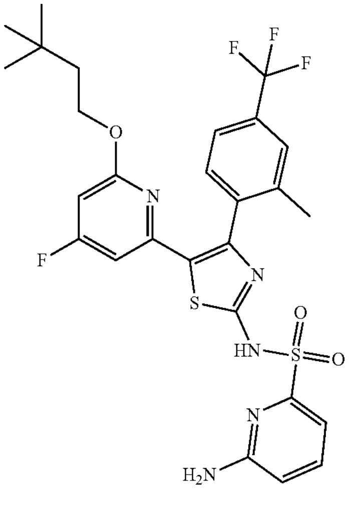 [SMILES: Cc1cc(C(F)(F)F)ccc1-c1nc(NS(=O)(=O)c2cccc(N)n2)sc1-c1cc(F)cc(OCCC(C)(C)C)n1] | 6-amino-N-[5-[6-(3,3-dimethylbutoxy)-4-fluoropyridin-2-yl]-4-[2-methyl-4-(trifluoromethyl)phenyl]-1,3-thiazol-2-yl]pyridine-2-sulfonamide |
| 143 | 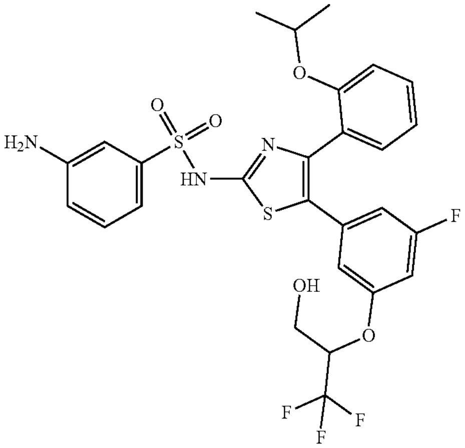 [SMILES: CC(C)Oc1ccccc1-c1nc(NS(=O)(=O)c2cccc(N)c2)sc1-c1cc(F)cc(OC(CO)C(F)(F)F)c1] | 3-amino-N-[5-[3-fluoro-5-(1,1,1-trifluoro-3-hydroxypropan-2-yl)oxyphenyl]-4-(2-propan-2-yloxyphenyl)-1,3-thiazol-2-yl]benzenesulfonamide |

TABLE 1-continued

| Compound Number | Compound Structural Formula | Compound Name |
|---|---|---|
| 114 | 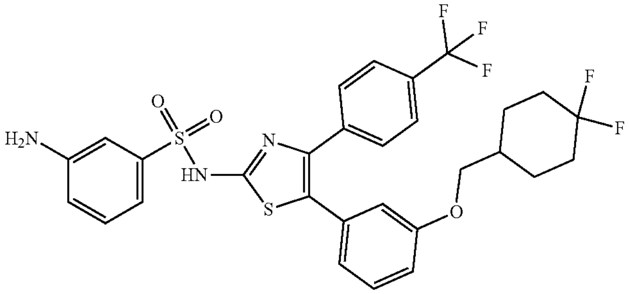 [SMILES: Nc1cccc(S(=O)(=O)Nc2nc(-c3ccc(C(F)(F)F)cc3)c(-c3cccc(OCC4CCC(F)(F)CC4)c3)s2)c1] | 3-amino-N-[5-[3-[(4,4-difluorocyclohexyl)methoxy]phenyl]-4-[4-(trifluoromethyl)phenyl]-1,3-thiazol-2-yl]benzenesulfonamide |
| 26 | 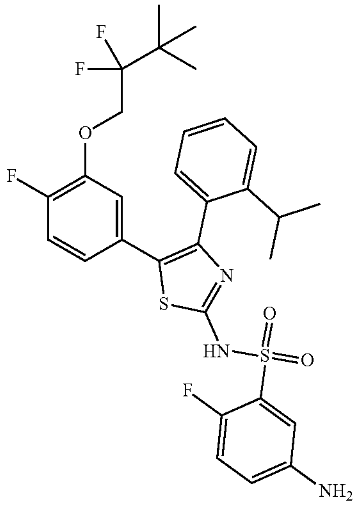 [SMILES: CC(C)c1ccccc1-c1nc(NS(=O)(=O)c2cc(N)ccc2F)sc1-c1ccc(F)c(OCC(F)(F)C(C)(C)C)c1] | 5-amino-N-[5-[3-(2,2-difluoro-3,3-dimethylbutoxy)-4-fluorophenyl]-4-(2-propan-2-ylphenyl)-1,3-thiazol-2-yl]-2-fluorobenzenesulfonamide |
| 495 | 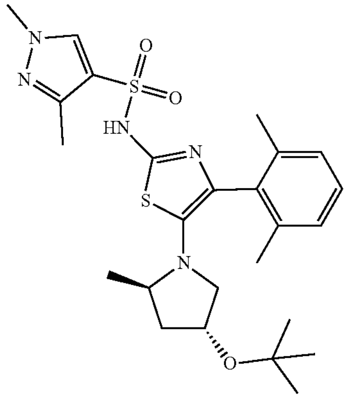 [SMILES: Cc1cccc(C)c1-c1nc(NS(=O)(=O)c2cn(C)nc2C)sc1N1C[C@H](OC(C)(C)C)C[C@H]1C] | N-[4-(2,6-dimethylphenyl)-5-[(2R,4R)-2-methyl-4-[(2-methylpropan-2-yl)oxy]pyrrolidin-1-yl]-1,3-thiazol-2-yl]-1,3-dimethylpyrazole-4-sulfonamide |

TABLE 1-continued

| Compound Number | Compound Structural Formula | Compound Name |
| --- | --- | --- |
| 362 | 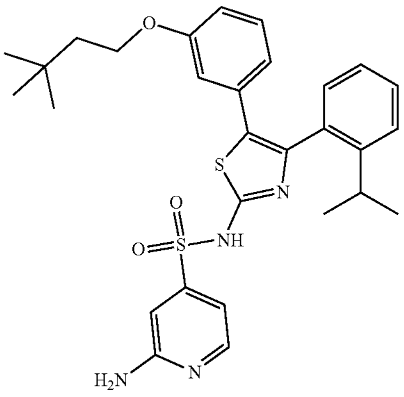 [SMILES: CC(C)c1ccccc1-c1nc(NS(=O)(=O)c2ccnc(N)c2)sc1-c1cccc(OCCC(C)(C)C)c1] | 2-amino-N-[5-[3-(3,3-dimethylbutoxy)phenyl]-4-(2-propan-2-ylphenyl)-1,3-thiazol-2-yl]pyridine-4-sulfonamide |
| 151 | 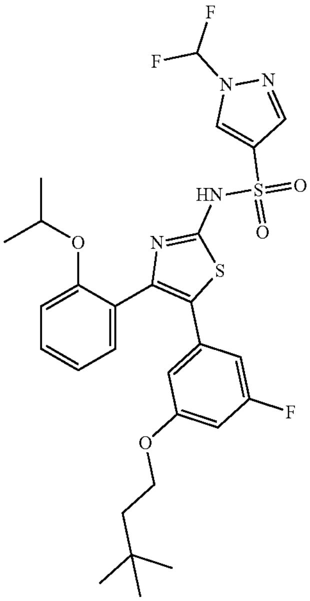 [SMILES: CC(C)Oc1ccccc1-c1nc(NS(=O)(=O)c2cnn(C(F)F)c2)sc1-c1cc(F)cc(OCCC(C)(C)C)c1] | 1-(difluoromethyl)-N-[5-[3-(3,3-dimethylbutoxy)-5-fluorophenyl]-4-(2-propan-2-yloxyphenyl)-1,3-thiazol-2-yl]pyrazole-4-sulfonamide |
| 589 | 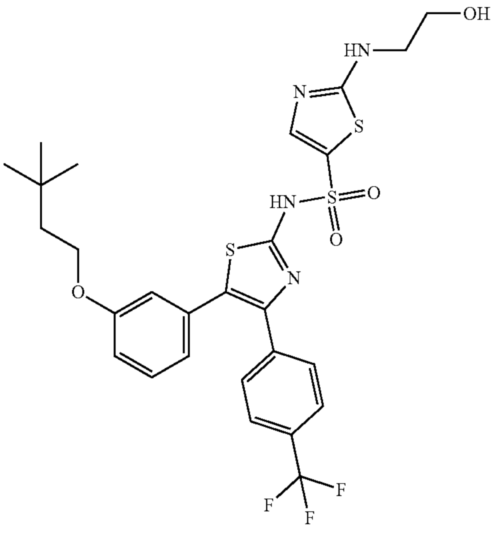 [SMILES: CC(C)(C)CCOc1cccc(-c2sc(NS(=O)(=O)c3cnc(NCCO)s3)nc2-c2ccc(C(F)(F)F)cc2)c1] | N-(5-(3-(3,3-dimethylbutoxy)phenyl)-4-(4-(trifluoromethyl)phenyl)thiazol-2-yl)-2-((2-hydroxyethyl)amino)thiazole-5-sulfonamide |

TABLE 1-continued

| Compound Number | Compound Structural Formula | Compound Name |
| --- | --- | --- |
| 166 | 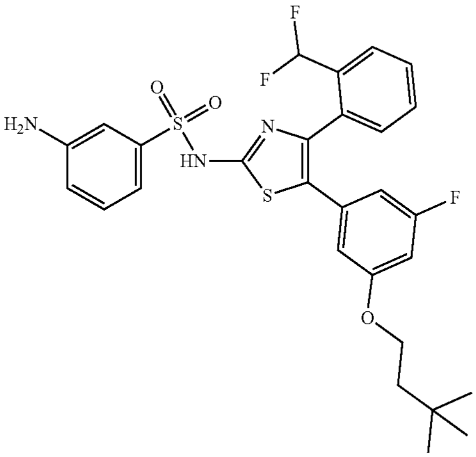 [SMILES: CC(C)(C)CCOc1cc(F)cc(-c2sc(NS(=O)(=O)c3cccc(N)c3)nc2-c2ccccc2C(F)F)c1] | 3-amino-N-[4-[2-(difluoromethyl)phenyl]-5-[3-(3,3-dimethylbutoxy)-5-fluorophenyl]-1,3-thiazol-2-yl]benzenesulfonamide |
| 397 | 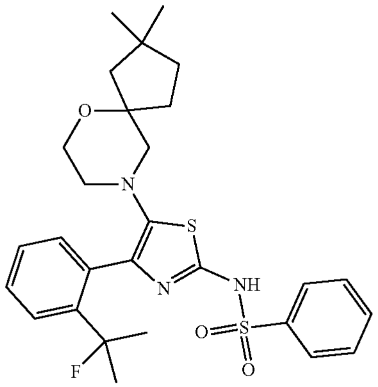 [SMILES: CC1(C)CCC2(CN(c3sc(NS(=O)(=O)c4ccccc4)nc3-c3ccccc3C(C)(C)F)CCO2)C1] | N-[5-(3,3-dimethyl-6-oxa-9-azaspiro[4.5]decan-9-yl)-4-[2-(2-fluoropropan-2-yl)phenyl]-1,3-thiazol-2-yl]benzenesulfonamide |
| 370 | 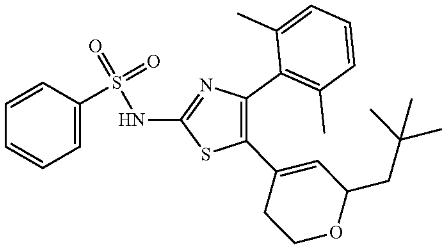 [SMILES: Cc1cccc(C)c1-c1nc(NS(=O)(=O)c2ccccc2)sc1C1=CC(CC(C)(C)C)OCC1] | N-[4-(2,6-dimethylphenyl)-5-[6-(2,2-dimethylpropyl)-3,6-dihydro-2H-pyran-4-yl]-1,3-thiazol-2-yl]benzenesulfonamide |
| 14 | 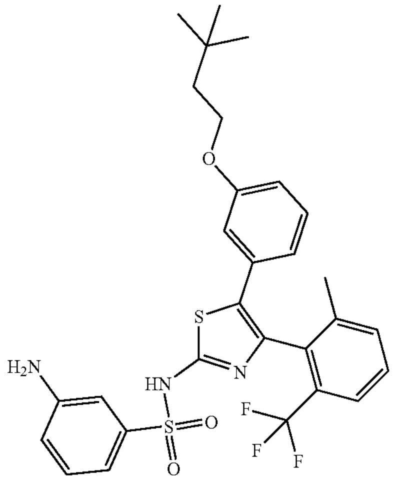 [SMILES: Cc1cccc(C(F)(F)F)c1-c1nc(NS(=O)(=O)c2cccc(N)c2)sc1-c1cccc(OCCC(C)(C)C)c1] | 3-amino-N-[5-[3-(3,3-dimethylbutoxy)phenyl]-4-[2-methyl-6-(trifluoromethyl)phenyl]-1,3-thiazol-2-yl]benzenesulfonamide |

TABLE 1-continued

| Compound Number | Compound Structural Formula | Compound Name |
| --- | --- | --- |
| 177 | 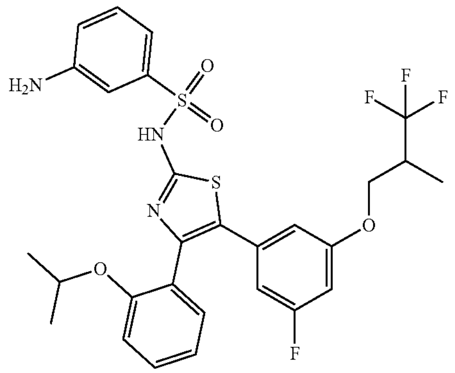 [SMILES: CC(C)Oc1ccccc1-c1nc(NS(=O)(=O)c2cccc(N)c2)sc1-c1cc(F)cc(OCC(C)C(F)(F)F)c1] | 3-amino-N-[5-[3-fluoro-5-(3,3,3-trifluoro-2-methylpropoxy)phenyl]-4-(2-propan-2-yloxyphenyl)-1,3-thiazol-2-yl]benzenesulfonamide |
| 590 | 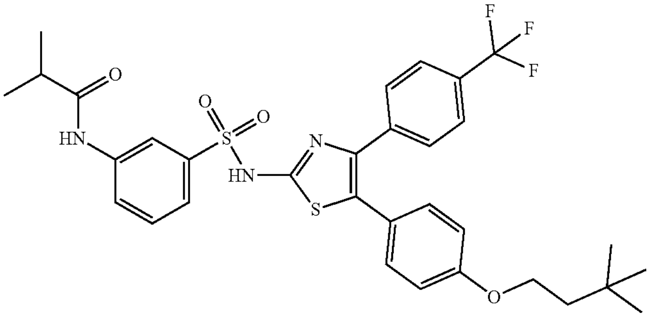 [SMILES: CC(C)C(=O)Nc1cccc(S(=O)(=O)Nc2nc(-c3ccc(C(F)(F)F)cc3)c(-c3ccc(OCCC(C)(C)C)cc3)s2)c1] | N-(3-(N-(5-(4-(3,3-dimethylbutoxy)phenyl)-4-(4-(trifluoromethyl)phenyl)thiazol-2-yl)sulfamoyl)phenyl)isobutyramide |
| 591 | 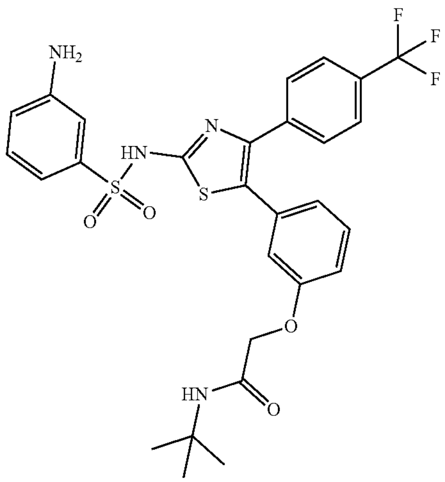 [SMILES: CC(C)(C)NC(=O)COc1cccc(-c2sc(NS(=O)(=O)c3cccc(N)c3)nc2-c2ccc(C(F)(F)F)cc2)c1] | 2-(3-(2-((3-aminophenyl)sulfonamido)-4-(4-(trifluoromethyl)phenyl)thiazol-5-yl)phenoxy)-N-(tert-butyl)acetamide |

TABLE 1-continued

| Compound Number | Compound Structural Formula | Compound Name |
|---|---|---|
| 344 | 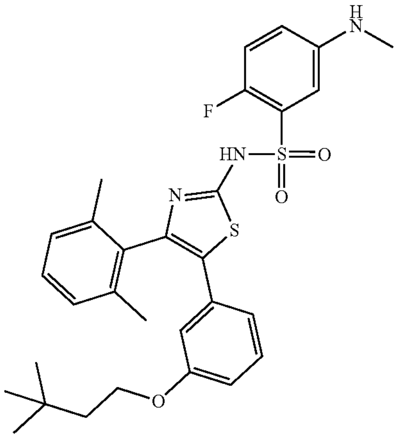 [SMILES: CNc1ccc(F)c(S(=O)(=O)Nc2nc(-c3c(C)cccc3C)c(-c3cccc(OCCC(C)(C)C)c3)s2)c1] | N-[5-[3-(3,3-dimethylbutoxy)phenyl]-4-(2,6-dimethylphenyl)-1,3-thiazol-2-yl]-2-fluoro-5-(methylamino)benzenesulfonamide |
| 499 | 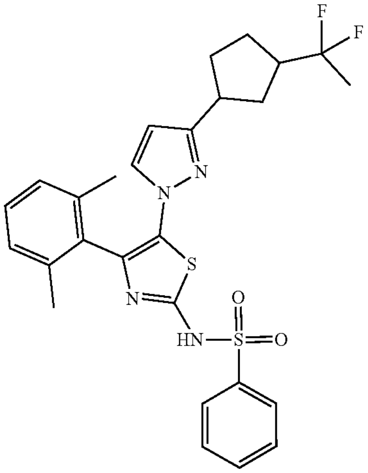 [SMILES: Cc1cccc(C)c1-c1nc(NS(=O)(=O)c2ccccc2)sc1-n1ccc(C2CCC(C(C)(F)F)C2)n1] | N-[5-[3-[3-(1,1-difluoroethyl)cyclopentyl]pyrazol-1-yl]-4-(2,6-dimethylphenyl)-1,3-thiazol-2-yl]benzenesulfonamide |
| 329 | 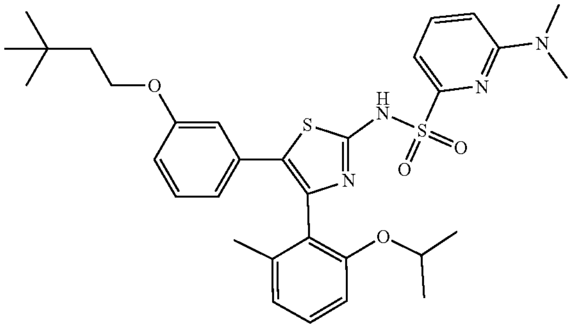 [SMILES: Cc1cccc(OC(C)C)c1-c1nc(NS(=O)(=O)c2cccc(N(C)C)n2)sc1-c1cccc(OCCC(C)(C)C)c1] | 6-(dimethylamino)-N-[5-[3-(3,3-dimethylbutoxy)phenyl]-4-(2-methyl-6-propan-2-yloxyphenyl)-1,3-thiazol-2-yl]pyridine-2-sulfonamide |

TABLE 1-continued

| Compound Number | Compound Structural Formula | Compound Name |
|---|---|---|
| 312 | 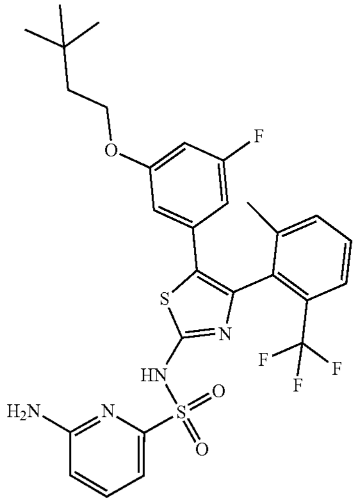 [SMILES: Cc1cccc(C(F)(F)F)c1-c1nc(NS(=O)(=O)c2cccc(N)n2)sc1-c1cc(F)cc(OCCC(C)(C)C)c1] | 6-amino-N-[5-[3-(3,3-dimethylbutoxy)-5-fluorophenyl]-4-[2-methyl-6-(trifluoromethyl)phenyl]-1,3-thiazol-2-yl]pyridine-2-sulfonamide |
| 473 | 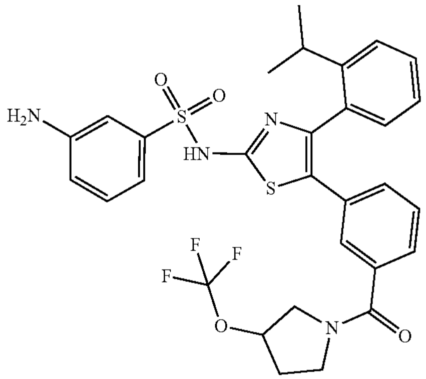 [SMILES: CC(C)c1ccccc1-c1nc(NS(=O)(=O)c2cccc(N)c2)sc1-c1cccc(C(=O)N2CCC(OC(F)(F)F)C2)c1] | 3-amino-N-[4-(2-propan-2-ylphenyl)-5-[3-[3-(trifluoromethoxy)pyrrolidine-1-carbonyl]phenyl]-1,3-thiazol-2-yl]benzenesulfonamide |
| 165 | 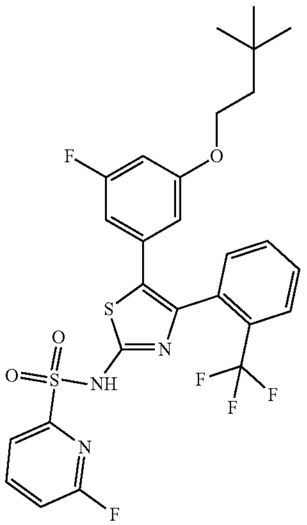 [SMILES: CC(C)(C)CCOc1cc(F)cc(-c2sc(NS(=O)(=O)c3cccc(F)n3)nc2-c2ccccc2C(F)(F)F)c1] | N-[5-[3-(3,3-dimethylbutoxy)-5-fluorophenyl]-4-[2-(trifluoromethyl)phenyl]-1,3-thiazol-2-yl]-6-fluoropyridine-2-sulfonamide |

TABLE 1-continued

| Compound Number | Compound Structural Formula | Compound Name |
|---|---|---|
| 453 | 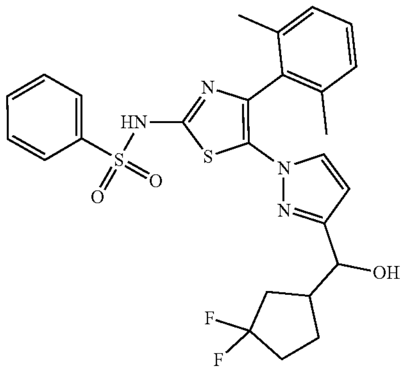 [SMILES: Cc1cccc(C)c1-c1nc(NS(=O)(=O)c2ccccc2)sc1-n1ccc(C(O)C2CCC(F)(F)C2)n1] | N-[5-[3-[(3,3-difluorocyclopentyl)-hydroxymethyl]pyrazol-1-yl]-4-(2,6-dimethylphenyl)-1,3-thiazol-2-yl]benzenesulfonamide |
| 372 | 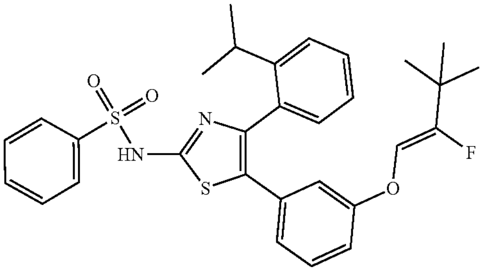 [SMILES: CC(C)c1ccccc1-c1nc(NS(=O)(=O)c2ccccc2)sc1-c1cccc(O/C=C(\F)C(C)(C)C)c1] | N-[5-[3-(2-fluoro-3,3-dimethylbut-1-enoxy)phenyl]-4-(2-propan-2-ylphenyl)-1,3-thiazol-2-yl]benzenesulfonamide |
| 356 | 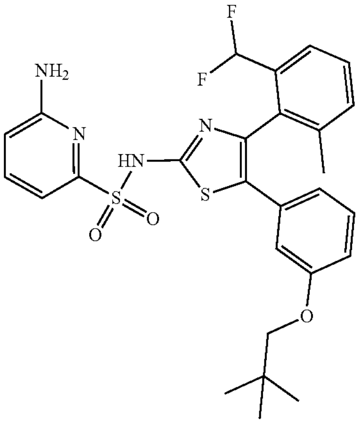 [SMILES: Cc1cccc(C(F)F)c1-c1nc(NS(=O)(=O)c2cccc(N)n2)sc1-c1cccc(OCC(C)(C)C)c1] | 6-amino-N-[4-[2-(difluoromethyl)-6-methylphenyl]-5-[3-(2,2-dimethylpropoxy)phenyl]-1,3-thiazol-2-yl]pyridine-2-sulfonamide |
| 592 | 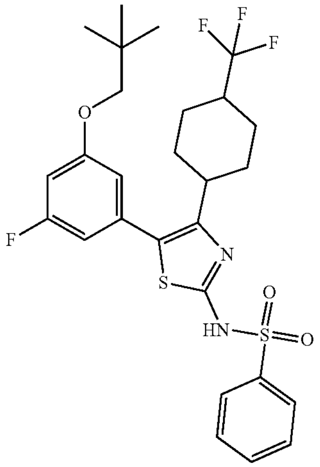 [SMILES: CC(C)(C)COc1cc(F)cc(-c2sc(NS(=O)(=O)c3ccccc3)nc2C2CCC(C(F)(F)F)CC2)c1] | N-(5-(3-fluoro-5-(neopentyloxy)phenyl)-4-(4-(trifluoromethyl)cyclohexyl)thiazol-2-yl)benzenesulfonamide |

TABLE 1-continued

| Compound Number | Compound Structural Formula | Compound Name |
|---|---|---|
| 227 | 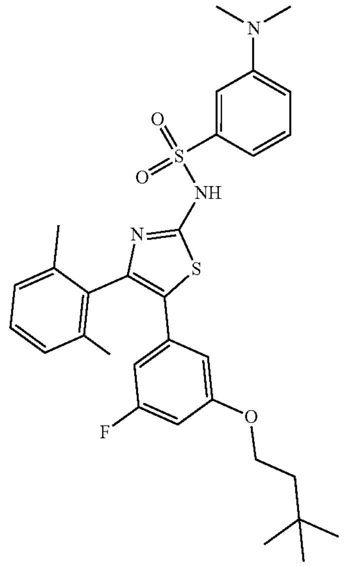 [SMILES: Cc1cccc(C)c1-c1nc(NS(=O)(=O)c2cccc(N(C)C)c2)sc1-c1cc(F)cc(OCCC(C)(C)C)c1] | 3-(dimethylamino)-N-[5-[3-(3,3-dimethylbutoxy)-5-fluorophenyl]-4-(2,6-dimethylphenyl)-1,3-thiazol-2-yl]benzenesulfonamide |
| 369 | 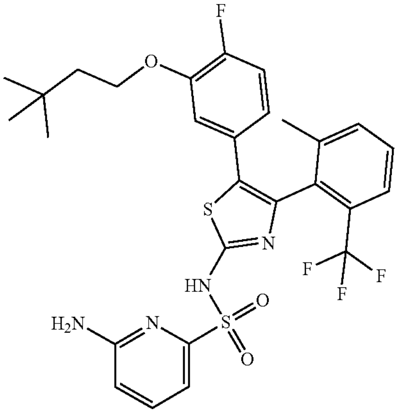 [SMILES: Cc1cccc(C(F)(F)F)c1-c1nc(NS(=O)(=O)c2cccc(N)n2)sc1-c1ccc(F)c(OCCC(C)(C)C)c1] | 6-amino-N-[5-[3-(3,3-dimethylbutoxy)-4-fluorophenyl]-4-[2-methyl-6-(trifluoromethyl)phenyl]-1,3-thiazol-2-yl]pyridine-2-sulfonamide |
| 593 | 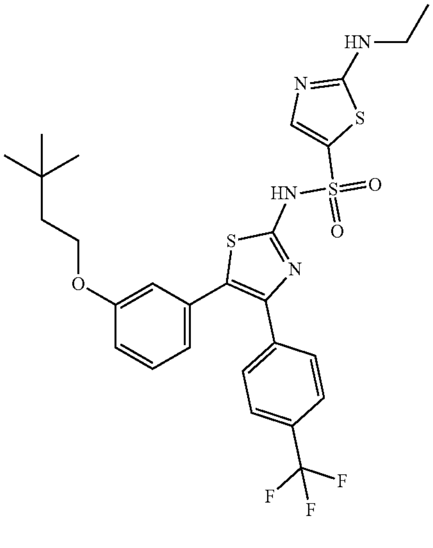 [SMILES: CCNc1ncc(S(=O)(=O)Nc2nc(-c3ccc(C(F)(F)F)cc3)c(-c3cccc(OCCC(C)(C)C)c3)s2)s1] | N-(5-(3-(3,3-dimethylbutoxy)phenyl)-4-(4-(trifluoromethyl)phenyl)thiazol-2-yl)-2-(ethylamino)thiazole-5-sulfonamide |

TABLE 1-continued
| Compound Number | Compound Structural Formula | Compound Name |
|---|---|---|
| 594 | 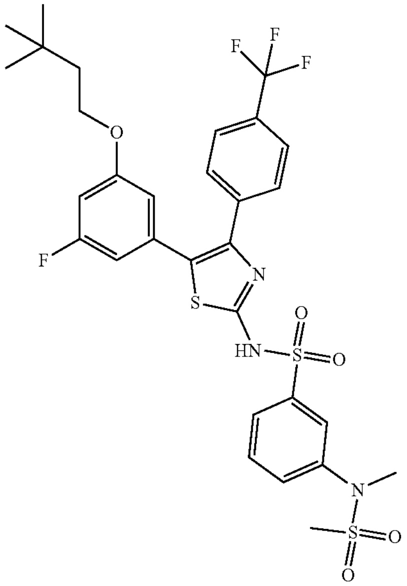 [SMILES: CN(c1cccc(S(=O)(=O)Nc2nc(-c3ccc(C(F)(F)F)cc3)c(-c3cc(F)cc(OCCC(C)(C)C)c3)s2)c1)S(C)(=O)=O] | N-(5-(3-(3,3-dimethylbutoxy)-5-fluorophenyl)-4-(4-(trifluoromethyl)phenyl)thiazol-2-yl)-3-(N-methylmethylsulfonamido)benzenesulfonamide |
| 326 | 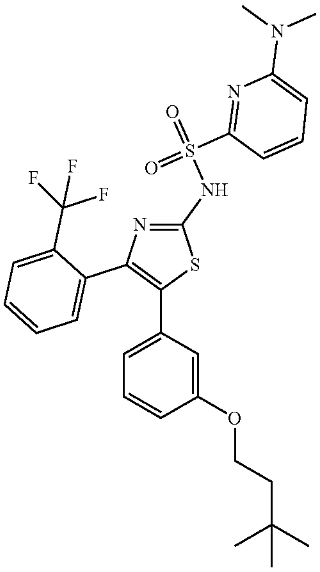 [SMILES: CN(C)c1cccc(S(=O)(=O)Nc2nc(-c3ccccc3C(F)(F)F)c(-c3cccc(OCCC(C)(C)C)c3)s2)n1] | 6-(dimethylamino)-N-[5-[3-(3,3-dimethylbutoxy)phenyl]-4-[2-(trifluoromethyl)phenyl]-1,3-thiazol-2-yl]pyridine-2-sulfonamide |

TABLE 1-continued
| Compound Number | Compound Structural Formula | Compound Name |
|---|---|---|
| 330 | 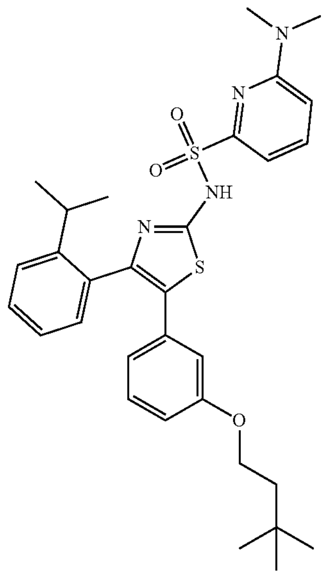 [SMILES: CC(C)c1ccccc1-c1nc(NS(=O)(=O)c2cccc(N(C)C)n2)sc1-c1cccc(OCCC(C)(C)C)c1] | 6-(dimethylamino)-N-[5-[3-(3,3-dimethylbutoxy)phenyl]-4-(2-propan-2-ylphenyl)-1,3-thiazol-2-yl]pyridine-2-sulfonamide |
| 412 | 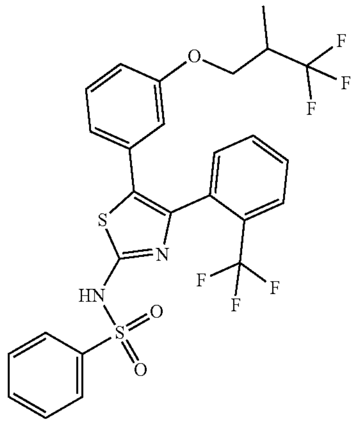 [SMILES: CC(COc1cccc(-c2sc(NS(=O)(=O)c3ccccc3)nc2-c2ccccc2C(F)(F)F)c1)C(F)(F)F] | N-[4-[2-(trifluoromethyl)phenyl]-5-[3-(3,3,3-trifluoro-2-methylpropoxy)phenyl]-1,3-thiazol-2-yl]benzenesulfonamide |
| 121 | 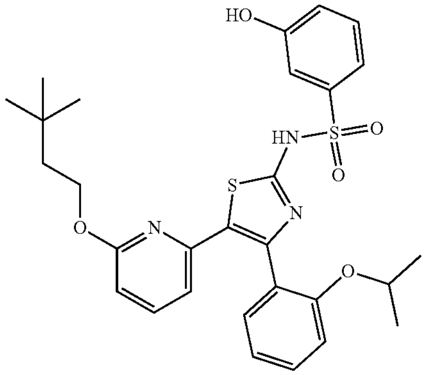 [SMILES: CC(C)Oc1ccccc1-c1nc(NS(=O)(=O)c2cccc(O)c2)sc1-c1cccc(OCCC(C)(C)C)n1] | N-[5-[6-(3,3-dimethylbutoxy)pyridin-2-yl]-4-(2-propan-2-yloxyphenyl)-1,3-thiazol-2-yl]-3-hydroxybenzenesulfonamide |

TABLE 1-continued

| Compound Number | Compound Structural Formula | Compound Name |
|---|---|---|
| 95 | 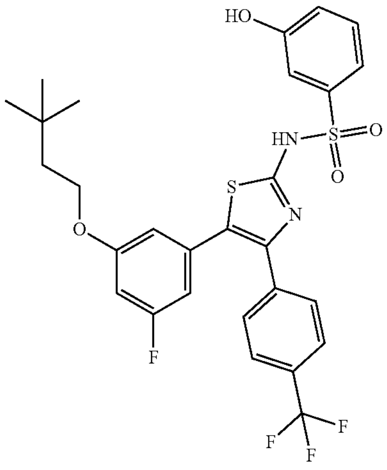 [SMILES: CC(C)(C)CCOc1cc(F)cc(-c2sc(NS(=O)(=O)c3cccc(O)c3)nc2-c2ccc(C(F)(F)F)cc2)c1] | N-[5-[3-(3,3-dimethylbutoxy)-5-fluorophenyl]-4-[4-(trifluoromethyl)phenyl]-1,3-thiazol-2-yl]-3-hydroxybenzenesulfonamide |
| 39 | 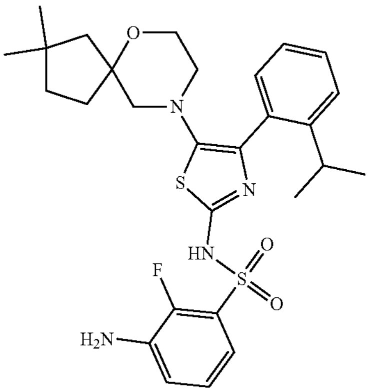 [SMILES: CC(C)c1ccccc1-c1nc(NS(=O)(=O)c2cccc(N)c2F)sc1N1CCOC2(CCC(C)(C)C2)C1] | 3-amino-N-[5-(3,3-dimethyl-6-oxa-9-azaspiro[4.5]decan-9-yl)-4-(2-propan-2-ylphenyl)-1,3-thiazol-2-yl]-2-fluorobenzenesulfonamide |
| 235 | 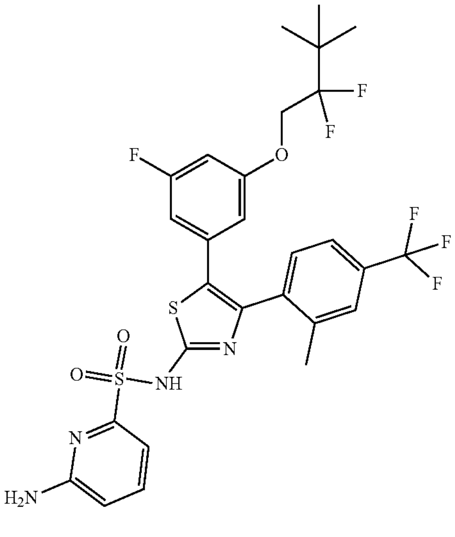 [SMILES: Cc1cc(C(F)(F)F)ccc1-c1nc(NS(=O)(=O)c2cccc(N)n2)sc1-c1cc(F)cc(OCC(F)(F)C(C)(C)C)c1] | 6-amino-N-[5-[3-(2,2-difluoro-3,3-dimethylbutoxy)-5-fluorophenyl]-4-[2-methyl-4-(trifluoromethyl)phenyl]-1,3-thiazol-2-yl]pyridine-2-sulfonamide |

TABLE 1-continued

| Compound Number | Compound Structural Formula | Compound Name |
|---|---|---|
| 406 | 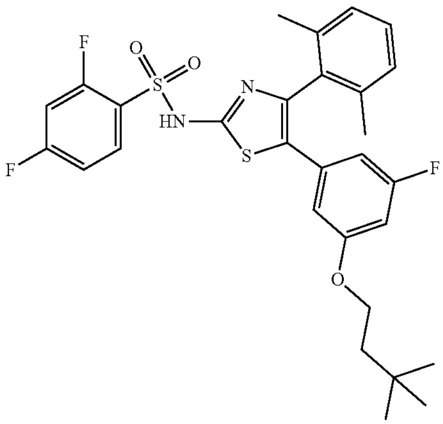 [SMILES: Cc1cccc(C)c1-c1nc(NS(=O)(=O)c2ccc(F)cc2F)sc1-c1cc(F)cc(OCCC(C)(C)C)c1] | N-[5-[3-(3,3-dimethylbutoxy)-5-fluorophenyl]-4-(2,6-dimethylphenyl)-1,3-thiazol-2-yl]-2,4-difluorobenzenesulfonamide |
| 324 | 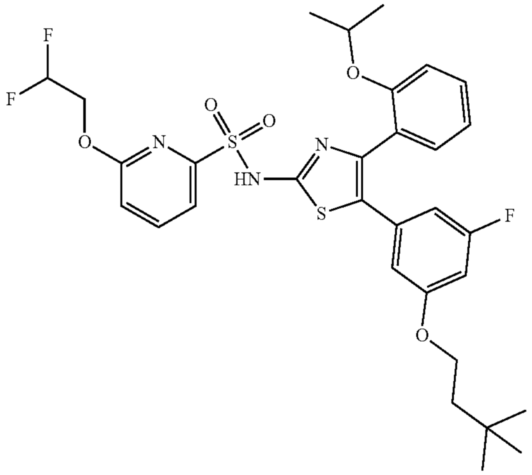 [SMILES: CC(C)Oc1ccccc1-c1nc(NS(=O)(=O)c2cccc(OCC(F)F)n2)sc1-c1cc(F)cc(OCCC(C)(C)C)c1] | 6-(2,2-difluoroethoxy)-N-[5-[3-(3,3-dimethylbutoxy)-5-fluorophenyl]-4-(2-propan-2-yloxyphenyl)-1,3-thiazol-2-yl]pyridine-2-sulfonamide |
| 35 | 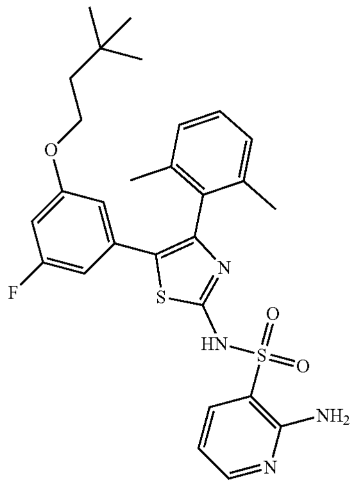 [SMILES: Cc1cccc(C)c1-c1nc(NS(=O)(=O)c2cccnc2N)sc1-c1cc(F)cc(OCCC(C)(C)C)c1] | 2-amino-N-[5-[3-(3,3-dimethylbutoxy)-5-fluorophenyl]-4-(2,6-dimethylphenyl)-1,3-thiazol-2-yl]pyridine-3-sulfonamide |

TABLE 1-continued

| Compound Number | Compound Structural Formula | Compound Name |
|---|---|---|
| 464 | 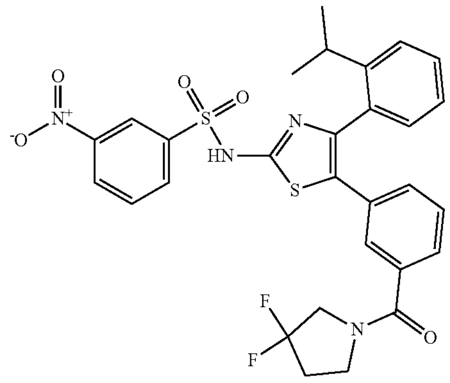 | N-[5-[3-(3,3-difluoropyrrolidine-1-carbonyl)phenyl]-4-(2-propan-2-ylphenyl)-1,3-thiazol-2-yl]-3-nitrobenzenesulfonamide |
| 175 | 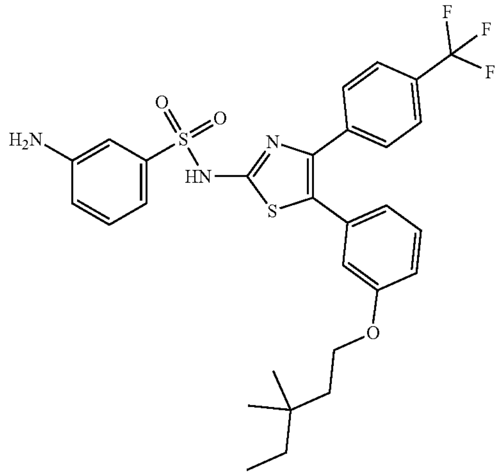 [SMILES: CCC(C)(C)CCOc1cccc(-c2sc(NS(=O)(=O)c3cccc(N)c3)nc2-c2ccc(C(F)(F)F)cc2)c1] | 3-amino-N-[5-[3-(3,3-dimethylpentoxy)phenyl]-4-[4-(trifluoromethyl)phenyl]-1,3-thiazol-2-yl]benzenesulfonamide |
| 12 | 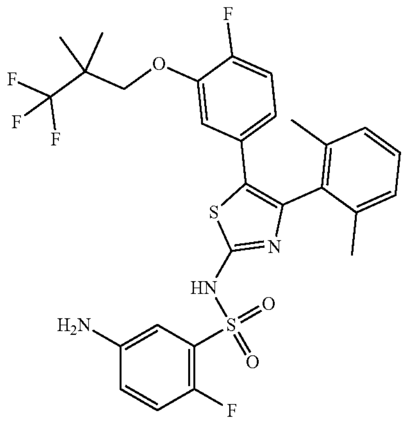 [SMILES: Cc1cccc(C)c1-c1nc(NS(=O)(=O)c2cc(N)ccc2F)sc1-c1ccc(F)c(OCC(C)(C)C(F)(F)F)c1] | 5-amino-N-[4-(2,6-dimethylphenyl)-5-[4-fluoro-3-(3,3,3-trifluoro-2,2-dimethylpropoxy)phenyl]-1,3-thiazol-2-yl]-2-fluorobenzenesulfonamide |

TABLE 1-continued

| Compound Number | Compound Structural Formula | Compound Name |
|---|---|---|
| 476 | 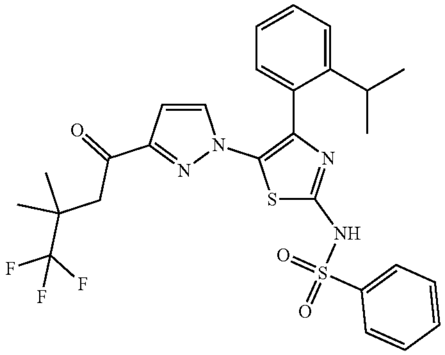 [SMILES: CC(C)c1ccccc1-c1nc(NS(=O)(=O)c2ccccc2)sc1-n1ccc(C(=O)CC(C)(C)C(F)(F)F)n1] | N-[4-(2-propan-2-ylphenyl)-5-[3-(4,4,4-trifluoro-3,3-dimethylbutanoyl)pyrazol-1-yl]-1,3-thiazol-2-yl]benzenesulfonamide |
| 455 | 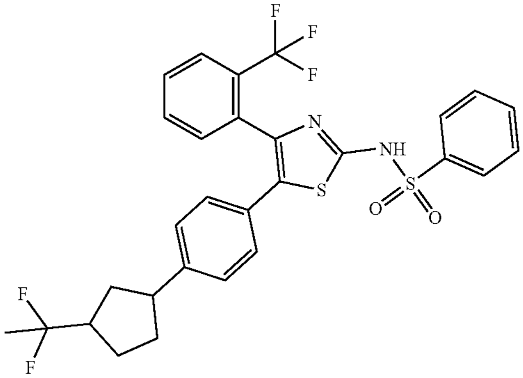 [SMILES: CC(F)(F)C1CCC(c2ccc(-c3sc(NS(=O)(=O)c4ccccc4)nc3-c3ccccc3C(F)(F)F)cc2)C1] | N-[5-[4-[3-(1,1-difluoroethyl)cyclopentyl]phenyl]-4-[2-(trifluoromethyl)phenyl]-1,3-thiazol-2-yl]benzenesulfonamide |
| 422 | 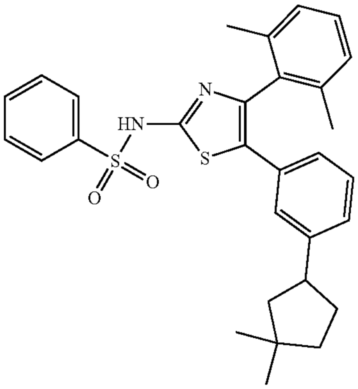 [SMILES: Cc1cccc(C)c1-c1nc(NS(=O)(=O)c2ccccc2)sc1-c1cccc(C2CCC(C)(C)C2)c1] | N-[5-[3-(3,3-dimethylcyclopentyl)phenyl]-4-(2,6-dimethylphenyl)-1,3-thiazol-2-yl]benzenesulfonamide |
| 176 | 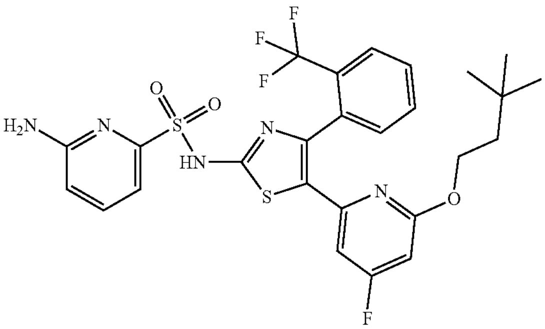 [SMILES: CC(C)(C)CCOc1cc(F)cc(-c2sc(NS(=O)(=O)c3cccc(N)n3)nc2-c2ccccc2C(F)(F)F)n1] | 6-amino-N-[5-[6-(3,3-dimethylbutoxy)-4-fluoropyridin-2-yl]-4-[2-(trifluoromethyl)phenyl]-1,3-thiazol-2-yl]pyridine-2-sulfonamide |

TABLE 1-continued

| Compound Number | Compound Structural Formula | Compound Name |
|---|---|---|
| 596 | 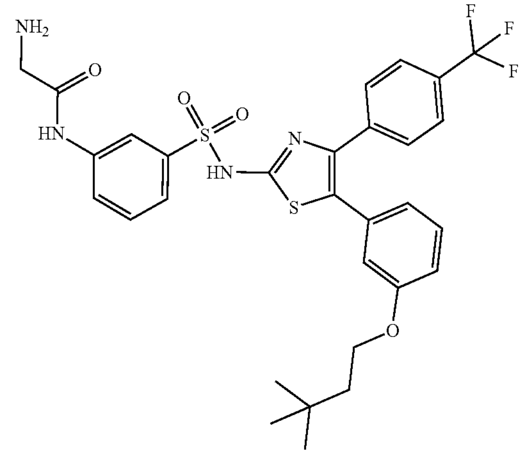 [SMILES: CC(C)(C)CCOc1cccc(-c2sc(NS(=O)(=O)c3cccc(NC(=O)CN)c3)nc2-c2ccc(C(F)(F)F)cc2)c1] | 2-amino-N-(3-(N-(5-(3-(3,3-dimethylbutoxy)phenyl)-4-(4-(trifluoromethyl)phenyl)thiazol-2-yl)sulfamoyl)phenyl)acetamide |
| 417 | 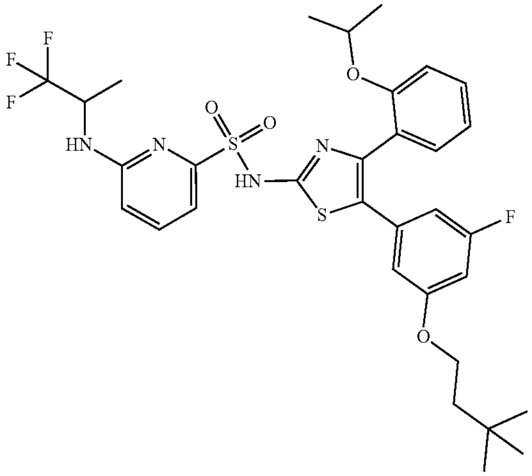 [SMILES: CC(C)Oc1ccccc1-c1nc(NS(=O)(=O)c2cccc(NC(C)C(F)(F)F)n2)sc1-c1cc(F)cc(OCCC(C)(C)C)c1] | N-[5-[3-(3,3-dimethylbutoxy)-5-fluorophenyl]-4-(2-propan-2-yloxyphenyl)-1,3-thiazol-2-yl]-6-(1,1,1-trifluoropropan-2-ylamino)pyridine-2-sulfonamide |
| 300 | 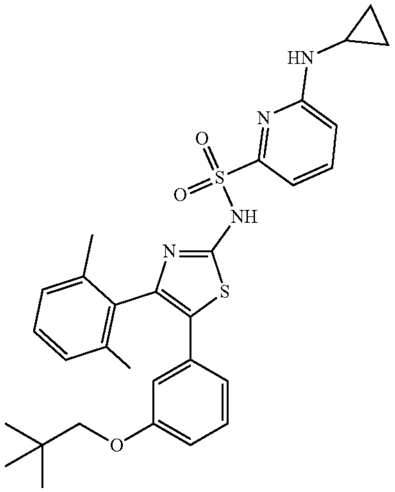 [SMILES: Cc1cccc(C)c1-c1nc(NS(=O)(=O)c2cccc(NC3CC3)n2)sc1-c1cccc(OCC(C)(C)C)c1] | 6-(cyclopropylamino)-N-[4-(2,6-dimethylphenyl)-5-[3-(2,2-dimethylpropoxy)phenyl]-1,3-thiazol-2-yl]pyridine-2-sulfonamide |

TABLE 1-continued

| Compound Number | Compound Structural Formula | Compound Name |
|---|---|---|
| 77 | 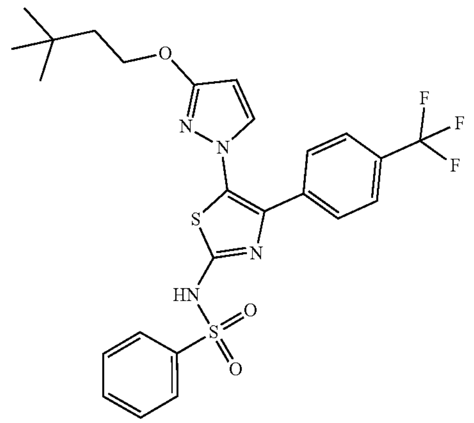 [SMILES: CC(C)(C)CCOc1ccn(-c2sc(NS(=O)(=O)c3ccccc3)nc2-c2ccc(C(F)(F)F)cc2)n1] | N-[5-[3-(3,3-dimethylbutoxy)pyrazol-1-yl]-4-[4-(trifluoromethyl)phenyl]-1,3-thiazol-2-yl]benzenesulfonamide |
| 478 | 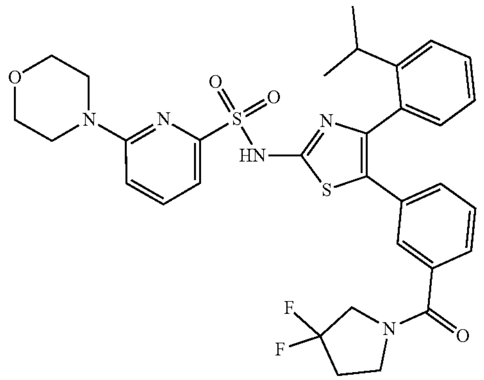 [SMILES: CC(C)c1ccccc1-c1nc(NS(=O)(=O)c2cccc(N3CCOCC3)n2)sc1-c1cccc(C(=O)N2CCC(F)(F)C2)c1] | N-[5-[3-(3,3-difluoropyrrolidine-1-carbonyl)phenyl]-4-(2-propan-2-ylphenyl)-1,3-thiazol-2-yl]-6-morpholin-4-ylpyridine-2-sulfonamide |
| 597 | 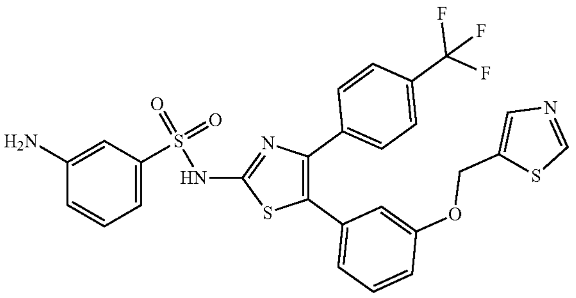 [SMILES: Nc1cccc(S(=O)(=O)Nc2nc(-c3ccc(C(F)(F)F)cc3)c(-c3cccc(OCc4cncs4)c3)s2)c1] | 3-amino-N-(5-(3-(thiazol-5-ylmethoxy)phenyl)-4-(4-(trifluoromethyl)phenyl)thiazol-2-yl)benzenesulfonamide |
| 598 | 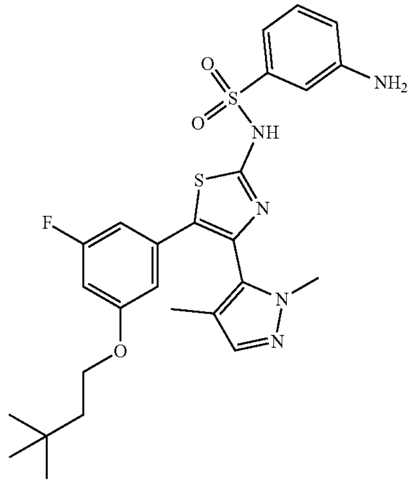 [SMILES: Cc1cnn(C)c1-c1nc(NS(=O)(=O)c2cccc(N)c2)sc1-c1cc(F)cc(OCCC(C)(C)C)c1] | 3-amino-N-(4-(1,4-dimethyl-1H-pyrazol-5-yl)-5-(3-(3,3-dimethylbutoxy)-5-fluorophenyl)thiazol-2-yl)benzenesulfonamide |

TABLE 1-continued

| Compound Number | Compound Structural Formula | Compound Name |
|---|---|---|
| 210 | 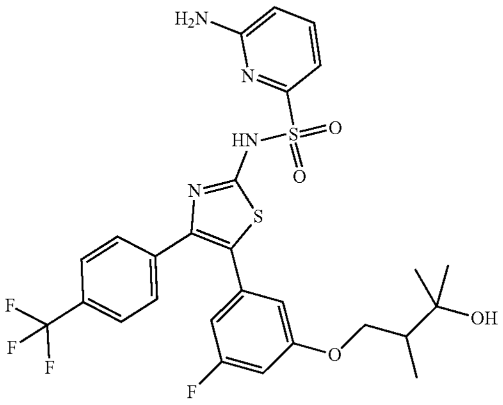 [SMILES: CC(COc1cc(F)cc(-c2sc(NS(=O)(=O)c3cccc(N)n3)nc2-c2ccc(C(F)(F)F)cc2)c1)C(C)(C)O] | 6-amino-N-[5-[3-fluoro-5-(3-hydroxy-2,3-dimethylbutoxy)phenyl]-4-[4-(trifluoromethyl)phenyl]-1,3-thiazol-2-yl]pyridine-2-sulfonamide |
| 492 | 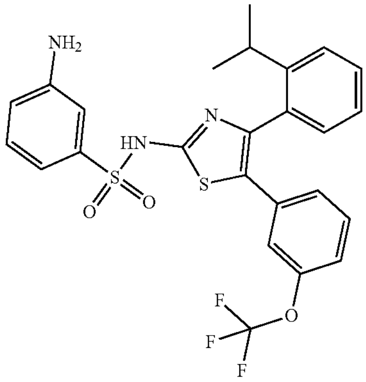 [SMILES: CC(C)c1ccccc1-c1nc(NS(=O)(=O)c2cccc(N)c2)sc1-c1cccc(OC(F)(F)F)c1] | 3-amino-N-[4-(2-propan-2-ylphenyl)-5-[3-(trifluoromethoxy)phenyl]-1,3-thiazol-2-yl]benzenesulfonamide |
| 376 | 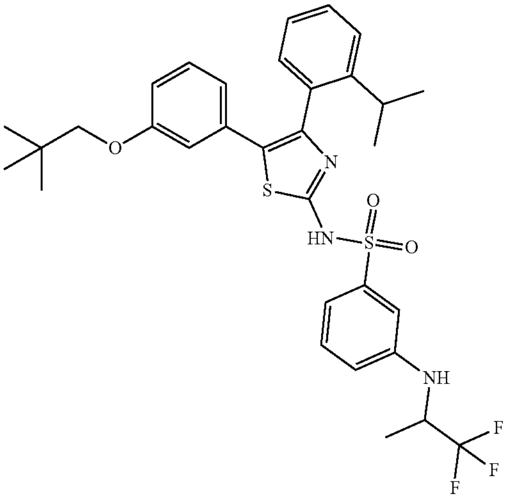 [SMILES: CC(C)c1ccccc1-c1nc(NS(=O)(=O)c2cccc(NC(C)C(F)(F)F)c2)sc1-c1cccc(OCC(C)(C)C)c1] | N-[5-[3-(2,2-dimethylpropoxy)phenyl]-4-(2-propan-2-ylphenyl)-1,3-thiazol-2-yl]-3-(1,1,1-trifluoropropan-2-ylamino)benzenesulfonamide |
| 335 | 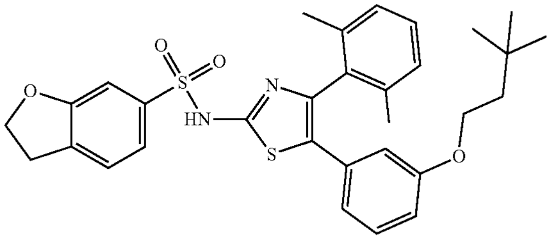 [SMILES: Cc1cccc(C)c1-c1nc(NS(=O)(=O)c2ccc3c(c2)OCC3)sc1-c1cccc(OCCC(C)(C)C)c1] | N-[5-[3-(3,3-dimethylbutoxy)phenyl]-4-(2,6-dimethylphenyl)-1,3-thiazol-2-yl]-2,3-dihydro-1-benzofuran-6-sulfonamide |

TABLE 1-continued
| Compound Number | Compound Structural Formula | Compound Name |
|---|---|---|
| 18 | 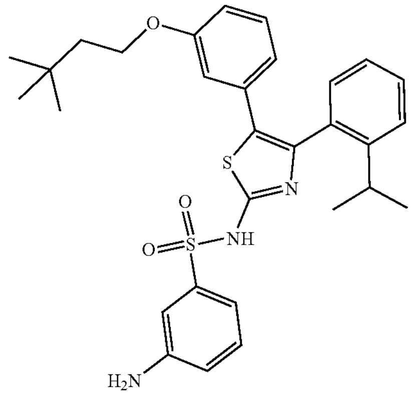 [SMILES: CC(C)c1ccccc1-c1nc(NS(=O)(=O)c2cccc(N)c2)sc1-c1cccc(OCCC(C)(C)C)c1] | 3-amino-N-[5-[3-(3,3-dimethylbutoxy)phenyl]-4-(2-propan-2-ylphenyl)-1,3-thiazol-2-yl]benzenesulfonamide |
| 28 | 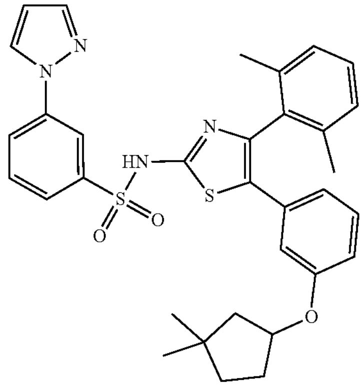 [SMILES: Cc1cccc(C)c1-c1nc(NS(=O)(=O)c2cccc(-n3cccn3)c2)sc1-c1cccc(OC2CCC(C)(C)C2)c1] | N-[5-[3-(3,3-dimethylcyclopentyl)oxyphenyl]-4-(2,6-dimethylphenyl)-1,3-thiazol-2-yl]-3-pyrazol-1-ylbenzenesulfonamide |
| 498 | 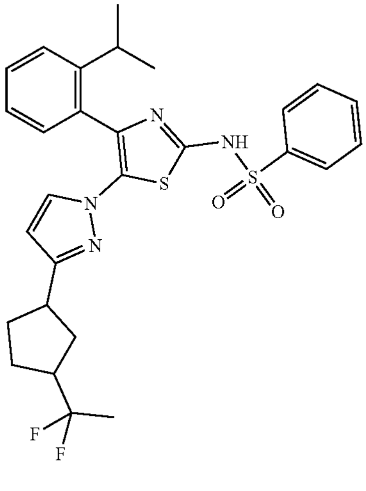 [SMILES: CC(C)c1ccccc1-c1nc(NS(=O)(=O)c2ccccc2)sc1-n1ccc(C2CCC(C(C)(F)F)C2)n1] | N-[5-[3-[3-(1,1-difluoroethyl)cyclopentyl]pyrazol-1-yl]-4 (2-propan-2-ylphenyl)-1,3-thiazol-2-yl]benzenesulfonamide |

TABLE 1-continued

| Compound Number | Compound Structural Formula | Compound Name |
|---|---|---|
| 489 | 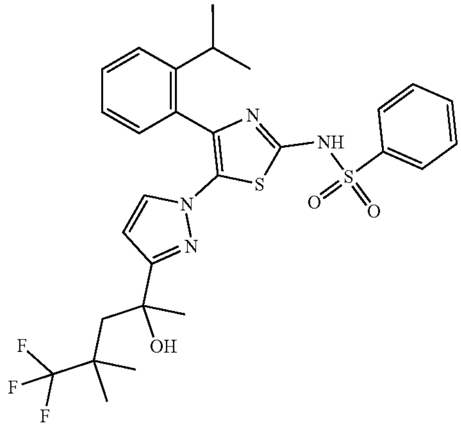 [SMILES: CC(C)c1ccccc1-c1nc(NS(=O)(=O)c2ccccc2)sc1-n1ccc(C(C)(O)CC(C)(C)C(F)(F)F)n1] | N-[4-(2-propan-2-ylphenyl)-5-[3-(5,5,5-trifluoro-2-hydroxy-4,4-dimethylpentan-2-yl)pyrazol-1-yl]-1,3-thiazol-2-yl]benzenesulfonamide |
| 599 | 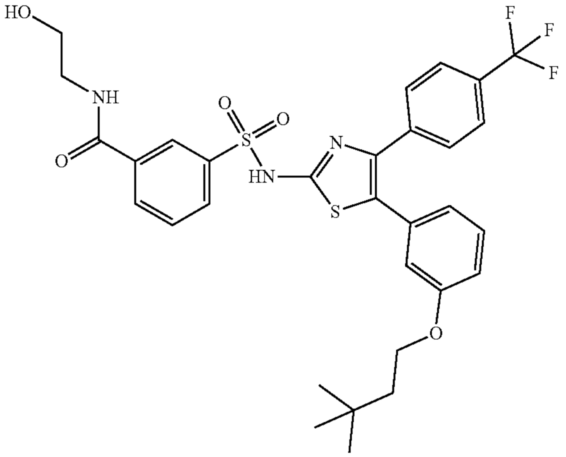 [SMILES: CC(C)(C)CCOc1cccc(-c2sc(NS(=O)(=O)c3cccc(C(=O)NCCO)c3)nc2-c2ccc(C(F)(F)F)cc2)c1] | 3-(N-(5-(3-(3,3-dimethylbutoxy)phenyl)-4-(4-(trifluoromethyl)phenyl)thiazol-2-yl)sulfamoyl)-N-(2-hydroxyethyl)benzamide |
| 436 | 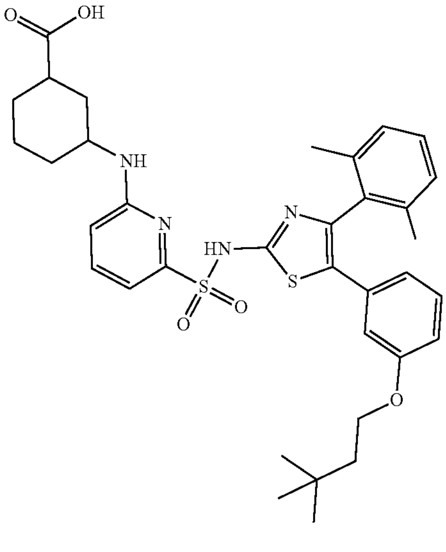 [SMILES: Cc1cccc(C)c1-c1nc(NS(=O)(=O)c2cccc(NC3CCCC(C(=O)O)C3)n2)sc1-c1cccc(OCCC(C)(C)C)c1] | 3-[6-[[5-[3-(3,3-dimethylbutoxy)phenyl]-4-(2,6-dimethylphenyl)-1,3-thiazol-2-yl]sulfamoyl]pyridin-2-yl]amino]cyclohexane-1-carboxylic acid |

TABLE 1-continued
| Compound Number | Compound Structural Formula | Compound Name |
|---|---|---|
| 284 | 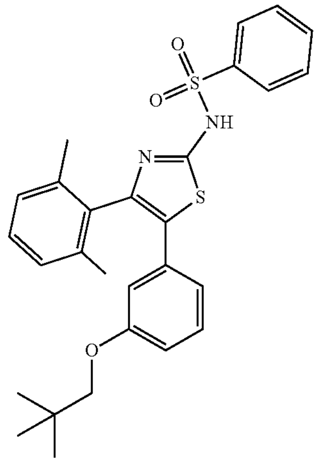 [SMILES: Cc1cccc(C)c1-c1nc(NS(=O)(=O)c2ccccc2)sc1-c1cccc(OCC(C)(C)C)c1] | N-[4-(2,6-dimethylphenyl)-5-[3-(2,2-dimethylpropoxy)phenyl]-1,3-thiazol-2-yl]benzenesulfonamide |
| 25 | 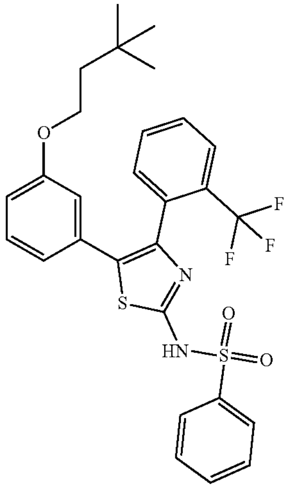 [SMILES: CC(C)(C)CCOc1cccc(-c2sc(NS(=O)(=O)c3ccccc3)nc2-c2ccccc2C(F)(F)F)c1] | N-[5-[3-(3,3-dimethylbutoxy)phenyl]-4-[2-(trifluoromethyl)phenyl]-1,3-thiazol-2-yl]benzenesulfonamide |
| 600 | 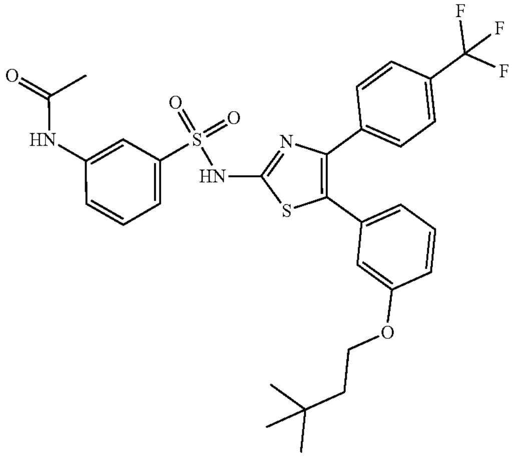 [SMILES: CC(=O)Nc1cccc(S(=O)(=O)Nc2nc(-c3ccc(C(F)(F)F)cc3)c(-c3cccc(OCCC(C)(C)C)c3)s2)c1] | N-(3-(N-(5-(3-(3,3-dimethylbutoxy)phenyl)-4-(4-(trifluoromethyl)phenyl)thiazol-2-yl)sulfamoyl)phenyl)acetamide |

TABLE 1-continued

| Compound Number | Compound Structural Formula | Compound Name |
| --- | --- | --- |
| 373 | 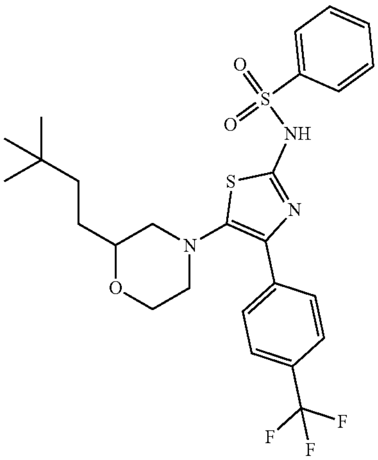 [SMILES: CC(C)(C)CCC1CN(c2sc(NS(=O)(=O)c3ccccc3)nc2-c2ccc(C(F)(F)F)cc2)CCO1] | N-[5-[2-(3,3-dimethylbutyl)morpholin-4-yl]-4-[4-(trifluoromethyl)phenyl]-1,3-thiazol-2-yl]benzenesulfonamide |
| 127 | 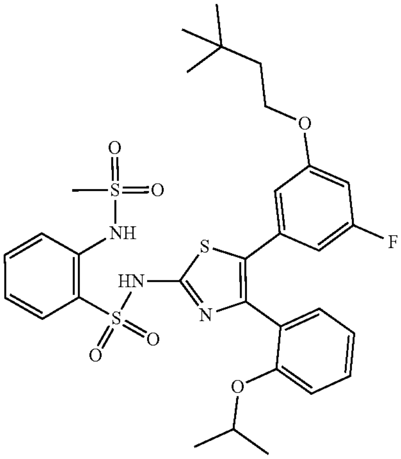 [SMILES: CC(C)Oc1ccccc1-c1nc(NS(=O)(=O)c2ccccc2NS(C)(=O)=O)sc1-c1cc(F)cc(OCCC(C)(C)C)c1] | N-[5-[3-(3,3-dimethylbutoxy)-5-fluorophenyl]-4-(2-propan-2-yloxyphenyl)-1,3-thiazol-2-yl]-2-(methanesulfonamido) benzenesulfonamide |
| 337 | 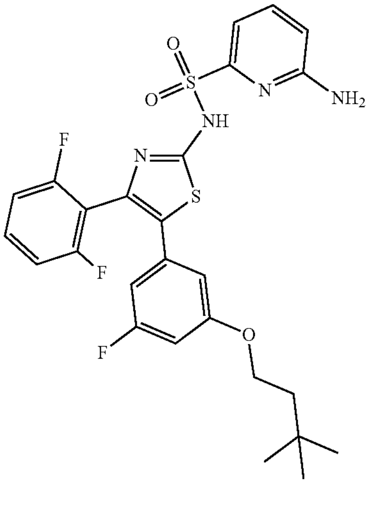 [SMILES: CC(C)(C)CCOc1cc(F)cc(-c2sc(NS(=O)(=O)c3cccc(N)n3)nc2-c2c(F)cccc2F)c1] | 6-amino-N-[4-(2,6-difluorophenyl)-5-[3-(3,3-dimethylbutoxy)-5-fluorophenyl]-1,3-thiazol-2-yl]pyridine-2-sulfonamide |

TABLE 1-continued

| Compound Number | Compound Structural Formula | Compound Name |
|---|---|---|
| 45B1 | 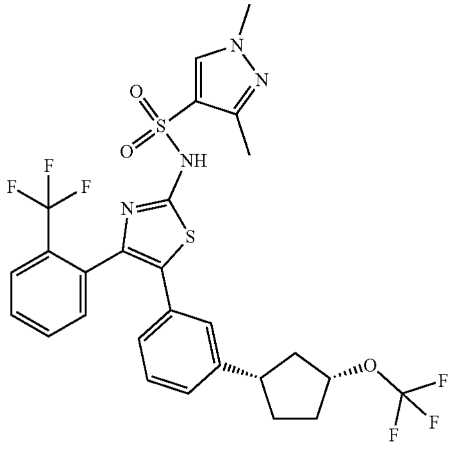 [SMILES: Cc1nn(C)cc1S(=O)(=O)Nc1nc(-c2ccccc2C(F)(F)F)c(-c2cccc([C@H]3CC[C@@H](OC(F)(F)F)C3)c2)s1] | 1,3-dimethyl-N-[5-[3-[(1S, 3R)-3-(trifluoromethoxy)cyclopentyl]phenyl]-4-[2-(trifluoromethyl)phenyl]-1,3-thiazol-2-yl]pyrazole-4-sulfonamide |
| 21 | 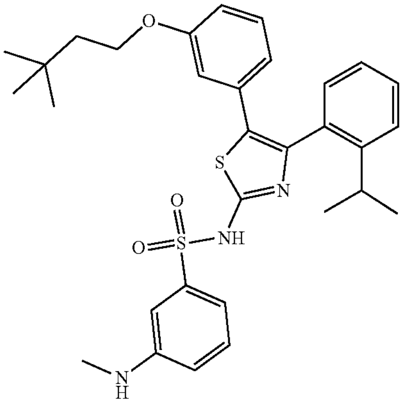 [SMILES: CNc1cccc(S(=O)(=O)Nc2nc(-c3ccccc3C(C)C)c(-c3cccc(OCCC(C)(C)C)c3)s2)c1] | N-[5-[3-(3,3-dimethylbutoxy)phenyl]-4-(2-propan-2-ylphenyl)-1,3-thiazol-2-yl]-3-(methylamino)benzenesulfonamide |
| 240 | 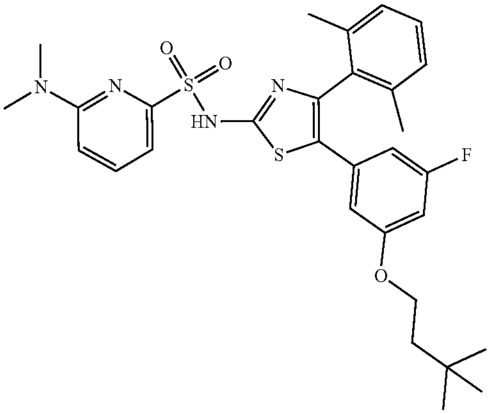 [SMILES: Cc1cccc(C)c1-c1nc(NS(=O)(=O)c2cccc(N(C)C)n2)sc1-c1cc(F)cc(OCCC(C)(C)C)c1] | 6-(dimethylamino)-N-[5-[3-(3,3-dimethylbutoxy)-5-fluorophenyl]-4-(2,6-dimethylphenyl)-1,3-thiazol-2-yl]pyridine-2-sulfonamide |

TABLE 1-continued

| Compound Number | Compound Structural Formula | Compound Name |
|---|---|---|
| 232 | 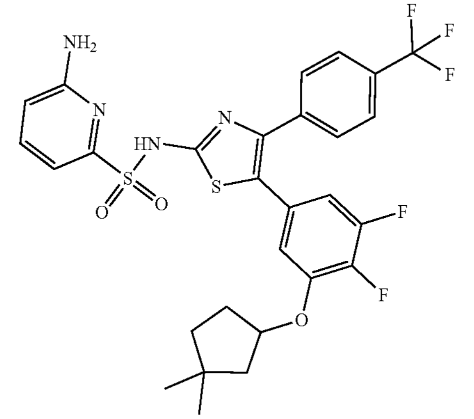 [SMILES: CC1(C)CCC(Oc2cc(-c3sc(NS(=O)(=O)c4cccc(N)n4)nc3-c3ccc(C(F)(F)F)cc3)cc(F)c2F)C1] | 6-amino-N-[5-[3-(3,3-dimethylcyclopentyl)oxy-4,5-difluorophenyl]-4-[4-(trifluoromethyl)phenyl]-1,3-thiazol-2-yl]pyridine-2-sulfonamide |
| 181 | 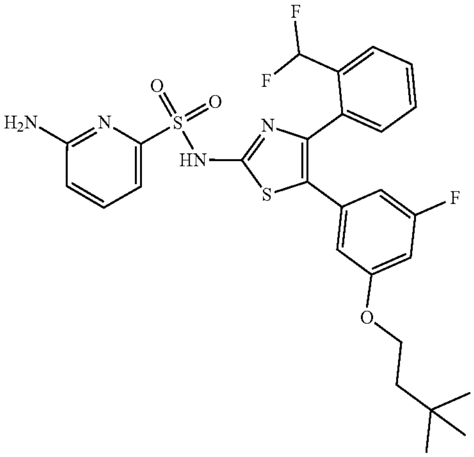 [SMILES: CC(C)(C)CCOc1cc(F)cc(-c2sc(NS(=O)(=O)c3cccc(N)n3)nc2-c2ccccc2C(F)F)c1] | 6-amino-N-[4-[2-(difluoromethyl)phenyl]-5-[3-(3,3-dimethylbutoxy)-5-fluorophenyl]-1,3-thiazol-2-yl]pyridine-2-sulfonamide |
| 601 | 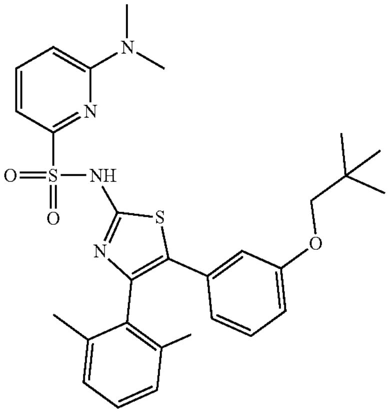 [SMILES: Cc1cccc(C)c1-c1nc(NS(=O)(=O)c2cccc(N(C)C)n2)sc1-c1cccc(OCC(C)(C)C)c1] | 6-(dimethylamino)-N-(4-(2,6-dimethylphenyl)-5-(3-(neopentyloxy)phenyl)thiazol-2-yl)pyridine-2-sulfonamide |

TABLE 1-continued
| Compound Number | Compound Structural Formula | Compound Name |
|---|---|---|
| 602 | 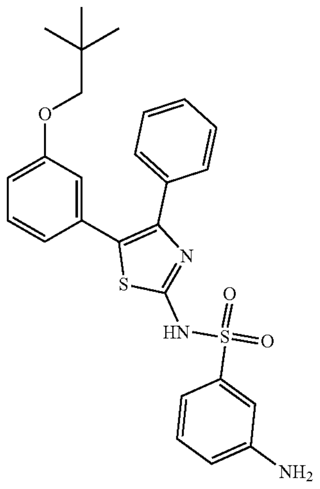 [SMILES: CC(C)(C)COc1cccc(-c2sc(NS(=O)(=O)c3cccc(N)c3)nc2-c2ccccc2)c1] | 3-amino-N-(5-(3-(neopentyloxy)phenyl)-4-phenylthiazol-2-yl)benzenesulfonamide |
| 140 | 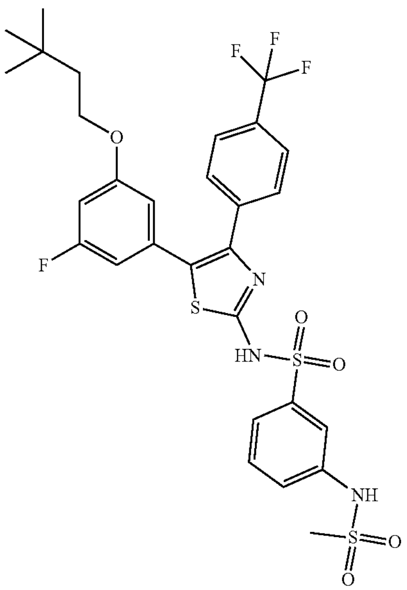 [SMILES: CC(C)(C)CCOc1cc(F)cc(-c2sc(NS(=O)(=O)c3cccc(NS(C)(=O)=O)c3)nc2-c2ccc(C(F)(F)F)cc2)c1] | N-[5-[3-(3,3-dimethylbutoxy)-5-fluorophenyl]-4-[4-(trifluoromethyl)phenyl]-1,3-thiazol-2-yl]-3-(methanesulfonamido) benzenesulfonamide |

TABLE 1-continued
| Compound Number | Compound Structural Formula | Compound Name |
|---|---|---|
| 350 | 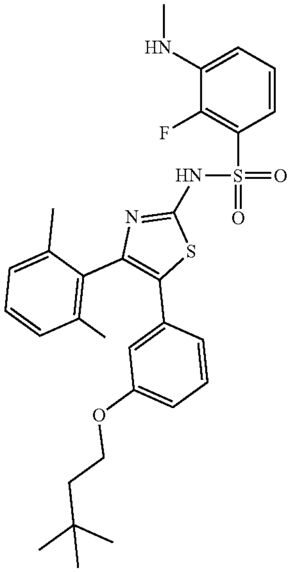 [SMILES: CNc1cccc(S(=O)(=O)Nc2nc(-c3c(C)cccc3C)c(-c3cccc(OCCC(C)(C)C)c3)s2)c1F] | N-[5-[3-(3,3-dimethylbutoxy)phenyl]-4-(2,6-dimethylphenyl)-1,3-thiazol-2-yl]-2-fluoro-3-(methylamino)benzenesulfonamide |
| 603 | 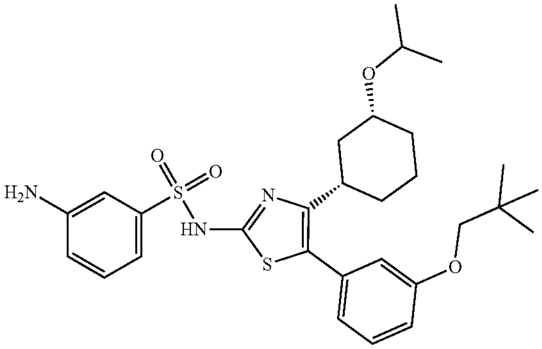 [SMILES: CC(C)O[C@@H]1CCC[C@H](c2nc(NS(=O)(=O)c3cccc(N)c3)sc2-c2cccc(OCC(C)(C)C)c2)C1] | 3-amino-N-(4-((1S,3R)-3-isopropoxycyclohexyl)-5-(3-(neopentyloxy)phenyl)thiazol-2-yl)benzenesulfonamide |
| 260 | 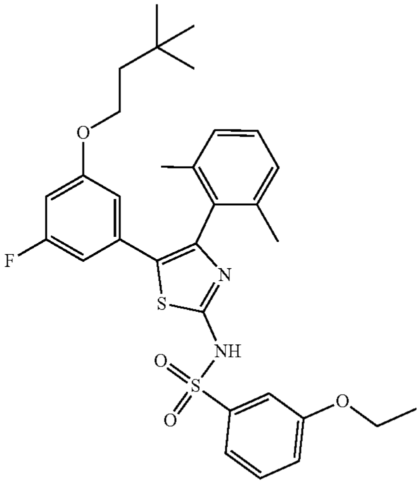 [SMILES: CCOc1cccc(S(=O)(=O)Nc2nc(-c3c(C)cccc3C)c(-c3cc(F)cc(OCCC(C)(C)C)c3)s2)c1] | N-[5-[3-(3,3-dimethylbutoxy)-5-fluorophenyl]-4-(2,6-dimethylphenyl)-1,3-thiazol-2-yl]-3-ethoxybenzenesulfonamide |

TABLE 1-continued

| Compound Number | Compound Structural Formula | Compound Name |
|---|---|---|
| 435 | 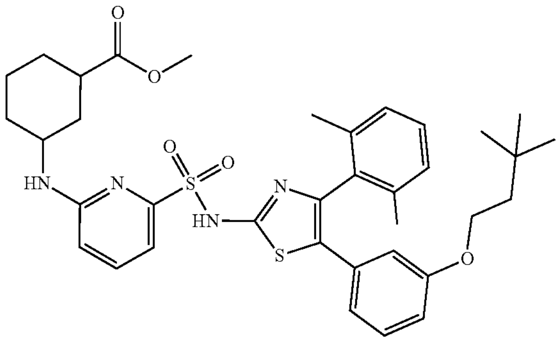 [SMILES: COC(=O)C1CCCC(Nc2cccc(S(=O)(=O)Nc3nc(-c4c(C)cccc4C)c(-c4cccc(OCCC(C)(C)C)c4)s3)n2)C1] | methyl 3-[6-[5-[3-(3,3-dimethylbutoxy)phenyl]-4-(2,6-dimethylphenyl)-1,3-thiazol-2-yl]sulfamoyl]pyridin-2-yl]amino]cyclohexane-1-carboxylate |
| 168 | 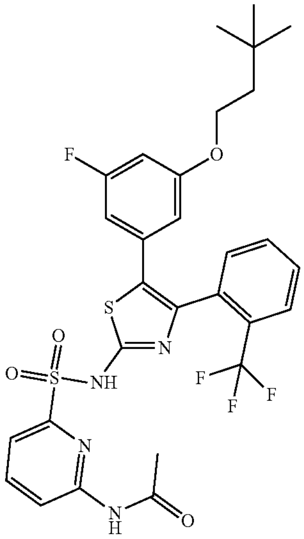 [SMILES: CC(=O)Nc1cccc(S(=O)(=O)Nc2nc(-c3ccccc3C(F)(F)F)c(-c3cc(F)cc(OCCC(C)(C)C)c3)s2)n1] | N-[6-[[5-[3-(3,3-dimethylbutoxy)-5-fluorophenyl]-4-[2-(trifluoromethyl)phenyl]-1,3-thiazol-2-yl]sulfamoyl]pyridin-2-yl]acetamide |
| 170 | 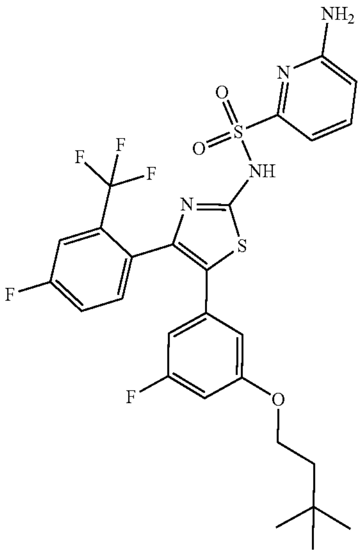 [SMILES: CC(C)(C)CCOc1cc(F)cc(-c2sc(NS(=O)(=O)c3cccc(N)n3)nc2-c2ccc(F)cc2C(F)(F)F)c1] | 6-amino-N-[5-[3-(3,3-dimethylbutoxy)-5-fluorophenyl]-4-[4-fluoro-2-(trifluoromethyl)phenyl]-1,3-thiazol-2-yl]pyridine-2-sulfonamide |

TABLE 1-continued

| Compound Number | Compound Structural Formula | Compound Name |
|---|---|---|
| 247 | 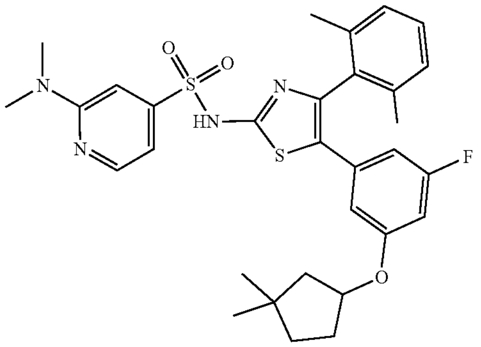 [SMILES: Cc1cccc(C)c1-c1nc(NS(=O)(=O)c2ccnc(N(C)C)c2)sc1-c1cc(F)cc(OC2CCC(C)(C)C2)c1] | 2-(dimethylamino)-N-[5-[3-(3,3-dimethylcyclopentyl)oxy-5-fluorophenyl]-4-(2,6-dimethylphenyl)-1,3-thiazol-2-yl]pyridine-4-sulfonamide |
| 604 | 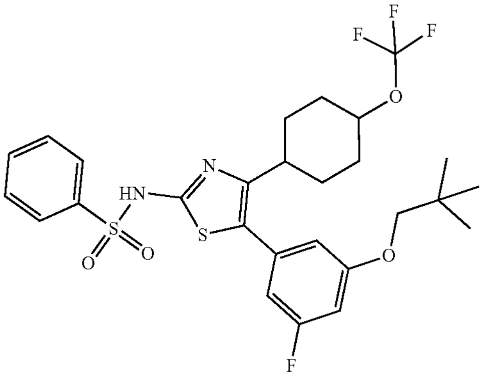 [SMILES: CC(C)(C)COc1cc(F)cc(-c2sc(NS(=O)(=O)c3ccccc3)nc2C2CCC(OC(F)(F)F)CC2)c1] | N-(5-(3-fluoro-5-(neopentyloxy)phenyl)-4-(4-(trifluoromethoxy)cyclohexyl)thiazol-2-yl)benzenesulfonamide |
| 216 | 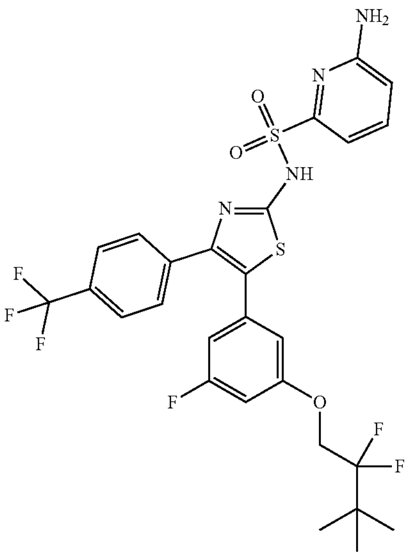 [SMILES: CC(C)(C)C(F)(F)COc1cc(F)cc(-c2sc(NS(=O)(=O)c3cccc(N)n3)nc2-c2ccc(C(F)(F)F)cc2)c1] | 6-amino-N-[5-[3-(2,2-difluoro-3,3-dimethylbutoxy)-5-fluorophenyl]-4-[4-(trifluoromethyl)phenyl]-1,3-thiazol-2-yl]pyridine-2-sulfonamide |

TABLE 1-continued

| Compound Number | Compound Structural Formula | Compound Name |
| --- | --- | --- |
| 286 | 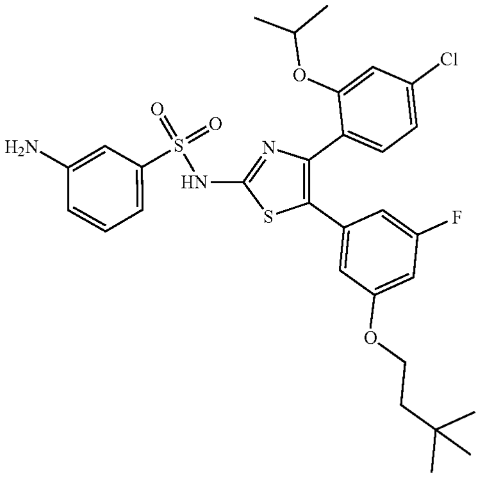 [SMILES: CC(C)Oc1cc(Cl)ccc1-c1nc(NS(=O)(=O)c2cccc(N)c2)sc1-c1cc(F)cc(OCCC(C)(C)C)c1] | 3-amino-N-[4-(4-chloro-2-propan-2-yloxyphenyl)-5-[3-(3,3-dimethylbutoxy)-5-fluorophenyl]-1,3-thiazol-2-yl]benzenesulfonamide |
| 605 | 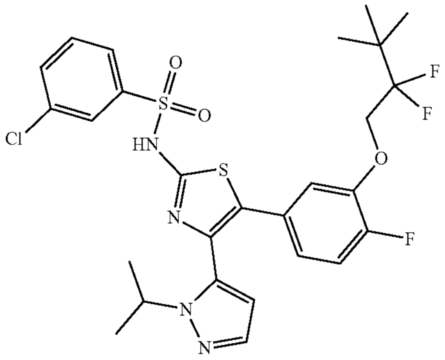 [SMILES: CC(C)n1nccc1-c1nc(NS(=O)(=O)c2cccc(Cl)c2)sc1-c1ccc(F)c(OCC(F)(F)C(C)(C)C)c1] | 3-chloro-N-(5-(3-(2,2-difluoro-3,3-dimethylbutoxy)-4-fluorophenyl)-4-(1-isopropyl-1H-pyrazol-5-yl)thiazol-2-yl)benzenesulfonamide |
| 141 | 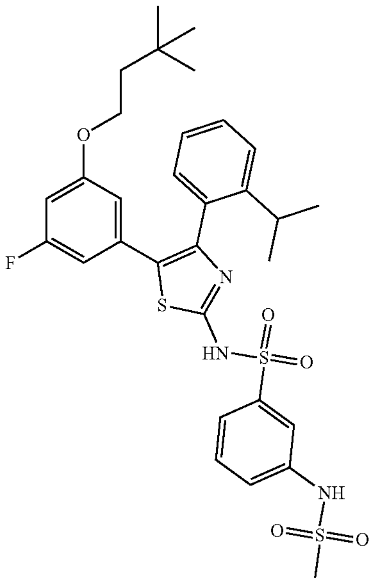 [SMILES: CC(C)c1ccccc1-c1nc(NS(=O)(=O)c2cccc(NS(C)(=O)=O)c2)sc1-c1cc(F)cc(OCCC(C)(C)C)c1] | N-[5-[3-(3,3-dimethylbutoxy)-5-fluorophenyl]-4-(2-propan-2-ylphenyl)-1,3-thiazol-2-yl]-3-(methanesulfonamido) benzenesulfonamide |

TABLE 1-continued

| Compound Number | Compound Structural Formula | Compound Name |
|---|---|---|
| 606 | 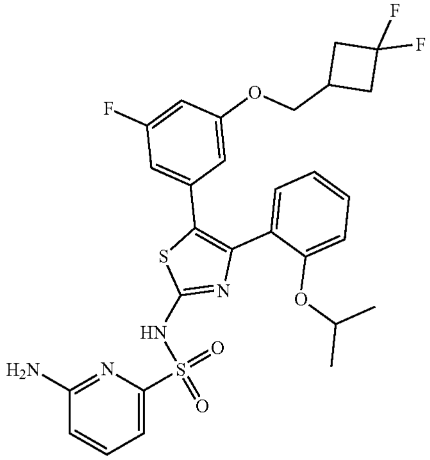 [SMILES: CC(C)Oc1ccccc1-c1nc(NS(=O)(=O)c2cccc(N)n2)sc1-c1cc(F)cc(OCC2CC(F)(F)C2)c1] | 6-amino-N-(5-(3-((3,3-difluorocyclobutyl)methoxy)-5-fluorophenyl)-4-(2-isopropoxyphenyl)thiazol-2-yl)pyridine-2-sulfonamide |
| 393 | 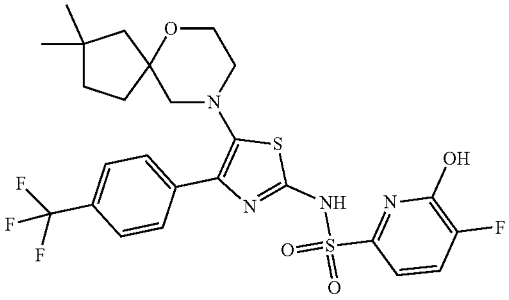 [SMILES: CC1(C)CCC2(CN(c3sc(NS(=O)(=O)c4ccc(F)c(O)n4)nc3-c3ccc(C(F)(F)F)cc3)CCO2)C1] | N-[5-(3,3-dimethyl-6-oxa-9-azaspiro[4.5]decan-9-yl)-4-[4-(trifluoromethyl)phenyl]-1,3-thiazol-2-yl]-5-fluoro-6-hydroxypyridine-2-sulfonamide |
| 409 | 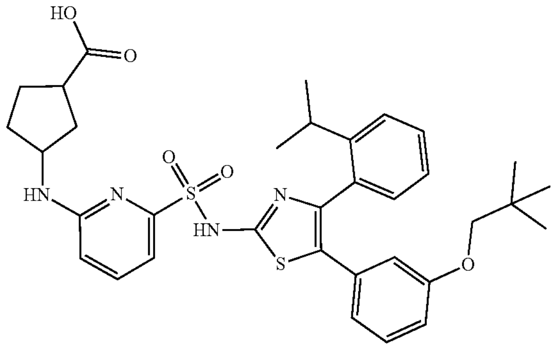 [SMILES: CC(C)c1ccccc1-c1nc(NS(=O)(=O)c2cccc(NC3CCC(C(=O)O)C3)n2)sc1-c1cccc(OCC(C)(C)C)c1] | 3-[6-[5-[3-(2,2-dimethylpropoxy)phenyl]-4-(2-propan-2-ylphenyl)-1,3-thiazol-2-yl]sulfamoyl]pyridin-2-yl]amino]cyclopentane-1-carboxylic acid |
| 607 | 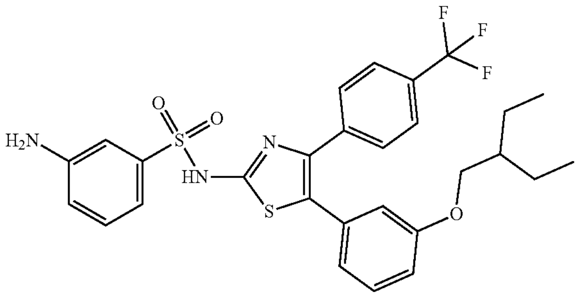 [SMILES: CCC(CC)COc1cccc(-c2sc(NS(=O)(=O)c3cccc(N)c3)nc2-c2ccc(C(F)(F)F)cc2)c1] | 3-amino-N-(5-(3-(2-ethylbutoxy)phenyl)-4-(4-(trifluoromethyl)phenyl)thiazol-2-yl)benzenesulfonamide |

TABLE 1-continued

| Compound Number | Compound Structural Formula | Compound Name |
|---|---|---|
| 78 | 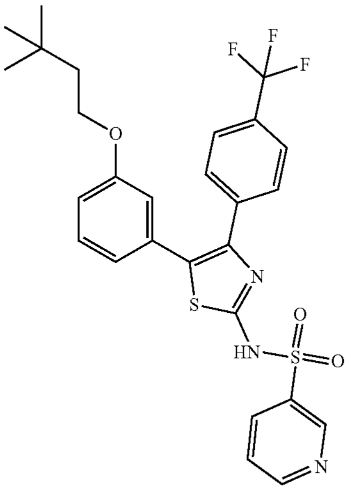 [SMILES: CC(C)(C)CCOc1cccc(-c2sc(NS(=O)(=O)c3cccnc3)nc2-c2ccc(C(F)(F)F)cc2)c1] | N-[5-[3-(3,3-dimethylbutoxy)phenyl]-4-[4-(trifluoromethyl)phenyl]-1,3-thiazol-2-yl]pyridine-3-sulfonamide |
| 429 | 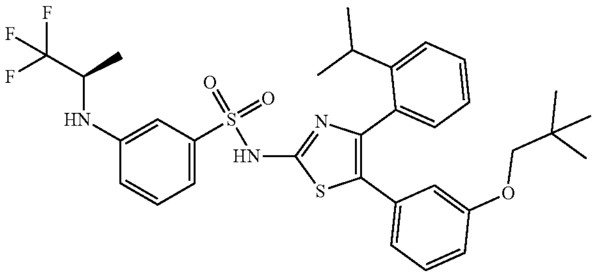 [SMILES: CC(C)c1ccccc1-c1nc(NS(=O)(=O)c2cccc(N[C@H](C)C(F)(F)F)c2)sc1-c1cccc(OCC(C)(C)C)c1] | N-[5-[3-(2,2-dimethylpropoxy)phenyl]-4-(2-propan-2-ylphenyl)-1,3-thiazol-2-yl]-3-[[(2R)-1,1,1-trifluoropropan-2-yl]amino]benzenesulfonamide |
| 44A1 | 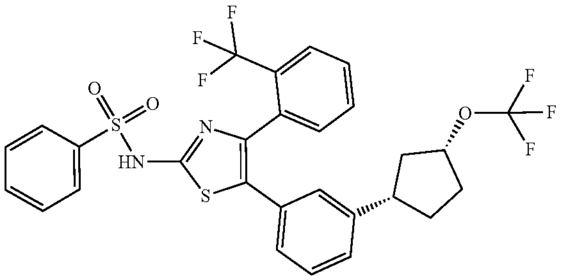 [SMILES: O=S(=O)(Nc1nc(-c2ccccc2C(F)(F)F)c(-c2cccc([C@H]3CC[C@@H](OC(F)(F)F)C3)c2)s1)c1ccccc1] | N-[5-[3-[(1R,3S)-3-(trifluoromethoxy)cyclopentyl]phenyl]-4-[2-(trifluoromethyl)phenyl]-1,3-thiazol-2-yl]benzenesulfonamide |
| 157 | 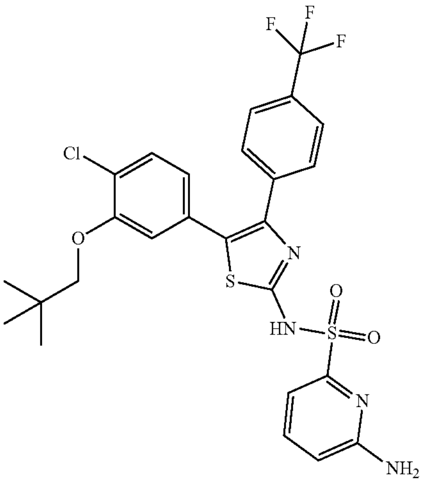 [SMILES: CC(C)(C)COc1cc(-c2sc(NS(=O)(=O)c3cccc(N)n3)nc2-c2ccc(C(F)(F)F)cc2)ccc1Cl] | 6-amino-N-[5-[4-chloro-3-(2,2-dimethylpropoxy)phenyl]-4-[4-(trifluoromethyl)phenyl]-1,3-thiazol-2-yl]pyridine-2-sulfonamide |

TABLE 1-continued

| Compound Number | Compound Structural Formula | Compound Name |
|---|---|---|
| 109 | 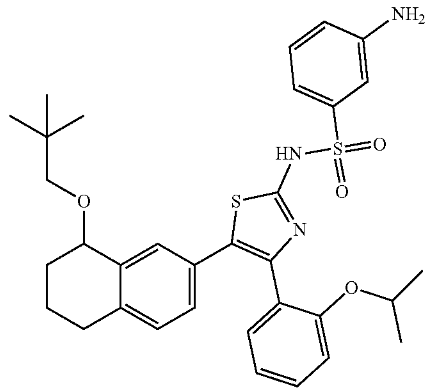 [SMILES: CC(C)Oc1ccccc1-c1nc(NS(=O)(=O)c2cccc(N)c2)sc1-c1ccc2c(c1)C(OCC(C)(C)C)CCC2] | 3-amino-N-[5-[8-(2,2-dimethylpropoxy)-5,6,7,8-tetrahydronaphthalen-2-yl]-4-(2-propan-2-yloxyphenyl)-1,3-thiazol-2-yl]benzenesulfonamide |
| 392 | 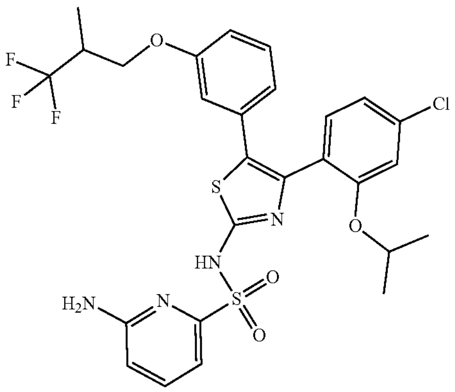 [SMILES: CC(C)Oc1cc(Cl)ccc1-c1nc(NS(=O)(=O)c2cccc(N)n2)sc1-c1cccc(OCC(C)C(F)(F)F)c1] | 6-amino-N-[4-(4-chloro-2-propan-2-yloxyphenyl)-5-[3-(3,3,3-trifluoro-2-methylpropoxy)phenyl]-1,3-thiazol-2-yl]pyridine-2-sulfonamide |
| 153 | 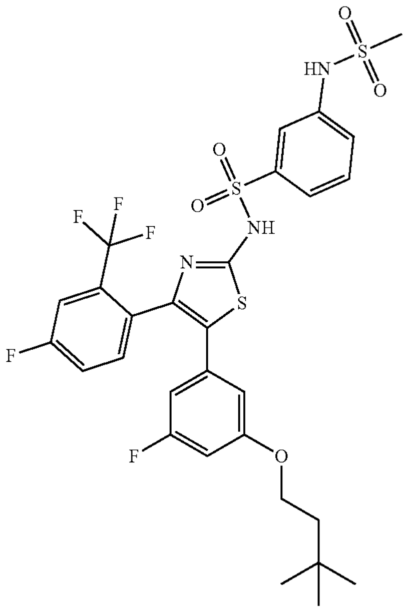 [SMILES: CC(C)(C)CCOc1cc(F)cc(-c2sc(NS(=O)(=O)c3cccc(NS(C)(=O)=O)c3)nc2-c2ccc(F)cc2C(F)(F)F)c1] | N-[5-[3-(3,3-dimethylbutoxy)-5-fluorophenyl]-4-[4-fluoro-2-(trifluoromethyl)phenyl]-1,3-thiazol-2-yl]-3-(methanesulfonamido)benzenesulfonamide |

TABLE 1-continued

| Compound Number | Compound Structural Formula | Compound Name |
|---|---|---|
| 608 | 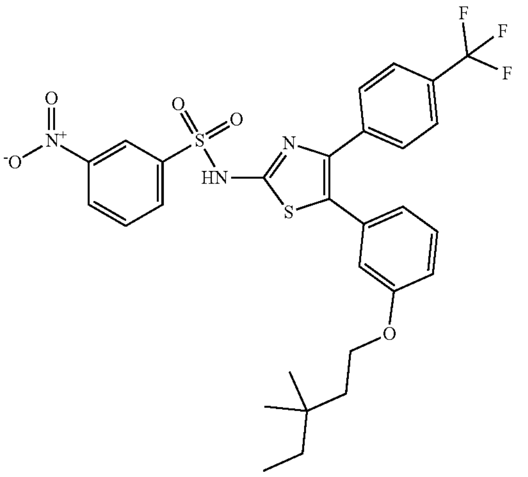 | N-(5-(3-((3,3-dimethylpentyl)oxy)phenyl)-4-(4-(trifluoromethyl)phenyl)thiazol-2-yl)-3-nitrobenzenesulfonamide |
| 195 | 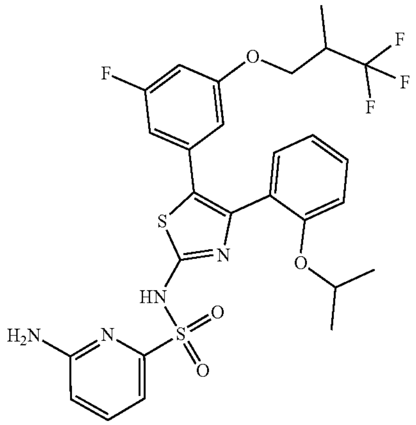 [SMILES: CC(C)Oc1ccccc1-c1nc(NS(=O)(=O)c2cccc(N)n2)sc1-c1cc(F)cc(OCC(C)C(F)(F)F)c1] | 6-amino-N-[5-[3-fluoro-5-(3,3,3-trifluoro-2-methylpropoxy)phenyl]-4-(2-propan-2-yloxyphenyl)-1,3-thiazol-2-yl]pyridine-2-sulfonamide |
| 366 | 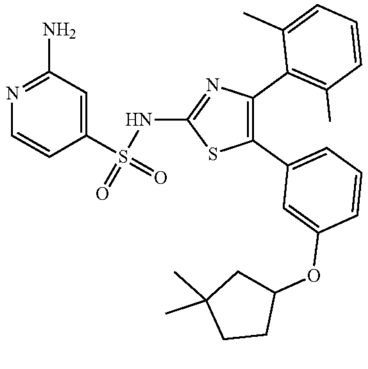 [SMILES: Cc1cccc(C)c1-c1nc(NS(=O)(=O)c2ccnc(N)c2)sc1-c1cccc(OC2CCC(C)(C)C2)c1] | 2-amino-N-[5-[3-(3,3-dimethylcyclopentyl)oxyphenyl]-4-(2,6-dimethylphenyl)-1,3-thiazol-2-yl]pyridine-4-sulfonamide |
| 486 | 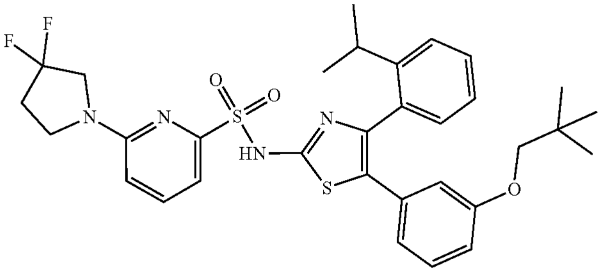 [SMILES: CC(C)c1ccccc1-c1nc(NS(=O)(=O)c2cccc(N3CCC(F)(F)C3)n2)sc1-c1cccc(OCC(C)(C)C)c1] | 6-(3,3-difluoropyrrolidin-1-yl)-N-[5-[3-(2,2-dimethylpropoxy)phenyl]-4-(2-propan-2-ylphenyl)-1,3-thiazol-2-yl]pyridine-2-sulfonamide |

TABLE 1-continued

| Compound Number | Compound Structural Formula | Compound Name |
|---|---|---|
| 90 | 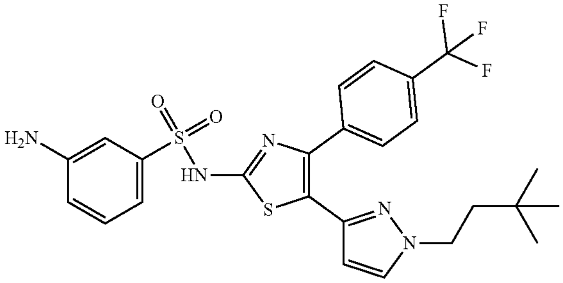 [SMILES: CC(C)(C)CCn1ccc(-c2sc(NS(=O)(=O)c3cccc(N)c3)nc2-c2ccc(C(F)(F)F)cc2)n1] | 3-amino-N-[5-[1-(3,3-dimethylbutyl)pyrazol-3-yl]-4-[4-(trifluoromethyl)phenyl]-1,3-thiazol-2-yl]benzenesulfonamide |
| 223 | 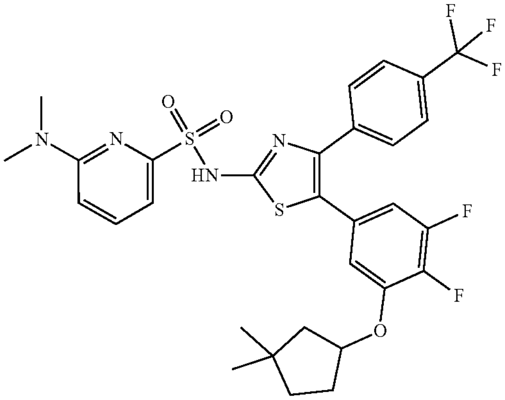 [SMILES: CN(C)c1cccc(S(=O)(=O)Nc2nc(-c3ccc(C(F)(F)F)cc3)c(-c3cc(F)c(F)c(OC4CCC(C)(C)C4)c3)s2)n1] | 6-(dimethylamino)-N-[5-[3-(3,3-dimethylcyclopentyl)oxy-4,5-difluorophenyl]-4-[4-(trifluoromethyl)phenyl]-1,3-thiazol-2-yl]pyridine-2-sulfonamide |
| 86 | 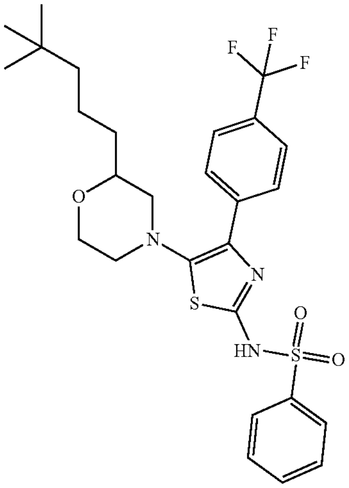 [SMILES: CC(C)(C)CCCC1CN(c2sc(NS(=O)(=O)c3ccccc3)nc2-c2ccc(C(F)(F)F)cc2)CCO1] | N-[5-[2-(4,4-dimethylpentyl)morpholin-4-yl]-4-[4-(trifluoromethyl)phenyl]-1,3-thiazol-2-yl]benzenesulfonamide |
| 208 | 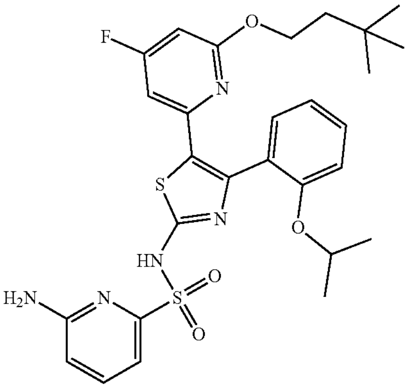 [SMILES: CC(C)Oc1ccccc1-c1nc(NS(=O)(=O)c2cccc(N)n2)sc1-c1cc(F)cc(OCCC(C)(C)C)n1] | 6-amino-N-[5-[6-(3,3-dimethylbutoxy)-4-fluoropyridin-2-yl]-4-(2-propan-2-yloxyphenyl)-1,3-thiazol-2-yl]pyridine-2-sulfonamide |

TABLE 1-continued

| Compound Number | Compound Structural Formula | Compound Name |
|---|---|---|
| 197 | 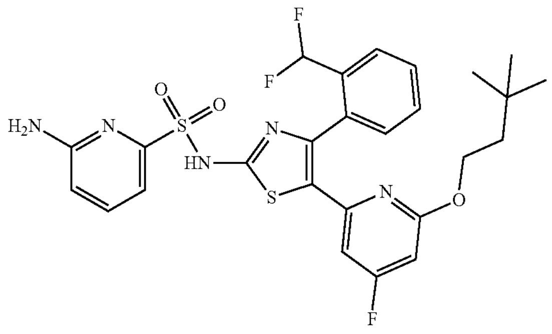 [SMILES: CC(C)(C)CCOc1cc(F)cc(-c2sc(NS(=O)(=O)c3cccc(N)n3)nc2-c2ccccc2C(F)F)n1] | 6-amino-N-[4-[2-(difluoromethyl)phenyl]-5-[6-(3,3-dimethylbutoxy)-4-fluoropyridin-2-yl]-1,3-thiazol-2-yl]pyridine-2-sulfonamide |
| 130 | 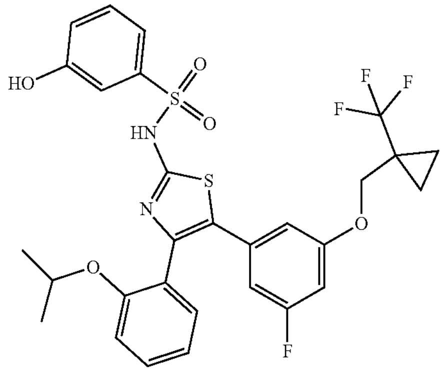 [SMILES: CC(C)Oc1ccccc1-c1nc(NS(=O)(=O)c2cccc(O)c2)sc1-c1cc(F)cc(OCC2(C(F)(F)F)CC2)c1] | N-[5-[3-fluoro-5-[[1-(trifluoromethyl)cyclopropyl]methoxy]phenyl]-4-(2-propan-2-yloxyphenyl)-1,3-thiazol-2-yl]-3-hydroxybenzenesulfonamide |
| 609 | 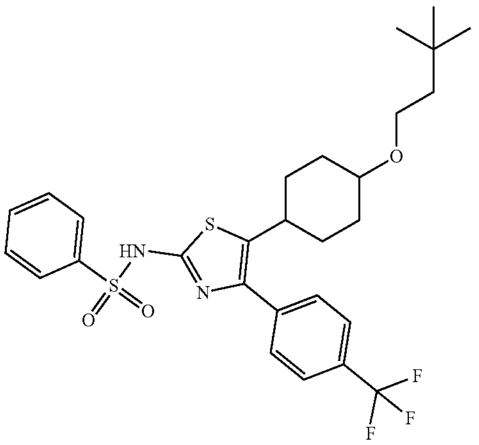 [SMILES: CC(C)(C)CCOC1CCC(c2sc(NS(=O)(=O)c3ccccc3)nc2-c2ccc(C(F)(F)F)cc2)CC1] | N-(5-(4-(3,3-dimethylbutoxy)cyclohexyl)-4-(4-(trifluoromethyl)phenyl)thiazol-2-yl)benzenesulfonamide |

TABLE 1-continued

| Compound Number | Compound Structural Formula | Compound Name |
| --- | --- | --- |
| 345 | 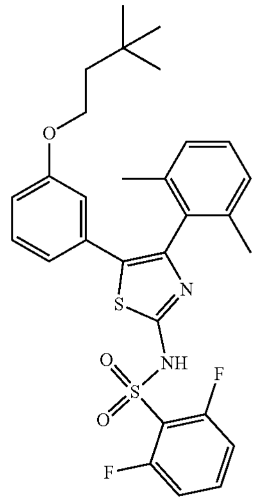 [SMILES: Cc1cccc(C)c1-c1nc(NS(=O)(=O)c2c(F)cccc2F)sc1-c1cccc(OCCC(C)(C)C)c1] | N-[5-[3-(3,3-dimethylbutoxy)phenyl]-4-(2,6-dimethylphenyl)-1,3-thiazol-2-yl]-2,6-difluorobenzenesulfonamide |
| 150 | 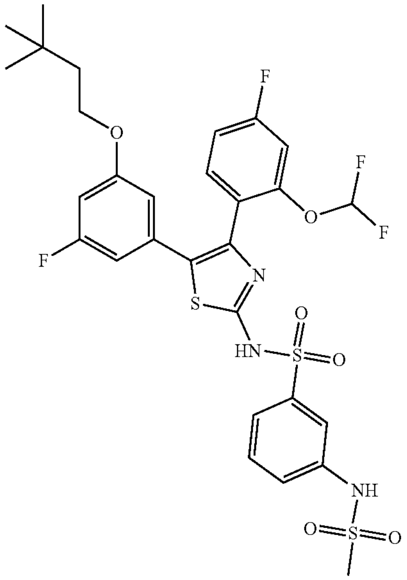 [SMILES: CC(C)(C)CCOc1cc(F)cc(-c2sc(NS(=O)(=O)c3cccc(NS(C)(=O)=O)c3)nc2-c2ccc(F)cc2OC(F)F)c1] | N-[4-[2-(difluoromethoxy)-4-fluorophenyl]-5-[3-(3,3-dimethylbutoxy)-5-fluorophenyl]-1,3-thiazol-2-yl]-3-(methanesulfonamido)benzenesulfonamide |
| 466 | 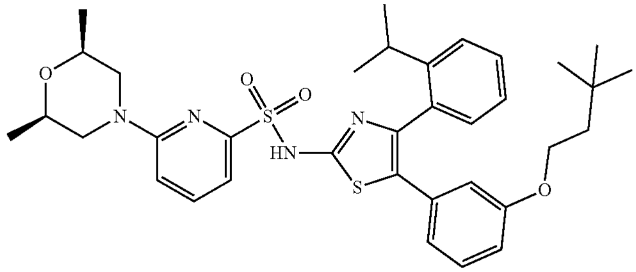 [SMILES: CC(C)c1ccccc1-c1nc(NS(=O)(=O)c2cccc(N3C[C@@H](C)O[C@@H](C)C3)n2)sc1-c1cccc(OCCC(C)(C)C)c1] | N-[5-[3-(3,3-dimethylbutoxy)phenyl]-4-(2-propan-2-ylphenyl)-1,3-thiazol-2-yl]-6-[(2S,6R)-2,6-dimethylmorpholin-4-yl]pyridine-2-sulfonamide |

TABLE 1-continued

| Compound Number | Compound Structural Formula | Compound Name |
|---|---|---|
| 273 | 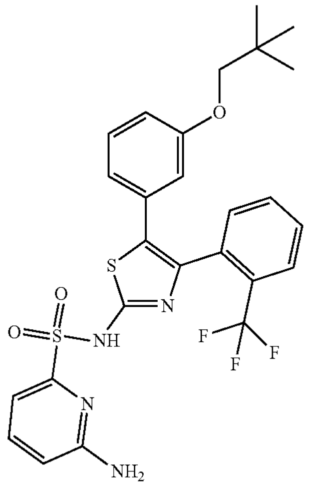 [SMILES: CC(C)(C)COc1cccc(-c2sc(NS(=O)(=O)c3cccc(N)n3)nc2-c2ccccc2C(F)(F)F)c1] | 6-amino-N-[5-[3-(2,2-dimethylpropoxy)phenyl]-4-[2-(trifluoromethyl)phenyl]-1,3-thiazol-2-yl]pyridine-2-sulfonamide |
| 610 | 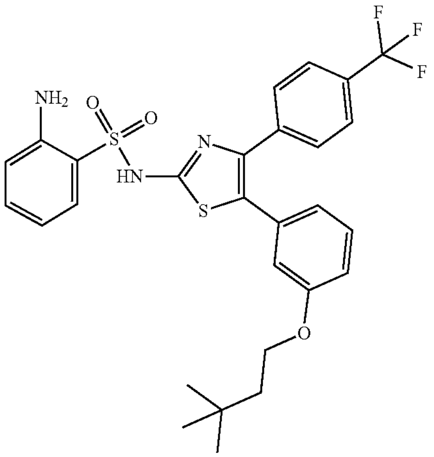 [SMILES: CC(C)(C)CCOc1cccc(-c2sc(NS(=O)(=O)c3ccccc3N)nc2-c2ccc(C(F)(F)F)cc2)c1] | 2-amino-N-(5-(3-(3,3-dimethylbutoxy)phenyl)-4-(4-(trifluoromethyl)phenyl)thiazol-2-yl)benzenesulfonamide |
| 481 | 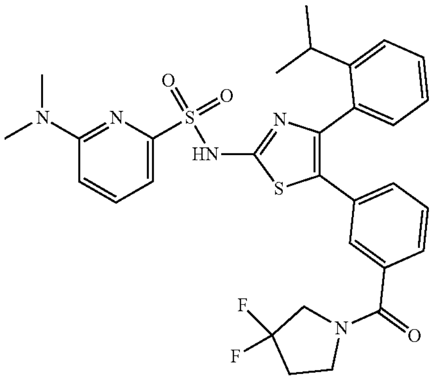 [SMILES: CC(C)c1ccccc1-c1nc(NS(=O)(=O)c2cccc(N(C)C)n2)sc1-c1cccc(C(=O)N2CCC(F)(F)C2)c1] | N-[5-[3-(3,3-difluoropyrrolidine-1-carbonyl)phenyl]-4-(2-propan-2-ylphenyl)-1,3-thiazol-2-yl]-6-(dimethylamino)pyridine-2-sulfonamide |

TABLE 1-continued

| Compound Number | Compound Structural Formula | Compound Name |
|---|---|---|
| 20 | 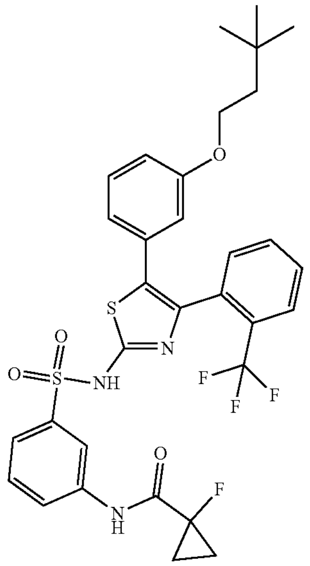 [SMILES: CC(C)(C)CCOc1cccc(-c2sc(NS(=O)(=O)c3cccc(NC(=O)C4(F)CC4)c3)nc2-c2ccccc2C(F)(F)F)c1] | N-[3-[[5-[3-(3,3-dimethylbutoxy)phenyl]-4-[2-(trifluoromethyl)phenyl]-1,3-thiazol-2-yl]sulfamoyl]phenyl]-1-fluorocyclopropane-1-carboxamide |
| 193 | 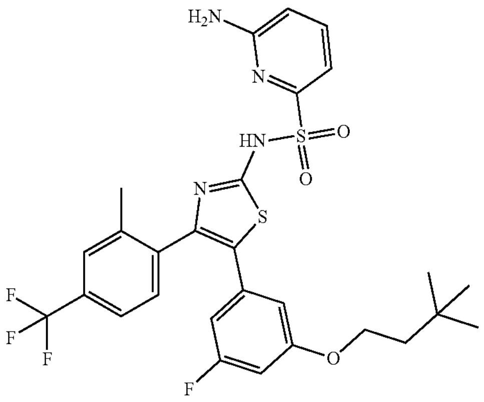 [SMILES: Cc1cc(C(F)(F)F)ccc1-c1nc(NS(=O)(=O)c2cccc(N)n2)sc1-c1cc(F)cc(OCCC(C)(C)C)c1] | 6-amino-N-[5-[3-(3,3-dimethylbutoxy)-5-fluorophenyl]-4-[2-methyl-4-(trifluoromethyl)phenyl]-1,3-thiazol-2-yl]pyridine-2-sulfonamide |
| 347 | 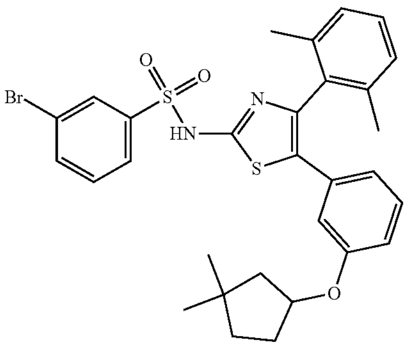 [SMILES: Cc1cccc(C)c1-c1nc(NS(=O)(=O)c2cccc(Br)c2)sc1-c1cccc(OC2CCC(C)(C)C2)c1] | 3-bromo-N-[5-[3-(3,3-dimethylcyclopentyl)oxyphenyl]-4-(2,6-dimethylphenyl)-1,3-thiazol-2-yl]benzenesulfonamide |

TABLE 1-continued

| Compound Number | Compound Structural Formula | Compound Name |
| --- | --- | --- |
| 479 | 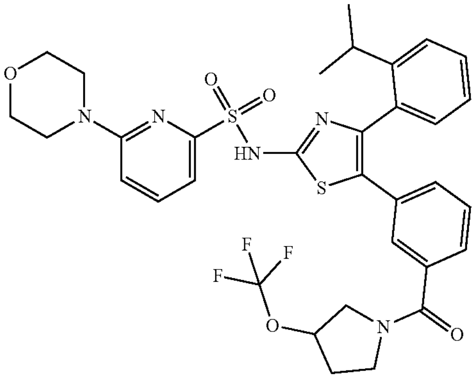 [SMILES: CC(C)c1ccccc1-c1nc(NS(=O)(=O)c2cccc(N3CCOCC3)n2)sc1-c1cccc(C(=O)N2CCC(OC(F)(F)F)C2)c1] | 6-morpholin-4-yl-N-[4-(2-propan-2-ylphenyl)-5-[3-[3-(trifluoromethoxy)pyrrolidine-1-carbonyl]phenyl]-1,3-thiazol-2-yl]pyridine-2-sulfonamide |
| 105 | 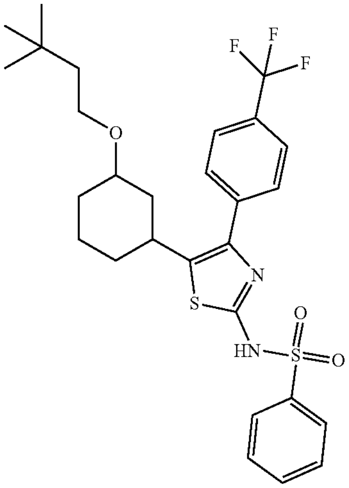 [SMILES: CC(C)(C)CCOC1CCCC(c2sc(NS(=O)(=O)c3ccccc3)nc2-c2ccc(C(F)(F)F)cc2)C1] | N-[5-[3-(3,3-dimethylbutoxy)cyclohexyl]-4-[4-(trifluoromethyl)phenyl]-1,3-thiazol-2-yl]benzenesulfonamide |
| 198 | 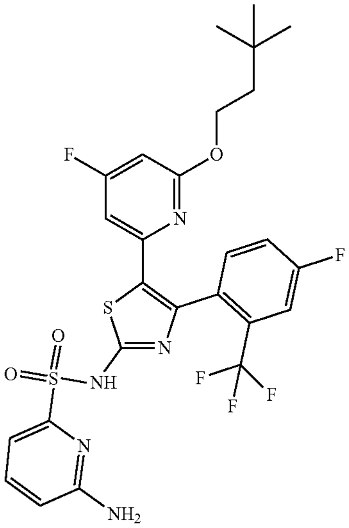 [SMILES: CC(C)(C)CCOc1cc(F)cc(-c2sc(NS(=O)(=O)c3cccc(N)n3)nc2-c2ccc(F)cc2C(F)(F)F)n1] | 6-amino-N-[5-[6-(3,3-dimethylbutoxy)-4-fluoropyridin-2-yl]-4-[4-fluoro-2-(trifluoromethyl)phenyl]-1,3-thiazol-2-yl]pyridine-2-sulfonamide |

TABLE 1-continued
| Compound Number | Compound Structural Formula | Compound Name |
|---|---|---|
| 611 | 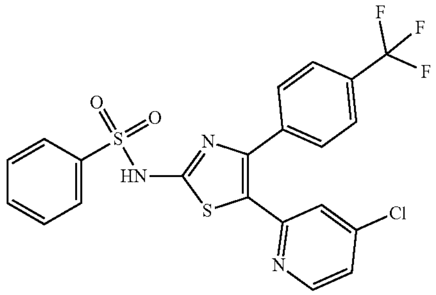 [SMILES: O=S(=O)(Nc1nc(-c2ccc(C(F)(F)F)cc2)c(-c2cc(Cl)ccn2)s1)c1ccccc1] | N-(5-(4-chloropyridin-2-yl)-4-(4-(trifluoromethyl)phenyl)thiazol-2-yl)benzenesulfonamide |
| 612 | 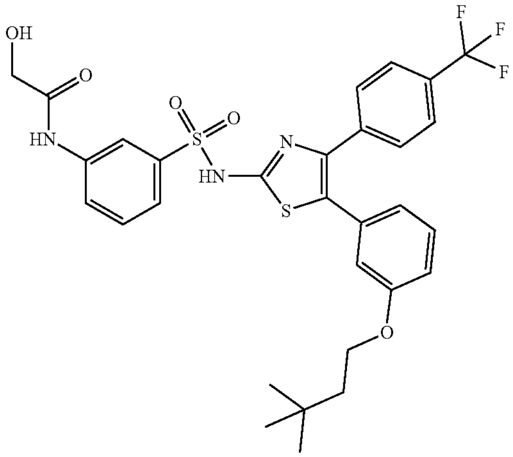 [SMILES: CC(C)(C)CCOc1cccc(-c2sc(NS(=O)(=O)c3cccc(NC(=O)CO)c3)nc2-c2ccc(C(F)(F)F)cc2)c1] | N-(3-(N-(5-(3-(3,3-dimethylbutoxy)phenyl)-4-(4-(trifluoromethyl)phenyl)thiazol-2-yl)sulfamoyl)phenyl)-2-hydroxyacetamide |
| 361 | 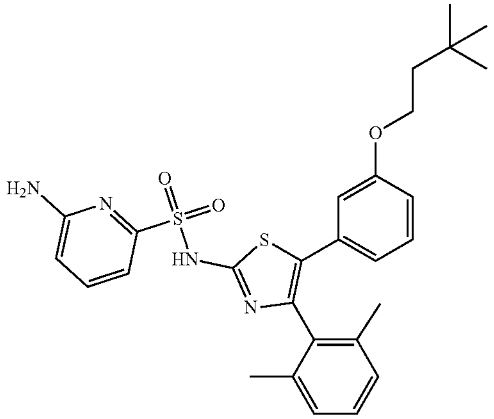 [SMILES: Cc1cccc(C)c1-c1nc(NS(=O)(=O)c2cccc(N)n2)sc1-c1cccc(OCCC(C)(C)C)c1] | 6-amino-N-[5-[3-(3,3-dimethylbutoxy)phenyl]-4-(2,6-dimethylphenyl)-1,3-thiazol-2-yl]pyridine-2-sulfonamide |

TABLE 1-continued

| Compound Number | Compound Structural Formula | Compound Name |
| --- | --- | --- |
| 248 | 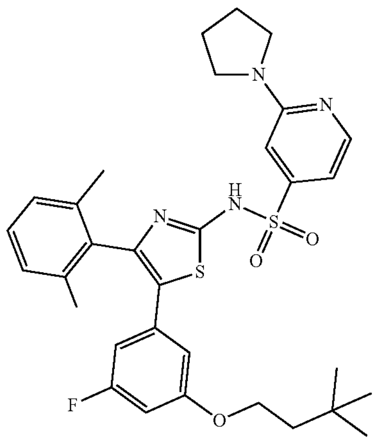 [SMILES: Cc1cccc(C)c1-c1nc(NS(=O)(=O)c2ccnc(N3CCCC3)c2)sc1-c1cc(F)cc(OCCC(C)(C)C)c1] | N-[5-[3-(3,3-dimethylbutoxy)-5-fluorophenyl]-4-(2,6-dimethylphenyl)-1,3-thiazol-2-yl]-2-pyrrolidin-1-ylpyridine-4-sulfonamide |
| 309 | 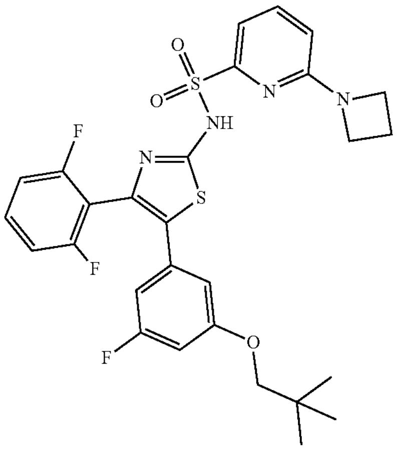 [SMILES: CC(C)(C)COc1cc(F)cc(-c2sc(NS(=O)(=O)c3cccc(N4CCC4)n3)nc2-c2c(F)cccc2F)c1] | 6-(azetidin-1-yl)-N-[4-(2,6-difluorophenyl)-5-[3-(2,2-dimethylpropoxy)-5-fluorophenyl]-1,3-thiazol-2-yl]pyridine-2-sulfonamide |
| 390 | 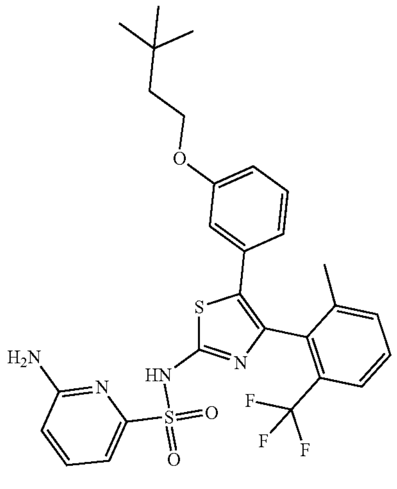 [SMILES: Cc1cccc(C(F)(F)F)c1-c1nc(NS(=O)(=O)c2cccc(N)n2)sc1-c1cccc(OCCC(C)(C)C)c1] | 6-(azetidin-1-yl)-N-[4-(2,6-difluorophenyl)-5-[3-(2,2-dimethylpropoxy)-5-fluorophenyl]-1,3-thiazol-2-yl]pyridine-2-sulfonamide |

TABLE 1-continued

| Compound Number | Compound Structural Formula | Compound Name |
|---|---|---|
| 51 | 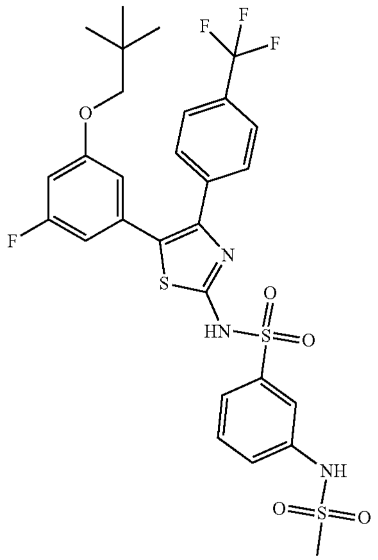 [SMILES: CC(C)(C)COc1cc(F)cc(-c2sc(NS(=O)(=O)c3cccc(NS(C)(=O)=O)c3)nc2-c2ccc(C(F)(F)F)cc2)c1] | N-[5-[3-(2,2-dimethylpropoxy)-5-fluorophenyl]-4-[4-(trifluoromethyl)phenyl]-1,3-thiazol-2-yl]-3-(methanesulfonamido)benzenesulfonamide |
| 613 | 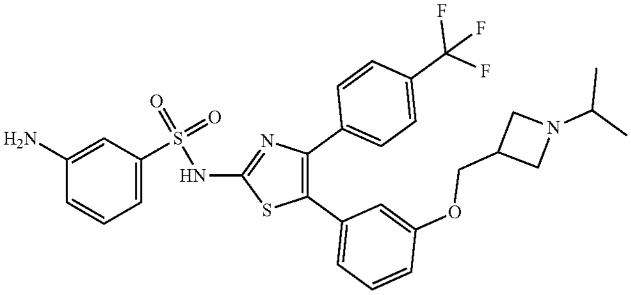 [SMILES: CC(C)N1CC(COc2cccc(-c3sc(NS(=O)(=O)c4cccc(N)c4)nc3-c3ccc(C(F)(F)F)cc3)c2)C1] | 3-amino-N-(5-(3-((1-isopropylazetidin-3-yl)methoxy)phenyl)-4-(4-(trifluoromethyl)phenyl)thiazol-2-yl)benzenesulfonamide |
| 614 | 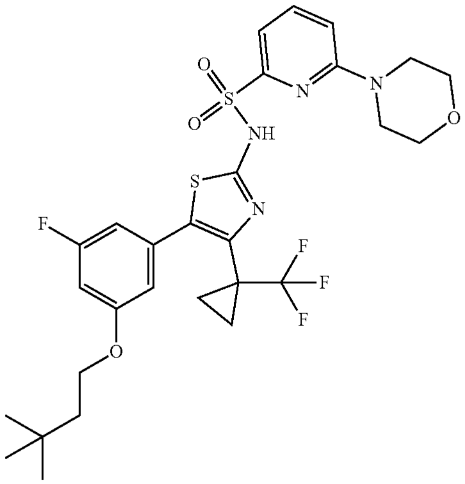 [SMILES: CC(C)(C)CCOc1cc(F)cc(-c2sc(NS(=O)(=O)c3cccc(N4CCOCC4)n3)nc2C2(C(F)(F)F)CC2)c1] | N-(5-(3-(3,3-dimethylbutoxy)-5-fluorophenyl)-4-(1-(trifluoromethyl)cyclopropyl)thiazol-2-yl)-6-morpholinopyridine-2-sulfonamide |

TABLE 1-continued

| Compound Number | Compound Structural Formula | Compound Name |
| --- | --- | --- |
| 411 | 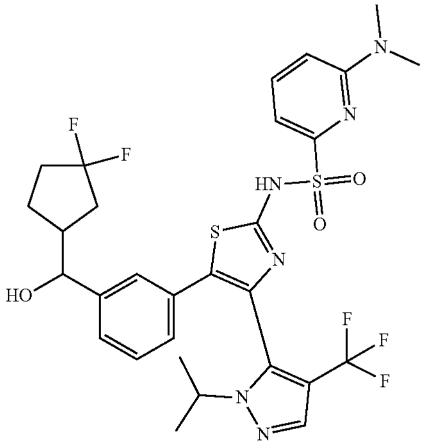 | N-[5-[3-[(3,3-difluorocyclopentyl)-hydroxymethyl]phenyl]-4-[2-propan-2-yl-4-(trifluoromethyl)pyrazol-3-yl]-1,3-thiazol-2-yl]-6-(dimethylamino)pyridine-2-sulfonamide |
| 120 | 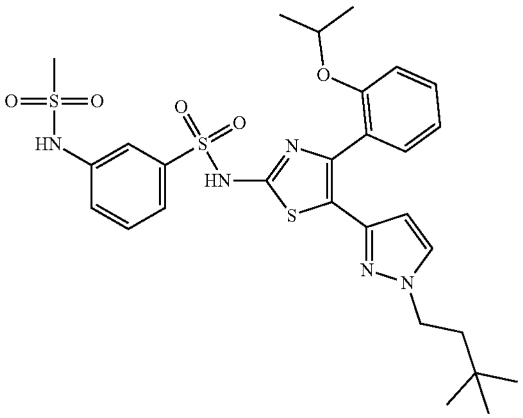 [SMILES: CC(C)Oc1ccccc1-c1nc(NS(=O)(=O)c2cccc(NS(C)(=O)=O)c2)sc1-c1ccn(CCC(C)(C)C)n1] | N-[5-[1-(3,3-dimethylbutyl)pyrazol-3-yl]-4-(2-propan-2-yloxyphenyl)-1,3-thiazol-2-yl]-3-(methanesulfonamido)benzenesulfonamide |
| 36 | 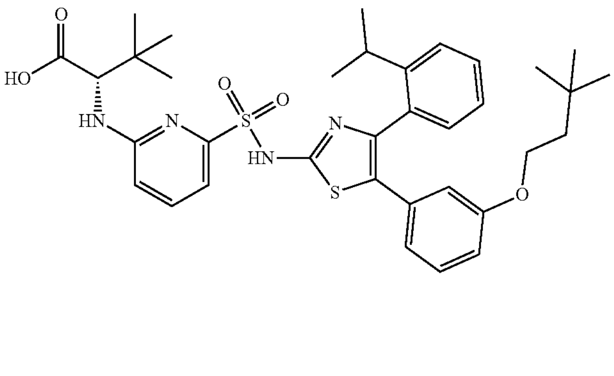 [SMILES: CC(C)c1ccccc1-c1nc(NS(=O)(=O)c2cccc(N[C@H](C(=O)O)C(C)(C)C)n2)sc1-c1cccc(OCCC(C)(C)C)c1] | (2S)-2-[6-[[5-[3-(3,3-dimethylbutoxy)phenyl]-4-(2-propan-2-ylphenyl)-1,3-thiazol-2-yl]sulfamoyl]pyridin-2-yl]amino]-3,3-dimethylbutanoic acid |

TABLE 1-continued

| Compound Number | Compound Structural Formula | Compound Name |
|---|---|---|
| 161 | 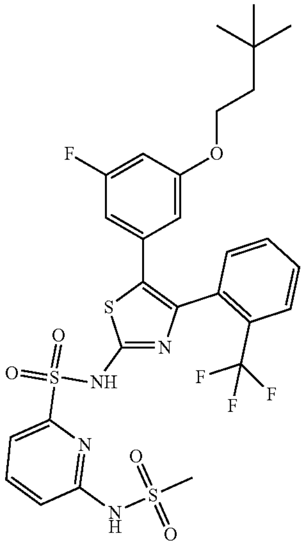 [SMILES: CC(C)(C)CCOc1cc(F)cc(-c2sc(NS(=O)(=O)c3cccc(NS(C)(=O)=O)n3)nc2-c2ccccc2C(F)(F)F)c1] | N-[5-[3-(3,3-dimethylbutoxy)-5-fluorophenyl]-4-[2-(trifluoromethyl)phenyl]-1,3-thiazol-2-yl]-6-(methanesulfonamido)pyridine-2-sulfonamide |
| 56 | 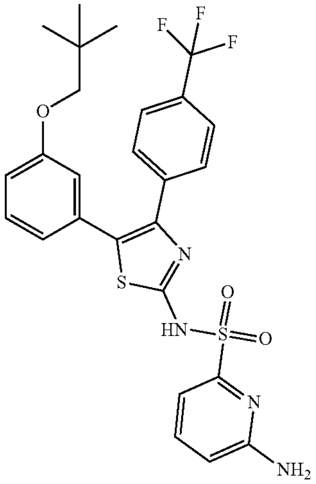 [SMILES: CC(C)(C)COc1cccc(-c2sc(NS(=O)(=O)c3cccc(N)n3)nc2-c2ccc(C(F)(F)F)cc2)c1] | 6-amino-N-[5-[3-(2,2-dimethylpropoxy)phenyl]-4-[4-(trifluoromethyl)phenyl]-1,3-thiazol-2-yl]pyridine-2-sulfonamide |
| 477 | 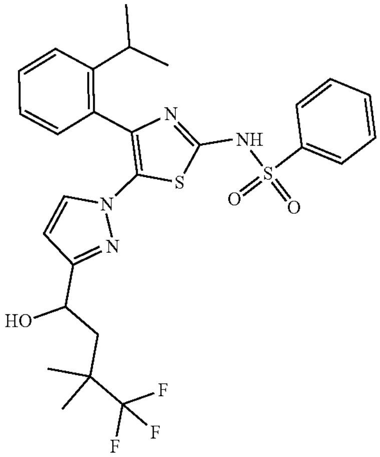 [SMILES: CC(C)c1ccccc1-c1nc(NS(=O)(=O)c2ccccc2)sc1-n1ccc(C(O)CC(C)(C)C(F)(F)F)n1] | N-[4-(2-propan-2-ylphenyl)-5-[3-(4,4,4-trifluoro-1-hydroxy-3,3-dimethylbutyl)pyrazol-1-yl]-1,3-thiazol-2-yl]benzenesulfonamide |

TABLE 1-continued

| Compound Number | Compound Structural Formula | Compound Name |
| --- | --- | --- |
| 343 | 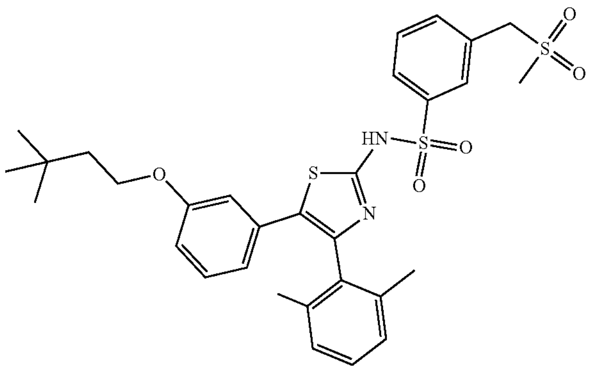 [SMILES: Cc1cccc(C)c1-c1nc(NS(=O)(=O)c2cccc(CS(C)(=O)=O)c2)sc1-c1cccc(OCCC(C)(C)C)c1] | N-[5-[3-(3,3-dimethylbutoxy)phenyl]-4-(2,6-dimethylphenyl)-1,3-thiazol-2-yl]-3-(methylsulfonylmethyl)benzenesulfonamide |
| 615 | 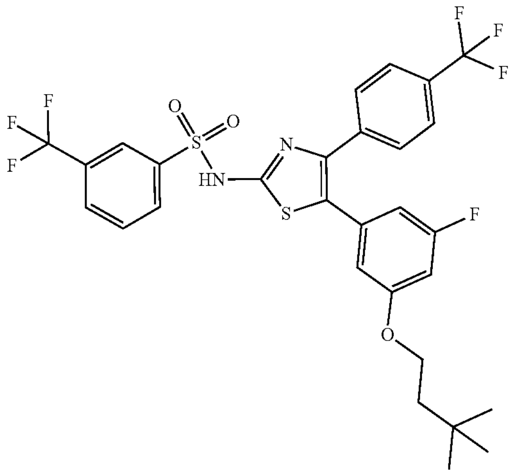 [SMILES: CC(C)(C)CCOc1cc(F)cc(-c2sc(NS(=O)(=O)c3cccc(C(F)(F)F)c3)nc2-c2ccc(C(F)(F)F)cc2)c1] | N-(5-(3-(3,3-dimethylbutoxy)-5-fluorophenyl)-4-(4-(trifluoromethyl)phenyl)thiazol-2-yl)-3-(trifluoromethyl)benzenesulfonamide |
| 49 | 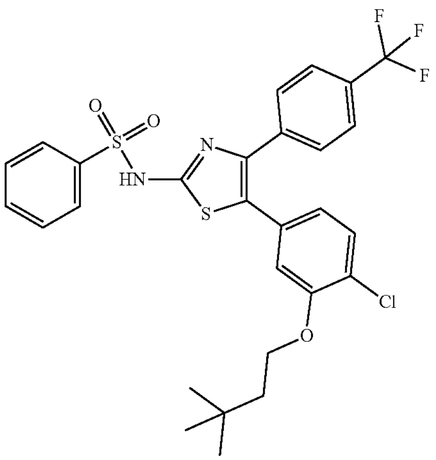 [SMILES: CC(C)(C)CCOc1cc(-c2sc(NS(=O)(=O)c3ccccc3)nc2-c2ccc(C(F)(F)F)cc2)ccc1Cl] | N-[5-[4-chloro-3-(3,3-dimethylbutoxy)phenyl]-4-[4-(trifluoromethyl)phenyl]-1,3-thiazol-2-yl]benzenesulfonamide |

TABLE 1-continued

| Compound Number | Compound Structural Formula | Compound Name |
|---|---|---|
| 471 | 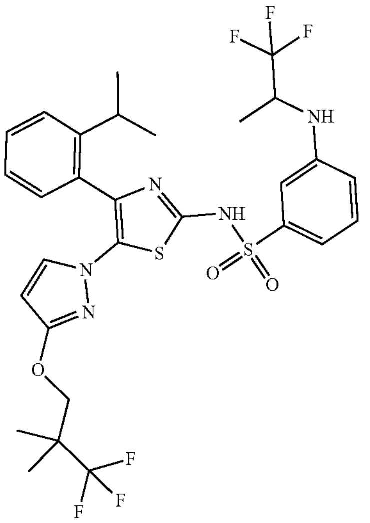 [SMILES: CC(C)c1ccccc1-c1nc(NS(=O)(=O)c2cccc(NC(C)C(F)(F)F)c2)sc1-n1ccc(OCC(C)(C)C(F)(F)F)n1] | N-[4-(2-propan-2-ylphenyl)-5-[3-(3,3,3-trifluoro-2,2-dimethylpropoxy)pyrazol-1-yl]-1,3-thiazol-2-yl]-3-(1,1,1-trifluoropropan-2-ylamino)benzenesulfonamide |
| 92 | 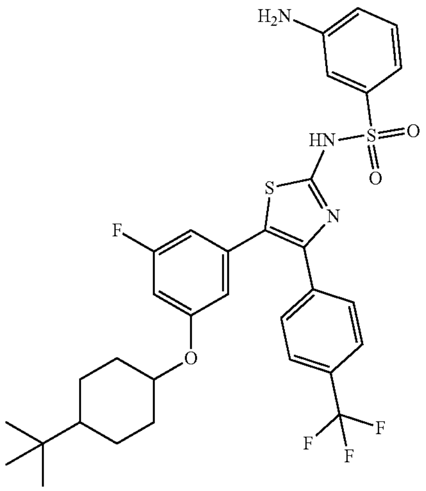 [SMILES: CC(C)(C)C1CCC(Oc2cc(F)cc(-c3sc(NS(=O)(=O)c4cccc(N)c4)nc3-c3ccc(C(F)(F)F)cc3)c2)CC1] | 3-amino-N-[5-[3-(4-tert-butylcyclohexyl)oxy-5-fluorophenyl]-4-[4-(trifluoromethyl)phenyl]-1,3-thiazol-2-yl]benzenesulfonamide |
| 387 | 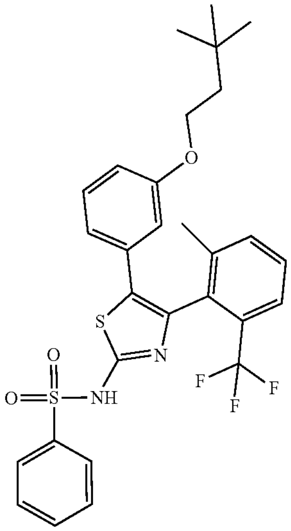 [SMILES: Cc1cccc(C(F)(F)F)c1-c1nc(NS(=O)(=O)c2ccccc2)sc1-c1cccc(OCCC(C)(C)C)c1] | N-[5-[3-(3,3-dimethylbutoxy)phenyl]-4-[2-methyl-6-(trifluoromethyl)phenyl]-1,3-thiazol-2-yl]benzenesulfonamide |

TABLE 1-continued
| Compound Number | Compound Structural Formula | Compound Name |
|---|---|---|
| 304 | 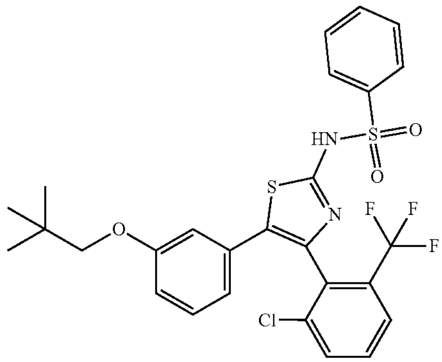 [SMILES: CC(C)(C)COc1cccc(-c2sc(NS(=O)(=O)c3ccccc3)nc2-c2c(Cl)cccc2C(F)(F)F)c1] | N-[4-[2-chloro-6-(trifluoromethyl)phenyl]-5-[3-(2,2-dimethylpropoxy)phenyl]-1,3-thiazol-2-yl]benzenesulfonamide |
| 288 | 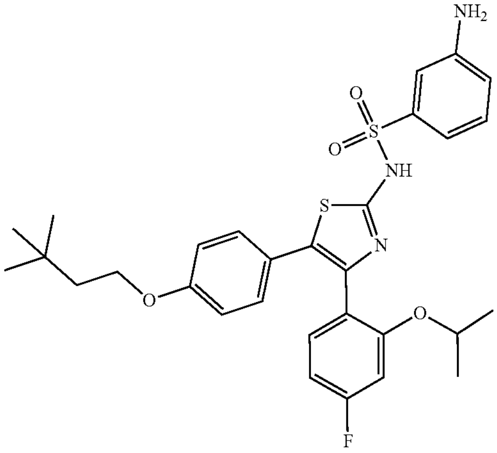 [SMILES: CC(C)Oc1cc(F)ccc1-c1nc(NS(=O)(=O)c2cccc(N)c2)sc1-c1ccc(OCCC(C)(C)C)cc1] | 3-amino-N-[5-[4-(3,3-dimethylbutoxy)phenyl]-4-(4-fluoro-2-propan-2-yloxyphenyl)-1,3-thiazol-2-yl]benzenesulfonamide |
| 616 | 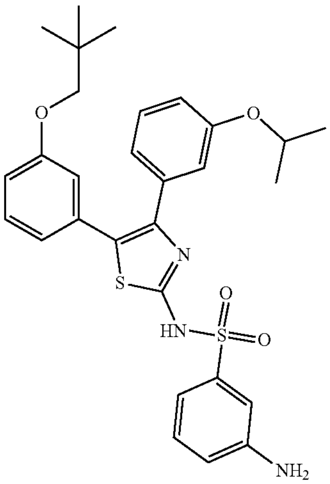 [SMILES: CC(C)Oc1cccc(-c2nc(NS(=O)(=O)c3cccc(N)c3)sc2-c2cccc(OCC(C)(C)C)c2)c1] | 3-amino-N-(4-(3-isopropoxyphenyl)-5-(3-(neopentyloxy)phenyl)thiazol-2-yl)benzenesulfonamide |

TABLE 1-continued

| Compound Number | Compound Structural Formula | Compound Name |
|---|---|---|
| 617 | 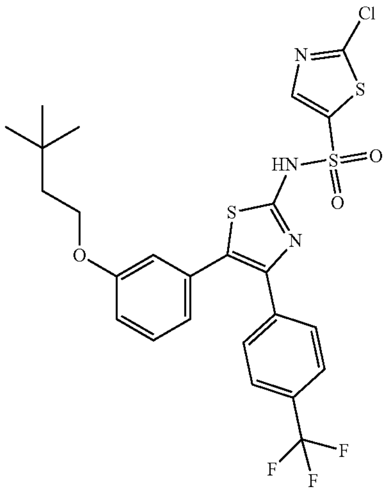 [SMILES: CC(C)(C)CCOc1cccc(-c2sc(NS(=O)(=O)c3cnc(Cl)s3)nc2-c2ccc(C(F)(F)F)cc2)c1] | 2-chloro-N-(5-(3-(3,3-dimethylbutoxy)phenyl)-4-(4-(trifluoromethyl)phenyl)thiazol-2-yl)thiazole-5-sulfonamide |
| 618 | 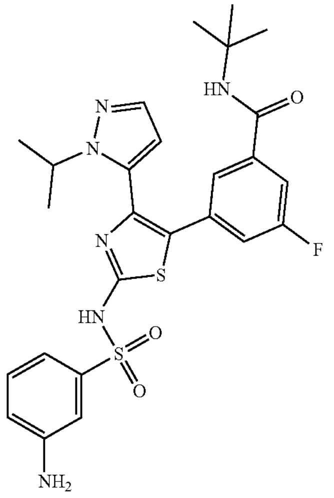 [SMILES: CC(C)n1nccc1-c1nc(NS(=O)(=O)c2cccc(N)c2)sc1-c1cc(F)cc(C(=O)NC(C)(C)C)c1] | 3-(2-((3-aminophenyl)sulfonamido)-4-(1-isopropyl-1H-pyrazol-5-yl)thiazol-5-yl)-N-(tert-butyl)-5-fluorobenzamide |
| 322 | 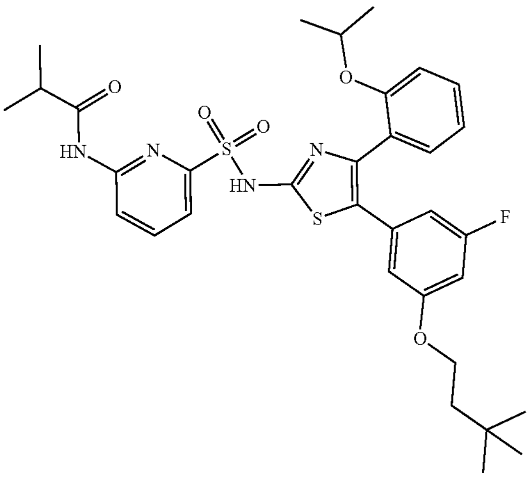 [SMILES: CC(C)Oc1ccccc1-c1nc(NS(=O)(=O)c2cccc(NC(=O)C(C)C)n2)sc1-c1cc(F)cc(OCCC(C)(C)C)c1] | N-[6-[[5-[3-(3,3-dimethylbutoxy)-5-fluorophenyl]-4-(2-propan-2-yloxyphenyl)-1,3-thiazol-2-yl]sulfamoyl]pyridin-2-yl]-2-methylpropanamide |

TABLE 1-continued

| Compound Number | Compound Structural Formula | Compound Name |
|---|---|---|
| 41 | 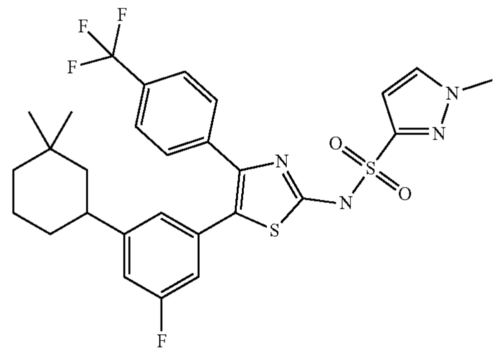 | N-(5-(3-(3,3-dimethylcyclohexyl)-5-fluorophenyl)-4-(4-(trifluoromethyl)phenyl)thiazol-2-yl)-1-methyl-1H-pyrazole-3-sulfonamide |
| 354 | 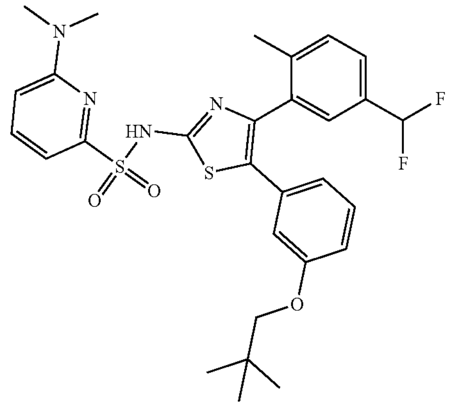 [SMILES: Cc1ccc(C(F)F)cc1-c1nc(NS(=O)(=O)c2cccc(N(C)C)n2)sc1-c1cccc(OCC(C)(C)C)c1] | N-[4-[5-(difluoromethyl)-2-methylphenyl]-5-[3-(2,2-dimethylpropoxy)phenyl]-1,3-thiazol-2-yl]-6-(dimethylamino)pyridine-2-sulfonamide |
| 224 | 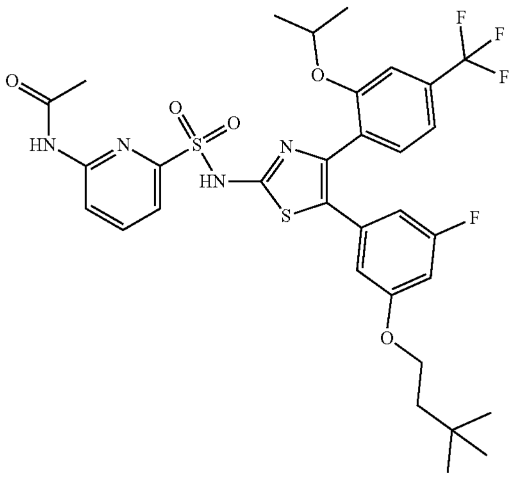 [SMILES: CC(=O)Nc1cccc(S(=O)(=O)Nc2nc(-c3ccc(C(F)(F)F)cc3OC(C)C)c(-c3cc(F)cc(OCCC(C)(C)C)c3)s2)n1] | N-[6-[5-[3-(3,3-dimethylbutoxy)-5-fluorophenyl]-4-[2-propan-2-yloxy-4-(trifluoromethyl)phenyl]-1,3-thiazol-2-yl]sulfamoyl]pyridin-2-yl]acetamide |

TABLE 1-continued

| Compound Number | Compound Structural Formula | Compound Name |
|---|---|---|
| 619 | 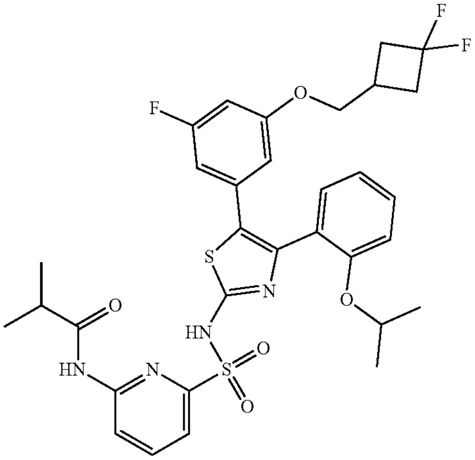 [SMILES: CC(C)Oc1ccccc1-c1nc(NS(=O)(=O)c2cccc(NC(=O)C(C)C)n2)sc1-c1cc(F)cc(OCC2CC(F)(F)C2)c1] | N-(6-(N-(5-(3-((3,3-difluorocyclobutyl)methoxy)-5-fluorophenyl)-4-(2-isopropoxyphenyl)thiazol-2-yl)sulfamoyl)pyridin-2-yl)isobutyramide |
| 42 | 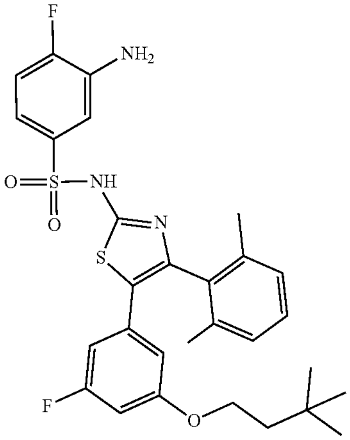 [SMILES: Cc1cccc(C)c1-c1nc(NS(=O)(=O)c2ccc(F)c(N)c2)sc1-c1cc(F)cc(OCCC(C)(C)C)c1] | 3-amino-N-[5-[3-(3,3-dimethylbutoxy)-5-fluorophenyl]-4-(2,6-dimethylphenyl)-1,3-thiazol-2-yl]-4-fluorobenzenesulfonamide |
| 271 | 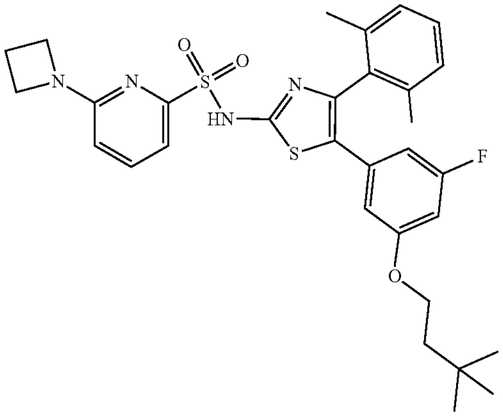 [SMILES: Cc1cccc(C)c1-c1nc(NS(=O)(=O)c2cccc(N3CCC3)n2)sc1-c1cc(F)cc(OCCC(C)(C)C)c1] | 6-(azetidin-1-yl)-N-[5-[3-(3,3-dimethylbutoxy)-5-fluorophenyl]-4-(2,6-dimethylphenyl)-1,3-thiazol-2-yl]pyridine-2-sulfonamide |

TABLE 1-continued

| Compound Number | Compound Structural Formula | Compound Name |
|---|---|---|
| 38 | 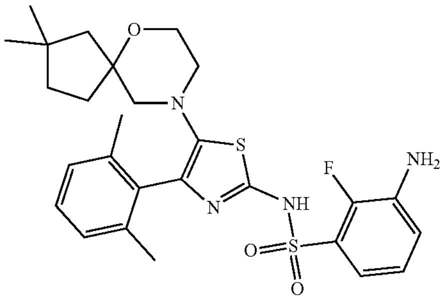 [SMILES: Cc1cccc(C)c1-c1nc(NS(=O)(=O)c2cccc(N)c2F)sc1N1CCOC2(CCC(C)(C)C2)C1] | 3-amino-N-[5-(3,3-dimethyl-6-oxa-9-azaspiro[4.5]decan-9-yl)-4-(2,6-dimethylphenyl)-1,3-thiazol-2-yl]-2-fluorobenzenesulfonamide |
| 460 | 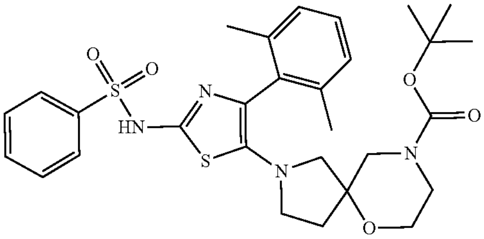 [SMILES: Cc1cccc(C)c1-c1nc(NS(=O)(=O)c2ccccc2)sc1N1CCC2(CN(C(=O)OC(C)(C)C)CCO2)C1] | tert-butyl 2-[2-(benzenesulfonamido)-4-(2,6-dimethylphenyl)-1,3-thiazol-5-yl]-6-oxa-2,9-diazaspiro[4.5]decane-9-carboxylate |
| 307 | 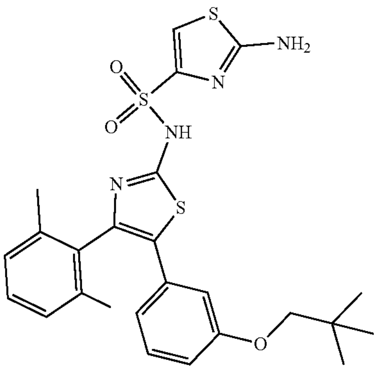 [SMILES: Cc1cccc(C)c1-c1nc(NS(=O)(=O)c2csc(N)n2)sc1-c1cccc(OCC(C)(C)C)c1] | 2-amino-N-[4-(2,6-dimethylphenyl)-5-[3-(2,2-dimethylpropoxy)phenyl]-1,3-thiazol-2-yl]-1,3-thiazole-4-sulfonamide |
| 620 | 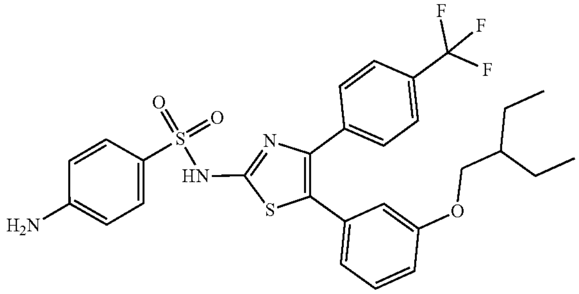 [SMILES: CCC(CC)COc1cccc(-c2sc(NS(=O)(=O)c3ccc(N)cc3)nc2-c2ccc(C(F)(F)F)cc2)c1] | 4-amino-N-(5-(3-(2-ethylbutoxy)phenyl)-4-(4-(trifluoromethyl)phenyl)thiazol-2-yl)benzenesulfonamide |

TABLE 1-continued

| Compound Number | Compound Structural Formula | Compound Name |
|---|---|---|
| 399 | 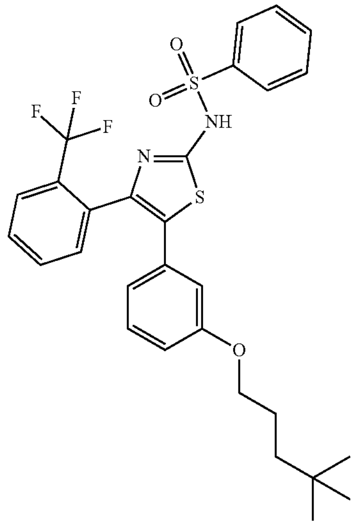 [SMILES: CC(C)(C)CCCOc1cccc(-c2sc(NS(=O)(=O)c3ccccc3)nc2-c2ccccc2C(F)(F)F)c1] | N-[5-[3-(4,4-dimethylpentoxy)phenyl]-4-[2-(trifluoromethyl)phenyl]-1,3-thiazol-2-yl]benzenesulfonamide |
| 46B2 | 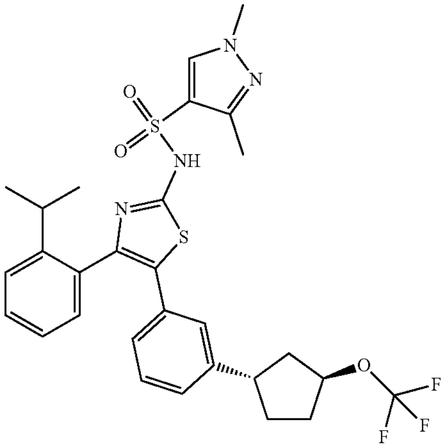 [SMILES: Cc1nn(C)cc1S(=O)(=O)Nc1nc(-c2ccccc2C(C)C)c(-c2cccc([C@H]3CC[C@H](OC(F)(F)F)C3)c2)s1] | 1,3-dimethyl-N-[4-(2-propan-2-ylphenyl)-5-[3-[(1S,3S)-3-(trifluoromethoxy)cyclopentyl]phenyl]-1,3-thiazol-2-yl]pyrazole-4-sulfonamide |
| 415 | 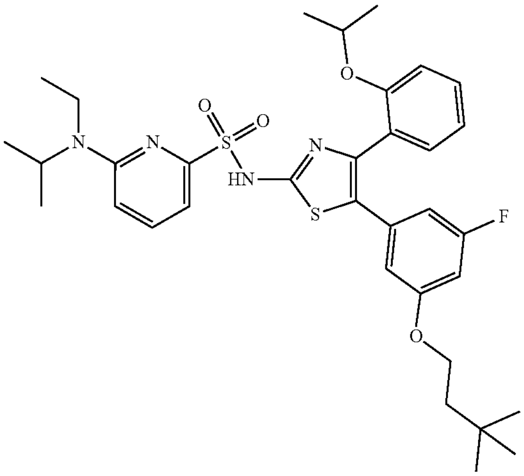 [SMILES: CCN(c1cccc(S(=O)(=O)Nc2nc(-c3ccccc3OC(C)C)c(-c3cc(F)cc(OCCC(C)(C)C)c3)s2)n1)C(C)C] | N-[5-[3-(3,3-dimethylbutoxy)-5-fluorophenyl]-4-(2-propan-2-yloxyphenyl)-1,3-thiazol-2-yl]-6-[ethyl(propan-2-yl)amino]pyridine-2-sulfonamide |

TABLE 1-continued
| Compound Number | Compound Structural Formula | Compound Name |
|---|---|---|
| 301 | 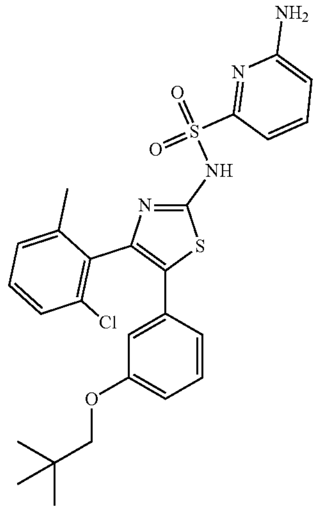 [SMILES: Cc1cccc(Cl)c1-c1nc(NS(=O)(=O)c2cccc(N)n2)sc1-c1cccc(OCC(C)(C)C)c1] | 6-amino-N-[4-(2-chloro-6-methylphenyl)-5-[3-(2,2-dimethylpropoxy)phenyl]-1,3-thiazol-2-yl]pyridine-2-sulfonamide |
| 621 | 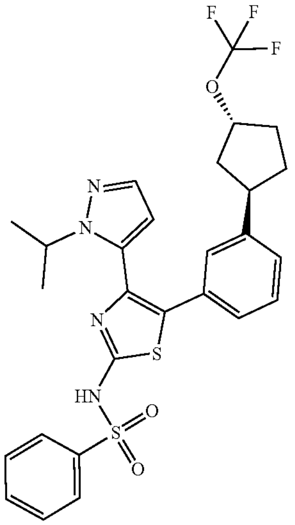 [SMILES: CC(C)n1nccc1-c1nc(NS(=O)(=O)c2ccccc2)sc1-c1cccc([C@@H]2CC[C@@H](OC(F)(F)F)C2)c1] | N-(4-(1-isopropyl-1H-pyrazol-5-yl)-5-(3-((1R,3R)-3-(trifluoromethoxy)cyclopentyl)phenyl)thiazol-2-yl)benzenesulfonamide |
| 319 | 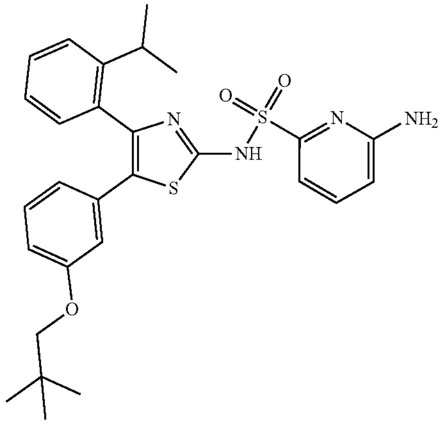 [SMILES: CC(C)c1ccccc1-c1nc(NS(=O)(=O)c2cccc(N)n2)sc1-c1cccc(OCC(C)(C)C)c1] | 6-amino-N-[5-[3-(2,2-dimethylpropoxy)phenyl]-4-(2-propan-2-ylphenyl)-1,3-thiazol-2-yl]pyridine-2-sulfonamide |

TABLE 1-continued

| Compound Number | Compound Structural Formula | Compound Name |
|---|---|---|
| 10 | 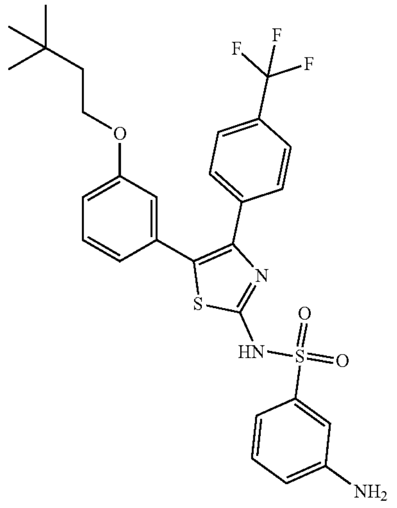 [SMILES: CC(C)(C)CCOc1cccc(-c2sc(NS(=O)(=O)c3cccc(N)c3)nc2-c2ccc(C(F)(F)F)cc2)c1] | 3-amino-N-[5-[3-(3,3-dimethylbutoxy)phenyl]-4-[4-(trifluoromethyl)phenyl]-1,3-thiazol-2-yl]benzenesulfonamide |
| 500 | 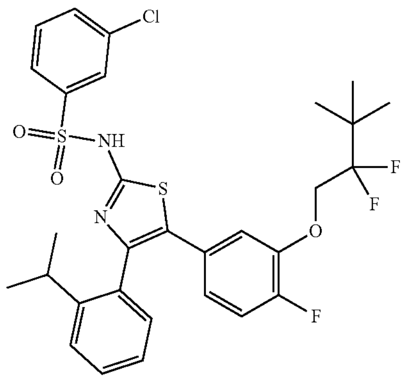 [SMILES: CC(C)c1ccccc1-c1nc(NS(=O)(=O)c2cccc(Cl)c2)sc1-c1ccc(F)c(OCC(F)(F)C(C)(C)C)c1] | 3-chloro-N-[5-[3-(2,2-difluoro-3,3-dimethylbutoxy)-4-fluorophenyl]-4-(2-propan-2-ylphenyl)-1,3-thiazol-2-yl]benzenesulfonamide |
| 374 | 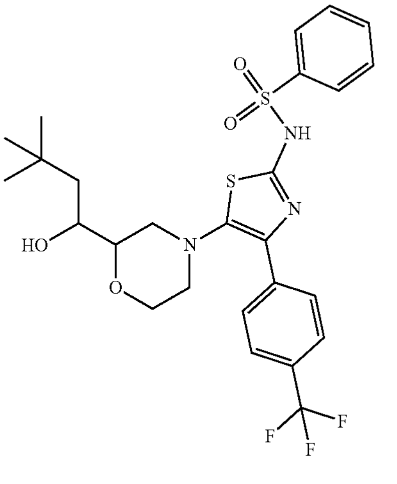 [SMILES: CC(C)(C)CC(O)C1CN(c2sc(NS(=O)(=O)c3ccccc3)nc2-c2ccc(C(F)(F)F)cc2)CCO1] | N-[5-[2-(1-hydroxy-3,3-dimethylbutyl)morpholin-4-yl]-4-[4-(trifluoromethyl)phenyl]-1,3-thiazol-2-yl]benzenesulfonamide |

TABLE 1-continued
| Compound Number | Compound Structural Formula | Compound Name |
|---|---|---|
| 93 | 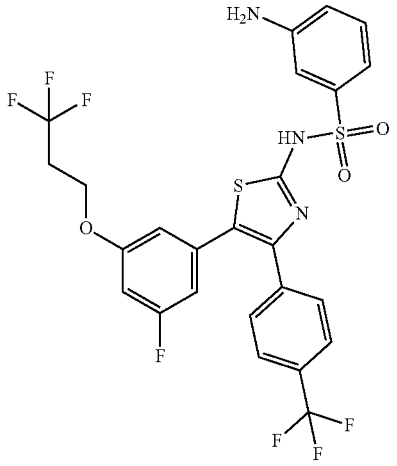 [SMILES: Nc1cccc(S(=O)(=O)Nc2nc(-c3ccc(C(F)(F)F)cc3)c(-c3cc(F)cc(OCCC(F)(F)F)c3)s2)c1] | 3-amino-N-[5-[3-fluoro-5-(3,3,3-trifluoropropoxy)phenyl]-4-[4-(trifluoromethyl)phenyl]-1,3-thiazol-2-yl]benzenesulfonamide |
| 311 | 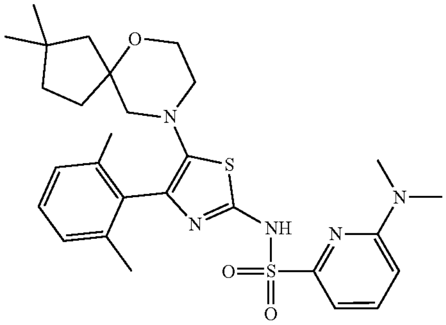 | 6-(dimethylamino)-N-[5-(3,3-dimethyl-6-oxa-9-azaspiro[4.5]decan-9-yl)-4-(2,6-dimethylphenyl)-1,3-thiazol-2-yl]pyridine-2-sulfonamide |
| 1 | 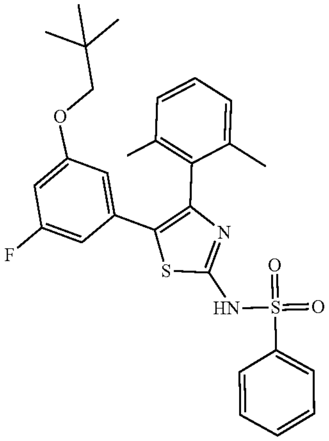 [SMILES: Cc1cccc(C)c1-c1nc(NS(=O)(=O)c2ccccc2)sc1-c1cc(F)cc(OCC(C)(C)C)c1] | N-(4-(2,6-dimethylphenyl)-5-(3-fluoro-5-(neopentyloxy)phenyl)thiazol-2-yl)benzenesulfonamide |

TABLE 1-continued

| Compound Number | Compound Structural Formula | Compound Name |
|---|---|---|
| 179 | 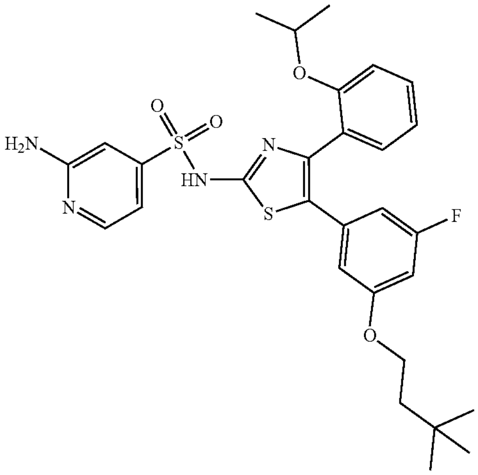 [SMILES: CC(C)Oc1ccccc1-c1nc(NS(=O)(=O)c2ccnc(N)c2)sc1-c1cc(F)cc(OCCC(C)(C)C)c1] | 2-amino-N-[5-[3-(3,3-dimethylbutoxy)-5-fluorophenyl]-4-(2-propan-2-yloxyphenyl)-1,3-thiazol-2-yl]pyridine-4-sulfonamide |
| 32 | 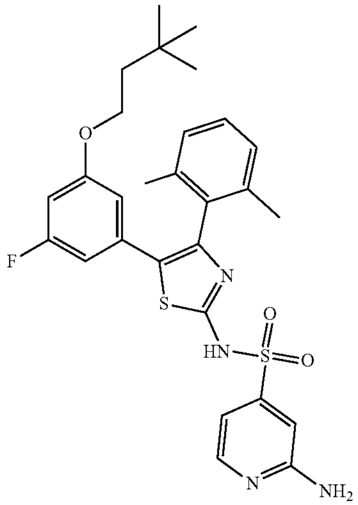 [SMILES: Cc1cccc(C)c1-c1nc(NS(=O)(=O)c2ccnc(N)c2)sc1-c1cc(F)cc(OCCC(C)(C)C)c1] | 2-amino-N-[5-[3-(3,3-dimethylbutoxy)-5-fluorophenyl]-4-(2,6-dimethylphenyl)-1,3-thiazol-2-yl]pyridine-4-sulfonamide |
| 431 | 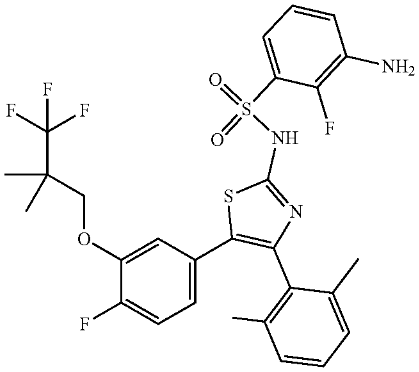 [SMILES: Cc1cccc(C)c1-c1nc(NS(=O)(=O)c2cccc(N)c2F)sc1-c1ccc(F)c(OCC(C)(C)C(F)(F)F)c1] | 3-amino-N-[4-(2,6-dimethylphenyl)-5-[4-fluoro-3-(3,3,3-trifluoro-2,2-dimethylpropoxy)phenyl]-1,3-thiazol-2-yl]-2-fluorobenzenesulfonamide |

TABLE 1-continued

| Compound Number | Compound Structural Formula | Compound Name |
|---|---|---|
| 474 | 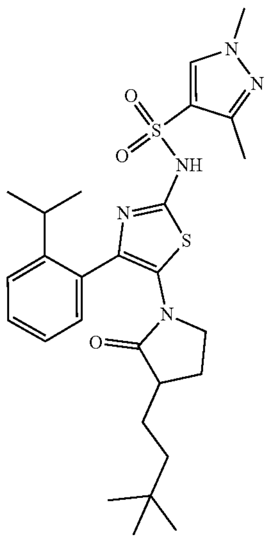 [SMILES: Cc1nn(C)cc1S(=O)(=O)Nc1nc(-c2ccccc2C(C)C)c(N2CCC(CCC(C)(C)C)C2=O)s1] | N-[5-[3-(3,3-dimethylbutyl)-2-oxopyrrolidin-1-yl]-4-(2-propan-2-ylphenyl)-1,3-thiazol-2-yl]-1,3-dimethylpyrazole-4-sulfonamide |
| 385 | 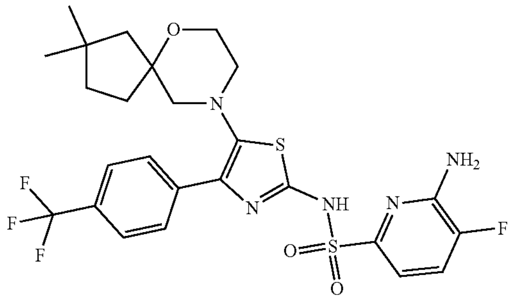 [SMILES: CC1(C)CCC2(CN(c3sc(NS(=O)(=O)c4ccc(F)c(N)n4)nc3-c3ccc(C(F)(F)F)cc3)CCO2)C1] | 6-amino-N-[5-(3,3-dimethyl-6-oxa-9-azaspiro[4.5]decan-9-yl)-4-[4-(trifluoromethyl)phenyl]-1,3-thiazol-2-yl]-5-fluoropyridine-2-sulfonamide |
| 54 | 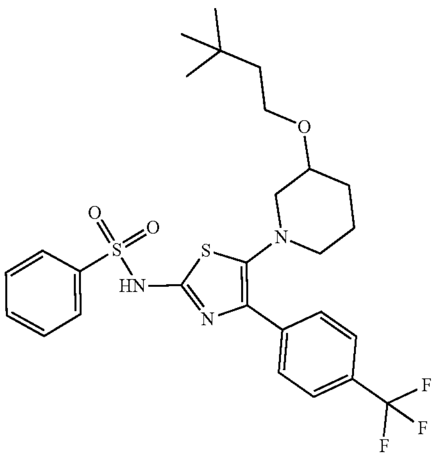 [SMILES: CC(C)(C)CCOC1CCCN(c2sc(NS(=O)(=O)c3ccccc3)nc2-c2ccc(C(F)(F)F)cc2)C1] | N-[5-[3-(3,3-dimethylbutoxy)piperidin-1-yl]-4-[4-(trifluoromethyl)phenyl]-1,3-thiazol-2-yl]benzenesulfonamide |

TABLE 1-continued
| Compound Number | Compound Structural Formula | Compound Name |
|---|---|---|
| 103 | 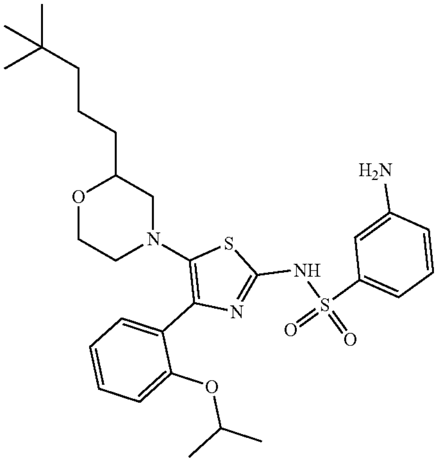 [SMILES: CC(C)Oc1ccccc1-c1nc(NS(=O)(=O)c2cccc(N)c2)sc1N1CCOC(CCCC(C)(C)C)C1] | 3-amino-N-[5-[2-(4,4-dimethylpentyl)morpholin-4-yl]-4-(2-propan-2-yloxyphenyl)-1,3-thiazol-2-yl]benzenesulfonamide |
| 367 | 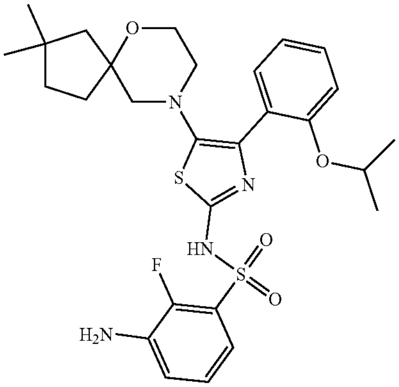 [SMILES: CC(C)Oc1ccccc1-c1nc(NS(=O)(=O)c2cccc(N)c2F)sc1N1CCOC2(CCC(C)(C)C2)C1] | 3-amino-N-[5-(3,3-dimethyl-6-oxa-9-azaspiro[4.5]decan-9-yl)-4-(2-propan-2-yloxyphenyl)-1,3-thiazol-2-yl]-2-fluorobenzenesulfonamide |
| 419 | 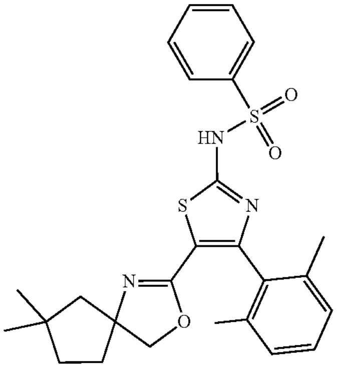 [SMILES: Cc1cccc(C)c1-c1nc(NS(=O)(=O)c2ccccc2)sc1C1=NC2(CCC(C)(C)C2)CO1] | N-[5-(8,8-dimethyl-3-oxa-1-azaspiro[4.4]non-1-en-2-yl)-4-(2,6-dimethylphenyl)-1,3-thiazol-2-yl]benzenesulfonamide |

In some embodiments, the compound of formula (I) is selected from the following compounds represented in Table 2 below:

TABLE 2

| Compound Number | Compound Structural Formula | Compound Name |
|---|---|---|
| 16 | 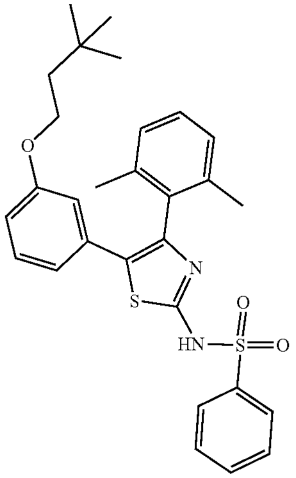 [SMILES: Cc1cccc(C)c1-c1nc(NS(=O)(=O)c2ccccc2)sc1-c1cccc(OCCC(C)(C)C)c1] | N-[5-[3-(3,3-dimethylbutoxy)phenyl]-4-(2,6-dimethylphenyl)-1,3-thiazol-2-yl]benzenesulfonamide |
| 30 | 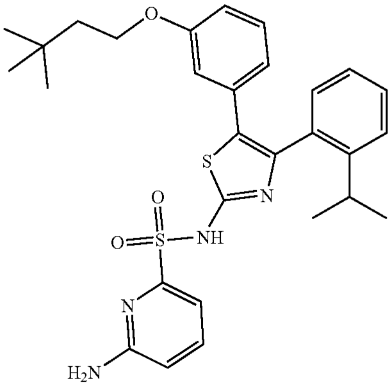 [SMILES: CC(C)c1ccccc1-c1nc(NS(=O)(=O)c2cccc(N)n2)sc1-c1cccc(OCCC(C)(C)C)c1] | 6-amino-N-[5-[3-(3,3-dimethylbutoxy)phenyl]-4-(2-propan-2-ylphenyl)-1,3-thiazol-2-yl]pyridine-2-sulfonamide |
| 242 | 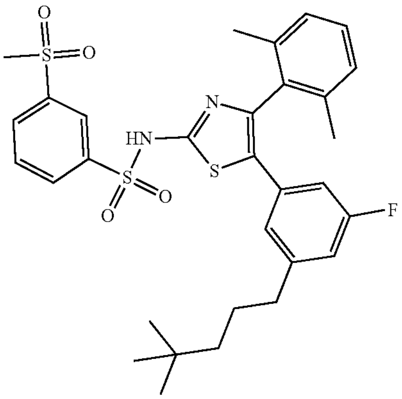 [SMILES: Cc1cccc(C)c1-c1nc(NS(=O)(=O)c2cccc(S(C)(=O)=O)c2)sc1-c1cc(F)cc(CCCC(C)(C)C)c1] | N-[5-[3-(3,3-dimethylbutoxy)-5-fluorophenyl]-4-(2,6-dimethylphenyl)-1,3-thiazol-2-yl]-3-methylsulfonylbenzenesulfonamide |

TABLE 2-continued
| Compound Number | Compound Structural Formula | Compound Name |
|---|---|---|
| 40 | 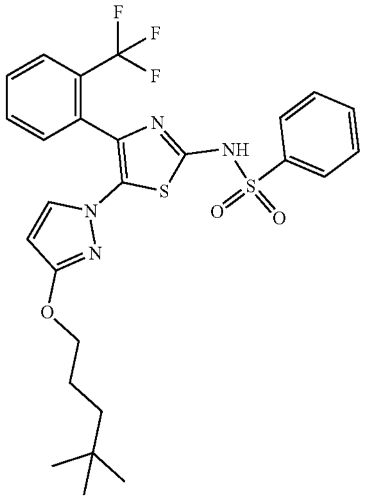 [SMILES: CC(C)(C)CCCOc1ccn(-c2sc(NS(=O)(=O)c3ccccc3)nc2-c2ccccc2C(F)(F)F)n1] | N-[5-[3-(4,4-dimethylpentoxy)pyrazol-1-yl]-4-[2-(trifluoromethyl)phenyl]-1,3-thiazol-2-yl]benzenesulfonamide |
| 25 | 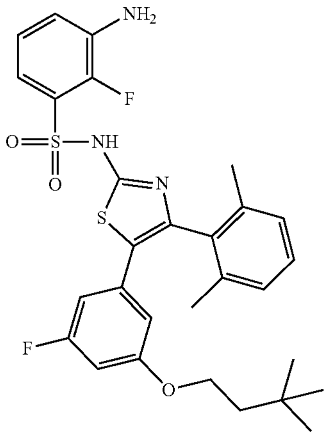 [SMILES: Cc1cccc(C)c1-c1nc(NS(=O)(=O)c2cccc(N)c2F)sc1-c1cc(F)cc(OCCC(C)(C)C)c1] | 3-amino-N-[5-[3-(3,3-dimethylbutoxy)-5-fluorophenyl]-4-(2,6-dimethylphenyl)-1,3-thiazol-2-yl]-2-fluorobenzenesulfonamide |
| 342 | 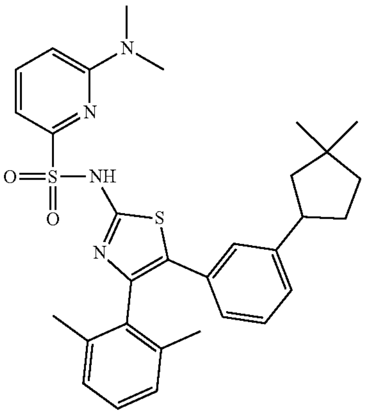 [SMILES: Cc1cccc(C)c1-c1nc(NS(=O)(=O)c2cccc(N(C)C)n2)sc1-c1cccc(C2CCC(C)(C)C2)c1] | 6-(dimethylamino)-N-[5-[3-(3,3-dimethylcyclopentyl)phenyl]-4-(2,6-dimethylphenyl)-1,3-thiazol-2-yl]pyridine-2-sulfonamide |

TABLE 2-continued

| Compound Number | Compound Structural Formula | Compound Name |
|---|---|---|
| 2 | 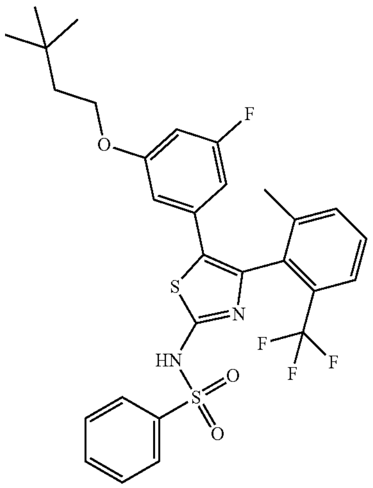 [SMILES: Cc1cccc(C(F)(F)F)c1-c1nc(NS(=O)(=O)c2ccccc2)sc1-c1cc(F)cc(OCCC(C)(C)C)c1] | N-(5-(3-(3,3-dimethylbutoxy)-5-fluorophenyl)-4-(2-methyl-6-(trifluoromethyl)phenyl)thiazol-2-yl)benzenesulfonamide |
| 37 | 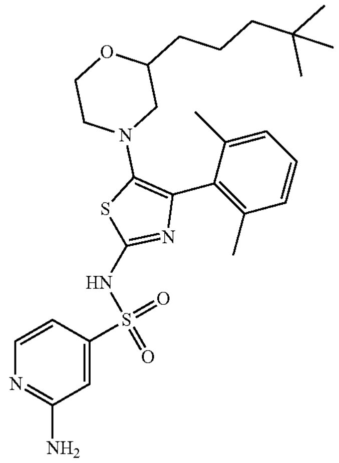 [SMILES: Cc1cccc(C)c1-c1nc(NS(=O)(=O)c2ccnc(N)c2)sc1N1CCOC(CCCC(C)(C)C)C1] | 2-amino-N-[5-[2-(4,4-dimethylpentyl)morpholin-4-yl]-4-(2,6-dimethylphenyl)-1,3-thiazol-2-yl]pyridine-4-sulfonamide |
| 389 | 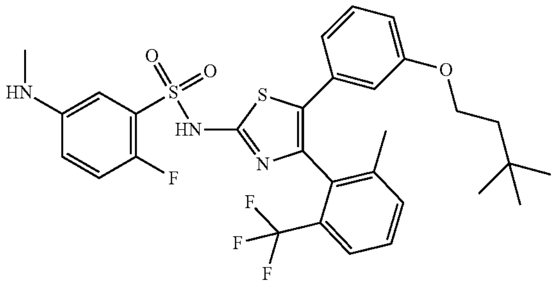 [SMILES: CNc1ccc(F)c(S(=O)(=O)Nc2nc(-c3c(C)cccc3C(F)(F)F)c(-c3cccc(OCCC(C)(C)C)c3)s2)c1] | N-[5-[3-(3,3-dimethylbutoxy)phenyl]-4-[2-methyl-6-(trifluoromethyl)phenyl]-1,3-thiazol-2-yl]-2-fluoro-5-(methylamino)benzenesulfonamide |

TABLE 2-continued
| Compound Number | Compound Structural Formula | Compound Name |
|---|---|---|
| 27 | 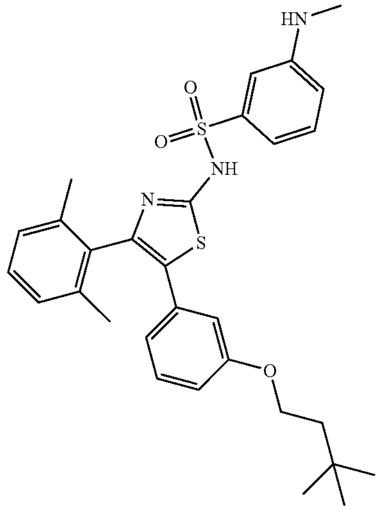 [SMILES: CNc1cccc(S(=O)(=O)Nc2nc(-c3c(C)cccc3C)c(-c3cccc(OCCC(C)(C)C)c3)s2)c1] | N-[5-[3-(3,3-dimethylbutoxy)phenyl]-4-(2,6-dimethylphenyl)-1,3-thiazol-2-yl]-3-(methylamino)benzenesulfonamide |
| 11 | 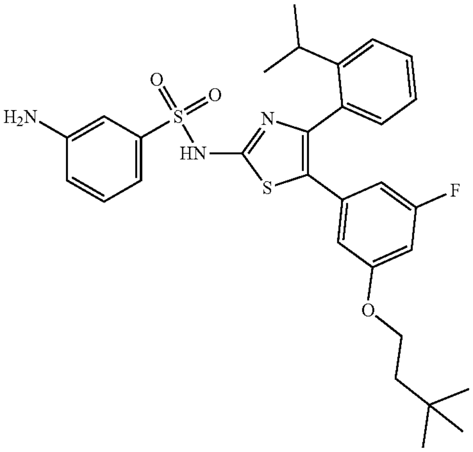 [SMILES: CC(C)c1ccccc1-c1nc(NS(=O)(=O)c2cccc(N)c2)sc1-c1cc(F)cc(OCCC(C)(C)C)c1] | 3-amino-N-[5-[3-(3,3-dimethylbutoxy)-5-fluorophenyl]-4-(2-propan-2-ylphenyl)-1,3-thiazol-2-yl]benzenesulfonamide |
| 490 | 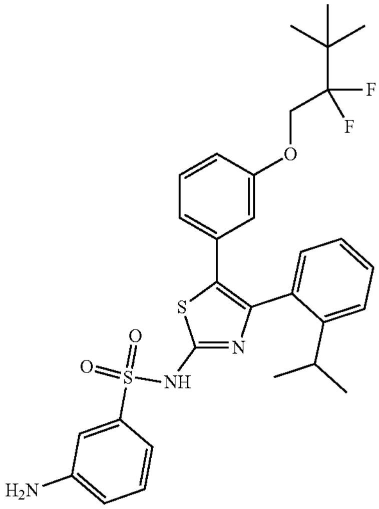 [SMILES: CC(C)c1ccccc1-c1nc(NS(=O)(=O)c2cccc(N)c2)sc1-c1cccc(OCC(F)(F)C(C)(C)C)c1] | 3-amino-N-[5-[3-(2,2-difluoro-3,3-dimethylbutoxy)phenyl]-4-(2-propan-2-ylphenyl)-1,3-thiazol-2-yl]benzenesulfonamide |

TABLE 2-continued

| Compound Number | Compound Structural Formula | Compound Name |
| --- | --- | --- |
| 259 | 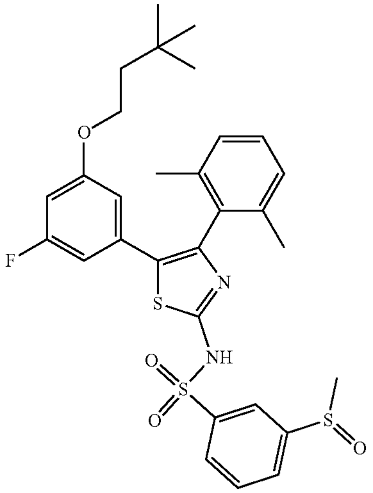 [SMILES: Cc1cccc(C)c1-c1nc(NS(=O)(=O)c2cccc(S(C)=O)c2)sc1-c1cc(F)cc(OCCC(C)(C)C)c1] | N-[5-[3-(3,3-dimethylbutoxy)-5-fluorophenyl]-4-(2,6-dimethylphenyl)-1,3-thiazol-2-yl]-3-methylsulfinylbenzenesulfonamide |
| 22 | 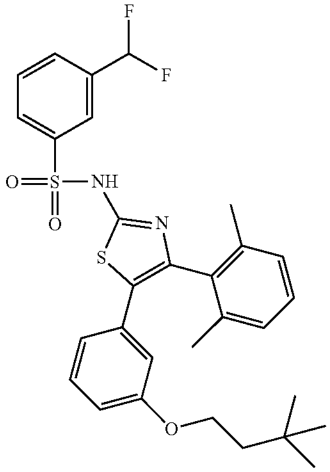 [SMILES: Cc1cccc(C)c1-c1nc(NS(=O)(=O)c2cccc(C(F)F)c2)sc1-c1cccc(OCCC(C)(C)C)c1] | 3-(difluoromethyl)-N-[5-[3-(3,3-dimethylbutoxy)phenyl]-4-(2,6-dimethylphenyl)-1,3-thiazol-2-yl]benzenesulfonamide |
| 46B1 | 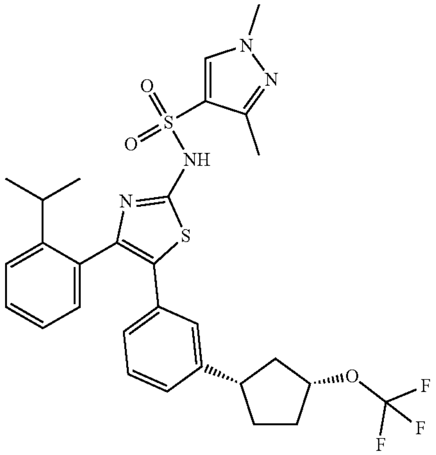 [SMILES: Cc1nn(C)cc1S(=O)(=O)Nc1nc(-c2ccccc2C(C)C)c(-c2cccc([C@H]3CC[C@@H](OC(F)(F)F)C3)c2)s1] | 1,3-dimethyl-N-[4-(2-propan-2-ylphenyl)-5-[3-[(1S,3R)-3-(trifluoromethoxy)cyclopentyl]phenyl]-1,3-thiazol-2-yl]pyrazole-4-sulfonamide |

TABLE 2-continued

| Compound Number | Compound Structural Formula | Compound Name |
|---|---|---|
| 7 | 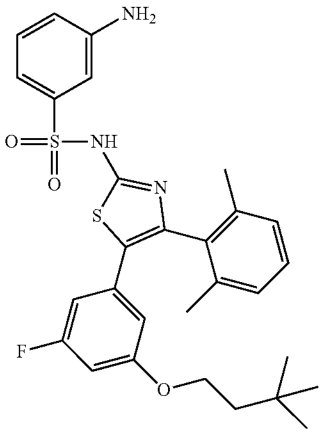 [SMILES: Cc1cccc(C)c1-c1nc(NS(=O)(=O)c2cccc(N)c2)sc1-c1cc(F)cc(OCCC(C)(C)C)c1] | 3-amino-N-(5-(3-(3,3-dimethylbutoxy)-5-fluorophenyl)-4-(2,6-dimethylphenyl)thiazol-2-yl)benzenesulfonamide |
| 13 | 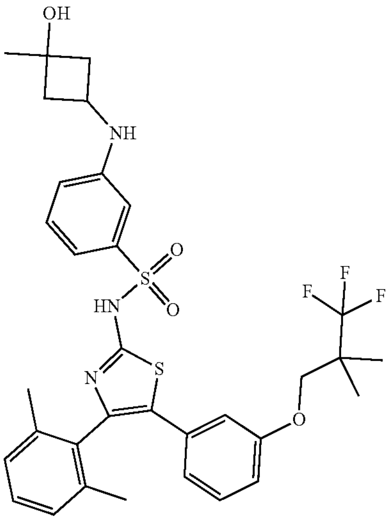 [SMILES: Cc1cccc(C)c1-c1nc(NS(=O)(=O)c2cccc(NC3CC(C)(O)C3)c2)sc1-c1cccc(OCC(C)(C)C(F)(F)F)c1] | N-[4-(2,6-dimethylphenyl)-5-[3-(3,3,3-trifluoro-2,2-dimethylpropoxy)phenyl]-1,3-thiazol-2-yl]-3-[(3-hydroxy-3-methylcyclobutyl)amino]benzenesulfonamide |
| 17 | 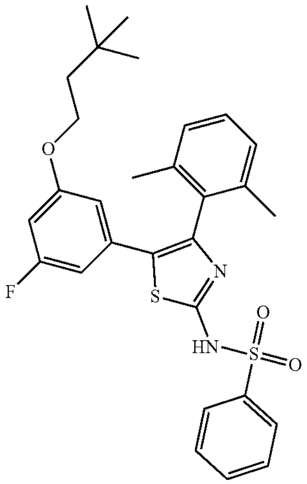 [SMILES: Cc1cccc(C)c1-c1nc(NS(=O)(=O)c2ccccc2)sc1-c1cc(F)cc(OCCC(C)(C)C)c1] | N-[5-[3-(3,3-dimethylbutoxy)-5-fluorophenyl]-4-(2,6-dimethylphenyl)-1,3-thiazol-2-yl]benzenesulfonamide |

TABLE 2-continued

| Compound Number | Compound Structural Formula | Compound Name |
|---|---|---|
| 382 | 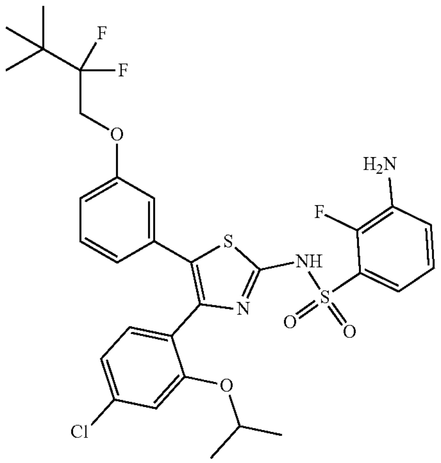 [SMILES: CC(C)Oc1cc(Cl)ccc1-c1nc(NS(=O)(=O)c2cccc(N)c2F)sc1-c1cccc(OCC(F)(F)C(C)(C)C)c1] | 6-amino-N-[5-[1-(3,3-dimethylbutyl)pyrazol-3-yl]-4-(2-propan-2-yloxyphenyl)-1,3-thiazol-2-yl]pyridine-2-sulfonamide |
| 4 | 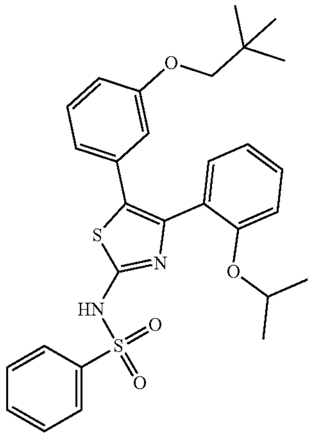 [SMILES: CC(C)Oc1ccccc1-c1nc(NS(=O)(=O)c2ccccc2)sc1-c1cccc(OCC(C)(C)C)c1] | N-(4-(2-isopropoxyphenyl)-5-(3-(neopentyloxy)phenyl)thiazol-2-yl)benzenesulfonamide |
| 48B2 | 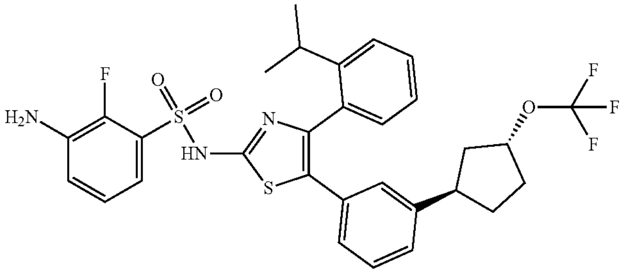 [SMILES: CC(C)c1ccccc1-c1nc(NS(=O)(=O)c2cccc(N)c2F)sc1-c1cccc([C@@H]2CC[C@@H](OC(F)(F)F)C2)c1] | 3-amino-2-fluoro-N-[4-(2-propan-2-ylphenyl)-5-[3-[(1R,3R)-3-(trifluoromethoxy)cyclopentyl]phenyl]-1,3-thiazol-2-yl]benzenesulfonamide |
| 334 | 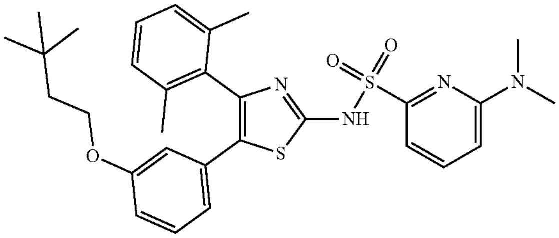 [SMILES: Cc1cccc(C)c1-c1nc(NS(=O)(=O)c2cccc(N(C)C)n2)sc1-c1cccc(OCCC(C)(C)C)c1] | 6-(dimethylamino)-N-[5-[3-(3,3-dimethylbutoxy)phenyl]-4-(2,6-dimethylphenyl)-1,3-thiazol-2-yl]pyridine-2-sulfonamide |

TABLE 2-continued
| Compound Number | Compound Structural Formula | Compound Name |
|---|---|---|
| 358 | 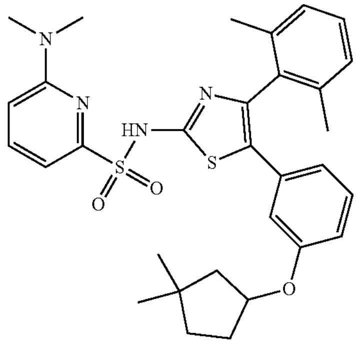 [SMILES: Cc1cccc(C)c1-c1nc(NS(=O)(=O)c2cccc(N(C)C)n2)sc1-c1cccc(OC2CCC(C)(C)C2)c1] | 6-(dimethylamino)-N-[5-[3-(3,3-dimethylcyclopentyl)oxyphenyl]-4-(2,6-dimethylphenyl)-1,3-thiazol-2-yl]pyridine-2-sulfonamide |
| 8 | 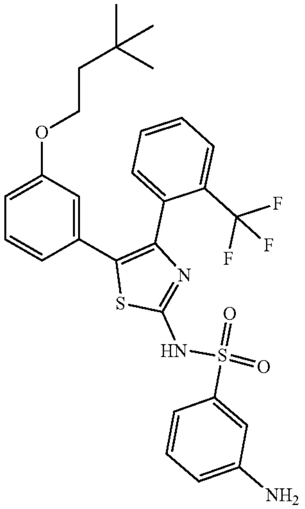 [SMILES: CC(C)(C)CCOc1cccc(-c2sc(NS(=O)(=O)c3cccc(N)c3)nc2-c2ccccc2C(F)(F)F)c1] | 3-amino-N-(5-(3-(3,3-dimethylbutoxy)phenyl)-4-(2-(trifluoromethyl)phenyl)thiazol-2-yl)benzenesulfonamide |
| 31 | 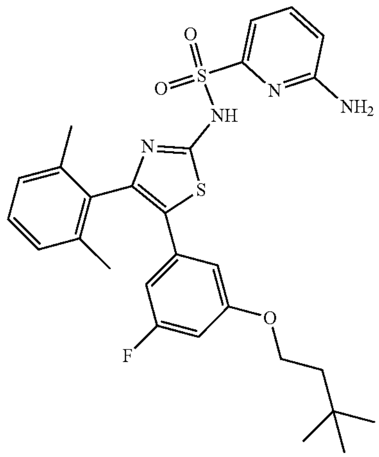 [SMILES: Cc1cccc(C)c1-c1nc(NS(=O)(=O)c2cccc(N)n2)sc1-c1cc(F)cc(OCCC(C)(C)C)c1] | 6-amino-N-[5-[3-(3,3-dimethylbutoxy)-5-fluorophenyl]-4-(2,6-dimethylphenyl)-1,3-thiazol-2-yl]pyridine-2-sulfonamide |

TABLE 2-continued

| Compound Number | Compound Structural Formula | Compound Name |
|---|---|---|
| 402 | 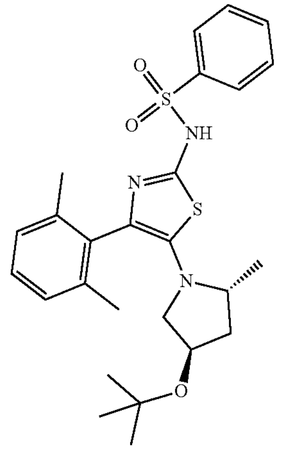 [SMILES: Cc1cccc(C)c1-c1nc(NS(=O)(=O)c2ccccc2)sc1N1C[C@H](OC(C)(C)C)C[C@H]1C] | N-[4-(2,6-dimethylphenyl)-5-[(2R,4R)-2-methyl-4-[(2-methylpropan-2-yl)oxy]pyrrolidin-1-yl]-1,3-thiazol-2-yl]benzenesulfonamide |
| 45A1 | 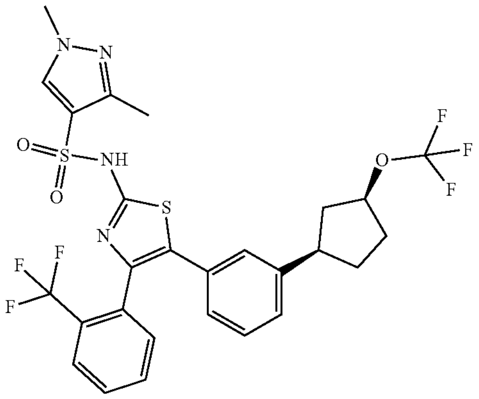 [SMILES: Cc1nn(C)cc1S(=O)(=O)Nc1nc(-c2ccccc2C(F)(F)F)c(-c2cccc([C@@H]3CC[C@H](OC(F)(F)F)C3)c2)s1] | 1,3-dimethyl-N-[5-[3-[(1R, 3S)-3-(trifluoromethoxy)cyclopentyl]phenyl]-4-[2-(trifluoromethyl)phenyl]-1,3-thiazol-2-yl]pyrazole-4-sulfonamide |
| 380 | 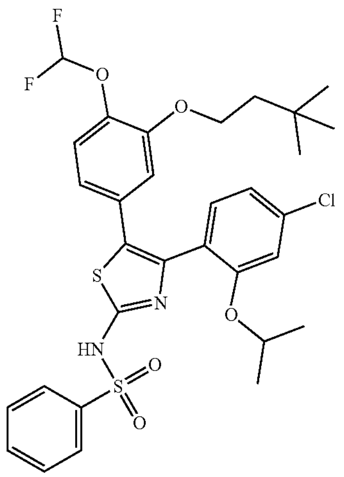 [SMILES: CC(C)Oc1cc(Cl)ccc1-c1nc(NS(=O)(=O)c2ccccc2)sc1-c1ccc(OC(F)F)c(OCCC(C)(C)C)c1] | N-[4-(4-chloro-2-propan-2-yloxyphenyl)-5-[4-(difluoromethoxy)-3-(3,3-dimethylbutoxy)phenyl]-1,3-thiazol-2-yl]benzenesulfonamide |

TABLE 2-continued

| Compound Number | Compound Structural Formula | Compound Name |
|---|---|---|
| 44B1 | 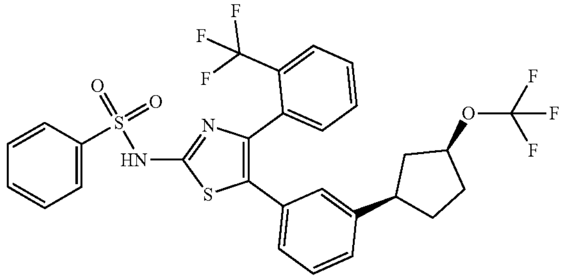 [SMILES: O=S(=O)(Nc1nc(-c2ccccc2C(F)(F)F)c(-c2cccc([C@@H]3CC[C@H](OC(F)(F)F)C3)c2)s1)c1ccccc1] | N-[5-[3-[(1S, 3R)-3-(trifluoromethoxy)cyclopentyl]phenyl]-4-[2-(trifluoromethyl)phenyl]-1,3-thiazol-2-yl]benzenesulfonamide |
| 24 | 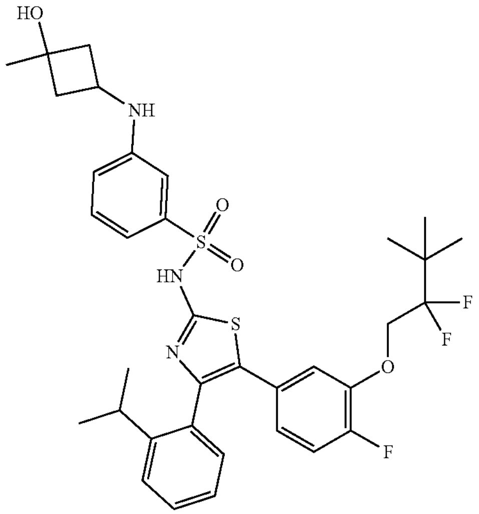 [SMILES: CC(C)c1ccccc1-c1nc(NS(=O)(=O)c2cccc(NC3CC(C)(O)C3)c2)sc1-c1ccc(F)c(OCC(F)(F)C(C)(C)C)c1] | N-[5-[3-(2,2-difluoro-3,3-dimethylbutoxy)-4-fluorophenyl]-4-(2-propan-2-ylphenyl)-1,3-thiazol-2-yl]-3-[(3-hydroxy-3-methylcyclobutyl)amino]benzenesulfonamide |
| 576 | 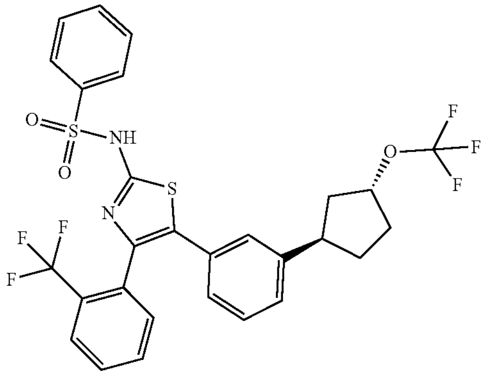 [SMILES: O=S(=O)(Nc1nc(-c2ccccc2C(F)(F)F)c(-c2cccc([C@@H]3CC[C@@H](OC(F)(F)F)C3)c2)s1)c1ccccc1] | N-(5-(3-((1R,3R)-3-(trifluoromethoxy)cyclopentyl)phenyl)-4-(2-(trifluoromethyl)phenyl)thiazol-2-yl)benzenesulfonamide |
| 349 | 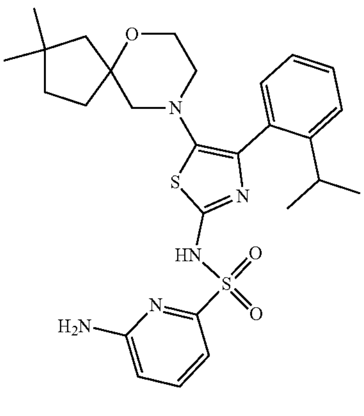 [SMILES: CC(C)c1ccccc1-c1nc(NS(=O)(=O)c2cccc(N)n2)sc1N1CCOC2(CCC(C)(C)C2)C1] | 6-amino-N-[5-(3,3-dimethyl-6-oxa-9-azaspiro[4.5]decan-9-yl)-4-(2-propan-2-ylphenyl)-1,3-thiazol-2-yl]pyridine-2-sulfonamide |

TABLE 2-continued

| Compound Number | Compound Structural Formula | Compound Name |
|---|---|---|
| 491 | 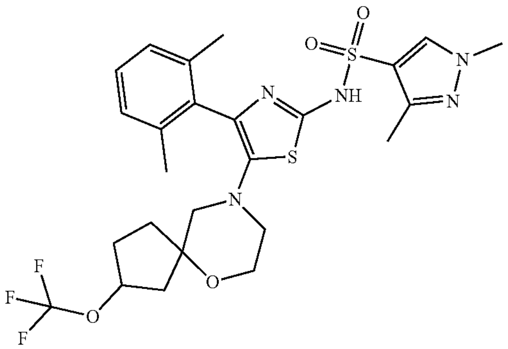 [SMILES: Cc1cccc(C)c1-c1nc(NS(=O)(=O)c2cn(C)nc2C)sc1N1CCOC2(CCC(OC(F)(F)F)C2)C1] | N-[4-(2,6-dimethylphenyl)-5-[3-(trifluoromethoxy)-6-oxa-9-azaspiro[4.5]decan-9-yl]-1,3-thiazol-2-yl]-1,3-dimethylpyrazole-4-sulfonamide |
| 23 | 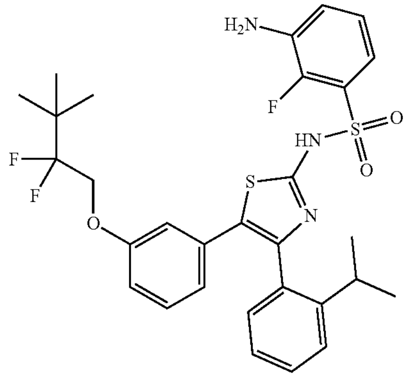 [SMILES: CC(C)c1ccccc1-c1nc(NS(=O)(=O)c2cccc(N)c2F)sc1-c1cccc(OCC(F)(F)C(C)(C)C)c1] | 3-amino-N-[5-[3-(2,2-difluoro-3,3-dimethylbutoxy)phenyl]-4-(2-propan-2-ylphenyl)-1,3-thiazol-2-yl]-2-fluorobenzenesulfonamide |
| 15 | 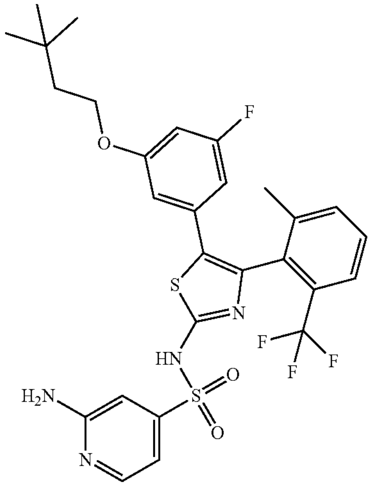 [SMILES: Cc1cccc(C(F)(F)F)c1-c1nc(NS(=O)(=O)c2ccnc(N)c2)sc1-c1cc(F)cc(OCCC(C)(C)C)c1] | 2-amino-N-[5-[3-(3,3-dimethylbutoxy)-5-fluorophenyl]-4-[2-methyl-6-(trifluoromethyl)phenyl]-1,3-thiazol-2-yl]pyridine-4-sulfonamide |

TABLE 2-continued
| Compound Number | Compound Structural Formula | Compound Name |
|---|---|---|
| 9 | 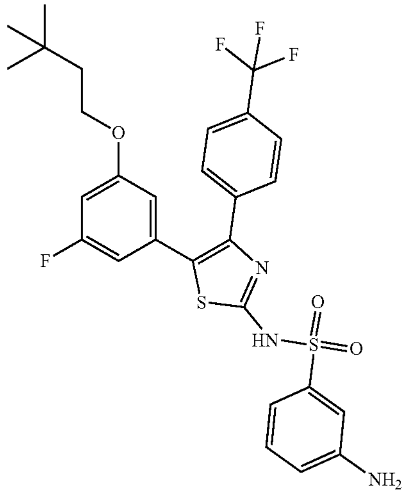 [SMILES: CC(C)(C)CCOc1cc(F)cc(-c2sc(NS(=O)(=O)c3cccc(N)c3)nc2-c2ccc(C(F)(F)F)cc2)c1] | 3-amino-N-(5-(3-(3,3-dimethylbutoxy)-5-fluorophenyl)-4-(4-(trifluoromethyl)phenyl)thiazol-2-yl)benzenesulfonamide |
| 3 | 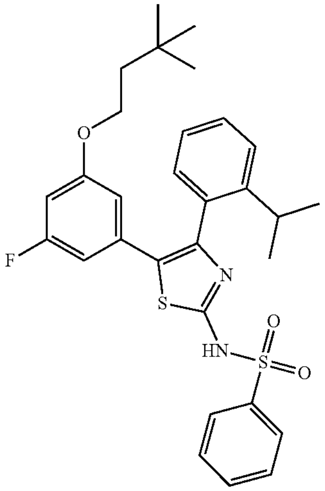 [SMILES: CC(C)c1ccccc1-c1nc(NS(=O)(=O)c2ccccc2)sc1-c1cc(F)cc(OCCC(C)(C)C)c1] | N-(5-(3-(3,3-dimethylbutoxy)-5-fluorophenyl)-4-(2-isopropylphenyl)thiazol-2-yl)benzenesulfonamide |
| 33 | 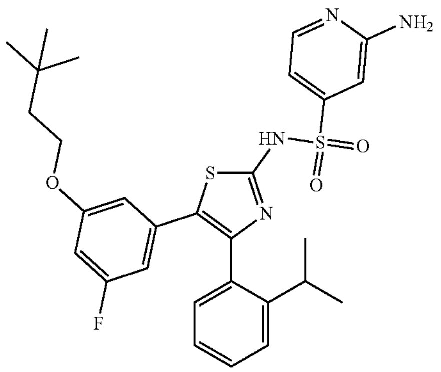 [SMILES: CC(C)c1ccccc1-c1nc(NS(=O)(=O)c2ccnc(N)c2)sc1-c1cc(F)cc(OCCC(C)(C)C)c1] | 2-amino-N-[5-[3-(3,3-dimethylbutoxy)-5-fluorophenyl]-4-(2-propan-2-ylphenyl)-1,3-thiazol-2-yl]pyridine-4-sulfonamide |

TABLE 2-continued

| Compound Number | Compound Structural Formula | Compound Name |
| --- | --- | --- |
| 34 | 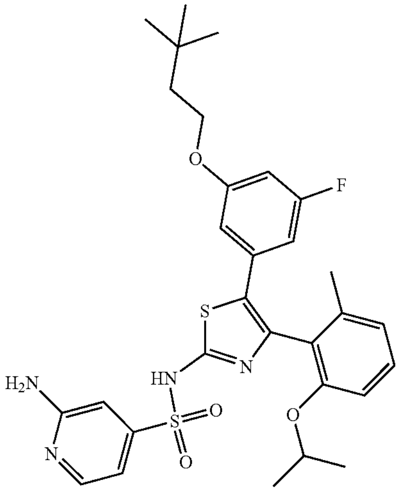 [SMILES: Cc1cccc(OC(C)C)c1-c1nc(NS(=O)(=O)c2ccnc(N)c2)sc1-c1cc(F)cc(OCCC(C)(C)C)c1] | 2-amino-N-[5-[3-(3,3-dimethylbutoxy)-5-fluorophenyl]-4-(2-methyl-6-propan-2-yloxyphenyl)-1,3-thiazol-2-yl]pyridine-4-sulfonamide |
| 26 | 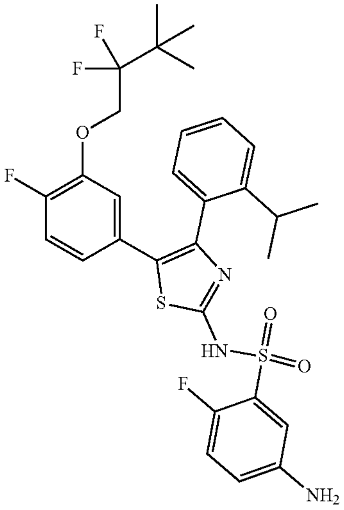 [SMILES: CC(C)c1ccccc1-c1nc(NS(=O)(=O)c2cc(N)ccc2F)sc1-c1ccc(F)c(OCC(F)(F)C(C)(C)C)c1] | 5-amino-N-[5-[3-(2,2-difluoro-3,3-dimethylbutoxy)-4-fluorophenyl]-4-(2-propan-2-ylphenyl)-1,3-thiazol-2-yl]-2-fluorobenzenesulfonamide |
| 495 | 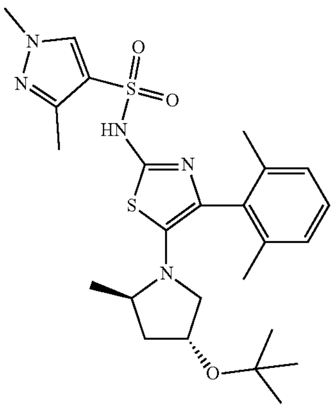 [SMILES: Cc1cccc(C)c1-c1nc(NS(=O)(=O)c2cn(C)nc2C)sc1N1C[C@H](OC(C)(C)C)C[C@H]1C] | N-[4-(2,6-dimethylphenyl)-5-[(2R,4R)-2-methyl-4-[(2-methylpropan-2-yl)oxy]pyrrolidin-1-yl]-1,3-thiazol-2-yl]-1,3-dimethylpyrazole-4-sulfonamide |

TABLE 2-continued

| Compound Number | Compound Structural Formula | Compound Name |
| --- | --- | --- |
| 362 | 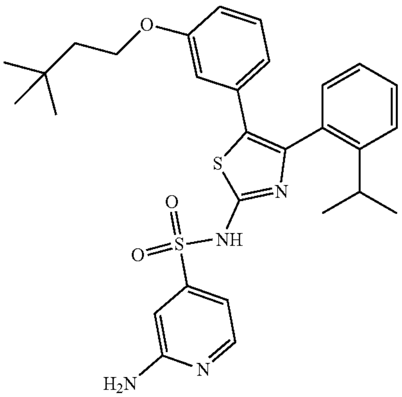 [SMILES: CC(C)c1ccccc1-c1nc(NS(=O)(=O)c2ccnc(N)c2)sc1-c1cccc(OCCC(C)(C)C)c1] | 2-amino-N-[5-[3-(3,3-dimethylbutoxy)phenyl]-4-(2-propan-2-ylphenyl)-1,3-thiazol-2-yl]pyridine-4-sulfonamide |
| 370 | 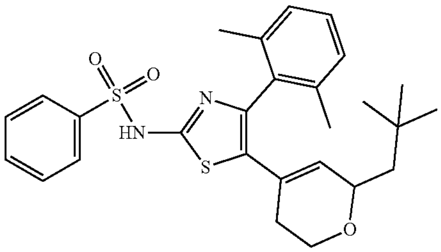 [SMILES: Cc1cccc(C)c1-c1nc(NS(=O)(=O)c2ccccc2)sc1C1=CC(CC(C)(C)C)OCC1] | N-[4-(2,6-dimethylphenyl)-5-[6-(2,2-dimethylpropyl)-3,6-dihydro-2H-pyran-4-yl]-1,3-thiazol-2-yl]benzenesulfonamide |
| 14 | 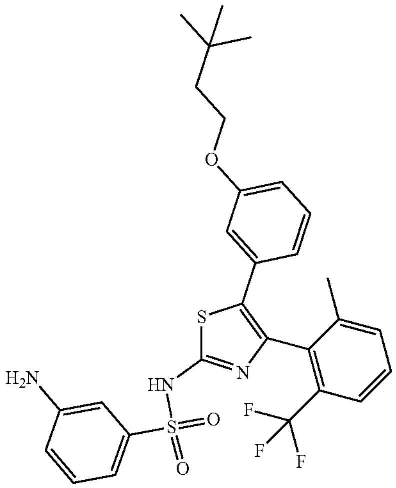 [SMILES: Cc1cccc(C(F)(F)F)c1-c1nc(NS(=O)(=O)c2cccc(N)c2)sc1-c1cccc(OCCC(C)(C)C)c1] | 3-amino-N-[5-[3-(3,3-dimethylbutoxy)phenyl]-4-[2-methyl-6-(trifluoromethyl)phenyl]-1,3-thiazol-2-yl]benzenesulfonamide |
| 329 | 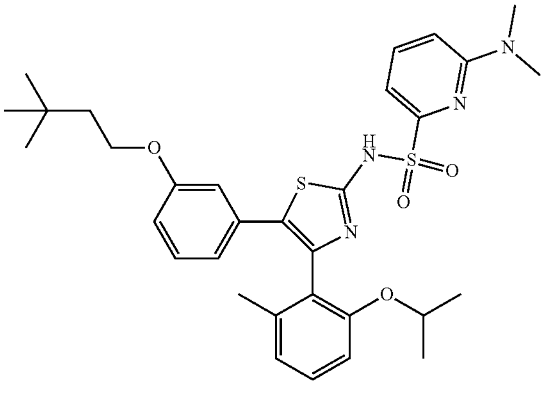 [SMILES: Cc1cccc(OC(C)C)c1-c1nc(NS(=O)(=O)c2cccc(N(C)C)n2)sc1-c1cccc(OCCC(C)(C)C)c1] | 6-(dimethylamino)-N-[5-[3-(3,3-dimethylbutoxy)phenyl]-4-(2-methyl-6-propan-2-yloxyphenyl)-1,3-thiazol-2-yl]pyridine-2-sulfonamide |

TABLE 2-continued

| Compound Number | Compound Structural Formula | Compound Name |
|---|---|---|
| 312 | 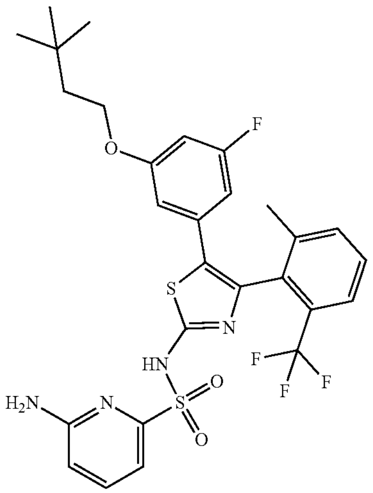 [SMILES: Cc1cccc(C(F)(F)F)c1-c1nc(NS(=O)(=O)c2cccc(N)n2)sc1-c1cc(F)cc(OCCC(C)(C)C)c1] | 6-amino-N-[5-[3-(3,3-dimethylbutoxy)-5-fluorophenyl]-4-[2-methyl-6-(trifluoromethyl)phenyl]-1,3-thiazol-2-yl]pyridine-2-sulfonamide |
| 35 | 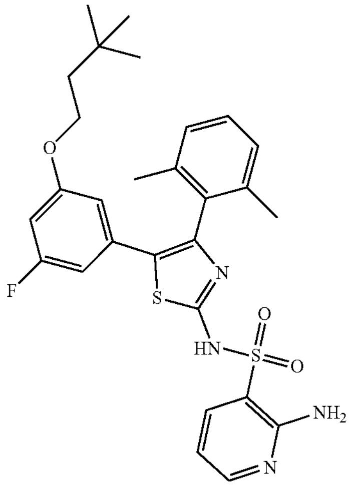 [SMILES: Cc1cccc(C)c1-c1nc(NS(=O)(=O)c2cccnc2N)sc1-c1cc(F)cc(OCCC(C)(C)C)c1] | 2-amino-N-[5-[3-(3,3-dimethylbutoxy)-5-fluorophenyl]-4-(2,6-dimethylphenyl)-1,3-thiazol-2-yl]pyridine-3-sulfonamide |
| 12 | 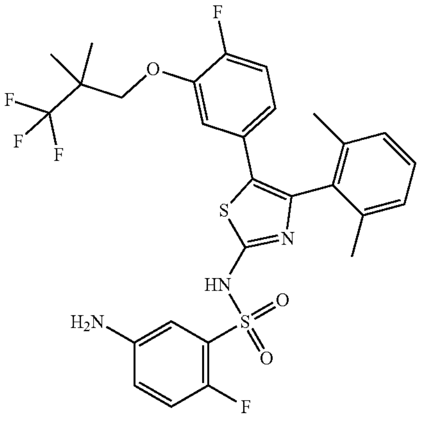 [SMILES: Cc1cccc(C)c1-c1nc(NS(=O)(=O)c2cc(N)ccc2F)sc1-c1ccc(F)c(OCC(C)(C)C(F)(F)F)c1] | 5-amino-N-[4-(2,6-dimethylphenyl)-5-[4-fluoro-3-(3,3,3-trifluoro-2,2-dimethylpropoxy)phenyl]-1,3-thiazol-2-yl]-2-fluorobenzenesulfonamide |

TABLE 2-continued
| Compound Number | Compound Structural Formula | Compound Name |
|---|---|---|
| 18 | 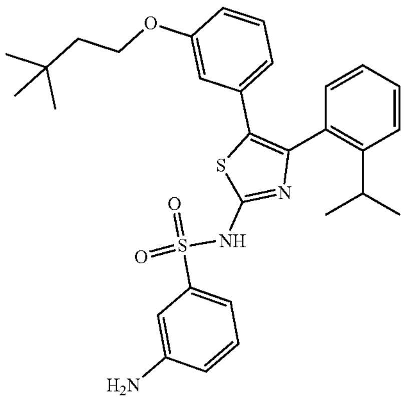 [SMILES: CC(C)c1ccccc1-c1nc(NS(=O)(=O)c2cccc(N)c2)sc1-c1cccc(OCCC(C)(C)C)c1] | 3-amino-N-[5-[3-(3,3-dimethylbutoxy)phenyl]-4-(2-propan-2-ylphenyl)-1,3-thiazol-2-yl]benzenesulfonamide |
| 28 | 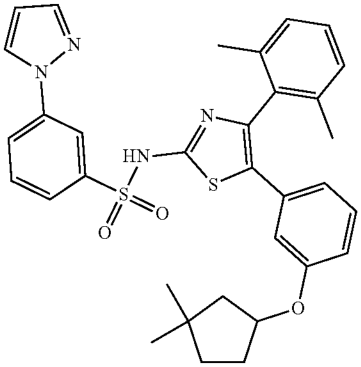 [SMILES: Cc1cccc(C)c1-c1nc(NS(=O)(=O)c2cccc(-n3cccn3)c2)sc1-c1cccc(OC2CCC(C)(C)C2)c1] | N-[5-[3-(3,3-dimethylcyclopentyl)oxyphenyl]-4-(2,6-dimethylphenyl)-1,3-thiazol-2-yl]-3-pyrazol-1-ylbenzenesulfonamide |
| 21 | 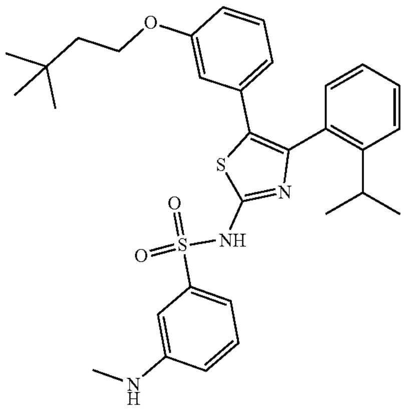 [SMILES: CNc1cccc(S(=O)(=O)Nc2nc(-c3ccccc3C(C)C)c(-c3cccc(OCCC(C)(C)C)c3)s2)c1] | N-[5-[3-(3,3-dimethylbutoxy)phenyl]-4-(2-propan-2-ylphenyl)-1,3-thiazol-2-yl]-3-(methylamino)benzenesulfonamide |

TABLE 2-continued

| Compound Number | Compound Structural Formula | Compound Name |
|---|---|---|
| 240 | 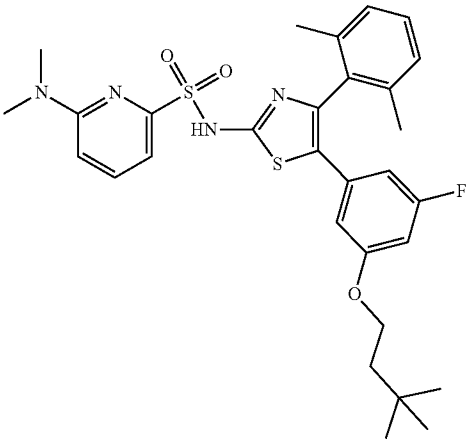 [SMILES: Cc1cccc(C)c1-c1nc(NS(=O)(=O)c2cccc(N(C)C)n2)sc1-c1cc(F)cc(OCCC(C)(C)C)c1] | 6-(dimethylamino)-N-[5-[3-(3,3-dimethylbutoxy)-5-fluorophenyl]-4-(2,6-dimethylphenyl)-1,3-thiazol-2-yl]pyridine-2-sulfonamide |
| 435 | 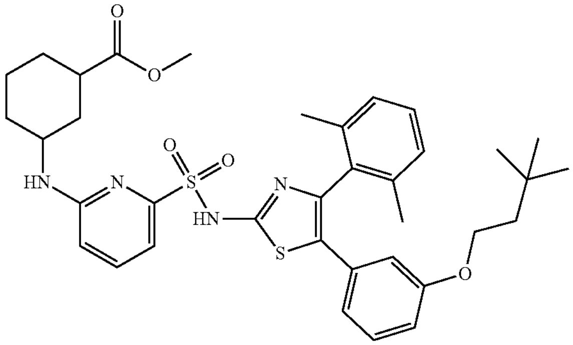 [SMILES: COC(=O)C1CCCC(Nc2cccc(S(=O)(=O)Nc3nc(-c4c(C)cccc4C)c(-c4cccc(OCCC(C)(C)C)c4)s3)n2)C1] | methyl 3-[[6-[[5-[3-(3,3-dimethylbutoxy)phenyl]-4-(2,6-dimethylphenyl)-1,3-thiazol-2-yl]sulfamoyl]pyridin-2-yl]amino]cyclohexane-1-carboxylate |
| 429 | 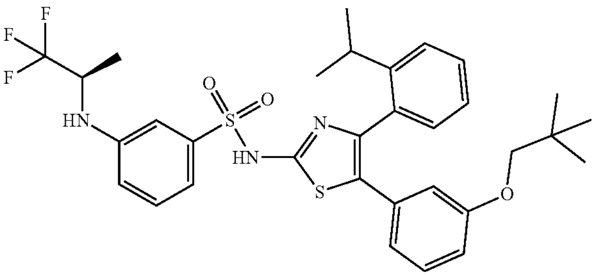 [SMILES: CC(C)c1ccccc1-c1nc(NS(=O)(=O)c2cccc(N[C@H](C)C(F)(F)F)c2)sc1-c1cccc(OCC(C)(C)C)c1] | N-[5-[3-(2,2-dimethylpropoxy)phenyl]-4-(2-propan-2-ylphenyl)-1,3-thiazol-2-yl]-3-[[(2R)-1,1,1-trifluoropropan-2-yl]amino]benzenesulfonamide |
| 44A1 | 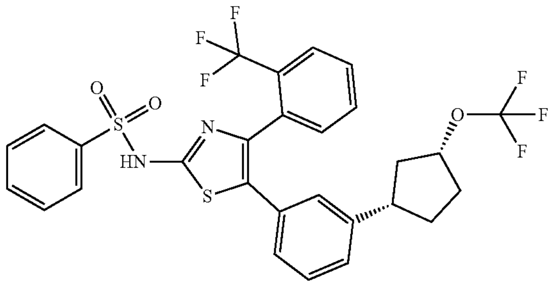 [SMILES: O=S(=O)(Nc1nc(-c2ccccc2C(F)(F)F)c(-c2cccc([C@H]3CC[C@@H](OC(F)(F)F)C3)c2)s1)c1ccccc1] | N-[5-[3-[(1R,3S)-3-(trifluoromethoxy)cyclopentyl]phenyl]-4-[2-(trifluoromethyl)phenyl]-1,3-thiazol-2-yl]benzenesulfonamide |

TABLE 2-continued

| Compound Number | Compound Structural Formula | Compound Name |
| --- | --- | --- |
| 20 | 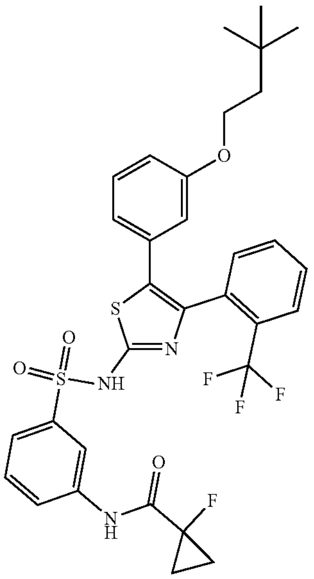 [SMILES: CC(C)(C)CCOc1cccc(-c2sc(NS(=O)(=O)c3cccc(NC(=O)C4(F)CC4)c3)nc2-c2ccccc2C(F)(F)F)c1] | N-[3-[[5-[3-(3,3-dimethylbutoxy)phenyl]-4-[2-(trifluoromethyl)phenyl]-1,3-thiazol-2-yl]sulfamoyl]phenyl]-1-fluorocyclopropane-1-carboxamide |
| 36 | 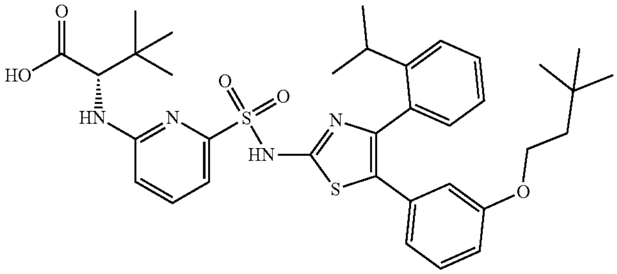 [SMILES: CC(C)c1ccccc1-c1nc(NS(=O)(=O)c2cccc(N[C@H](C(=O)O)C(C)(C)C)n2)sc1-c1cccc(OCCC(C)(C)C)c1] | (2S)-2-[[6-[[5-[3-(3,3-dimethylbutoxy)phenyl]-4-(2-propan-2-ylphenyl)-1,3-thiazol-2-yl]sulfamoyl]pyridin-2-yl]amino]-3,3-dimethylbutanoic acid |
| 471 | 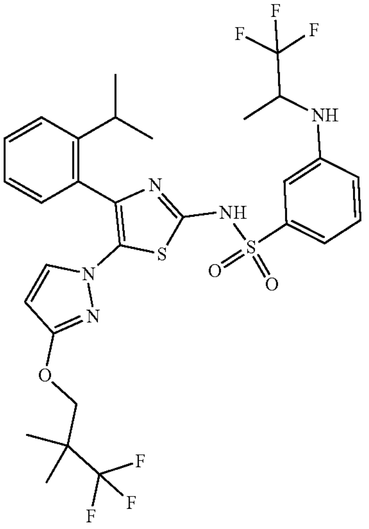 [SMILES: CC(C)c1ccccc1-c1nc(NS(=O)(=O)c2cccc(NC(C)C(F)(F)F)c2)sc1-n1ccc(OCC(C)(C)C(F)(F)F)n1] | N-[4-(2-propan-2-ylphenyl)-5-[3-(3,3,3-trifluoro-2,2-dimethylpropoxy)pyrazol-1-yl]-1,3-thiazol-2-yl]-3-(1,1,1-trifluoropropan-2-ylamino)benzenesulfonamide |

TABLE 2-continued
| Compound Number | Compound Structural Formula | Compound Name |
|---|---|---|
| 10 | 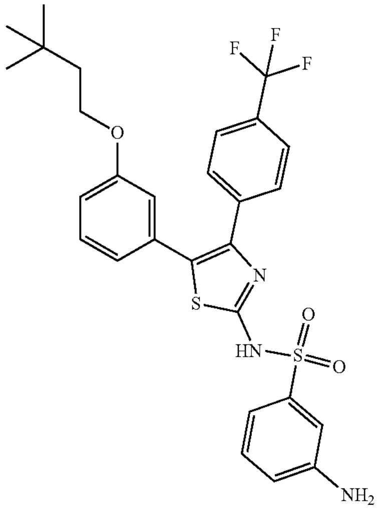 [SMILES: CC(C)(C)CCOc1cccc(-c2sc(NS(=O)(=O)c3cccc(N)c3)nc2-c2ccc(C(F)(F)F)cc2)c1] | 3-amino-N-[5-[3-(3,3-dimethylbutoxy)phenyl]-4-[4-(trifluoromethyl)phenyl]-1,3-thiazol-2-yl]benzenesulfonamide |
| 1 | 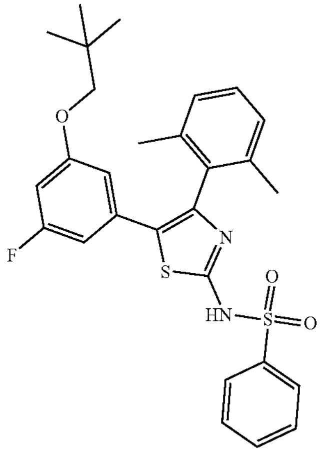 | N-(4-(2,6-dimethylphenyl)-5-(3-fluoro-5-(neopentyloxy)phenyl)thiazol-2-yl)benzenesulfonamide |
| 32 | 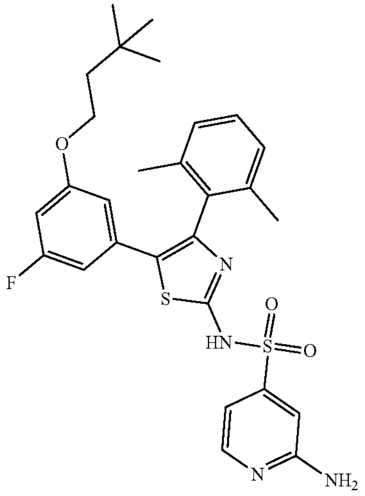 | 2-amino-N-[5-[3-(3,3-dimethylbutoxy)-5-fluorophenyl]-4-(2,6-dimethylphenyl)-1,3-thiazol-2-yl]pyridine-4-sulfonamide |

Definitions

Unless defined otherwise, all technical and scientific terms used herein have the meaning commonly understood by a person skilled in the art of the present disclosure. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Unless specifically stated or obvious from context, as used herein, the term "or" is understood to be inclusive. Unless specifically stated or obvious from context, as used herein, the terms "a", "an", and "the" are understood to be singular or plural.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10, more preferably from 1-6. unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "haloalkyl", as used herein, refers to an alkyl group in which at least one hydrogen has been replaced with a halogen, such as fluoro, chloro, bromo, or iodo. Exemplary haloalkyl groups include trifluoromethyl, difluoromethyl, fluoromethyl, 2-fluoroethyl, 2,2-difluoroethyl, and 2,2,2-trifluoroethyl.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

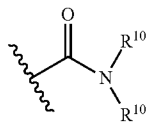

wherein each $R^{10}$ independently represents a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

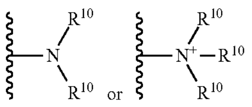

wherein each $R^{10}$ independently represents a hydrogen or a hydrocarbyl group, or two $R^{10}$ are taken together with the N atom to which they are attached complete a heterocycle having from 4 to 8 atoms in the ring structure. The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably, the ring is a 5- to 6-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

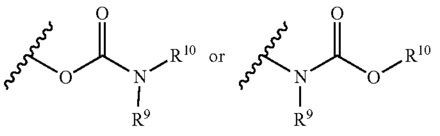

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond.

The term "carbocycle" includes 3-10 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 9 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings.

A "cycloalkenyl" group is a cyclic hydrocarbon containing one or more double bonds. The cycloalkenyl ring may have 3 to 10 carbon atoms. As such, cycloalkenyl groups can be monocyclic or multicyclic. Individual rings of such multicyclic cycloalkenyl groups can have different connectivities, e.g., fused, bridged, spiro, etc. in addition to covalent bond substitution. Exemplary cycloalkenyl groups include cyclopropenyl, cyclobutenyl, cyclopentyl, cyclohexenyl, cycloheptenyl, 1,3-cyclohexadienyl, 1,4-cyclohexadienyl and 1,5-cyclooctadienyl.

Exemplary cycloalkyl groups include cyclopropyl, cyclobutyl, cyclopentyl, cyclohexyl, norbornanyl, bicyclo[3.2.1]octanyl, octahydro-pentalenyl, spiro[4.5]decanyl, cyclopropyl, and adamantyl.

The term "carbocyclylalkyl", as used herein, refers to an alkyl group substituted with a carbocycle group.

The term "carbonate" is art-recognized and refers to a group $—OCO_2—R^{10}$, wherein $R^{10}$ represents a hydrocarbyl group.

The term "carboxy", as used herein, refers to a group represented by the formula $—CO_2H$.

The term "ester", as used herein, refers to a group $—C(O)OR^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 3- to 10-membered rings, more preferably 5- to 9-membered rings, such as 5-6 membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

Individual rings of such multicyclic heteroaryl groups can have different connectivities, e.g., fused, etc. in addition to covalent bond substitution. Exemplary heteroaryl groups include furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl and benzoxazinyl, etc. In general, the heteroaryl group typically is attached to the main structure via a carbon atom.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

Individual rings of such multicyclic heterocycloalkyl groups can have different connectivities, e.g., fused, bridged, spiro, etc. in addition to covalent bond substitution. Exemplary heterocycloalkyl groups include pyrrolidinyl, tetrahydrofuranyl, dihydrofuranyl, tetrahydropyranyl, pyranyl, thiopyranyl, azindinyl, azetidinyl, oxiranyl, methylenedioxyl, chromenyl, barbituryl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, piperizin-2-onyl, piperizin-3-onyl, chromanyl, 2-pyrrolinyl, 3-pyrrolinyl, imidazolidinyl, 2-imidazolidinyl, 1,4-dioxanyl, 8-azabicyclo[3.2.1]octanyl, 3-azabicyclo[3.2.1]octanyl, 3,8-diazabicyclo[3.2.1]octanyl, 2,5-diazabicyclo[2.2.1]heptanyl, 2,5-diazabicyclo[2.2.2]octanyl, octahydro-2H-pyrido[1,2-a]pyrazinyl, 3-azabicyclo[4.1.0]heptanyl, 3-azabicyclo[3.1.0]hexanyl 2-azaspiro[4.4]nonanyl, 7-oxa-1-aza-spiro[4.4]nonanyl, 7-azabicyclo[2.2.2]heptanyl, octahydro-1H-indolyl, etc. In general, the heterocycloalkyl group typically is attached to the main structure via a carbon atom or a nitrogen atom.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —$OSO_3H$, or a pharmaceutically acceptable salt thereof.

The term "sulfonamide" is art-recognized and refers to the group represented by the general formulae

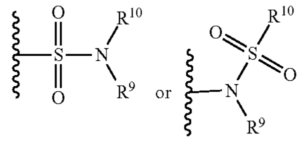

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group —S(O)—$R^{10}$, wherein $R^{10}$ represents a hydrocarbyl.

The term "sulfonate" is art-recognized and refers to the group $SO_3H$, or a pharmaceutically acceptable salt thereof.

The term "sulfone" is art-recognized and refers to the group —$S(O)_2$—$R^{10}$, wherein $R^{10}$ represents a hydrocarbyl.

The term "thioalkyl", as used herein, refers to an alkyl group substituted with a thiol group.

The term "thioester", as used herein, refers to a group —C(O)S$R^{10}$ or —SC(O)$R^{10}$ wherein $R^{10}$ represents a hydrocarbyl.

The term "thioether", as used herein, is equivalent to an ether, wherein the oxygen is replaced with a sulfur.

The term "urea" is art-recognized and may be represented by the general formula

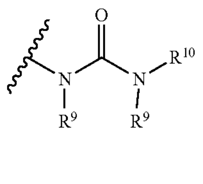

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

The term "protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry,* 3rd Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The invention also includes various isomers and mixtures thereof. Certain of the compounds of the present invention may exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms. When a chiral center is not defined as R or S, either a pure enantiomer or a mixture of both configurations is present.

"Racemate" or "racemic mixture" means a compound of equimolar quantities of two enantiomers, wherein such mixtures exhibit no optical activity; i.e., they do not rotate the plane of polarized light. In certain embodiments, compounds of the invention may be racemic.

In certain embodiments, compounds of the invention may be enriched in one enantiomer. For example, a compound of the invention may have greater than about 30% ee, about 40% ee, about 50% ee, about 60% ee, about 70% ee, about 80% ee, about 90% ee, or even about 95% or greater ee. In certain embodiments, compounds of the invention may have more than one stereocenter. In certain such embodiments, compounds of the invention may be enriched in one or more diastereomer. For example, a compound of the invention may have greater than about 30% de, about 40% de, about 50% de, about 60% de, about 70% de, about 80% de, about 90% de, or even about 95% or greater de.

In certain embodiments, the therapeutic preparation may be enriched to provide predominantly one enantiomer of a compound (e.g., of Formula (I)). An enantiomerically enriched mixture may comprise, for example, at least about 60 mol percent of one enantiomer, or more preferably at least about 75, about 90, about 95, or even about 99 mol percent. In certain embodiments, the compound enriched in one enantiomer is substantially free of the other enantiomer, wherein substantially free means that the substance in question makes up less than about 10%, or less than about 5%, or less than about 4%, or less than about 3%, or less than about 2%, or less than about 1% as compared to the amount of the other enantiomer, e.g., in the composition or compound mixture. For example, if a composition or compound mixture contains about 98 grams of a first enantiomer and about 2 grams of a second enantiomer, it would be said to contain about 98 mol percent of the first enantiomer and only about 2% of the second enantiomer.

In certain embodiments, the therapeutic preparation may be enriched to provide predominantly one diastereomer of a compound (e.g., of Formula (I)). A diastereomerically enriched mixture may comprise, for example, at least about 60 mol percent of one diastereomer, or more preferably at least about 75, about 90, about 95, or even about 99 mol percent.

The compounds of the invention may be prepared as individual isomers by either isomer specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least about 60%, about 70%, about 80%, about 90%, about 99% or about 99.9% by weight pure relative to the other stereoisomers. When a single enantiomer is named or depicted by structure, the depicted or named enantiomer is at least about 60%, about 70%, about 80%, about 90%, about 99% or about 99.9% by weight optically pure. Percent optical purity by weight is the ratio of the weight of the enantiomer that is present divided by the combined weight of the enantiomer that is present and the weight of its optical isomer.

In the pictorial representation of the compounds given through this application, a thickened tapered line ( ) indicates a substituent which is above the plane of the ring to which the asymmetric carbon belongs and a dotted line ( ) indicates a substituent which is below the plane of the ring to which the asymmetric carbon belongs.

As used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

An isotope-labelled form of a disclosed compound has one or more atoms of the compound replaced by an atom or atoms having an atomic mass or mass number different that that which usually occurs in greater natural abundance. Examples of isotopes which are readily commercially available and which can be incorporated into a disclosed compound by well-known methods include isotopes of hydrogen, carbon, nitrogen, oxygen, phosphorus, fluorine and chlorine, for example, 2H, 3H, 13C, 14C, 15N, 18O, 17O, 31P, 32P, 35S, 18F and 36Cl, respectively. An isotope-labelled compound provided herein can usually be prepared by carrying out the procedures disclosed herein, replacing a non-isotope-labelled reactant by an isotope-labelled reactant.

The concentration of such a heavier isotope, specifically deuterium, may be defined by the isotopic enrichment factor. The term "isotopic enrichment factor" as used herein means the ratio between the isotopic abundance and the natural abundance of a specified isotope. If a hydrogen atom in a compound of this invention is replaced with deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

An isotope-labelled compound as provided herein can be used in a number of beneficial ways. Compounds having 14C incorporated are suitable for medicament and/or substrate tissue distribution assays. Tritium (3H) and carbon-14 (14C), are preferred isotopes owing to simple preparation and excellent detectability. Heavier isotopes, for example deuterium (2H), has therapeutic advantages owing to the higher metabolic stability. Metabolism is affected by the primary kinetic isotope effect, in which the heavier isotope has a lower ground state energy and causes a reduction in the rate-limiting bond breakage. Slowing the metabolism can lead to an increased in vivo half-life or reduced dosage requirements or an improvement in therapeutic index.

For a further discussion, see S. L. Harbeson and R. D. Tung, Deuterium In Drug Discovery and Development, Ann. Rep. Med. Chem. 2011, 46, 403-417, Foster, A. B., "Deuterium Isotope Effects in Studies of Drug Metabolism," Trends in Pharmacological Sciences, 5: 524-527 (1984) AND Foster, A. B., "Deuterium Isotope Effects in the Metabolism of Drugs and Xenobiotics: Implications for Drug Design," Advances in Drug Research, 14: 1-40 (1985).

Metabolic stability can be affected by the compound's processing in different organs of the body. For example, compounds with poor pharmacokinetic profiles are susceptible to oxidative metabolism. In vitro liver microsomal assays currently available provide valuable information on the course of oxidative metabolism of this type, which in turn assists in the rational design of deuterated compounds as disclosed herein. Improvements can be measured in a number of assays known in the art, such as increases in the in vivo half-life (t1/2), concentration at maximum therapeutic effect (Cmax), area under the dose response curve (AUC), and bioavailability; and in terms of reduced clearance, dose and materials costs.

Another effect of deuterated compounds can be diminishing or eliminating undesired toxic metabolites. For example, if a toxic metabolite arises through oxidative carbon-hydrogen (C—H) bond cleavage, the deuterated analogue will have a slower reaction time and slow the production of the unwanted metabolite, even if the particular oxidation is not a rate-determining step. See, e.g., Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33 (10) 2927-2937, 1994, and Jarman et al. Carcinogenesis 16(4), 683-688, 1993.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. Preferred subjects are humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" means to decrease, suppress, attenuate, diminish, arrest, or stabilize the development or progression of a disease (e.g., a disease or disorder delineated herein), lessen the severity of the disease or improve the symptoms associated with the disease. Treatment includes treating a symptom of a disease, disorder or condition. Without being bound by any theory, in some embodiments, treating includes augmenting deficient CFTR activity. If it is administered prior to clinical manifestation of the unwanted condition (e.g., disease or other unwanted state of the subject) then the treatment is prophylactic (i.e., it protects the subject against developing the unwanted condition), whereas if it is administered after manifestation of the unwanted condition, the treatment is therapeutic, (i.e., it is intended to diminish, ameliorate, or stabilize the existing unwanted condition or side effects thereof).

As used herein, the term "prodrug" means a pharmacological derivative of a parent drug molecule that requires biotransformation, either spontaneous or enzymatic, within the organism to release the active drug. For example, prodrugs are variations or derivatives of the compounds of the invention that have groups cleavable under certain metabolic conditions, which when cleaved, become the compounds of the invention. Such prodrugs then are pharmaceutically active in vivo, when they undergo solvolysis under physiological conditions or undergo enzymatic degradation. Prodrug compounds herein may be called single, double, triple, etc., depending on the number of biotransformation steps required to release the active drug within the organism, and the number of functionalities present in a precursor-type form. Prodrug forms often offer advantages of solubility, tissue compatibility, or delayed release in the mammalian organism (See, Bundgard, Design of Prodrugs, pp. 7-9, 21-24, Elsevier, Amsterdam 1985 and Silverman, The Organic Chemistry of Drug Design and Drug Action, pp. 352-401, Academic Press, San Diego, CA, 1992). Prodrugs commonly known in the art include well-known acid derivatives, such as, for example, esters prepared by reaction of the parent acids with a suitable alcohol, amides prepared by reaction of the parent acid compound with an amine, basic groups reacted to form an acylated base derivative, etc. Of course, other prodrug derivatives may be combined with other features disclosed herein to enhance bioavailability.

As such, those of skill in the art will appreciate that certain of the presently disclosed compounds having free amino, amido, hydroxy or carboxylic groups can be converted into prodrugs. Prodrugs include compounds having an amino acid residue, or a polypeptide chain of two or more (e.g., two, three or four) amino acid residues which are covalently joined through peptide bonds to free amino, hydroxy or carboxylic acid groups of the presently disclosed compounds. The amino acid residues include the 20 naturally occurring amino acids commonly designated by three letter symbols and also include 4-hydroxyproline, hydroxylysine, demosine, isodemosine, 3-methylhistidine, norvalin, beta-alanine, gamma-aminobutyric acid, citrullinehomocysteine, homoserine, ornithine and methionine sulfone. Prodrugs also include compounds having a carbonate, carbamate, amide or alkyl ester moiety covalently bonded to any of the above substituents disclosed herein.

A "therapeutically effective amount", as used herein refers to an amount that is sufficient to achieve a desired therapeutic effect. For example, a therapeutically effective amount can refer to an amount that is sufficient to improve at least one sign or symptom of cystic fibrosis.

A "response" to a method of treatment can include a decrease in or amelioration of negative symptoms, a decrease in the progression of a disease or symptoms thereof, an increase in beneficial symptoms or clinical outcomes, a lessening of side effects, stabilization of disease, partial or complete remedy of disease, among others.

As used herein, "CFTR" means cystic fibrosis transmembrane conductance regulator. Defects in the function of the CFTR ion channel result from loss of function mutations of CFTR. Such mutations lead to exocrine gland dysfunction, abnormal mucociliary clearance, and cause cystic fibrosis. The most common CFTR mutation in Cystic Fibrosis (CF) patients leads to the specific deletion of three nucleotides of the codon for phenylalanine at position 508. This mutation, which is found in ~70% of CF patients worldwide, is referred to as "ΔF508". The ΔF508 mutation decreases the stability of the CFTR NBD1 domain and limits CFTR interdomain assembly. Since CF is an autosomal recessive disease, a CF patient harboring the ΔF508 CFTR mutation must also carry a second defective copy of CFTR. Approximately 2000 different CF-causing CFTR mutations have been identified in CF patients. CF patients harboring the ΔF508 CFTR mutation can be homozygous for that mutation (ΔF508/ΔF508). CF patients can also be ΔF508 heterozygous, if the second CFTR allele such patients carry instead contains a different CFTR loss of function mutation. Such CFTR mutations include, but are not limited to, G542X, G551D, N1303K, W1282X, R553X, R117H, R1162X, R347P, G85E, R560T, A455E, A1507, G178R, S549N, S549R, G551S, G970R, G1244E, S1251N, S1255P, and G1349D.

As used herein, the term "CFTR modulator" refers to a compound that increases the activity of CFTR. In certain aspects, a CFTR modulator is a CFTR corrector or a CFTR poteniator or a dual-acting compound having activities of a corrector and a poteniator. These dual acting agents are useful when the mutations result in absence or reduced amount of synthesized CFTR protein.

As used herein, the term "CFTR corrector" refers to a compound that increases the amount of functional CFTR protein at the cell surface, thus enhancing ion transport through CFTR. CFTR correctors partially "rescue" misfolding of CFTR protein, particularly such misfolding that results from mutations within CFTR, thereby permitting CFTR maturation and functional expression on the cell surface. CFTR correctors may modify the folding environment of the cell in a way that promotes CFTR folding, and include compounds that interact directly with CFTR protein to modify its folding, conformational maturation or stability. Examples of correctors include, but are not limited to, VX-809, VX-661, VX-152, VX-440, VX-445, VX-659, VX-121, VX-983, compounds described in US20190248809A1, GLPG2222, GLPG2737, GLPG3221, GLPG2851, FDL169, FDL304, FDL2052160, FD2035659, and PTI-801.

As used herein, the term "CFTR potentiator" refers to a compound that increases the ion channel activity of CFTR protein located at the cell surface, resulting in enhanced ion transport. CFTR potentiators restore the defective channel functions that results from CFTR mutations, or that otherwise increase the activity of CFTR at the cell surface. Examples of potentiators include, but are not limited to, ivacaftor (VX770), deuterated ivacaftor (CPT 656, VX-561), PTI-808, QBW251, GLPG1837, GLPG2451, ABBV-3067, ABBV-974, ABBV-191, FDL176, and genistein.

As used herein, "CFTR disease or condition" refers to a disease or condition associated with deficient CFTR activity, for example, cystic fibrosis, congenital bilateral absence of vas deferens (CBAVD), acute, recurrent, or chronic pancreatitis, disseminated bronchiectasis, asthma, allergic pulmonary aspergillosis, smoking-related lung diseases, such as chronic obstructive pulmonary disease (COPD), rhinosinusitis, congenital pneumonia, intestinal malabsorption, celiac disease, nasal polyposis, non-tuberculous mycobacterial infection, pancreatic steatorrhea, intestinal atresia, dry eye disease, protein C deficiency, A.beta.-lipoproteinemia, lysosomal storage disease, type 1 chylomicronemia, mild pulmonary disease, lipid processing deficiencies, type 1 hereditary angioedema, coagulation-fibrinolyis, hereditary hemochromatosis, CFTR-related metabolic syndrome, chronic bronchitis, constipation, pancreatic insufficiency, hereditary emphysema, and Sjogren's syndrome.

Methods of Use

Disclosed herein are methods of treating deficient CFTR activity in a cell, comprising contacting the cell with a compound of formula (I), or a pharmaceutically acceptable salt thereof. In certain embodiments, contacting the cell occurs in a subject in need thereof, thereby treating a disease or disorder mediated by deficient CFTR activity.

Also, disclosed herein are methods of treating a disease or a disorder mediated by deficient CFTR activity comprising administering a compound of Formula (I) or a pharmaceutically acceptable salt thereof. In some embodiments, the subject is a mammal, preferably a human. In some embodiments, the disease is associated with the regulation of fluid volumes across epithelial membranes, particularly an obstructive airway disease such as CF or COPD. Such diseases and conditions include, but are not limited to, cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), congenital pneumonia, intestinal malabsorption, celiac disease, nasal polyposis, non-tuberculous mycobacterial infection, pancreatic steatorrhea, intestinal atresia, liver disease, hereditary emphysema, hereditary hemochromatosis, coagulation-fibrinolysis deficiencies, protein C deficiency, Type 1 hereditary angioedema, lipid processing deficiencies, familial hypercholesterolemia, Type 1 chylomicronemia, abetalipoproteinemia, lysosomal storage diseases, I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases, Alzheimer's disease, Parkinson's disease, amyotrophic lateral sclerosis, progressive supranuclear plasy, Pick's disease, several polyglutamine neurological disorders, Huntington's, spinocerebullar ataxia type I, spinal and bulbar muscular atrophy, dentatorubal pallidoluysian, myotonic dystrophy, spongiform encephalopathies, hereditary Creutzfeldt-Jakob disease, Fabry disease, Straussler-Scheinker syndrome, COPD, dry-eye disease, Sjogren's disease, Osteoporosis, Osteopenia, bone healing and bone growth, bone repair, bone regeneration, reducing bone resorption, increasing bone deposition, Gorham's Syndrome, chloride channelopathies, myotonia congenita, Bartter's syndrome type III, Dent's disease, hyperekplexia, epilepsy, hyperekplexia, lysosomal storage disease, Angelman syndrome, Primary Ciliary Dyskinesia (PCD), PCD with situs inversus, PCD without situs inversus and ciliary aplasia.

Such diseases and conditions include, but are not limited to, cystic fibrosis, congenital bilateral absence of vas deferens (CBAVD), acute, recurrent, or chronic pancreatitis, disseminated bronchiectasis, asthma, allergic pulmonary aspergillosis, chronic obstructive pulmonary disease (COPD), chronic rhinosinusitis, congenital pneumonia, intestinal malabsorption, celiac disease, nasal polyposis, non-tuberculous mycobacterial infection, pancreatic steatorrhea, intestinal atresia, dry eye disease, protein C deficiency, Abetalipoproteinemia, lysosomal storage disease, type 1 chylomicronemia, mild pulmonary disease, lipid processing deficiencies, type 1 hereditary angioedema, coagulation-fibrinolyis, hereditary hemochromatosis, CFTR-related metabolic syndrome, chronic bronchitis, constipation, pancreatic insufficiency, hereditary emphysema, and Sjogren's syndrome. In some embodiments, the disease is cystic fibrosis.

Provided herein are methods of treating cystic fibrosis, comprising administering to a subject in need thereof, a compound as disclosed herein or a pharmaceutically acceptable salt thereof. Also provided herein are methods of lessening the severity of cystic fibrosis, comprising administering to a subject in need thereof, a compound as disclosed herein or a pharmaceutically acceptable salt thereof. In some embodiments, the subject is a human. In some embodiments, the subject is at risk of developing cystic fibrosis, and administration is carried out prior to the onset of symptoms of cystic fibrosis in the subject.

Provided herein are compounds as disclosed herein for use in treating a disease or condition mediated by deficient CFTR activity. Also provided herein are uses of a compound as disclosed herein for the manufacture of a medicament for treating a disease or condition mediated by deficient CFTR activity.

The compounds and methods described herein can be used to treat subjects who have deficient CFTR activity and harbor CFTR mutations like ΔF508. The ΔF508 mutation impedes normal CFTR folding, stability, trafficking, and function by decreasing the stability of CFTR's NBD1 domain, the competency of CFTR domain-domain assembly, or both. Due their impact on the ICL4 interface, a CFTR corrector with an ICL4-directed mechanism can be effective in subjects harboring the following mutations: ΔF508-CFTR (>70% of all CF patients harbor at least one copy) and mutations that cause ICL4 interface instability for example: G85E, H139R, H1054D, L1065P, L1077P, R1066C and other CFTR mutations where ICL4 interface stability is compromised.

Provided herein are kits for use in measuring the activity of CFTR or a fragment thereof in a biological sample in vitro or in vivo. The kit can contain: (i) a compound as disclosed herein, or a pharmaceutical composition comprising the disclosed compound, and (ii) instructions for: a) contacting the compound or composition with the biological sample; and b) measuring activity of said CFTR or a fragment thereof. In some embodiments, the biological sample is biopsied material obtained from a mammal or extracts thereof; blood, saliva, urine, feces, semen, tears, other body fluids, or extracts thereof. In some embodiments, the mammal is a human.

Combination Treatments

As used herein, the term "combination therapy" means administering to a subject (e.g., human) two or more CFTR modulators, or a CFTR modulator and an agent such as antibiotics, ENaC inhibitors, GSNO (S-nitrosothiol s-nitroglutanthione) reductase inhibitors, and a CRISPR Cas correction therapy or system (as described in US 2007/0022507 and the like).

In certain embodiments, the method of treating or preventing a disease or condition mediated by deficient CFTR activity comprises administering a compound as disclosed herein conjointly with one or more other therapeutic agent (s). In some embodiments, one other therapeutic agent is administered. In other embodiments, at least two other therapeutic agents are administered.

Additional therapeutic agents include, for example, ENaC inhibitors, mucolytic agents, bronchodilators, antibiotics, anti-infective agents, anti-inflammatory agents, ion channel modulating agents, therapeutic agents used in gene therapy, agents that reduce airway surface liquid and/or reduce airway surface PH, CFTR correctors, and CFTR potentiators, or other agents that modulate CFTR activity.

In some embodiments, at least one additional therapeutic agent is selected from one or more CFTR modulators, one or more CFTR correctors and one or more CFTR potentiators.

Non-limiting examples of CFTR modulators, correctors and potentiators include VX-770 (Ivacaftor), VX-809 (Lumacaftor, 3-(6-(I-(2,2-5 difluorobenzo[d][1, 3]dioxol-5-yl) cyclopropanecarboxamido)-3-methylpyridin-2-yl) benzoic acid, VX-661 (Tezacaftor, I-(2,2-difluoro-1, 3-benzodioxol-5-yl)-N—[I-[(2R)-2,3-dihydroxypropyl]-6-fluoro-2-(2-hydroxy-1, I-dimethylethyl)-1H-indol-5-yl]-cyclopropanecarboxamide), VX-983, VX-152, VX-440, VX-445, VX-659, VX-371, VX-121, Orkambi, compounds described in US20190248809A1, Ataluren (PTC 124) (3-[5-(2-fluorophenyl)-1, 2,4-oxadiazol-3-yl]benzoic acid), PTI-130 (Proteostasis), PTI-801, PTI-808, PTI-428, N91115.74 (cavosonstat), QBW251 (Novartis) compounds described in WO2011113894, compounds N30 Pharmaceuticals (e.g., WO 2014/186704), deuterated ivacaftor (e.g., CTP-656 or VX-561), GLPG2222, GLPG3221, GLPG2451, GLPG3067, GLPG2851, GLPG2737, GLPG1837 (N-(3-carbamoyl-5,5,7,7-tetramethyl-5,7-dihydro-4H-thieno[2,3-c]pyran-2-yl)-1H-pyrazole-5-carboxamide), GLPG2665 (Galapagos), ABBV-191 (Abbvie), ABBV-974, FDL 169 (Flatley Discovery lab), FDL 176, FDL438, FDL304, FD2052160, FD1881042, FD2027304, FD2035659, FD2033129, FD1860293, CFFT-Pot01, CFFT-Pot-02, P-1037, glycerol, phenylbutyrate, and the like. Non-limiting examples of anti-inflammatory agents are N6022 (3-(5-(4-(1H-imidazol-1-yl)10 phenyl)-1-(4-carbamoyl-2-methylphenyl)-1H-pyrrol-2-yl) propanoic acid), Ibuprofen, Lenabasum (anabasum), Acebilustat (CTX-4430), LAU-7b, POL6014, docosahexaenoic acid, alpha-1 anti-trypsin, sildenafil. Additional therapeutic agents also include, but are not limited to a mucolytic agent, a modifier of mucus rheology (such as hypertonic saline, mannitol, and oligosaccharide based therapy), a bronchodialator, an anti-infective (such as tazobactam, piperacillin, rifampin, meropenum, ceftazidime, aztreonam, tobramycin, fosfomycin, azithromycin, vancomycin, gallium and colistin), an anti-infective agent, an anti-inflammatory agent, a CFTR modulator other than a compound of the present invention, and a nutritional agent. Additional therapeutic agents can include treatments for comorbid conditions of cyctic fibrosis, such as exocrine pancreatic insufficiency which can be treated with Pancrelipase or Liprotamase.

Examples of CFTR potentiators include, but are not limited to, Ivacaftor (VX-770), CTP-656, NVS-QBW251, PTI-808. ABBV-3067, ABBV-974, ABBV-191, FDL176, FD1860293, GLPG2451, GLPG1837, and N-(3-carbamoyl-5,5,7,7-tetramethyl-5,7-dihydro-4H-thieno[2,3-c]pyran-2-yl)-1H-pyrazole-5-carboxarnide. Examples of potentiators are also disclosed in publications: WO2005120497, WO2008147952, WO2009076593, WO2010048573, WO2006002421, WO2008147952, WO2011072241, WO2011113894, WO2013038373, WO2013038378, WO2013038381, WO2013038386, WO2013038390, WO2014180562, WO2015018823, and U.S. patent application Ser. Nos. 14/271,080, 14/451,619 and 15/164,317.

Non-limiting examples of correctors include Lumacaftor (VX-809), 1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropane carboxamide (VX-661), VX-983, GLPG2222, GLPG2665, GLPG2737, GLPG3221, GLPG2851, VX-152, VX-440, VX-121, VX-445, VX-659, PTI-801, FDL169, FDL304, FD2052160, and FD2035659. Examples of correctors are also disclosed in US20160095858A1, US20190248809A1, and US, application Ser. Nos. 14/925,649 and 14/926,727.

In certain embodiments, the additional therapeutic agent is a CFTR amplifier. CFTR amplifiers enhance the effect of known CFTR modulators, such as potentiators and correctors. Examples of CFTR amplifier include PTI130 and PTI-428. Examples of amplifiers are also disclosed in publications: WO2015138909 and WO2015138934.

In certain embodiments, the additional therapeutic agent is an agent that reduces the activity of the epithelial sodium channel blocker (ENaC) either directly by blocking the channel or indirectly by modulation of proteases that lead to an increase in ENaC activity (e.g., serine proteases, channel-activating proteases). Exemplary of such agents include camostat (a trypsin-like protease inhibitor), QAU145, 552-02, ETD001, GS-9411, INO-4995, Aerolytic, amiloride, AZD5634, and VX-371. Additional agents that reduce the activity of the epithelial sodium channel blocker (ENaC) can be found, for example, in PCT Publication No. WO2009074575 and WO2013043720; and U.S. Pat. No. 8,999,976.

In one embodiment, the ENaC inhibitor is VX-371 In one embodiment, the ENaC inhibitor is SPX-101 (S18).

In certain embodiments, the additional therapeutic agent is an agent that modulates the activity of the non-CFTR Cl-channel TMEM16A. Non-limiting examples of such agents include TMEM16A activators, denufosol, Melittin, Cinnamaldehyde, 3,4,5-Trimethoxy-N-(2-methoxyethyl)-N-(4-phenyl-2-thiazolyl)benzamide, INO-4995, CLCA1, ETX001, ETD002 and phosphatidylinositol diC8-PIP2, and TMEM16A inhibitors, 10bm, Arctigenin, dehydroandrographolide, Ani9, Niclosamide, and benzbromarone.

In certain embodiments, the combination of a compound of Formula (I), with a second therapeutic agent may have a synergistic effect in the treatment of cancer and other diseases or disorders mediated by adenosine. In other embodiments, the combination may have an additive effect.

Pharmaceutical Compositions

The compositions and methods of the present invention may be utilized to treat a subject in need thereof. In certain embodiments, the subject is a mammal such as a human, or a non-human mammal. When administered to subject, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the subject being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the subject being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the subject's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

In certain embodiments, the dosing follows a 3+3 design. The traditional 3+3 design requires no modeling of the dose-toxicity curve beyond the classical assumption for cytotoxic drugs that toxicity increases with dose. This rule-based design proceeds with cohorts of three patients; the first cohort is treated at a starting dose that is considered to be safe based on extrapolation from animal toxicological data, and the subsequent cohorts are treated at increasing dose levels that have been fixed in advance. In some embodiments, the three doses of a compound of formula (I) range from about 100 mg to about 1000 mg orally, such as about 200 mg to about 800 mg, such as about 400 mg to about 700 mg, such as about 100 mg to about 400 mg, such as about 500 mg to about 1000 mg, and further such as about 500 mg to about 600 mg. Dosing can be three times a day when taken with without food, or twice a day when taken with food. In certain embodiments, the three doses of a compound of formula (I) range from about 400 mg to about 800 mg, such as about 400 mg to about 700 mg, such as about 500 mg to about 800 mg, and further such as about 500 mg to about 600 mg twice a day. In certain preferred embodiments, a dose of greater than about 600 mg is dosed twice a day.

If none of the three patients in a cohort experiences a dose-limiting toxicity, another three patients will be treated at the next higher dose level. However, if one of the first three patients experiences a dose-limiting toxicity, three more patients will be treated at the same dose level. The dose escalation continues until at least two patients among a cohort of three to six patients experience dose-limiting toxicities (i.e., ≥about 33% of patients with a dose-limiting toxicity at that dose level). The recommended dose for phase II trials is conventionally defined as the dose level just below this toxic dose level.

In certain embodiments, the dosing schedule can be about 40 $mg/m^2$ to about 100 $mg/m^2$, such as about 50 $mg/m^2$ to about 80 $mg/m^2$, and further such as about 70 $mg/m^2$ to about 90 $mg/m^2$ by IV for 3 weeks of a 4 week cycle.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one h, 12 h, 24 h, 36 h, 48 h, 72 h, or a week of one another. Thus, a subject who receives such treatment can benefit from a combined effect of different therapeutic compounds.

In certain embodiments, conjoint administration of compounds of the invention with one or more additional therapeutic agent(s) (e.g., one or more additional chemotherapeutic agent(s)) provides improved efficacy relative to each individual administration of the compound of the invention (e.g., compound of formula I or Ia) or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

This invention includes the use of pharmaceutically acceptable salts of compounds of the invention in the compositions and methods of the present invention. A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, 3-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Although specific embodiments of the present disclosure will now be described with reference to the preparations and schemes, it should be understood that such embodiments are by way of example only and merely illustrative of but a small number of the many possible specific embodiments which can represent applications of the principles of the present disclosure. Various changes and modifications will be obvious to those of skill in the art given the benefit of the present disclosure and are deemed to be within the spirit and scope of the present disclosure as further defined in the appended claims.

Unless defined otherwise, all technical and scientific terms used herein have the same meaning as commonly understood by one having ordinary skill in the art to which this disclosure belongs. Although other compounds or methods can be used in practice or testing, certain preferred methods are now described in the context of the following preparations and schemes.

A number of synthetic protocols were used to produce the compounds described herein. These synthetic protocols (see schemes below) have common intersections and can be used alternatively for synthesis of the compounds described herein.

EXAMPLES

General Schemes

Compounds of Formula (I) and the Intermediates may be prepared by the general procedures depicted in Schemes 1-9.

Scheme 1.

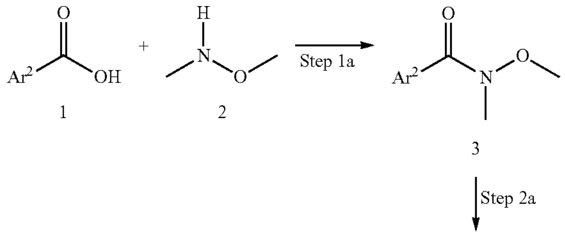

-continued

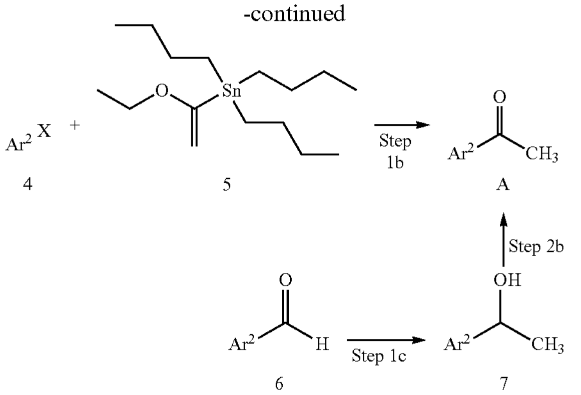

Scheme 1 illustrates the synthesis of the Intermediate A, an aryl methyl ketone. Any commercially available starting materials which may be converted into an aryl methyl ketone are applicable in this case using conventional chemical reactions well known in the art. For example, the acid 1 may be converted (Step 1a) into a Weinreb amide (3) by coupling the acid with methoxy(methyl)amine (2). Then, methyl anion sources, such as a Grignard reagent or methyllithium, may be added to the Weinreb amides (Step 2a) to form the desired aryl methyl ketone, Intermediate A. Alternatively, an aryl halide derivative (4) can undergo Stille coupling (Step 1b) to form the aryl methyl ketone Intermediate A. Alternatively yet, an aldehyde may be converted into alcohol (7) (Step 1c) in a reaction with a Grignard reagent or methyllithium followed by oxidation (Step 2b).

Scheme 2.

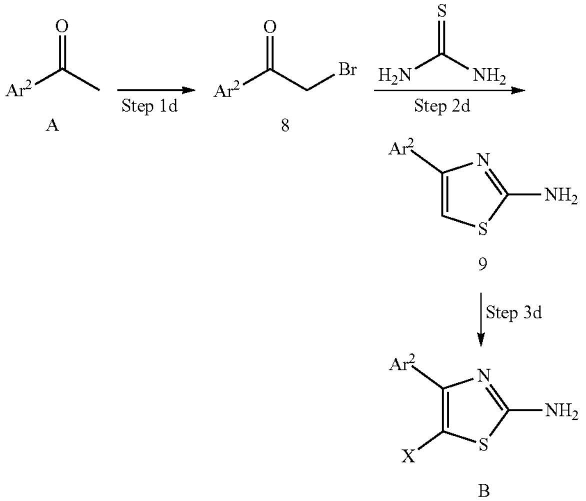

In Scheme 2, an aryl methyl ketone (Intermediate A) may be transformed into an aryl bromomethyl ketone (8) by treating Intermediate A with a brominating agent, such as pyridinium tribromide (Step 1d). Condensation of 8 with thiourea in a polar solvent, such as ethanol, at room temperature or elevated temperature, yields aryl amino thiazole 9 (Step 2d). A halogen (X=bromine or iodine) substituent may be introduced into position 5 of the aryl amino thiazole by treating 9 with a proper halogenating agent, such as NBS or NIS (Step 3d), to give Intermediate B.

Scheme 3.

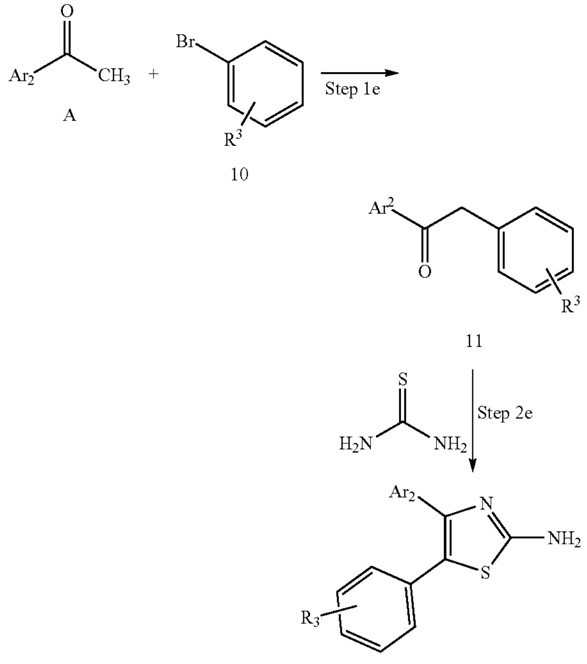

A 10 11 C

Scheme 3 illustrates a method of preparation of an aryl amino thiazole (Intermediate C). Aryl methyl ketone (Intermediate A) is coupled with an aryl bromide (10) using a catalyst, such as X-phos-Pd, at an elevated temperature to yield ketone 11 (Step 1e). The aryl bromide 10 is obtained in an appropriate reaction, such as alkylation of a substituted phenol with an alkyl halide or an alkyl triflate (for illustrative examples, see "Preparation of the Intermediates"). Condensation of 11 with thiourea (Step 2e) gives Intermediate C.

Scheme 4.

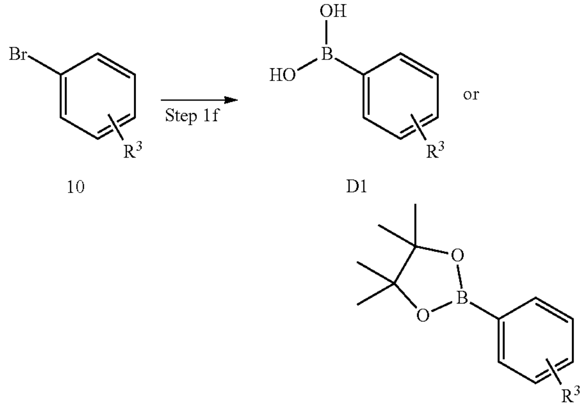

10 D1 or D2

In Scheme 4, the aryl bromide 10 is converted to an aryl boronic acid or a pinacol boron ester (Intermediates D1 or D2) by conventional chemical reactions well known in the art (Step 1f). Both D1 and D1 can be used in the synthesis of Intermediate C interchangeably.

Scheme 5.

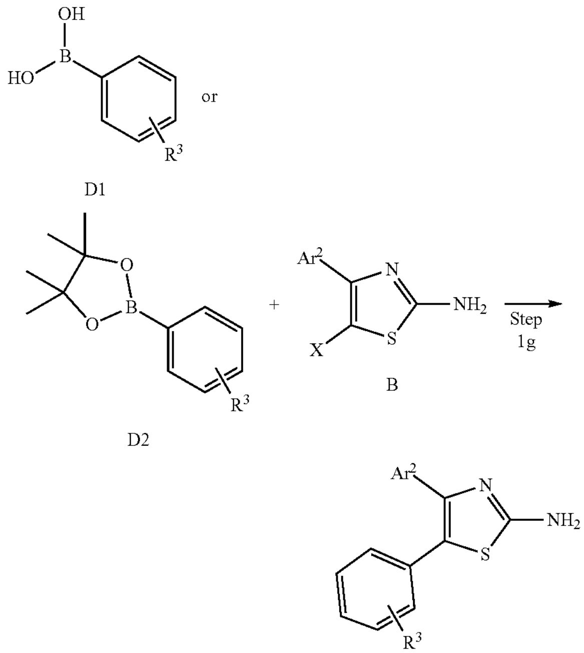

D1 or D2 + B C

Scheme 5 illustrates an alternative method to prepare Intermediate C by coupling of the boronic acid or the pinacol boron ester (D1 or D2) with Intermediate B (Step 1g).

Scheme 6.

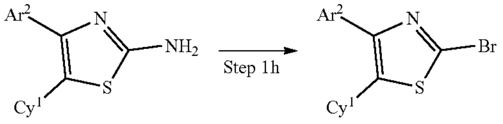

C G

In Scheme 6, the amino group in Intermediate C is converted to a bromine substituent in Intermediate G by a $CuBr_2$ catalyzed reaction at elevated temperature (Step 1h).

Scheme 7.

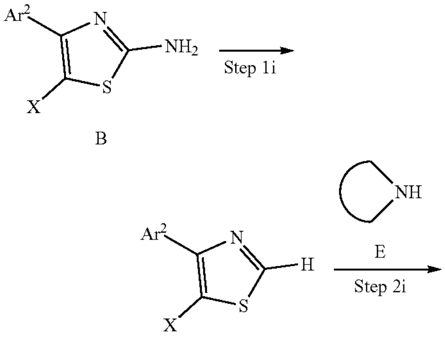

B 12

-continued

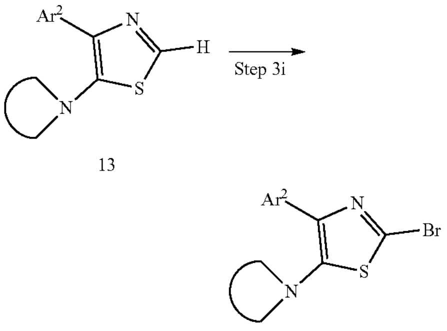

13

G

Scheme 7 illustrates preparation of Intermediate G, where substituent $Cy^1$ contains a nitrogen connecting group. In Step 1i, the amino group in thiazole (Intermediate B) may be removed via a tert-butyl nitrite-mediated reaction to avoid complication of the next step 5-position haligen replacement reaction. After the halogen at the 5 position is replaced by an amino group (Step 2i), the halogen at the 2 position may be re-introduced via a simple bromination or iodination reaction (Step 3i) to obtain Intermediate G.

Scheme 8.

Synthesis of the compounds of Formula (I), Method 1.

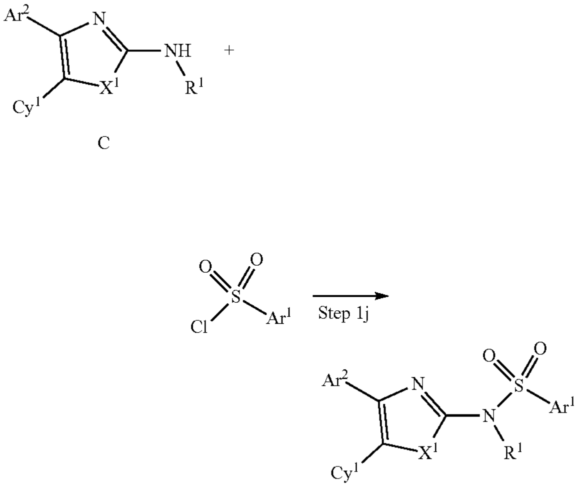

C (I)

Scheme 8 illustrates Method 1 of the synthesis of a compound of Formula (I) by a direct sulfonamide formation reaction of amino thiazoles (Intermediate C) with aryl sulfonyl chloride (Step 1j).

Scheme 9.

Synthesis of the compounds of Formula (I), Method 2.

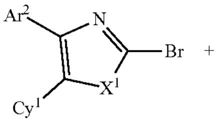

G

-continued

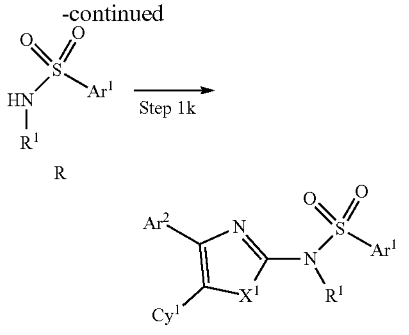

R (I)

Scheme 9 illustrates Method 2 of the synthesis of a compound of Formula (I) by Buchwald coupling reaction (Step 1k) of the bromide derivative (Intermediate G) with sulfonamides (Intermediate R). For the synthesis of the commercially unavailable sulfonamides (Intermediate R), see the section titled "Preparation of Intermediates".

Analytical Procedures

The $^1H$ NMR spectra are run at 400 MHz on a Gemini 400 or Varian Mercury 400 spectrometer with an ASW 5 mm probe, and usually recorded at ambient temperature in a deuterated solvent, such as $D_2O$, DMSO-$D_6$ or $CDCl_3$ unless otherwise noted. Chemical shifts values (6) are indicated in parts per million (ppm) with reference to tetramethylsilane (TMS) as the internal standard.

High Pressure Liquid Chromatography-Mass Spectrometry (LCMS) experiments to determine retention times (RT) and associated mass ions were performed using one of the following methods.

Mass Spectra (MS) were recorded using a Micromass mass spectrometer. Generally, the method used was positive electro-spray ionization, scanning mass m/z from 100 to 1000. Liquid chromatography was performed on a Hewlett Packard 1100 Series Binary Pump & Degasser; Auxiliary detectors used were: Hewlett Packard 1100 Series UV detector, wavelength=220 nm and Sedere SEDEX 75 Evaporative Light Scattering (ELS) detector temperature=46° C., N2 pressure=4 bar.

LCT: Grad (AcN+0.05% TFA):($H_2O$+0.05% TFA)=5:95 (0 min) to 95:5 (2.5 min) to 95:5 (3 min). Column: YMC Jsphere 33×2 4 μM, 1 ml/min MUX: Column: YMC Jsphere 33×2, 1 ml/min Grad (AcN+0.05% TFA):($H_2O$+0.05% TFA)=5:95 (0 min) to 95:5 (3.4 min) to 95:5 (4.4 min).

LCT2: YMC Jsphere 33×2 4 μM, (AcN+0.05% TFA):($H_2O$+0.05% TFA)=5:95 (0 min) to 95:5 (3.4 min) to 95:5 (4.4 min).

QU: YMC Jsphere 33×2 1 ml/min, (AcN+0.08% formic acid):($H_2O$+0.1% formic acid)=5:95 (0 min) to 95:5 (2.5 min) to 95:5 (3.0 min).

Preparation of Intermediates

This section "Preparation of Intermediates" illustrates the synthesis of the common intermediates used in the preparation of the examples. It is not intended to list all the intermediates. Rather, the procedures shown here are only for illustration purpose. It should not bear any limitations or restrictions for the methods used for the synthesis of the examples.

Intermediate A-1

1-(2-Isopropylphenyl)ethan-1-one

Step 1.

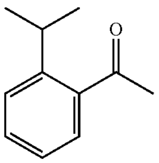

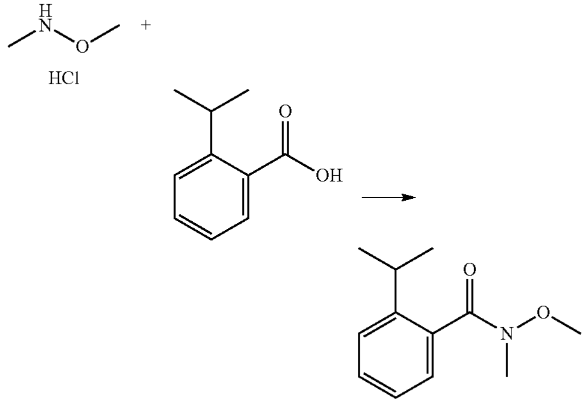

To a solution of 2-isopropylbenzoic acid (1.39 g, 8.45 mmol) in DMF (13 mL) was added HATU (6.42 g, 16.89 mmol), N,O-dimethylhydroxylamine hydrochloride (1.25 g, 12.88 mmol) and TEA (2.57 g, 25.46 mmol) at room temperature. The resulting mixture was stirred at the same temperature for 3 h. The mixture was poured into water (100 mL) and extracted with ethyl acetate (100 mL×2). The extracts were washed with water (100 mL×2), dried over sodium sulfate and evaporated. The crude product thus obtained was purified by silica gel chromatography (PE/EA=5/1) to give 2-isopropyl-N-methoxy-N-methylbenzamide (1.50 g, 85.5%) as a colorless oil.

LCMS: MS (ESI): m/z 208 $[M+H]^+$.

Step 2.

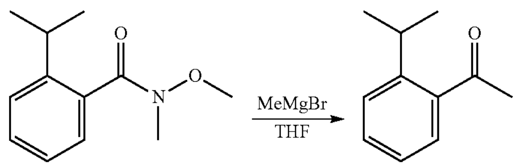

To a solution of 2-isopropyl-N-methoxy-N-methylbenzamide (1.75 g, 8.44 mmol) in THF (17 mL) was added MeMgBr (8.5 mL, 25.5 mmol, 3.0 M) under $N_2$ at 0° C. The resulting mixture was stirred at room temperature for 2 h. The mixture was poured into water (50 mL) and extracted with ethyl acetate (50 mL×2). The extracts were washed with water (40 mL×2), dried over sodium sulfate and evaporated. The resulting residue was purified by silica gel chromatography (PE/EA=10/1) to afford 1-(2-isopropylphenyl)ethan-1-one (1.25 g, 91.3%) as a colorless oil.

LCMS: MS (ESI): m/z 163 $[M+H]^+$.

Intermediate A-2

1-(2-isopropoxy-6-methylphenyl)ethan-1-one

Step 1.

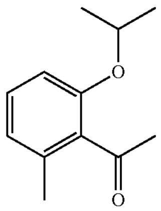

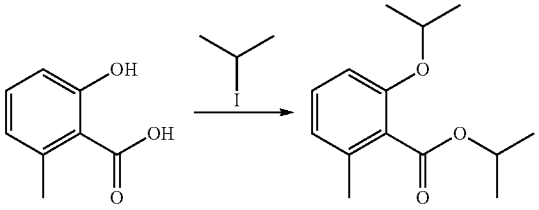

A mixture of 2-hydroxy-6-methylbenzoic acid (5.0 g, 32.9 mmol), potassium carbonate (18.16 g, 131.6 mmol), and 2-iodopropane (19.58 g, 115 mmol) in DMF (90 mL) was stirred at 50° C. overnight. LCMS indicated 2-hydroxy-6-methyl-benzoic acid was remained, 2-iodopropane (11.19 g, 65.8 mmol) and potassium carbonate (9.08 g, 65.8 mmol) were added additionally at room temperature, and the reaction mixture was stirred at 50° C. for another 4 h. After cooling to room temperature, water (250 mL) was added, and extracted with ethyl acetate (80 mL×3). The combined organic layers were washed with brine (100 mL×3), dried over sodium sulfate, filtered and concentrated under reduced pressure, the residue was purified by silica gel chromatography (8% ethyl acetate in petroleum ether) to give the product isopropyl 2-isopropoxy-6-methylbenzoate as a colorless oil (7.648 g, 99% yield).

LCMS: Retention time 2.24 min. MS (ESI) m/z 237 $[M+H]^+$.

Step 2.

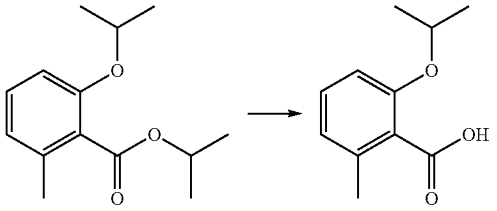 [SMILES: Cc1cccc(OC(C)C)c1C(=O)OC(C)C ; Cc1cccc(OC(C)C)c1C(=O)O]

Potassium hydroxide (54.5 g, 971 mmol) was added to the mixture of isopropyl 2-isopropoxy-6-methylbenzoate (7.65 g, 32.4 mmol) in dimethyl sulfoxide (27 mL) and water (30 mL) at room temperature, the resulting mixture was stirred at 100° C. overnight. Diluted with water (30 mL), the mixture was acidified to pH=2 with 6 N HCl at 0° C., then extracted with ethyl acetate (80 mL×3), washed with brine (80 mL×3), dried over sodium sulfate, filtered and concentrated under reduced pressure to give the crude product 2-isopropoxy-6-methylbenzoic acid as a light yellow oil (5.28 g).

$^1H$ NMR (400 MHz, chloroform-d) δ 7.30 (t, J=8.0 Hz, 1H), 6.90 (d, J=7.6 Hz, 1H), 6.86 (d, J=8.0 Hz, 1H), 4.69 (m, 1H), 2.54 (s, 3H), 1.41 (d, J=6.0 Hz, 6H) ppm.

LCMS: Retention time 1.84 min. MS (ESI) m/z 177 $[M-OH]^+$.

Step 3.

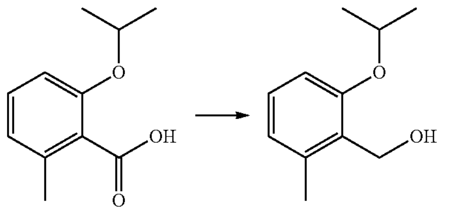

Borane-methyl sulfide complex (52.5 mL, 105 mmol, 2.0 M) was added dropwise to the solution of 2-isopropoxy-6-methylbenzoic acid (5.1 g, 26.3 mmol) in tetrahydrofuran (45 mL) at 0° C. under argon atmosphere. The resulting mixture was stirred at 60° C. for 3 h. After cooling to room temperature, the reaction mixture was adjusted to about pH=8 with 2.0 M sodium hydroxide solution, diluted with water (100 mL), extracted with diethyl ether (80 mL×3), the combined organic layers were washed with brine (100 mL), dried over sodium sulfate, filtered and concentrated under reduced pressure to afford the crude product (2-isopropoxy-6-methylphenyl)methanol as a yellow oil (4.21 g), which was used directly for the next step without further purification.

LCMS: LC retention time 1.95 min. MS (ESI) m/z 163 $[M-OH]^+$.

Step 4.

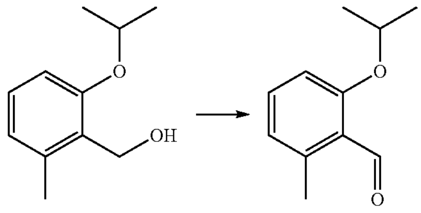

To a stirred solution of (2-isopropoxy-6-methylphenyl) methanol (4.21 g, 23.4 mmol) in dichloromethane (50 mL) was added activated manganese dioxide (40.7 g, 468 mmol). The resulting mixture was stirred at 50° C. for 3 h. Additional activated manganese dioxide (40.7 g, 468 mmol) and dichloromethane (10 mL) were added. The resulting mixture was stirred at 50° C. for 18 h. Manganese dioxide was filtered off through Celite, washed with ethyl acetate and the filtrate was evaporated under reduced pressure to give the crude product 2-isopropoxy-6-methylbenzaldehyde as a yellow oil (3.6 g).

LCMS: LC retention time 2.15 min. MS (ESI) m/z 179 $[M+H]^+$.

Step 5.

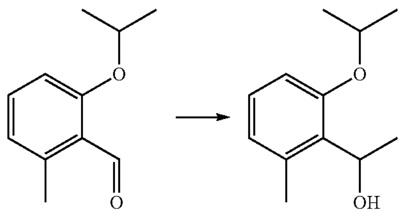

To a solution of 2-isopropoxy-6-methylbenzaldehyde (3.60 g, 20.2 mmol) in tetrahydrofuran (30.0 mL) was added methylmagnesium bromide (20.2 mL, 3.0 M solution in diethyl ether, 60.6 mmol) at 0° C. under argon atmosphere. The resulting mixture was stirred at room temperature for 3 h. Quenched with saturated aqueous ammonium chloride solution (30 mL), diluted with water (120 mL), and extracted with ethyl acetate (60 mL×3), the combined organic layers were washed with brine (100 mL), dried over sodium sulfate, filtered and concentrated under reduced pressure to give the crude product 1-(2-isopropoxy-6-methylphenyl)ethan-1-ol as a light yellow oil (3.82 g).

LCMS: LC retention time 2.07 min. MS (ESI) m/z 177 $[M-OH]^+$

Step 6.

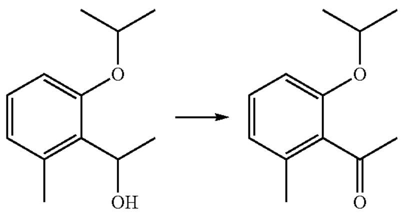

Activated manganese dioxide (44 g, 506 mmol) was added to the solution of 1-(2-isopropoxy-6-methylphenyl) ethan-1-ol (3.82 g, 19.7 mmol) in dichloromethane (50 mL). The resulting mixture was stirred at 50° C. for 14 h, and activated manganese dioxide (17 g, 195.5 mmol) and dichloromethane (10 mL) were added additionally. The resulting mixture was stirred at 50° C. for 3 h. Manganese dioxide was filtered through Celite, washed with ethyl acetate and the solvent was evaporated under reduced pressure to give the crude product, which was purified by silica gel chromatography (5% ethyl acetate in petroleum ether) to give 1-(2-isopropoxy-6-methylphenyl)ethan-1-one as a light yellow oil (3.14 g, 62% yield over 4 steps).

LCMS: LC retention time 2.12 min. MS (ESI) m/z 193 $[M+H]^+$.

$^1H$ NMR (400 MHz, chloroform-d) δ 7.17 (t, J=8.0 Hz, 1H), 6.73-6.77 (m, 2H), 4.56 (m, 1H), 2.49 (s, 3H), 2.22 (s, 3H), 1.32 (d, J=6.0 Hz, 6H) ppm.

Intermediate A-3

1-(2-Isopropoxy-4-(trifluoromethyl)phenyl)ethan-1-one

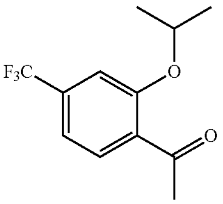 [SMILES: CC(=O)c1ccc(C(F)(F)F)cc1OC(C)C]

Step 1.

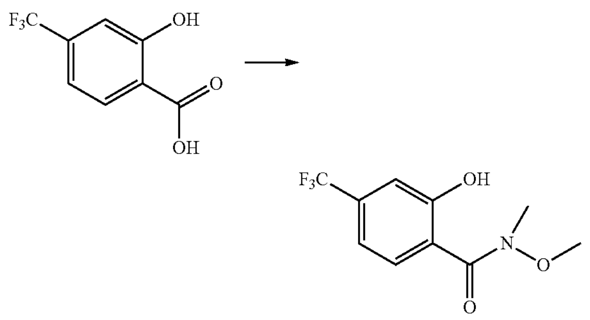

To a solution of 2-hydroxy-4-(trifluoromethyl)benzoic acid (2.50 g, 12.1 mmol) in THF (30 mL) was added N,O-dimethylhydroxylamine (1.18 g, 12.1 mmol), HATU (4.61 g, 12.1 mmol) and DIPEA (7.82 g, 60.6 mmol). The mixture was stirred at rt for 2 h. Then diluted with EtOAc (50 mL) and $H_2O$ (50 mL). The two layers were separated and the aqueous was extracted with EtOAc (10 mL×3). The combined organic phase was washed with brine (50 mL), dried over anhydrous sodium sulphate, filtered, concentrated in vacuo to purified by SGC (PE/EA=5/1) to afford the desired compound 2-hydroxy-N-methoxy-N-methyl-4-(trifluoromethyl)benzamide as a colorless oil (2.40 g, 79.4%).

LC retention time 1.77 min. MS (ESI) m/z 250 $[M+H]^+$.

Step 2.

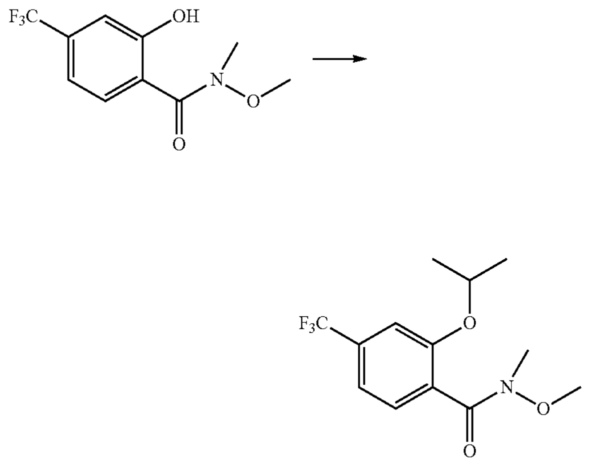

To a solution of 2-hydroxy-N-methoxy-N-methyl-4-(trifluoromethyl)benzamide (3.80 g, 15.2 mmol) in THF (50 mL) was added 2-iodopropane (2.59 g, 15.2 mmol), and $K_2CO_3$ (4.21 g, 30.5 mmol). The mixture was stirred at 40° C. overnight. Then extracted with EA (50 mL) twice and $H_2O$ (50 mL). The combined organic phase was washed with brine (50 mL), dried over anhydrous sodium sulphate, filtered, concentrated in vacuo and purified by silica gel chromatography (PE/EA=20/1) to afford 2-isopropoxy-N-methoxy-N-methyl-4-(trifluoromethyl)benzamide (3.60 g, 81%) as a light yellow oil.

LC retention time 2.03 min. MS (ESI) m/z 292 $[M+H]^+$.

Step 3.

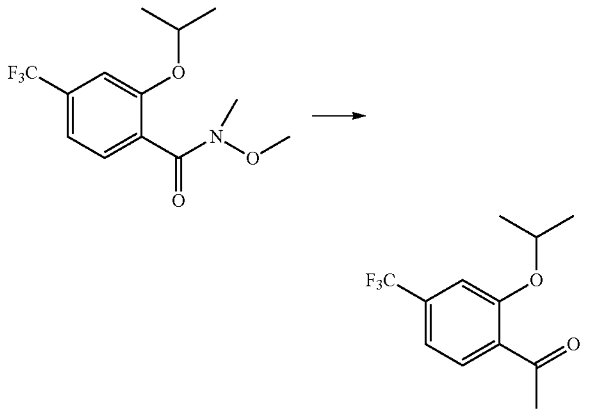

To a solution of 2-isopropoxy-N-methoxy-N-methyl-4-(trifluoromethyl)benzamide (2.00 g, 6.87 mmol) in THF (20 mL) was added MeMgBr (3.42 mL, 10.3 mmol). The mixture was stirred at room temperature for 2 h. Then quenched with $NH_4Cl$ aq (50 mL), extracted with EA (50 mL×2). The combined organic phase was washed with brine (50 mL), dried over anhydrous sodium sulphate, filtered, concentrated in vacuo and purified by silica gel column chromatography (PE/EA=20/1) to afford the title intermediate (1.20 g, 71%) as a light yellow oil.

LCMS: LC retention time 2.22 min. MS (ESI) m/z 247 $[M+H]^+$.

Intermediate A-4

1-(2-Cyclopropylphenyl)ethan-1-one

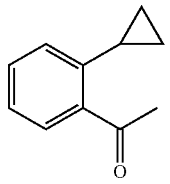

Step 1.

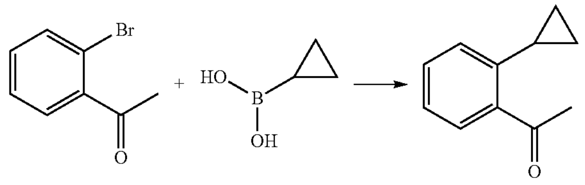

To a solution of 1-(2-bromophenyl)ethan-1-one (2.00 g, 10.0 mmol), cyclopropylboronic acid (1.12 g, 13.0 mmol), $K_3PO_4$ (7.46 g, 35.0 mmol), and tricyclohexyl phosphine (280 mg, 1.0 mmol) in toluene (40 mL) and water (4.0 mL) under a nitrogen atmosphere was added palladium acetate (113 mg, 0.5 mmol). The mixture was heated to 100° C. and stirred at the same temperature for 3 h and then cooled to room temperature. Water (100 mL) was added and the mixture was extracted with ethyl acetate (100 mL×2). The combined organic phase was washed with brine, dried over anhydrous $Na_2SO_4$, and filtered. The filtrate was concentrated under reduced pressure to give the crude. The crude was purified by silica gel column chromatography (PE/EA=10/1) to give the title intermediate (1.40 g, 87.0% yield) as a yellow oil.

LCMS: LC retention time 2.02 min. MS (ESI) m/z 161 $[M+H]^+$.

Intermediate A-5

1-(2-Methyl-6-(trifluoromethyl)phenyl)ethan-1-one

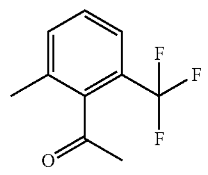

Step 1.

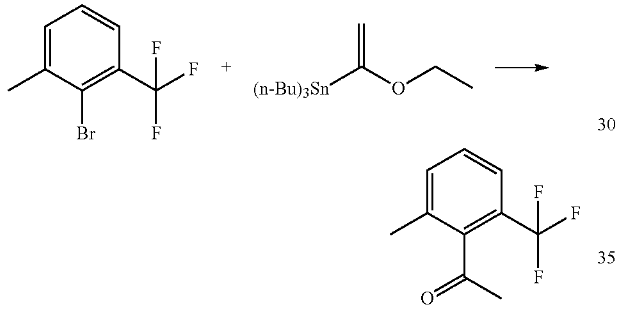

A mixture of 2-bromo-1-methyl-3-(trifluoromethyl)benzene (2.00 g, 8.37 mmol), tributyl(1-ethoxyvinyl)stannane (4.30 g, 11.9 mmol), $Pd(PPh_3)_4$ (194 mg, cat.) in toluene (50 mL) was stirred at 120° C. for 16 h under $N_2$ atmosphere. The mixture was concentrated and the residue was purified by SGC (PE/EA=10/1) to give the intermediate as a light oil. Then it was treated with THF (40 mL) and 6N HCl aqueous (80 mL), the mixture was stirred at room temperature for 6 h. The mixture was extracted with EA (50 mL×3). The organic layers were combined and washed with brine (50 mL×2), dried over $Na_2SO_4$, concentrated to give 1-(2-methyl-6-(trifluoromethyl)phenyl)ethan-1-one as a yellow oil (1.50 g, 88.7%).

Intermediate A-6

1-(2-(Difluoromethyl)-6-methylphenyl)ethan-1-one

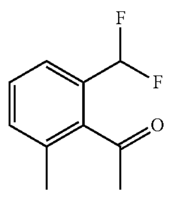

Step 1.

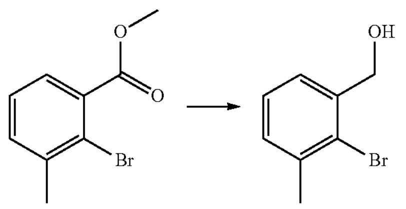

To a solution of methyl 2-bromo-3-methyl-benzoate (7.50 g, 32.7 mmol) in THF (53.6 mL) was added $LiAlH_4$ (1.87 g, 49.1 mmol) at 0° C. The mixture was stirred at room temperature for 3 h. Then added $H_2O$/15% NaOH/$H_2O$ (1:1:3). The mixture was diluted with water (10 mL), and extracted with EtOAc (10 mL×2). The combined organic phases were dried over anhydrous sodium sulfate, filtered, and concentrated in vacuo. The mixture was purified by reversed phase column chromatography to afford the title product (2-bromo-3-methylphenyl)methanol (6.00 g, 91.1%).

LCMS (acid): LC retention time 2.01 min. MS (ESI) m/z 200 $[M+H]^+$.

Step 2.

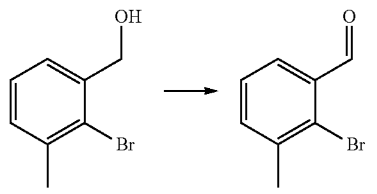

To a solution of (2-bromo-3-methyl-phenyl)methanol (6.00 g, 0.0298 mol) in $CH_2Cl_2$ (60.0 mL) was added Dess-martin Periodinane (12.7 g, 29.8 mol) at 0° C. The mixture was stirred at room temperature for 3 h. Then washed with hydrogen carbonate ammonia solution. The mixture was diluted with water (10 mL), and extracted with EtOAc (10 mL×2). The combined organic phases were dried over anhydrous sodium sulfate, filtered, and concentrated in vacuo. The residue was purified by reversed phase column chromatography to afford the title product 2-bromo-3-methylbenzaldehyde (5.60 g, 94.2%).

LCMS (acid): LC retention time 2.09 min. MS (ESI) m/z 199 $[M+H]^+$.

Step 3.

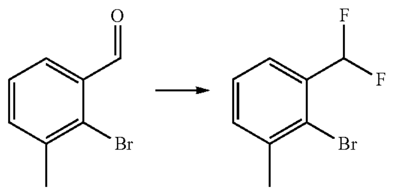

To a solution of 2-bromo-3-methyl-benzaldehyde (5.60 g, 28.1 mmol) in $CH_2Cl_2$ (30.0 mL) was added DAST (6.79 g, 42.2 mmol) at 0° C. The mixture was stirred at room temperature for 3 h. Then the DCM solution was washed with hydrogen carbonate ammonia solution. The mixture was diluted with water (10 mL) and extracted with EtOAc (10 mL×2). The combined organic phases were dried over anhydrous sodium sulfate, filtered, and concentrated in vacuo. The residue was purified by SGC (PE) to afford the title product 2-bromo-1-(difluoromethyl)-3-methylbenzene (4.00 g, 64.3%).

LCMS (acid): LC retention time 2.09 min. MS (ESI) m/z 221 $[M+H]^+$.

Step 4.

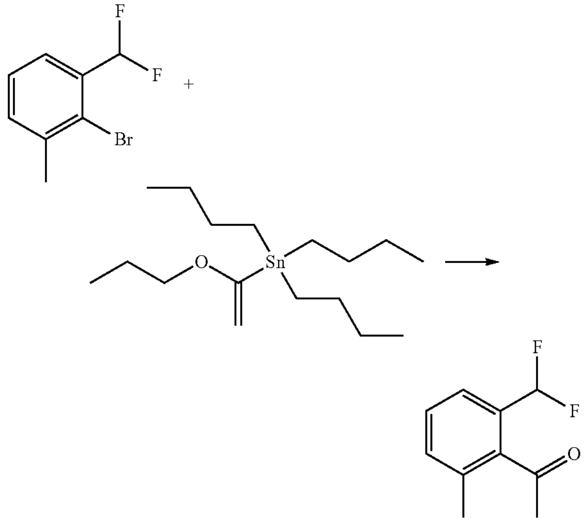

To a solution of 2-bromo-1-(difluoromethyl)-3-methylbenzene (4.00 g, 18.1 mmol) in toluene (20.0 mL) was added Pd $(PPh_3)_4$ (1.05 g, 0.905 mmol) and tributyl (1-ethoxyvinyl)stannane (7.84 g, 21.7 mmol). The mixture was stirred at room temperature for 3 h. Then was added potassium fluoride aqueous solution. The mixture was stirred at room temperature for 3 h. The mixture was diluted with water (10 mL) and extracted with EtOAc (10 mL×2). The combined organic phases were dried over anhydrous sodium sulfate, filtered, and concentrated in vacuo. The mixture was added HCl (12 N) in THF and stirred for 3 h. The mixture was then diluted with water (10 mL) and extracted with EtOAc (10 mL×2). The combined organic phases were dried over anhydrous sodium sulfate, filtered, and concentrated in vacuo. The mixture was purified by SGC (PE) to afford the title product 1-(2-(difluoromethyl)-6-methylphenyl)ethan-1-one (3.00 g).

LCMS (acid): LC retention time 1.97 min. MS (ESI) m/z 184 $[M+H]^+$.

Intermediate A-7

1-(2,6-Dimethyl-4-(trifluoromethyl)phenyl)ethan-1-one

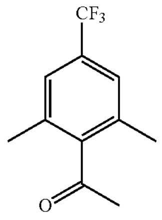

Step 1.

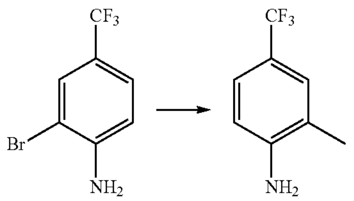

To a solution of 2-bromo-4-(trifluoromethyl)aniline (9.0 g, 37.5 mmol) in 1,4-dioxane (100 mL) and $H_2O$ (50 mL) was added methylboronic acid (3.37 g, 56.2 mmol) and Pd(dppf)$Cl_2$·DCM (613 mg, 0.750 mmol), $Cs_2CO_3$ (18.3 g, 56.2 mmol). The mixture was stirred at 100° C. for 16 h. To the mixture was added water (200 mL). Then, the aqueous solution was extracted with ethyl acetate (200 mL×2). The organic layer was washed with brine (200 mL), dried over sodium sulfate and concentrated in vacuo to obtain 2-methyl-4-(trifluoromethyl)aniline (5.20 g, 63.3%) as a yellow oil.

LCMS: LC retention time 1.92 min. MS (ESI) m/z 176 $[M+H]^+$.

Step 2.

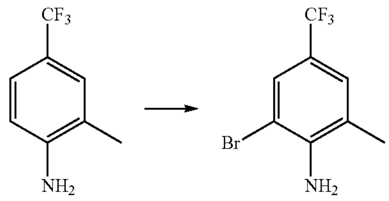

To a solution of 2-methyl-4-(trifluoromethyl)aniline (5.20 g, 23.8 mmol) in $CH_3CN$ (100 mL) was added NBS (6.27 g, 35.6 mmol). The mixture was stirred at rt for 16 h. To the mixture was added water (100 mL) and extracted with ethyl acetate (100 mL×2). The organic layer was washed with brine (100 mL), dried over sodium sulfate and concentrated in vacuo and to give 2-bromo-6-methyl-4-(trifluoromethyl) aniline (5.10 g, 71.8% yield) as a yellow oil.

LCMS: LC retention time 2.19 min. MS (ESI) m/z 256 $[M+H]^+$.

Step 3.

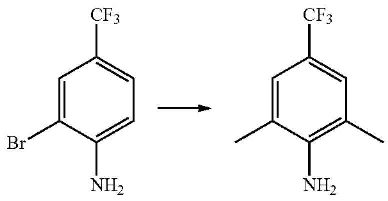

To a solution of 2-bromo-6-methyl-4-(trifluoromethyl) aniline (5.1 g, 20.1 mmol) in 1,4-dioxane (100 mL) and $H_2O$ (50 mL) was added methylboronic acid (1.81 g, 30.1 mmol) and Pd(dppf)$Cl_2$·DCM (328 mg, 0.402 mmol), $Cs_2CO_3$ (9.82 g, 30.1 mmol). The mixture was stirred at 100° C. for 16 h. To the mixture was added water (200 mL), then extracted with ethyl acetate (200 mL×2). The organic layer was washed with brine (200 mL), dried over sodium sulfate and concentrated in vacuo and to give 2,6-dimethyl-4-(trifluoromethyl)aniline (3.60 g, 75.8% yield) as a yellow oil. The crude was used next step directly without further purification.

LCMS: LC retention time 2.01 min. MS (ESI) m/z 190 $[M+H]^+$.

Step 4.

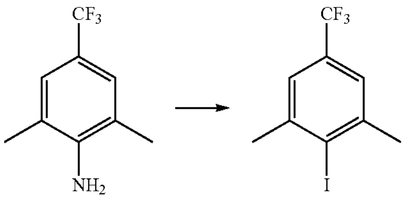

To a solution of 2,6-dimethyl-4-(trifluoromethyl)aniline (3.6 g, 19.0 mmol) in HCl (50 mL) and water (50 mL) was cooled at 0° C. Sodium nitrite (3.94 g, 57.1 mmol) aqueous solution was added dropwise. The mixture was stirred at current temperature for 20 min. KI (6.32 g, 38.1 mmol) aqueous solution was added dropwise. The mixture was stirred at room temperature for 3 h. To the mixture was added water (100 mL) and extracted with ethyl acetate (100 mL×2). The organic layer was washed with brine (200 mL), dried over sodium sulfate and concentrated in vacuo. The residue was purified by SGC (PE/EA=10:1) to give 2-iodo-1,3-dimethyl-5-(trifluoromethyl)benzene (3.00 g, 52.5% yield) as a yellow oil.

Step 5.

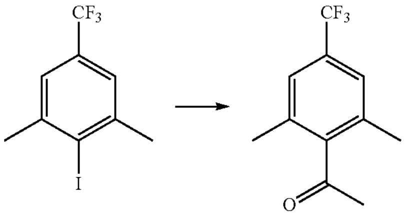

To a solution of 2-iodo-1,3-dimethyl-5-(trifluoromethyl)benzene (3.0 g, 10.0 mmol) in toluene (80 mL) were added tributyl(1-ethoxyvinyl)stannane (5.42 g, 15.0 mmol) and $Pd(PPh_3)_4$ (119 mg, 0.1 mmol). The mixture was stirred at 100° C. for 16 h under Ar. Then, the reaction was cooled to rt and concentrated HCl (20.0 mL) was added. The mixture was stirred at rt for 6 h and extracted with $Et_2O$ (100 mL). The organic layer was washed with water (100 mL), brine (100 mL), dried over $Na_2SO_4$, filtered and concentrated. The residue was purified by silica gel column chromatography (PE) to afford the title compound (1.70 g, 77.9%) as a colorless oil.

$^1H$ NMR (400 MHz, chloroform-d): δ 7.29 (s, 2H), 2.49 (s, 3H), 2.30 (s, 6H) ppm.

Intermediate A-8

1-(2-Chloro-6-(trifluoromethyl)phenyl)ethan-1-one

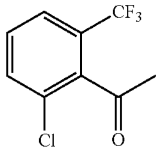

Step 1.

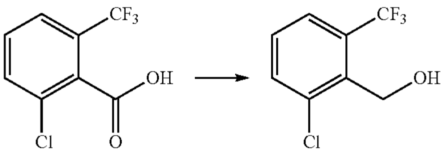 [SMILES: O=C(O)c1c(Cl)cccc1C(F)(F)F ; OCc1c(Cl)cccc1C(F)(F)F]

Borane-methyl sulfide complex (44.6 mL, 89.2 mmol, 2.0 M) was added dropwise to the solution of 2-chloro-6-(trifluoromethyl)benzoic acid (5.0 g, 22.3 mmol) at 0° C. under argon atmosphere. The resulting mixture was stirred at 60° C. for 27 h. LCMS indicated the reactant was remained. Then, borane-methyl sulfide complex (33.5 mL, 66.9 mmol, 2.0 M) was added dropwise at 0° C. The resulting mixture was reacted at 60° C. for 65 h. After cooling to room temperature, the reaction mixture was adjusted to about pH=11 with 2.0 M sodium hydroxide solution, diluted with water (200 mL), extracted with diethyl ether (100 mL×3). The combined organic layers were washed with brine (100 mL×2), dried over sodium sulfate, filtered and concentrated under reduced pressure to afford the product (2-chloro-6-(trifluoromethyl)phenyl)methanol as a brown solid (6.23 g).

LCMS: LC retention time 1.89 min. MS (ESI) m/z 193 $[M-17]^+$.

Step 2.

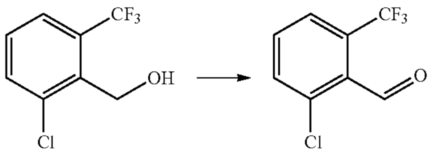 [SMILES: OCc1c(Cl)cccc1C(F)(F)F ; O=Cc1c(Cl)cccc1C(F)(F)F]

Dess-Martin Periodinane (18.9 g, 44.6 mmol) was added to the solution of (2-chloro-6-(trifluoromethyl)phenyl)methanol (6.23 g, 22.3 mmol) in dichloromethane (50 mL) at room temperature. The resulting reaction mixture was stirred at room temperature for 19 h. The solvent was removed under reduced pressure, the residue was suspended in diethyl ether (50 mL), and stirred for 10 min. Then the white solid resulting was filtered through Celite, washed with diethyl ether and the solvent was evaporated under reduced pressure. The residue was purified by silica gel chromatography (6% ethyl acetate in petroleum ether) to give 2-chloro-6-(trifluoromethyl)benzaldehyde as a light yellow oil (3.47 g, 75% yield, two steps).

LCMS: LC retention time 1.95 min. MS (ESI) m/z not observed.

$^1H$ NMR (400 MHz, chloroform-d) δ 10.50 (s, 1H), 7.72-7.66 (m, 2H), 7.58 (t, J=8.0 Hz, 1H) ppm.

Step 3.

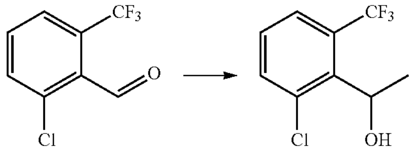

MeMgBr (27.8 mL, 3.0 M solution in diethyl ether, 83.4 mmol) was added dropwise to the solution of 2-chloro-6-(trifluoromethyl)benzaldehyde (3.47 g, 16.7 mmol) in anhydrous tetrahydrofuran (40.0 mL) at 0° C. under argon atmosphere. The resulting mixture was stirred at room temperature overnight. Quenched with saturated aqueous ammonium chloride solution (40 mL), and diluted with water (30 mL), extracted with ethyl acetate (40 mL×3). The combined organic layers were washed with brine (70 mL), dried over sodium sulfate, filtered and concentrated under reduced pressure to give the desired product 1-(2-chloro-6-(trifluoromethyl)phenyl)ethan-1-ol as a light yellow oil (3.78 g).

LCMS: LC retention time 2.08 min. MS (ESI) m/z 207 $[M-OH]^+$.

Step 4.

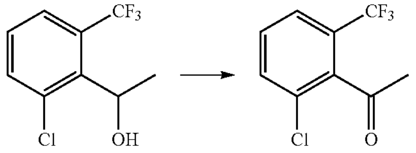

Dess-Martin Periodinane (14.2 g, 33.4 mmol) was added portion-wise to the solution of 1-(2-chloro-6-(trifluoromethyl)phenyl)ethan-1-ol (3.78 g, crude, 16.7 mmol) in dichloromethane (40.0 mL) at 0° C. The resulting reaction mixture was stirred at room temperature for 3 h. The solvent was removed under reduced pressure. The residue was suspended in diethyl ether (40 mL). The resulting mixture was stirred for 10 min. Then the resulting white solid was filtered through Celite, washed with diethyl ether. The filtrate was evaporated under reduced pressure. The crude product was purified by silica gel chromatography (10% ethyl acetate in petroleum ether) to give 1-(2-chloro-6-(trifluoromethyl)phenyl)ethan-1-one as a light yellow oil (2.63 g, 71% yield, two steps).

LCMS: LC retention time 2.15 min. MS (ESI) m/z 223 $[M+H]^+$.

Intermediate A-9

1-(2-Isopropoxyphenyl)ethan-1-one

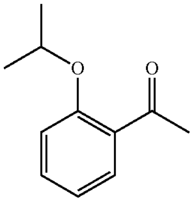

Step 1.

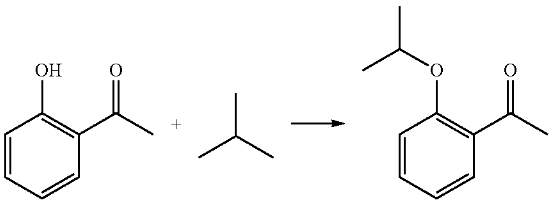

A mixture of 1-(2-hydroxyphenyl)ethan-1-one (4.0 g, 29.4 mmol), 2-iodopropane (6.49 g, 38.2 mmol) and $K_2CO_3$ (8.12 g, 58.8 mmol) in DMF (60 mL) was stirred at 80° C. for 16 h. The mixture was quenched with brine (300 mL), extracted with ethyl acetate (150 mL×2), dried over anhydrous $Na_2SO_4$, and then filtered and concentrated. The crude product was purified by silica gel chromatography (PE/EA=10/1) to give the desired compound 1-(2-isopropoxyphenyl)ethan-1-one (4.41 g, 84.2%) as a light yellow oil.

$^1$H NMR (400 MHz, chloroform-d) δ 7.72 (dd, J=7.9, 1.8 Hz, 1H), 7.42 (td, J=8.1, 1.8 Hz, 1H), 6.95 (t, J=7.6 Hz, 2H), 4.69 (dt, J=12.1, 6.1 Hz, 1H), 2.622 (s, 3H), 1.40 (d, J=6.1 Hz, 1H) ppm.

Intermediate B-1

5-Iodo-4-(2-isopropylphenyl)thiazol-2-amine

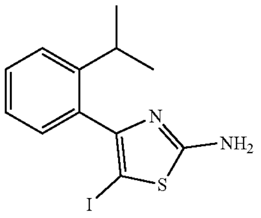 [SMILES: CC(C)c1ccccc1-c1nc(N)sc1I]

Step 1.

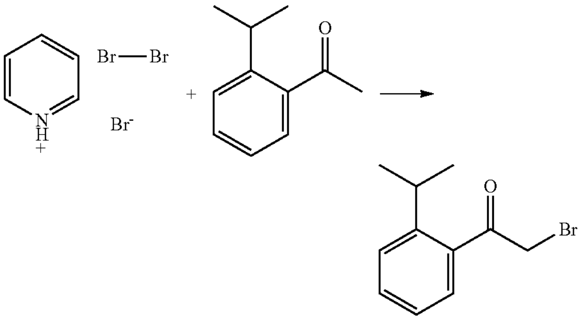

To a solution of 1-(2-isopropylphenyl)ethan-1-one (835 mg, 5.15 mmol) in DCM (8.0 mL) was added pyridine hydrobromide perbromide (1.64 g, 5.15 mmol). The resulting mixture was stirred at room temperature for 2 h. The mixture was poured into water (50 mL) and extracted with DCM (50 mL×2). The extracts were washed with water (40 mL×2), dried over sodium sulfate and evaporated. The resulting crude product was purified by silica gel chromatography (PE/EA=10/1) to afford 2-bromo-1-(2-isopropylphenyl)ethan-1-one (1167 mg, 93.9%) as colorless oil.

LCMS: MS (ESI): m/z 243 $[M+H]^+$.

Step 2.

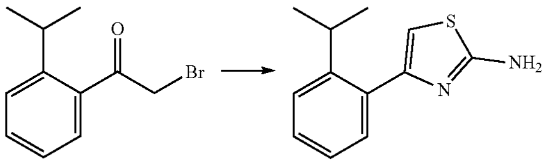

To a solution of 2-bromo-1-(2-isopropylphenyl)ethan-1-one (1.17 g, 4.84 mmol) in ethanol (12 mL) was added thiourea (741 mg, 9.74 mmol). The resulting mixture was stirred at room temperature overnight. The mixture was basified by aqueous NaOH (2.0 M) to pH=12, extracted with ethyl acetate (10 mL×4). The combined organic phases were washed with aqueous $Na_2S_2O_3$ (20 mL×2), $H_2O$ (20 mL), brine (20 mL), dried over anhydrous sodium sulphate, filtered, and concentrated in vacuo. The resulting residue was purified by silica gel chromatography (PE/EA=5/1) to afford 4-(2-isopropylphenyl)thiazol-2-amine (1.00 g, 94.7%) as a light yellow solid.

LCMS: Retention time 2.24 min; MS (ESI): m/z 219 $[M+H]^+$.

Step 3.

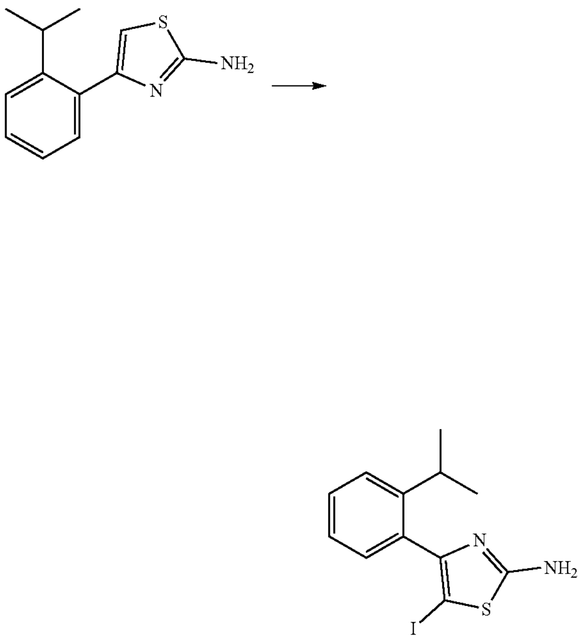

To a solution of 4-(2-isopropylphenyl)thiazol-2-amine (1250 mg, 5.73 mmol) in DCM (20 mL) was added NIS (1.48 mg, 6.61 mmol) and AIBN (150 mg, 0.914 mmol) at room temperature. Then the reaction mixture was stirred at the same temperature for 3 h. The mixture was extracted with EA (200 mL×2), washed with brine (200 mL) and dried over anhydrous $Na_2SO_4$. The filtrate was concentrated and purified by silica gel chromatography (PE/EA=5/1) to afford 5-iodo-4-(2-isopropylphenyl)thiazol-2-amine (1286 mg, 65.2%) as a yellow solid.

LCMS: MS (ESI) m/z 345 $[M+H]^+$

Intermediate B-2a

5-Bromo-4-(2,6-dimethylphenyl)thiazol-2-amine

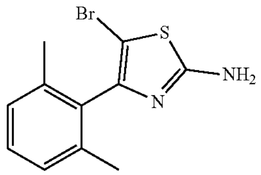

Intermediate B-2b 4-(2,6-Dimethylphenyl)-5-iodothiazol-2-amine

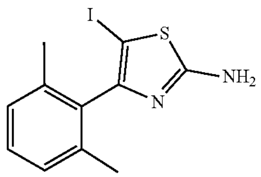

Step 1.

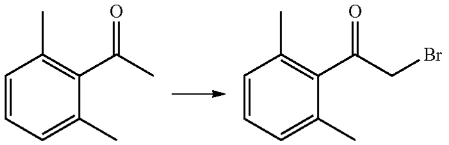

1-(2,6-dimethylphenyl)ethan-1-one (5.00 g, 33.78 mmol) was dissolved in acetonitrile (60 mL). To this solution was added pyridinium tribromide (10.81 g, 33.78 mmol). The mixture was stirred overnight at room temperature until the solution turned light yellow or colorless. The solvent was extracted with dichloromethane (200 mL) and washed with water (300 mL). The organic layers were combined and concentrated under vacuum to provide 2-bromo-1-(2,6-dimethylphenyl)ethan-1-one (7.29 g, 82.1%) as a yellow oil.

LCMS: LC retention time 2.06 min. MS (ESI) m/z 229 $[M+H]^+$.

Step 2.

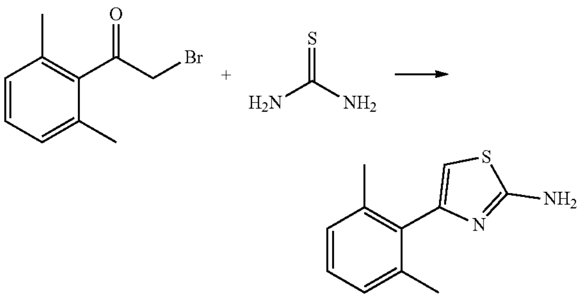

To a solution of 2-bromo-1-(2,6-dimethylphenyl)ethan-1-one (7.29 g, 32.11 mmol) in ethanol (75 mL) was added thiourea (2.44 g, 32.11 mmol) and the reaction mixture was refluxed for 2 h. After the solvent was removed, the resulting white precipitate was suspended and washed in water/saturated aqueous $NaHCO_3$ (30/70, 250 mL) for 1 h. The solution was extracted with ethyl acetate (200 mL×3). The combined organic phase was dried over anhydrous $Na_2SO_4$, filtered, and the filtrate was concentrated to give the crude which was purified by silica gel chromatography (PE/EA=1/1) to give 4-(2,6-dimethylphenyl)thiazol-2-amine (5.30 g, 80.8%) as a yellow solid.

LCMS: LC retention time 1.45 min. MS (ESI) m/z 205 $[M+H]^+$.

Step 3a.

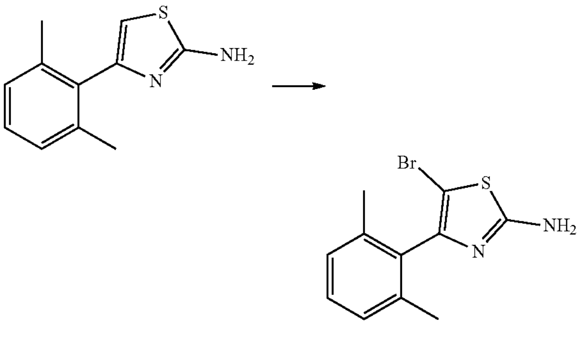

To a solution of 4-(2,6-dimethylphenyl)thiazol-2-amine (1.0 g, 4.90 mmol) in anhydrous tetrahydrofuran (20 mL) was added NBS (872.5 mg, 4.90 mmol). After stirring at room temperature overnight, the mixture was partitioned between ethyl acetate (100 mL) and water (80 mL). The organic phase was washed with water (150 mL×2), dried over anhydrous $Na_2SO_4$, filtered, and the filtrate was concentrated under reduced pressure to give the crude, which was purified by silica gel chromatography (PE/EA=3/1) to give 5-bromo-4-(2,6-dimethylphenyl)thiazol-2-amine (0.964 g, 69.5%) as a light yellow solid.

LCMS: LC retention time 1.92 min. MS (ESI) m/z 285 $[M+H]^+$.

Step 3b.

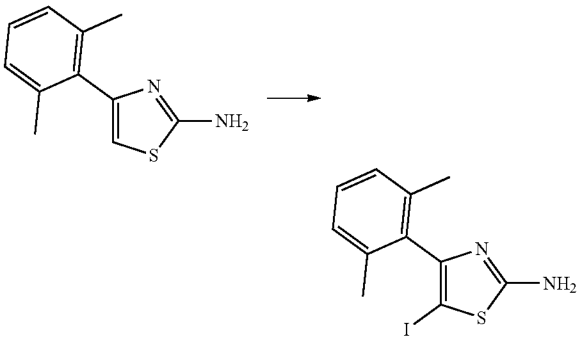

To a solution of 4-(2,6-dimethylphenyl)thiazol-2-amine (500 mg, 2.45 mmol) in tetrahydrofuran (5.0 mL) was added N-iodosuccinimide (551 mg, 2.45 mmol), and the resulting mixture was reacted at room temperature for 3 h. The reaction was quenched by addition of water (50 mL), extracted with ethyl acetate (50 mL×2). The combined organic layers were washed with brine, dried over anhydrous sodium sulfate, concentrated in vacuo (control the temperature around 40° C.) and purified by silica gel column chromatography (PE/EA=5/1) to provide the title compound, 4-(2,6-dimethylphenyl)-5-iodothiazol-2-amine (600 mg, 74%) as a brown solid.

LCMS: LC retention time 1.85 min. MS (ESI) m/z 331 $[M+H]^+$.

Intermediate B-3

4-(2,6-Dimethyl-4-(trifluoromethyl)phenyl)-5-iodothiazol-2-amine

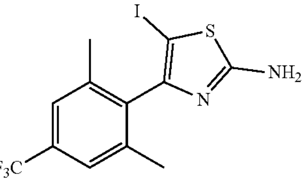

Step 1.

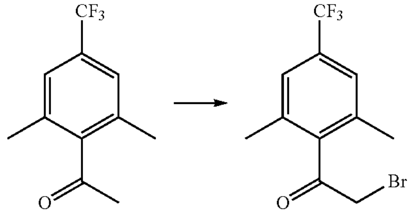

To a solution of 1-(2,6-dimethyl-4-(trifluoromethyl)phenyl)ethan-1-one (Intermediate A-7) (1.7 g, 6.29 mmol) in acetonitrile (60 mL), was added pyridinium tribromide (2.01 g, 6.29 mmol). The mixture was stirred overnight at room temperature. The solvent was removed in vacuo; the residue was extracted with dichloromethane (50 mL×2) and washed with water (100 mL). The organic layers were combined and concentrated under vacuum to provide the crude 2-bromo-1-(2,6-dimethyl-4-(trifluoromethyl)phenyl)ethan-1-one (1.90 g).

Step 2.

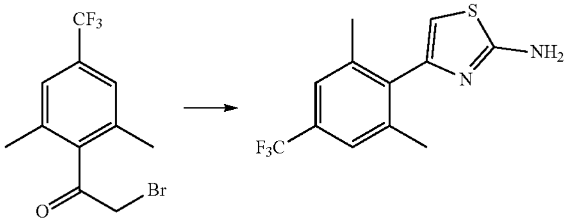 [SMILES: Cc1cc(C(F)(F)F)cc(C)c1C(=O)CBr ; Cc1cc(C(F)(F)F)cc(C)c1-c1csc(N)n1]

To a solution of 2-bromo-1-(2,6-dimethyl-4-(trifluoromethyl)phenyl)ethan-1-one (1.90 g, 4.51 mmol) in ethanol (50.0 mL) was added thiourea (377 mg, 4.96 mmol) and the mixture was refluxed for 4 h. After the solvent was removed in vacuo. The residue was stirred with saturated aqueous sodium bicarbonate (40 mL) for 20 min. Then, the mixture was extracted with ethyl acetate (50 mL×2). The combined organic solution was washed with brine, dried over anhydrous sodium sulfate, concentrated in vacuo and purified by silica gel column chromatography (silica gel, PE/EA=3:1) to obtain the title compound, 4-(2,6-dimethyl-4-(trifluoromethyl)phenyl)thiazol-2-amine (1.10 g, 89.6% yield) as a colorless solid.

LCMS: LC retention time 1.68 min. MS (ESI) m/z 273 $[M+H]^+$.

Step 3.

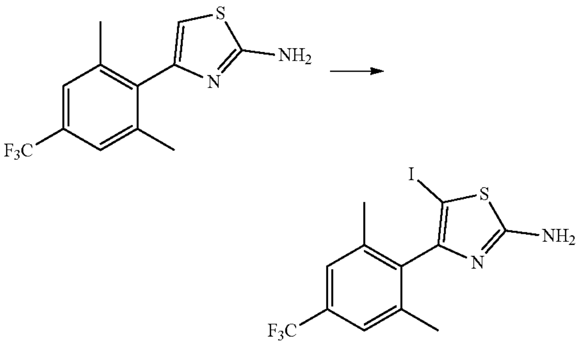

To a solution of 4-(2,6-dimethyl-4-(trifluoromethyl)phenyl)thiazol-2-amine (1.30 g, 4.77 mmol) in $CH_3CN$ (60 mL) was added NIS (1.07 g, 4.77 mmol). The mixture was stirred at rt for 16 h. Then, the solvent was removed on a rotavapor. To the residue was added water (100 mL) and extracted with EA (100 mL). The organic layer was washed with brine (100 mL), dried over $Na_2SO_4$, filtered and to purified by silica gel column chromatography (PE/EA=3:1) to obtain 4-(2,6-dimethyl-4-(trifluoromethyl)phenyl)-5-iodothiazol-2-amine (1.30 g, 61.5%) as a yellow solid.

LCMS: LC retention time 2.15 min. MS (ESI) m/z 399 $[M+H]^+$.

Intermediate B-4

5-Iodo-4-(2-methyl-6-(trifluoromethyl)phenyl)thiazol-2-amine

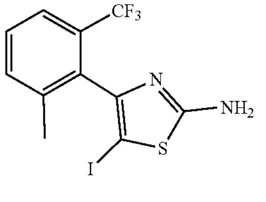 [SMILES: Cc1cccc(C(F)(F)F)c1-c1nc(N)sc1I]

Step 1.

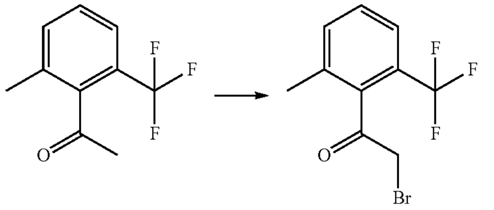

To a mixture of 1-[2-methyl-6-(trifluoromethyl)phenyl]ethanone (Intermediate A5) (1.50 g, 7.42 mmol) in $CH_3CN$ (40 mL) was slowly added pyridinium tribromide (2.37 g, 7.42 mmol) at 0° C. The resulting mixture was stirred at room temperature for 12 h, The mixture was concentrated. The residue was diluted with brine (70 mL), extracted with EA (50 mL×3), dried over $Na_2SO_4$, concentrated to give 2-bromo-1-[2-methyl-6-(trifluoromethyl)phenyl]ethanone as a brown solid (1.80 g, 86.3%).

LCMS: LC retention time 2.109 min. MS (ESI) m/z 281 $[M+H]^+$.

Step 2.

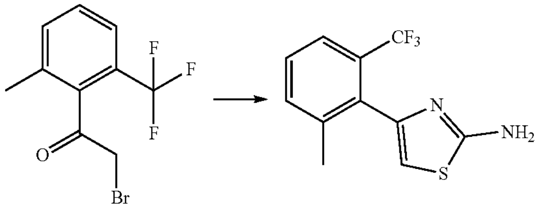 [SMILES: Cc1cccc(C(F)(F)F)c1C(=O)CBr ; Cc1cccc(C(F)(F)F)c1-c1csc(N)n1]

A solution of 2-bromo-1-[2-methyl-6-(trifluoromethyl)phenyl]ethanone (1.8 g, 6.4 mmol), thiourea (487 mg, 6.4 mmol) in ethanol (30 mL) was stirred at 80° C. for 16 h. The mixture was concentrated and the residue was purified by SGC (PE/EA=2/1) to give 4-[2-methyl-6-(trifluoromethyl)phenyl]thiazol-2-amine as a yellow solid (700 mg, 42.3%).

LCMS: LC retention time 1.85 min. MS (ESI) m/z 259 $[M+H]^+$.

Step 3.

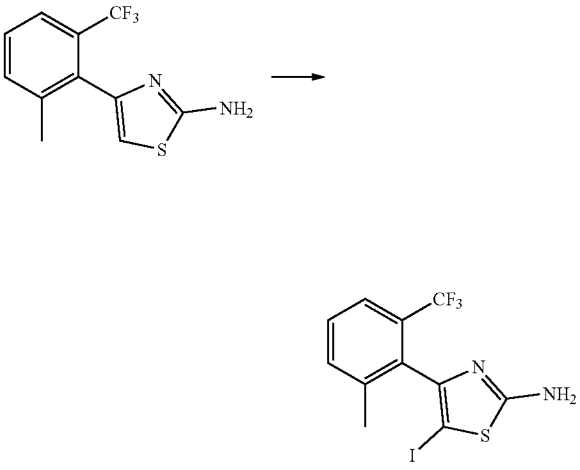

To a solution of 4-[2-methyl-6-(trifluoromethyl)phenyl]thiazol-2-amine (700 mg, 2.71 mmol) in THF (20 mL) was added NIS (732 mg, 3.25 mmol) at room temperature. After addition, the mixture was stirred for 12 h. The mixture was dried with blowing $N_2$. The residue was diluted with brine (60 mL), extracted with EA (40 mL×3), the organic layers were combined and washed with brine (40 mL×3), dried over $Na_2SO_4$, concentrated to give 5-iodo-4-(2-methyl-6-(trifluoromethyl)phenyl)thiazol-2-amine as a brown solid (960 mg, 92.2%).

LCMS: LC retention time 1.686 min. MS (ESI) m/z 385 $[M+H]^+$.

Intermediate B-5

5-Bromo-4-(2-(difluoromethyl)-6-methylphenyl)thiazol-2-amine

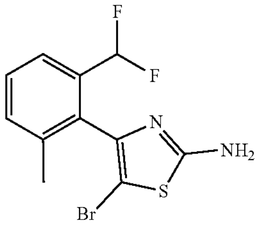 [SMILES: Cc1cccc(C(F)F)c1-c1nc(N)sc1Br]

Step 1.

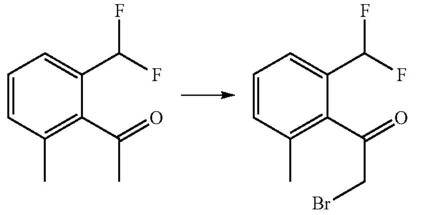

To a solution of 1-[2-(difluoromethyl)-6-methyl-phenyl]ethanone (Intermediate A-6) (3.00 g, 0.0163 mol) in $CH_2Cl_2$ (30.0 mL) was added pyridinium tribromide (3.19 g, 0.0179 mol). The mixture was stirred at room temperature for 1 h. The mixture was diluted with water (10 mL). The aqueous solution was extracted with EtOAc (10 mL×2). The combined organic phases were dried over anhydrous sodium sulfate, filtered, and concentrated in vacuo to afford the title compound 2-bromo-1-(2-(difluoromethyl)-6-methylphenyl)ethan-1-one (3.70 g).

LCMS (acid): LC retention time 2.03 min. MS (ESI) m/z 262 $[M+H]^+$.

Step 2.

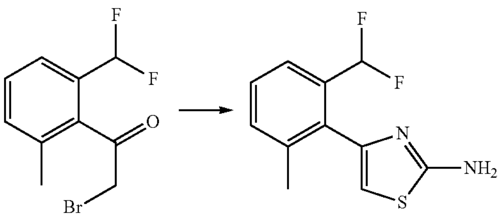 [SMILES: Cc1cccc(C(F)F)c1C(=O)CBr ; Cc1cccc(C(F)F)c1-c1csc(N)n1]

To a solution of 2-bromo-1-(2-(difluoromethyl)-6-methylphenyl)ethan-1-one (3.70 g, 14.1 mmol) in EtOH (30.0 mL) was added thiourea (1.07 g, 14.1 mmol). The mixture was stirred at room temperature for 1 h. The mixture was diluted with water (10 mL). The aqueous solution was extracted with EtOAc (10 mL×2). The combined organic phases were dried over anhydrous sodium sulfate, filtered, and concentrated in vacuo. The crude product was purified by SGC (PE/EA=3/1) to afford the title product 4-(2-(difluoromethyl)-6-methylphenyl)thiazol-2-amine (2.70 g).

LCMS (acid): LC retention time 1.60 min. MS (ESI) m/z241 $[M+H]^+$.

Step 3.

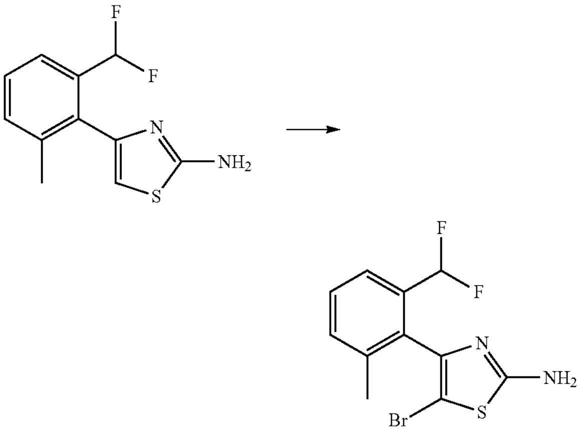 [SMILES: Cc1cccc(C(F)F)c1-c1csc(N)n1 ; Cc1cccc(C(F)F)c1-c1nc(N)sc1Br]

To a solution of 4-[2-(difluoromethyl)-6-methyl-phenyl]thiazol-2-amine (2.70 g, 0.0112 mol) in THF (30.0 mL) was added NBS (2.00 g, 11.2 mmol). The mixture was stirred at room temperature for 1 h. The mixture was diluted with water (10 mL). The aqueous solution was extracted with EtOAc (10.0 mL×2). The combined organic phases were dried over anhydrous sodium sulfate, filtered, and concentrated in vacuo. The crude product was purified by SGC (PE/EA=3/1) to afford the title product 5-bromo-4-(2-(difluoromethyl)-6-methylphenyl)thiazol-2-amine (2.20 g, 61.3%).

LCMS (acid): LC retention time 2.04 min. MS (ESI) m/z320 $[M+H]^+$.

Intermediate B-6

5-Iodo-4-(2-isopropoxy-6-methylphenyl)thiazol-2-amine

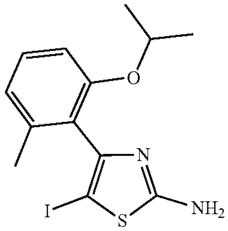 [SMILES: Cc1cccc(OC(C)C)c1-c1nc(N)sc1I]

Step 1.

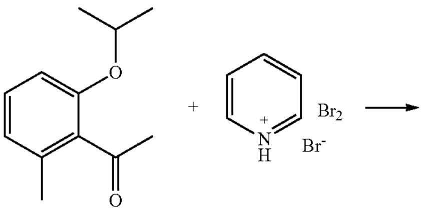

-continued

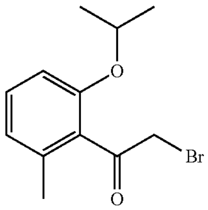

To a solution of 1-(2-isopropoxy-6-methylphenyl)ethan-1-one (3.14 mg, 16.3 mmol) in acetonitrile (30 mL) was added pyridinium tribromide (5.21 g, 16.3 mmol) at room temperature. The resulting mixture was stirred at room temperature for 17 h. LCMS indicated 1-(2-isopropoxy-6-methylphenyl)ethanone was remained, and pyridinium tribromide (1.56 g, 4.89 mmol) was added additionally at room temperature. The resulting mixture was stirred at room temperature for another 3 h. The reaction was quenched with saturated aqueous sodium bicarbonate solution (30 mL), diluted with water (50 mL), and extracted with ethyl acetate (40 mL×3). The combined organic layers were washed with brine (60 mL), dried over sodium sulfate, filtered and concentrated under reduced pressure to afford the crude product 2-bromo-1-(2-isopropoxy-6-methylphenyl)ethan-1-one as a yellow oil (4.882 g).

LCMS: LC retention time 2.20 min. MS (ESI) m/z 273 $[M+H]^+$.

Step 2.

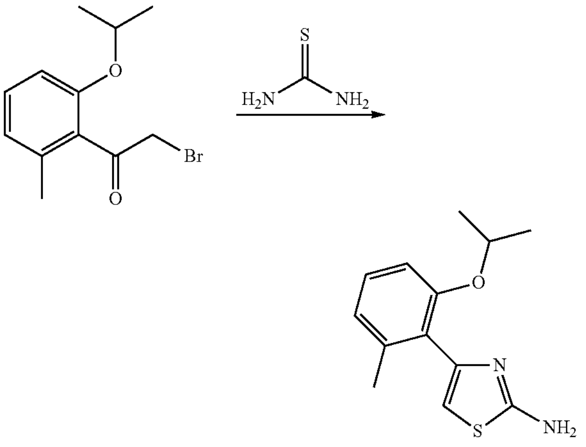

To a solution of 2-bromo-1-(2-isopropoxy-6-methylphenyl)ethan-1-one (4.88 g, crude, 16.4 mmol) in ethanol (25 mL) was added thiourea (1.87 g, 24.6 mmol). The resulting mixture was stirred at 80° C. for 3 h. The solvent was removed under reduced pressure, diluted with water (30 mL), and saturated aqueous sodium bicarbonate solution (40 mL). The aqueous solution was extracted with ethyl acetate (40 mL×3) The combined organic layers were washed with brine (60 mL), dried over sodium sulfate, filtered and concentrated under reduced pressure, the residue was purified by silica gel chromatography (35% ethyl acetate in petroleum ether) to give 4-(2-isopropoxy-6-methylphenyl)thiazol-2-amine as a white solid (3.21 g, 80% yield over 2 steps).

LCMS: LC retention time 2.05 min. MS (ESI) m/z 387 $[M+H]^+$ $^1$H NMR (400 MHz, chloroform-d) δ 7.16 (t, J=8.0 Hz, 1H), 6.84 (d, J=7.6 Hz, 1H), 6.80 (d, J=8.4 Hz, 1H), 6.40 (s, 1H), 4.96 (s, 2H), 4.32 (m, 1H), 2.21 (s, 3H), 1.19 (d, J=6.0 Hz, 6H) ppm.

Step 3.

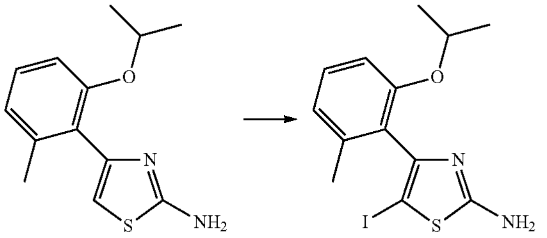 [SMILES: Cc1cccc(OC(C)C)c1-c1csc(N)n1 ; Cc1cccc(OC(C)C)c1-c1nc(N)sc1I]

To a solution of 4-(2-isopropoxy-6-methylphenyl)thiazol-2-amine (3.21 g, 12.9 mmol) in tetrahydrofuran (30 mL) was added 1-iodopyrrolidine-2,5-dione (2.9 g, 12.9 mmol) at 0° C. The resulting mixture was stirred at room temperature for 1.5 h, and additional 1-iodopyrrolidine-2,5-dione (0.871 g, 3.87 mmol) was added at room temperature. The resulting reaction mixture was stirred at room temperature for another 40 min. The reaction was quenched with saturated aqueous sodium bicarbonate solution (30 mL), diluted with water (40 mL), and extracted with ethyl acetate (3×30 mL), the combined organic layers were washed with saturated aqueous sodium bicarbonate solution (60 mL), and brine (60 mL), dried over anhydrous sodium sulfate, filtered and concentrated under reduced pressure to give the product 5-iodo-4-(2-isopropoxy-6-methylphenyl)thiazol-2-amine as a brown solid (5.54 g).

LCMS: LC retention time 1.79 min. MS (ESI) m/z 375 $[M+H]^+$.

$^1$H NMR (400 MHz, chloroform-d) δ 7.22 (t, J=8.0 Hz, 1H), 6.85 (d, J=7.6 Hz, 1H), 6.79 (d, J=8.4 Hz, 1H), 5.36 (br, 2H), 4.38 (m, 1H), 2.09 (s, 3H), 1.22 (d, J=5.2 Hz, 6H) ppm.

Intermediate B-7

4-(2-Chloro-6-(trifluoromethyl)phenyl)-5-iodothiazol-2-amine

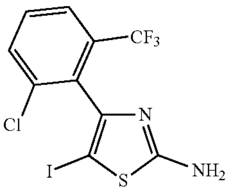 [SMILES: Nc1nc(-c2c(Cl)cccc2C(F)(F)F)c(I)s1]

Step 1.

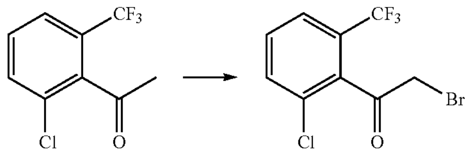

To a solution of 1-(2-chloro-6-(trifluoromethyl)phenyl) ethan-1-one (2.625 g, 11.8 mmol) in acetonitrile (20.0 mL)

was added pyridinium tribromide (4.53 g, 14.2 mmol) at room temperature. The resulting mixture was stirred at room temperature overnight. The solvent was removed. Saturated aqueous sodium bicarbonate solution (50 mL) and water (40 mL) were added. The aqueous solution was then extracted with ethyl acetate (40 mL×3). The combined organic layers were washed with brine (80 mL), dried over sodium sulfate, filtered and concentrated under reduced pressure to afford the product 2-bromo-1-(2-chloro-6-(trifluoromethyl)phenyl) ethan-1-one as yellow oil (3.32 g).

LCMS: LC retention time 2.17 min. MS (ESI) m/z 301 $[M+H]^+$.

Step 2.

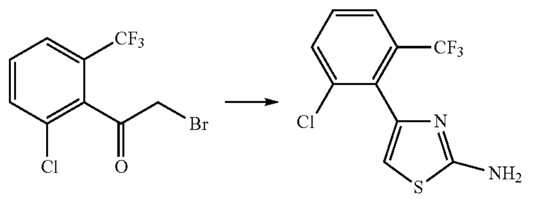 [SMILES: O=C(CBr)c1c(Cl)cccc1C(F)(F)F ; Nc1nc(-c2c(Cl)cccc2C(F)(F)F)cs1]

To a solution of 2-bromo-1-(2-chloro-6-(trifluoromethyl) phenyl)ethan-1-one (3.32 g, 11.0 mmol) in ethanol (24 mL) was added thiourea (1.26 g, 16.5 mmol). The reaction was stirred at 80° C. for 70 h. The solvent was removed under reduced pressure, diluted with water (70 mL), and saturated aqueous sodium bicarbonate solution (40 mL). The aqueous solution was extracted with ethyl acetate (40 mL×3). The combined organic layers were washed with brine (80 mL), dried over sodium sulfate, filtered and concentrated under reduced pressure. The residue was purified by silica gel chromatography (33% ethyl acetate in petroleum ether) to give 4-(2-chloro-6-(trifluoromethyl)phenyl)thiazol-2-amine as a brown solid (2.17 g, 67% yield over two steps).

LCMS: LC retention time 1.81 min. MS (ESI) m/z 279 $[M+H]^+$.

$^1$H NMR (400 MHz, chloroform-d) δ 7.65-7.63 (m, 2H), 7.42 (m, 1H), 6.49 (s, 1H), 5.06 (s, 2H) ppm.

Step 3.

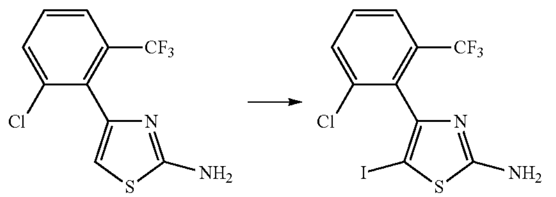 [SMILES: Nc1nc(-c2c(Cl)cccc2C(F)(F)F)cs1 ; Nc1nc(-c2c(Cl)cccc2C(F)(F)F)c(I)s1]

To a solution of 4-(2-chloro-6-(trifluoromethyl)phenyl) thiazol-2-amine (2.18 g, 7.81 mmol) in tetrahydrofuran (20 mL) was added 1-iodopyrrolidine-2,5-dione (2.11 g, 9.37 mmol) at 0° C. The resulting mixture was stirred at room temperature for 1 h. The reaction was quenched with saturated aqueous sodium bicarbonate solution (30 mL), diluted with water (30 mL), and extracted with ethyl acetate (30 mL×3) The combined organic layers were washed with brine (60 mL), dried over anhydrous sodium sulfate, filtered and concentrated under reduced pressure to give a brown solid, which was suspended in petroleum ether (30 mL) and dichloromethane (0.5 mL), and stirred for 30 min. at room temperature. After filtration, the product 4-(2-chloro-6-(trifluoromethyl)phenyl)-5-iodothiazol-2-amine was obtained as a brown solid (3.14 g).

LCMS: LC retention time=2.04 min. MS (ESI) m/z=405 $[M+H]^+$.

$^1$H NMR (400 MHz, chloroform-d) δ 7.68 (m, 2H), 7.48 (t, J=8.0 Hz, 1H), 5.22 (br, s, 2H) ppm.

Intermediate B-8

5-Bromo-4-(2-isopropoxyphenyl)thiazol-2-amine

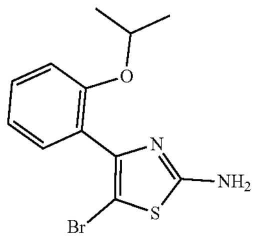 [SMILES: CC(C)Oc1ccccc1-c1nc(N)sc1Br]

Step 1.

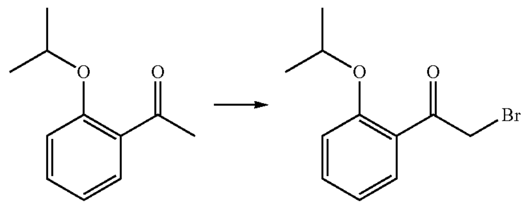

To a solution of 1-(2-isopropoxyphenyl)ethan-1-one (1.78 g, 10 mmol) in acetonitrile (50 mL), was added pyridinium tribromide (3.20 g, 10 mmol). The mixture was stirred overnight under room temperature until the solution turned light yellow or colorless. The solution was extracted with dichloromethane (100 mL×3). The DCM solution was washed with water (80 mL). The organic layers were combined and concentrated under vacuum to provide 2-bromo-1-(2-isopropoxyphenyl)ethan-1-one (2.41 g, 93.8%) as a yellow oil.

LCMS: LC retention time 2.10 min. MS (ESI) m/z 257 $[M+H]^+$.

Step 2.

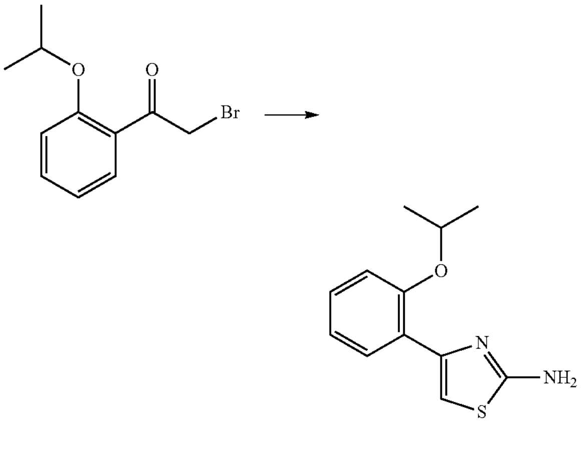

To a solution of 2-bromo-1-(2-isopropoxyphenyl)ethan-1-one (2.41 g, 9.38 mmol) in ethanol (50 mL) was added thiourea (742 mg, 9.75 mmol) and the reaction mixture was refluxed for 2 h. After the solvent was removed, the resulting white precipitate was suspended and washed in saturated aqueous $NaHCO_3$ (100 mL) for 1 h. The solution was extracted with ethyl acetate (80 mL×3). The organic phase was dried over anhydrous $Na_2SO_4$ and filtered. The filtrate was concentrated to give the desired compound 4-(2-isopropoxyphenyl)thiazol-2-amine (2.20 g, 100% yield) as a yellow oil.

LCMS: LC retention time 1.56 min. MS (ESI) m/z 235 $[M+H]^+$.

Step 3.

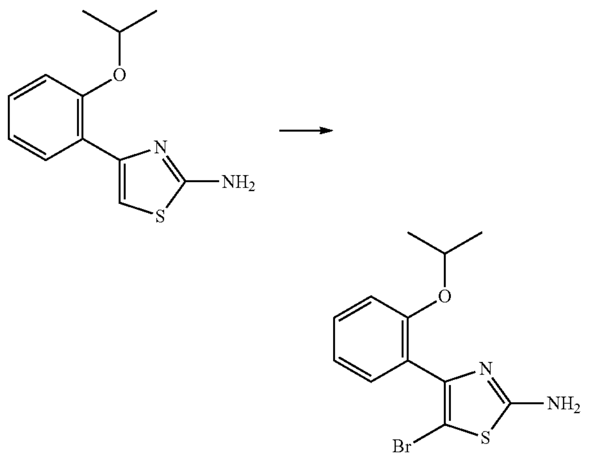

To a solution of 4-(2-isopropoxyphenyl)thiazol-2-amine (2.20 g, 9.4 mmol) in anhydrous tetrahydrofuran (50 mL) was added NBS (1.67 g, 9.4 mmol). After stirring at room temperature overnight, the mixture was partitioned between ethyl acetate (200 mL) and water (150 mL). The organic phase was washed with water (150 mL×2), dried over anhydrous $Na_2SO_4$ and filtered. The filtrate was concentrated under reduced pressure to give the crude which was purified by silica gel chromatography (PE/EA=3/1) to give the desired compound 5-bromo-4-(2-isopropoxyphenyl)thiazol-2-amine (1.70 g, 58%) as a red-brown oil.

LCMS: LC retention time 1.85 min. MS (ESI) m/z 315 $[M+H]^+$.

Intermediate B-9

5-Iodo-4-(2-(trifluoromethyl)phenyl)thiazol-2-amine

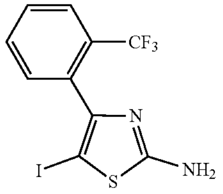 [SMILES: Nc1nc(-c2ccccc2C(F)(F)F)c(I)s1]

Intermediate B-9 was prepared in essentially the same way as Intermediate B-7.

Intermediate B-10

4-(2,2-Dimethylcyclopentyl)thiazol-2-amine

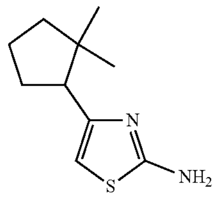

Step 1.

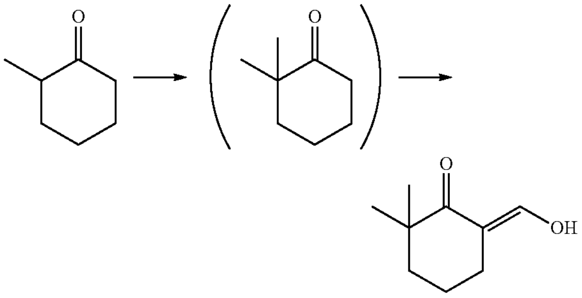

To a stirred suspension of NaH (5.12 g, 134 mmol of 60% mineral oil dispersion) in dry toluene (180 mL) was added 2-methylcyclohexan-1-one (10.00 g, 89.2 mol) dropwise during 2 h at 100° C. To this was added $CH_3I$ (19.00 g, 134 mol) dropwise over 2 h at 60° C. The mixture was stirred for an additional 2 h at 60° C. After cooling, a mixture of NaOMe (10.60 g, 196 mmol) and $HCO_2Me$ (11.2 g, 152 mmol) were added to the mixture at 5° C., and the reaction mixture stirred for 12 h at room temperature before being poured into ice water (100 mL). The aqueous layer was acidified with 10% HCl aqueous and extracted with ether. The combined organic phases were washed with brine, dried over $MgSO_4$ and concentrated to afford (E)-6-(hydroxymethylene)-2,2-dimethylcyclohexan-1-one (9.00 g, 65%) as a brown oil.

LCMS: LC retention time 2.09 min. MS (ESI) m/z 155 $[M+H]^+$.

Step 2.

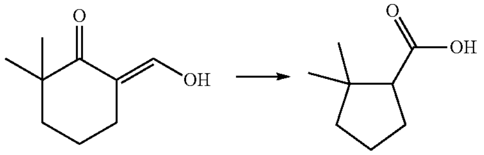

To a solution of (E)-6-(hydroxymethylene)-2,2-dimethylcyclohexan-1-one (7.50 g, 48.6 mmol) in 13 mL of t-BuOH was added 30% $H_2O_2$ (6.06 g, 53.5 mmol) dropwise. The reaction mixture was stirred at room temperature overnight. The resulting solution was heated at 100° C. for 4 h. The reaction mixture was cooled to room temperature. To this solution was added 80 mL of water and then extracted with ether. The organics were washed with 2 N NaOH solution (200 mL×5). The extracts were acidified by 4 N HCl, then extracted with $Et_2O$ (150 mL×2), dried over $Na_2SO_4$, filtered and concentrated to afford 2,2-dimethylcyclopentane-1-carboxylic acid (5.5 g, 79%) as a yellow oil.

$^1$H NMR (400 MHz, chloroform-d) δ 2.09-1.49 (m, 7H), 1.21 (s, 3H), 0.96 (s, 3H) ppm.

Step 3.

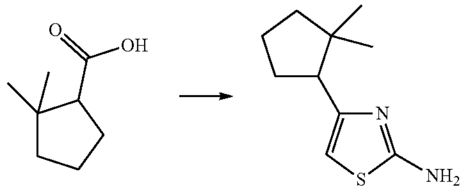

The reaction mixture of 2,2-dimethylcyclopentane-1-carboxylic acid (2.50 g, 17.6 mmol) in $SOCl_2$ (10 mL) was heated at 50° C. for 2 h. The reaction mixture was then concentrated. The resulting residue was dissolved in $CH_3CN$ (10 mL). To this solution was added 2 M diazomethyl (trimethyl) silane (22 mL, 44 mmol). The reaction mixture was stirred at room temperature for 2 h, cooled to 0° C., 40% HBr in AcOH (10.50 g, 52.7 mmol) was added dropwise. The mixture was stirred at 0° C. for 20 min. The mixture was filtered, and the filtrate was concentrated. The resulting residue was dissolved in EtOH (12 mL). To this solution was added thiourea (1.34 g, 17.6 mmol). The reaction was heated at 70° C. for 1 h. The reaction mixture was concentrated and diluted with water, adjusted pH with $NaHCO_3$. The aqueous solution was extracted with EtOAc (50 mL×2). The ethyl acetate solution was concentrated and purified by Prep-TLC (DCM:MeOH=10:1) to afford 4-(2,2-dimethylcyclopentyl)thiazol-2-amine (750 mg, 21%) as a brown oil.

LCMS: LC retention time 1.32 min. MS (ESI) m/z 197 $[M+H]^+$.

Intermediate C-1

5-(3-(3,3-Dimethylbutoxy)phenyl)-4-(2-isopropylphenyl)thiazol-2-amine

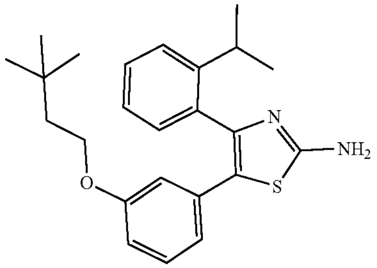 [SMILES: CC(C)c1ccccc1-c1nc(N)sc1-c1cccc(OCCC(C)(C)C)c1]

STep 1.

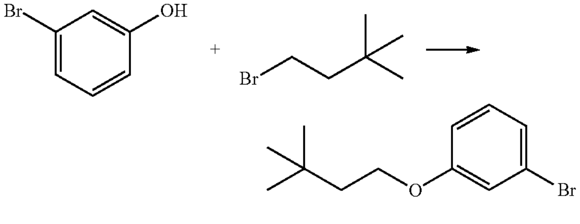

To a solution of 3-bromophenol (5.00 g, 28.9 mmol) in 1.4-dioxane (80 mL) were added 1-bromo-3,3-dimethylbutane (6.20 g, 37.6 mmol) and $Cs_2CO_3$ (14.1 g, 43.4 mmol). The resulting mixture was stirred at 100° C. under Ar atmosphere overnight. The reaction mixture was cooled to rt and was extracted with EA (20 mL×3). The organic layers were combined, washed with brine (20 mL) and dried over anhydrous $Na_2SO_4$. The combined organic layers were concentrated in vacuo. The crude product thus obtained was purified by silica gel chromatography (100% P E) to afford 1-bromo-3-(3,3-dimethylbutoxy)benzene (7.40 g, 99.6%) as a yellow oil.

LCMS: LC retention time 2.73 min. MS (ESI) m/z 280 $[M+Na]^+$

Step 2.

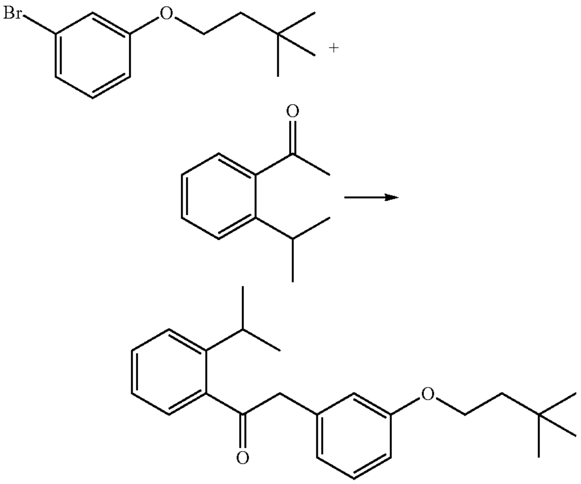

To a solution of 1-bromo-3-(3,3-dimethylbutoxy)benzene (1.80 g, 7.0 mmol) in toluene (20 mL) was added 1-(2-isopropylphenyl)ethanone (1.14 g, 7 mmol), followed by t-BuOK (1.57 g, 14 mmol) and X-phos-Pd (55.2 mg, 0.07 mmol). The resulting mixture was stirred at 65° C. under Ar atmosphere for 4 h. The reaction mixture was cooed to rt and quenched with $NH_4Cl$ (30 mL). The mixture was extracted with EA (10 mL×3). The organic layers were combined and washed with brine (20 mL) and dried over anhydrous $Na_2SO_4$. The combined organic layers were concentrated in vacuo. The crude product was purified by silica gel chromatography (PE/EA=4%) to afford 2-[3-(3,3-dimethylbutoxy)phenyl]-1-(2-isopropyl phenyl)ethanone (1.80 g, 76.0%) as a yellow oil.

LCMS: LC retention time 2.6 min. MS (ESI) m/z 339 $[M+H]^+$.

Step 3.

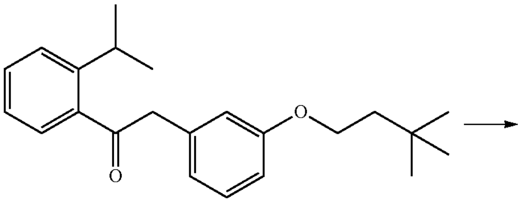

-continued

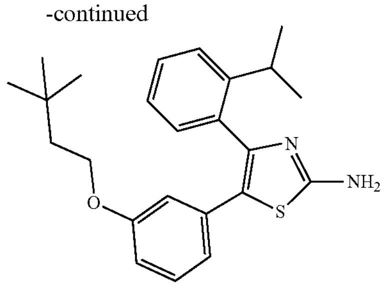

To a solution of 2-[3-(3,3-dimethylbutoxy)phenyl]-1-(2-isopropyl phenyl)ethanone (1.80 g, 5.32 mmol) in DMF (20 mL) was added thiourea (486 mg, 6.38 mmol), followed by $KHCO_3$ (638 mg, 6.38 mmol) and $BrCCl_3$ (2.11 g, 10.6 mmol). The resulting mixture was stirred at 80° C. under Ar atmosphere for 2 h. The reaction mixture was cooled and quenched with aqueous solution of $NH_4Cl$ (30 mL) and extracted with EA (10 mL×3). The organic layers were combined and washed with brine (20 mL) and dried over anhydrous $Na_2SO_4$. The organic layers were concentrated in vacuo. The crude was purified by silica gel chromatography (PE/EA=40%) to afford 5-(3-(3,3-dimethylbutoxy)phenyl)-4-(2-isopropylphenyl)thiazol-2-amine (800 mg, 38.1%) as a brown oil.

LCMS: LC retention time 2.6 min. MS (ESI) m/z 395 $[M+H]^+$.

Intermediate C-2

5-(3-(2,2-Difluoro-3,3-dimethylbutoxy)-4-fluorophenyl)-4-(2-isopropylphenyl)thiazol-2-amine

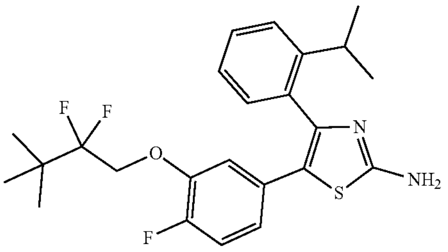 [SMILES: CC(C)c1ccccc1-c1nc(N)sc1-c1ccc(F)c(OCC(F)(F)C(C)(C)C)c1]

Step 1.

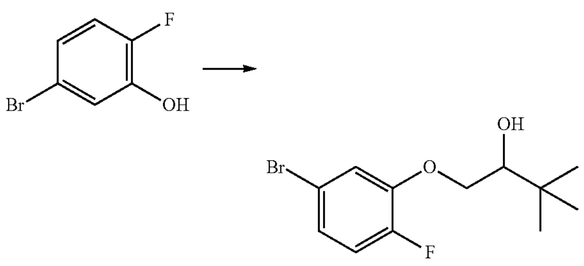

To a solution of 5-bromo-2-fluorophenol (5.00 g, 26.2 mmol) in N,N-dimethylformamide (60 mL) were added 2-tert-butyloxirane (3.93 g, 39.3 mmol) and cesium carbonate (17.08 g, 52.4 mmol) at room temperature. The resulting mixture was stirred at 80° C. overnight. The mixture was cooled to room temperature, diluted with water (350 mL), extracted with ethyl acetate (80 mL×3), washed with water (100 mL×2), and brine (100 mL), dried over anhydrous sodium sulfate, filtered and concentrated under reduced pressure. The residue was purified by silica gel chromatography (5% ethyl acetate in petroleum ether) to give 1-(5-bromo-2-fluorophenoxy)-3,3-dimethylbutan-2-ol as a colorless oil (4.068 g, 53% yield).

LCMS: LC retention time 2.19 min. MS (ESI) m/z 275 $[M-OH]^+$ $^1H$ NMR (400 MHz, chloroform-d) δ 7.11-7.08 (m, 1H), 7.06-7.02 (m, 1H), 69.8-6.93 (m, 1H), 4.16-4.13 (m, 1H), 3.91 (t, J=8.8 Hz, 1H), 3.73-3.71 (m, 1H), 2.47 (s, 1H), 1.01 (s, 9H) ppm.

Step 2.

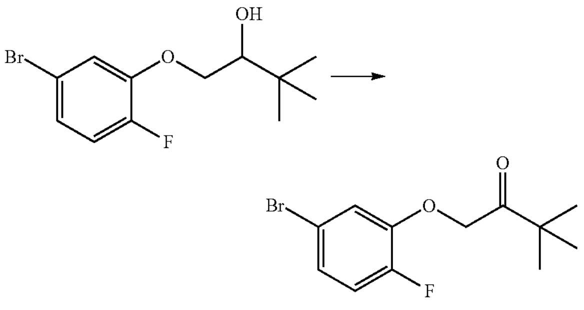

To a solution of 1-(5-bromo-2-fluorophenoxy)-3,3-dimethylbutan-2-ol (4.07 g, 14 mmol) in dichloromethane (60 mL) was added (1,1-diacetoxy-3-oxo-1lambda5,2-benziodoxol-1-yl) acetate (8.89 g, 21 mmol) at 0° C. The resulting reaction mixture was stirred at room temperature for 18 h. The solvent was removed under reduced pressure. To the residue was added diethyl ether (60 mL) and the resulting mixture was stirred at room temperature for 3 h, filtered through Celite, washed with diethyl ether. The filtrate was concentrated, and the residue was purified by silica gel chromatography (5% ethyl acetate in petroleum ether) to give 1-(5-bromo-2-fluorophenoxy)-3,3-dimethylbutan-2-one as a yellow oil (3.50 g, 87% yield).

LCMS: LC retention time 2.28 min. MS (ESI) m/z 291 $[M+H]^+$.

$^1H$ NMR (400 MHz, chloroform-d): δ 7.07-7.03 (m, 1H), 6.99-6.94 (m, 2H), 4.94 (s, 2H), 1.25 (s, 9H) ppm.

Step 3.

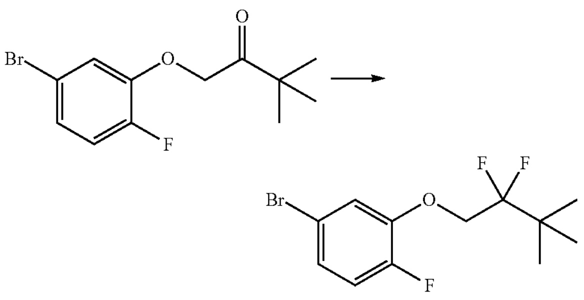

To a solution of 1-(5-bromo-2-fluorophenoxy)-3,3-dimethylbutan-2-one (3.5 g, 12.1 mmol) in anhydrous dichloromethane (40 mL) was added N-ethyl-N-(trifluoro-lambda4-sulfanyl)ethanamine (9.76 g, 60.5 mmol) at 0° C. under argon atmosphere. The resulting mixture was stirred at room temperature for 40 h. The reaction was quenched with saturated aqueous sodium bicarbonate solution. After $CO_2$ evolution ceased, the aqueous was extracted with dichloromethane (50 mL×3). The combined organic layers were washed with brine (100 mL), dried over sodium sulfate, filtered and concentrated under reduced pressure. The residue was purified by silica gel chromatography (10% ethyl acetate in petroleum ether) to give the crude product 4-bromo-2-(2,2-difluoro-3,3-dimethylbutoxy)-1-fluorobenzene as yellow oil (2.83 g, 75% yield).

LCMS: LC retention time 2.36 min. MS (ESI) m/z not observed.

Step 4.

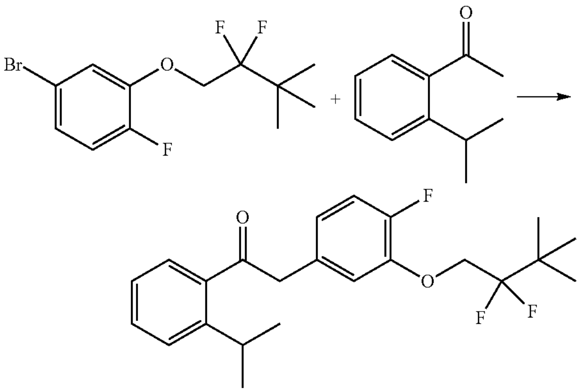

To a solution of 4-bromo-2-(2,2-difluoro-3,3-dimethylbutoxy)-1-fluorobenzene (1.00 g, 3.24 mmol) in anhydrous toluene (12 mL) were added 1-(2-isopropylphenyl)ethanone (500 mg, 3.09 mmol) and potassium tert-butoxide (830 mg, 6.2 mmol), followed by XPhos precatalyst (25 mg, 0.0309 mmol). The reaction was stirred at 60° C. under nitrogen atmosphere in a sealed tube for 6 h. After cooling to room temperature, the mixture was filtered through Celite. The filtrate was concentrated. The residue was purified by silica gel chromatography (10% ethyl acetate in petroleum ether) to give the desired product 2-(3-(2,2-difluoro-3,3-dimethylbutoxy)-4-fluorophenyl)-1-(2-isopropylphenyl)ethan-1-one as a light yellow oil (977 mg, 81% yield).

LCMS: LC retention time 2.41 min. MS (ESI) m/z 393 $[M+H]^+$.

Step 5.

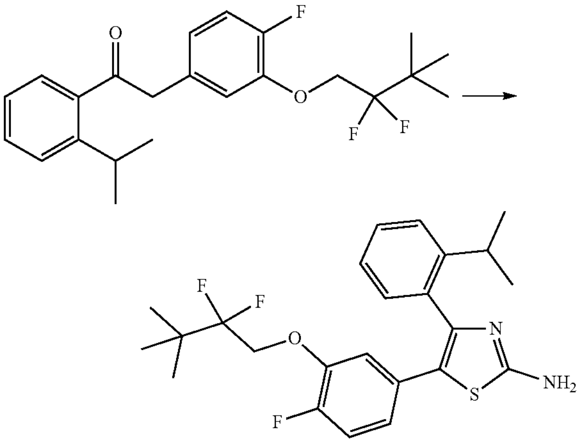

To a solution of 2-(3-(2,2-difluoro-3,3-dimethylbutoxy)-4-fluorophenyl)-1-(2-isopropylphenyl)ethan-1-one (977 mg, 2.49 mmol) in DMF (8.0 mL) were added thiourea (227 mg, 2.99 mmol), potassium bicarbonate (324 mg, 3.24 mmol), and bromotrichloromethane (0.49 mL, 4.98 mmol). The reaction was stirred at 70° C. for 4 h. After cooling to room temperature, the reaction was diluted with water (80 mL) and saturated aqueous sodium bicarbonate solution (80 mL). The aqueous was extracted with ethyl acetate (30 mL×3). The combined organic layers were washed with brine (60 mL), dried over anhydrous sodium sulfate, filtered and concentrated under reduced pressure. The residue was purified by prep-HPLC to afford the product 5-(3-(2,2-difluoro-3,3-dimethylbutoxy)-4-fluorophenyl)-4-(2-isopropylphenyl)thiazol-2-amine as a white solid (195 mg, 18% yield).

LCMS: LC retention time 2.16 min. MS (ESI) m/z 449 $[M+H]^+$.

Intermediate C-3

5-(3-(2,2Ddifluoro-3,3-dimethylbutoxy)phenyl)-4-(2-isopropylphenyl)thiazol-2-amine

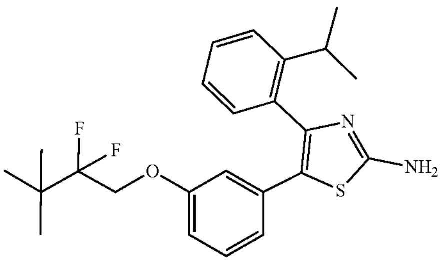 [SMILES: CC(C)c1ccccc1-c1nc(N)sc1-c1cccc(OCC(F)(F)C(C)(C)C)c1]

Step 1.

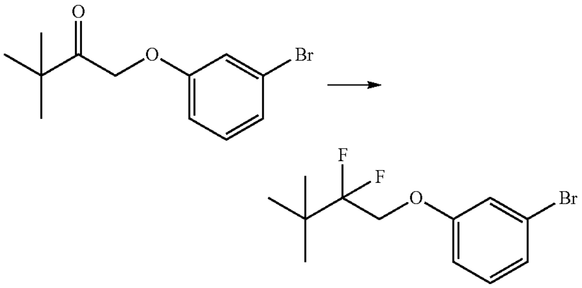

To a cooled (0° C.) and stirred solution of 1-(3-bromophenoxy)-3,3-dimethylbutan-2-one (4.36 g, 1.61 mmol) in DCM (50 mL) was added DAST (5.18 g, 3.22 mmol). The mixture was warmed to room temperature and stir overnight. LCMS showed that the starting materials were consumed. To the mixture was added saturated $NaHCO_3$ (50 mL), extracted with DCM (120 mL), washed with water (100 mL), dried over anhydrous $Na_2SO_4$, filtered and the filtrate was concentrated to dryness under reduced pressure. The crude was purified by silica gel column chromatography (PE/EA=20/1) to give the mixture compound 1-bromo-3-(2,2-difluoro-3,3-dimethylbutoxy)benzene which contained the desired compound about 50% (1.22 g, 25.9%) as a colorless oil.

LCMS: LC retention time 2.39 min. MS (ESI) m/z 294 $[M+H]^+$.

Step 2.

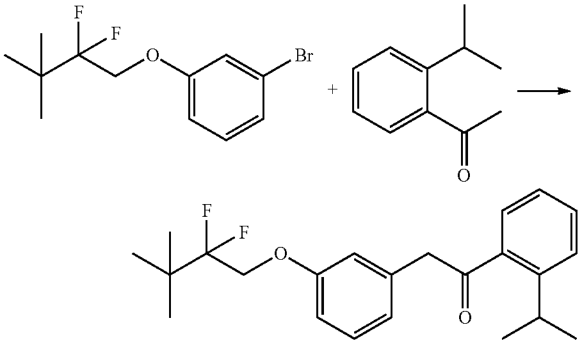

To a solution of 1-bromo-3-(2,2-difluoro-3,3-dimethylbutoxy)benzene (1.22 g, 4.16 mmol) in toluene (15 mL) were added 1-(2-isopropylphenyl)ethan-1-one (743 mg, 4.58 mmol) and t-BuOK (932 mg, 8.32 mmol), followed by X-phos-Pd (30.8 mg, 0.04 mmol). The reaction was stirred at 60° C. for 5 h under Ar. After cooling to room temperature, saturated aqueous $NH_4Cl$ (50 mL) was added. The resulting solution was stirred thoroughly. The mixture was poured into water (100 mL) and extracted with ethyl acetate (80 mL×3). The combined organic washes were dried over anhydrous $Na_2SO_4$, filtered and the filtrate was concentrated under reduced pressure to give the crude. The crude was purified by silica gel chromatography (PE/EA=20/1) to give the desired compound 2-(3-(2,2-difluoro-3,3-dimethylbutoxy)phenyl)-1-(2-isopropylphenyl)ethan-1-one (1.23 g, 78.9%) as a light yellow oil.

LCMS: LC retention time 2.46 min. MS (ESI) m/z 397 $[M+Na]^+$.

Step 3.

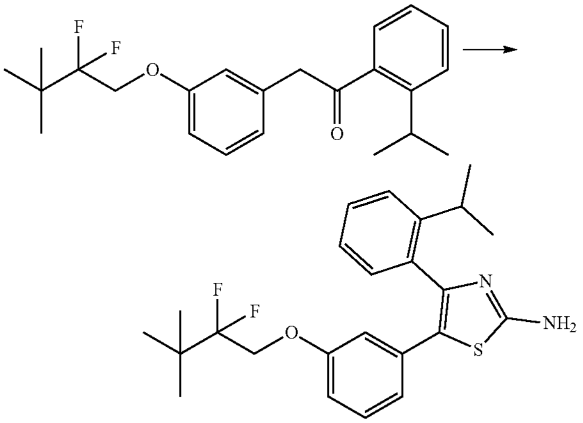

To a solution of 2-(3-(2,2-difluoro-3,3-dimethylbutoxy)phenyl)-1-(2-isopropylphenyl)ethan-1-one (1.23 g, 3.28 mmol) in DMF (40 mL) were added thiourea (300 mg, 3.94 mmol), $KHCO_3$ (394 mg, 3.94 mmol), and $BrCCl_3$ (1.30 g, 6.57 mmol). The reaction mixture was heated to 80° C. and stirred for 2 h. After cooling to room temperature, the mixture was poured into water (80 mL), extracted with ethyl acetate (80 mL×3), washed with brine (150 mL), dried over anhydrous $Na_2SO_4$, and filtered. The filtrate was concentrated under reduced pressure to give the crude which was purified by prep. HPLC give the desired compound 5-(3-(2,2-difluoro-3,3-dimethylbutoxy)phenyl)-4-(2-isopropylphenyl)thiazol-2-amine (320 mg, 22.6% yield) as a white solid.

LCMS: LC retention time 2.08 min. MS (ESI) m/z 431 $[M+H]^+$.

Intermediate C-4

5-(3-(3,3-Dimethylbutoxy)phenyl)-4-(2-(trifluoromethyl)phenyl)thiazol-2-amine

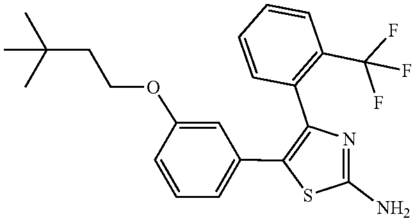 [SMILES: CC(C)(C)CCOc1cccc(-c2sc(N)nc2-c2ccccc2C(F)(F)F)c1]

Step 1.

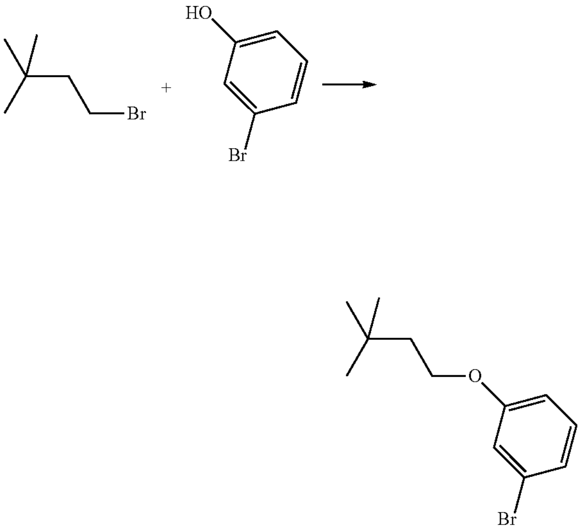

To a stirred solution of 1-bromo-3,3-dimethylbutane (3.64 g, 22.06 mmol) in DMF (10 mL) were added 3-bromophenol (3.43 g, 19.83 mmol) and $Cs_2CO_3$ (12.93 g, 39.69 mmol). The resulting mixture was stirred at room temperature for 20 h. Then, the rection was diluted with water (100 mL) and extracted with EA (200 mL×2). The organic solution was washed with brine (200 mL), dried over anhydrous $Na_2SO_4$, filtered and concentrated in vacuo. The residue was purified by silica gel chromatography (EA/PE=1/10) to afford (4.61 g; 90.4%) of 1-bromo-3-(3,3-dimethylbutoxy)benzene as a colorless oil.

LCMS: LC retention time 2.64 min. MS (ESI) m/z 282 $[M+Na]^+$.

$^1H$ NMR (400 MHz, chloroform-d): 7.15 (t, J=8.4 Hz, 1H), 7.10-7.07 (m, 2H), 6.86-6.83 (m, 1H), 4.02 (t, J=7.6 Hz, 2H), 1.74 (t, J=7.6 Hz, 2H), 1.01 (s, 9H) ppm.

Step 2.

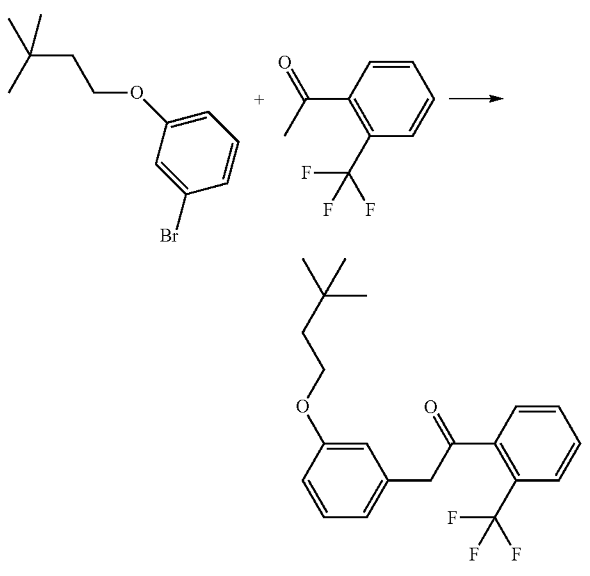

XPhos precatalyst (22 mg, 0.029 mmol) and $C_4H9OK$ (662 mg, 5.91 mmol) were added to a test tube equipped with a stir bar. The test tube was sealed with a Teflon septum-lined screw cap and evacuated/backfilled with argon. 1-(2-(trifluoromethyl)phenyl)ethan-1-one (558 mg, 2.96 mmol) and 1-bromo-3-(3,3-dimethylbutoxy)benzene (756 mg, 2.94 mmol) and toluene (6.0 mL) were added to the reaction vessel in succession via syringe. The reaction mixture was heated to 60° C. for 5 h. After cooling to room temperature, saturated aqueous $NH_4Cl$ (4.0 mL) was added to the reaction mixture and the resulting mixture was vigorously shaken. This mixture was then poured into a reparatory funnel and extracted with ethyl acetate (100 mL×3). The combined organic was washed with brine and dried over sodium sulfate and evaporated. The resulting residue was purified by silica gel chromatography with a Biotage instrument (PE/EA=10/1) to afford 2-(3-(3,3-dimethylbutoxy)phenyl)-1-(2-(trifluoromethyl)phenyl)ethan-1-one (820 mg, 76.6%) as a light yellow oil.

LCMS: LC retention time 2.34 min. MS (ESI) m/z 387 $[M+Na]^+$.

Step 3.

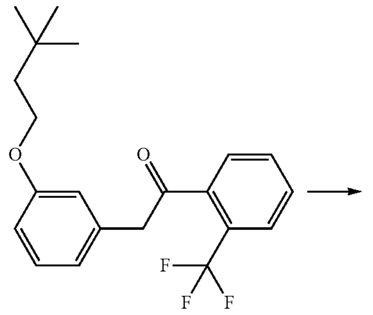

-continued

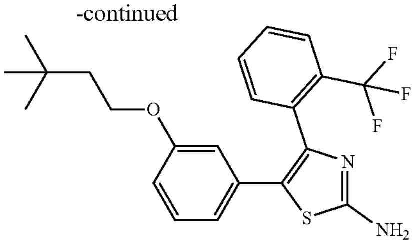

To a solution of 2-(3-(3,3-dimethylbutoxy)phenyl)-1-(2-(trifluoromethyl)phenyl)ethan-1-one (820 mg, 2.25 mmol) in DMF (5 mL) were added $KHCO_3$ (339 mg, 3.39 mmol), thiourea (259 mg, 3.4 mmol), and $CBrCl_3$ (852 mg, 4.3 mmol). The mixture was stirred at 70° C. for 1h. The mixture was diluted with water (50 mL) and extracted with EA (50 mL×3). The combined organic phases were dried over anhydrous sodium sulfate, filtered and concentrated in vacuo. The residue was purified by silica gel chromatography (EA/PE=1/1) to afford 5-(3-(3,3-dimethylbutoxy)phenyl)-4-(2-(trifluoromethyl)phenyl)thiazol-2-amine (130 mg, 13.7%) as light yellow solid.

LCMS: LC retention time 2.22 min. MS (ESI) m/z 421 $[M+H]^+$.

Intermediate C-5

4-(2,6Diimethylphenyl)-5-(3-(3,3,3-trifluoro-2,2-dimethylpropoxy)phenyl)thiazol-2-amine

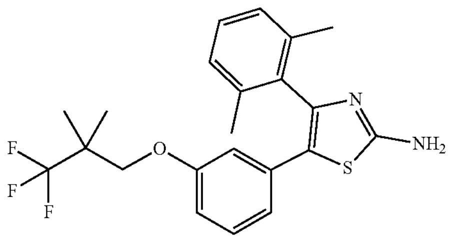 [SMILES: Cc1cccc(C)c1-c1nc(N)sc1-c1cccc(OCC(C)(C)C(F)(F)F)c1]

Intermediate C-5 was prepared in essentially the same protocol as Intermediate C-3.

Intermediate C-6a 5-(3-(3,3-Dimethylbutoxy)-5-fluorophenyl)-4-(2,6-dimethylphenyl)thiazol-2-amine

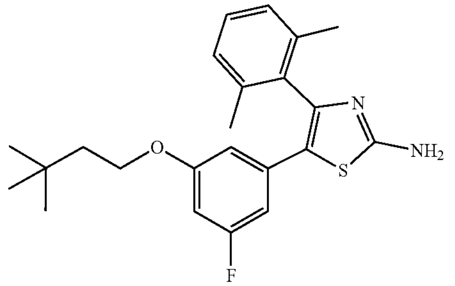 [SMILES: Cc1cccc(C)c1-c1nc(N)sc1-c1cc(F)cc(OCCC(C)(C)C)c1]

Intermediate C-6a was prepared in essentially the same protocol as Intermediate C-3.

Intermediate C-6b 5-(3-(3,3-Dimethylbutoxy)phenyl)-4-(2,6-dimethylphenyl)thiazol-2-amine

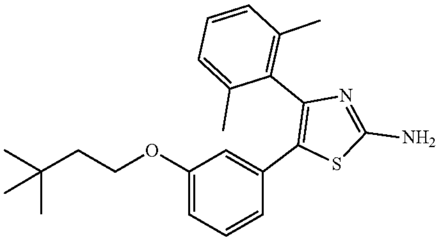 [SMILES: Cc1cccc(C)c1-c1nc(N)sc1-c1cccc(OCCC(C)(C)C)c1]

Intermediate C-6b was prepared in essentially the same protocol as Intermediate C-3.

Intermediate C-7

5-(3-(3,3-Dimethylbutoxy)-5-fluorophenyl)-4-(2-isopropylphenyl)thiazol-2-amine

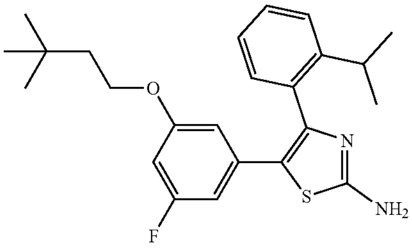 [SMILES: CC(C)c1ccccc1-c1nc(N)sc1-c1cc(F)cc(OCCC(C)(C)C)c1]

Step 1.

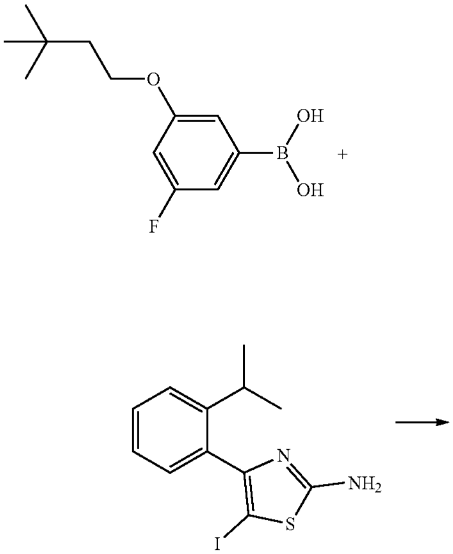

-continued

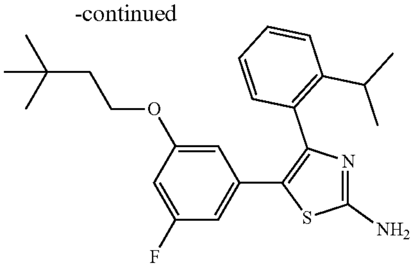

To a solution of (3-(3,3-dimethylbutoxy)-5-fluorophenyl) boronic acid (Intermediate D-1) (512 mg, 2.13 mmol) in toluene (40 mL), EtOH (20 mL) and water (10 mL)) were added $Na_2CO_3$ (106 mg, 4.87 mmol) and 5-iodo-4-(2-isopropylphenyl)thiazol-2-amine (Intermediate B-1) (555 mg, 1.61 mmol). The mixture was bubbled with $N_2$ for 5 min. Then charged with $Pd(Ph_3P)_4$ (188 mg, 0.163 mmol). The mixture was stirred at 80° C. for 12 h and then cooled to room temperature. The mixture was partitioned between EtOAc and water. The organic layer was dried and filtered. The filtrate was concentrated and purified by silica gel chromatography on silica gel chromatography (PE/EA=5/1) to give 5-(3-(3,3-dimethylbutoxy)-5-fluorophenyl)-4-(2-isopropylphenyl)thiazol-2-amine (500 mg; 75.3%) as a yellow solid.

LCMS: MS (ESI): m/z 413 $[M+H]^+$.

Intermediate C-8

5-(3-(3,3-dimethylbutoxy)-5-fluorophenyl)-4-(2-methyl-6-(trifluoromethyl)phenyl)thiazol-2-amine

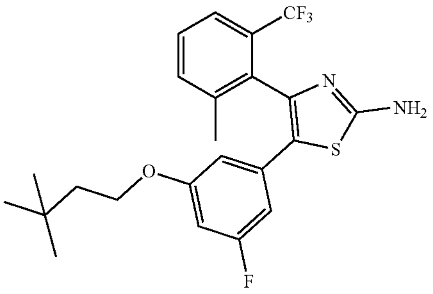 [SMILES: Cc1cccc(C(F)(F)F)c1-c1nc(N)sc1-c1cc(F)cc(OCCC(C)(C)C)c1]

Step 1.

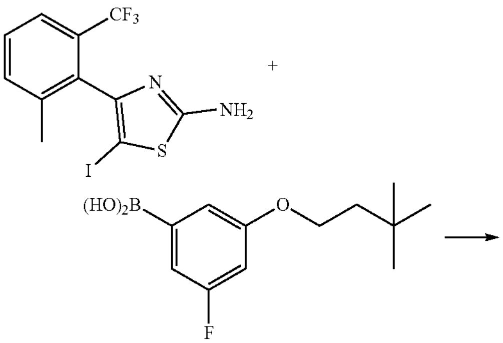

-continued

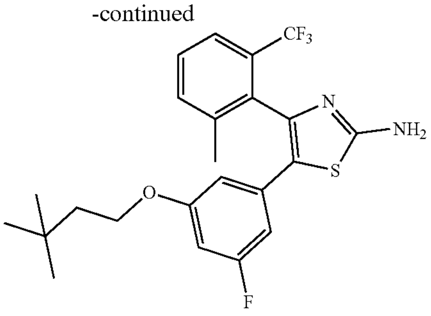

A mixture of 5-iodo-4-[2-methyl-6-(trifluoromethyl)phenyl]thiazol-2-amine (Intermediate B-4) (960 mg, 2.5 mmol), (3-(3,3-dimethylbutoxy)-5-fluorophenyl)boronic acid (Intermediate D-1) (720 mg, 3 mmol), $Pd(PPh_3)_4$ (579 mg, cat.), and $Na_2CO_3$ (795 mg, 7.5 mmol) in toluene (20 mL), ethanol (10 mL) and water (5 mL) was stirred 80° C. for 12 h under $N_2$ atmosphere. The mixture was concentrated and the residue was purified by SGC (PE/EA=2/1) to give the title intermediate as a yellow solid (400 mg, 36%).

LCMS: LC retention time 2.234 min. MS (ESI) m/z 453 $[M+H]^+$.

Intermediate C-9

5-(3-(3,3-Dimethylbutoxy)phenyl)-4-(2-methyl-6-(trifluoromethyl)phenyl)thiazol-2-amine

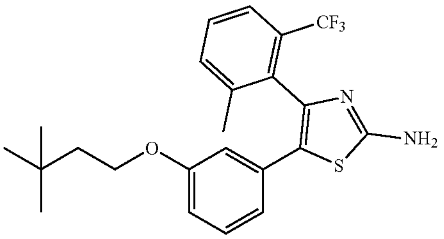 [SMILES: Cc1cccc(C(F)(F)F)c1-c1nc(N)sc1-c1cccc(OCCC(C)(C)C)c1]

Intermediate C-9 was prepared in the same way as Intermediate C-8.

Intermediate C-10

4-(2,6-dimethylphenyl)-5-(3-fluoro-5-(neopentyloxy)phenyl)thiazol-2-amine

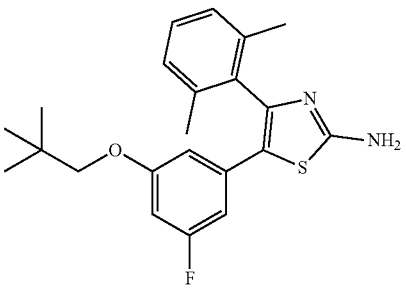 [SMILES: Cc1cccc(C)c1-c1nc(N)sc1-c1cc(F)cc(OCC(C)(C)C)c1]

Step 1.

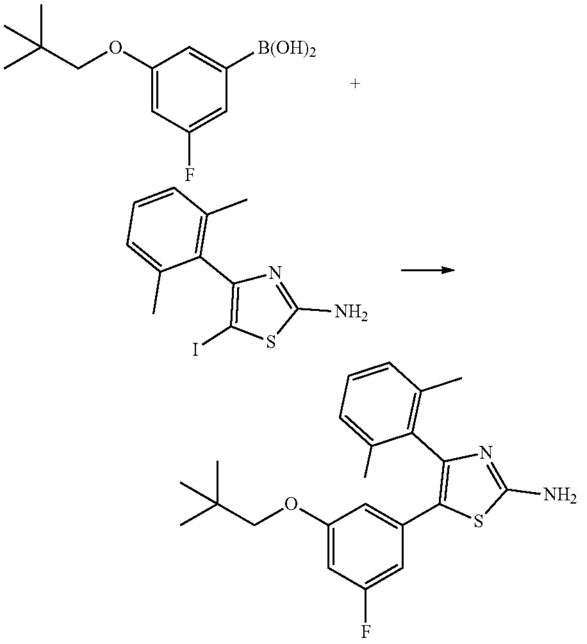

To a stirred solution of (3-fluoro-5-(neopentyloxy)phenyl)boronic acid (Intermediate D-6) (800 mg, 2.42 mmol) in toluene/ethanol/$H_2O$ (30/15/7.5 mL) were added 4-(2,6-dimethylphenyl)-5-iodothiazol-2-amine (Intermediate B-2b) (602 mg, 2.67 mmol), $Pd(Ph_3P)_4$ (280 mg, 0.24 mmol) and $Na_2CO_3$ (770 mg, 7.27 mmol). The resulting mixture was stirred at 80° C. for 16 h. The reaction mixture was diluted with water (50 mL) and extracted with ethyl acetate (50 mL×3). The organic layers were combined, dried over anhydrous sodium sulfate and concentrated in vacuo. The residue was purified by silica gel chromatography (PE/EA=1/1) to afford product 4-(2,6-dimethylphenyl)-5-(3-fluoro-5-(neopentyloxy)phenyl)thiazol-2-amine (510 mg, 55%) as a brown oil.

LC retention time 2.27 min. MS (ESI) m/z 385 $[M+H]^+$.

Intermediate C-11

5-(3-(3,3-Dimethylbutoxy)-5-fluorophenyl)-4-(2,6-dimethylphenyl)thiazol-2-amine

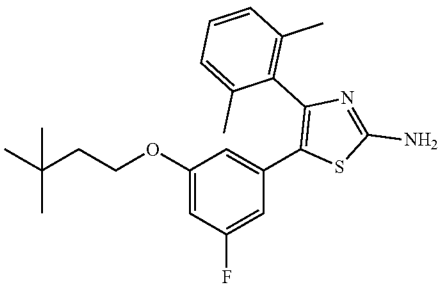 [SMILES: Cc1cccc(C)c1-c1nc(N)sc1-c1cc(F)cc(OCCC(C)(C)C)c1]

Step 1.

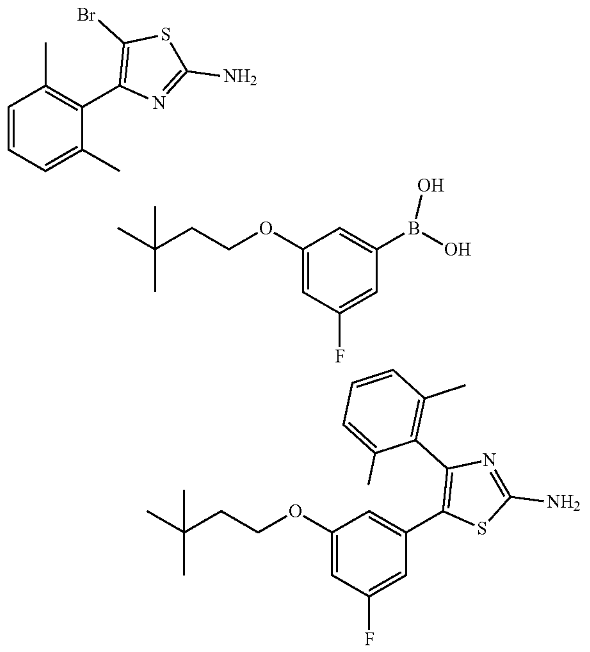

To a solution of 5-bromo-4-(2,6-dimethylphenyl)thiazol-2-amine (Intermediate B-2a) (964 mg, 3.41 mmol) in toluene/ethanol/$H_2O$ (52.5 mL, v/v/v=4/2/1) were added (3-(3,3-dimethylbutoxy)-5-fluorophenyl)boronic acid (Intermediate D-1) (981 mg, 4.09 mmol), $Pd(Ph_3P)_4$ (393 mg, 0.34 mmol), and $Na_2CO_3$ (1.08 g, 10.22 mmol). The resulting mixture was stirred at 80° C. under argon atmosphere for 16 h. The reaction mixture was cooled to rt and filtered. The filtrate was concentrated in vacuo. The residue was dissolved in water (150 mL) and brine (150 mL). The aqueous solution was extracted with ethyl acetate (80 mL×3), dried over anhydrous $Na_2SO_4$, filtered. The filtrate was concentrated to dryness under reduced pressure to give the crude which was purified by silica gel chromatography (PE/EA=3/1) to give the desired compound 5-(3-(3,3-dimethylbutoxy)-5-fluorophenyl)-4-(2,6-dimethylphenyl)thiazol-2-amine (670 mg, 49.4%) as a yellow solid.

LCMS: LC retention time 2.49 min. MS (ESI) m/z 400 $[M+H]^+$.

Intermediate C-12

5-(3-(2,2-Difluoro-3,3-dimethylbutoxy)phenyl)-4-(2-isopropoxy-6-methylphenyl)thiazol-2-amine

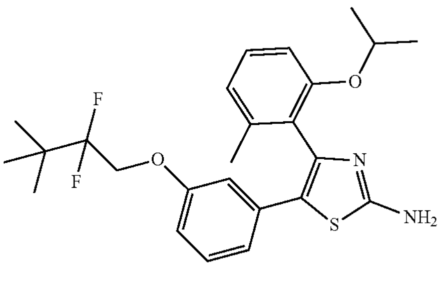 [SMILES: Cc1cccc(OC(C)C)c1-c1nc(N)sc1-c1cccc(OCC(F)(F)C(C)(C)C)c1]

This intermediate was prepared in the same way as Intermediate C-11

Intermediate D-1

(3-(3,3-Dimethylbutoxy)-5-fluorophenyl)boronic acid

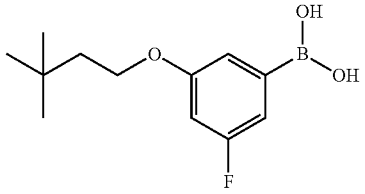 [SMILES: CC(C)(C)CCOc1cc(F)cc(B(O)O)c1]

Step 1.

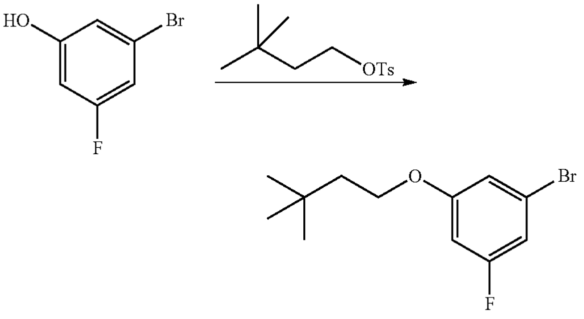

To a solution of 3-bromo-5-fluorophenol (4.80 g, 25.1 mmol) in NMP (22 mL) was added $Cs_2CO_3$ (16.4 g, 50.3 mmol) and 3,3-dimethylbutyl 4-methylbenzenesulfonate (7.73 g, 30.2 mmol). The mixture was stirred at 138° C. overnight. The volatiles were removed under reduced pressure. The residue was purified by SGC (PE=100%) to afford 1-bromo-3-(3,3-dimethylbutoxy)-5-fluorobenzene as a colorless oil (6.55 g, 93.5%).

LCMS: LC retention time 2.18 min. Molecular ion not observed.

Step 2.

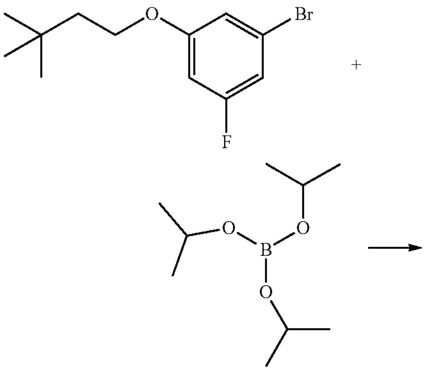

-continued

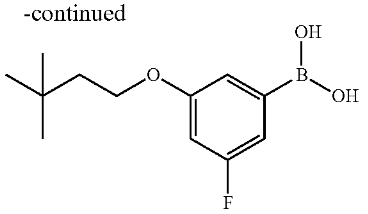

To a cooled (−78° C.) and stirred solution of 1-bromo-3-(3,3-dimethylbutoxy)-5-fluorobenzene (6.55 g, 23.8 mmol) in anhydrous THF (65 mL) was added n-BuLi (2.5M in hexane, 26.2 mmol) dropwise. The reaction mixture was stirred for 30 min. Triisopropyl borate (6.72 g, 35.7 mmol,) was added drop-wise while keeping the temperature of the reaction at −78° C. The reaction was allowed to warm to rt and stirred at rt for 2h. To the reaction mixture was added water and 2N HCl (50 mL) and stirred for 2 h more. After completion of reaction, ethyl acetate (60 mL) and water (40 mL) were added. The two layers were separated and the organic solution was dried over $MgSO_4$ and concentrated to afford (3-(3,3-dimethylbutoxy)-5-fluorophenyl)boronic acid (5.30 g).

LCMS: LC retention time 2.12 min. MS (ESI) m/z 241 $[M+H]^+$.

Intermediate D-2

[3-(3,3-Dimethylbutoxy)phenyl]boronic acid

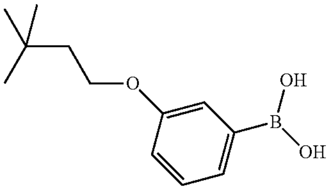 [SMILES: CC(C)(C)CCOc1cccc(B(O)O)c1]

Step 1.

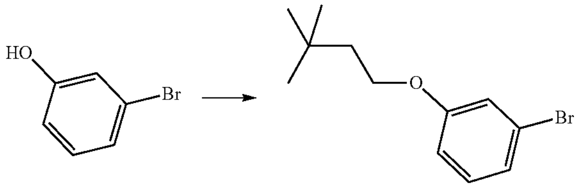

A mixture of 3-bromophenol (7 g, 40.5 mmol), 1-bromo-3,3-dimethylbutane (8.68 g, 52.6 mol), $K_2CO_3$ (11.2 g, 80.9 mol) in DMF (80 mL) was stirred at 100° C. for 12 h. The mixture was filtered and diluted with brine (400 mL), then extracted with ethyl acetate (200 mL×3). The organic solution was washed with brine (200 mL), dried over $Na_2SO_4$, concentrated. The residue was purified by combi-flash (elute with PE/EA=20/1) to give 1-bromo-3-(3,3-dimethylbutoxy) benzene (6.90 g, 66.3%) as a light oil.

LCMS: LC retention time 2.47 min. MS (ESI) m/z 257 $[M+H]^+$.

Step 2.

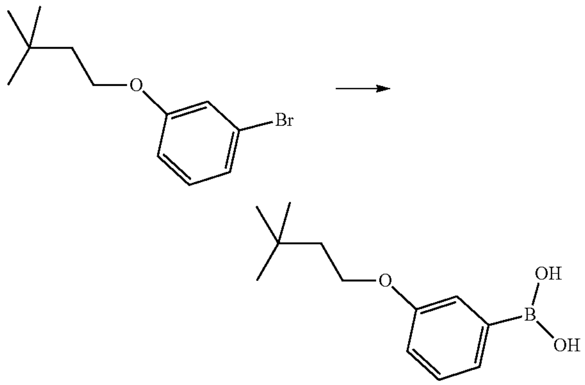

1-Bromo-3-(3,3-dimethylbutoxy)benzene (3.0 g, 11.7 mmol) was dissolved in 30 mL tetrahydrofuran and the solution was cooled to −70° C. in a cooling bath (acetone/dry ice). n-Butyllithium solution (5.13 mL, 2.5 M in hexane) was added dropwise under argon such that the temperature did not rise above −60° C. After stirring at −70° C. for 1.5 h, trimethyl borate (3.64 g, 35 mmol) was also added dropwise such that the temperature did not rise above −60° C. After stirring in the cold for 1 h, the mixture was warmed to 25° C. in the course of 2 h. To the reaction solution was added 500 mL hydrochloric acid (6 N). The mixture was stirred at 25° C. for 15 h. Then, the mixture was extracted with ethyl acetate (100 mL×3). The organic phases were combined, washed with saturated sodium chloride solution, dried over anhydrous sodium sulfate and filtered. The filtrate was concentrated on a rotary evaporator. The residue was purified by silica gel column chromatography (on silica gel, PE/EA=5/1) to obtain the title compound, [3-(3,3-dimethylbutoxy)phenyl]boronic acid (1.67 g, 64.5%) as a white solid.

LCMS: LC retention time 1.99 min. MS (ESI) m/z 223 $[M+H]^+$.

Intermediate D-3

2-(2-Fluoro-5-(neopentyloxy)phenyl)-4,4,5,5-tetramethyl-1,3,2-dioxaborolane

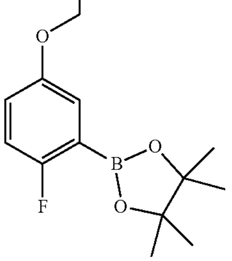

Step 1.

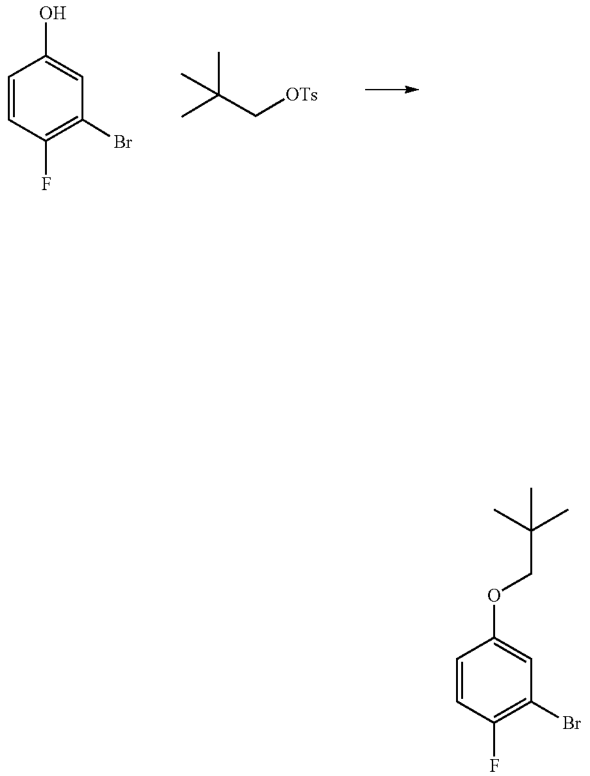

To a solution of 3-bromo-4-fluorophenol (2.00 g, 10.47 mmol), neopentyl 4-methylbenzenesulfonate (3.00 g, 12.56 mmol) in NMP (10 mL) was added $K_2CO_3$ (2.90 g, 20.94 mmol). The reaction was stirred at 150° C. overnight. After cooling to rt, the reaction was diluted with water (50 mL) and extracted with EA (50 mL). The organic solution was washed with brine (50 mL), dried over anhydrous $Na_2SO_4$, filtered and concentrated in vacuo. The residue was purified by silica gel chromatography (EA/PE=1/50) to afford 2-bromo-1-fluoro-4-(neopentyloxy)benzene (2.40 g, 88%) as a colorless oil.

LCMS: MS (ESI) m/z 261 $[M+H]^+$.

Step 2.

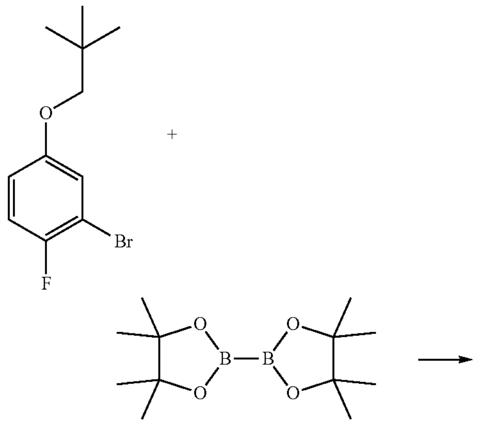

-continued

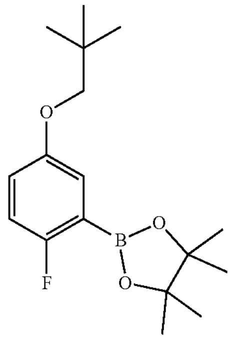

To a stirred solution of 2-bromo-1-fluoro-4-(neopentyloxy)benzene (1.0 g, 3.83 mmol) in 1,4-dioxane (10 mL) were added 4,4,4',4',5,5,5',5'-octamethyl-2,2'-bi(1,3,2-dioxaborolane) (1.46 g, 5.75 mmol), KOAc (1.13 g, 11.49 mmol) and $Pd(dppf)Cl_2$ (280 mg, 0.38 mmol). The solution was stirred at 80° C. for 3 h. To the reaction mixture was added water (50 mL) and then extracted with EA (50 mL). The organic solution was washed with brine (50 mL), dried over anhydrous $Na_2SO_4$, filtered and concentrated in vacuo. The residue was purified by silica gel chromatography (PE) to afford 2-(2-fluoro-5-(neopentyloxy)phenyl)-4,4,5,5-tetramethyl-1,3,2-dioxaborolane (960 mg, crude) as a colorless oil.

LCMS: MS (ESI) m/z 309 $[M+H]^+$.

The following intermediates were synthesized similarly using the procedures detailed above:

Intermediate D-4

4,4,5,5-Tetramethyl-2-(3-(neopentyloxy)phenyl)-1,3,2-dioxaborolane

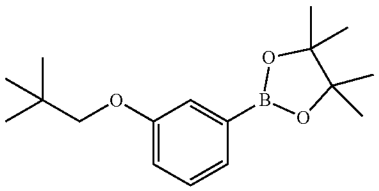 [SMILES: CC(C)(C)COc1cccc(B2OC(C)(C)C(C)(C)O2)c1]

Intermediate D-5

2-(3-Fluoro-5-(2,2,2-trifluoroethoxy)phenyl)-4,4,5,5-tetramethyl-1,3,2-dioxaborolane

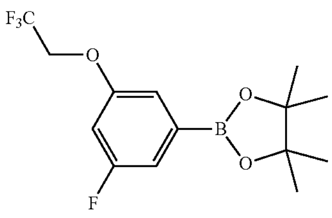 [SMILES: CC1(C)OB(c2cc(F)cc(OCC(F)(F)F)c2)OC1(C)C]

Intermediate D-6

(3-Fluoro-5-(neopentyloxy)phenyl)boronic acid

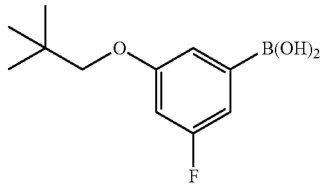 [SMILES: CC(C)(C)COc1cc(F)cc(B(O)O)c1]

Intermediate D-7

2-(4-Chloro-3-(neopentyloxy)phenyl)-4,4,5,5-tetramethyl-1,3,2-dioxaborolane

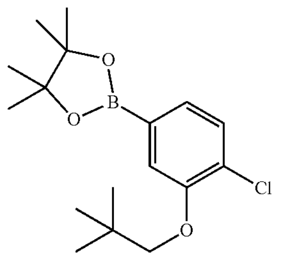 [SMILES: CC(C)(C)COc1cc(B2OC(C)(C)C(C)(C)O2)ccc1Cl]

Intermediate D-8

(4-Fluoro-3-(3,3,3-trifluoro-2,2-dimethylpropoxy)phenyl)boronic acid

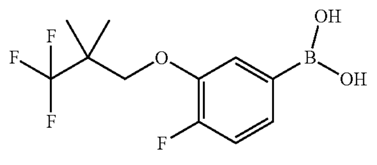 [SMILES: CC(C)(COc1cc(B(O)O)ccc1F)C(F)(F)F]

Intermediate D-9

2-(3-((4-(tert-Butyl)cyclohexyl)oxy)-5-fluorophenyl)-4,4,5,5-tetramethyl-1,3,2-dioxaborolane

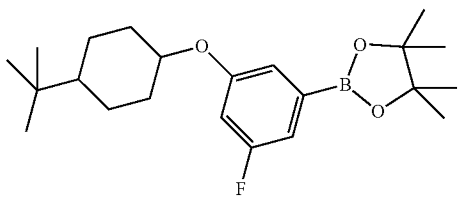 [SMILES: CC(C)(C)C1CCC(Oc2cc(F)cc(B3OC(C)(C)C(C)(C)O3)c2)CC1]

Intermediate D-10

1-Bromo-3-(2-(1-(trifluoromethyl)cyclopropyl)ethoxy)benzene

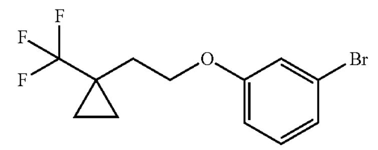 [SMILES: FC(F)(F)C1(CCOc2cccc(Br)c2)CC1]

Step 1.

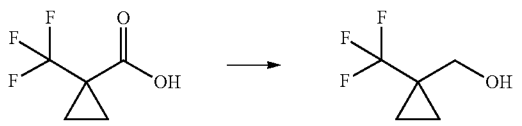 [SMILES: O=C(O)C1(C(F)(F)F)CC1 ; OCC1(C(F)(F)F)CC1]

To a stirred solution of 1-(trifluoromethyl)cyclopropane-1-carboxylic acid (6.0 g, 38.96 mmol) in anhydrous tetrahydrofuran (35 mL) was added borane-methyl sulfide complex (29.2 mL, 2.0 M solution in THF, 58.4 mmol) at room temperature under argon atmosphere. The resulting reaction mixture was stirred at 40° C. for 18 h. The reaction was quenched by adding saturated aqueous ammonium chloride solution (120 mL). The resulting solid was filtered off. The filtrate was extracted with diethyl ether (50 mL×3). The combined organic solution was washed with saturated aqueous sodium bicarbonate solution (100 mL) and brine (100 mL). Then, the organic solution was dried over anhydrous sodium sulfate, filtered and concentrated under vacuum to give (1-(trifluoromethyl)cyclopropyl)methanol as a light yellow oil (5.11 g).

LCMS: MS (ESI) m/z was not observed.

$^1$H NMR (400 MHz, chloroform-d) δ 3.73 (s, 2H), 1.05-1.02 (m, 2H), 0.78 (m, 2H) ppm.

Step 2.

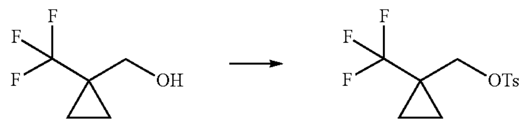 [SMILES: OCC1(C(F)(F)F)CC1 ; Cc1ccc(S(=O)(=O)OCC2(C(F)(F)F)CC2)cc1]

To a stirred solution of (1-(trifluoromethyl)cyclopropyl)methanol (5.11 g, 38.96 mmol) in anhydrous dichloromethane (80 mL) was added triethylamine (16.3 mL, 116.9 mmol) at 0° C. under argon atmosphere, followed by 4-methylbenzenesulfonyl chloride (9.62 g, 50.6 mmol) and 4-dimethylaminopyridine (436 mg, 3.9 mmol). The reaction mixture was stirred at room temperature for 15 h. The reaction mixture was diluted with dichloromethane (80 mL), and organic layer was washed with 2 M HCl (90 mL), saturated aqueous sodium bicarbonate solution (80 mL), and brine (80 mL). The organic solution was dried over anhydrous sodium sulfate, filtered and concentrated to give (1-(trifluoromethyl)cyclopropyl)methyl 4-methylbenzenesulfonate as a light yellow oil (7.30 g, 64% over two steps).

LCMS: LC retention time 2.08 min. MS (ESI) m/z 295 $[M+H]^+$.

$^1$H NMR (400 MHz, chloroform-d) δ 7.79 (d, J=8.0 Hz, 2H), 7.36 (d, J=8.0 Hz, 2H), 4.10 (s, 2H), 2.46 (s, 3H), 1.12 (m, 2H), 0.84 (m, 2H) ppm.

Step 3.

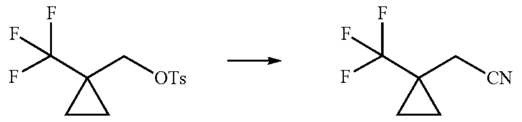 [SMILES: Cc1ccc(S(=O)(=O)OCC2(C(F)(F)F)CC2)cc1 ; N#CCC1(C(F)(F)F)CC1]

A mixture of (1-(trifluoromethyl)cyclopropyl)methyl 4-methylbenzenesulfonate (3.00 g, 10.2 mmol), potassium cyanide (0.995 g, 15.3 mmol), and 18-crown-6 (4.04 g, 15.3 mmol) in DMF (30 mL) was stirred at 55° C. for 18 h. The resulting mixture was diluted with water (200 mL) and extracted with ethyl acetate (40 mL×3). The combined organic layers were washed with water (80 mL×2) and brine (80 mL). The organic solution was then dried over sodium sulfate, filtered and concentrated under reduced pressure to give 2-(1-(trifluoromethyl)cyclopropyl)acetonitrile as a yellow oil (1.31 g).

LCMS: LC retention time 2.08 min. MS (ESI) m/z not observed.

$^1$H NMR (400 MHz, chloroform-d) δ 2.81 (s, 2H), 1.18 (m, 2H), 0.94 (m, 2H) ppm.

Step 4.

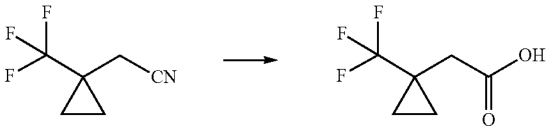 [SMILES: N#CCC1(C(F)(F)F)CC1 ; O=C(O)CC1(C(F)(F)F)CC1]

A mixture of 2-(1-(trifluoromethyl)cyclopropyl)acetonitrile (1.31 g, 8.79 mmol), and sodium hydroxide (7.03 g, 176 mmol) in ethanol (30 mL) and water (10 mL) was stirred at 80° C. for 18 h. The resulting mixture was concentrated under reduced pressure. The residue was dissolved in water (20 mL). The pH was adjusted to pH 2.0 with hydrogen chloride (4 N). The mixture was extracted with ethyl acetate (30 mL×3). The combined organic layers were washed with brine (60 mL), dried over anhydrous sodium sulfate, filtered and concentrated under vacuum to give 2-(1-(trifluoromethyl)cyclopropyl)acetic acid as a brown oil (1.31 g).

LCMS: LC retention time 2.50 min. MS (ESI) m/z was not observed.

$^1$H NMR (400 MHz, chloroform-d) δ 2.60 (s, 2H), 1.12 (m, 2H), 0.86 (m, 2H) ppm.

Step 5.

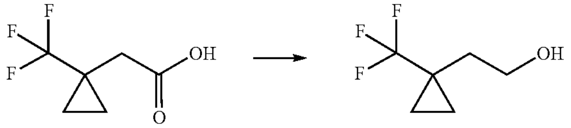 [SMILES: O=C(O)CC1(C(F)(F)F)CC1 ; OCCC1(C(F)(F)F)CC1]

To a solution of 2-(1-(trifluoromethyl)cyclopropyl)acetic acid (1.31 g, 7.79 mmol) in anhydrous tetrahydrofuran (15 mL) was added borane-methyl sulfide complex (7.8 mL, 2.0 M solution in THF, 15.6 mmol) at 0° C. under argon atmosphere. The resulting reaction mixture was stirred for 18 h at 40° C. The reaction was quenched by saturated aqueous ammonium chloride solution (50 mL). The resulting solid was filtered off after cooled to rt. The filtrate was extracted with diethyl ether (30 mL×3), washed with saturated aqueous sodium bicarbonate solution (50 mL), and brine (50 mL), dried over anhydrous sodium sulfate, filtered and concentrated under vacuum to give 2-(1-(trifluoromethyl)cyclopropyl)ethan-1-ol as a light yellow oil (1.21 g).

LCMS: LC retention time 2.56 min. MS (ESI) m/z not observed.

$^1$H NMR (400 MHz, chloroform-d) δ 3.79 (t, J=7.2 Hz, 2H), 1.84 (t, J=7.2 Hz, 2H), 0.98 (m, 2H), 0.67 (m, 2H) ppm.

Step 6.

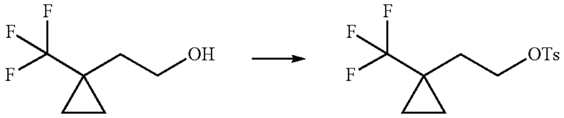 [SMILES: OCCC1(C(F)(F)F)CC1 ; Cc1ccc(S(=O)(=O)OCCC2(C(F)(F)F)CC2)cc1]

To a stirred solution of 2-(1-(trifluoromethyl)cyclopropyl) ethan-1-ol (0.91 g, crude, 5.9 mmol) in anhydrous dichloromethane (12 mL) was added triethylamine (1.79 g, 17.7 mmol) at 0° C. under argon atmosphere followed by 4-methylbenzenesulfonyl chloride (1.69 g, 8.86 mmol) and 4-dimethylaminopyridine (72 mg, 0.59 mmol). The reaction mixture was stirred at room temperature for about 65 h. The reaction mixture was diluted with dichloromethane (50 mL), and organic layer was washed with 2 M HCl (40 mL), saturated aqueous sodium bicarbonate solution (50 mL), and brine (50 mL), dried over anhydrous sodium sulfate and concentrated to give 2-(1-(trifluoromethyl)cyclopropyl) ethyl 4-methylbenzenesulfonate as a yellow oil (1.26 g).

LCMS: LC retention time 2.14 min. MS (ESI) m/z 331 $[M+Na]^+$

$^1$H NMR (400 MHz, chloroform-d) δ 7.79 (d, J=8.0 Hz, 2H), 7.36 (d, J=8.0 Hz, 2H), 4.16 (t, J=7.2 Hz, 2H), 2.46 (s, 3H), 1.94 (t, J=7.2 Hz, 2H), 0.97 (m, 2H), 0.65 (m, 2H) ppm.

Step 7

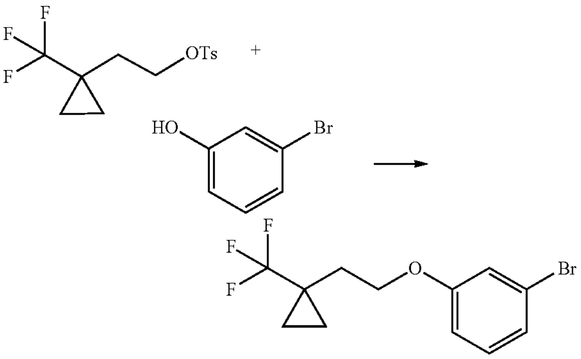

To a solution of 2-(1-(trifluoromethyl)cyclopropyl)ethyl 4-methylbenzenesulfonate (1.26 g, crude, 4.07 mmol) in DMF (15 mL) were added 3-bromophenol (916 mg, 5.3 mmol) and cesium carbonate (3.98 g, 12.2 mmol). The reaction was stirred at 120° C. overnight. The reaction was diluted with water (120 mL). The aqueous was extracted with ethyl acetate (30 mL×3). The combined organic layers were washed with water (50 mL×2) and brine (50 mL), dried over anhydrous sodium sulfate, filtered and concentrated under reduced pressure. The residue was purified by silica gel chromatography (petroleum ether) to give 1-bromo-3-

(2-(1-(trifluoromethyl)cyclopropyl)ethoxy)benzene as a yellow oil (757 mg, 36% yield over 5 steps).

LCMS: LC retention time 2.40 min. MS (ESI) m/z 309 $[M+H]^+$.

$^1H$ NMR (400 MHz, chloroform-d) δ 7.16-7.03 (m, 3H), 6.82-6.80 (m, 1H), 4.08 (t, J=7.2 Hz, 2H), 1.03 (t, J=7.2 Hz, 2H), 1.03 (m, 2H), 0.73 (m, 2H) ppm.

Intermediate D-11a

2-[3-(3,3-Dimethylcyclopentoxy)-5-fluoro-phenyl]-4,4,5,5-tetramethyl-1,3,2-dioxaborolane

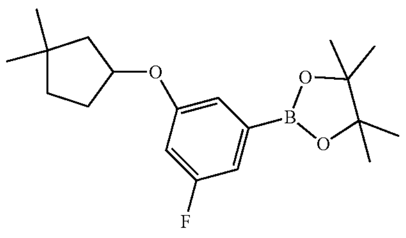

Step 1.

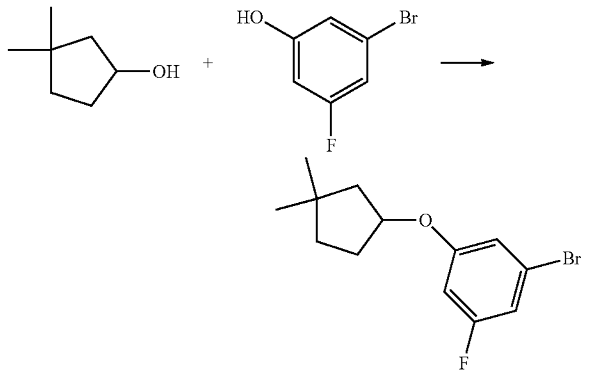

To a solution of 3-bromo-5-fluoro-phenol (836 mg, 4.38 mmol) in THF (50 mL) were added 3,3-dimethylcyclopentanol (500 mg, 4.38 mmol) and triphenylphosphine (1.72 g, 6.57 mmol), followed by diisopropyl azodicarboxylate (1.29 mL, 6.57 mmol) under argon at 0° C. The resultant mixture was reacted at room temperature overnight. The solvent was removed under vacuum. The residue was purified by FCC (PE=100%) to afford the desired compound, 1-bromo-3-(3,3-dimethylcyclopentoxy)-5-fluoro-benzene (890 mg, 71%) as a colorless oil.

LCMS: LC retention time 2.67 min. MS (ESI) m/z 287 $[M+H]^+$.

Step 2.

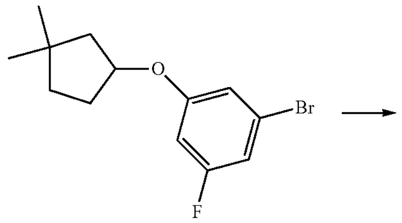

-continued

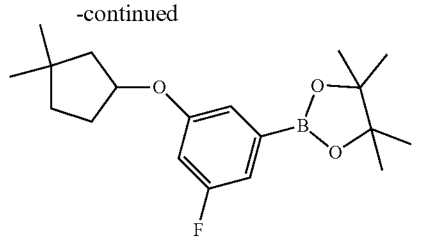

To a solution of 1-bromo-3-(3,3-dimethylcyclopentoxy)-5-fluoro-benzene (480 mg, 1.67 mmol), bis(pinacolato)diboron (509 g, 2.01 mmol) in DMSO (10 mL) were added Pd(dppf)$Cl_2$ (62 mg, cat.) and potassium acetate (491 mg, 5.01 mmol). The reaction was heated at 80° C. under Ar for 3 h. After cooling to rt, the reaction mixture was diluted with water (50 mL) and extracted with AcOEt (40 mL×2). The combined organic layers were washed with brine and dried over $Na_2SO_4$and filtered. The filtrate was concentrated in vacuo. The residue was purified by FCC (PE/EA=10/1) to afford the desired compound, 2-[3-(3,3-dimethylcyclopentoxy)-5-fluoro-phenyl]-4,4,5,5-tetramethyl-1,3,2-dioxaborolane (730 mg, 71%) as a colorless oil.

$^1H$ NMR (400 MHz, chloroform-d) δ 7.12-7.01 (m, 2H), 6.66 (dt, J=10.9, 2.4 Hz, 1H), 4.82 (tt, J=6.9, 3.6 Hz, 1H), 2.25-2.10 (m, 1H), 1.90 (dd, J=13.8, 6.9 Hz, 2H), 1.69 (dt, J=10.1, 6.7 Hz, 2H), 1.53-1.41 (m, 1H), 1.35 (s, 12H), 1.14 (s, 3H), 1.05 (s, 3H) ppm.

Intermediate D-11b 2-(3-((3,3-Dimethylcyclopentyl)oxy)phenyl)-4,4,5,5-tetramethyl-1,3,2-dioxaborolane

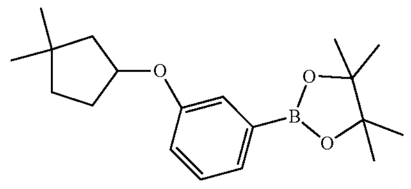

Intermediate D-11b was prepared in essentially the same protocol as Intermediate D-11a.

Intermediate D-12

(3-(3,3-Dimethylcyclopentyl)phenyl)boronic acid

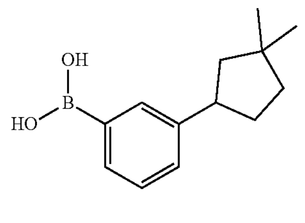 [SMILES: CC1(C)CCC(c2cccc(B(O)O)c2)C1]

Step 1.

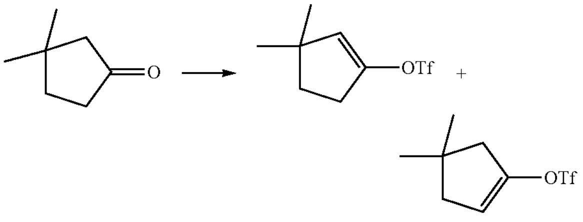

A solution of diisopropylamine (5.2 g, 51.4 mmol) in anhydrous THF (40 mL) under Ar was cooled to 0° C., n-BuLi (2.5M in hexane, 18.8 mL, 47.1 mmol) was added, and the solution was stirred at 0° C. for 15 min, and then cooled to −78° C. A solution of 3,3-dimethylcyclopentanone (7.37 g, 40 mmol) in anhydrous THF (40 mL) was added and the mixture was stirred at −78° C. for 2 h. A solution of PhNTf2 (16.80 g, 47.1 mmol) in anhydrous THF (80 mL) was added, and the mixture was warmed to 0° C. and stirred overnight. The mixture was poured into saturated aqueous $NH_4Cl$ and extracted with $Et_2O$. The combined organic layers were washed with water and brine, dried, and concentrated and to give a mixture of 3,3-dimethylcyclopent-1-en-1-yl trifluoromethanesulfonate and 4,4-dimethylcyclopent-1-en-1-yl trifluoromethanesulfonate (8.00 g, 76.6%) as a colorless oil.

$^1$H NMR (400 MHz, chloroform-d) δ 5.56-5.49 (m, 1H), 2.66-2.62 (m, 1H), 2.42-2.40 (m, 1H), 2.23-2.21 (m, 1H), 1.85 (t, J=8.1 Hz, 1H), 1.15 (s, 3H), 1.14 (s, 3H) ppm.

Step 2.

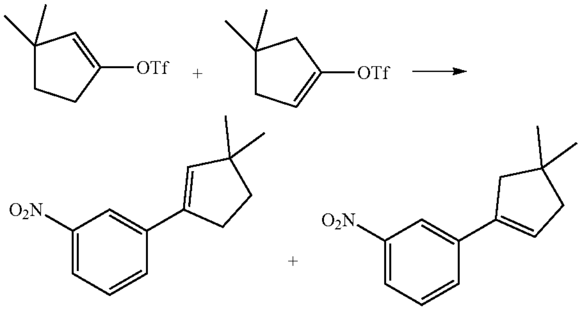

To a solution of 3,3-dimethylcyclopent-1-en-1-yl trifluoromethanesulfonate in toluene/EtOH/water (60 mL/30 mL/15 mL) were added 4,4-dimethylcyclopent-1-en-1-yl trifluoromethanesulfonate (2.00 g, 8.18 mmol), (3-nitrophenyl)boronic acid (1.71 g, 10.2 mmol), tetrakis (triphenylphosphine)palladium (236 mg, 0.205 mmol), and sodium carbonate (2.60 g, 24.6 mmol). The mixture was stirred at 90° C. for 16 h. Then, the mixture was concentrated. The residue was taken in water (50 mL) and extracted with ethyl acetate (50 mL×2). The organic layers were washed with brine (100 mL), dried over sodium sulfate and concentrated in vacuo. The residue was purified by silica gel column chromatography (PE) to obtain 1-(3,3-dimethylcyclopent-1-en-1-yl)-3-nitrobenzene and 1-(4,4-dimethylcyclopent-1-en-1-yl)-3-nitrobenzene (1.30 g, 73.1%) as a yellow oil.

$^1$HNMR (400 MHz, chloroform-d) δ 8.23-8.20 (m, 1H), 8.06-8.03 (m, 1H), 7.72-7.69 (m, 1H), 7.48 (t, J=8.0 Hz, 1H), 6.24-6.14 (m, 1H), 2.80-2.76 (m, 1H), 2.57-2.55 (m, 1H), 2.40-2.39 (m, 1H), 1.89 (t, J=7.2 Hz, 1H), 1.19 (s, 3H), 1.16 (s, 3H) ppm.

Step 3.

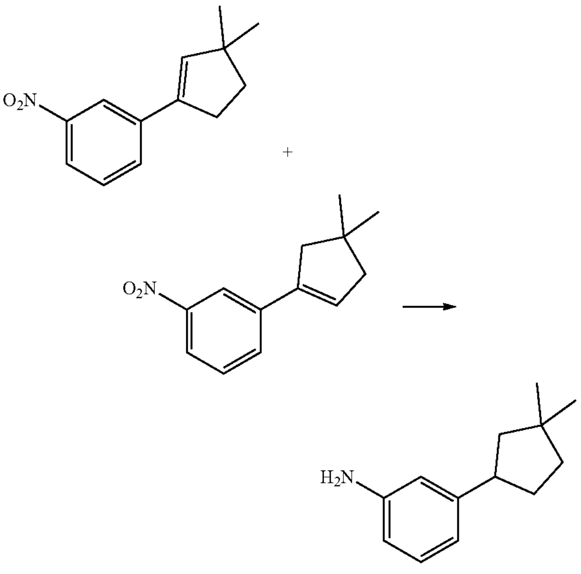

To a solution of 1-(3,3-dimethylcyclopent-1-en-1-yl)-3-nitrobenzene and 1-(4,4-dimethylcyclopent-1-en-1-yl)-3-nitrobenzene (1.30 g, 6.00 mmol) in MeOH (50 mL) was added 10 wt % Pd/C (130 mg) under Ar atmosphere at room temperature. The flask was purged with hydrogen and stirred under hydrogen atmosphere (1 atm) for 16 h. The reaction mixture was filtrate and the filtrate was concentrated to obtain 3-(3,3-dimethylcyclopentyl)aniline (700 mg, 62%) as a yellow oil.

LCMS: LC retention time 1.953 min. MS (ESI) m/z 190 $[M+H]^+$.

$^1$HNMR (400 MHz, chloroform-d) δ 7.09 (t, J=7.6 Hz, 1H), 6.67 (d, J=7.6 Hz, 1H), 6.59 (s, 1H), 6.52-6.49 (m, 1H), 3.59 (br, 2H), 3.14-3.09 (m, 1H), 2.10-2.06 (m, 1H), 1.85-1.47 (m, 5H), 1.16 (s, 3H), 1.14 (s, 3H) ppm.

Step 4.

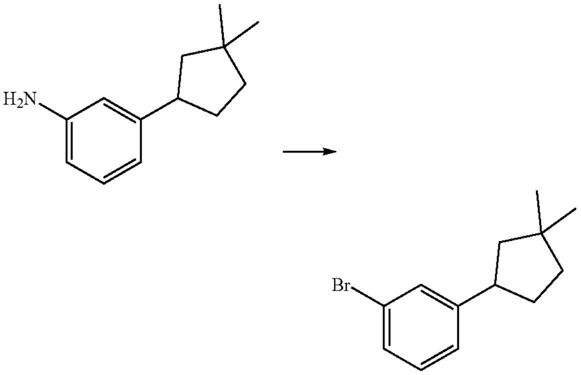

To a solution 3-(3,3-dimethylcyclopentyl)aniline (700 mg, 3.33 mmol) in anhydrous MeCN (20 mL) was added $CuBr_2$ (445 mg, 2.00 mmol) and tert-butylnitrite (343 mg, 3.33 mmol) at room temperature. The resulting mixture was stirred at reflux for 15 min. An aliquot checked by LCMS analysis indicated that the reaction was completed. The reaction was quenched by addition of water (80 mL). The aqueous was extracted with ethyl acetate (80 mL×3). The combined organic layers were washed with brine (100 mL), dried over anhydrous sodium sulfate, filtered and concentrated to dryness to give the crude product which was purified by silica gel column chromatography (PE/EA=50/1) to give the desired compound 1-bromo-3-(3,3-dimethylcyclopentyl)benzene (478 mg, 53.9%) as a yellow oil.

$^1$HNMR (400 MHz, chloroform-d): δ 7.41-7.13 (m, 4H), 3.57-3.12 (m, 1H), 2.17-1.50 (m, 6H), 1.12 (s, 3H), 1.10 (s, 3H) ppm.

Step 5.

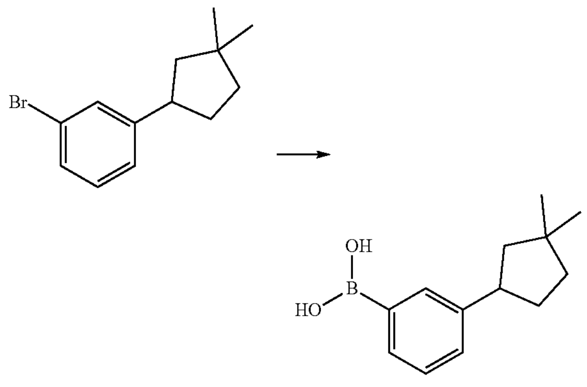

To a cooled and stirred solution of 1-bromo-3-(3,3-dimethylcyclopentyl)benzene (470 mg, 1.67 mmol) in anhydrous tetrahydrofuran (20 mL) was added n-butyllithium (1.34 mL, 3.34 mmol, 2.5 M solution in hexanes) dropwise at −78° C. After addition, the reaction mixture was stirred at −78° C. for 0.5 h. Then, trimethyl borate (347 mg, 3.34 mmol) was added dropwise at −78° C., The resulting mixture was stirred at −78° C. for 1 h. The reaction was then warmed to room temperature gradually over 2 h. To this solution was added hydrochloric acid (6.0 N, 5 mL) at 0° C. The resulting mixture was stirred at room temperature overnight. The reaction was diluted with water (50 mL). The aqueous was extracted with ethyl acetate (20 mL×3). The combined organic layers were washed with brine (60 mL), dried over sodium sulfate, filtered and concentrated under reduce pressure to give the product (3-(3,3-dimethylcyclopentyl)phenyl)boronic acid (400 mg, crude) as a yellow solid.

$^1$HNMR (400 MHz, chloroform-d): δ 7.68-7.23 (m, 4H), 3.20-3.15 (m, 1H), 2.07-1.30 (m, 6H), 1.16 (s, 3H), 1.14 (s, 3H) ppm.

Intermediate D-13

4,4,5,5-Tetramethyl-2-(3-(3,3,3-trifluoro-2,2-dimethylpropoxy)phenyl)-1,3,2-dioxaborolane

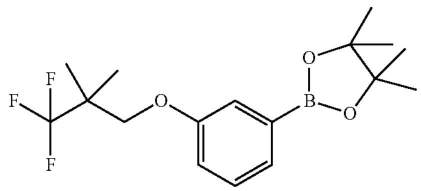 [SMILES: CC(C)(COc1cccc(B2OC(C)(C)C(C)(C)O2)c1)C(F)(F)F]

Step 1.

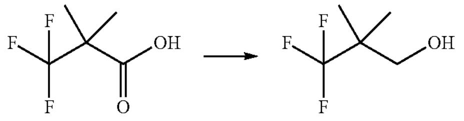

To a cooled stirred solution of 3,3,3-trifluoro-2,2-dimethylpropanoic acid (10.0 g, 64.1 mmol) in $Et_2O$ (150 mL) was added $LiAlH_4$ (4.87 g, 128 mmol) at 0° C. The mixture was stirred at room temperature overnight. When the reaction was completed, the reaction was quenched with $H_2O$ (5 mL), NaOH (15%, 5 mL) and $H_2O$ (15 mL). The mixture was filtered through a Celite pad. The filtrate was concentrated to give 3,3,3-trifluoro-2,2-dimethylpropan-1-ol (8.40 g, 92.3%) as a yellow oil.

Step 2.

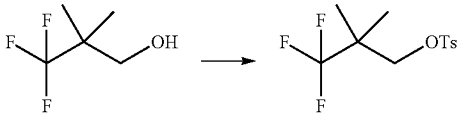

To a solution of 3,3,3-trifluoro-2,2-dimethylpropan-1-ol (8.4 g, 59.1 mmol) in $Et_2O$ (100 mL) was added NaOH (4.73 g, 118 mmol), followed by 4-methylbenzenesulfonyl chloride (12.4 g, 65.0 mmol). The result mixture was stirred at temperature overnight. The two layers were separated and the organic layer was washed with water (120 mL×3) and $NaHCO_3$ (50 mL). The organic solution was concentrated in vacuo and the residue was purified by silica gel column chromatography using PE:EA (5:1) as eluent to give 3,3,3-trifluoro-2,2-dimethylpropyl-4-methylbenzenesulfonate (12.6 g, 71.9% yield) as a yellow oil.

LCMS (acidic): LC retention time 2.130 min. MS (ESI) m/z 297 $[M+H]^+$.

Step 3.

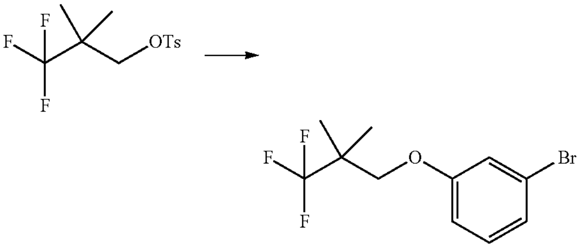

To a solution of 3,3,3-trifluoro-2,2-dimethylpropyl 4-methylbenzenesulfonate (6.00 g, 20.2 mmol) in DMSO (60 mL) were added 3-bromophenol (3.50 g, 20.2 mmol) and $Cs_2CO_3$ (19.8 g, 60.7 mmol). The mixture was heated with stirring at 130° C. overnight. When the reaction completed, the mixture was cooled to rt and diluted with EA (100 mL). The organic solution was washed with $H_2O$ (100 mL×3). The organic solution was concentrated in vacuo and purified by silica gel column chromatography using PE as eluent to give 1-bromo-3-(3,3,3-trifluoro-2,2-dimethylpropoxy)benzene (4.20 g, 69.8%) as a yellow oil.

LCMS (acidic): LC retention time 2.337 min. MS (ESI) m/z: not observed.

Step 4.

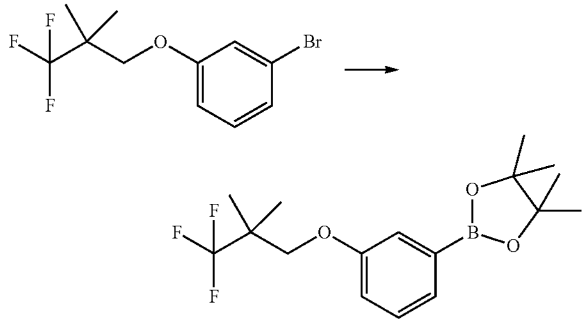

To a solution of 1-bromo-3-(3,3,3-trifluoro-2,2-dimethylpropoxy)benzene (4 g, 13.5 mmol) in 1,4-dioxane (50 mL) were added bis(pinacolato)diboron (5.13 g, 20.2 mmol), $CH_3COOK$ (3.30 g, 33.7 mmol), and Pd (dppf)$Cl_2$ (985 mg, 1.35 mmol). The reaction was heated at 80° C. under argon overnight. The reaction mixture was concentrated and purified by SGC (PE:EA=10:1) to give 4,4,5,5-tetramethyl-2-(3-(3,3,3-trifluoro-2,2-dimethylpropoxy)phenyl)-1,3,2-dioxaborolane (2.93 g, 63.2% yield) as a yellow oil.

LCMS (acidic): LC retention time 2.539 min. MS (ESI) m/z 345 $[M+H]^+$.

Intermediate D-14

2-(3-(2,2-Difluoro-3,3-dimethylbutoxy)phenyl)-4,4,5,5-tetramethyl-1,3,2-dioxaborolane

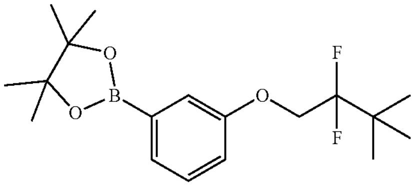 [SMILES: CC(C)(C)C(F)(F)COc1cccc(B2OC(C)(C)C(C)(C)O2)c1]

Step 1.

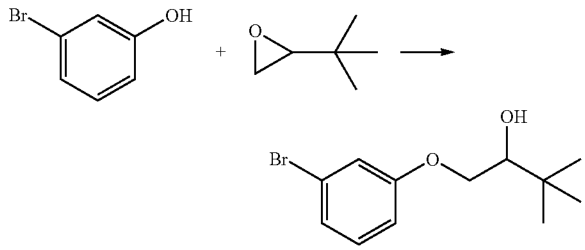

To the solution of 3-bromophenol (1.9 g, 11.0 mmol) in DMF (20 mL) were added 2-(tert-butyl)oxirane (1.65 g, 16.5 mmol) and cesium carbonate (7.16 g, 22.0 mmol) at room temperature. The resulting mixture was stirred at 80° C. overnight. The mixture was cooled to room temperature, diluted with water (150 mL), extracted with ethyl acetate (40 mL×3). The organic solution was washed with brine (60 mL), dried over anhydrous sodium sulfate, filtered and concentrated under reduced pressure. The residue was purified by silica gel chromatography (9% ethyl acetate in petroleum ether) to give 1-(3-bromophenoxy)-3,3-dimethylbutan-2-ol as a colorless oil (2.46 g, 82% yield).

LCMS: LC retention time 2.24 min. MS (ESI) m/z 275 $[M+H]^+$.

$^1$HNMR (400 MHz, chloroform-d) δ 7.17-7.06 (m, 3H), 6.87-6.84 (m, 1H), 4.10-4.07 (m, 1H), 3.85 (t, J=9.2 Hz, 1H) 3.69-3.66 (m, 1H), 2.36 (d, J=3.2 Hz, 1H), 1.01 (s, 9H) ppm.

Step 2.

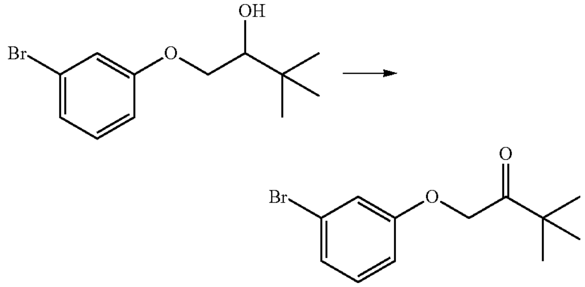

To a solution of 1-(3-bromophenoxy)-3,3-dimethylbutan-2-ol (2.46 g, 9.01 mmol) in dichloromethane (30 mL) was added (1,1-diacetoxy-3-oxo-1lambda5,2-benziodoxol-1-yl) acetate (5.73 g, 13.5 mmol) at room temperature. The resulting reaction mixture was stirred at room temperature for 18 h. The solvent was removed under reduced pressure. The residue was purified by silica gel chromatography (10% ethyl acetate in petroleum ether) to give 1-(3-bromophenoxy)-3,3-dimethylbutan-2-one as a colorless oil (2.18 g, 89% yield).

LCMS: LC retention time 2.18 min. MS (ESI) m/z 273 $[M+H]^+$.

$^1$HNMR (400 MHz, chloroform-d) δ 7.16-7.10 (m, 2H), 7.02 (s, 1H), 6.81 (d, J=7.2 Hz, 1H), 4.85 (s, 2H), 1.25 (s, 9H) ppm.

Step 3.

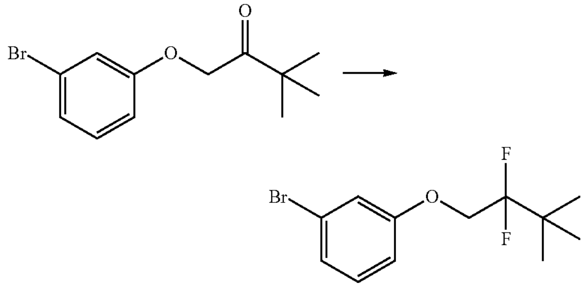

To a solution of 1-(3-bromophenoxy)-3,3-dimethylbutan-2-one (2.18 g, 8.04 mmol) in anhydrous dichloromethane (20 mL) was added N-ethyl-N-(trifluoro-lambda4-sulfanyl) ethanamine (5.18 g, 32.2 mmol) dropwise at 0° C. under argon atmosphere. The resulting mixture was stirred at room temperature for 65 h. The reaction was quenched with saturated aqueous sodium bicarbonate solution. After $CO_2$ evolution ceased, the solution was extracted with dichloromethane (30 mL×3). The combined organic layers were washed with brine (50 mL), dried over sodium sulfate, filtered and concentrated under reduced pressure. The residue was purified by silica gel chromatography (petroleum ether) to give 1-bromo-3-(2,2-difluoro-3,3-dimethylbutoxy) benzene as a colorless oil (1.56 g, 66% yield).

LCMS: LC retention time 2.35 min. MS (ESI) m/z not observation.

$^1$HNMR (400 MHz, chloroform-d) δ 7.18-7.10 (m, 3H), 6.88 (m, 1H), 4.23 (t, J=13.2 Hz, 2H), 1.14 (s, 9H) ppm.

Step 4.

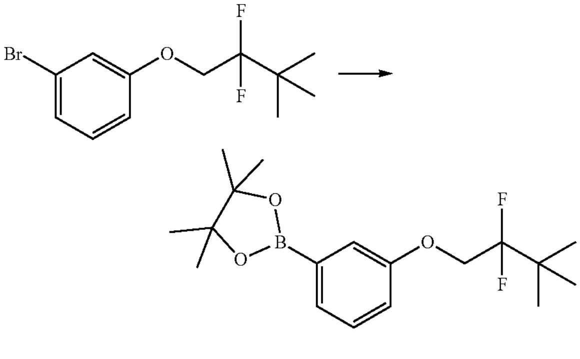

To a solution of 1-bromo-3-(2,2-difluoro-3,3-dimethylbutoxy)benzene (1.56 g, 5.32 mmol) in anhydrous 1,4-dioxane (20.0 mL) were added 4,4,4',4',5,5,5',5'-octamethyl-2,2'-bi(1,3,2-dioxaborolane) (2.03 g, 7.99 mmol), potassium acetate (1.56 g, 15.96 mmol), and [1,1'-bis (diphenylphosphino)ferrocene]dichloropalladium (II) (389 mg, 0.532 mmol). The reaction was stirred at 90° C. under argon atmosphere overnight. The solid was filtered off, diluted with water (120 mL), extracted with ethyl acetate (50 mL×3). The combined organic layers were washed with brine (100 mL), dried over sodium sulfate, filtered and concentrated under reduced pressure. The residue was purified by silica gel chromatography (3% ethyl acetate in petroleum ether) to give 2-(3-(2,2-difluoro-3,3-dimethylbutoxy)phenyl)-4,4,5,5-tetramethyl-1,3,2-dioxaborolane as a colorless oil (1.34 g, 74% yield).

LCMS: LC retention time 2.42 min. MS (ESI) m/z 340 $[M+H]^+$.

Intermediate D-15

2-(4-(Difluoromethoxy)-3-(3,3-dimethylbutoxy)phenyl)-4,4,5,5-tetramethyl-1,3,2-dioxaborolane

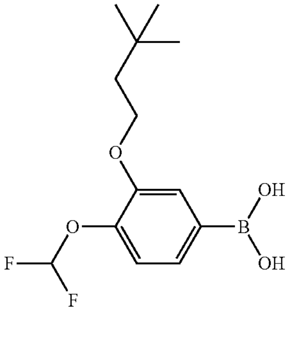 [SMILES: CC(C)(C)CCOc1cc(B(O)O)ccc1OC(F)F]

Step 1.

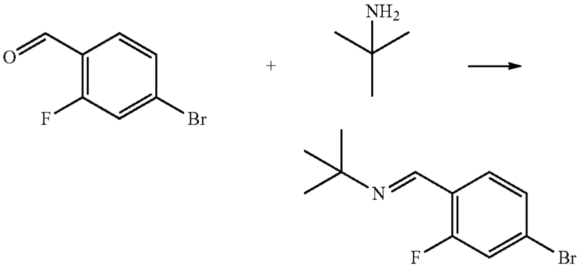

To a solution of 4-bromo-2-fluorobenzaldehyde (8.0 g, 39.4 mmol) in dichloromethane (60 mL) was added 2-methylpropan-2-amine (14.4 g, 197 mmol) and magnesium sulfate (33.2 g, 276 mmol). The resulting mixture was stirred at room temperature for 43 h. The solution was filtered and concentrated to give (E)-1-(4-bromo-2-fluorophenyl)-N-(tert-butyl)methanimine as a yellow oil (10.2 g).

LCMS: LC retention time 2.04 min. MS (ESI) m/z 258 $[M+H]^+$.

Step 2.

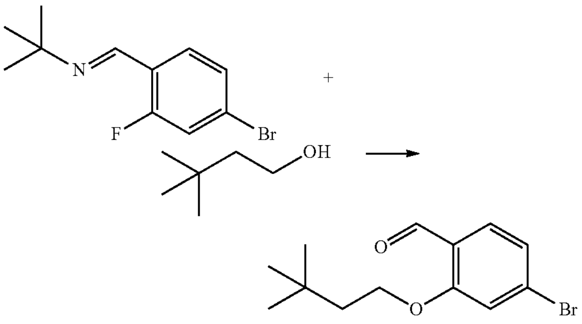

To a suspension of sodium hydride (60 wt % in mineral oil, 4.74 g, 119 mmol) in DMF (40 mL) was added a solution of 3,3-dimethylbutan-1-ol (4.84 g, 47.4 mmol) in DMF (30 mL) dropwise at 0° C. under argon atmosphere. The resulting mixture was stirred at room temperature for 30 min, then the solution of (E)-1-(4-bromo-2-fluorophenyl)-N-(tert-butyl)methanimine (10.2 g, 39.5 mmol) in DMF (30 mL) was added dropwise at 0° C. The resulting reaction mixture was stirred at room temperature overnight. The reaction was quenched with water (30 mL) at 0° C., diluted with water (250 mL), and extracted with tert-butyl methyl ether (3×100 mL). The combined organic layers were washed with water (150 mL), brine (150 mL), dried over sodium sulfate, filtered and concentrated under reduced pressure to give a yellow solid which was treated with tetrahydrofuran (50 mL), water (50 mL) and acetic acid (12 mL). After 18 h, this solution was made basic with saturated aqueous sodium carbonate solution and extracted with ethyl acetate (100 mL×2). The combined organic layers were washed with brine (100 mL) and dried over sodium sulfate, filtered and concentrated under reduced pressure. The residue was purified by silica gel chromatography (4% ethyl acetate in petroleum ether) to give 4-bromo-2-(3,3-dimethylbutoxy)benzaldehyde as a white solid (9.54 g, 85% yield over 2 steps).

LCMS: LC retention time 2.56 min. MS (ESI) m/z 287 $[M+H]^+$.

$^1$H NMR (400 MHz, chloroform-d) δ 10.4 (s, 1H), 7.70-7.68 (m, 1H), 7.17-7.15 (m, 2H), 4.13 (t, J=7.2 Hz, 2H), 1.80 (t, J=7.2 Hz, 2H), 1.02 (s, 9H) ppm.

Step 3.

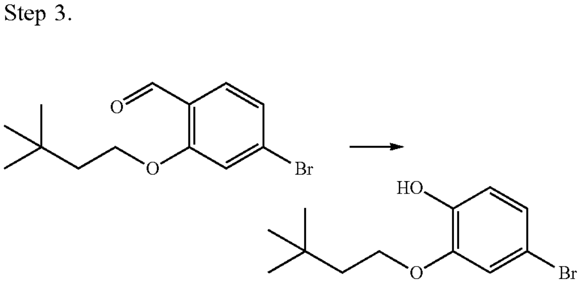

To a solution of 4-bromo-2-(3,3-dimethylbutoxy)benzaldehyde (6.9 g, 24.2 mmol) in dichloromethane (70 mL) was added 3-chlorobenzenecarboperoxoic acid (85 wt %, 7.37 g, 36.3 mmol). After 15 h stirring, saturated aqueous sodium sulfite solution was added at 0° C. and the solution allowed to stir until the aqueous was K1 paper negative. The aqueous was then extracted with dichloromethane (100 mL×2). The combined organic layers were washed with saturated sodium bicarbonate solution (100 mL), concentrated and treated with methanol (40 mL) and 1N sodium hydroxide (70 mL) at 0° C. The resulting mixture was stirred at room temperature for 4 h. The reaction mixture was acidified with 1 M potassium bisulfate solution (pH about 4), then extracted with dichloromethane (100 mL×2). The combined organic layers were washed with brine (100 mL) and dried over sodium sulfate, filtered and concentrated under reduced pressure The residue was purified by silica gel chromatography (4% ethyl acetate in petroleum ether) to give 4-bromo-2-(3,3-dimethylbutoxy)phenol as a yellow oil (5.77 g, 87% yield).

LCMS: LC retention time 2.34 min. MS (ESI) m/z not observed.

$^1$H NMR (400 MHz, chloroform-d) δ 6.98-6.96 (m, 2H), 6.79 (d, J=8.8 Hz, 1H), 5.57 (s, 1H), 4.07 (t, J=7.2 Hz, 2H), 1.75 (t, J=7.2 Hz, 2H), 1.00 (s, 9H) ppm.

Step 4.

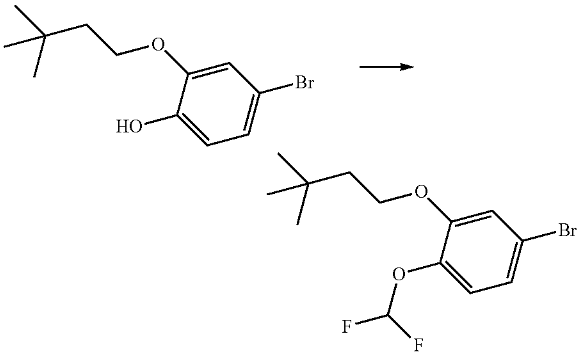

To a solution of 4-bromo-2-(3,3-dimethylbutoxy)phenol (1.25 g, 4.58 mmol) in MeCN (27 mL) was added a solution of KOH (5.0 g, 89.1 mmol) in $H_2O$ (27 mL). The mixture was immediately cooled in a −78° C. bath and diethyl (bromodifluoromethyl) phosphonate (2.44 g, 9.15 mmol) was added. The flask was sealed and the cold bath was removed. The mixture was stirred for 5 h. The reaction was diluted with EtOAc and the layers were separated. The aqueous layer was extracted with EtOAc and the combined organics were washed with 1 M NaOH, $H_2O$ and brine then dried over $Na_2SO_4$ and concentrated in vacuo. The residue was purified by Prep-TLC (100% PE) to afford 4-bromo-1-(difluoromethoxy)-2-(3,3-dimethylbutoxy)benzene (1.30 g, 87.9%) as a colorless oil.

$^1$H NMR (400 MHz, chloroform-d): δ 7.10-7.05 (m, 3H), 6.71-6.34 (t, 1H), 4.08-4.05 (m, 2H), 1.80-1.76 (m, 2H), 1.02 (s, 9H) ppm.

$^{19}$F NMR (400 MHz, chloroform-d): 6-81.709 ppm.

Step 5.

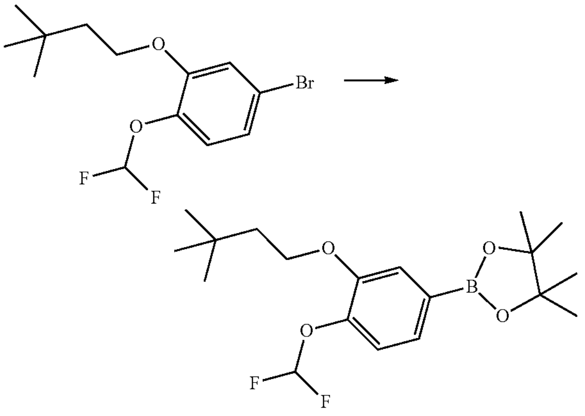

To a solution of 4-bromo-1-(difluoromethoxy)-2-(3,3-dimethylbutoxy)benzene (800 mg, 2.48 mmol) in 25 mL of dioxane were added 4, 4, 5, 5-tetramethyl-2-(4, 4, 5, 5-tetramethyl-1, 3, 2-dioxaborolan-2-yl)-1, 3, 2-dioxaborolane (1.26 g, 4.95 mmol), KOAc (729 mg, 7.43 mmol), Pd (dppf) $Cl_2$ (90.5 mg, 0.124 mmol). The reaction was heated at 90° C. under Ar for 5 h. The reaction mixture was cooled to room temperature and then filtered. The filtrate was concentrated to afford 2-(4-(difluoromethoxy)-3-(3,3-dimethylbutoxy)phenyl)-4,4,5,5-tetramethyl-1,3,2-dioxaborolane (917 mg, 100% yield) as a brown oil.

LCMS: LC retention time 1.955 min. MS (ESI) m/z 371.2 $[M+H]^+$.

Intermediate D-16

4,4,5,5-Tetramethyl-2-(6-neopentyl-3,6-dihydro-2H-pyran-4-yl)-1,3,2-dioxaborolane

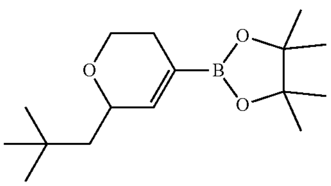 [SMILES: CC(C)(C)CC1C=C(B2OC(C)(C)C(C)(C)O2)CCO1]

Step 1.

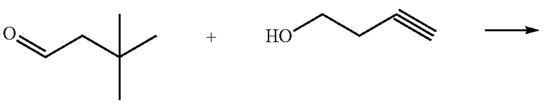

-continued

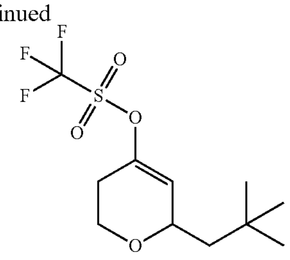

To a stirring solution of 3,3-dimethylbutanal (1.0 g, 9.98 mmol) in dry dichloromethane (50.0 mL) was added triflic acid (1.8 g, 12.0 mmol) dropwise, followed by but-3-yn-1-ol (1.05 g, 15.0 mmol) at 0° C. The reaction mixture was stirred at room temperature for 12 h. After completion of the reaction, the reaction mixture was treated with saturated sodium bicarbonate solution (100 mL). Then, extracted with DCM (80 mL×2). The organic layer was washed with brine and dried over anhydrous $Na_2SO_4$. The organic was then concentrated to dryness. The residue was purified by FCC (PE:EA=10:1) to give 6-neopentyl-3,6-dihydro-2H-pyran-4-yl trifluoromethanesulfonate (1.70 g, 56.3%) as a yellow oil.

Step 2.

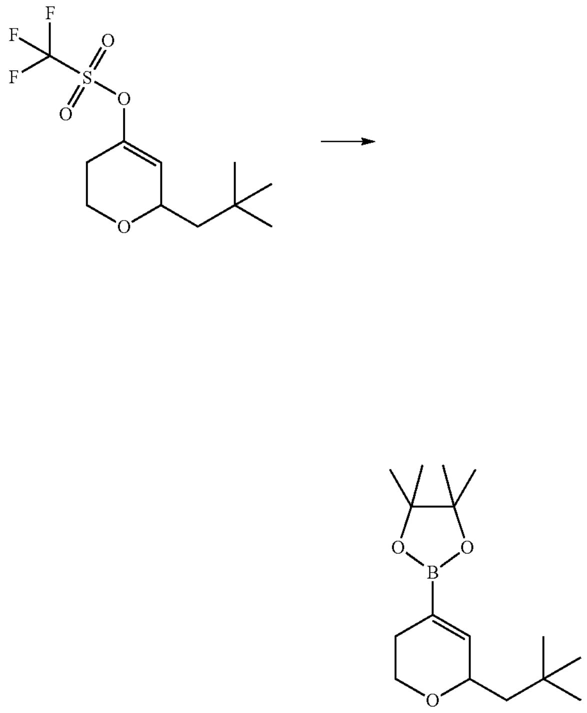

The reaction mixture of 6-neopentyl-3,6-dihydro-2H-pyran-4-yl trifluoromethanesulfonate (1.7 g, 5.62 mmol), bis(pinacolato)diboron (2.14 g, 8.44 mmol), $CH_3COOK$ (1.10 g, 11.2 mmol), Pd (dppf)$Cl_2$ (411 mg, 0.562 mmol) in 1,4-dioxane (60 mL) was heated at 80° C. under Ar overnight. The reaction mixture was concentrated to afford 4,4,5,5-tetramethyl-2-(6-neopentyl-3,6-dihydro-2H-pyran-4-yl)-1,3,2-dioxaborolane.

LCMS: LC retention time 2.50 min. MS (ESI) m/z 281 $[M+H]^+$.

Intermediate D-17

(6-(3,3-Dimethylbutoxy)pyridin-2-yl)boronic acid

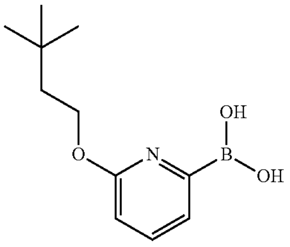 [SMILES: CC(C)(C)CCOc1cccc(B(O)O)n1]

Step 1.

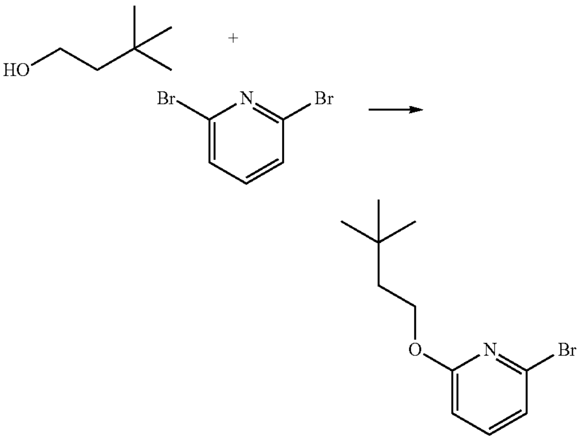

To a stirred solution of 3,3-dimethylbutan-1-ol (500 mg, 4.89 mmol) in dry THF (10 mL) was added NaH (293.58 mg, 7.34 mmol, 60%) at 0° C. The reaction mixture was stirred at room temperature for 0.5 h. To the reaction mixture was added 2,6-dibromopyridine (1.16 g, 4.89 mmol). Then, the mixture was stirred at room temperature for 12 h. The reaction was diluted with EA (20 mL) and washed with water (10 mL×2). The organic phase was dried over $Na_2SO_4$, filtered and concentrated to dryness to give the crude product which was purified by silica gel chromatography (petroleum ether) to give 2-bromo-6-(3,3-dimethylbutoxy)pyridine (1.8 g, 71% two batches) as a colorless oil.

LCMS: MS (ESI) m/z 260 $[M+H]^+$

Step 2.

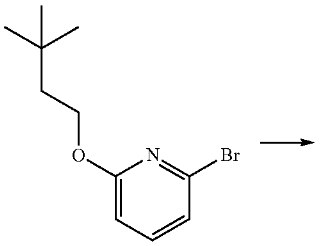

-continued

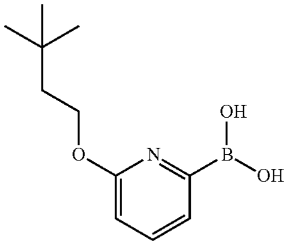

To a stirred solution of 2-bromo-6-(3,3-dimethylbutoxy) pyridine (0.5 g, 1.93 mmol) in THF (6 mL) was added n-butyllithium (1.42 mL, 2.9 mmol) at −78° C. under N2 atmosphere. The reaction was stirred at this temperature for 1 h, then triisopropyl borate (436.3 mg, 2.32 mmol) was added. The mixture was warmed to room temperature and stirred at this temperature for 13 h. TLC (PE/EA=8/1) showed the starting material was consumed. To the mixture was added MeOH (3 mL) and adjusted the pH to 3 with HCl (2 M), evaporated to remove the organic solvent, adjusted the pH to 7 with $NaHCO_3$, extracted with EA (15 mL×3). The combined organic layers were dried over $Na_2SO_4$, filtered and concentrated to dryness. The residue was suspended in PE (10 mL) and filtered to give (6-(3,3-dimethylbutoxy)pyridin-2-yl)boronic acid (0.20 g, 46.29%) as a yellow solid.

$^1$H NMR (400 MHz, methanol-d) 8 8.19 (t, J=7.8 Hz, 1H), 7.46 (d, J=7.4 Hz, 1H), 7.22 (d, J=8.2 Hz, 1H), 4.46 (t, J=7.2 Hz, 2H), 1.97-1.81 (m, 2H), 1.06 (s, 9H) ppm.

Intermediate D-18

2-(3-(1,1-Difluoro-4,4-dimethylpentyl)phenyl)-4,4,5,5-tetramethyl-1,3,2-dioxaborolane

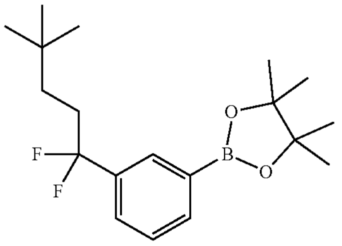 [SMILES: CC(C)(C)CCC(F)(F)c1cccc(B2OC(C)(C)C(C)(C)O2)c1]

Step 1.

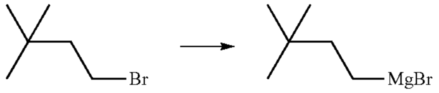

Magnesium turnings (2.10 g, 86.42 mmol) were initially charged in 60 mL of $Et_2O$. A spatula tip of iodine was added and a solution of (17.500 g, 106 mmol) of 1-bromo-3,3-dimethylbutane in 10 mL of $Et_2O$ was slowly added. The reaction mixture was stirred under reflux for 2 h. After cooling to rt, the reaction solution (3,3-dimethylbutyl)magnesium bromide was used directly for the next step.

Step 2.

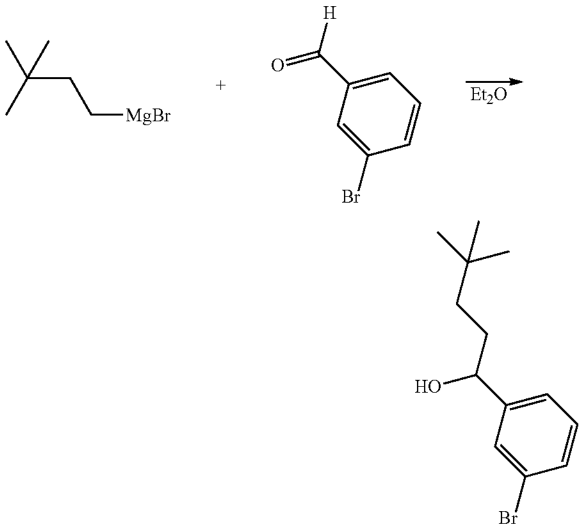

To a solution of 3-bromobenzaldehyde (5.42 g, 29.3 mmol) in $Et_2O$ (30 mL) was added (3,3-dimethylbutyl) magnesium bromide (70 mL, 86.42 mmol) under $N_2$ at room temperature. The resulting mixture was stirred at room temperature for 2 h. The mixture was poured into ammonium chloride solution (50 mL) and extracted with DCM (30 mL×2). The extracts were washed with brine (20 mL×2) and dried over sodium sulfate. The filtrate 1-(3-bromophenyl)-4,4-dimethylpentan-1-ol was used directly for the next step.

LCMS: LC retention time 2.34 min. MS (ESI) m/z 272 [M+H$^+$.

Step 3.

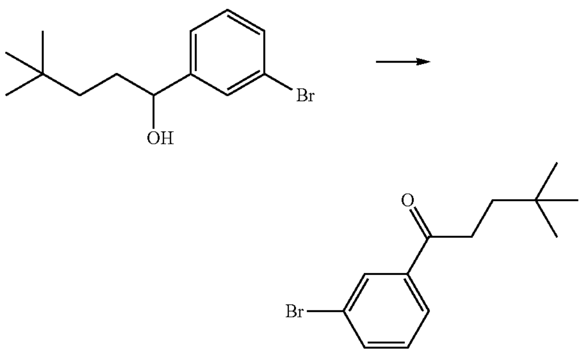

To a stirred solution of 1-(3-bromophenyl)-4,4-dimethylpentan-1-ol (7.95 g, 29.3 mmol) in dry DCM (150 mL) was added PCC (17.60 g, 81.7 mmol) at 0° C. under nitrogen for 2 h. The resulting mixture was stirred at room temperature for 12 h. The mixture was filtered. The filtrate was concentrated. The residue was purified by silica gel chromatography (PE/EA=98/2) to give 1-(3-bromophenyl)-4,4-dimethylpentan-1-one (6.95 g, three steps 88.1%) as a light yellow oil.

LCMS: LC retention time 2.33 min. MS (ESI) m/z 271 [M+H]$^+$.

Step 4.

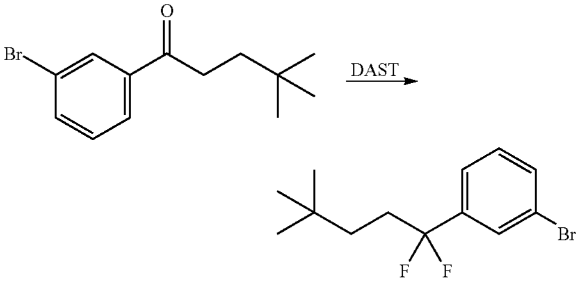

To a stirred solution of 1-(3-bromophenyl)-4,4-dimethyl-pentan-1-one (1.74 g, 6.84 mmol) in DCM (20 mL) was added DAST (4.50 g, 27.9 mmol) at room temperature under nitrogen. The reaction mixture was stirred at 86° C. for 14 h. The mixture was poured into ice water. The aqueous layer was adjusted to pH 8. Then, the aqueous was extracted with EA. The organic layer was then dried over $Na_2SO_4$, filtered and concentrated. The crude residue was purified via flash chromatography (PE) to afford 1-bromo-3-(1,1-difluoro-4,4-dimethylpentyl)benzene (1.59 g, 79.9%) as a colorless oil.

$^1$H NMR (400 MHz, Chloroform-d) δ 7.64 (s, 1H), 7.58 (d, J=8.0 Hz, 1H), 7.41 (d, J=7.6 Hz, 1H), 7.32 (t, J=8.0 Hz, 1H), 2.11-2.03 (m, 2H), 1.35-1.30 (m, 2H), 0.90 (s, 9H) ppm.

Step 5.

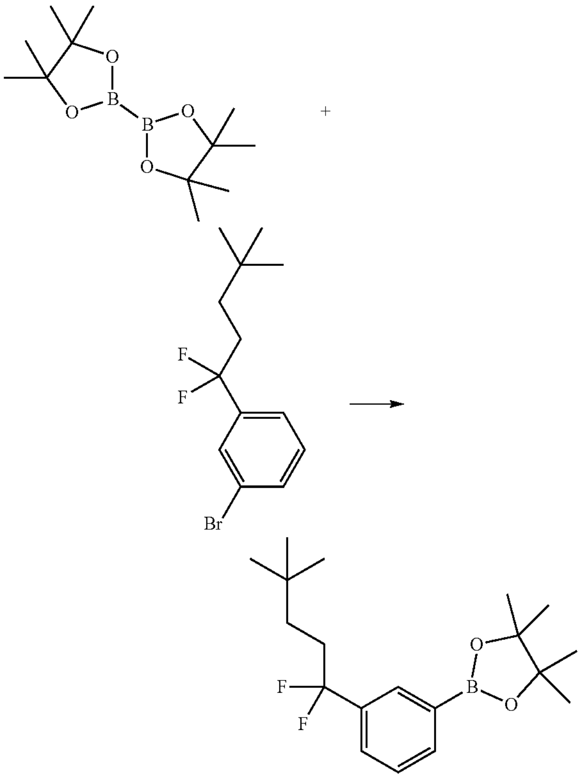

A mixture of 1-bromo-3-(1,1-difluoro-4,4-dimethylpentyl)benzene (266 mg, 0.913 mmol), AcOK (270 mg, 2.75 mmol), 4,4,4',4',5,5,5',5'-octamethyl-2,2'-bi(1,3,2-dioxaborolane) (255 mg, 1.0 mmol), tricyclohexylphosphane (27 mg, 0.096 mmol) and $Pd_2$ $(dba)_3$ (84 mg, 0.092 mmol) in 1,4-dioxane (10 mL) under $N_2$ protection was stirred at 85° C. for 20 h. The reaction mixture was cooled to room temperature and filtered through Celite. The filtrate was concentrated to give 2-(3-(1,1-difluoro-4,4-dimethylpentyl)phenyl)-4,4,5,5-tetramethyl-1,3,2-dioxaborolane (235 mg, 100%) as a colorless oil.

LCMS: LC retention time 2.19 min. MS (ESI) m/z 256.8 $[M+H]^+$.

Intermediate D-19

3-(3-(4,4,5,5-Tetramethyl-1,3,2-dioxaborolan-2-yl)phenyl)-5-(trifluoromethyl)isoxazole

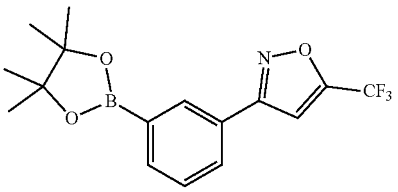 [SMILES: CC1(C)OB(c2cccc(-c3cc(C(F)(F)F)on3)c2)OC1(C)C]

Step 1.

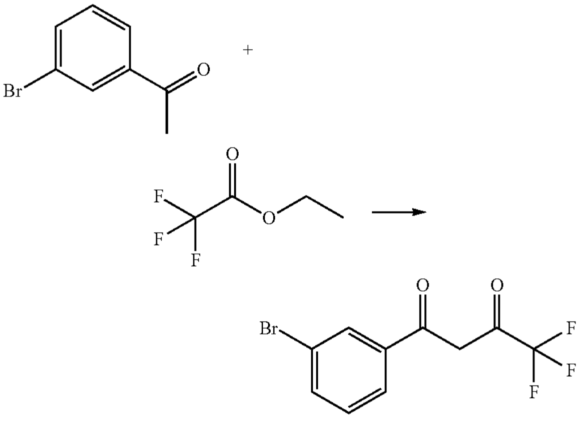

Sodium (347 mg, 15.1 mmol) was dissolved in ethanol (10 mL) under inert conditions. To this solution was added a solution of ethyl 2,2,2-trifluoroacetate (2.86 g, 20.1 mmol) in ethanol (10 mL), followed by a solution of 1-(3-bromophenyl) ethanone (2.00 g, 10.0 mmol) in ethanol (10 mL). The reaction mixture was refluxed at 85° C. overnight. After the completion of the reaction, the reaction was quenched with aq. HCl (1 N) (30 mL). The solution was extracted with ethyl acetate (50 mL) and washed with brine (50 mL×2). The solution was dried over anhydrous $Na_2SO_4$ and filtered. The filtrate was concentrated under reduced pressure to get crude product which was purified by silica gel chromatography (15% ethyl acetate/Petroleum ether) to afford 1-(3-bromophenyl)-4,4,4-trifluoro-butane-1,3-dione (4.12 g) as a red oil.

LCMS: LC retention time 1.18 min. MS (ESI) m/z 297 $[M+H]^+$.

Step 2.

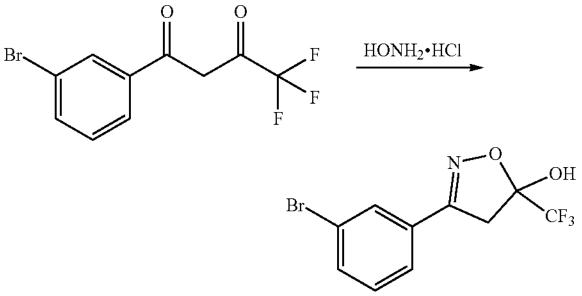

To a solution of hydroxylamine hydrochloride (236 mg, 3.39 mmol) in aq. NaOH (142 mg, 3.56 mmol) was added 1-(3-bromophenyl)-4,4,4-trifluoro-butane-1,3-dione (1 g, 3.39 mmol) at 20-30° C. over 1 h. The resulting mixture was heated under reflux for 45 min. After cooling to room temperature, the mixture was poured into ice water (50 mL). The precipitate was filtered off. The solution was extracted with ethyl acetate (30 mL) and dried over anhydrous $Na_2SO_4$ and filtered. The filtrate was concentrated under reduced pressure to get 3-(3-bromophenyl)-5-(trifluoromethyl)-4,5-dihydroisoxazol-5-ol (810 mg).

LCMS: LC retention time 2.02 min. MS (ESI) m/z 311 $[M+H]^+$.

Step 3.

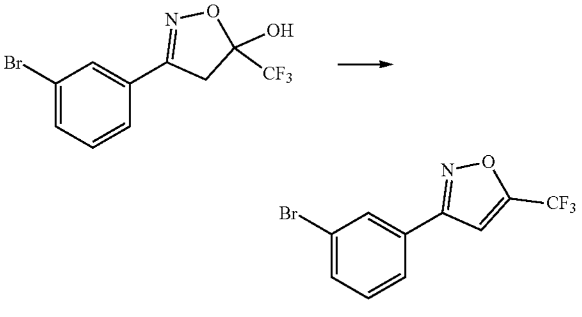

The solution of 3-(3-bromophenyl)-5-(trifluoromethyl)-4,5-dihydroisoxazol-5-ol (810 mg, 3.36 mmol) in trifluoroacetic acid (20 mL) was refluxed at 80° C. overnight. After completion of reaction, the reaction was quenched with aq. $NaHCO_3$ (40 mL). The aqueous solution was extracted with ethyl acetate (40 mL). The organic solution was then washed with water (30 mL). The solution was dried over anhydrous $Na_2SO_4$ and filtered. The solution was concentrated under reduced pressure to get crude product which was purified by silica gel chromatography (11% ethyl acetate/petroleum ether) to afford the product (190 mg).

LCMS: LC retention time 1.54 min. MS (ESI) m/z not observed.

Step 4.

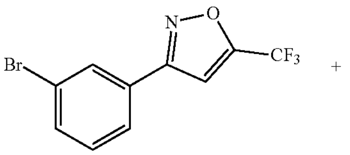

-continued

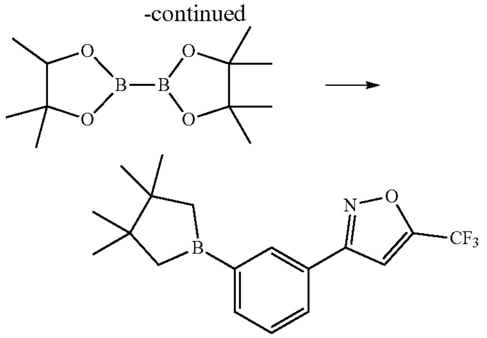

The mixture of 3-(3-bromophenyl)-5-(trifluoromethyl)isoxazole (200 mg, 0.685 mmol), 4,4,5,5-tetramethyl-2-(4,4,5,5-tetramethyl-1,3,2-dioxaborolan-2-yl)-1,3,2-dioxaborolane (174 mg, 0.685 mmol), $Pd(dppf)Cl_2$ (25.1 mg, 0.034 mmol), and potassium acetate (134 mg, 1.37 mmol) in 1,4-dioxane (10 mL) were heated at 80° C. under the atmosphere of nitrogen overnight. After the completion of reaction, the mixture was filtered. The filtrate was extracted with ethyl acetate (25 mL). The organic solution was washed with water (25 mL) and brine (25 mL). The solution was dried over anhydrous $Na_2SO_4$ and filtered. The solution was concentrated under reduced pressure to get 3-(3-(4,4,5,5-tetramethyl-1,3,2-dioxaborolan-2-yl)phenyl)-5-(trifluoromethyl)isoxazole as a brown oil.

LCMS: LC retention time 1.59 min. MS (ESI) m/z 340 $[M+H]^+$.

Intermediate D-20

4,4,5,5-Tetramethyl-2-(3-((1S)-3-(trifluoromethoxy)cyclopentyl)phenyl)-1,3,2-dioxaborolane

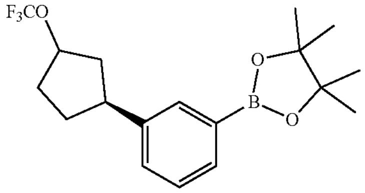 [SMILES: CC1(C)OB(c2cccc([C@H]3CCC(OC(F)(F)F)C3)c2)OC1(C)C]

Step 1.

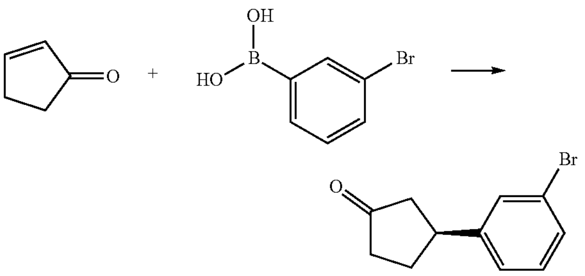

To a mixture of 6.84 g (34.2 mmol) of (3-bromophenyl)boronic acid, 188.6 mg (0.74 mmol) of acetylacetonatobis(ethylene)rhodium (I) and 455 mg (0.74 mmol) of S-BINAP in 40 mL of dioxane and 4 mL of $H_2O$ under nitrogen was added 2.0 g (24.4 mmol) of cyclopent-2-en-1-one. After refluxing for 5.0 h, the reaction was concentrated. The residue was partitioned between 100 mL of EtOAc and 100 mL of 1N $NaHCO_3$. After separating phases, the organic layer was washed with 100 mL of brine, dried over $Na_2SO_4$ and concentrated. The residue was purified by silica gel column chromatography (PE/EA=5/1) to afford 4.70 g of (S)-3-(3-bromophenyl)cyclopentan-1-one as a light yellow solid.

LCMS: LC retention time 2.14 min. MS (ESI) m/z 241 $[M+H]^+$.

Step 2.

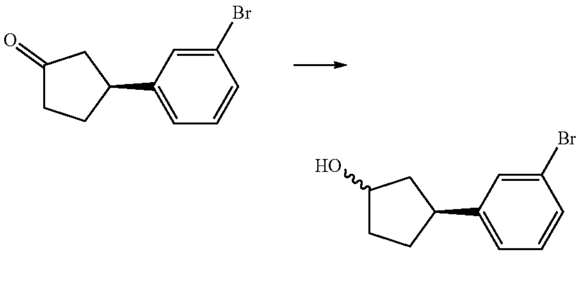

A solution of (S)-3-(3-bromophenyl)cyclopentan-1-one (4.58 g, 19.2 mmol) in anhydrous tetrahydrofuran (40.0 mL) was cooled to −78° C. and added DIBAL (1M in toluene) (76.7 mL) at the same temperature under argon atmosphere. Then the mixture was allowed to warm to room temperature slowly and stirred at room temperature overnight. Then saturated potassium sodium tartrate tetrahydrate solution (80 mL) was added and stirred for another 1 h, and the mixture was filtered through a celite plug. The filtrate was concentrated under reduced pressure to give the crude product which was purified by flash reversed phase column to give (3S)-3-(3-bromophenyl)cyclopentan-1-ol (3.25 g, 70.4%) as colorless oil.

LCMS: LC retention time 2.05 min. MS (ESI) m/z 225 $[M-H_2O]^+$.

Step 3.

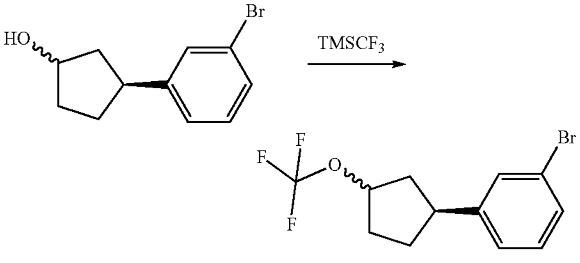

To a flask was charged AgOTf (3.20 g, 12.4 mmol), Select-F® (2.20 g, 6.22 mmol), KF (964 mg, 16.6 mmol) and (3S)-3-(3-bromophenyl)cyclopentan-1-ol (1.0 g, 4.15 mmol) was purged with argon, then EtOAc (20 mL) was added, followed by $TMSCF_3$ (1.77 g, 12.4 mmol), 2-fluoropyridine (1.21 g, 12.4 mmol). The reaction mixture was stirred at room temperature overnight under argon. The reaction mixture was filtered through a celite pad. The filtrate was concentrated and purified by silica gel column chromatography (100% PE) to afford 1-bromo-3-((1S)-3-(trifluoromethoxy)cyclopentyl)benzene (402 mg, 31.4%) as a colorless oil.

$^1H$ NMR (400 MHz, chloroform-d) δ 7.36 (dd, J=16.2, 9.0 Hz, 2H), 7.16 (dd, J=15.8, 6.8 Hz, 2H), 4.85 (d, J=28.0 Hz, 1H), 3.39-2.95 (m, 1H), 2.61-2.21 (m, 2H), 2.16-1.59 (m, 5H) ppm.

Step 4.

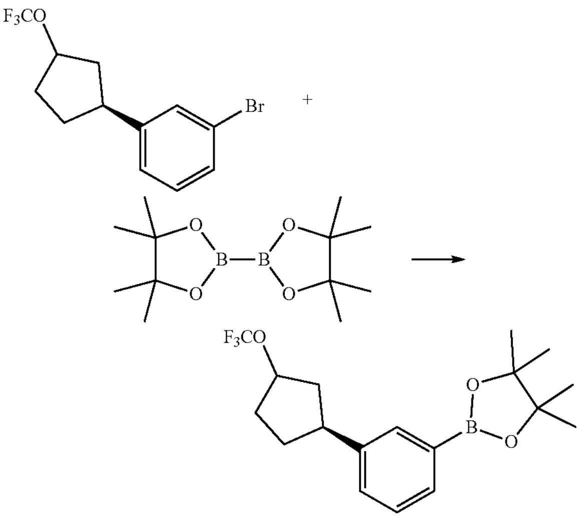

The reaction mixture of 1-bromo-3-[(1S)-3-(trifluoromethoxy) cyclopentyl]benzene (1.0 g, 3.23 mmol) in dioxane (20 mL) was added 2,4,4,5,5-pentamethyl-1,3,2-dioxaborolane (1.38 g, 4.85 mmol), KOAc (793 mg, 8.09 mmol), $Pd(dppf)Cl_2$ (70.9 mg, $9.70\times10^{-5}$ mol) and stirred at 90° C. overnight under argon. The mixture was concentrated and extracted with EA (10 mL×3), the organic phase was washed with brine (20 mL), the organic phase was concentrated and purified by SGC (PE:EA=10:1) to give 4,4,5,5-tetramethyl-2-[3-[(1S)-3-(trifluoromethoxy)cyclopentyl] phenyl]-1,3,2-dioxaborolane (720 mg, 62.5% yield) as a light oil.

LCMS (acidic): LC retention time 2.41, MS (ESI): m/z 357 $[M+H]^+$.

Intermediate D-21

1-Bromo-3-((JR)-3-(trifluoromethoxy)cyclopentyl) benzene

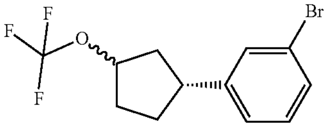 [SMILES: FC(F)(F)OC1CC[C@@H](c2cccc(Br)c2)C1]

Step 1.

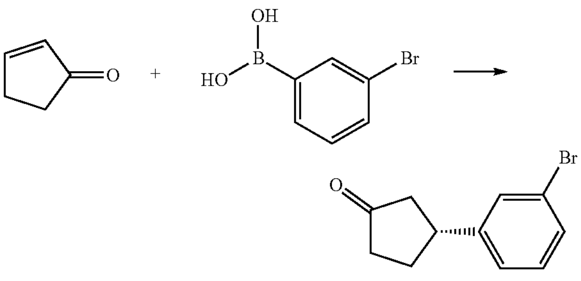

Cyclopent-2-en-1-one (1.0 g, 12.2 mmol) was added to the mixture of (3-bromophenyl)boronic acid (2.94 g, 14.6 mmol), acetylacetonatobis(ethylene)rhodium(I) (189 mg, 0.731 mmol), and (R)-(+)-2,2'-Bis(diphenylphosphino)-1,1'-binaphthyl (758 mg, 1.22 mmol) in 1,4-dioxane (20 mL) and water (2.0 mL) under argon atmosphere at room temperature. The resulting reaction mixture was stirred at 105° C. for 5.5 hrs. After cooling to room temperature, the mixture was concentrated under reduced pressure. Saturated aqueous sodium bicarbonate solution (100 mL) was added, and extracted with ethyl acetate (3×30 mL), the combined organic layers were washed with brine (60 mL), dried over sodium sulfate, filtered and concentrated under reduced pressure, the residue was purified by silica gel column chromatography (petroleum ether:ethyl acetate=5:1) to afford (R)-3-(3-bromophenyl)cyclopentan-1-one as light yellow oil (2.55 g, 88% yield).

LCMS: LC retention time 2.00 min. MS (ESI) m/z 239 $[M+H]^+$ $^1H$ NMR (400 MHz, chloroform-d) δ 7.40-7.37 (m, 2H), 7.23-7.17 (m, 2H), 3.43-3.35 (m, 1H), 2.70-2.63 (m, 1H), 2.51-2.41 (m, 2H), 2.35-2.26 (m, 2H), 2.02-1.92 (m, 1H) ppm.

Step 2.

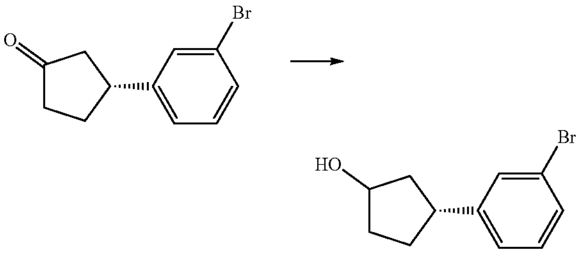

Diisobutylaluminium hydride (6.3 mL, 1 M solution in toluene, 6.3 mmol) was added to the solution of (R)-3-(3-bromophenyl)cyclopentan-1-one (1.0 g, 4.18 mmol) in anhydrous tetrahydrofuran (10.0 mL) at −78° C. under argon atmosphere, the resulting reaction mixture was stirred at the same temperature for 2.0 h. The reaction was quenched by adding methanol (5.0 mL) dropwise at −78° C. Then the mixture was warmed to room temperature, and saturated aqueous potassium sodium tartrate tetrahydrate solution (50 mL) was added. The resulting mixture was stirred overnight at room temperature. Extracted with ethyl acetate (30 mL×3), the combined organic layers were washed with brine (30 mL), dried over sodium sulfate, filtered and concentrated under reduced pressure, the residue was purified by silica gel chromatography (30% ethyl acetate in petroleum ether) to give (3R)-3-(3-bromophenyl)cyclopentan-1-ol as colorless oil (798 mg, 79% yield).

LCMS: LC retention time 1.97 min. MS (ESI) m/z 223 $[M-H_2O]+$ $^1H$ NMR (400 MHz, chloroform-d) δ 7.44-7.37 (m, 1H), 7.33-7.30 (m, 1H), 7.23-7.14 (m, 2H), 4.55-4.43 (m, 1H), 3.41-2.97 (m, 1H), 2.49-2.07 (m, 2H), 1.95-1.79 (m, 2H), 1.74-1.58 (m, 2H) ppm.

Step 3.

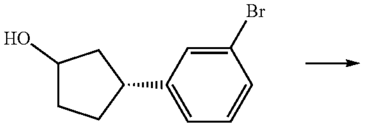

-continued

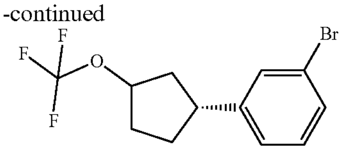

(Trifluoromethyl)trimethylsilane (1.41 g, 9.93 mmol) was added to the mixture of (3R)-3-(3-bromophenyl)cyclopentan-1-ol (798 mg, 3.31 mmol), silver trifluoromethane sulfonate (2.55 g, 9.93 mmol), 1-chloromethyl-4-fluoro-1,4-diazoniabicyclo[2.2.2]octane bis(tetrafluoroborate) (1.758 g, 4.97 mmol) and potassium fluoride (0.768 g, 13.24 mmol) in ethyl acetate (15.0 mL) under argon atmosphere at room temperature, followed by 2-fluoropyridine (0.963 g, 9.93 mmol). The resulting reaction mixture was stirred at room temperature for 94 h. Filtered through a celite pad, the filtrate was concentrated and purified by silica gel chromatography (100% petroleum ether) to afford 1-bromo-3-((1R)-3-(trifluoromethoxy)cyclopentyl)benzene as a colorless oil (468 mg, 46% yield).

LCMS: LC retention time 2.74 min. MS (ESI) not observed.

$^1H$ NMR (400 MHz, chloroform-d) δ 7.40-7.33 (m, 2H), 7.19-7.13 (m, 2H), 4.90-4.79 (m, 1H), 3.37-2.98 (m, 1H), 2.59-2.32 (m, 1H), 2.29-1.63 (m, 5H) ppm.

Intermediate D-22

2-(3-(3-(1,1-Difluoroethyl)cyclopentyl)phenyl)-4,4,5,5-tetramethyl-1,3,2-dioxaborolane

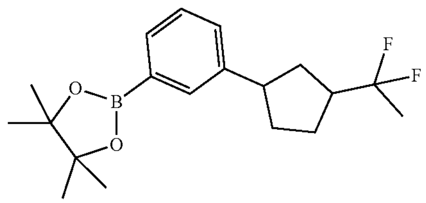 [SMILES: CC(F)(F)C1CCC(c2cccc(B3OC(C)(C)C(C)(C)O3)c2)C1]

Step 1.

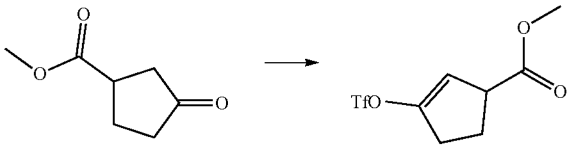

To a solution of methyl 3-oxocyclopentane-1-carboxylate (2.56 g, 18.0 mmol) in toluene (50 mL) was added DIEA (9.35 g, 72.3 mmol) at room temperature, followed by $Tf_2O$ (12.80 g, 45.4 mmol) at 0° C. under $N_2$ atmosphere. The resulting mixture was stirred at 50° C. for 2 h. The mixture was poured into water (400 mL) and extracted with ethyl acetate (100 mL×2). The extracts were washed with water (100 mL×2), dried over sodium sulfate, filtered and evaporated. The crude product thus obtained was purified by silica gel chromatography (PE/EA=10/1) to give methyl 3-(((trifluoromethyl)sulfonyl)oxy)cyclopent-2-ene-1-carboxylate (4.93 g, 100%) as a yellow oil.

$^1H$ NMR (400 MHz, chloroform-d) δ 5.74-5.61 (m, 1H), 3.75 (s, 3H), 3.82-3.62 (m, 1H), 3.35-2.96 (m, 1H), 2.87-2.64 (m, 2H), 2.37-2.30 (m, 1H) ppm.

Step 2.

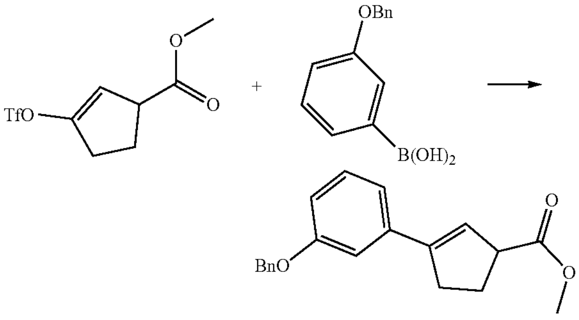

To a solution of methyl 3-(((trifluoromethyl)sulfonyl)oxy)cyclopent-2-ene-1-carboxylate (4930 mg, 18.0 mmol) in 1,2-dimethoxyethane/$H_2O$ (60 mL, v/v=5/1) were added (3-(benzyloxy)phenyl)boronic acid (4.18 g, 18.3 mmol), Pd$(Ph_3P)_4$ (520 mg, 0.45 mmol), and $NaHCO_3$ (4.57 g, 54.49 mmol). The resulting mixture was stirred at 80° C. under argon atmosphere for 16 h, filtered and concentrated in vacuo. The residue was washed with water (200 mL) and brine (200 mL), extracted with ethyl acetate (20 mL×2), dried over anhydrous $Na_2SO_4$, filtered, and the filtrate was concentrated to dryness under reduced pressure. The crude product thus obtained was purified by silica gel chromatography on silica gel (PE/EA=10:1) to give methyl 3-(3-(benzyloxy)phenyl)cyclopent-2-ene-1-carboxylate (2.63 g; 47.5% two steps) as a yellow oil.

LCMS: LC retention time 2.27 min. MS (ESI) m/z 309 $[M+H]^+$.

Step 3.

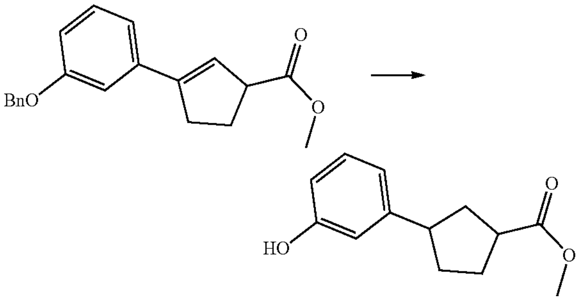

To a solution of methyl 3-(3-(benzyloxy)phenyl)cyclopent-2-ene-1-carboxylate (2.63 g, 8.53 mmol) in MeOH (150 mL) was added Pd/C (1210 mg). The resulting mixture was stirred at room temperature for 16 h. The reaction mixture was filtered through a Celite plug. The filtrate was concentrated and purified by silica gel chromatography (PE/EA=5/1) to give methyl 3-(3-hydroxyphenyl)cyclopentane-1-carboxylate (1.45 g, 77.2%) as a yellow oil.

LCMS: LC retention time 1.54 min. MS (ESI) m/z 221 $[M+H]^+$.

Step 4.

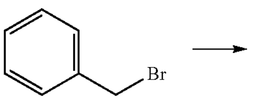

-continued

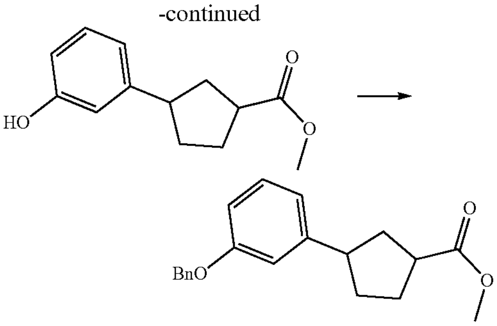

To a solution of methyl 3-(3-hydroxyphenyl)cyclopentane-1-carboxylate (1.45 g, 6.58 mmol) in acetone (30 mL) were added (bromomethyl)benzene (2220 mg, 12.98 mmol) and $K_2CO_3$ (2735 mg, 19.79 mmol). The resulting mixture was stirred at 55° C. under N2 atmosphere for 16 h. The mixture was extracted with ethyl acetate (50 mL×2), washed with water (50 mL) and brine (50 mL), dried over anhydrous $Na_2SO_4$, filtered, and the filtrate was concentrated to dryness under reduced pressure. The crude product thus obtained was purified by silica gel chromatography (PE/EA=10/1) to give methyl 3-(3-(benzyloxy)phenyl)cyclopentane-1-carboxylate (2.04 g, 100%) as a yellow oil.

LCMS: LC retention time 2.26 min. MS (ESI) m/z 333 $[M+Na]^+$.

Step 5.

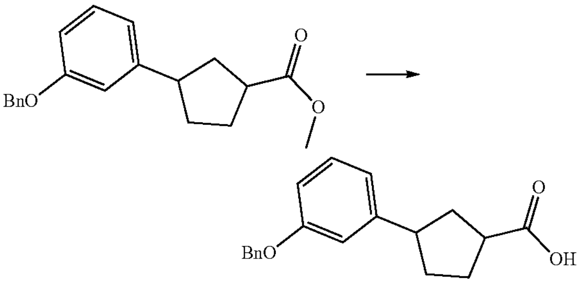

To a stirred solution of methyl 3-(3-(benzyloxy)phenyl)cyclopentane-1-carboxylate (2.04 g, 6.57 mmol) in THF (8 mL) MeOH (4 mL) and water (0.75 mL), LiOH·$H_2O$ (2060 mg, 49.05 mmol) was added slowly at room temperature. The reaction was stirred at room temperature for 16 h. Hydrochloric acid (2N) was added to the solution until pH 4. Then the mixture was extracted with ethyl acetate (50 mL×2), washed with brine (50 mL), dried over anhydrous $Na_2SO_4$, filtered. The filtrate was concentrated under reduced and gave 3-(3-(benzyloxy)phenyl)cyclopentane-1-carboxylic acid (2.17 g; 100%) as a yellow solid.

LCMS: LC retention time 1.38 min. MS (ESI) m/z 297 $[M+H]^+$.

Step 6.

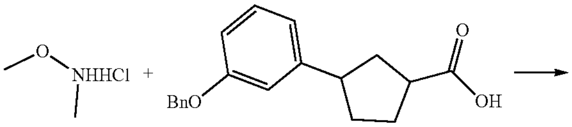

-continued

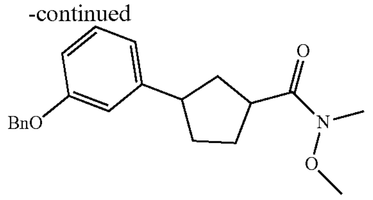

To a solution of 3-(3-(benzyloxy)phenyl)cyclopentane-1-carboxylic acid (2175 mg, 7.34 mmol) in DCM (40 mL) was added HATU (5580 mg, 14.68 mmol), N,O-dimethylhydroxylamine hydrochloride (1.08 g, 11.12 mmol) and DIEA (2850 mg, 22.05 mmol) at room temperature. The resulting mixture was stirred at the same temperature for 16 h. The mixture was poured into water (100 mL) and extracted with ethyl acetate (100 mL×2). The extracts were washed with water (100 mL×2), dried over sodium sulfate and evaporated. The crude product thus obtained was purified by silica gel chromatography (PE/EA=10/1) to give 3-(3-(benzyloxy)phenyl)-N-methoxy-N-methylcyclopentane-1-carboxamide (2.19 g, 88%) as a colorless oil.

LCMS: LC retention time 2.16 min. MS (ESI) m/z 340 $[M+H]^+$.

Step 7.

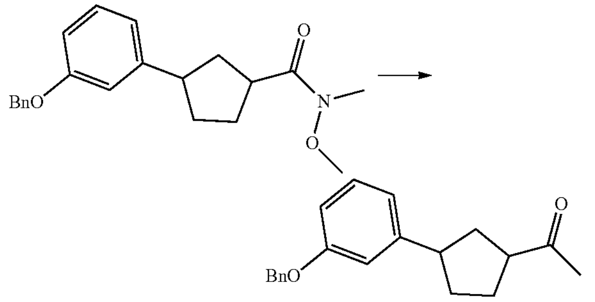

To a solution of 3-(3-(benzyloxy)phenyl)-N-methoxy-N-methylcyclopentane-1-carboxamide (2690 mg, 7.92 mmol) in THF (20 mL) was added MeMgBr (7.9 mL, 23.7 mmol, 3.0 M) under $N_2$ at 0° C. The resulting mixture was stirred at room temperature for 2 h. The mixture was poured into water (50 mL) and extracted with ethyl acetate (100 mL×2). The extracts were washed with water (100 mL×2), dried over sodium sulfate and evaporated. The resulting residue was purified by silica gel chromatography (PE/EA=10/1) to afford 1-(3-(3-(benzyloxy)phenyl)cyclopentyl)ethan-1-one (2.31 g, 99%) as a colorless oil.

LCMS: LC retention time 2.22 min. MS (ESI) m/z 295 $[M+H]^+$.

Step 8.

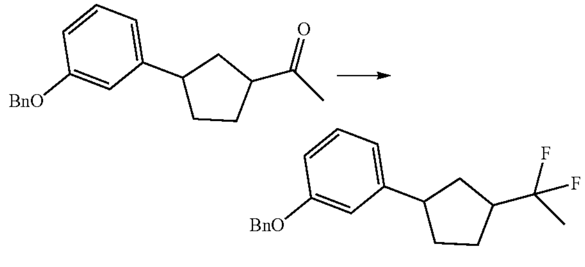

To a stirred solution of 1-(3-(3-(benzyloxy)phenyl)cyclopentyl)ethan-1-one (1.50 g, 5.1 mmol) in DCM (15 mL) was added DAST (4.0 mL) at 0° C. under nitrogen. The reaction mixture was stirred at room temperature for 16 h. The mixture was poured into water (100 mL) and extracted with ethyl acetate (100 mL×2). The extracts were washed with water (100 mL×2), dried over sodium sulfate and evaporated. The crude product obtained was purified by silica gel chromatography (PE/EA=95/5) to give 1-(benzyloxy)-3-(3-(1,1-difluoroethyl)cyclopentyl)benzene (1.36 g, 84.9%) as a colorless oil.

LCMS: LC retention time 2.47 min. MS (ESI) m/z 317 $[M+H]^+$.

Step 9.

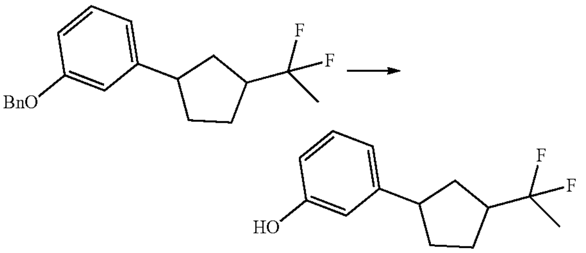

To a solution of 1-(benzyloxy)-3-(3-(1,1-difluoroethyl)cyclopentyl)benzene (2.04 g, 6.46 mmol) in EA (50 mL) was added Pd/C (1.04 g). The resulting mixture was stirred at room temperature for 16 h. The reaction fluid was filtered through a Celite plug. The filtrate was concentrated and purified by silica gel chromatography (PE/EA=6/1) to give 3-(3-(1,1-difluoroethyl)cyclopentyl)phenol (1.25 g, 85.6%) as a yellow oil.

LCMS: LC retention time 2.03 min. MS (ESI) m/z 227 $[M+H]^+$.

Step 10.

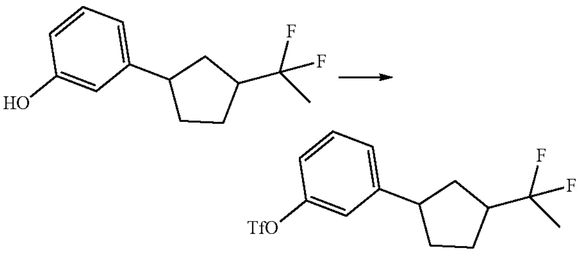

To a solution of 3-(3-(1,1-difluoroethyl)cyclopentyl)phenol (223 mg, 0.986 mmol) in DCM (2.5 mL) was added pyridine (80 mg, 1.01 mmol) and $Tf_2O$ (335 mg, 1.19 mmol) at 0° C. After the addition was completed the reaction mixture was stirred at room temperature overnight. The reaction solution was concentrated under reduced pressure. The residue was extracted with EA (20 mL×3). The organic solutions were combined, washed with $NaHCO_3$ (10 mL) and brine (20 mL), dried over anhydrous $Na_2SO_4$. The solvent was evaporated and purified by SGC (PE/EA=5%) to afford 3-(3-(1,1-difluoroethyl)cyclopentyl)phenyl trifluoromethanesulfonate (171 mg, 48.4%) as a colorless oil.

LCMS: LC retention time 2.37 min. MS (ESI) m/z 381 $[M+Na]^+$.

Step 11.

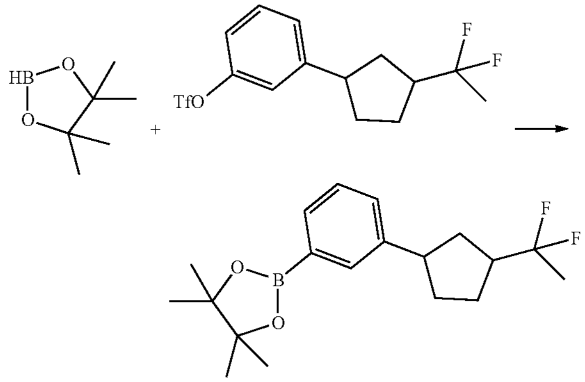

To a solution of 3-(3-(1,1-difluoroethyl)cyclopentyl)phenyl trifluoromethanesulfonate (171 mg, 0.48 mmol) in dioxane (2.5 mL) were added 4,4,5,5-tetramethyl-1,3,2-dioxaborolane (108 mg, 0.84 mmol), TEA (145 mg, 1.43 mmol) and $PdCl_2$(dppf) (22 mg, 0.03 mmol) at room temperature. The reaction was heated at reflux for 16 h until TLC indicated that the starting material was consumed. The mixture was extracted with EA (30 mL×2). The organic solution was washed with brine (30 mL×2) and dried over anhydrous $Na_2SO_4$. The filtrate was concentrated and gave 2-(3-(3-(1,1-difluoroethyl)cyclopentyl)phenyl)-4,4,5,5-tetramethyl-1,3,2-dioxaborolane (195 mg, 100%) as a yellow solid.

LCMS: LC retention time 1.96 min. MS (ESI) m/z 337 $[M+H]^+$.

Intermediate D-23

2-(3-(3-(2,2-Difluoropropyl)cyclopentyl)phenyl)-4,4,5,5-tetramethyl-1,3,2-dioxaborolane

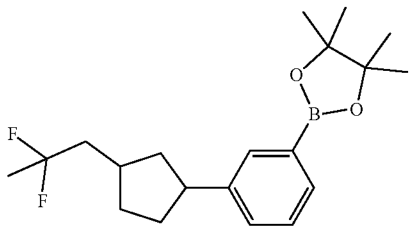 [SMILES: CC(F)(F)CC1CCC(c2cccc(B3OC(C)(C)C(C)(C)O3)c2)C1]

Step 1.

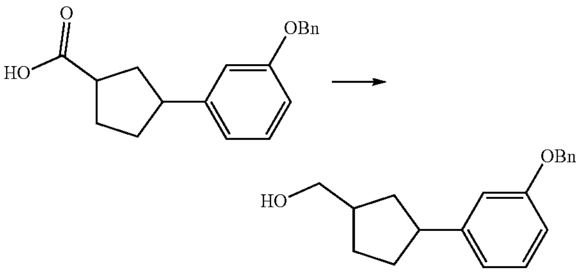

To a solution of 3-(3-(benzyloxy)phenyl)cyclopentane-1-carboxylic acid (2.10 g, 7.09 mmol) in anhydrous THF (60 mL) was added $LiAlH_4$ (808 mg, 21.3 mmol) slowly at 0° C. under argon atmosphere. After addition, the mixture was allowed to warm to room temperature and stirred at the same temperature for 1 h. LCMS showed that the starting material was consumed. The mixture was added $Na_2SO_4 \cdot 10H_2O$ and water at 0° C., and the mixture was stirred for another 1 h. The mixture was filtered through a Celite pad. The filtrate was extracted with ethyl acetate (150 mL). The organic solution was washed with water (100 mL) and brine (150 mL), dried over anhydrous sodium sulfate, filtered. The filtrate was concentrated under reduced pressure to give the crude which was purified by flash chromatography column (PE/EA=5/1) to give the desired compound (3-(3-(benzyloxy)phenyl)cyclopentyl)methanol (1.66 g, 83.0%) as a colorless oil.

LCMS: LC retention time 2.15 min. MS (ESI) m/z 283 $[M+H]^+$.

Step 2.

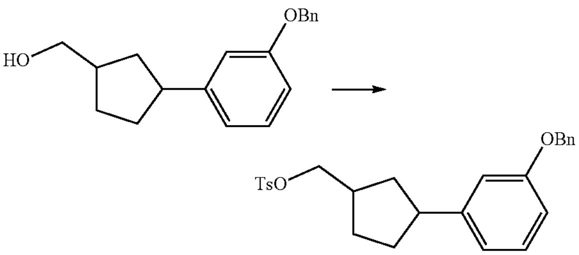

To a solution of (3-(3-(benzyloxy)phenyl)cyclopentyl)methanol (1.66 g, 5.88 mmol) in DCM (30 mL) were added DMAP (71.8 mg, 0.59 mmol), $Et_3N$ (1.78 g, 17.6 mmol), and TsCl (1.68 g, 8.82 mmol) under argon atmosphere at 0° C. The mixture was allowed to warm to room temperature and stirred at the same temperature for overnight. The mixture was poured into ice-water, extracted with DCM (60 mL). The DCM solution was washed with $NaHCO_3$ (30 mL) and brine (50 mL), dried over anhydrous sodium sulfate, filtered. The filtrate was concentrated under reduced pressure to give (3-(3-(benzyloxy)phenyl)cyclopentyl)methyl 4-methylbenzenesulfonate (2.47 g) as a yellow oil.

LCMS: LC retention time 2.38 min. MS (ESI) m/z 459 $[M+Na]^+$.

Step 3.

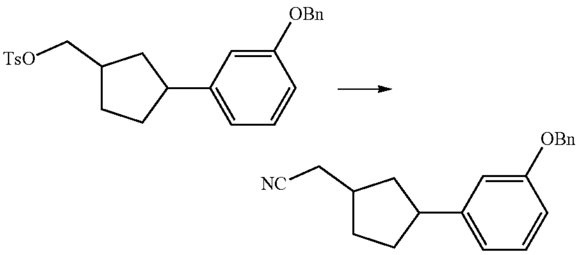

To a solution of (3-(3-(benzyloxy)phenyl)cyclopentyl)methyl 4-methylbenzenesulfonate (2.47 g, 5.66 mmol) in DMF (30.0 mL) were added 18-Crown-6 (2.24 g, 8.49 mmol) and KCN (552 mg, 8.49 mmol). The solution was stirred at 55° C. in an oil bath overnight. The resulting solution was cooled to rt, then diluted with ethyl acetate (150 mL), washed with brine (100 mL), dried over anhydrous sodium sulfate, filtered and the filtrate was concentrated under vacuum to give the crude which was purified by flash chromatography column (PE/EA=5/1) to give 2-(3-(3-(benzyloxy)phenyl)cyclopentyl)acetonitrile (1.49 g, 90.4%) as a colorless oil.

LCMS: LC retention time 2.22 min. MS (ESI) m/z 292 $[M+H]^+$.

Step 4.

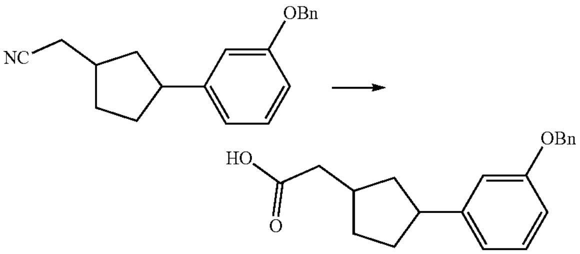

To a solution of 2-(3-(3-(benzyloxy)phenyl)cyclopentyl) acetonitrile (1.49 g, 5.11 mmol) in ethanol (30 mL) and $H_2O$ (3.0 mL) was added sodium hydroxide (4.09 g, 100.3 mg). The reaction was stirred for 12 h at 80° C. The resulting mixture was concentrated under vacuum. The residue was dissolved in water (60 mL). The pH was adjusted to 4 with hydrogen chloride (1N). The mixture was extracted with ethyl acetate (100 mL). The ethyl acetate solution was dried over anhydrous sodium sulfate, concentrated under vacuum to obtain the title compound 2-(3-(3-(benzyloxy)phenyl) cyclopentyl)acetic acid (1.48 g) as a light yellow solid.

LCMS: LC retention time 2.13 min. MS (ESI) m/z 311 $[M+H]^+$.

Step 5.

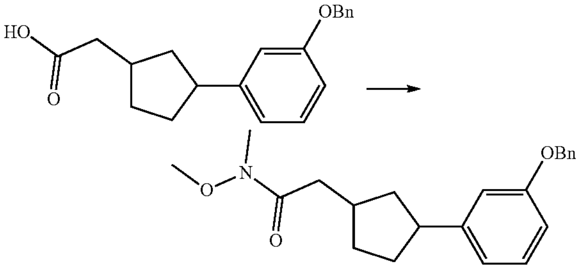

To a stirred solution of 2-(3-(3-(benzyloxy)phenyl)cyclopentyl)acetic acid (1.48 g, 4.77 mmol) in DCM (35 mL) were added N-methoxymethanamine hydrochloride (698 mg, 7.15 mmol), HATU (2.72 g, 7.15 mmol) and DIPEA (1.85 g, 14.3 mmol). The reaction mixture was stirred at room temperature overnight. The reaction was diluted with DCM (80 mL) and washed with brine (60 mL×2), dried over anhydrous $Na_2SO_4$, filtered. The filtrate was concentrated under reduced pressure. The crude product was purified by silica gel column chromatography (PE/EA=3/1) to afford the desired compound 2-(3-(3-(benzyloxy)phenyl)cyclopentyl)-N-methoxy-N-methylacetamide (1.43 g, 84.9%) as a colorless oil.

LCMS: LC retention time 2.24 min. MS (ESI) m/z 354 $[M+H]^+$.

Step 6.

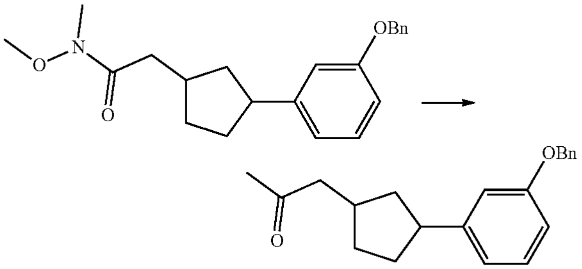

To a stirred solution of 2-(3-(3-(benzyloxy)phenyl)cyclopentyl)-N-methoxy-N-methylacetamide (1.43 g, 4.05 mmol) in dry tetrahydrofuran (25.0 mL) was added methyl magnesium bromide (3M in THF, 2.70 mL, 8.09 mmol) dropwise at 0° C. The reaction mixture was stirred at room temperature for 1 h. It was quenched with saturated ammonium chloride solution (60 mL) and extracted with ethyl acetate (80 mL×3). The organic layer was washed with brine (100 mL), dried over anhydrous $Na_2SO_4$ and concentrated under vacuum. The crude was purified by silica gel column chromatography (PE/EA=5/1) to afford the title compound 1-(3-(3-(benzyloxy)phenyl)cyclopentyl)propan-2-one (1.15 g, 92.2%) as a colorless oil.

LCMS: LC retention time 2.28 min. MS (ESI) m/z 309 $[M+H]^+$.

Step 7.

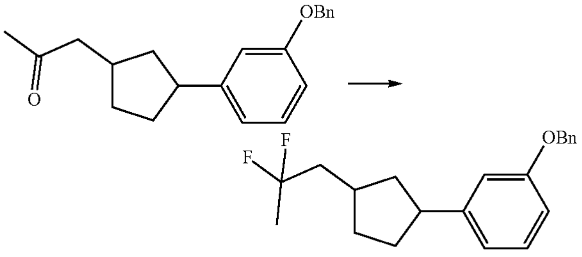

To a cooled (0° C.) stirred solution of 1-(3-(3-(benzyloxy) phenyl)cyclopentyl)propan-2-one (954 mg, 3.09 mmol) in DCM (20 mL) was added DAST (12.0 mL) under argon atmosphere. Then the mixture was allowed to warm to room temperature slowly and stirred at the same temperature overnight. The mixture was concentrated to dryness by blowing nitrogen gas. The crude was dissolved in ethyl acetate (80 mL), washed with saturated $NaHCO_3$ (60 mL) and brine (80 mL), dried over anhydrous $Na_2SO_4$, and filtered. The filtrate was concentrate to dryness under vacuum to the desired compound 1-(benzyloxy)-3-(3-(2,2-difluoropropyl)cyclopentyl)benzene (665 mg, 70.6%) as a light yellow oil.

LCMS: LC retention time 2.42 min. MS (ESI) m/z 331 $[M+H]^+$.

Step 8.

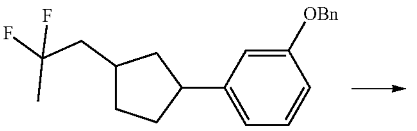

-continued

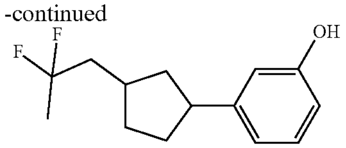

To a solution of 1-(benzyloxy)-3-(3-(2,2-difluoropropyl) cyclopentyl)benzene (665 mg, 2.01 mmol) in EtOAc (20.0 mL) was added Pd/C (600 mg) under nitrogen atmosphere. Then the mixture was stirred at room temperature overnight. LCMS showed that the starting materials consumed, the mixture was filtered through a Celite pad and the filtrate was concentrated to dryness under reduced pressure. The crude was diluted with ethyl acetate (150 mL), washed with water (80 mL) and brine (80 mL), dried over anhydrous sodium sulfate, filtered and the filtrate was concentrated under reduced pressure to give 3-(3-(2,2-difluoropropyl)cyclopentyl)phenol (315 mg) as a yellow oil.

LCMS: LC retention time 2.10 min. MS (ESI) m/z 241 $[M+H]^+$.

Step 9.

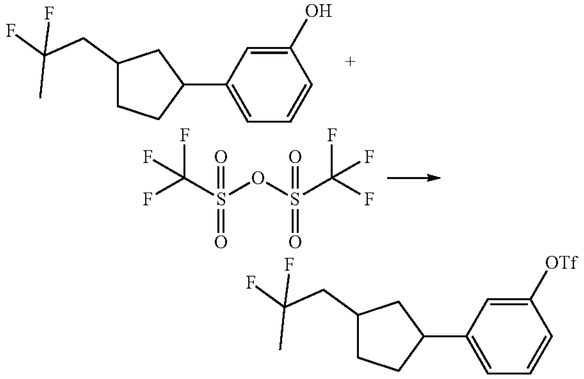

To a solution of 3-(3-(2,2-difluoropropyl)cyclopentyl) phenol (158 mg, 0.66 mmol) in DCM (3 mL) was added pyridine (51.9 mg, 0.66 mmol) at 0° C., followed by trifluoromethanesulfonic anhydride (223 mg, 0.79 mmol). After the addition was completed, the reaction mixture was stirred at temperature overnight. The reaction mixture was concentrated under vacuum. The residue was extracted with ethyl acetate (20 mL×3). The combined organic phases were washed with $NaHCO_3$ (10 mL) and brine (20 mL), dried over anhydrous $Na_2SO_4$, and filtered. The filtrate was evaporated and the residue was purified by flash chromatography column (PE/EA=10/1) to give the desired compound 3-(3-(2,2-difluoropropyl)cyclopentyl)phenyl trifluoromethanesulfonate (190 mg, 77.6%) as a light yellow oil.

$^1H$ NMR (400 MHz, chloroform-d) δ 7.35 (t, J=7.8 Hz, 1H), 7.24 (s, 1H), 7.09 (dd, J=11.8, 3.8 Hz, 2H), 3.11 (ddd, J=17.6, 13.2, 8.8 Hz, 1H), 2.43-1.75 (m, 10H), 1.74-1.44 (m, 11H), 1.39-1.16 (m, 3H) ppm.

Step 10.

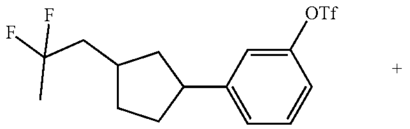

-continued

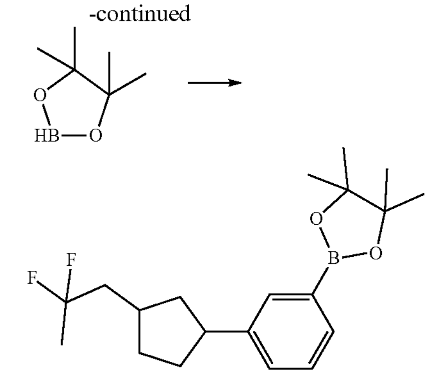

To a solution of 3-(3-(2,2-difluoropropyl)cyclopentyl) phenyl trifluoromethanesulfonate (170 mg, 0.457 mmol) in 1,4-dioxane (8.0 mL) were added 4,4,5,5-tetramethyl-1,3,2-dioxaborolane (174 mg, 0.685 mmol), potassium acetate (112 mg, 1.14 mmol) and 1,1'-bis(diphenylphosphino)ferrocene-palladium(II)-dichloridedichloromethane complex (11.2 mg, cat.) under Ar atmosphere. The solution was stirred at 90° C. overnight. After the completion of reaction, the solution was concentrated in vacuo. The residue was dissolved in ethyl acetate (50 mL) and filtered. The filtrate was washed with water (50 mL×3) and brine (50 mL). The aqueous phase was back extracted with ethyl acetate (50 mL). The combined organic phases were dried over anhydrous $Na_2SO_4$ and concentrated to dryness to afford 2-(3-(3-(2,2-difluoropropyl)cyclopentyl)phenyl)-4,4,5,5-tetramethyl-1,3,2-dioxaborolane (120 mg, 75.0% yield) as a yellow oil.

LCMS: LC retention time 2.45 min. MS (ESI) m/z 351 $[M+H]^+$.

Intermediate D-24

1-(3-Bromo-5-fluorophenyl)-3-(tert-butyl)pyrrolidine

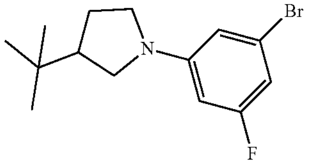 [SMILES: CC(C)(C)C1CCN(c2cc(F)cc(Br)c2)C1]

Step 1.

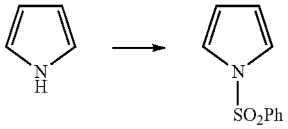

To a suspension of NaH (8.05 g, 201 mmol) in THF (100 mL) was added a solution of pyrrole (9.0 g, 134 mmol) in THF (100 mL) at 0° C. After 30 min, benzenesulfonyl chloride (23.70 g, 134 mmol) in THF (50 mL) was added. The mixture was stirred at rt for 5 h. The reaction was quenched with water (200 mL). THF was evaporated under reduced pressure. The residue was filtered, and the solid cake was washed with water, dried and to obtain 1-(phenylsulfonyl)-1H-pyrrole (26.00 g, 89.8%) as a white solid.

LCMS: LC retention time 2.04 min. MS (ESI) m/z 208 $[M+H]^+$

Step 2.

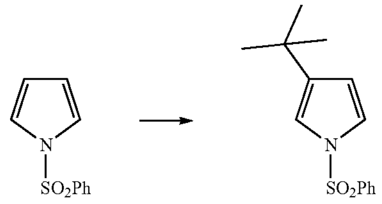

To a solution of 1-(phenylsulfonyl)-1H-pyrrole (9.0 g, 43.4 mmol) and 2-chloro-2-methylpropane (4.79 g, 52.1 mmol) in DCM (150 mL) was added $AlCl_3$ (8.68 g, 65.1 mmol) at 0° C. After addition, the mixture was stirred at rt for 6 h. The mixture was quenched with water (150 mL). The aqueous was extracted with DCM (100 mL). The organic layer was washed with water (100 mL), brine (100 mL), dried over $Na_2SO_4$, filtered and concentrated. The residue was purified by SGC (PE/EA=2:1) to give 3-(tert-butyl)-1-(phenylsulfonyl)-1H-pyrrole (6.00 g, 49.8% yield) as a yellow oil.

LCMS: LC retention time 2.25 min. MS (ESI) m/z 264.2 $[M+H]^+$.

Step 3.

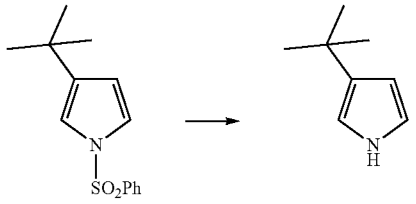

To a solution of 3-(tert-Butyl)-1-(phenylsulfonyl)-1H-pyrrole (6.0 g, 22.8 mmol) in EtOH/$H_2O$ (60 mL/60 mL) was added KOH (12.8 g, 228 mmol). The mixture was stirred at reflux for 5 h. Then the solvent was removed under reduced pressure. The residue was taken in water (50 mL). The aqueous solution was extracted with DCM (20 mL×3). The organic layer was washed with brine, dried $Na_2SO_4$, filtered and concentrated. The residue was purified by SGC (PE/EA=5:1) to give 3-(tert-butyl)-1H-pyrrole (2.20 g, 78.4% yield) as a yellow oil.

Step 4.

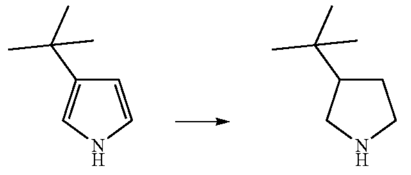

To a solution of 3-(tert-butyl)-1H-pyrrole (2.20 g, 17.9 mmol) in EtOH (100 mL) was added HCl (1N, 1.0 mL) and $PtO_2$ (203 mg) under Ar atmosphere at room temperature. The flask was purged with hydrogen and stirred at rt under hydrogen for 16 h. The reaction mixture was filtered and washed with ether. The filtrate was concentrated in vacuo to afford 3-(tert-butyl)pyrrolidine (1.80 g, 79.2%) as a yellow oil.

LCMS: LC retention time 1.43 min. MS (ESI) m/z 128 $[M+H]^+$

Step 5.

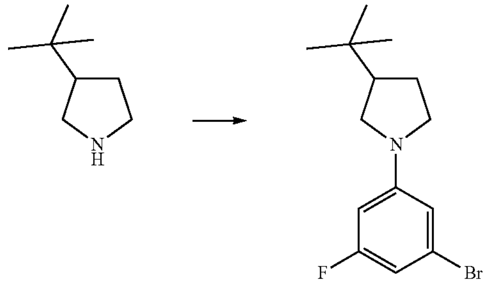

To a solution of 1-bromo-3,5-difluorobenzene (2.0 g, 10.4 mmol) in NMP (10.0 mL) in a tube were added 3-(tert-butyl)pyrrolidine (1.45 g, 11.4 mmol) and DIPEA (6.68 g, 51.8 mmol). The tube was sealed and stirred at 100° C. overnight. The reaction mixture was diluted with water and EtOAc (10 mL each) ppm. The aqueous layer was back-extracted with EtOAc (30 mL×3). The combined organic layers were then washed with $H_2O$ (150 mL), brine (150 mL), dried over $Na_2SO_4$, filtered and concentrated. The residue was purified by SGC (PE) to obtain 1-(3-bromo-5-fluorophenyl)-3-(tert-butyl)pyrrolidine (2.40 g, 51.7%) as a colorless oil.

LCMS: LC retention time 3.04 min. MS (ESI) m/z 302 $[M+H]^+$

Intermediate E-1a 3-(Neopentyloxy)-1H-pyrazole

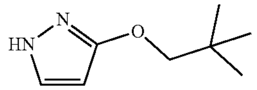

and

Intermediate E-1b 3-(3,3-dimethylbutoxy)-1H-pyrazole

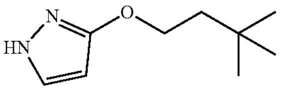

Step 1.

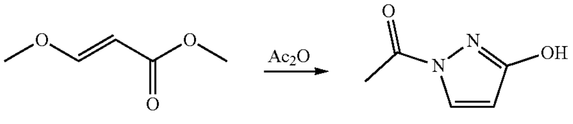

To a stirred solution of methyl (E)-3-methoxyacrylate (6.00 g, 51.72 mmol) in MeOH (50 mL) was added hydrazine hydrate (30 mL) at room temperature. The mixture solution was stirred under reflux for 16 h. After the reaction was completed, the solvent was removed. The residue (3.69 g, 43.93 mmol) was dissolved in pyridine (30 mL) and $Ac_2O$ (4.7 g, 46.12 mmol) was added slowly at 95° C. Then the mixture was stirred at 95° C. for 2 h. The solvent was removed under reduced pressure and the residue was taken in $Et_2O$ (60 mL). The slurry was stirred overnight at room temperature. The solid was collected via filtration and rinsed with $Et_2O$ (30 mL) to afford 1-(3-hydroxy-1H-pyrazol-1-yl)ethan-1-one (4.32 g, 78%) as a light yellow solid.

LCMS MS (ESI) m/z 127 $[M+H]^+$.

Step 2a.

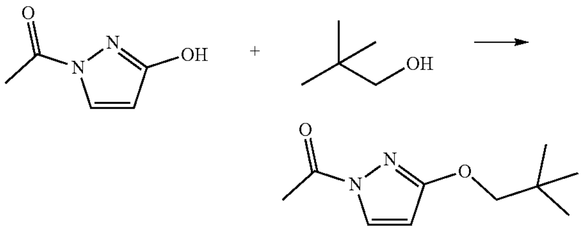

To a stirred solution of 1-(3-hydroxy-1H-pyrazol-1-yl)ethan-1-one (4.32 g, 34.29 mmol) in THF (100 mL) were added 2,2-dimethylpropan-1-ol (3.00 g, 34.29 mmol), $PPh_3$ (9.88 g, 37.72 mmol) and DIAD (7.62 g, 37.72 mmol) at room temperature. The mixture was stirred at room temperature for 16 h. The reaction was diluted with water (50 mL) and extracted with EA (30 mL×3). The organic solution was washed with brine (20 mL×2), dried over anhydrous $Na_2SO_4$, filtered and concentrated in vacuo. The residue was purified by silica gel chromatography (EA/PE=1/10) to afford 1-(3-(neopentyloxy)-1H-pyrazol-1-yl)ethan-1-one (3.3 g, 49%) as a light yellow solid.

LCMS MS (ESI) m/z 197 $[M+H]^+$.

Step 3a.

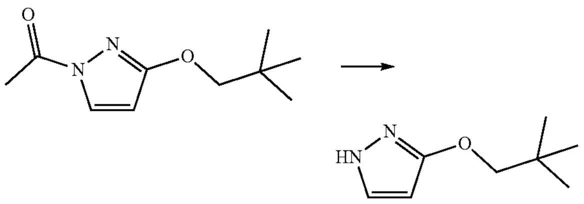

To a stirred solution of 1-(3-(neopentyloxy)-1H-pyrazol-1-yl)ethan-1-one (3.3 g, 16.84 mmol) in $MeOH/H_2O$ (30 mL/3 mL) was added NaOH (673 mg, 16.84 mmol) at room temperature. The mixture solution was stirred at room temperature for 16 h. The reaction was diluted with water (30 mL) and extracted with EA (20 mL×3). The organic was washed with brine (20 mL×2), dried over anhydrous $Na_2SO_4$, filtered and concentrated in vacuo. The residue was purified by silica gel chromatography (EA/PE=1/5) to afford 3-(neopentyloxy)-1H-pyrazole (2.00 g, 80%) as a yellow oil.

LCMS MS (ESI) m/z 155 $[M+H]^+$.

Step 2b

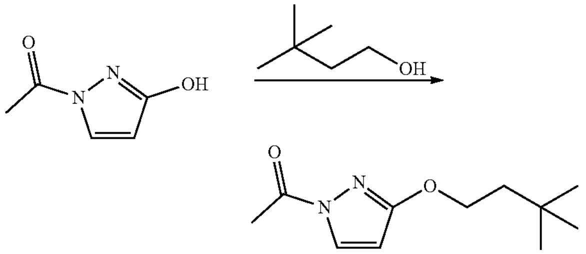

To a stirred solution of 1-(3-hydroxy-1H-pyrazol-1-yl)ethan-1-one (3.8 g, 30.16 mmol) in THF (200 mL) were added 2,2-dimethylpropan-1-ol (3.69 g, 36.19 mmol), $PPh_3$ (11.85 g, 45.24 mmol) and DIAD (9.14 g, 45.24 mmol) at room temperature. The mixture was stirred at room temperature for 16 h. Then, diluted with water (50 mL) and extracted with EA (30 mL×3). The organic solution was washed with brine (20 mL×2), dried over anhydrous $Na_2SO_4$, filtered and concentrated to afford 1-(3-(3,3-dimethylbutoxy)-1H-pyrazol-1-yl)ethan-1-one (8.80 g) as a yellow solid.

LCMS MS (ESI) m/z 211 $[M+H]^+$.

Step 3b.

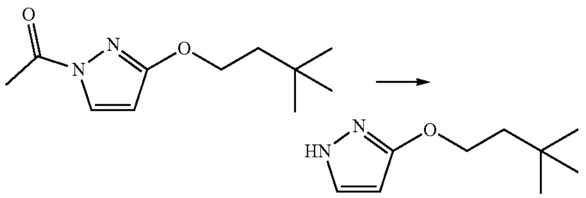

To a stirred solution of 1-(3-(3,3-dimethylbutoxy)-1H-pyrazol-1-yl)ethan-1-one (8.80 g, 41.9 mmol) in $MeOH/H_2O$ (100 mL/10 mL) was added NaOH (1.68 g, 41.9 mmol) at room temperature. The mixture was stirred at room temperature for 16 h. The reaction was diluted with water (50 mL) and extracted with EA (30 mL×3). The organic solution was washed with brine (30 mL×2), dried over anhydrous $Na_2SO_4$, filtered and concentrated in vacuo. The residue was purified by silica gel chromatography (EA/PE=1/4) to afford 3-(3,3-dimethylbutoxy)-1H-pyrazole (2.6 g, 51% over two steps) as a yellow oil.

LCMS MS (ESI) m/z 169 $[M+H]^+$.

Intermediate E-2

3-((4,4-Dimethylpentyl)oxy)-1H-pyrazole

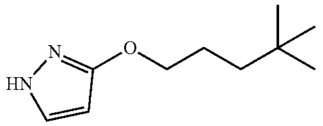

Step 1.

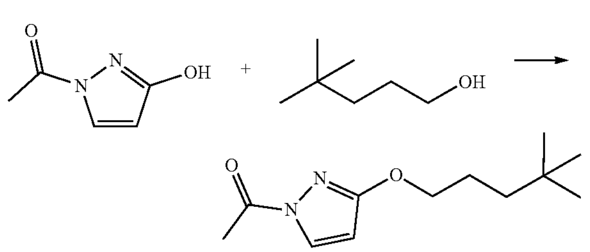

To a stirred solution of 4,4-dimethylpentan-1-ol (1.5 g, 12.9 mmol) in THF (30 mL) were added 1-(3-hydroxy-1H-pyrazol-1-yl)ethan-1-one (1.36 g, 10.8 mmol), $Ph_3P$ (4.24 g, 0.0162 mol) and DIAD (3.27 g, 16.2 mmol. Then the mixture was stirred at 60° C. for 16 h. The solvent was evaporated and the residue was purified by silica gel chromatography (petroleum ether/ethyl acetate=10/1) to afford 1-(3-((4,4-dimethylpentyl)oxy)-1H-pyrazol-1-yl)ethan-1-one (1.80 g, 74.4%) as a colorless oil.

LCMS: MS (ESI) m/z 225 $[M+H]^+$.

Step 2.

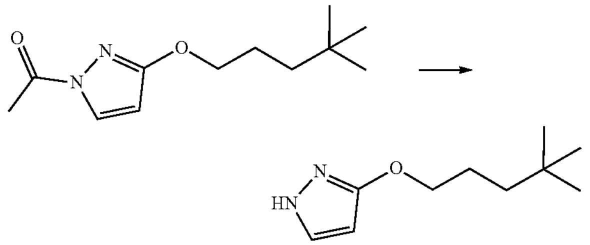

To a stirred solution of 1-(3-((4,4-dimethylpentyl)oxy)-1H-pyrazol-1-yl)ethan-1-one (1.80 g, 8.02 mmol) in MeOH (20 mL) and water (2 mL) was added NaOH (0.32 g, 8.02 mmol). Then the mixture was stirred at rt for 16 h. The solvent was evaporated to afford 3-((4,4-dimethylpentyl) oxy)-1H-pyrazole (1.2 g, 82%) as a colorless oil.

LCMS: MS (ESI) m/z 183 $[M+H]^+$.

Intermediate E-3

3-(3,3,3-Trifluoro-2,2-dimethylpropoxy)-1H-pyrazole

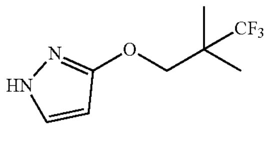

Step 1.

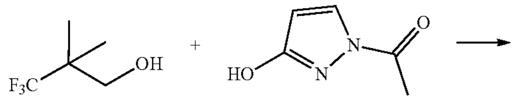

-continued

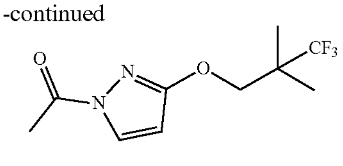

To a stirred solution of 3,3,3-trifluoro-2,2-dimethylpropan-1-ol (2.57 g, 20.4 mmol) in THF (30 mL) were added 1-(3-hydroxy-1H-pyrazol-1-yl)ethan-1-one (2.90 g, 20.4 mol), triphenyl phosphine (8.03 g, 30.6 mmol) and diisopropyl azodicarboxylate (6.19 g, 30.6 mmol). Then the mixture was stirred at 60° C. for 16 h. The solvent was removed under reduce pressure. The residue was purified by silica gel chromatography (petroleum ether/ethyl acetate=20/1) to afford 1-(3-(3,3,3-trifluoro-2,2-dimethylpropoxy)-1H-pyrazol-1-yl)ethan-1-one (3.50 g, 68.5%) as a yellow oil.

LCMS: MS (ESI) m/z 251 $[M+H]^+$.

Step 2.

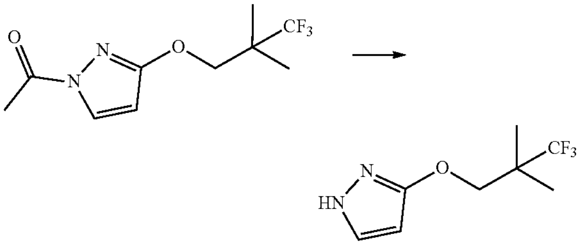

To a stirred solution of 1-(3-(3,3,3-trifluoro-2,2-dimethylpropoxy)-1H-pyrazol-1-yl)ethan-1-one (3.5 g, 0.014 mol) in MeOH (20 mL) and water (1 mL) was added NaOH (0.615 g, 15.4 mol). Then the mixture was stirred at rt for 16 h. The solvent was evaporated to afford 3-(3,3,3-trifluoro-2,2-dimethylpropoxy)-1H-pyrazole.

LCMS: LC retention time 1.58 min. MS (ESI) m/z 208.8 $[M+H]^+$.

$^1H$ NMR (400 MHz, chloroform-d) δ 7.37 (s, 1H), 5.76 (s, 1H), 4.13 (s, 2H), 1.26 (s, 6H) ppm.

Intermediate E-4

3-(3-(1,1-Difluoroethyl)cyclopentyl)-1H-pyrazole

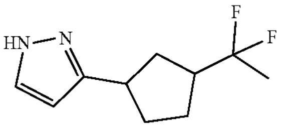

Step 1.

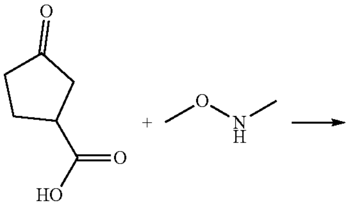

-continued

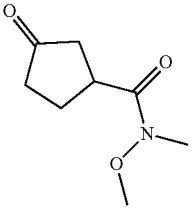

To a stirred solution of 3-oxocyclopentane-1-carboxylic acid (3.50 g, 27.3 mmol) in DCM (20 mL) were added oxalyl chloride (6.93 g, 54.6 mol) and DMF (0.2 mL). After the reaction was stirred at rt for 2 h, the solvent was removed. The residue was dissolved in DCM (30 mL). To this solution were added DIPEA (7.06 g, 54.6 mol) and N,O-dimethylhydroxylamine (2.00 g, 32.8 mmol) were added. Then the reaction was stirred at rt for 16 h and concentrated in vacuo to afford the desired product N-methoxy-N-methyl-3-oxocyclopentane-1-carboxamide (4.20 g, 89.8% yield) as a yellow solid.

Step 2.

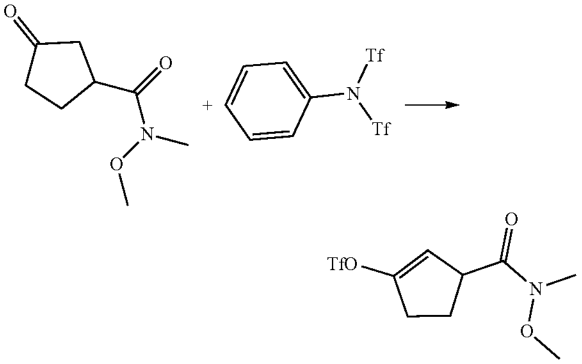

To a solution of N-methoxy-N-methyl-3-oxocyclopentane-1-carboxamide (3.60 g, 0.021 mol) in anhydrous THF (150 mL) was added LDA (27 mL, 1M in THF, 27 mol) slowly at −78° C. and the mixture was stirred at −78° C. for 2 h. A solution of 1,1,1-trifluoro-N-phenyl-N-((trifluoromethyl)sulfonyl)methanesulfonamide (9.02 g, 25.2 mmol) in anhydrous THF (50 mL) was added. The mixture was warmed to 0° C. and stirred overnight. The mixture was poured into saturated aqueous $NH_4Cl$ (30 mL) and extracted with $Et_2O$ (80 mL). The combined organic layers were washed with water (50 mL) and brine (80 mL), dried over anhydrous sodium sulfate, filtered. The filtrate was concentrated to afford 3-(methoxy(methyl)carbamoyl)cyclopent-1-en-1-yl trifluoromethanesulfonate (5.00 g) as a yellow solid.

Step 3.

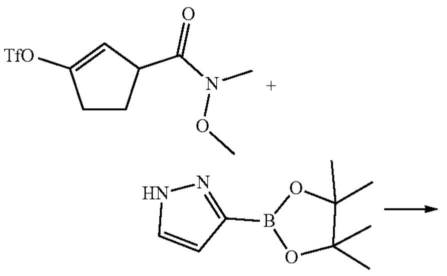

-continued

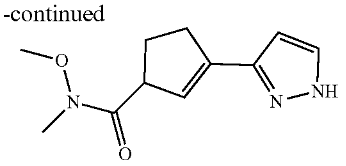

To a stirred solution of 3-(methoxy(methyl)carbamoyl) cyclopent-1-en-1-yl trifluoromethanesulfonate (3.50 g, 11.5 mmol) in toluene/ethanol/$H_2O$ (175 mL, v/v/v=4/2/1) was added 3-(4,4,5,5-tetramethyl-1,3,2-dioxaborolan-2-yl)-1H-pyrazole (1.79 g, 9.23 mmol), $Pd(Ph_3P)_4$ (1.33 g, 1.15 mmol) and $K_2CO_3$ (3.19 g, 23.1 mmol). The resulting mixture was stirred at 80° C. under argon atmosphere overnight, filtered and concentrated in vacuo. The residue was washed with water (100 mL) and brine (100 mL), extracted with ethyl acetate (100 mL×3), dried over anhydrous sodium sulfate, filtered, and the filtrate was concentrated to dryness under reduced pressure to give the crude. The crude was purified by flash reversed-phase column chromatography to afford N-methoxy-N-methyl-3-(1H-pyrazol-3-yl)cyclopent-2-ene-1-carboxamide (1.30 g, 50.9%) as a light yellow oil.

LCMS: MS m/z 222 $[M+H]^+$.

Step 4.

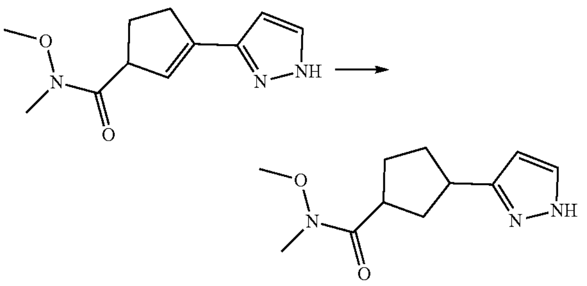

To a stirred solution of N-methoxy-N-methyl-3-(1H-pyrazol-3-yl)cyclopent-2-ene-1-carboxamide (1.30 g, 5.88 mmol) in EtOAc (20 mL) was added Pd/C (0.0625 g, 0.588 mmol). Then the reaction was stirred at rt under $H_2$ for 16 h. The solvent was concentrated to afford N-methoxy-N-methyl-3-(1H-pyrazol-3-yl)cyclopentane-1-carboxamide (1.10 g, 83.9%) as a yellow solid.

LCMS: MS m/z 224 $[M+H]^+$.

Step 5.

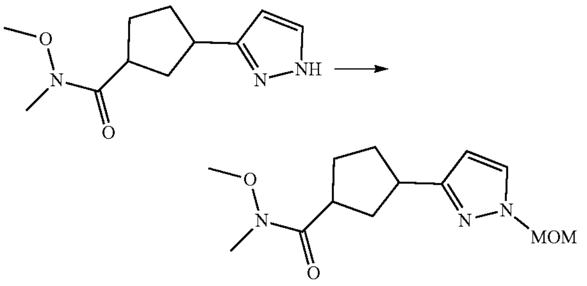

To a stirred solution of N-methoxy-N-methyl-3-(1H-pyrazol-3-yl)cyclopentane-1-carboxamide (1.1 g, 0.00493 mol) in DMF (20 mL) were added potassium carbonate (1.36 g, 9.85 mmol) and MOMBr (0.739 g, 5.91 mmol). Then the mixture was stirred at rt for 16 h. The solvent was evaporated. The residue was purified by prep-HPLC to afford N-methoxy-3-(1-(methoxymethyl)-1H-pyrazol-3-yl)-N-methylcyclopentane-1-carboxamide (1.20 g, 91%) as a yellow solid.

LCMS: MS (ESI) m/z 268 $[M+H]^+$.

Step 6.

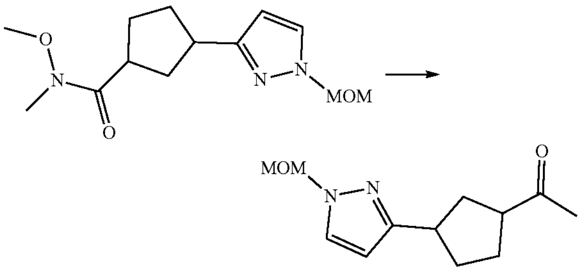

To a stirred solution of N-methoxy-3-(1-(methoxymethyl)-1H-pyrazol-3-yl)-N-methylcyclopentane-1-carboxamide (1.20 g, 4.49 mmol) in THF (50 mL) was added MeMgBr (4.49 mL, 13.5 mol) slowly at 0° C. Then the mixture was stirred at rt for 4 h. The solvent was evaporated. The residue was purified by prep-HPLC to afford 1-(3-(1-(methoxymethyl)-1H-pyrazol-3-yl)cyclopentyl)ethan-1-one (0.83 g, 83%) as a yellow solid.

LCMS: MS (ESI) m/z 223 $[M+H]^+$.

Step 7.

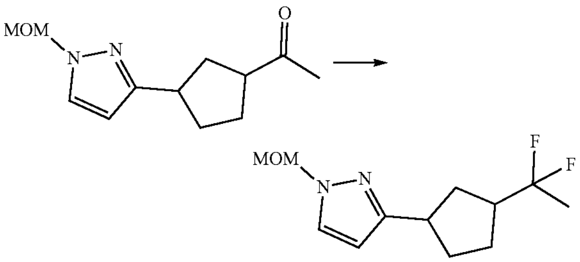

To a stirred solution of 1-(3-(1-(methoxymethyl)-1H-pyrazol-3-yl)cyclopentyl)ethan-1-one (0.73 g, 0.00328 mol) in DCM (5 mL) was added DAST (2.18 g, 9.85 mol). Then the mixture was stirred at rt for 16 h. The solvent was concentrated and purified by prep-HPLC to afford 3-(3-(1,1-difluoroethyl)cyclopentyl)-1-(methoxymethyl)-1H-pyrazole (0.25 g, 31%) as a yellow solid.

LCMS: MS (ESI) m/z 245 $[M+H]^+$.

Step 8.

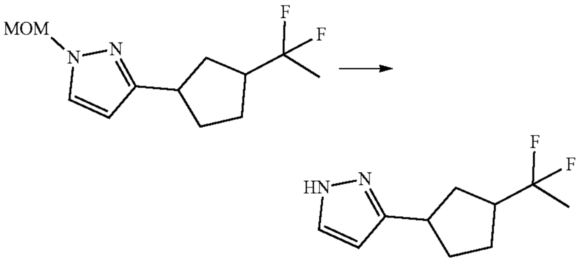

To a stirred solution of 3-(3-(1,1-difluoroethyl)cyclopentyl)-1-(methoxymethyl)-1H-pyrazole (0.2 g, 0.000819 mol) in MeOH (5 mL) was added HCl (0.5 mL). Then the mixture was stirred at 60° C. for 16 h. The solution was concentrated and the residue was purified by prep-HPLC to afford 3-(3-(1,1-difluoroethyl)cyclopentyl)-1H-pyrazole (0.11 g, 67.1%) as a yellow solid.

LCMS: MS (ESI) m/z 201 $[M+H]^+$.

Intermediate E-5

3-(3,3-Dimethylbutoxy)piperidine

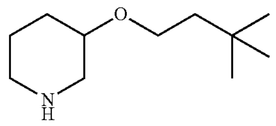

Step 1.

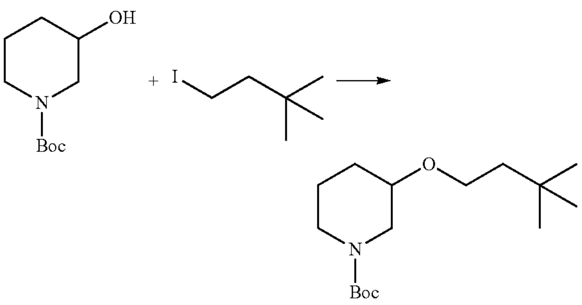

To a solution of tert-butyl 3-hydroxypiperidine-1-carboxylate (1.00 g, 5.0 mmol) in DMF (10 mL) was added NaH (400 mg, 10.0 mmol). The reaction mixture was stirred at rt for 30 min and 1-iodo-3,3-dimethylbutane (1.40 g, 6.5 mmol) was added. The mixture was stirred from 0° C. to rt for 16 h. To the reaction mixture was added water (50 mL), extracted with EA (50 mL×2). The organic solution was washed with brine (50 mL) and dried over anhydrous $Na_2SO_4$, filtered and concentrated. The residue was purified by silica gel chromatography using PE/EA (10/1) as eluent to give tert-butyl 3-(3,3-dimethylbutoxy)piperidine-1-carboxylate (130 mg, 7% yield) as a colorless oil.

LCMS: MS (ESI) m/z 308 $[M+Na]^+$.

Step 2.

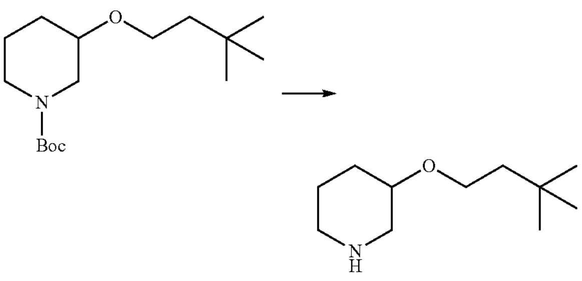

To a stirred solution of tert-butyl 3-(3,3-dimethylbutoxy)piperidine-1-carboxylate (130 mg, 0.5 mmol) in DCM (2 mL) were added HCl/dioxane (2 mL). The reaction mixture was stirred at rt for 1 h. Then the solution was concentrated to afford 3-(3,3-dimethylbutoxy)piperidine (80 mg, 95% yield) as a white solid.

Intermediate E-6

(S)-3-(3,3-Dimethylbutoxy)pyrrolidine hydrochloride

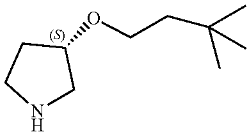

Step 1.

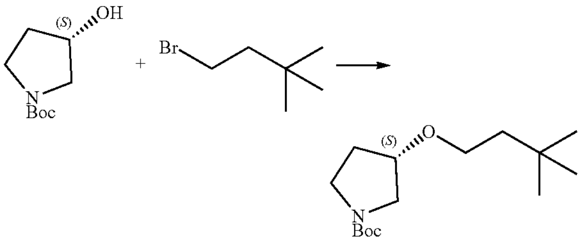

To a solution of tert-butyl (S)-3-hydroxypyrrolidine-1-carboxylate (2.00 g, 10.7 mmol) in NMP (20 mL) was added NaH (1 g, 25.7 mmol). The reaction mixture was stirred at rt for 30 min and 1-bromo-3,3-dimethylbutane (2.10 g, 12.8 mmol) was added. The mixture was stirred from 0° C. to rt for 16 h. To the reaction mixture was added water (100 mL). The aqueous solution was then extracted with EA (100 mL×2). The EA solution was washed with brine (100 mL) and dried over anhydrous $Na_2SO_4$, filtered and concentrated. The residue was purified by silica gel chromatography using PE/EA (8/1) as eluent to give tert-butyl (S)-3-(3,3-dimethylbutoxy)pyrrolidine-1-carboxylate (270 mg, 9% yield) as a colorless oil.

LCMS: MS (ESI) m/z 294 $[M+Na]^+$.

Step 2.

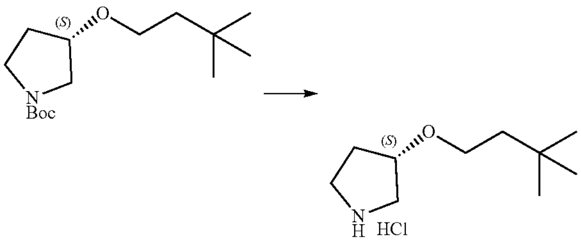

To a solution of tert-butyl (S)-3-(3,3-dimethylbutoxy) pyrrolidine-1-carboxylate (270 mg, 1.0 mmol) in DCM (2 mL) were added HCl/dioxane (4 mL). The reaction mixture was stirred at rt for 1 h. Then it was concentrated to afford (S)-3-(3,3-dimethylbutoxy)pyrrolidine hydrochloride (190 mg, 92% yield) as a white solid.

LCMS MS (ESI) m/z 172 $[M+H]^+$

Intermediate E-7

(R)-3-(3,3-Dimethylbutoxy)pyrrolidine hydrochloride

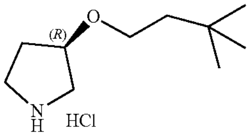

Intermediate E-7 was prepared by essentially the same method as Intermediate E-6.

Intermediate E-8

2,2-Dimethyl-6-oxa-9-azaspiro[4.5]decane hydrochloride

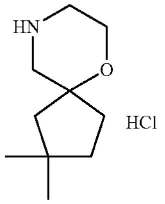

Step 1.

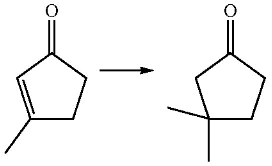

To a suspension of CuI (6.85 g, 36.0 mmol) in anhydrous ethyl ether (100 mL) was added a solution of methyllithium in diethoxymethane (47 mL, 75 mmol, 1.6 M) at 0° C. over a period of 30 min. The mixture was stirred at 0° C. for 30 min. To the above mixture was added 3-methylcyclopent-2-en-1-one (2.88 g, 30.0 mmol) dropwise over a period of 30 min at 0° C. The resulting mixture was stirred at 0° C. for another 2 h. The reaction was then quenched with saturated $NH_4Cl$ (150 mL) and filtered. The filtrate was extracted with ethyl ether (100 mL×2). The combined organic layer was dried over anhydrous $Mg_2SO_4$ and filtered. The filtrate was evaporated under reduced pressure to afford 3,3-dimethylcyclopentan-1-one (2.52 g).

Step 2.

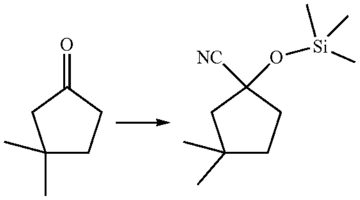

To a solution of 3,3-dimethylcyclopentan-1-one (2.52 g, 22.5 mmol) in 30 mL of THF were added trimethylsilylformonitrile (3.35 g, 33.8 mmol) and $ZnI_2$ (72 mg, 0.225 mmol) at 0° C. The mixture was stirred 3 h at 0° C. and 3 h at 60° C. The resulting solid was filtered off The filtrate was evaporated to obtain 3,3-dimethyl-1-((trimethylsilyl)oxy) cyclopentane-1-carbonitrile.

Step 3.

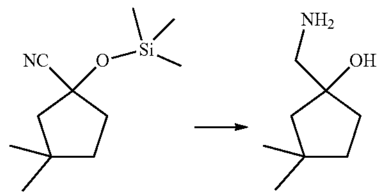

To a solution of 3,3-dimethyl-1-((trimethylsilyl)oxy)cyclopentane-1-carbonitrile (4.76 g, 22.5 mmol) in 50 mL of THF was added a solution of lithium aluminum hydride in THF (27 mL, 1.0 mol) dropwise at 0° C. under argon atmosphere. After stirring for 16 h at room temperature, a sodium hydroxide solution (20%) was added slowly with cooling. The solid was filtered off after dilution with ethyl acetate (30 mL). The filtrate was evaporated to give 1-(aminomethyl)-3,3-dimethylcyclopentan-1-ol (6.22 g).

LCMS: LC retention time 1.314 min. MS (ESI) m/z 144 $[M+H]^+$.

Step 4.

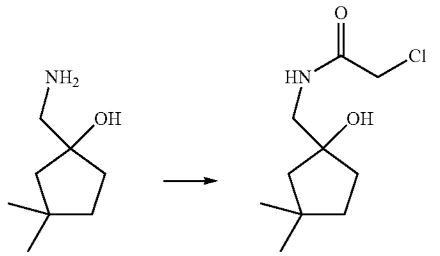

To a solution of potassium carbonate (6.22 g, 45.1 mmol) in water (30 mL) was added to a solution of 1-(aminomethyl)-3,3-dimethylcyclopentan-1-ol (3.23 g, 22.6 mmol) in ethyl acetate (30 mL). The mixture was cooled to 0° C., and then treated with 2-chloroacetyl chloride (2.8 g, 24.8 mmol) dropwise. After completion of the addition, the reaction mixture was warmed to 25° C. and allowed to stir for 16 h. The aqueous layer was extracted with ethyl acetate (50 mL×3). The combined organic layers were dried over sodium sulfate, filtered, and concentrated in vacuo to give 2-chloro-N-((1-hydroxy-3,3-dimethylcyclopentyl)methyl) acetamide (4.95 g).

Step 5.

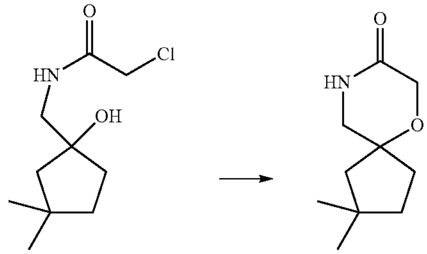

To a mixture of potassium tert-butoxide (5.06 g, 45.1 mmol) in tert-butanol (40 mL) was added 2-chloro-N-((1-hydroxy-3,3-dimethylcyclopentyl)methyl)acetamide (4.95 g, 22.5 mmol) in THF (30 mL) over 30 min. The resulting mixture was stirred for 16 h at room temperature before it was concentrated. The residue was diluted with EtOAc and water, the organic layer was separated, washed with brine, and concentrated to provide 2,2-dimethyl-6-oxa-9-azaspiro [4.5]decan-8-one (4.13 g).

Step 6.

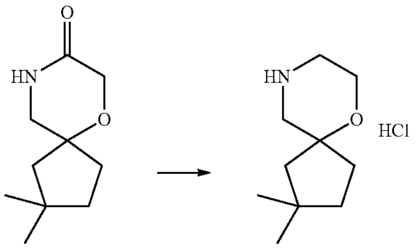

To a solution of 2,2-dimethyl-6-oxa-9-azaspiro[4.5]decan-8-one (4.13 g, 22.5 mmol) in THF (50 mL) was added tetrahydrofuran-borane (7.75 g, 90.2 mmol) at room temperature. The reaction mixture was refluxed for 2 h. Then, the reaction was cooled to room temperature. MeOH was carefully added and the mixture was concentrated under vacuum. To the resulting mixture was added MeOH (50 mL) and N,N,N',N'-tetramethylethylenediamine (10.5 g, 90.2 mmol) and the reaction was stirred at 78° C. overnight. The reaction was concentrated and the residue was diluted with EtOAc and water. The organic layer was separated, washed with brine, and concentrated in vacuo to give crude. To the crude product was added HCl/dioxane (5 mL) and stirred at rt for 1 h. Then it was concentrated to give 2,2-dimethyl-6-oxa-9-azaspiro[4.5]decane hydrochloride (566 mg, 7% yield for 6 steps) as a yellow solid.

LCMS (acidic): LC retention time 1.42 min. MS (ESI) m/z 170 $[M+H]^+$.

Intermediate E-9

2,2,8-Trimethyl-6-oxa-9-azaspiro[4.5]decane hydrochloride

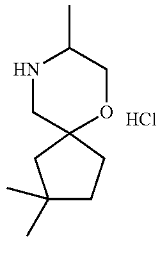

Intermediate E-9 was synthesized similarly to Intermediate E-8.

Intermediate E-10

2-(Trifluoromethoxy)-6-oxa-9-azaspiro[4.5]decane hydrochloride

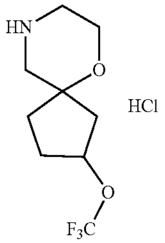 [SMILES: FC(F)(F)OC1CCC2(CNCCO2)C1 ; Cl]

Step 1.

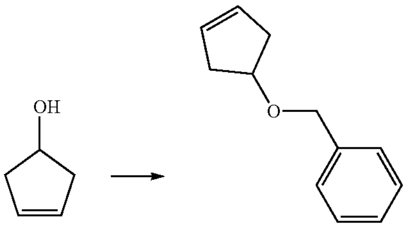 [SMILES: OC1CC=CC1 ; C1=CCC(OCc2ccccc2)C1]

To a cooled stirred suspension of sodium hydride (2.85 g, 71.3 mmol, 60% in paraffin oil) in 30 mL dry toluene was added a solution of cyclopent-3-en-1-ol (4.00 g, 47.6 mmol) in toluene (10 mL) under inert ($N_2$) atmosphere slowly. After gas formation had seized, a solution of BnBr (8.94 g, 52.3 mmol) in toluene (20 mL) was added drop wise and the resulting mixture was heated to reflux for 12 h. Methanol in toluene was added in small portions to decompose residual NaH. The reaction mixture was partitioned between water and ethyl acetate (20 mL each) and the two phases were separated. The organic phase was dried over sodium sulfate and the solvent was evaporated. The residue was purified by combi-flash (100% PE) to afford ((cyclopent-3-en-1-yloxy)methyl)benzene (8.00 g, 96.6% yield) as a yellow oil.

LCMS (acidic): LC retention time 2.18 min; MS (ESI) m/z not observed.

Step 2.

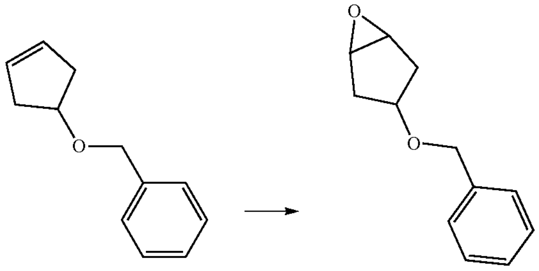 [SMILES: C1=CCC(OCc2ccccc2)C1 ; c1ccc(COC2CC3OC3C2)cc1]

To a stirred solution of ((cyclopent-3-en-1-yloxy)methyl)benzene (8.00 g, 45.9 mmol) in DCM (80 mL) at 0° C., m-CPBA (8.69 g, 50.5 mmol) was added in one portion. The reaction mixture was stirred at 0° C. for 2 h before it was slowly warmed to room temperature. The reaction mixture was slowly quenched with a saturated $NaHSO_3$ and $NaHCO_3$ solution (1:1, 150 mL). The reaction was diluted with EtOAc. The layers were separated. The aqueous layer was extracted with EtOAc (100 mL×2). The combined organic layers were dried over $MgSO_4$, filtered, and concentrated under reduced pressure. The crude product was purified by combi-flash (EA in PE=0-5%) to afford 3-(benzyloxy)-6-oxabicyclo[3.1.0]hexane (7.06 g, 80.8%) as a yellow oil.

LCMS (acidic): LC retention time 1.875, 1.95 min. MS (ESI) m/z 213 $[M+Na]^+$.

Step 3.

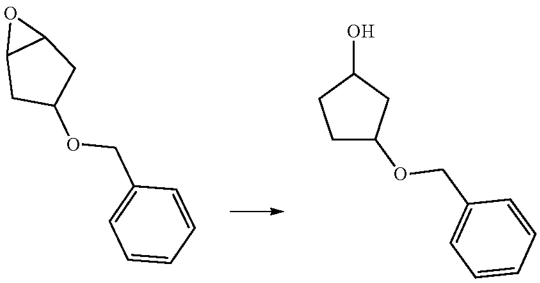 [SMILES: c1ccc(COC2CC3OC3C2)cc1 ; OC1CCC(OCc2ccccc2)C1]

To a solution of 3-(benzyloxy)-6-oxabicyclo[3.1.0]hexane (7.06 g, 37.1 mmol) in 80 mL of THF was added a solution of $LiAlH_4$ (44.5 mL, 44.5 mmol, 1.0 M in THF) dropwise at 0° C. The reaction mixture was stirred for 2 h at 0° C. and quickly warmed to room temperature for 5 min. To this a mixture was added Celite/$Na_2SO_4$ $10H_2O$ (1:1, 100 g total) until the gas stopped to evolve. The solid mixture was dissolved in ether and filtered through a plug of Celite to give 3-(benzyloxy)cyclopentan-1-ol (3.44 g, 48.2%) as a yellow oil.

LCMS (acidic): LC retention time 1.83 min. MS (ESI) m/z 193 $[M+H]^+$.

Step 4.

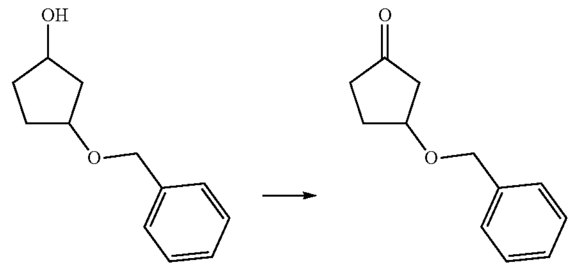 [SMILES: OC1CCC(OCc2ccccc2)C1 ; O=C1CCC(OCc2ccccc2)C1]

To a stirred solution of 3-(benzyloxy)cyclopentan-1-ol (3.44 g, 17.9 mmol) in 40 mL of THF was added Dess-Martin periodinane (15.20 g, 35.8 mmol) at 0° C. The reaction mixture was stirred for 4 h at 0° C. The reaction mixture was slowly quenched with a saturated $NaHSO_3$ and $NaHCO_3$ solution (1:1, 100 mL). The reaction was diluted with EtOAc. The layers were separated. The aqueous layer was extracted with EtOAc (150 mL×2). The combined organic layers were dried over $MgSO_4$, filtered, and concentrated under reduced pressure to afford 3-(benzyloxy) cyclopentan-1-one (2.67 g, 78.5%) as a yellow oil.

LCMS (acidic): LC retention time 1.896 min. MS (ESI) m/z 191 $[M+H]^+$.

Step 5.

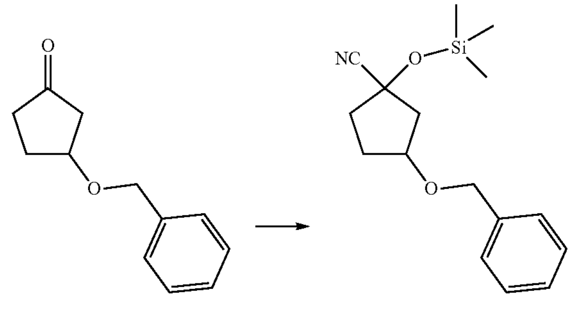 [SMILES: O=C1CCC(OCc2ccccc2)C1 ; C[Si](C)(C)OC1(C#N)CCC(OCc2ccccc2)C1]

To a solution of 3-(benzyloxy)cyclopentan-1-one (2.10 g, 11.0 mmol) in 25 mL of tetrahydrofuran were added trimethylsilylformonitrile (1.75 g, 17.7 mmol) and $ZnI_2$ (352 mg, 1.10 mmol) at 0° C. The mixture was stirred at 0° C. for 6 h and at 60° C. for 16 h. The solid was filtered off and the filtrate was evaporated. The residue was purified by SGC (PE:EA=20:1) to give 3-(benzyloxy)-1-((trimethylsilyl)oxy) cyclopentane-1-carbonitrile (2.25 g, 70.4%) as a yellow oil.

LCMS (acidic): LC retention time 2.66 min. MS (ESI) m/z 312 $[M+Na]^+$.

Step 6.

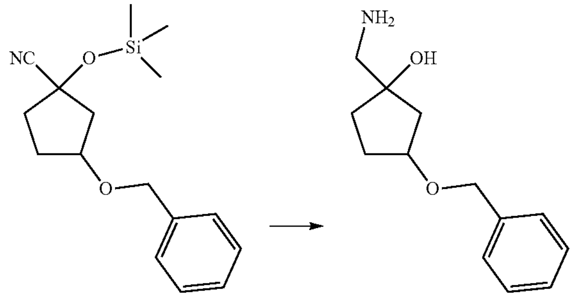 [SMILES: C[Si](C)(C)OC1(C#N)CCC(OCc2ccccc2)C1 ; NCC1(O)CCC(OCc2ccccc2)C1]

To a solution of 3-(benzyloxy)-1-((trimethylsilyl)oxy)cyclopentane-1-carbonitrile (2.25 g, 7.77 mmol) in 15 mL of tetrahydrofuran was added a solution of lithium aluminum hydride in tetrahydrofuran (9.33 mL, 9.33 mmol) drop wise under an argon atmosphere at 0° C. After stirring for 16 h at room temperature, a sodium hydroxide solution (20%) was slowly added with cooling. The solid was filtered after dilution with ethyl acetate and the organic filtrate was evaporated to give 1-(aminomethyl)-3-(benzyloxy)cyclopentan-1-ol (1.60 g, 93.0%) as a yellow oil.

LCMS (acidic): LC retention time 1.296 min. MS (ESI) m/z 222 $[M+H]^+$.

Step 7.

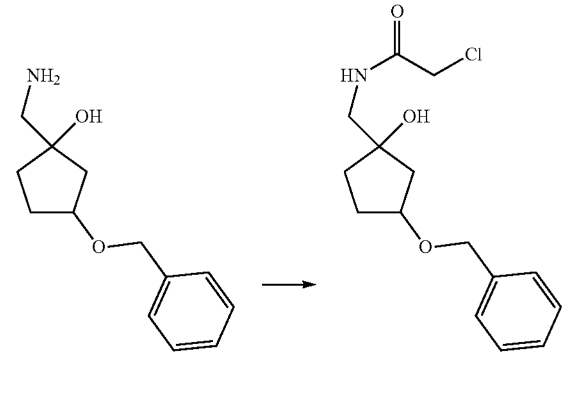 [SMILES: NCC1(O)CCC(OCc2ccccc2)C1 ; O=C(CCl)NCC1(O)CCC(OCc2ccccc2)C1]

To a solution of potassium carbonate (2.0 g, 14.5 mmol) in water (15 mL) was added to a solution of 1-(aminomethyl)-3-(benzyloxy)cyclopentan-1-ol (1.60 g, 7.23 mmol) in ethyl acetate (15 mL). The mixture was cooled to 0° C., and then treated with 2-chloroacetyl chloride (980 mg, 8.68 mmol). After completion of the addition, the reaction mixture was warmed to 25° C. and allowed to stir for 16 h. The aqueous layer was extracted with ethyl acetate (50 mL×3). The combined organic layers were dried over sodium sulfate, filtered, and concentrated in vacuo to give N-((3-(benzyloxy)-1-hydroxycyclopentyl)methyl)-2-chloroacetamide (1.90 g, 88.2%) as a yellow oil.

LCMS (acidic): LC retention time 1.86 min. MS (ESI) m/z 298 $[M+H]^+$.

Step 8.

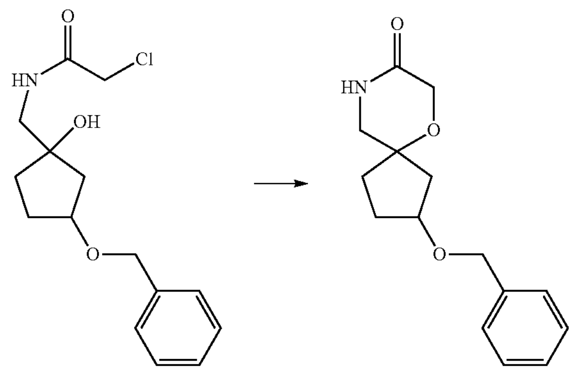 [SMILES: O=C(CCl)NCC1(O)CCC(OCc2ccccc2)C1 ; O=C1COC2(CCC(OCc3ccccc3)C2)CN1]

To a solution of potassium tert-butoxide (1.43 g, 12.8 mmol) in tert-butanol (15 mL) was added N-((3-(benzyloxy)-1-hydroxycyclopentyl)methyl)-2-chloroacetamide (1.90 g, 6.38 mmol) in THF (15 mL) over 10 min. and the resulting mixture was continued to stir for 16 h at room temperature before it was concentrated. The residue was partitioned between EtOAc (100 mL) and water (100 mL). The organic layer was separated, washed with brine (50 mL×2), and concentrated to provide 2-(benzyloxy)-6-oxa-9-azaspiro[4.5]decan-8-one (1.50 g, 90.0%).

LCMS (acidic): LC retention time 1.81, 1.84 min. MS (ESI) m/z 262 $[M+H]^+$.

Step 9.

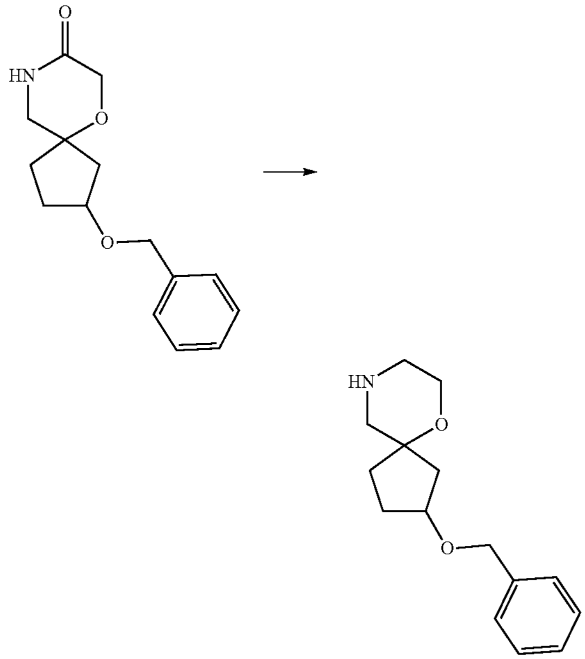

To a solution of 2-(benzyloxy)-6-oxa-9-azaspiro[4.5]decan-8-one (1.30 g, 4.97 mmol) in THF (15 mL) was added tetrahydrofuran-borane (14.9 mL, 14.9 mmol) at room temperature. The reaction mixture was refluxed for 2 h, then cooled to room temperature. MeOH was carefully added and the solvent was concentrated under reduced pressure. To the resulting mixture was added MeOH (15 mL) and N,N,N',N'-tetramethylethylenediamine (2.31 g, 19.9 mmol). The reaction was stirred at 75° C. overnight. The reaction was concentrated and the residue was diluted with EtOAc (50 mL) and water (50 mL). The organic layer was separated, washed with brine (50 mL×2), and concentrated in vacuo to give 2-(benzyloxy)-6-oxa-9-azaspiro[4.5]decane (1.15 g, 93.5%) as a yellow oil.

LCMS (acidic): LC retention time 1.531, 1.558 min. MS (ESI) m/z 248 $[M+H]^+$.

Step 10.

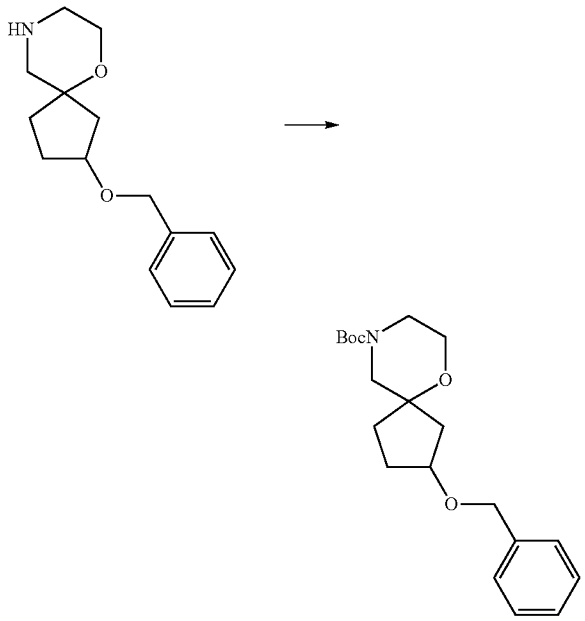

To reaction solution of 2-(benzyloxy)-6-oxa-9-azaspiro[4.5]decane (1.20 g, 4.85 mmol) in 1,4-dioxane (10 mL)/$H_2O$ (10 mL) was added di-tert-butyl dicarbonate (3.18 g, 14.6 mmol) and $Na_2CO_3$ (1.54 g, 14.6 mmol). The result mixture was stirred at room temperature overnight. The reaction solution was concentrated. The residue was taken in EA (50 mL). The EA solution was washed with brine (50 mL). The organic was concentrated and purified by SGC (PE:EA=5:1) to give tert-butyl 2-(benzyloxy)-6-oxa-9-azaspiro[4.5]decane-9-carboxylate (1.20 g, 71.2%) as a yellow oil.

LCMS (acidic): LC retention time 2.205, 2.242 min. MS (ESI) m/z 292 $[M-tBu]^+$

Step 11.

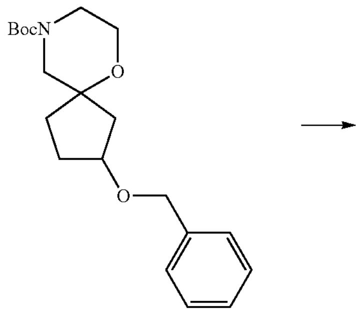

-continued

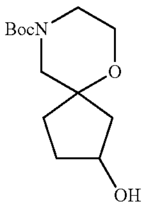

To a solution of tert-butyl 2-(benzyloxy)-6-oxa-9-azaspiro[4.5]decane-9-carboxylate (1.20 g, 3.45 mmol) in EtOAc (25 mL) was added Pd/C. The flask was attached to a hydrogenation apparatus. The system was stirred under hydrogen for 5 h. The catalyst was filtered off. The filtrate was concentrated to give tert-butyl 2-hydroxy-6-oxa-9-azaspiro[4.5]decane-9-carboxylate (810 mg, 91.1%) as a colorless oil.

LCMS (acidic): LC retention time 1.736 min. MS (ESI) m/z 202 $[M\text{-}t\text{-}Bu]^+$.

Step 12.

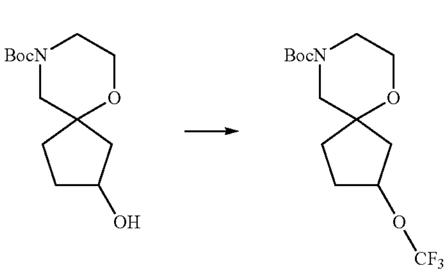 [SMILES: CC(C)(C)OC(=O)N1CCOC2(CCC(O)C2)C1 ; CC(C)(C)OC(=O)N1CCOC2(CCC(OC(F)(F)F)C2)C1]

To a flask was charged AgOTf (1.65 g, 6.41 mmol), Select-F (1.14 g, 3.21 mmol), KF (497 mg, 8.55 mmol) and tert-butyl 2-hydroxy-6-oxa-9-azaspiro[4.5]decane-9-carboxylate (550 mg, 2.14 mmol). The flask was purged with argon. Then, EtOAc (15 mL) was added, followed by $TMSCF_3$ (912 mg, 6.41 mmol) and 2-fluoropyridine (623 mg, 6.41 mmol). The reaction mixture was stirred at room temperature overnight under argon atmosphere. The mixture was filtered through a celite pad. The filtrate was concentrated and purified by combi-flash (100% PE) to afford tert-butyl 2-(trifluoromethoxy)-6-oxa-9-azaspiro[4.5]decane-9-carboxylate (420 mg, 60.4%) as a yellow oil.

LCMS: LC retention time 2.170 min. MS (ESI) m/z 270 $[M\text{-}t\text{-}Bu]^+$.

Step 13.

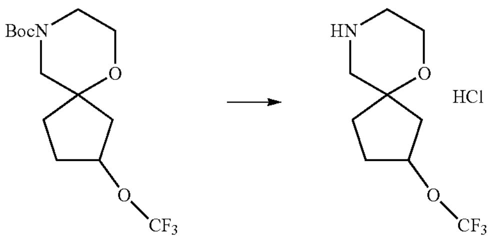 [SMILES: CC(C)(C)OC(=O)N1CCOC2(CCC(OC(F)(F)F)C2)C1 ; FC(F)(F)OC1CCC2(CNCCO2)C1 ; Cl]

To a solution of tert-butyl 2-(trifluoromethoxy)-6-oxa-9-azaspiro[4.5]decane-9-carboxylate (650 mg, 2.0 mmol) in dioxane (1 mL) was added HCl/1,4-dioxane (10.0 mL). The solution was stirred at room temperature for 2 h. The mixture was concentrated to give 2-(trifluoromethoxy)-6-oxa-9-azaspiro[4.5]decane hydrochloride (523 mg, 100%) as a yellow oil.

LCMS: LC retention time 1.28 min. MS (ESI) m/z 226 $[M+H]^+$.

Intermediate E-11 tert-Butyl 6-oxa-2,9-diazaspiro[4.5]decane-9-carboxylate

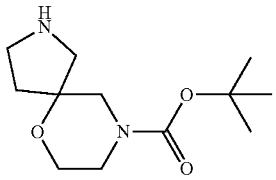 [SMILES: CC(C)(C)OC(=O)N1CCOC2(CCNC2)C1]

Step 1.

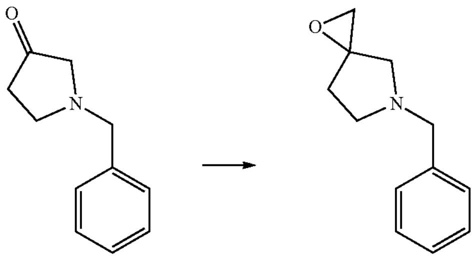 [SMILES: O=C1CCN(Cc2ccccc2)C1 ; c1ccc(CN2CCC3(CO3)C2)cc1]

To a suspension of NaH (3.01 g, 75.33 mmol) in DMSO (120 mL) was added trimethylsulfoxonium iodide (19.59 g, 89.03 mmol) followed by 1-benzylpyrrolidin-3-one (12.00 g, 68.48 mmol). The reaction mixture was stirred at room temperature for 3 h. The reaction mixture was quenched by the addition of water (500 mL) and the mixture was extracted with EtOAc (500 mL×2). The combined extracts were washed with water (300 mL×2), dried over $Na_2SO_4$, filtered and concentrated to afford 5-benzyl-1-oxa-5-azaspiro[2.4]heptane (12.00 g, 92.6%) as a brown oil.

LCMS: LC retention time 1.370 min. MS (ESI) m/z 190 $[M+H]^+$.

Step 2.

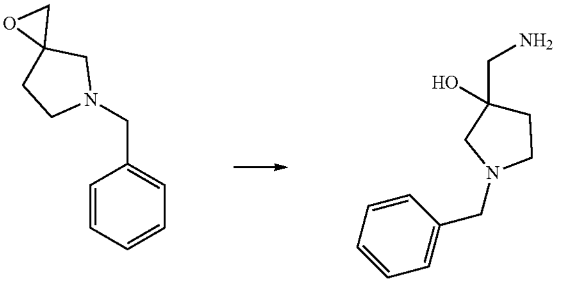 [SMILES: c1ccc(CN2CCC3(CO3)C2)cc1 ; NCC1(O)CCN(Cc2ccccc2)C1]

To a solution of 5-benzyl-1-oxa-5-azaspiro[2.4]heptane (12.00 g, 63.4 mmol) in 60 mL of MeOH was added 90 mL of 28% $NH_4OH$ dropwise at 0° C. The reaction mixture was stirred at room temperature overnight. The reaction mixture was concentrated, diluted with 500 mL of EtOAc, washed with water (200 mL×2), dried over $Na_2SO_4$, filtered, and concentrated. The residue was purified by combi-flash (MeOH in DCM=0-10%) to give 3-(aminomethyl)-1-benzylpyrrolidin-3-ol (5.93 g, 45.3%) as a yellow oil.

LCMS: LC retention time 1.10 min. MS (ESI) m/z 207 $[M+H]^+$.

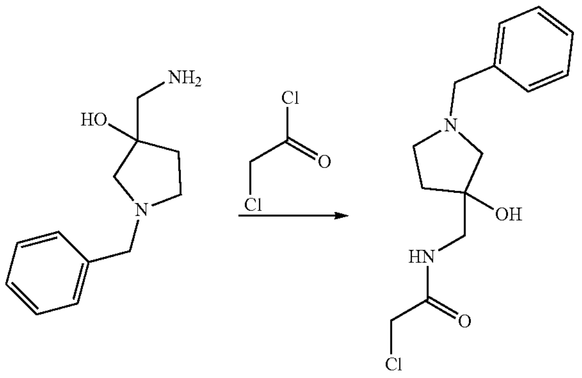 [SMILES: NCC1(O)CCN(Cc2ccccc2)C1 ; O=C(Cl)CCl ; O=C(CCl)NCC1(O)CCN(Cc2ccccc2)C1]

To a stirred solution of 3-(aminomethyl)-1-benzylpyrrolidin-3-ol (6.08 g, 29.5 mmol) in DCM (50 mL) was added triethylamine (8.95 g, 88.4 mmol) followed by 2-chloroacetyl chloride (3.33 g, 29.5 mmol) dropwise at −20° C. under Ar. The reaction mixture was stirred at the same temperature for 0.5 h and then warmed to r.t for 1 h. The reaction mixture was diluted with DCM (100 mL) and washed with saturated $NH_4Cl$ solution (100 mL) followed by saturated brine (100 mL). The organic layer was dried ($Na_2SO_4$) and concentrated in vacuo to give the crude product which was purified by automated flash chromatography (MeOH in DCM 0-5%) to give the product N-((1-benzyl-3-hydroxypyrrolidin-3-yl)methyl)-2-chloroacetamide (4.70 g, 56% yield) as a yellow oil.

LCMS: LC retention time 0.578 min. MS (ESI) m/z 283 $[M+H]^+$.

Step 3.

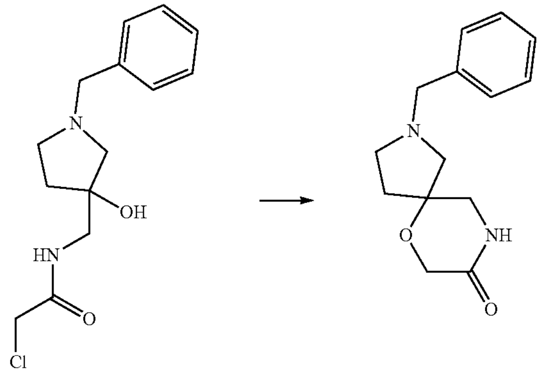 [SMILES: O=C(CCl)NCC1(O)CCN(Cc2ccccc2)C1 ; O=C1COC2(CCN(Cc3ccccc3)C2)CN1]

To the solution of N-((1-benzyl-3-hydroxypyrrolidin-3-yl)methyl)-2-chloroacetamide (0.35 g, 1.24 mmol, 1.0 eq) in THF (5 mL) was added the solution of t-BuOK in THF (1.0 M, 1.49 mL, 1.49 mmol) at 0° C. under Ar. The mixture was stirred at the same temperature for 15 min and then rt for 1 h. The reaction was diluted with $H_2O$ (20 mL) and extracted with EtOAc (20 mL×3). The combined extracts were washed with saturated brine (20 mL) followed by drying over $Na_2SO_4$. The solvent was removed in vacuo to give the crude product which was purified by automated flash chromatography (MeOH in DCM 0-5%) to give the product 2-benzyl-6-oxa-2,9-diazaspiro[4.5]decan-8-one (178 mg, 58% yield) as a white solid.

LCMS: LC retention time 1.251 min. MS (ESI) m/z 247 $[M+H]^+$.

Step 4.

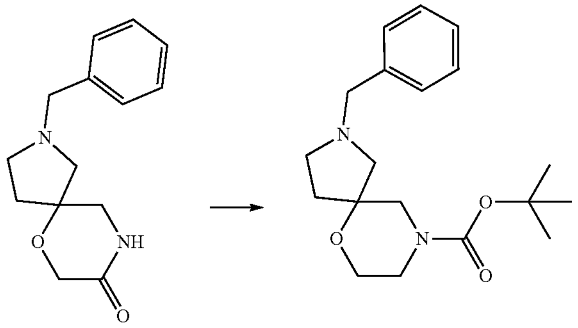 [SMILES: O=C1COC2(CCN(Cc3ccccc3)C2)CN1 ; CC(C)(C)OC(=O)N1CCOC2(CCN(Cc3ccccc3)C2)C1]

To a stirred solution of 2-benzyl-6-oxa-2,9-diazaspiro[4.5]decan-8-one (2.36 g, 9.58 mmol, 1.0 eq) in THF (150 mL) was added $LiAlH_4$ (14.4 mL, 1 M, 14.4 mmol, 1.5 eq) in THF at 0° C. under Ar. The mixture was heated to reflux for 1 h. Then, the reaction was cooled to 0° C. and quenched by the addition of $H_2O$ (5 mL), followed by $Na_2CO_3$ (2.03 g, 19.2 mmol, 2.0 eq) and $(Boc)_2O$ (4.18 g, 19.2 mmol, 2.0 eq). The mixture was stirred at rt for 3 h. The reaction was diluted with $H_2O$ (200 mL) and extracted with EtOAc (200 mL×2). The combined extracts were washed with saturated brine (200 mL) and dried over $Na_2SO_4$. The solvent was removed in vacuo to give the crude product which was purified by automated flash chromatography (EtOAc in heptane 0-20%) to give the product tert-butyl 2-benzyl-6-oxa-2,9-diazaspiro[4.5]decane-9-carboxylate (2.59 g, 82% yield) as a color-less oil.

LCMS: LC retention time 1.484 min. MS (ESI) m/z 333 $[M+H]^+$.

Step 5.

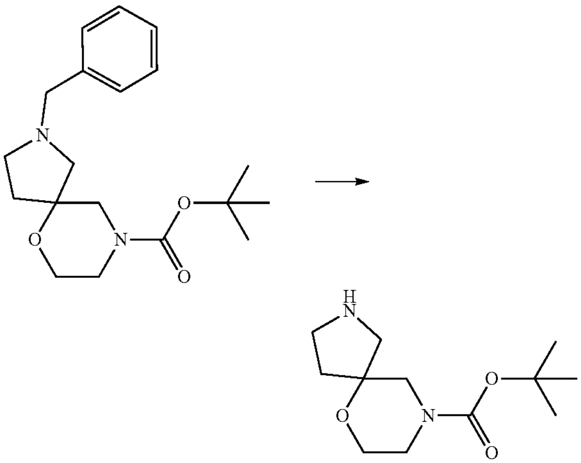

To a solution of tert-butyl 2-benzyl-6-oxa-2,9-diazaspiro[4.5]decane-9-carboxylate (3.00 g, 9.0 mmol, 1.0 eq) in MeOH (50 mL) was added Pd/C (10%, 2.0 g) and ammonium formate (4.00 g, 63.4 mmol, 7.0 eq) at rt. The mixture was heated to reflux for 1 h. The Pd/C was removed by filtration and the filtrate was concentrated in vacuo to give the product tert-butyl 6-oxa-2,9-diazaspiro[4.5]decane-9-carboxylate (2.0 g, 91.5% yield) as a color-less oil.

LCMS: LC retention time 1.417 min. MS (ESI) m/z 243 $[M+H]^+$.

Intermediate E-12

2-Neopentylmorpholine

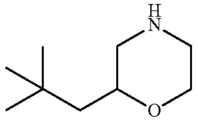

Step 1.

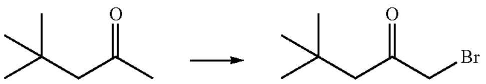

To a solution of 4, 4-dimethylpentan-2-one (1.0 g, 8.76 mmol) in 15 mL of MeOH was added $Br_2$ (1.40 g, 8.76 mmol) drop-wise at 0° C., the reaction mixture was stirred at room temperature overnight. The reaction mixture was concentrated to afford crude 1-bromo-4,4-dimethylpentan-2-one (1.69 g, 100%) as a brown oil.

Step 2.

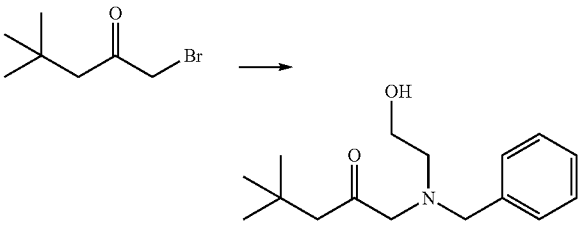

To a reaction solution of 1-bromo-4,4-dimethylpentan-2-one (1.69 g, 8.75 mmol) in 40 mL of $CH_3CN$ were added 2-(benzylamino)ethanol (1.99 g, 13.1 mmol) and $K_2C_{03}$ (1.81 g, 13.1 mmol). The reaction was then heated at 80° C. overnight. The reaction mixture was concentrated. The residue was dissolved in EtOAc (100 mL). The ethyl acetate solution was washed with brine (50 mL), water (50 mL), and then concentrated. The residue was purified by prep-TLC to afford 1-(benzyl(2-hydroxyethyl)amino)-4,4-dimethylpentan-2-one (500 mg, 21.7%) as a yellow oil.

LCMS: LC retention time 1.624 min. MS (ESI) m/z 264 $[M+H]^+$.

Step 3.

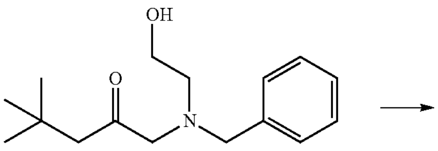

-continued

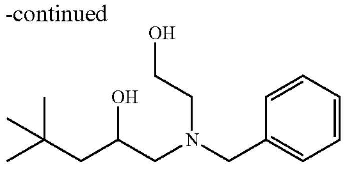

To a solution of 1-(benzyl(2-hydroxyethyl)amino)-4,4-dimethylpentan-2-one (500 mg, 1.90 mmol) in 10 mL of MeOH was added $NaBH_4$ (351 mg, 9.49 mmol) in portions. The reaction mixture was stirred at room temperature for 5 h. The reaction mixture was quenched with $NH_4Cl$ solution, concentrated, extracted with EtOAc (20 mL×4). The organic solution was washed with brine, water, and then dried over $Na_2SO_4$, filtered and concentrated to afford 1-(benzyl(2-hydroxyethyl)amino)-4,4-dimethylpentan-2-ol (430 mg, 85.3%) as a yellow oil.

LCMS: LC retention time 1.555 min. MS (ESI) m/z 266 $[M+H]^+$.

Step 4.

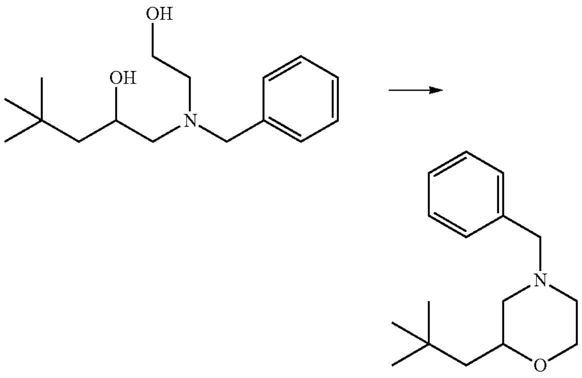

To a solution of 1-(benzyl(2-hydroxyethyl)amino)-4,4-dimethylpentan-2-ol (400 mg, 1.51 mmol) in 10 mL of THF were added and $Ph_3P$ (1.19 g, 4.52 mmol) and DIAD (913 mg, 4.52 mmol) drop-wise at room temperature. The reaction mixture was stirred at room temperature overnight. The reaction was quenched by $NH_4Cl$, extracted with EtOAc, concentrated, diluted with EtOAc. The solid was filtered off. The filtrate was concentrated and purified by Prep-TLC (PE:EA=3:1) to afford 4-benzyl-2-neopentylmorpholine (100 mg, 26.7%) as a pink oil.

LCMS: LC retention time 2.047 min. MS (ESI) m/z 248 $[M+H]^+$.

Step 5.

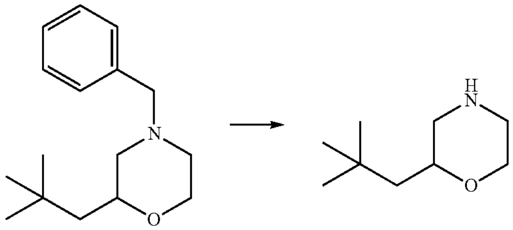 [SMILES: CC(C)(C)CC1CN(Cc2ccccc2)CCO1 ; CC(C)(C)CC1CNCCO1]

To a reaction solution of 4-benzyl-2-neopentylmorpholine (100 mg, 0.404 mmol) in 30 mL of MeOH was added 10% Pd/C (100 mg). The reaction was stirred at room temperature under $H_2$ for 4 h. The reaction mixture was filtered and concentrated to afford 2-neopentylmorpholine (45 mg, 70.8%) as a pink oil. LCMS: LC retention time 1.529 min. MS (ESI) m/z 158 $[M+H]^+$.

Intermediate E-13

2-(3,3-Dimethylbutyl)morpholine hydrochloride

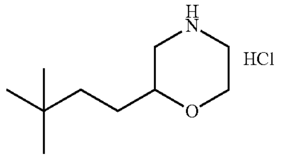

Step 1.

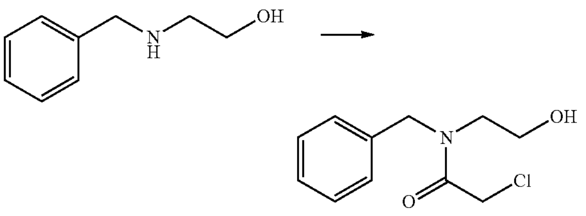

To a solution of 2-(benzylamino)ethan-1-ol (20.00 g, 132 mmol) in 50 mL of DCM were added NaOH (5.29 g, 132 mmol) in 50 mL of $H_2O$ and 2-chloroacetyl chloride (14.9 g, 132 mmol) dropwise. The reaction mixture was stirred at room temperature overnight. The reaction mixture was separated and washed with water. The organics were dried over $Na_2SO_4$, filtered and concentrated to afford N-benzyl-2-chloro-N-(2-hydroxyethyl)acetamide (29.00 g, 96%) as a yellow oil.

LCMS: LC retention time 1.523 min. MS (ESI) m/z 228 $[M+H]^+$.

Step 2.

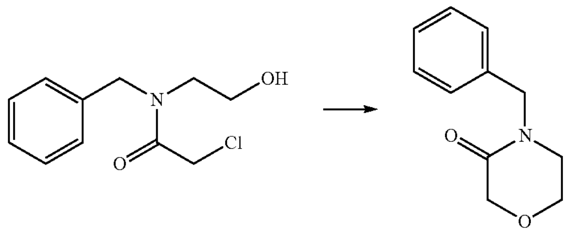 [SMILES: O=C(CCl)N(CCO)Cc1ccccc1 ; O=C1COCCN1Cc1ccccc1]

To a suspension of t-BuOK (23.70 g, 211 mmol) in 100 mL of t-BuOH was added N-benzyl-2-chloro-N-(2-hydroxyethyl)acetamide (24.00 g, 105 mmol) in 100 mL of THF dropwise. The reaction mixture was stirred at room temperature for 2 h. The reaction mixture was concentrated, diluted with 180 mL of EtOAc. The ethyl acetate solution was washed with water (100 mL×2), dried over $Na_2SO_4$, filtered and concentrated to afford 4-benzylmorpholin-3-one (18.00 g, 89.3%) as a yellow oil.

LCMS: LC retention time 1.512 min. MS (ESI) m/z 192 $[M+H]^+$.

Step 3.

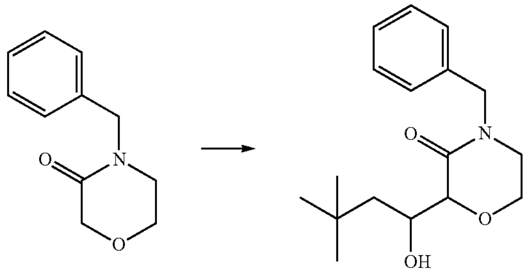 [SMILES: O=C1COCCN1Cc1ccccc1 ; CC(C)(C)CC(O)C1OCCN(Cc2ccccc2)C1=O]

To a solution of 4-benzylmorpholin-3-one (5.00 g, 26.1 mmol) in 60 mL of THF was added n-BuLi (2.5M in hexane, 12.6 mL, 31.4 mmol) at −78° C. After the reaction mixture was stirred at −78° C. for 45 min, 3,3-dimethylbutanal (3.14 g, 31.4 mmol) was added. The reaction mixture was stirred at −78° C. for 1 h, then allowed to warm to room temperature overnight. The reaction mixture was quenched by aqueous $NH_4Cl$. The aqueous was extracted with EA (100 mL×2). The organic solution was concentrated and purified by combi-flash (EA in PE=0-100%) to afford 4-benzyl-2-(1-hydroxy-3,3-dimethylbutyl)morpholin-3-one (3.78 g, 49%) as a yellow oil.

LCMS: LC retention time 2.006 min. MS (ESI) m/z 292 $[M+H]^+$.

Step 4.

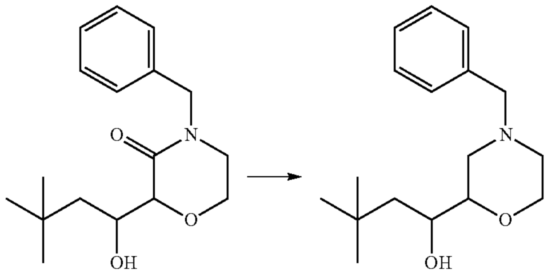 [SMILES: CC(C)(C)CC(O)C1OCCN(Cc2ccccc2)C1=O ; CC(C)(C)CC(O)C1CN(Cc2ccccc2)CCO1]

To a solution of 4-benzyl-2-(1-hydroxy-3,3-dimethylbutyl)morpholin-3-one (3.48 g, 11.9 mmol) in 20 mL of THF was added $BH_3$·THF (1M in THF, 35.8 mL, 35.8 mmol). The reaction mixture was heated at 55° C. for 2 h. The reaction mixture was cooled to room temperature, quenched by MeOH (1 mL), and then concentrated. The residue was dissolved in MeOH (30 mL). To the methanol solution was added TMEDA (5.54 g, 47.8 mmol). The reaction mixture was heated at 80° C. overnight. The reaction was concentrated. The residue was dissolved in EtOAc (100 mL). The EtOAc solution was washed with brine (80 mL×2) and concentrated to afford crude 1-(4-benzylmorpholin-2-yl)-3,3-dimethylbutan-1-ol (3.0 g, 90%) as a yellow oil.

LCMS: LC retention time 1.526 min. MS (ESI) m/z 278 $[M+H]^+$.

Step 5.

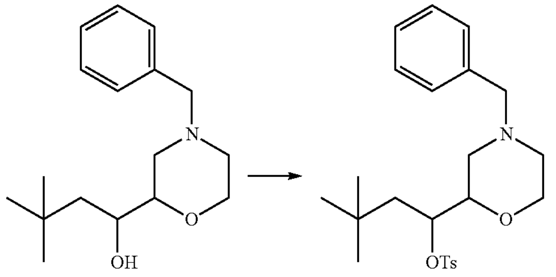 [SMILES: CC(C)(C)CC(O)C1CN(Cc2ccccc2)CCO1 ; Cc1ccc(S(=O)(=O)OC(CC(C)(C)C)C2CN(Cc3ccccc3)CCO2)cc1]

To a solution of 1-(4-benzylmorpholin-2-yl)-3,3-dimethylbutan-1-ol (1.0 g, 3.60 mmol) in DCM (10 mL) was added DMAP (88 mg, 0.721 mmol) and TEA (728 mg, 7.21 mmol). The reaction mixture was cooled to 0° C. TsCl (825 mg, 4.33 mmol) was added in portions. The reaction mixture was allowed to warm to room temperature and stirred overnight. The reaction mixture was quenched by water (20 mL), extracted with DCM (30 mL×2). The DCM solution was washed with water and concentrated. The residue was then purified by Prep-TLC (PE:EA=3:1) to afford 1-(4-benzylmorpholin-2-yl)-3,3-dimethylbutyl 4-methylbenzenesulfonate (840 mg, 54%) as a yellow oil.

LCMS: LC retention time 1.697 min. MS (ESI) m/z 432 $[M+H]^+$.

Step 6.

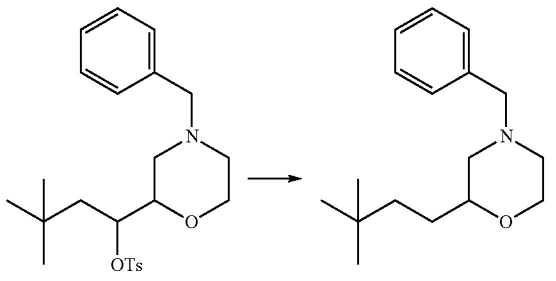 [SMILES: Cc1ccc(S(=O)(=O)OC(CC(C)(C)C)C2CN(Cc3ccccc3)CCO2)cc1 ; CC(C)(C)CCC1CN(Cc2ccccc2)CCO1]

To a solution of 1-(4-benzylmorpholin-2-yl)-3,3-dimethylbutyl 4-methylbenzenesulfonate (840 mg, 1.95 mmol) in THF (5 mL) was added $LiAlH_4$ (1M in THF, 5.84 mL) at 0° C. The reaction mixture was refluxed overnight. The reaction mixture was cooled to room temperature, quenched with aqueous $Na_2SO_4$ solution (2 mL) and filtered. The filtrate cake was washed with EtOAc. The combined EtOAc solution was dried over $Na_2SO_4$, filtered and concentrated. The residue was purified by Prep-TLC (PE:EA=4:1) to afford 4-benzyl-2-(3,3-dimethylbutyl)morpholine (283 mg, 55.6%) as a yellow oil.

LCMS: LC retention time 1.661 min. MS (ESI) m/z 262 $[M+H]^+$.

Step 7.

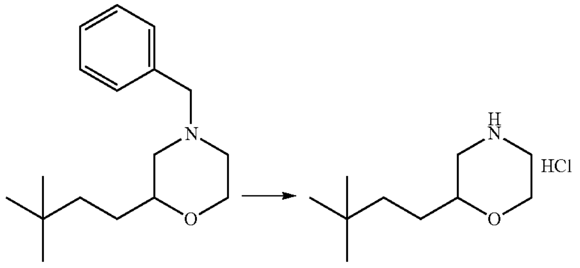 [SMILES: CC(C)(C)CCC1CN(Cc2ccccc2)CCO1 ; CC(C)(C)CCC1CNCCO1 ; Cl]

To a solution of 4-benzyl-2-(3,3-dimethylbutyl)morpholine (283 mg, 1.08 mmol) in 50 mL of MeOH was added 500 mg of 10% Pd/C. The reaction mixture was stirred under $H_2$ at room temperature overnight. The reaction mixture was filtered and the filtrate was concentrated. The residue was dissolved in 2 mL of DCM, 5 mL of 4 m HCl in dioxane was added. The reaction mixture was stirred at room temperature for 20 min, concentrated to afford 2-(3,3-dimethylbutyl)morpholine hydrochloride (200 mg, 88.9%) as a white solid.

LCMS: LC retention time 1.488 min. MS (ESI) m/z 172 $[M+H]^+$.

Intermediate E-14

2-(4,4-Dimethylpentyl)morpholine

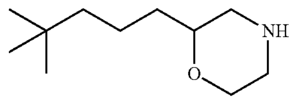

Step 1.

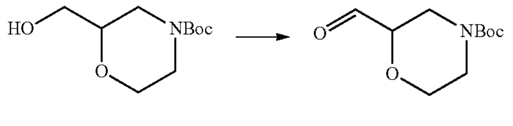 [SMILES: CC(C)(C)OC(=O)N1CCOC(CO)C1 ; CC(C)(C)OC(=O)N1CCOC(C=O)C1]

To a stirred solution of oxylyl chloride (1.93 g, 15.2 mmol) in DCM (40 mL) was slowly added DMSO (0.79 mL, 11.0 mmol) at −78° C., and the resulting mixture was stirred for 30 min at this temperature. A solution of tert-butyl 2-(hydroxymethyl)morpholine-4-carboxylate (3.00 g, 13.8 mmol) in DCM (10 mL) was added slowly over 10 min and stirred for 1 h. Then TEA (6.29 g, 62.1 mmol) was added dropwise and stirred for 0.5 h. The reaction mixture was allowed to warm slowly to rt, and then quenched with water (30 mL). After extraction with DCM (20 mL×3), the organic layer was washed successively with HCl (10 mL, 1 M), saturated aqueous $Na_2CO_3$ (30 mL), and then brine (30 mL). The organic layer was dried over anhydrous $Na_2SO_4$ and concentrated in vacuo to afford tert-butyl 2-formylmorpholine-4-carboxylate as a yellow oil (2 g, 67% yield).

LCMS: LC retention time 1.49 min; MS (ESI) m/z 160 $[M\text{-}t\text{-}Bu]^+$.

Step 2.

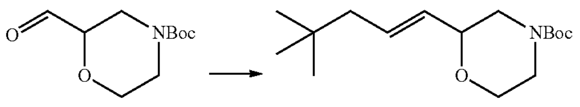 [SMILES: CC(C)(C)OC(=O)N1CCOC(C=O)C1 ; CC(C)(C)C/C=C/C1CN(C(=O)OC(C)(C)C)CCO1]

To a solution of (3,3-dimethylbutyl) (triphenyl)phosphonium methanesulfonate (2.05 g, 4.6 mmol) in THF (30 mL) was added sodium hydride (60% on mineral oil, 223 mg, 9.2 mmol) at 0° C. The mixture was stirred for 30 min. To the reaction mixture was added a solution of tert-butyl 2-formylmorpholine-4-carboxylate (1.0 g, 4.6 mmol) in THF (10 mL) dropwise and the mixture was stirred at 50° C. for 4 h. Hydrochloric acid (1N) was added and the mixture was extracted with ethyl acetate (50 mL). The extract was washed with saturated brine and dried over anhydrous sodium sulfate. The solvent was evaporated and the residue was purified by silica gel chromatography using PE/EA (20/1) as eluent to give tert-butyl (E)-2-(4,4-dimethylpent-1-en-1-yl)morpholine-4-carboxylate (490 mg, 37% yield) as a colorless oil.

LCMS: LC retention time 2.30 min; MS (ESI) m/z 228 $[M-t-Bu]^+$.

$^1H$ NMR (400 MHz, chloroform-d) (5.72-7.65 (m, 1H), 5.43-5.38 (m, 1H), 4.13 (t, J=8.4 Hz, 1H), 3.88-3.52 (m, 4H), 2.94 (t, J=11.2 Hz, 1H), 2.68 (s, 1H), 2.01 (d, J=8.0 Hz, 2H), 1.47 (s, 9H), 0.90 (s, 9H) ppm.

Step 3.

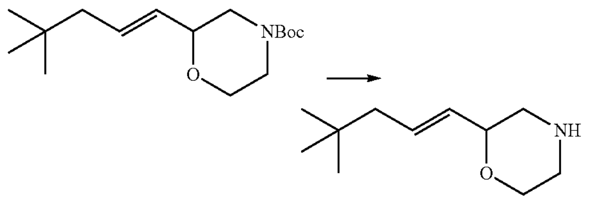

To a stirred solution of tert-butyl (E)-2-(4,4-dimethylpent-1-en-1-yl)morpholine-4-carboxylate (430 mg, 1.4 mmol) in DCM (3 mL) was added HCl/dioxane (4 mL). The reaction was stirred at rt for 1 h. Then the reaction solution was concentrated to give (E)-2-(4,4-dimethylpent-1-en-1-yl) morpholine (250 mg, 90% yield) as a white solid.

LCMS: LC retention time 1.48 min. MS (ESI) m/z 184 $[M+H]^+$.

Step 4.

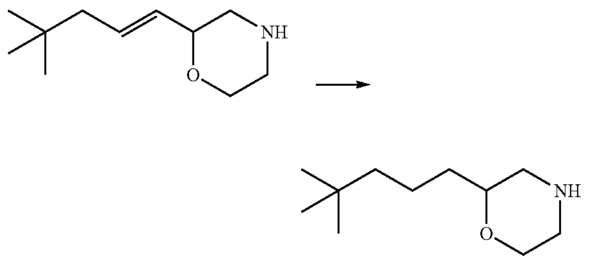

To a solution of (E)-2-(4,4-dimethylpent-1-en-1-yl)morpholine (250 mg, 0.77 mmol) in MeOH (6 mL) were added Pd/C (10%, 100 mg). The reaction mixture was stirred under $H_2$ at rt for 1 h. Then, the reaction mixture was filtered and concentrated to give 2-(4,4-dimethylpentyl)morpholine (220 mg, 87% yield) as a white solid.

LCMS: LC retention time 1.54 min. MS (ESI) m/z 186 $[M+H]^+$.

Intermediate E-15

4-(tert-Butoxy)-2-methylpyrrolidine

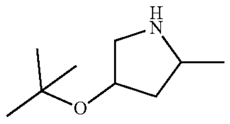

Step 1.

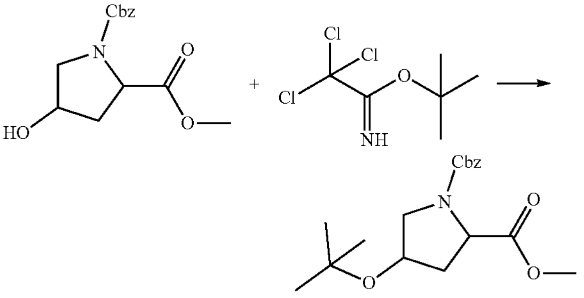

To a stirring solution of 1-benzyl 2-methyl 4-hydroxypyrrolidine-1,2-dicarboxylate (5.67 g, 20.3 mmol) in THF (60 mL) was added tert-butyl 2,2,2-trichloroethanimidate (3.6 mL). The mixture was stirred at room temperature for 3 h. Then additional tert-butyl 2,2,2-trichloroethanimidate (3.6 mL) was added and stirred at room temperature for 0.5 h. The remaining parts of tert-butyl 2,2,2-trichloroethanimidate (29.1 mL) were added in a few portions. After addition was completed, the solution was stirred at room temperature for 48 h. To the reaction mixture was added DCM (60 mL). The mixture was filtered through a celite plug and the filtrate was concentrated to dryness under reduced pressure to give the crude which was purified by reversed phase silica gel column chromatography to give the desired compound 1-benzyl 2-methyl 4-(tert-butoxy)pyrrolidine-1,2-dicarboxylate (1.75 g, 25.7%) as a colorless oil.

LCMS: LC retention time 2.12 min. MS (ESI) m/z 336 $[M+H]^+$.

Step 2.

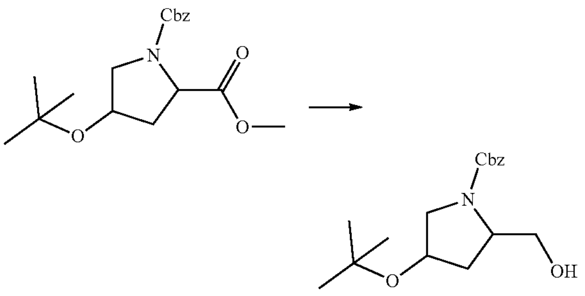

To a cooled stirred solution of 1-benzyl 2-methyl 4-(tert-butoxy)pyrrolidine-1,2-dicarboxylate (1.75 g, 4.17 mmol) in anhydrous tetrahydrofuran (40.0 mL) was added DIBAL-H (1M in toluene) (20.9 mL) at −78° C. The reaction was stirred at the same temperature under argon atmosphere. Then the mixture was allowed to warm to room temperature slowly and stirred at room temperature overnight. Then, saturated potassium sodium tartrate tetrahydrate solution (40 mL) was added and stirred for 1h. The mixture was filtered through a celite plug. The filtrate was concentrated under reduced pressure to give the crude which was purified by flash chromatography (PE/EA=2/1) to give the desired compound benzyl 4-(tert-butoxy)-2-(hydroxymethyl)pyrrolidine-1-carboxylate (850 mg, 53.0%) as a light yellow oil.

LCMS: LC retention time 1.99 min. MS (ESI) m/z 308 $[M+H]^+$.

Step 3.

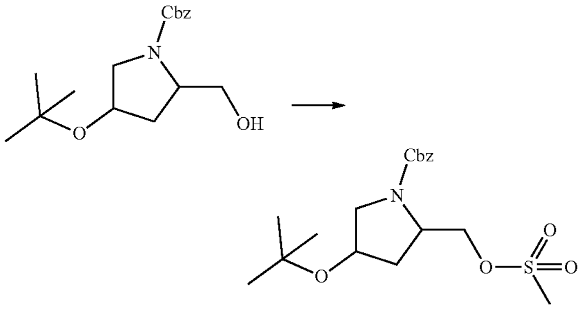

To a solution of benzyl 4-(tert-butoxy)-2-(hydroxymethyl)pyrrolidine-1-carboxylate (700 mg, 2.28 mmol) in DCM (30 mL) were added MsCl (521 mg, 4.55 mmol) and $Et_3N$ (690 mg, 6.83 mmol) at ice bath temperature. Then the mixture was stirred at room temperature overnight. The mixture was concentrated to dryness in vacuo and the residue was dissolved in ethyl acetate (80 mL). The ethyl acetate solution was washed with saturated $NaHCO_3$ solution (50 mL) and brine (50 mL), dried over anhydrous $Na_2SO_4$, and then filtered. The filtrate was concentrated under reduced pressure to give the crude which was purified by flash chromatography (PE/EA=2/1) to give the desired compound benzyl 4-(tert-butoxy)-2-(((methylsulfonyl)oxy)methyl)pyrrolidine-1-carboxylate (860 mg, 98.0%) as a colorless oil.

LCMS: LC retention time 2.08 min. MS (ESI) m/z 386 $[M+H]^+$.

Step 4.

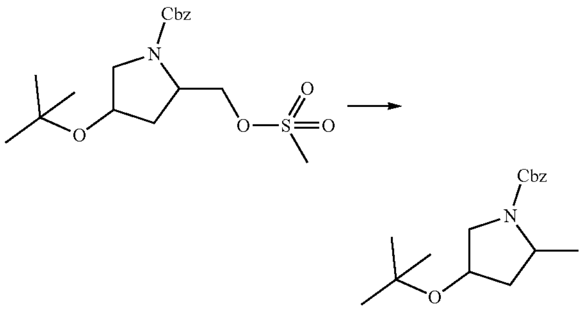

To a solution of benzyl 4-(tert-butoxy)-2-(((methylsulfonyl)oxy)methyl)pyrrolidine-1-carboxylate (860 mg, 2.23 mmol) in dioxane (30 mL) was added $(Bu_4N)BH_4$ (2.29 g, 9.92 mmol) under argon atmosphere. Then, the mixture was heated to 100° C. and stirred at the same temperature for 5 h. After cooling to room temperature, the mixture was diluted with ethyl acetate (150 mL). The ethyl acetate solution was washed with water (80 mL) and brine (150 mL). The aqueous phase was back extracted with ethyl acetate (80 mL×2). The combined organic phases were dried over anhydrous $Na_2SO_4$ and filtered. The filtrate was concentrated under reduced pressure to give the crude which was purified by silica gel chromatography (PE/EA=5/1) to give the desired compound benzyl 4-(tert-butoxy)-2-methylpyrrolidine-1-carboxylate (530 mg, 81.5%) as a colorless oil.

LCMS: LC retention time 2.22 min. MS (ESI) m/z 314 $[M+Na]^+$.

Step 5.

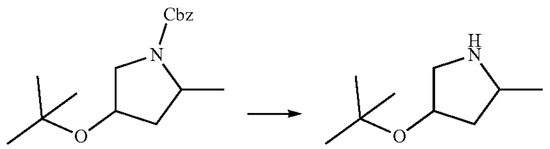 [SMILES: CC1CC(OC(C)(C)C)CN1C(=O)OCc1ccccc1 ; CC1CC(OC(C)(C)C)CN1]

To a solution of benzyl 4-(tert-butoxy)-2-methylpyrrolidine-1-carboxylate (530 mg, 1.82 mmol) in MeOH (20 mL) was added $Pd(OH)_2$ (150 mg). The mixture was stirred at room temperature overnight under hydrogen atmosphere. The mixture was diluted with MeOH (20 mL), filtered through a celite plug. The filtrate was concentrated to dryness to give the crude which was purified by silica gel column chromatography (100% EA) to give the desired compound 4-(tert-butoxy)-2-methylpyrrolidine (70 mg, 24.5%) as a light yellow oil.

LCMS: LC retention time 1.35 min. MS (ESI) m/z 158 $[M+H]^+$.

Intermediate E-16

(2R,4R)-4-(tert-Butoxy)-2-methylpyrrolidine

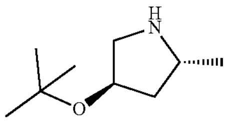

Intermediate E-16 was prepared in essentially the same way as Intermediate E-15 described above.

Intermediate E-17

3-(3,3-Dimethylbutyl)pyrrolidin-2-one

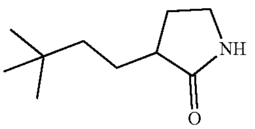

Step 1.

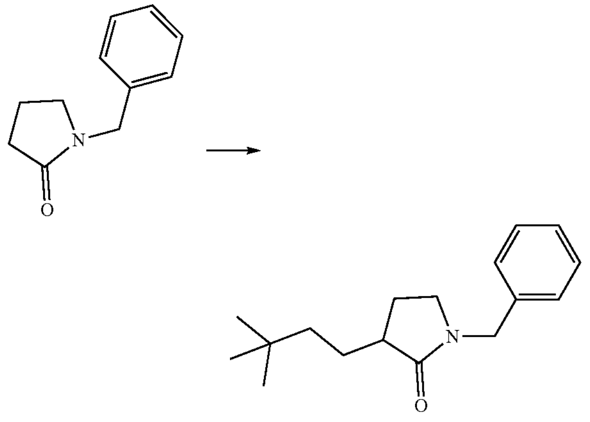

To a solution of diisopropylamine (3.18 g, 31.4 mmol) in THF (50 mL) was added n-BuLi (13.7 mL, 34.2 mmol) at 0° C. and stirred for 0.5 h. The mixture was cooled to −78° C. and 1-benzylpyrrolidin-2-one (5 g, 28.5 mmol) was added. The mixture was stirred for 0.5 h and then 1-bromo-3,3-dimethyl-butane (7.07 g, 42.8 mmol) was added and stirred for 16 h from −78° C. to rt. The reaction was quenched with water (2 mL), extracted with ethyl acetate (50 mL). The ethyl acetate solution was washed with brine (50 mL×2). The aqueous layer was back extracted with ethyl acetate. The combined organic extracts were dried over anhydrous sodium sulfate, filtered, and concentrated in vacuo. The residue was purified by combi-flash (EA in PE=0-10%) to give 1-benzyl-3-(3,3-dimethylbutyl)pyrrolidin-2-one (2.90 g, 39.2% yield) as a yellow oil.

LCMS (acidic): LC retention time 2.21 min. MS (ESI) m/z 260 [M+H]$^+$.

Step 2.

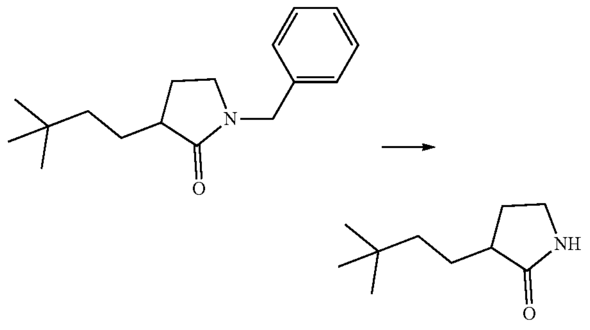

To a solution of 1-benzyl-3-(3,3-dimethylbutyl)pyrrolidin-2-one (1.8 g, 6.9 mmol) in toluene (6 mL) was added trifluoromethanesulfonic acid (4.17 g, 27.8 mmol). The reaction mixture was stirred in microwave oven at 195° C. for 40 min. The mixture was poured into a small amount of saturated $NaHCO_3$ (10 mL), extracted with EA (50 mL). The EA solution was washed with brine (50 mL×3). The combined organic extracts were dried over anhydrous sodium sulfate, filtered, and concentrated in vacuo. The crude residue was purified by combi-flash (EA in PE=60%-100%) to give 3-(3,3-dimethylbutyl)pyrrolidin-2-one (500 mg, 42.6% yield) as a yellow solid.

LCMS (acidic): LC retention time 1.89 min. MS (ESI) m/z 170 [M+H]$^+$.

Intermediate G-1a

2-Bromo-5-(3-(3,3-dimethylbutoxy)-5-fluorophenyl)-4-(2,6-dimethylphenyl)thiazole

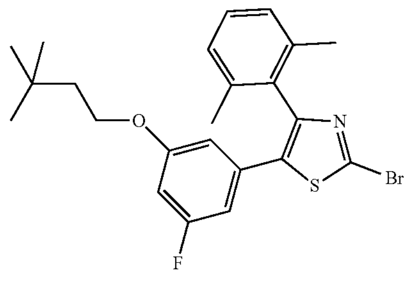 [SMILES: Cc1cccc(C)c1-c1nc(Br)sc1-c1cc(F)cc(OCCC(C)(C)C)c1]

Step 1.

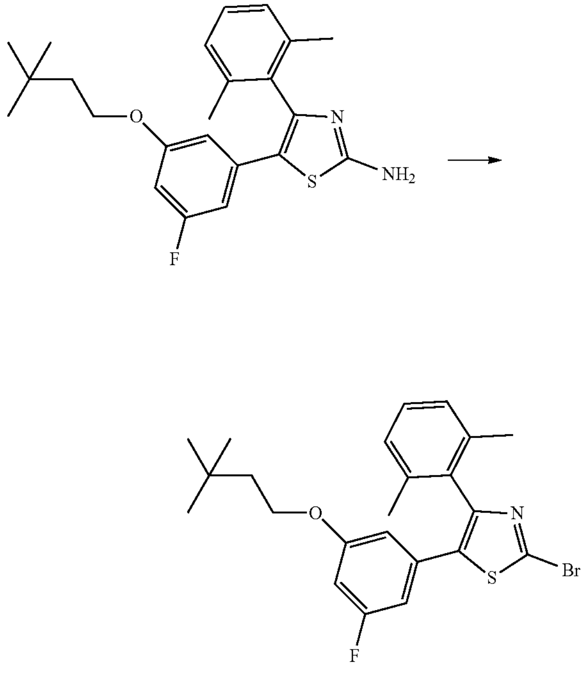

To a solution of 5-[3-(3,3-dimethylbutoxy)-5-fluoro-phenyl]-4-(2,6-dimethylphenyl)thiazol-2-amine (Intermediate C-11) (1.00 g, 2.52 mmol) in $CH_3CN$ (8.0 mL) were added $CuBr_2$ (561 mg, 2.52 mmol) and tert-butyl nitrite (259 mg, 2.52 mmol). The reaction was stirred at 80° C. for 15 min. The reaction mixture was concentrated to dryness. The residue was purified by SGC (PE/EA=50/1) to give 2-bromo-5-(3-(3,3-dimethylbutoxy)-5-fluorophenyl)-4-(2,6-dimethylphenyl)thiazole as a red solid (980 mg, 84%).

LCMS: LC retention time 1.95 min. MS (ESI) m/z 464 [M+H]$^+$.

The following intermediates were prepared in essentially the same protocol as Intermediate G-1a using the proper Intermediate C-xx.

Intermediate G-1b

2-Bromo-5-(3-(3,3-dimethylbutoxy)-5-phenyl)-4-(2,6-dimethylphenyl)thiazole

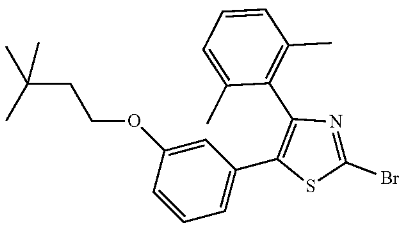 [SMILES: Cc1cccc(C)c1-c1nc(Br)sc1-c1cccc(OCCC(C)(C)C)c1]

Intermediate G-2a 2-bromo-5-(3-(3,3-dimethylbutoxy)-5-fluorophenyl)-4-(2-isopropylphenyl)thiazole

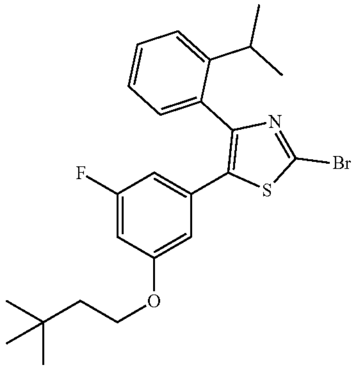 [SMILES: CC(C)c1ccccc1-c1nc(Br)sc1-c1cc(F)cc(OCCC(C)(C)C)c1]

Intermediate G-2b 2-bromo-5-(3-(3,3-dimethylbutoxy)phenyl)-4-(2-isopropylphenyl)thiazole

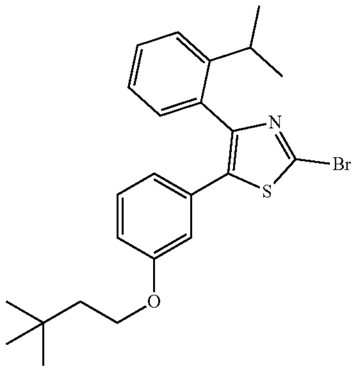 [SMILES: CC(C)c1ccccc1-c1nc(Br)sc1-c1cccc(OCCC(C)(C)C)c1]

Intermediate G-3

2-Bromo-5-(3-(2,2-difluoro-3,3-dimethylbutoxy)-4-fluorophenyl)-4-(2-isopropylphenyl)thiazole

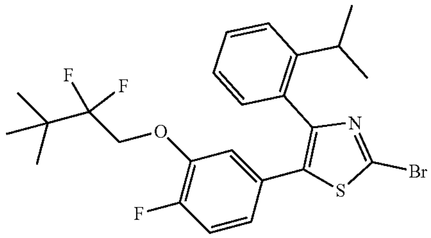 [SMILES: CC(C)c1ccccc1-c1nc(Br)sc1-c1ccc(F)c(OCC(F)(F)C(C)(C)C)c1]

Intermediate G-4

2-Bromo-5-(3-(2,2-difluoro-3,3-dimethylbutoxy)phenyl)-4-(2-isopropylphenyl)thiazole

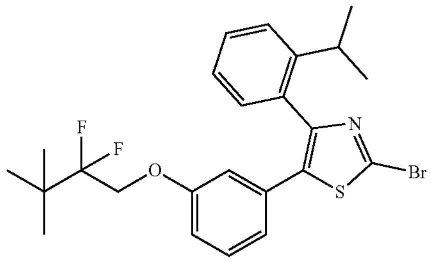 [SMILES: CC(C)c1ccccc1-c1nc(Br)sc1-c1cccc(OCC(F)(F)C(C)(C)C)c1]

Intermediate G-5

2-Bromo-5-(3-(3,3-dimethylbutoxy)phenyl)-4-(2-methyl-6-(trifluoromethyl)phenyl)thiazole

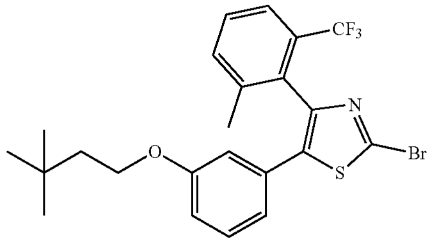 [SMILES: Cc1cccc(C(F)(F)F)c1-c1nc(Br)sc1-c1cccc(OCCC(C)(C)C)c1]

Intermediate G-6

2-bromo-5-(3-(2,2-difluoro-3,3-dimethylbutoxy)phenyl)-4-(2-isopropoxy-6-methylphenyl)thiazole

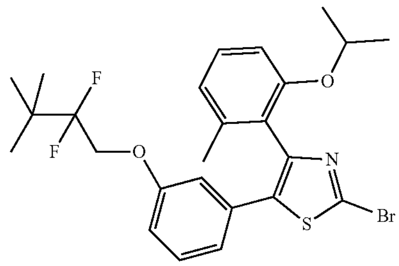 [SMILES: Cc1cccc(OC(C)C)c1-c1nc(Br)sc1-c1cccc(OCC(F)(F)C(C)(C)C)c1]

Intermediate G-7

2-Bromo-5-(3-(3,3-dimethylbutoxy)-5-fluorophenyl)-4-(2-isopropoxy-6-methylphenyl)thiazole

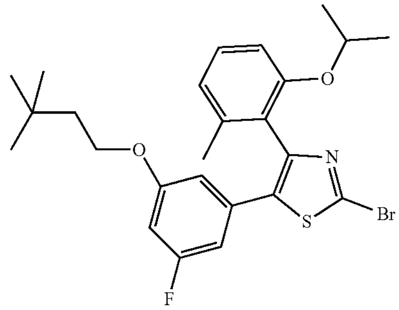 [SMILES: Cc1cccc(OC(C)C)c1-c1nc(Br)sc1-c1cc(F)cc(OCCC(C)(C)C)c1]

Intermediate R-1

3-Ethoxybenzenesulfonamide

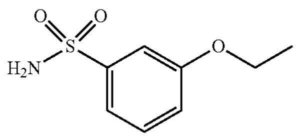

To a stirred solution of 1-bromo-3-ethoxy-benzene (1.10 g, 5.47 mmol) in THF (100 mL) was added n-BuLi (701 mg, 10.9 mmol) in THF (50 mL) slowly at −78° C. After the reaction was stirred at −78° C. for 2 h, S02 (1.75 g, 27.4 mmol) was added. Then the reaction was stirred at −78° C. for 1 h. The reaction was allowed to warm to rt. Then, the reaction was concentrated to dryness under reduced pressure. The residue was dissolved in DCM (50 mL). To this solution was added NCS (1.1 g, 8.21 mmol). After the reaction was stirred at rt for 2 h, concentrated $NH_4OH$ (20 mL) was added. The reaction was stirred at rt for 16 h. Then the mixture was extracted with ethyl acetate (20 mL×3). The ethyl acetate solution was washed with brine (20 mL), dried over anhydrous $Na_2SO_4$, and filtered. The filtrate was concentrated under reduced pressure to give 3-ethoxybenzenesulfonamide (829 mg, 75.3%).

LCMS: LC retention time 1.28 min. MS (ESI) m/z 218 $[M+NH_4]+$

Intermediate R-2

3-Isopropoxybenzenesulfonamide

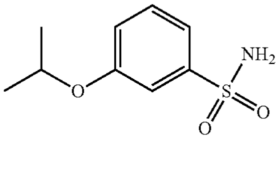

Step 1.

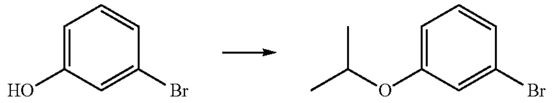

To a solution of 3-bromophenol (1.00 g, 5.78 mmol) and 2-iodopropane (1.18 g, 6.94 mmol) in DMF (20 mL) was added potassium carbonate (1.04 g, 7.51 mmol). The reaction was heated to 55° C. for 12 h and then cooled to rt. To the mixture was added water (20 mL). The resulting aqueous solution was then extracted with ethyl acetate (20 mL×2). The organic layer was washed with brine (20 mL), dried over sodium sulfate and concentrated in vacuo. The residue was purified by SGC (PE/EA=10:1) to give 1-bromo-3-isopropoxybenzene (880 mg, 70.8% yield) as a yellow solid.

LCMS: LC retention time 2.32 min. MS (ESI) m/z 216 $[M+H]^+$.

Step 2.

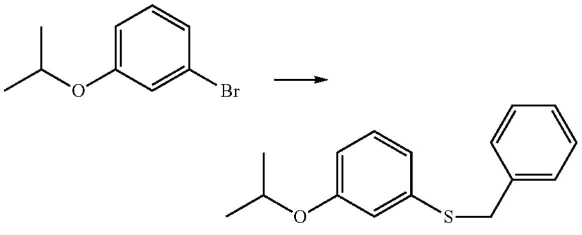

To a solution of 1-bromo-3-isopropoxybenzene (670 mg, 3.12 mmol) in toluene (20 mL) were added phenyl methanethiol (721 mg, 4.67 mmol), N,N-diisopropylethylamine (805 mg, 6.23 mmol), 4,5-bis(diphenylphosphino)-9, 9-dimethylxanthene (180 mg, 0.312 mmol) and tris (dibenzylideneacetone)dipalladium (143 mg, 0.156 mmol). The reaction was stirred at 100° C. under argon atmosphere for 3 h. The mixture was tested by TLC to confirm the starting materials were consumed. After cooling to room temperature, the reaction mixture was filtered through Celite. The filtrate was concentrated under reduced pressure. The residue was dissolved in water (60 mL). The aqueous was then extracted with ethyl acetate (20 mL×2). The combined organic layers were washed with water (50 mL) and brine (50 mL), dried over sodium sulfate, filtered and concentrated under reduced pressure. The residue was purified by silica gel chromatography (petroleum ether:ethyl acetate=20:1) to give benzyl(3-isopropoxyphenyl)sulfane (800 mg, 89% yield) as a colorless oil.

Step 3.

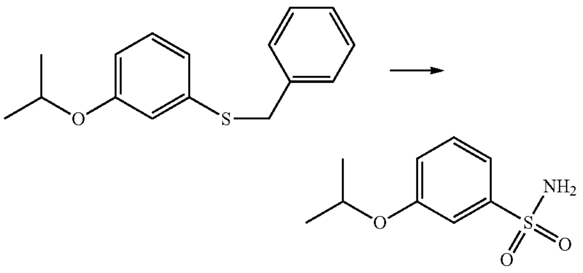

To the solution of benzyl(3-isopropoxyphenyl)sulfane (1.00 g, 3.47 mmol) in acetic acid/water (10 mL/5 mL) was added N-chlorosuccinimide (1.39 g, 10.4 mmol) at 0° C., and stirred at this temperature for 10 minutes. The resulting mixture was stirred at 25° C. until the reactant was consumed completely (about 3 h). The reaction was diluted with water (10 mL). The aqueous solution was extracted with dichloromethane (20 mL×2). The combined organic layers were washed with water (20 mL), brine (20 mL), and then concentrated under reduced pressure. The residue was re-dissolved in dichloromethane (10 mL). To this solution was added concentrated ammonium hydroxide (10 mL) at 0° C. The reaction mixture was stirred at room temperature for 12 h. The two layers were separated. The aqueous phase was extracted with dichloromethane (30 mL×2). The combined organic layers were washed with brine (30 mL), dried over sodium sulfate, filtered and concentrated under reduced pressure to afford 3-isopropoxybenzenesulfonamide (600 mg, 80.4% yield) as a while solid.

LCMS: LC: retention time 1.78 min. MS (ESI) m/z 216 $[M+H]^+$.

Intermediate R-3

3-(2,2,2-Trifluoro-1-hydroxyethyl)benzenesulfonamide

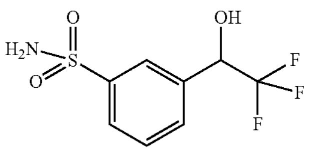 [SMILES: NS(=O)(=O)c1cccc(C(O)C(F)(F)F)c1]

Step 1.

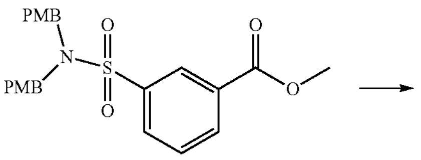

-continued

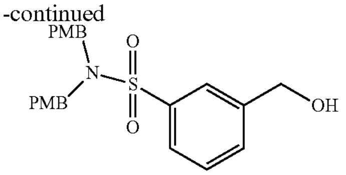

To a solution of methyl 3-[bis[(4-methoxyphenyl)methyl]sulfamoyl]benzoate (2.00 g, 4.39 mmol) in THF (15 mL) was added $LiBH_4$ (2.00 M, 22.0 mL, 0.0439 mol) dropwise at 0° C. After addition, the mixture was stirred at 18° C. for 16 h. LCMS showed the starting material was consumed and desired MS was detected. The reaction was quenched with HCl (15 mL, 2M). The aqueous solution was extracted with EA (10 mL×3). The combined organic layers were dried over $Na_2SO_4$, filtered and evaporated to dryness to give the crude product which was purified by silica gel chromatography (PE/EA=2/1) to give 3-(hydroxymethyl)-N,N-bis[(4-methoxyphenyl)methyl]benzenesulfonamide (1.80 g, 95.9% yield) as a yellow solid.

LCMS: LC retention time 1.93 min. MS (ESI) m/z 450 $[M+Na]^+$

Step 2.

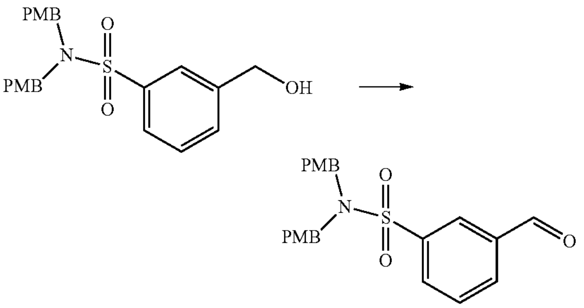

To a stirred solution of 3-(hydroxymethyl)-N,N-bis[(4-methoxyphenyl)methyl]-benzenesulfonamide (1.80 g, 4.21 mmol) in dry DCM (10 mL) was added Dess-Martin periodinane (10.7 g, 25.3 mol). The mixture was stirred at room temperature for 16 h. LCMS showed the starting material was consumed and desired MS was detected. To the mixture was added aqueous $Na_2CO_3$ (15 mL) and $Na_2SO_3$ (15 mL). The resulting aqueous solution was extracted with DCM (8 mL×3). The combined organic layers were dried over $Na_2SO_4$, filtered and concentrated to dryness to give crude which was purified by silica gel chromatography (PE/EA=2/1) to give 3-formyl-N,N-bis[(4-methoxyphenyl)methyl]-benzenesulfonamide (1.70 g, 94.9% yield) as a yellow solid.

LCMS: LC retention time 2.04 min. MS (ESI) m/z 448 $[M+Na]^+$

Step 3.

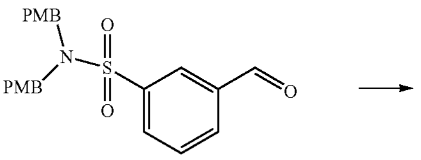

-continued

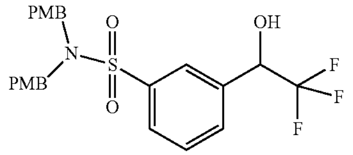

To a solution of 3-formyl-N,N-bis[(4-methoxyphenyl)methyl]benzenesulfonamide (1.70 g, 4.00 mmol) in THF (12 mL) was added trimethyl(trifluoromethyl)silane (2.27 g, 16.0 mmol) at 0° C., followed by TBAF (1 mL, 2 mmol). After addition, the mixture was stirred at room temperature for 16 h. An additional TBAF (15 mL, 30 mmol) was added and stirred for 10 min. To the reaction mixture was added HCl (1 M, 15 mL). The resulting aqueous solution was extracted with EA (15 mL×3). The combined organic layers were dried over $Na_2SO_4$, filtered and concentrated to dryness to give the crude product which was purified by prep-TLC (PE/EA=2/1) to give N,N-bis[(4-methoxyphenyl)methyl]-3-(2,2,2-trifluoro-1-hydroxy-ethyl)benzenesulfonamide (0.440 g, 17.3% yield) as a yellow solid.

LCMS: LC retention time 2.04 min. MS (ESI) m/z 518 $[M+Na]^+$

Step 4.

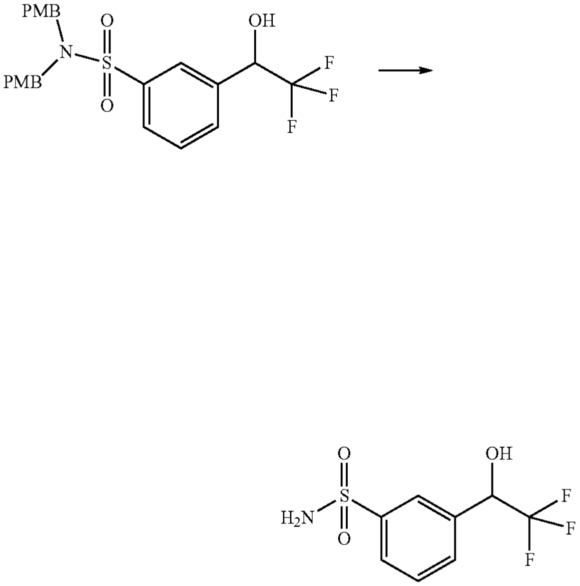

To a solution of N,N-bis[(4-methoxyphenyl)methyl]-3-(2,2,2-trifluoro-1-hydroxy-ethyl)benzenesulfonamide (0.440 g, 0.888 mmol) in DCM (5 mL) was added TFA (0.506 g, 4.44 mmol) at 0° C. The mixture was stirred at room temperature for 3 h. LCMS showed the starting material was consumed completely and desired MS was detected. The mixture was evaporated to dryness to give the crude product which was purified by prep-HPLC to give 3-(2,2,2-trifluoro-1-hydroxy-ethyl)benzenesulfonamide (0.0800 g, 35.3% yield) as a white solid.

$^1$H NMR (400 MHz, MeOD) δ 8.09 (s, 1H), 7.94 (d, J=8.0 Hz, 1H), 7.74 (d, J=8.0 Hz, 1H), 7.60 (t, J=8.0 Hz, 1H), 5.18 (m, 1H) ppm.

Intermediate R-4

Methyl 3-methyl-1-(3-sulfamoylphenyl)piperidine-3-carboxylate

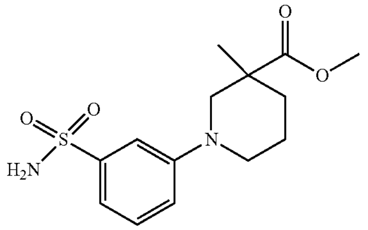 [SMILES: COC(=O)C1(C)CCCN(c2cccc(S(N)(=O)=O)c2)C1]

Step 1.

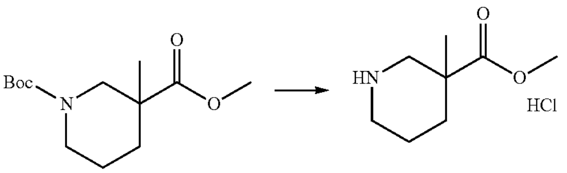 [SMILES: COC(=O)C1(C)CCCN(C(=O)OC(C)(C)C)C1 ; COC(=O)C1(C)CCCNC1 ; Cl]

To a solution of 1-(tert-butyl) 3-methyl 3-methylpiperidine-1,3-dicarboxylate (2.00 g, 7.77 mmol) in dioxane (10.0 mL) was added HCl in dioxane (4.00 M, 11.2 mL, 44.7 mmol). The mixture was stirred at room temperature for 12 h. TLC (PE/EA=8/1) showed the starting material was consumed completely and a new spot was formed. The mixture was evaporated to dryness to give methyl 3-methylpiperidine-3-carboxylate hydrochloride (0.140 g, 99.7% yield) as a white solid.

Step 2.

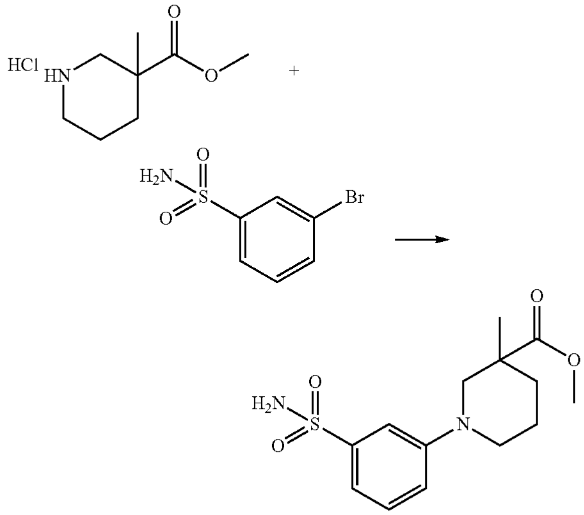

To a solution of methyl 3-methylpiperidine-3-carboxylate hydrochloride (0.500 g, 2.58 mmol) in DMSO (8.00 mL) were added 3-bromobenzenesulfonamide (0.508 g, 2.15 mmol), $K_2CO_3$ (0.714 g, 5.16 mmol), CuI (30.0%, 0.328 g, 0.516 mmol), and L-proline (0.0892 g, 0.775 mmol). The mixture was purged with $N_2$ three times. The mixture was stirred at 90° C. for 16 h. LCMS showed the desired MS. To the mixture was added $H_2O$ (16 mL). The resulting aqueous solution was extracted with EA (10 mL×3). The combined organic layers were dried over $Na_2SO_4$, filtered and concentrated to dryness to give the crude product which was purified by prep-HPLC to give methyl 3-methyl-1-(3-sulfamoylphenyl)piperidine-3-carboxylate (0.100 g, 12.4% yield) as a yellow solid.

LCMS: LC retention time 1.82 min. MS (ESI) m/z 313 $[M+H]^+$.

Intermediate R-6

3-(Dimethylphosphoryl)benzenesulfonamide

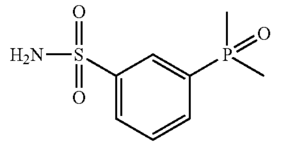

Step 1.

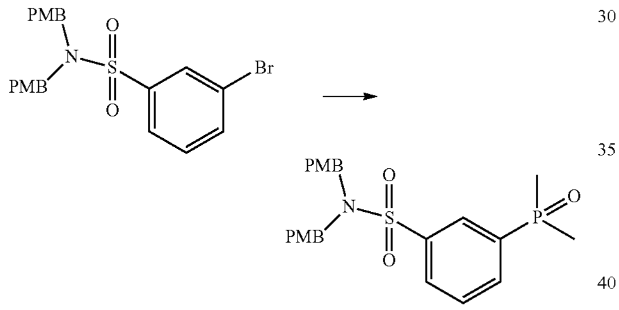

To a solution of 3-bromo-N,N-bis[(4-methoxyphenyl)methyl]benzenesulfonamide (476 mg, 1.0 mmol) in 1,4-dioxane (15.0 mL) were added dimethylphosphine oxide (78.1 mg, 1.0 mmol), TEA (152 mg, 1.5 mmol), $PdCl_2(dppf)_2$ (35.3 mg, 0.0483 mmol) and Xantphos (116 mg, 2.0 mmol). The mixture was stirred at room temperature for 1 day, at 60° C. for 1 day and at 100° C. for 1 day. The volatiles were removed in vacuo. The residue was purified by silica gel chromatography with a Biotage instrument (DCM/MeOH=20/1 to 10/1) to afford 3-dimethylphosphoryl-N,N-bis[(4-methoxyphenyl)methyl]benzenesulfonamide (400 mg, 84%) as a light yellow oil.

LCMS: LC retention time 1.82 min. MS (ESI) m/z 474 $[M+H]^+$.

Step 2.

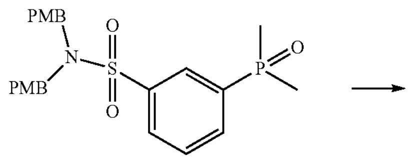

-continued

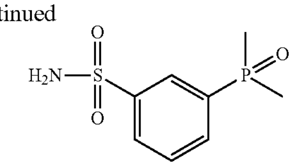

TFA (1.0 mL) was added to 3-dimethylphosphoryl-N,N-bis[(4-methoxyphenyl)methyl]benzenesulfonamide (400 mg, 0.845 mmol). The mixture was stirred at room temperature over weekend. The volatiles were removed in vacuo to afford 3-dimethylphosphorylbenzenesulfonamide (180 mg, 91%) as a light yellow solid.

LCMS: LC retention time 0.91 min. MS (ESI) m/z 234 $[M+H]^+$

Intermediate R-7

3-(JH-Pyrazol-1-yl)benzenesulfonamide

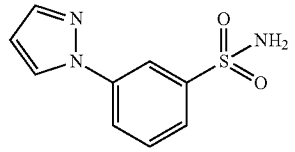 [SMILES: NS(=O)(=O)c1cccc(-n2cccn2)c1]

Step 1.

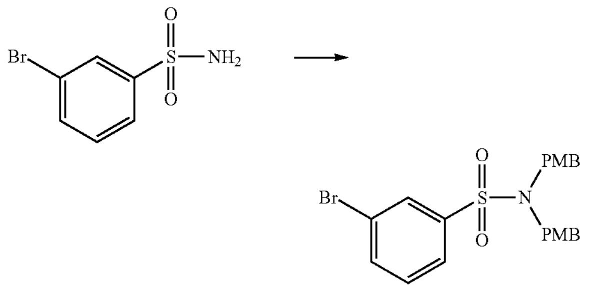

To a solution of 3-bromobenzenesulfonamide (5.37 g, 22.7 mmol) in 2-butanone (120 mL) were added PMBCl (10.68 g, 68.2 mmol), NaI (341 mg, 2.3 mmol), and $K_2CO_3$ (9.41 g, 68.2 mmol). The reaction mixture was stirred at 85° C. overnight under nitrogen atmosphere. After completion of the reaction, the reaction mixture was filtered and concentrated under reduced pressure. The residue was dissolved in DCM (80 mL). The DCM solution was washed with water (60 mL×3), dried over anhydrous $Na_2SO_4$ and concentrated under reduced pressure to afford 3-bromo-N,N-bis(4-methoxybenzyl)benzenesulfonamide (7.78 g, 71.8%) as a yellow solid.

LCMS: LC retention time 1.95 min. MS (ESI) m/z 500 $[M+Na]^+$.

Step 2.

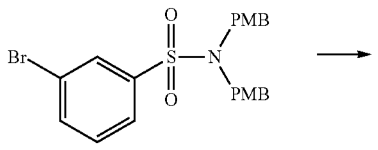

-continued

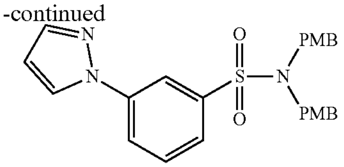

To a solution of 3-bromo-N,N-bis[(4-methoxyphenyl)methyl]benzenesulfonamide (1.43 g, 3.0 mmol) in 1,4-dioxane (15.0 mL) were added 1H-pyrazole (306 mg, 4.5 mmol), sodium tert-butoxide (721 mg, 7.5 mmol), CuI (57 mg, cat) and 1,10-phenanthroline (108 mg, cat) in a glove-box. The resulting mixture was reacted at 120° C. overnight. The solvent was removed under reduced pressure and the residue was diluted with dichloromethane (150 mL). The organic phase was washed with saturated aqueous $NaHCO_3$ (80 mL), water (80 mL) and brine. The combined organic solutions were dried over anhydrous sodium sulfate, filtered and concentrated. The crude was purified by FCC (PE/EA=1/1) to afford the target compound, N,N-bis[(4-methoxyphenyl)methyl]-3-pyrazol-1-yl-benzenesulfonamide (600 mg, 43%) as a white solid.

LCMS: LC retention time: 2.19 min. MS (ESI) m/z 464 $[M+H]^+$.

Step 3.

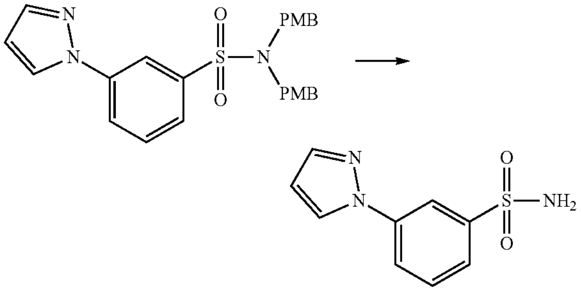

To a solution of N,N-bis[(4-methoxyphenyl)methyl]-3-pyrazol-1-yl-benzenesulfonamide (700 mg, 1.51 mmol) in DCM (5.0 mL) was added TFA (5.0 mL). The resulting mixture was reacted at room temperature overnight. The solvent was removed under reduced pressure. The residue was dissolved in DCM (50 mL). The DCM solution was washed with water (50 mL×2), saturated aqueous $NaHCO_3$ (50 mL), and brine. The DCM solution was dried over anhydrous sodium sulfate, filtered and concentrated to dryness. The residue was purified by FCC (PE/EA=1/1) to afford the target compound, 3-(1H-pyrazol-1-yl)benzenesulfonamide (230 mg, 68%) as a pale yellow solid.

LCMS: LC retention time: 1.59 min. MS (ESI) m/z 224 $[M+H]^+$.

Intermediate R-8

3-(Difluoromethyl)benzenesulfonamide

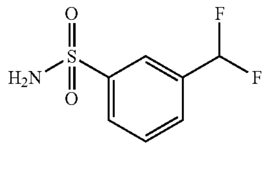 [SMILES: NS(=O)(=O)c1cccc(C(F)F)c1]

Step 1.

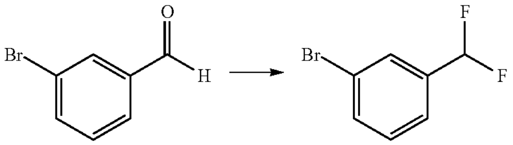 [SMILES: O=Cc1cccc(Br)c1 ; FC(F)c1cccc(Br)c1]

To a solution of 3-bromobenzaldehyde (2.0 g, 10.8 mmol) in DCM (60 mL) was added diethylaminosulfur trifluoride (2.86 mL, 21.6 mmol) in a ice bath. The resulting solution was stirred at ambient temperature overnight before quenching by addition of saturated sodium bicarbonate aqueous (80 mL). After separation, the organic solution was washed with brine, dried over anhydrous sodium sulfate, filtered, and concentrated. The residual oil was purified by FCC (PE=100%) to afford the desired compound, 1-bromo-3-(difluoromethyl)benzene (1.20 g, 54%) as colorless oil.

LCMS: LC retention time: 1.36 min. MS (ESI) m/z 207 $[M+H]^+$.

$^1H$ NMR (400 MHz, chloroform-d) δ 7.69 (s, 1H), 7.64 (d, J=8 Hz, 1H), 7.46 (d, J=7.6 Hz, 1H), 7.36 (t, J=8 Hz, 1H), 6.77-6.49 (t, J=56.4 Hz; 56 Hz, 1H) ppm.

Step 2.

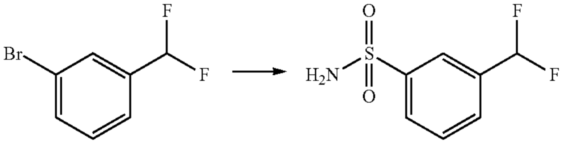 [SMILES: FC(F)c1cccc(Br)c1 ; NS(=O)(=O)c1cccc(C(F)F)c1]

To a solution of 1-bromo-3-(difluoromethyl)benzene (1.2 g, 5.80 mmol) in dry THF (12.0 mL) was added n-BuLi (2.5 M in THF, 2.96 mL) dropwise at −78° C. After stirring for 1 h, sulfur dioxide (liquid) was poured into the flask. The reaction was allowed to warm to room temperature and stirred for 5 h. The solvent was removed under reduced pressure, and the residue was diluted with DCM (12.0 mL). To this solution was added NCS (1.16 g, 8.7 mmol). After 30 min, concentrated $NH_4OH$ (12.0 mL) was added. The resulting mixture was stirred overnight at room temperature. The solvent was removed under reduced pressure. The residue was dissolved in ethyl acetate (80 mL). The ethyl acetate solution was washed with water (100 mL×2), brine and dried with anhydrous sodium sulfate, filtered, and concentrated. The crude was purified by FCC (DCM/MeOH=20/1) to afford the desired compound, 3-(difluoromethyl)benzenesulfonamide (780 mg, 65%) as a yellow solid.

LCMS: LC retention time 0.81 min. MS (ESI) m/z was not observed.

$^1H$ NMR (400 MHz, DMSO-$d_6$) δ 8.04-7.76 (m, 4H), 7.54 (s, 2H), 7.33-7.06 (t, J=55.6 Hz; 55.2 Hz, 1H) ppm.

Intermediate R-9

3-((1,1,1-Trifluoropropan-2-yl)amino)benzenesulfonamide

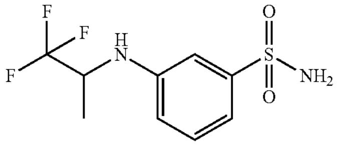 [SMILES: CC(Nc1cccc(S(N)(=O)=O)c1)C(F)(F)F]

Step 1.

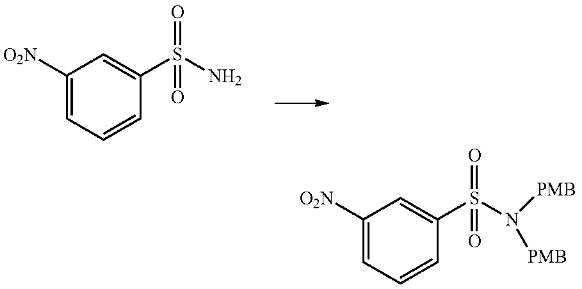

To a solution of 3-nitrobenzenesulfonamide (5.05 g, 25.0 mmol) in 2-butanone (100 mL) were added PMBCl (11.75 g, 75.0 mmol), NaI (375 mg, 2.50 mmol), and $K_2CO_3$ (10.35 g, 75.0 mmol). Then the mixture was stirred at 85° C. overnight under nitrogen atmosphere. After the completion of the reaction, the mixture was filtered. The filtrate was concentrated under reduced pressure. The residue was dissolved in DCM (150 mL). The DCM solution was washed with water (200 mL), dried over anhydrous $Na_2SO_4$, filtered. The filtrate was concentrated to dryness under reduced pressure to give the desired compound N,N-bis(4-methoxybenzyl)-3-nitrobenzenesulfonamide (9.2 g, 83.17%) as a white solid.

LCMS: LC retention time 2.22 min. MS (ESI) m/z 465 $[M+Na]^+$.

Step 2.

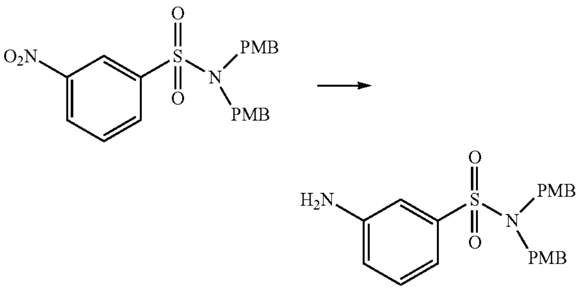

To a solution of N,N-bis(4-methoxybenzyl)-3-nitrobenzenesulfonamide (9.20 g, 20.8 mmol) in methanol (60 mL) and water (12 mL) were added iron powder (11.6 g, 207.9 mmol) and $NH_4Cl$ (11.10 g, 207.9 mmol). The reaction mixture was heated to reflux and stirred for 30 min. Then the mixture was concentrated to dryness under reduced pressure. The residue was dissolved in ethyl acetate (300 mL), filtered through a Celite plug. The filtrate was washed with water (200 mL) and brine (200 mL), dried over anhydrous $Na_2SO_4$, and then filtered. The filtrate was concentrated to dryness in vacuo and the crude was purified by reversed-phase column to give 3-amino-N,N-bis(4-methoxybenzyl)benzenesulfonamide (4.26 g, 49.7% yield) as a white solid.

LCMS: LC retention time 2.10 min. MS (ESI) m/z 413 $[M+H]^+$.

Step 3.

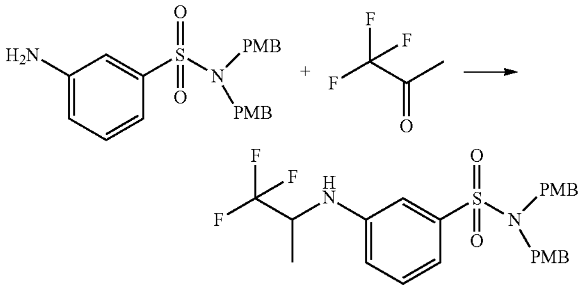

To a slurry of 3-amino-N,N-bis(4-methoxybenzyl)benzenesulfonamide (824 mg, 2.0 mmol) and $NaBH_3CN$ (264 mg, 5.0 mmol) in $CH_2Cl_2$ (15 mL) in ice bath was added neat TFA (2.22 mL, 30.0 mmol) dropwise at a rate such that the internal temperature below 5° C. 1,1,1-trifluoropropan-2-one (560 mg, 5.0 mmol) was then added over 5 min under argon atmosphere. After overnight stirring, the mixture was slowly poured into saturated $NaHCO_3$ (60 mL) at 0° C. The mixture was then neutralized by portion-wise addition of solid $NaHCO_3$. The mixture was stirred 30 min and precipitated solid was filtered off. The two phases of the filtrate were separated, and the aqueous layer was extracted with $CH_2Cl_2$ (50 mL×3). The combined organic extracts were concentrated to dryness to give N,N-bis(4-methoxybenzyl)-3-((1,1,1-trifluoropropan-2-yl)amino)benzenesulfonamide (755 mg) as a yellow oil.

LCMS: LC retention time 2.17 min. MS (ESI) m/z 509 $[M+H]^+$.

Step 4.

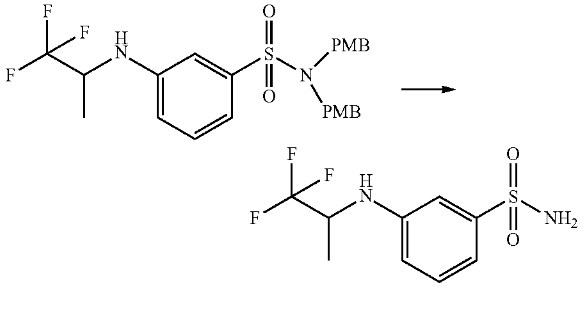

To a solution of N,N-bis(4-methoxybenzyl)-3-((1,1,1-trifluoropropan-2-yl)amino)-benzenesulfonamide (755 mg, 1.48 mmol) in DCM (10 mL) was added TFA (10 mL). The resulting mixture was stirred at room temperature overnight. An aliquot checked by LCMS analysis indicated that the reaction was completed. The reaction was concentrated to dryness by blowing nitrogen, and then poured into water (60 mL). The aqueous was then extracted with DCM (60 mL×2). The combined organic layers were dried over anhydrous sodium sulfate, concentrated to dryness under reduced pressure to give the crude which was purified by silica gel column chromatography (PE/EA=2/1) to give the desired compound 3-((1,1,1-trifluoropropan-2-yl)amino)benzenesulfonamide (170 mg, 42.7% yield) as a yellow oil.

LCMS: LC retention time 1.83 min. MS (ESI) m/z 269 $[M+H]^+$.

Intermediate R-10

3-[bis[(4-Methoxyphenyl)methyl]amino]-2-fluoro-benzenesulfonamide

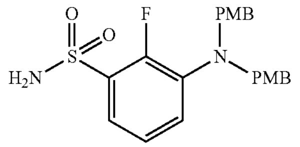

Step 1.

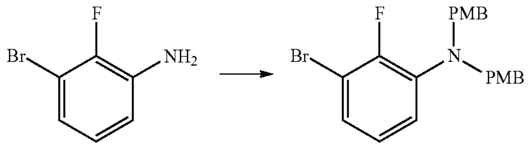

To a solution of 3-bromo-2-fluoro-aniline (2.5 g, 13.2 mmol) in DMF (25 mL) was added NaH (1.32 g, 32.9 mmol) at 0° C. in the ice bath. After the mixture was stirred for 30 min, 1-(chloromethyl)-4-methoxy-benzene (4.28 mL, 31.6 mol) was added dropwise. The reaction mixture was warmed to room temperature and stirred at rt overnight. The reaction was carefully poured into 100 mL of ice. The two layers were separated and the aqueous phase was extracted with ethyl acetate (100 mL). The combined organic layers were dried over anhydrous sodium sulfate and concentrated in vacuo. The crude was purified by flash chromatography on silica gel (PE/EA=10/1) to give the title compound, 3-bromo-2-fluoro-N,N-bis[(4-methoxyphenyl)methyl]aniline (5.86 g, 98%) as a yellow solid.

LCMS: LC retention time 2.45 min. MS (ESI) m/z 432 $[M+H]^+$.

Step 2.

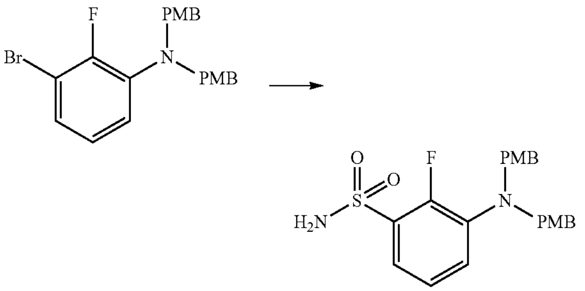

To a solution of 3-bromo-2-fluoro-N,N-bis(4-methoxybenzyl)aniline (2.0 g, 4.65 mmol) in dry THF (12.0 mL) was added n-BuLi (2.5 M in hexane, 2.23 mL) dropwise at −78° C. After stirring for 1 h, sulfur dioxide (liquid) was poured into the flask. The reaction was allowed to warm to room temperature and stirred for 5 h. The solvent was removed under reduced pressure, and the residue was diluted with DCM (20.0 mL). To the DCM solution was added NCS (931 mg, 6.97 mmol). After 30 mins, conc. $NH_4OH$ (20.0 mL) was added. The resulting mixture was stirred overnight at room temperature. The solvent was removed by blowing nitrogen. The residue was dissolved in DCM (100 mL). The DCM solution was washed with water (100 mL×2), brine and dried over anhydrous sodium sulfate. After filtration and concentration, the crude was purified by FCC (DCM/MeOH=10/1) to afford the desired compound, 3-[bis[(4-methoxyphenyl)methyl]amino]-2-fluoro-benzenesulfonamide (1.20 g, 60%) as a yellow solid.

LCMS: LC retention time: 1.72 min. MS (ESI) m/z 431 $[M+H]^+$.

Intermediate R-11

3-Amino-2-fluorobenzenesulfonamide

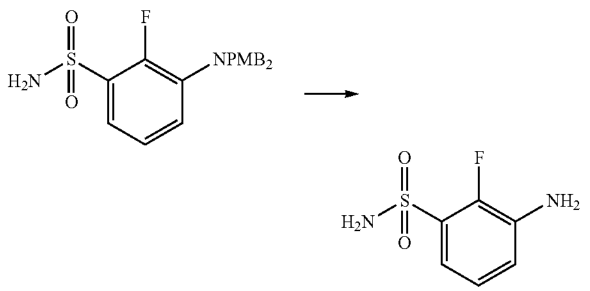

To a solution of Intermediate R-10 (2.5 g, 5.81 mmol) in DCM (10 mL) was added TFA (10.0 mL). The reaction solution was stirred at 75° C. for 2 h. The solvent was removed under reduced pressure. The residue was dissolved in DCM (100 mL) and washed with saturated aqueous sodium bicarbonate (50 mL×2) and brine (50 mL). The organic phase was dried over anhydrous $Na_2SO_4$, filtered and concentrated under vacuum. The crude was purified by SGC (PE:EA=1:1) to give the title compound (860 mg, 77.9%) as a yellow solid.

LCMS (acidic): LC retention time 1.390, MS (ESI): m/z 191.1 $[M+H]^+$.

Intermediate R-12

3-(bis(4-Methoxybenzyl)amino)-4-fluorobenzenesulfonamide

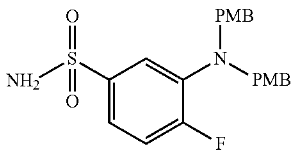

Intermediate R-12 was prepared in the same way as Intermediate R-10.

Intermediate R-13

3-Amino-4-fluorobenzenesulfonamide

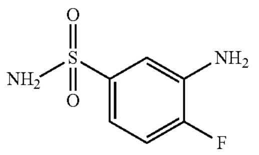 [SMILES: Nc1cc(S(N)(=O)=O)ccc1F]

Intermediate R-13 was prepared in the same way as Intermediate R-11.

PREPARATION OF EXAMPLES

Example 1

N-(4-(2,6-Dimethylphenyl)-5-(3-fluoro-5-(neopentyloxy)phenyl)thiazol-2-yl)benzenesulfonamide

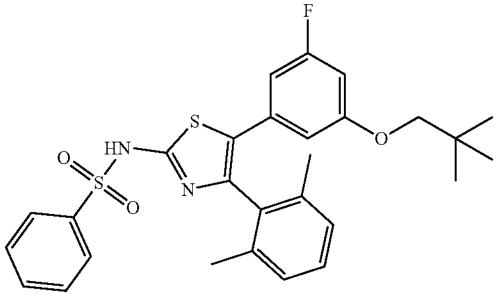 [SMILES: Cc1cccc(C)c1-c1nc(NS(=O)(=O)c2ccccc2)sc1-c1cc(F)cc(OCC(C)(C)C)c1]

Step 1.

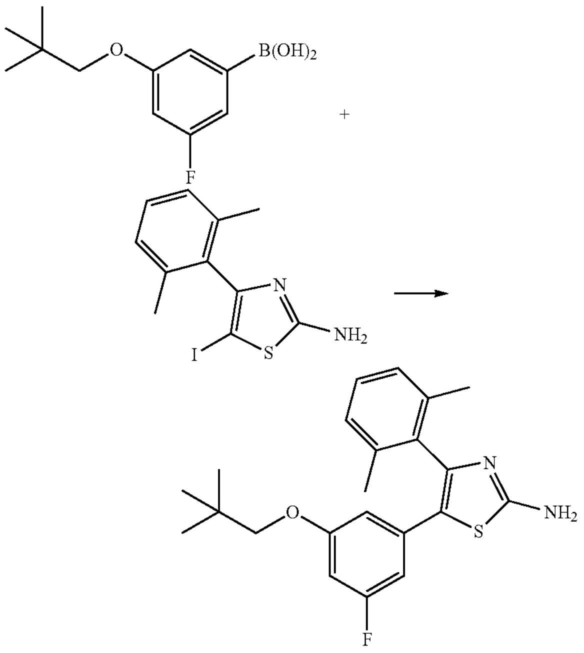

To a stirred solution of Intermediate D-6 (800 mg, 2.42 mmol) in toluene/ethanol/$H_2O$ (30/15/7.5 mL) was added Intermediate B-2b (602 mg, 2.67 mmol), $Pd(Ph_3P)_4$ (280 mg, 0.24 mmol) and $Na_2CO_3$ (770 mg, 7.27 mmol). The resulting mixture was stirred at 80° C. for 16 h. The reaction mixture was diluted with water (50 mL). The resulting aqueous solution was extracted with ethyl acetate (50 mL×3). The organic layers were combined, dried over anhydrous sodium sulfate and concentrated in vacuo. The residue was purified by silica gel chromatography (PE/EA=1/1) to afford the title compound (510 mg, 55%) as a brown oil.

LCMS: LC retention time 2.27 min. MS (ESI) m/z 385 $[M+H]^+$.

Step 2.

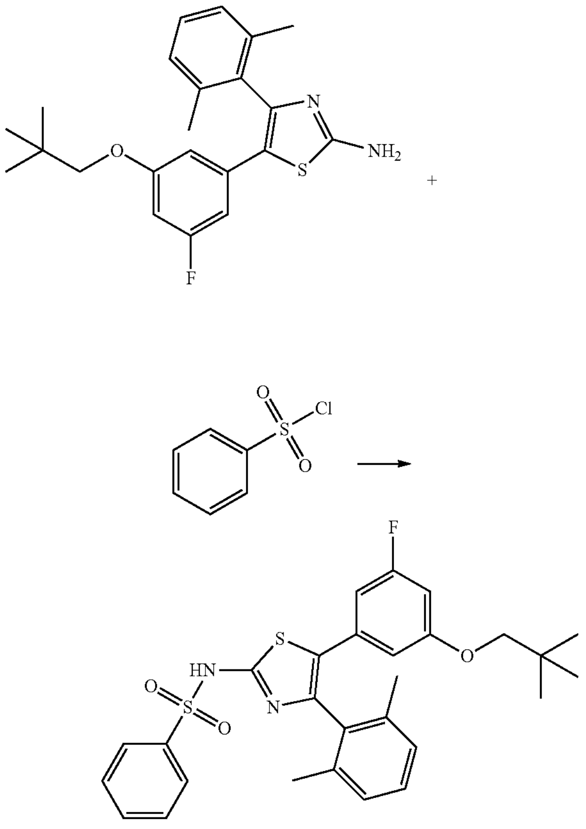

To a solution of 4-(2,6-dimethylphenyl)-5-(3-fluoro-5-(neopentyloxy)phenyl)thiazol-2-amine (510 mg, 1.3 mmol) in pyridine (8 mL) was added benzenesulfonyl chloride (1.17 g, 6.63 mmol) at 25° C. The resulting solution was stirred at rt for 16 h. After that, the reaction mixture was diluted with water (10 mL) and extracted with ethyl acetate (8 mL×3). The organic layers were combined, dried over anhydrous sodium sulfate, filtered, and concentrated in vacuo. The residue was purified by Prep-HPLC to afford the title compound (184 mg, 26.5%) as a yellow solid.

LC retention time 2.42 min. MS (ESI) m/z 525 $[M+H]^+$.

$^1H$ NMR (400 MHz, chloroform-d) δ 7.98-8.11 (m, 2H), 7.48-7.56 (m, 3H), 7.28-7.31 (m, 1H), 7.13-7.15 (m, 2H), 6.45-6.49 (m, 1H) 6.37-3.38 (m, 1H), 6.25-6.38 (m, 1H), 3.27 (s, 2H), 2.13 (s, 6H), 0.96 (s, 9H) ppm.

Example 2

N-(5-(3-(3,3-Dimethylbutoxy)-5-fluorophenyl)-4-(2-methyl-6-(trifluoromethyl)phenyl)thiazol-2-yl)benzenesulfonamide

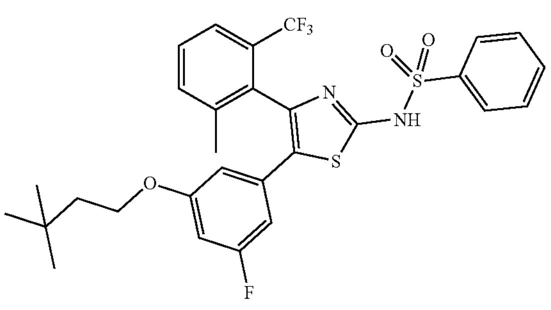 [SMILES: Cc1cccc(C(F)(F)F)c1-c1nc(NS(=O)(=O)c2ccccc2)sc1-c1cc(F)cc(OCCC(C)(C)C)c1]

Step 1.

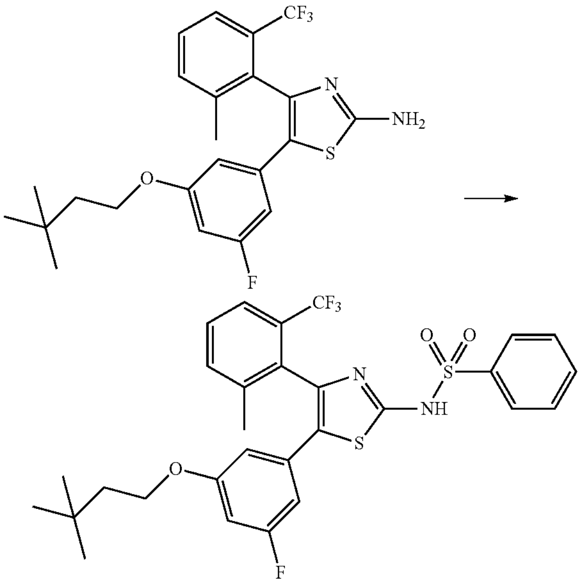

To a solution of 5-[3-(3,3-dimethylbutoxy)-5-fluoro-phenyl]-4-[2-methyl-6-(trifluoromethyl) phenyl]thiazol-2-amine (Intermediate C-8) (130 mg, 0.287 mmol) in pyridine (10 mL) was added benzenesulfonyl chloride (75.8 mg, 0.431 mmol). The reaction was stirred at room temperature for 3 h. The mixture was concentrated. The residue was diluted with brine (30 mL). The resulting aqueous solution was extracted with EA (30 mL×3). The organic layers were combined and washed with brine (40 mL), dried over $Na_2SO_4$, and concentrated. The crude product was treated with $K_2CO_3$ (690 mg, 5 mmol) in MeOH. The resulting solution was stirred for 1 h. The mixture was concentrated and the crude was purified by prep-HPLC to give the title compound as a yellow solid (62.5 mg, 36.7%).

LCMS: LC retention time 2.424 min. MS (ESI) m/z 593 $[M+H]^+$.

$^1H$ NMR (400 MHz, chloroform-d) δ 9.80 (s, 1H), 7.92 (m, 2H), 7.67-7.48 (m, 6H), 6.48 (d, J=10.4 Hz, 1H), 6.31 (m, 2H), 3.73 (m, 2H), 2.18 (s, 3H), 1.62 (t, J=7.2 Hz, 2H), 0.95 (s, 9H) ppm.

Example 3

N-(5-(3-(3,3-Dimethylbutoxy)-5-fluorophenyl)-4-(2-isopropylphenyl)thiazol-2-yl)benzenesulfonamide

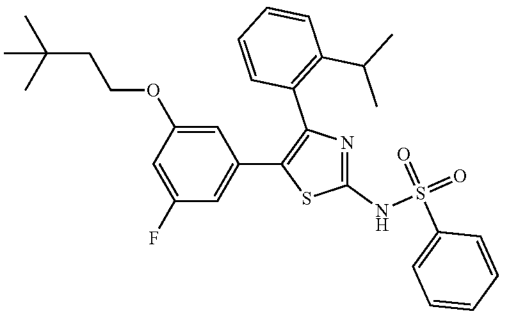 [SMILES: CC(C)c1ccccc1-c1nc(NS(=O)(=O)c2ccccc2)sc1-c1cc(F)cc(OCCC(C)(C)C)c1]

Step 1.

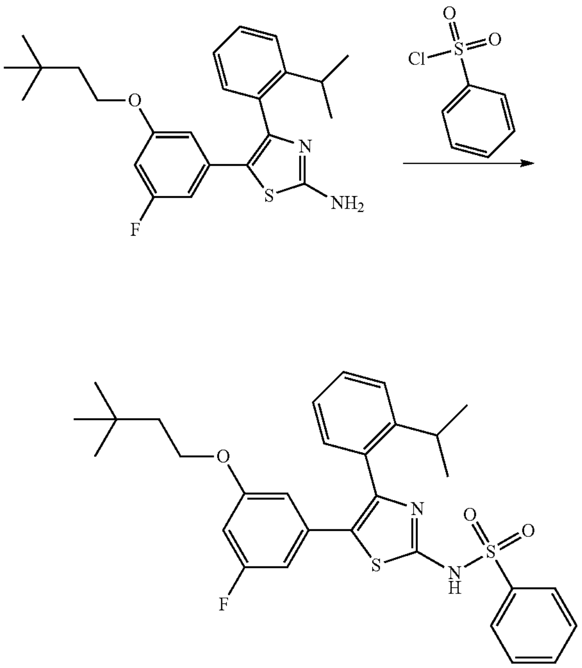

To a solution of Intermediate C-7 (220.0 mg, 0.53 mmol) in pyridine (5.0 mL) was added DMAP (65.1 mg, 0.53 mmol), followed by benzenesulfonyl chloride (283.0 mg, 1.6 mmol). The mixture was stirred at 50° C. for 16 h. The solution was quenched with $H_2O$ (30 mL). The aqueous solution was extracted with ethyl acetate (30 mL×2). The combined organic layer was washed with aqueous brine (30 mL), dried over anhydrous sodium sulfate, filtered and concentrated. The residue was purified by Prep-HPLC to give the title compound (40.6 mg, 13.8%) as a yellow solid.

LCMS: LC retention time 2.51 min. MS (ESI) m/z 554 $[M+H]^+$.

$^1H$ NMR (400 MHz, chloroform-d) δ 8.04-7.97 (m, 2H), 7.61-7.38 (m, 5H), 7.25-7.21 (m, 2H), 6.49-6.36 (m, 2H), 6.33-6.31 (s, 1H), 3.65 (t, J=7.2 Hz, 2H), 2.85-2.78 (m, 1H), 1.58 (t, J=7.2 Hz, 3H), 1.10-1.02 (m, 6H), 0.91 (s, 9H) ppm.

Example 4

N-(4-(2-Isopropoxyphenyl)-5-(3-(neopentyloxy)phenyl)thiazol-2-yl)benzenesulfonamide

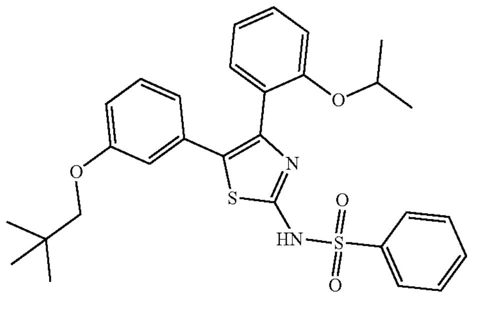 [SMILES: CC(C)Oc1ccccc1-c1nc(NS(=O)(=O)c2ccccc2)sc1-c1cccc(OCC(C)(C)C)c1]

Step 1.

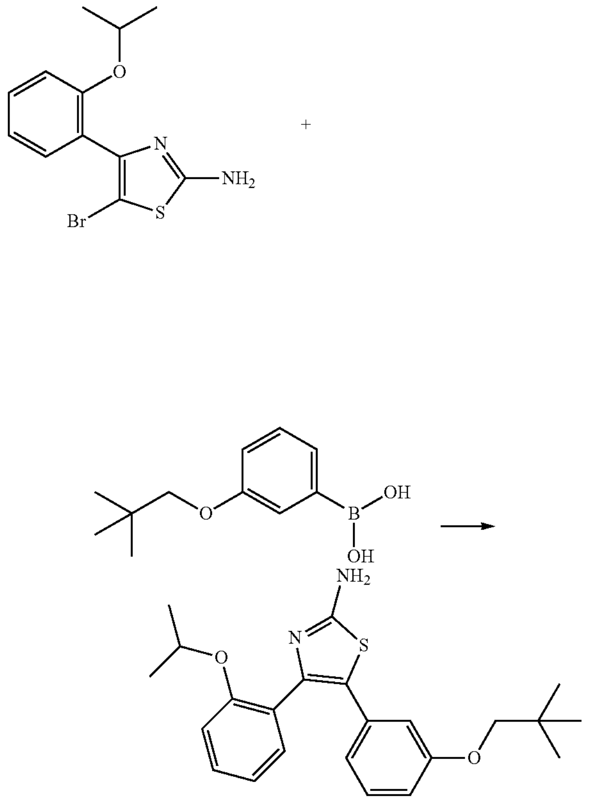

To a solution of Intermediate B-8 (500 mg, 1.60 mmol) in toluene/ethanol/$H_2O$ (3.5 mL, v/v/v=4/2/1) was added (3-(neopentyloxy)phenyl)boronic acid (400 mg, 1.92 mmol), $Pd(Ph_3P)_4$ (185 mg, 0.16 mmol), $Na_2CO_3$ (510 mg, 4.81 mmol). The resulting mixture was stirred at 80° C. under argon atmosphere for 16 h. The reaction was cooled to rt, then filtered. The filtrate was concentrated in vacuo. The residue was purified by silica gel chromatography (PE/EA=3/1) to afford the title compound (580 mg, 91.6%) as a red-brown oil.

LCMS: LC retention time 1.97 min. MS (ESI) m/z 397 $[M+H]^+$.

Step 2.

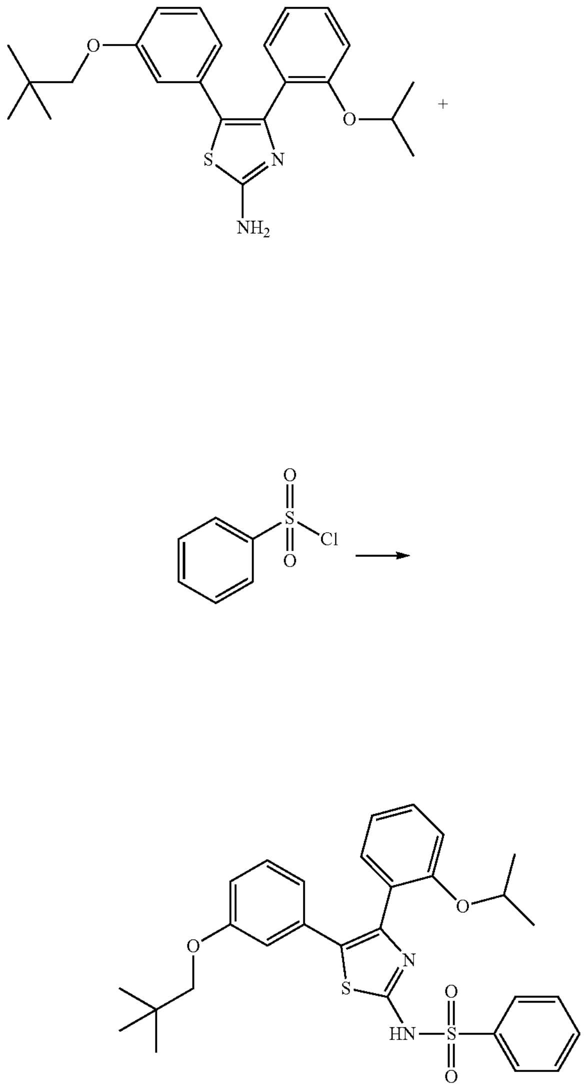

To a solution of 4-(2-isopropoxyphenyl)-5-(3-(neopentyloxy)phenyl)thiazol-2-amine (100 mg, 0.25 mmol) in anhydrous pyridine (3 mL) was added benzenesulfonyl chloride (88.5 mg, 0.5 mmol) after purged by argon atmosphere and cooled to 0° C. in an ice-bath. The reaction mixture was heated to 100° C. and stirred overnight. The reaction mixture cooled to rt and diluted with water (80 mL). The aqueous was extracted with ethyl acetate (80 mL). The organic layer was washed with water (80 mL) again and brine (80 mL), dried over anhydrous $Na_2SO_4$, filtered, and concentrated under reduced pressure to give the crude. The crude was purified by silica gel chromatography (PE/EA=2/1) to give the title compound (66.8 mg, 49.4%) as light yellow solid.

LCMS: LC retention time 2.33 min. MS (ESI) m/z 537 $[M+H]^+$.

$^1H$ NMR (400 MHz, chloroform-d)) (8.01 (d, J=7.4 Hz, 2H), 7.54-7.45 (m, 3H), 7.32 (t, J=7.3 Hz, 1H), 7.26 (s, 2H), 7.13 (dd, J=16.1, 7.9 Hz, 2H), 6.98 (d, J=8.4 Hz, 1H), 6.84-6.73 (m, 4H), 4.62 (dt, J=12.0, 6.0 Hz, 1H), 3.43 (s, 2H), 1.33 (d, J=6.0 Hz, 6H), 0.99 (s, 9H) ppm.

Example 5

N-(5-(3-(3,3-Dimethylbutoxy)-5-fluorophenyl)-4-(4-fluoro-2-((1,1,1-trifluoropropan-2-yl)oxy)phenyl)thiazol-2-yl)-1-methyl-1H-pyrazole-3-sulfonamide

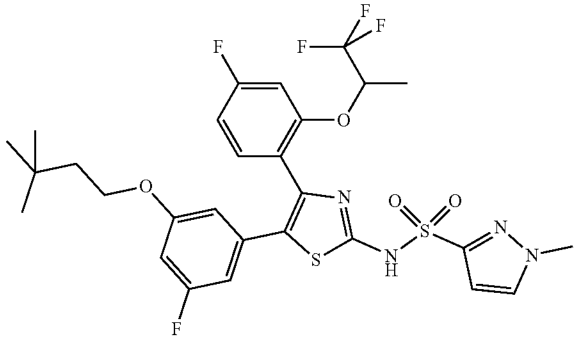 [SMILES: CC(Oc1cc(F)ccc1-c1nc(NS(=O)(=O)c2ccn(C)n2)sc1-c1cc(F)cc(OCCC(C)(C)C)c1)C(F)(F)F]

Step 1.

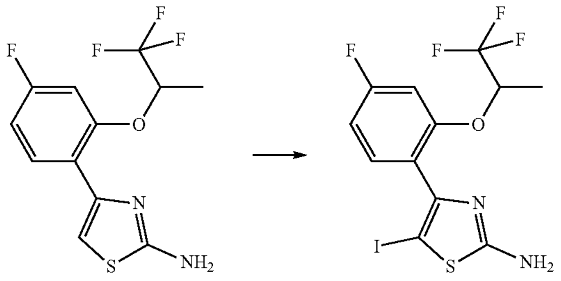 [SMILES: CC(Oc1cc(F)ccc1-c1csc(N)n1)C(F)(F)F ; CC(Oc1cc(F)ccc1-c1nc(N)sc1I)C(F)(F)F]

To a solution of 4-(4-fluoro-2-((1,1,1-trifluoropropan-2-yl)oxy)phenyl)thiazol-2-amine (1.4 g, 4.6 mmol) in DMF (20 mL) was added 1-iodopyrrolidine-2,5-dione (1.00 g, 4.6 mmol) at 0° C. The resulting solution was stirred at rt for 2 h. Then water (70 mL) was added and stirred at rt for 2 h. The mixture was filtered to give 4-(4-fluoro-2-((1,1,1-trifluoropropan-2-yl)oxy)phenyl)-5-iodothiazol-2-amine (1.50 g, 76% yield) as a brown solid.

LCMS: LC retention time 1.95 min. MS (ESI) m/z 433 $[M+H]^+$.

Step 2.

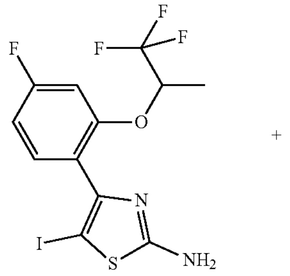

-continued

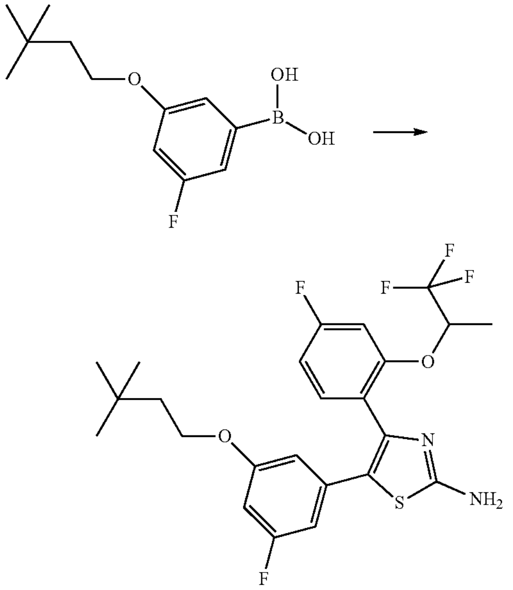

To a stirred solution of 4-(4-fluoro-2-((1,1,1-trifluoropropan-2-yl)oxy)phenyl)-5-iodothiazol-2-amine (1.40 g, 3.2 mmol) in toluene/EtOH/$H_2O$ (80 mL/40 mL/20 mL) were added [3-(3,3-dimethylbutoxy)-5-fluoro-phenyl]boronic acid (Intermediate D-1) (1.56 g, 6.50 mmol) and $Na_2CO_3$ (858 mg, 8.1 mmol) while purging with Ar at rt for 1 min. To this system was added $Pd(PPh_3)_4$ (374 mg, 0.32 mmol). The reaction was heated to 100° C. with stirring for 3 h. Then, the reaction was cooled to rt and concentrated under reduced pressure. The residue was purified by combi-flash (EA in PE=0-30%) to give the title compound (1.30 g, 64% yield) as a brown solid.

LCMS: LC retention time 2.21 min. MS (ESI) m/z 501 $[M+H]^+$.

Step 3.

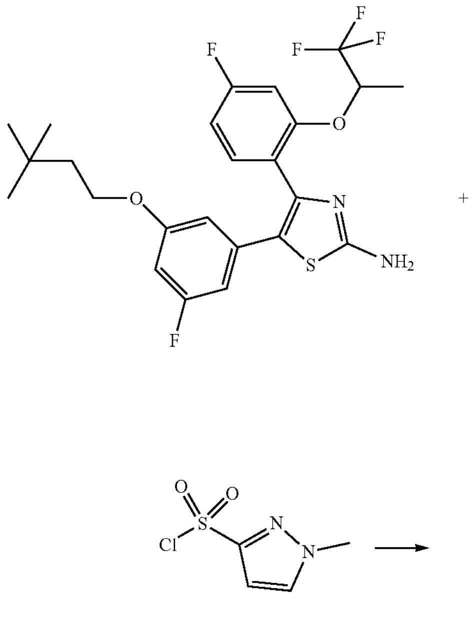

-continued

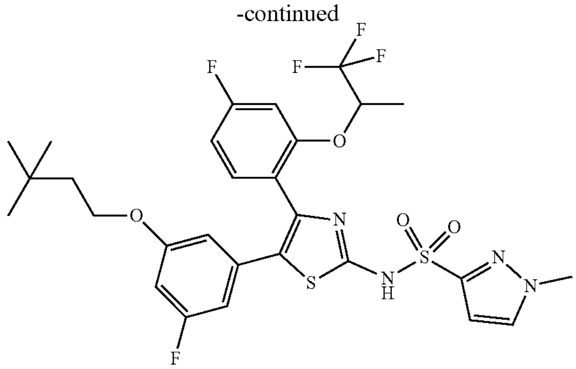

To a solution of 5-(3-(3,3-dimethylbutoxy)-5-fluorophenyl)-4-(4-fluoro-2-((1,1,1-trifluoropropan-2-yl)oxy)phenyl) thiazol-2-amine (300 mg, 0.6 mmol) in pyridine (3 mL) was added 1-methyl-1H-pyrazole-3-sulfonyl chloride (325 mg, 1.8 mmol). The mixture was stirred at 130° C. in microwave oven for 2 h. Then, the reaction was quenched with water (50 mL). The resulting aqueous solution was extracted with EA (50 mL×2). The EA solution was washed with brine (50 mL), dried over anhydrous $Na_2SO_4$, filtered and concentrated. The residue was purified by Prep-HPLC (MeCN—$H_2O$/0.05% TFA) to give the title compound (115 mg, 30% yield) as a white solid.

LCMS (acidic): LC retention time 2.22 min, m/z 645 $[M+H]^+$.

$^1$H NMR (400 MHz, methanol-$d_4$): 7.70 (d, J=2.4 Hz, 1H), 7.41-7.38 (m, 1H), 7.13 (dd, J=2.4, 6.8 Hz, 1H), 6.93-6.88 (m, 1H), 6.71 (d, J=2.4 Hz, 1H), 6.61-6.57 (m, 1H), 6.53-6.50 (m, 1H), 6.44 (s, 1H), 5.06-5.00 (m, 1H), 3.96 (s, 3H), 3.87-3.76 (m, 2H), 1.62 (t, J=6.8 Hz, 2H), 1.26 (d, J=6.4 Hz, 3H), 0.95 (s, 9H) ppm.

Example 6

N-(4-(2,6-Dimethylphenyl)-5-(3-(3,3,3-trifluoro-2,2-dimethylpropoxy)phenyl)thiazol-2-yl)-1,3-dimethyl-1H-pyrazole-4-sulfonamide

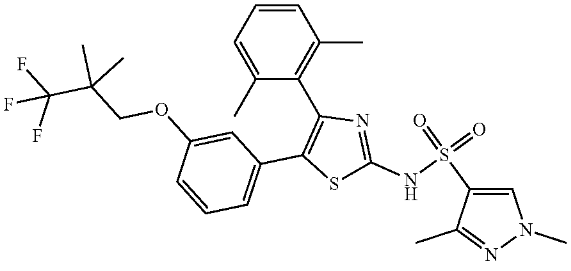 [SMILES: Cc1cccc(C)c1-c1nc(NS(=O)(=O)c2cn(C)nc2C)sc1-c1cccc(OCC(C)(C)C(F)(F)F)c1]

The title compound was synthesized in the same way as Example 5, step 3 by coupling Intermediate C-5 with 1-methyl-1H-pyrazole-3-sulfonyl chloride.

LCMS: LC retention time 2.21 min. MS (ESI) m/z 579 $[M+H]^+$.

$^1$H NMR (400 MHz, chloroform-d) δ 9.13 (s, 1H), 7.84 (s, 1H), 7.33-7.29 (m, 1H), 7.17-7.14 (m, 3H), 6.80-6.78 (m, 1H), 6.73-6.71 (m, 1H), 8.50 (s, 1H), 3.86 (s, 3H), 3.52 (s, 2H), 2.45 (s, 3H), 2.16 (s, 6H), 1.21 (s, 6H) ppm.

Example 7

3-Amino-N-(5-(3-(3,3-dimethylbutoxy)-5-fluorophenyl)-4-(2,6-dimethylphenyl)thiazol-2-yl)benzenesulfonamide

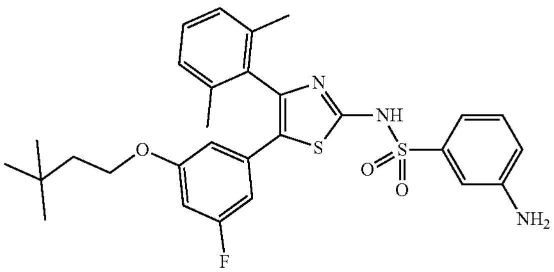 [SMILES: Cc1cccc(C)c1-c1nc(NS(=O)(=O)c2cccc(N)c2)sc1-c1cc(F)cc(OCCC(C)(C)C)c1]

Step 1.

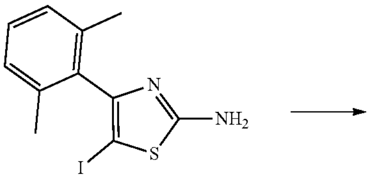

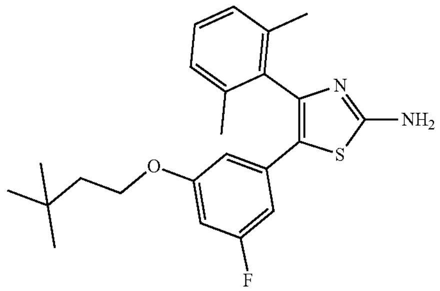

To a solution of 4-(2,6-dimethylphenyl)-5-iodo-thiazol-2-amine (Intermediate B-2b) (1.00 g, 3.03 mmol), in toluene (30 mL), ethanol (15 mL) and water (8 mL) were added [3-(3,3-dimethylbutoxy)-5-fluoro-phenyl]boronic acid (Intermediate D-1) (873 mg, 3.63 mmol), sodium carbonate (963 mg, 9.09 mmol), tetrakis(triphenylphosphine) palladium (350 mg, cat.). The reaction was heated to 80° C. for 12 h under Ar atmosphere. The mixture was concentrated under reduced pressure. The residue was diluted with ethyl acetate (100 mL) and washed with brine. The organics were dried over anhydrous sodium sulfate, concentrated in vacuo and the residue was purified by combi-flash (PE/EA=3/1) to give the title compound (1.30 g, 86%) as a brown oil.

LCMS: LC retention time 2.15 min. MS (ESI) m/z 399 $[M+H]^+$.

Step 2.

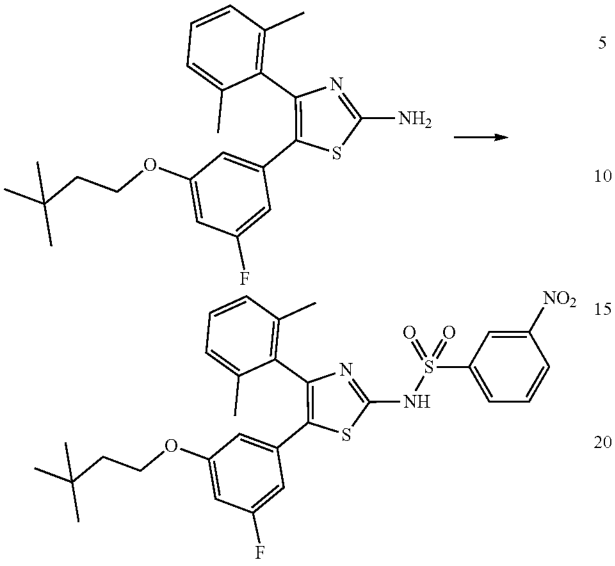

To a solution of 5-[3-(3,3-dimethylbutoxy)-5-fluoro-phenyl]-4-(2,6-dimethylphenyl)thiazol-2-amine (1.0 g, 2.51 mmol) in pyridine (10.0 mL) was added 3-nitrobenzenesulfonyl chloride (1.67 g, 7.53 mmol). The reaction was heated at 130° C. in a microwave oven for 2 h. The reaction was quenched by addition of aqueous saturated $NaHCO_3$ (80 mL). The aqueous solution was extracted with ethyl acetate (80 mL×2). After separation of the two layers, the organic solution was washed with brine, dried over anhydrous sodium sulfate, filtered and concentrated in vacuo. The residue was purified by silica gel column chromatography (PE/EA=2/1) to afford the title compound (780 mg, 53%) as a brown oil.

LCMS: LC retention time 2.35 min. MS (ESI) m/z 584 $[M+H]^+$.

Step 3.

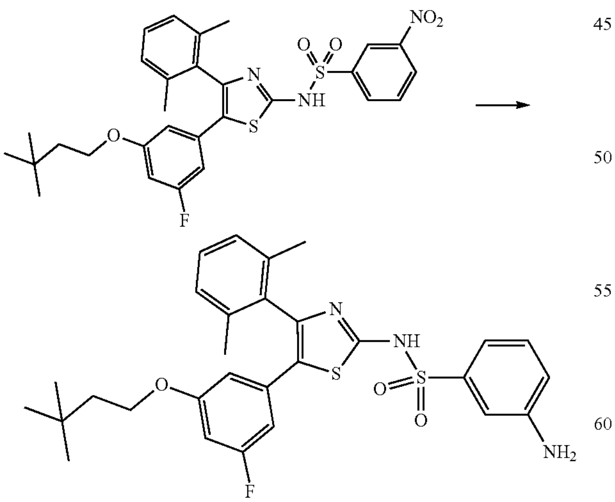

To a solution of N-[5-[3-(3,3-dimethylbutoxy)-5-fluoro-phenyl]-4-(2,6-dimethylphenyl)thiazol-2-yl]-3-nitro-benzenesulfonamide (780 mg, 1.34 mmol) in MeOH (9.0 mL) and $H_2O$ (2.0 mL) were added Zn (3.47 g, 53.5 mmol) and $NH_4Cl$ (2.89 g, 53.5 mmol). The reaction was stirred at reflux for 3 h. The resulting mixture was filtered. The filtrate was concentrated. The residue was diluted in water (100 mL). The resulting aqueous solution was extracted with ethyl acetate (80 mL×2). The combined organic layers were washed with brine, dried over anhydrous sodium sulfate, filtered and concentrated in vacuo to give the title compound (550 mg, 74%) as a white solid.

LCMS: LC retention time 2.27 min. MS (ESI) m/z 554 $[M+H]^+$.

$^1H$ NMR (400 MHz, chloroform-d) 7.37 (d, J=7.7 Hz, 1H), 7.34-7.29 (m, 2H), 7.27 (d, J=7.9 Hz, 1H), 7.15 (d, J=7.6 Hz, 2H), 6.84 (dd, J=8.0, 1.4 Hz, 1H), 6.47 (dt, J=10.4, 2.2 Hz, 1H), 6.40-6.30 (m, 2H), 3.68 (t, J=7.3 Hz, 2H), 2.15 (s, 6H), 1.62 (s, 2H), 0.95 (s, 9H) ppm.

Example 8

3-Amino-N-[5-[3-(3,3-dimethylbutoxy)phenyl]-4-[2-(trifluoromethyl)phenyl]thiazol-2-yl]benzenesulfonamide

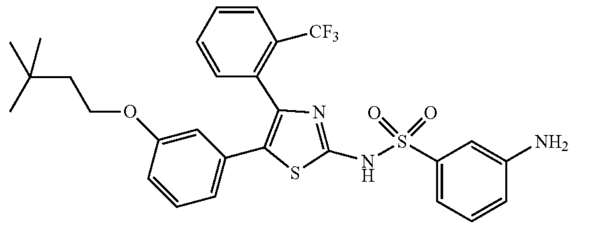 [SMILES: CC(C)(C)CCOc1cccc(-c2sc(NS(=O)(=O)c3cccc(N)c3)nc2-c2ccccc2C(F)(F)F)c1]

Step 1.

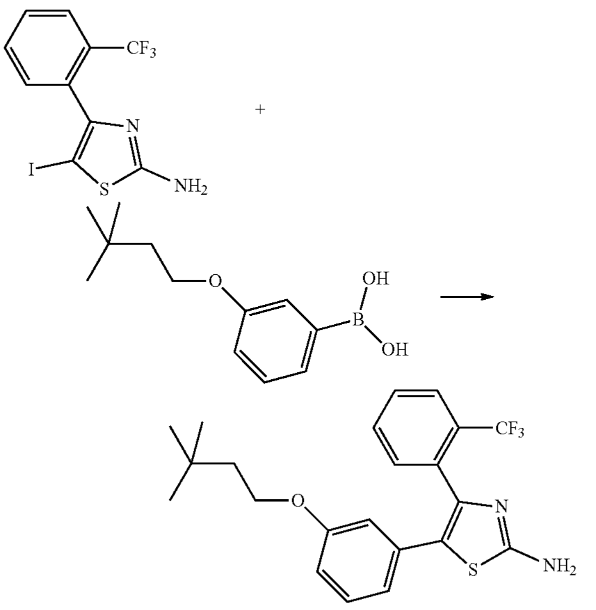

A mixture of 5-iodo-4-[2-(trifluoromethyl)phenyl]thiazol-2-amine (Intermediate B-9) (700 mg, 1.89 mmol), [3-(3,3-dimethylbutoxy)phenyl]boronic acid (Intermediate D-2) (546 mg, 2.46 mmol), $Na_2CO_3$ (601 mg, 5.67 mmol), tetrakis (triphenylphosphine)palladium (235 mg, cat.) in toluene (20 mL), ethanol (10 mL) and water (5 mL) was heated to 80° C. and stirred for 12 h under argon atmosphere. The mixture was concentrated and the residue was purified by combi-flash (PE/EA=2/1) to give the title compound (700 mg, 88%) as a brown solid.

LCMS: LC retention time 2.09 min. MS (ESI) m/z 421 $[M+H]^+$.

Step 2.

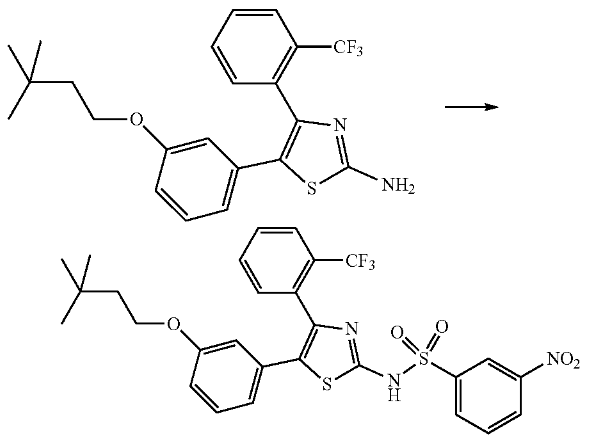

To a solution of 5-[3-(3,3-dimethylbutoxy)phenyl]-4-[2-(trifluoromethyl)phenyl]thiazol-2-amine (750 mg, 1.78 mmol) in pyridine (10.0 mL) was added 3-nitrobenzenesulfonyl chloride (1.19 g, 5.35 mmol). The reaction was heated at 130° C. in a microwave oven for 3 h. After removal of the solvent by blowing nitrogen, the residue was diluted with water (100 mL) and extracted with ethyl acetate (50 mL×2). The combined organics were washed with brine and dried over anhydrous sodium sulfate, concentrated in vacuo. The residue was purified by silica gel column chromatography (PE/EA=2/1) to afford the desired compound, N-[5-[3-(3,3-dimethylbutoxy)phenyl]-4-[2-(trifluoromethyl)phenyl]thiazol-2-yl]-3-nitro-benzenesulfonamide (570 mg, 53%) as a brown solid.

LCMS: LC retention time 2.28 min. MS (ESI) m/z 606 $[M+H]^+$.

Step 3.

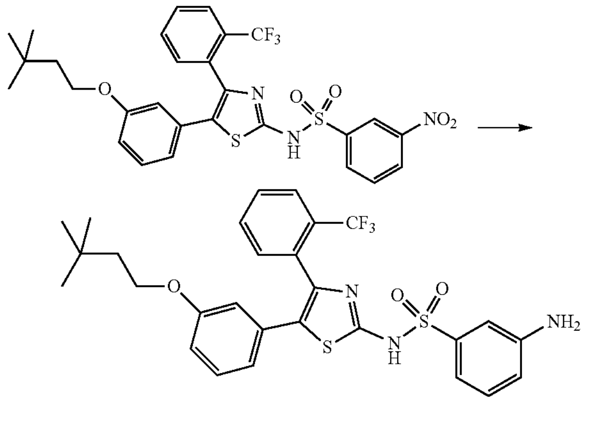

The mixture of N-[5-[3-(3,3-dimethylbutoxy)phenyl]-4-[2-(trifluoromethyl)phenyl]thiazol-2-yl]-3-nitro-benzenesulfonamide (400 mg, 0.66 mmol), Zn powder (1.72 g, 26.4 mmol), $NH_4Cl$ (1.43 g, 26.4 mmol) in MeOH (9.0 mL) and $H_2O$ (3.0 mL) was stirred at reflux for 1 h. The resulting mixture was filtered and concentrated. The residue was dissolved in water (80 mL). The aqueous was extracted with ethyl acetate (50 mL×2). The combined organic layers were combined and washed with brine, dried over anhydrous sodium sulfate, and filtered. The filtrate was concentrated in vacuo to give the title compound (350 mg, 92%) as a yellow solid.

LCMS: LC retention time 2.18 min. MS (ESI) m/z 576 $[M+H]^+$.

$^1H$ NMR (400 MHz, chloroform-d) (7.74 (s, 1H), 7.51 (s, 2H), 7.31 (s, 5H), 7.10 (dd, J=25.1, 17.1 Hz, 2H), 6.68 (dd, J=34.2, 7.3 Hz, 3H), 6.47 (s, 1H), 3.69 (s, 2H), 1.61 (t, J=7.3 Hz, 2H), 1.28 (s, 1H), 0.94 (s, 9H) ppm.

Example 9

3-Amino-N-(5-(3-(3,3-dimethylbutoxy)-5-fluorophenyl)-4-(4-(trifluoromethyl)phenyl)thiazol-2-yl)benzenesulfonamide

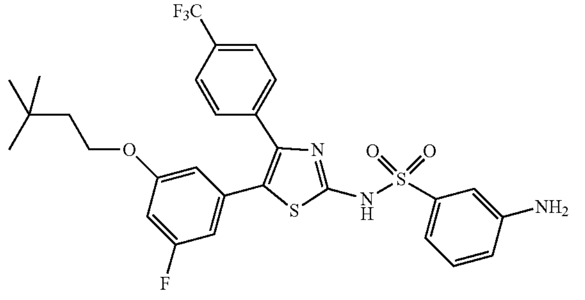 [SMILES: CC(C)(C)CCOc1cc(F)cc(-c2sc(NS(=O)(=O)c3cccc(N)c3)nc2-c2ccc(C(F)(F)F)cc2)c1]

Step 1.

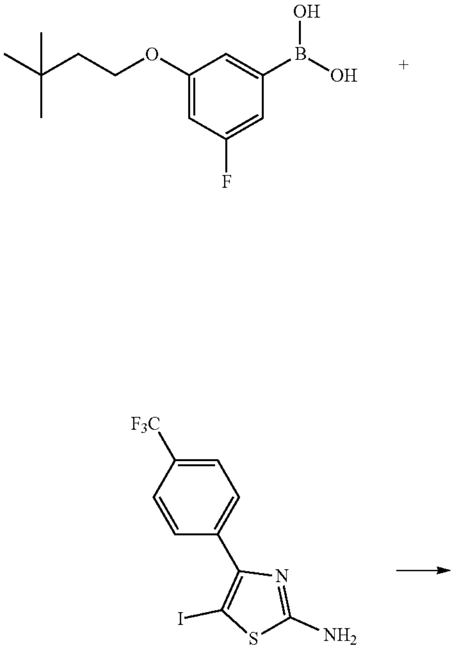

-continued

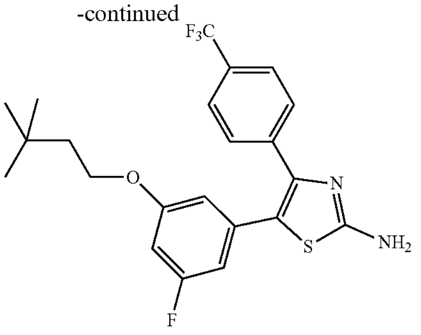

To a solution of 5-iodo-4-[4-(trifluoromethyl)phenyl]thiazol-2-amine (1.67 g, 4.51 mmol), Intermediate D-1 (3.06 g, 13.5 mmol), $Na_2CO_3$ (1.43 g, 13.5 mmol), and $Pd(PPh_3)_4$ (300 mg) in toluene/EtOH/$H_2O$ (4/2/1) (7 mL) was stirred at 80° C. overnight. The reaction was cooled to rt and then concentrated under reduced pressure. The residue was purified with SGC (PE:EA=5:1) to afford a crude which was purified by Prep-HPLC to afford 5-(3-(3,3-dimethylbutoxy)-5-fluorophenyl)-4-(4-(trifluoromethyl)phenyl)thiazol-2-amine (239 mg, 12.1% yield) as a brown solid.

LCMS: LC retention time 2.26 min. MS (ESI) m/z 439 $[M+H]^+$.

Step 2.

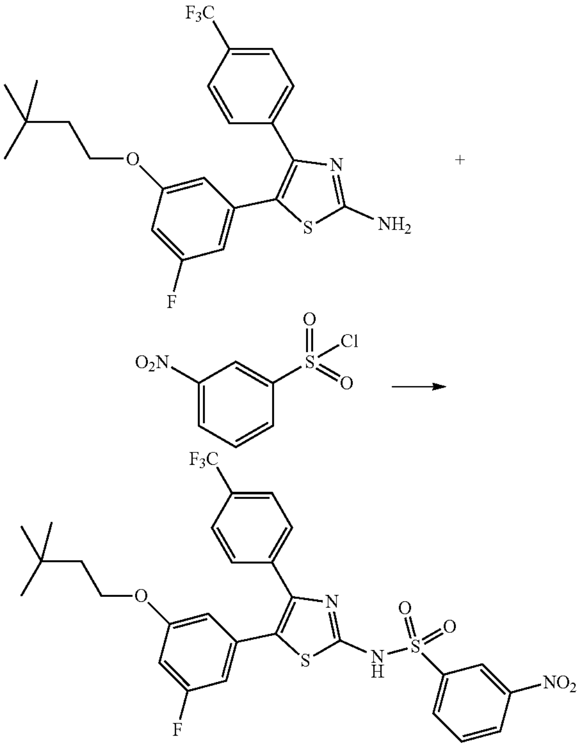

To a solution of 5-(3-(3,3-dimethylbutoxy)-5-fluorophenyl)-4-(4-(trifluoromethyl)phenyl)thiazol-2-amine (90 mg, 0.21 mmol) in pyridine (2 mL) was added 3-nitrobenzenesulfonyl chloride (136 mg, 0.62 mmol). The reaction was stirred at room temperature for 2 h and at 55° C. for 5 h. The reaction was cooled to rt. The solvent was evaporated. The residue was purified by Prep-TLC to afford N-(5-(3-(3,3-dimethylbutoxy)-5-fluorophenyl)-4-(4-(trifluoromethyl)phenyl)thiazol-2-yl)-3-nitrobenzenesulfonamide (110 mg, 86% yield) as a yellow solid.

LCMS: LC retention time 2.33 min. MS (ESI) m/z not observed.

Step 3.

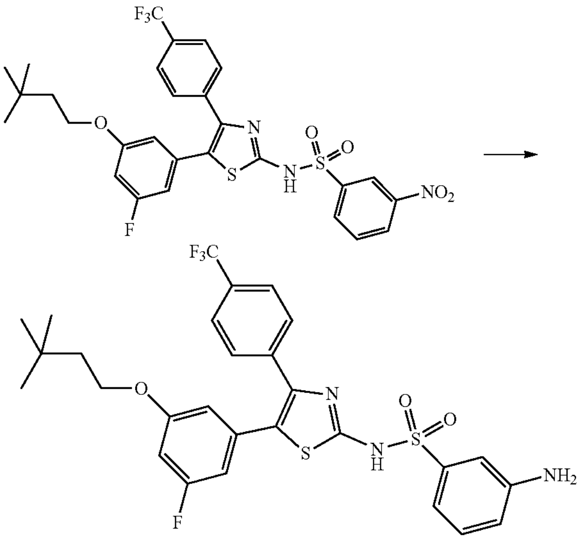

To a solution of N-(5-(3-(3,3-dimethylbutoxy)-5-fluorophenyl)-4-(4-(trifluoromethyl)phenyl)thiazol-2-yl)-3-nitrobenzenesulfonamide (110 mg, 0.176 mmol) methanol (10 mL) was added Pd/C. The reaction flask was mounted to a hydrogenation apparatus. The reaction was stirred under hydrogen for 12 h at rt. The reaction mixture was filtered. The filtrate was concentrated. The residue was purified by Prep-HPLC to afford 3-amino-N-(5-(3-(3,3-dimethylbutoxy)-5-fluorophenyl)-4-(4-(trifluoromethyl)phenyl)thiazol-2-yl)benzenesulfonamide (44 mg, 42%) as a white solid.

LCMS: LC retention time 2.24 min. MS (ESI) m/z 594 $[M+H]^+$.

$^1H$ NMR (400 MHz, chloroform-d) δ 7.54 (d, J=8.2 Hz, 2H), 7.48-7.37 (m, 3H), 7.31 (d, J=7.6 Hz, 1H), 7.20 (t, J=7.9 Hz, 1H), 6.78 (d, J=7.3 Hz, 1H), 6.55 (d, J=10.5 Hz, 1H), 6.45 (d, J=10.8 Hz, 2H), 3.83 (t, J=7.1 Hz, 2H), 1.63 (t, J=7.1 Hz, 2H), 0.92 (s, 9H) ppm.

Example 10

3-Amino-N-(5-(3-(3,3-dimethylbutoxy)phenyl)-4-(4-(trifluoromethyl)phenyl)thiazol-2-yl)benzenesulfonamide

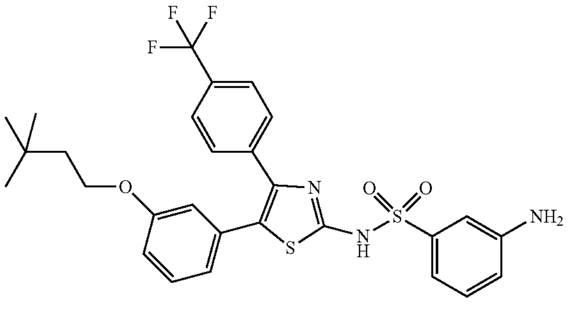 [SMILES: CC(C)(C)CCOc1cccc(-c2sc(NS(=O)(=O)c3cccc(N)c3)nc2-c2ccc(C(F)(F)F)cc2)c1]

The title compound was synthesized similarly as Example 8 described above.

LCMS: LC retention time 2.27 min. MS (ESI) m/z 576 $[M+H]^+$.

$^1H$ NMR (400 MHz, chloroform-d) δ 7.50 (s, 2H), 7.48 (s, 1H), 7.40 (d, J=8.4 Hz, 2H), 7.33 (d, J=8.0 Hz, 1H), 7.21-7.15 (m, 2H), 6.85 (d, J=8.0 Hz, 1H), 6.75 (d, J=8.8 Hz, 2H), 6.67 (s, 1H), 3.85 (t, J=7.6 Hz, 2H), 1.65 (t, J=7.2 Hz, 2H), 0.94 (s, 9H) ppm.

Example 11

3-Amino-N-(5-(3-(3,3-dimethylbutoxy)-5-fluorophenyl)-4-(2-isopropylphenyl)thiazol-2-yl)benzenesulfonamide

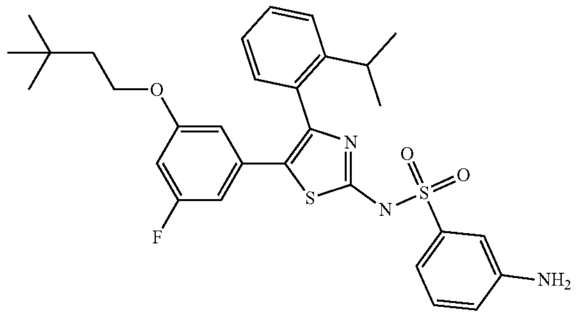 [SMILES: CC(C)c1ccccc1-c1nc(NS(=O)(=O)c2cccc(N)c2)sc1-c1cc(F)cc(OCCC(C)(C)C)c1]

Step 1.

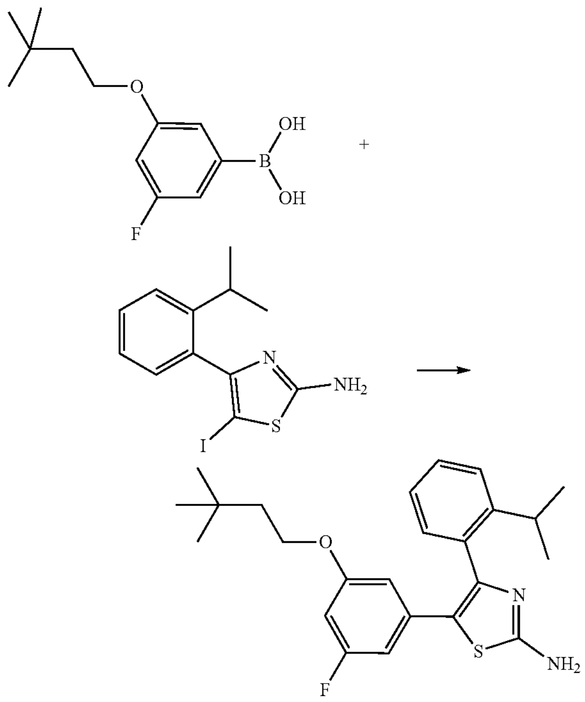

To a solution of Intermediate D-1 (512 mg, 2.13 mmol), $Na_2CO_3$ (106 mg, 4.87 mmol) and Intermediate B-1 (555 mg, 1.61 mmol) were suspended in toluene (40 mL), EtOH (20 mL) and water (10 mL). The mixture was bubbled with $N_2$ for 5 min then charged with $Pd(Ph_3P)_4$ (188 mg, 0.163 mmol). The mixture was stirred at 80° C. for 12 h and then cooled to room temperature. The mixture was partitioned between EtOAc (10 mL) and water (10 mL). The organic layer was dried, filtered, and concentrated. The residue was purified by silica gel chromatography (PE/EA=5/1) to give 5-(3-(3,3-dimethylbutoxy)-5-fluorophenyl)-4-(2-isopropylphenyl)thiazol-2-amine (500 mg, 75.3%) as a yellow solid.

LCMS: MS (ESI) m/z 413 $[M+H]^+$.

Step 2.

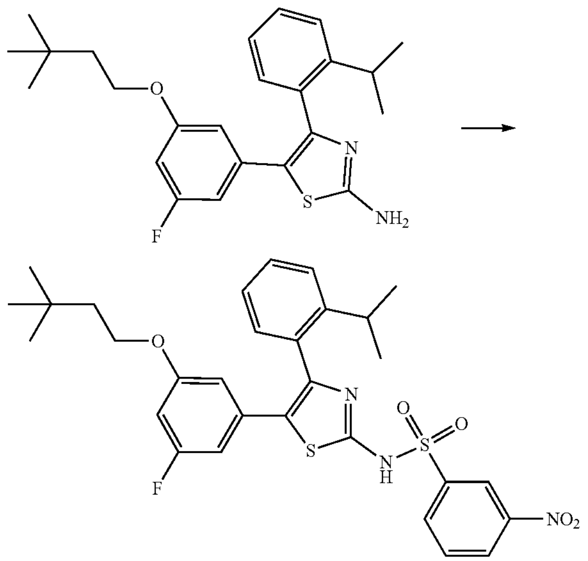

To a solution of 5-(3-(3,3-dimethylbutoxy)-5-fluorophenyl)-4-(2-isopropylphenyl)thiazol-2-amine (300 mg, 0.727 mmol) in pyridine (2.0 mL) was added 3-nitrobenzenesulfonyl chloride (580 mg, 2.62 mmol). The mixture was stirred at 130° C. in a microwave reactor for 2 h. The solution was quenched with $H_2O$ (50 mL). The aqueous solution was extracted with ethyl acetate (50 mL×2). The combined organic layer was dried over anhydrous sodium sulfate and filtered. The filtrate was concentrated to obtain N-(5-(3-(3,3-dimethylbutoxy)-5-fluorophenyl)-4-(2-isopropylphenyl)thiazol-2-yl)-3-nitrobenzenesulfonamide (400 mg; 91.9%) as a yellow oil.

LCMS: LC retention time 2.16 min. MS (ESI) m/z 598 $[M+H]^+$.

Step 3.

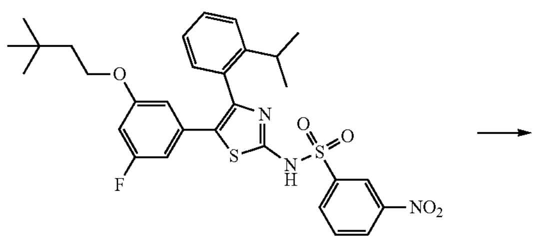

-continued

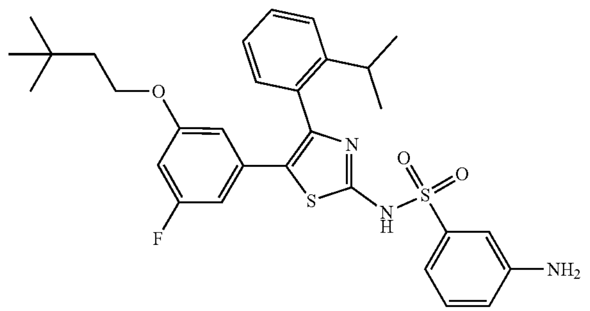

To a solution of N-(5-(3-(3,3-dimethylbutoxy)-5-fluorophenyl)-4-(2-isopropylphenyl)thiazol-2-yl)-3-nitrobenzenesulfonamide (400 mg, 0.67 mmol) in MeOH (30 mL) and $H_2O$ (0.3 mL) was added $NH_4Cl$ (800 mg, 9.1 mmol) and Fe (1.22 g, 21.9 mmol). The resulting mixture was stirred at 60° C. for 3 h. The mixture was poured into water (50 mL) and extracted with DCM (50 mL x 2). The extracts were washed with water (40 mL×2), dried over sodium sulfate and evaporated. The resulting residue was purified by silica gel chromatography (PE/EA=10/1) to afford the title compound (295 mg, 77.8% yield) as a colorless oil.

LCMS: MS (ESI) m/z 568 $[M+H]^+$.

Example 12

5-Amino-N-(4-(2,6-dimethylphenyl)-5-(4-fluoro-3-(3,3,3-trifluoro-2,2-dimethylpropoxy)phenyl)thiazol-2-yl)-2-fluorobenzenesulfonamide

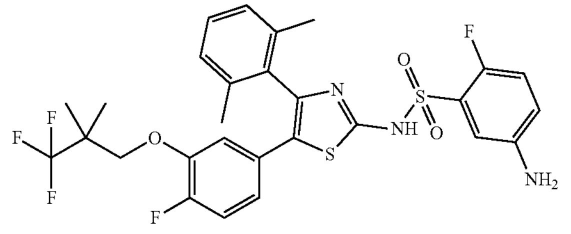 [SMILES: Cc1cccc(C)c1-c1nc(NS(=O)(=O)c2cc(N)ccc2F)sc1-c1ccc(F)c(OCC(C)(C)C(F)(F)F)c1]

Step 1.

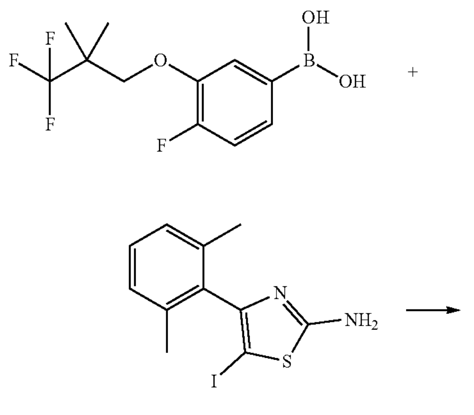

-continued

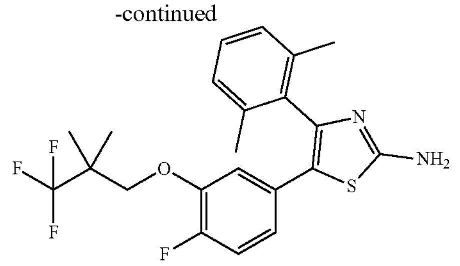

To a solution of Intermediate B-2b (632 mg, 1.91 mmol) in toluene/ethanol/$H_2O$ (52.5 mL, v/v/v=4/2/1) were added Intermediate D-8 (643 mg, 2.30 mmol), Pd $(Ph_3P)_4$ (221 mg, 0.19 mmol) and $Na_2CO_3$ (608.6 mg, 5.74 mmol). The resulting mixture was stirred at 80° C. under argon atmosphere overnight. The reaction was cooled to rt and then filtered. The filtrate was concentrated in vacuo. The residue was dissolved in water (50 mL) and brine (50 mL). The resulting aqueous solution was extracted with ethyl acetate (80 mL×3). The ethyl acetate extracts were combined and dried over anhydrous sodium sulfate, and then filtered. The filtrate was concentrated to dryness under reduced pressure to give the crude product which was purified by flash reversed-phase column chromatography to give the desired compound (270 mg, 46.0% yield) as a white solid.

LCMS: LC retention time 2.13 min. MS (ESI) m/z 439 $[M+H]^+$.

Step 2.

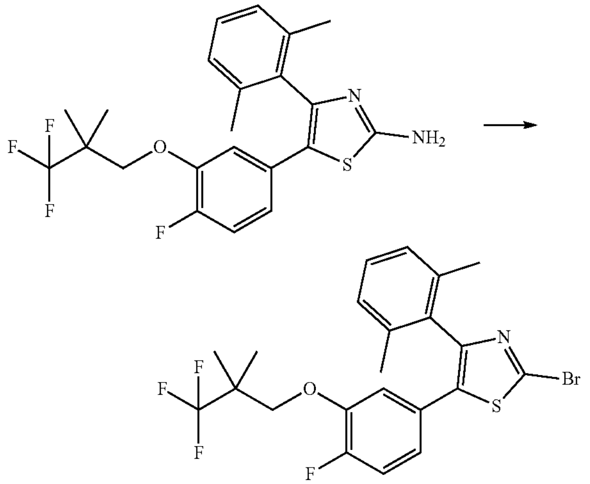

To a solution of 4-(2,6-dimethylphenyl)-5-(4-fluoro-3-(3,3,3-trifluoro-2,2-dimethylpropoxy)phenyl)thiazol-2-amine (270 mg, 0.62 mmol) in anhydrous MeCN (5.0 mL) was added $CuBr_2$ (82.4 mg, 0.37 mmol) and tert-butyl nitrite (63.4 mg, 0.62 mmol) at room temperature. The resulting mixture was stirred at 80° C. for 15 min. An aliquot was checked by LCMS analysis which indicated that the reaction was completed. The reaction was quenched by addition of water (20 mL). The aqueous solution was extracted with ethyl acetate (30 mL×3). The combined organic layers were washed with brine (50 mL), dried over anhydrous sodium sulfate, filtered and concentrated to dryness to give the crude. The crude was purified by silica gel column chromatography (PE/EA=20/1) to give 2-bromo-4-(2,6-dimethylphenyl)-5-(4-fluoro-3-(3,3,3-trifluoro-2,2-dimethylpropoxy)phenyl)thiazole (210 mg, 67.9%) as a yellow oil.

LCMS: LC retention time 2.25 min. MS (ESI) m/z 504 $[M+H]^+$.

Step 3.

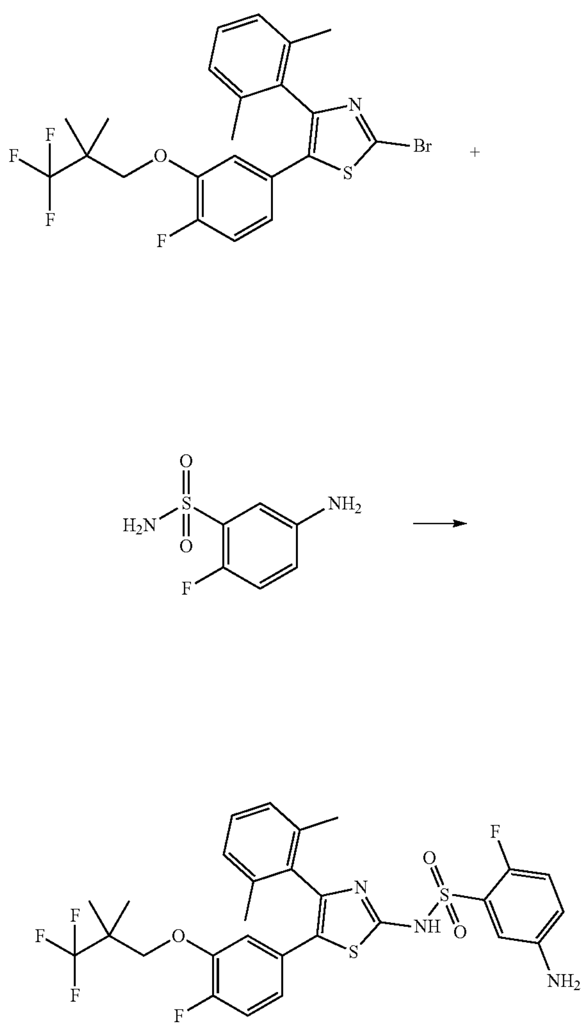

To a solution of 2-bromo-4-(2,6-dimethylphenyl)-5-(4-fluoro-3-(3,3,3-trifluoro-2,2-dimethylpropoxy)phenyl)thiazole (105 mg, 0.21 mmol) in anhydrous DMF (2.0 mL) were added 5-amino-2-fluorobenzenesulfonamide (59.6 mg, 0.31 mmol)), CuI (4.0 mg, 0.021 mmol), $K_2CO_3$ (86.5 mg, 0.63 mL) and N,N'-dimethyl-1,2-ethanediamine (9.3 mg, 0.11 mmol) under nitrogen in a glove-box. The reaction was heated to 100° C. and stirred at the same temperature overnight. Then the mixture was cooled to room temperature and poured into water (20 mL). The resulting aqueous solution was extracted with ethyl acetate (20 mL×3). The ethyl acetate solution was washed with brine (20 mL), dried over anhydrous sodium sulfate, filtered and concentrated to dryness under reduced pressure. The crude was purified by prep-HPLC to give the desired compound (61.8 mg, 48.3%) as a white solid.

LCMS: LC retention time 2.22 min. MS (ESI) m/z 612 $[M+H]^+$.

$^1H$ NMR (400 MHz, chloroform-d) 7.30 (d, J=7.8 Hz, 2H), 7.14 (d, J=7.4 Hz, 2H), 6.95 (t, J=9.0 Hz, 2H), 6.75 (d, J=8.2 Hz, 2H), 6.47 (d, J=8.8 Hz, 1H), 3.44 (s, 2H), 2.16 (s, 6H), 1.21 (s, 6H) ppm.

Example 13

N-(4-(2,6-Dimethylphenyl)-5-(3-(3,3,3-trifluoro-2,2-dimethylpropoxy)phenyl)thiazol-2-yl)-3-((3-hydroxy-3-methylcyclobutyl)amino)benzenesulfonamide

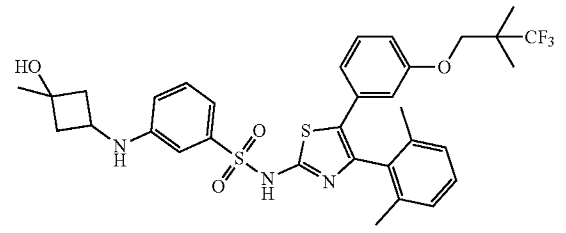 [SMILES: Cc1cccc(C)c1-c1nc(NS(=O)(=O)c2cccc(NC3CC(C)(O)C3)c2)sc1-c1cccc(OCC(C)(C)C(F)(F)F)c1]

Step 1.

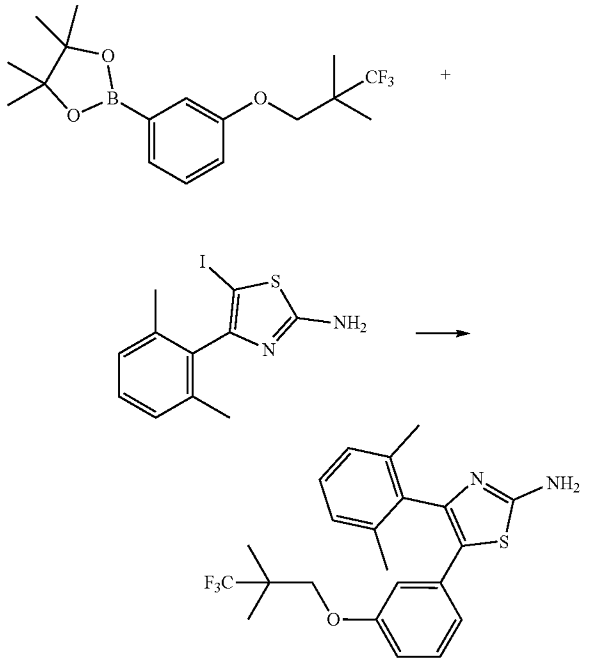

To a stirred solution of 4,4,5,5-tetramethyl-2-[3-(3,3,3-trifluoro-2,2-dimethyl-propoxy)phenyl]-1,3,2-dioxaborolane (600 mg, 1.74 mmol) in toluene:ethanol:$H_2O$=4:2:1 (8 mL, 4 mL, 2 mL) were added Intermediate B-2b (574 mg, 1.74 mmol), $Na_2CO_3$ (554 mg, 5.23 mmol), and $Pd(PPh_3)_4$ (101 mg, 0.087 mmol). The reaction was heated at 90° C. with stirring overnight. When the reaction was completed, the mixture was partitioned between EA (20 mL) and $H_2O$ (5 mL). The aqueous was extracted with EA (20 mL×3). The organic solution was concentrated in vacuo to give the crude product which was purified by a silica gel chromatography (PE/EA=10%) to give the desired product 4-(2,6-dimethylphenyl)-5-[3-(3,3,3-trifluoro-2,2-dimethyl-propoxy)phenyl]thiazol-2-amine (400 mg, 54.6%) as a yellow solid.

LCMS: LC retention time 1.93 min. MS (ESI) m/z 423 $[M+H]^+$.

Step 2.

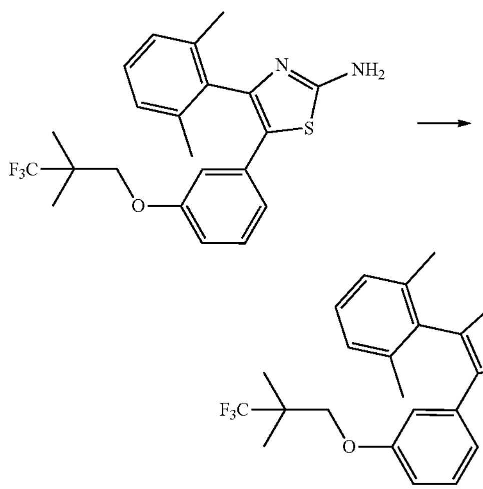

To a mixture of 4-(2,6-dimethylphenyl)-5-[3-(3,3,3-trifluoro-2,2-dimethyl-propoxy)phenyl]thiazol-2-amine (400 mg, 0.951 mmol) in $CH_3CN$ (8 mL) were added $CuBr_2$ (149 mg, 0.666 mmol), tert-butyl nitrite (98 mg, 0.951 mmol) at room temperature under Ar atmosphere. Then the mixture was heated to 80° C. for 15 min. The mixture was concentrated and the residue was purified by SGC (PE/EA=20/1) to give 2-bromo-4-(2,6-dimethylphenyl)-5-(3-(3,3,3-trifluoro-2,2-dimethylpropoxy)phenyl)thiazole as a yellow solid (300 mg, 65.1% yield).

LCMS: LC retention time 2.32 min. MS (ESI) m/z 485 $[M+H]^+$.

Step 3.

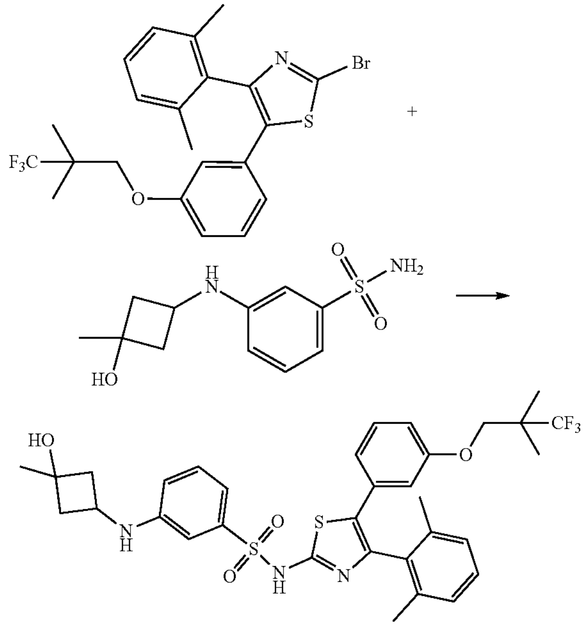

To a stirred solution of 2-bromo-4-(2,6-dimethylphenyl)-5-(3-(3,3,3-trifluoro-2,2-dimethylpropoxy)phenyl)thiazole (120 mg, 0.248 mol) in DMF (2 mL) were added 3-[(3-hydroxy-3-methyl-cyclobutyl)amino]benzenesulfonamide (63.5 mg, 0.248 mmol), CuI (4.71 mg, cat.), $K_2CO_3$ (103 mg, 0.743 mmol), and N,N'-dimethyl-1, 2-ethanediamine (53.7 mg, cat.) under nitrogen in a glove-box. The reaction mixture was heated to 100° C. and stirred overnight. Then the mixture was cooled to room temperature and poured into water (100 mL), extracted with ethyl acetate (40 mL×3). The organic was washed with brine (40 mL), dried over anhydrous $Na_2SO_4$, filtered and concentrated. The residue was purified by prep-HPLC to give the title compound as a yellow solid (53.7 mg, 32.9%).

LCMS: LC retention time 1.67 min. MS (ESI) m/z 661 $[M+H]^+$.

$^1$H NMR (400 MHz, chloroform-d) δ 7.33-7.30 (m, 2H), 7.15-7.14 (d, 1H), 6.80-6.79 (d, 1H), 6.77-6.69 (m, 3H), 6.80-6.77 (m, 1H), 6.73-6.70 (m, 2H), 6.50 (s, 1H), 3.59-3.56 (m, 1H), 3.51 (s, 1H), 2.67-2.62 (m, 2H), 2.14 (s, 6H), 1.96-1.80 (m, 4H), 1.45-1.40 (m, 3H), 1.21 (s, 6H) ppm.

Example 14

3-Amino-N-(5-(3-(3,3-dimethylbutoxy)phenyl)-4-(2-methyl-6-(trifluoromethyl)phenyl)thiazol-2-yl)benzenesulfonamide

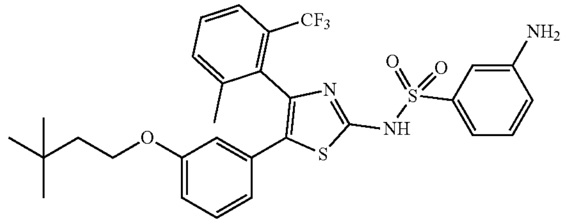 [SMILES: Cc1cccc(C(F)(F)F)c1-c1nc(NS(=O)(=O)c2cccc(N)c2)sc1-c1cccc(OCCC(C)(C)C)c1]

Step 1.

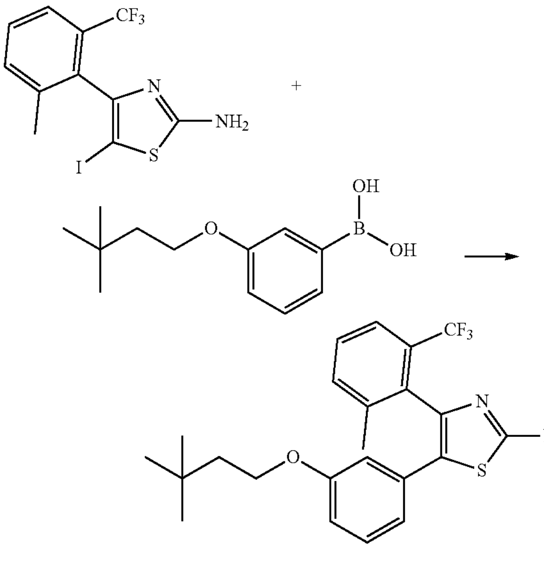

To a solution of Intermediate B-4 (1.00 g, 2.60 mmol) in toluene/ethanol/$H_2O$ (70 mL, v/v/v=4/2/1) were added Intermediate D-2 (697 mg, 3.13 mmol), Pd $(Ph_3P)_4$ (301 mg, 0.26 mmol), $Na_2CO_3$ (828 mg, 7.81 mmol). The resulting mixture was stirred at 80° C. under argon atmosphere for 16 h. After cooled to rt, the mixture was filtered. The filtrate was concentrated in vacuo. The residue was taken in water (150 mL) and brine (200 mL). The resulting aqueous was extracted with ethyl acetate (150 mL×3). The combined organic solutions were dried over anhydrous $Na_2SO_4$, filtered. The filtrate was concentrated to dryness under reduced pressure to give the crude which was purified by reversed phase silica gel column chromatography to give 5-(3-(3,3-dimethylbutoxy)phenyl)-4-(2-methyl-6-(trifluoromethyl)phenyl)thiazol-2-amine (230 mg, 20.3%) as a white solid.

LCMS: LC retention time 2.32 min. MS (ESI) m/z 435 $[M+H]^+$.

Step 2.

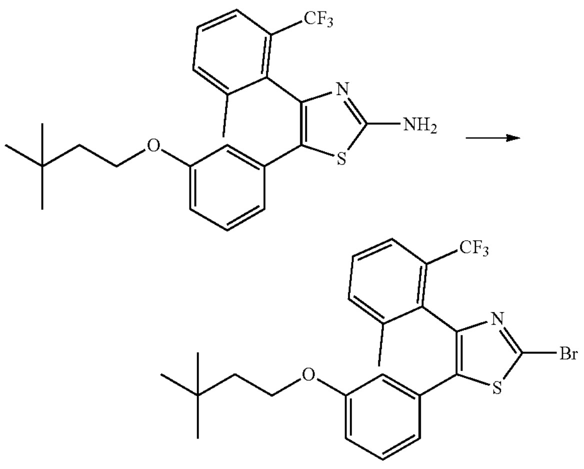

To a solution of 5-(3-(3,3-dimethylbutoxy)phenyl)-4-(2-methyl-6-(trifluoromethyl)phenyl)thiazol-2-amine (230 mg, 0.53 mmol) in anhydrous MeCN (10 mL) were added $CuBr_2$ (71 mg, 0.32 mmol) and tert-butyl nitrite (54.5 mg, 0.53 mmol) at room temperature. The resulting mixture was stirred at 80° C. for 15 min. An aliquot checked by LCMS analysis indicated that the reaction was completed. The reaction was quenched by addition of water (100 mL). The aqueous solution was extracted with ethyl acetate (100 mL×3). The combined organic layers were washed with brine (150 mL), dried over anhydrous sodium sulfate, concentrated to dryness to give the crude which was purified by silica gel column chromatography (PE/EA=20/1) to give 2-bromo-5-(3-(3,3-dimethylbutoxy)phenyl)-4-(2-methyl-6-(trifluoromethyl)phenyl)thiazole (150 mg, 56.8%) as a light yellow oil.

LCMS: LC retention time 2.36 min. MS (ESI) m/z 498 $[M+H]^+$.

Step 3.

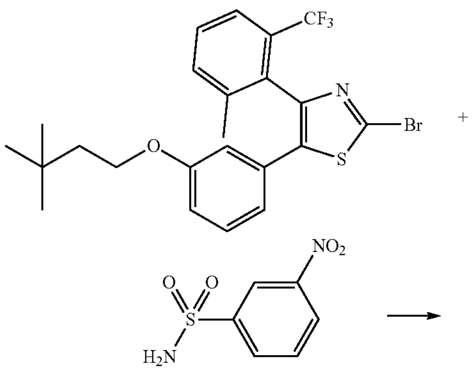

-continued

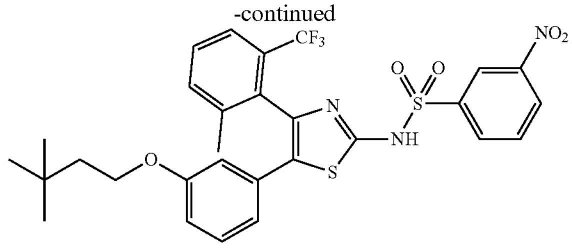

To a solution of 2-bromo-5-(3-(3,3-dimethylbutoxy)phenyl)-4-(2-methyl-6-(trifluoromethyl)phenyl)thiazole (150 mg, 0.30 mmol) in DMF (2 mL) were added 3-nitrobenzenesulfonamide (91.3 mg, 0.45 mmol), CuI (5.7 mg, 0.03 mmol), $K_2CO_3$ (124.2 mg, 0.9 mmol), N,N'-dimethyl-1,2-ethanediamine (13.3 mg, 0.15 mmol) under nitrogen in a glove-box. The reaction mixture was heated to 100° C. and stirred overnight. Then the mixture was cooled to room temperature and poured into water (100 mL). The resulting aqueous solution was extracted with ethyl acetate (80 mL×3). The organic solution was washed with brine (100 mL), dried over anhydrous $Na_2SO_4$, filtered and concentrated to dryness under reduced pressure to give the crude. The crude was purified by reversed-phase silica gel column chromatography to give the desired compound N-(5-(3-(3,3-dimethylbutoxy)phenyl)-4-(2-methyl-6-(trifluoromethyl)phenyl)thiazol-2-yl)-3-nitrobenzenesulfonamide (100 mg, 80.5%) as a white solid.

LCMS: LC retention time 2.39 min. MS (ESI) m/z 620 $[M+H]^+$.

Step 4.

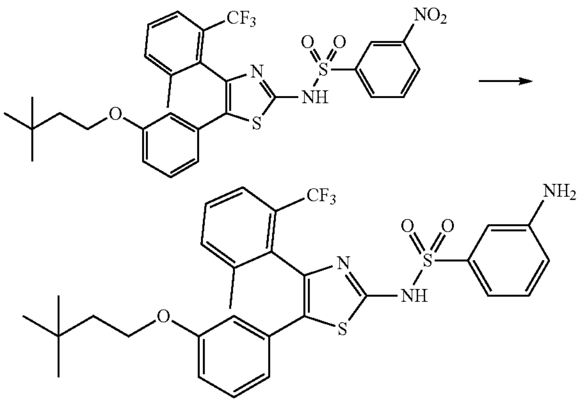

To a solution of N-(5-(3-(3,3-dimethylbutoxy)phenyl)-4-(2-methyl-6-(trifluoromethyl)phenyl)thiazol-2-yl)-3-nitrobenzenesulfonamide (100 mg, 0.16 mmol) in methanol (10 mL) and water (3 mL) were added iron powder (1.80 g, 3.23 mmol) and $NH_4Cl$ (1.73 g, 3.23 mmol). The reaction mixture was refluxed with stirring for 30 min. Then the mixture was concentrated to dryness under reduced pressure. The residue was diluted with ethyl acetate (80 mL), filtered through a Celite plug. The filtrate was washed with water (100 mL) and brine (100 mL), dried over anhydride $Na_2SO_4$ and filtered. The filtrate was concentrated to dryness in vacuo and the crude was purified by reversed-phase column and prep-TLC to give the title compound (18.9 mg, 19.9% yield) as a white solid.

LCMS: LC retention time 2.32 min. MS (ESI) m/z 590 $[M+H]^+$.

$^1$HNMR (400 MHz, chloroform-d) δ 7.65 (d, J=6.6 Hz, 1H), 7.52 (d, J=7.4 Hz, 2H), 7.34-7.27 (m, 2H), 7.11 (t, J=8.0 Hz, 1H), 6.78 (dd, J=25.4, 6.8 Hz, 2H), 6.63 (d, J=7.6 Hz, 1H), 6.45 (s, 1H), 3.74-3.60 (m, 2H), 2.15 (s, 3H), 1.60 (t, J=7.3 Hz, 2H), 0.92 (s, 9H) ppm.

Example 15

2-Amino-N-(5-(3-(3,3-dimethylbutoxy)-5-fluorophenyl)-4-(2-methyl-6-(trifluoromethyl)phenyl)thiazol-2-yl)pyridine-4-sulfonamide

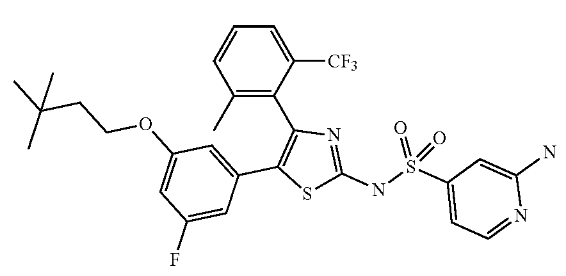 [SMILES: Cc1cccc(C(F)(F)F)c1-c1nc(NS(=O)(=O)c2ccnc(N)c2)sc1-c1cc(F)cc(OCCC(C)(C)C)c1]

Step 1.

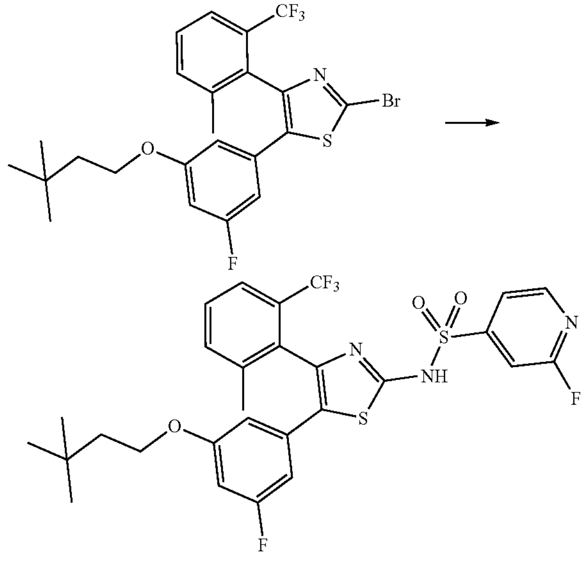

To a solution of 2-bromo-5-(3-(3,3-dimethylbutoxy)-5-fluorophenyl)-4-(2-methyl-6-(trifluoromethyl)phenyl)thiazole (obtained by the same protocol as synthesis of Example 14, step 1 and 2) (115 mg, 0.22 mmol) in NMP (1 mL) were added 2-fluoropyridine-4-sulfonamide, CuI (4.24 mg, cat.), (1S,2S)—N1,N2-dimethylcyclohexane-1,2-diamine (6.32 mg, cat.), and $Na_2CO_3$ (70.8 mg, 0.66 mmol). The reaction was stirred at 100° C. for 5 h under $N_2$ atmosphere. The mixture was diluted with brine (20 mL) after cooled to rt. The resulting aqueous solution was then extracted with EA (20 mL×3). The organic layers were combined and washed with brine (20 mL), dried over $Na_2SO_4$, and then concentrated. The residue was purified by prep-HPLC to give N-(5-(3-(3,3-dimethylbutoxy)-5-fluorophenyl)-4-(2-methyl-6-(trifluoromethyl)phenyl)thiazol-2-yl)-2-fluoropyridine-4-sulfonamide (60 mg, 44%) as a white solid.

LCMS: LC retention time 2.41 min. MS (ESI) m/z 612 $[M+H]^+$.

Step 2.

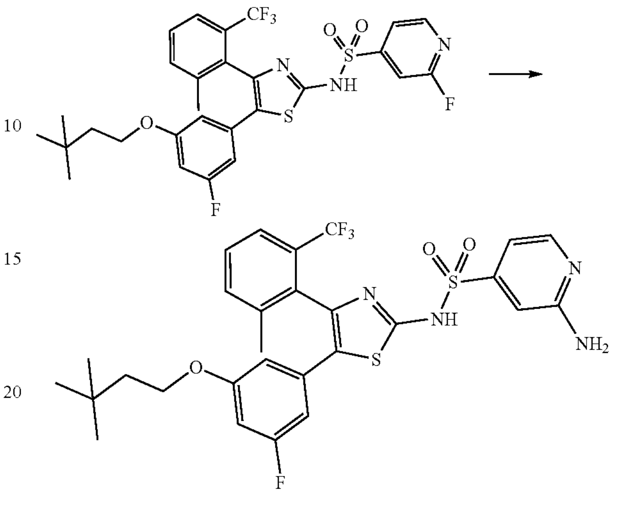

To a solution of N-(5-(3-(3,3-dimethylbutoxy)-5-fluorophenyl)-4-(2-methyl-6-(trifluoromethyl)phenyl)thiazol-2-yl)-2-fluoropyridine-4-sulfonamide (60 mg) in NMP (2 mL) was added $NH_3$—$H_2O$ (20 mL). The reaction was stirred at 130° C. for 16 h. The mixture was concentrated. The residue was purified by prep-HPLC to give 2-amino-N-(5-(3-(3,3-dimethylbutoxy)-5-fluorophenyl)-4-(2-methyl-6-(trifluoromethyl)phenyl)thiazol-2-yl)pyridine-4-sulfonamide (21.8 mg, 36.5%) as a yellow solid.

LCMS: LC retention time 1.4 min. MS (ESI) m/z 609 $[M+H]^+$.

$^1$HNMR (400 MHz, chloroform-d) δ 7.71 (d, J=6.8 Hz, 1H), 7.60 (m, 2H), 7.06 (s, 1H), 6.83 (m, 2H), 6.50 (d, J=10.4 Hz, 1H), 6.32 (m, 2H), 6.05 (s, 2H), 3.75 (m, 2H), 3.15 (s, 3H), 2.17 (s, 3H), 1.65 (t, J=7.2 Hz, 2H), 0.93 (s, 9H) ppm.

Example 16

N-(5-(3-(3,3-Dimethylbutoxy)phenyl)-4-(2,6-dimethylphenyl)thiazol-2-yl)benzenesulfonamide

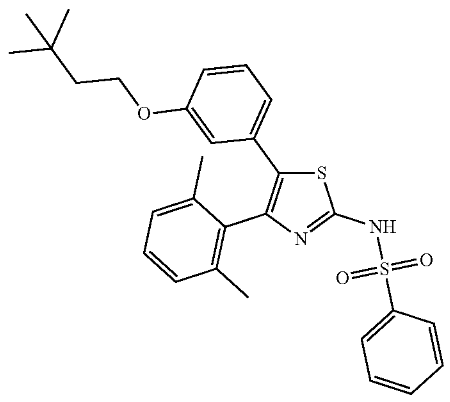 [SMILES: Cc1cccc(C)c1-c1nc(NS(=O)(=O)c2ccccc2)sc1-c1cccc(OCCC(C)(C)C)c1]

Step 1.

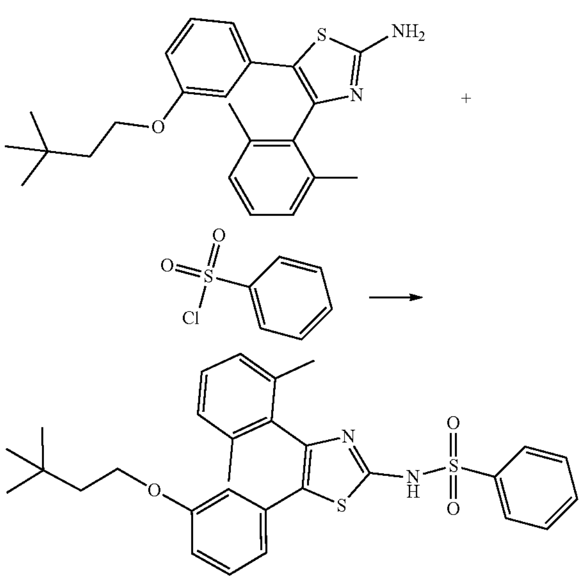

To a solution of 5-[3-(3,3-dimethylbutoxy)phenyl]-4-(2,6-dimethylphenyl)thiazol-2-amine (0.200 g, 0.526 mmol) (Intermediate C-6b) in pyridine (5.0 mL) was added benzenesulfonyl chloride (0.278 g, 1.58 mmol). The mixture was stirred at room temperature for 5 h. The mixture was diluted with water (10 mL). The resulting aqueous solution was extracted with EtOAc (10 mL×2). The combined organic phases were dried over anhydrous sodium sulfate, filtered, and concentrated in vacuo. The residue was purified by reversed phase column chromatography to afford the title compound (0.11 g, 61.3%).

LCMS (acid): LC retention time 2.36 min. MS (ESI) m/z 521 $[M+H]^+$.

$^1$HNMR (400 MHz, Chloroform-d) (8.00-7.94 (m, 2H), 7.59-7.45 (m, 3H), 7.30-7.26 (m, 1H), 7.15-7.09 (m, 3H), 6.76-6.66 (m, 2H), 6.47 (t, J=2.0 Hz, 1H), 3.62 (t, J=7.2 Hz, 2H), 2.13 (s, 6H), 1.59 (t, J=7.2 Hz, 2H), 0.92 (s, 9H) ppm.

Example 17

N-(5-(3-(3,3-Dimethylbutoxy)-5-fluorophenyl)-4-(2,6-dimethylphenyl)thiazol-2-yl)benzenesulfonamide

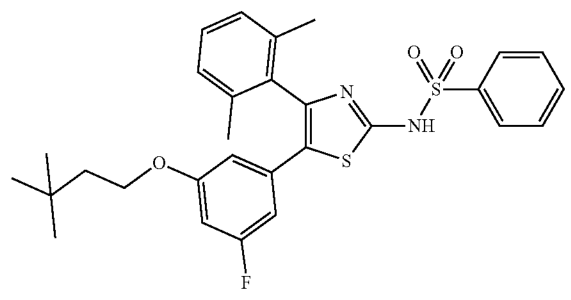 [SMILES: Cc1cccc(C)c1-c1nc(NS(=O)(=O)c2ccccc2)sc1-c1cc(F)cc(OCCC(C)(C)C)c1]

Step 1.

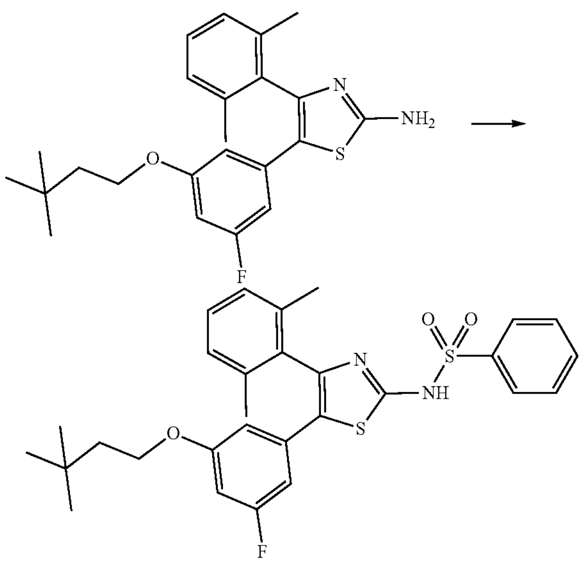

The mixture of 5-[3-(3,3-dimethylbutoxy)-5-fluoro-phenyl]-4-(2,6-dimethylphenyl)thiazol-2-amine (Intermediate C-6a) (300 mg, 0.75 mmol) in pyridine (3.0 mL) was added benzenesulfonyl chloride (0.192 mL, 1.51 mmol). The reaction was stirred at 130° C. in a microwave oven for 3 h. The reaction was cooled to rt and then diluted with brine (20 mL). The aqueous solution was extracted with ethyl acetate (40 mL×2). The combined organics were dried over anhydrous sodium sulfate, filtered and concentrated. The residue was purified by Prep-HPLC to afford the title compound, N-[5-[3-(3,3-dimethylbutoxy)-5-fluoro-phenyl]-4-(2,6-dimethylphenyl)thiazol-2-yl]benzenesulfonamide (206 mg, 51%) as a white solid.

LCMS: LC retention time 1.76 min. MS (ESI) m/z 539 $[M+H]^+$.

$^1$H NMR (400 MHz, chloroform-d) δ 9.73 (s, 1H), 7.91 (d, J=7.5 Hz, 2H), 7.52 (dt, J=32.1, 7.3 Hz, 3H), 7.35-7.04 (m, 3H), 6.55-6.21 (m, 3H), 3.66 (t, J=7.2 Hz, 2H), 2.13 (s, 6H), 1.61 (t, J=7.1 Hz, 2H), 0.95 (s, 9H) ppm.

Example 18

3-Amino-N-(5-(3-(3,3-dimethylbutoxy)phenyl)-4-(2-isopropylphenyl)thiazol-2-yl)benzenesulfonamide

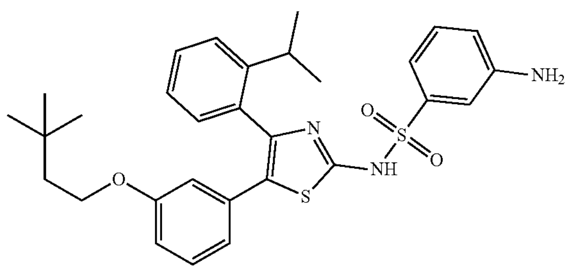 [SMILES: CC(C)c1ccccc1-c1nc(NS(=O)(=O)c2cccc(N)c2)sc1-c1cccc(OCCC(C)(C)C)c1]

Step 1.

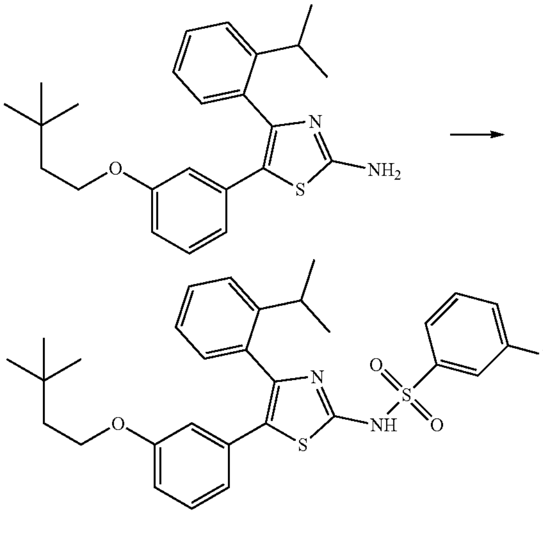

To a solution of Intermediate C-1 (300 mg, 0.76 mmol) in pyridine (10 mL) was added 3-nitrobenzenesulfonyl chloride (336 mg, 1.52 mmol). The reaction was stirred at room temperature for 4 h. The mixture was diluted with brine (50 mL). The resulting aqueous solution was extracted with EA (50 mL×3). The organic layers were combined and washed with brine (100 mL×2), dried over $Na_2SO_4$, filtered and concentrated. The residue was purified by SGC (PE/EA=3/1) to obtain N-(5-(3-(3,3-dimethylbutoxy)phenyl)-4-(2-isopropylphenyl)thiazol-2-yl)-3-nitrobenzenesulfonamide (350 mg, 79.4%) as a yellow oil.

LCMS: LC retention time 2.545 min. MS (ESI) m/z 580 $[M+H]^+$.

Step 2.

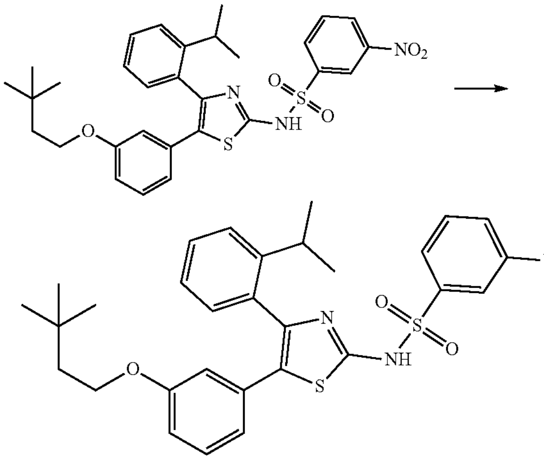

To a solution of N-(5-(3-(3,3-dimethylbutoxy)phenyl)-4-(2-isopropylphenyl)thiazol-2-yl)-3-nitrobenzenesulfonamide (350 mg, 0.604 mmol) in $MeOH/H_2O$ (20 mL/20 mL) were added $NH_4Cl$ (640 mg, 1.21 mmol) and Fe powder (664 mg, 1.21 mmol). The reaction was stirred at reflux for 1 h. Then, the solvent was evaporated. To the residue was added EA (50 mL) and filtered. The filtrate was concentrated and the crude was purified by Prep-HPLC ($CH_3CN/H_2O$: 80/20) to obtain 3-amino-N-(5-(3-(3,3-dimethylbutoxy)phenyl)-4-(2-isopropylphenyl)thiazol-2-yl)benzenesulfonamide (320 mg, 96.4%) as a white solid.

LCMS: LC retention time 2.393 min. MS (ESI) m/z 550 $[M+H]^+$.

$^1H$ NMR (400 MHz, chloroform-d) δ 7.50-7.35 (m, 4H), 7.29-7.25 (m, 3H), 7.16 (t, J=8.0 Hz, 1H), 6.85-6.82 (m, 1H), 6.77-6.72 (m, 2H), 6.51-6.50 (m, 1H), 3.65 (t, J=7.6 Hz, 2H), 2.88-2.85 (m, 1H), 1.62 (t, J=7.6 Hz, 2H), 1.08 (s, 6H), 0.93 (s, 9H) ppm.

Example 19

N-(3-(N-(5-(3-(3,3-Dimethylbutoxy)phenyl)-4-(2-(trifluoromethyl)phenyl)thiazol-2-yl)sulfamoyl)phenyl)cyclopropanecarboxamide

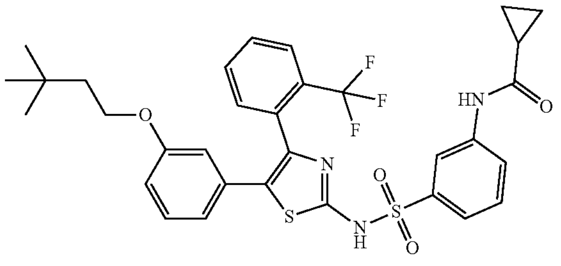 [SMILES: CC(C)(C)CCOc1cccc(-c2sc(NS(=O)(=O)c3cccc(NC(=O)C4CC4)c3)nc2-c2ccccc2C(F)(F)F)c1]

Step 1.

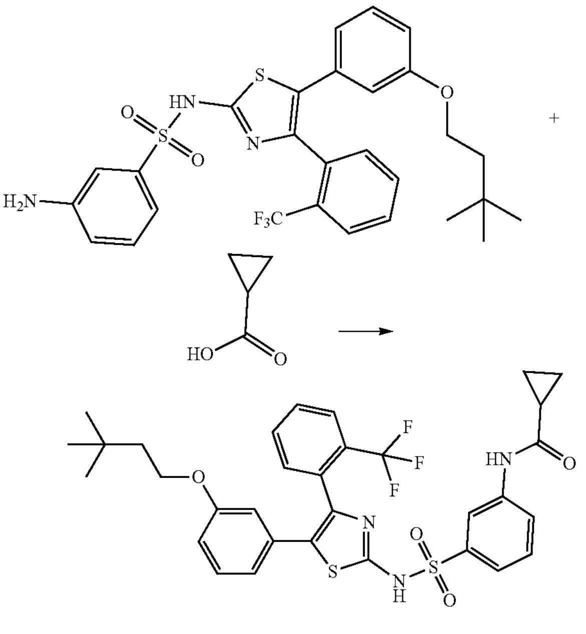

To a solution of Example 8 (80 mg, 0.139 mmol) in $CH_2Cl_2$ (5 mL) were added HATU (110 mg, 0.289 mmol), cyclopropanecarboxylic acid (20 mg, 0.232 mmol) and TEA (85 mg, 0.842 mmol) at room temperature. The resulting solution was stirred at room temperature for 2.5 h and then concentrated. The crude product thus obtained was purified by Prep-HPLC to give the title compound (80 mg, 90%) as a yellow solid.

LCMS: LC retention time 2.24 min. MS (ESI) m/z 644 $[M+H]^+$.

$^1$H NMR (400 MHz, methanol-$d_4$) δ 8.28 (s, 1H), 7.87 (t, J=5.2 Hz, 1H), 7.79 (d, J=7.6 Hz, 1H), 7.72 (t, J=4.0 Hz, 2H), 7.66 (d, J=7.6 Hz, 1H), 7.58-7.57 (m, 1H), 7.49 (t, J=8.0 Hz, 1H), 7.17 (t, J=8.0 Hz, 1H), 6.79-6.76 (m, 2H), 6.49 (s, 1H), 3.70 (t, J=7.2 Hz, 2H), 1.82-1.76 (m, 1H), 1.59 (t, J=7.2 Hz, 2H), 0.99-0.98 (m, 2H), 0.94 (s, 9H), 0.90-0.87 (m, 2H) ppm.

Example 20

N-(3-(N-(5-(3-(3,3-Dimethylbutoxy)phenyl)-4-(2-(trifluoromethyl)phenyl)thiazol-2-yl)sulfamoyl)phenyl)-1-fluorocyclopropane-1-carboxamide

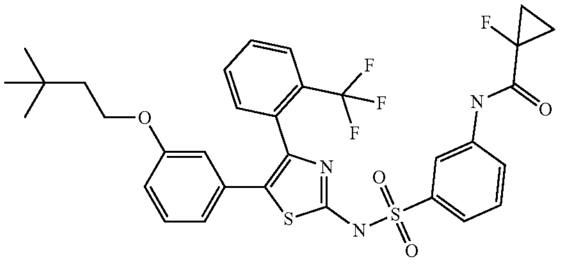 [SMILES: CC(C)(C)CCOc1cccc(-c2sc(NS(=O)(=O)c3cccc(NC(=O)C4(F)CC4)c3)nc2-c2ccccc2C(F)(F)F)c1]

Example 20 was synthesized in essentially the same protocols as Example 19.

LCMS: LC retention time 2.26 min. MS (ESI) m/z 662 $[M+H]^+$.

$^1$HNMR (400 MHz, methanol-$d_4$) δ 8.39 (s, 1H), 7.89-7.85 (m, 2H), 7.74-7.72 (m, 3H), 7.58 (t, J=4.0 Hz, 1H), 7.53 (t, J=8.0 Hz, 1H), 7.17 (t, J=8.0 Hz, 1H), 6.79 (d, J=8.0 Hz, 2H), 6.49 (s, 1H), 3.71 (t, J=6.8 Hz, 2H), 1.59 (t, J=7.2 Hz, 2H), 1.44-1.41 (m, 2H), 0.95 (s, 9H) ppm.

Example 21

N-(5-(3-(3,3-Dimethylbutoxy)phenyl)-4-(2-isopropylphenyl)thiazol-2-yl)-3-(methylamino)benzenesulfonamide

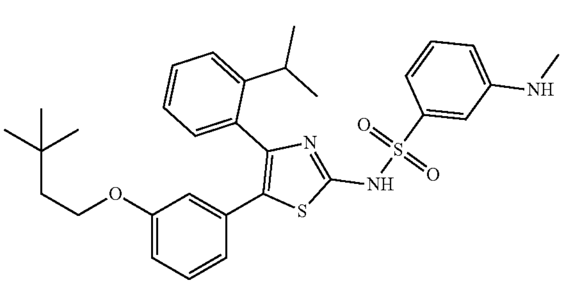 [SMILES: CNc1cccc(S(=O)(=O)Nc2nc(-c3ccccc3C(C)C)c(-c3cccc(OCCC(C)(C)C)c3)s2)c1]

Step 1.

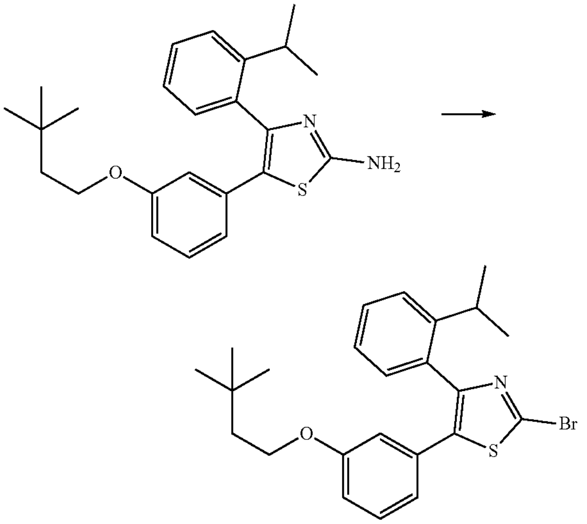

To a solution of Intermediate C-1 (1.0 g, 2.53 mmol) in anhydrous MeCN (20 mL) were added $CuBr_2$ (339 mg, 1.52 mmol) and tert-butylnitrite (261 mg, 2.53 mmol) at room temperature. The resulting mixture was stirred and refluxed for 15 min. An aliquot was checked by LCMS analysis which indicated that the reaction was completed. The reaction was quenched by addition of water (80 mL). The resulting aqueous solution was extracted with ethyl acetate (80 mL×3). The combined organic layers were washed with brine (100 mL), dried over anhydrous sodium sulfate, concentrated to dryness to give the crude product which was purified by silica gel column chromatography (PE/EA=3/1) to give 2-bromo-5-(3-(3,3-dimethylbutoxy)phenyl)-4-(2-isopropylphenyl)thiazole (1.0 g, 81.8%) as a yellow solid.

LCMS: LC retention time 2.627 min. MS (ESI) m/z 458 $[M+H]^+$.

Step 2.

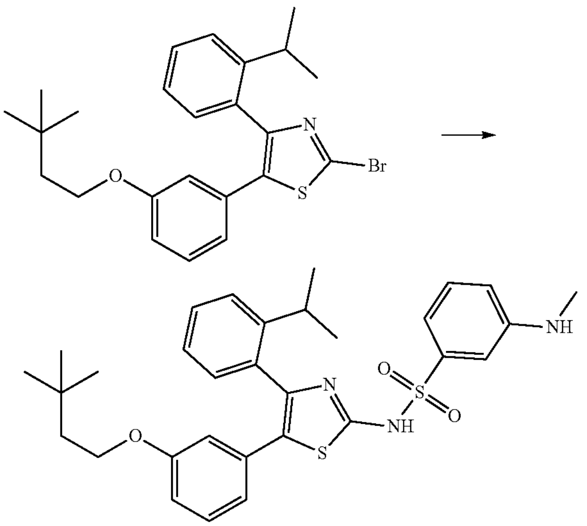

To a solution of 2-bromo-5-(3-(3,3-dimethylbutoxy)phenyl)-4-(2-isopropylphenyl)thiazole (300 mg, 0.654 mmol) in NMP (8 mL) were added 3-(methylamino)benzenesulfonamide (158 mg, 0.849 mmol), $Na_2CO_3$ (208 mg, 19.6 mmol), (1R,2R)—$N_1$,$N_2$-dimethylcyclohexane-1,2-diamine (18.6 mg, 0.131 mmol) and CuI (12.4 mg, 0.0654 mmol) at rt under nitrogen. The mixture was stirred at 100° C. for 16 h. Then, the reaction was cooled to rt. To the mixture was added water (20 mL). The resulting aqueous was extracted with ethyl acetate (60 mL×2). The combined organic solutions were washed with brine (80 mL), dried over sodium sulfate, filtered and concentrated. The residue was purified by Prep-HPLC to obtain N-(5-(3-(3,3-dimethylbutoxy)phenyl)-4-(2-isopropylphenyl)thiazol-2-yl)-3-(methylamino) benzenesulfonamide (280 mg, 75.1%) as a yellow solid.

LCMS: LC retention time 2.534 min. MS (ESI) m/z 564 $[M+H]^+$.

$^1$HNMR (400 MHz, chloroform-d) δ 7.49-7.41 (m, 2H), 7.33-7.24 (m, 5H), 7.15 (t, J=8.0 Hz, 1H), 6.78-6.72 (m, 3H), 6.51 (m, 1H), 3.65 (t, J=7.2 Hz, 2H), 2.89 (s, 3H), 2.87-2.85 (m, 1H), 1.62 (t, J=7.2 Hz, 2H), 1.08 (s, 6H), 0.94 (s, 9H) ppm.

Example 22

3-(Difluoromethyl)-N-(5-(3-(3,3-dimethylbutoxy)phenyl)-4-(2,6-dimethylphenyl)thiazol-2-yl)benzenesulfonamide

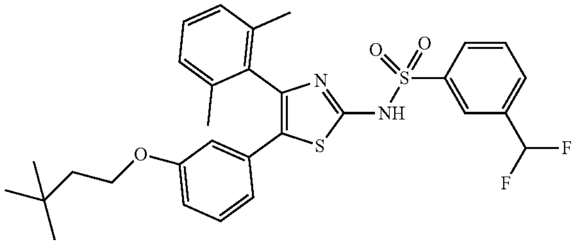 [SMILES: Cc1cccc(C)c1-c1nc(NS(=O)(=O)c2cccc(C(F)F)c2)sc1-c1cccc(OCCC(C)(C)C)c1]

Step 1.

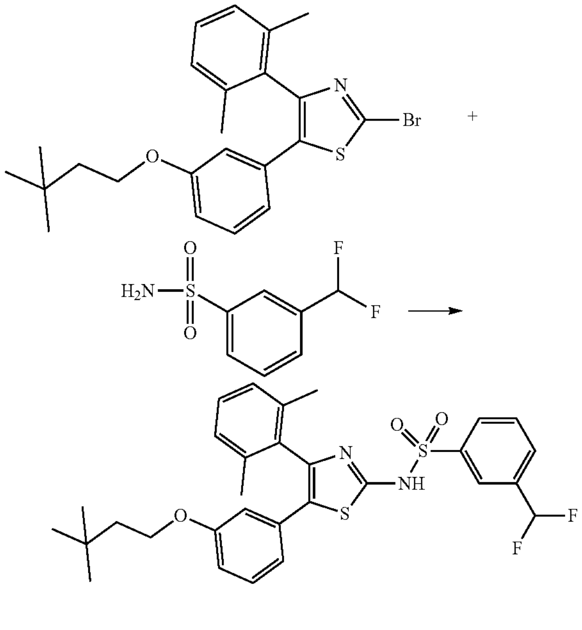

To a solution of 2-bromo-5-[3-(3,3-dimethylbutoxy)phenyl]-4-(2,6-dimethylphenyl)thiazole (Intermediate G-1b) (100 mg, 0.23 mmol) in DMF (2.0 mL) were added 3-(difluoromethyl)benzenesulfonamide (Intermediate R-8) (56 mg, 0.27 mmol), potassium carbonate (78 mg, 0.56 mmol), cuprous iodide (5 mg, cat.) and N,N'-dimethyl-1,2-ethanediamine (4 mg, cat.) in a glove-box. The resulting mixture was heated at 100° C. overnight. The mixture was cooled to rt and then diluted with ethyl acetate (80 mL). The organic was washed with saturated aqueous $NaHCO_3$ (50 mL), water (50 mL) and brine. The organic solution was concentrated under reduced pressure, and the residue was purified by prep-HPLC to afford the title compound (49.4 mg, 39%) as a white solid.

LCMS: LC retention time 2.43 min. MS (ESI) m/z 571 $[M+H]^+$.

$^1$HNMR (400 MHz, chloroform-d) δ 9.06 (s, 1H), 8.15-8.12 (m, 2H), 7.73 (d, J=8 Hz, 1H), 7.65-7.61 (t, J=8 Hz; 7.6 Hz, 1H), 7.33-7.29 (t, J=8 Hz; 7.2 Hz, 1H), 7.17-7.13 (m, 3H), 6.87-6.59 (m, 3H), 6.50 (m, 1H), 3.67-3.63 (t, J=7.2 Hz; 7.6 Hz, 2H), 2.16 (s, 6H), 1.64-1.60 (t, J=7.6 Hz; 7.2 Hz, 2H), 0.95 (s, 9H) ppm.

Example 23

3-Amino-N-(5-(3-(2,2-difluoro-3,3-dimethylbutoxy)phenyl)-4-(2-isopropylphenyl)thiazol-2-yl)-2-fluorobenzenesulfonamide

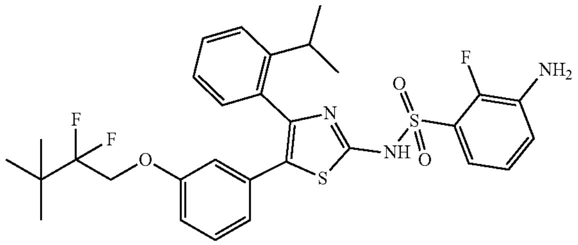 [SMILES: CC(C)c1ccccc1-c1nc(NS(=O)(=O)c2cccc(N)c2F)sc1-c1cccc(OCC(F)(F)C(C)(C)C)c1]

Step 1.

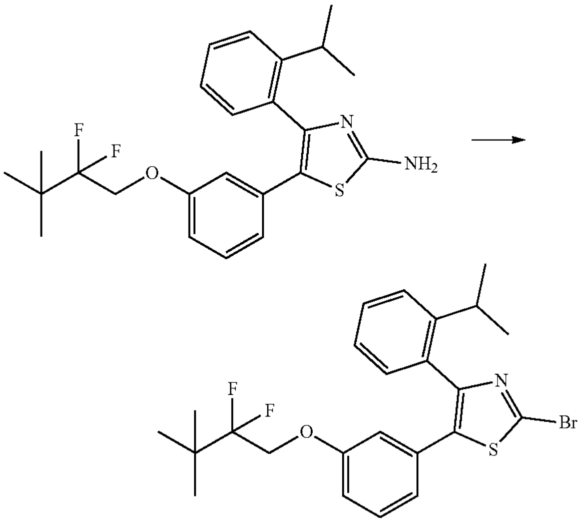

To a solution of Intermediate C-3 (320 mg, 0.74 mmol) in anhydrous MeCN (10 mL) was added $CuBr_2$ (84.7 mg, 0.45 mmol) and tert-butyl nitrite (76.6 mg, 0.74 mmol) at room temperature. The resulting mixture was stirred at 80° C. for 15 min. An aliquot was checked by LCMS analysis which indicated that the reaction was completed. The reaction was quenched by addition of water (80 mL). The resulting aqueous was extracted with ethyl acetate (80 mL×3). The combined organic layers were washed with brine (100 mL), dried over anhydrous sodium sulfate, concentrated to dryness to give the crude product which was purified by silica gel column chromatography (PE/EA=20/1) to give the desired compound, 2-bromo-5-(3-(2,2-difluoro-3,3-dimethylbutoxy)phenyl)-4-(2-isopropylphenyl)thiazole (250 mg, 68.0%) as a light yellow oil.

LCMS: LC retention time 2.32 min. MS (ESI) m/z 495 $[M+H]^+$.

Step 2.

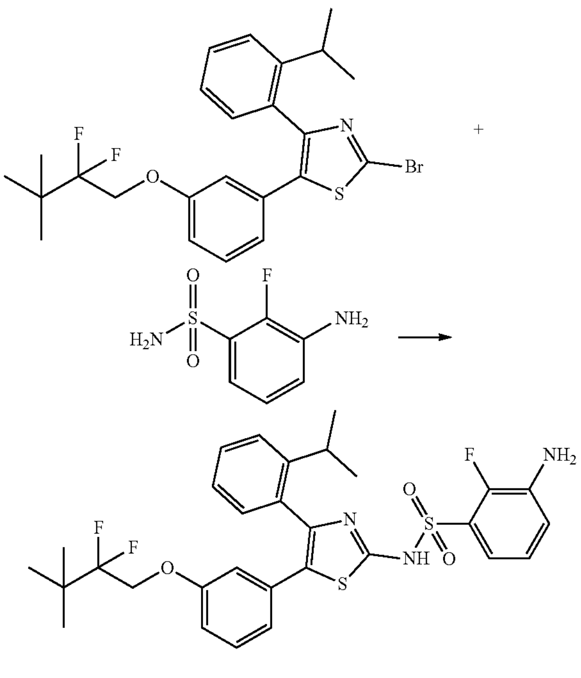

To a solution of 2-bromo-5-(3-(2,2-difluoro-3,3-dimethylbutoxy)phenyl)-4-(2-isopropylphenyl)thiazole (200 mg, 0.41 mmol) in DMF (8 mL) were added 3-amino-2-fluorobenzenesulfonamide (115.0 mg, 0.61 mmol), CuI (7.7 mg, 0.04 mmol), $K_2CO_3$ (167 mg, 1.21 mmol), and N, N'-dimethyl-1,2-ethanediamine (17.9 mg, 0.21 mmol) under nitrogen in a glove-box. The reaction mixture was heated to 100° C. and stirred overnight. Then, the mixture was cooled to room temperature and poured into water (50 mL). The resulting aqueous solution was extracted with ethyl acetate (30 mL×3). The ethyl acetate extracts were combined and washed with brine (30 mL), dried over anhydrous $Na_2SO_4$, and filtered. The filtrate was concentrated to dryness under reduced pressure to give the crude product which was purified by reversed-phase column chromatography to give the title compound 3-amino-N-(5-(3-(2,2-difluoro-3,3-dimethylbutoxy)phenyl)-4-(2-isopropylphenyl)thiazol-2-yl)-2-fluorobenzenesulfonamide (54.9 mg, 22.5%) as a white solid.

LCMS: LC retention time 2.32 min. MS (ESI) m/z 604 $[M+H]^+$.

$^1$HNMR (400 MHz, chloroform-d) 7.53-7.45 (m, 1H), 7.41 (d, J=7.6 Hz, 1H), 7.36 (t, J=6.8 Hz, 1H), 7.32-7.27 (m, 2H), 7.16 (t, J=8.0 Hz, 1H), 7.03 (t, J=8.0 Hz, 1H), 6.95 (t, J=8.0 Hz, 1H), 6.81 (dd, J=19.6, 10.8 Hz, 2H), 6.55 (d, J=18.0 Hz, 1H), 3.87 (t, J=13.2 Hz, 2H), 2.85 (dd, J=13.6, 7.0 Hz, 1H), 0.99 (d, J=55.3 Hz, 15H) ppm.

Example 24

N-(5-(3-(2,2-Difluoro-3,3-dimethylbutoxy)-4-fluorophenyl)-4-(2-isopropylphenyl)thiazol-2-yl)-3-((3-hydroxy-3-methylcyclobutyl)amino)benzenesulfonamide

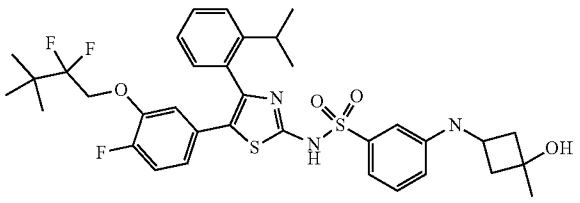 [SMILES: CC(C)c1ccccc1-c1nc(NS(=O)(=O)c2cccc(NC3CC(C)(O)C3)c2)sc1-c1ccc(F)c(OCC(F)(F)C(C)(C)C)c1]

Step 1.

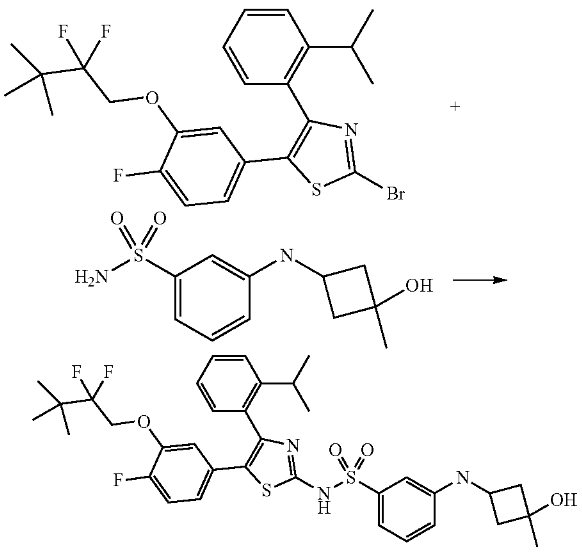

To a solution of Intermediate G-3 (100 mg, 0.195 mmol) in DMF (3 mL) were added 3-[(3-hydroxy-3-methyl-cyclobutyl)amino]benzenesulfonamide (60 mg, 0.234 mmol), potassium carbonate (81 mg, 0.585 mmol), cuprous iodide (4 mg, 0.0195 mmol) and N,N'-dimethyl-1,2-ethanediamine (5 mg, 0.0585 mmol). The resulting reaction mixture was stirred at 100° C. in a sealed tube under nitrogen atmosphere for 18 h. After cooling to room temperature, the reaction was diluted with water (60 mL). The resulting aqueous solution was extracted with ethyl acetate (30 mL×2). The combined organic layers were washed with brine (40 mL), dried over sodium sulfate, filtered and concentrated under reduced pressure. The residue was purified by prep-PLC to give the title compound as a white solid (72.5 mg, 54% yield).

LCMS: LC retention time 2.24 min. MS (ESI) m/z 688 $[M+H]^+$.

$^1$H NMR (400 MHz, chloroform-d) δ 7.48-7.39 (m, 2H), 7.30-7.21 (m, 4H), 7.17 (s, 1H), 6.99-6.94 (m, 1H), 6.78-6.75 (m, 1H), 6.68 (d, J=8.0 Hz, 1H), 6.57-6.54 (m, 1H), 3.85 (t, J=13.2 Hz, 2H), 3.56-3.50 (m, 1H), 2.84-2.77 (s, 1H), 2.63-2.58 (m, 2H), 1.98-1.93 (m, 2H), 1.37 (s, 3H), 1.06 (s, 9H), 1.03 (s, 6H) ppm.

Example 25

3-Amino-N-(5-(3-(3,3-dimethylbutoxy)-5-fluorophenyl)-4-(2,6-dimethylphenyl)thiazol-2-yl)-2-fluorobenzenesulfonamide

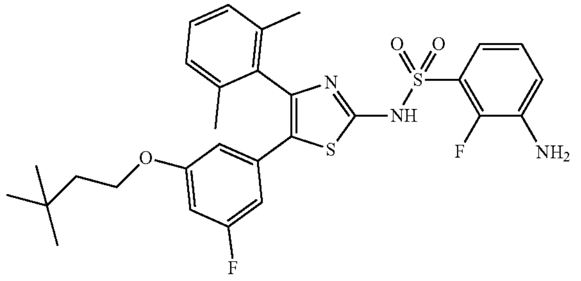 [SMILES: Cc1cccc(C)c1-c1nc(NS(=O)(=O)c2cccc(N)c2F)sc1-c1cc(F)cc(OCCC(C)(C)C)c1]

Step 1.

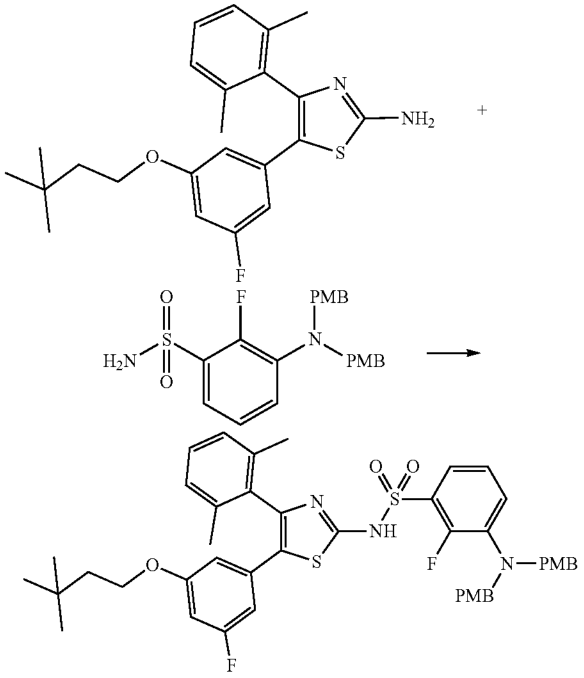

To a solution of 2-bromo-5-[3-(3,3-dimethylbutoxy)-5-fluoro-phenyl]-4-(2,6-dimethylphenyl)thiazole (Intermediate G-1a) (500 mg, 1.08 mmol) in NMP (10.0 mL) were added 3-[bis[(4-methoxyphenyl)methyl]amino]-2-fluoro-benzenesulfonamide (Intermediate R-10) (698 mg, 1.62 mmol), potassium carbonate (374 mg, 2.7 mmol), cuprous iodide (21 mg, cat.) and N,N'-dimethyl-1,2-ethanediamine (19 mg, cat.) in a glovebox. The resulting mixture was heated at 100° C. with stirring overnight. The mixture was cooled to rt, then diluted with ethyl acetate (80 mL). The organic solution was washed with saturated aqueous $NaHCO_3$ (50 mL), water (50 mL) and brine. The organic solution was then concentrated under reduced pressure. The residue was purified by FCC (DCM/MeOH=15/1) to afford the target compound, 3-[bis[(4-methoxyphenyl)methyl]amino]-N-[5-[3-(3,3-dimethylbutoxy)-5-fluoro-phenyl]-4-(2,6-dimethylphenyl)thiazol-2-yl]-2-fluoro-benzenesulfonamide (400 mg, 46%) as a yellow oil.

LCMS: LC retention time 2.67 min. MS (ESI) m/z 812 $[M+H]^+$

Step 2.

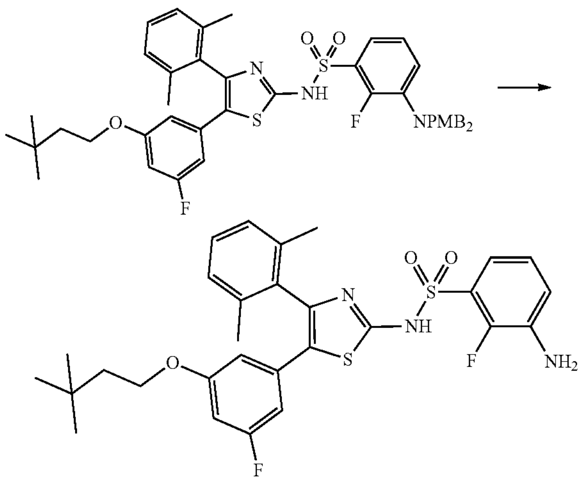

To a solution of 3-[bis[(4-methoxyphenyl)methyl]amino]-N-[5-[3-(3,3-dimethylbutoxy)-5-fluoro-phenyl]-4-(2,6-dimethylphenyl)thiazol-2-yl]-2-fluoro-benzenesulfonamide (50 mg, 0.06 mmol) in DCM (2.0 mL) was added TFA (2.0 mL). The resulting mixture was reacted at room temperature overnight. The solvent was removed under reduced pressure. The residue was dissolved in water (50 mL). The resulting aqueous was extracted with DCM (40 mL×2). The organic phase was evaporated to dryness. The residue was purified by prep-HPLC to afford the desired compound, 3-amino-N-[5-[3-(3,3-dimethylbutoxy)-5-fluoro-phenyl]-4-(2,6-dimethylphenyl)thiazol-2-yl]-2-fluoro-benzenesulfonamide (96 mg, 34%) as a white solid.

LCMS: LC retention time 2.36 min. MS (ESI) m/z=572 $[M+H]^+$.

$^1$H NMR (400 MHz, chloroform-d) δ 7.35-7.23 (m, 2H), 7.14 (d, J=7.6 Hz, 2H), 6.96 (dt, J=14.5, 7.8 Hz, 2H), 6.51-6.27 (m, 3H), 3.65 (t, J=7.2 Hz, 2H), 2.14 (s, 6H), 1.61 (t, J=7.2 Hz, 2H), 0.94 (s, 9H) ppm.

Example 26

5-Amino-N-(5-(3-(2,2-difluoro-3,3-dimethylbutoxy)-4-fluorophenyl)-4-(2-isopropylphenyl)thiazol-2-yl)-2-fluorobenzenesulfonamide

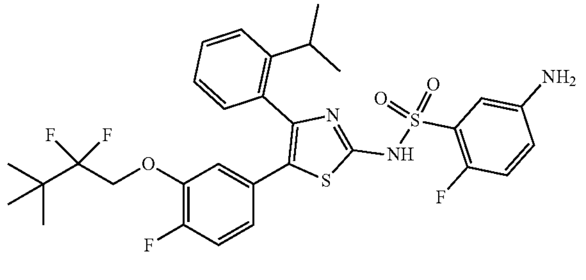 [SMILES: CC(C)c1ccccc1-c1nc(NS(=O)(=O)c2cc(N)ccc2F)sc1-c1ccc(F)c(OCC(F)(F)C(C)(C)C)c1]

Step 1.

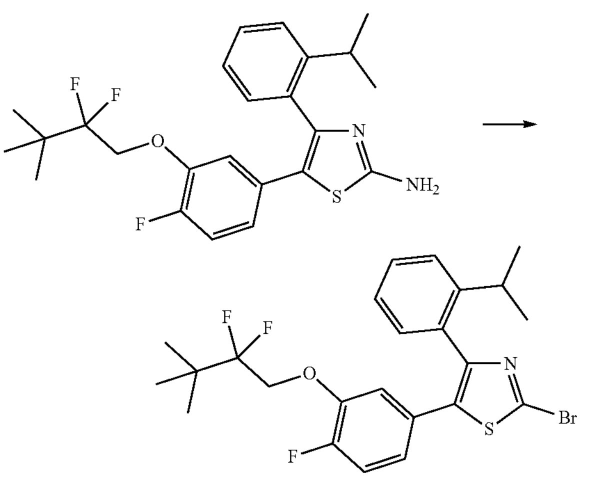

to the mixture of Intermediate C-2 (195 mg, 0.435 mmol) in acetonitrile (9 mL) were added cupric bromide (58 mg, 0.261 mmol) tert-butyl nitrite (45 mg, 0.435 mmol) under argon atmosphere at room temperature. The resulting mixture was stirred at 80° C. for 15 min. The reaction mixture was concentrated under reduced pressure and purified by silica gel chromatography (10% ethyl acetate in petroleum ether) to give the product 2-bromo-5-(3-(2,2-difluoro-3,3-dimethylbutoxy)-4-fluorophenyl)-4-(2-isopropylphenyl)thiazole (171 mg, 77% yield) as a yellow oil.

LCMS: LC retention time 2.27 min. MS (ESI) m/z 512 $[M+H]^+$.

Step 2.

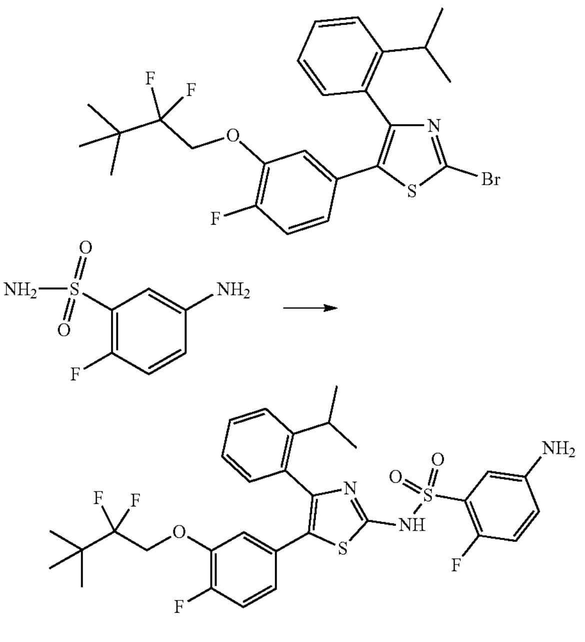

To a solution of 2-bromo-5-(3-(2,2-difluoro-3,3-dimethylbutoxy)-4-fluorophenyl)-4-(2-isopropylphenyl)thiazole (171 mg, 0.334 mmol) in anhydrous DMF (3 mL) were added 5-amino-2-fluoro-benzenesulfonamide (76 mg, 0.4 mmol), potassium carbonate (138 mg, 1.0 mmol), cuprous iodide (6 mg, 0.0334 mmol) and N,N'-dimethyl-1,2-ethanediamine (9 mg, 0.1 mmol). The resulting solution was stirred at 100° C. in a sealed tube under nitrogen atmosphere for 5 h. After cooling to room temperature, the reaction was diluted with water (30 mL). The aqueous was extracted with ethyl acetate (20 mL×2). The combined organic layers were washed with brine (40 mL), dried over sodium sulfate, filtered and concentrated under reduced pressure. The residue was purified by prep-HPLC to give 5-amino-N-(5-(3-(2,2-difluoro-3,3-dimethylbutoxy)-4-fluorophenyl)-4-(2-isopropylphenyl)thiazol-2-yl)-2-fluorobenzenesulfonamide as a white solid (123.2 mg, 59% yield).

LCMS: LC retention time 2.25 min. MS (ESI) m/z 622 $[M+H]^+$.

$^1$H NMR (400 MHz, chloroform-d) δ 7.49-7.40 (m, 2H), 7.31-7.25 (m, 3H), 7.00-6.92 (m, 2H), 6.80-6.74 (m, 2H), 6.58-6.56 (m, 1H), 1.07 (t, J=13.2 Hz, 2H), 2.87-2.80 (m, 1H), 1.08 (m, 15H) ppm.

Example 27

N-(5-(3-(3,3-Dimethylbutoxy)phenyl)-4-(2,6-dimethylphenyl)thiazol-2-yl)-3-(methylamino)benzenesulfonamide

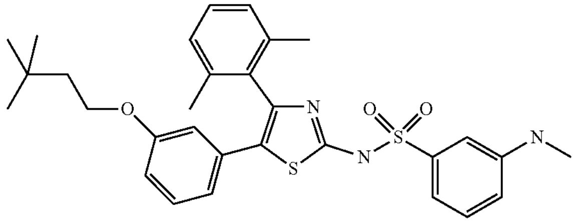 [SMILES: CNc1cccc(S(=O)(=O)Nc2nc(-c3c(C)cccc3C)c(-c3cccc(OCCC(C)(C)C)c3)s2)c1]

Step 1.

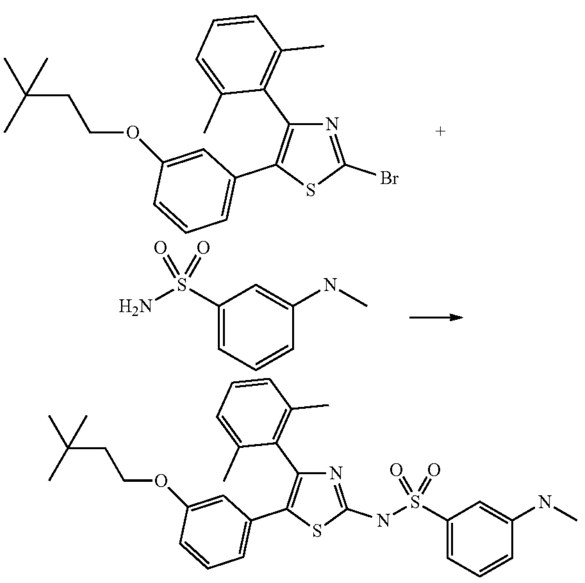

To a solution of 2-bromo-5-(3-(3,3-dimethylbutoxy)phenyl)-4-(2,6-dimethylphenyl)thiazole (Intermediate G-1a) (300 mg, 0.68 mmol) in NMP (5 mL) were added 3-(methylamino)benzenesulfonamide (126 mg, 0.68 mmol), $K_2CO_3$ (233 mg, 1.7 mmol), CuI (12.8 mg, 0.07 mmol), and N1,N2-dimethylcyclohexane-1,2-diamine (19.2 mg, 0.14 mmol). The resulting reaction mixture was stirred at 110° C. for 11 h. The mixture was then poured into water (10 mL). The resulting aqueous was extracted with EtOAc (10 mL×3). The combined organic extracts were dried over $Na_2SO_4$, filtered and concentrated. The residue was purified by reversed phase flash chromatography to give N-[5-[3-(3,3-dimethylbutoxy)phenyl]-4-(2,6-dimethylphenyl)thiazol-2-yl]-3-(methylamino)benzenesulfonamide (226 mg, 61%) as a light yellow solid.

LCMS: LC retention time 1.80 min. MS (ESI) m/z 550 $[M+H]^+$.

$^1$HNMR (400 MHz, chloroform-d) (7.26 (s, 4H), 7.12-7.08 (m, 2H), 6.73-6.66 (m, 3H), 6.45 (s, 1H), 3.59 (t, J=6.4 Hz, 2H), 2.81 (s, 3H), 2.09 (s, 6H), 1.58 (t, J=7.2 Hz, 2H), 0.92 (s, 9H) ppm.

Example 28

N-(5-(3-((3,3-Dimethylcyclopentyl)oxy)phenyl)-4-(2,6-dimethylphenyl)thiazol-2-yl)-3-(1H-pyrazol-1-yl)benzenesulfonamide

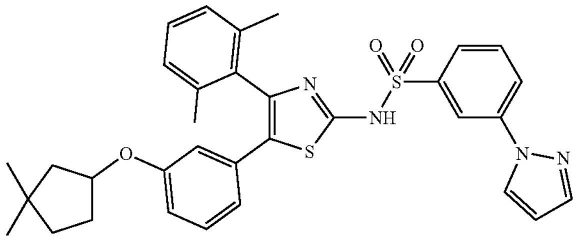 [SMILES: Cc1cccc(C)c1-c1nc(NS(=O)(=O)c2cccc(-n3cccn3)c2)sc1-c1cccc(OC2CCC(C)(C)C2)c1]

Step 1.

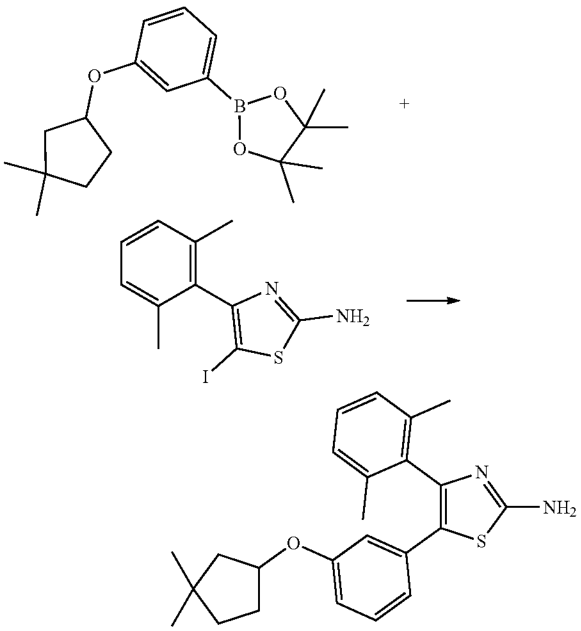

To a solution of 2-[3-(3,3-dimethylcyclopentoxy)phenyl]-4,4,5,5-tetramethyl-1,3,2-dioxaborolane (Intermediate D-11b) (4.11 g, 13.0 mmol) in toluene/EtOH/$H_2O$ (4/2/1, 175 mL) were added 4-(2,6-dimethylphenyl)-5-iodo-thiazol-2-amine (Intermediate B-2b) (3.30 g, 10.0 mmol), sodium carbonate (3.18 g, 30.0 mmol) and tetrakis (triphenylphosphine)palladium (O) (809 mg, 0.70 mmol). The reaction was heated at 90° C. overnight. The solvent was removed under reduced pressure. The residue was dissolved in ethyl acetate (80 mL). The organic solution was washed with brine (50 mL×2). The combined organic extracts were dried over anhydrous sodium sulfate, filtered and concentrated. The residue was purified by FCC (PE/EA=3/1) to afford the crude product which was purified by prep-HPLC (ACN/water=70%) to obtain the desired compound 5-[3-(3,3-dimethylcyclopentoxy)phenyl]-4-(2,6-dimethylphenyl) thiazol-2-amine (700 mg, 18% yield) as a brown oil.

LCMS: LC retention time 1.48 min. MS (ESI) m/z 393 $[M+H]^+$.

Step 2.

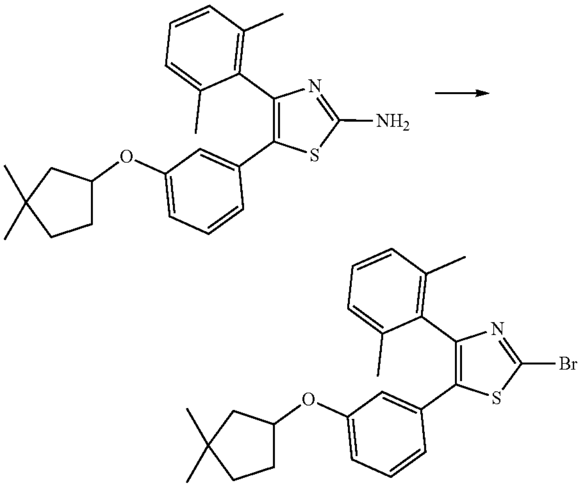

To a suspension of 5-[3-(3,3-dimethylcyclopentoxy)phenyl]-4-(2,6-dimethylphenyl)thiazol-2-amine (320 mg, 0.82 mmol) in acetonitrile (10 mL) were added $CuBr_2$ (145 mg, 0.65 mmol) and tert-butyl nitrite (84 mg, 0.82 mmol) under argon atmosphere. The resulting mixture was heated up to 80° C. for 15 min. The reaction was cooled to rt and concentrated under reduced pressure. The residue was purified by FCC (PE/EA=20/1) to afford the desired compound 2-bromo-5-[3-(3,3-dimethylcyclopentoxy)phenyl]-4-(2,6-dimethylphenyl)thiazole (240 mg, 65%) as a colorless oil.

LCMS: LC retention time 1.97 min. MS (ESI) m/z 456 $[M+H]^+$.

Step 3.

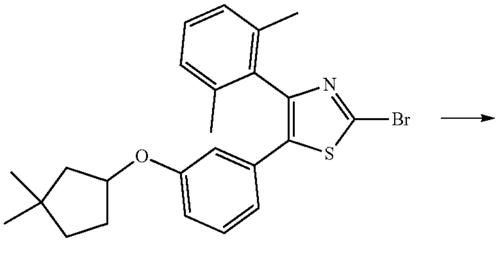

-continued

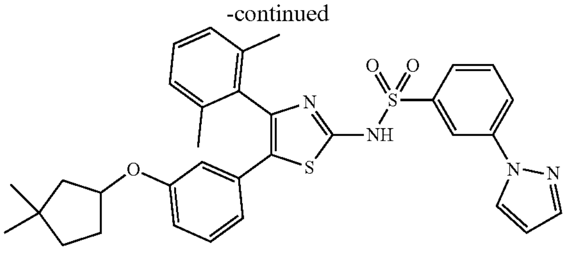

To a solution of 2-bromo-5-[3-(3,3-dimethylcyclopentoxy)phenyl]-4-(2,6-dimethylphenyl)thiazole (120 mg, 0.26 mmol) in DMF (5.0 mL) were added 3-pyrazol-1-ylbenzenesulfonamide (Intermediate R-7) (70 mg, 0.32 mmol), potassium carbonate (109 mg, 0.79 mmol), cuprous iodide (5 mg, 0.02 mmol) and N,N'-dimethyl-1,2-ethanediamine (5 mg, 0.05 mmol) under nitrogen atmosphere. The resulting mixture was heated up to 100° C. overnight before cooling to rt and quenching with water (150 mL). The aqueous was extracted with ethyl acetate (50 mL×2). The combined organics were washed with brine (10 mL) and concentrated to dryness under reduced pressure. The residue was purified by prep-HPLC to afford the target compound N-(5-(3-((3,3-dimethylcyclopentyl)oxy)phenyl)-4-(2,6-dimethylphenyl)thiazol-2-yl)-3-(1H-pyrazol-1-yl)benzenesulfonamide (29.1 mg, 19%) as a white solid.

$^1$H NMR (400 MHz, chloroform-d) δ 9.28 (s, 1H), 8.26 (s, 1H), 8.02-7.89 (m, 3H), 7.72 (s, 1H), 7.60 (t, 1H), 7.29 (m, 1H), 7.16-7.12 (m, 3H), 6.75-6.69 (m, 2H), 6.51 (s, 1H), 6.46 (s, 1H), 4.33 (m, 1H), 2.14 (d, J=6.4 Hz, 6H), 1.91-1.84 (m, 1H), 1.72-1.58 (m, 3H), 1.47-1.34 (m, 2H), 1.08 (s, 3H), 0.98 (s, 3H) ppm.

Example 29

N-(5-(3-((3,3-Dimethylcyclopentyl)oxy)phenyl)-4-(2,6-dimethylphenyl)thiazol-2-yl)-3-(1H-pyrazol-5-yl)benzenesulfonamide

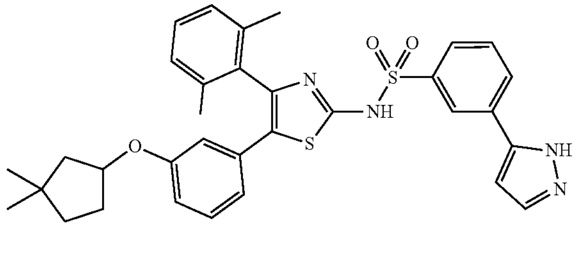 [SMILES: Cc1cccc(C)c1-c1nc(NS(=O)(=O)c2cccc(-c3ccn[nH]3)c2)sc1-c1cccc(OC2CCC(C)(C)C2)c1]

Step 1.

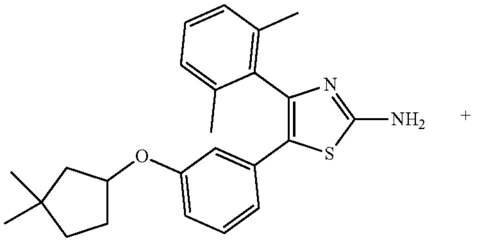

-continued

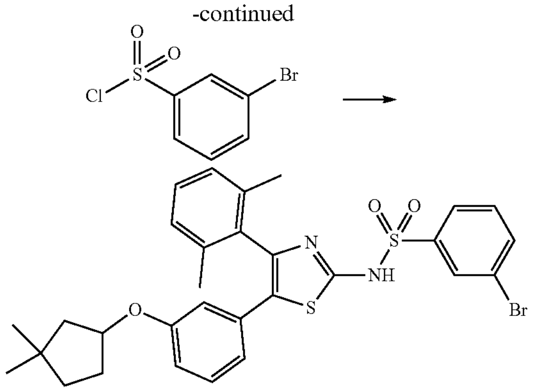

To a solution of 5-[3-(3,3-dimethylcyclopentoxy)phenyl]-4-(2,6-dimethylphenyl)thiazol-2-amine (380 mg, 0.97 mmol) in pyridine (4.0 mL) was added 3-bromobenzenesulfonyl chloride (495 mg, 1.94 mmol). The resulting solution was stirred at room temperature overnight. The solvent was removed by blowing nitrogen. The residue was diluted with ethyl acetate (50 mL). The organic phase was washed with saturated aqueous sodium bicarbonate (50 mL), brine, and then dried over anhydrous $Na_2SO_4$. After filtration and concentration, the residue was purified by FCC (PE/EA=3/1) to afford the desired compound, 3-bromo-N-(5-(3-((3,3-dimethylcyclopentyl)oxy)phenyl)-4-(2,6-dimethylphenyl)thiazol-2-yl)benzenesulfonamide (320 mg, 54%) as a yellow solid.

LCMS: LC retention time 1.82 min. MS (ESI) m/z 611 $[M+H]^+$.

$^1$HNMR (400 MHz, chloroform-d) δ 8.10 (s, 1H), 7.91 (d, J=8 Hz, 1H), 7.67 (d, J=7.6 Hz, 1H), 7.39-7.28 (m, 2H), 7.14 (m, 3H), 6.75-6.70 (m, 2H), 6.46 (s, 1H), 4.32 (m, 1H), 2.15 (d, J=5.6 Hz, 6H), 1.94-1.86 (m, 1H), 1.74-1.54 (m, 3H), 1.48-1.35 (m, 2H), 1.09 (s, 3H), 0.98 (s, 3H) ppm.

Step 2.

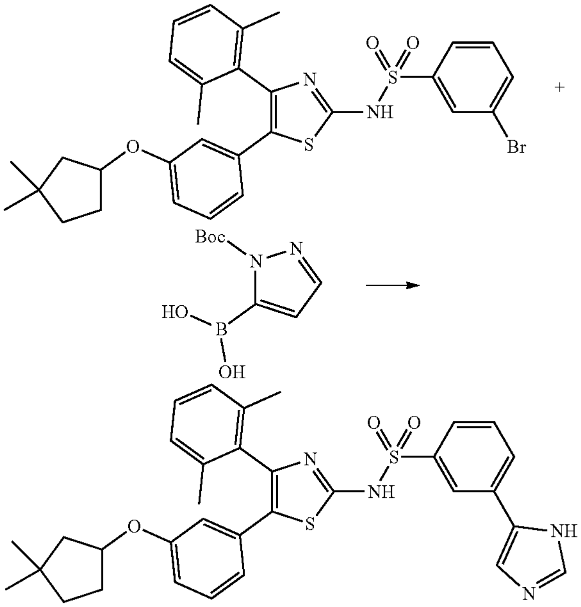

To a solution of 3-bromo-N-[5-[3-(3,3-dimethylcyclopentoxy)phenyl]-4-(2,6-dimethylphenyl)thiazol-2-yl]benzenesulfonamide (270 mg, 0.44 mmol) in toluene/ethanol/water=4/2/1 (total 17.5 ml) were added (2-tert-butoxycarbonylpyrazol-3-yl)boronic acid (112 mg, 0.53 mmol), sodium carbonate (140 mg, 1.32 mmol), and tetrakis (triphenylphosphine)palladium(O) (26 mg, cat.). The resulting mixture was heated up to reflux and stirred overnight. The solvent was removed under reduced pressure. The residue was diluted with ethyl acetate (80 ml), washed with brine (50 mL×2). The organics were dried over anhydrous sodium sulfate, filtered and concentrated. The residue was purified by Prep-HPLC to afford the desired compound, N-(5-(3-((3,3-dimethylcyclopentyl)oxy)phenyl)-4-(2,6-dimethylphenyl)thiazol-2-yl)-3-(1H-pyrazol-5-yl)benzenesulfonamide (53.9 mg, 20%) as a white solid.

LCMS: LC retention time 1.68 min. MS (ESI) m/z 599 $[M+H]^+$.

$^1H$ NMR (400 MHz, chloroform-d) δ 8.31 (s, 1H), 7.95 (d, J=7.6 Hz, 1H), 7.66 (d, J=7.6 Hz, 1H), 7.40 (t, 1H), 7.30 (m, 1H), 7.15-7.09 (m, 3H), 6.72 (m, 1H), 6.54 (s, 1H), 6.45 (s, 1H), 4.31 (m, 1H), 2.09 (d, J=5.6 Hz, 6H), 1.92-1.83 (m, 1H), 1.70-1.55 (m, 3H), 1.47-1.32 (m, 2H), 1.08 (s, 3H), 0.99 (s, 3H) ppm.

Example 30

6-Amino-N-(5-(3-(3,3-Dimethylbutoxy)phenyl)-4-(2-isopropylphenyl)thiazol-2-yl)pyridine-2-sulfonamide

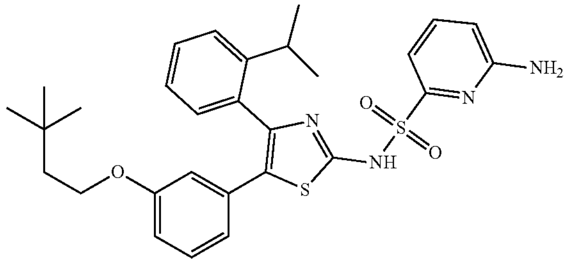 [SMILES: CC(C)c1ccccc1-c1nc(NS(=O)(=O)c2cccc(N)n2)sc1-c1cccc(OCCC(C)(C)C)c1]

Step 1.

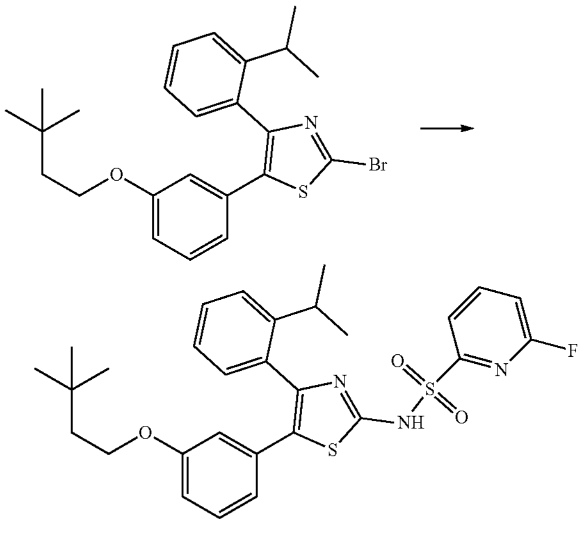

To a solution of 2-bromo-5-[3-(3,3-dimethylbutoxy)phenyl]-4-(2-isopropylphenyl)thiazole (Intermediate G-2b) (300 mg, 0.654 mmol) in NMP (6 mL) was added 6-fluoropyridine-2-sulfonamide (158 mg, 0.897 mmol), sodium carbonate (208 mg, 1.96 mmol), CuI (12.4 mg, 0.0654 mmol) and (1R,2R)—N1,N2-dimethylcyclohexane-1,2-diamine (18.6 mg, 0.131 mmol) under nitrogen. The mixture was stirred at 100° C. for 16 h. The mixture was cooled to rt and diluted with water (20 mL). The aqueous solution was extracted with ethyl acetate (40 mL×2). The combined organic layers were washed with brine (40 mL), dried over sodium sulfate and concentrated in vacuo. The residue was purified by prep-HPLC to obtain N-[5-[3-(3,3-dimethylbutoxy)phenyl]-4-(2-isopropylphenyl)thiazol-2-yl]-6-fluoro-pyridine-2-sulfonamide (250 mg, 66.9%) as a yellow solid.

LCMS: LC retention time 2.495 min. MS (ESI) m/z 554 $[M+H]^+$.

Step 2.

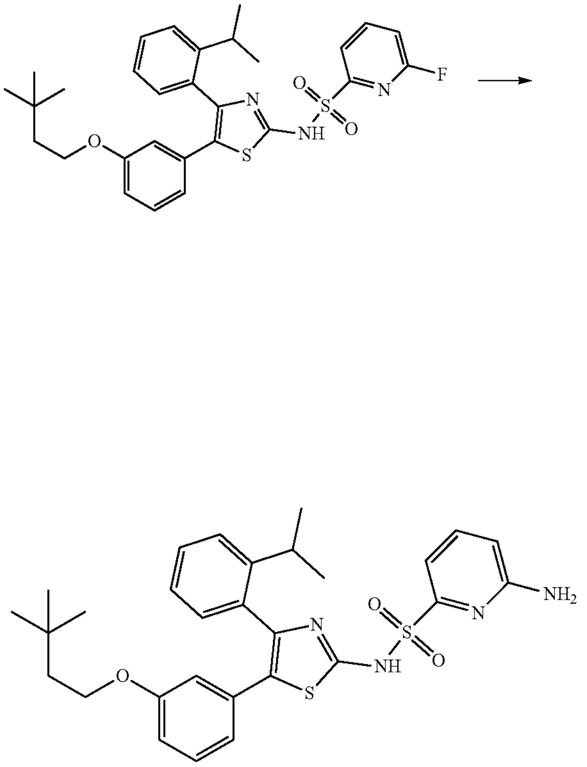

To a solution of N-[5-[3-(3,3-dimethylbutoxy)phenyl]-4-(2-isopropylphenyl)thiazol-2-yl]-6-fluoro-pyridine-2-sulfonamide (300 mg, 0.654 mmol) in NMP (6 mL) was added $NH_3 \cdot H_2O$ (3 mL). The solution was stirred at 130° C. in a sealed tube for 18 h. The mixture was diluted with water (10 mL). The resulting aqueous solution was extracted with EA (40 mL×3). The organic layers were combined and washed with brine (10 mL) and then concentrated. The residue was purified by prep-HPLC to give the title compound 6-amino-N-(5-(3-(3,3-dimethylbutoxy)phenyl)-4-(2-isopropylphenyl)thiazol-2-yl)pyridine-2-sulfonamide (53.2 mg, 11% yield) as a white solid.

LCMS: LC retention time 2.273 min. MS (ESI) m/z 551 $[M+H]^+$.

Example 31

6-Amino-N-(5-(3-(3,3-dimethylbutoxy)-5-fluorophenyl)-4-(2,6-dimethylphenyl)thiazol-2-yl)pyridine-2-sulfonamide

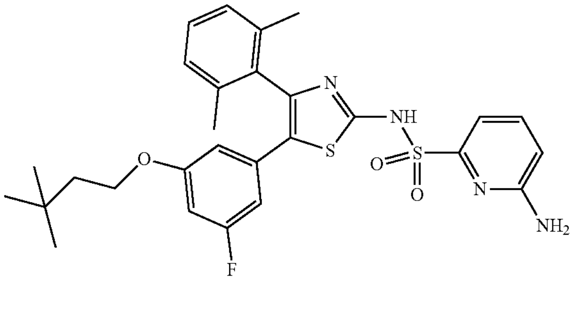 [SMILES: Cc1cccc(C)c1-c1nc(NS(=O)(=O)c2cccc(N)n2)sc1-c1cc(F)cc(OCCC(C)(C)C)c1]

Step 1.

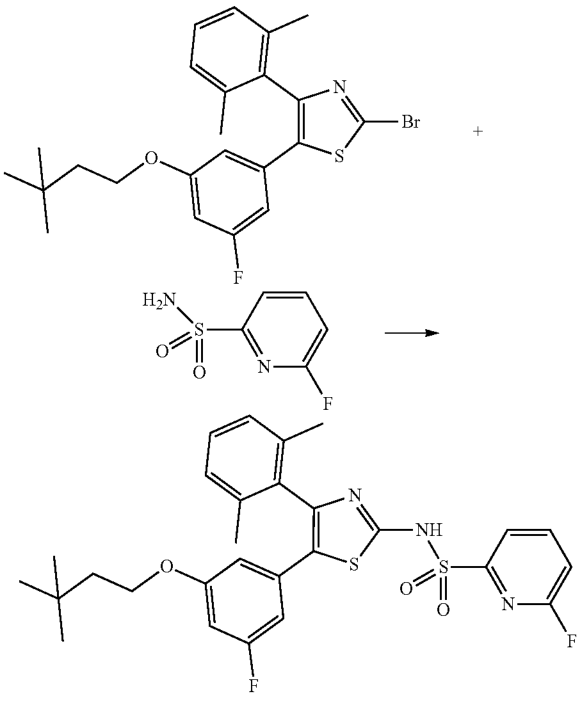

To a stirred solution of 2-bromo-5-[3-(3,3-dimethylbutoxy)-5-fluoro-phenyl]-4-(2,6-dimethylphenyl)thiazole (Intermediate G-1a) (400 mg, 0.87 mmol) in NMP (8.0 mL) were added 6-fluoropyridine-2-sulfonamide (229 mg, 1.3 mmol), sodium carbonate (229 mg, 2.16 mmol), trans-N1, N2-dimethylcyclohexane-1,2-diamine (61 mg, cat.), and copper(I) iodide (16 mg, cat.) in a glovebox. The reaction was heated at 100° C. for 5 h. The reaction was diluted with brine (80 mL) and extracted with ethyl acetate (50 mL×2). The combined organic solution was dried over anhydrous sodium sulfate, filtered and concentrated. The residue was purified by prep-HPLC to afford the desired compound, N-[5-[3-(3,3-dimethylbutoxy)-5-fluoro-phenyl]-4-(2,6-dimethylphenyl)thiazol-2-yl]-6-fluoro-pyridine-2-sulfonamide (380 mg, 79%) as a colorless oil.

LCMS: LC retention time 2.40 min. MS (ESI) m/z 558 $[M+H]^+$.

Step 2.

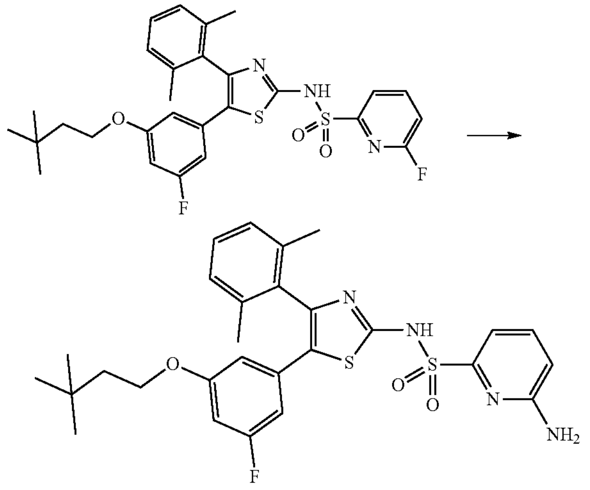

A solution of N-[5-[3-(3,3-dimethylbutoxy)-5-fluoro-phenyl]-4-(2,6-dimethylphenyl)thiazol-2-yl]-6-fluoro-pyridine-2-sulfonamide (380 mg, 0.68 mmol) in $NH_4OH$ (40.0 mL) was heated up to 130° C. in a steel bomb for 16 h. After cooling to room temperature, the solvent was removed under reduced pressure. The residue was extracted with ethyl acetate (50 mL×2). The combined organic extracts were washed with brine, dried over anhydrous sodium sulfate, filtered and concentrated. The crude product was purified by prep-HPLC to afford the title compound, 6-amino-N-(5-(3-(3,3-dimethylbutoxy)-5-fluorophenyl)-4-(2,6-dimethylphenyl)thiazol-2-yl)pyridine-2-sulfonamide (82.1 mg, 22%) as a white solid.

LCMS: LC retention time 2.34 min. MS (ESI) m/z 555 $[M+H]^+$.

$^1H$ NMR (400 MHz, chloroform-d) δ 7.60 (t, J=7.8 Hz, 1H), 7.44 (d, J=7.3 Hz, 1H), 7.31 (t, J=7.6 Hz, 1H), 7.16 (d, J=7.6 Hz, 2H), 6.62 (d, J=8.2 Hz, 1H), 6.47 (dt, J=10.4, 2.1 Hz, 1H), 6.42-6.27 (m, 2H), 3.67 (t, J=7.3 Hz, 2H), 2.16 (s, 6H), 1.61 (t, J=7.3 Hz, 2H), 0.94 (s, 9H) ppm.

Example 32

2-Amino-N-(5-(3-(3,3-dimethylbutoxy)-5-fluorophenyl)-4-(2,6-dimethylphenyl)thiazol-2-yl)pyridine-4-sulfonamide

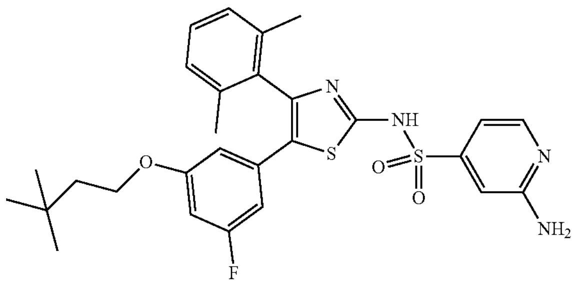 [SMILES: Cc1cccc(C)c1-c1nc(NS(=O)(=O)c2ccnc(N)c2)sc1-c1cc(F)cc(OCCC(C)(C)C)c1]

Step 1.

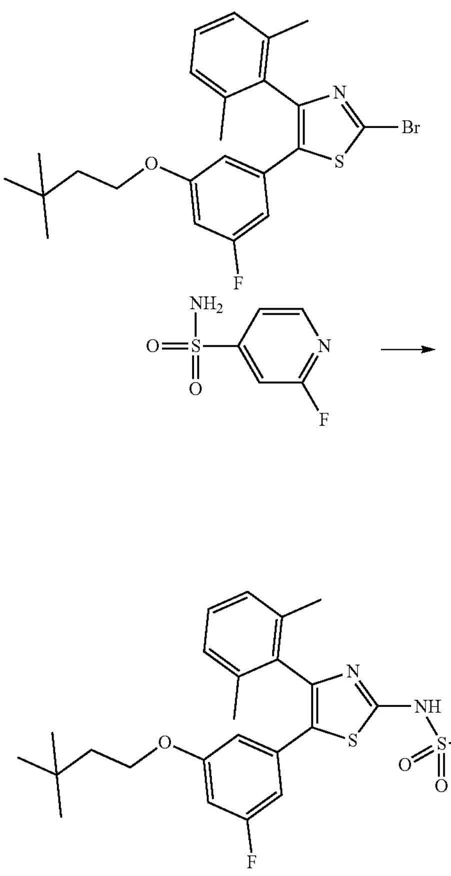

To a solution of 2-bromo-5-[3-(3,3-dimethylbutoxy)-5-fluoro-phenyl]-4-(2,6-dimethylphenyl)thiazole (Intermediate G-1a) (150 mg, 0.324 mmol) in NMP (2 mL) was added 2-fluoropyridine-4-sulfonamide (114 mg, 0.649 mmol), sodium carbonate (86 mg, 0.81 mmol), trans-N1,N2-dimethylcyclohexane-1,2-diamine (23 mg, cat.), and copper(I) iodide (6 mg, cat.) in in glove box. The solution was heated at 100° C. for 5 h. The reaction was diluted with brine (10 mL). The resulting aqueous was extracted with ethyl acetate (10 mL×2). The organic extracts were combined and concentrated under reduced pressure. The residue was purified by FCC ($ACN/H_2O=1/1$) to afford the desired compound, N-[5-[3-(3,3-dimethylbutoxy)-5-fluoro-phenyl]-4-(2,6-dimethylphenyl)thiazol-2-yl]-2-fluoro-pyridine-4-sulfonamide (120 mg, 39.8%) as a brown oil.

LCMS: LC retention time 1.70 min. MS (ESI) m/z 558 $[M+H]^+$.

Step 2.

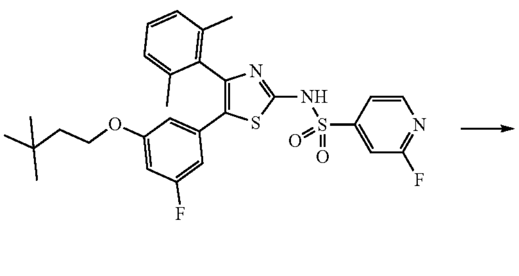

-continued

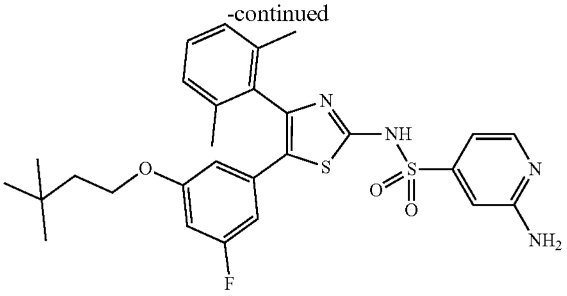

To a solution of N-[5-[3-(3,3-dimethylbutoxy)-5-fluoro-phenyl]-4-(2,6-dimethylphenyl) thiazol-2-yl]-2-fluoro-pyridine-4-sulfonamide (120 mg, 0.22 mmol) in NMP (3 mL) was added conc. ammonium hydroxide (20 mL) in a steel bomb. The reaction was stirred at 130° C. for 12 h. The mixture was extracted with EA (30 mL×3). The organic layers were combined and washed with brine (10 mL×3) and concentrated. The residue was purified by prep-HPLC to give the title compound as a yellow solid (52.1 mg, 43.6%).

LCMS: LC retention time 1.627 min. MS (ESI) m/z 555 $[M+H]^+$.

$^1$H NMR (400 MHz, chloroform-d) δ 8.09-8.07 (d, J=5.6 Hz, 1H), 7.35-7.31 (t, J=7.6 Hz, 1H), 7.23 (m, 1H), 7.10 (s, 1H), 6.91 (m, 1H), 6.77-6.74 (d, J=10.8 Hz, 1H), 6.50-6.48 (d, J=9.6 Hz, 1H), 6.26 (s, 1H), 3.69 (t, J=7.2 Hz, 2H), 2.02 (s, 6H), 1.51 (t, J=7.2 Hz, 2H), 0.84 (s, 9H) ppm.

Example 33

2-Amino-N-(5-(3-(3,3-dimethylbutoxy)-5-fluorophenyl)-4-(2-isopropylphenyl)thiazol-2-yl)pyridine-4-sulfonamide

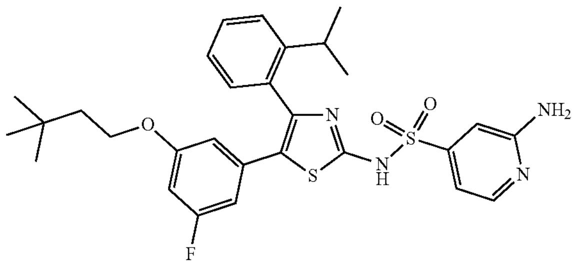 [SMILES: CC(C)c1ccccc1-c1nc(NS(=O)(=O)c2ccnc(N)c2)sc1-c1cc(F)cc(OCCC(C)(C)C)c1]

Step 1.

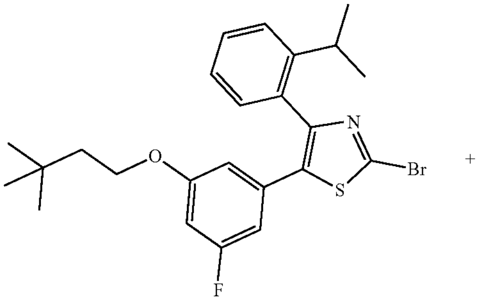

-continued

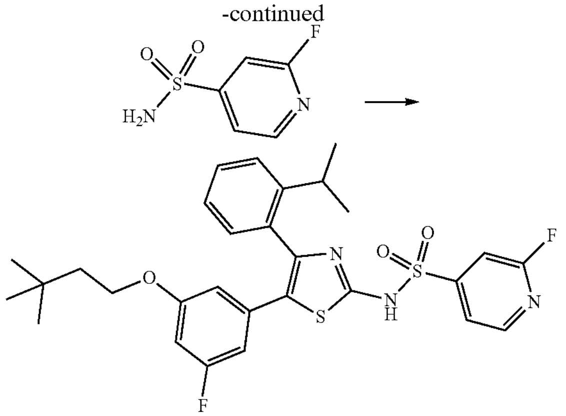

To a solution of Intermediate G-2a (533 mg, 1.11 mmol) in 1-methyl-2-pyrrolidinone (12.0 mL) were added 2-fluoropyridine-4-sulfonamide (236 mg, 1.34 mmol), sodium carbonate (353 mg, 3.33 mmol), cuprous iodide (21 mg, 0.111 mmol) and trans-(1R,2R)—N, N'-dimethylcyclohexane-1,2-diamine (47 mg, 0.333 mmol) in a sealed tube under nitrogen atmosphere. The reaction was stirred at 100° C. for 5 h. After cooling to room temperature, the reaction was diluted with water (50 mL). The resulting aqueous solution was extracted with ethyl acetate (20 mL×3). The combined organic layers were washed with brine (30 mL×2), dried over sodium sulfate, filtered and concentrated under reduced pressure. The residue was purified by prep-HPLC to give the desired product N-(5-(3-(3,3-dimethylbutoxy)-5-fluorophenyl)-4-(2-isopropylphenyl)thiazol-2-yl)-2-fluoropyridine-4-sulfonamide as a yellow solid (108 mg, 17% yield).

LCMS: LC retention time 2.05 min. MS (ESI) m/z 572 $[M+H]^+$.

Step 2.

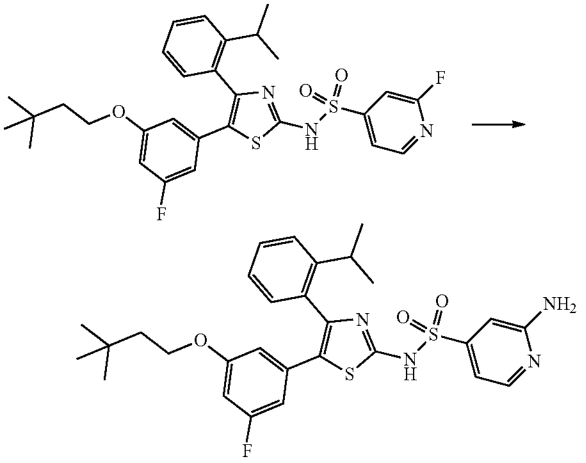

A suspension of N-(5-(3-(3,3-dimethylbutoxy)-5-fluorophenyl)-4-(2-isopropylphenyl)thiazol-2-yl)-2-fluoropyridine-4-sulfonamide (108 mg, 0.189 mmol) in ammonium hydroxide (30 mL) was sealed in a tube and heated at 130° C. overnight. The solvent was removed under reduced pressure. The residue was dissolved in water (15 mL) and saturated aqueous ammonium chloride solution (15 mL). The resulting aqueous solution was extracted with ethyl acetate (15 mL×3). The combined organic layers were washed with brine (30 mL), dried over sodium sulfate, filtered and concentrated. The residue was purified by prep-HPLC to give the title compound (21.6 mg, 20% yield) as a light yellow solid.

LCMS: LC retention time 1.98 min. MS (ESI) m/z 569 $[M+H]^+$.

$^1H$ NMR (400 MHz, chloroform-d) δ 7.54 (m, 1H), 7.45 (d, J=8.0 Hz, 1H), 7.30 (d, J=7.6 Hz, 1H), 7.19 (d, J=7.6 Hz, 1H), 7.00 (s, 1H), 6.75 (d, J=5.6 Hz, 1H), 6.45 (d, J=10.0 Hz, 2H), 6.36 (s, 2H), 6.13 (br, 2H), 3.63 (t, J=7.2 Hz, 2H), 2.79 (m, 1H), 1.58 (t, J=7.2 Hz, 2H), 0.98 (s, 6H), 0.92 (s, 9H) ppm.

Example 34

2-Amino-N-(5-(3-(3,3-dimethylbutoxy)-5-fluorophenyl)-4-(2-isopropoxy-6-methylphenyl)thiazol-2-yl) pyridine-4-sulfonamide

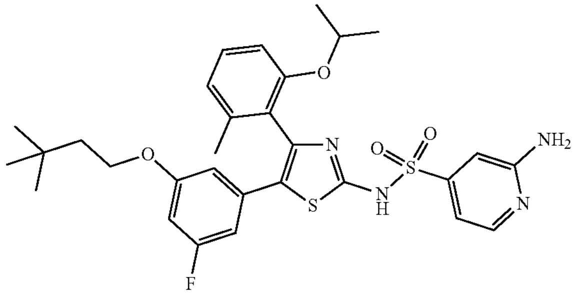 [SMILES: Cc1cccc(OC(C)C)c1-c1nc(NS(=O)(=O)c2ccnc(N)c2)sc1-c1cc(F)cc(OCCC(C)(C)C)c1]

Step 1.

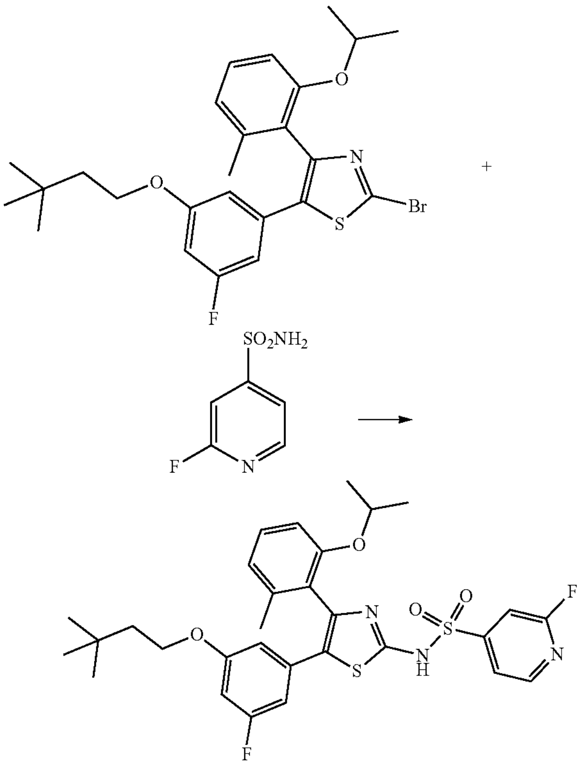

To a solution of Intermediate G-7 (405 mg, 0.8 mmol in NMP (9 mL) were added 2-fluoropyridine-4-sulfonamide (169 mg, 0.96 mmol), sodium carbonate (254 mg, 2.4 mmol), cuprous iodide (15 mg, 0.08 mmol) and trans-(1R, 2R)N,N'-dimethyl-cyclohexane-1,2-diamine (34 mg, 0.24 mmol). The reaction was stirred at 100° C. in a sealed tube under nitrogen atmosphere for 5 h. After cooling to room temperature, the reaction was diluted with water (60 mL). The resulting aqueous was extracted with ethyl acetate (40 mL×2). The combined organic layers were washed with brine (50 mL), dried over sodium sulfate, filtered and concentrated under reduced pressure. The residue was purified by prep-HPLC to give N-(5-(3-(3,3-dimethylbutoxy)-5-fluorophenyl)-4-(2-isopropoxy-6-methylphenyl)thiazol-2-yl)-2-fluoropyridine-4-sulfonamide (125 mg, 26% yield) as a brown oil.

LCMS: LC retention time 2.64 min. MS (ESI) m/z 602 $[M+H]^+$.

Step 2.

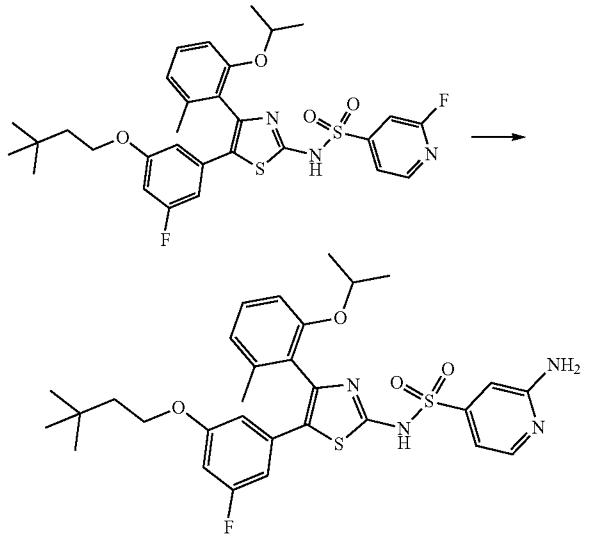

To a solution of N-(5-(3-(3,3-dimethylbutoxy)-5-fluorophenyl)-4-(2-isopropoxy-6-methylphenyl)thiazol-2-yl)-2-fluoropyridine-4-sulfonamide (125 mg, 0.208 mmol) in NMP (3.0 mL) was added ammonium hydroxide (20 mL). The reaction was heated in a sealed tube at 130° C. overnight. The solvent was removed under reduced pressure. The residue was taken in water (40 mL). The aqueous was extracted with ethyl acetate (20 mL×3). The combined organic layers were washed with brine (20 mL), dried over sodium sulfate, filtered and concentrated. The residue was purified by prep-HPLC to give 2-amino-N-(5-(3-(3,3-dimethylbutoxy)-5-fluorophenyl)-4-(2-isopropoxy-6-methylphenyl)thiazol-2-yl)pyridine-4-sulfonamide (40.4 mg, 32% yield) as a white solid.

LCMS: LC retention time 1.99 min. MS (ESI) m/z 599 $[M+H]^+$.

$^1$H NMR (400 MHz, chloroform-d) δ 7.32 (t, J=8.0 Hz, 1H), 7.05-7.02 (m, 2H), 6.87-6.78 (m, 3H), 6.46-6.42 (m, 3H), 5.79 (s, 2H), 4.45-4.39 (m, 1H), 3.75-3.64 (m, 2H), 1.97 (s, 3H), 1.61 (t, J=7.2 Hz, 2H), 1.11 (d, J=6.4 Hz, 3H), 1.06 (d, J=6.0 Hz, 3H), 0.93 (s, 9H) ppm.

Example 35

2-Amino-N-(5-(3-(3,3-dimethylbutoxy)-5-fluorophenyl)-4-(2,6-dimethylphenyl)thiazol-2-yl)pyridine-3-sulfonamide

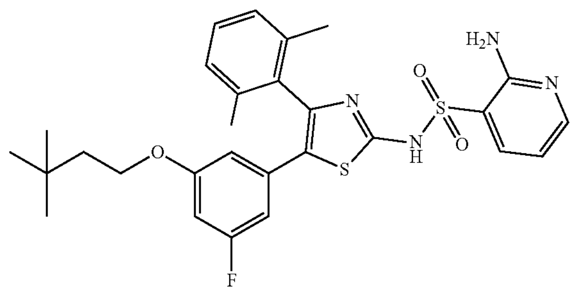 [SMILES: Cc1cccc(C)c1-c1nc(NS(=O)(=O)c2cccnc2N)sc1-c1cc(F)cc(OCCC(C)(C)C)c1]

Step 1.

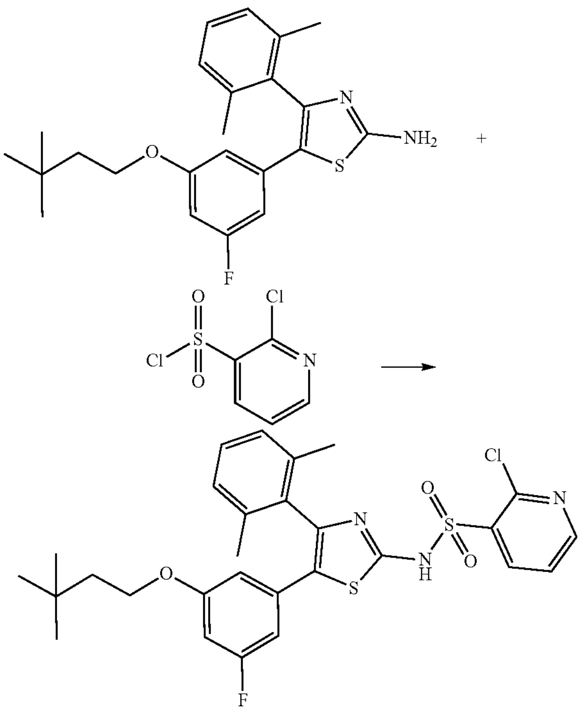

To a solution of Intermediate C-11 (600 mg, 1.51 mmol) in pyridine (15 mL) was added 2-chloropyridine-3-sulfonyl chloride (958 mg, 4.52 mol) and DMAP (37 mg, 0.3 mmol). The mixture was heated to 50° C. and stirred at the same temperature for 2 h. Then the reaction mixture was cooled to room temperature and poured into water (80 mL), extracted with ethyl acetate (100 mL×2). The combined ethyl acetate solution was washed with water (80 mL) and brine (100 mL), dried over anhydrous $Na_2SO_4$, filtered, and concentrated to dryness under reduced pressure. The crude was purified by flash reversed-phase column to give the desired compound 2-chloro-N-(5-(3-(3,3-dimethylbutoxy)-5-fluorophenyl)-4-(2,6-dimethylphenyl)thiazol-2-yl)pyridine-3-sulfonamide (330 mg, 38.2%) as a brown solid.

LCMS: LC retention time 2.44 min. MS (ESI) m/z 574 $[M+H]^+$.

Step 2.

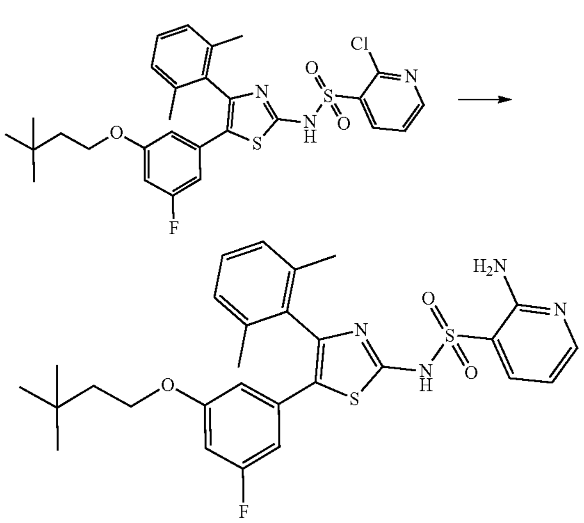

2-Chloro-N-(5-(3-(3,3-dimethylbutoxy)-5-fluorophenyl)-4-(2,6-dimethylphenyl)thiazol-2-yl)pyridine-3-sulfonamide (330 mg, 0.57 mmol) was placed in a sealed stuffy tank and ammonium hydroxide (25 mL) was added. The mixture was heated to 130° C. and stirred at the same temperature overnight. After cooling to room temperature, the mixture was concentrated under reduced pressure. The residue was taken in ethyl acetate (80 mL). The ethyl acetate solution was washed with water (80 mL) and brine (100 mL), then dried over anhydrous $Na_2SO_4$, filtered. The filtrate was concentrated to dryness to give the crude product which was purified by prep-HPLC to give the desired compound 2-amino-N-(5-(3-(3,3-dimethylbutoxy)-5-fluorophenyl)-4-(2,6-dimethylphenyl)thiazol-2-yl)pyridine-3-sulfonamide (56.1 mg, 17.6%) as a white solid.

LCMS: LC retention time 2.44 min. MS (ESI) m/z 555 $[M+H]^+$.

$^1$HNMR (400 MHz, chloroform-d) δ 8.08 (dd, J=7.7, 1.7 Hz, 1H), 7.33 (t, J=7.6 Hz, 1H), 7.16 (d, J=7.6 Hz, 2H), 6.78 (s, 2H), 6.51 (d, J=3.9 Hz, 1H), 6.45 (dt, J=10.4, 2.2 Hz, 1H), 6.37 (ddd, J=8.6, 7.0, 3.5 Hz, 3H), 3.66 (t, J=7.3 Hz, 2H), 2.09 (s, 6H), 1.60 (t, J=7.3 Hz, 2H), 0.93 (s, 9H) ppm.

Example 36

(S)-2-((6-(N-(5-(3-(3,3-Dimethylbutoxy)phenyl)-4-(2-isopropylphenyl)thiazol-2-yl)sulfamoyl)pyridin-2-yl)amino)-3,3-dimethylbutanoic acid

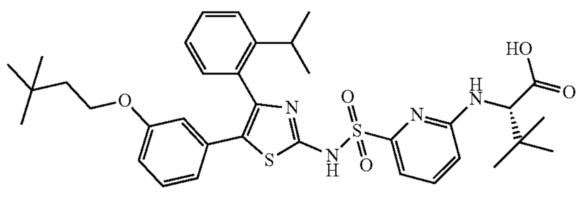 [SMILES: CC(C)c1ccccc1-c1nc(NS(=O)(=O)c2cccc(N[C@H](C(=O)O)C(C)(C)C)n2)sc1-c1cccc(OCCC(C)(C)C)c1]

Step 1.

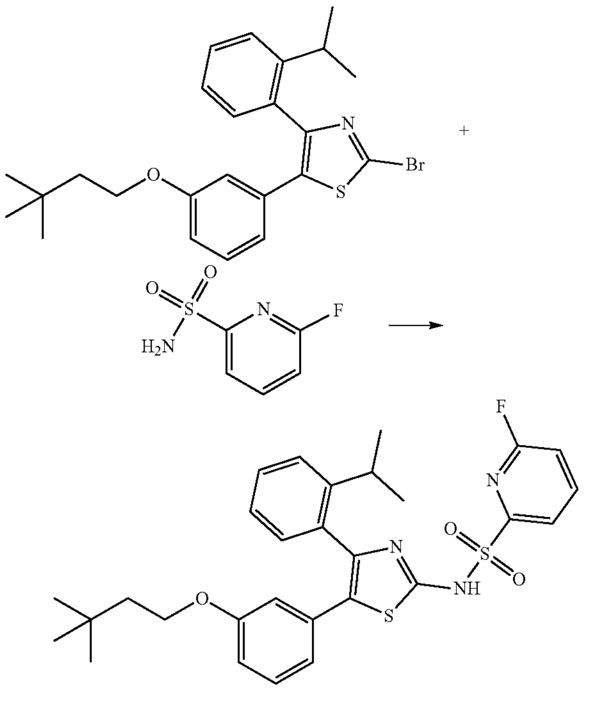

To a solution of 2-bromo-5-[3-(3,3-dimethylbutoxy)phenyl]-4-(2-isopropylphenyl) thiazole (Intermediate G-2b) (140 mg, 0.305 mmol) in anhydrous NMP (3.0 mL) was added 6-fluoropyridine-2-sulfonamide (80.7 mg, 0.458 mmol)), CuI (5.8 mg, 3.1 mmol), $Na_2CO_3$ (129 mg, 1.22 mmol) and $N^1,N^2$-dimethylcyclohexane-1,2-diamine (13.0 mg, 0.092 mmol) under nitrogen in a glove-box. The reaction was heated to 100° C. and stirred at the same temperature overnight. Then the mixture was cooled to room temperature and poured into water (30 mL). The resulting aqueous solution was extracted with ethyl acetate (50 mL×3). The combined organic extracts were washed with brine (30 mL), dried over anhydrous sodium sulfate, filtered and concentrated to dryness under reduced pressure. The crude was purified by prep-HPLC to give the desired compound (90 mg, 53.2%) as a white solid.

LCMS: LC retention time 2.51 min. MS (ESI) m/z 554 $[M+H]^+$.

Step 2.

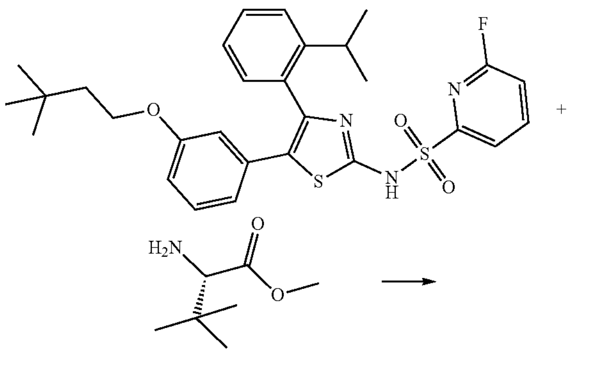

-continued

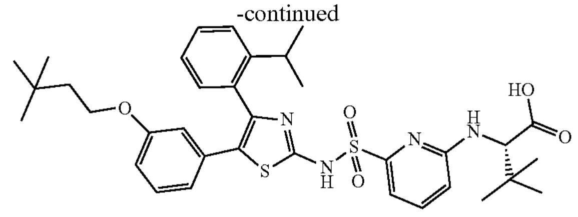

To a solution of N-[5-[3-(3,3-dimethylbutoxy)phenyl]-4-(2-isopropylphenyl)thiazol-2-yl]-6-fluoro-pyridine-2-sulfonamide (90.0 mg, 0.163 mmol) in DMSO (2.0 mL) were added methyl (2S)-2-amino-3,3-dimethyl-butanoate (70.8. mg, 0.488 mmol) and $Cs_2CO_3$ (211 mg, 0.65 mmol). The mixture was stirred at 100° C. overnight. The mixture was diluted with water (50 mL), extracted with ethyl acetate (80 mL×3). The combined organic extracts were washed with water (50 mL) and brine (80 mL), dried over anhydrous $Na_2SO_4$, and then filtered. The filtrate was concentrated to dryness to give the crude product which was purified by prep-HPLC to give the title compound (10.9 mg, 10.1%) as white solid.

LCMS: LC retention time 2.3 min, MS (ESI) 665 $[M+H]^+$.

$^1$H NMR (400 MHz, chloroform-d) δ 7.49-7.41 (m, 2H), 7.33-7.31 (m, 1H), 7.13 (s, 2H), 7.12-7.09 (m, 1H), 6.73-6.71 (m, 2H), 6.50-6.48 (m, 2H), 5.07 (s, 1H), 3.61-3.57 (m, 2H), 2.86 (s, 1H), 1.59-1.56 (t, 2H), 1.02-0.91 (m, 24H) ppm.

Example 37

2-Amino-N-(5-(2-(4,4-dimethylpentyl)morpholino)-4-(2,6-dimethylphenyl)thiazol-2-yl)pyridine-4-sulfonamide

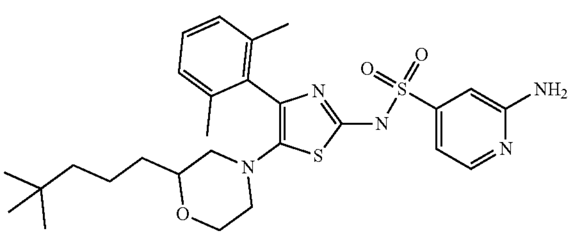 [SMILES: Cc1cccc(C)c1-c1nc(NS(=O)(=O)c2ccnc(N)c2)sc1N1CCOC(CCCC(C)(C)C)C1]

Step 1.

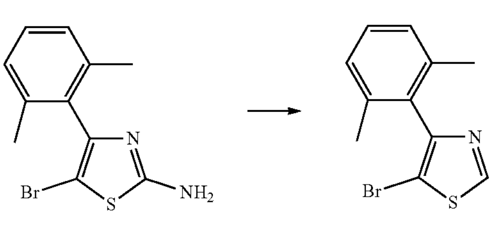

To a solution of Intermediate B-2a (800 mg, 2.8 mmol) in THF (10 mL) was added t-BuONO (378 mg, 3.6 mmol). The reaction solution was stirred at 50° C. for 4 h. The reaction was then quenched with water (10 mL). The resulting aqueous was extracted with EA (50 mL). The EA solution was washed with brine (50 mL) and then concentrated to give 5-bromo-4-(2,6-dimethylphenyl)thiazole (0.60 g, 79.2% yield) as a brown solid.

LCMS (acidic): LC retention time 2.17 min. MS (ESI) m/z 268 $[M+H]^+$.

Step 2.

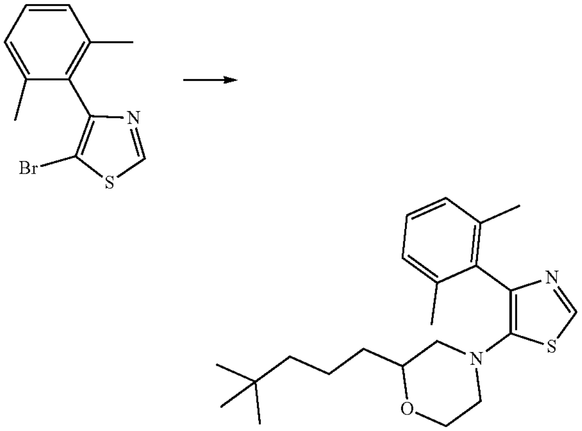

To the stirred solution of 5-bromo-4-(2,6-dimethylphenyl)thiazole (1.00 g, 3.7 mmol) in MeCN (20 mL) was added 2-(4,4-dimethylpentyl)morpholine hydrochloride (Intermediate E-14) (992 mg, 4.5 mmol) and $Cs_2CO_3$ (3.0 mg, 9.3 mmol). The reaction was stirred at 80° C. for 16 h. To the reaction mixture was added EA (50 mL). The organic solution was washed with brine (50 mL×2) and concentrated to give 2-(4,4-dimethylpentyl)-4-(4-(2,6-dimethylphenyl)thiazol-5-yl)morpholine (1.20 g, 86% yield) as a red solid.

LCMS (acidic): LC retention time 2.62 min. MS (ESI) m/z 373 (M+H)+.

Step 3.

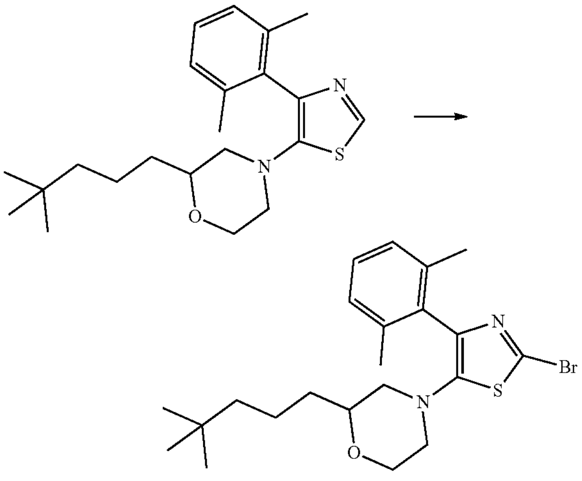

The reaction mixture of 2-(4,4-dimethylpentyl)-4-(4-(2,6-dimethylphenyl)thiazol-5-yl)morpholine (1.20 g, 3.2 mmol) in DMF (10 mL) was added NBS (573 mg, 3.2 mmol). The reaction was stirred at rt for 2 h. Then, the reaction was diluted with EA (50 mL), washed with brine (100 mL×3), and then concentrated. The residue was purified by combi-flash (EA in PE=0-10%) to give 4-(2-bromo-4-(2,6-dimethylphenyl)thiazol-5-yl)-2-(4,4-dimethylpentyl)morpholine (0.90 g, 61.9% yield) as a yellow oil.

LCMS (acidic): LC retention time 2.93 min; MS (ESI) m/z 450, 452. [M+H]+.

Step 4.

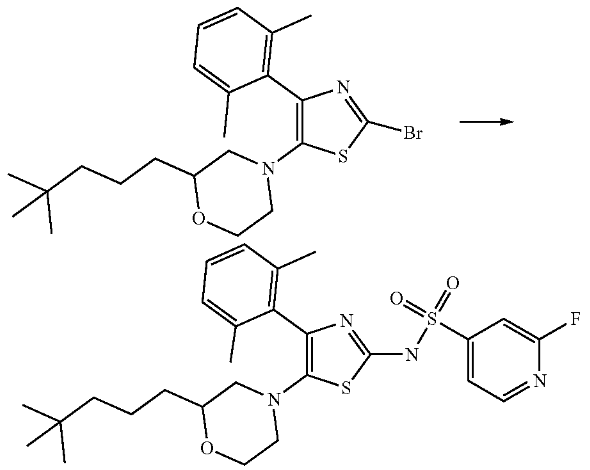

The reaction mixture of 4-(2-bromo-4-(2,6-dimethylphenyl)thiazol-5-yl)-2-(4,4-dimethylpentyl)morpholine (480 mg, 1.06 mmol), 2-fluoropyridine-4-sulfonamide (375 mg, 2.1 mmol), $Na_2CO_3$ (282 mg, 2.7 mmol), $N^1$, $N^2$-dimethylcyclohexane-1, 2-diamine (75 mg, 0.53 mmol), and CuI (20 mg, 0.1 mmol) in 5 mL of NMP was heated at 110° C. overnight in a glove-box. The reaction mixture was diluted with DCM (20 mL), then washed with water (10 mL). The DCM solution was concentrated. The residue was purified by prep-HPLC to give N-(5-(2-(4,4-dimethylpentyl)morpholino)-4-(2,6-dimethylphenyl)thiazol-2-yl)-2-fluoropyridine-4-sulfonamide (200 mg, 36.6% yield) as a white solid.

LCMS (acidic): LC retention time 2.40 min. MS (ESI) m/z 547 [M+H]+.

Step 5.

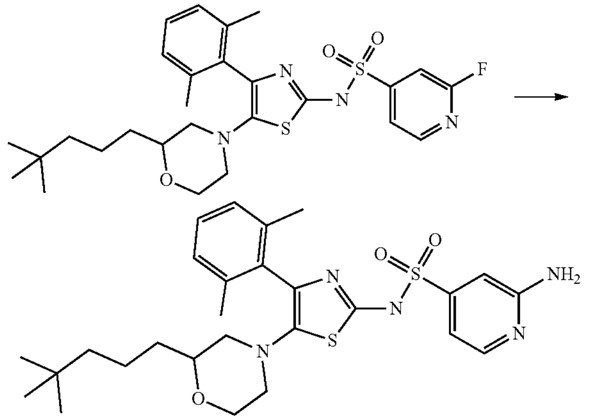

The reaction mixture of N-(5-(2-(4,4-dimethylpentyl) morpholino)-4-(2,6-dimethylphenyl)thiazol-2-yl)-2-fluoropyridine-4-sulfonamide (70 mg, 0.13 mmol) in NMP (2 mL) and $NH_{40}H$ (20 mL) was sealed in a stuffy tank and stirred at 130° C. for 12 h. Then the reaction mixture was concentrated. The residue was purified by prep-HPLC (MeCN—$H_2O$/0.05% FA) to give the title compound (30 mg, 43% yield) as a yellow solid.

LCMS (acidic): LC retention time 1.95 min. MS (ESI) m/z 544 [M+H]+.

$^1H$ NMR (400 MHz, methanol-$d_4$): δ 8.04 (d, J=5.6 Hz, 1H), 7.26 (t, J=7.6 Hz, 1H), 7.16-7.14 (m, 2H), 7.05 (s, 1H), 6.97 (dd, J=5.6, 1.2 Hz, 1H), 3.81-3.78 (m, 1H), 3.51-3.45 (m, 1H), 2.84-2.80 (m, 3H), 2.46-2.41 (m, 1H), 2.21 (s, 6H), 1.39-1.07 (m, 7H), 0.86 (s, 9H) ppm.

Example 38

3-Amino-N-(5-(2,2-dimethyl-6-oxa-9-azaspiro[4.5]decan-9-yl)-4-(2,6-dimethylphenyl)thiazol-2-yl)-2-fluorobenzenesulfonamide

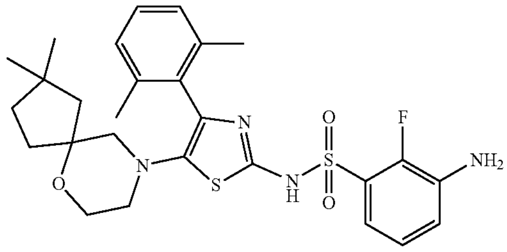 [SMILES: Cc1cccc(C)c1-c1nc(NS(=O)(=O)c2cccc(N)c2F)sc1N1CCOC2(CCC(C)(C)C2)C1]

Step 1.

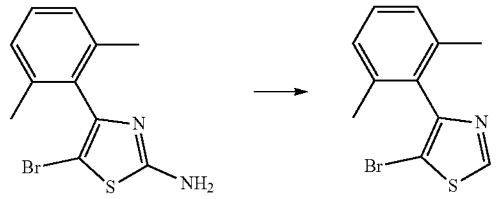

To a solution of Intermediate B-2a (500 mg, 1.77 mmol) in THF (25 mL) was added tert-butyl nitrite (236 mg, 0.2.30 mmol). The reaction mixture was stirred at 50° C. for 4 h. The reaction was then quenched with water (50 mL). The resulting aqueous solution was extracted with EtOAc (50 mL). The EtOAc solution was washed with brine (50 mL) and concentrated to dryness. The residue was purified by SGC (PE:EA=10:1) to give 5-bromo-4-(2,6-dimethylphenyl)thiazole (299 mg, 63.1%) as a yellow oil.

LCMS (acidic): LC retention time 2.198 min. MS (ESI) m/z 268 [M+H]+.

Step 2.

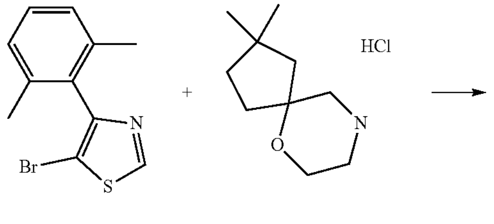

-continued

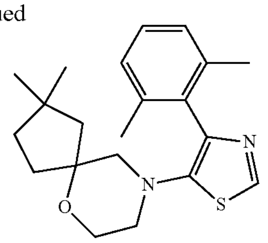

To a solution of 5-bromo-4-(2,6-dimethylphenyl)thiazole (299 mg, 1.11 mmol) in MeCN (5 mL) were added 3,3-dimethyl-6-oxa-9-azaspiro[4.5]decane hydrochloride (Intermediate E-8) (298 mg, 1.45 mmol) and $Cs_2CO_3$ (1.09 g, 3.34 mmol). The reaction was stirred at 90° C. for 16 h. After cooling to rt, the reaction was diluted with EA (50 mL). The EA solution was washed with brine (50 mL×2) and concentrated. The residue was purified by prep-TLC (PE:EA=10:1) to give 9-(4-(2,6-dimethylphenyl)thiazol-5-yl)-2,2-dimethyl-6-oxa-9-azaspiro[4.5]decane (286 mg, 71.9% yield) as a yellow solid.

LCMS (acidic): LC retention time 2.471 min. MS (ESI) m/z 357 $[M+H]^+$.

Step 3.

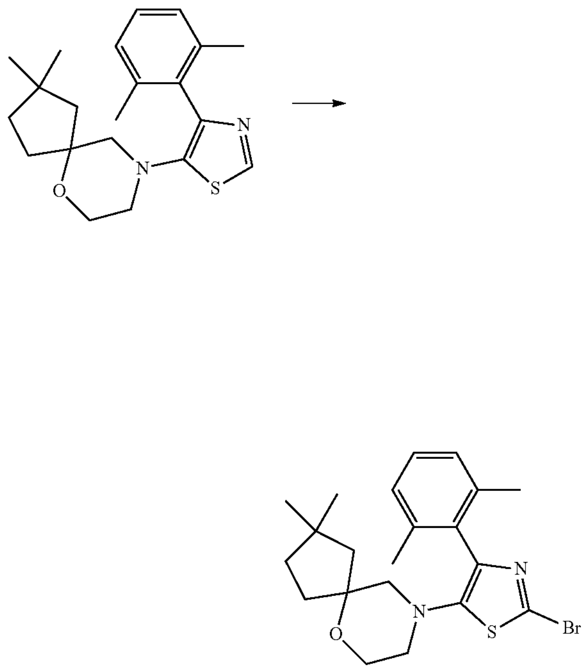

To a solution of 9-(4-(2,6-dimethylphenyl)thiazol-5-yl)-2,2-dimethyl-6-oxa-9-azaspiro[4.5]decane (286 mg, 0.802 mmol) in 10 mL of THF was added NBS (150 mg, 0.842 mmol). The reaction mixture was stirred at room temperature for 3 h. The reaction mixture was extracted with EtOAc (50 mL×3). The EtOAc combined extracts were washed with brine (50 mL×2), dried over $Na_2SO_4$, filtered and concentrated to afford crude which was purified by prep-TLC (PE:EA=10:1) to give 9-(2-bromo-4-(2,6-dimethylphenyl)thiazol-5-yl)-2,2-dimethyl-6-oxa-9-azaspiro[4.5]decane (302 mg, 86.5%) as a colorless oil.

LCMS: LC retention time 4.388 min. MS (ESI) m/z 435 $[M+H]^+$.

Step 4.

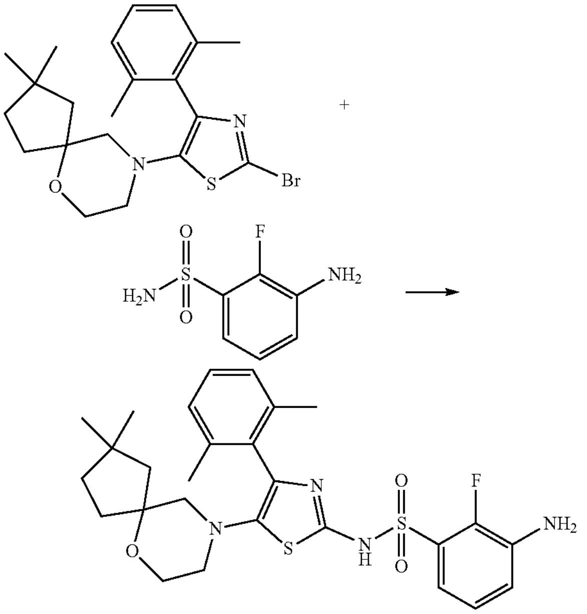

The mixture of 9-(2-bromo-4-(2,6-dimethylphenyl)thiazol-5-yl)-2,2-dimethyl-6-oxa-9-azaspiro[4.5]decane (275 mg, 0.632 mmol), 3-amino-2-fluoro-benzenesulfonamide (Intermediate R-11) (144 mg, 0.758 mmol), sodium carbonate (167 mg, 1.58 mmol), N,N'-dimethylethane-1,2-diamine (11.1 mg, cat.) and copper (I) iodide (12 mg, cat.) was heated with stirring in a glove box at 100° C. overnight. The reaction was cooled to rt and diluted with brine (50 mL), then extracted with ethyl acetate (40 mL×2). The combined organic extracts were concentrated under reduced pressure. The residue was purified by prep-HPLC to afford 3-amino-N-(5-(2,2-dimethyl-6-oxa-9-azaspiro[4.5]decan-9-yl)-4-(2,6-dimethylphenyl)thiazol-2-yl)-2-fluorobenzenesulfonamide (93.0 mg, 27.0%) as a white solid.

LCMS (acidic): LC retention time 2.212 min. MS (ESI) m/z 545 $[M+H]^+$.

$^1$HNMR (400 MHz, methanol-$d_4$) δ 7.27 (t, J=7.6 Hz, 1H), 7.17 (d, J=7.2 Hz, 3H), 7.11-6.93 (m, 2H), 3.63 (d, J=2.4 Hz, 2H), 2.84 (t, J=4.7 Hz, 2H), 2.56 (dd, 2H), 2.23 (d, J=2.6 Hz, 6H), 1.77-1.60 (m, 1H), 1.45 (m, 3H), 1.10 (m, 2H), 0.97 (s, 3H), 0.74 (s, 3H) ppm.

Example 39

3-Amino-N-(5-(2,2-dimethyl-6-oxa-9-azaspiro[4.5]decan-9-yl)-4-(2-isopropylphenyl)thiazol-2-yl)-2-fluorobenzenesulfonamide

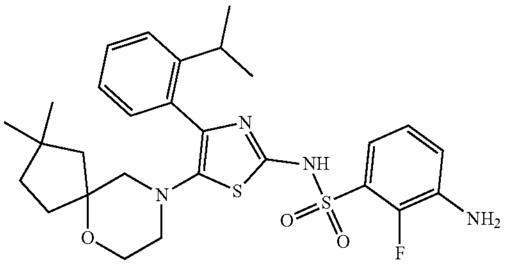 [SMILES: CC(C)c1ccccc1-c1nc(NS(=O)(=O)c2cccc(N)c2F)sc1N1CCOC2(CCC(C)(C)C2)C1]

Example 39 was synthesized starting from Intermediate B-1 by following the same protocol as Example 38 described above.

LCMS (acidic): LC retention time 2.27 min. MS (ESI) m/z 559 [M+H]$^+$.

$^1$HNMR (400 MHz, $CD_3OD$): 7.49-7.45 (m, 2H), 7.29-7.26 (m, 2H), 7.18-7.14 (m, 1H), 7.06-6.99 (m, 2H), 3.62-3.60 (m, 2H), 2.98-2.95 (m, 1H), 2.82-2.80 (m, 2H), 2.63-2.56 (m, 2H), 1.70-1.65 (m, 1H), 1.51-1.38 (m, 3H), 1.25-1.00 (m, 8H), 0.97 (s, 3H), 0.79 (s, 3H) ppm.

Example 40

N-(5-(3-((4,4-Dimethylpentyl)oxy)-1H-pyrazol-1-yl)-4-(2-(trifluoromethyl)phenyl)thiazol-2-yl)benzenesulfonamide

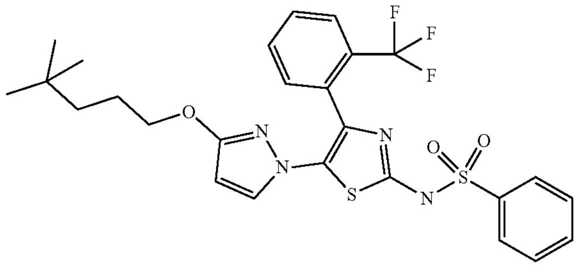 [SMILES: CC(C)(C)CCCOc1ccn(-c2sc(NS(=O)(=O)c3ccccc3)nc2-c2ccccc2C(F)(F)F)n1]

Step 1.

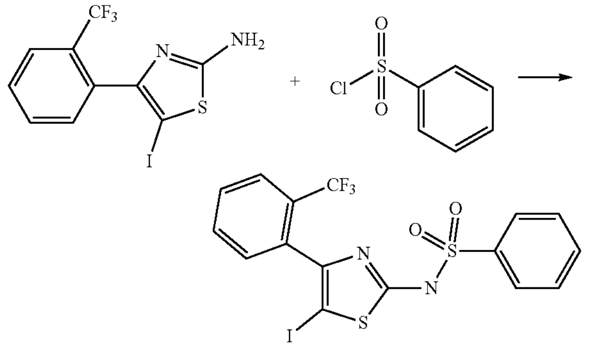

To a stirred solution of Intermediate B-9 (1.3 g, 3.51 mmol) in pyridine (10 mL) was added benzenesulfonyl chloride (0.744 g, 0.00421 mol). The reaction mixture was stirred at rt for 16 h. The solvent was removed on a rotavapor and the residue was purified by silica gel chromatography (petroleum ether/ethyl acetate=2/1) to afford N-(5-iodo-4-(2-(trifluoromethyl)phenyl)thiazol-2-yl)benzenesulfonamide (1.8 g, 74.4%) as a brown solid.

LCMS: MS (ESI) m/z 511 [M+H]$^+$.

Step 2.

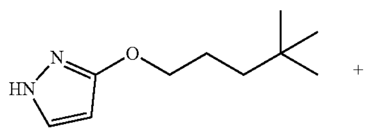

-continued

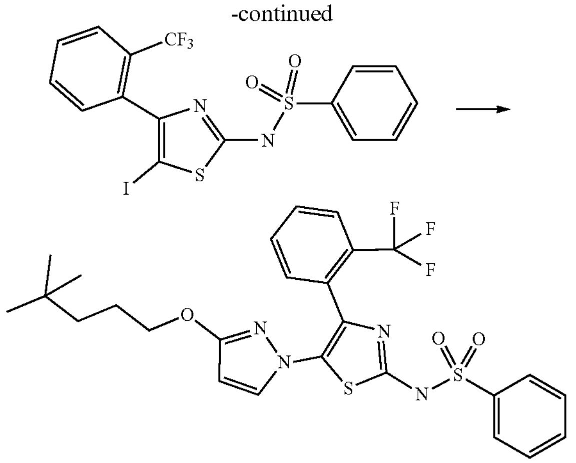

To a stirred solution of N-(5-iodo-4-(2-(trifluoromethyl)phenyl)thiazol-2-yl)benzenesulfonamide (0.84 g, 1.65 mmol) in DMF (6 mL) were added Intermediate E-2 (0.25 g, 1.37 mmol), CuI (0.0261 g, 0.137 mmol) and N$^1$,N$^2$-dimethylethane-1,2-diamine (0.0121 g, 0.137 mmol). Then the mixture was stirred at 100° C. for 16 h. The solvent was removed by distillation under reduced pressure. The residue was purified by prep-HPLC to afford N-(5-(3-((4,4-dimethylpentyl)oxy)-1H-pyrazol-1-yl)-4-(2-(trifluoromethyl)phenyl)thiazol-2-yl)benzenesulfonamide (0.053 g, 6.8% yield) as a yellow solid.

LCMS: MS (ESI) m/z 565 [M+H]$^+$.

$^1$H NMR (400 MHz, chloroform-d) δ 7.94 (d, J=7.2 Hz, 2H), 7.84-7.81 (m, 1H), 7.64-7.45 (m, 7H), 6.71 (d, J=2.0 Hz, 1H), 5.63 (d, J=2.0 Hz, 1H), 4.10 (t, J=6.4 Hz, 2H), 1.73-1.68 (m, 2H), 1.31-1.26 (m, 2H), 0.91 (s, 9H) ppm.

Example 41

N-(4-(2,6-Dimethylphenyl)-5-(3-(neopentyloxy)phenyl)thiazol-2-yl)thiophene-3-sulfonamide

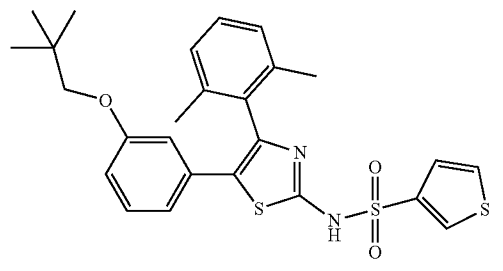 [SMILES: Cc1cccc(C)c1-c1nc(NS(=O)(=O)c2ccsc2)sc1-c1cccc(OCC(C)(C)C)c1]

Step 1.

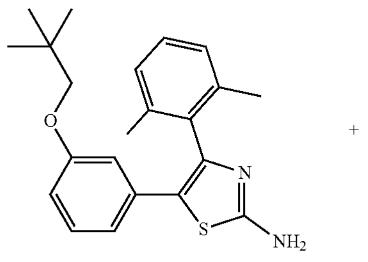

-continued

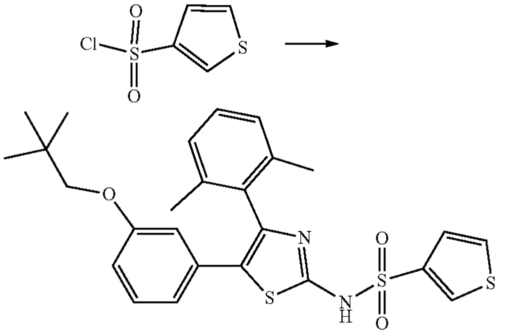

To a solution of 4-(2,6-dimethylphenyl)-5-(3-fluoro-5-(neopentyloxy)phenyl)thiazol-2-amine (210 mg, 0.573 mmol) in DCM (8 mL) were added thiophene-3-sulfonyl chloride (153 mg, 0.672 mmol), DMAP (215 mg, 1.76 mmol) and TEA (0.5 mL) at room temperature. The resulting mixture was stirred at the same temperature for 16 h. The mixture was poured into water (100 mL) and extracted with ethyl acetate (100 mL×2). The combined extracts were washed with water (100 mL×2), dried over sodium sulfate and evaporated. The crude product thus obtained was purified by prep-HPLC to give N-(4-(2,6-dimethylphenyl)-5-(3-(neopentyloxy)phenyl)thiazol-2-yl)thiophene-3-sulfonamide (65 mg) as a white solid.

LCMS: LC retention time 2.32 min. MS (ESI) m/z 513 $[M+H]^+$.

$^1H$ NMR (400 MHz, methanol-$d_4$) δ 8.17 (s, 1H), 7.58 (s, 1H), 7.44 (s, 1H), 7.32 (s, 1H), 7.20 (s, 3H), 6.78 (s, 2H), 6.49 (s, 1H), 3.20 (s, 2H), 2.12 (s, 6H), 0.95 (s, 9H) ppm.

Example 42

3-Amino-N-(5-(3-(3,3-dimethylbutoxy)-5-fluorophenyl)-4-(2,6-dimethylphenyl)thiazol-2-yl)-4-fluorobenzenesulfonamide

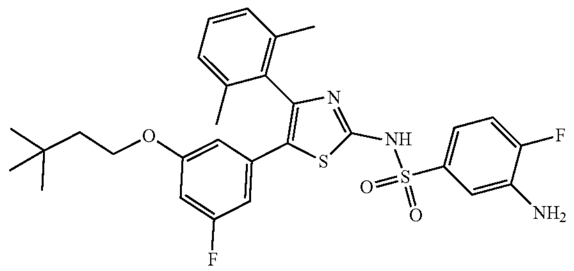 [SMILES: Cc1cccc(C)c1-c1nc(NS(=O)(=O)c2ccc(F)c(N)c2)sc1-c1cc(F)cc(OCCC(C)(C)C)c1]

Step 1.

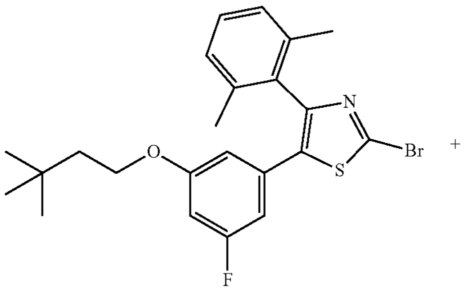

-continued

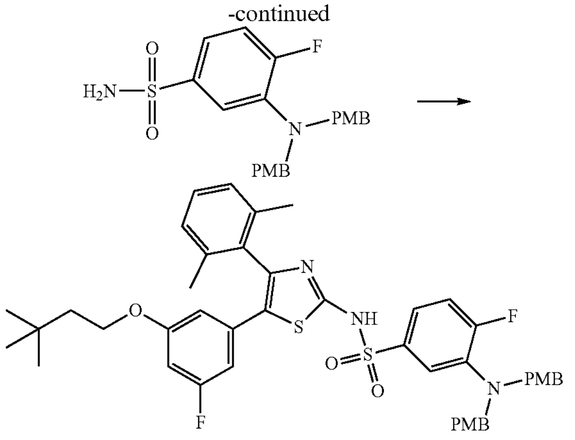

To a solution of 2-bromo-5-[3-(3,3-dimethylbutoxy)-5-fluoro-phenyl]-4-(2,6-dimethyl phenyl)thiazole (Intermediate G-1a) (130 mg, 0.281 mmol) in DMF (10 mL) were added 3-[bis[(4-methoxy phenyl)methyl]amino]-4-fluoro-benzenesulfonamide (Intermediate R-12) (145 mg, 0.337 mmol), CuI (5.34 mg, 0.0281 mmol), $Na_2CO_3$ (89.4 mg, 0.843 mmol), $N^1$, $N^2$-dimethyl cyclohexane-1,2-diamine (3.99 mg, 0.0281 mmol) under nitrogen in a glove-box. The reaction mixture was heated to 100° C. with stirring for 5 h. Then the mixture was cooled to room temperature and poured into water (20 mL), and then extracted with ethyl acetate (20 mL×3). The combined ethyl acetate extracts were washed with brine (20 mL), dried over anhydrous $Na_2SO_4$, and then filtered. The filtrate was concentrated under reduced pressure to give 3-(bis(4-methoxybenzyl)amino)-N-(5-(3-(3,3-dimethylbutoxy)-5-fluorophenyl)-4-(2,6-dimethylphenyl)thiazol-2-yl)-4-fluorobenzenesulfonamide (141 mg, 29.6%) as a yellow solid.

LCMS: LC retention time 1.869 min. MS (ESI) m/z 812 $[M+H]^+$.

Step 2

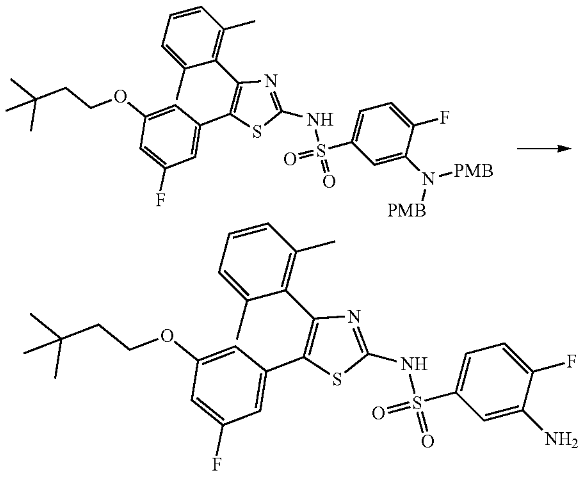

To a stirred solution of 3-(bis(4-methoxybenzyl)amino)-N-(5-(3-(3,3-dimethylbutoxy)-5-fluorophenyl)-4-(2,6-dimethylphenyl)thiazol-2-yl)-4-fluorobenzenesulfonamide (0.14 g, 0.172 mmol) in DCM was added $CF_3CO_2H$ (5 mL). Then the reaction was stirred at rt for 32 h. Then the mixture was poured into water (20 mL) and the pH of the aqueous was adjusted to pH 7.0. The aqueous was then extracted with ethyl acetate (10 mL×3). The combined organic extracts were washed with brine (10 mL), dried over anhydrous $Na_2SO_4$, and filtered. The filtrate was concentrated under reduced pressure. The residue was purified by prep-HPLC to give 3-amino-N-(5-(3-(3,3-dimethylbutoxy)-5-fluorophenyl)-4-(2,6-dimethylphenyl)thiazol-2-yl)-4-fluorobenzenesulfonamide (20 mg, 20.3%) as light yellow solid.

LCMS: LC retention time 1.705 min. MS (ESI) m/z 572 $[M+H]^+$.

$^{1}$H NMR (400 MHz, chloroform-d) δ 7.54-7.51 (m, 1H), 7.30-7.25 (m, 1H), 7.24-7.21 (m, 1H), 7.07-6.97 (m, 3H), 6.42 (d, J=10.8 Hz, 1H), 6.32 (d, J=9.6 Hz, 1H), 6.26 (s, 1H), 3.63 (t, J=9.6 Hz, 2H), 2.04 (s, 6H), 1.58 (t, J=9.6 Hz, 2H), 0.92 (s, 9H) ppm.

Example 43A

3-Amino-N-(5-(3-fluoro-5-(((1S)-3-(trifluoromethoxy)cyclopentyl)oxy)phenyl)-4-(4-(trifluoromethyl)phenyl)thiazol-2-yl)benzenesulfonamide

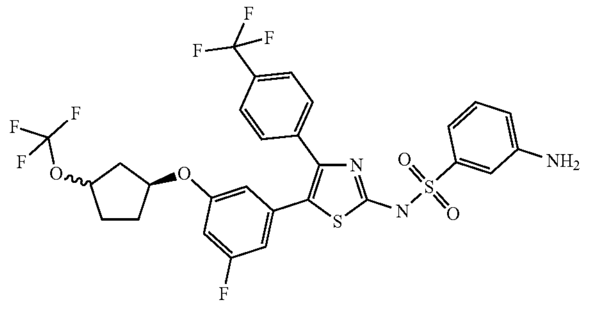 [SMILES: Nc1cccc(S(=O)(=O)Nc2nc(-c3ccc(C(F)(F)F)cc3)c(-c3cc(F)cc(O[C@H]4CCC(OC(F)(F)F)C4)c3)s2)c1]

and

Example 43B

3-Amino-N-(5-(3-fluoro-5-(((1R)-3-(trifluoromethoxy)cyclopentyl)oxy)phenyl)-4-(4-(trifluoromethyl)phenyl)thiazol-2-yl)benzenesulfonamide

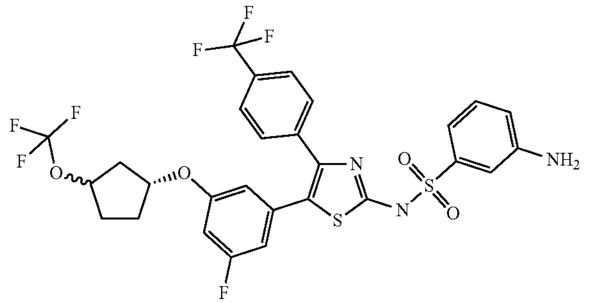 [SMILES: Nc1cccc(S(=O)(=O)Nc2nc(-c3ccc(C(F)(F)F)cc3)c(-c3cc(F)cc(O[C@@H]4CCC(OC(F)(F)F)C4)c3)s2)c1]

Step 1.

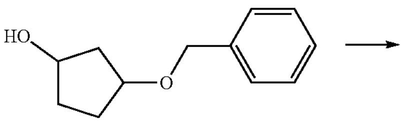

-continued

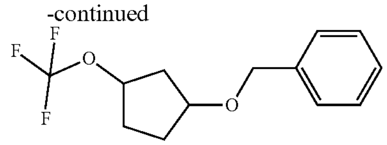

A flask were charged with AgOTf (12 g, 46.8 mmol), Select-F (8.29 g, 23.4 mmol), KF (3.62 g, 62.4 mmol) and 3-(benzyloxy)cyclopentan-1-ol (3.0 g, 15.6 mmol). After purged with Ar, EtOAc (80 mL) was added, followed by $TMSCF_3$ (6.65 g, 46.8 mmol), and 2-fluoropyridine (4.55 g, 46.8 mmol). The reaction mixture was stirred at room temperature overnight under Ar. The reaction mixture was filtered through a celite pad. The filtrate was concentrated and purified by combi-flash (100% PE) to afford (((3-(trifluoromethoxy)cyclopentyl)oxy)methyl)benzene (1.5 g, 36% yield) as a yellow oil.

LCMS: LC retention time 2.253, 2.293 min.

$^{1}$HNMR: (400 MHz, chloroform-d) (1.57-1.81 (m, 1H), 1.91-2.05 (m, 4H), 2.23-2.27 (m, 1H), 3.95-3.98 (m, 1H), 4.48 (d, J=4.0 Hz, 2H), 4.62-4.65 (m, 1H), 7.23-7.37 (m, 5H);

$^{19}$FNMR (400 MHz, chloroform-d) 8-58.549.

Step 2.

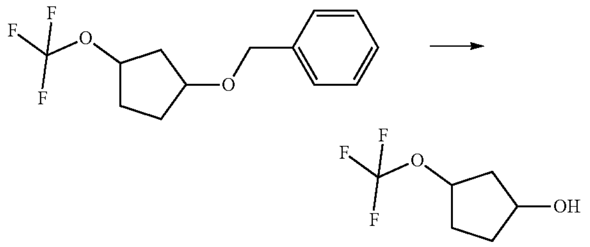

To a solution of (((3-(trifluoromethoxy)cyclopentyl)oxy)methyl)benzene (3.0 g, 11.5 mmol) in $Et_2O$ (150 mL) was added 10% Pd/C (1 g). The reaction mixture was stirred at room temperature under $H_2$ for 2 days. The catalyst was filtered off. The filtrate was concentrated to afford 3-(trifluoromethoxy)cyclopentan-1-ol (1.96 g, 100%) as a yellow oil.

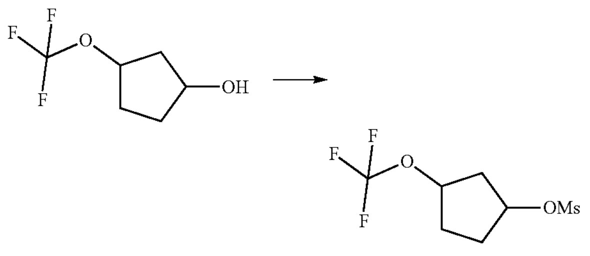

To a solution of 3-(trifluoromethoxy)cyclopentan-1-ol (500 mg, 2.94 mmol) in 5 mL of DCM was added methanesulfonyl chloride (438 mg, 3.82 mmol) dropwise at 0° C. The reaction mixture was stirred at 0° C. for 2 h. The reaction mixture was then diluted with DCM. The DCM solution was washed with aqueous $NaHCO_3$, brine, dried over $Na_2SO_4$, filtered and concentrated to afford crude 3-(trifluoromethoxy)cyclopentyl methanesulfonate (730 mg, 100%) as a brown oil.

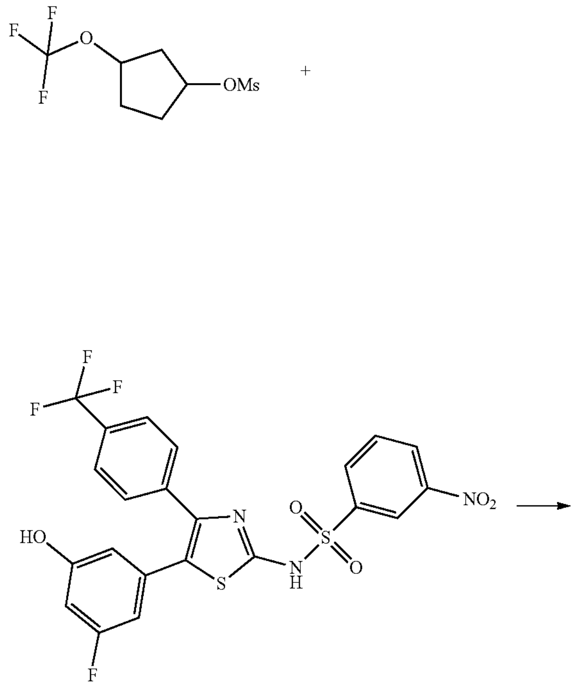

-continued

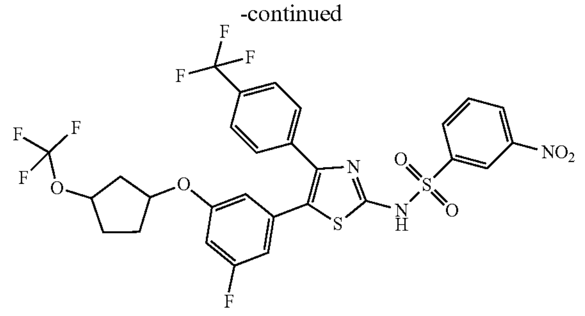

To a solution of 3-(trifluoromethoxy)cyclopentyl methanesulfonate (730 mg, 2.94 mmol) in 2 mL of NMP were added N-[5-(3-fluoro-5-hydroxy-phenyl)-4-[4-(trifluoromethyl)phenyl]thiazol-2-yl]-3-nitro-benzenesulfonamide (150 mg, 0.28 mmol), $Cs_2CO_3$ (226 mg, 0.695 mmol) in a sealed tube. The reaction was heated at 100° C. overnight. The reaction was cooled to rt and then poured into water (20 mL). The resulting aqueous solution was then extracted with EA. The combined EA extracts were washed with water (10 mL) and then concentrated. The residue was purified by prep-TLC (PE:EA=1:1) to afford N-(5-(3-fluoro-5-((3-(trifluoromethoxy)cyclopentyl)oxy)phenyl)-4-(4-(trifluoromethyl)phenyl)thiazol-2-yl)-3-nitrobenzenesulfonamide (90 mg, 46.8%) as a yellow oil.

LCMS: LC retention time 1.684, 1.703 min. MS (ESI) m/z 692 $[M+H]^+$.

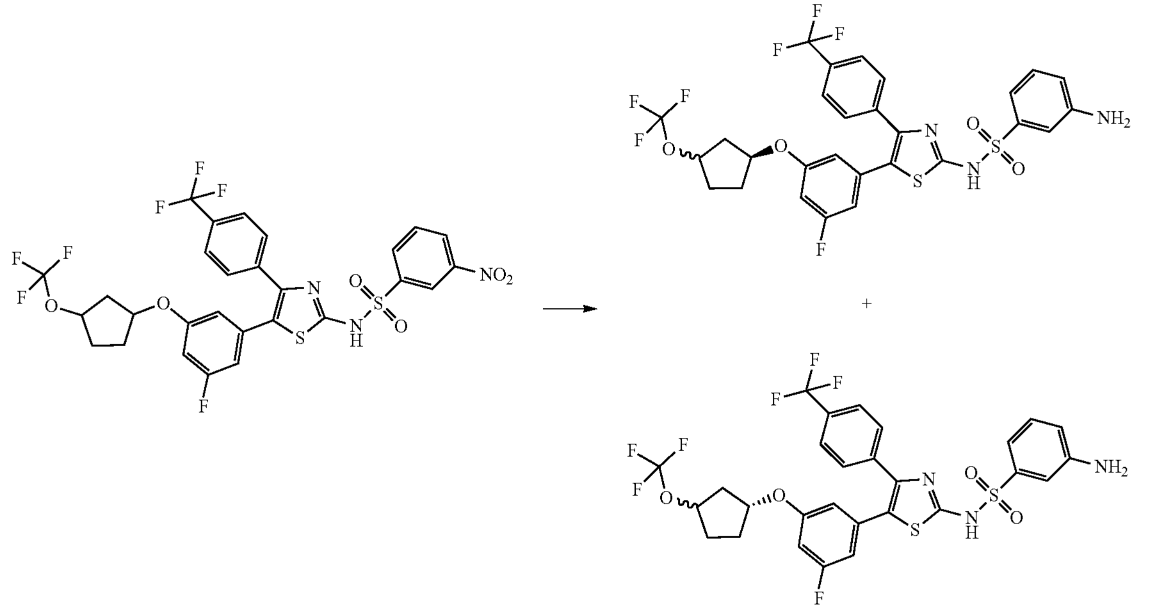 [SMILES: O=[N+]([O-])c1cccc(S(=O)(=O)Nc2nc(-c3ccc(C(F)(F)F)cc3)c(-c3cc(F)cc(OC4CCC(OC(F)(F)F)C4)c3)s2)c1 ; Nc1cccc(S(=O)(=O)Nc2nc(-c3ccc(C(F)(F)F)cc3)c(-c3cc(F)cc(O[C@@H]4CCC(OC(F)(F)F)C4)c3)s2)c1 ; Nc1cccc(S(=O)(=O)Nc2nc(-c3ccc(C(F)(F)F)cc3)c(-c3cc(F)cc(O[C@H]4CCC(OC(F)(F)F)C4)c3)s2)c1]

To a reaction of N-(5-(3-fluoro-5-((3-(trifluoromethoxy)cyclopentyl)oxy)phenyl)-4-(4-(trifluoromethyl)phenyl)thiazol-2-yl)-3-nitrobenzenesulfonamide (90 mg, 0.13 mmol) in MeOH (5 mL) and saturated $NH_4Cl$ solution (2 mL) was added Fe (72.7 mg, 1.3 mmol). The reaction was then refluxed for 1 h. The reaction mixture was cooled to room temperature and filtered. The filtrate was concentrated. The residue was purified by prep-HPLC to give two fractions. The first eluted compound was designated as Example 43A (5.8 mg, 6.7% yield) as a white solid; and the second eluted compound was designated as Example 43B (2.8 mg, 3.24% yield), as a yellow solid.

Example 43A: LCMS: LC retention time 1.932 min. MS (ESI) m/z 662 $[M+H]^+$.

$^1H$ NMR (400 MHz, methanol-d) δ 8.45 (s, 1H), 7.69 (d, J=8.0 Hz, 2H), 7.57 (d, J=8.0 Hz, 2H), 7.20-7.27 (m, 3H), 6.86-6.89 (m, 1H), 6.62-6.66 (m, 2H), 6.45 (s, 1H), 4.95-4.97 (m, 1H), 4.72-4.73 (m, 1H), 2.05-2.11 (m, 3H), 1.87-1.97 (m, 2H), 1.70-1.72 (m, 1H) ppm.

Example 43B: LCMS: LC retention time 1.899 min. MS (ESI) m/z 662 $[M+H]^+$.

$^1$HNMR (400 MHz, methanol-d) δ 8.45 (s, 1H), 7.69 (d, J=8.0 Hz, 2H), 7.57 (d, J=8.0 Hz, 2H), 7.20-7.35 (m, 3H), 6.85-6.88 (m, 1H), 6.62-6.65 (m, 2H), 6.47 (s, 1H), 4.75-4.77 (m, 1H), 4.60-4.63 (m, 1H), 2.18-2.25 (m, 1H), 1.96-2.01 (m, 2H), 1.82-1.86 (m, 3H) ppm.

The absolute stereochemistry is unknown.

Example 44A1

N-(5-(3-((1S,3R)-3-(Trifluoromethoxy)cyclopentyl)phenyl)-4-(2-(trifluoromethyl)phenyl)thiazol-2-yl)benzenesulfonamide

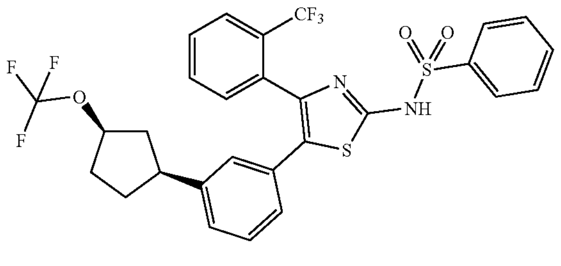 [SMILES: O=S(=O)(Nc1nc(-c2ccccc2C(F)(F)F)c(-c2cccc([C@H]3CC[C@@H](OC(F)(F)F)C3)c2)s1)c1ccccc1]

and

Example 44A2

N-(5-(3-((1S,3S)-3-(Trifluoromethoxy)cyclopentyl)phenyl)-4-(2-(trifluoromethyl)phenyl)thiazol-2-yl)benzenesulfonamide

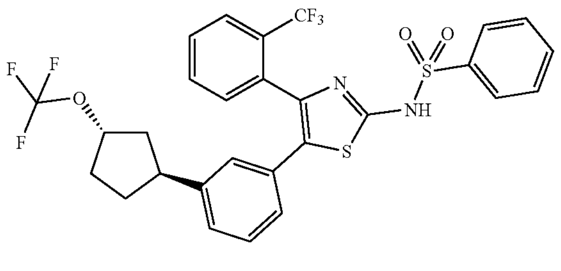 [SMILES: O=S(=O)(Nc1nc(-c2ccccc2C(F)(F)F)c(-c2cccc([C@H]3CC[C@H](OC(F)(F)F)C3)c2)s1)c1ccccc1]

Step 1.

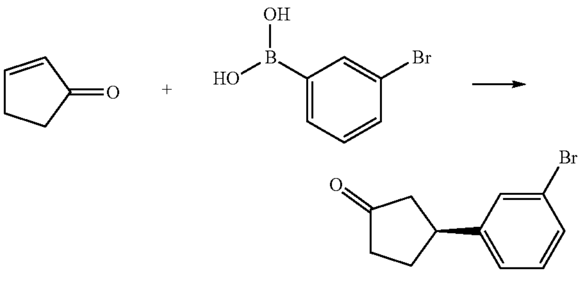

To a solution of (3-bromophenyl)boronic acid (6.84 g, 34.2 mmol) in 40 mL of dioxane and 4 mL of $H_2O$ were added acetylacetonatobis(ethylene)rhodium (I) (188.6 mg, 0.74 mmol), (S)-(+)-2,2'-bis(diphenylphosphino)-1,1'-binaphthyl (S-BINAP) (455 mg, 0.74 mmol), and cyclopent-2-en-1-one (2.00 g, 24.4 mmol) under nitrogen. The reaction mixture was heated to reflux. After refluxing for 5.0 h, the mixture was concentrated. The residue was partitioned between 100 mL of EtOAc and 100 mL of 1N $NaHCO_3$. After separating phases, the organic layer was washed with 100 mL of brine, dried over $Na_2SO_4$, filtered, and concentrated. The residue was purified by silica gel column chromatography (PE/EA=5/1) to afford 4.70 g of the title compound (S)-3-(3-bromophenyl)cyclopentan-1-one as a light yellow solid.

LCMS: LC retention time 2.14 min. MS (ESI) m/z 241 $[M+H]^+$.

Step 2.

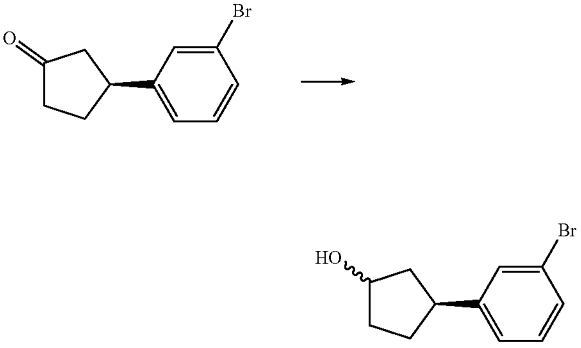

To a cooled solution of (S)-3-(3-bromophenyl)cyclopentan-1-one (4.58 g, 19.2 mmol) in anhydrous tetrahydrofuran (40.0 mL) was added DIBAL (1M in toluene, 76.7 mL) at −78° C. The reaction was stirred at the same temperature under argon atmosphere. Then the mixture was allowed to warm to room temperature slowly and stirred at room temperature overnight. Then saturated potassium sodium tartrate tetrahydrate solution (80 mL) was added and stirred for another 1 h. The mixture was filtered through a celite plug. The filtrate was concentrated under reduced pressure to give the crude which was purified by flash reversed phase column to give the desired compound (3S)-3-(3-bromophenyl)cyclopentan-1-ol (3.25 g, 70.4%) as colorless oil.

LCMS: LC retention time 2.05 min. MS (ESI) m/z 225 $[M-OH]^+$.

Step 3.

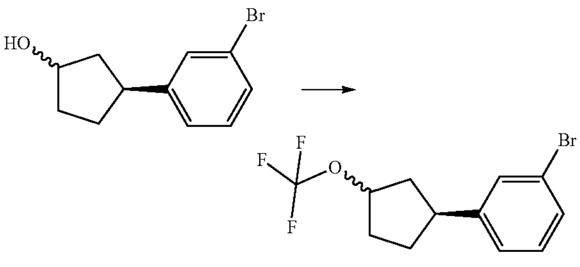

A flask were charged with AgOTf (3.20 g, 12.4 mmol), Select-F (2.20 g, 6.22 mmol), KF (964 mg, 16.6 mmol) and (3S)-3-(3-bromophenyl)cyclopentan-1-ol (1.0 g, 4.15 mmol), and then was purged with Ar. To this flask was added EtOAc (20 mL), followed by $TMSCF_3$ (1.77 g, 12.4 mmol) and 2-fluoropyridine (1.21 g, 12.4 mmol). The reaction mixture was stirred at room temperature overnight under Ar. The mixture was then filtered through a celite pad. The filtrate was concentrated to dryness. The residue was purified by combi-flash (100% PE) to afford the desired compound 1-bromo-3-((1S)-3-(trifluoromethoxy)cyclopentyl)benzene (402 mg, 31.4%) as a colorless oil.

$^1$H NMR (400 MHz, chloroform-d) δ 7.36 (dd, J=16.2, 9.0 Hz, 2H), 7.16 (dd, J=15.8, 6.8 Hz, 2H), 4.85 (d, J=28.0 Hz, 1H), 3.39-2.95 (m, 1H), 2.61-2.21 (m, 2H), 2.16-1.59 (m, 5H) ppm.

Step 4.

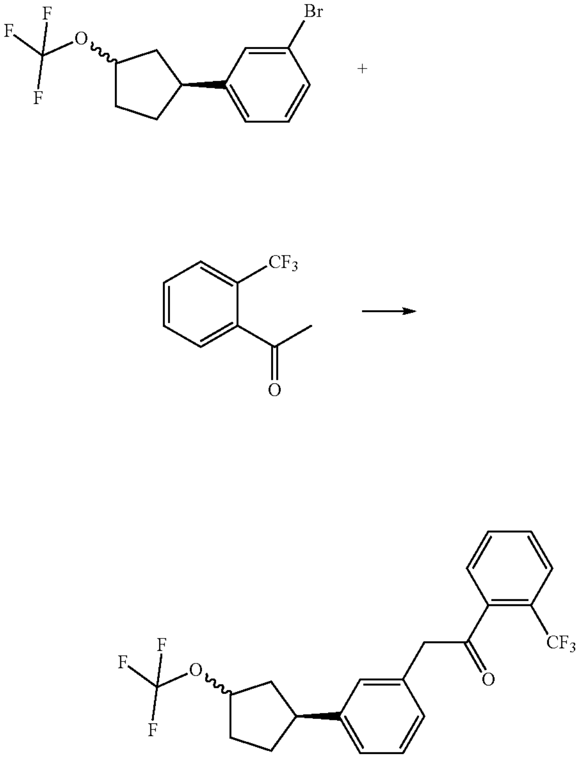

To a solution of 1-bromo-3-((1S)-3-(trifluoromethoxy)cyclopentyl)benzene (400 mg, 1.29 mmol) in toluene (2.5 mL) was added 1-(2-(trifluoromethyl)phenyl)ethan-1-one (243 mg, 1.29 mmol), t-BuOK (290 mg, 2.59 mmol). The reaction flask was purged with argon. Then, Xphos-Pd (10.2 mg, 0.0129 mmol) was added to the mixture. The reaction was heated to 65° C. and stirred for 4 h. After cooling to room temperature, saturated aqueous $NH_4Cl$ (30 mL) was added to the reaction solution. The resulting mixture was stirred thoroughly. The mixture was poured into water (50 mL) and extracted with ethyl acetate (50 mL×3). The combined organic extracts were dried over anhydrous $Na_2SO_4$ and filtered. The filtrate was concentrated under reduced pressure to give the crude. The crude was purified by silica gel chromatography (PE/EA=b20/1) to give the desired compound 2-(3-((1S)-3-(trifluoromethoxy)cyclopentyl)phenyl)-1-(2-(trifluoromethyl)phenyl)ethan-1-one (435 mg, 80.7%) as a light yellow oil.

LCMS: LC retention time 2.34 min. MS (ESI) m/z 418 $[M+H]^+$.

Step 5.

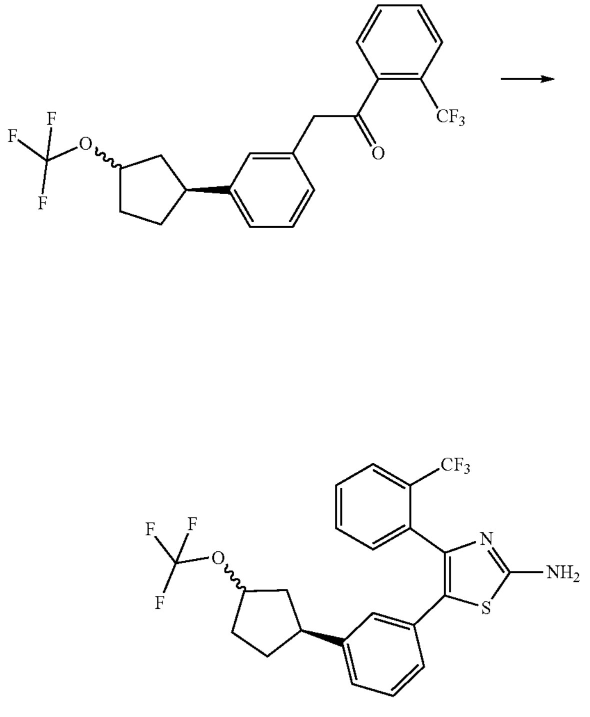

To a solution of 2-(3-((1S)-3-(trifluoromethoxy)cyclopentyl)phenyl)-1-(2-(trifluoromethyl)phenyl)ethan-1-one (400 mg, 0.96 mmol) in DMF (5 mL) were added thiourea (87.6 mg, 1.15 mmol), $KHCO_3$ (115 mg, 1.15 mmol), and $BrCCl_3$ (380 mg, 1.92 mmol). The reaction mixture was heated to 80° C. and stirred for 2 h. After cooling to room temperature, the mixture was poured into water (60 mL). the resulting aqueous solution was extracted with ethyl acetate (80 mL×3). The combined ethyl acetate extracts were washed with brine (100 mL), dried over anhydrous $Na_2SO_4$, and filtered and the filtrate was concentrated under reduced pressure to give the crude. The crude was purified by silica gel column chromatography (PE/EA=2/1) to give the desired compound 5-(3-((1S)-3-(trifluoromethoxy)cyclopentyl)phenyl)-4-(2-(trifluoromethyl)phenyl)thiazol-2-amine (220 mg, 48.5%) as a light yellow solid.

LCMS: LC retention time 2.17 min. MS (ESI) m/z 473 $[M+H]^+$.

Step 6.

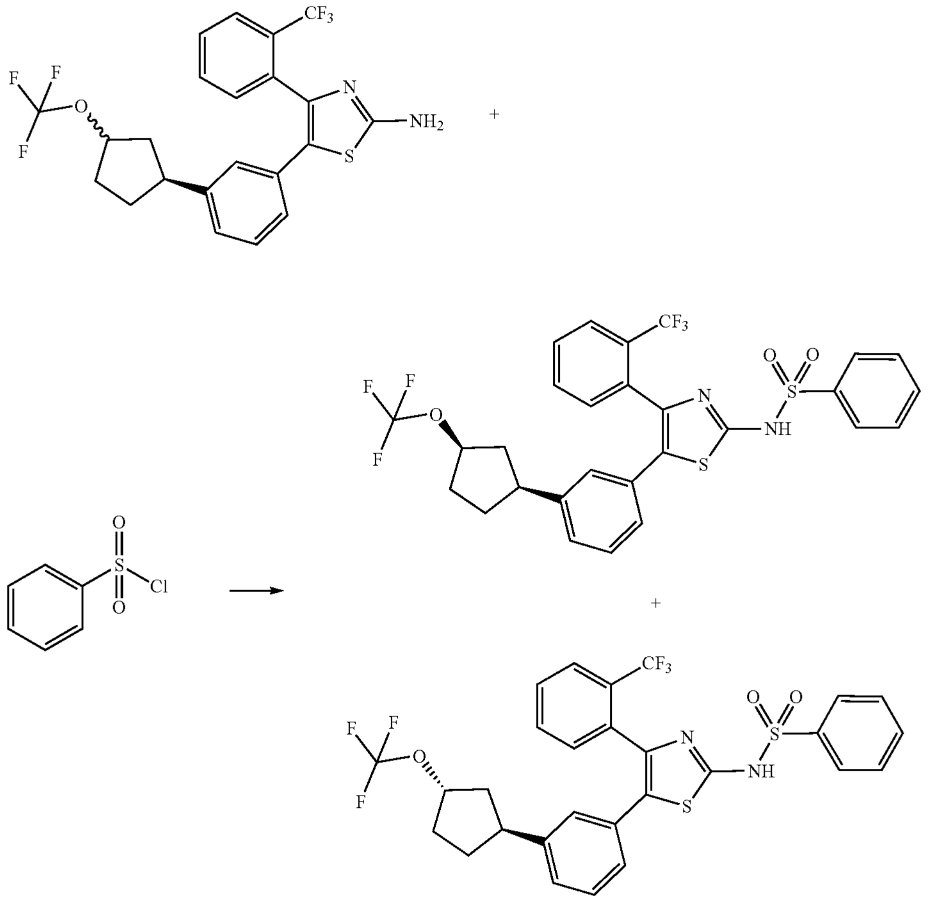

To a solution of 5-(3-((1S)-3-(trifluoromethoxy)cyclopentyl)phenyl)-4-(2-(trifluoromethyl)phenyl)thiazol-2-amine (220 mg, 0.466 mmol) in anhydrous pyridine (2.0 mL) was added benzenesulfonyl chloride at 0° C. (ice-bath) under argon atmosphere. The reaction mixture was allowed to stir overnight at room temperature. To the reaction mixture was added water (30 mL). The aqueous solution was extracted with ethyl acetate (50 mL×2). The organic layers were combined and washed with water (30 mL) and brine (30 mL), dried over anhydrous $Na_2SO_4$ and filtered. The filtrate was concentrated under reduced pressure. The crude residue was purified by prep-HPLC to give two fractions. The first compound eluted out was designated as Example 44A1 (48.0 mg, 16.8%), as a light yellow solid; The second compound eluted was designated as Example 44A2 (26.3 mg, 9.2%), as a light yellow solid. The absolute stereochemistry is unknown.

Example 44A1: LCMS: LC retention time: 2.26 min. MS (ESI) m/z 613 $[M+H]^+$.

$^1H$ NMR (400 MHz, chloroform-d) δ 7.90 (d, J=7.8 Hz, 2H), 7.75 (d, J=7.2 Hz, 1H), 7.52 (dt, J=14.0, 7.2 Hz, 3H), 7.43 (t, J=7.6 Hz, 2H), 7.30 (d, J=7.4 Hz, 1H), 7.10 (t, J=7.8 Hz, 1H), 7.03 (d, J=7.6 Hz, 1H), 6.87 (d, J=7.4 Hz, 1H), 6.81 (s, 1H), 4.66 (s, 1H), 2.87-2.75 (m, 1H), 2.37-2.25 (m, 1H), 2.01-1.86 (m 2H), 1.49 (dd, J=19.2, 10.8 Hz, 2H), 0.80 (d, J=6.8 Hz, 1H) ppm.

Example 44A2: LCMS: LC retention time 2.28 min. MS (ESI) m/z 613 $[M+H]^+$.

$^1H$ NMR (400 MHz, chloroform-d) δ 7.96 (d, J=7.6 Hz, 2H), 7.82 (d, J=7.6 Hz, 1H), 7.66-7.53 (m, 3H), 7.49 (t, J=7.6 Hz, 2H), 7.36 (d, J=7.2 Hz, 1H), 7.15 (t, J=7.8 Hz, 1H), 7.07 (d, J=7.8 Hz, 1H), 6.92 (d, J=8.0 Hz, 1H), 6.83 (s, 1H), 4.75 (s, 1H), 3.30-3.11 (m, 1H), 2.19-2.06 (m, 3H), 1.92 (s, 1H), 1.67-1.54 (m, 1H), 1.45-1.31 (m, 1H) ppm.

Example 44B1

N-(5-(3-((1R,3R)-3-(Trifluoromethoxy)cyclopentyl)phenyl)-4-(2-(trifluoromethyl)phenyl)thiazol-2-yl)benzenesulfonamide

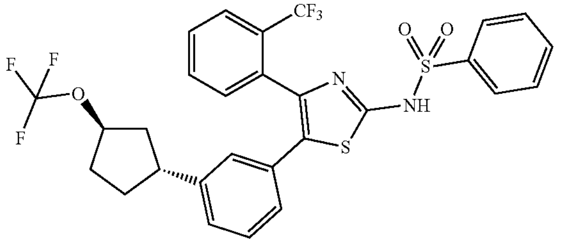 [SMILES: O=S(=O)(Nc1nc(-c2ccccc2C(F)(F)F)c(-c2cccc([C@@H]3CC[C@@H](OC(F)(F)F)C3)c2)s1)c1ccccc1]

and

Example 44B2

N-(5-(3-((1R,3S)-3-(Trifluoromethoxy)cyclopentyl)phenyl)-4-(2-(trifluoromethyl)phenyl)thiazol-2-yl)benzenesulfonamide

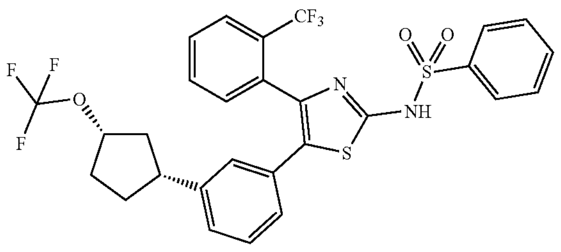 [SMILES: O=S(=O)(Nc1nc(-c2ccccc2C(F)(F)F)c(-c2cccc([C@@H]3CC[C@H](OC(F)(F)F)C3)c2)s1)c1ccccc1]

Example 44B1 and Example 44B2 were synthesized in essentially the identical protocols as Example 44A1 and Example 44A2 except using (R)-(+)-2,2'-bis(diphenylphosphino)-1,1'-binaphthyl (R-BINAP) instead of (S)-(+)-2,2'-bis(diphenylphosphino)-1,1'-binaphthyl (S-BINAP) in step 1. The same as Example 44A1 and Example 44A2 where the crude product was purified by prep-HPLC to obtain two fractions. The first compound eluted was designated as Example 44B1 (123.9 mg, 27% yield); The second compound eluted was designated as Example 44B2 (89.3 mg, 20% yield). The absolute stereochemistry is unknown.

Example 44B1: LCMS: LC retention time 2.28 min. MS (ESI) m/z 613 $[M+H]^+$.

$^1H$ NMR (400 MHz, chloroform-d) δ 7.94 (d, J=7.6 Hz, 2H), 7.82 (d, J=7.2 Hz, 1H), 7.63-7.53 (m, 3H), 7.50-7.46 (m, 2H), 7.37 (d, J=6.8 Hz, 1H), 7.16 (t, J=7.6 Hz, 1H), 7.10 (d, J=8.0 Hz, 1H), 6.94 (d, J=7.6 Hz, 1H), 6.88 (s, 1H), 4.76-4.71 (m, 1H), 2.90-2.83 (m, 1H), 2.40-2.35 (m, 1H), 1.99-1.86 (m, 3H), 1.61-1.52 (m, 2H) ppm.

Example 44B2: LCMS: LC retention time 2.30 min. MS (ESI) m/z 613 $[M+H]^+$.

$^1H$ NMR (400 MHz, chloroform-d) δ 7.96 (d, J=7.6 Hz, 2H), 7.83 (d, J=7.6 Hz, 1H), 7.65-7.54 (m, 3H), 7.51-7.47 (m, 2H), 7.37 (d, J=7.2 Hz, 1H), 7.15 (t, J=7.6 Hz, 1H), 7.08 (d, J=8.0 Hz, 1H), 6.92 (d, J=7.2 Hz, 1H), 6.84 (s, 1H), 4.77-4.74 (m, 1H), 3.21-3.14 (m, 1H), 2.20-2.06 (m, 3H), 1.95-1.91 (m, 1H), 1.65-1.57 (m, 2H) ppm.

Example 45 (A1, A2, B1, B2)

Example 45A1 and Example 45A2 in the following were similarly synthesized following procedures described in Example 44A1 and 44A2using (S)-(+)-2,2'-bis(diphenylphosphino)-1,1'-binaphthyl (S-BINAP) in step 1; Example 45B1 and Example 45B2 using (R)-(+)-2,2'-bis(diphenylphosphino)-1,1'-binaphthyl (R-BINAP) in step 1. In both cases, using 1,3-dimethyl-1H-pyrazole-4-sulfonyl chloride instead of phenyl sulfonyl chloride in Step 6.

ST1-HM7803-A, B

Example 45A1

1,3-Dimethyl-N-(5-(3-((1S,3R)-3-(trifluoromethoxy)cyclopentyl)phenyl)-4-(2-(trifluoromethyl)phenyl)thiazol-2-yl)-1H-pyrazole-4-sulfonamide

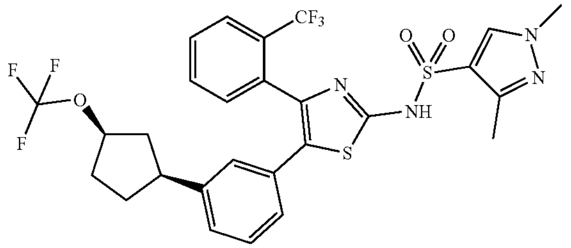 [SMILES: Cc1nn(C)cc1S(=O)(=O)Nc1nc(-c2ccccc2C(F)(F)F)c(-c2cccc([C@H]3CC[C@@H](OC(F)(F)F)C3)c2)s1]

LCMS: LC retention time 2.17 min. MS (ESI) m/z 631 $[M+H]^+$.

$^1H$ NMR (400 MHz, chloroform-d) δ 7.83 (d, J=7.2 Hz, 1H), 7.78 (s, 1H), 7.60 (dd, J=14.0, 7.2 Hz, 2H), 7.39 (d, J=6.8 Hz, 1H), 7.17 (t, J=7.6 Hz, 1H), 7.10 (d, J=7.8 Hz, 1H), 6.95 (d, J=7.8 Hz, 1H), 6.88 (s, 1H), 4.74 (s, 1H), 3.84 (s, 3H), 2.95-2.83 (m, 1H), 2.44-2.34 (m, 4H), 2.04-1.83 (m, 3H), 1.56 (dd, J=17.8, 8.0 Hz, 2H) ppm.

Example 45A2

1,3-Dimethyl-N-(5-(3-((1S,3S)-3-(trifluoromethoxy)cyclopentyl)phenyl)-4-(2-(trifluoromethyl)phenyl)thiazol-2-yl)-1H-pyrazole-4-sulfonamide

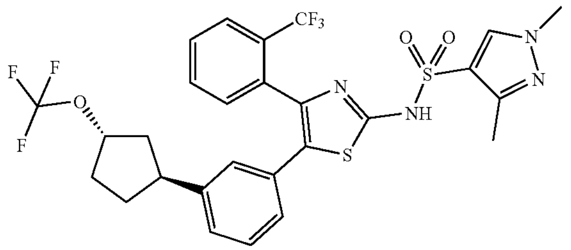 [SMILES: Cc1nn(C)cc1S(=O)(=O)Nc1nc(-c2ccccc2C(F)(F)F)c(-c2cccc([C@H]3CC[C@H](OC(F)(F)F)C3)c2)s1]

LCMS: LC retention time 2.19 min. MS (ESI) m/z 631 $[M+H]^+$.

$^1HNMR$ (400 MHz, chloroform-d) δ 7.84 (d, J=8.2 Hz, 1H), 7.79 (s, 1H), 7.68-7.56 (m, 2H), 7.38 (d, J=7.2 Hz, 1H), 7.15 (t, J=8.0 Hz, 1H), 7.08 (d, J=7.6 Hz, 1H), 6.93 (d, J=7.0 Hz, 1H), 6.84 (s, 1H), 4.76 (s, 1H), 3.85 (s, 3H), 3.18 (d, J=9.0 Hz, 1H), 2.42 (s, 3H), 2.20-2.14 (m, 3H), 1.93 (s, 1H), 1.67-1.55 (m, 2H), 1.36 (d, J=10.2 Hz, 1H) ppm.

Assignment of the stereochemistry was arbitrarily. The first eluted compound was designated as Example 45A1, and second eluted compound was designated as Example 45A2.

Example 45B1

1,3-Dimethyl-N-(5-(3-((1R,3S)-3-(trifluoromethoxy)cyclopentyl)phenyl)-4-(2-(trifluoromethyl)phenyl)thiazol-2-yl)-1H-pyrazole-4-sulfonamide

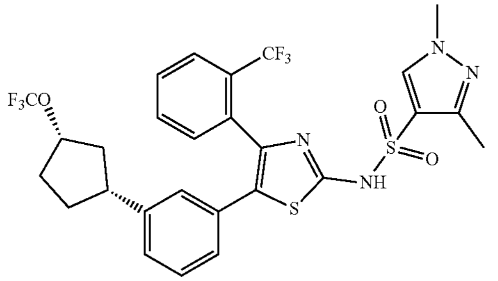 [SMILES: Cc1nn(C)cc1S(=O)(=O)Nc1nc(-c2ccccc2C(F)(F)F)c(-c2cccc([C@@H]3CC[C@H](OC(F)(F)F)C3)c2)s1]

45B1: LCMS: LC retention time 2.16 min. MS (ESI) m/z 631.2 $[M+H]^+$.

P1: $^1H$ NMR (400 MHz, chloroform-d) δ 7.83 (d, J=6.8 Hz, 1H), 7.79 (s, 1H), 7.64-7.57 (m, 2H), 7.38 (d, J=7.2 Hz, 1H), 7.15 (t, J=15.6, 8.0 Hz, 1H), 7.10 (d, J=7.6 Hz, 1H), 6.94 (d, J=7.6 Hz, 1H), 6.88 (s, 1H), 4.74 (s, 1H), 3.84 (s, 3H), 2.91-2.83 (m, 1H), 2.42 (s, 3H), 2.00-1.90 (m, 3H), 1.60-1.55 (m, 2H), 1.48 (d, J=6.8 Hz, 1H) ppm.

Example 45B2

1,3-Dimethyl-N-(5-(3-((1R,3R)-3-(trifluoromethoxy)cyclopentyl)phenyl)-4-(2-(trifluoromethyl)phenyl)thiazol-2-yl)-1H-pyrazole-4-sulfonamide

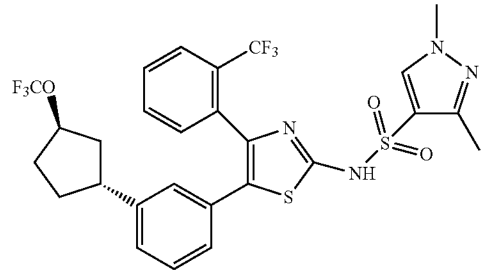 [SMILES: Cc1nn(C)cc1S(=O)(=O)Nc1nc(-c2ccccc2C(F)(F)F)c(-c2cccc([C@@H]3CC[C@@H](OC(F)(F)F)C3)c2)s1]

45B2:

LCMS: LC retention time 2.18 min. MS (ESI) m/z 631 $[M+H]^+$.

$^1H$ NMR (400 MHz, chloroform-d) δ 7.82 (d, J=7.6 Hz, 1H), 7.77 (s, 1H), 7.65-7.57 (m, 2H), 7.38 (d, J=7.2 Hz, 1H), 7.15 (t, J=15.6, 8.0 Hz, 1H), 7.07 (d, J=8 Hz, 1H), 6.93 (d, J=8 Hz, 1H), 6.83 (s, 1H), 4.76 (s, 1H), 3.83 (s, 3H), 3.23-3.14 (m, 1H), 2.38 (s, 3H), 2.19-2.06 (m, 3H), 1.96-1.92 (m, 1H), 1.64-1.56 (m, 1H), 1.41-1.34 (m, 1H) ppm.

Assignment of the stereochemistry was arbitrarily. The first eluted compound was designated as Example 45B1, and second eluted compound was designated as Example 45B2.

Example 46 (A1, A2, B1, B2)

Example 46 (A1, A2, B1, B2) was similarly synthesized following procedures described in Example 45 (A1, A2, B1, B2) by selecting the corresponding starting materials and the chiral catalyst.

Example 46A1

N-(4-(2-Isopropylphenyl)-5-(3-((1S,3R)-3-(trifluoromethoxy)cyclopentyl)phenyl)thiazol-2-yl)-1,3-dimethyl-1H-pyrazole-4-sulfonamide

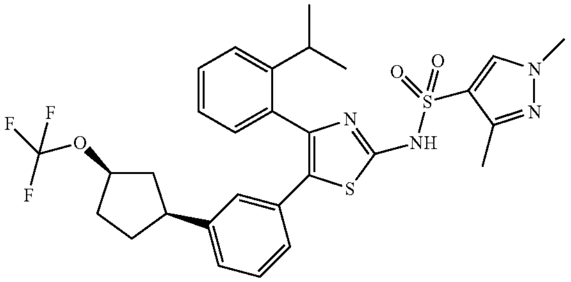 [SMILES: Cc1nn(C)cc1S(=O)(=O)Nc1nc(-c2ccccc2C(C)C)c(-c2cccc([C@H]3CC[C@@H](OC(F)(F)F)C3)c2)s1]

LCMS: LC retention time 2.29 min. MS (ESI) m/z 605 $[M+H]^+$.

$^1H$ NMR (400 MHz, chloroform-d) δ 7.82 (s, 1H), 7.50-7.44 (m, 1H), 7.39 (d, J=7.8 Hz, 1H), 7.30-7.23 (m, 2H), 7.17 (t, J=7.6 Hz, 1H), 7.08 (d, J=7.8 Hz, 1H), 6.99 (d, J=8.0 Hz, 1H), 6.89 (s, 1H), 4.71 (dd, J=9.6, 5.4 Hz, 1H), 3.84 (s, 3H), 2.90-2.77 (m, 2H), 2.45 (s, 3H), 2.40-2.31 (m, 1H), 2.00-1.84 (m, 3H), 1.59-1.50 (m, 2H), 1.00 (d, J=6.6 Hz, 6H) ppm.

Example 46A2

N-(4-(2-Isopropylphenyl)-5-(3-((1S,3S)-3-(trifluoromethoxy)cyclopentyl)phenyl)thiazol-2-yl)-1,3-dimethyl-1H-pyrazole-4-sulfonamide

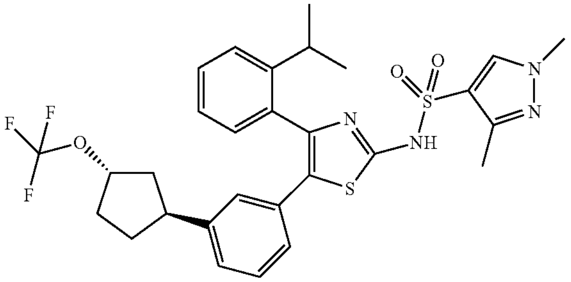 [SMILES: Cc1nn(C)cc1S(=O)(=O)Nc1nc(-c2ccccc2C(C)C)c(-c2cccc([C@H]3CC[C@H](OC(F)(F)F)C3)c2)s1]

LCMS: LC retention time 2.32 min. MS (ESI) m/z 605 $[M+H]^+$.

$^1H$ NMR (400 MHz, chloroform-d) δ 7.82 (s, 1H), 7.50-7.45 (m, 1H), 7.40 (d, J=7.8 Hz, 1H), 7.30-7.23 (m, 2H), 7.17 (t, J=7.6 Hz, 1H), 7.05 (d, J=7.8 Hz, 1H), 6.99 (d, J=8.0 Hz, 1H), 6.81 (s, 1H), 4.74-4.68 (m, 1H), 3.83 (s, 3H), 3.21-3.11 (m, 1H), 2.82 (dt, J=13.6, 6.8 Hz, 1H), 2.43 (s, 3H), 2.17-1.99 (m, 3H), 1.90 (dd, J=14.8, 7.8 Hz, 1H), 1.59-1.49 (m, 1H), 1.34-1.30 (m, 1H), 0.99 (d, J=6.8 Hz, 6H) ppm.

Example 46B1

N-(4-(2-Isopropylphenyl)-5-(3-((1R,3S)-3-(trifluoromethoxy)cyclopentyl)phenyl)thiazol-2-yl)-1,3-dimethyl-1H-pyrazole-4-sulfonamide

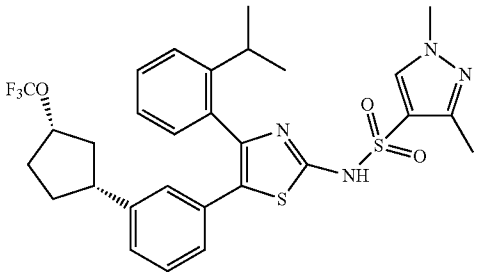 [SMILES: Cc1nn(C)cc1S(=O)(=O)Nc1nc(-c2ccccc2C(C)C)c(-c2cccc([C@@H]3CC[C@H](OC(F)(F)F)C3)c2)s1]

LCMS: LC retention time 2.26 min. MS (ESI) m/z 605 $[M+H]^+$.

$^1H$ NMR (400 MHz, chloroform-d) δ 7.82 (s, 1H), 7.48 (m, 1H), 7.40 (d, J=8 Hz, 1H), 7.30 (m, 2H), 7.19-7.15 (t, J=16.0, 8.4 Hz, 1H), 7.08 (d, J=7.6 Hz, 1H), 6.99 (d, J=7.6 Hz, 1H), 6.89 (s, 1H), 4.72 (s, 1H), 3.84 (s, 3H), 2.90-2.79 (m, 2H), 2.46 (s, 3H), 2.40-2.32 (m, 1H), 1.96-1.87 (m, 3H), 1.59 (m, 2H), 0.10 (s, 6H) ppm.

Example 46B2

N-(4-(2-Isopropylphenyl)-5-(3-((1R,3R)-3-(trifluoromethoxy)cyclopentyl)phenyl)thiazol-2-yl)-1,3-dimethyl-1H-pyrazole-4-sulfonamide

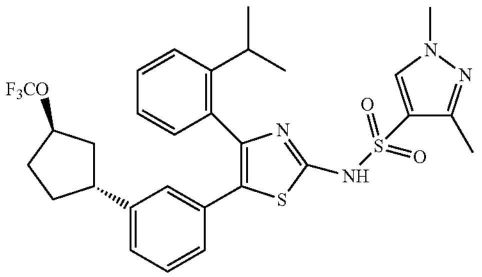 [SMILES: Cc1nn(C)cc1S(=O)(=O)Nc1nc(-c2ccccc2C(C)C)c(-c2cccc([C@@H]3CC[C@@H](OC(F)(F)F)C3)c2)s1]

LCMS: LC retention time 2.27 min. MS (ESI) m/z 605 $[M+H]^+$.

$^1H$ NMR (400 MHz, chloroform-d) δ 7.84 (s, 1H), 7.50 (m, 1H), 7.42 (d, J=7.6 Hz, 1H), 7.32 (s, 2H), 7.21-7.17 (t, J=15.6, 7.6 Hz, 1H), 7.09 (s, 1H), 7.01 (d, J=8 Hz, 1H), 6.84 (s, 1H), 4.75 (s, 1H), 3.86 (s, 3H), 3.21-3.14 (m, 1H), 2.87-2.82 (m, 1H), 2.47 (s, 3H), 2.18-2.03 (m, 3H), 1.93-1.88 (m, 1H), 1.60-1.56 (m, 1H), 1.37-1.27 (m, 1H), 1.01 (s, 6H) ppm.

Example 47A1

3-Amino-2-fluoro-N-(5-(3-((1S,3R)-3-(trifluoromethoxy)cyclopentyl)phenyl)-4-(2-(trifluoromethyl)phenyl)thiazol-2-yl)benzenesulfonamide

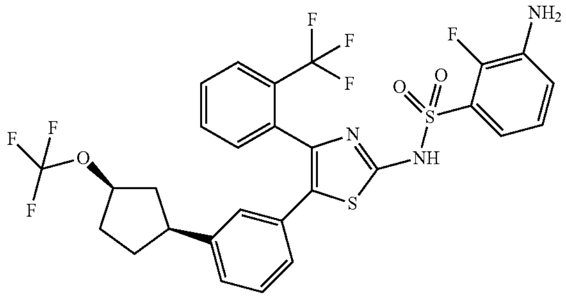 [SMILES: Nc1cccc(S(=O)(=O)Nc2nc(-c3ccccc3C(F)(F)F)c(-c3cccc([C@H]4CC[C@@H](OC(F)(F)F)C4)c3)s2)c1F]

And

Example 47A2

3-Amino-2-fluoro-N-(5-(3-((1S,3S)-3-(trifluoromethoxy)cyclopentyl)phenyl)-4-(2-(trifluoromethyl)phenyl)thiazol-2-yl)benzenesulfonamide

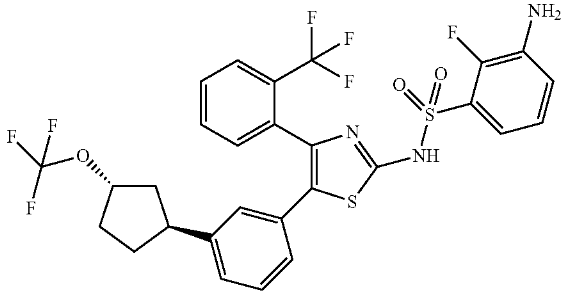 [SMILES: Nc1cccc(S(=O)(=O)Nc2nc(-c3ccccc3C(F)(F)F)c(-c3cccc([C@H]4CC[C@H](OC(F)(F)F)C4)c3)s2)c1F]

Step 1.

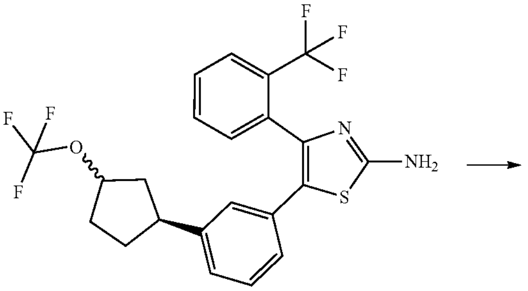

-continued

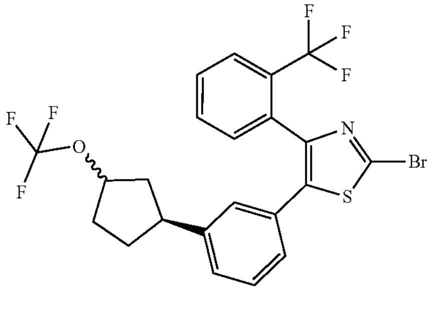

To a solution of 5-(3-((1S)-3-(trifluoromethoxy)cyclopentyl)phenyl)-4-(2-(trifluoromethyl)phenyl)thiazol-2-amine (obtained from the synthesis of Example 44A, step 5) (330 mg, 0.698 mmol) in anhydrous MeCN (5.0 mL) were added $CuBr_2$ (93.5 mg, 0.419 mmol) and tert-butyl nitrite (71.9 mg, 0.698 mmol) at room temperature. The resulting mixture was stirred at 80° C. for 15 min. An aliquot checked by LCMS analysis indicated that the reaction was completed. The reaction was quenched by addition of water (20 mL). The aqueous solution was extracted with ethyl acetate (30 mL×3). The combined organic layers were washed with brine (50 mL), dried over anhydrous sodium sulfate, filtered, and concentrated to dryness. The crude residue was purified by silica gel column chromatography (PE/EA=10/1) to give the desired compound 2-bromo-5-(3-((1S)-3-(trifluoromethoxy)cyclopentyl)phenyl)-4-(2-(trifluoromethyl)phenyl)thiazole (220 mg, 58.7%) as a light yellow oil.

LCMS: LC retention time 2.18 min. MS (ESI) m/z 536 $[M+H]^+$.

Step 2.

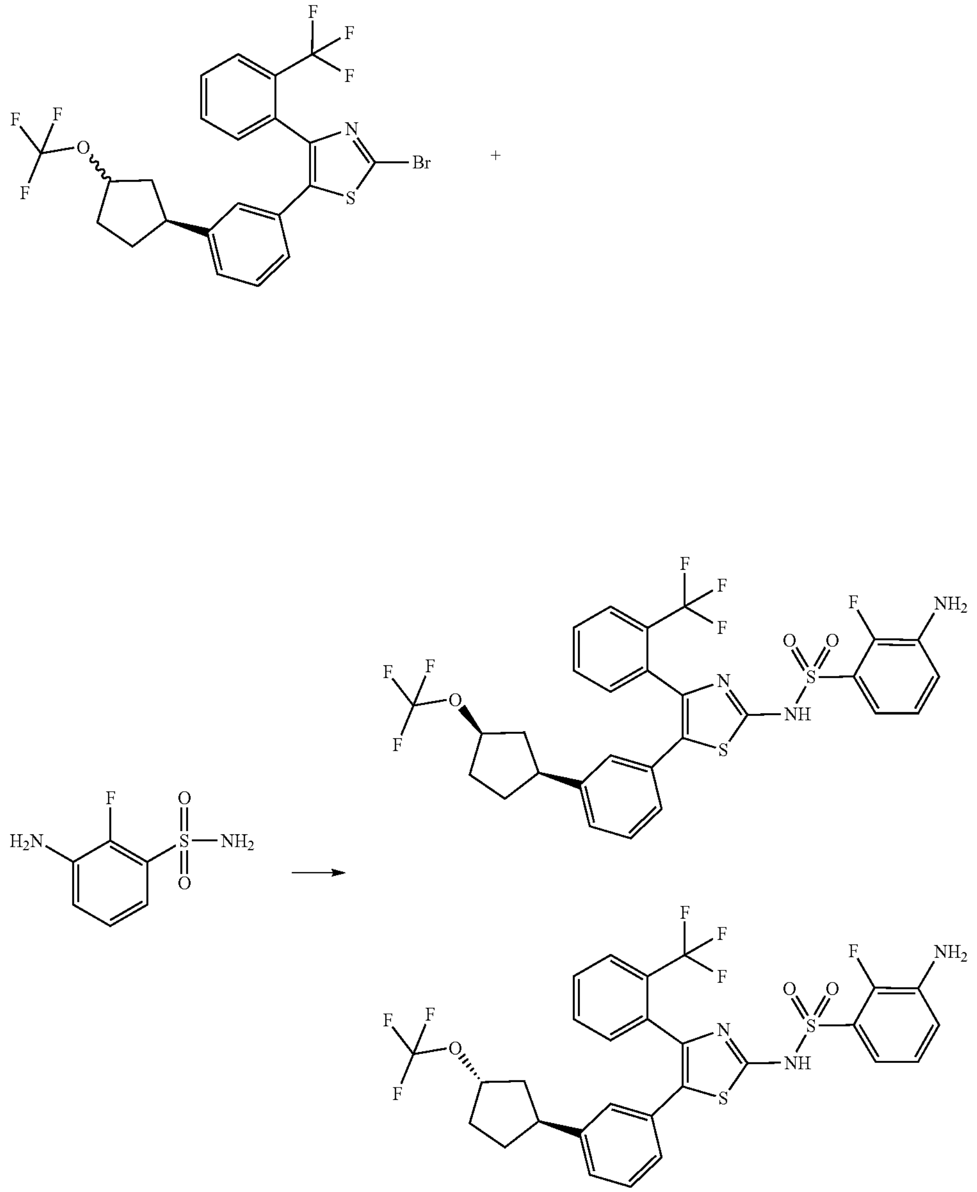

To a solution of 2-bromo-5-(3-((1S)-3-(trifluoromethoxy)cyclopentyl)phenyl)-4-(2-(trifluoromethyl)phenyl)thiazole (220 mg, 0.41 mmol) in anhydrous DMF (3.0 mL) were added Intermediate R-11 (117 mg, 0.615 mmol), CuI (7.8 mg, 0.041 mmol), $K_2CO_3$ (170 mg, 1.23 mmol) and N,N'-dimethyl-1,2-ethanediamine (18.2 mg, 0.205 mmol) under nitrogen in a glove-box. The reaction was heated to 100° C. and stirred at the same temperature overnight. Then the reaction mixture was cooled to room temperature and poured into water (20 mL). The resulting aqueous solution was extracted with ethyl acetate (20 mL×3). The combined organic extracts were washed with brine (20 mL), dried over anhydrous sodium sulfate, filtered and concentrated to dryness under reduced pressure. The crude was purified by prep-HPLC to give Example 47A1 (29.8 mg, 11.3%) as a light yellow solid and Example 47A2 (13.9 mg, 5.25%), also a light yellow solid.

Assignment of the stereochemistry was arbitrarily. The first eluted compound was designated as Example 47A1, and second eluted compound was designated as Example 47A2. The absolute stereochemistry is unknown.

Example 47A1

LCMS: LC retention time 2.18 min. MS (ESI) m/z 646 $[M+H]^+$.

$^1H$ NMR (400 MHz, chloroform-d) δ 7.83 (d, J=7.4 Hz, 1H), 7.66-7.56 (m, 2H), 7.40 (d, J=7.2 Hz, 1H), 7.33 (t, J=6.4 Hz, 1H), 7.17 (t, J=7.6 Hz, 1H), 7.11 (d, J=7.4 Hz, 1H), 7.02 (t, J=8.0 Hz, 1H), 6.96 (d, J=8.0 Hz, 1H), 6.89 (s, 1H), 4.73 (s, 1H), 3.89 (s, 1H), 2.95-2.81 (m, 1H), 2.45-2.33 (m, 1H), 2.04-1.83 (m, 2H), 1.72-1.45 (m, 2H), 1.25 (s, 1H) ppm.

Example 47A2

LCMS: LC retention time 2.20 min. MS (ESI) m/z 646 $[M+H]^+$.

$^1H$ NMR (400 MHz, chloroform-d) δ 7.83 (d, J=7.6 Hz, 1H), 7.67-7.56 (m, 2H), 7.40 (d, J=7.4 Hz, 1H), 7.32 (t, J=6.6 Hz, 1H), 7.15 (t, J=7.8 Hz, 1H), 7.07 (d, J=7.8 Hz, 1H), 7.02 (t, J=7.8 Hz, 1H), 6.94 (t, J=8.6 Hz, 2H), 6.85 (s, 1H), 4.76 (s, 1H), 3.89 (s, 1H), 3.18 (dd, J=17.6, 8.0 Hz, 1H), 2.20-2.07 (m, 3H), 1.92 (s, 1H), 1.68-1.54 (m, 1H), 1.39 (dd, J=16.4, 8.6 Hz, 1H) ppm.

Example 47B1 and Example 47B2

Example 47B1 and Example 47B2 were synthesized similarly following the protocol in synthesis of Example 47A1 and 47A2 by using the intermediate 2-bromo-5-(3-((1R)-3-(trifluoromethoxy)cyclopentyl)phenyl)-4-(2-(trifluoromethyl)phenyl)thiazole obtained from the synthesis of Example 44B, step 5.

Example 47B1

3-Amino-2-fluoro-N-(5-(3-((1R,3S)-3-(trifluoromethoxy)cyclopentyl)phenyl)-4-(2-(trifluoromethyl)phenyl)thiazol-2-yl)benzenesulfonamide

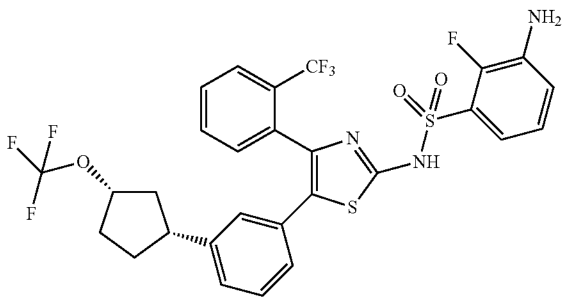 [SMILES: Nc1cccc(S(=O)(=O)Nc2nc(-c3ccccc3C(F)(F)F)c(-c3cccc([C@@H]4CC[C@H](OC(F)(F)F)C4)c3)s2)c1F]

LCMS: LC retention time 2.17 min. MS (ESI) m/z 646 $[M+H]^+$.

$^1H$ NMR (400 MHz, chloroform-d) δ 7.84-7.82 (m, 1H), 7.64-7.57 (m, 2H), 7.41-7.39 (m, 1H), 7.34-7.30 (m, 1H), 7.19-7.15 (m, 1H), 7.11-7.09 (m, 1H), 7.03-6.99 (m, 1H), 6.96-6.92 (m, 2H), 6.89 (s, 1H), 4.76-4.71 (m, 1H), 3.89 (br, 2H), 2.93-2.84 (m, 1H), 2.42-2.35 (m, 1H), 1.99-1.86 (m, 3H), 1.61-1.53 (m, 2H) ppm.

Example 47B2

3-Amino-2-fluoro-N-(5-(3-((1R,3R)-3-(trifluoromethoxy)cyclopentyl)phenyl)-4-(2-(trifluoromethyl)phenyl)thiazol-2-yl)benzenesulfonamide

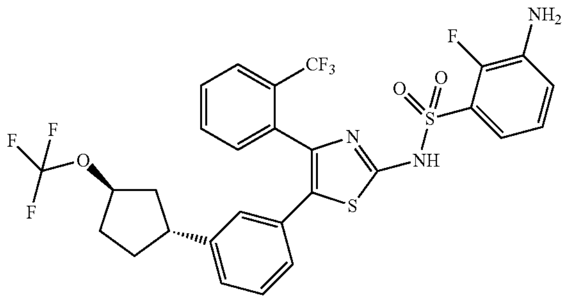 [SMILES: Nc1cccc(S(=O)(=O)Nc2nc(-c3ccccc3C(F)(F)F)c(-c3cccc([C@@H]4CC[C@@H](OC(F)(F)F)C4)c3)s2)c1F]

LCMS: LC retention time 2.21 min. MS (ESI) m/z 646 $[M+H]^+$.

$^1H$ NMR (400 MHz, chloroform-d) δ 7.83 (d, J=7.2 Hz, 1H), 7.65-7.57 (m, 2H), 7.40 (d, J=6.8 Hz, 1H), 7.30 (t, J=6.4 Hz, 1H), 7.17-7.13 (m, 1H), 7.08-7.06 (m, 1H), 7.03-6.99 (m, 1H), 6.96-6.92 (m, 2H), 6.85 (s, 1H), 4.76-4.75 (m, 1H), 3.21-3.14 (m, 1H), 2.20-2.06 (m, 3H), 1.96-1.89 (m, 1H), 1.65-1.57 (m, 1H), 1.40-1.35 (m, 1H) ppm.

Example 48 (A1, A2, B1, and B2)

Example 48 (A1, A2, B1, and B2) were synthesized analogously to Example 47 (A1, A2, B1, and B2) by the protocols detailed above.

Example 48A1

3-Amino-2-fluoro-N-(4-(2-isopropylphenyl)-5-(3-((1S,3R)-3-(trifluoromethoxy)cyclopentyl)phenyl)thiazol-2-yl)benzenesulfonamide

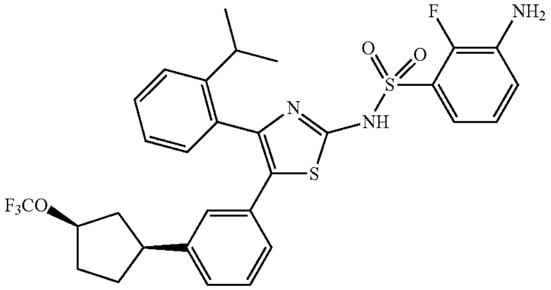 [SMILES: CC(C)c1ccccc1-c1nc(NS(=O)(=O)c2cccc(N)c2F)sc1-c1cccc([C@H]2CC[C@@H](OC(F)(F)F)C2)c1]

LCMS: LC retention time 2.337 min. MS (ESI) m/z 620 $[M+H]^+$.

$^1$H NMR (400 MHz, chloroform-d) δ 7.47 (m, 1H), 7.38 (m, 2H), 7.27 (m, 1H), 7.19 (m, 1H), 7.05 (m, 5H), 6.89 (s, 1H), 4.71 (m, 1H), 3.88 (s, 2H), 2.85 (m, 2H), 1.92 (m, 1H), 1.89 (m, 3H), 1.54 (m, 2H), 1.02 (s, 6H) ppm.

Example 48A2

3-Amino-2-fluoro-N-(4-(2-isopropylphenyl)-5-(3-((1S,3S)-3-(trifluoromethoxy)cyclopentyl)phenyl)thiazol-2-yl)benzenesulfonamide

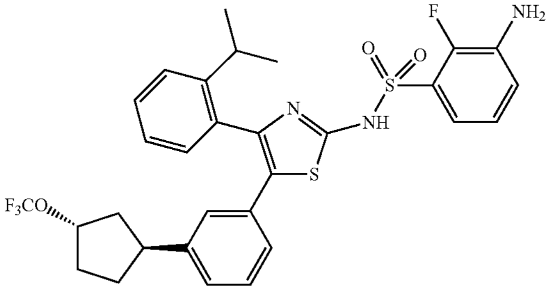 [SMILES: CC(C)c1ccccc1-c1nc(NS(=O)(=O)c2cccc(N)c2F)sc1-c1cccc([C@H]2CC[C@H](OC(F)(F)F)C2)c1]

LCMS: LC retention time 2.362 min. MS (ESI) m/z 620 $[M+H]^+$.

$^1$H NMR (400 MHz, chloroform-d) δ 7.56 (m, 1H), 7.39 (m, 2H), 7.28 (m, 2H), 7.19 (m, 1H), 7.02 (m, 5H), 6.84 (s, 1H), 4.74 (m, 1H), 3.90 (s, 2H), 3.18 (m, 1H), 2.80 (m, 1H), 2.15 (m, 3H), 2.04 (m, 1H), 1.34 (m, 1H), 1.02 (s, 6H) ppm.

Example 48B1

3-Amino-2-fluoro-N-(4-(2-isopropylphenyl)-5-(3-((1R,3S)-3-(trifluoromethoxy)cyclopentyl)phenyl)thiazol-2-yl)benzenesulfonamide

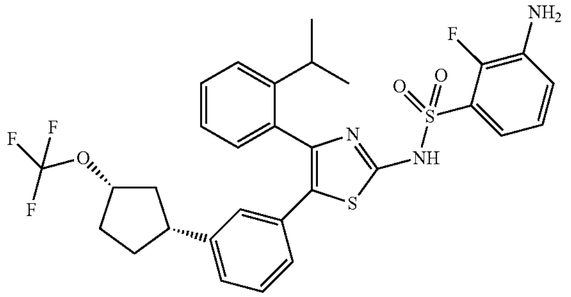 [SMILES: CC(C)c1ccccc1-c1nc(NS(=O)(=O)c2cccc(N)c2F)sc1-c1cccc([C@@H]2CC[C@H](OC(F)(F)F)C2)c1]

LCMS: LC retention time 2.26 min. MS (ESI) m/z 620 $[M+H]^+$.

$^1$H NMR (400 MHz, chloroform-d) δ 7.49-7.45 (m, 1H), 7.40-7.33 (m, 2H), 7.30-7.26 (m, 2H), 7.19-7.15 (m, 1H), 7.08 (d, J=7.6 Hz, 1H), 7.04-6.89 (m, 4H), 4.74-4.69 (m, 1H), 3.90 (br, 2H), 2.89-2.80 (m, 2H), 2.39-2.32 (m, 1H), 1.99-1.85 (m, 3H), 1.60-1.48 (m, 2H), 1.01 (s, 6H) ppm.

Example 48B2

3-Amino-2-fluoro-N-(4-(2-isopropylphenyl)-5-(3-((1R,3R)-3-(trifluoromethoxy)cyclopentyl)phenyl)thiazol-2-yl)benzenesulfonamide

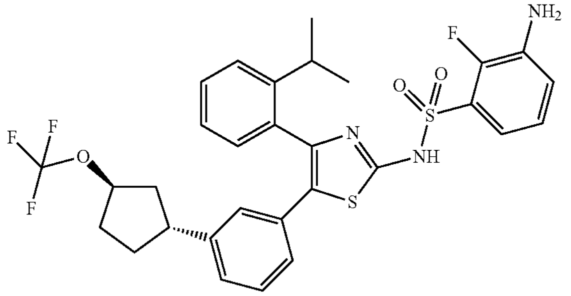 [SMILES: CC(C)c1ccccc1-c1nc(NS(=O)(=O)c2cccc(N)c2F)sc1-c1cccc([C@@H]2CC[C@@H](OC(F)(F)F)C2)c1]

LCMS: LC retention time 2.30 min. MS (ESI) m/z 620 $[M+H]^+$.

$^1$H NMR (400 MHz, chloroform-d) δ 7.50-7.46 (m, 1H), 7.41-7.35 (m, 2H), 7.30-7.28 (m, 2H), 7.19-7.15 (m, 1H), 7.07-6.94 (m, 4H), 6.82 (s, 1H), 4.73-4.70 (s, 1H), 3.89 (br, 2H), 3.21-3.12 (m, 1H), 2.87-2.81 (m, 1H), 2.16-2.00 (m, 3H), 1.93-1.86 (m, 1H), 1.59-1.51 (m, 1H), 1.37-1.30 (m, 1H), 1.00 (s, 6H) ppm.

Table 3. Example 49-509

The following examples were synthesized by the methods illustrated in the synthesis of Example 1 to 48 or analogously to Example 1 to 48 using the proper Intermediates described in the section of "Preparation of Intermediates" and the commercially available starting materials.

TABLE 3

| Example 49-509 | | | |
|---|---|---|---|
| Compound Number | NMR | LCMS retention time (min.) | LCMS MS (ESI) m/z $[M + H]^+$ |
| 49 | $^1$H NMR (400 MHz, DMSO) δ 13.40 (s, 1H), 7.89 (d, J = 6.8 Hz, 2H), 7.79 (d, J = 8.4 Hz, 2H), 7.66-7.56 (m, 5H), 7.42 (d, J = 8.4 Hz, 1H), 6.85 (d, J = 8.0 Hz, 1H), 6.79 (s, 1H), 3.37 (s, 2H), 0.93 (s, 9H) ppm. | 1.12 | 595 |
| 50 | $^1$H NMR (400 MHz, DMSO) δ 13.40 (s, 1H), 7.89 (d, J = 6.8 Hz, 2H), 7.79 (d, J = 8.4 Hz, 2H), 7.66-7.56 (m, 5H), 7.42 (d, J = 8.4 Hz, 1H), 6.85 (d, J = 8.0 Hz, 1H), 6.79 (s, 1H), 3.37 (s, 2H), 0.93 (s, 9H) ppm. | 1.75 | 582 |
| 51 | $^1$H NMR (400 MHz, $CDCl_3$) δ 8.18 (brs, 1H), 8.01 (s, 1H), 7.72 (d, J = 8.0 Hz, 1H), 7.60-7.56 (m, 3H), 7.49-7.46 (m, 2H), 7.41 (t, J = 8.0 Hz, 1H), 6.61-6.54 (m, 2H), 6.44-6.41 (m, 1H), 3.44 (s, 2H), 3.00 (s, 3H), 0.98 (s, 9H) ppm. | ND | 658 |
| 52 | $^1$H NMR (400 MHz, $CDCl_3$) δ 8.01 (s, 1H), 7.75 (d, J = 8.0 Hz, 1H), 7.58 (d, J = 8.8 Hz, 1H), 7.50-7.37 (m, 5H), 7.24 (d, J = 8.4 Hz, 1H), 6.64 (s, 1H), 3.38 (s, 2H), 2.99 (s, 3H), 1.01 (s, 9H) ppm. | 2.45 | 674 |
| 53 | $^1$H NMR (400 MHz, $CDCl_3$) δ 7.44-7.29 (m, 6H), 7.24-7.20 (m, 1H), 6.80-6.78 (m, 1H), 6.53-6.50 (m, 1H), 6.42-6.38 (m, 2H), 4.16-3.83 (m, 1H), 1.96-1.72 (m, 1H), 1.33-1.21 (m, 3H), 1.00-0.86 (m, 6H) ppm. | 1.68 | 580 |
| 54 | $^1$H NMR (400 MHz, $CD_3OD$) δ 8.04 (d, 2H), 7.95 (d, 2H), 7.72 (d, 2H), 7.61-7.52 (m, 3H), 3.51-3.41 (m, 3H), 3.33-3.32 (m, 1H), 3.07-3.04 (m, 1H), 2.92-2.88 (m, 1H), 2.80-2.67 (m, 2H), 1.92-1.86 (m, 2H), 1.63-1.44 (m, 4H), 0.89(s, 9H) ppm. | ND | 568 |
| 55 | $^1$H NMR (400 MHz, DMSO-$d_6$) δ 7.89-7.88 (m, 2H), 7.87-7.76 (m, 2H), 7.74-7.56 (m, 5H), 7.26-7.30 (m, 1H), 6.72 (m, 1H), 6.92-6.85 (m, 2H), 6.67 (m, 1H), 1.54-1.5 (m, 2H), 0.9 (s, 9H) ppm. | ND | 560 |
| 56 | $^1$H NMR (400 MHz, $CDCl_3$) δ 7.59-7.55 (m, 3H), 7.50-7.42 (m, 3H), 7.22 (dd, J = 8.0 Hz & 8.0 Hz, 1H), 6.89-6.87 (m, 1H), 6.74 (m, 2H), 6.23 (d, J = 8 Hz, 1H), 3.46 (s, 3H), 1.01 (m, 9H) ppm. | 1.67 | 563 |
| 57 | $^1$H NMR (400 MHz, DMSO) δ 8.11 (dd, J = 7.6 Hz & 8 Hz, 1H), 8.00 (d, J = 7.6 Hz, 1H), 7.74-7.72 (m, 3H), 7.60 (d, J = 8.0 Hz, 2H), 7.26 (dd, J = 8.0 Hz & 8 Hz, 1H), 6.89 (dd, J = 2.0 Hz & 8 Hz, 1H), 6.80 (d, J = 7.6 Hz, 1H), 6.67 (s, 1H), 3.41 (s, 2H), 0.91 (m, 9H) ppm. | 2.32 | 582 |
| 58 | $^1$H NMR (400 MHz, $CDCl_3$) 8.02 (s, 1H), 7.80 (d, J = 7.6 Hz, 1H), 7.61-7.40 (m, 6H), 6.76-6.75 (m, 1H), 3.46 (s, 2H), 3.01 (s, 3H), 1.00 (s, 9H) ppm. | 1.67 | 568 |
| 59 | $^1$H NMR (400 MHz, $CDCl_3$) 7.53 (d, J = 8.4 Hz, 1H), 7.44 (s, 1H), 7.37 (d, J = 8.0 Hz, 3H), 7.25 (t, J = 7.6 Hz, 1H), 6.96 (t, J = 9.2 Hz, | 2.19 | 580 |

TABLE 3-continued

Example 49-509

| Compound Number | NMR | LCMS retention time (min.) | LCMS MS (ESI) m/z $[M + H]^+$ |
|---|---|---|---|
| | 1H), 6.89-6.76 (m, 2H), 6.74 (t, J = 2.8 Hz, 1H), 3.46 (s, 2H), 1.01 (s, 9H) ppm. | | |
| 60 | $^1$H NMR (400 MHz, chloroform-d) δ 7.52 (s, 1H), 7.43 (d, J = 8.4 Hz, 2H), 7.34 (d, J = 7.6 Hz, 3H), 7.20-7.13 (m, 2H), 6.85 (m, 1H), 6.76 (m, 1H), 6.68 (m, 2H), 3.43 (s, 2H), 1.00 (s, 9H). | 2.22 | 562 |
| 61 | $^1$H NMR (400 MHz, DMSO-$d_6$) δ 13.42 (br s, 1H), 7.77-7.75 (m, 2H), 7.58-7.54 (m, 3H), 7.18 (d, J = 9.6 Hz, 1H), 7.09 (d, J = 7.2 Hz, 1H), 7.01-6.97 (m, 1H), 6.86-6.83 (m, 1H), 6.62 (d, J = 8.4 Hz, 1H), 6.47 (s, 2H), 3.47 (s, 2H), 0.93 (s, 9H) ppm. | ND | 581 |
| 62 | $^1$H NMR (400 MHz, DMSO-$d_6$) δ 8.16-8.11 (m, 1H), 8.02-8.00 (m, 1H), 7.81-7.75 (m, 3H), 7.57-7.55 (m, 2H), 7.18 (t, J = 9.2 Hz, 1H), 7.01-6.97 (m, 1H), 6.84-6.82 (m, 1H), 3.46 (s, 2H), 0.93 (s, 9H) ppm. | ND | 600 |
| 63 | $^1$H NMR (400 MHz, $CDCl_3$) δ 8.01-7.99 (m, 1H), 7.79-7.77 (m, 1H), 7.61-7.58 (m, 3H), 7.48-7.45 (m, 3H), 6.58-6.56 (m, 1H), 6.49-6.46 (m, 2H), 3.93-3.90 (m, 1H), 3.01 (s, 3H), 1.82-1.76 (m, 1H), 1.29-1.10 (m, 3H), 0.90-0.88 (m, 6H) ppm. | 1.67 | 658 |
| 64 | $^1$H NMR (400 MHz, $CDCl_3$) δ 8.07-8.04 (m, 1H), 7.90 (t, J = 8.0 Hz, 1H), 7.67-7.59 (m, 4H), 7.50 (d, J = 8.0 Hz, 1H), 6.63-6.58 (m, 2H), 6.49 (d, J = 8.8 Hz, 1H), 3.47 (s, 2H), 1.01 (s, 9H) ppm. | ND | 600 |
| 65 | $^1$H NMR (400 MHz, $CDCl_3$) 7.99 (s, 1H), 7.71 (d, J = 8.0 Hz, 1H), 7.57 (d, J = 8.0 Hz, 1H), 7.43-7.32 (m, 5H), 6.63-6.49 (m, 3H), 4.24 (q, J = 8.0 Hz, 2H), 2.99 (s, 3H) ppm. | 2.07 | 670 |
| 66 | $^1$H NMR (400 MHz, chloroform-d) δ 7.52 (s, 1H), 7.43 (d, J = 8.4 Hz, 2H), 7.34 (d, J = 7.6 Hz, 3H), 7.20-7.13 (m, 2H), 6.85 (m, 1H), 6.76 (m, 1H), 6.68 (m, 2H), 3.43 (s, 2H), 1.00 (s, 9H). | 2.06 | 592 |
| 67 | $^1$H NMR (400 MHz, $CDCl_3$) δ 8.04 (s, 1H), 7.77 (d, J = 7.6 Hz, 1H), 7.63 (d, J = 7.6 Hz, 1H), 7.45-7.37 (m, 5H), 7.18 (dd, J = 8.0 Hz & 8 Hz, 1H), 6.87 (dd, J = 8.0 Hz & 1.6 Hz, 1H), 6.68-6.66 (m, 2H), 3.45 (s, 2H), 3.00 (s, 3 H), 1.00 (s, 9 H) ppm. | 1.67 | 640 |
| 68 | $^1$H NMR (400 MHz, $CD_3OD$) δ 7.94 (d, 2H), 7.81 (d, 2H), 7.71 (d, 2H), 7.62-7.52 (m, 3H), 4.09-4.08 (m, 1H), 3.53-3.43 (m, 2H), 3.26-3.20 (m, 2H), 3.12-3.02 (m, 2H), 2.12-2.01 (m, 2H), 1.53 (t, 2H), 0.95(s, 9H) ppm. | ND | 554 |
| 69 | $^1$H NMR (400 MHz, $CD_3OD$) δ 7.94 (d, 2H), 7.81 (d, 2H), 7.71 (d, 2H), 7.62-7.52 (m, 3H), 4.09-4.08 (m, 1H), 3.53-3.43 (m, 2H), 3.26-3.20 (m, 2H), 3.12-3.02 (m, 2H), 2.12-2.01 (m, 2H), 1.53 (t, 2H), 0.95(s, 9H) ppm. | ND | 554 |
| 70 | $^1$H NMR (400 MHz, $CD_3OD$) δ 7.57-7.54 (m, 2H), 7.48-7.44 (m, 3H), 7.15 (d, J = 7.2 Hz, 1H), 6.57 | ND | 581 |

TABLE 3-continued

| Compound Number | NMR | LCMS retention time (min.) | LCMS MS (ESI) m/z $[M+H]^+$ |
|---|---|---|---|
| Example 49-509 | | | |
| | (d, J = 8.8 Hz, 1H), 6.53-6.49 (m, 1H), 6.46-6.41 (m, 2H), 3.31 (s, 2H), 0.86 (s, 9H) ppm. | | |
| 71 | $^1$H NMR (400 MHz, $CDCl_3$) 7.97 (s, 1H), 7.82 (d, J = 8.8 Hz, 1H), 7.85-7.42 (m, 6H), 6.62-6.46(m, 3H), 3.76-3.58 (m, 2H), 3.03 (s, 1H), 1.28-1.27 (m, 2H), 0.94 (d, J = 7.6 Hz, 6H), 0.87 (d, J = 6.0 Hz, 3H) ppm. | ND | 672 |
| 72 | $^1$H NMR (400 MHz, $CDCl_3$) 7.39-7.32 (m, 6H), 7.17-7.16 (m, 1H), 6.75-6.74 (m, 1H), 6.53-6.24 (m, 3H), 3.68-3.55 (m, 2H), 1.72-1.71 (m, 2H), 0.88-0.84 (m, 9 H) ppm. | ND | 594 |
| 73 | $^1$H NMR (400 MHz, $CDCl_3$) δ 7.63 (d, J = 8.0 Hz, 2H), 7.52 (d, J = 8.0 Hz, 2H), 7.41 (d, J = 2.0 Hz, 1H), 7.31 (d, J = 8.0 Hz, 1H), 6.80 (d, J = 2.0 Hz, 1H), 6.76 (dd, J = 8.0 Hz & J = 2.0 Hz, 1H), 6.71 (d, J = 2.0 Hz, 1H), 3.93 (s, 3H), 3.83 (t, J = 6.8 Hz, 2H), 1.71 (t, J = 7.2 Hz, 2H), 0.95 (s, 9H) ppm. | ND | 599 |
| 74 | $^1$H NMR (400 MHz, $CDCl_3$) δ 7.97-7.95 (m, 2H) 7.70-7.68 (m, 2H) 7.56-7.52 (m, 3H), 7.46-7.42 (m, 2H), 7.26-7.20 (m, 1H), 6.72 (m, 1H), 6.70 (m, 1H), 6.64 (m, 1H), 3.56 (s, 2H), 1.03 (s, 9H) ppm. | ND | 563 |
| 75 | $^1$H NMR (400 MHz, chloroform-d) δ 7.64 (d, J = 8.4 Hz, 2H), 7.48 (d, J = 8.4 Hz, 2H), 7.26 (t, J = 8.0 Hz, 1H), 6.92-6.89 (m, 1H), 6.80 (d, J = 7.6 Hz, 1H), 6.73-6.72 (m, 1H), 3.89 (t, J = 7.2 Hz, 2H), 2.72 (s, 3H), 2.48 (s, 3H), 1.67 (t, J = 7.2 Hz, 2H), 0.96 (s, 9H) ppm. | 1.73 | 580 |
| 76 | $^1$H NMR (400 MHz, chloroform-d) δ 7.97 (d, J = 7.5 Hz, 2H), 7.71 (d, J = 8.1 Hz, 2H), 7.60 (d, J = 8.1 Hz, 2H), 7.51 (dt, J = 29.6, 7.4 Hz, 3H), 7.36 (t, J = 7.9 Hz, 1H), 6.62-6.53 (m, 2H), 4.25 (t, J = 7.3 Hz, 2H), 1.66 (t, J = 7.4 Hz, 2H), 0.99 (s, 9H) ppm. | 2.38 | 562 |
| 77 | $^1$H NMR (400 MHz, chloroform-d) δ 7.99 (d, J = 7.6 Hz, 2H), 7.65-7.59 (m, 3 H), 7.54-7.50 (m, 2H), 7.40 (d, J = 8.0 Hz, 2 H), 7.12 (d, J = 2.8 Hz, 1H), 5.83 (d, J = 2.4 Hz, 1 H), 4.25 (t, J = 7.2 Hz, 2 H), 1.73 (t, J = 7.2 Hz, 2 H), 1.00 (s, 9H) ppm. | 2.30 | 551 |
| 78 | $^1$H NMR (400 MHz, chloroform-d) δ 9.42 (m, 1H), 8.51-8.50 (m, 1H), 8.44-8.42 (m, 1H), 7.63-7.61 (m, 2H), 7.51-7.49 (m, 2H), 7.47-7.44 (m, 2H), 7.24-7.20 (m, 1H), 6.88-6.85 (m, 1H), 6.78-6.77 (m, 1H), 6.71 (m, 1H), 3.88-3.85 (m, 2H), 1.67-1.63 (m, 2H), 0.93 (s, 9H) ppm. | 2.25 | 562 |
| 79 | $^1$H NMR (400 MHz, DMSO-d6) δ ppm 13.2 (bs, 1 H), 7.82 (d, J = 8.29 Hz, 2 H), 7.74 (d, J = 8.20 Hz, 2 H), 7.16 (t, J = 7.82 Hz, 1 H), 7.06 (t, J = 1.86 Hz, 1 H), 6.96 (d, J = 7.73 Hz, 1 H), 6.91 (s, 1 H), 6.74 (dd, J = 8.14 Hz, J = 1.59 Hz, 1 H), 5.58 (bs, 2 H), 4.94 (q, J = 8.69 Hz, 2 H) | 0.86 | 581 |
| 80 | $^1$H NMR (400 MHz, chloroform-d) δ 8.02 (d, J = 7.2 Hz, 2H), 7.60 (t, J = 8.0 Hz, 3H), 7.52 (t, J = 7.6 | 1.67 | 561 |

TABLE 3-continued

| Compound Number | NMR | LCMS retention time (min.) | LCMS MS (ESI) m/z $[M + H]^+$ |
|---|---|---|---|
| Example 49-509 | | | |
| | Hz, 2H), 7.43 (d, J = 7.6 Hz, 2H), 7.25 (d, J = 6.4 Hz, 2H), 7.14 (s, 1H), 7.07 (s, 1H), 3.46 (t, J = 7.6 Hz, 2H), 2.77 (t, J = 7.2 Hz, 2H), 1.45 (s, 9H) ppm. | | |
| 81 | $^1$H NMR (400 MHz, DMSO-d6) δ ppm 13.08 (bs, 1 H), 7.82 (d, J = 8.26 Hz, 2 H), 7.74 (d, J = 8.26 Hz, 2 H), 7.17 (t, J = 7.87 Hz, 1 H), 7.06 (t, J = 1.93 Hz, 1 H), 6.95 (d, J = 7.59 Hz, 1 H), 6.75 (s, 1 H), 6.73 (dd, J = 8.32 Hz, J = 1.85 Hz, 1 H), 5.56 (bs, 2 H), 4.26 (t, J = 6.63 Hz, 2 H), 1.55 (q, J = 6.74 Hz, 2 H), 0.76-0.63 (m, 1 H), 0.44-0.34 (m, 2 H), 0.09-0.02 (m, 2 H) | 0.93 | 567 |
| 82 | $^1$H NMR (400 MHz, DMSO-d6) δ ppm 13.08 (bs, 1 H), 7.81 (d, J = 8.20 Hz, 2 H), 7.73 (d, J = 8.26 Hz, 2 H), 7.17 (t, J = 7.87 Hz, 1 H), 7.06 (t, J = 1.93 Hz, 1 H), 6.95 (d, J = 7.77 Hz, 1H), 6.78 (s, 1H), 6.73 (dd, J = 8.02 Hz, J = 1.70 Hz, 1 H), 5.56 (bs, 2 H), 1.96 (s, 2 H), 0.91 (s, 9 H) | 0.97 | 569 |
| 83 | $^1$H NMR (400 MHz, chloroform-d) δ 7.81-7.79 (m, 1H), 7.70-7.68 (m, 1H), 7.52-7.50 (m, 2H), 7.48-7.46 (m, 3H), 6.91-6.88 (m, 1H), 6.81-6.79 (m, 1H), 6.73 (m, 1H), 3.91-3.87 (m, 2H), 1.69-1.65 (m, 2H), 0.96 (s, 9H) ppm. | 2.41 | 579 |
| 84 | $^1$H NMR (400 MHz, chloroform-d) δ 7.56 (d, J = 8.4 Hz, 2H), 7.41 (d, J = 8.8 Hz, 3H), 7.36 (d, J = 8.0 Hz, 1H), 7.25-7.17 (m, 2H), 6.82 (d, J = 8.0 Hz, 2H), 6.77 (d, J = 7.6 Hz, 1H), 6.58 (s, 1H), 4.55-4.53 (m, 1H), 1.98-1.89 (m, 1H), 1.79-1.71 (m, 1H), 1.69-1.57 (m, 2H), 1.52-1.48 (m, 1H), 1.41-1.34 (m, 1H), 1.07 (s, 3H), 0.96 (s, 3H) ppm. | 2.24 | 588 |
| 85 | $^1$H NMR (400 MHz, chloroform-d) δ 8.06 (s, 1H), 7.78 (d, J = 8.0 Hz, 1H), 7.64-7.57 (m, 3H), 7.50-7.43 (m, 3H), 7.24 (t, J = 8.0 Hz, 1H), 6.89 (d, J = 8.4 Hz, 1H), 6.80 (d, J = 7.6 Hz, 1H), 6.73 (s, 1H), 3.89 (t, J = 7.6 Hz, 2H), 3.02 (s, 3H), 1.67 (t, J = 7.2 Hz, 2H), 0.95 (s, 9H) ppm. | 2.06 | 654 |
| 86 | $^1$H NMR (400 MHz, methanol-d) δ 7.98-7.94 (m, 4H), 7.77 (s, 1H), 7.75 (s, 1H), 7.63-7.53 (m, 3H), 3.91 (d, J = 11.2 Hz, 1H), 3.76-3.70 (m, 1H), 3.58 (s, 1H), 2.96-2.79 (m, 3H), 2.49 (t, J = 10.4 Hz, 1H), 1.49-1.11 (m, 6H), 0.87 (s, 9H) ppm. | 2.39 | 568 |
| 87 | $^1$H NMR (400 MHz, chloroform-d) δ 7.57 (d, 2H), 7.44-7.35 (m, 4H), 7.27-7.19 (m, 2H), 6.84-6.82 (m, 2H), 6.77 (d, J = 7.6 Hz, 1H), 6.61 (s, 1H), 4.53 (m, 1H), 2.24-2.07 (m, 2H), 1.99-1.84 (m, 3H), 1.78-1.67 (m, 2H), 1.06-0.99 (m, 3H) ppm. | 2.22 | 574 |
| 88 | $^1$H NMR (400 MHz, $CDCl_3$-d) δ 7.38-7.28 (m, 3H), 7.13 (dd, J = 14.8, 7.0 Hz, 2H), 6.97 (d, J = 8.5 Hz, 1H), 6.84-6.65 (m, 6H), 4.61 (dt, J = 12.1, 6.0 Hz, 1H), 3.85 (s, 2H), 3.43 (s, 2H), 1.32 (d, J = 6.1 Hz, 6H), 0.99 (s, 9H) ppm. | 2.22 | 552 |

TABLE 3-continued

| Example 49-509 | | | |
|---|---|---|---|
| Compound Number | NMR | LCMS retention time (min.) | LCMS MS (ESI) m/z $[M + H]^+$ |
| 89 | $^1$H NMR (400 MHz, chloroform-d) δ 8.00 (d, J = 7.6 Hz, 2H), 7.58-7.54 (m, 3 H), 7.50-7.43 (m, 4H), 7.00 (d, J = 7.6 Hz, 1 H), 6.96 (s, 1H), 6.88 (d, J = 7.6 Hz, 1H), 3.87-3.84 (m, 1H), 2.91-2.82 (m, 3H), 2.71-2.64 (m, 1H), 1.99-1.96 (m, 1 H), 1.78-1.75 (m, 1 H), 1.25 (s, 9H) ppm. | 2.36 | 687 |
| 90 | $^1$H NMR (400 MHz, DMSO-d6) δ ppm 13.03 (bs, 1 H), 7.83 (d, J = 8.28 Hz, 2 H), 7.77-7.67 (m, 3 H), 7.16 (t, J = 7.82 Hz, 1 H), 7.06 (t, J = 1.93 Hz, 1 H), 6.94 (d, J = 7.65 Hz, 1 H), 6.72 (dd, J = 8.07 Hz, J = 1.72 Hz, 1 H), 5.7 (d, J = 2.10 Hz, 1 H), 5.57 (bs, 2 H), 4.15-4.04 (m, 2 H), 1.72-1.62 (m, 2 H), 0.91 (s, 9 H) | 0.89 | 550 |
| 91 | $^1$H NMR (400 MHz, methanol-d): δ 7.97-7.94 (m, 2H), 7.77-7.75 (m, 2H), 7.68-7.53 (m, 5H), 6.89 (s, 1H), 4.07 (t, J = 7.2 Hz, 2H), 1.63 (t, J = 7.2 Hz, 2H), 0.97 (s, 9H) ppm. | 2.45 | 600 $[M - H]^-$ |
| 92 | $^1$H NMR (400 MHz, chloroform-d) δ 7.57-7.55 (m, 2H), 7.42-7.39 (m, 3H), 7.33 (d, J = 8.0 Hz, 1H), 7.24-7.20 (t, 1H), 6.81-6.79 (m, 1H), 6.59-6.54 (m, 1H), 6.48-6.42 (m, 2H), 4.31-4.29 (m, 0.5H), 3.88-3.82 (m, 0.5H), 1.96-1.87 (m, 2.0H), 1.79-1.75 (m, 1.0H), 1.53-1.50 (m, 1.0H), 1.42-1.25 (m, 4.0H), 1.05-0.94 (m, 1.0H), 0.85 (m, 9.0H) ppm. | 2.41 | 648 |
| 93 | $^1$H NMR (400 MHz, chloroform-d) δ 7.45 (s, 1H), 7.33-7.28 (m, 1H), 7.15-7.06 (m, 5H), 6.66 (d, J = 6.8 Hz, 1H), 6.46 (d. J = 10.4, 1H), 6.34 (s, 2H), 3.97 (t, J = 6.4 Hz, 2H), 2.54-2.50 (m, 2H) ppm. | 2.14 | 606 |
| 94 | $^1$H NMR (400 MHz, chloroform-d) δ 7.98-7.96 (m, 2H), 7.63 (d, J = 8.0 Hz, 2 H), 7.59-7.51 (m, 4H), 7.43 (d, J = 8.4 Hz, 2 H), 7.34 (s, 1H), 3.91 (t, J = 7.2 Hz, 2 H), 1.63 (t, J = 7.2 Hz, 2 H), 0.95 (s, 9H) ppm. | 2.32 | 551 |
| 95 | $^1$H NMR (400 MHz, chloroform-d) δ 7.83 (s, 1H), 7.52 (d, J = 8.3 Hz, 2H), 7.42 (t, J = 9.6 Hz, 3H), 7.28 (d, J = 8.0 Hz, 1H), 6.99 (dd, J = 8.2, 1.6 Hz, 1H), 6.55 (dt, J = 10.5, 2.2 Hz, 1H), 6.42 (dd, J = 8.0, 2.0 Hz, 2H), 3.82 (t, J = 7.2 Hz, 2H), 1.62 (t, J = 7.2 Hz, 2H), 0.92 (s, 9H) ppm. | 2.28 | 595 |
| 96 | $^1$H NMR (400 MHz, DMSO-d) δ 13.3 (s, 1H), 8.33 (d, J = 5.6 Hz, 1H), 7.88-7.77 (m, 6H), 7.61-7.54 (m, 3H), 6.83 (d, J = 4.0 Hz, 1H), 6.35 (s, 1H), 3.69 (t, J = 7.2 Hz, 2H), 1.46 (t, J = 7.2 Hz, 2H), 0.81 (s, 9H) ppm. | 2.19 | 562 |
| 97 | $^1$HNMR (400 MHz, chloroform-d) δ 7.33 (m, 3H), 7.23 (t, J = 7.9 Hz, 1H), 7.11 (dd, J = 7.7, 1.6 Hz, 1H), 6.95 (d, J = 8.4 Hz, 1H), 6.87-6.74 (m, 2H), 6.55-6.42 (m, 3H), 4.57 (dq, J = 12.1, 6.1 Hz, 1H), 3.82 (t, J = 7.2 Hz, 2H), 1.63 (t, J = 7.2 Hz, 2H), 1.32-1.22 (m, 6H), 0.96 (s, 9H) ppm. | 2.23 | 584 |
| 98 | $^1$HNMR (400 MHz, chloroform-d) δ 7.87 (t, J = 1.9 Hz, 1H), 7.80 (d, J = | 2.26 | 662 |

TABLE 3-continued

| Example 49-509 | | | |
|---|---|---|---|
| Compound Number | NMR | LCMS retention time (min.) | LCMS MS (ESI) m/z $[M + H]^+$ |
| | 7.8 Hz, 1H), 7.59-7.53 (m, 1H), 7.47 (t, J = 7.9 Hz, 1H), 7.38-7.31 (m, 1H), 7.15 (dd, J = 7.7, 1.6 Hz, 1H), 6.96 (d, J = 8.3 Hz, 1H), 6.85 (t, J = 7.5 Hz, 1H), 6.51 (m, 3H), 4.58 (dt, J = 12.1, 6.1 Hz, 1H), 3.83 (t, J = 7.2 Hz, 2H), 3.02 (s, 3H), 1.63 (t, J = 7.2 Hz, 2H), 1.27 (d, J = 6.1 Hz, 6H), 0.92 (s, 9H) ppm. | | |
| 99 | $^1$H NMR (400 MHz, methanol-d): δ 7.67 (s, 4H), 7.28-7.17 (m, 3H), 6.86-6.83 (m, 1H), 6.71 (s, 1H), 4.02 (t, J = 7.2 Hz, 2H), 1.61 (t, J = 7.2 Hz, 2H), 0.96 (s, 9H) ppm. | 2.35 | 615 $[M - H]^-$ |
| 100 | $^1$H NMR (400 MHz, chloroform-d) δ 7.60-7.53 (m, 3H), 7.52-7.49 (m, 1H), 7.38 (t, J = 7.2 Hz, 3H), 7.08 (dd, J = 8.0, 2.2 Hz, 1H), 6.57 (dt, J = 10.5, 2.2 Hz, 1H), 6.52-6.41 (m, 2H), 3.92-3.76 (m, 5H), 1.64 (t, J = 7.2 Hz, 2H), 0.93 (s, 9H) ppm. | 2.35 | 609 |
| 101 | $^1$H NMR (400 MHz, DMSO-d) 7.83 (d, J = 8.0 Hz, 2H), 7.24 (d, J = 8.0 Hz, 2H), 7.56 (t, J = 8.0 Hz, 1H), 7.14 (t, J = 8.0 Hz, 1H), 7.05 (t, J = 2.0 Hz, 1H), 6.68-6.96 (m, 1H), 6.73 (d, J = 7.6 Hz, 1H), 6.63 (t, J = 7.2 Hz, 1H), 5.54 (bs, 1H), 4.12 (t, J = 7.2 Hz, 2H), 1.58 (t, J = 7.2 Hz, 2H), 0.93 (s, 9H) ppm. | 2.34 | 577 |
| 102 | $^1$H NMR (400 MHz, DMSO-d) δ 8.33 (d, J = 6.0 Hz, 2H), 7.87-7.77 (m, 4H), 7.14 (t, J = 7.6 Hz, 1H), 7.07 (t, J = 1.6 Hz, 1H), 6.95 (d, J = 6.8 Hz, 1H), 6.83-6.81 (m, 1H), 6.72 (dd, J = 8.0 Hz, J = 1.6 Hz, 1H), 6.35 (d, J = 2.0 Hz, 1H), 5.54 (bs, 1H), 3.69 (t, J = 7.2 Hz, 2H), 1.46 (t, J = 7.2 Hz, 2H), 0.81 (s, 9H) ppm. | 2.14 | 577 |
| 103 | $^1$H NMR (400 MHz, chloroform-d) 10.13 (br, 1H), 8.00 (dd, J = 7.6, 1.6 Hz, 1H), 7.37-7.32 (m, 2H), 7.29-7.28 (m, 1H), 7.24 (t, J = 7.6 Hz, 1H), 7.04-7.00 (m, 2H), 6.82-6.79 (m, 1H), 4.69-4.63 (m, 1H), 3.93-3.53 (m, 5H), 2.93-2.83 (m, 3H), 2.56-2.51 (m, 1H), 1.53-1.13 (m, 12H), 0.87 (s, 9H) ppm. | 2.27 | 573 |
| 104 | $^1$H NMR (400 MHz, DMSO-d) & 8.31-8.30 (m, 1 H), 8.08-7.99 (m, 2 H), 7.78-7.71 (m, 3 H), 7.63-7.56 (m, 4 H), 7.27 (t, J = 8.0 Hz, 1 H), 6.89-6.83 (m, 2 H), 6.67-6.66 (m, 1 H), 3.80 (t, J = 7.2 Hz, 2 H), 1.52 (t, J = 7.6 Hz, 2 H), 0.86 (s, 9 H) ppm. | 2.19 | 640 |
| 105 | $^1$HNMR (400 MHz, chloroform-d) δ 7.97 (d, J = 7.3 Hz, 2H), 7.49 (m, 5H), 7.30 (m, 2H), 3.57-3.37 (m, 2H), 3.16 (m, 1H), 2.73 (m, 1H), 1.81 (m, 4H), 1.47 (m, 2H), 1.35-1.26 (m, 4H), 0.92-0.73 (s, 9H) ppm. | 2.40 | 567 |
| 106 | $^1$H NMR (400 MHz, chloroform-d) δ 8.00 (dd, J = 7.6, 1.6 Hz, 1H), 7.80-7.78 (m, 2H), 7.56-7.53 (m, 1H), 7.50-7.46 (m, 1H), 7.37-7.32 (m, 1H), 7.04-7.00 (m, 2H), 4.69-4.63 (m, 1H), 3.93-3.91 (m, 1H), 3.74-3.67 (m, 1H), 3.57-3.53 (m, 1H), 3.06 (s, 3H), 2.94-2.84 (m, 3H), 2.56-2.51 (m, 1H), 1.48-1.25 (m, 12H), 0.87 (s, 9H) ppm. | 2.26 | 651 |

TABLE 3-continued

| Compound Number | NMR | LCMS retention time (min.) | LCMS MS (ESI) m/z [M + H]+ |
|---|---|---|---|
| Example 49-509 | | | |
| 107 | $^1$H NMR (400 MHz, chloroform-d) δ 7.49-7.43 (m, 1H), 7.37-7.32 (m, 1H), 7.29-7.21 (m, 3H), 7.16 (t, J = 8.0 Hz, 1H), 6.80 (dd, J = 8.0, 2.3 Hz, 1H), 6.71 (d, J = 7.7 Hz, 1H), 3.77 (t, J = 7.3 Hz, 1H), 1.62 (t, J = 7.3 Hz, 1H), 0.92 (s, 5H) ppm. | 2.23 | 592 |
| 108 | $^1$H NMR (400 MHz, chloroform-d) 87.92 (s, 1H), 7.80 (dd, J = 10.6, 7.4 Hz, 2H), 7.67-7.56 (m, 3H), 7.52-7.38 (m, 2H), 7.13 (t, J = 8.0 Hz, 1H), 6.78 (dd, J = 8.1, 2.1 Hz, 1H), 6.67 (d, J = 7.9 Hz, 1H), 6.53 (s, 1H), 3.74 (t, J = 7.3 Hz, 2H), 3.01 (s, 3H), 1.63 (t, J = 7.3 Hz, 2H), 0.95 (s, 9H) ppm. | 2.19 | 654 |
| 109 | $^1$H NMR (400 MHz, chloroform-d) δ 7.34-7.38 (t, J = 7.2 Hz, 1H), = 7.25-7.27 (d, J = 8.0 Hz, 1H), 6.89-7.15 (m, 8H), 6.70-6.73 (d, J 12.0 Hz, 1H), 5.51 (s, 2H), 4.42-4.46 (m, 1H) 4.14 (m, 1H), 3.39 (s, 1H), 3.15-3.27 (d, J = 8.4 Hz, 1H), 2.93-2.95 (d, J = 8.4 Hz, 1H), 2.61-2.66 (m, 2H), 1.61-1.81 (m, 4H), 0.99-1.00 (d, J = 4.0 Hz, 3H), 0.94-0.96 (d, J = 6.0 Hz, 3H), 0.82 (s, 9H) ppm. | 2.35 | 606 |
| 110 | $^1$H NMR (400 MHz, methanol-d) & 7.71 (d, J = 8.3 Hz, 2H), 7.58 (d, J = 8.1 Hz, 2H), 7.31-7.14 (m, 3H), 6.88 (dd, J = 7.6, 2.3, 1.5 Hz, 1H), 6.74 (dt, J = 10.7, 2.2 Hz, 1H), 6.65 (d, J = 1.9 Hz, 1H), 6.63-6.56 (m, 1H), 4.20-3.99 (m, 3H), 2.13-2.02 (m, 1H), 1.91-1.79 (m, 1H) ppm. | 2.03 | 635 |
| 111 | $^1$H NMR (400 MHz, chloroform-d) δ 7.89 (s, 1H), 7.80 (d, J = 8.2 Hz, 1H), 7.57 (d, J = 9.4 Hz, 1H), 7.53-7.43 (m, 2H), 7.39-7.29 (m, 3H), 7.27 (d, J = 5.4 Hz, 11H), 7.17 (t, J = 8.0 Hz, 1H), 7.00 (s, 1H), 6.82 (dd, J = 8.3, 2.4 Hz, 1H), 6.72 (d, J = 7.7 Hz, 1H), 6.61 (d, J = 2.1 Hz, 1H), 3.78 (t, J = 7.3 Hz, 2H), 3.01 (s, 3H), 1.62 (t, J = 7.3 Hz, 6H), 0.93 (s, 11H) ppm. | 1.63 | 670 |
| 112 | $^1$H NMR (400 MHz, DMSO-d) 8 8.35 (s, 1H), 7.84 (s, 1H), 7.40 (dd, J = 8.4 Hz & 7.2 Hz, 1H), 7.34 (dd, J = 7.6 Hz & 1.2 Hz, 1H), 7.07 (d, J = 8.4 Hz, 1H), 7.01 (dd, J = 7.6 Hz & 7.2 Hz, 1H), 6.71 (d, J = 10.8 Hz, 1H), 6.54 (d, J = 9.6 Hz, 1H), 6.40 (s, 1H), 5.10-5.08 (m, 1H), 4.49-4.46 (m, 1H), 3.98-3.74 (m, 6H), 2.37-2.29 (m, 2H), 1.54 (t, J = 6.8 Hz, 2H), 0.99 (d, J = 6.0 Hz, 6H), 0.89 (s, 9H) ppm. | 2.27 | 629 |
| 113 | $^1$H NMR (400 MHz, chloroform-d) δ 7.83 (s, 1H), 7.52 (d, J = 8.3 Hz, 2H), 7.42 (t, J = 9.6 Hz, 3H), 7.28 (d, J = 8.0 Hz, 1H), 6.99 (dd, J = 8.2, 1.6 Hz, 1H), 6.55 (dt, J = 10.5, 2.2 Hz, 1H), 6.42 (dd, J = 8.0, 2.0 Hz, 2H), 3.82 (t, J = 7.2 Hz, 2H), 1.62 (t, J = 7.2 Hz, 2H), 0.92 (s, 9H) ppm. | 2.00 | 596 |
| 114 | $^1$H NMR (400 MHz, DMSO-d6) 8 ppm 13.18 (bs, 1 H), 7.75 (d, J = 8.11 Hz, 2 H), 7.58 (d, J = 8.08 Hz, | 0.92 | 624 |

TABLE 3-continued

| Compound Number | NMR | LCMS retention time (min.) | LCMS MS (ESI) m/z [M + H]$^+$ |
|---|---|---|---|
| Example 49-509 | | | |
| | 2 H), 7.27 (t, J = 8.02 Hz, 1 H), 7.16 (t, J = 7.80 Hz, 1 H), 7.08 (bs, 1H), 6.96 (d, J = 7.77 Hz, 1 H), 6.92 (d, J = 8.06 Hz, 1 H), 6.81 (d, J = 7.48 Hz, 1 H), 6.76-6.68 (m, 2 H), 5.56 (bs, 2 H), 3.69 (d, J = 5.92 Hz, 2 H), 2.07-1.93 (m, 2 H), 1.90-1.67 (m, 5 H), 1.30-1.15 (m, 2 H) | | |
| 115 | $^1$H NMR (400 MHz, chloroform-d): 7.49-7.43 (m, 2H), 7.32-7.19 (m, 4H), 7.13 (d, J = 8.4 Hz, 1H), 7.03-6.99 (m, 1H), 6.89-6.86 (m, 1H), 5.58 (d, J = 2.4 Hz, 1H), 4.58-4.52 (m, 1H), 4.16-4.12 (m, 2H), 1.78-1.74 (m, 2H), 1.18 (d, J = 6.0 Hz, 6H), 0.99 (s, 9H) ppm. | 2.10 | 540 |
| 116 | $^1$H NMR (400 MHz, DMSO-d) & 8.69 (d, J = 4.0 Hz, 1H), 8.05-7.99 (m, 2H), 7.75-7.58 (m, 5H), 7.27 (t, J = 8.0 Hz, 1H), 6.91-6.85 (m, 2H), 6.67 (s, 1H), 3.81 (t, J = 7.2 Hz, 2H), 1.52 (t, J = 7.2 Hz, 2H), 0.87 (s, 9H) ppm. | 2.27 | 562 |
| 117 | $^1$H NMR (400 MHz, chloroform-d) δ 7.52 (dd, J = 18.2, 4.4 Hz, 2H), 7.40 (td, J = 8.0, 4.3 Hz, 1H), 7.31 (d, J = 7.5 Hz, 1H), 7.14 (d, J = 7.6 Hz, 2H), 7.09 (dd, J = 8.1, 2.0 Hz, 1H), 3.86 (d, J = 3.6 Hz, 3H), 3.67 (t, J = 7.2 Hz, 2H), 2.14 (s, 6H), 1.62 (t, J = 7.3 Hz, 2H), 0.95 (s, 9H); | 2.37 | 569 |
| 118 | $^1$H NMR (400 MHz, chloroform-d) δ 7.36 (t, J = 7.0 Hz, 2H), 7.30 (s, 1H), 7.10 (d, J = 7.7 Hz, 1H), 6.98 (s, 1H), 6.91-6.73 (m, 2H), 6.55 (d, J = 9.6 Hz, 3H), 4.60 (dt, J = 12.1, 6.0 Hz, 1H), 4.01 (d, J = 10.2 Hz, 1H), 3.92 (d, J = 17.5 Hz, 1H), 3.85 (t, J = 8.7 Hz, 1H), 3.62 (s, 3H), 1.29 (d, J = 6.1 Hz, 6H) ppm. | 2.06 | 626 |
| 119 | $^1$H NMR (400 MHz, chloroform-d) δ 7.44-7.35 (m, 2H), 7.34-7.30 (m, 1H), 7.26 (d, J = 7.9 Hz, 1H), 7.12 (dd, J = 7.7, 1.7 Hz, 1H), 7.01 (d, J = 8.3 Hz, 1H), 6.92-6.79 (m, 2H), 6.62 (ddd, J = 10.6, 4.6, 1.3 Hz, 3H), 4.64 (dt, J = 12.1, 6.1 Hz, 1H), 4.21 (q, J = 8.0 Hz, 2H), 1.33 (d, J = 6.1 Hz, 6H) ppm. | 2.05 | 582 |
| 120 | $^1$H NMR (400 MHz, methanol-d) δ 7.87 (t, J = 1.7 Hz, 1H), 7.72 (dt, J = 7.5, 1.5 Hz, 1H), 7.56-7.37 (m, 4H), 7.31 (dd, J = 7.6, 1.7 Hz, 1H), 7.11 (d, J = 8.3 Hz, 1H), 7.01 (td, J = 7.5, 0.9 Hz, 1H), 5.57 (d, J = 2.4 Hz, 1H), 4.56-4.47 (m, 1H), 4.18-4.09 (m, 2H), 3.00 (s, 3H), 1.15 (d, J = 6.0 Hz, 6H), 0.99 (s, 9H) ppm. | 1.85 | 618 |
| 121 | $^1$H NMR (400 MHz, chloroform-d) δ 7.75-7.74 (m, 1H), 7.53-7.51 (m, 1H), 7.41-7.26 (m, 4H), 6.98-6.94 (m, 3H), 6.57-6.50 (m, 2H), 4.50-4.47(m, 1H), 4.32-4.29(m, 2H), 1.69-1.65 (m, 2H), 1.18-1.17 (m, 6H), 0.92 (m, 6H), 0.99 (s, 9H) ppm. | 2.24 | 568 |
| 122 | $^1$H NMR (400 MHz, chloroform-d) δ 7.65 (s, 1H), 7.52 (d, J = 7.6 Hz, 1H), 7.31 (dd, J = 12.5, 7.5 Hz, 2H), 7.12 (d, J = 7.7 Hz, 1H), 6.95 (dd, J = 20.3, 8.3 Hz, 2H), 6.83 (t, J = 7.6 | 2.27 | 585 |

TABLE 3-continued

| Compound Number | NMR | LCMS retention time (min.) | LCMS MS (ESI) m/z $[M + H]^+$ |
|---|---|---|---|
| Example 49-509 | | | |
| | Hz, 1H), 6.52-6.44 (m, 3H), 4.56-4.48 (m, 1H), 3.80 (t, J = 7.2 Hz, 2H), 1.62 (t, J = 7.2 Hz, 2H), 1.22 (d, J = 6.0 Hz, 6H), 0.93 (s, 9H) ppm. | | |
| 123 | $^1H$ NMR (400 MHz, chloroform-d) δ 7.92 (d, J = 1.8 Hz, 1H), 7.88-7.73 (m, 2H), 7.69-7.55 (m, 3H), 7.53-7.40 (m, 2H), 6.49 (dt, J = 10.5, 2.1 Hz, 1H), 6.40-6.28 (m, 2H), 3.76 (t, J = 7.2 Hz, 2H), 3.00 (s, 3H), 1.63 (t, J = 7.2 Hz, 2H), 0.95 (s, 9H) ppm. | 2.19 | 672 |
| 124 | $^1H$ NMR (400 MHz, DMSO-d6) δ ppm 13.91 (bs, 1 H), 7.75 (d, J = 8.34 Hz, 2 H), 7.57 (d, J = 8.18 Hz, 2 H), 7.25 (t, J = 7.93 Hz, 1 H), 7.16 (t, J = 7.86 Hz, 1 H), 7.08 (t, J = 1.72 Hz, 1 H), 6.96 (d, J = 7.83 Hz, 1 H), 6.89 (dd, J = 8.38 Hz, J = 2.12 Hz, 1 H), 6.78 (d, J = 7.66 Hz, 1 H), 6.73 (dd, J = 8.07 Hz, J = 1.16 Hz, 1 H), 6.69 (t, J = 1.75 Hz, 1 H), 5.56 (bs, 2 H), 3.57 (s, 2 H), 1.09 (s, 3 H), 0.44-0.3 (m, 4 H) | 0.93 | 560 |
| 125 | $^1H$ NMR (400 mHz, methanol-$d_4$): δ 0.89 (s, 9H), 1.16 (d, J = 6.0 Hz, 6H), 1.74-1.79 (m, 2H), 4.12-4.16 (m, 2H), 4.52-4.54 (m, 1H), 5.58 (d, J = 2.4 Hz 1H), 6.98-7.03 (m, 2H), 7.12-7.14 (m, 1H), 7.30-7.58 (m, 6H) ppm. | 2.07 | 539 $[M - H]^-$ |
| 126 | $^1H$ NMR (400 MHz, chloroform-d) δ 7.73 (d, J = 8.0 Hz, 2H), 7.60 (d, J = 8.0 Hz, 2H), 7.36-7.34 (m, 2H), 7.24 (t, J = 8.0 Hz, 1H), 6.82-6.81 (m, 1H), 6.36-6.27 (m, 2H), 4.27 (t, J = 7.2 Hz, 2H), 1.67 (t, J = 7.2 Hz, 2H), 1.00 (s, 9H) ppm | 2.26 | 595 |
| 127 | $^1H$ NMR (400 MHz, chloroform-d) δ 8.05 (d, J = 9.2 Hz, 1H), 7.85 (d, J = 8.4 Hz, 1H), 7.56 (t, J = 7.6 Hz, 1H), 7.40 (t, J = 8.8 Hz, 1H), 7.30 (s, 1H), 7.15 (d, J = 9.2 Hz, 1H), 7.02 (d, J = 8.4 Hz, 1H), 6.89 (t, J = 6.0 Hz, 1H), 6.56~6.49 (m, 3H), 4.66~4.63 (m, 1H), 3.88 (t, J = 7.2 Hz, 2H), 3.12 (s, 3H), 1.67 (t, J = 7.2, 2H), 1.36 (d, J = 6.0 Hz, 6H), 0.96 (s, 9H) ppm. | 2.34 | 662 |
| 128 | $^1H$ NMR (400 MHz, chloroform-d) 7.97 (t, J = 1.8 Hz, 1H), 7.81 (d, J = 7.8 Hz, 1H), 7.61 (dd, J = 8.2, 1.3 Hz, 1H), 7.49 (t, J = 8.0 Hz, 1H), 7.40-7.35 (m, 1H), 7.28-7.18 (m, 2H), 6.95 (d, J = 7.8 Hz, 1H), 6.56-6.35 (m, 3H), 3.71 (t, J = 7.2 Hz, 2H), 3.03 (s, 3H), 1.69 (dd, J = 9.4, 4.2 Hz, 1H), 1.62 (t, J = 7.2 Hz, 2H), 0.94 (s, 9H), 0.85-0.77 (m, 2H), 0.64-0.57 (m, 2H) ppm. | 2.44 | 644 |
| 129 | $^1H$ NMR (400 MHz, chloroform-d) 7.97 (s, 1H), 7.82 (d, J = 7.7 Hz, 1H), 7.61 (d, J = 8.2 Hz, 1H), 7.50 (t, J = 8.0 Hz, 1H), 7.30 (d, J = 7.6 Hz, 1H), 7.14 (d, J = 7.7 Hz, 2H), 6.48 (dt, J = 10.3, 2.1 Hz, 1H), 6.41-6.29 (m, 2H), 3.68 (t, J = 7.3 Hz, 2H), 3.03 (s, 3H), 2.14 (s, 6H), 1.62 (t, J = 7.3 Hz, 2H), 0.95 (s, 9H) ppm. | 2.24 | 632 |
| 130 | $^1H$ NMR (400 MHz, chloroform-d) δ 7.80-7.79 (m, 1 H), 7.53 (d, J = 7.6 Hz, 1 H), 7.37-7.29 (m, 2 H), 7.17 (dd, J = 1.6 Hz & 7.6 Hz, 1 | 2.19 | 623 |

TABLE 3-continued

| Example 49-509 | | | |
|---|---|---|---|
| Compound Number | NMR | LCMS retention time (min.) | LCMS MS (ESI) m/z $[M + H]^+$ |
| | H), 7.02 (dd, J = 2.4 Hz& 8.0 Hz, 1 H), 6.95 (d, J = 8.0 Hz, 1 H), 6.88 (dd, J = 7.6 Hz & 7.6 Hz, 1 H), 6.55-6.47 (m, 3H), 4.55-4.52 (m, 1 H), 3.91 (s, 2 H), 1.22 (d, J = 6.0 Hz, 6 H), 1.15-1.12 (m, 2 H), 0.90-0.87(m, 2 H) | | |
| 131 | $^1$H NMR (400 MHz, chloroform-d) δ 7.38-7.34 (m, 3 H), 7.25 (dd, J = 8.0 Hz & 8.0 Hz, 1 H), 7.32 (d, J = 7.2 Hz, 1 H), 6.98 (d, J = 8.4 Hz, 1 H), 6.88 (dd, J = 7.6 Hz, 7.2 Hz, 1 H), 6.81 (d, J = 7.6 Hz, 1 H), 6.54-6.50 (m, 3 H) 4.60-4.57 (m, 1 H), 3.92 (s, 2 H), 1.28 (d, J = 6.0 Hz, 6 H), 1.16-1.13 (m, 2 H), 0.88 (m, 2 H) | 1.63 | 622 |
| 132 | $^1$H NMR (400 MHz, chloroform-d) δ 9.64 (s, 1H), 8.01 (d, J = 9.2 Hz, 1H), 7.89 (s, 1H), 7.64 (d, J = 7.5 Hz, 1H), 7.46-7.24 (m, 3H), 7.06 (d, J = 7.9 Hz, 1H), 6.90 (d, J = 8.4 Hz, 1H), 6.77 (t, J = 7.4 Hz, 1H), 6.43 (m, J = 12.9 Hz, 3H), 4.53 (m, 1H), 3.76 (t, J = 7.2 Hz, 2H), 3.57 (m, J = 7.0 Hz, 1H), 1.56 (t, J = 7.3 Hz, 2H), 1.35 (d, J = 7.0 Hz, 3H), 1.23 (d, J = 5.9 Hz, 6H), 0.86 (s, 9H) ppm. | 2.11 | 655 |
| 133 | $^1$H NMR (400 MHz, chloroform-d) δ 7.89 (s, 1H), 7.79 (d, J = 7.7 Hz, 1H), 7.56 (d, J = 8.3 Hz, 1H), 7.48 (d, J = 7.9 Hz, 1H), 7.13 (dd, J = 8.6, 6.6 Hz, 1H), 6.66 (dd, J = 10.8, 2.2 Hz, 1H), 6.63-6.55 (m, 1H), 6.53 (d, J = 10.5 Hz, 1H), 6.50 (s, 1H), 3.86 (t, J = 7.2 Hz, 2H), 3.02 (s, 2H), 1.64 (d, J = 7.2 Hz, 2H), 1.26 (d, J = 6.1 Hz, 6H), 0.95 (s, 9H) ppm. | 2.24 | 680 |
| 134 | $^1$H NMR (400 MHz, chloroform-d) δ 7.93 (s, 1H), 7.81 (d, J = 7.1 Hz, 1H), 7.59 (d, J = 7.6 Hz, 1H), 7.37 (ddd, J = 30.3, 16.5, 8.2 Hz, 4H), 7.05-6.83 (m, 2H), 6.56 (dd, J = 24.9, 7.7Hz, 2H), 4.55 (d, J = 5.6 Hz, 1H), 4.33 (t, J = 6.9 Hz, 2H), 3.00(s, 3H), 1.72-1.66 (m, 2H), 1.22 (d, J = 5.5 Hz, 6H), 1.00 (s, 9H) ppm. | 2.24 | 645 |
| 135 | $^1$H NMR (400 MHz, methanol-d4) δ 7.44-7.39 (m, 1H), 7.37-7.30 (m, 5H), 7.29-7.19 (m, 4H), 7.05 (d, J = 8.4 Hz, 1H), 6.98 (d, J = 7.5 Hz, 1H), 6.91-6.86 (m, 1H), 6.65-6.53 (m, 2H), 6.48 (s, 1H), 4.82 (d, J = 11.5 Hz, 1H), 4.71 (d, J = 11.5 Hz, 1H), 4.58-4.48 (m, 1H), 4.27 (s, 1H), 4.08-4.01 (m, 1H), 3.93 (d, J = 7.1 Hz, 1H), 1.11 (d, J = 6.0 Hz, 6H) ppm. | 2.17 | 702 |
| 136 | $^1$H NMR (400 MHz, chloroform-d) 7.99-7.80 (m, 3H), 7.65 (p, J = 7.2 Hz, 3H), 7.54 (t, J = 7.9 Hz, 1H), 7.42 (d, J = 6.4 Hz, 1H), 6.50 (dd, J = 10.5, 2.1 Hz, 1H), 6.41-6.29 (m, 2H), 3.78 (t, J = 7.2 Hz, 2H), 3.38 (s, 3H), 2.89 (s, 3H), 1.63 (t, J = 7.2 Hz, 3H), 0.95 (s, 9H) ppm. | 2.24 | 686 |
| 137 | $^1$H NMR (400 MHz, chloroform-d) δ 7.93 (m, 1H), 7.90 (d, J = 7.9 Hz, 1H), 7.67-7.59 (m, 1H), 7.50 (t, J = 7.9 Hz, 1H), 7.38-7.31 (m, 1H), 7.12 (dd, J = 7.7, 1.5 Hz, 1H), 6.98 (d, J = 8.4 Hz, 1H), 6.84 (t, J = 7.5 | 2.30 | 676 |

TABLE 3-continued

| Example 49-509 | | | |
|---|---|---|---|
| Compound Number | NMR | LCMS retention time (min.) | LCMS MS (ESI) m/z $[M + H]^+$ |
| | Hz, 1H), 6.56-6.44 (m, 3H), 4.63 (dt, J = 12.2, 6.1 Hz, 1H), 3.84 (t, J = 7.2 Hz, 2H), 3.36 (s, 3H), 2.89 (s, 3H), 1.64 (t, J = 7.2 Hz, 2H), 1.33 (d, J = 6.1 Hz, 6H), 0.94 (s, 9H) ppm. | | |
| 138 | $^1H$ NMR (400 MHz, DMSO-$d_6$) δ 7.88-7.77 (m, 4H), 7.18-6.97 (m, 4H), 6.75 (d, J = 7.6 Hz, 1H), 6.66 (s, 1H), 5.54 (bs, 1H), 4.20 (t, J = 7.2 Hz, 2H), 1.61 (t, J = 7.2 Hz, 2H), 0.94 (s, 9H) ppm. | 2.44 | 645 |
| 139 | $^1H$ NMR (400 MHz, chloroform-d) δ 7.90 (s, 1H), 7.76 (d, J = 7.7 Hz, 1H), 7.52 (d, J = 8.1 Hz, 1H), 7.42 (t, J = 8.0 Hz, 1H), 7.32 (t, J = 7.2 Hz, 1H), 7.12 (d, J = 6.4 Hz, 1H), 6.91 (d, J = 8.4 Hz, 1H), 6.83 (t, J = 7.7 Hz, 1H), 6.53-6.42 (m, 3H), 4.51 (dt, J = 11.9, 6.0 Hz, 1H), 3.80 (t, J = 7.2 Hz, 2H), 1.62 (t, J = 7.2 Hz, 2H), 1.19 (d, J = 6.0 Hz, 6H), 0.92 (s, 9H) ppm. | 2.34 | 716 |
| 140 | $^1H$ NMR (400 MHz, chloroform-d) δ 8.00 (s, 1 H), 7.71 (d, J = 8.0 Hz, 1 H), 7.57 (dd, J = 8.0, 1.6 Hz, 1 H), 7.51 (d, J = 8.0 Hz, 2 H), 7.38-7.43 (m, 3 H), 6.55 (m, 1 H), 6.45 (m, 2 H), 3.84 (t, J = 7.2 Hz, 2 H), 2.98 (s, 3 H), 1.63 (t, J = 7.2 Hz, 2 H), 0.93 (s, 9 H) ppm. | 2.28 | 672 |
| 141 | $^1H$ NMR (400 MHz, DMSO-$d_6$) δ 13.16 (s, 1H), 10.18 (s, 1H), 7.77 (s, 1H), 7.60 (d, J = 8.0 Hz, 1H), 7.54 (t, J = 8.0 hz, 1H), 7.49-7.44 (m, 3H), 7.35-7.28 (m, 2H), 6.71 (d, J = 10.8 Hz, 1H), 6.53 (d, J = 9.6 Hz, 1H), 6.30 (s, 1H), 3.67 (t, J = 7.6 Hz, 2H), 3.05 (s, 3H), 2.75-2.69 (m, 1H), 2.08 (s, 1H), 1.50 (t, J = 7.2 Hz, 2H), 1.09 (s, 3H), 0.88 (s, 12H) ppm. | ND | 646 |
| 142 | $^1H$ NMR (400 MHz, methanol-$d_4$) 7.51-7.50 (m, 1H), 7.29-7.14 (m, 5H), 7.03-6.99 (m, 1H), 6.91-6.89 (m, 1H), 6.42-6.37 (m, 2H), 6.22-6.19 (m, 1H), 4.70-4.67 (m, 1H), 4.24-4.14 (m, 2H), 3.92-3.90 (m, 1H), 1.29 (s, 3H), 1.14 (s, 3H) ppm. | 1.94 | 612 |
| 143 | $^1H$ NMR (400 MHz, methanol-$_{d4}$) 7.53-7.51(m, 1H), 7.35-7.20 (m, 4H), 7.14-7.12 (m, 1H), 7.02-6.98 (m, 1H), 6.91-6.88 (m, 1H), 6.43-6.37 (m, 2H), 6.22-6.20 (m, 1H), 4.70-4.65 (m, 1H), 4.48-4.44 (m, 2H), 3.69-3.63 (m, 1H), 3.33-3.32 (m, 1H), 1.29 (s, 3H), 1.14 (s, 3H) ppm. | 1.96 | 612 |
| 144 | $^1H$ NMR (400 MHz, chloroform-d) δ 7.60 (d, J = 8.0 Hz, 1H), 7.45 (d, J = 7.2 Hz, 1H), 7.38 (t, J = 8.0 Hz, 1H), 7.20 (d, J = 8.0 Hz, 1H), 6.99 (d, J = 8.4 Hz, 1H), 6.89 (t, J = 7.6 Hz, 1H), 6.61 (d, J = 8.4 Hz, 1H), 6.59-6.48 (m, 3H), 4.61-4.58 (br, 3H), 3.85 (t, J = 6.8 Hz, 2H), 1.65 (t, J = 7.2 Hz, 2H), 1.30 (d, J = 6.0 Hz, 6H), 0.93 (s, 9H) ppm. | 2.26 | 585 |
| 145 | $^1H$ NMR (400 MHz, chloroform-d) δ 7.86-7.80 (m, 2H), 7.38-7.34 (m, 2H), 7.21 (d, J = 7.6 Hz, 1H), 7.00 (d, J = 8.4 Hz, 1H), 6.90 (t, J = 7.2 Hz, 1H),, 6.55-6.50 (m, 3H), 4.61-4.58 (m, 1H), 3.86 (t, J = 7.6 Hz, | 2.25 | 663 |

TABLE 3-continued

| Example 49-509 | | | |
|---|---|---|---|
| Compound Number | NMR | LCMS retention time (min.) | LCMS MS (ESI) m/z $[M + H]^+$ |
| | 2H), 3.13 (s, 3H), 1.68 (t, J = 8.8 Hz, 2H), 1.30 (d, J = 6.0 Hz, 6H), 0.94 (s, 9H) ppm. | | |
| 146 | $^1$H NMR (400 MHz, chloroform-d) δ 7.98 (s, 1 H), 7.66 (d, J = 7.2 Hz, 1 H), 7.46 (m, 3 H), 7.34 (m, 3 H), 6.55 (m, 1 H), 6.40 (m, 2 H), 3.82 (t, J = 7.2 Hz, 2 H), 1.62 (t, J = 7.2 Hz, 2 H), 0.92 (s, 9 H) ppm. | 1.55 | 726 |
| 147 | $^1$H NMR (400 MHz, DMSO-d6) δ ppm 13.15 (bs, 1 H), 11.54 (s, 1 H), 7.99 (s, 1 H), 7.73 (d, J = 8.29 Hz, 2 H), 7.70 (d, J = 8.45 Hz, 1 H), 7.61 (t, J = 2.71 Hz, 1 H), 7.55 (d, J = 8.18 Hz, 2 H), 7.48 (dd, J = 8.34 Hz, J = 1.50 Hz, 1 H), 7.28 (t, J = 7.97 Hz, 1 H), 6.89 (dd, J = 8.31 Hz, J = 1.97 Hz, 1 H), 6.85 (d, J = 8.00 Hz, 1 H), 6.64 (t, J = 1.94 Hz, 1 H), 6.55 (t, J = 2.01 Hz, 1 H), 3.79 (t, J = 7.19 Hz, 2 H), 1.51 (t, J = 7.21 Hz, 2 H), 0.85 (s, 9 H) | 1.02 | 600 |
| 148 | $^1$H NMR (400 MHz, methanol-d4): δ 7.90 (t, J = 2.0 Hz, 1H), 7.70-7.68 (m, 1H), 7.52 (t, J = 8.0 Hz, 1H), 7.47-7.44 (m, 1H), 7.40-7.36 (m, 1H), 7.11 (dd, J = 10.8, 2.4 Hz, 1H), 6.92-6.87(m, 1H), 6.61-6.57 (m, 1H), 6.54-6.51 (m, 1H), 6.45 (s, 1H), 5.04-4.97 (m, 1H), 3.88-3.77 (m, 2H), 3.00 (s, 3H), 1.62 (t, J = 6.4 Hz, 2H), 1.25 (d, J = 6.4 Hz, 3H), 0.96 (s, 9H) ppm. | 2.23 | 734 |
| 149 | $^1$H NMR (400 MHz, chloroform-d) δ 9.74 (s, 1H), 8.02 (t, J = 3.8 Hz, 2H), 7.57 (dd, J = 4.3, 2.2 Hz, 2H), 7.42-7.32 (m, 1H), 7.13 (dd, J = 7.7, 1.6 Hz, 1H), 7.01 (d, J = 8.4 Hz, 1H), 6.86 (t, J = 7.5 Hz, 1H), 6.54 (ddd, J = 10.7, 7.2, 1.9 Hz, 3H), 4.65 (dt, J = 12.1, 6.1 Hz, 1H), 3.87 (t, J = 7.2 Hz, 2H), 3.52 (s, 3H), 1.66 (t, J = 7.2 Hz, 2H), 1.35 (d, J = 6.1 Hz, 6H), 0.96 (s, 9H) ppm. | 2.40 | 730 |
| 150 | $^1$H NMR (400 MHz, chloroform-d) δ 7.89 (s, 1H), 7.76 (d, J = 7.6 Hz, 1H), 7.57 (d, J = 8.4 Hz, 1H), 7.46 (t, J = 8.0 Hz, 1H), 7.02-6.99 (m, 1H), 6.94-6.89 (m, 1H), 6.69-6.32 (m, 5H), 3.83 (t, J = 7.2 Hz, 2H), 3.01 (s, 3H), 1.64 (t, J = 7.2 Hz, 2H), 0.94 (s, 9H) ppm. | 2.29 | 688 |
| 151 | $^1$H NMR (400 MHz, chloroform-d) δ 8.30 (s, 1H), 8.00 (s, 1H), 7.36-7.33 (m, 1H), 7.19-6.49 (m, 7H), 4.65-4.62 (m, 1H), 3.85 (t, J = 7.2 Hz, 2H), 1.64 (t, J = 7.2 Hz, 2H), 1.34 (d, J = 6.0 Hz, 6H), 0.94 (s, 9H) ppm. | 2.33 | 609 |
| 152 | $^1$H NMR (400 MHz, methanol-$d_4$) δ 7.73-7.64 (m, 2H), 7.54 (td, J = 8.3, 2.5 Hz, 1H), 7.28-7.17 (m, 3H), 6.90 (ddd, J = 7.8, 2.2, 1.1 Hz, 1H), 6.60 (dd, J = 8.5, 2.2 Hz, 1H), 6.53-6.45 (m, 1H), 6.35 (s, 1H), 3.81 (t, J = 7.0 Hz, 2H), 1.62 (t, J = 7.0 Hz, 2H), 0.96 (s, 9H) ppm. | 2.27 | 612 |
| 153 | $^1$H NMR (400 MHz, methanol-$d_4$) δ 7.90 (s, 1H), 7.73-7.60 (m, 3H), 7.52 (t, J = 7.9 Hz, 2H), 7.46 (d, J = 8.2 Hz, 1H), 6.56 (d, J = 10.6 Hz, 1H), 6.47 (d, J = 9.5 Hz, 1H), 6.36 (s, 1H), 3.80 (t, J = 7.0 Hz, 2H), | 2.16 | 690 |

TABLE 3-continued

| Compound Number | NMR | LCMS retention time (min.) | LCMS MS (ESI) m/z $[M+H]^+$ |
|---|---|---|---|
| Example 49-509 | | | |
| | 3.00 (s, 3H), 1.62 (t, J = 7.0 Hz, 2H), 0.96 (s, 9H) ppm. | | |
| 154 | $^1$HNMR (400 MHz, chloroform-d) δ 7.65~7.60 (m, 3H), 7.53 (d, J = 8.4 Hz, 2H), 7.47 (d, J = 7.2 Hz, 1H), 6.65 (d, J = 8.4 Hz, 1H), 6.61~6.58 (m, 1H), 6.53~6.49 (m, 2 H), 3.90 (t, J = 7.2 Hz, 2H), 1.68 (t, J = 4.0 Hz, 2H), 0.99 (s, 9H) ppm. | 2.29 | 595 |
| 155 | $^1$H NMR (400 MHz, chloroform-d) δ 9.12 (s, 1H), 8.71 (s, 1H), 8.36 (s, 1H), 7.41 (t, J = 8.0 Hz, 1H), 7.26 (d, J = 3.2 Hz, 1H), 7.00~6.90 (m, 2 H), 6.55 (m, J = 10.0 Hz, 1H), 4.59~4.56 (m, 1H), 3.86 (t, J = 7.2 Hz, 2H), 3.12 (s, 3H), 1.67~1.61 (m, 3H), 1.23 (d, J = 6.0 Hz, 6H), 0.95 (s, 9H) ppm. | 2.13 | 585 |
| 156 | $^1$H NMR (400 MHz, chloroform-d) 7.45-7.36 (m, 2H), 7.35-7.31 (m, 1H), 7.27 (d, J = 8.0 Hz, 1H), 7.23 (d, J = 4.1 Hz, 2H), 6.96 (d, J = 7.9 Hz, 1H), 6.84 (dd, J = 8.0, 1.5 Hz, 1H), 6.53-6.38 (m, 3H), 3.72 (t, J = 7.2 Hz, 2H), 1.70 (d, J = 5.1 Hz, 1H), 1.62 (s, 2H), 0.94 (s, 9H), 0.87 (dt, J = 6.2, 4.6 Hz, 2H), 0.67-0.61 (m, 2H) ppm. | 2.26 | 566 |
| 157 | $^1$H NMR (400 MHz, DMSO-d6) δ 13.33 (s, 1H), 7.79 (d, J = 8.2 Hz, 2H), 7.62-7.52 (m, 3H), 7.41 (d, J = 8.2 Hz, 1H), 7.08 (d, J = 7.2 Hz, 1H), 6.87-6.78 (m, 2H), 6.61 (d, J = 8.3 Hz, 1H), 6.44 (s, 2H), 3.38 (s, 2H), 0.93 (s, 9H) ppm. | 2.32 | 598 |
| 158 | $^1$H NMR (400 MHz, chloroform-d) δ 7.83 (dd, J = 5.3, 3.8 Hz, 1H), 7.61 (ddd, J = 29.5, 11.0, 6.2 Hz, 3H), 7.46 (dd, J = 5.1, 3.8 Hz, 1H), 7.38 (d, J = 7.4 Hz, 1H), 6.62 (d, J = 8.3 Hz, 1H), 6.48 (dt, J = 10.5, 2.2 Hz, 1H), 6.39-6.27 (m, 2H), 4.70 (s, 2H), 3.76 (t, J = 7.2 Hz, 2H), 1.63 (t, J = 7.2 Hz, 2H), 0.95 (s, 9H) ppm. | 2.20 | 595 |
| 159 | | 1.59 | 618 |
| 160 | $^1$H NMR (400 MHz, methanol-$d_4$): δ 7.40-7.36 (m, 1H), 7.26-7.25 (m, 1H), 7.22 (d, J = 7.6 Hz, 1H), 7.20-7.17 (m, 1H), 7.11 (dd, J = 10.4, 2.4 Hz, 1H), 6.92-6.87 (m, 2H), 6.60-6.58(m, 1H), 6.54-6.50 (m, 1H), 6.42 (t, J = 1.6 Hz, 1H), 5.04-4.97 (m, 1H), 3.87-3.76 (m, 2H), 1.62 (t, J = 6.8 Hz, 2H), 1.25 (d, J = 6.4 Hz, 3H), 0.95 (s, 9H) ppm. | 2.23 | 656 |
| 161 | $^1$H NMR (400 MHz, chloroform-d) δ 7.81 (s, 3H), 7.62 (s, 2H), 7.46 (s, 2H), 6.47 (d, J = 10.6 Hz, 1H), 6.34 (s, 2H), 3.74 (t, J = 7.2 Hz, 2H), 3.16 (s, 3H), 1.62 (t, J = 7.2 Hz, 2H), 0.95 (s, 9H) ppm. | 1.59 | 673 |
| 162 | $^1$H NMR (400 MHz, methanol-$d_4$) δ 8.04 (s, 1H), 7.89 (d, J = 7.6 Hz, 1H), 7.71-7.53 (m, 5H), 6.60-6.57 (m, 1H), 6.46 (d, J = 9.6 Hz, 1H), 6.37 (s, 1H), 3.83-3.80 (m, 2H), 3.38 (s, 3H), 2.93 (s, 3H), 1.639-1.604 (m, 2H), 0.96 (s, 9H) ppm. | 1.67 | 704 |
| 163 | $^1$H NMR (400 MHz, methanol-$d_4$) δ 8.201-8.161 (m, 1H), 7.998-7.975 (m, 1H), 7.727-7.700(m, 2H), 7.563-7.557 (m, 1H), 7.33-7.30 (m, | 1.67 | 616 |

TABLE 3-continued

| Example 49-509 | | | |
|---|---|---|---|
| Compound Number | NMR | LCMS retention time (min.) | LCMS MS (ESI) m/z $[M+H]^+$ |
| | 1H), 6.62-6.60 (m, 1H), 6.528-6.500 (m, 1H), 6.390 (s, 1H), 3.842-3.806 (m, 2H), 1.642-1.607 (m, 2H), 0.96 (s, 9H) ppm. | | |
| 164 | $^1$H NMR (400 MHz, methanol-$d_4$) δ 7.60 (dd, J = 8.4, 7.3 Hz, 2H), 7.36-7.22 (m, 4H), 6.90 (dd, J = 11.4, 2.3 Hz, 2H), 6.75 (ddd, J = 14.7, 10.3, 5.4 Hz, 4H), 6.63-6.52 (m, 4H), 6.47 (s, 2H), 4.89 (s, 39H), 4.56 (dt, J = 12.0, 6.1 Hz, 2H), 3.82 (t, J = 7.0 Hz, 4H), 3.33 (dt, J = 3.2, 1.6 Hz, 72H), 1.62 (t, J = 7.0 Hz, 4H), 1.14 (d, J = 6.0 Hz, 12H), 1.05-0.93 (m, 9H) ppm. | 2.23 | 603 |
| 165 | $^1$HNMR (400 MHz, chloroform-d) δ 8.05-7.79 (m, 3H), 7.74-7.56 (m, 2H), 7.52-7.43 (m, 1H), 7.12 (dd, J = 8.1, 1.8 Hz, 1H), 6.49 (dt, J = 10.5, 2.2 Hz, 1H), 6.42-6.29 (m, 2H), 3.77 (t, J = 7.2 Hz, 2H), 1.63 (t, J = 7.2 Hz, 2H), 0.95 (s, 9H) ppm. | 2.27 | 598 |
| 166 | $^1$H NMR (400 MHz, chloroform-d) δ 7.71 (d, J = 7.5 Hz, 1H), 7.56 (m, J = 13.9, 6.6 Hz, 2H), 7.33 (d, J = 8.0 Hz, 2H), 7.27 (d, J = 10.0 Hz, 2H), 6.82 (d, J = 7.5 Hz, 1H), 6.69-6.22 (m, 4H), 3.72 (t, J = 7.2 Hz, 2H), 1.60 (t, J = 7.2 Hz, 2H), 0.93 (s, 9H) ppm. | 2.19 | 576 |
| 167 | $^1$H NMR (400 MHz, chloroform-d) δ 8.55 (s, 1 H), 8.19 (s, 1 H), 7.98 (d, J = 8.4 Hz, 1 H), 7.68 (d, J = 7.6 Hz, 1 H), 7.53 (d, J = 8.4 Hz, 2 H), 7.42 (d, J = 8.4 Hz, 2 H), 7.36 (t, J = 8.0 Hz, 1 H), 6.54 (m, 1 H), 6.42 (m, 2 H), 3.82 (t, J = 7.2 Hz, 2 H), 2.04 (s, 3 H), 1.62 (t, J = 7.2 Hz, 2 H), 0.92 (s, 9 H) ppm. | 2.27 | 636 |
| 168 | $^1$H NMR (400 MHz, chloroform-d) δ 8.38 (d, J = 8.4 Hz, 1H), 8.30 (s, 1H), 7.95-7.80 (m, 2H), 7.76 (d, J = 7.5 Hz, 1H), 7.70-7.59 (m, 2H), 7.44 (d, J = 6.3 Hz, 1H), 6.49 (dt, J = 10.5, 2.1 Hz, 1H), 6.40-6.26 (m, 2H), 3.77 (t, J = 7.2 Hz, 2H), 2.20 (s, 3H), 1.63 (t, J = 7.2 Hz, 2H), 0.95 (s, 9H) ppm. | 2.22 | 637 |
| 169 | $^1$H NMR (400 MHz, chloroform-d) δ 7.28-7.26 (m, 1H), 7.25-7.18 (m, 3H), 6.99 (d, J = 8.4 Hz, 1H), 6.89 (t, J = 8.0 Hz, 1H), 6.80-6.78 (m, 1H), 6.67-6.30 (m, 4H), 3.82 (t, J = 7.2 Hz, 2H), 1.63 (t, J = 7.2 Hz, 2H), 0.94 (s, 9H) ppm. | ND | 610 |
| 170 | $^1$H NMR (400 MHz, methanol-$d_4$) 7.71-7.67 (m, 2H), 7.62-7.54 (m, 2H), 7.25 (d, J = 7.6 Hz, 1H), 6.73 (d, J = 8.8 Hz, 1H), 6.61-6.57 (m, 1H), 6.50-6.47 (m, 1H), 6.36 (s, 1H), 3.82-3.79 (m, 2H), 1.64-1.60 (m, 2H), 0.96 (s, 9H) ppm. | 1.65 | 613 |
| 171 | $^1$H NMR (400 MHz, chloroform-d) δ 7.83 (t, J = 7.9 Hz, 1H), 7.77 (d, J = 7.2 Hz, 1H), 7.29 (d, J = 8.3 Hz, 1H), 7.17 (dd, J = 8.6, 6.6 Hz, 1H), 6.67 (d, J = 10.7 Hz, 1H), 6.60 (t, J = 8.2 Hz, 1H), 6.51 (ddd, J = 16.4, 10.7, 5.5 Hz, 3H), 4.52 | 1.65 | 681 |

TABLE 3-continued

| Compound Number | NMR | LCMS retention time (min.) | LCMS MS (ESI) m/z $[M + H]^+$ |
|---|---|---|---|
| Example 49-509 | | | |
| | (dd, J = 12.0, 5.9 Hz, 1H), 3.85 (t, J = 7.2 Hz, 2H), 3.13 (s, 3H), 1.64 (t, J = 7.2 Hz, 2H), 1.25 (d, J = 6.0 Hz, 6H), 0.94 (s, 9H) ppm. | | |
| 172 | $^1$H NMR (400 MHz, chloroform-d) δ 7.77 (d, J = 8.4 Hz, 2H), 7.69 (d, J = 8.0 Hz, 2H), 7.60 (t, J = 7.2 Hz, 1H), 7.45 (d, J = 7.2 Hz, 1H), 6.62 (d, J = 8.4Hz, 1H), 6.34 (d, J = 8.8 Hz, 1H), 6.28 (d, J = 9.6 Hz, 1H), 4.27 (t, J = 7.6 Hz, 2H), 1.66 (t, J = 7.2 Hz, 2H), 0.98 (s, 9H) ppm. | 2.23 | 596 |
| 173 | $^1$H NMR (400 MHz, chloroform-d) δ 8.05-7.95 (m, 2H), 7.75 (d, J = 7.3 Hz, 1H), 7.60 (dt, J = 21.2, 7.6 Hz, 2H), 7.42 (d, J = 7.3 Hz, 1H), 7.13 (d, J = 7.1 Hz, 1H), 6.77-6.32 (m, 4H), 3.73 (t, J = 7.3 Hz, 2H), 1.61 (t, J = 7.2 Hz, 2H), 0.93 (s, 9H) ppm. | 2.23 | 580 |
| 174 | $^1$H NMR (400 MHz, DMSO-$d_6$) δ 13.42 (s, 1H), 7.81 (d, J = 8.1 Hz, 2H), 7.63-7.52 (m, 3H), 7.08 (d, J = 7.2 Hz, 1H), 6.95 (d, J = 9.4 Hz, 1H), 6.68-6.58 (m, 2H), 6.47 (s, 2H), 3.40 (s, 2H), 0.93 (s, 9H) ppm. | 2.29 | 616 |
| 175 | $^1$H NMR (400 MHz, DMSO-d6) δ ppm 13.18 (bs, 1 H), 7.75 (d, J = 8.32 Hz, 2 H), 7.57 (d, J = 8.12 Hz, 2 H), 7.28 (t, J = 7.93 Hz, 1 H), 7.15 (t, J = 7.81 Hz, 1 H), 7.08 (t, J = 1.94 Hz, 1 H), 6.96 (d, J = 7.69 Hz, 1 H), 6.90 (dd, J = 8.22 Hz, J = 2.03 Hz, 1 H), 6.85 (d, J = 7.88 Hz, 1 H), 6.73 (dd, J = 7.87 Hz, J = 1.37 Hz, 1 H), 6.66 (t, J = 1.96 Hz, 1 H), 5.56 (bs, 2 H), 3.78 (t, J = 7.25 Hz, 2 H), 1.51 (t, J = 7.25 Hz, 2 H), 1.22-1.14 (m, 2 H), 0.80 (s, 6 H), 0.76 (t, J = 7.40 Hz, 3 H) | 1.02 | 590 |
| 176 | $^1$H NMR (400 MHz, chloroform-d) δ 7.92 (d, J = 5.3 Hz, 1H), 7.83-7.68 (m, 2H), 7.59 (t, J = 7.6 Hz, 2H), 7.42 (d, J = 7.1 Hz, 1H), 6.63 (d, J = 8.2 Hz, 1H), 6.22 (d, J = 9.5 Hz, 1H), 5.81 (d, J = 9.0 Hz, 1H), 4.25 (t, J = 7.2 Hz, 2H), 1.65 (t, J = 7.3 Hz, 2H), 0.99 (s, 9H) ppm. | 2.18 | 596 |
| 177 | $^1$H NMR (400 MHz, chloroform-d) δ 7.32-7.37 (m, 3H), 7.21-7.26 (m, 1H), 7.09-7.11 (m, 1H), 6.96 (d, J = 8.0 Hz, 1H), 6.78-6.86 (m, 2H), 6.51-6.63 (m, 3H), 4.55-4.61 (m, 1H), 3.96-3.99 (m, 1H), 3.70-3.74 (m, 1H), 2.58-2.62 (m, 1H), 1.27 (d, J = 4.0 Hz, 6H), 1.22 (d, J = 4.0 Hz, 3H) ppm. | 2.13 | 610 |
| 178 | $^1$H NMR (400 MHz, DMSO-$d_6$) δ 13.07 (s, 1H), 7.68 (d, J = 8.0 Hz, 1H), 7.53 (t, J = 8.0 Hz, 1H), 7.41-7.39 (m, 2H), 7.08 (d, J = 7.2 Hz, 1H), 6.61-6.64 (m, 2H), 6.34 (s, 2H), 6.33 (d, J = 9.2 Hz, 1H), 6.69 (bs, 1H), 4.08 (t, J = 7.2 Hz, 2H), 1.55 (t, J = 7.2 Hz, 2H), 1.01 (d, J = 4.4 Hz, 6H), 0.92 (s, 9H) ppm. | 2.43 | 654 |
| 179 | $^1$H NMR (400 MHz, chloroform-d) δ 8.10 (d, J = 5.2 Hz, 1H), 7.40 (t, J = 7.2 Hz, 1H), 7.13 (t, J = 6.0 Hz, 2H), 7.01 (t, J = 5.2 Hz, 2H), 6.87 (t, J = 7.6 Hz, 3H), 4.86 (s, 2 H), | 2.13 | 585 |

TABLE 3-continued

| Example 49-509 | | | |
|---|---|---|---|
| Compound Number | NMR | LCMS retention time (min.) | LCMS MS (ESI) m/z $[M + H]^+$ |
| | 4.65~4.62 (m, 1H), 3.88 (t, J = 6.8 Hz, 2H), 1.33 (d, J = 6.0 Hz, 6H), 1.29 (t, J = 4.0 Hz, 2H), 0.96 (s, 9H) ppm. | | |
| 180 | $^1$H NMR (400 MHz, chloroform-d) δ 7.65-7.56 (m, 1H), 7.46 (d, J = 7.3 Hz, 1H), 7.42-7.33 (m, 1H), 6.76 (dd, J = 13.5, 9.4 Hz, 2H), 6.62 (d, J = 8.3 Hz, 1H), 6.34 (dd, J = 9.2, 1.7 Hz, 1H), 6.25 (dd, J = 9.6, 1.8 Hz, 1H), 4.67-4.47 (m, 3H), 4.35 (t, J = 7.4 Hz, 2H), 1.69 (t, J = 7.5 Hz, 2H), 1.29 (d, J = 6.0 Hz, 6H), 1.00 (s, 9H) ppm. | 2.19 | 604 |
| 181 | $^1$H NMR (400 MHz, chloroform-d) δ 7.67 (d, J = 7.7 Hz, 1H), 7.56-7.42 (m, 3H), 7.33 (d, J = 7.3 Hz, 1H), 7.29 (d, J = 7.7 Hz, 1H), 6.68-6.38 (m, 3H), 6.35-6.26 (m, 2H), 3.68 (t, J = 7.3 Hz, 2H), 1.58 (t, J = 7.3 Hz, 2H), 0.91 (s, 9H) ppm. | 2.17 | 577 |
| 182 | $^1$H NMR (400 MHz, chloroform-d) δ 7.58-7.54 (m, 1H), 7.45-7.38 (m, 3H), 7.22-7.20 (m, 1H), 7.02 (d, J = 8.3 Hz, 1H), 6.96-6.92 (m, 1H), 6.58 (d, J = 8.1 Hz, 1H), 5.86-5.84 (m, 1H), 4.58-4.56 (m, 3H), 4.14-4.00 (m, 2H), 1.79 (d, J = 8.3 Hz, 2H), 1.32-1.30 (m, 6H), 0.96 (s, 9H) ppm. | 2.04 | 541 |
| 183 | HNMR (DMSO-d6, 400 MHz) 7.61 (d, J = 7.6 Hz, 1 H), 7.57 (dd, J = 7.6 Hz & 8.0 Hz, 1 H), 7.36-7.33 (m, 2 H), 7.09 (d, J = 7.2 Hz, 1 H), 6.77 (d, J = 10.8 Hz, 1 H), 6.45 (s, 1 H), 6.36 (s, 1 H), 4.67 (m, 1H), 3.78 (t, J = 6.8 Hz, 2 H), 1.52 (t, J = 6.8 Hz, 2 H), 0.99 (d, J = 5.6 Hz, 6 H), 0.85 (s, 9 H) ppm. | 2.33 | 653 |
| 184 | $^1$HNMR (400 MHz, DMSO-$d_6$) 7.69 (dd, J = 7.6 Hz & 8.0 Hz, 1 H), 7.56 (d, J = 8.0 Hz, 1 H), 7.36-7.34 (m, 2 H), 7.07 (d, J = 7.2 Hz, 1 H), 6.84 (d, J = 8.8 Hz, 1 H), 6.78 (d, J = 11.2 Hz, 1 H), 6.54 (d, J = 9.2 Hz, 1 H), 6.34 (s, 1H), 4.68 (m, 1H), 3.80 (t, J = 6.8 Hz, 2 H), 2.99 (s, 6H), 1.53 (t, J = 6.8 Hz, 2 H), 0.99 (d, J = 5.6 Hz, 6 H), 0.86 (s, 9 H) ppm. | 2.43 | 681 |
| 185 | $^1$H NMR (400 MHz, methanol-$d_4$): 8.18 (q, J = 7.6 Hz, 1H), 7.98 (d, J = 7.2 Hz, 1H), 7.43-7.39 (m, 1H), 7.31 (d, J = 7.6 Hz, 1H), 7.13 (d, J = 9.6 Hz, 1H), 6.93-6.89 (m, 1H), 6.61-6.52 (m, 2H), 6.46 (s, 1H), 5.03-4.99 (m, 1H), 3.86-3.80 (m, 2H), 1.62 (t, J = 6.8 Hz, 2H), 1.30-1.26 (m, 3H) 0.92 (s, 9H) ppm. | 2.24 | 660 |
| 186 | $^1$H NMR (400 MHz, methanol-$d_4$): 7.60-7.56 (m, 1H), 7.42-7.38 (m, 1H), 7.24 (d, J = 7.2 Hz, 1H), 7.11-7.08 (m, 1H), 6.92-6.88 (m, 1H), 6.70 (d, J = 8.8 Hz, 1H), 6.58-6.51 (m, 2H), 6.43 (s, 1H), 5.01-4.95 (m, 1H), 3.86-3.75 (m, 2H), 1.62 (t, J = 6.8 Hz, 2H), 1.29-1.11 (m, 3H) 0.95 (s, 9H) ppm. | 2.18 | 657 |
| 187 | $^1$H NMR (400 MHz, chloroform-d) δ 8.18 (d, J = 9.2 Hz, 1H), 7.40-7.36 (m, 2H), 7.23 (d, J = 6.4 Hz, 1H), 7.00 (d, J = 8.4 Hz, 1H), 6.92 (t, J = 8.0 Hz, 1H), 6.60-6.50 (m, | 2.02 | 585 |

TABLE 3-continued

| Compound Number | NMR | LCMS retention time (min.) | LCMS MS (ESI) m/z $[M + H]^+$ |
|---|---|---|---|
| Example 49-509 | | | |
| | 4H), 4.60-4.52 (m, 3H), 3.86 (t, J = 7.2 Hz, 2H), 1.68 (t, J = 8.8 Hz, 2H), 1.27 (d, J = 6.0 Hz, 6H), 0.95 (s, 9H) ppm. | | |
| 188 | $^1H$ NMR (400 MHz, chloroform-d) δ 7.64-7.49 (m, 3H), 7.41 (dd, J = 16.5, 7.6 Hz, 2H), 6.58 (d, J = 8.3 Hz, 1H), 6.22 (d, J = 9.2 Hz, 1H), 5.99 (d, J = 9.1 Hz, 1H), 4.24 (t, J = 7.2 Hz, 2H), 2.27 (s, 3H), 1.65 (t, J = 7.3 Hz, 2H), 1.00 (s, 9H) ppm. | 2.28 | 610 |
| 189 | $^1H$ NMR (400 MHz, chloroform-d) δ 7.61-7.59 (m, 2H), 7.56-7.54 (m, 1H), 7.52-7.49 (m, 2H), 7.41 (d, J = 7.6 Hz, 1H), 6.62-6.55 (m, 2H), 6.50-6.45 (m, 2H), 3.90 (dd, J = 8.8, 4.0 Hz, 1H), 3.51 (t, J = 8.8 Hz, 1H), 1.68-1.60 (m, 1H), 0.95 (d, J = 6.8 Hz, 3H), 0.89 (s, 9H) ppm. | ND | 609 |
| 190 | $^1H$ NMR (400 MHz, chloroform-d) δ 8.23 (dd, J = 4.0 Hz, 1H), 7.60 (t, J = 7.6 Hz, 1H), 7.44 (t, J = 8.0 Hz, 2H), 7.19 (t, J = 8.0 Hz, 1H), 6.83-6.77 (m, 2H), 6.68 (s, 1H), 6.64 (d, J = 8.4 Hz, 1H), 6.61-6.58 (m, 1H), 4.71 (d, J = 8.8 Hz, 1H), 3.79 (t, J = 7.6 Hz, 2H), 3.41-3.37 (m, 1H), 2.97-2.87 (m, 1H), 2.51-2.45 (m, 1H), 1.65 (t, J = 7.2 Hz, 2H), 1.57 (s, 3H), 1.44 (s, 3H), 0.96 (s, 9H), 0.84 (d, J = 6.4 Hz, 3H) ppm. | 2.02 | 621 |
| 191 | $^1H$ NMR (400 MHz, chloroform-d) δ 8.20 (dd, J = 4.8 Hz, 1.2 Hz, 1H), 7.61 (t, J = 8.0 Hz, 1H), 7.37 (dd, J = 7.2 Hz, 1.6 Hz, 1H), 7.33 (d, J = 7.2 Hz, 1H), 7.20 (t, J = 8.0 Hz, 1H), 6.83 (dd, J = 2.0 Hz, 1.2 Hz, 1H), 6.78 (d, J = 8.0 Hz, 1H), 6.69-6.65 (m, 2H), 6.61-6.58 (m, 1H), 4.74 (d, J = 9.6 Hz, 1H), 4.49 (s, 1H), 3.80 (t, J = 7.2 Hz, 2H), 3.43-3.37 (m, 1H), 2.95 (s, 6H), 2.51-2.47 (m, 1H), 1.65 (t, J = 7.6 Hz, 2H), 1.60 (s, 3H), 1.49 (s, 3H), 0.96 (s, 9H), 0.87 (d, J = 6.8 Hz, 3H) ppm. | 2.11 | 649 |
| 192 | $^1H$ NMR (400 MHz, chloroform-d) δ 7.51 (dd, J = 24.0, 7.9 Hz, 3H), 7.40 (d, J = 2.2 Hz, 1H), 6.75 (d, J = 2.2 Hz, 1H), 6.51 (d, J = 10.5 Hz, 1H), 6.35 (d, J = 6.9 Hz, 2H), 3.94 (s, 3H), 3.77 (t, J = 7.1 Hz, 2H), 2.21 (s, 3H), 1.63 (t, J = 7.1 Hz, 2H), 0.94 (s, 9H) ppm. | 2.26 | 597 |
| 193 | $^1H$ NMR (400 MHz, chloroform-d) δ 7.49 (t, J = 7.8 Hz, 1H), 7.39 (s, 1H), 7.32 (dd, J = 12.8, 7.7 Hz, 3H), 6.49 (dd, J = 24.0, 9.4 Hz, 2H), 6.32-6.25 (m, 2H), 3.72 (t, J = 7.1 Hz, 2H), 2.00 (s, 3H), 1.60 (t, J = 7.1 Hz, 2H), 0.92 (s, 9H) ppm. | 2.33 | 609 |
| 194 | $^1H$ NMR (400 MHz, chloroform-d) δ 8.06 (d, J = 6.8 Hz, 1H), 7.72-7.71 (m, 1H), 7.38-7.34 (m, 1H), 7.15 (d, J = 7.2 Hz, 1H), 6.96 (d, J = 8.7 Hz, 1H), 6.89-6.85 (m, 1H), 6.61-6.58 (m, 1H), 6.50-6.46 (m, 3H), 6.02 (m, 2H), 4.65-4.38 (m, 1H), 3.80 (t, J = 7.2 Hz, 2H), 1.62 (t, J = 7.2 Hz, 2H), 1.23-1.21 (d, J = 6.0 Hz, 6H), 0.93 (s, 9H) ppm. | 2.25 | 585 |
| 195 | $^1H$ NMR (400 MHz, chloroform-d) δ 7.55-7.59 (m, 1H), 7.43-7.45 (m, | 2.15 | 611 |

TABLE 3-continued

| Compound Number | NMR | LCMS retention time (min.) | LCMS MS (ESI) m/z $[M + H]^+$ |
|---|---|---|---|
| Example 49-509 | | | |
| | 1H), 7.34-7.39 (m, 1H), 7.16-7.18 (m, 1H), 6.97-6.99 (m, 1H) 6.85-6.89 (m, 1H), 6.58-6.61 (m, 1H), 6.50-6.55 (m, 3H), 4.55-4.64 (m, 1H), 3.96-4.00 (m, 1H), 3.70-3.75 (m, 1H), 2.57-2.64 (m, 1H), 1.29 (d, J = 8.0 Hz, 6H), 1.23 (d, J = 8.0 Hz, 3H) ppm. | | |
| 196 | $^1$HNMR (400 MHz, chloroform-d) 7.60 (dd, J = 7.6 Hz & 8.0 Hz, 1 H), 7.43 (d, J = 7.2 Hz, 1 H), 7.32 (m, 1 H), 7.13 (d, J = 8 Hz, 1 H), 6.61-6.55 (m, 3H), 6.50 (d, J = 8.8 Hz, 1 H); 4.68 (br S, 1H), 4.66 (m, 1H), 4.05 (t, J = 6.4 Hz, 2 H), 1.96 (t, J = 6.4 Hz, 2 H), 1.33 (d, J = 6.0 Hz, 6 H), 1.24 (s, 6 H) ppm | 2.17 | 655 |
| 197 | $^1$H NMR (400 MHz chloroform-d) δ 7.75 (d, J = 7.7 Hz, 1H), 7.65-7.54 (m, 2H), 7.50 (t, J = 7.8 Hz, 1H), 7.41 (d, J = 7.3 Hz, 1H), 7.34 (d, J = 7.1 Hz, 1H), 6.70-6.40 (m, 2H), 6.14 (d, J = 7.9 Hz, 1H), 5.87 (d, J = 9.0 Hz, 1H), 4.14 (t, J = 7.4 Hz, 2H), 1.56 (t, J = 7.3 Hz, 2H), 0.90 (s, 9H) ppm. | 2.24 | 578 |
| 198 | $^1$H NMR (400 MHz, methanol-d4) δ 7.71 (dd, J = 9.0, 2.5 Hz, 1H), 7.65 (dd, J = 8.5, 5.4 Hz, 1H), 7.57 (ddd, J = 11.3, 7.9, 3.5 Hz, 2H), 7.26 (d, J = 7.3 Hz, 1H), 6.69 (d, J = 8.3 Hz, 1H), 6.27 (dd, J = 9.9, 1.8 Hz, 1H), 6.03 (dd, J = 9.6, 1.8 Hz, 1H), 4.14 (t, J = 7.0 Hz, 2H), 1.64 (t, J = 7.1 Hz, 2H), 1.01 (s, 9H) ppm. | 2.19 | 614 |
| 199 | $^1$H NMR (400 MHz, chloroform-d) δ 7.48 (ddd, J = 13.7, 8.5, 3.9 Hz, 2H), 7.37 (d, J = 2.2 Hz, 1H), 7.34-7.27 (m, 1H), 6.67 (d, J = 2.3 Hz, 1H), 6.48 (dt, J = 10.5, 2.2 Hz, 1H), 6.35 (s, 1H), 6.30 (dd, J = 9.1, 1.8 Hz, 1H), 3.93 (s, 3H), 3.78 (t, J = 7.2 Hz, 2H), 1.63 (t, J = 7.2 Hz, 2H), 0.94 (s, 9H) ppm. | 2.25 | 601 |
| 200 | $^1$H NMR (400 MHz, chloroform-d) δ 7.52 (s, 1H), 7.40-7.34 (m, 2H), 7.30 (d, J = 3.2 Hz, 2H), 6.83 (d, J = 7.9 Hz, 1H), 6.52 (d, J = 10.5 Hz, 1H), 6.43 (s, 2H), 3.80 (t, J = 7.2 Hz, 2H), 1.63 (s, 2H), 0.93 (s, 9H) ppm. | 1.66 | 610 |
| 201 | $^1$H NMR (400 MHz, DMSO) δ 13.33 (s, 1H), 7.78 (d, J = 8.4 Hz, 2H), 7.64-7.48 (m, 3H), 7.09 (d, J = 6.9 Hz, 1H), 6.89-6.77 (m, 1H), 6.71-6.64 (m, 1H), 6.61 (d, J = 8.4 Hz, 1H), 6.57 (s, 1H), 6.46 (s, 2H), 4.35 (s, 1H), 3.95 (t, J = 7.1 Hz, 2H), 1.72 (t, J = 7.1 Hz, 2H), 1.08 (s, 6H) ppm. | 1.94 | 597 |
| 202 | $^1$H NMR (400 MHz, chloroform-d) δ 7.57-7.55 (m, 2H), 7.39-7.37 (m, 3H), 7.33-7.32 (m, 1H), 7.23-7.22 (m, 1H), 6.81-6.79 (m, 1H), 6.59(dd, J = 4.0 Hz, 1H), 6.49-6.48 (m, 2H), 4.00-3.98 (m, 1H), 3.77-3.76 (m, 1H), 2.63-2.62 (m, 1H), 1.23 (d, J = 7.0 Hz, 3H) ppm. | 2.18 | 620 |
| 203 | $^1$H NMR (400 MHz, chloroform-d) 7.49 (d, J = 11.7 Hz, 5H), 7.36 (s, 1H), 6.62-6.44 (m, 3H), 6.37 (s, | 1.68 | 609 |

TABLE 3-continued

| Example 49-509 | | | |
|---|---|---|---|
| Compound Number | NMR | LCMS retention time (min.) | LCMS MS (ESI) m/z $[M + H]^+$ |
| | 1H), 4.19 (s, 1H), 1.72-1.63 (m, 1H), 1.32 (s, 1H), 1.08 (d, J = 4.3Hz, 3H), 0.84 (s, 9H) ppm. | | |
| 204 | $^1$H NMR (400 MHz, chloroform-d) δ 8.05 (s, 1H), 7.86 (d, J = 7.6 Hz, 1H), 7.58 (d, J = 8.2 Hz, 2H), 7.39 (d, J = 7.5 Hz, 1H), 6.63 (d, J = 8.3 Hz, 1H), 6.49 (d, J = 10.4 Hz, 1H), 6.35-6.28 (m, 2H), 3.79 (t, J = 7.1 Hz, 2H), 1.61 (d, J = 7.2 Hz, 2H), 0.93 (s, 9H) ppm. | 2.32 | 663 |
| 205 | $^1$H NMR (400 MHz, chloroform-d) δ 7.64-7.55 (m, 2H), 7.52 (s, 2H), 7.48-7.30 (m, 8H), 6.62 (d, J = 8.4 Hz, 2H), 6.53 (d, J = 10.5 Hz, 2H), 6.44 (s, 3H), 3.80 (t, J = 7.2 Hz, 5H), 0.98-0.87 (m, 23H) | 2.20 | 611 |
| 206 | $^1$H NMR (400 MHz, DMSO-$d_6$) δ 13.38 (s, 1H), 7, 90 (d, J = 7.2 Hz, 2H), 7.78 (d, J = 8.4 Hz, 2H), 7.64-7.56 (m, 5H), 6.87 (d, J = 10.8Hz, 1H), 6.69 (d, J = 9.3 Hz, 1H), 6.58 (s, 1H), 4.32 (s, 1H), 3.74 (d, J = 9.6Hz, 1H), 3.67 (d, J = 9.6 Hz, 1H), 1.09 (s, 3H), 0.86 (s, 9H) ppm. | 2.19 | 609 |
| 207 | $^1$H NMR (400 MHz, chloroform-d) δ 7.60-7.51 (m, 4H), 7.40 (d, J = 7.2 Hz, 1H), 6.63 (d, J = 8.4 Hz, 1H), 6.53 (d, J = 8.4 Hz, 1H), 6.39-6.35 (m, 2H), 4.00-3.91 (m, 2H), 2.19 (s, 3H), 2.17-2.04 (m, 2H), 1.39 (s, 3H) ppm. | 2.01 | 665 |
| 208 | $^1$H NMR (400 MHz, DMSO-$d_6$) δ 12.95 (s, 1H), 7.47-7.45 (m, 3H), 7.13-7.11 (m, 3H), 6.51-6.50 (m, 4H), 6.12 (s, 1H), 4.54 (s, 1H), 4.28 (s, 2H), 1.63 (s, 2H), 1.00-0.97 (m, 15H) ppm | 2.30 | 586 |
| 209 | $^1$H NMR (400 MHz, chloroform-d) δ 7.57-7.52 (m, 2H), 7.43 (s, 2H), 7.31-7.26 (m, 1H), 6.76-6.40 (m, 5H), 3.81 (t, J = 7.2 Hz, 2H), 1.63 (t, J = 7.2 Hz, 2H), 0.93 (s, 9H) ppm. | ND | 661 |
| 210 | $^1$H NMR (400 MHz, $CD_3OD$): 7.73-7.71 (m, 2H), 7.62-7.58 (m, 3H), 7.26 (d, J = 6.8 Hz, 1H), 6.72-6.68 (m, 2H), 6.61-6.59 (m, 2H), 4.08-4.05 (m, 1H), 3.66-3.62 (m, 1H), 1.92-1.87 (m, 1H), 1.19 (s, 3H), 1.15 (s, 3H), 1.02 (d, J = 6.8 Hz, 3H) ppm. | 2.07 | 611 |
| 211 | $^1$H NMR (400 MHz, DMSO-d6) δ ppm 13.34 (bs, 1 H), 10.14 (bs, 1 H), 8.28 (t, J = 1.90 Hz, 1 H), 7.78 (dt, J = 7.86 Hz, J = 1.72 Hz, 1H), 7.75 (d, J = 8.39 Hz, 2 H), 7.57 (d, J = 8.39 Hz, 2 H), 7.54-7.45 (m, 2 H), 7.28 (t, J = 7.96 Hz, 1 H), 6.90 (dd, J = 8.26 Hz, J = 2.20 Hz, 1 H), 6.85 (d, J = 7.84 Hz, 1 H), 6.67 (t, J = 1.90 Hz, 1 H), 3.80 (t, J = 7.15 Hz, 2 H), 2.59 (sept., J = 6.85 Hz, 1 H), 1.52 (t, J = 7.20 Hz, 2 H), 1.10 (d, J = 3.81 Hz, 6 H), 0.86 (s, 9 H) | 1.05 | 646 |
| 212 | $^1$H NMR (400 MHz, chloroform-d) δ 8.00-7.91 (m, 2H), 7.64-7.53 (m, 3H), 7.46 (dd, J = 16.3, 8.2 Hz, 4H), 6.66-6.59 (m, 1H), 6.52 (d, J = 6.6 Hz, 1H), 3.84 (t, J = 7.2 Hz, 2H), 1.66 (t, J = 7.2 Hz, 2H), 0.91 (s, 9H) ppm. | 2.36 | 597 |

TABLE 3-continued

| Example 49-509 | | | |
|---|---|---|---|
| Compound Number | NMR | LCMS retention time (min.) | LCMS MS (ESI) m/z $[M + H]^+$ |
| 213 | $^1H$ NMR (400 MHz, chloroform-d) δ 7.49 (d, J = 8.1 Hz, 2H), 7.37 (d, J = 7.6 Hz, 3H), 6.78 (d, J = 2.2 Hz, 1H), 6.61 (d, J = 10.1 Hz, 1H), 6.52 (d, J = 8.8 Hz, 2H), 4.09 (t, J = 13.2 Hz, 2H), 3.91 (s, 3H), 1.07 (s, 9H) ppm. | 1.60 | 619 |
| 214 | $^1H$ NMR (400 MHz, chloroform-d) δ 7.98-7.94 (m, 2H), 7.64-7.54 (m, 3H), 7.51-7.41 (m, 4H), 6.69-6.62 (m, 1H), 6.36 (d, J = 6.6 Hz, 1H), 4.51-4.44 (m, 1H), 1.89-1.68 (m, 2H), 1.65-1.54 (m, 2H), 1.48 (dd, J = 13.9, 3.7 Hz, 1H), 1.40-1.32 (m, 1H), 1.07 (s, 3H), 0.93 (s, 3H) ppm. | 2.38 | 609 |
| 215 | $^1H$ NMR (400 MHz, chloroform-d) δ 7.48 (t, J = 8.0 Hz, 1 H), 7.41 (d, J = 8.0 Hz, 2 H), 7.35 (d, J = 7.6 Hz, 1 H), 7.30 (d, J = 8.0 Hz, 2 H), 6.53-6.40 (m, 3 H), 6.32 (s, 1 H), 4.49 (m, 1 H), 1.95-1.86 (m, 1 H), 1.75-1.68 (m, 1 H), 1.66-1.54 (m, 2 H), 1.46 (m, 1 H), 1.39-1.33 (m, 1 H), 1.05 (s, 3 H), 0.94 (s, 3 H) ppm. | 2.34 | 607 |
| 216 | $^1H$ NMR (400 MHz, chloroform-d) δ 7.63-7.50 (m, 3H), 7.41 (dd, J = 15.6, 7.7 Hz, 3H), 6.59 (dd, J = 25.6, 17.6 Hz, 4H), 4.09 (t, J = 13.2 Hz, 2H), 1.07 (s, 9H) ppm. | 2.16 | 631 |
| 217 | $^1H$ NMR (400 MHz, chloroform-d) δ 7.53-7.45 (m, 2H), 7.39 (d, J = 2.0 Hz, 2H), 6.76 (d, J = 2.0 Hz, 1H), 6.55 (d, J = 12.0 Hz, 1H), 6.43-6.34 (m, 2H), 4.00 (t, J = 12.0 Hz, 2H), 3.94 (s, 3H), 2.15 (s, 3H), 1.06 (s, 9H) ppm. | 1.62 | 633 |
| 218 | $^1H$ NMR (400 MHz, chloroform-d) δ 7.86 (d, J = 8.0 Hz, 1H) 7.52-7.54 (m, 1H), 7.43-7.46 (m, 2H), 7.19-7.26 (m, 2H), 6.99 (d, J = 8.0 Hz, 1H), 6.89-6.91 (m, 1H), 6.38-6.74 (m, 4H), 3.82 (t, J = 8.0 Hz, 2H), 1.63 (t, J = 8.0 Hz, 2H), 0.94 (s, 9H) ppm. | ND | ND |
| 219 | $^1H$ NMR (400 MHz, chloroform-d) δ 7.97 (d, J = 7.4 Hz, 2H), 7.57 (t, J = 7.2 Hz, 1H), 7.53-7.44 (m, 4H), 7.37 (d, J = 7.2 Hz, 1H), 6.49 (d, J = 10.4 Hz, 1H), 6.33 (d, J = 7.6 Hz, 2H), 3.75 (t, J = 7.1 Hz, 2H), 2.14 (s, 3H), 1.61 (t, J = 7.1 Hz, 2H), 0.92 (s, 9H) ppm. | 2.36 | 593 |
| 220 | $^1H$ NMR (400 MHz, chloroform-d) δ 7.58-7.52 (m, 3H), 7.44 (d, J = 7.6 Hz, 1H), 7.13 (d, J = 7.2 Hz, 1H), 6.65 (d, J = 8.8 Hz, 1H), 6.54 (d, J = 9.2 Hz, 1H), 6.40-6.35 (m, 2H),, 4.01-3.92 (m, 2H), 2.96 (s, 6H), 2.21 (s, 3H), 2.18-2.07 (m, 2H), 1.40 (s, 3H) ppm. | 2.11 | 693 |
| 221 | $^1H$ NMR (400 MHz, methanol-$d_4$) δ 7.69-7.56 (m, 5H), 7.26 (d, J = 7.2 Hz, 1 H), 6.73-6.61 (m, 4 H), 3.77 (s, 2 H), 1.23 (s, 3 H), 0.96 (s, 9 H) ppm. | 1.56 | 625 |
| 222 | $^1H$ NMR (400 MHz, chloroform-d) δ 7.56 (m, J = 7.9 Hz, 1H), 7.45 (m, J = 29.0, 15.5 Hz, 3H), 7.32 (d, J = 8.0 Hz, 2H), 6.58 (d, J = 8.6 Hz, 2H), 6.47 (d, J = 6.4 Hz, 1H), 3.82 (t, J = 7.3 Hz, 2H), 1.64 (t, J = 7.2 Hz, 2H), 0.90 (s, 9H) ppm. | 2.25 | 613 |

TABLE 3-continued

| Compound Number | NMR | LCMS retention time (min.) | LCMS MS (ESI) m/z $[M + H]^+$ |
|---|---|---|---|
| | Example 49-509 | | |
| 223 | $^1$H NMR (400 MHz, chloroform-d) δ 7.61-7.53 (m, 3H), 7.46 (d, J = 8.1 Hz, 2H), 7.40 (d, J = 7.3 Hz, 1H), 6.63 (dd, J = 16.0, 8.0 Hz, 2H), 6.37 (d, J = 6.3 Hz, 1H), 4.50-4.45 (m, 1H), 1.79 (m, J = 27.9, 11.4, 5.3 Hz, 2H), 1.64-1.53 (m, 2H), 1.47 (dd, J = 13.7, 3.7 Hz, 1H), 1.39-1.31 (m, 1H), 1.06 (s, 3H), 0.93 (s, 3H) ppm. | 2.35 | 625 |
| 224 | $^1$HNMR (400 MHz, chloroform-d) 8.41-8.33 (m, 2H), 7.89-7.77 (m, 2 H), 7.28 (m, 1H), 7.15-7.10 (m, 2H), 6.58-6.46 (m, 3 H), 4.66-4.63 (m, 1 H), 3.88 (t, J = 7.2 Hz, 2 H), 2.32-2.18 (m, 3 H), 1.67 (t, J = 7.2 Hz, 2 H), 1.30 (d, J = 6.0 Hz, 6 H), 0.95 (s, 9 H) ppm. | 2.44 | 695 |
| 225 | $^1$H NMR (400 MHz, chloroform-d) δ 7.64-7.56 (m, 1H), 7.54 (d, J = 8.0 Hz, 2H), 7.49-7.38 (m, 2H), 6.63 (d, J = 8.0 Hz, 1H), 6.48 (d, J = 12.0 Hz, 1H), 6.47-6.27 (m, 2H), 4.03 (dd, J = 12.0, 8.0 Hz, 1H), 2.21 (s, 3H), 1.23 (dd, J = 32.0, 16.0 Hz, 8H), 0.90 (d, J = 24.0 Hz, 6H) ppm. | 2.39 | 635 |
| 226 | $^1$H NMR (400 MHz, chloroform-d) δ 7.68-7.44 (m, 4H), 7.40 (d, J = 7.3 Hz, 1H), 6.62 (d, J = 8.3 Hz, 1H), 6.47 (d, J = 10.5 Hz, 1H), 6.37 (d, J = 9.0 Hz, 1H), 6.23 (s, 1H), 4.43-4.35 (m, 1H), 2.19 (s, 3H), 1.91-1.28 (m, 6H), 1.06 (s, 3H), 0.97 (s, 3H) ppm. | 2.39 | 621 |
| 227 | $^1$H NMR (400 MHz, chloroform-d) δ 7.40-7.29 (m, 4H), 7.16 (d, J = 7.6 Hz, 2H), 6.88 (d, J = 9.0 Hz, 1H), 6.47 (d, J = 10.4 Hz, 1H), 6.41-6.27 (m, 2H), 3.67 (t, J = 7.3 Hz, 2H), 3.03 (s, 6H), 2.15 (s, 6H), 1.63 (d, J = 7.2 Hz, 2H), 0.95 (s, 9H) ppm. | 2.53 | 582 |
| 228 | $^1$HNMR (400 MHz, chloroform-d) δ 7.52-7.56 (m, 1H), 7.33-7.35 (m, 2H), 6.99-7.01 (m, 1H), 6.90-6.92 (m, 1H), 6.64-6.65 (m, 1H), 6.42-6.53 (m, 4H), 2.01 (t, J = 8.0 Hz, 2H), 1.63 (t, J = 8.0 Hz, 2H), 0.94 (s, 9H) ppm. | 2.24 | 611 |
| 229 | $^1$HNMR (400 MHz, chloroform-d) δ 7.64~7.58 (m, 3H), 7.52 (d, J = 8.0 Hz, 2H), 7.44 (d, J = 7.2 Hz, 1H), 6.64~6.59 (m, 2H), 6.53 (d, J = 2.0 Hz, 2H), 4.13~4.04 (m, 2H), 2.21~2.12 (m, 2 H), 1.43 (s, 3H) ppm. | 2.08 | 651 |
| 230 | $^1$H NMR (400 MHz, chloroform-d) δ 7.32 (t, J = 7.4 Hz, 3H), 7.22 (s, 1H), 7.16 (d, J = 7.6 Hz, 2H), 6.81-6.71 (m, 1H), 6.47 (d, J = 10.4 Hz, 1H), 6.40-6.26 (m, 2H), 3.68 (t, J = 7.3 Hz, 2H), 2.90 (s, 3H), 2.15 (s, 6H), 1.62 (s, 2H), 0.95 (s, 9H) ppm. | 2.44 | 568 |
| 231 | | 1.04 | 644 |
| 232 | $^1$H NMR (400 MHz, chloroform-d) δ 7.61-7.53 (m, 3H), 7.46 (d, J = 8.1 Hz, 2H), 7.40 (d, J = 7.3 Hz, 1H), 6.63 (dd, J = 16.0, 8.0 Hz, 2H), 6.37 (d, J = 6.3 Hz, 1H), 4.50-4.45 (m, 1H), 1.79 (m, J = 27.9, 11.4, 5.3 Hz, 2H), 1.64-1.53 (m, 2H), 1.47 (dd, J = 13.7, 3.7 Hz, | 2.35 | 625 |

TABLE 3-continued

| Example 49-509 | | | |
|---|---|---|---|
| Compound Number | NMR | LCMS retention time (min.) | LCMS MS (ESI) m/z $[M + H]^+$ |
| | 1H), 1.39-1.31 (m, 1H), 1.06 (s, 3H), 0.93 (s, 3H) ppm. | | |
| 233 | | 0.57 | 605 |
| 234 | $^1$H NMR (400 MHz, chloroform-d) δ 8.00 (d, J = 7.5 Hz, 2H), 7.53-7.49 (m, 1H), 7.45-7.41 (m, 2H), 7.39-7.28 (m, 5H), 7.26-7.07 (m, 4H), 6.62-6.58 (m, 1H), 6.53-6.51 (m, 1H), 6.41-6.38 (m, 1H), 4.89 (s, 2H) ppm. | 2.29 | 585 |
| 235 | $^1$H NMR (400 MHz, chloroform-d) δ 7.63-7.56 (m, 1H), 7.50 (d, J = 12.0 Hz, 2H), 7.44-7.37 (m, 2H), 6.62 (d, J = 8.0 Hz, 1H), 6.55 (d, J = 12.0 Hz, 1H), 6.36 (s, 2H), 4.00 (t, J = 12.0 Hz, 2H), 2.16 (s, 3H), 1.06 (s, 9H) ppm. | 2.15 | 645 |
| 236 | $^1$H NMR (400 MHz, methanol-$d_4$) δ 8.04-7.86 (m, 4H), 7.77 (d, J = 8.3 Hz, 2H), 7.66-7.46 (m, 3H), 3.86-3.71(m, 2H), 2.84 (t, J = 4.8 Hz, 2H), 2.68 (q, J = 11.1 Hz, 2H), 1.93 (dd, J = 13.9, 7.0 Hz, 1H), 1.80-1.64 (m, 2H), 1.61-1.48 (m, 1H), 1.42 (d, J = 14.0 Hz, 1H), 1.36-1.25 (m, 1H), 1.07 (s, 3H), 0.86 (s, 3H) ppm. | 2.35 | 552 |
| 237 | $^1$H NMR (400 MHz, methanol-$d_4$) δ 7.95 (d, J = 8.2 Hz, 2H), 7.78 (d, J = 8.4 Hz, 2H), 7.60 (dd, J = 8.3, 7.4 Hz, 1H), 7.24 (d, J = 7.2 Hz, 1H), 6.71 (d, J = 8.3 Hz, 1H), 3.79 (dd, J = 8.0, 4.3 Hz, 2H), 2.86 (t, J = 4.7 Hz, 2H), 2.70 (q, J = 11.1 Hz, 2H), 1.94 (dd, J = 13.8, 7.0 Hz, 1H), 1.82-1.64 (m, 2H), 1.64-1.49 (m, 1H), 1.44 (d, J = 13.6 Hz, 1H), 1.32 (dt, J = 12.5, 7.3 Hz, 1H), 1.07 (s, 3H), 0.87 (s, 3H) ppm. | 2.32 | 568 |
| 238 | | 0.85 | 593 |
| 239 | $^1$H NMR (400 MHz, chloroform-d) δ 7.66-7.58 (m, 1H), 7.43-7.30 (m, 2H), 7.18 (d, J = 7.6 Hz, 2H), 6.59-6.43 (m, 2H), 6.41-6.30 (m, 2H), 3.68 (t, J = 7.3 Hz, 2H), 2.76 (s, 3H), 2.17 (s, 6H), 1.62 (t, J = 7.3 Hz, 2H), 0.95 (s, 9H) ppm. | 2.35 | 569 |
| 240 | $^1$H NMR (400 MHz, chloroform-d) δ 7.60 (dd, J = 8.5, 7.4 Hz, 1H), 7.32 (dd, J = 13.7, 6.0 Hz, 2H), 7.17 (d, J = 7.6 Hz, 2H), 6.65 (d, J = 8.6 Hz, 1H), 6.48 (dt, J = 10.4, 2.1 Hz, 1H), 6.41-6.28 (m, 2H), 3.67 (t, J = 7.3 Hz, 2H), 2.96 (s, 6H), 2.16 (s, 6H), 1.62 (t, J = 7.3 Hz, 2H), 0.95 (s, 9H) ppm. | 2.44 | 583 |
| 241 | $^1$H NMR (400 MHz, chloroform-d) δ 8.08-7.98 (m, 2H), 7.65-7.48 (m, 3H), 7.45-7.36 (m, 1H), 7.23 (d, J = 4.0 Hz, 2H), 6.97 (d, J = 8.0 Hz, 1H), 6.56-6.37 (m, 3H), 3.73 (t, J = 7.3 Hz, 2H), 1.71 (ddd, J = 13.4, 8.4, 5.3 Hz, 1H), 1.62 (t, J = 7.3 Hz, 2H), 0.95 (s, 9H), 0.90-0.83 (m, 2H), 0.69-0.61 (m, 2H) ppm. | 2.47 | 551 |
| 242 | $^1$H NMR (400 MHz, chloroform-d) δ 8.55 (d, J = 2.0 Hz, 1H), 8.29 (d, J = 8.0 Hz, 1H), 8.13 (d, J = 8.0 Hz, 1H), 7.74 (t, J = 8.0 Hz, 1H), 7.35-7.28 (m, 1H), 7.15 (d, J = 8.0 Hz, 2H), 6.47 (d, J = 12.0 Hz, 1H), 6.33 (d, J = 8.0 Hz, 2H), 3.67 | 2.35 | 617 |

TABLE 3-continued

| Compound Number | NMR | LCMS retention time (min.) | LCMS MS (ESI) m/z $[M + H]^+$ |
|---|---|---|---|
| Example 49-509 | | | |
| | (s, 2H), 3.11 (s, 3H), 2.14 (s, 6H), 1.61 (d, J = 8.0 Hz, 2H), 0.93 (s, 9H) ppm. | | |
| 243 | $^1$H NMR (400 MHz, chloroform-d) δ 8.12 (s, 1H), 7.88 (d, J = 8.0 Hz, 1H), 7.71 (d, J = 8.0 Hz, 1H), 7.49 (s, 1H), 7.34-7.28 (m, 1H), 7.14 (d, J = 8.0 Hz, 2H), 6.46 (d, J = 12.0Hz, 1H), 6.38-6.26 (m, 2H), 3.66 (t, J = 8.0 Hz, 2H), 2.14 (s, 6H), 1.62-1.58 (m, 8H), 0.93 (s, 9H) ppm. | 2.40 | 597 |
| 244 | $^1$H NMR (400 MHz, chloroform-d) δ 7.38-7.33 (m, 1H), 7.19 (d, J = 7.6 Hz, 2H), 7.05 (s, 1H), 6.80 (d, J = 30.0 Hz, 2H), 6.40 (dd, J = 32.5, 17.2 Hz, 3H), 5.93 (s, 2H), 4.39-4.30 (m, 1H), 2.10 (d, J = 4.3 Hz, 6H), 1.90 (d, J = 7.3 Hz, 2H), 1.66 (dd, J = 13.6, 6.7 Hz, 2H), 1.40 (d, J = 4.6 Hz, 2H), 1.08 (s, 3H), 1.00 (s, 3H) ppm. | 1.96 | 567 |
| 245 | | ND | ND |
| 246 | $^1$HNMR (400 MHz, chloroform-d) δ 8.71 (s, 1H), 8.46 (s, 1H), 8.24 (d, J = 5.2 Hz, 1H), 7.56 (dd, J = 5.2 Hz & 1.2 Hz, 1H), 7.32 (d, J = 8 Hz, 1H), 7.18 (s, 1H), 7.15 (d, J = 8 Hz, 1H), 6.59-6.49 (m, 3 H), 4.67-4.64 (m, 1 H), 3.90 (t, J = 6.8 Hz, 2H), 2.24 (s, 3 H), 1.68(t, J = 7.2 Hz, 2H), 1.32 (d, J = 6 Hz, 6H), 0.96 (s, 9 H) ppm. | 2.44 | 695 |
| 247 | $^1$H NMR (400 MHz, chloroform-d) δ 8.30 (d, J = 5.2 Hz, 1H), 7.35-7.29 (m, 1H), 7.16 (d, J = 7.6 Hz, 2H), 7.06 (s, 1H), 7.00 (dd, J = 5.2, 1.3 Hz, 1H), 6.52-6.40 (m, 1H), 6.36 (d, J = 9.4 Hz, 1H), 6.30 (s, 1H), 4.35 (td, J = 7.1, 3.5 Hz, 1H), 3.16 (s, 6H), 2.15 (d, J = 4.8 Hz, 6H), 1.90 (dd, J = 14.6, 7.4 Hz, 1H), 1.74-1.60 (m, 3H), 1.46-1.36 (m, 2H), 1.08 (s, 3H), 0.99 (s, 3H) ppm. | 2.14 | 595 |
| 248 | $^1$H NMR (400 MHz, chloroform-d) δ 8.23 (d, J = 5.3 Hz, 1H), 7.35-7.29 (m, 1H), 7.15 (d, J = 7.6 Hz, 2H), 7.02-6.81 (m, 2H), 6.48 (dt, J = 10.4, 2.1 Hz, 1H), 6.42-6.28 (m, 2H), 3.68 (t, J = 7.3 Hz, 2H), 3.47 (t, J = 6.3 Hz, 4H), 2.15 (s, 6H), 2.03 (t, J = 6.5 Hz, 4H), 1.62 (t, J = 7.3 Hz, 2H), 0.95 (s, 9H) ppm. | 2.04 | 609 |
| 249 | $^1$H NMR (400 MHz, chloroform-d) δ 7.59-7.57 (m, 1H), 7.52-7.51 (m, 1H), 7.49-7.45 (m, 1H), 7.42-7.38 (m, 2H), 7.24-7.21 (m, 2H), 7.09-7.07 (m, 1H), 6.45-6.38 (m, 2H), 6.33-6.31 (m, 1H), 3.86 (s, 3H), 3.64 (t, J = 7.2 Hz, 2H), 2.86-2.79 (m, 1H), 1.58 (t, J = 7.2 Hz, 2H), 1.21-0.98 (m, 6H), 0.91 (s, 9H) ppm. | 1.76 | 583 |
| 250 | $^1$HNMR (400 MHz, chloroform-d) δ 7.91-7.93 (m, 2H), 7.63-7.65 (m, 2H), 7.52-7.56 (m, 3H), 7.44-7.48 (m, 2H), 3.67-3.68 (s, 1H), 3.50-3.54 (m, 1H), 3.36-3.39 (m, 1H), 3.04-3.06 (m, 1H), 2.87-2.90 (m, 1H), 2.61-2.66 (m, 1H), 2.44-2.50 (m, 1H), 2.14-2.15 (m, 1H), 1.87-1.88 (m, 1H), 0.84 (s, 9H) ppm. | 2.13 | 568 |

TABLE 3-continued

| Compound Number | NMR | LCMS retention time (min.) | LCMS MS (ESI) m/z $[M + H]^+$ |
|---|---|---|---|
| | Example 49-509 | | |
| 251 | $^1$H NMR (400 MHz, chloroform-d) δ 8.27 (d, J = 5.2 Hz, 1H), 7.30 (t, J = 7.6 Hz, 1H), 7.14 (d, J = 7.6 Hz, 2H), 7.04 (s, 1H), 6.98 (dd, J = 5.2, 1.4 Hz, 1H), 6.46 (dt, J = 10.4, 2.2 Hz, 1H), 6.38-6.28 (m, 2H), 3.66 (t, J = 7.3 Hz, 2H), 3.14 (s, 6H), 2.13 (s, 6H), 1.60 (t, J = 7.3 Hz, 2H), 0.93 (s, 9H) ppm. | 2.08 | 583 |
| 252 | | ND | ND |
| 253 | $^1$H NMR (400 MHz, chloroform-d) δ 10.62 (s, 1H), 7.65 (d, J = 5.1 Hz, 1H), 7.54 (d, J = 13.2 Hz, 2H), 7.46-7.31 (m, 3H), 7.07 (d, J = 7.3 Hz, 1H), 6.48 (d, J = 10.2 Hz, 1H), 6.32 (d, J = 8.2 Hz, 2H), 3.83 (s, 3H), 3.77-3.63 (m, 2H), 2.19 (s, 3H), 1.62 (t, J = 7.1 Hz, 2H), 0.95 (s, 9H) ppm. | 2.43 | 623 |
| 254 | $^1$H NMR (400 MHz, chloroform-d) δ 9.43 (d, J = 7.2 Hz, 2H), 7.83 (d, J = 7.2 Hz, 1H), 7.61 (t, J = 6.4 Hz, 2H), 7.56 (d, J = 7.2 Hz, 1H), 7.49 (t, J = 8.0 Hz, 2H), 7.41 (d, J = 6.8 Hz, 1H), 7.13 (t, J = 8.0 Hz, 1H), 6.77 (d, J = 8.4 Hz, 2H), 6.67 (d, J = 7.6 Hz, 1H), 6.53 (s, 1H), 3.74 (t, J = 7.2 Hz, 2H), 1.63 (t, J = 7.2 Hz, 2H), 0.95 (s, 9H) ppm. | 2.29 | 561 |
| 255 | $^1$H NMR (400 MHz, chloroform-d) δ 8.00 (d, J = 8.0 Hz, 2H), 7.58-7.44 (m, 3H), 7.34 (t, J = 4.0 Hz, 1H), 7.11 (d, J = 8.0 Hz, 1H), 6.98 (d, J = 4.0 Hz, 1H), 6.83 (t, J = 4.0 Hz, 1H), 6.57-6.44 (m, 3H), 4.62 (dd, J = 8.0, 8.0 Hz, 1H), 3.84 (t, J = 8.0 Hz, 2H), 1.64 (t, J = 8.0 Hz, 2H), 1.33 (d, J = 4.0 Hz, 6H), 0.94 (s, 9H) ppm. | 2.46 | 569 |
| 256 | | ND | ND |
| 257 | $^1$H NMR (400 MHz, chloroform-d) δ 7.98-8.00 (m, 2H), 7.48-7.61 (m, 5H), 7.42-7.44 (m, 2H), 7.17-7.21 (m, 1H), 6.86-6.88 (m, 1H), 6.71-6.75 (m, 2H), 3.45 (s, 2H), 0.99 (s, 9H) ppm. | 2.35 | 547 |
| 258 | $^1$H NMR (400 MHz, chloroform-d) δ 8.07(m, 2H), 7.58 (m, 6H), 6.48 (d, J = 10.4 Hz, 1H), 6.32 (d, J = 2 Hz, 1H), 6.25 (d, J = 9. 2 Hz, 1H), 3.74 (t, J = 7.2 Hz, 2H), 3.15 (s, 3H), 2.19 (s, 3H), 1.64 (t, J = 7.2 Hz, 2H), 0.96 (s, 9H) ppm. | 2.12 | 60 |
| 259 | $^1$H NMR (400 MHz, chloroform-d) 8.20 (s, 1H), 8.13 (d, J = 7.6 Hz, 1H), 7.90 (d, J = 8.0 Hz, 1H), 7.71 (t, J = 8.0 Hz, 1H), 7.32-7.28 (m, 1H), 7.16-7.13 (m, 2H), 6.48-6.45 (m, 1H), 6.37-6.31 (m, 2H), 3.66 (t, J = 7.2 Hz, 2H), 2.77 (s, 3H), 2.14 (s, 6H), 1.60 (t, J = 7.2 Hz, 2H), 0.93 (s, 9H) ppm. | 1.63 | 601 |
| 260 | $^1$H NMR (400 MHz, chloroform-d) δ 9.03 (br s, 1H), 7.54 (d, J = 8.0 Hz, 1H), 7.48-7.47 (m, 1H), 7.38 (t, J = 8.0 Hz, 1H), 7.30 (t, J = 8.0 Hz, 1H), 7.14 (d, J = 7.6 Hz, 2H), 7.08-7.05 (m, 1H), 6.47-6.43 (m, 1H), 6.35-6.30 (m, 2H), 4.08 (q, J = 7.2 Hz, 2H), 3.65 (t, J = 7.2 Hz, 2H), 2.13 (s, 6H), 1.60 (t, J = 7.2 Hz, 2H), 1.43 (t, J = 7.2 Hz, 3H), 0.93 (s, 9H) ppm. | 2.57 | 583 |

TABLE 3-continued

| Example 49-509 | | | |
|---|---|---|---|
| Compound Number | NMR | LCMS retention time (min.) | LCMS MS (ESI) m/z $[M + H]^+$ |
| 261 | $^1$HNMR (400 MHz, methanol-$d_4$) δ 7.93 (d, J = 5.6 Hz, 1 H), 7.40 (d, J = 8.4 Hz, 1 H), 7.19-7.18 (m, 2 H, 6.96 (s, 1 H), 6.88-6.87 (m, 1H), 6.51-6.48 (m, 2 H), 6.31 (s, 1H), 4.54-4.51(m, 1H), 3.70 (t, J = 6 Hz, 2 H), 1.50 (t, J = 6.8 Hz, 2 H), 1.02 (d, J = 6 Hz, 6 H), 0.81 (s, 9H) ppm. | 1.63 | 653 |
| 262 | $^1$H NMR (400 MHz, chloroform-d) δ 7.47-7.50 (m, 2 H), 7.36 (t, J = 8.0 Hz, 1 H), 7.28 (t, J = 7.6 Hz, 1 H), 7.11-7.13 (m, 2 H), 7.04 (dd, J = 8.0, 2.0 Hz, 1 H), 6.45 (d, J = 10.4 Hz, 1 H), 6.34 (d, J = 9.2 Hz, 1 H), 6.29 (s, 1 H), 4.57-4.66 (m, 1 H), 3.64 (t, J = 7.2 Hz, 2 H), 2.11 (s, 6 H), 1.60 (t, J = 7.2 Hz, 2 H), 1.34 (d, J = 6.0 Hz, 6 H), 0.93 (s, 9 H) ppm. | 2.77 | 597 |
| 263 | $^1$H NMR (400 MHz, methanol-$d_4$) δ 8.04 (d, J = 8.8 Hz, 2H), 7.96-7.94 (m, 2H), 7.72 (d, J = 8.0 Hz, 2H), 7.58-7.50 (m, 3H), 3.89-3.85 (m, 1H), 3.76-3.65 (m, 2H), 2.91-2.74 (m, 3H), 2.49-2.43 (m, 1H), 1.45-1.39 (m, 1H), 1.20-1.15 (m, 1H), 0.91 (s, 9H) ppm. | 2.36 | 540 |
| 264 | | 1.05 | 592 |
| 265 | $^1$H NMR (400 MHz, chloroform-d) δ 7.50 (t, J = 7.1 Hz, 1H), 7.43 (d, J = 7.4 Hz, 1H), 7.37-7.31 (m, 1H), 7.24 (d, J = 6.9 Hz, 3H), 7.16 (s, 1H), 6.72 (d, J = 6.4 Hz, 1H), 6.44 (dd, J = 21.4, 9.8 Hz, 2H), 6.33 (s, 1H), 3.66 (t, J = 7.2 Hz, 2H), 3.35 (s, 4H), 2.87-2.80 (m, 1H), 2.04 (t, J = 6.5 Hz, 4H), 1.60 (s, 2H), 1.18 (d, J = 74.6 Hz, 6H), 0.93 (s, 9H) ppm. | 2.66 | 622 |
| 266 | $^1$H NMR (400 MHz, chloroform-d) δ 7.29 (t, J = 7.8 Hz, 2H), 7.19 (d, J = 7.7 Hz, 1H), 7.13 (d, J = 7.6 Hz, 3H), 6.71 (dd, J = 8.3, 2.0 Hz, 1H), 6.44 (dt, J = 10.4, 2.1 Hz, 1H), 6.33 (dd, J = 11.8, 9.9 Hz, 2H), 3.99-3.86 (m, 1H), 3.65 (t, J = 7.3 Hz, 2H), 3.45 (t, J = 8.3 Hz, 1H), 3.20 (dd, J = 16.7, 8.0 Hz, 1H), 2.16-1.95 (m, 9H), 1.72 (m, J = 2.7 Hz, 1H), 1.60 (t, J = 7.3 Hz, 2H), 1.17 (d, J = 6.2 Hz, 3H), 0.93 (s, 9H) ppm. | 2.87 | 622 |
| 267 | $^1$HNMR (400 MHz, chloroform-d) δ 7.99 (d, J = 7.2 Hz, 2H), 7.57-7.548 (m, 3H), 7.23-7.16 (m, 3H), 6.91-6.89 (m, 2H), 6.79 (s, 1H), 4.10-4.06 (t, J = 7.2 Hz, 2H), 1.64-1.61 (t, J = 7.2 Hz, 2H), 0.926 (s, 9H) ppm. | 2.45 | 663 |
| 268 | $^1$HNMR (400 MHz, chloroform-d) δ 7.96 (d, J = 7.6 Hz, 2H), 7.56 (d, J = 7.2 Hz, 1H), 7.49 (t, J = 7.6 Hz, 2H), 7.32 (s, 2H), 6.48 (dd, J = 2.8 Hz, 8.0 Hz, 1H), 6.30 (d, J = 8.0 Hz, 1H), 6.25 (s, 1H), 3.73 (t, J = 6.8 Hz, 2H), 2.07 (s, 6H), 1.63 (t, J = 7.2 Hz, 2H), 0.94 (s, 9H) ppm. | 1.76 | 607 |
| 269 | $^1$H NMR (400 MHz, chloroform-d) δ 7.35-7.28 (m, 2H), 7.21 (d, J = 7.9 Hz, 1H), 7.16-7.10 (m, 3H), 6.68 (dd, J = 8.2, 1.8 Hz, 1H), 6.44 (d, J = 10.4 Hz, 1H), 6.37-6.27 (m, | 2.60 | 608 |

TABLE 3-continued

| Compound Number | NMR | LCMS retention time (min.) | LCMS MS (ESI) m/z [M + H]+ |
|---|---|---|---|
| Example 49-509 | | | |
| | 2H), 3.65 (t, J = 7.3 Hz, 2H), 3.32 (t, J = 6.5 Hz, 4H), 2.12 (s, 6H), 2.02 (t, J = 6.5 Hz, 4H), 1.60 (t, J = 7.3 Hz, 2H), 0.93 (s, 9H) | | |
| 270 | $^1$H NMR (400 MHz, chloroform-d) δ 8.04 (s, 1H), 7.90-7.88 (d, J = 8 Hz, 1H), 7.62 (d, J = 8 Hz, 1H), 7.46 (t, 1H), 7.26 (t, J = 8 Hz, 1H), 7.10 (d, J = 8 Hz, 2H), 6.45 (d, J = 4 Hz, 1H), 6.33 (d, J = 8 Hz, 1H), 6.28 (s, 1H), 5.05 (m, 1H), 3.64 (t, J = 8 Hz, 2H), 2.09 (s, 6H), 0.92 (s, 9H) ppm. | 1.72 | 637 |
| 271 | $^1$H NMR (400 MHz, chloroform-d) δ 7.57 (t, J = 7.7 Hz, 1H), 7.38-7.29 (m, 2H), 7.18 (d, J = 7.3 Hz, 2H), 6.47 (d, J = 10.3 Hz, 1H), 6.42-6.25 (m, 3H), 3.70 (dt, J = 14.3, 6.9 Hz, 6H), 2.38-2.03 (m, 8H), 1.61 (t, J = 7.0 Hz, 2H), 0.94 (s, 9H) ppm. | 2.45 | 595 |
| 272 | | 1.03 | 602 |
| 273 | $^1$H NMR (400 MHz, chloroform-d) δ 7.82-7.79 (m, 1H), 7.62-7.60 (m, 2H), 7.56 (t, J = 8 Hz, 1H), 7.45-7.43 (m, 1H), 7.39 (d, J = 7.2 Hz, 1H), 7.09-7.05 (m, 1H), 6.77-6.75 (m, 1H), 6.61-6.55 (m, 3H), 3.33 (s, 2H), 0.93 (s, 9H) ppm. | 2.12 | 563 |
| 274 | $^1$H NMR (400 MHz, chloroform-d) δ 7.96 (d, J = 7.2 Hz, 2 H), 7.45-7.55 (m, 3 H), 7.29 (t, J = 8.0 Hz, 1 H), 6.80 (d, J = 8.0 Hz, 2 H), 6.37-6.46 (m, 3 H), 4.47-4.56 (m, 1 H), 3.63-3.75 (m, 2 H), 1.99 (s, 3 H), 1.60 (t, J = 7.2 Hz, 2 H), 1.25 (d, J = 6.4 Hz, 3 H), 1.11 (d, J = 6.0 Hz, 3 H), 0.93 (s, 9 H) ppm. | 2.48 | 583 |
| 275 | $^1$H NMR (400 MHz, chloroform-d) δ 7.55 (d, J = 7.2 Hz, 1 H), 7.50 (s, 1 H), 7.38 (t, J = 8.0 Hz, 1 H), 7.29 (t, J = 8.0 Hz, 1 H), 7.06 (dd, J = 8.4, 2.4 Hz, 1 H), 6.80 (d, J = 8.4 Hz, 2 H), 6.37-6.47 (m, 3 H), 4.47-4.56 (m, 1 H), 3.85 (s, 3 H), 3.63-3.75 (m, 2 H), 1.99 (s, 3 H), 1.60 (t, J = 7.2 Hz, 2 H), 1.26 (d, J = 6.0 Hz, 3 H), 1.12 (d, J = 6.0 Hz, 3 H), 0.93 (s, 9 H) ppm. | 2.48 | 613 |
| 276 | | 1.08 | 618 |
| 277 | $^1$H NMR (400 MHz, chloroform-d) δ 7.53 (t, J = 8.0 Hz, 1H), 7.34 (dd, J = 8.0, 8.0 Hz, 2H), 7.18 (d, J = 8.0 Hz, 1H), 6.96 (d, J = 8.0 Hz, 1H), 6.86 (t, J = 8.0 Hz, 1H), 6.50 (t, J = 8.0 Hz, 3H), 6.32 (d, J = 8.0 Hz, 1H), 4.60 (dt, J = 12.0, 6.0 Hz, 1H), 3.82 (t, J = 8.0 Hz, 2H), 3.76 (t, J = 8.0 Hz, 4H), 2.23-2.13 (m, 2H), 1.63 (d, J = 8.0 Hz, 2H), 1.29 (d, J = 8.0 Hz, 6H), 0.93 (s, 9H) ppm. | 2.45 | 625 |
| 278 | $^1$H NMR (400 MHz, chloroform-d) δ 9.06 (s, 1H), 8.05-7.97 (m, 2H), 7.60-7.38 (m, 5H), 7.28 (d, J = 1.4 Hz, 1H), 7.25-7.21 (m, 1H), 7.09 (t, J = 8.0 Hz, 1H), 6.77-6.74 (m, 1H), 6.65-6.63 (m, 1H), 6.58-6.53 (m, 1H), 3.24 (s, 2H), 2.84 (m, 1H), 1.04 (m, 6H), 0.94 (s, 9H) ppm. | 2.44 | 521 |

TABLE 3-continued

| Compound Number | NMR | LCMS retention time (min.) | LCMS MS (ESI) m/z $[M + H]^+$ |
|---|---|---|---|
| | Example 49-509 | | |
| 279 | $^1$HNMR (400 MHz, chloroform-d): δ 8.02-7.91 (m, 2H), 7.64-7.38 (m, 7H), 6.57-6.54 (m, 1H), 6.49-6.41 (m, 2H), 4.05-3.85 (m, 2H), 3.77 (s, 3H), 1.46 (s, 3H) ppm. | 2.08 | 611 |
| 280 | | 0.98 | 576 |
| 281 | $^1$H NMR (400 MHz, chloroform-d) δ 7.90-7.92 (d, J = 8.0 Hz, 1H), 7.82 (s, 1H), 7.53 (t, J = 8.0 Hz, 2H), 7.62-7.64 (m, 1H), 7.39-7.45 (m, 3H), 7.26-7.29 (m, 1H), 6.68-6.70 (m, 2H), 6.67-6.69 (m, 2H), 3.39 (s, 2H), 1.02 (s, 9H) ppm. | 4.14 | 665 |
| 282 | $^1$H NMR (400 MHz, $CD_3OD$) 7.84-7.82 (m, 1 H), 7.66-7.64 (m, 1 H), 7.54 (dd, J = 7.6 Hz& 7.6 Hz, 1H), 7.47-7.18 (m, 1 H), 7.18 (d, J = 7.6 Hz, 1H), 6.50 (d, J = 10 Hz, 1H), 6.42 (s, 1H), 6.36(d, J = 8.4 Hz, 1H), 6.25 (d, J = 9.2 Hz, 1H), 3.90 (t, J = 7.2 Hz, 4 H), 3.36 (s, 2H), 2.32-2.28 (m, 2H), 0.98 (s, 9 H) ppm | 2.35 | 621 |
| 283 | $^1$H NMR (400 MHz, $CD_3OD$) 7.82-7.81 (m, 1 H), 7.65-7.62 (m, 1 H), 7.56 (dd, J = 7.6 Hz& 8.0 Hz, 1H), 7.47-7.45 (m, 1 H), 7.34-7.33 (m, 1H), 6.61 (d, J = 8.4 Hz, 1H), 6.50 (d, J = 10.4 Hz, 1H), 6.42(s, 1H), 6.26 (dd, J = 9.2 Hz & 2 Hz, 1H), 3.36 (s, 2 H), 0.98 (s, 9 H) ppm | 2.21 | 581 |
| 284 | $^1$H NMR (400 MHz, chloroform-d) δ 9.16 (s, 1H), 8.00 (d, J = 8.8 Hz, 2H), 7.60-7.50 (m, 3H), 7.31 (d, J = 8.0 Hz, 1H), 7.16-7.10 (m, 3H), 6.79 (d, J = 8.0 Hz, 1H), 6.63 (d, J = 8.0 Hz, 1H), 6.56 (s, 1H), 3.25 (s, 2H), 2.15 (s, 6H), 0.98 (s, 9H) ppm. | 2.34 | 507 |
| 285 | $^1$H NMR (400 MHz, chloroform-d) δ 7.56 (dd, J = 8.4, 7.4 Hz, 1H), 7.39-7.28 (m, 2H), 7.17 (d, J = 7.6 Hz, 2H), 6.47 (dt, J = 10.5, 2.2 Hz, 1H), 6.38-6.31 (m, 2H), 6.30-6.22 (m, 1H), 3.72 (t, J = 7.4 Hz, 4H), 3.26 (s, 2H), 2.26-2.12 (m, 8H), 0.95 (s, 9H) | 2.41 | 581 |
| 286 | | 1.07 | 618 |
| 287 | | 1.05 | 612 |
| 288 | | 1.03 | 584 |
| 289 | $^1$H NMR (400 MHz, chloroform-d) δ 8.53-8.54 (m, 1H), 8.27-8.29 (d, J = 8.0Hz, 1H), 8.10-8.12 (m, 1H), 7.73 (t, J = 8.0 Hz, 1H), 7.62-7.64(m, 2H), 7.44-7.46(m, 2H), 7.27-7.29 (m, 1H), 6.68-6.70 (m, 2H), 3.40 (m, 1H), 3.11 (s, 2H), 1.02 (s, 9H) ppm. | 2.39 | 659 |
| 290 | $^1$H NMR (400 MHz, chloroform-d) δ 7.59 (t, J = 8.4 Hz, 1 H), 7.44 (d, J = 7.2 Hz, 1 H), 7.31 (t, J = 8.0 Hz, 1 H), 6.83-6.81 (m, 2 H), 6.60 (d, J = 8.0 Hz, 1 H), 6.48-6.40 (m, 3 H), 4.55-4.47 (m, 3 H), 3.76-3.65 (m, 2 H), 2.05 (s, 3 H), 1.61 (t, J = 7.2 Hz, 2 H), 1.27 (d, J = 6.0 Hz, 3 H), 1.12 (d, J = 6.0 Hz, 3 H), 0.93 (s, 9 H) ppm. | 1.74 | 599 |
| 291 | $^1$H NMR (400 MHz, chloroform-d) δ 7.54 (t, J = 7.2 Hz, 1H), 7.46 (t, J = 8.8 Hz, 1H), 7.39-7.36 (m, 2H), 7.31-7.25 (m, 2H), 6.57 (d, J = 8.4 Hz, 1H), 6.12-6.07 (m, 2H), 5.98 (s, 1H), 3.20 (t, J = 9.2 Hz, 1H), 3.11-3.09 (m, 1H), 3.17 (t, J = 8.8 Hz, 1H), 2.83 (t, J = 9.6 Hz, 1H), | 2.39 | 636 |

TABLE 3-continued

| Compound Number | NMR | LCMS retention time (min.) | LCMS MS (ESI) m/z $[M + H]^+$ |
|---|---|---|---|
| Example 49-509 | | | |
| | 2.11-2.10 (m, 1H), 1.96-1.90 (m, 1H), 1.76-1.68 (m, 1H), 0.93 (s, 9H) ppm. | | |
| 292 | $^1$H NMR (400 MHz, methanol-$d_4$): 7.94-7.92 (m, 2H), 7.63-7.53 (m, 3H), 7.48-7.43 (m, 2H), 7.28-7.22 (m, 2H), 3.62-3.57 (m, 2H), 2.97-2.90 (m, 1H), 2.82-2.80 (m, 2H), 2.63-2.55 (m, 2H), 1.72-1.65 (m, 1H), 1.50-1.35 (m, 3H), 1.24-1.10 (m, 8H), 0.94 (s, 3H), 0.78 (s, 3H) ppm. | 2.36 | 526 |
| 293 | $^1$H NMR (400 MHz, chloroform-d) δ 7.53 (m, J = 8.3, 7.4 Hz, 1H), 7.38 (dd, J = 7.4, 0.6 Hz, 1H), 7.27-7.21 (t, 1H), 7.07 (dd, J = 16.7, 7.7 Hz, 2H), 6.55 (dd, J = 8.3, 0.6 Hz, 1H), 6.40 (dt, J = 10.4, 2.2 Hz, 1H), 6.31 (t, J = 1.8 Hz, 1H), 6.24-6.15 (dt, 1H), 3.20 (s, 2H), 2.10 (s, 6H), 0.89 (s, 9H) ppm. | 2.26 | 541 |
| 294 | $^1$H NMR (400 MHz, methanol-$d_4$): 7.93-7.91 (m, 2H), 7.61-7.51 (m, 3H), 7.43-7.37 (m, 2H), 7.10 (d, J = 8.4 Hz, 1H), 7.03-6.99 (m, 1H), 4.62-4.56 (m, 1H), 3.65-3.63 (m, 2H), 2.81-2.79 (m, 2H), 2.64-2.55 (m, 2H), 1.76-1.71 (m, 1H), 1.64-1.57 (m, 1H), 1.53-1.44 (m, 2H), 1.27-1.15(m, 8H), 0.99 (s, 3H), 0.81 (s, 3H) ppm. | 2.25 | 542 |
| 295 | $^1$H NMR (400 MHz, chloroform-d) δ 8.0-7.95 (m, 2 H), 7.66-7.43 (m, 7H), 6.87-6.48 (m, 3H), 4.04 (d, J = 9.6 Hz, 1H), 3.80 (d, J = 6.4 Hz, 1H), 1.36-1.40 (m, 9H) ppm. | 1.47 | 611 |
| 296 | $^1$H NMR (400 MHz, chloroform-d) δ 7.33 (t, J = 15.2 Hz, 1H), 7.6 (d, J = 7.7 Hz, 2H), 7.07 (s, 1H), 6.81 (d, J = 4.8 Hz, 1H), 6.64 (s, 1H), 6.51-6.42 (m, 2H), 6.31 (d, J = 7.6 Hz, 1H), 3.28 (s, 2H), 2.07 (s, 6H), 0.97 (s, 9H) ppm. | 1.96 | 541 |
| 297 | $^1$H NMR (400 MHz, chloroform-d) δ 7.61-7.55 (m, 1H), 7.45 (d, J = 8.0 Hz, 1H), 7.33 (d, J = 8.0 Hz, 1H), 7.18 (dd, J = 4.0, 2.0 Hz, 1H), 7.13 (d, J = 8.0 Hz, 1H), 6.98 (d, J = 8.0 Hz, 1H), 6.83 (d, J = 8.0 Hz, 2H), 6.76 (d, J = 8.0 Hz, 2H), 6.60 (d, J = 8.0 Hz, 1H), 4.62-4.58 (m, 1H), 3.42 (s, 2H), 1.31 (d, J = 4.0 Hz, 6H), 0.98 (s, 9H) ppm. | 2.23 | 553 |
| 298 | $^1$H NMR (400 MHz, chloroform-d) δ 8.23-8.15 (m, 2H), 7.91-7.86 (m, 1H), 7.61 (td, J = 7.6 Hz & 2.0 Hz, 1H), 7.30-7.26 (m, 1H), 7.14-7.08 (m, 3H), 6.77 (dd, J = 7.6 Hz & 2.0 Hz, 1H), 6.63 (d, J = 8.0 Hz, 1H), 6.55 (m, 1H), 3.25 (s, 2H), 2.13 (s, 6H), 1.70 (s, 3H), 1.66 (s, 3H), 0.97 (s, 9H) ppm. | 2.20 | 583 |
| 299 | $^1$H NMR (400 MHz, chloroform-d) δ 7.55 (t, J = 7.6 Hz, 1H), 7.32-7.26 (m, 2H), 7.15-7.14 (m, 2H), 7.09 (t, J = 7.6 Hz, 1H), 6.77-6.76 (m, 1H), 6.61-6.60 (m, 1H), 6.52 (s, 1H), 6.34 (d, J = 8.4 Hz, 1H), 3.72 (t, J = 7.2 Hz, 4H), 3.22 (s, 2H), 2.21-2.19 (m, 2H), 2.17 (s, 6H), 0.95 (s, 9H) ppm. | 2.34 | 563 |
| 300 | $^1$H NMR (400 MHz, chloroform-d) δ 9.16 (s, 1H), 8.00 (d, J = 8.8 Hz, 2H), 7.60-7.50 (m, 3H), 7.31 (d, | 2.30 | 563 |

TABLE 3-continued

| Compound Number | NMR | LCMS retention time (min.) | LCMS MS (ESI) m/z $[M + H]^+$ |
|---|---|---|---|
| Example 49-509 | | | |
| | J = 8.0 Hz, 1H), 7.16-7.10 (m, 3H), 6.79 (d, J = 8.0 Hz, 1H), 6.63 (d, J = 8.0 Hz, 1H), 6.56 (s, 1H), 3.25 (s, 2H), 2.15 (s, 6H), 0.98 (s, 9H) ppm. | | |
| 301 | $^1$H NMR (400 MHz, chloroform-d) δ 7.38-7.34 (m, 2H), 7.22-7.20 (m, 1H), 7.13-7.07 (m, 2H), 6.86-6.77 (m, 3H), 6.68-6.66 (m, 2H), 5.99 (br, 2H), 3.38 (dd, J = 8.8 Hz, 16.8 Hz, 2H), 0.97 (s, 9H) ppm. | 1.99 | 543 |
| 302 | $^1$H NMR (400 MHz, chloroform-d) δ 7.99-7.96 (t, 3H), 7.58-7.48 (m, 3H), 7.28-7.24 (m, 1H), 7.14-7.12 (m, 2H), 3.63-3.60 (m, 2H), 2.78-2.75 (t, 2H), 2.60-2.51 (m, 2H), 2.21 (d, J = 2.8Hz, 6H), 1.76-1.65 (m, 2H), 1.47-1.42 (m, 2H), 1.16-1.06 (m, 2H), 0.99 (s, 3H), 0.75 (s, 3H) ppm. | 2.30 | 512 |
| 303 | $^1$HNMR (400 MHz, Chloroform-d) δ 7.32 (t, J = 7.6 Hz, 1H), 7.15 (d, J = 7.6 Hz, 2H), 7.09 (t, J = 8.0 Hz, 1H), 7.04 (s, 1H), 6.81-6.73 (m, 2H), 6.65 (d, J = 8.0 Hz, 1H), 6.60 (s, 1H), 6.12 (s, 2H), 3.25 (s, 2H), 2.07 (s, 6H), 0.96 (s, 9H) ppm. | 2.44 | 523 |
| 304 | $^1$HNMR (400 MHz, chloroform-d) δ 7.84-7.81 (m, 2 H), 7.71-7.66 (m, 2 H), 7.56-7.50 (m, 2 H), 7.43 (m, 2 H), 7.09 (t, J = 8.0 Hz, 1 H), 6.79-6.77 (m, 1 H), 6.61 (m, 2 H), 3.34 (dd, J = 16.4, 8.4 Hz, 2 H), 0.97 (s, 9 H) ppm. | 2.40 | 581 |
| 305 | $^1$HNMR (400 MHz, chloroform-d) δ 7.83 (d, J = 8.0 Hz, 1 H), 7.75-7.68 (m, 3 H), 7.57 (t, J = 8.0 Hz, 1 H), 7.51 (t, J = 8.4 Hz, 1 H), 7.38 (d, J = 8.8 Hz, 1 H), 7.10 (t, J = 8.4 Hz, 1 H), 6.81-6.78 (m, 1 H), 6.62-6.60 (m, 2 H), 3.36 (dd, J = 15.2, 8.4 Hz, 2 H), 0.97 (s, 9 H) ppm. | 2.43 | 665 |
| 306 | $^1$HNMR (400 MHz, chloroform-d) δ 7.97-7.89 (m, 2H), 7.65 (d, J = 6.8 Hz, 1H), 7.58-7.44 (m, 5H), 7.07 (t, J = 8.0 Hz, 1H), 6.76 (dd, J = 8.4, 1.8 Hz, 1H), 6.54 (dd, J = 10.2, 5.0 Hz, 2H), 3.28 (dd, J = 21.6, 8.4 Hz, 2H), 2.16 (s, 3H), 0.96 (s, 9H) ppm. | 2.43 | 561 |
| 307 | $^1$HNMR (400 MHz, methanol-$d_4$) □ δ 7.53 (s, 1H), 7.30 (t, J = 7.6 Hz, 1H), 7.21-7.16 (m, 3H), 6.79 (d, J = 7.6 Hz, 1H), 6.49 (s, 1H), 3.20 (s, 2H), 2.14 (s, 6H), 0.96 (s, 9H) ppm. | 2.13 | 529 |
| 308 | $^1$HNMR (400 MHz, Chloroform-d) δ 8.00-7.98 (m, 1 H), 7.58-7.48 (m, 3 H), 7.35-7.18 (m, 1 H), 7.17 (d, J = 7.6 Hz, 2 H) 5.79 (s, 1 H), 4.73 (q, J = 8.4 Hz, 2 H), 2.14 (s, 6 H) ppm. | 2.21 | 526 |
| 309 | $^1$HNMR (400 MHz, DMSO-$d_6$) 7.68-7.66 (m, 2H), 7.32-7.30 (m, 1H), 7.14 (d, J = 7.6 Hz, 1H), 6.56 (d, J = 8.4 Hz, 1H), 6.51-6.50 (m, 3H), 3.93 (t, J = 7.2 Hz, 4 H), 3.48 (s, 2 H), 2.30 (m, 2 H), 0.94 (s, 9H) ppm. | 2.32 | 589 |
| 310 | $^1$HNMR (400 MHz, DMSO-$d_6$) 8.14 (s, 1H), 8.06 (d, J = 5.6 Hz, 1 H), 7.65-7.59 (m, 1 H), 7.28 (m, 1 H), 6.93 (s, 1H), 6.84-6.76 (m, 2 H), 6.57-6.49 (m, 4 H), 3.46 (s, 2 H), 0.93 (s, 9 H) ppm. | 1.90 | 549 |

TABLE 3-continued

| Example 49-509 | | | |
|---|---|---|---|
| Compound Number | NMR | LCMS retention time (min.) | LCMS MS (ESI) m/z $[M+H]^+$ |
| 311 | $^1$HNMR (400 MHz, Chloroform-d) δ 7.60-7.55 (t, 1H), 7.26-7.23 (m, 2H), 7.12 (d, J = 7.2 Hz, 2H), 6.63 (d, J = 8.8 Hz, 1H), 3.60 (d, J = 2.4 Hz, 2H), 2.93 (s, 6H), 2.76-2.73 (m, 2H), 2.59-2.49 (m, 2H), 2.20 (s, 6H), 1.74-1.69 (m, 1H), 1.46-1.39 (m, 1H), 1.28 (d, 2H), 1.13-1.07 (m, 2H), 0.97 (s, 3H), 0.72 (s, 3H) ppm. | 2.28 | 556 |
| 312 | $^1$HNMR (400 MHz, chloroform-d) δ 7.70-7.57 (m, 4H), 7.42 (d, J = 7.6 Hz, 2H), 6.63 (d, J = 8.0 Hz, 2H), 6.48 (d, J = 10.4 Hz, 1H), 6.32-6.28 (m, 2H), 4.61 (s, 1H), 3.73 (dt, J = 14.0, 7.2 Hz, 2H), 2.31 (s, 3H), 1.65-1.61 (t, J = 7.2 Hz, 2H), 0.95 (s, 9H) ppm. | ND | ND |
| 313 | $^1$HNMR (400 MHz, DMSO-$d_6$) 8.25 (d, J = 5.2 Hz, 1 H), 7.64-7.61 (m, 1 H), 7.28-7.24 (m, 2 H), 6.78 (d, J = 10.8 Hz, 1 H), 6.50 (m, 2 H), 3.46 (s, 2 H), 3.07 (s, 6 H), 0.93 (s, 9 0H) ppm. | 2.04 | 577 |
| 314 | $^1$HNMR (400 MHz, chloroform-d) δ 7.92 (d, J = 7.6 Hz, 1H), 7.84 (s, 1H), 7.68 (d, J = 6.4 Hz, 1H), 7.56 (m, 3H), 7.43 (d, J = 7.6 Hz, 1H), 7.11 (t, J = 8 Hz, 1H), 6.79 (m, 1H), 6.55 (m, 2H), 3.32 (dd, $J_1$ = 8.8 Hz, $J_2$ = 23.2 Hz, 2H), 2.18 (s, 3H), 0.98 (s, 9H) ppm. | 1.77 | 645 |
| 315 | $^1$HNMR (400 MHz, chloroform-d) δ 7.79 (d, J = 7.6 Hz, 1H), 7.71 (m, 2H), 7.75 (m, 3H), 7.34 (d, J = 8 Hz, 1H), 7.10 (t, J = 8 Hz, 1H), 6.57~6.39 (m, 4H), 3.32 (dd, $J_1$ = 8.4 Hz, $J_2$ = 22 Hz, 2H), 2.18 (s, 3H), 0.90 (s, 9H) ppm. | 1.72 | 627 |
| 316 | $^1$HNMR (400 MHz, MeOD) δ 7.62-7.57 (t, 3H), 7.29-7.15 (m, 4H), 6.71 (d, J = 8.4 Hz, 1H), 3.63 (s, 2H), 2.85-2.83 (t, 3H), 2.62-2.52 (m, 2H), 2.23 (s, 6H), 1.74-1.66 (m, 1H), 1.52-1.38 (m, 3H), 1.15-1.05 (m, 2H), 0.97 (s, 3H), 0.75 (s, 3H). | 2.13 | 528 |
| 317 | $^1$HNMR (400 MHz, chloroform-d) δ 7.74-7.68 (m, 2 H), 7.59-7.54 (m, 2 H), 7.38 (d, J = 6.8 Hz, 1 H), 7.08 (t, J = 8.0 Hz, 1 H), 6.78 (d, J = 7.2 Hz, 1 H), 6.60 (m, 3 H), 3.35 (dd, J = 16.0, 8.0 Hz, 2 H), 0.97 (s, 9 H) ppm. | 1.53 | 597 |
| 318 | $^1$HNMR (400 MHz, chloroform-d) 7.57 (t, J = 7.2 Hz, 1 H), 7.41-7.34 (m, 4 H), 7.12 (t, J = 8.0 Hz, 1 H), 6.80 (d, J = 7.6 Hz, 1H), 6.67-6.65 (m, 2 H), 6.60 (d, J = 8.0 Hz, 1 H), 3.38 (s, 2 H), 0.98 (s, 9 H) ppm. | 2.20 | 563 |
| 319 | $^1$HNMR (400 MHz, chloroform-d) 7.60 (t, J = 8.4 Hz, 1 H), 7.49-7.42 (m, 3 H), 7.32-7.29 (m, 2 H), 7.10 (t, J = 8.0 Hz, 1 H), 6.75 (d, J = 8.0 Hz, 1 H), 6.66 (d, J = 8.0 Hz, 1 H), 6.61-6.57 (m, 2 H), 4.45 (s, 2 H), 3.25 (s, 2 H), 2.92 (m, 1 H), 1.07 (s, 5H), 0.94 (s, 9 H) ppm. | 1.59 | 537 |
| 320 | $^1$HNMR (400 MHz, Chloroform-d) δ 7.56 (t, J = 7.6 Hz, 1 H), 7.33 (t, J = 7.2 Hz, 2 H), 7.20 (d, J = 7.6 Hz, 2 H), 6.36 (d, J = 8.4 Hz, 1 H), 5.81 (s, 1 H), 4.71 (q, J = 8.0 Hz, 2 | 2.25 | 582 |

TABLE 3-continued

| Example 49-509 | | | |
|---|---|---|---|
| Compound Number | NMR | LCMS retention time (min.) | LCMS MS (ESI) m/z $[M + H]^+$ |
| | H), 3.74 (t, J = 7.6 Hz, 4 H) 2.22-2.16 (m, 8 H) ppm. | | |
| 321 | $^1$HNMR (400 MHz, Chloroform-d) δ 8.25-8.23 (m, 1 H), 8.13 (dd, J = 8.0 Hz, J = 2.0 Hz, 2 H), 7.32 (t, J = 7.6 Hz, 1 H), 7.18 (d, J = 7.6 Hz, 2 H), 6.59-6.56 (m, 1H), 5.80 (s, 1 H), 4.71 (q, J = 8.0 Hz, 2 H), 4.45 (t, J = 7.6 Hz, 4 H), 2.31-2.24 (m, 2H), 2.14 (s, 6 H) ppm. | 2.01 | 582 |
| 322 | | 1.10 | 655 |
| 323 | | 1.15 | 628 |
| 324 | | 1.10 | 650 |
| 325 | | 1.13 | 690 |
| 326 | $^1$HNMR (400 MHz, methanol-$d_4$) δ 7.86 (d, J = 7.2 Hz, 1H), 7.75-7.62 (m, 3H), 7.54-7.50 (m, 1H), 7.20-7.11 (m, 2H), 6.82-6.75 (m, 3H), 6.48 (s, 1H), 3.70-3.67 (m, 2H), 3.08 (s, 6H), 1.60-1.57 (m, 2H), 0.95 (s, 9H) ppm. | 1.74 | 605 |
| 327 | $^1$HNMR (400 MHz, chloroform-d) δ 7.51 (t, J = 8.0 Hz, 1 H), 7.37-7.28 (m, 2 H), 7.09 (t, J = 8.0 Hz, 1 H), 7.02 (d, J = 7.6 Hz, 1 H), 6.96 (t, J = 8.4 Hz, 1 H), 6.79-6.75 (dd, J = 8.4, 2.0 Hz, 1 H), 6.65-6.61 (m, 2 H), 6.55 (d, J = 8.0 Hz, 1 H), 3.35-3.28 (dd, J = 22.4, 8.4 Hz, 2 H), 2.06 (s, 3 H), 0.96 (s, 9 H) ppm. | 2.25 | 527 |
| 328 | | 1.10 | 664 |
| 329 | $^1$HNMR (400 MHz, chloroform-d) δ 7.56 (t, J = 8.0 Hz, 1 H), 7.28 (m, 2 H), 7.13 (t, J = 8.0 Hz, 1 H), 6.80-6.71 (m, 4 H), 6.61 (d, J = 8.4 Hz, 1 H), 6.55 (s, 1 H), 4.56-4.47 (s, 2 H), 3.73-3.60 (m, 2 H), 2.93 (s, 6 H), 2.00 (s, 3 H), 1.60 (t, J = 7.2 Hz, 2 H), 1.28 (d, J = 6.0 Hz, 3 H), 1.11 (d, J = 6.0 Hz, 3 H), 0.92 (s, 9 H) ppm. | 1.75 | 609 |
| 330 | $^1$HNMR (400 MHz, chloroform-d) δ 7.59-7.55 (m, 1H), 7.48-7.41 (m, 2H), 7.32 (d, J = 7.2 Hz, 1H), 7.25-7.24 (m, 2H), 7.14 (t, J = 8.0 Hz, 1H), 6.75-6.69 (m, 2H), 6.63 (d, J = 8.4 Hz, 1H), 6.50-6.49 (m, 1H), 3.63 (t, J = 7.2 Hz, 2H), 2.94-2.92 (m, 1H), 2.90 (s, 6H), 1.60 (t, J = 7.2 Hz, 2H), 1.08 (s, 6H), 0.91 (s, 9H) ppm. | 2.58 | 579 |
| 331 | $^1$HNMR (400 MHz, chloroform-d) δ 9.68 (s, 1H), 8.54 (s, 1H), 8.27 (d, J = 7.6 Hz, 1H), 8.14 (d, J = 7.2 Hz, 1H), 7.75 (t, J = 8 Hz, 1H), 7.69 (d, J = 7.2 Hz, 1H), 7.56 (m, 2H), 7.11 (t, J = 8 Hz, 1H), 6.76 (m, 1H), 6.55 (m, 2H), 3.34 (dd, $J_1$ = 8.4 Hz, $J_2$ = 22 Hz, 2H), 3.11 (s, 3H), 2.18 (s, 3H), 0.90 (s, 9H). | 2.26 | 639 |
| 332 | $^1$HNMR (400 MHz, Chloroform-d) δ 7.60-7.54 (m, 1H), 7.48 (d, J = 8.0 Hz, 1H), 7.35 (d, J = 8.0 Hz, 2H), 7.30 (d, J = 8.0 Hz, 2H), 7.16 (t, J = 8.0 Hz, 1H), 6.81 (d, J = 8.0 Hz, 1H), 6.71 (d, J = 8.0 Hz, 1H), 6.62 (d, J = 8.0 Hz, 2H), 3.78 (t, J = 8.0 Hz, 2H), 2.95 (s, 6H), 1.62 (s, 2H), 0.93 (s, 9H) ppm. | 1.70 | 621 |
| 333 | $^1$HNMR (400 MHz, DMSO-$d_6$) 8.36 (m. 1H), 8.23-8.23 (m, 1H), 7.46 (m, 1H), 7.02-6.98 (m, 2 H), 6.93-6.90 (m, 1 H), 6.58-6.55 (m, 2 | 2.30 | ND |

TABLE 3-continued

| Compound Number | NMR | LCMS retention time (min.) | LCMS MS (ESI) m/z $[M + H]^+$ |
|---|---|---|---|
| | Example 49-509 | | |
| | H), 6.42-6.40 (m, 1 H), 3.45 (s, 2 h), 2.97 (s, 6 H), 1.00 (s, 9H) ppm | | |
| 334 | $^1$HNMR (400 MHz, Chloroform-d) δ 9.87 (bs, 1H), 7.60-7.56 (m, 1H), 7.30-7.26 (m, 2H), 7.14-7.10 (m, 3H), 6.76-6.47 (m, 3H), 6.47 (s, 1H), 3.62 (t, J = 7.2 Hz, 2H), 2.93 (s, 6H), 2.15 (s, 6H), 1.59 (t, J = 7.6 Hz, 2H), 0.92 (s, 9H) ppm. | 1.87 | 565 |
| 335 | | 1.81 | 563 |
| 336 | $^1$HNMR (400 MHz, chloroform-d) δ 8.06 (s, 2H), 7.68 (d, J = 8 Hz, 1H), 7.59 (t, J = 8 Hz; 8.4 Hz, 1H), 7.30 (m, 1H), 7.16-7.09 (m, 3H), 6.80-6.78 (d, J = 8 Hz, 1H), 6.63 (d, J = 7.6 Hz, 2H), 6.56 (s, 1 H), 4.35 (s, 2H), 3.26 (s, 2H), 2.83 (s, 3H), 2.15 (s, 6H), 0.98 (s, 9H) ppm. | 1.57 | 599 |
| 337 | $^1$HNMR (400 MHz, DMSO-$d_6$) 8.14 (s, 1H), 8.06 (d, J = 5.6 Hz, 1 H), 7.65-7.59 (m, 1 H), 7.28 (m, 1 H), 6.93 (s, 1H), 6.84-6.76 (m, 2 H), 6.57-6.49 (m, 4 H), 3.46 (s, 2 H), 0.93 (s, 9 H) ppm. | 1.90 | 549 |
| 338 | $^1$HNMR (400 MHz, Chloroform-d) δ 7.65-7.49 (m, 4H), 7.20 (d, J = 7.2 Hz, 1H), 6.61 (d, J = 8.4 Hz, 1H), 5.83 (s, 1H), 5.53 (q, J = 8.0 Hz, 2H), 2.98 (s, 6H), 2.20 (s, 3H) ppm. | 1.62 | 624 |
| 339 | $^1$HNMR (400 MHz, methanol-$d_4$) δ 7.53 (s, 1H), 7.32 (t, J = 7.2 Hz, 1H), 7.21-7.16 (m, 3H), 6.83 (d, J = 7.6 Hz, 1H), 6.75 (d, J = 8.0 Hz, 1H), 6.43 (s, 1H), 4.30 (s, 1H), 2.15 (s, 3H), 2.13 (s, 3H), 1.93-1.85 (m, 1H), 1.64-1.52 (m, 3H), 1.40-1.35 (m, 2H), 1.06 (s, 3H), 1.00 (s, 3H) ppm. | 2.19 | 555 |
| 340 | $^1$HNMR (400 MHz, chloroform-d) δ 7.57 (t, J = 16.0 Hz, 1H), 7.36 (t, J = 6.8 Hz, 1H), 7.30 (d, J = 7.4 Hz, 1H), 7.17 (ddd, J = 20.8, 15.0, 7.2 Hz, 3H), 6.95 (d, J = 7.6 Hz, 1H), 6.79-6.70 (m, 2H), 6.66-6.53 (m, 2H), 3.68 (t, J = 7.2 Hz, 2H), 2.89 (s, 6H), 1.77 (dd, J = 12.0, 6.8 Hz, 1H), 1.59 (t, J = 7.4 Hz, 2H), 0.97-0.85 (m, 11H), 0.67-0.58 (m, 2H) ppm. | 2.50 | 577 |
| 341 | | 1.13 | 626 |
| 342 | $^1$HNMR (400 MHz, chloroform-d) δ 7.60 (t, J = 7.6 Hz, 1H), 7.32-7.29 (m, 2H), 7.14-7.05 (m, 4H), 6.90-6.87 (m, 2H), 6.35 (d, J = 8.4 Hz, 1H), 3.04-2.99 (m, 1H), 2.93 (s, 6H), 2.13 (s, 6H), 1.96-1.93 (m, 1H), 1.69-1.63 (m, 1H), 1.47-1.36 (m, 3H), 1.12-1.01 (m, 1H), 1.00 (s, 6H) ppm. | 2.60 | 561 |
| 343 | $^1$HNMR (400 MHz, Chloroform-d) δ 8.12~8.02 (d, 2H), 7.64~7.57 (d, 1H), 7.57~7.55 (t, 1H), 7.28~7.24 (s, 1H), 7.14~7.01 (m, 3H), 6.77~6.69 (m, 2 H), 6.48~6.47 (d, 1H), 4.39 (s, 2H), 3.64~3.61 (m, 2H), 2.81 (s, 3H), 2.14~2.02 (d, 6H), 1.62~1.59 (m, 2H), 1.36-1.48 (m, 1 H), 0.94~0.92 (d, 9 H) ppm. | 1.93 | 613 |
| 344 | $^1$HNMR (400 MHz, chloroform-d) δ 7.33-7.26 (m, 1H), 7.23-7.21 (dd, J = 5.6 Hz, 3.2 Hz, 1H), 7.17-7.13 (m, 3H), 7.03-6.98 (m, 1H), 6.78-6.51 (m, 3H), 6.50 (s, 1H), 3.64 (t, J = 7.6 Hz, 2H), 2.87 (s, | 1.67 | 568 |

TABLE 3-continued

| Compound Number | NMR | LCMS retention time (min.) | LCMS MS (ESI) m/z [M + H]$^+$ |
|---|---|---|---|
| Example 49-509 | | | |
| | 3H), 2.19 (s, 6H), 1.62 (t, J = 7.6 Hz, 2H), 0.95 (s, 9H) ppm. | | |
| 345 | $^1$HNMR (400 MHz, Chloroform-d) δ 7.44-7.46 (m, 2H), 7.28-7.30 (m, 2H), 7.11-7.15 (m, 3H), 6.74-6.78 (m, 1H), 6.68-6.70 (m, 1H), 6.47-6.48 (m, 1H), 3.62 (t, J = 8.0 Hz, 2H), 2.16 (s, 6H), 1.59-1.61 (m, 2H), 0.923 (s, 9H) ppm. | 2.41 | 557 |
| 346 | $^1$HNMR (400 MHz, Chloroform-d) δ 7.44-7.46 (m, 2H), 7.28-7.30 (m, 2H), 7.11-7.15 (m, 3H), 6.74-6.78 (m, 1H), 6.68-6.70 (m, 1H), 6.47-6.48 (m, 1H), 3.62 (t, J = 8.0 Hz, 2H), 2.16 (s, 6H), 1.59-1.61 (m, 2H), 0.923 (s, 9H) ppm. | 2.45 | 590 |
| 347 | $^1$HNMR (400 MHz, chloroform-d) δ 8.10 (s, 1H), 7.91 (d, J = 8 Hz, 1H), 7.67 (d, J = 7.6 Hz, 1H), 7.39-7.28 (m, 2H), 7.14 (m, 3H), 6.75-6.70 (m, 2H), 6.46 (s, 1H), 4.32 (m, 1H), 2.15 (d, J = 5.6 Hz, 6H), 1.94-1.86 (m, 1H), 1.74-1.54 (m, 3H), 1.48-1.35 (m, 2H), 1.09 (s, 3H), 0.98 (s, 3H) ppm. | 1.82 | 611 |
| 348 | $^1$HNMR (400 MHz, chloroform-d) δ 7.39-7.34 (m, 1H), 7.26-7.17 (m, 3H), 7.13 (t, J = 8.0 Hz, 1H), 7.01-6.94 (m, 2H), 6.78-6.72 (m, 2H), 6.69-6.64 (m, 1H), 6.59-6.56 (m, 1H), 3.67 (t, J = 7.2 Hz, 2H), 2.85 (s, 3H), 1.76-1.71 (m, 1H), 1.59 (t, J = 7.2 Hz, 3H), 0.92 (s, 9H), 0.89-0.84 (m, 2H), 0.65-0.60 (m, 2H) ppm. | 2.37 | 580 |
| 349 | $^1$HNMR (400 MHz, $CD_3OD$): 7.60 (t, J = 8.0 Hz, 1H), 7.49-7.47 (m, 2H), 7.26-7.22 (m, 3H), 6.71 (d, J = 8.4 Hz, 1H), 3.61-3.60 (m, 2H), 3.01-2.94 (m, 1H), 2.83-2.81 (m, 2H), 2.65-2.57 (m, 2H), 1.73-1.66 (m, 1H), 1.51-1.39 (m, 3H), 1.25-1.11 (m, 8H), 0.97 (s, 3H), 0.79 (s, 3H) ppm. | 2.19 | 542 |
| 350 | $^1$HNMR (400 MHz, chloroform-d)δ 9.507 (s, 1H), 7.31~7.29 (d, 2H), 7.16~7.13 (m, 4H), 6.87~6.50 (m, 4H), 4.11 (s, 1H), 3.67~3.63 (m, 2H), 2.92 (s, 3H), 2.18 (s, 6H), 1.63~1.60 (m, 2H), 0.95 (s, 9H) | 2.45 | 568 |
| 351 | $^1$HNMR (400 MHz, Chloroform-d) δ 7.60-7.49 (m, 3H), 7.45 (d, J = 7.4 Hz, 1H), 7.17 (d, J = 7.2 Hz, 1H), 7.08 (t, J = 8.0 Hz, 1H), 6.78-6.77 (m, 1H), 6.63-6.62 (m, 1H), 6.59-6.26 (m, 3H), 3.25 (q, J = 8.5 Hz, 2H), 2.96 (s, 6H), 2.20 (s, 3H), 0.95 (s, 9H) ppm. | 2.26 | 587 |
| 352 | $^1$HNMR (400 MHz, methanol-$d_4$) δ 7.71-7.55 (m, 1H), 7.30-7.25 (m, 1H), 7.20-7.16 (m, 3H), 6.52 (d, J = 8.4Hz, 1H), 4.03 (t, J = 7.5 Hz, 4H), 3.65-3.62 (m, 2H), 2.84 (t, J = 4.8 Hz, 2H), 2.62-2.52 (m, 2H), 2.47-2.31 (m, 2H), 2.25 (d, J = 2.3 Hz, 6H), 1.77-1.63 (m, 1H), 1.54-1.36 (m, 3H), 1.18-1.03 (m, 2H), 0.98 (s, 3H), 0.76 (s, 3H) ppm. | 2.33 | 568 |
| 353 | $^1$HNMR (400 MHz, Chloroform-d) δ 7.51~7.46 (m, 1H), 7.44~7.42 (d, 1H), 7.30~7.28 (d, 2H), 7.23~7.21 (m, 4H), 7.16~7.12 (t, 1H), 7.04~6.99 (t, 1H), 6.77~6.75 (m, | 2.40 | 582 |

TABLE 3-continued

| Example 49-509 | | | |
|---|---|---|---|
| Compound Number | NMR | LCMS retention time (min.) | LCMS MS (ESI) m/z [M + H]+ |
| | 2H), 6.71~6.67 (m, 1H), 6.53~6.52 (t, 1H), 3.65~3.62 (m, 2H), 2.93~2.91 (m, 1H), (s, 3H), 2.90 (s, 3H), 1.62~1.58 (t, 2H), 1.27~1.08 (d, 6H), 0.93 (s, 9H) | | |
| 354 | $^1$HNMR (400 MHz, Chloroform-d) δ 7.63-7.51 (m, 2H), 7.46 (s, 1H), 7.39 (d, J = 8.0 Hz, 1H), 7.29 (s, 1H), 7.11 (t, J = 8.0 Hz, 1H), 6.81-6.75 (m, 1H), 6.57 (dd, J = 56.0 8.0 Hz, 4H), 3.29 (s, 2H), 2.93 (s, 6H), 2.19 (s, 3H), 0.95 (s, 9H) ppm. | 2.36 | 587 |
| 355 | $^1$HNMR (400 MHz, Chloroform-d) δ 7.44-7.54 (m, 2H), 7.50-7.40 (m, 3H), 7.37-7.36 m, 1H), 7.12-7.02 (m, 2H), 6.78-6.77 (m, 1H), 6.60-6.28 (m, 3H), 4.62-4.61 (m, 1H), 3.27-3.26 (m, 2H), 2.17 (s, 3H), 1.34 (d, J = 6.0 Hz, 6H), 0.95 (s, 9H) ppm. | 2.34 | 601 |
| 356 | $^1$HNMR (400 MHz, Chloroform-d) δ 7.56-7.55 (m, 3H), 7.47-7.45 (m, 1H), 7.42-7.40 (m, 1H), 7.10-7.09 (m, 1H), 6.80-6.73 (m, 1H), 6.65-6.31 (m, 4H), 3.31-3.20 (m, 2H), 2.23 (s, 3H), 0.95 (s, 9H) ppm. | 2.13 | 559 |
| 357 | $^1$HNMR (400 MHz, Chloroform-d) δ 8.00-7.94 (m, 2H), 7.59-7.45 (m, 3H), 7.30-7.26 (m, 1H), 7.15-7.09 (m, 3H), 6.76-6.66 (m, 2H), 6.47 (t, J = 2.0 Hz, 1H), 3.62 (t, J = 7.2 Hz, 2H), 2.13 (s, 6H), 1.59 (t, J = 7.2 Hz, 2H), 0.92 (s, 9H) ppm. | 2.60 | 535 |
| 358 | $^1$HNMR (400 MHz, Chloroform-d) δ 7.65-7.49 (m, 4H), 7.20 (d, J = 7.2 Hz, 1H), 6.61 (d, J = 8.4 Hz, 1H), 5.83 (s, 1H), 5.53 (q, J = 8.0 Hz, 2H), 2.98 (s, 6H), 2.20 (s, 3H) ppm. | 2.43 | 577 |
| 359 | $^1$HNMR (400 MHz, chloroform-d) δ 7.99 (d, J = 7.2 Hz, 2 H), 7.55-7.46 (m, 3 H), 7.19 (t, J = 8.0 Hz, 1 H), 7.03 (d, J = 8.4 Hz, 1 H), 6.95 (s, 1 H), 6.83-6.76 (m, 3 H), 6.70 (s, 1 H), 4.59 (m, 1 H), 3.87 (t, J = 7.2 Hz, 2 H), 1.65 (t, J = 7.2 Hz, 2 H), 1.33 (d, J = 6.0 Hz, 6 H), 0.95 (s, 9 H) ppm. | 1.82 | 585 |
| 360 | $^1$HNMR (400 MHz, $CD_3OD$): 7.58 (t, J = 7.6 Hz, 1H), 7.44-7.39 (m, 2H), 7.21 (d, J = 7.6 Hz, 1H), 7.11 (d, J = 8.0 Hz, 1H), 7.02 (t, J = 7.6 Hz, 1H), 6.70 (d, J = 8.4 Hz, 1H), 4.62-4.58 (m, 1H), 3.66-3.65 (m, 2H), 2.83-2.81 (m, 2H), 2.66-2.58 (m, 2H), 1.78-1.44 (m, 4H), 1.31-1.16 (m, 8H), 1.00 (s, 3H), 0.82 (s, 3H) ppm. | 2.17 | 558 |
| 361 | $^1$HNMR (400 MHz, Chloroform-d)δ 7.60 (t, J = 8 Hz, 1H), 7.45 (d, J = 8 Hz, 1H), 7.32-7.27 (m, 2H), 7.18-7.08 (m, 3H), 6.78-6.58 (m, 3H), 6.49 (s, 1H), 3.63 (t, J = 8 Hz, 2H), 2.17 (s, 6H), 1.59 (t, J = 8 Hz, 2H), 0.92 (s, 9H) ppm. | 1.70 | 537 |
| 362 | $^1$HNMR (400 MHz, chloroform-d) δ 7.55-7.52 (m, 1H), 7.47 (d, J = 7.2 Hz, 1H), 7.32 (d, J = 8.0 Hz, 1H), 7.25 (d, J = 7.6 Hz, 1H), 7.17 (t, J = 8.0 Hz, 1H), 7.05 (s, 1H), 6.79-6.74 (m, 3H), 6.57-6.56 (m, 1H), 6.45 (br, 1H), 6.12 (br, 2H), 3.64 (t, J = 6.8 Hz, 2H), 2.86-2.82 | 2.12 | 551 |

TABLE 3-continued

Example 49-509

| Compound Number | NMR | LCMS retention time (min.) | LCMS MS (ESI) m/z $[M + H]^+$ |
|---|---|---|---|
| | (m, 1H), 1.62 (t, J = 7.2 Hz, 2H), 1.08 (s, 6H), 0.96 (s, 9H) ppm. | | |
| 363 | $^1$HNMR (400 MHz, chloroform-d) δ 7.30 (t, J = 8.0 Hz, 1 H), 7.17-7.11 (m, 2 H), 7.06 (s, 1 H), 6.90 (m, 1 H), 6.81-6.73 (m, 4 H), 6.58 (m, 1 H), 5.65 (s, 2 H), 4.46-4.37 (m, 1 H), 3.72-3.60 (m, 2 H), 1.96 (s, 3 H), 1.60 (t, J = 7.2 Hz, 2 H), 1.12 (d, J = 6.0 Hz, 3 H), 1.05 (d, J = 6.0 Hz, 3 H), 0.92 (s, 9 H) ppm. | 2.09 | 581 |
| 364 | $^1$HNMR (400 MHz, methanol-d4) δ 7.33-7.18 (m, 7H), 6.90 (d, J = 8.0 Hz, 1H), 6.82 (d, J = 7.6 Hz, 1H), 6.78 (d, J = 8.0 Hz, 1H), 6.45 (s, 1H), 3.61 (t, J = 6.8 Hz, 2H), 2.13 (s, 6H), 1.57 (t, J = 7.2 Hz, 2H), 0.95 (s, 9H) ppm. | 2.27 | 536 |
| 365 | LCMS (acid): LC retention time 2.28 min. MS (ESI) m/z 600.7 $[M + H]^+$ $^1$HNMR (400 MHz, Chloroform-d) δ 7.62-7.40 (m, 4H), 7.137.11 (m, 2H), 6.76-6.75 (m, 1H), 6.69-6.25 (m, 4H), 3.72-3.54 (m, 2H), 2.95 (s, 6H), 2.18 (s, 3H), 1.59 (t, J = 7.3 Hz, 2H), 0.92 (s, 9H) ppm. | 2.28 | 601 |
| 366 | $^1$HNMR (400 MHz, chloroform-d) δ 7.35 (t, J = 7.6 Hz, 1H), 7.19-7.12 (m, 3H), 7.06 (s, 1H), 6.81-6.72 (m, 3H), 6.51 (s, 2H), 6.15 (s, 2H), 4.34-4.30 (m, 1H), 2.09 (d, J = 5.6 Hz, 6H), 1.93-1.84 (m, 1H), 1.74-1.58 (m, 3H), 1.49-1.34 (m, 2H), 1.08 (s, 3 H), 0.99 (s, 3 H) ppm. | 1.36 | 549 |
| 367 | $^1$HNMR (400 MHz, $CD_3OD$): 7.43-7.40 (m, 2H), 7.17-7.09 (m, 2H), 7.04-6.98 (m, 3H), 4.61-4.58 (m, 1H), 3.65-3.64 (m, 2H), 2.82-2.79 (m, 2H), 2.65-2.56 (m, 2H), 1.77-1.72 (m, 1H), 1.65-1.43 (m, 3H), 1.30-1.18 (m, 8H), 1.00 (s, 3H), 0.81 (s, 3H) ppm. | 2.25 | 575 |
| 368 | | 0.90 | 634 |
| 369 | $^1$HNMR (400 MHz, chloroform-d) δ 7.61 (m, 4H), 7.44 (d, J = 7.2 Hz, 1H), 6.96 (t, J = 8.4 Hz, 1H), 6.65 (m, 2H), 6.52 (m, 1H), 4.59 (s, 2H), 3.64 (m, 2H), 2.24 (s, 3H), 1.64 (m, 2H), 0.95 (s, 9H) ppm. | 1.64 | 609 |
| 370 | $^1$HNMR (400 MHz, methanol-$d_4$) δ 7.94 (d, J = 7.2 Hz, 2H), 7.69-7.47 (m, 3H), 7.28 (t, J = 7.5 Hz, 1H), 7.17-7.14 (m, 2H), 5.63 (s, 1H), 4.22-4.20 (m, 1H), 3.82-3.76 (m, 1H), 3.57-3.40 (m, 1H), 2.15 (d, J = 5.2 Hz, 6H), 2.00-1.93 (m, 1H), 1.74 (d, J = 17.6 Hz, 1H), 1.44-1.38 (m, 1H), 1.23-1.18 (m, 1H), 0.92 (s, 9H) ppm. | 2.51 | 497 |
| 371 | $^1$HNMR (400 MHz, chloroform-d) δ 7.77 (d, J = 6.4 Hz, 1 H), 7.43 (s, 1 H), 7.23 (d, J = 7.6 Hz, 1 H), 7.10 (t, J = 8.0 Hz, 1 H), 6.96 (d, J = 5.2 Hz, 1 H), 6.78-6.71 (m, 4 H), 6.52 (s, 1 H), 6.34 (s, 2 H), 4.38-4.31 (m, 1 H), 3.69-3.57 (m, 2 H), 1.97 (s, 3 H), 1.58 (t, J = 7.2 Hz, 2 H), 1.10 (d, J = 5.6 Hz, 3 H), 0.94-0.91 (m, 12 H) ppm. | 2.24 | 597 |
| 372 | $^1$HNMR (400 MHz, chloroform-d)δ 8.03~8.01 (d, 2H), 7.59~7.46 (m, 5H), 7.43~7.41 (m, 3H), 7.29~7.18 (m, 1H), 6.92~6.84 (m, | 2.36 | 551 |

TABLE 3-continued

| Compound Number | NMR | LCMS retention time (min.) | LCMS MS (ESI) m/z $[M + H]^+$ |
|---|---|---|---|
| Example 49-509 | | | |
| | 2H), 6.67 (s, 1H), 5.70~5.65 (d, 1H), 2.87~2.84 (m, 1H), 1.14 (s, 9H), 1.06~0.99 (d, 4H) ppm. | | |
| 373 | $^1$HNMR (400 MHz, methanol-$d_4$) 7.99-7.94 (m, 4H), 7.75 (d, J = 8.4 Hz, 2H), 7.59-7.52 (m, 3H), 3.91-3.88 (m, 1H), 3.74-3.68 (m, 1H), 3.53-3.51 (m, 1H), 2.97-2.80 (m, 3H), 2.52-2.47 (m, 1H), 1.49-1.36 (m, 3H), 1.16-1.11 (m, 1H), 0.88 (s, 9H) ppm. | 1.71 | 554 |
| 374 | $^1$HNMR (400 MHz, methanol-$d_4$) 7.99-7.94 (m, 4H), 7.75 (d, J = 8.0 Hz, 2H), 7.62-7.52 (m, 3H), 3.94-3.91 (m, 1H), 3.75-3.70 (m, 1H), 3.62-3.59 (m, 1H), 3.14-3.11 (m, 1H), 2.91-2.79 (m, 2H), 2.64-2.59 (m, 1H), 1.60-1.57 (m, 1H), 1.31-1.18 (m, 2H), 0.89 (s, 9H) ppm. | 2.23 | 670 |
| 375 | | 0.96 | 560 |
| 376 | $^1$HNMR (400 MHz, chloroform-d) 7.48-7.43 (m, 1H), 7.42-7.37 (m, 2H), 7.33-7.28 (m, 2H), 7.24 (dt, J = 7.0, 3.4 Hz, 2H), 7.08 (t, J = 8.0 Hz, 1H), 6.78 (ddd, J = 25.2, 8.2, 2.0 Hz, 2H), 6.63 (d, J = 7.8 Hz, 1H), 6.58-6.53 (m, 1H), 4.09 (tt, J = 13.2, 6.4 Hz, 1H), 3.93 (d, J = 9.2 Hz, 1H), 3.24 (s, 2H), 2.84 (dt, J = 13.6, 6.8 Hz, 1H), 1.41 (d, J = 6.8 Hz, 3H), 0.99 (m, 15H) ppm. | 2.54 | 632 |
| 377 | $^1$HNMR (400 MHz, methanol-$d_4$) δ 7.95 (d, J = 8.1 Hz, 2H), 7.76 (d, J = 7.9 Hz, 2H), 7.26 (t, J = 7.9 Hz, 1H), 7.21-7.02 (m, 2H), 6.79 (d, J = 7.1 Hz, 1H), 3.78 (s, 2H), 2.85-2.78 (m, 3H), 2.68 (q, 2H), 1.96-1.91 (m, 1H), 1.83-1.63 (m, 2H), 1.60-1.55 (m, 1H), 1.43 (d, J = 14.0 Hz, 1H), 1.35-1.23 (m, 1H), 1.07 (s, 3H), 0.86 (s, 3H) ppm. | 2.30 | 581 |
| 378 | | 1.61 | 593 |
| 379 | $^1$HNMR (400 MHz, Chloroform-d) δ 7.73 (s, 1H), 7.52 (d, J = 7.2 Hz, 1H), 7.43-7.35 (m, 3H), 7.26-7.19 (m, 2H), 7.17 (d, J = 8.0 Hz, 1H), 6.96 (t, J = 7.6 Hz, 2H), 6.85-6.77 (m, 2H), 6.60 (s, 1H), 4.56-4.50 (m, 1H), 3.71 (t, J = 7.2 Hz, 2H), 3.20 (s, 3H), 1.59 (t, J = 7.2 Hz, 2H), 1.11 (d, J = 6.4 Hz, 6H), 0.92 (s, 9H) | 2.24 | 643 |
| 380 | $^1$HNMR (400 MHz, Chloroform-d) δ 8.00-7.98 (m, 2H), 7.58-7.48 (m, 3H), 7.10-7.05 (m, 2H), 6.97 (d, J = 1.6 Hz, 1H), 6.86-6.84 (m, 1H), 6.80-6.77 (m, 1H), 6.74 (d, J = 2Hz, 1H), 6.74-6.37 (t, 1H), 4.61-4.58 (m, 1H), 3.85-3.81 (m, 2H), 1.69-1.65 (m, 2H), 1.32 (d, J = 6Hz, 6H), 0.92 (s, 9H) ppm. | 2.45 | 651 |
| 381 | $^1$HNMR (400 MHz, chloroform-d) δ 7.67-7.60 (m, 1H), 7.56-7.49 (m, 3H), 7.15-7.05 (m, 2H), 6.74 (dd, J = 8.2, 1.8 Hz, 1H), 6.62 (t, J = 7.0 Hz, 2H), 6.44 (s, 1H), 3.74-3.56 (m, 2H), 2.98 (s, 6H), 2.17 (s, 3H), 1.60 (t, J = 7.4 Hz, 2H), 0.92 (s, 9H) ppm. | 2.36 | 619 |
| 382 | $^1$HNMR (400 MHz, chloroform-d) δ 7.36 (t, J = 6.4 Hz, 1 H), 7.23 (t, J = 8.0 Hz, 1 H), 7.04-6.77 (m, 8 H), 4.64-4.57 (m, 1 H), 4.12 (t, J = | 1.61 | 654 |

TABLE 3-continued

| Compound Number | NMR | LCMS retention time (min.) | LCMS MS (ESI) m/z [M + H]$^+$ |
|---|---|---|---|
| Example 49-509 | | | |
| | 13.2 Hz, 2 H), 3.86 (s, 2 H), 1.34 (d, J = 6.0 Hz, 6 H), 1.10 (s, 9 H) ppm. | | |
| 383 | $^1$HNMR (400 MHz, methanol-$d_4$) δ 8.01-7.85 (m, 2H), 7.65-7.42 (m, 3H), 7.24 (t, J = 7.6 Hz, 1H), 7.13 (d, J = 7.7 Hz, 2H), 3.95-3.92 (m, 1H), 3.71 (t, 2H), 2.91-2.87 (m, 1H), 2.10 (d, J = 8.6 Hz, 6H), 1.77-1.73 (m, 1H), 1.69-1.60 (m, 1H), 1.61-1.42 (m, 3H), 0.91 (s, 9H) ppm. | 1.76 | 499 |
| 384 | $^1$HNMR (400 MHz, methanol-$d_4$) δ 7.94 (d, J = 7.1 Hz, 2H), 7.66-7.48 (m, 3H), 7.29 (t, 1H), 7.17 (d, J = 7.6 Hz, 2H), 3.98-3.82 (m, 1H), 3.36-3.30 (m, 2H), 2.66-2.60 (m, 1H), 2.14 (s, 6H), 1.69-1.50 (m, 3H), 1.46-1.31 (m, 2H), 1.24-1.19 (m, 1H), 0.90 (s, 9H) ppm. | 1.82 | 499 |
| 385 | $^1$HNMR (400 MHz, methanol-$d_4$) δ 7.96 (d, J = 8.1 Hz, 2H), 7.78 (d, J = 8.1 Hz, 2H), 7.43 (t, 1H), 6.81-6.69 (m, 1H), 3.79 (d, J = 3.5 Hz, 2H), 2.86-2.84 (m, 2H), 2.69 (q, 2H), 2.00-1.88 (m, 1H), 1.84-1.65 (m, 2H), 1.60-1.53 (m, 1H), 1.44 (d, J = 14.0 Hz, 1H), 1.34-1.28 (m, 1H), 1.07 (s, 3H), 0.87 (s, 3H) ppm. | 2.20 | 586 |
| 386 | $^1$HNMR (400 MHz, methanol-$d_4$) δ 7.98 (d, J = 7.2 Hz, 2H), 7.64-7.55 (m, 3H), 7.42-7.30 (m, 4H), 7.18 (d, J = 7.6 Hz, 2H), 7.04 (s, 1H), 2.10 (s, 6H), 1.92-1.80 (m, 2H), 1.09-1.05 (m, 2H), 0.84 (s, 9H) ppm. | 2.47 | 555 |
| 387 | $^1$HNMR (400 MHz, chloroform-d) δ 7.36 (t, J = 6.4 Hz, 1 H), 7.23 (t, J = 8.0 Hz, 1 H), 7.04-6.77 (m, 8 H), 4.64-4.57 (m, 1 H), 4.12 (t, J = 13.2 Hz, 2 H), 3.86 (s, 2 H), 1.34 (d, J = 6.0 Hz, 6 H), 1.10 (s, 9 H) ppm. | 2.38 | 575 |
| 388 | $^1$HNMR (400 MHz, Chloroform-d) δ 7.97-7.99 (m, 2H), 7.46-7.55 (m, 3H), 6.18-7.22 (m, 1 H), 6.95-7.01 (m, 2H), 6.77-6.84 (m, 3H), 6.71-6.62 (m, 1H), 4.56-4.62 (m, 1 H), 4.03-4.06 (m, 1H), 3.76-3.80 (m, 1H), 2.60-2.67 (m, 1 H), 1.32-1.33 (d, J = 4.0 Hz, 1H), 1.24-1.26 (d, J = 8.0 Hz, 3H) ppm | 2.31 | 611 |
| 389 | $^1$HNMR (400 MHz, chloroform-d) δ 7.70-7.61 (m, 1H), 7.56-7.48 (m, 2H), 7.17 (dd, J = 5.6, 3.0 Hz, 1H), 7.11 (t, J = 8.0 Hz, 1H), 6.97 (t, J = 9.2 Hz, 1H), 6.75 (dd, J = 8.2, 2.4 Hz, 1H), 6.66 (td, J = 7.0, 3.6 Hz, 2H), 6.46 (t, J = 2.0 Hz, 1H), 3.74-3.59 (m, 2H), 2.84 (s, 3H), 2.19 (s, 3H), 1.60 (t, J = 7.2 Hz, 2H), 0.92 (s, 9H) ppm. | 2.36 | 622 |
| 390 | $^1$HNMR (400 MHz, chloroform-d) 7.69-7.62 (m, 1H), 7.61-7.51 (m, 3H), 7.41 (d, J = 7.4 Hz, 1H), 7.11 (t, J = 8.0 Hz, 1H), 6.75 (d, J = 6.2 Hz, 1H), 6.67-6.57 (m, 2H), 6.45 (s, 1H), 4.59 (s, 2H), 3.66 (dt, 1.60 (t, J = 7.2 Hz, 2H), 0.92 (s, 9H) ppm. | 2.27 | 591 |
| 391 | $^1$HNMR (400 MHz, chloroform-d) δ 7.37-7.29 (m, 2 H), 7.17 (t, J = 8.0 Hz, 1 H), 7.01 (t, J = 8.0 Hz, 1 H), 6.94 (t, J = 7.2 Hz, 1 H), 6.82-6.78 (m, 4 H), 6.58 (s, 1 H), 4.56- | 2.25 | 634 |

TABLE 3-continued

| Example 49-509 | | | |
|---|---|---|---|
| Compound Number | NMR | LCMS retention time (min.) | LCMS MS (ESI) m/z $[M+H]^+$ |
| | 4.50 (m, 1 H), 3.99-3.83 (m, 4 H), 2.00 (s, 3 H), 1.29 (d, J = 6.0 Hz, 3 H), 1.14 (d, J = 6.0 Hz, 3 H), 1.07 (s, 9 H) ppm. | | |
| 392 | $^1$H NMR (400 MHz, chloroform-d) δ 7.58 (t, J = 8.0 Hz, 1H), 7.43-6.96-6.97 (m, 1H), 6.79-6.83 (m, 3H), 6.72-6.73 (m, 1H), 6.59-6.61 (m, 1H), 4.53-4.56(m, 1H), 4.02-4.06 (m, 1H), 3.75-3.79 (m, 3H), 2.60-2.65 (m, 2H), 1.30-1.31 (d, J = 4.0 Hz, 6H), 1.24-1.25 (d, J = 4.0 Hz, 3H) ppm. | 2.19 | 627 |
| 393 | $^1$HNMR (400 MHz, DMSO) δ 11.38 (s, 1H), 8.13 (s, 2H), 7.70 (m, 3H), 6.78 (s, 1H), 3.72-3.69 (m, 2H), 2.68 (s, 2H), 2.64-2.55 (m, 2H), 1.91-1.86 (m, 1H), 1.77-1.61 (m, 2H), 1.52-1.31 (m, 2H), 1.30-1.24 (m, 1H), 1.03 (s, 3H), 0.84 (s, 3H) ppm. | 2.21 | 587 |
| 394 | | 1.14 | 574 |
| 395 | $^1$H NMR (400 MHz, chloroform-d) δ 10.01 (s, 1H), 7.58 (m, 1H), 7.31~7.23 (m, 4H), 7.13 (d, J = 7.6 Hz, 2H), 7.05 (m, 1H), 6.90 (m, 1H), 6.65 (d, J = 8.8 Hz, 2H), 4.33 (m, 1H), 2.95 (s, 6H), 2.14~1.57 (m, 12H), 1.29 (m, 1H) ppm. | 2.07 | 599 |
| 396 | $^1$H NMR (400 MHz, chloroform-d) δ 7.64-7.51 (m, 3H), 7.26 (m, 1H), 7.14 (t, J = 8.0 Hz, 1H), 7.01-6.93 (m, 2H), 6.81 (d, J = 8.0 Hz, 1H), 6.70 (d, J = 7.2 Hz, 1H), 6.50 (s, 1H), 1.07 (m, 2H), 2.17 (s, 3H), 1.07 (s, 9H) ppm. | 2.19 | 644 |
| 397 | $^1$H NMR (400 MHz, methanol-$d_4$) δ7.93-7.91 (m, 2H), 7.62-7.48 (m, 5H), 7.39-7.35 (m, 1H), 7.27-7.25 (m, 1H), 3.59-3.58 (m, 2H), 2.81-2.79 (m, 2H), 2.67-2.60 (m, 2H), 1.71-1.63 (m, 7H), 1.47-1.38 (m, 3H), 1.17-1.11 (m, 2H), 0.96 (s, 3H), 0.83 (s, 3H) ppm. $^{19}$F NMR (400 MHz, methanol-$d_4$) δ −135.106. | 2.27 | 544 |
| 398 | $^1$H NMR (400 MHz, methanol-$d_4$)□ δ 7.34-7.11 (m, 5H), 6.88-6.73 (m, 2H), 6.63-6.34 (m, 2H), 4.33-4.29 (m, 1H), 2.21-2.09 (m, 6H), 1.93-1.84 (m, 1H), 1.68-1.50 (m, 3H), 1.41-1.32 (m, 2H), 1.06 (s, 3H), 1.00 (s, 3H) ppm. | 2.33 | 554 |
| 399 | $^1$H NMR (400 MHz, chloroform-d) δ 7.94 (m, 2H), 7.83 (m, 1H), 7.65-7.48 (m, 5H), 7.40 (d, J = 7.2 Hz, 1H), 7.13 (t, J = 8.0 Hz, 1H), 6.79-6.76 (dd, J = 8.0, 2.0 Hz, 1H), 6.60 (m, 2H), 3.72 (t, J = 6.8 Hz, 2H), 1.70-1.64 (m, 2H), 1.29-1.24 (m, 2H), 0.92 (s, 9H) ppm. | 2.48 | 575 |
| 400 | | 1.10 | 689 |
| 401 | | 1.11 | 621 |
| 402 | $^1$H NMR (400 MHz, chloroform-d) 8.00-7.95 (m, 2H), 7.51 (dq, J = 14.4, 7.2 Hz, 3H), 7.22 (t, J = 7.6 Hz, 1H), 7.08 (d, J = 7.6 Hz, 2H), 4.05-4.01(m, 1H), 3.35 (dd, J = 13.8, 6.6 Hz, 1H), 3.20 (dd, J = 10.2, 5.8 Hz, 1H), 2.70 (dd, J = 10.2, 3.6 Hz, 1H), 2.20 (d, J = 7.2 | 2.27 | 500 |

TABLE 3-continued

| Compound Number | NMR | LCMS retention time (min.) | LCMS MS (ESI) m/z $[M + H]^+$ |
|---|---|---|---|
| Example 49-509 | | | |
| | Hz, 6H), 1.89 (dd, J = 9.8, 6.6 Hz, 1H), 1.27 (s, 1H), 1.11 (s, 9H), 0.99 (d, J = 6.2 Hz, 3H) ppm. | | |
| 403 | $^1$H NMR (400 MHz, methanol-$d_4$) δ 7.94 (d, J = 7.6 Hz, 2H), 7.63-7.53 (m, 3H), 7.32 (t, 1H), 7.18-7.12 (m, 2H), 3.59-3.53 (m, 1H), 3.27-3.20 (m, 1H), 2.82-2.76 (m, 1H), 2.69-2.58 (m, 2H), 2.25 (d, J = 4.8 Hz, 3H), 2.15 (d, J = 2.8 Hz, 3H), 1.75-1.19 (m, 5H), 1.05-0.68 (m, 10H) ppm. | 2.32 | 526 |
| 404 | $^1$H NMR(400 MHz, chloroform-d) δ 7.95 (d, J = 7.4 Hz, 2H), 7.82 (d, J = 7.4 Hz, 1H), 7.66-7.53 (m, 3H), 7.49 (t, 2H), 7.38 (d, J = 7.0 Hz, 1H), 7.10 (t, J = 8.0 Hz, 1H), 6.76 (m, 1H), 6.63 (d, J = 7.6 Hz, 1H), 6.56 (s, 1H), 3.84 (s, 2H), 1.09 (t, J = 6.1 Hz, 2H), 0.85 (t, 2H) ppm. | ND | ND |
| 405 | $^1$H NMR (400 MHz, chloroform-d) δ 7.95 (d, J = 7.2 Hz, 2H), 7.82 (d, J = 6.8 Hz, 1H), 7.64-7.47 (m, 5H), 7.38 (d, J = 6.8 Hz, 1H), 7.11 (t, J = 8.0 Hz, 1H), 6.76 (dd, J = 8.0, 2.4 Hz, 1H), 6.65 (d, J = 8.0 Hz, 1H), 6.54 (d, J = 2.4 Hz, 1H), 3.83-3.74 (m, 2H), 2.45-2.35 (m, 1H), 2.14-2.04 (m, 1H), 1.47-1.35 (m, 1H), 1.12 (d, J = 7.2 Hz, 3H) ppm. | 2.58 | 601 |
| 406 | | 1.10 | 576 |
| 407 | | 1.04 | 620 |
| 408 | | 1.88 | 677 |
| 409 | | 1.67 | 649 |
| 410 | | 0.93 | 668 |
| 411 | $^1$H NMR (400 MHz, chloroform-d) δ 7.81 (s, 1H), 7.59 (m, 1H), 7.30 (m, 1H), 7.26 (m, 2H), 7.06 (s, 2H), 6.65 (d, J = 8.4 Hz, 1H), 4.44 (m, 1H), 4.19 (m, 1H), 3.01 (s, 6H), 2.29~1.84 (m, 7H), 1.37 (m, 3H), 1.02 (m, 3H) ppm. | 2.10 | 671 |
| 412 | $^1$H NMR (400 MHz, chloroform-d) δ 7.95-7.97 (m, 2H), 7.80-7.82 (m, 1H), 7.47-7.63 (m, 5H), 7.36-7.38 (d, J = 8.0 Hz, 1H), 7.10-7.14 (m, 1H), 6.75-6.77 (m, 1H), 6.67-6.75 (m, 1H), 6.51-6.52 (m, 1H), 3.87-3.90 (m, 1H), 3.60-3.64 (m, 1H), 2.54-2.61 (m, 1H), 1.20-1.22 (d, J = 8.0 Hz, 3H) ppm. | 2.28 | 587 |
| 413 | | 1.54 | 539 |
| 414 | | 1.12 | 683 |
| 415 | | 1.14 | 656 |
| 416 | $^1$H NMR (400 MHz, chloroform-d) δ 7.93-7.91 (m, 2H), 7.83-7.80 (m, 1H), 7.63-7.53 (m, 3H), 7.49-7.45 (m, 2H), 7.39 (d, J = 6.8 Hz, 1H), 7.12 (t, J = 8.0 Hz, 1H), 6.75-6.73 (dd, J = 8.4, 2.0 Hz, 1H), 6.67 (d, J = 7.6 Hz, 1H), 6.49 (m, 1H), 3.80 (t, J = 7.2 Hz, 2H), 1.95 (t, J = 7.2 Hz, 2H), 1.01-0.98 (m, 2H), 0.66 (m, 2H) ppm. | 2.27 | 613 |
| 417 | | 1.08 | 682 |
| 418 | | 1.15 | 634 |
| 419 | $^1$H NMR (400 MHz, methanol-d4) δ 7.96 (d, J = 7.2 Hz, 2H), 7.63 (t, J = 7.2 Hz, 1H), 7.56 (t, J = 8.0 Hz, 2H), 7.23 (t, J = 7.6 Hz, 1H), 7.09 (d, J = 7.6 Hz, 2H), 4.07-4.01 (m, 2H), 2.11 (s, 6H), 1.98-1.92 (m, 1H), 1.81-1.74 (m, 2H), | 1.57 | 496 |

TABLE 3-continued

| Compound Number | NMR | LCMS retention time (min.) | LCMS MS (ESI) m/z $[M + H]^+$ |
|---|---|---|---|
| Example 49-509 | | | |
| | 1.69-1.64 (m, 1H), 1.56-1.53 (m, 1H), 1.49-1.42 (m, 1H), 1.10 (s, 3H), 0.99 (s, 3H) ppm. | | |
| 420 | | 1.07 | 662 |
| 421 | $^1$H NMR (400 MHz, chloroform-d) δ 7.97 (d, J = 8.0 Hz, 2H), 7.85 (d, J = 8.0 Hz, 1H), 7.70-7.61 (m, 3H), 7.57 (t, J = 8.0 Hz, 1H), 7.51 (dd, J = 8.0, 4.0 Hz, 3H), 7.42 (d, J = 8.0 Hz, 1H), 7.34 (t, J = 8.0 Hz, 1H), 7.16 (d, J = 8.0 Hz, 1H), 6.80 (s, 1H) ppm. | 1.60 | 596 |
| 422 | $^1$H NMR (400 MHz, chloroform-d) δ 8.01-7.98 (d, 1H), 7.57-7.49 (m, 3H), 7.32-7.28 (m, 1H), 7.16-7.09 (m, 3H), 7.12-7.07 (m, 1H), 7.07-6.89(m, 2H), 3.06-3.01 (m, 1H), 2.14 (s, 6H), 2.03-1.95 (m, 1H), 1.70-1.67 (m, 1H), 1.68-1.14 (m, 4H), 1.03 (s, 6H) ppm. | 2.50 | 517 |
| 423 | | 1.70 | 690 |
| 424 | | 1.57 | 662 |
| 425 | $^1$H NMR (400 MHz, chloroform-d) δ 7.91-7.88 (m, 3H), 7.79-7.73 (m, 2H), 7.57-7.53 (m, 1H), 7.49-7.44 (m, 3H), 2.93-2.89 (m, 2H), 1.55-1.51 (m, 2H), 0.90 (s, 9H) ppm. | | |
| 426 | $^1$H NMR (400 MHz, chloroform-d) δ 7.83-7.80 (m, 1H), 7.77 (s, 1H), 7.64-7.64 (m, 2H), 7.45-7.42 (m, 1H), 6.75 (d, J = 2.4 Hz, 1H), 5.66 (d, J = 2.4 Hz, 1H), 4.09 (s, 2H), 3.83 (s, 3H), 2.34 (s, 3H), 1.22 (s, 6H) ppm. | 1.96 | 609 |
| 427 | | 1.08 | 682 |
| 428 | | 1.04 | 656 |
| 429 | | ND | ND |
| 430 | | ND | ND |
| 431 | $^1$H NMR (400 MHz, chloroform-d) δ 7.36 (t, J = 6.4 Hz, 1H), 7.32-7.27 (m, 1H), 7.14 (d, J = 7.6 Hz, 2H), 7.03 (t, J = 8.0Hz, 1H), 6.95 (t, J = 8.6 Hz, 2H), 6.74 (s, 1H), 6.47 (d, J = 7.8 Hz, 1H), 3.88 (s, 2H), 3.44 (s, 2H), 2.15 (s, 6H), 1.21 (s, 6H) ppm. | 2.25 | 612 |
| 432 | $^1$H NMR (400 MHz, chloroform-d) δ 7.81 (s, 1H), 7.50-7.41 (m, 2H), 7.31-7.24 (m, 2H), 7.00-6.95 (m, 1H), 6.79-6.76 (m, 1H), 6.57 (dd, J = 8.0, 2.0 Hz, 1H), 3.89-3.83 (m, 5H), 2.85-2.79 (m, 1H), 2.45 (s, 3H), 1.06 (s, 15H) ppm. | 2.27 | 607 |
| 433 | $^1$H NMR (400 MHz, chloroform-d) δ 7.92 (d, J = 7.2 Hz, 2H), 7.82 (d, J = 7.2 Hz, 1H), 7.65-7.54 (m, 3H), 7.50-7.44 (m, 3H), 6.82 (d, J = 2.4 Hz, 1H), 6.03 (d, J = 2.4 Hz, 1H), 3.15-3.08 (m, 1H), 2.22-2.15 (m, 1H), 2.08-2.00 (m, 2H), 1.87-1.80 (m, 2H), 1.68-1.65 (m, 2H), 1.60 (t, J = 18.4 Hz, 3H) ppm. | ND | 583 |
| 434 | $^1$H NMR (400 MHz, DMSO-$d_6$) δ 8.32 (d, J = 8.0 Hz, 1H), 7.90 (t, J = 8.0 Hz, 1H), 7.51 (d, J = 7.6 Hz, 1H), 7.12 (t, J = 7.2 Hz, 1H), 7.05 (d, J = 7.6 Hz, 3H), 6.61 (d, J = 8.0 Hz, 1H), 6.55 (d, J = 7.2 Hz, 1H), 6.33 (s, 1H), 4.69 (s, 1H), 3.53 (t, J = 7.2 Hz, 2H), 2.56 (s, 1H), 2.14 (s, 1H), 2.07-2.04 (m, 1H), 1.94 (s, 6H), 1.67 (s, 1H), 1.57-1.48 (m, 5H), 1.33-1.21 (m, 2H), 0.89 (s, 9H) ppm. | 1.78 | 645 |

TABLE 3-continued

| Compound Number | NMR | LCMS retention time (min.) | LCMS MS (ESI) m/z [M + H]$^+$ |
|---|---|---|---|
| | Example 49-509 | | |
| 435 | $^1$H NMR (400 MHz, methanol-$d_4$) δ 7.54-6.46 (m, 10H), 3.83-3.77 (m, 1H), 3.67-3.58 (m, 4H), 2.19-2.14 (m, 6H), 2.09-2.02 (m, 1H), 1.98-1.94 (m, 1H), 1.70-1.43 (m, 5H), 1.23-1.00 (m, 3H), 0.96 (s, 9H) ppm. | 1.83 | 677 |
| 436 | $^1$H NMR (400 MHz, DMSO-$d_6$) δ δ 7.49 (t, J = 7.6 Hz, 1H), 7.32 (t, J = 7.6 Hz, 1H), 7.20 (d, J = 7.2 Hz, 3H), 7.08 (d, J = 7.2 Hz, 1H), 6.87 (d, J = 7.6 Hz, 1H), 6.78 (d, J = 7.6 Hz, 1H), 6.59 (d, J = 8.4 Hz, 1H), 6.51 (s, 1H), 3.83-3.77 (m, 1H), 3.66-3.56 (m, 2H), 2.18-2.02 (m, 9H), 1.59-1.56 (m, 4H), 1.30-1.00 (m, 4H), 0.95(s, 9H) ppm. | 1.52 | 663 |
| 437 | | 1.10 | 701 |
| 438 | $^1$H NMR (400 MHz, chloroform-d) δ 7.85-7.83 (m, 2H), 7.64-7.62 (m, 1H), 7.61-7.59 (m, 3H), 7.57-7.36(m, 2H), 7.52-7.50 (m, 1H), 7.42-7.40 (m, 1H), 7.13-7.11 (m, 1H), 6.81-6.80(m, 1H), 6.57-6.56(s, 1H), 3.62(s, 2H), 1.22 (s, 6H) ppm. | 2.23 | 601 |
| 439 | | 1.14 | 717 |
| 440 | | 1.16 | 725 |
| 441 | | 1.13 | 647 |
| 442 | $^1$H NMR (400 MHz, chloroform-d) δ 7.97 (d, J = 7.6 Hz, 2H), 7.58-7.46 (m, 4H), 7.42-7.40 (m, 1H), 7.30-7.26 (m, 1H), 7.25-7.23 (m, 1H), 6.73 (d, J = 2.4 Hz, 1H), 5.65 (d, J = 2.4 Hz, 1H), 4.13 (s, 2H), 2.87-2.83 (m, 1H), 1.23 (s, 6H), 1.07 (d, J = 6.8 Hz, 6H) ppm. | 2.31 | 565 |
| 443 | | 1.07 | 621 |
| 444 | | 0.95 | 605 |
| 445 | | 0.88 | 535 |
| 446 | | 1.07 | 625 |
| 447 | | 1.13 | 661 |
| 448 | | 1.14 | 656 |
| 449 | | 1.15 | 678 |
| 450 | | 0.91 | 619 |
| 451 | | 1.11 | 627 |
| 452 | $^1$H NMR (400 MHz, chloroform-d) δ 7.99 (d, J = 7.6 Hz, 2H), 7.59-7.50 (m, 3H), 7.34 (t, J = 7.6 Hz, 1H), 7.17 (d, J = 7.2 Hz, 2H), 6.95 (d, J = 2.4 Hz, 1H), 6.76 (d, J = 2.4 Hz, 1H), 4.08-4.01 (m, 1H), 2.54-2.31 (m, 2H), 2.22-2.15 (m, 8H), 1.98-1.90 (m, 2H) ppm. | ND | 543 |
| 453 | $^1$H NMR (400 MHz, chloroform-d) δ 7.94 (d, J = 7.2 Hz, 2H), 7.56-7.44 (m, 3H), 7.30-7.26 (m, 1H), 7.10 (d, J = 7.6 Hz, 2H), 6.82 (d, J = 2.4 Hz, 1H), 6.12 (d, J = 2.4 Hz, 1H), 4.60 (d, J = 7.2 Hz, 1H), 2.52-2.45 (m, 1H), 2.12 (s, 6H), 2.11-1.90 (m, 3H), 1.89-1.81 (m, 2H), 1.75-1.68 (m, 1H) ppm. | ND | 545 |
| 454 | $^1$HNMR (400 MHz, chloroform-d) δ 7.39-7.29 (m, 2H), 7.16 (d, J = 7.8 Hz, 2H), 6.99-6.88 (m, 2H), 6.74 (ddd, J = 8.6, 4.0, 2.2 Hz, 1H), 6.47 (dd, J = 8.0, 2.2 Hz, 1H), 3.89 (s, 2H), 3.43 (s, 2H), 2.16 (s, 6H), 1.19 (s, 6H) ppm. | 2.27 | 630 |
| 455 | $^1$H NMR (400 MHz, methanol-$d_4$) δ 7.97 (d, J = 7.6 Hz, 2H), 7.87 (t, J = 4.0 Hz, 1H), 7.70 (t, J = 4.0 Hz, | 2.23 | 593 |

TABLE 3-continued

| Example 49-509 | | | |
|---|---|---|---|
| Compound Number | NMR | LCMS retention time (min.) | LCMS MS (ESI) m/z $[M + H]^+$ |
| | 2H), 7.61-7.50 (m, 4H), 7.19 (t, J = 7.6 Hz, 1H), 7.11 (d, J = 7.6 Hz, 1H), 7.04 (d, J = 7.6 Hz, 1H), 6.86 (s, 1H), 2.96-2.84 (m, 1H), 2.52-2.37 (m, 1H), 1.98-1.84 (m, 2H), 1.82-1.73 (m, 2H), 1.56 (t, J = 18.4 Hz, 3H), 1.34-1.20 (m, 2H) ppm. | | |
| 456 | | 1.09 | 621 |
| 457 | | 1.10 | 631 |
| 458 | | 1.13 | 680 |
| 459 | | 0.97 | 647 |
| 460 | $^1$HNMR (400 mHz, chloroform-d) δ 8.62 (s, 1H), 7.98-7.96 (m, 2H), 7.57-7.47 (m, 3H), 7.28-7.21 (m, 1H), 7.10-7.08 (m, 2H), 3.66-3.62 (m, 1H), 3.55-3.51 (m, 1H), 3.37-3.24 (m, 4H), 3.10-2.96 (m, 4H), 2.22 (s, 6H), 1.99-1.92 (m, 1H), 1.86-1.81 (m, 1H), 1.45 (s, 9H) ppm. | 2.13 | 585 |
| 461 | $^1$HNMR (400 MHz, chloroform-d) δ 9.66 (s, 1H), 8.03-7.80 (m, 3H), 7.70-7.33 (m, 6H), 7.21-7.06 (m, 2H), 6.94-6.71 (m, 2H), 3.03-2.81 (m, 1H), 2.25-2.05 (m, 2H), 2.05-1.79 (m, 4H), 1.65-1.56 (m, 3H), 1.46-1.19 (m, 2H), 1.05-0.95 (m, 1H) ppm. | 2.63 | 607 |
| 462 | | 1.11 | 690 |
| 463 | | 1.11 | 641 |
| 464 | | 0.84 | 613 |
| 465 | | 0.88 | 661 |
| 466 | | 1.13 | 649 |
| 467 | | ND | ND |
| 468 | | 1.06 | 607 |
| 469 | | 0.92 | 620 |
| 470 | $^1$H NMR (400 MHz, methanol-$d_4$)□ δ 7.96 (d, J = 7.2 Hz, 2H), 7.54 (t, J = 8.0 Hz, 2H), 7.49 (t, J = 6.8 Hz, 2H), 7.41 (t, J = 7.6 Hz, 1H), 7.30-7.24 (m, 2H), 7.00 (d, J = 2.4 Hz, 1 H), 5.67 (d, J = 2.8 Hz, 1H), 4.41 (t, J = 14.4 Hz, 2H), 1.53 (s, 3H), 1.47 (s, 3H), 1.10 (s, 9H) ppm. | 1.68 | 579 |
| 471 | $^1$H NMR (400 MHz, chloroform-d) δ 7.50-7.26 (m, 7H), 6.82 (dd, J = 8.0, 1.6 Hz, 1H), 6.73 (d, J = 2.4 Hz, 1H), 5.65 (d, J = 2.4 Hz, 1H), 4.13 (s, 2H), 3.90-3.87 (m, 1H), 2.87-2.83 (m, 1H), 1.42 (d, J = 6.4 Hz, 3H), 1.28 (s, 6H), 1.07 (d, J = 6.8 Hz, 6H) ppm. | ND | 676 |
| 472 | | 0.71 | 584 |
| 473 | | 0.75 | 631 |
| 474 | $^1$H NMR (400 MHz, chloroform-d) δ: 7.80 (s, 1H), 7.51-7.42 (m, 2H), 7.26-7.25 (m, 2H), 3.85 (s, 3H), 3.16-3.12 (m, 2H), 2.92-2.89 (m, 1H), 2.43 (s, 3H), 2.39-2.36 (m, 1H), 2.16-2.11 (m, 1H), 1.86-1.79 (m, 1H), 1.65-1.55 (m, 1H), 1.33-1.24 (m, 2H), 1.22-1.20(m, 6H), 1.16-1.10 (m, 1H), 0.87 (s, 9H) ppm. | 2.17 | 544 |
| 475 | | 0.69 | 584 |
| 476 | $^1$H NMR (400 MHz, chloroform-d) δ 8.02-8.00 (m, 2H), 7.63-7.51 (m, 4H), 7.46-7.44 (m, 1H), 7.33-7.26 (m, 2H), 7.03 (d, J = 2.8 Hz, 1H), 6.73 (d, J = 2.8 Hz, 1H), 3.17 (s, 2H), 2.86-2.82 (m, 1H), 1.28 (s, 6H), 1.09-1.07 (m, 6H) ppm. | 2.25 | 577 |
| 477 | $^1$H NMR (400 MHz, methanol-$d_4$) δ 7.97-7.95 (m, 2H), 7.58-7.51 (m, 3H), 7.41-7.37 (m, 2H), 7.30-7.28 | 2.14 | 579 |

TABLE 3-continued

| Example 49-509 | | | |
|---|---|---|---|
| Compound Number | NMR | LCMS retention time (min.) | LCMS MS (ESI) m/z $[M + H]^+$ |
| | (m, 1H), 7.23-7.20 (m, 1H), 7.16 (s, 1H), 6.27 (s, 1H), 4.87 (t, J = 6.4 Hz, 1H), 2.91-2.88 (m, 1H), 1.93-1.92 (m, 2H), 1.22 (s, 3H), 1.10 (s, 3H), 1.04 (t, J = 7.2 Hz, 6H) ppm. | | |
| 478 | | 0.78 | 654 |
| 479 | | 0.82 | 702 |
| 480 | | 0.89 | 760 |
| 481 | | 0.81 | 612 |
| 482 | | 0.83 | 679 |
| 483 | | 0.86 | 727 |
| 484 | $^1$H NMR (400 MHz, DMSO-d6) δ ppm 12.83-13.12 (m, 1 H) 12.30-12.71 (m, 1 H) 7.52-7.58 (m, 1 H) 7.24-7.51 (m, 7 H) 7.06-7.24 (m, 2 H) 7.00 (br d, J = 7.14 Hz, 1 H) 6.94 (d, J = 8.34 Hz, 1 H) 4.87-5.17 (m, 1 H) 4.52-4.72 (m, 1 H) 3.47-3.76 (m, 2 H) 2.63-3.11 (m, 3 H) 1.76-2.26 (m, 2 H) 1.02-1.24 (m, 3 H) 0.63-0.94 (m, 12 H) | 0.82 | 746 |
| 485 | | 0.92 | 610 |
| 486 | | 1.09 | 627 |
| 487 | | 1.09 | 613 |
| 488 | | 0.76 | 632 |
| 489 | $^1$H NMR (400 MHz, methanol-$d_4$) δ 7.97-7.95 (m, 2H), 7.65-7.55 (m, 3H), 7.50-7.43 (m, 2H), 7.37-7.35 (m, 1H), 7.30-7.27 (m, 1H), 7.18 (m, 1H), 6.32-6.31 (m, 1H), 2.88-2.81 (m, 1H), 2.23 (d, J = 14.4 Hz, 1H), 2.00 (d, J = 14.8 Hz, 1H), 1.52 (s, 3H), 1.17 (s, 3H), 1.11-1.06(m, 6H), 0.68 (s, 3H) ppm. | 2.18 | 593 |
| 490 | $^1$H NMR (400 MHz, chloroform-d) δ 7.48-7.44 (m, 1 H), 7.40-7.34 (m, 3 H), 7.26-7.23 (m, 3 H), 7.15 (t, J = 8.0 Hz, 1 H), 6.81-6.76 (m, 3 H), 6.51 (s, 1 H), 3.87 (t, J = 13.2 Hz, 2 H), 2.86-2.79 (m, 1 H), 1.06 (m, 15 H) ppm. | 2.21 | 586 |
| 491 | $^1$H NMR (400 MHz, chloroform-d) δ 7.804 (s, 1H), 7.284 (s, 1H), 7.144-7.125 (m, 2H), 4.657 (s, 1H), 3.858 (s, 3H), 3.608-3.596 (m, 2H), 2.666 (s, 1H), 2.649-2.530 (m, 3H), 2.492 (s, 2H), 2.214 (s, 6H), 1.980-1.827 (m, 3H), 1.530-1.506 (m, 2H), 1.381-1.349 (m, 1H) ppm. | 2.07 | 586 |
| 492 | $^1$H NMR (400 MHz, chloroform-d) δ 7.49 (m, 1H), 7.38 (m, 2H), 7.32-7.27 (m, 3H), 7.25 (s, 1H), 7.24-7.20 (m, 1H), 7.06 (t, J = 7.9 Hz, 2H), 6.85-6.81 (m, 2H), 2.85-2.72 (m, 1H), 1.01 (s, 6H) | 2.20 | 534 |
| 493 | $^1$H NMR (400 MHz, methanol-$d_4$) δ 7.93 (d, J = 7.6 Hz, 2H), 7.63-7.53 (m, 3H), 7.49-7.43 (m, 2H), 7.29-7.21 (m, 2H), 4.72-4.48 (m, 1H), 3.66-3.59 (m, 2H), 3.57-2.93 (m, 1H), 2.92-2.89 (m, 2H), 2.88-2.61 (m, 2H), 2.06-1.93 (m, 1H), 1.84-1.41 (m, 5H), 1.22 (d, J = 6.8Hz, 6H) ppm. | 2.21 | 582 |
| 494 | $^1$H NMR (400 MHz, chloroform-d) δ 7.49 (m, 1H), 7.40 (m, 1H), 7.34-7.27 (m, 3H), 7.25 (s, 1H), 7.22 (m, 2H), 7.06 (t, J = 8.0 Hz, 2H), 6.83 (s, 1H), 6.74 (d, J = 7.8 Hz, 1H), 4.13 (s, 1H), 3.94 (m, 2H), 3.83 (m, 1H), 3.72 (m, 1H), 2.86-2.73 (m, 1H), 2.28 (m, 1H), 1.97-1.81 (m, 2H), 1.01 (s, 6H) ppm. | 2.26 | 604 |

TABLE 3-continued

| Example 49-509 | | | |
|---|---|---|---|
| Compound Number | NMR | LCMS retention time (min.) | LCMS MS (ESI) m/z $[M + H]^+$ |
| 495 | $^1H$ NMR (400 MHz, chloroform-d) δ 7.78 (s, 1H), 7.23 (t, J = 7.6 Hz, 1H), 7.09 (d, J = 6.8 Hz, 2H), 4.08-3.99 (m, 1H), 3.83 (s, 3H), 3.40-3.29 (m, 1H), 3.21 (dd, J = 10.0, 5.8 Hz, 1H), 2.70 (dd, J = 10.0, 4.0 Hz, 1H), 2.42 (s, 3H), 2.21 (d, J = 7.2 Hz, 6H), 1.89 (ddd, J = 12.8, 6.6, 3.2 Hz, 1H), 1.58 (ddd, J = 13.0, 8.2, 6.6 Hz, 1H), 1.11 (s, 9H), 0.99 (d, J = 6.1 Hz, 3H) ppm. | 2.15 | 518 |
| 496 | $^1H$ NMR (400 MHz, chloroform-d) δ 7.48-7.38 (m, 2 H), 7.33-7.21 (m, 5 H), 7.15 (t, J = 8.0 Hz, 1 H), 6.81-6.71 (m, 3 H), 6.51 (m, 1 H), 4.13-4.09 (m, 1 H), 3.95-3.69 (m, 6 H), 2.86-2.79 (m, 1 H), 2.30-2.21 (m, 1 H), 1.91-1.84 (m, 1 H), 1.06-1.03 (m, 15 H) ppm. | 2.30 | 656 |
| 497 | $^1H$ NMR (400 MHz, chloroform-d) δ 7.96 (t, J = 3.2, 1.6 Hz, 1 H), 7.89 (d, J = 7.6 Hz, 1 H), 7.54 (d, J = 2.0 Hz, 1 H), 7.50 (t, J = 15.6, 7.6 Hz, 1 H), 7.31 (m, 1 H), 7.19-7.13 (m, 3 H), 6.84-6.81 (dd, J = 8.0, 2.0 Hz, 1 H), 6.75 (d, J = 8.8 Hz, 1 H), 6.50 (t, J = 4.4, 2.0 Hz, 1 H), 3.88 (t, J = 26, 12.8 Hz, 2 H), 2.13 (s, 6 H), 1.08 (s, 9 H) ppm. | 2.37 | 592 |
| 498 | $^1H$ NMR (400 MHz, chloroform-d) δ 7.99 (d, J = 7.6 Hz, 2H), 7.59-7.47 (m, 5H), 7.31-7.26 (m, 2H), 6.83 (d, J = 2.4 Hz, 1H), 6.03 (d, J = 2.4 Hz, 1H), 3.14-3.08 (m, 1H), 2.85-2.81 (m, 1H), 2.51-2.45 (m, 1H), 2.23-2.15 (m, 1H), 2.09-2.01 (m, 1H), 1.88-1.80 (m, 2H), 1.72-1.65 (m, 2H), 1.60 (t, J = 18.4 Hz, 3H), 1.04 (d, J = 6.8 Hz, 6H) ppm. | ND | 557 |
| 499 | $^1H$ NMR (400 MHz, chloroform-d) δ 8.01-8.00 (m, 2H), 7.58-7.50 (m, 3H), 7.34-7.30 (m, 1H), 7.17-7.14 (m, 2H), 6.74 (d, J = 2.0 Hz, 1H), 6.04 (d, J = 2.0 Hz, 1H), 3.17-3.07 (m, 1H), 2.54-2.41 (m, 1H), 2.24-2.05 (m, 8H), 1.87-1.81 (m, 2H), 1.73-1.65 (m, 2H), 1.60 (t, J = 18.4 Hz, 3H) ppm. | ND | 543 |
| 500 | $^1H$ NMR (400 MHz, chloroform-d) δ 7.97 (t, J = 2.0 Hz, 1H), 7.91-7.85 (m, 1H), 7.52 (s, 1H), 7.51-7.47 (m, 1H), 7.46 (d, J = 8.0 Hz, 1H), 7.43 (s, 1H), 7.28 (d, J = 8.0 Hz, 1H), 7.24 (s, 1H), 6.98 (d, J = 12.0 Hz, 1H), 6.78 (ddd, J = 8.0, 4.0, 2.0 Hz, 1H), 6.57 (dd, J = 8.0, 2.2 Hz, 1H), 3.86 (t, J = 12.0 Hz, 2H), 2.81 (s, 1H), 1.06 (s, 15H) ppm. | 2.36 | 623 |
| 501 | $^1H$NMR (400 MHz, chloroform-d) δ 8.00-7.95 (m, 2H), 7.57-7.46 (m, 3H), 7.44-7.36 (m, 2H), 7.24-7.19 (m, 1H), 7.18-7.14 (m, 1H), 4.09-3.99 (m, 1H), 3.33-3.20 (m, 2H), 2.98-2.88 (m, 1H), 2.72 (dd, J = 10.0, 4.2 Hz, 1H), 1.87 (ddd, J = 12.8, 6.6, 3.2 Hz, 1H), 1.57 (ddd, J = 13.0, 8.6, 6.8 Hz, 1H), 1.20 (dd, J = 6.8, 5.6 Hz, 6H), 1.12 (s, 9H), 0.94 (d, J = 6.2 Hz, 3H) ppm. | 2.29 | 514 |
| 502 | $^1H$ NMR (400 MHz, methanol-$d_4$) 8 7.97-7.95 (m, 2H), 7.65-7.55 (m, 3H), 7.50-7.43 (m, 2H), 7.37-7.35 (m, 1H), 7.30-7.27 (m, 1H), 7.18 | 2.18 | ND |

TABLE 3-continued

| Compound Number | NMR | LCMS retention time (min.) | LCMS MS (ESI) m/z $[M + H]^+$ |
|---|---|---|---|
| Example 49-509 | | | |
| | (m, 1H), 6.32-6.31 (m, 1H), 2.88-2.81 (m, 1H), 2.23 (d, J = 14.4 Hz, 1H), 2.00 (d, J = 14.8 Hz, 1H), 1.52 (s, 3H), 1.17 (s, 3H), 1.11-1.06(m, 6H), 0.68 (s, 3H) ppm. | | |
| 503 | $^1$HNMR (400 MHz, chloroform-d) δ 7.93 (d, J = 7.8 Hz, 2H), 7.77 (d, J = 7.4 Hz, 1H), 7.64-7.51 (m, 3H), 7.50-7.41 (m, 3H), 4.03 (s, 1H), 3.33-3.22 (m, 2H), 2.73 (dd, J = 10.2, 3.8 Hz, 1H), 1.87 (ddd, J = 9.6, 6.4, 2.6 Hz, 1H), 1.59-1.50 (m, 1H), 1.12 (s, 9H), 0.95 (d, J = 6.2 Hz, 3H) ppm. | 2.31 | 540 |
| 504 | $^1$H NMR (400 MHz, chloroform-d) δ 7.48 (t, J = 7.4 Hz, 1H), 7.39 (t, J = 7.9 Hz, 2H), 7.23 (dd, J = 11.0, 7.8 Hz, 2H), 7.16 (d, J = 7.2 Hz, 2H), 7.04 (d, J = 7.8 Hz, 2H), 6.81 (s, 1H), 6.74 (d, J = 8.6 Hz, 1H), 4.50-4.11 (m, 2H), 2.73 (m, 3H), 2.15 (m, 1H), 1.45 (m, 2H), 1.26 (m, 2H), 1.13 (m, 3H), 0.93 (d, J = 6.4 Hz, 6H) ppm. | 2.23 | 661 |
| 505 | $^1$H NMR (400 MHz, chloroform-d) δ 7.92 (d, J = 7.6 Hz, 2H), 7.82 (d, J = 6.8 Hz, 1H), 7.65-7.43 (m, 6H), 6.82 (d, J = 1.6 Hz, 1H), 6.01 (d, J = 1.6 Hz, 1H), 3.15-3.11 (m, 1H), 2.40-2.24 (m, 3H), 2.11-2.03 (m, 2H), 1.75 (d, J = 12.4 Hz, 3H), 1.69-1.65 (m, 2H) ppm. | ND | 563 |
| 506 | $^1$H NMR (400 MHz, chloroform-d) δ 7.99 (d, J = 7.2 Hz, 2H), 7.59-7.40 (m, 5H), 7.31-7.26 (m, 2H), 6.84-6.82 (m, 1H), 6.02-6.01 (m, 1H), 3.19-3.17 (m, 1H), 2.87-2.77 (m, 1H), 2.39-2.29 (m, 2H), 2.15-2.03 (m, 1H), 1.88 (d, J = 17.2 Hz, 3H), 1.76-1.65 (m, 2H), 1.04 (d, J = 7.2 Hz, 6H) ppm. | ND | 537 |
| 507 | $^1$H NMR (400 MHz, chloroform-d) δ 8.04-8.01 (m, 2H), 7.57-7.50 (m, 3H), 7.34-7.30 (m, 1H), 7.17-7.14 (m, 2H), 6.74 (s, 1H), 6.02 (s, 1H), 3.17-3.11 (m, 1H), 2.61-2.50 (m, 2H), 2.37-2.19 (m, 8H), 1.88 (d, J = 18.0 Hz, 3H), 1.81-1.73 (m, 2H) ppm. | ND | 523 |
| 508 | $^1$H NMR (400 MHz, methanol-$d_4$) δ 7.92-7.87 (m, 2H), 7.63-7.61 (m, 1H), 7.57-7.52 (m, 3H), 7.46-7.37 (m, 2H), 7.22 (t, J = 8.0 Hz, 1H), 6.89-6.83 (m, 2H), 6.55-6.54 (m, 1H), 4.00-3.89 (m, 2H), 1.59 (d, J = 22.8 Hz, 3H), 1.44 (d, J = 22.4 Hz, 3H), 1.07 (s, 9H) ppm. | 2.29 | 623 |
| 509 | $^1$H NMR (400 MHz, chloroform-d) δ 7.48 (t, J = 7.4 Hz, 1H), 7.39 (t, J = 7.9 Hz, 2H), 7.23 (dd, J = 11.0, 7.8 Hz, 2H), 7.16 (d, J = 7.2 Hz, 2H), 7.04 (d, J = 7.8 Hz, 2H), 6.81 (s, 1H), 6.74 (d, J = 8.6 Hz, 1H), 4.50-4.11 (m, 2H), 2.73 (m, 3H), 2.15 (m, 1H), 1.45 (m, 2H), 1.26 (m, 2H), 1.13 (m, 3H), 0.93 (d, J = 6.4 Hz, 6H) ppm. | 2.23 | 661 $(M - Me]^+$ |

Biological Assays

Example 510: TECC24 AUC Fold Over DMSO @3 μM

The effects of a test agent on CFTR-mediated transepithelial chloride transport was measured using TECC24 recording analysis. Test agents were solubilized in DMSO. Solubilized test agents were mixed with incubation medium containing DMEM/F12, Ultroser G (2%; Crescent Chemical, catalog #67042), Hyclone Fetal Clone II (2%; GE Healthcare, catalog #SH30066.02), bovine brain extract (0.25%; Lonza, catalog #CC-4098), insulin (2.5 μg/mL), IL-13 (10 ng/mL), hydrocortisone (20 nM), transferrin (2.5 μg/mL), triiodothyronine (500 nM), ethanolamine (250 nM), epinephrine (1.5 μM), phosphoethanolamine (250 nM), and retinoic acid (10 nM). Primary human bronchial epithelial cells from a ΔF508 homozygous CF donor (CF-HBE cells; from University of North Carolina Cystic Fibrosis Tissue Procurement Center), grown on Transwell HTS 24-well cell culture inserts (Costar, catalog #3378), were exposed to test agents or controls dissolved in incubation medium. The CF-HBE cells were cultured at 36.5° C. for 48 h before TECC24 recordings were performed in the presence or absence of test agent, a positive control or vehicle (DMSO).

Following incubation, the transwell cell culture inserts containing the test agent or control-treated CF-HBE cells were loaded onto a TECC24 apparatus (TECC v7 or MTECC v2; EP Design) to record the transepithelial voltage (VT) and resistance (TEER) using 4 AgCl electrodes per well configured in current-clamp mode. The apical and basolateral bath solutions both contained (in mM) 140 NaCl, 5 KCl, 2 CaCl2), 1 MgCl2, 10 Hepes, and 10 glucose (adjusted to pH 7.4 with NaOH) ppm. To inhibit basal Na+ absorption, the ENaC inhibitor benzamil (10 μM) was added to the bath. Then, the adenylate cyclase activator, forskolin (10 μM), was added to the bath to activate CFTR. The forskolin-stimulated Cl-transport was halted by addition of The forskolin-stimulated Cl transport was halted by addition of bumetanide (20 μM), an inhibitor of the basolateral chloride co-transporter NKCC1, to the bath to confirm that the detected signal was chloride dependent. VT and TEER recordings were digitally acquired at routine intervals using TECC or MTECC software (EP Design). VT and TEER were transformed into equivalent transepithelial Cl current (IEQ), and the Area Under the Curve (AUC) of the IEQ time course between forskolin and bumetanide addition is generated using Excel (Microsoft). Efficacy is expressed as the ratio of the test agent AUC divided by vehicle AUC. EC50s based on AUC are generated using the non-linear regression log(agonist) vs. response function in Prism software (GraphPad) with Hill Slope fixed=1.

If a test agent increased the AUC of the forskolin-stimulated IEQ relative to vehicle in CF-HBE cells, and this increase was inhibited by bumetanide, then the test agent was considered a CFTR corrector.

Biological data for Compounds 1-509 are provided in Table 4 below.

TABLE 4

Biological data for Compounds 1-509

| EX. No. | TECC AUC vs. DMSO @ 3 uM |
|---|---|
| 1 | A |
| 2 | A |
| 3 | A |
| 4 | B |
| 5 | B |
| 6 | B |
| 7 | A |
| 8 | A |
| 9 | B |
| 10 | A |
| 11 | A |
| 12 | A |
| 13 | A |
| 14 | A |
| 15 | A |
| 16 | A |
| 17 | B |
| 18 | A |
| 19 | A |
| 20 | A |
| 21 | A |
| 22 | A |
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | A |
| 39 | B |
| 40 | A |
| 41 | A |
| 42 | B |
| 43A | B |
| 43B | A |
| 44A1 | B |
| 44A2 | C |
| 44B1 | B |
| 44B2 | C |
| 45A1 | B |
| 45A2 | B |
| 45B1 | A |
| 45B2 | C |
| 46A1 | C |
| 46A2 | B |
| 46B1 | A |
| 46B2 | C |
| 47A1 | C |
| 47A2 | C |
| 47B1 | A |
| 47B2 | C |
| 48A1 | A |
| 48A2 | A |
| 48B1 | B |
| 48B2 | B |
| 49 | B |
| 50 | B |
| 51 | A |
| 52 | C |
| 53 | B |
| 54 | B |
| 55 | B |
| 56 | B |
| 57 | C |
| 58 | B |
| 59 | B |
| 60 | B |

TABLE 4-continued

| Biological data for Compounds 1-509 | |
|---|---|
| EX. No. | TECC AUC vs. DMSO @ 3 uM |
| 61 | B |
| 62 | C |
| 63 | C |
| 64 | B |
| 65 | C |
| 66 | B |
| 67 | B |
| 68 | B |
| 69 | B |
| 70 | B |
| 71 | C |
| 72 | B |
| 73 | B |
| 74 | C |
| 75 | C |
| 76 | B |
| 77 | B |
| 78 | C |
| 79 | A |
| 80 | B |
| 81 | A |
| 82 | B |
| 83 | C |
| 84 | A |
| 85 | A |
| 86 | B |
| 87 | A |
| 88 | A |
| 89 | C |
| 90 | B |
| 91 | C |
| 92 | B |
| 93 | B |
| 94 | C |
| 95 | B |
| 96 | B |
| 97 | B |
| 98 | A |
| 99 | C |
| 100 | B |
| 101 | A |
| 102 | A |
| 103 | B |
| 104 | C |
| 105 | C |
| 106 | A |
| 107 | A |
| 108 | A |
| 109 | B |
| 110 | A |
| 111 | A |
| 112 | B |
| 113 | B |
| 114 | A |
| 115 | B |
| 116 | C |
| 117 | A |
| 118 | B |
| 119 | B |
| 120 | B |
| 121 | A |
| 122 | B |
| 123 | B |
| 124 | B |
| 125 | B |
| 126 | B |
| 127 | C |
| 128 | B |
| 129 | A |
| 130 | B |
| 131 | A |
| 132 | B |
| 133 | B |
| 134 | A |
| 135 | B |

TABLE 4-continued

| Biological data for Compounds 1-509 | |
|---|---|
| EX. No. | TECC AUC vs. DMSO @ 3 uM |
| 136 | B |
| 137 | B |
| 138 | C |
| 139 | B |
| 140 | B |
| 141 | A |
| 142 | C |
| 143 | C |
| 144 | B |
| 145 | B |
| 146 | C |
| 147 | C |
| 148 | B |
| 149 | B |
| 150 | B |
| 151 | B |
| 152 | A |
| 153 | B |
| 154 | B |
| 155 | B |
| 156 | A |
| 157 | B |
| 158 | B |
| 159 | B |
| 160 | A |
| 161 | B |
| 162 | C |
| 163 | B |
| 164 | B |
| 165 | B |
| 166 | A |
| 167 | B |
| 168 | C |
| 169 | A |
| 170 | B |
| 171 | B |
| 172 | B |
| 173 | B |
| 174 | B |
| 175 | B |
| 176 | B |
| 177 | B |
| 178 | B |
| 179 | A |
| 180 | B |
| 181 | B |
| 182 | B |
| 183 | B |
| 184 | A |
| 185 | B |
| 186 | B |
| 187 | B |
| 188 | B |
| 189 | B |
| 190 | B |
| 191 | B |
| 192 | B |
| 193 | B |
| 194 | B |
| 195 | B |
| 196 | C |
| 197 | B |
| 198 | B |
| 199 | B |
| 200 | B |
| 201 | C |
| 202 | B |
| 203 | B |
| 204 | C |
| 205 | C |
| 206 | B |
| 207 | C |
| 208 | B |
| 209 | B |
| 210 | C |

TABLE 4-continued

Biological data for Compounds 1-509

| EX. No. | TECC AUC vs. DMSO @ 3 uM |
|---|---|
| 211 | A |
| 212 | B |
| 213 | B |
| 214 | B |
| 215 | B |
| 216 | B |
| 217 | B |
| 218 | B |
| 219 | B |
| 220 | B |
| 221 | C |
| 222 | B |
| 223 | B |
| 224 | C |
| 225 | C |
| 226 | B |
| 227 | A |
| 228 | B |
| 229 | C |
| 230 | A |
| 231 | A |
| 232 | B |
| 233 | B |
| 234 | B |
| 235 | B |
| 236 | A |
| 237 | A |
| 238 | B |
| 239 | A |
| 240 | A |
| 241 | B |
| 242 | A |
| 243 | A |
| 244 | A |
| 245 | B |
| 246 | B |
| 247 | B |
| 248 | B |
| 249 | B |
| 250 | B |
| 251 | B |
| 252 | C |
| 253 | A |
| 254 | B |
| 255 | B |
| 256 | B |
| 257 | B |
| 258 | C |
| 259 | B |
| 260 | B |
| 261 | A |
| 262 | A |
| 263 | B |
| 264 | C |
| 265 | B |
| 266 | B |
| 267 | B |
| 268 | C |
| 269 | B |
| 270 | A |
| 271 | A |
| 272 | B |
| 273 | B |
| 274 | A |
| 275 | A |
| 276 | B |
| 277 | A |
| 278 | A |
| 279 | C |
| 280 | A |
| 281 | C |
| 282 | B |
| 283 | B |
| 284 | B |
| 285 | A |

TABLE 4-continued

Biological data for Compounds 1-509

| EX. No. | TECC AUC vs. DMSO @ 3 uM |
|---|---|
| 286 | A |
| 287 | A |
| 288 | B |
| 289 | C |
| 290 | A |
| 291 | B |
| 292 | B |
| 293 | B |
| 294 | B |
| 295 | B |
| 296 | B |
| 297 | B |
| 298 | B |
| 299 | B |
| 300 | B |
| 301 | B |
| 302 | B |
| 303 | B |
| 304 | B |
| 305 | B |
| 306 | B |
| 307 | B |
| 308 | B |
| 309 | C |
| 310 | C |
| 311 | B |
| 312 | A |
| 313 | C |
| 314 | B |
| 315 | C |
| 316 | A |
| 317 | B |
| 318 | B |
| 319 | A |
| 320 | B |
| 321 | C |
| 322 | B |
| 323 | A |
| 324 | ND |
| 325 | A |
| 326 | B |
| 327 | B |
| 328 | B |
| 329 | A |
| 330 | A |
| 331 | B |
| 332 | B |
| 333 | C |
| 334 | A |
| 335 | B |
| 336 | B |
| 337 | B |
| 338 | B |
| 339 | A |
| 340 | A |
| 341 | B |
| 342 | A |
| 343 | A |
| 344 | A |
| 345 | A |
| 346 | B |
| 347 | B |
| 348 | B |
| 349 | A |
| 350 | B |
| 351 | A |
| 352 | A |
| 353 | B |
| 354 | B |
| 355 | B |
| 356 | B |
| 357 | A |
| 358 | A |
| 359 | B |
| 360 | B |

TABLE 4-continued

| Biological data for Compounds 1-509 | |
|---|---|
| EX. No. | TECC AUC vs. DMSO @ 3 uM |
| 361 | A |
| 362 | A |
| 363 | A |
| 364 | A |
| 365 | B |
| 366 | A |
| 367 | B |
| 368 | B |
| 369 | A |
| 370 | A |
| 371 | C |
| 372 | A |
| 373 | B |
| 374 | B |
| 375 | B |
| 376 | A |
| 377 | B |
| 378 | ND |
| 379 | A |
| 380 | A |
| 381 | B |
| 382 | A |
| 383 | A |
| 384 | B |
| 385 | B |
| 386 | B |
| 387 | A |
| 388 | B |
| 389 | A |
| 390 | A |
| 391 | A |
| 392 | A |
| 393 | B |
| 394 | A |
| 395 | B |
| 396 | B |
| 397 | A |
| 398 | B |
| 399 | A |
| 400 | A |
| 401 | B |
| 402 | A |
| 403 | B |
| 404 | B |
| 405 | B |
| 406 | B |
| 407 | A |
| 408 | A |
| 409 | B |
| 410 | B |
| 411 | C |
| 412 | B |
| 413 | B |
| 414 | B |
| 415 | A |
| 416 | B |
| 417 | A |
| 418 | B |
| 419 | B |
| 420 | A |
| 421 | B |
| 422 | A |
| 423 | B |
| 424 | A |
| 425 | C |
| 426 | C |
| 427 | A |
| 428 | A |
| 429 | A |
| 430 | A |
| 431 | B |
| 432 | B |
| 433 | C |
| 434 | A |
| 435 | A |

TABLE 4-continued

| Biological data for Compounds 1-509 | |
|---|---|
| EX. No. | TECC AUC vs. DMSO @ 3 uM |
| 436 | B |
| 437 | B |
| 438 | B |
| 439 | B |
| 440 | B |
| 441 | A |
| 442 | B |
| 443 | A |
| 444 | A |
| 445 | A |
| 446 | A |
| 447 | B |
| 448 | A |
| 449 | B |
| 450 | A |
| 451 | A |
| 452 | C |
| 453 | C |
| 454 | B |
| 455 | B |
| 456 | C |
| 457 | A |
| 458 | A |
| 459 | A |
| 460 | B |
| 461 | B |
| 462 | B |
| 463 | A |
| 464 | C |
| 465 | C |
| 466 | A |
| 467 | C |
| 468 | A |
| 469 | B |
| 470 | C |
| 471 | B |
| 472 | C |
| 473 | C |
| 474 | C |
| 475 | C |
| 476 | C |
| 477 | C |
| 478 | C |
| 479 | C |
| 480 | B |
| 481 | C |
| 482 | C |
| 483 | C |
| 484 | C |
| 485 | B |
| 486 | A |
| 487 | A |
| 488 | C |
| 489 | C |
| 490 | B |
| 491 | B |
| 492 | C |
| 493 | C |
| 494 | B |
| 495 | B |
| 496 | C |
| 497 | B |
| 498 | B |
| 499 | B |
| 500 | B |
| 501 | B |
| 502 | A |
| 503 | B |
| 504 | B |
| 505 | C |
| 506 | C |

TABLE 4-continued

| Biological data for Compounds 1-509 | |
|---|---|
| EX. No. | TECC AUC vs. DMSO @ 3 uM |
| 507 | B |
| 508 | B |
| 509 | A |

ND refers to Not determined;
"A" refers to AUC > 5;
"B" refers to AUC 2-5;
"C" refers to AUC < 2.

The invention claimed is:

1. A compound of Formula (I):

(I)

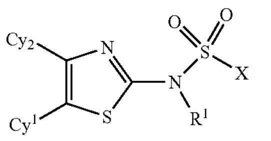

or a tautomer, or a pharmaceutically acceptable salt thereof, wherein:

$R^1$ is hydrogen or $C_{1-6}$ alkyl;

X is phenyl substituted with 0-3 occurrences of $R^2$;

$Cy^1$ is phenyl substituted with 0-3 occurrences of $R^3$;

$Cy^2$ is phenyl substituted with 1-3 occurrences of $R^4$;

each $R^2$ is independently halo, —$NH_2$, nitro, $C_{1-6}$ alkyl, $C_{1-6}$ alkoxy, $C_{1-6}$ haloalkyl, $C_{1-6}$ haloalkoxy, 4-10 membered heterocycloalkyl, 5-6 membered heteroaryl, $C_{3-9}$ cycloalkyl, $C_{3-9}$ cycloalkoxy, —C(O)$NH_2$, —N($R^a$)($R^5$), —N($R^a$)C(O)—$R^5$, —N($R^a$)$SO_2$—$R^5$, —$SO_2$—$R^5$, —C(O)N($R^a$)($R^5$), —S(O)—$R^5$, —N($R^a$)S(O)(NH)—$R^5$ or —P(O)$(R^5)_2$, wherein each $C_{1-6}$ alkyl, $C_{1-6}$ alkoxy, $C_{1-6}$ haloalkyl, $C_{3-9}$ cycloalkyl or 4-10 membered heterocycloalkyl is further substituted by 0-3 occurrences of $R^5$;

each $R^3$ is independently halo, $C_{1-8}$ alkyl, $C_{1-8}$ alkenyl, $C_{1-8}$ alkoxy, $C_{1-8}$ haloalkyl, $C_{1-8}$ haloalkoxy, $C_{3-9}$ cycloalkyl, $C_{1-4}$ alkyl-$C_{3-9}$ cycloalkyl, $C_{1-4}$ alkoxy-$C_{3-9}$ cycloalkyl, $C_{3-9}$ cycloalkoxy, $C_{3-9}$ cycloalkenyl, 5-6 membered aryl, aralkyl, aralkoxy, 5-6 membered heteroaryl, 4-10 membered heterocycloalkyl, —C(O)—$R^7$, —C(O)N($R^a$)($R^7$) or —N($R^a$)($R^8$), wherein each $C_{3-9}$ cycloalkyl, $C_{3-9}$ cycloalkoxy, $C_{1-8}$ haloalkoxy, $C_{1-6}$ alkoxy, 4-10 membered heterocycloalkyl, 5-6 membered aryl, 5-6 membered heteroaryl, cycloalkenyl, $C_{1-4}$ alkyl-$C_{3-9}$ cycloalkyl or $C_{1-4}$ alkoxy-$C_{3-9}$ cycloalkyl is further substituted with 0-3 occurrences of $R^7$;

each $R^4$ is independently halo, $C_{1-6}$ alkyl, $C_{1-6}$ alkoxy, $C_{1-6}$ haloalkyl, $C_{1-6}$ haloalkoxy, $C_{3-6}$ cycloalkyl, $N(R^a)_2$ or 4-10 membered heterocycloalkyl, wherein each 4-10 membered heterocycloalkyl may be further substituted with 0-3 $R^b$;

each $R^5$ is independently $C_{1-6}$ alkyl, $C_{1-6}$ haloalkyl, $C_{3-9}$ cycloalkyl, hydroxyl, —$SO_2$—$R^6$, —$CO_2H$, —$NH_2$, —$CO_2$—$C_{1-4}$ alkyl or 4-10 membered heterocycloalkyl, wherein each $C_{1-6}$ alkyl, $C_{3-9}$ cycloalkyl or 4-10 membered heterocycloalkyl is further substituted by 0-3 occurrences of $R^6$;

each $R^6$ is independently hydroxyl, —$NH_2$, halo, $C_{1-4}$ alkyl, $C_{1-4}$ haloalkyl, —$CO_2H$ or —$CO_2$—($C_{1-4}$ alkyl);

each $R^7$ is independently halo, $C_{1-5}$ alkyl, $C_{1-5}$ alkoxy, $C_{1-5}$ haloalkyl, $C_{1-5}$ haloalkoxy, $C_{1-5}$ haloalkenyl, $C_{3-7}$ cycloalkyl, hydroxyl, 5-6 membered aryl, aralkyl, aralkoxy, —C(O)—O—$C_{1-4}$alkyl, —C(O)N($R^a$)($C_{1-4}$ alkyl), 5-6 membered heteroaryl or 4-10 membered heterocycloalkyl, wherein each $C_{3-7}$ cycloalkyl, 5-6 membered aryl or 4-10 membered heterocycloalkyl is further substituted by 0-3 occurrences of $R^8$;

each $R^8$ is independently halo, $C_{1-4}$ alkyl, $C_{1-4}$ haloalkoxy, C(O)—$C_{1-4}$ alkyl or C(O)N($R^a$)($C_{1-4}$ alkyl);

each $R^a$ is independently H or $C_{1-6}$ alkyl; and each $R^b$ is $C_{1-4}$ alkyl;

wherein a) if $Cy^1$ has 3 occurrences of $R^3$, then each $R^3$ is not methoxy;

b) $R^2$ and $R^4$ are not each methyl;

c) $R^3$ and $R^4$ are not simultaneously tert-butyl or simultaneously methoxy; and d) when $Cy^1$ and $Cy^2$ are mono-substituted, then $R^3$ is not Cl and $R^4$ is not OMe.

2. The compound of claim 1, wherein $R^1$ is H.

3. The compound of claim 1, wherein $R^1$ is $C_{1-6}$ alkyl.

4. The compound of claim 1, wherein X is phenyl substituted with 0 occurrences of $R^2$.

5. The compound of claim 1, wherein X is phenyl substituted with 1 occurrence of $R^2$.

6. The compound of claim 5, wherein $R^2$ is —N($R^a$)($R^5$).

7. The compound of claim 6, wherein $R^a$ is H or $C_{1-6}$ alkyl, and $R^5$ is $C_{1-6}$ alkyl.

8. The compound of claim 6, wherein $R^a$ is H and $R^5$ is selected from $C_{1-6}$ haloalkyl, wherein each 4-10 membered heterocycloalkyl or $C_{3-9}$ cycloalkyl is substituted with 0 or 1 $R^6$.

9. The compound of claim 8, wherein $R^6$ is selected from —$CO_2H$, —$C(O)_2$—$C_{1-4}$ alkyl, hydroxyl, and $C_{1-4}$ alkyl.

10. The compound of claim 5, wherein $R^2$ is —N($R^a$)C(O)—$R^5$.

11. The compound of claim 10, wherein $R^a$ is H and $R^5$ is selected from $C_{1-6}$ alkyl and $C_{3-9}$ cycloalkyl, each substituted with 0-3 occurrences of $R^6$.

12. The compound of claim 11, wherein $R^6$ is selected from —$NH_2$, hydroxyl, halo, and $C_{1-4}$ haloalkyl.

13. The compound of claim 5, wherein $R^2$ is 4-10 membered heterocycloalkyl substituted with 0-3 occurrences of $R^5$.

14. The compound of claim 13, wherein each $R^5$ is selected from $C_{1-6}$ alkyl substituted with 0-3 occurrences of $R^6$.

15. The compound of claim 5, wherein $R^2$ is —C(O)—N($R^a$)($R^5$).

16. The compound of claim 15, wherein $R^a$ is H and $R^5$ is $C_{1-6}$ alkyl substituted with 0-3 occurrences of $R^6$.

17. The compound of claim 5, wherein $R^2$ is —N($R^a$)S(O)(NH)—$R^5$.

18. The compound of claim 17, wherein $R^a$ is H and $R^5$ is $C_{1-6}$ alkyl substituted with 0-3 occurrences of $R^6$.

19. The compound of claim 5, wherein X is

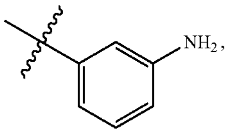

,

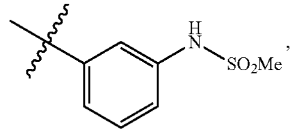

,

-continued
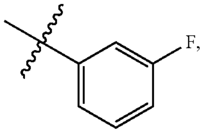
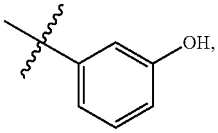
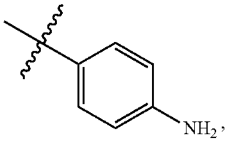
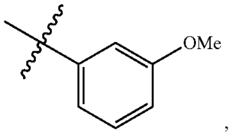
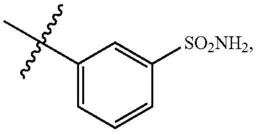
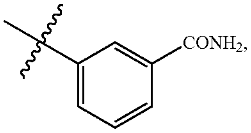
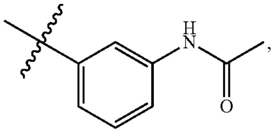
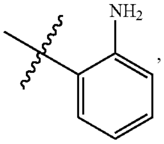
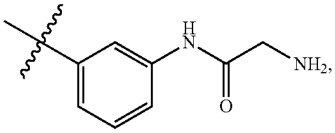
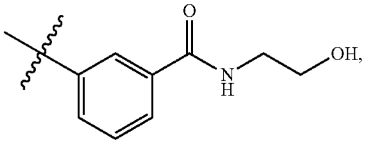
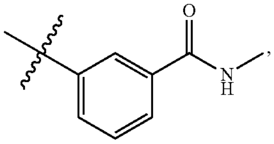
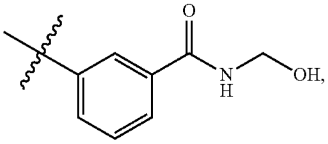
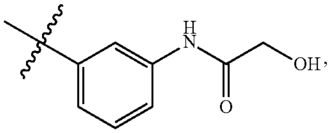
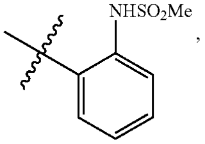
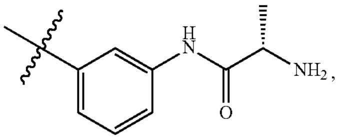
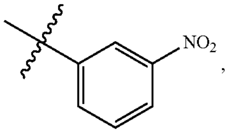
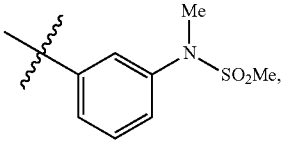
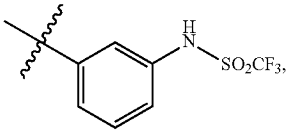
-continued
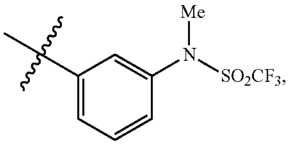
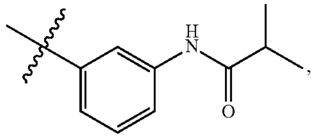
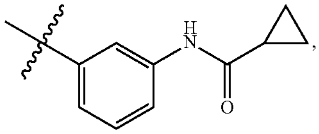
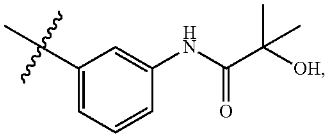
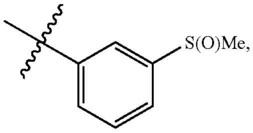
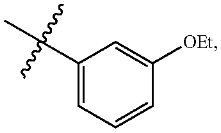
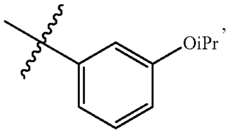
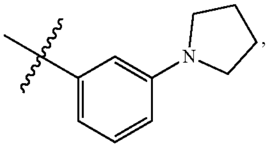
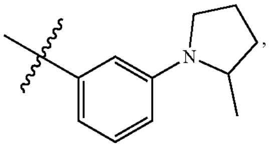
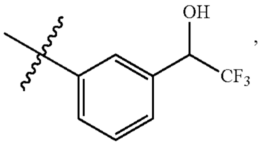
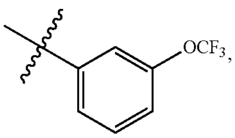
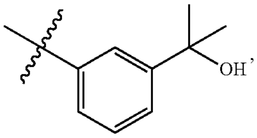
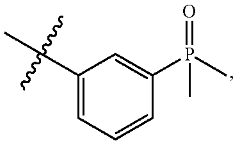
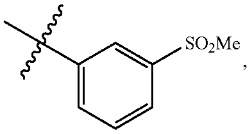
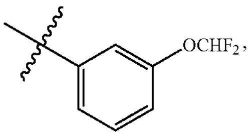
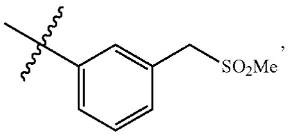
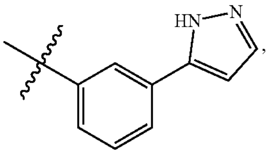
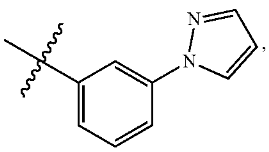
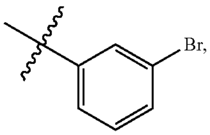
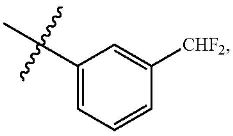

-continued

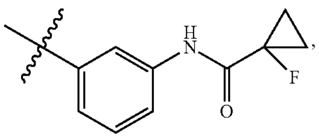
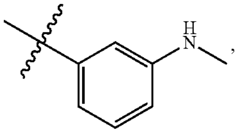
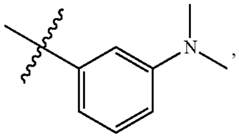
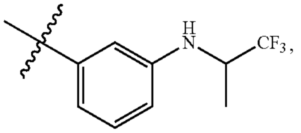
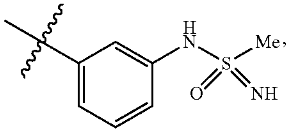
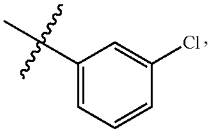
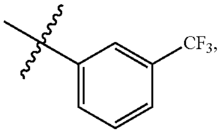
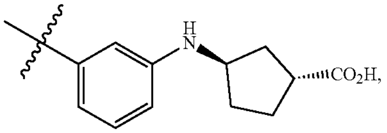
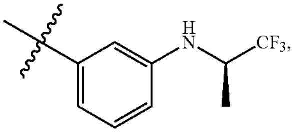
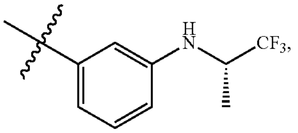
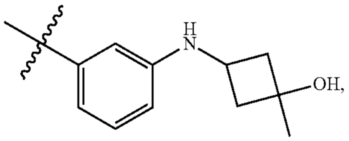
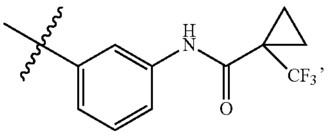
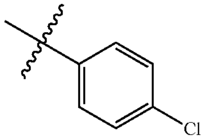
,
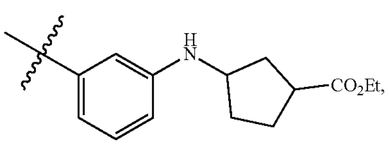
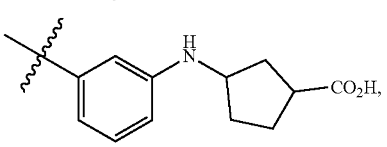
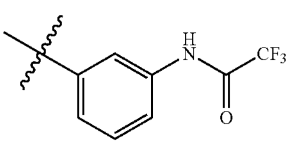
or -continued

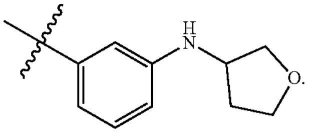

20. The compound of claim 1, wherein $R^4$ is selected from $C_{1-6}$ alkyl, $C_{1-6}$ haloalkyl, $C_{1-6}$ alkoxy, $C_{1-6}$ haloalkoxy and $C_{3-6}$ cycloalkyl.

21. The compound of claim 20, wherein $Cy^2$ is

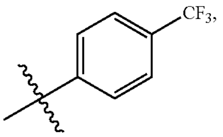
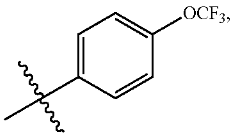
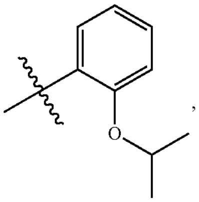
,
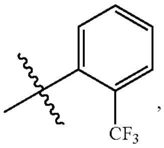
,
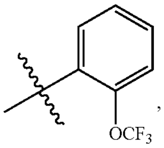
,
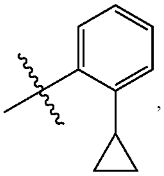
,
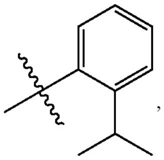
,
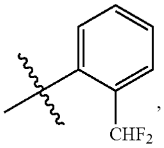
,
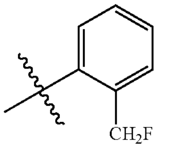
or
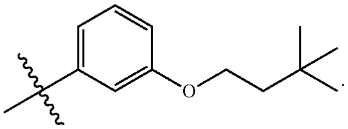

22. The compound of claim 1, wherein $Cy^2$ is phenyl substituted with 2 or 3 occurrences of $R^4$.

23. The compound of claim 22, wherein $R^4$ is selected from halo, $C_{1-6}$ haloalkyl, $C_{1-6}$ alkyl, $C_{1-6}$ alkoxy, $C_{1-6}$ haloalkoxy and $—N(R^a)_2$.

24. The compound of claim 23, wherein $Cy^2$ is

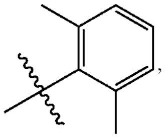
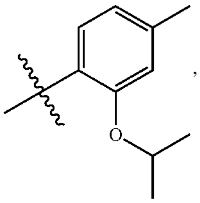
,
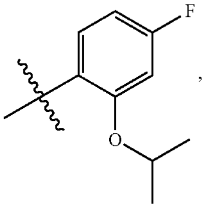
,

-continued
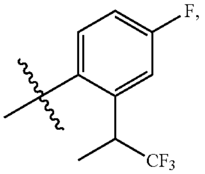
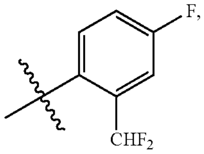
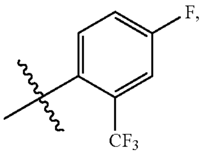
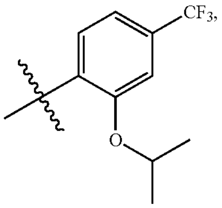
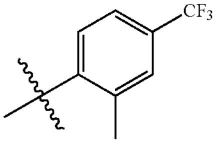,
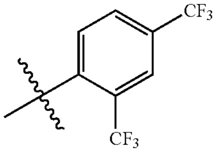,
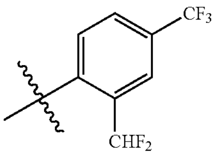,
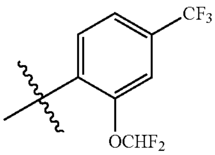,
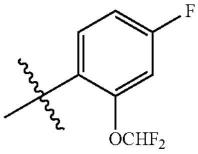,
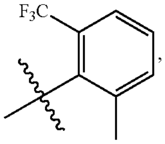
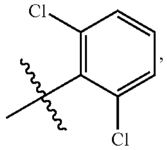
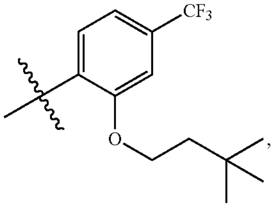
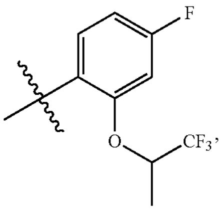
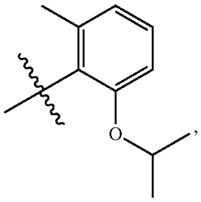
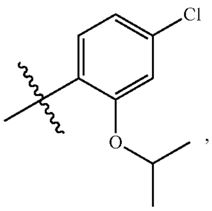,
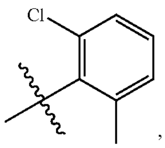,
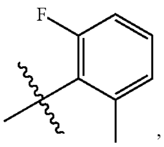,
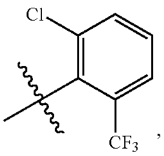,
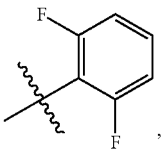,
-continued
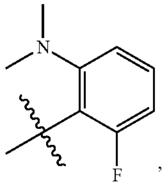,
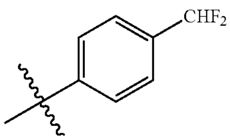,
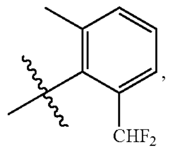
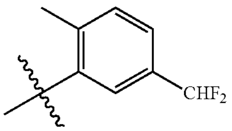
or
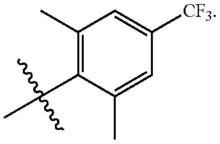
25. The compound of claim 1, wherein $Cy^2$ is
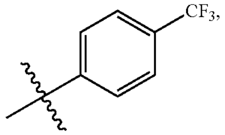
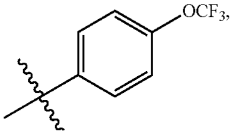
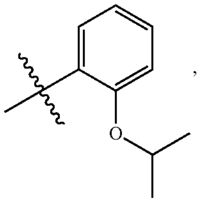,
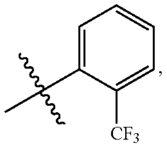
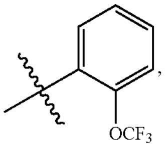
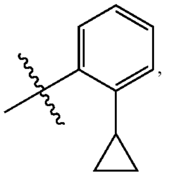
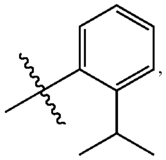
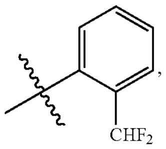
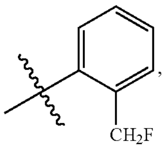
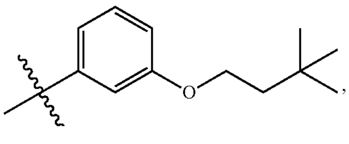
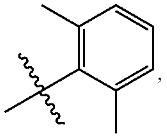
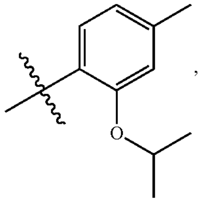,
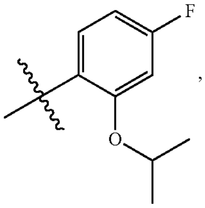, -continued
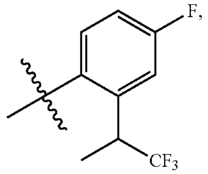
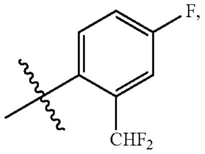
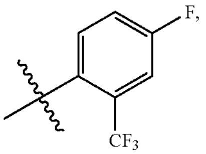
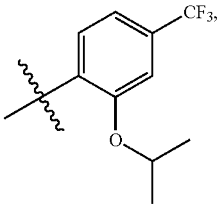
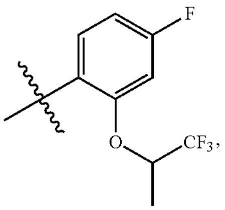
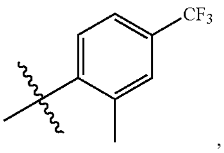
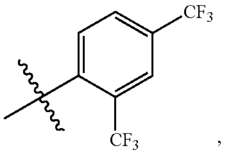
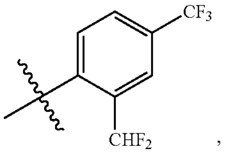
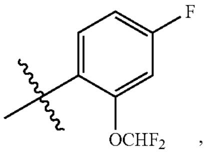
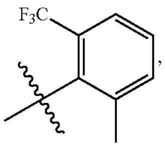
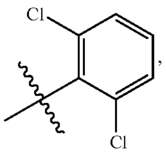
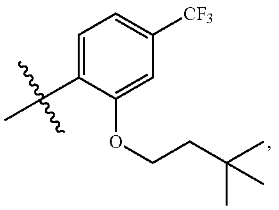
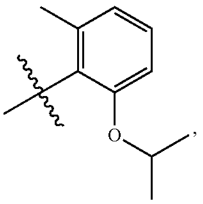
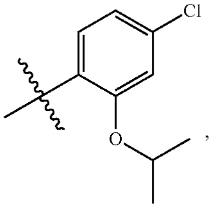
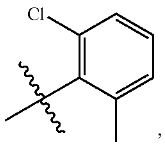
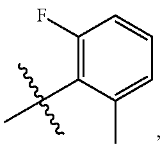
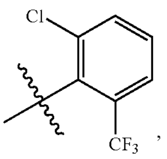
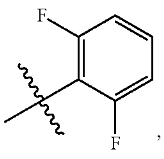
-continued
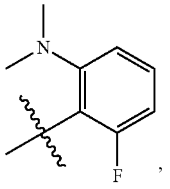
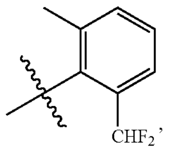
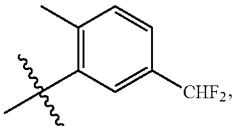
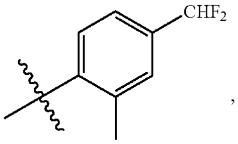
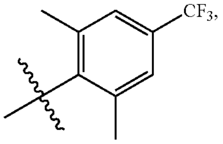
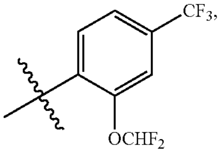
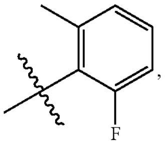
or
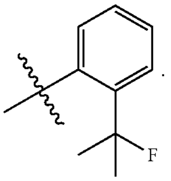
26. The compound of claim 1, wherein $R^3$ is selected from $C_{1-8}$ alkyl, $C_{1-8}$ haloalkyl, and $C_{1-8}$ alkoxy.
27. The compound of claim 1, wherein $Cy^1$ is
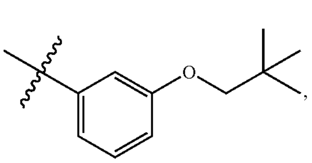
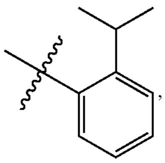
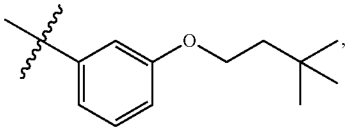
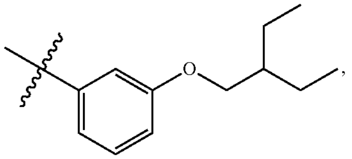
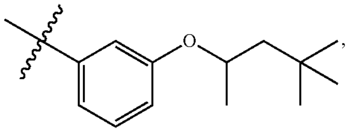
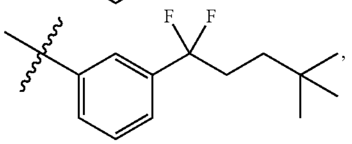
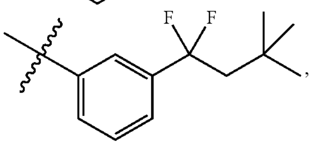

-continued
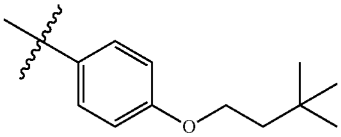
or
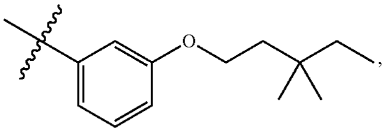
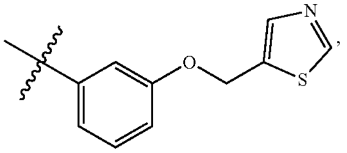
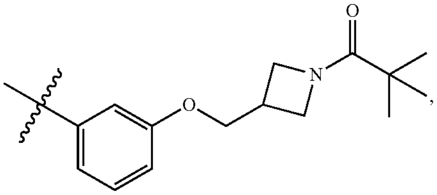
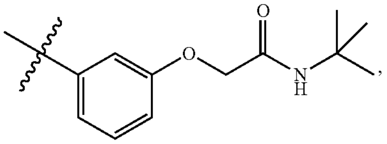
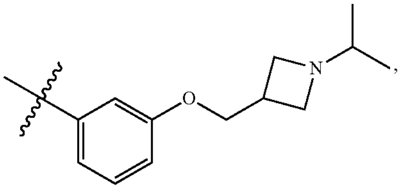
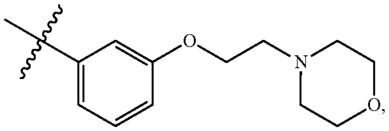
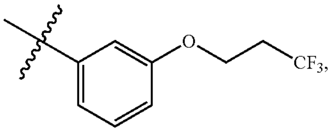
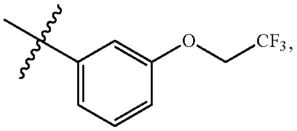
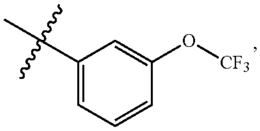
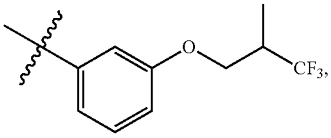
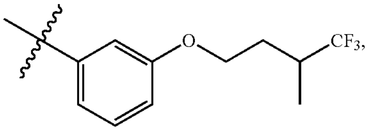
-continued
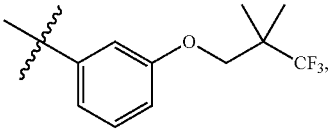
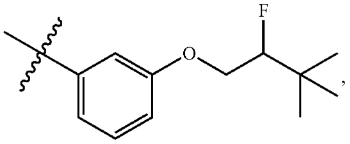
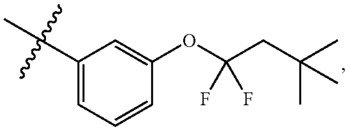
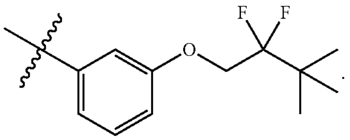
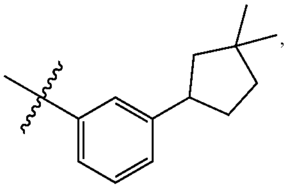
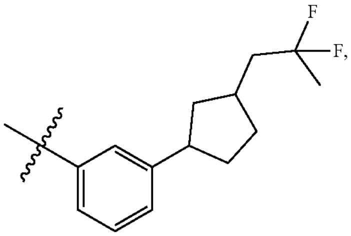
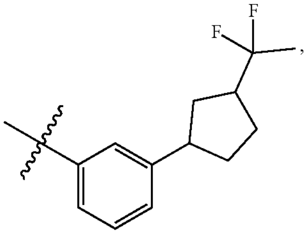
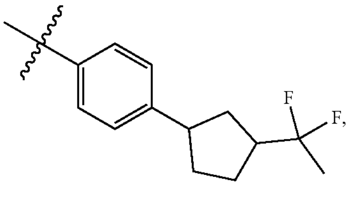
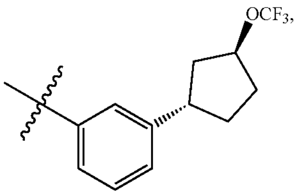

-continued

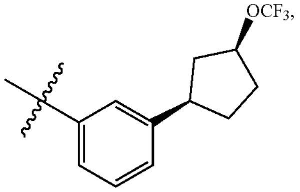

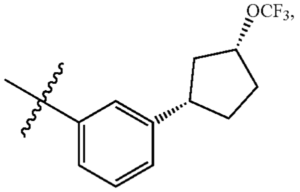

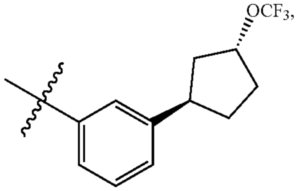

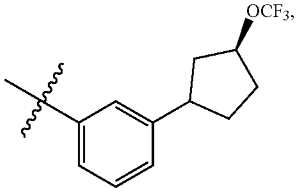

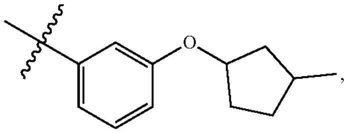

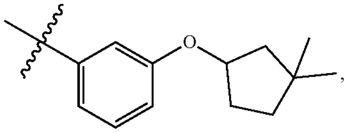

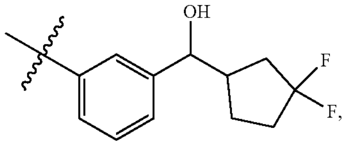

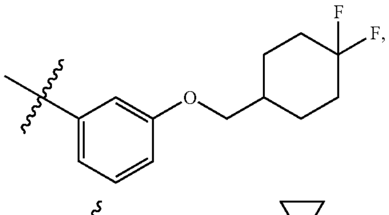

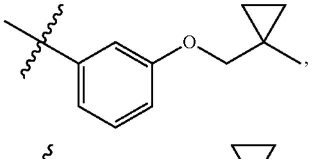

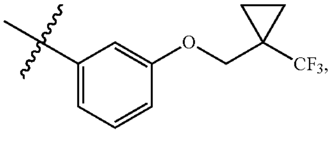

-continued

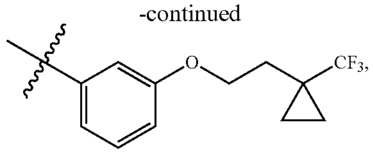

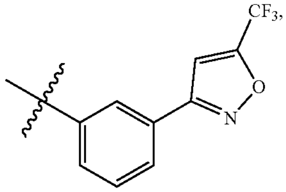

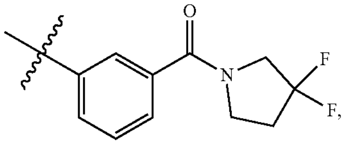

or

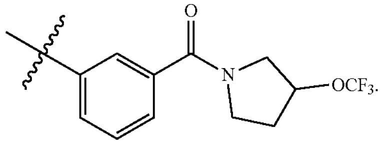

28. The compound of claim 1, wherein $Cy^1$ is phenyl substituted with 2 occurrences of $R^3$.

29. The compound of claim 28, wherein each $R^3$ is independently selected from halo, $C_{1-8}$ alkyl, $C_{1-8}$ haloalkyl, $C_{3-9}$ cycloalkyl, $C_{1-8}$ alkoxy, $C_{3-9}$ cycloalkoxy, $C_{1-8}$ haloalkoxy, $C_{1-4}$ alkoxy-$C_{3-9}$ cycloalkyl, $C_{3-9}$ cycloalkenyl, aryl, 4-10 membered heterocycloalkyl, —C(O)$R^7$, and —C(O)N($R^a$)($R^7$).

30. The compound of claim 29, wherein $R^3$ is further substituted with at least one $R^7$ selected from hydroxyl, —C(O)—O—$C_{1-4}$ alkyl, $C_{1-4}$ alkyl, $C_{1-8}$ alkenyl, $C_{1-4}$ alkoxy, aralkoxy, $C_{1-4}$ haloalkoxy, and 4-10 membered heterocycloalkyl.

31. The compound of claim 28, wherein $Cy^1$ is

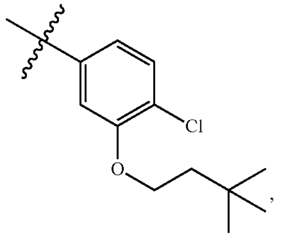

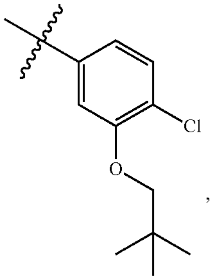

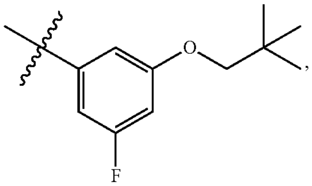

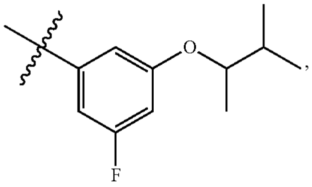

-continued
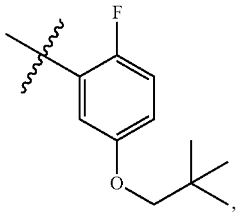
,
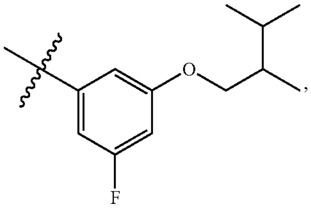
,
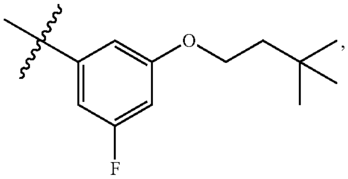
,
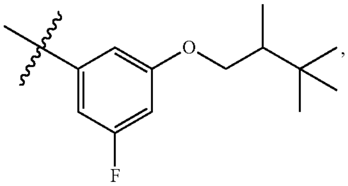
,
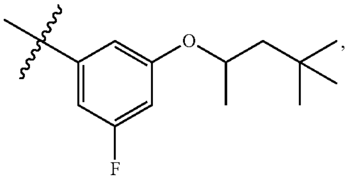
,
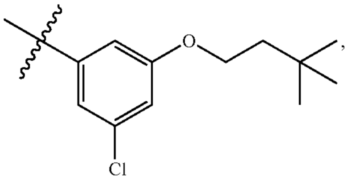
,
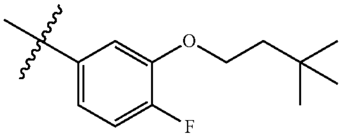
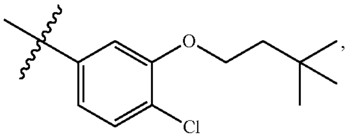
,
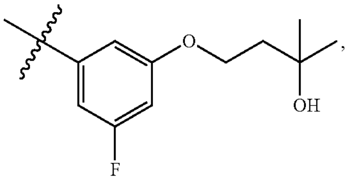
,
-continued
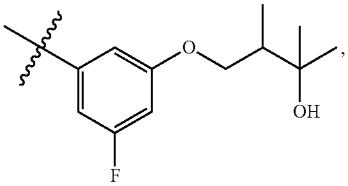
,
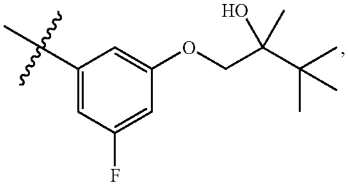
,
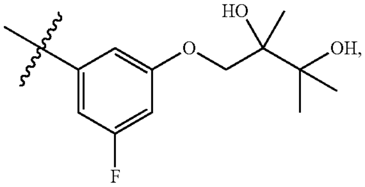
,
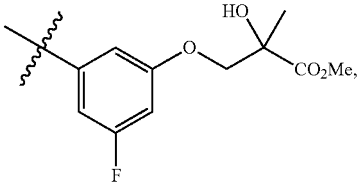
,
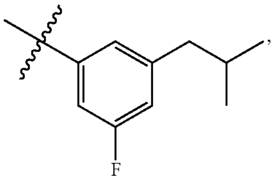
,
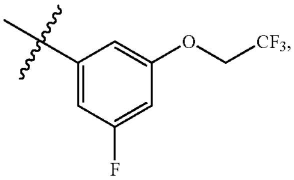
,
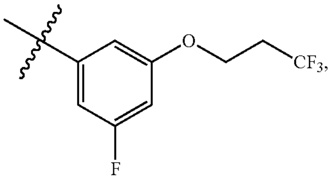
,
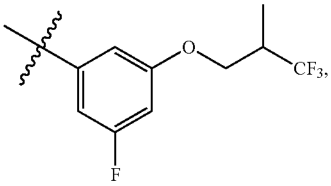
,
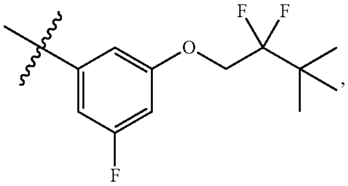
,
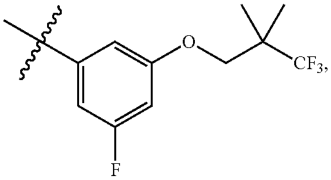
, -continued
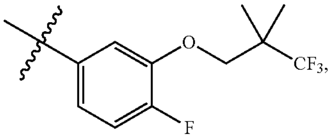
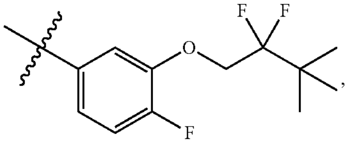
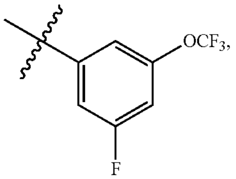
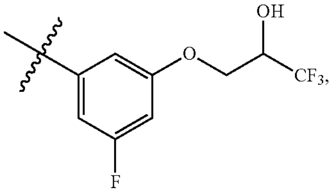
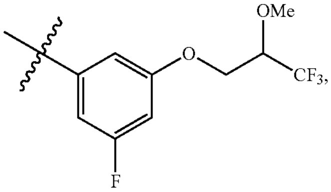
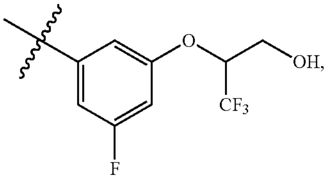
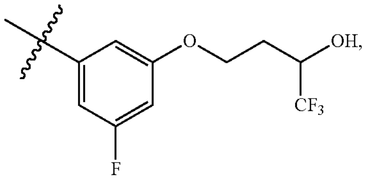
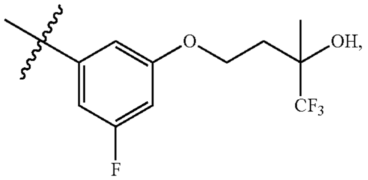
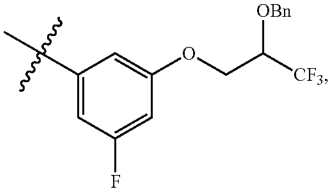
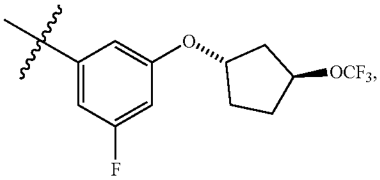
-continued
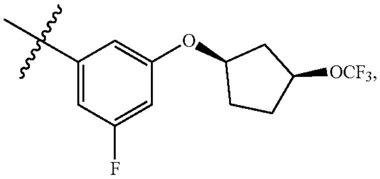
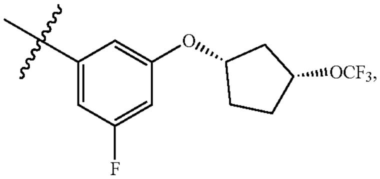
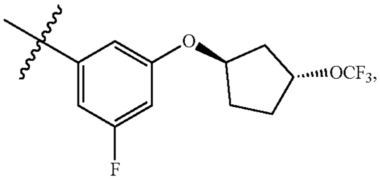
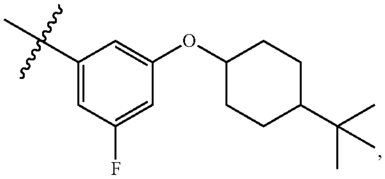
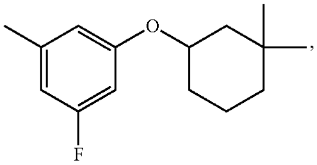
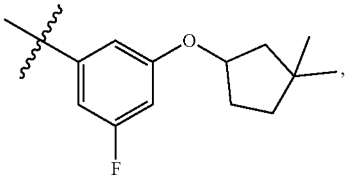
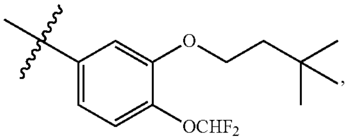
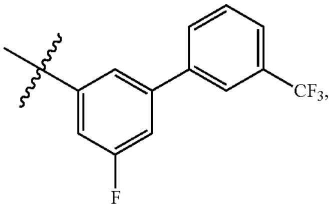
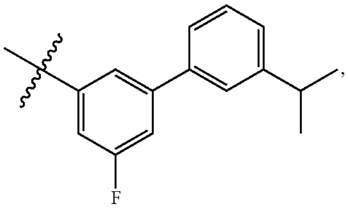

-continued

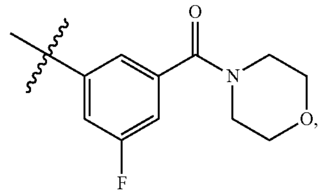

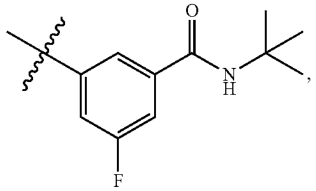

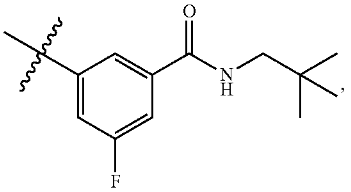

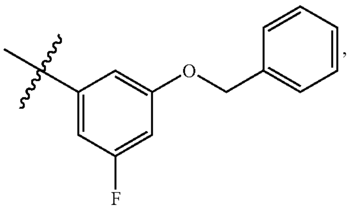

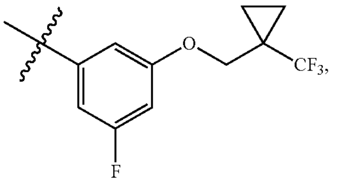

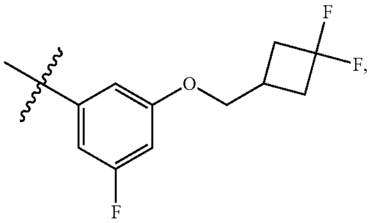

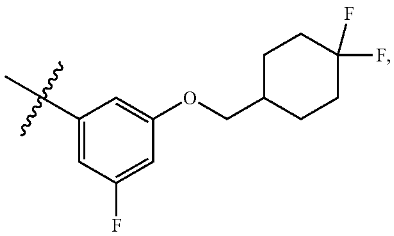

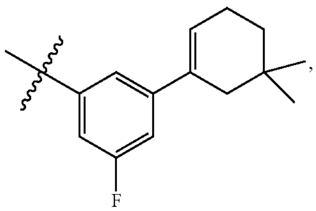

-continued

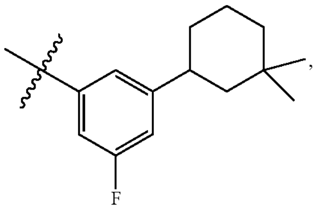

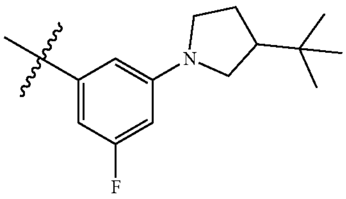

or

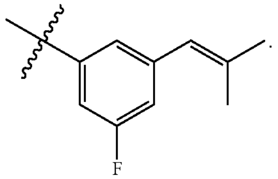

32. The compound of claim 26, wherein $Cy^1$ is phenyl substituted with 3 occurrences of $R^3$.

33. The compound of claim 32, wherein each $R^3$ is independently selected from halo, $C_{1-8}$ alkoxy, and $C_{3-9}$ cycloalkoxy.

34. The compound of claim 33, wherein $R^3$ is further substituted with at least one $R^7$ selected from $C_{1-5}$ alkyl.

35. The compound of claim 33, wherein $Cy^1$ is

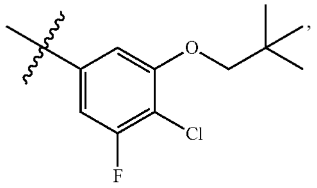

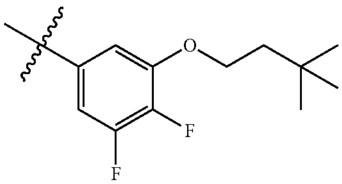

or

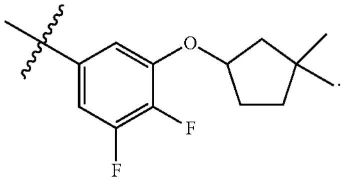

36. A compound selected from the group consisting of
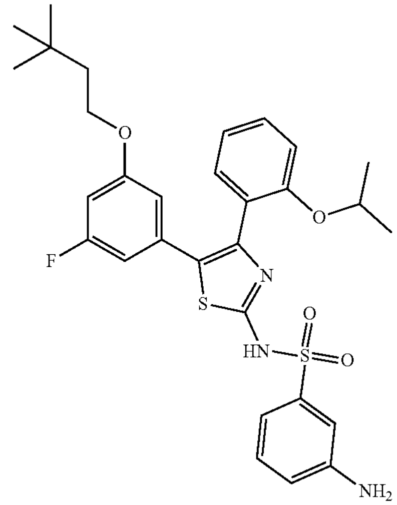 [SMILES: CC(C)Oc1ccccc1-c1nc(NS(=O)(=O)c2cccc(N)c2)sc1-c1cc(F)cc(OCCC(C)(C)C)c1]
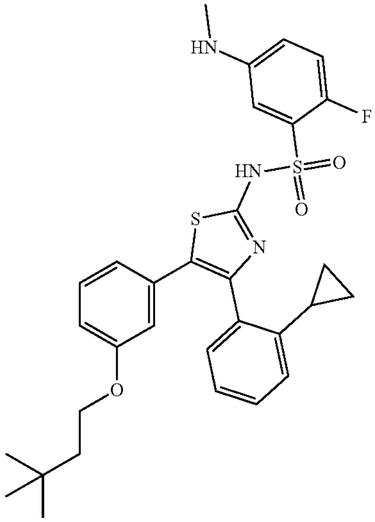 [SMILES: CNc1ccc(F)c(S(=O)(=O)Nc2nc(-c3ccccc3C3CC3)c(-c3cccc(OCCC(C)(C)C)c3)s2)c1]
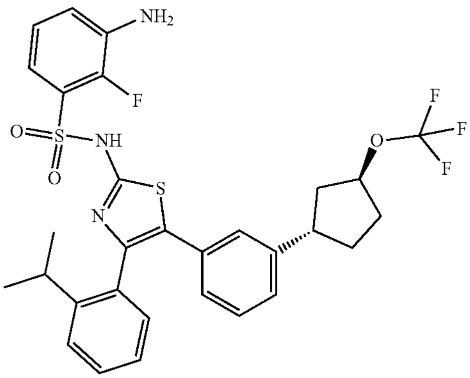 [SMILES: CC(C)c1ccccc1-c1nc(NS(=O)(=O)c2cccc(N)c2F)sc1-c1cccc([C@H]2CC[C@H](OC(F)(F)F)C2)c1]
-continued
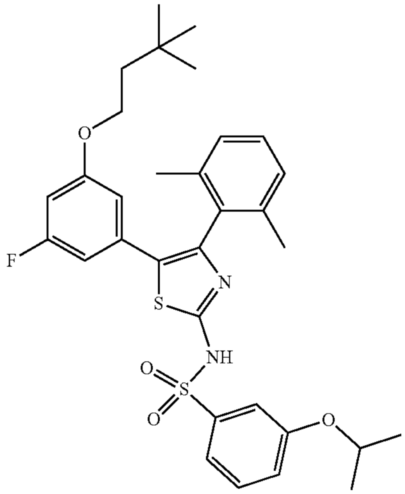 [SMILES: Cc1cccc(C)c1-c1nc(NS(=O)(=O)c2cccc(OC(C)C)c2)sc1-c1cc(F)cc(OCCC(C)(C)C)c1]
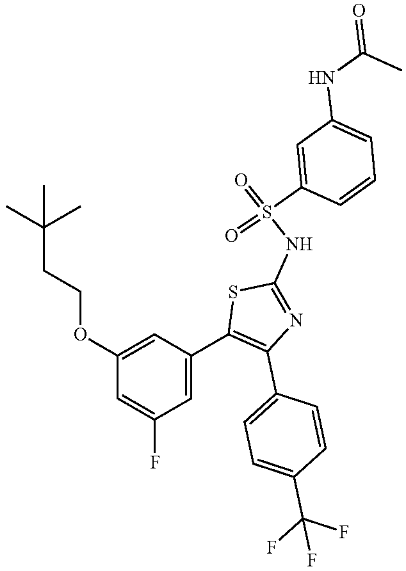 [SMILES: CC(=O)Nc1cccc(S(=O)(=O)Nc2nc(-c3ccc(C(F)(F)F)cc3)c(-c3cc(F)cc(OCCC(C)(C)C)c3)s2)c1]
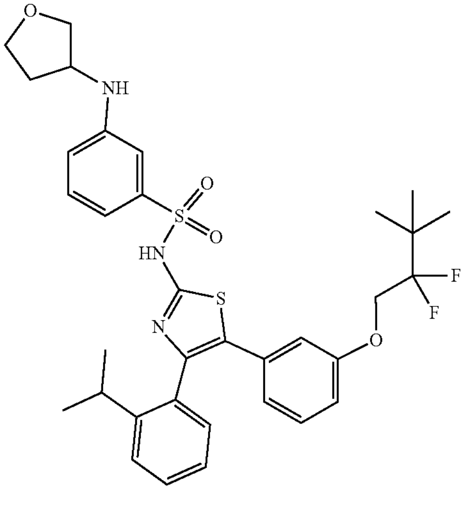 [SMILES: CC(C)c1ccccc1-c1nc(NS(=O)(=O)c2cccc(NC3CCOC3)c2)sc1-c1cccc(OCC(F)(F)C(C)(C)C)c1]

-continued
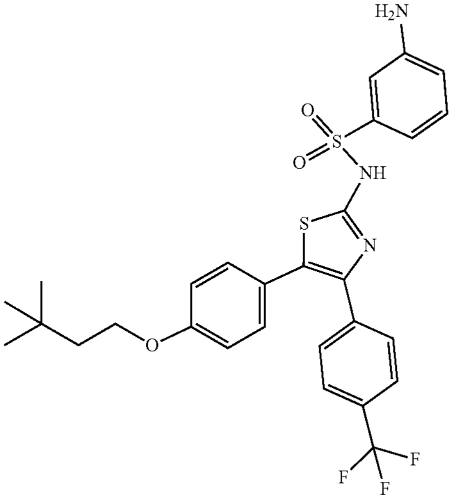 [SMILES: CC(C)(C)CCOc1ccc(-c2sc(NS(=O)(=O)c3cccc(N)c3)nc2-c2ccc(C(F)(F)F)cc2)cc1]
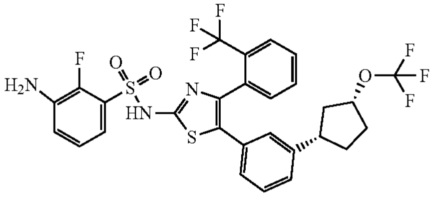 [SMILES: Nc1cccc(S(=O)(=O)Nc2nc(-c3ccccc3C(F)(F)F)c(-c3cccc([C@H]4CC[C@@H](OC(F)(F)F)C4)c3)s2)c1F]
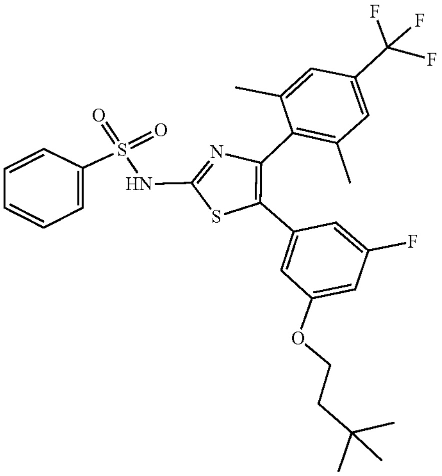 [SMILES: Cc1cc(C(F)(F)F)cc(C)c1-c1nc(NS(=O)(=O)c2ccccc2)sc1-c1cc(F)cc(OCCC(C)(C)C)c1]
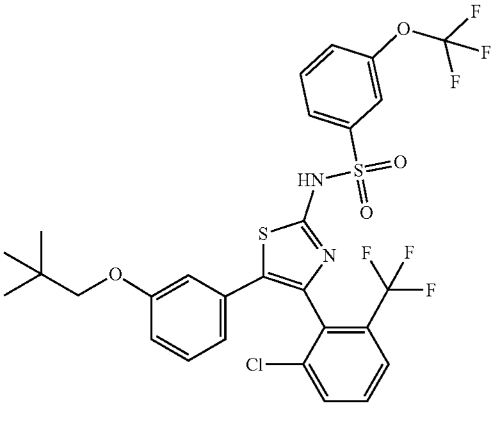 [SMILES: CC(C)(C)COc1cccc(-c2sc(NS(=O)(=O)c3cccc(OC(F)(F)F)c3)nc2-c2c(Cl)cccc2C(F)(F)F)c1]
-continued
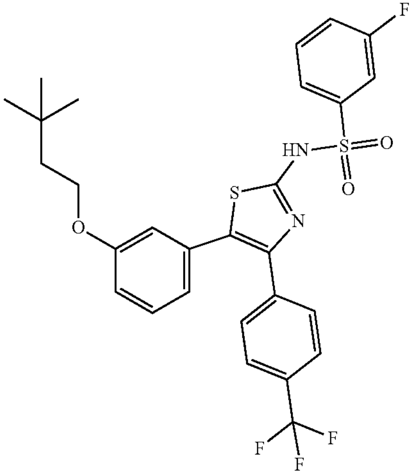 [SMILES: CC(C)(C)CCOc1cccc(-c2sc(NS(=O)(=O)c3cccc(F)c3)nc2-c2ccc(C(F)(F)F)cc2)c1]
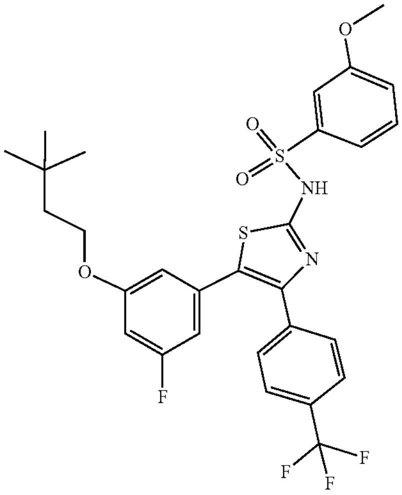 [SMILES: COc1cccc(S(=O)(=O)Nc2nc(-c3ccc(C(F)(F)F)cc3)c(-c3cc(F)cc(OCCC(C)(C)C)c3)s2)c1]
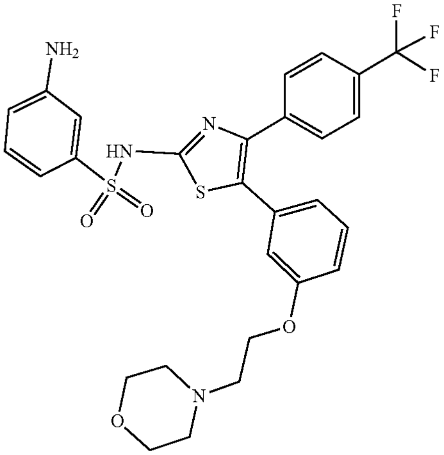 [SMILES: Nc1cccc(S(=O)(=O)Nc2nc(-c3ccc(C(F)(F)F)cc3)c(-c3cccc(OCCN4CCOCC4)c3)s2)c1]

-continued
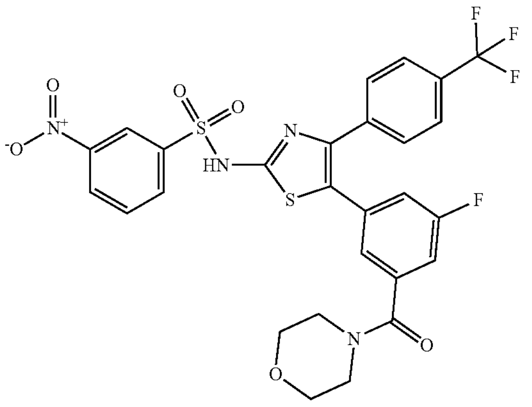
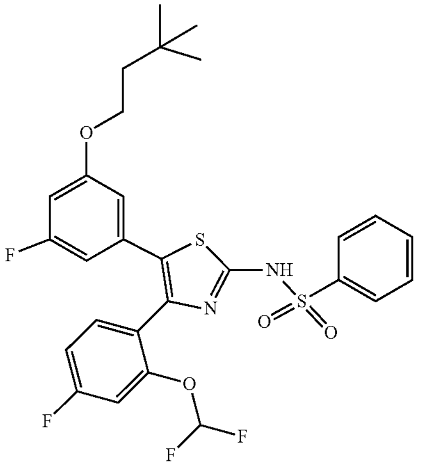 [SMILES: CC(C)(C)CCOc1cc(F)cc(-c2sc(NS(=O)(=O)c3ccccc3)nc2-c2ccc(F)cc2OC(F)F)c1]
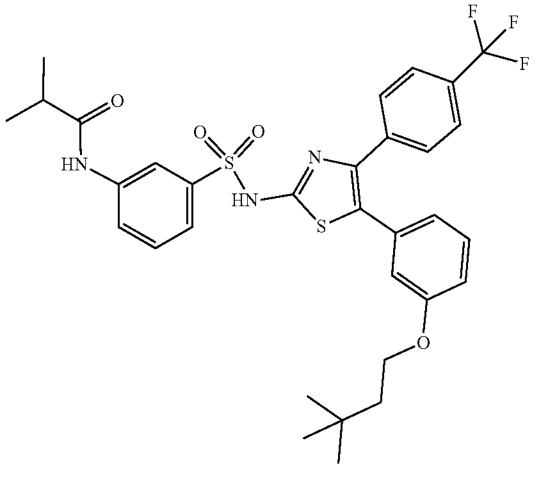 [SMILES: CC(C)C(=O)Nc1cccc(S(=O)(=O)Nc2nc(-c3ccc(C(F)(F)F)cc3)c(-c3cccc(OCCC(C)(C)C)c3)s2)c1]
-continued
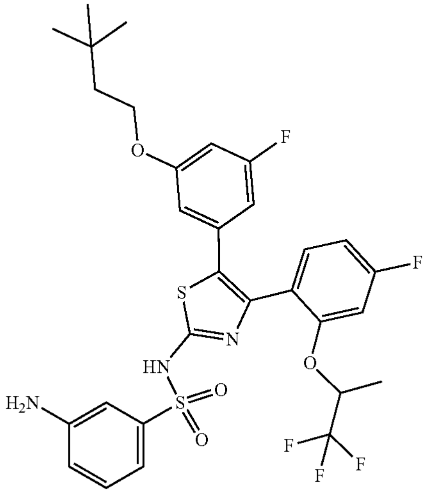 [SMILES: CC(Oc1cc(F)ccc1-c1nc(NS(=O)(=O)c2cccc(N)c2)sc1-c1cc(F)cc(OCCC(C)(C)C)c1)C(F)(F)F]
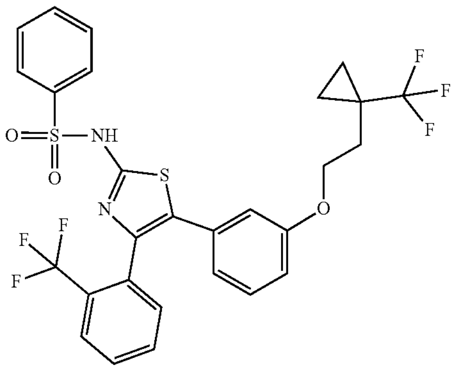 [SMILES: O=S(=O)(Nc1nc(-c2ccccc2C(F)(F)F)c(-c2cccc(OCCC3(C(F)(F)F)CC3)c2)s1)c1ccccc1]
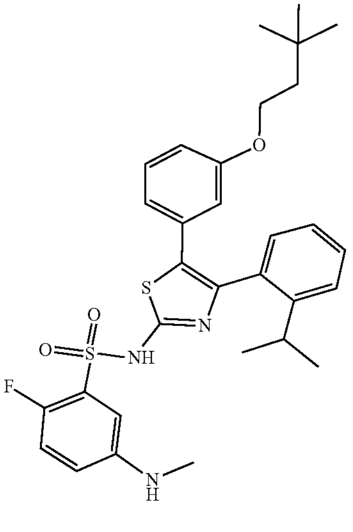 [SMILES: CNc1ccc(F)c(S(=O)(=O)Nc2nc(-c3ccccc3C(C)C)c(-c3cccc(OCCC(C)(C)C)c3)s2)c1]

-continued
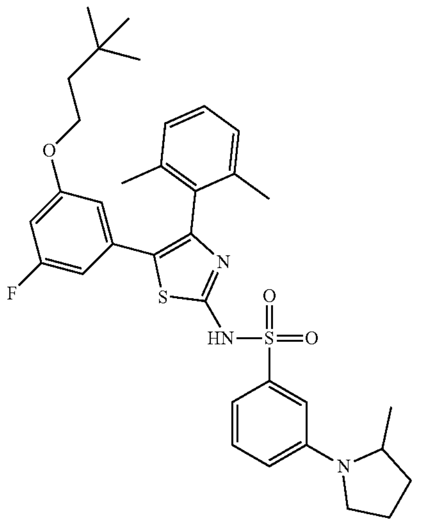 [SMILES: Cc1cccc(C)c1-c1nc(NS(=O)(=O)c2cccc(N3CCCC3C)c2)sc1-c1cc(F)cc(OCCC(C)(C)C)c1]
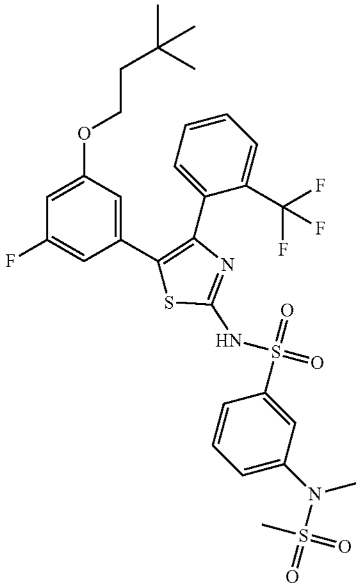 [SMILES: CN(c1cccc(S(=O)(=O)Nc2nc(-c3ccccc3C(F)(F)F)c(-c3cc(F)cc(OCCC(C)(C)C)c3)s2)c1)S(C)(=O)=O]
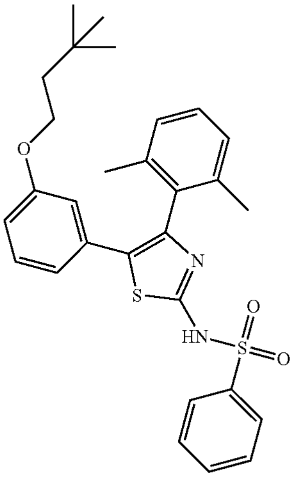 [SMILES: Cc1cccc(C)c1-c1nc(NS(=O)(=O)c2ccccc2)sc1-c1cccc(OCCC(C)(C)C)c1]
-continued
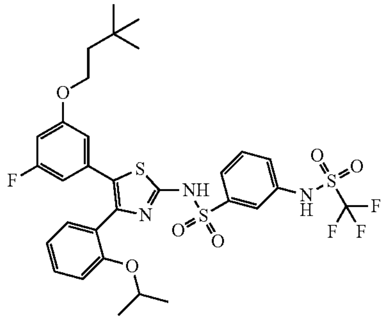 [SMILES: CC(C)Oc1ccccc1-c1nc(NS(=O)(=O)c2cccc(NS(=O)(=O)C(F)(F)F)c2)sc1-c1cc(F)cc(OCCC(C)(C)C)c1]
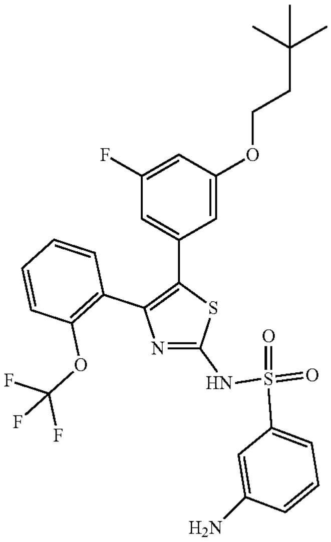 [SMILES: CC(C)(C)CCOc1cc(F)cc(-c2sc(NS(=O)(=O)c3cccc(N)c3)nc2-c2ccccc2OC(F)(F)F)c1]
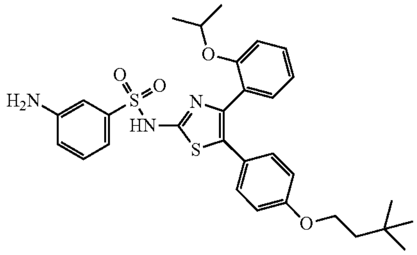 [SMILES: CC(C)Oc1ccccc1-c1nc(NS(=O)(=O)c2cccc(N)c2)sc1-c1ccc(OCCC(C)(C)C)cc1]
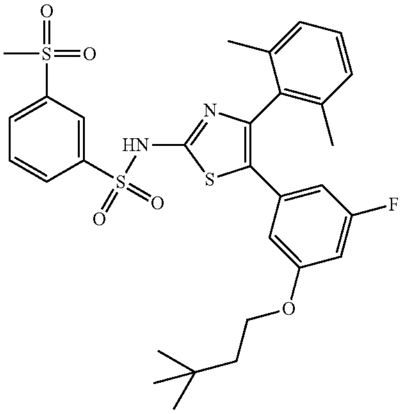 [SMILES: Cc1cccc(C)c1-c1nc(NS(=O)(=O)c2cccc(S(C)(=O)=O)c2)sc1-c1cc(F)cc(OCCC(C)(C)C)c1]

-continued
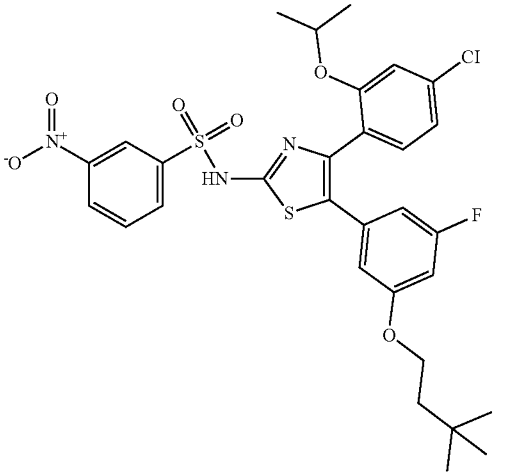
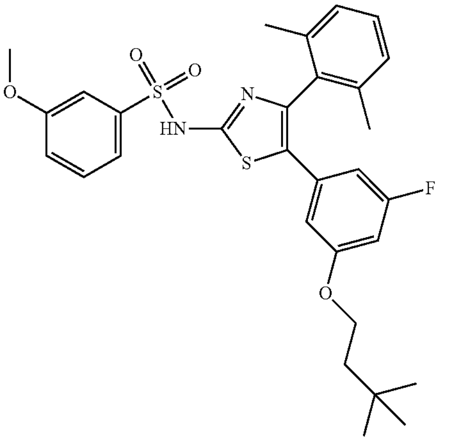 [SMILES: COc1cccc(S(=O)(=O)Nc2nc(-c3c(C)cccc3C)c(-c3cc(F)cc(OCCC(C)(C)C)c3)s2)c1]
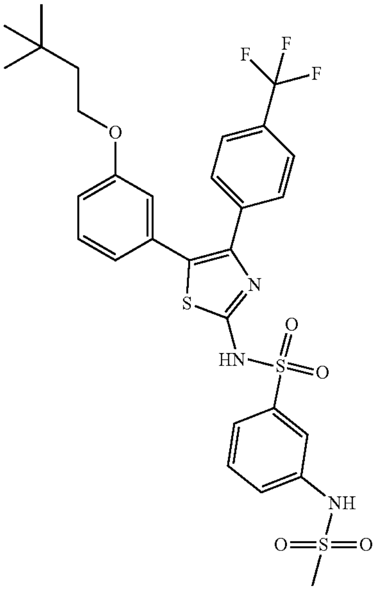 [SMILES: CC(C)(C)CCOc1cccc(-c2sc(NS(=O)(=O)c3cccc(NS(C)(=O)=O)c3)nc2-c2ccc(C(F)(F)F)cc2)c1]
-continued
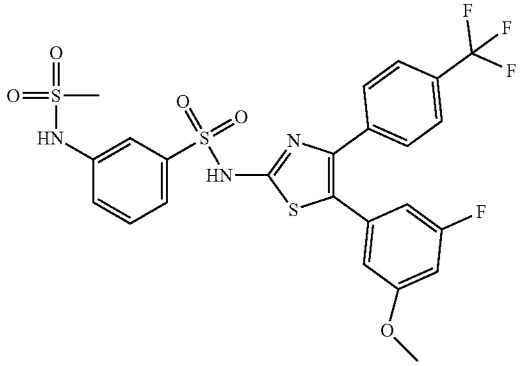 [SMILES: COc1cc(F)cc(-c2sc(NS(=O)(=O)c3cccc(NS(C)(=O)=O)c3)nc2-c2ccc(C(F)(F)F)cc2)c1]
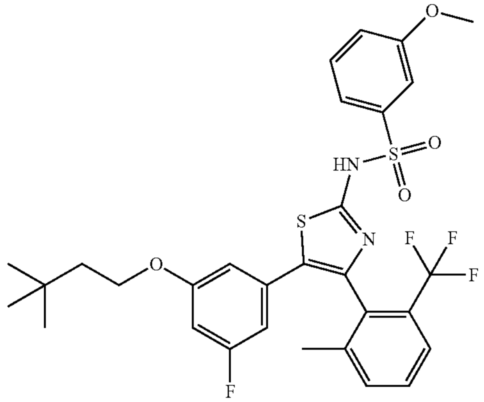 [SMILES: COc1cccc(S(=O)(=O)Nc2nc(-c3c(C)cccc3C(F)(F)F)c(-c3cc(F)cc(OCCC(C)(C)C)c3)s2)c1]
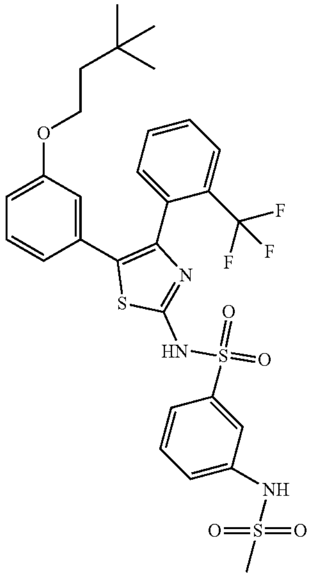 [SMILES: CC(C)(C)CCOc1cccc(-c2sc(NS(=O)(=O)c3cccc(NS(C)(=O)=O)c3)nc2-c2ccccc2C(F)(F)F)c1]

-continued
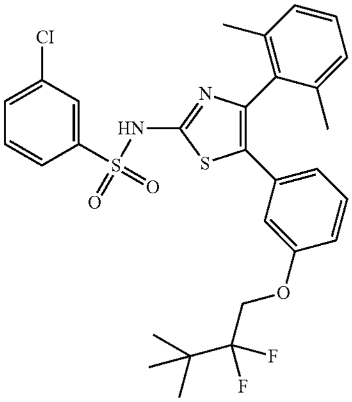
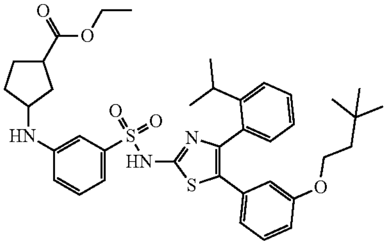 [SMILES: CCOC(=O)C1CCC(Nc2cccc(S(=O)(=O)Nc3nc(-c4ccccc4C(C)C)c(-c4cccc(OCCC(C)(C)C)c4)s3)c2)C1]
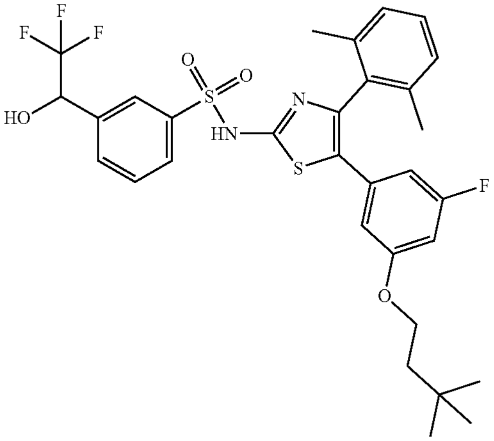 [SMILES: Cc1cccc(C)c1-c1nc(NS(=O)(=O)c2cccc(C(O)C(F)(F)F)c2)sc1-c1cc(F)cc(OCCC(C)(C)C)c1]
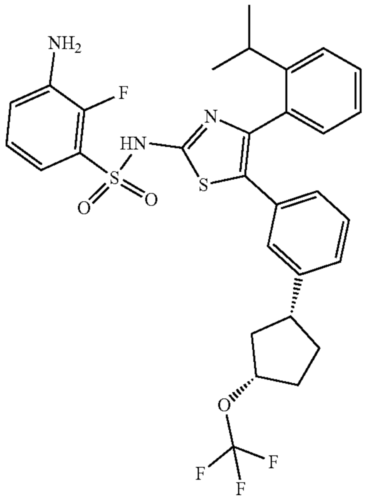 [SMILES: CC(C)c1ccccc1-c1nc(NS(=O)(=O)c2cccc(N)c2F)sc1-c1cccc([C@@H]2CC[C@H](OC(F)(F)F)C2)c1]
-continued
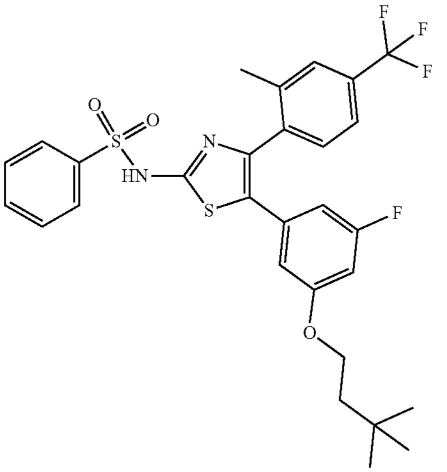 [SMILES: Cc1cc(C(F)(F)F)ccc1-c1nc(NS(=O)(=O)c2ccccc2)sc1-c1cc(F)cc(OCCC(C)(C)C)c1]
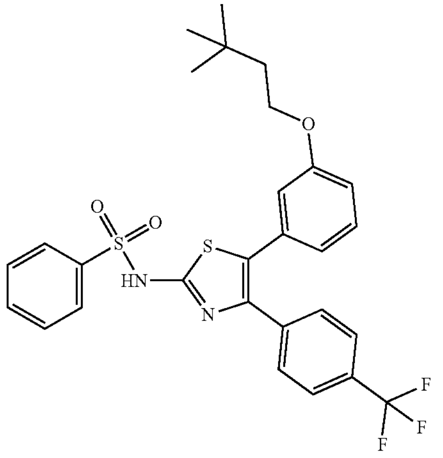 [SMILES: CC(C)(C)CCOc1cccc(-c2sc(NS(=O)(=O)c3ccccc3)nc2-c2ccc(C(F)(F)F)cc2)c1]
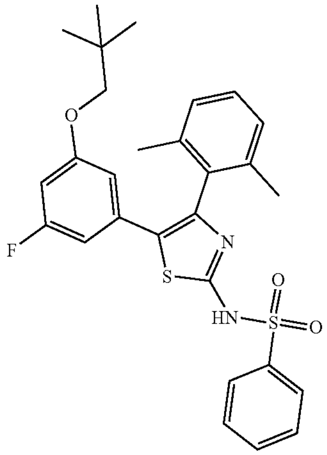 [SMILES: Cc1cccc(C)c1-c1nc(NS(=O)(=O)c2ccccc2)sc1-c1cc(F)cc(OCC(C)(C)C)c1]

-continued
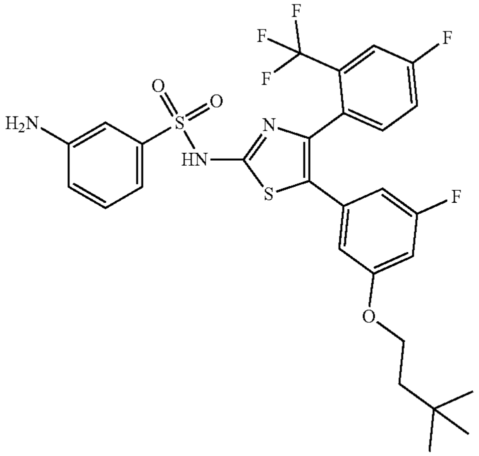 [SMILES: CC(C)(C)CCOc1cc(F)cc(-c2sc(NS(=O)(=O)c3cccc(N)c3)nc2-c2ccc(F)cc2C(F)(F)F)c1]
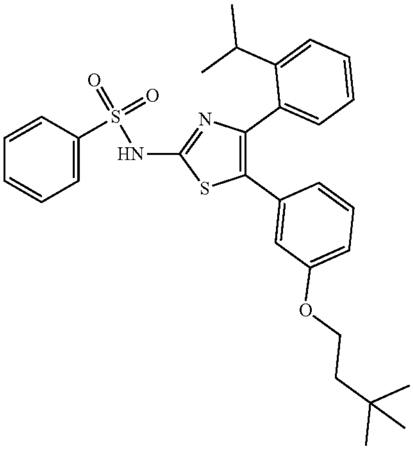 [SMILES: CC(C)c1ccccc1-c1nc(NS(=O)(=O)c2ccccc2)sc1-c1cccc(OCCC(C)(C)C)c1]
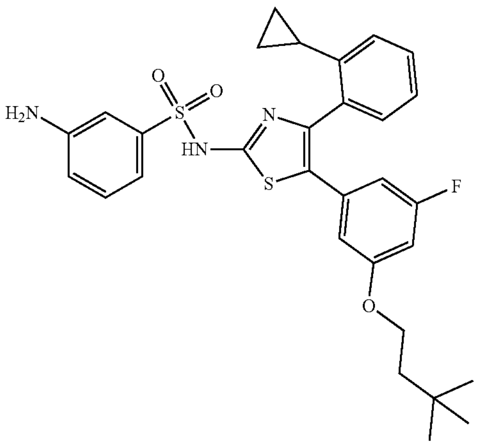 [SMILES: CC(C)(C)CCOc1cc(F)cc(-c2sc(NS(=O)(=O)c3cccc(N)c3)nc2-c2ccccc2C2CC2)c1]
-continued
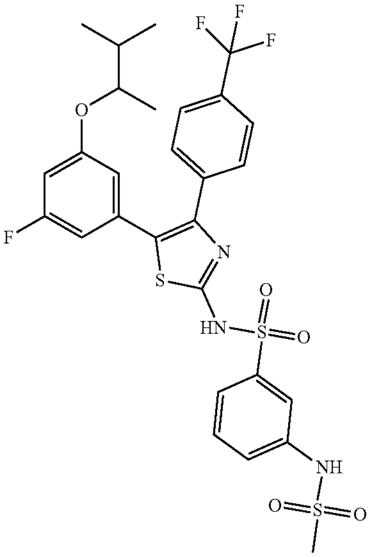 [SMILES: CC(C)C(C)Oc1cc(F)cc(-c2sc(NS(=O)(=O)c3cccc(NS(C)(=O)=O)c3)nc2-c2ccc(C(F)(F)F)cc2)c1]
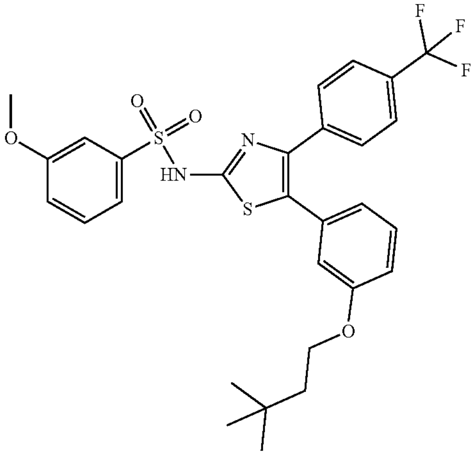 [SMILES: COc1cccc(S(=O)(=O)Nc2nc(-c3ccc(C(F)(F)F)cc3)c(-c3cccc(OCCC(C)(C)C)c3)s2)c1]
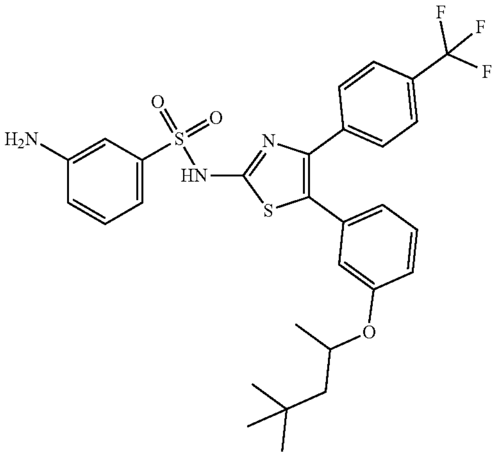 [SMILES: CC(CC(C)(C)C)Oc1cccc(-c2sc(NS(=O)(=O)c3cccc(N)c3)nc2-c2ccc(C(F)(F)F)cc2)c1]

-continued
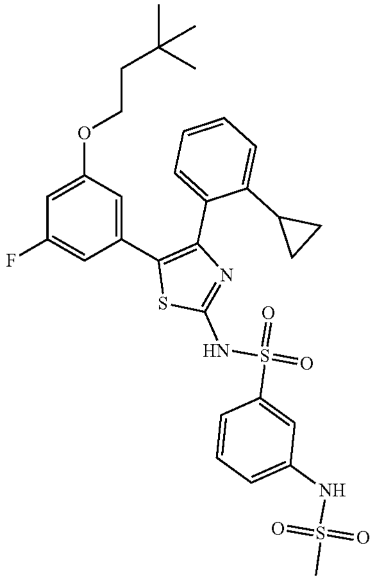 [SMILES: CC(C)(C)CCOc1cc(F)cc(-c2sc(NS(=O)(=O)c3cccc(NS(C)(=O)=O)c3)nc2-c2ccccc2C2CC2)c1]
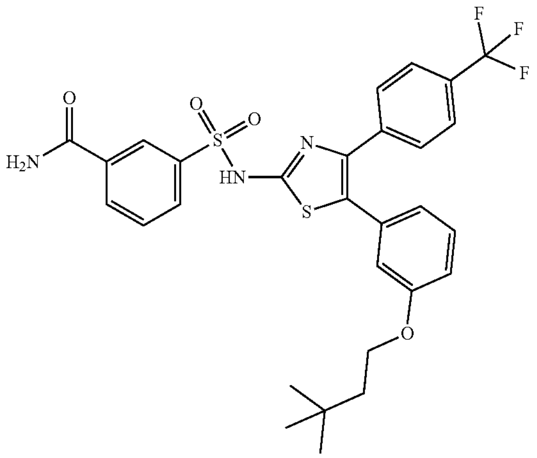 [SMILES: CC(C)(C)CCOc1cccc(-c2sc(NS(=O)(=O)c3cccc(C(N)=O)c3)nc2-c2ccc(C(F)(F)F)cc2)c1]
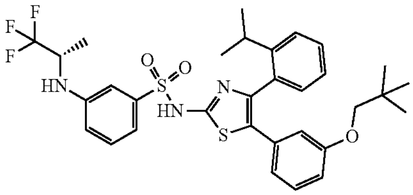 [SMILES: CC(C)c1ccccc1-c1nc(NS(=O)(=O)c2cccc(N[C@@H](C)C(F)(F)F)c2)sc1-c1cccc(OCC(C)(C)C)c1]
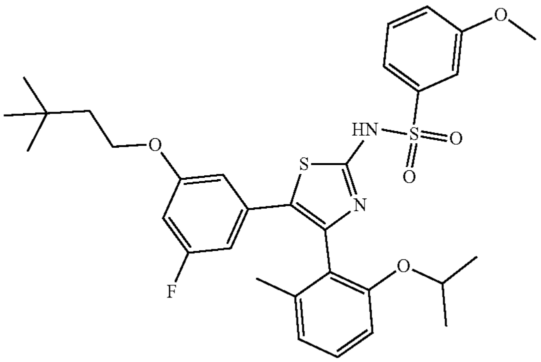 [SMILES: COc1cccc(S(=O)(=O)Nc2nc(-c3c(C)cccc3OC(C)C)c(-c3cc(F)cc(OCCC(C)(C)C)c3)s2)c1]
-continued
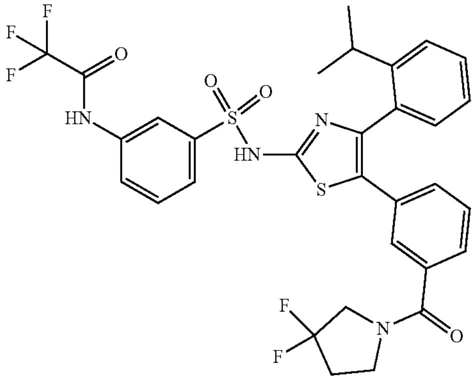 [SMILES: CC(C)c1ccccc1-c1nc(NS(=O)(=O)c2cccc(NC(=O)C(F)(F)F)c2)sc1-c1cccc(C(=O)N2CCC(F)(F)C2)c1]
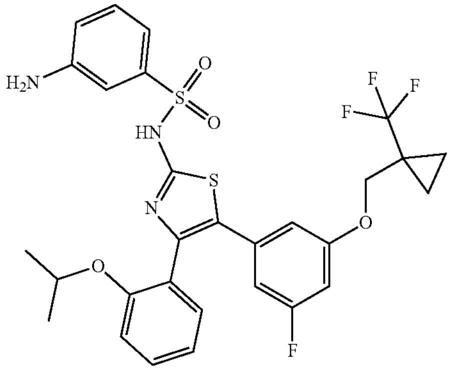 [SMILES: CC(C)Oc1ccccc1-c1nc(NS(=O)(=O)c2cccc(N)c2)sc1-c1cc(F)cc(OCC2(C(F)(F)F)CC2)c1]
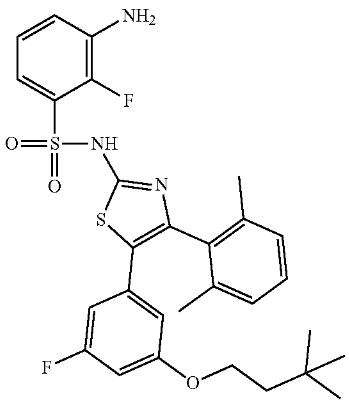 [SMILES: Cc1cccc(C)c1-c1nc(NS(=O)(=O)c2cccc(N)c2F)sc1-c1cc(F)cc(OCCC(C)(C)C)c1]
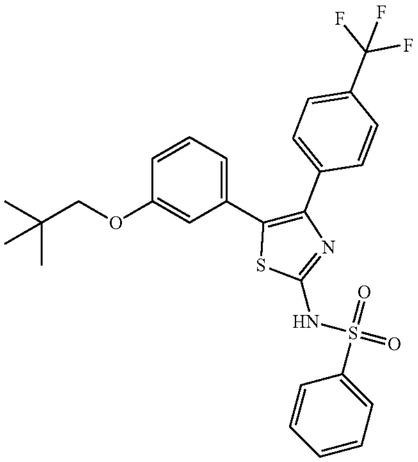 [SMILES: CC(C)(C)COc1cccc(-c2sc(NS(=O)(=O)c3ccccc3)nc2-c2ccc(C(F)(F)F)cc2)c1]

-continued
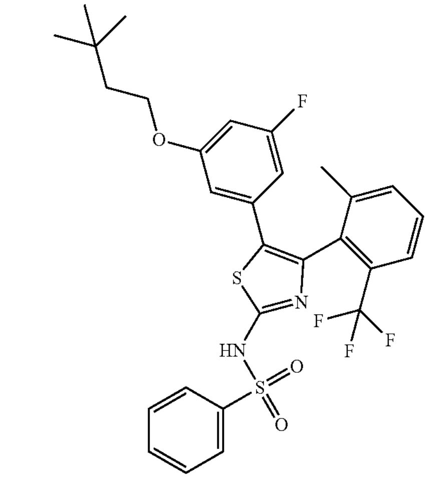 [SMILES: Cc1cccc(C(F)(F)F)c1-c1nc(NS(=O)(=O)c2ccccc2)sc1-c1cc(F)cc(OCCC(C)(C)C)c1]
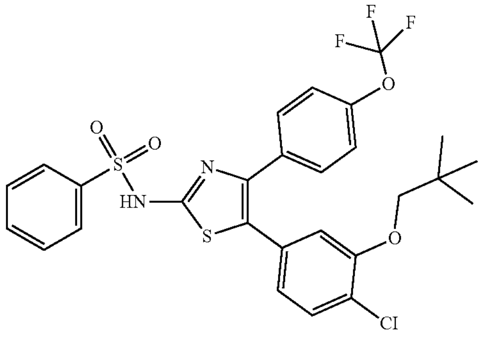
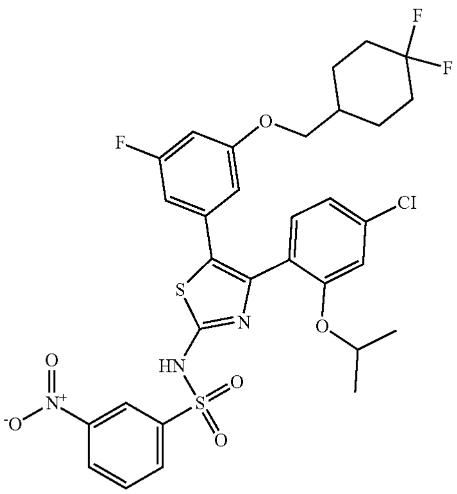
-continued
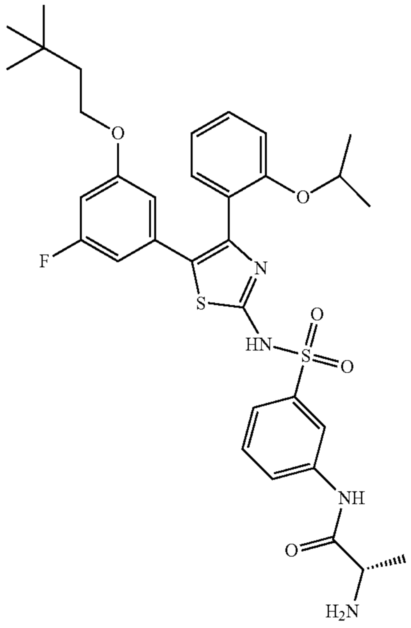 [SMILES: CC(C)Oc1ccccc1-c1nc(NS(=O)(=O)c2cccc(NC(=O)[C@H](C)N)c2)sc1-c1cc(F)cc(OCCC(C)(C)C)c1]
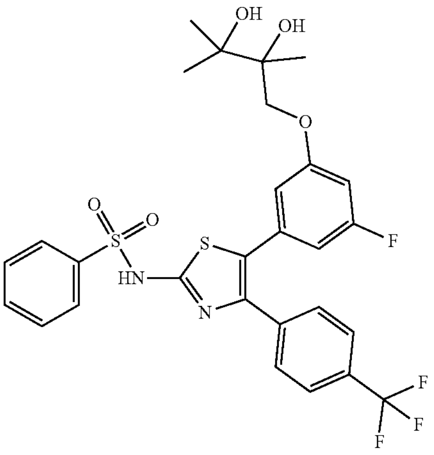 [SMILES: CC(C)(O)C(C)(O)COc1cc(F)cc(-c2sc(NS(=O)(=O)c3ccccc3)nc2-c2ccc(C(F)(F)F)cc2)c1]
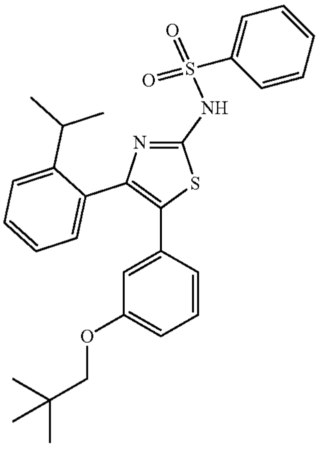 [SMILES: CC(C)c1ccccc1-c1nc(NS(=O)(=O)c2ccccc2)sc1-c1cccc(OCC(C)(C)C)c1]

-continued
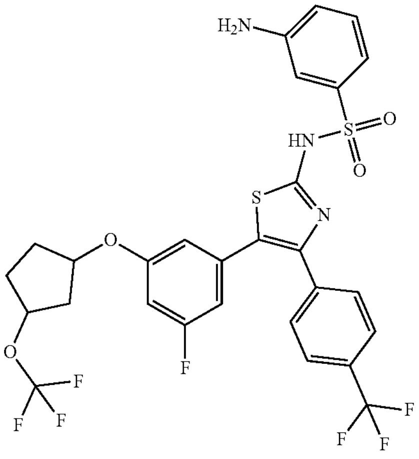 [SMILES: Nc1cccc(S(=O)(=O)Nc2nc(-c3ccc(C(F)(F)F)cc3)c(-c3cc(F)cc(OC4CCC(OC(F)(F)F)C4)c3)s2)c1]
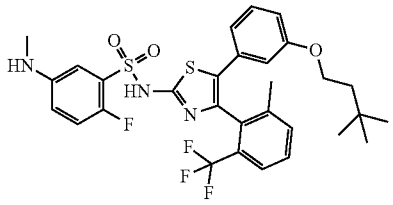 [SMILES: CNc1ccc(F)c(S(=O)(=O)Nc2nc(-c3c(C)cccc3C(F)(F)F)c(-c3cccc(OCCC(C)(C)C)c3)s2)c1]
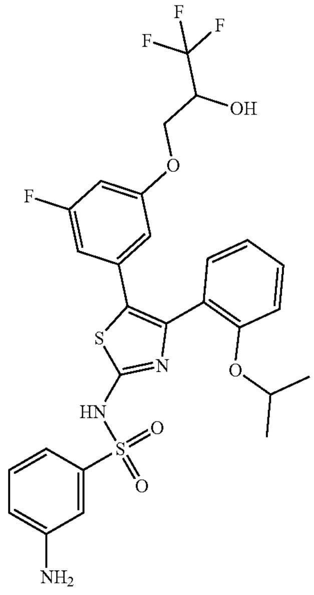 [SMILES: CC(C)Oc1ccccc1-c1nc(NS(=O)(=O)c2cccc(N)c2)sc1-c1cc(F)cc(OCC(O)C(F)(F)F)c1]
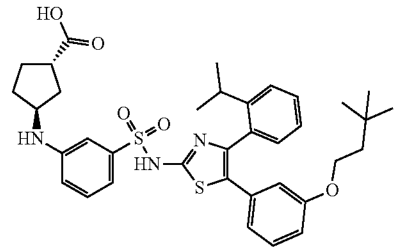 [SMILES: CC(C)c1ccccc1-c1nc(NS(=O)(=O)c2cccc(N[C@H]3CC[C@H](C(=O)O)C3)c2)sc1-c1cccc(OCCC(C)(C)C)c1]
-continued
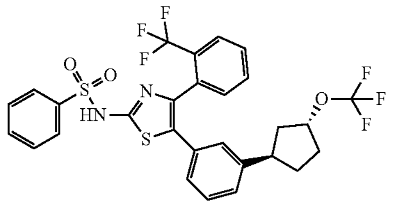 [SMILES: O=S(=O)(Nc1nc(-c2ccccc2C(F)(F)F)c(-c2cccc([C@@H]3CC[C@@H](OC(F)(F)F)C3)c2)s1)c1ccccc1]
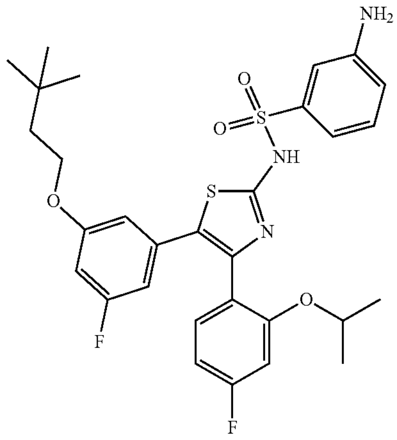 [SMILES: CC(C)Oc1cc(F)ccc1-c1nc(NS(=O)(=O)c2cccc(N)c2)sc1-c1cc(F)cc(OCCC(C)(C)C)c1]
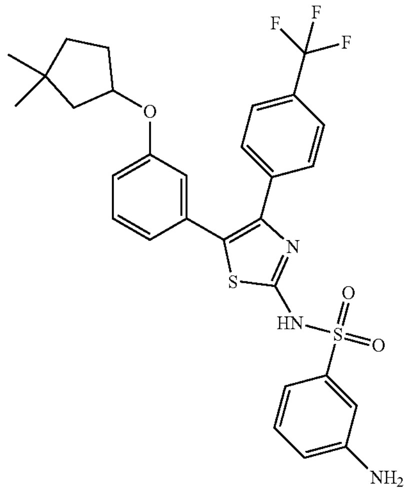 [SMILES: CC1(C)CCC(Oc2cccc(-c3sc(NS(=O)(=O)c4cccc(N)c4)nc3-c3ccc(C(F)(F)F)cc3)c2)C1]
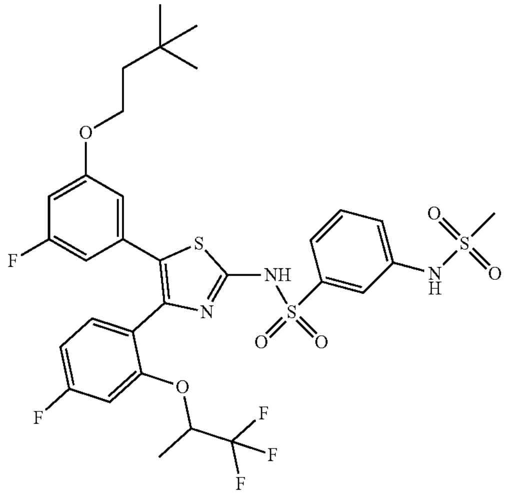 [SMILES: CC(Oc1cc(F)ccc1-c1nc(NS(=O)(=O)c2cccc(NS(C)(=O)=O)c2)sc1-c1cc(F)cc(OCCC(C)(C)C)c1)C(F)(F)F]

-continued
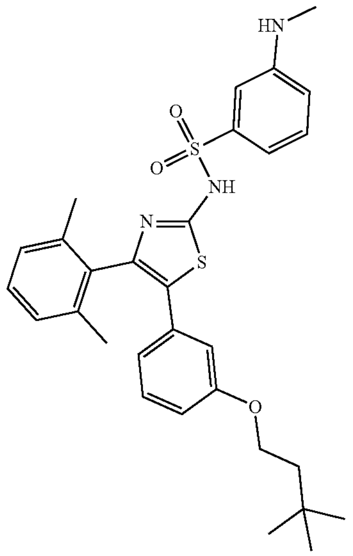 [SMILES: CNc1cccc(S(=O)(=O)Nc2nc(-c3c(C)cccc3C)c(-c3cccc(OCCC(C)(C)C)c3)s2)c1]
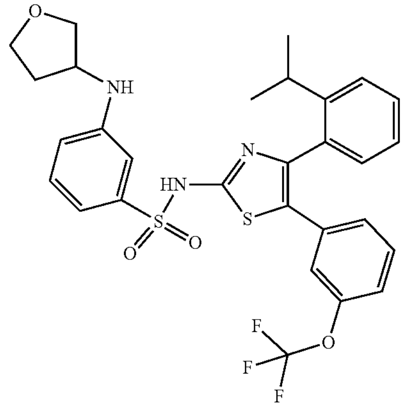 [SMILES: CC(C)c1ccccc1-c1nc(NS(=O)(=O)c2cccc(NC3CCOC3)c2)sc1-c1cccc(OC(F)(F)F)c1]
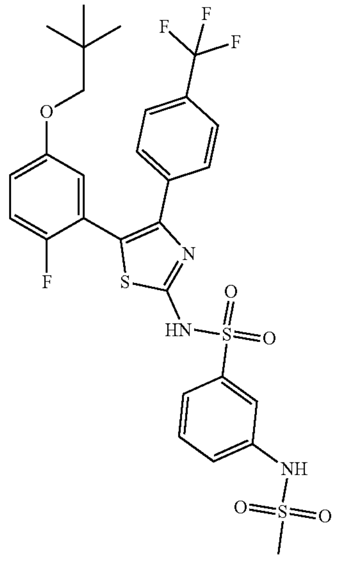 [SMILES: CC(C)(C)COc1ccc(F)c(-c2sc(NS(=O)(=O)c3cccc(NS(C)(=O)=O)c3)nc2-c2ccc(C(F)(F)F)cc2)c1]
-continued
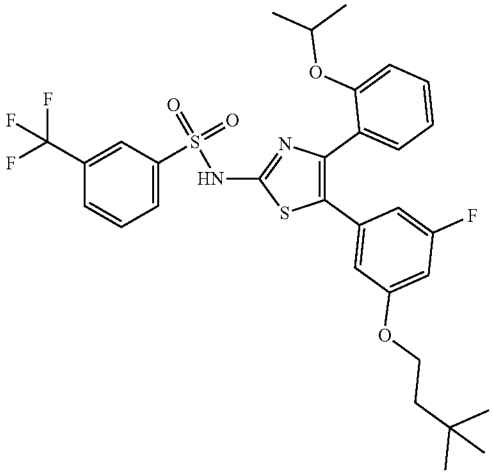 [SMILES: CC(C)Oc1ccccc1-c1nc(NS(=O)(=O)c2cccc(C(F)(F)F)c2)sc1-c1cc(F)cc(OCCC(C)(C)C)c1]
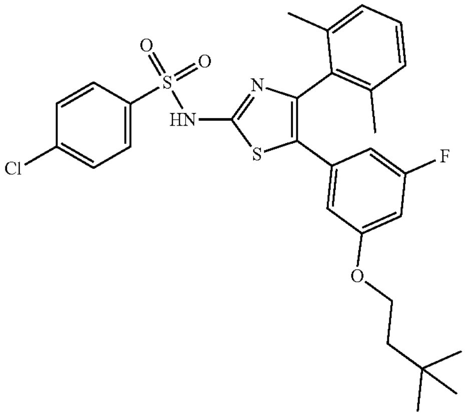 [SMILES: Cc1cccc(C)c1-c1nc(NS(=O)(=O)c2ccc(Cl)cc2)sc1-c1cc(F)cc(OCCC(C)(C)C)c1]
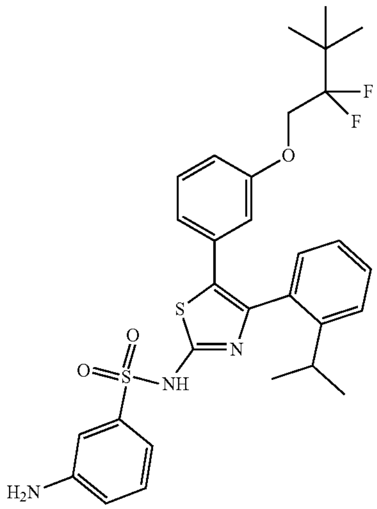 [SMILES: CC(C)c1ccccc1-c1nc(NS(=O)(=O)c2cccc(N)c2)sc1-c1cccc(OCC(F)(F)C(C)(C)C)c1]

-continued
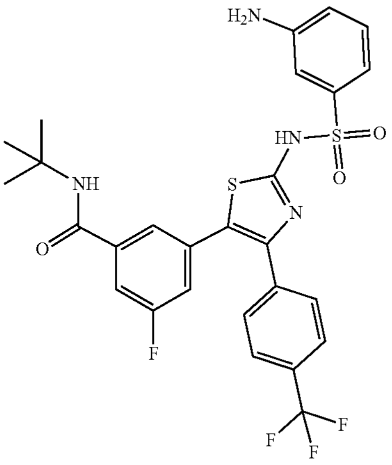 [SMILES: CC(C)(C)NC(=O)c1cc(F)cc(-c2sc(NS(=O)(=O)c3cccc(N)c3)nc2-c2ccc(C(F)(F)F)cc2)c1]
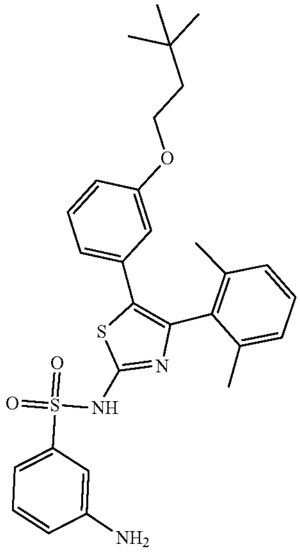 [SMILES: Cc1cccc(C)c1-c1nc(NS(=O)(=O)c2cccc(N)c2)sc1-c1cccc(OCCC(C)(C)C)c1]
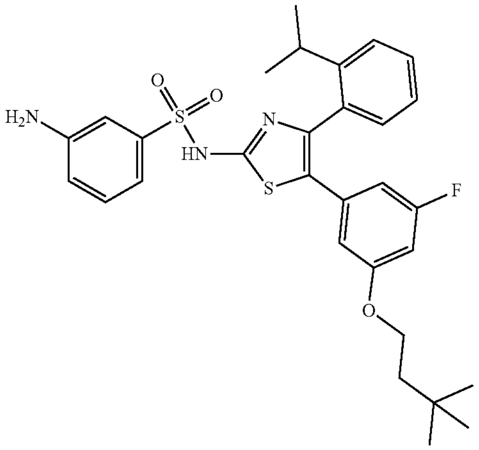 [SMILES: CC(C)c1ccccc1-c1nc(NS(=O)(=O)c2cccc(N)c2)sc1-c1cc(F)cc(OCCC(C)(C)C)c1]
-continued
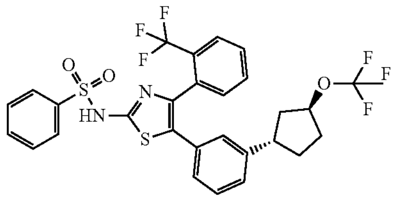
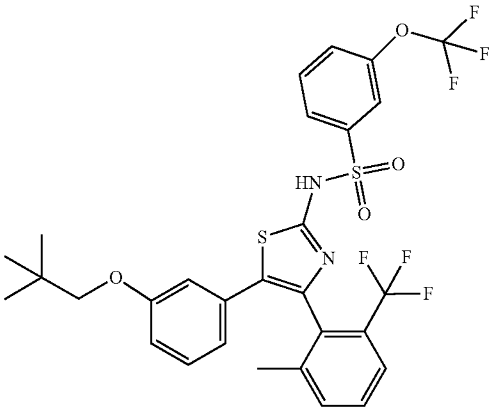 [SMILES: Cc1cccc(C(F)(F)F)c1-c1nc(NS(=O)(=O)c2cccc(OC(F)(F)F)c2)sc1-c1cccc(OCC(C)(C)C)c1]
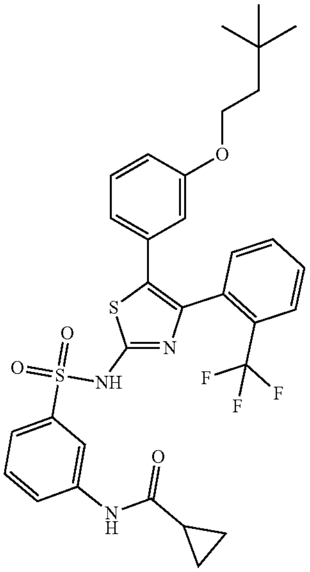 [SMILES: CC(C)(C)CCOc1cccc(-c2sc(NS(=O)(=O)c3cccc(NC(=O)C4CC4)c3)nc2-c2ccccc2C(F)(F)F)c1]
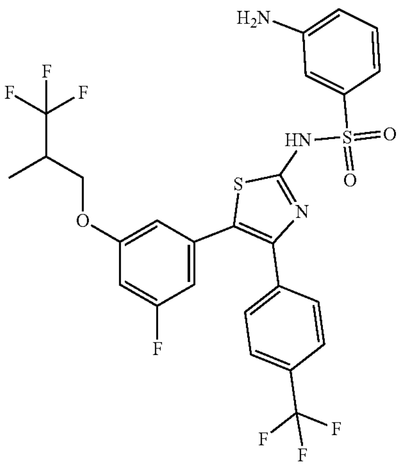 [SMILES: CC(COc1cc(F)cc(-c2sc(NS(=O)(=O)c3cccc(N)c3)nc2-c2ccc(C(F)(F)F)cc2)c1)C(F)(F)F]

-continued
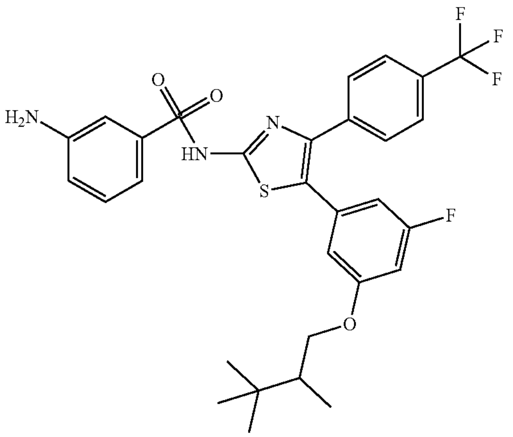
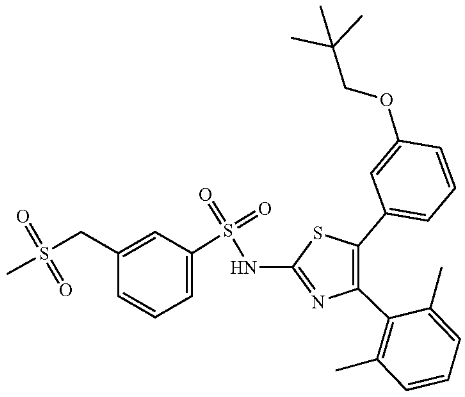 [SMILES: Cc1cccc(C)c1-c1nc(NS(=O)(=O)c2cccc(CS(C)(=O)=O)c2)sc1-c1cccc(OCC(C)(C)C)c1]
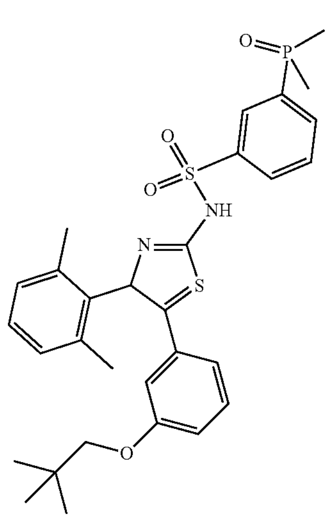
-continued
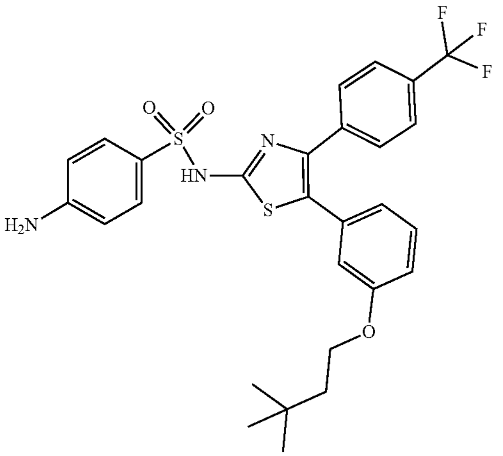 [SMILES: CC(C)(C)CCOc1cccc(-c2sc(NS(=O)(=O)c3ccc(N)cc3)nc2-c2ccc(C(F)(F)F)cc2)c1]
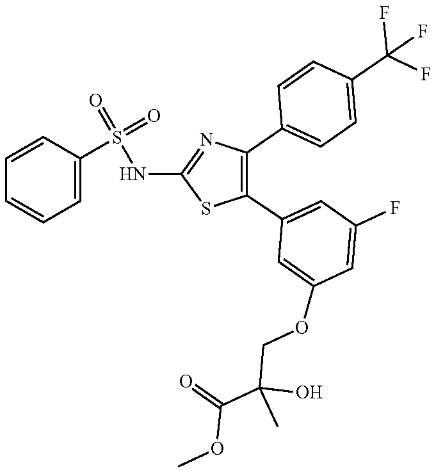 [SMILES: COC(=O)C(C)(O)COc1cc(F)cc(-c2sc(NS(=O)(=O)c3ccccc3)nc2-c2ccc(C(F)(F)F)cc2)c1]
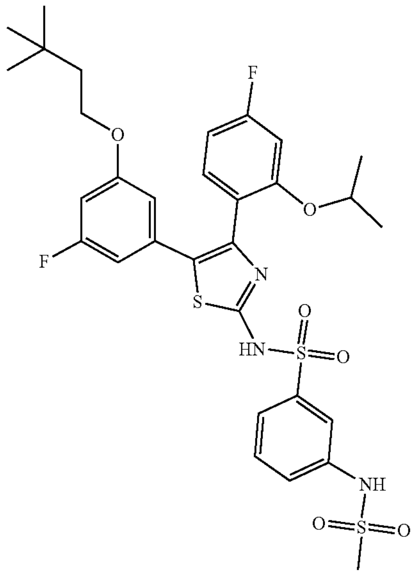 [SMILES: CC(C)Oc1cc(F)ccc1-c1nc(NS(=O)(=O)c2cccc(NS(C)(=O)=O)c2)sc1-c1cc(F)cc(OCCC(C)(C)C)c1]

-continued
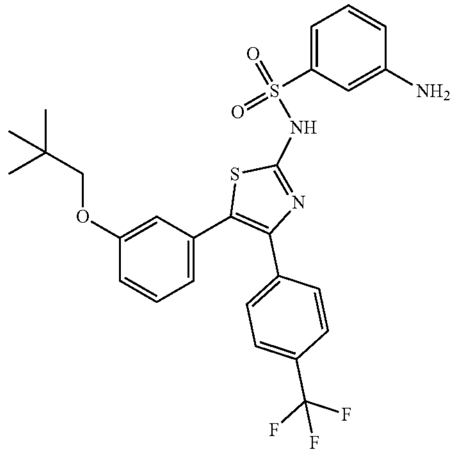 [SMILES: CC(C)(C)COc1cccc(-c2sc(NS(=O)(=O)c3cccc(N)c3)nc2-c2ccc(C(F)(F)F)cc2)c1]
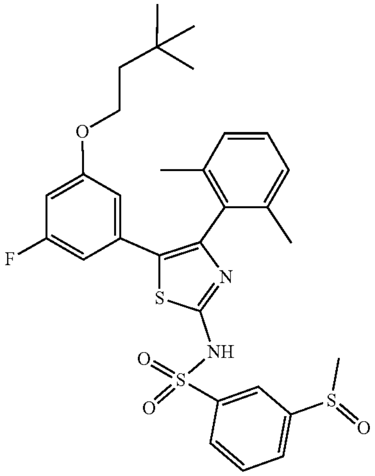 [SMILES: Cc1cccc(C)c1-c1nc(NS(=O)(=O)c2cccc(S(C)=O)c2)sc1-c1cc(F)cc(OCCC(C)(C)C)c1]
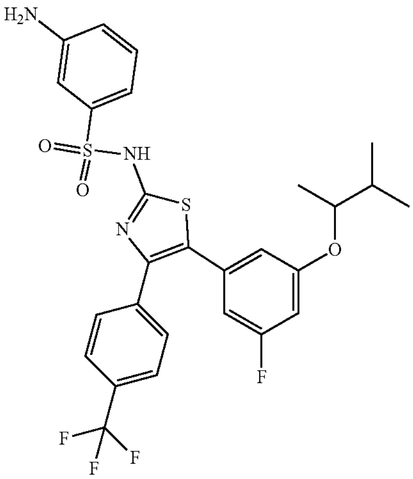 [SMILES: CC(C)C(C)Oc1cc(F)cc(-c2sc(NS(=O)(=O)c3cccc(N)c3)nc2-c2ccc(C(F)(F)F)cc2)c1]
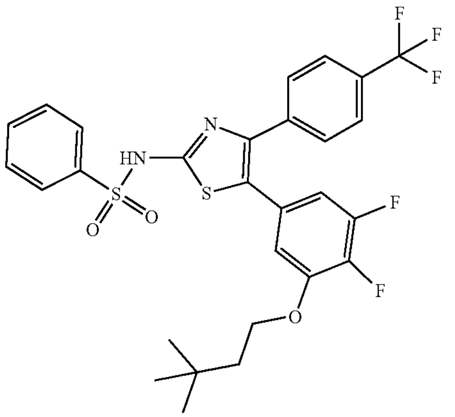 [SMILES: CC(C)(C)CCOc1cc(-c2sc(NS(=O)(=O)c3ccccc3)nc2-c2ccc(C(F)(F)F)cc2)cc(F)c1F]
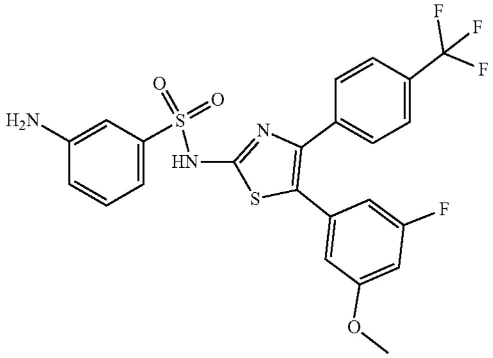 [SMILES: COc1cc(F)cc(-c2sc(NS(=O)(=O)c3cccc(N)c3)nc2-c2ccc(C(F)(F)F)cc2)c1]
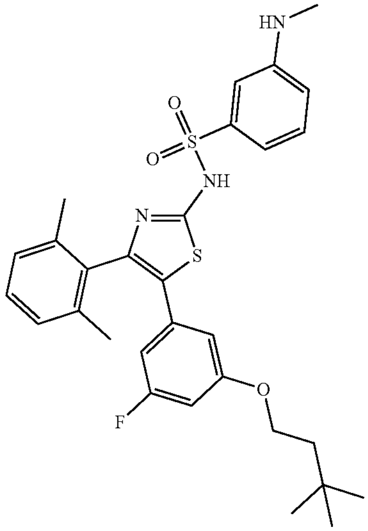 [SMILES: CNc1cccc(S(=O)(=O)Nc2nc(-c3c(C)cccc3C)c(-c3cc(F)cc(OCCC(C)(C)C)c3)s2)c1]

-continued
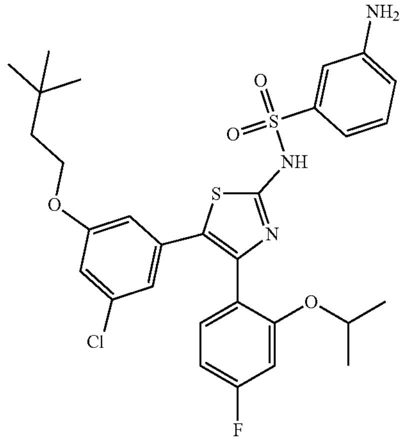 [SMILES: CC(C)Oc1cc(F)ccc1-c1nc(NS(=O)(=O)c2cccc(N)c2)sc1-c1cc(Cl)cc(OCCC(C)(C)C)c1]
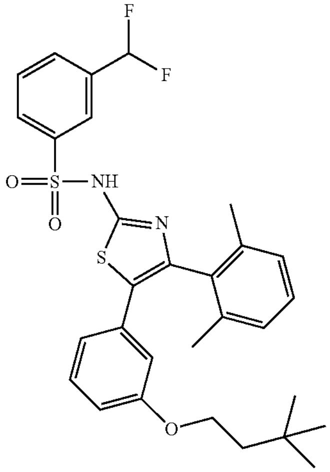 [SMILES: Cc1cccc(C)c1-c1nc(NS(=O)(=O)c2cccc(C(F)F)c2)sc1-c1cccc(OCCC(C)(C)C)c1]
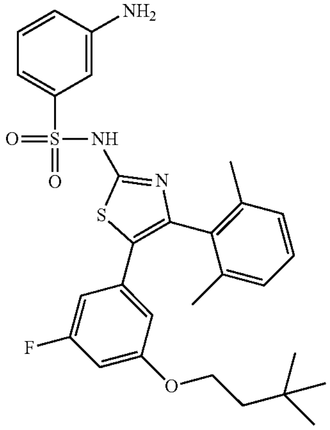 [SMILES: Cc1cccc(C)c1-c1nc(NS(=O)(=O)c2cccc(N)c2)sc1-c1cc(F)cc(OCCC(C)(C)C)c1]
-continued
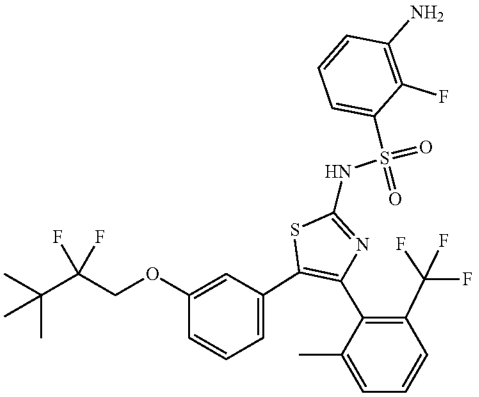 [SMILES: Cc1cccc(C(F)(F)F)c1-c1nc(NS(=O)(=O)c2cccc(N)c2F)sc1-c1cccc(OCC(F)(F)C(C)(C)C)c1]
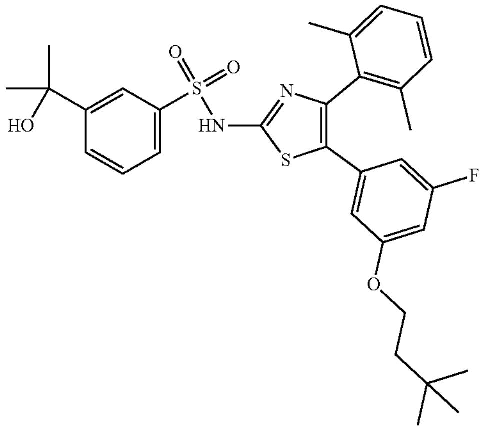 [SMILES: Cc1cccc(C)c1-c1nc(NS(=O)(=O)c2cccc(C(C)(C)O)c2)sc1-c1cc(F)cc(OCCC(C)(C)C)c1]
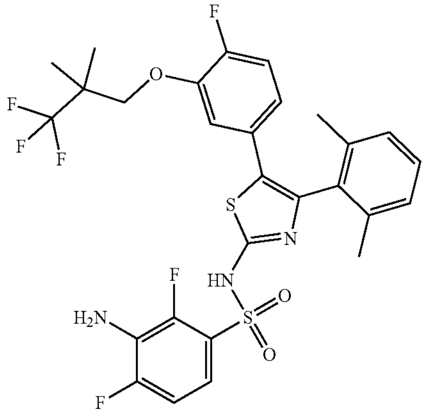 [SMILES: Cc1cccc(C)c1-c1nc(NS(=O)(=O)c2ccc(F)c(N)c2F)sc1-c1ccc(F)c(OCC(C)(C)C(F)(F)F)c1]
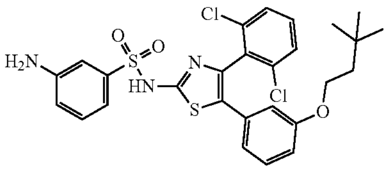 [SMILES: CC(C)(C)CCOc1cccc(-c2sc(NS(=O)(=O)c3cccc(N)c3)nc2-c2c(Cl)cccc2Cl)c1]

-continued
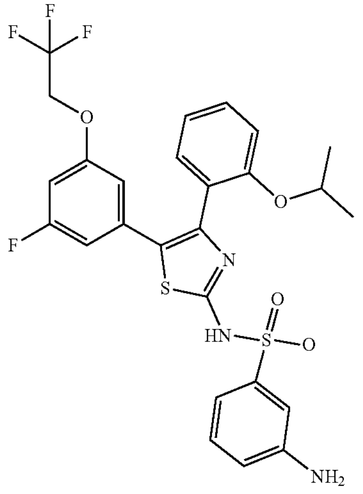
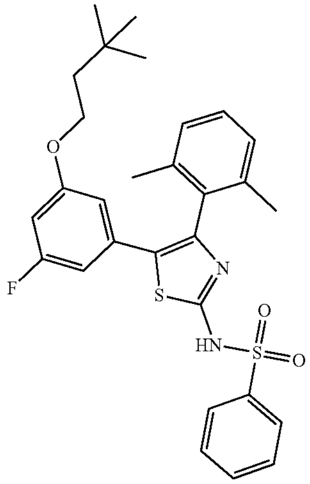 [SMILES: Cc1cccc(C)c1-c1nc(NS(=O)(=O)c2ccccc2)sc1-c1cc(F)cc(OCCC(C)(C)C)c1]
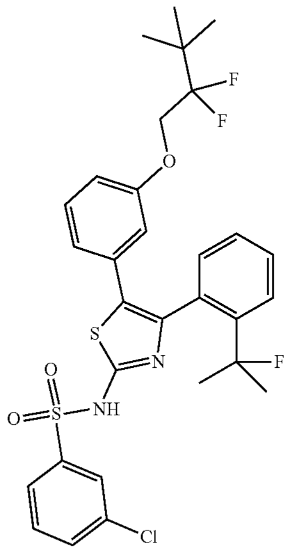 [SMILES: CC(C)(F)c1ccccc1-c1nc(NS(=O)(=O)c2cccc(Cl)c2)sc1-c1cccc(OCC(F)(F)C(C)(C)C)c1]
-continued
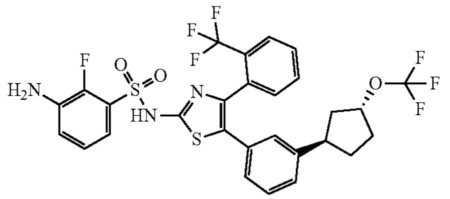 [SMILES: Nc1cccc(S(=O)(=O)Nc2nc(-c3ccccc3C(F)(F)F)c(-c3cccc([C@@H]4CC[C@@H](OC(F)(F)F)C4)c3)s2)c1F]
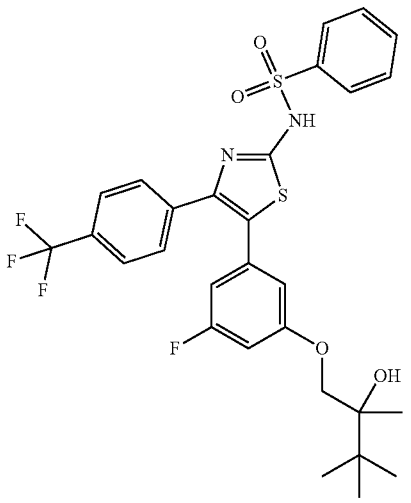 [SMILES: CC(C)(C)C(C)(O)COc1cc(F)cc(-c2sc(NS(=O)(=O)c3ccccc3)nc2-c2ccc(C(F)(F)F)cc2)c1]
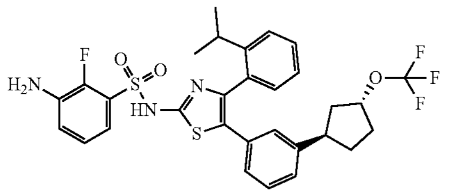 [SMILES: CC(C)c1ccccc1-c1nc(NS(=O)(=O)c2cccc(N)c2F)sc1-c1cccc([C@@H]2CC[C@@H](OC(F)(F)F)C2)c1]
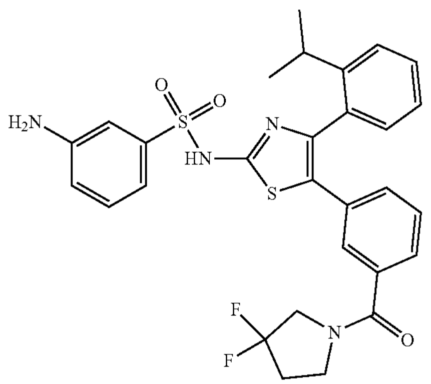 [SMILES: CC(C)c1ccccc1-c1nc(NS(=O)(=O)c2cccc(N)c2)sc1-c1cccc(C(=O)N2CCC(F)(F)C2)c1]

-continued
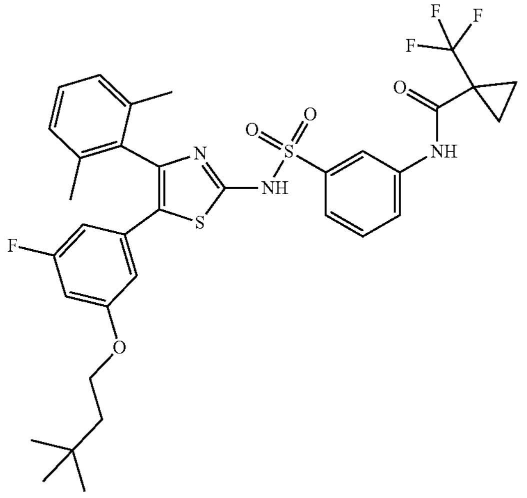 [SMILES: Cc1cccc(C)c1-c1nc(NS(=O)(=O)c2cccc(NC(=O)C3(C(F)(F)F)CC3)c2)sc1-c1cc(F)cc(OCCC(C)(C)C)c1]
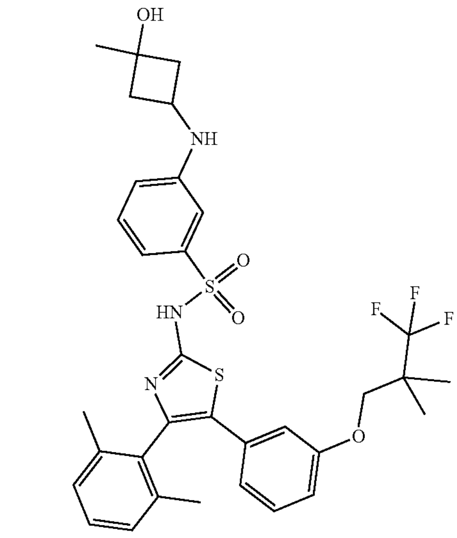 [SMILES: Cc1cccc(C)c1-c1nc(NS(=O)(=O)c2cccc(NC3CC(C)(O)C3)c2)sc1-c1cccc(OCC(C)(C)C(F)(F)F)c1]
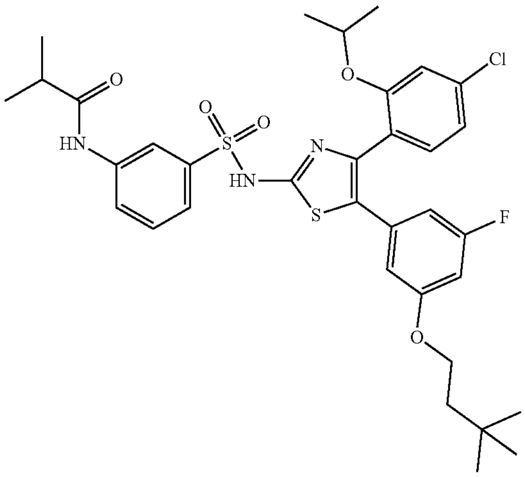 [SMILES: CC(C)Oc1cc(Cl)ccc1-c1nc(NS(=O)(=O)c2cccc(NC(=O)C(C)C)c2)sc1-c1cc(F)cc(OCCC(C)(C)C)c1]
-continued
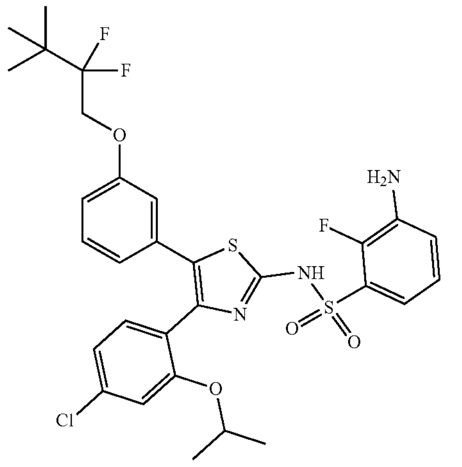 [SMILES: CC(C)Oc1cc(Cl)ccc1-c1nc(NS(=O)(=O)c2cccc(N)c2F)sc1-c1cccc(OCC(F)(F)C(C)(C)C)c1]
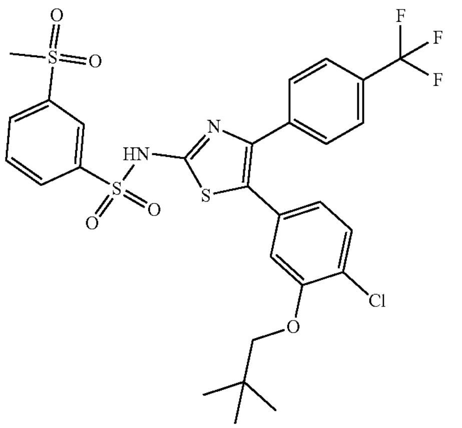 [SMILES: CC(C)(C)COc1cc(-c2sc(NS(=O)(=O)c3cccc(S(C)(=O)=O)c3)nc2-c2ccc(C(F)(F)F)cc2)ccc1Cl]
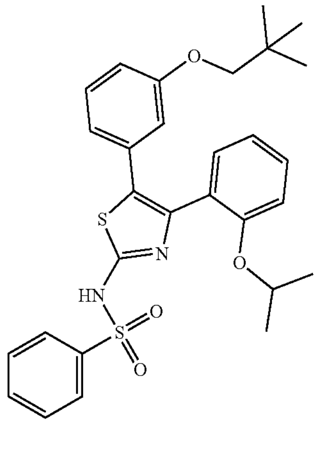 [SMILES: CC(C)Oc1ccccc1-c1nc(NS(=O)(=O)c2ccccc2)sc1-c1cccc(OCC(C)(C)C)c1]

-continued
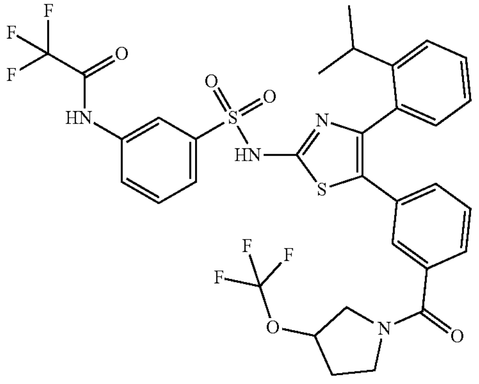 [SMILES: CC(C)c1ccccc1-c1nc(NS(=O)(=O)c2cccc(NC(=O)C(F)(F)F)c2)sc1-c1cccc(C(=O)N2CCC(OC(F)(F)F)C2)c1]
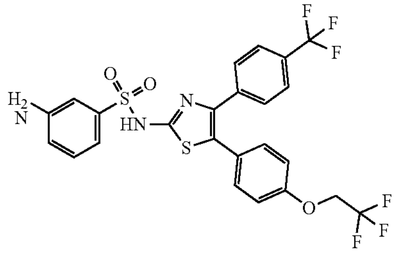 [SMILES: Nc1cccc(S(=O)(=O)Nc2nc(-c3ccc(C(F)(F)F)cc3)c(-c3ccc(OCC(F)(F)F)cc3)s2)c1]
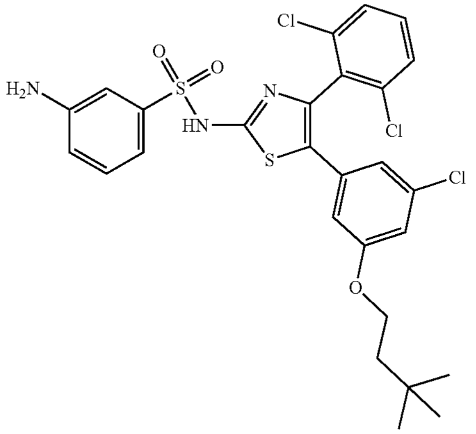 [SMILES: CC(C)(C)CCOc1cc(Cl)cc(-c2sc(NS(=O)(=O)c3cccc(N)c3)nc2-c2c(Cl)cccc2Cl)c1]
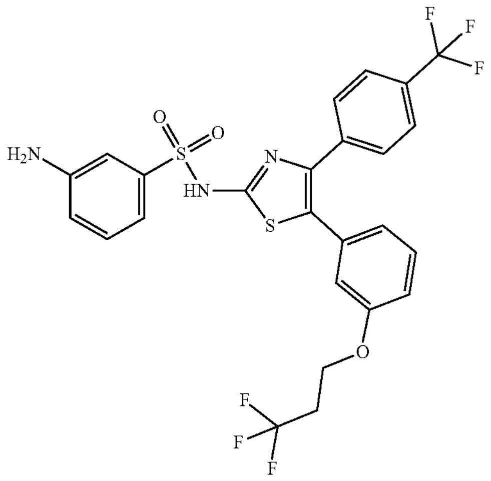 [SMILES: Nc1cccc(S(=O)(=O)Nc2nc(-c3ccc(C(F)(F)F)cc3)c(-c3cccc(OCCC(F)(F)F)c3)s2)c1]
-continued
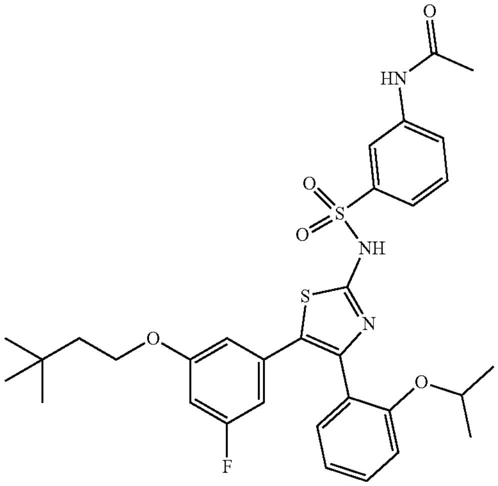 [SMILES: CC(=O)Nc1cccc(S(=O)(=O)Nc2nc(-c3ccccc3OC(C)C)c(-c3cc(F)cc(OCCC(C)(C)C)c3)s2)c1]
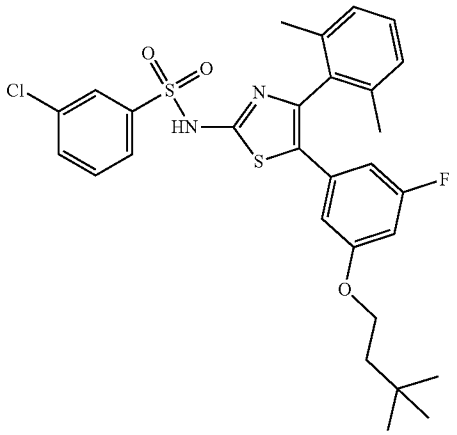 [SMILES: Cc1cccc(C)c1-c1nc(NS(=O)(=O)c2cccc(Cl)c2)sc1-c1cc(F)cc(OCCC(C)(C)C)c1]
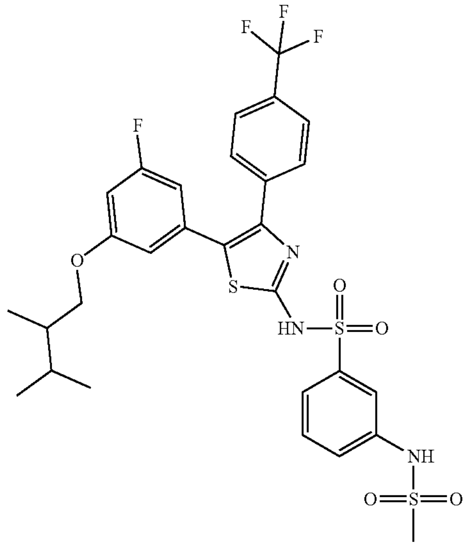 [SMILES: CC(C)C(C)COc1cc(F)cc(-c2sc(NS(=O)(=O)c3cccc(NS(C)(=O)=O)c3)nc2-c2ccc(C(F)(F)F)cc2)c1]

-continued
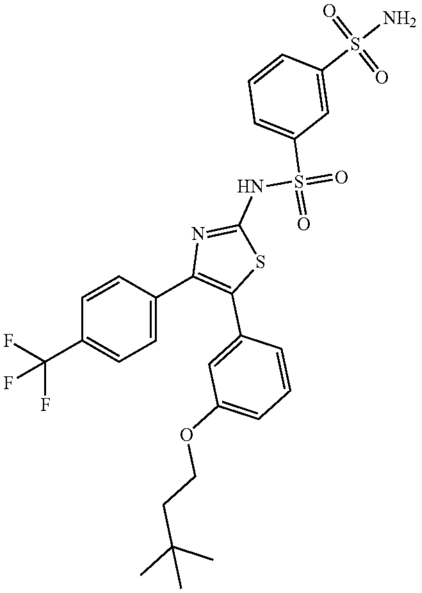 [SMILES: CC(C)(C)CCOc1cccc(-c2sc(NS(=O)(=O)c3cccc(S(N)(=O)=O)c3)nc2-c2ccc(C(F)(F)F)cc2)c1]
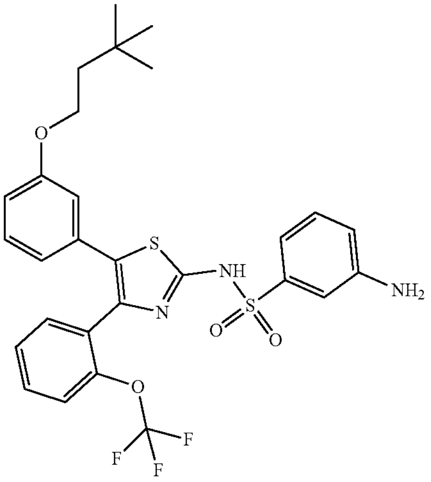 [SMILES: CC(C)(C)CCOc1cccc(-c2sc(NS(=O)(=O)c3cccc(N)c3)nc2-c2ccccc2OC(F)(F)F)c1]
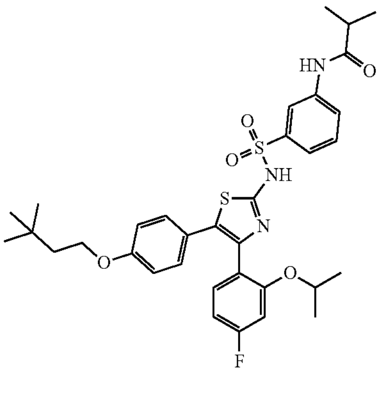 [SMILES: CC(C)Oc1cc(F)ccc1-c1nc(NS(=O)(=O)c2cccc(NC(=O)C(C)C)c2)sc1-c1ccc(OCCC(C)(C)C)cc1]
-continued
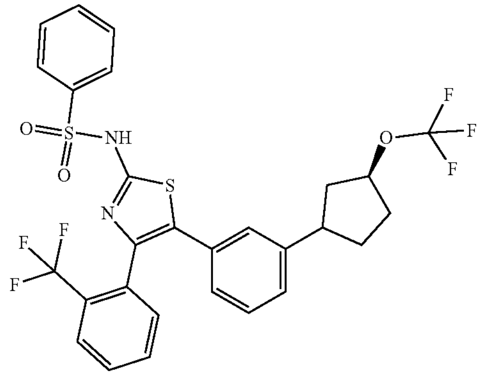 [SMILES: O=S(=O)(Nc1nc(-c2ccccc2C(F)(F)F)c(-c2cccc(C3CC[C@H](OC(F)(F)F)C3)c2)s1)c1ccccc1]
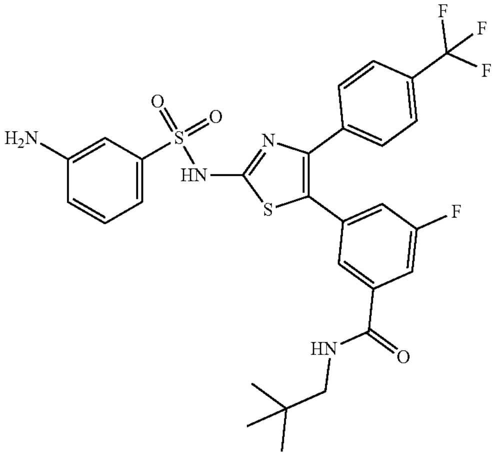 [SMILES: CC(C)(C)CNC(=O)c1cc(F)cc(-c2sc(NS(=O)(=O)c3cccc(N)c3)nc2-c2ccc(C(F)(F)F)cc2)c1]
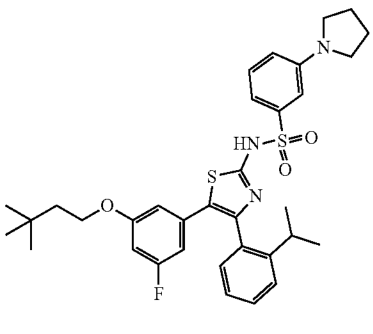 [SMILES: CC(C)c1ccccc1-c1nc(NS(=O)(=O)c2cccc(N3CCCC3)c2)sc1-c1cc(F)cc(OCCC(C)(C)C)c1]

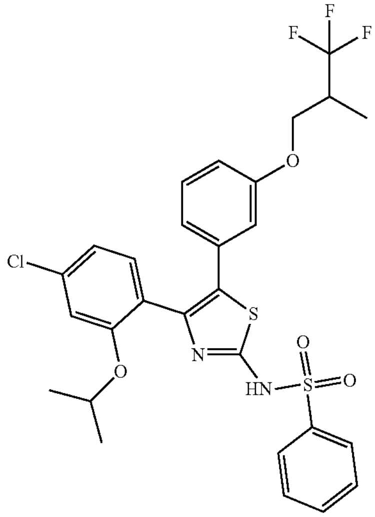 [SMILES: CC(C)Oc1cc(Cl)ccc1-c1nc(NS(=O)(=O)c2ccccc2)sc1-c1cccc(OCC(C)C(F)(F)F)c1]
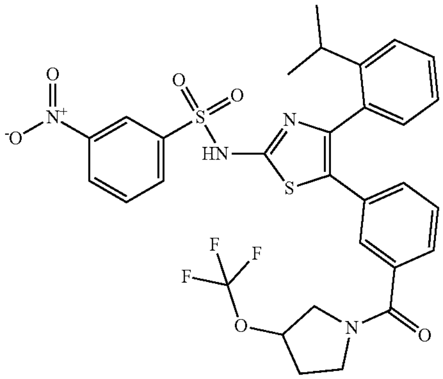
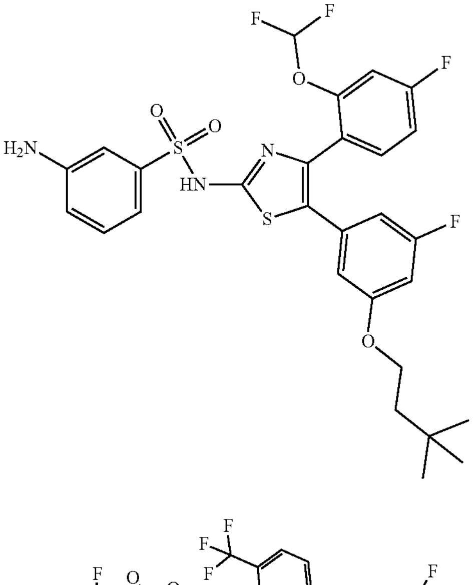
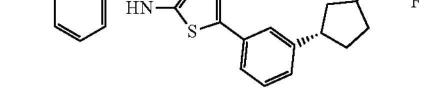
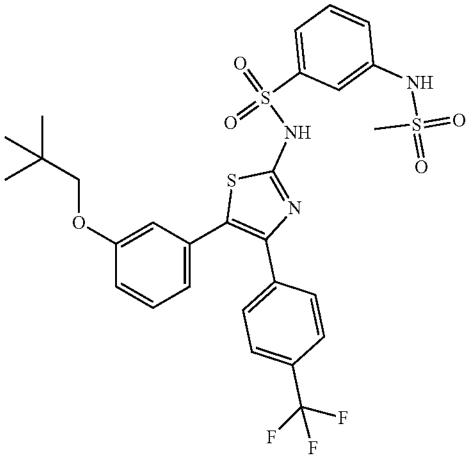 [SMILES: CC(C)(C)COc1cccc(-c2sc(NS(=O)(=O)c3cccc(NS(C)(=O)=O)c3)nc2-c2ccc(C(F)(F)F)cc2)c1]
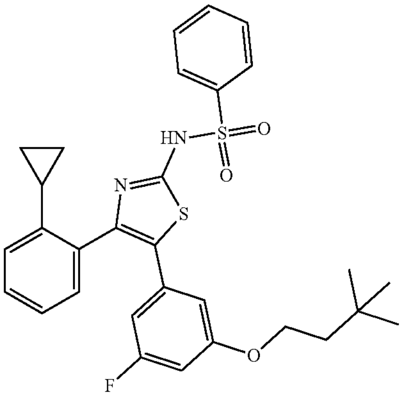 [SMILES: CC(C)(C)CCOc1cc(F)cc(-c2sc(NS(=O)(=O)c3ccccc3)nc2-c2ccccc2C2CC2)c1]
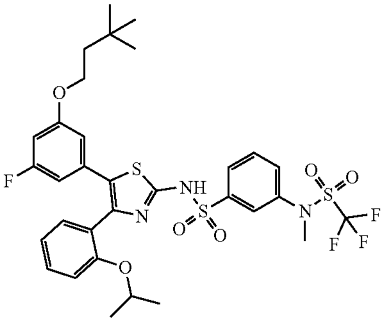 [SMILES: CC(C)Oc1ccccc1-c1nc(NS(=O)(=O)c2cccc(N(C)S(=O)(=O)C(F)(F)F)c2)sc1-c1cc(F)cc(OCCC(C)(C)C)c1]

-continued
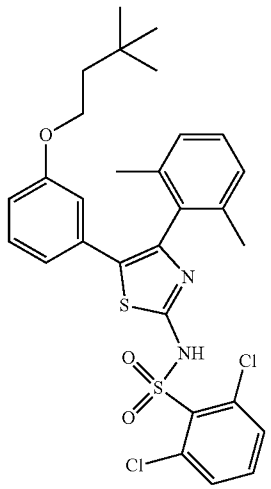 [SMILES: Cc1cccc(C)c1-c1nc(NS(=O)(=O)c2c(Cl)cccc2Cl)sc1-c1cccc(OCCC(C)(C)C)c1]
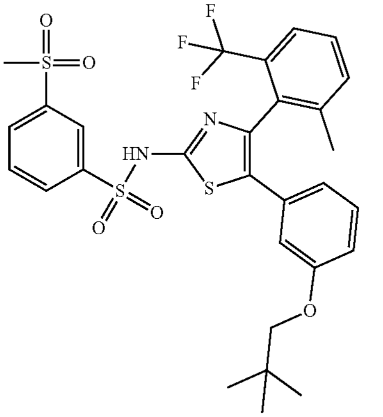 [SMILES: Cc1cccc(C(F)(F)F)c1-c1nc(NS(=O)(=O)c2cccc(S(C)(=O)=O)c2)sc1-c1cccc(OCC(C)(C)C)c1]
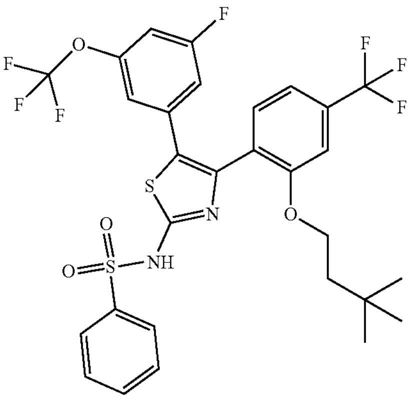 [SMILES: CC(C)(C)CCOc1cc(C(F)(F)F)ccc1-c1nc(NS(=O)(=O)c2ccccc2)sc1-c1cc(F)cc(OC(F)(F)F)c1]
-continued
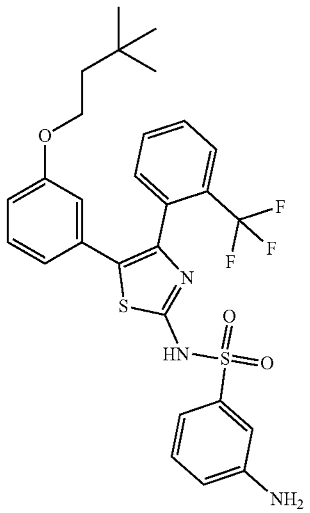 [SMILES: CC(C)(C)CCOc1cccc(-c2sc(NS(=O)(=O)c3cccc(N)c3)nc2-c2ccccc2C(F)(F)F)c1]
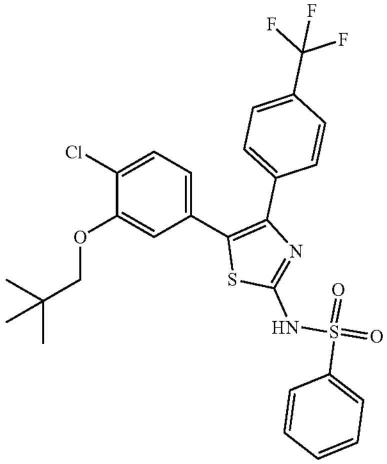 [SMILES: CC(C)(C)COc1cc(-c2sc(NS(=O)(=O)c3ccccc3)nc2-c2ccc(C(F)(F)F)cc2)ccc1Cl]
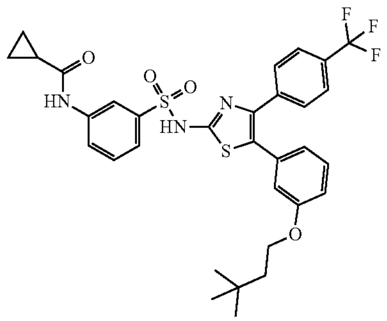 [SMILES: CC(C)(C)CCOc1cccc(-c2sc(NS(=O)(=O)c3cccc(NC(=O)C4CC4)c3)nc2-c2ccc(C(F)(F)F)cc2)c1]

-continued
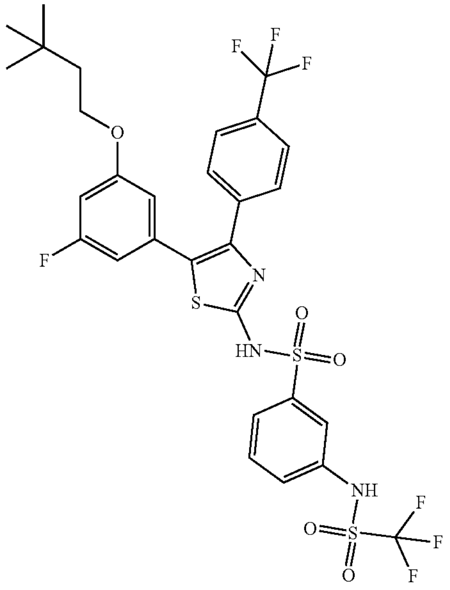 [SMILES: CC(C)(C)CCOc1cc(F)cc(-c2sc(NS(=O)(=O)c3cccc(NS(=O)(=O)C(F)(F)F)c3)nc2-c2ccc(C(F)(F)F)cc2)c1]
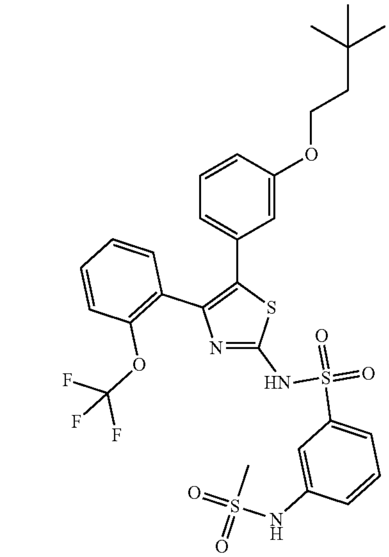 [SMILES: CC(C)(C)CCOc1cccc(-c2sc(NS(=O)(=O)c3cccc(NS(C)(=O)=O)c3)nc2-c2ccccc2OC(F)(F)F)c1]
-continued
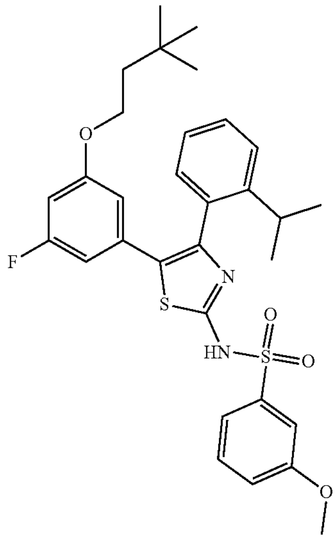 [SMILES: COc1cccc(S(=O)(=O)Nc2nc(-c3ccccc3C(C)C)c(-c3cc(F)cc(OCCC(C)(C)C)c3)s2)c1]
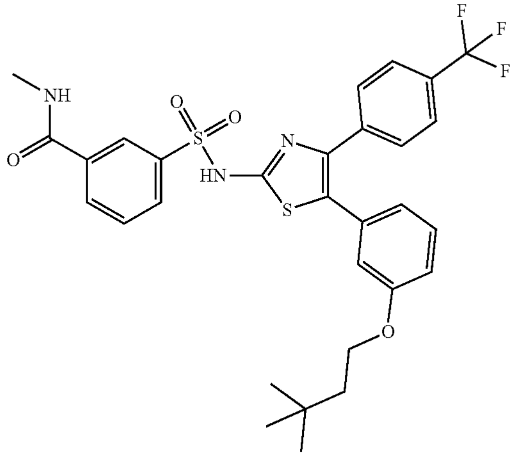 [SMILES: CNC(=O)c1cccc(S(=O)(=O)Nc2nc(-c3ccc(C(F)(F)F)cc3)c(-c3cccc(OCCC(C)(C)C)c3)s2)c1]
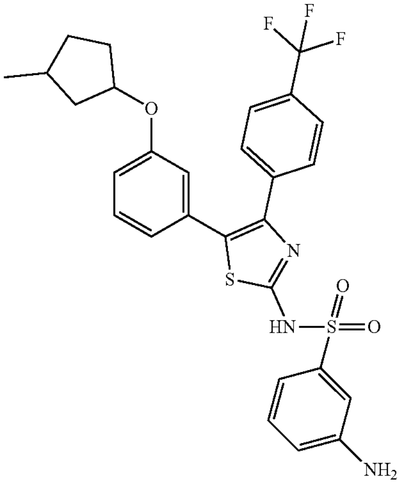 [SMILES: CC1CCC(Oc2cccc(-c3sc(NS(=O)(=O)c4cccc(N)c4)nc3-c3ccc(C(F)(F)F)cc3)c2)C1]

-continued
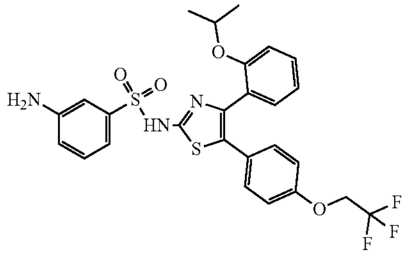 [SMILES: CC(C)Oc1ccccc1-c1nc(NS(=O)(=O)c2cccc(N)c2)sc1-c1ccc(OCC(F)(F)F)cc1]
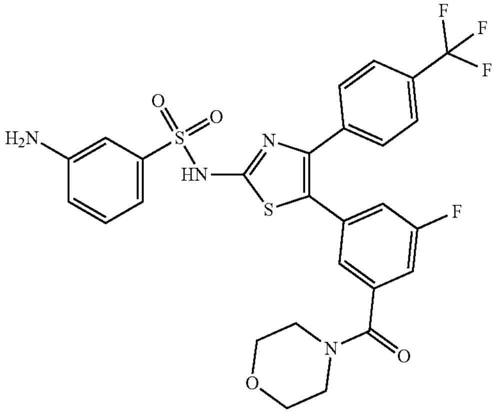 [SMILES: Nc1cccc(S(=O)(=O)Nc2nc(-c3ccc(C(F)(F)F)cc3)c(-c3cc(F)cc(C(=O)N4CCOCC4)c3)s2)c1]
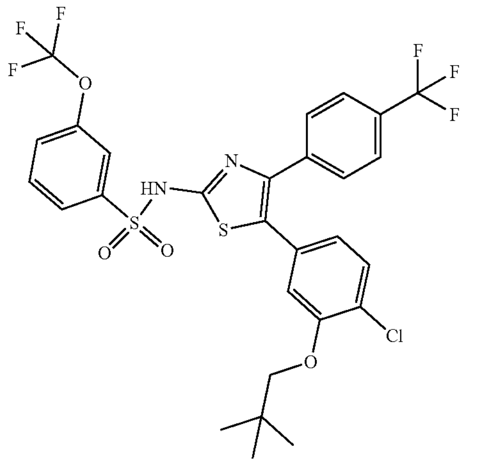 [SMILES: CC(C)(C)COc1cc(-c2sc(NS(=O)(=O)c3cccc(OC(F)(F)F)c3)nc2-c2ccc(C(F)(F)F)cc2)ccc1Cl]
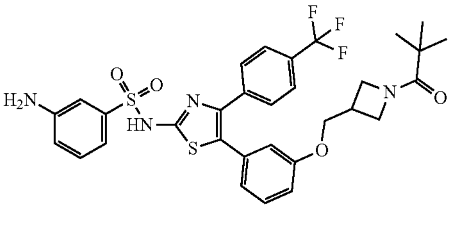 [SMILES: CC(C)(C)C(=O)N1CC(COc2cccc(-c3sc(NS(=O)(=O)c4cccc(N)c4)nc3-c3ccc(C(F)(F)F)cc3)c2)C1]
-continued
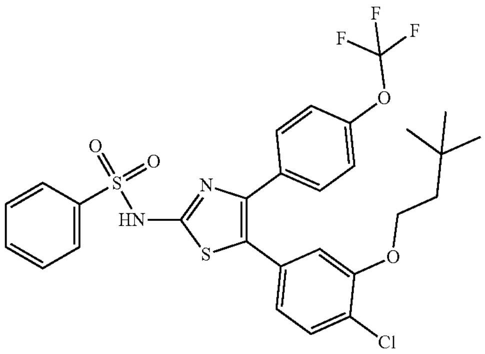 [SMILES: CC(C)(C)CCOc1cc(-c2sc(NS(=O)(=O)c3ccccc3)nc2-c2ccc(OC(F)(F)F)cc2)ccc1Cl]
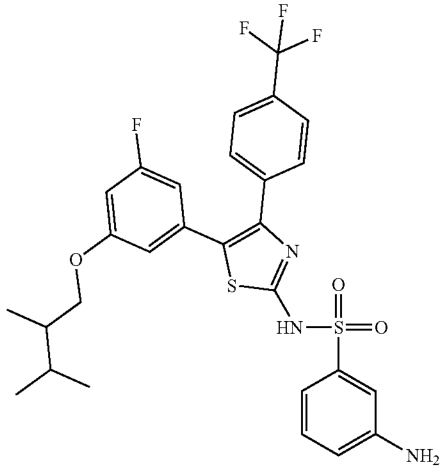 [SMILES: CC(C)C(C)COc1cc(F)cc(-c2sc(NS(=O)(=O)c3cccc(N)c3)nc2-c2ccc(C(F)(F)F)cc2)c1]
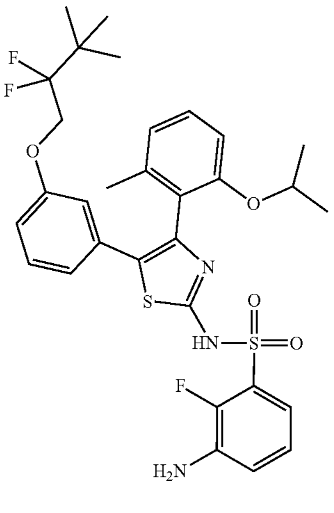 [SMILES: Cc1cccc(OC(C)C)c1-c1nc(NS(=O)(=O)c2cccc(N)c2F)sc1-c1cccc(OCC(F)(F)C(C)(C)C)c1]

-continued
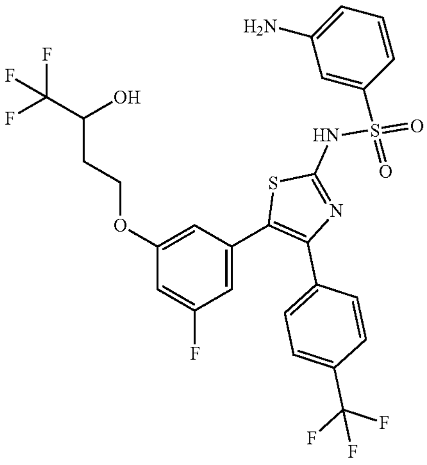 [SMILES: Nc1cccc(S(=O)(=O)Nc2nc(-c3ccc(C(F)(F)F)cc3)c(-c3cc(F)cc(OCCC(O)C(F)(F)F)c3)s2)c1]
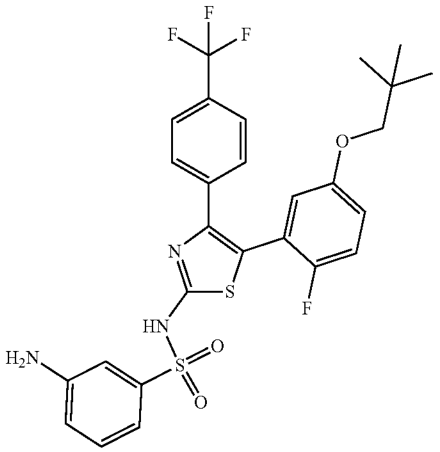 [SMILES: CC(C)(C)COc1ccc(F)c(-c2sc(NS(=O)(=O)c3cccc(N)c3)nc2-c2ccc(C(F)(F)F)cc2)c1]
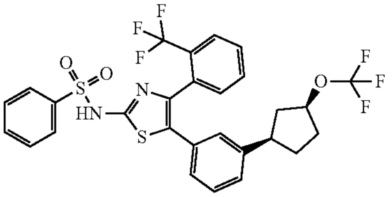 [SMILES: O=S(=O)(Nc1nc(-c2ccccc2C(F)(F)F)c(-c2cccc([C@@H]3CC[C@H](OC(F)(F)F)C3)c2)s1)c1ccccc1]
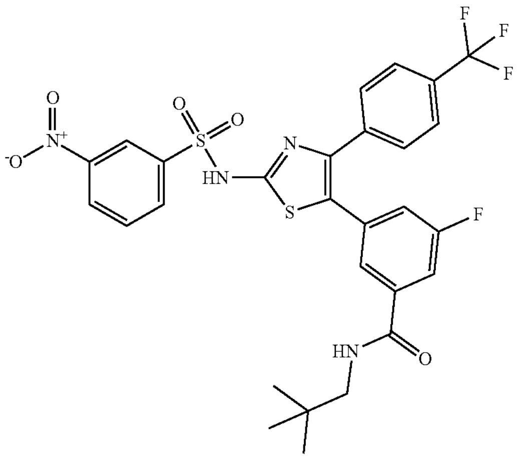
-continued
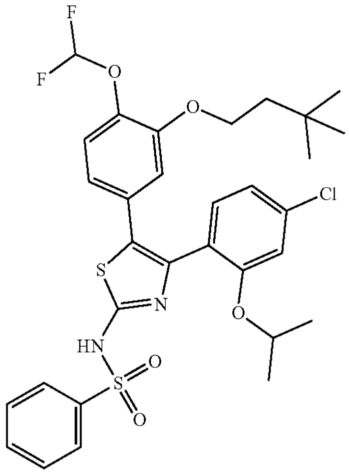 [SMILES: CC(C)Oc1cc(Cl)ccc1-c1nc(NS(=O)(=O)c2ccccc2)sc1-c1ccc(OC(F)F)c(OCCC(C)(C)C)c1]
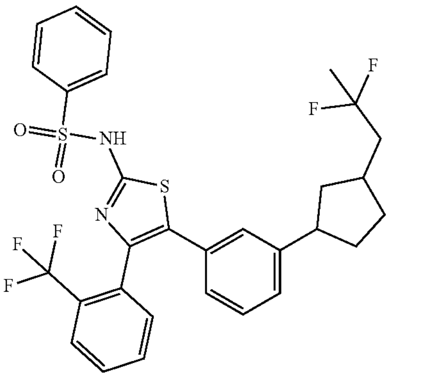 [SMILES: CC(F)(F)CC1CCC(c2cccc(-c3sc(NS(=O)(=O)c4ccccc4)nc3-c3ccccc3C(F)(F)F)c2)C1]
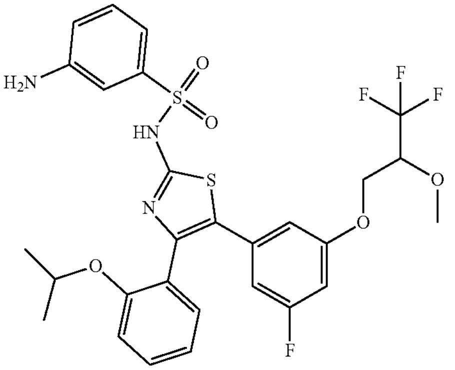 [SMILES: COC(COc1cc(F)cc(-c2sc(NS(=O)(=O)c3cccc(N)c3)nc2-c2ccccc2OC(C)C)c1)C(F)(F)F]
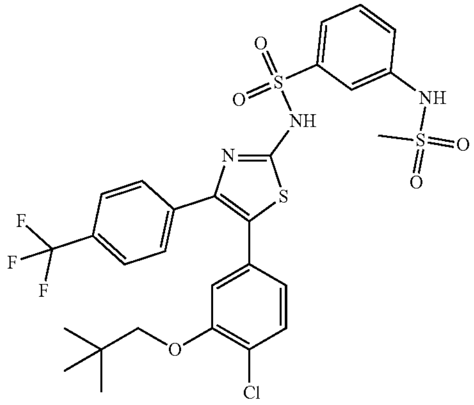 [SMILES: CC(C)(C)COc1cc(-c2sc(NS(=O)(=O)c3cccc(NS(C)(=O)=O)c3)nc2-c2ccc(C(F)(F)F)cc2)ccc1Cl]

-continued
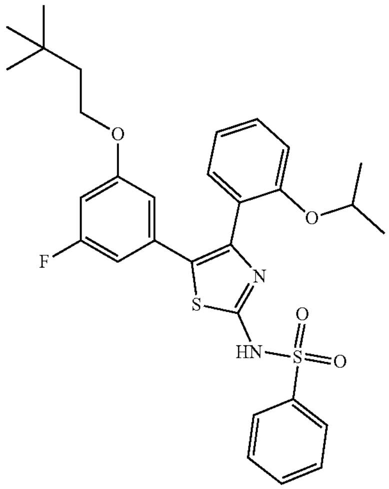 [SMILES: CC(C)Oc1ccccc1-c1nc(NS(=O)(=O)c2ccccc2)sc1-c1cc(F)cc(OCCC(C)(C)C)c1]
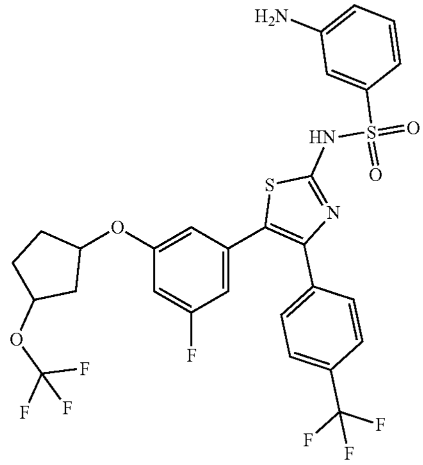 [SMILES: Nc1cccc(S(=O)(=O)Nc2nc(-c3ccc(C(F)(F)F)cc3)c(-c3cc(F)cc(OC4CCC(OC(F)(F)F)C4)c3)s2)c1]
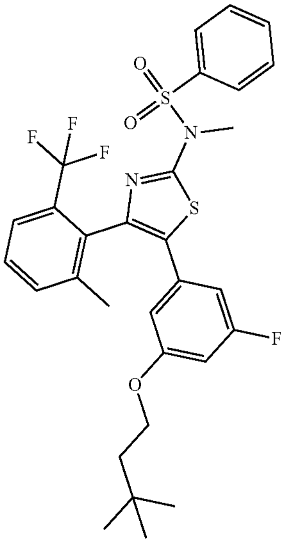 [SMILES: Cc1cccc(C(F)(F)F)c1-c1nc(N(C)S(=O)(=O)c2ccccc2)sc1-c1cc(F)cc(OCCC(C)(C)C)c1]
-continued
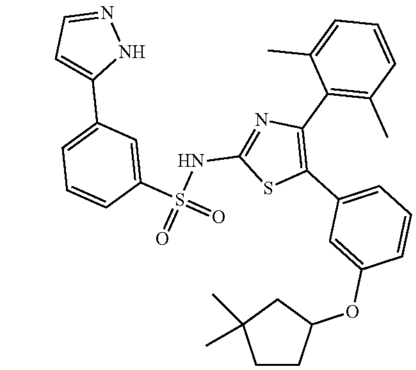 [SMILES: Cc1cccc(C)c1-c1nc(NS(=O)(=O)c2cccc(-c3ccn[nH]3)c2)sc1-c1cccc(OC2CCC(C)(C)C2)c1]
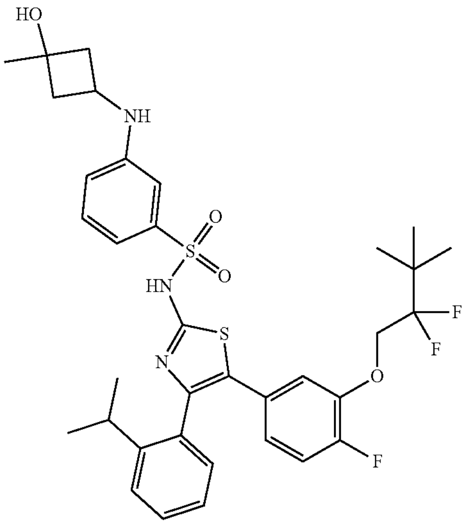 [SMILES: CC(C)c1ccccc1-c1nc(NS(=O)(=O)c2cccc(NC3CC(C)(O)C3)c2)sc1-c1ccc(F)c(OCC(F)(F)C(C)(C)C)c1]
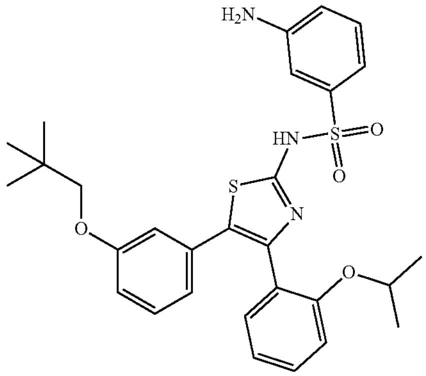 [SMILES: CC(C)Oc1ccccc1-c1nc(NS(=O)(=O)c2cccc(N)c2)sc1-c1cccc(OCC(C)(C)C)c1]
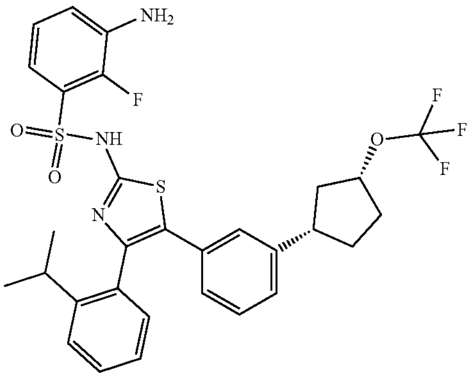 [SMILES: CC(C)c1ccccc1-c1nc(NS(=O)(=O)c2cccc(N)c2F)sc1-c1cccc([C@H]2CC[C@@H](OC(F)(F)F)C2)c1]

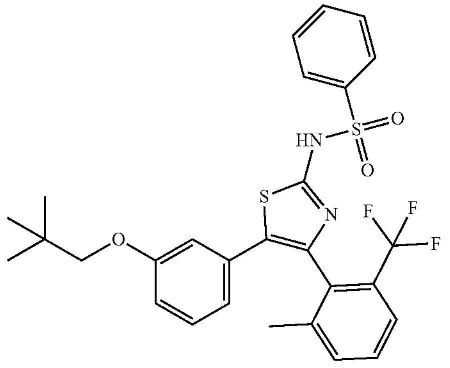 [SMILES: Cc1cccc(C(F)(F)F)c1-c1nc(NS(=O)(=O)c2ccccc2)sc1-c1cccc(OCC(C)(C)C)c1]
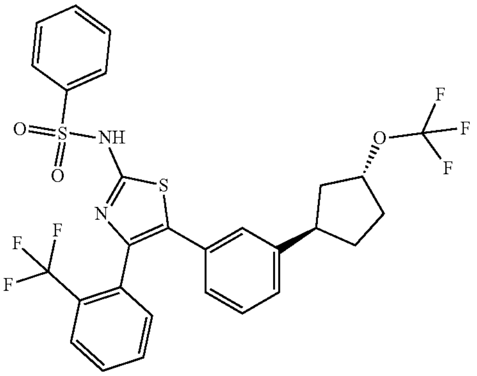 [SMILES: O=S(=O)(Nc1nc(-c2ccccc2C(F)(F)F)c(-c2cccc([C@@H]3CC[C@@H](OC(F)(F)F)C3)c2)s1)c1ccccc1]
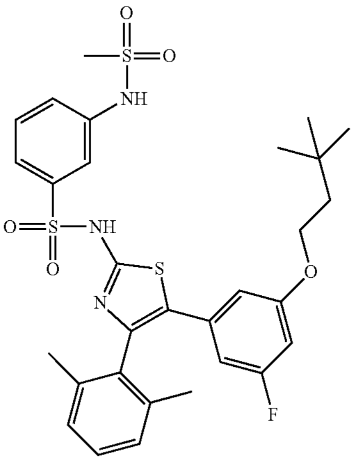 [SMILES: Cc1cccc(C)c1-c1nc(NS(=O)(=O)c2cccc(NS(C)(=O)=O)c2)sc1-c1cc(F)cc(OCCC(C)(C)C)c1]
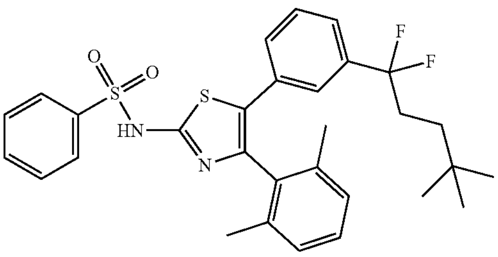 [SMILES: Cc1cccc(C)c1-c1nc(NS(=O)(=O)c2ccccc2)sc1-c1cccc(C(F)(F)CCC(C)(C)C)c1]
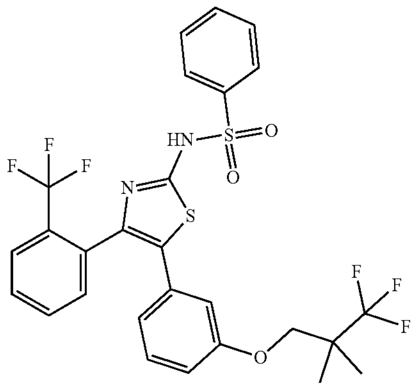 [SMILES: CC(C)(COc1cccc(-c2sc(NS(=O)(=O)c3ccccc3)nc2-c2ccccc2C(F)(F)F)c1)C(F)(F)F]
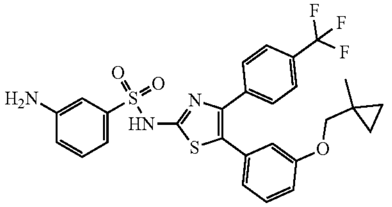 [SMILES: CC1(COc2cccc(-c3sc(NS(=O)(=O)c4cccc(N)c4)nc3-c3ccc(C(F)(F)F)cc3)c2)CC1]
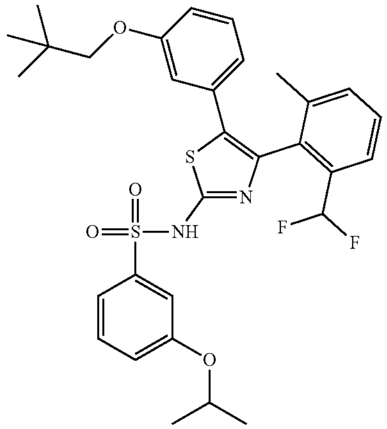 [SMILES: Cc1cccc(C(F)F)c1-c1nc(NS(=O)(=O)c2cccc(OC(C)C)c2)sc1-c1cccc(OCC(C)(C)C)c1]
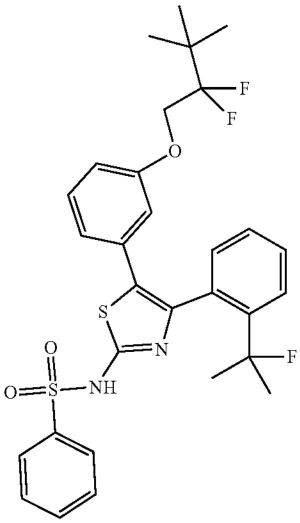 [SMILES: CC(C)(F)c1ccccc1-c1nc(NS(=O)(=O)c2ccccc2)sc1-c1cccc(OCC(F)(F)C(C)(C)C)c1]

-continued
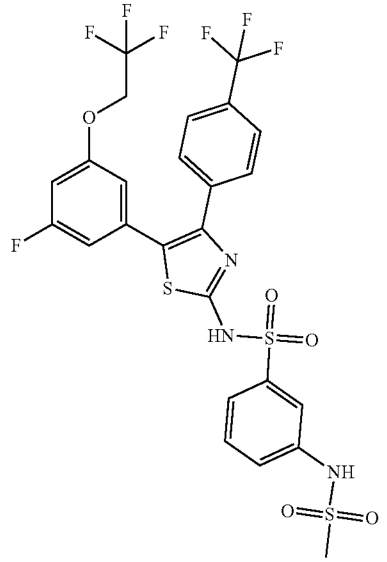 [SMILES: CS(=O)(=O)Nc1cccc(S(=O)(=O)Nc2nc(-c3ccc(C(F)(F)F)cc3)c(-c3cc(F)cc(OCC(F)(F)F)c3)s2)c1]
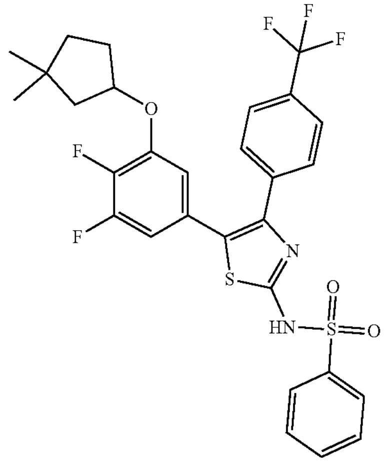 [SMILES: CC1(C)CCC(Oc2cc(-c3sc(NS(=O)(=O)c4ccccc4)nc3-c3ccc(C(F)(F)F)cc3)cc(F)c2F)C1]
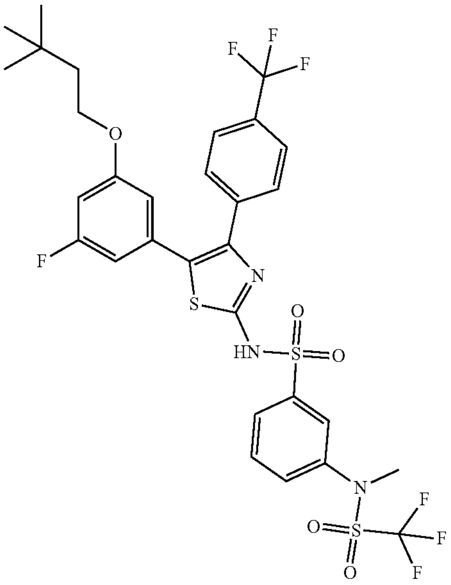 [SMILES: CN(c1cccc(S(=O)(=O)Nc2nc(-c3ccc(C(F)(F)F)cc3)c(-c3cc(F)cc(OCCC(C)(C)C)c3)s2)c1)S(=O)(=O)C(F)(F)F]
-continued
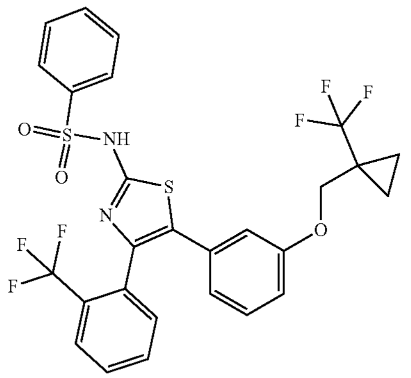 [SMILES: O=S(=O)(Nc1nc(-c2ccccc2C(F)(F)F)c(-c2cccc(OCC3(C(F)(F)F)CC3)c2)s1)c1ccccc1]
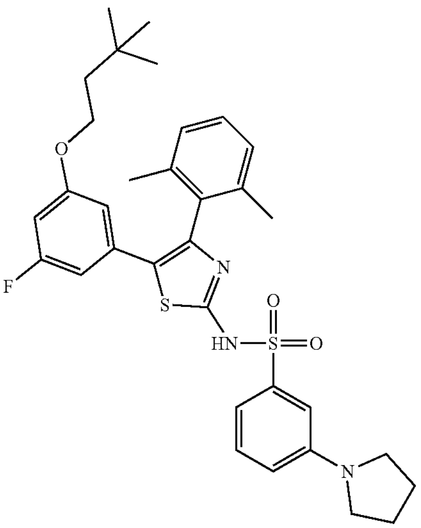 [SMILES: Cc1cccc(C)c1-c1nc(NS(=O)(=O)c2cccc(N3CCCC3)c2)sc1-c1cc(F)cc(OCCC(C)(C)C)c1]
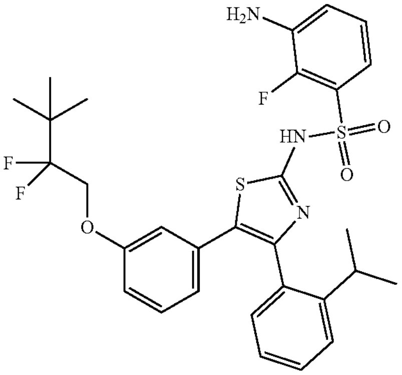 [SMILES: CC(C)c1ccccc1-c1nc(NS(=O)(=O)c2cccc(N)c2F)sc1-c1cccc(OCC(F)(F)C(C)(C)C)c1]

-continued
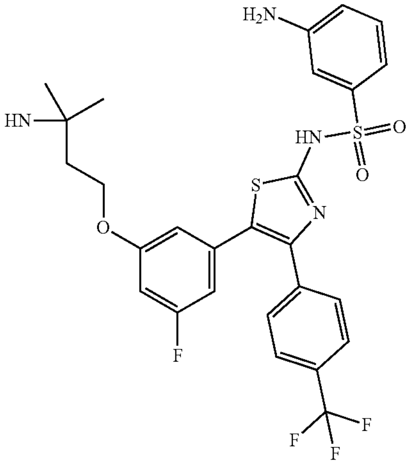 [SMILES: CC(C)(N)CCOc1cc(F)cc(-c2sc(NS(=O)(=O)c3cccc(N)c3)nc2-c2ccc(C(F)(F)F)cc2)c1]
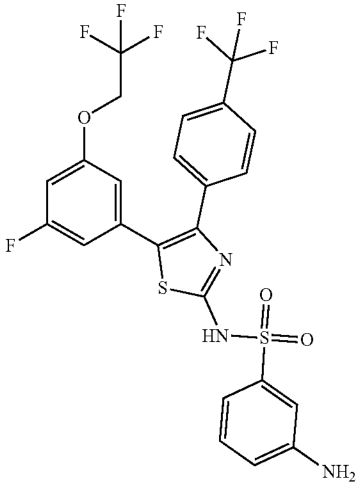 [SMILES: Nc1cccc(S(=O)(=O)Nc2nc(-c3ccc(C(F)(F)F)cc3)c(-c3cc(F)cc(OCC(F)(F)F)c3)s2)c1]
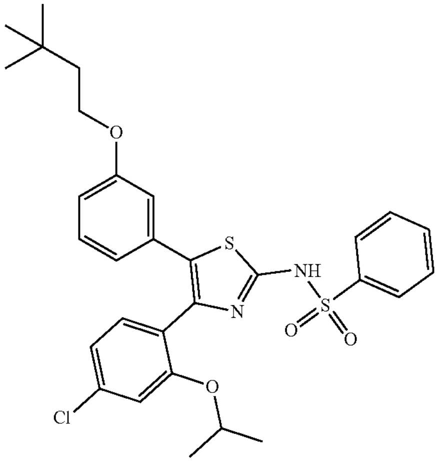 [SMILES: CC(C)Oc1cc(Cl)ccc1-c1nc(NS(=O)(=O)c2ccccc2)sc1-c1cccc(OCCC(C)(C)C)c1]
-continued
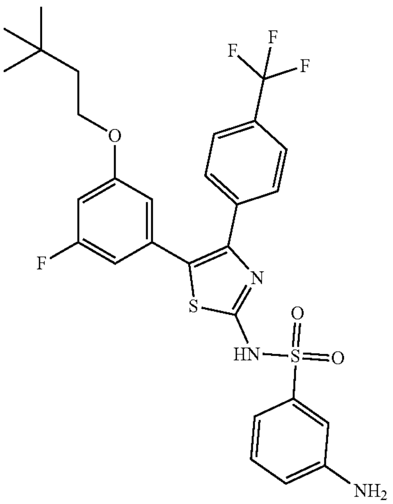 [SMILES: CC(C)(C)CCOc1cc(F)cc(-c2sc(NS(=O)(=O)c3cccc(N)c3)nc2-c2ccc(C(F)(F)F)cc2)c1]
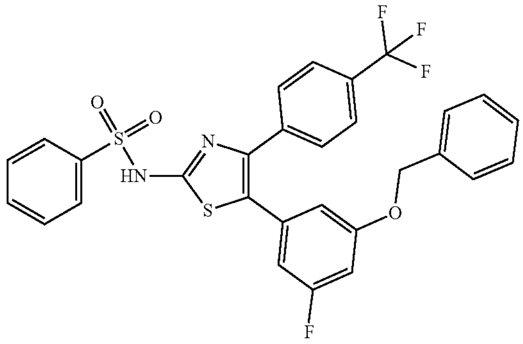 [SMILES: O=S(=O)(Nc1nc(-c2ccc(C(F)(F)F)cc2)c(-c2cc(F)cc(OCc3ccccc3)c2)s1)c1ccccc1]
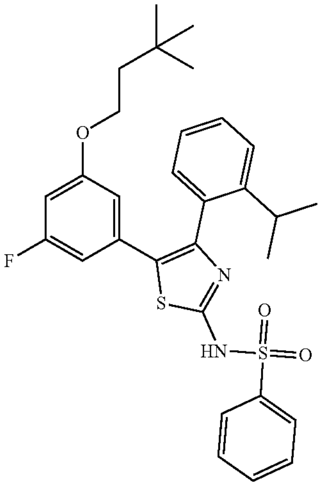 [SMILES: CC(C)c1ccccc1-c1nc(NS(=O)(=O)c2ccccc2)sc1-c1cc(F)cc(OCCC(C)(C)C)c1]

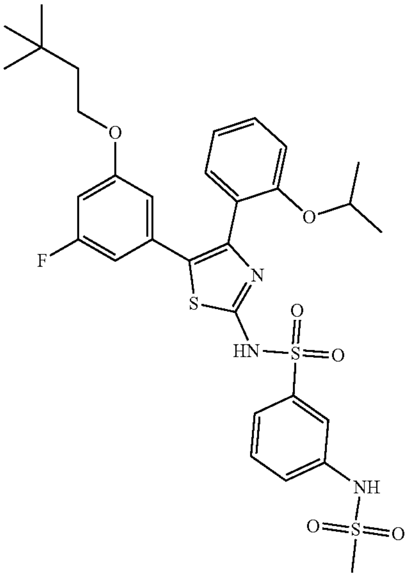 [SMILES: CC(C)Oc1ccccc1-c1nc(NS(=O)(=O)c2cccc(NS(C)(=O)=O)c2)sc1-c1cc(F)cc(OCCC(C)(C)C)c1]
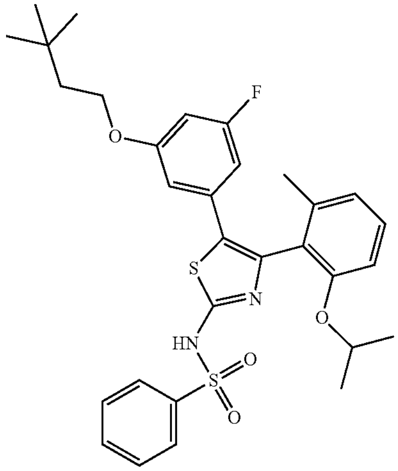 [SMILES: Cc1cccc(OC(C)C)c1-c1nc(NS(=O)(=O)c2ccccc2)sc1-c1cc(F)cc(OCCC(C)(C)C)c1]
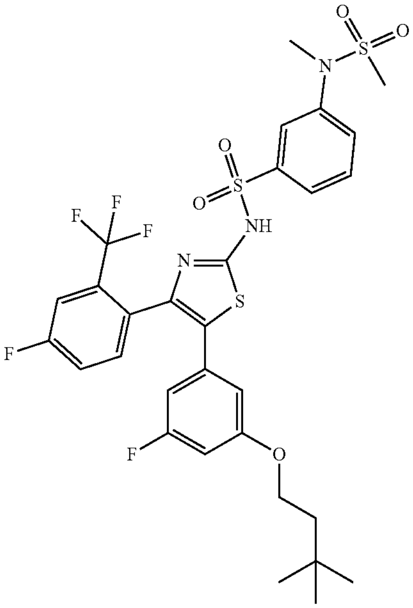 [SMILES: CN(c1cccc(S(=O)(=O)Nc2nc(-c3ccc(F)cc3C(F)(F)F)c(-c3cc(F)cc(OCCC(C)(C)C)c3)s2)c1)S(C)(=O)=O]
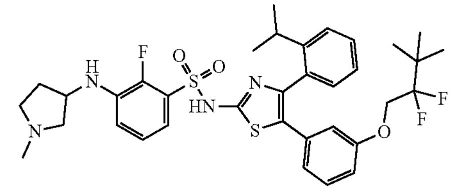 [SMILES: CC(C)c1ccccc1-c1nc(NS(=O)(=O)c2cccc(NC3CCN(C)C3)c2F)sc1-c1cccc(OCC(F)(F)C(C)(C)C)c1]
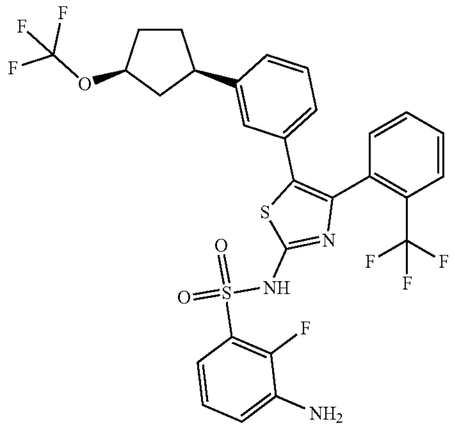 [SMILES: Nc1cccc(S(=O)(=O)Nc2nc(-c3ccccc3C(F)(F)F)c(-c3cccc([C@@H]4CC[C@H](OC(F)(F)F)C4)c3)s2)c1F]
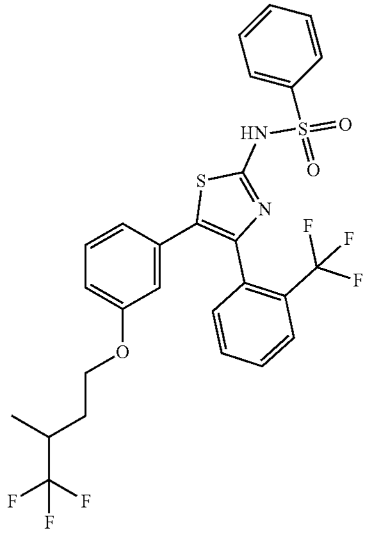 [SMILES: CC(CCOc1cccc(-c2sc(NS(=O)(=O)c3ccccc3)nc2-c2ccccc2C(F)(F)F)c1)C(F)(F)F]
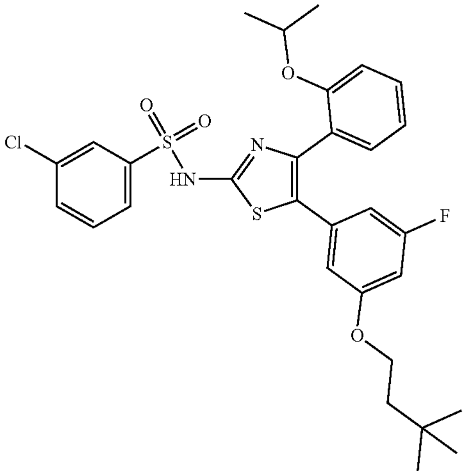 [SMILES: CC(C)Oc1ccccc1-c1nc(NS(=O)(=O)c2cccc(Cl)c2)sc1-c1cc(F)cc(OCCC(C)(C)C)c1]

-continued
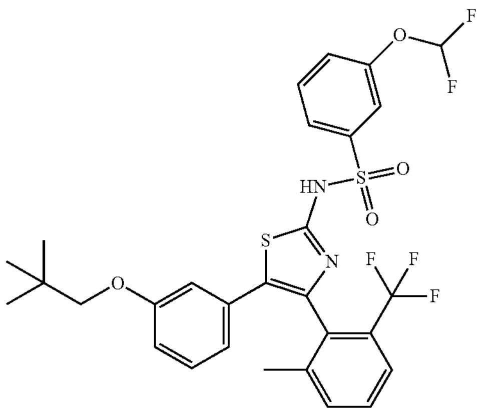 [SMILES: Cc1cccc(C(F)(F)F)c1-c1nc(NS(=O)(=O)c2cccc(OC(F)F)c2)sc1-c1cccc(OCC(C)(C)C)c1]
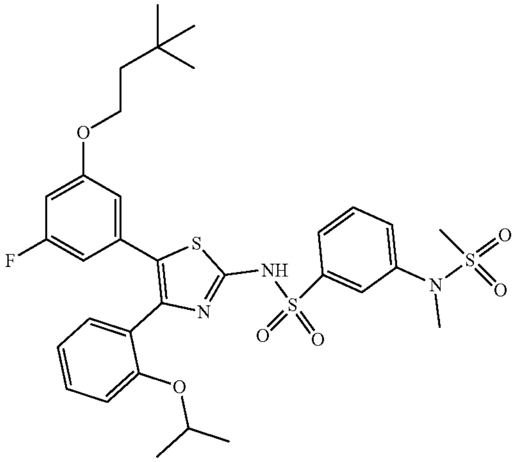 [SMILES: CC(C)Oc1ccccc1-c1nc(NS(=O)(=O)c2cccc(N(C)S(C)(=O)=O)c2)sc1-c1cc(F)cc(OCCC(C)(C)C)c1]
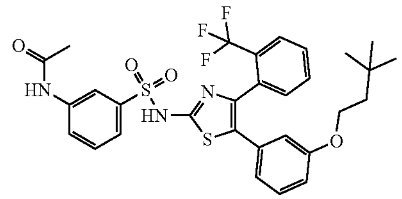 [SMILES: CC(=O)Nc1cccc(S(=O)(=O)Nc2nc(-c3ccccc3C(F)(F)F)c(-c3cccc(OCCC(C)(C)C)c3)s2)c1]
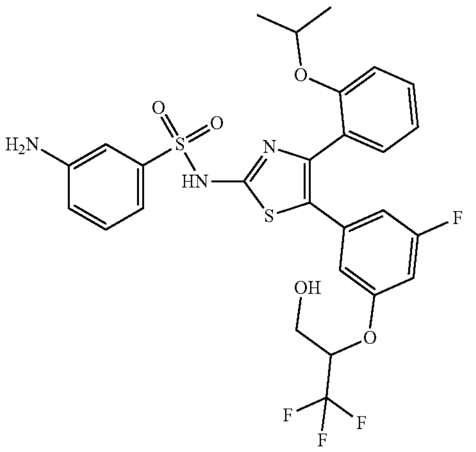 [SMILES: CC(C)Oc1ccccc1-c1nc(NS(=O)(=O)c2cccc(N)c2)sc1-c1cc(F)cc(OC(CO)C(F)(F)F)c1]
-continued
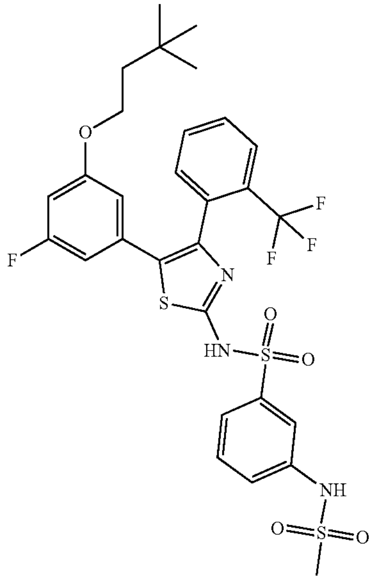
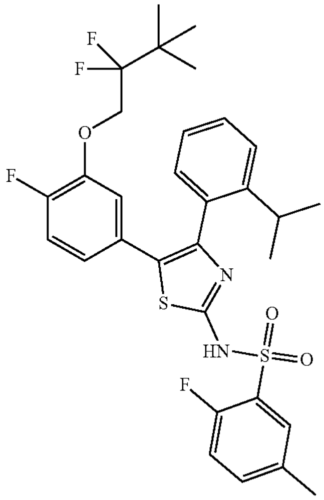 [SMILES: Cc1ccc(F)c(S(=O)(=O)Nc2nc(-c3ccccc3C(C)C)c(-c3ccc(F)c(OCC(F)(F)C(C)(C)C)c3)s2)c1]
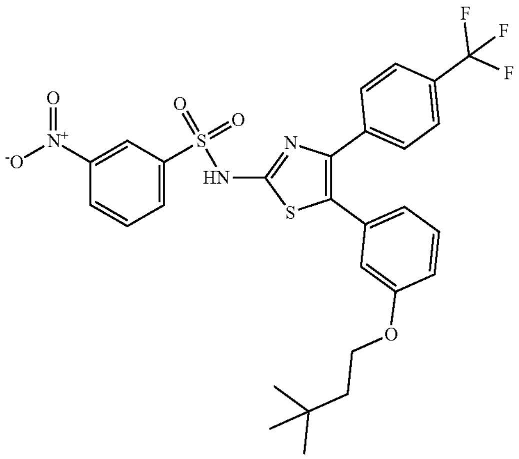

-continued
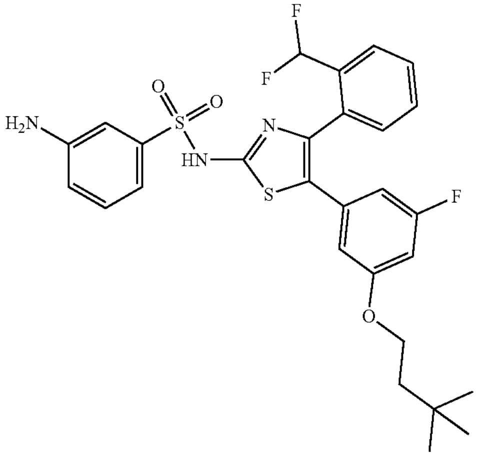 [SMILES: CC(C)(C)CCOc1cc(F)cc(-c2sc(NS(=O)(=O)c3cccc(N)c3)nc2-c2ccccc2C(F)F)c1]
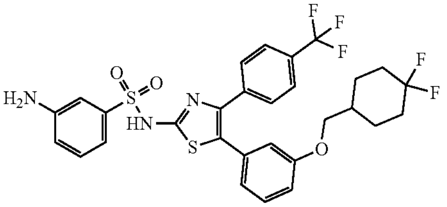 [SMILES: Nc1cccc(S(=O)(=O)Nc2nc(-c3ccc(C(F)(F)F)cc3)c(-c3cccc(OCC4CCC(F)(F)CC4)c3)s2)c1]
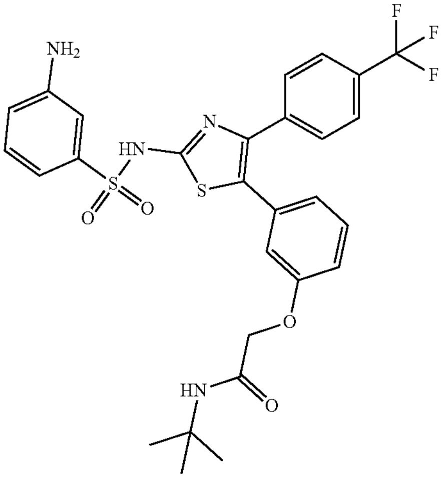 [SMILES: CC(C)(C)NC(=O)COc1cccc(-c2sc(NS(=O)(=O)c3cccc(N)c3)nc2-c2ccc(C(F)(F)F)cc2)c1]
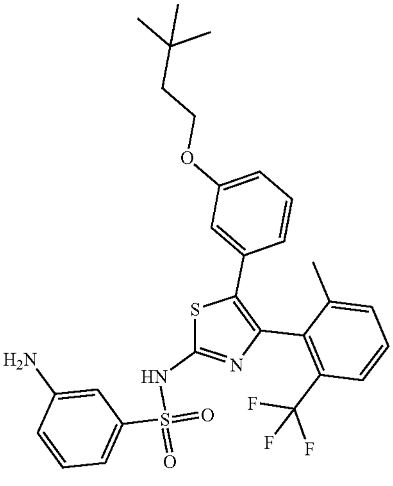 [SMILES: Cc1cccc(C(F)(F)F)c1-c1nc(NS(=O)(=O)c2cccc(N)c2)sc1-c1cccc(OCCC(C)(C)C)c1]
-continued
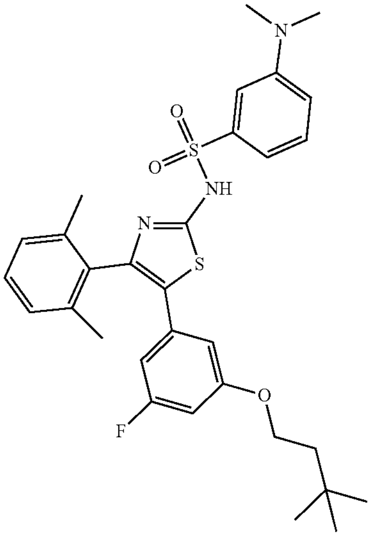 [SMILES: Cc1cccc(C)c1-c1nc(NS(=O)(=O)c2cccc(N(C)C)c2)sc1-c1cc(F)cc(OCCC(C)(C)C)c1]
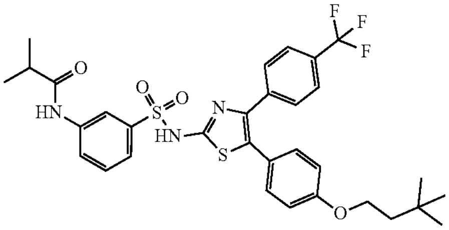 [SMILES: CC(C)C(=O)Nc1cccc(S(=O)(=O)Nc2nc(-c3ccc(C(F)(F)F)cc3)c(-c3ccc(OCCC(C)(C)C)cc3)s2)c1]
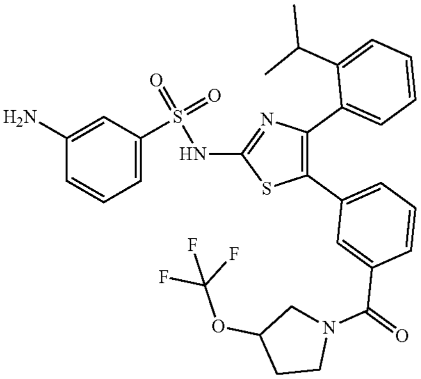 [SMILES: CC(C)c1ccccc1-c1nc(NS(=O)(=O)c2cccc(N)c2)sc1-c1cccc(C(=O)N2CCC(OC(F)(F)F)C2)c1]
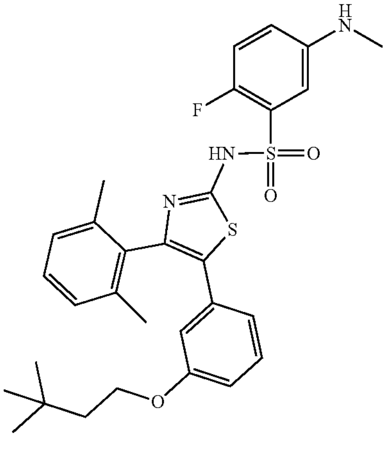 [SMILES: CNc1ccc(F)c(S(=O)(=O)Nc2nc(-c3c(C)cccc3C)c(-c3cccc(OCCC(C)(C)C)c3)s2)c1]

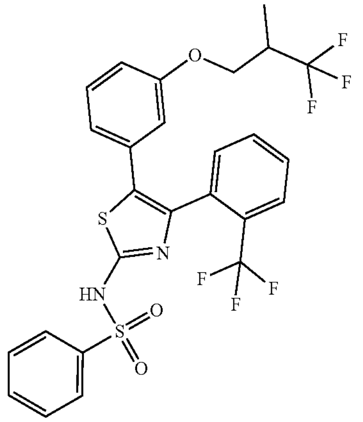 [SMILES: CC(COc1cccc(-c2sc(NS(=O)(=O)c3ccccc3)nc2-c2ccccc2C(F)(F)F)c1)C(F)(F)F]
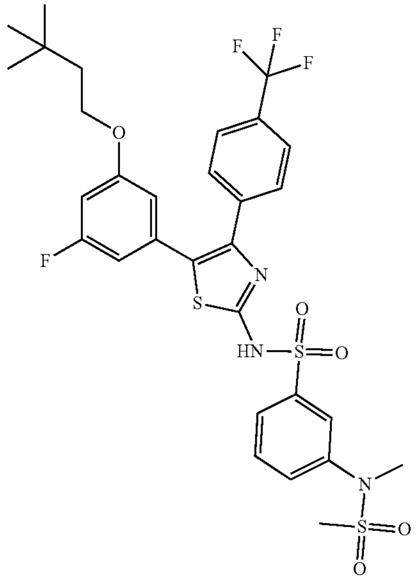 [SMILES: CN(c1cccc(S(=O)(=O)Nc2nc(-c3ccc(C(F)(F)F)cc3)c(-c3cc(F)cc(OCCC(C)(C)C)c3)s2)c1)S(C)(=O)=O]
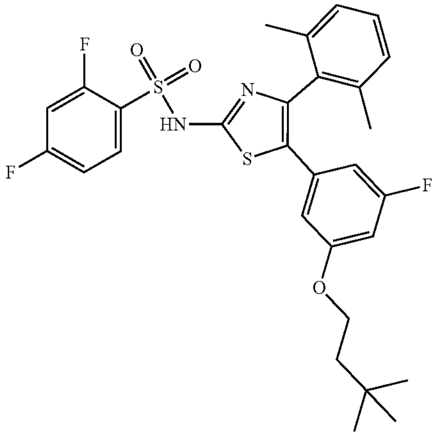 [SMILES: Cc1cccc(C)c1-c1nc(NS(=O)(=O)c2ccc(F)cc2F)sc1-c1cc(F)cc(OCCC(C)(C)C)c1]
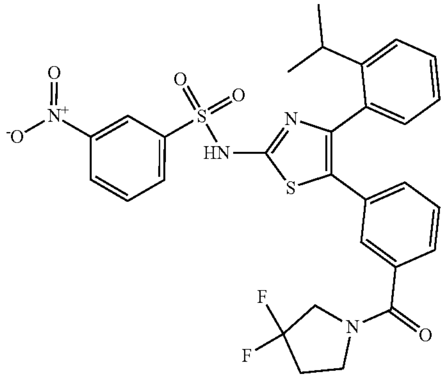
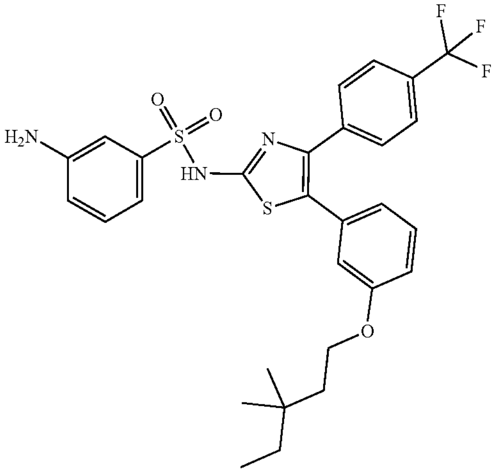 [SMILES: CCC(C)(C)CCOc1cccc(-c2sc(NS(=O)(=O)c3cccc(N)c3)nc2-c2ccc(C(F)(F)F)cc2)c1]
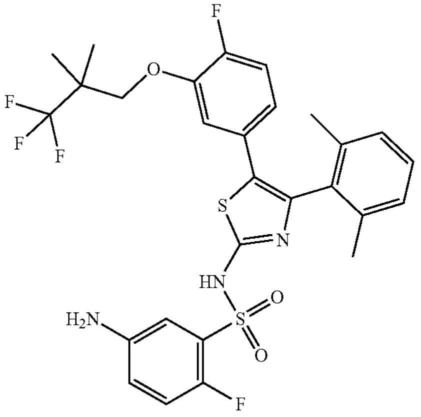 [SMILES: Cc1cccc(C)c1-c1nc(NS(=O)(=O)c2cc(N)ccc2F)sc1-c1ccc(F)c(OCC(C)(C)C(F)(F)F)c1]
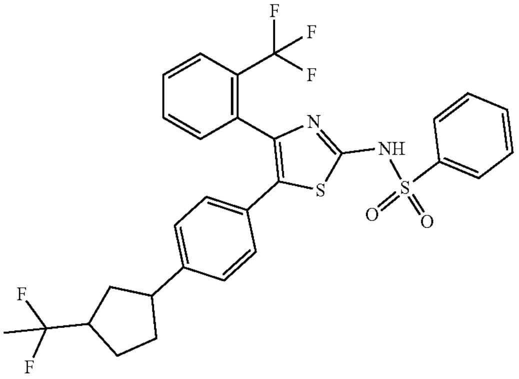 [SMILES: CC(F)(F)C1CCC(c2ccc(-c3sc(NS(=O)(=O)c4ccccc4)nc3-c3ccccc3C(F)(F)F)cc2)C1]

-continued
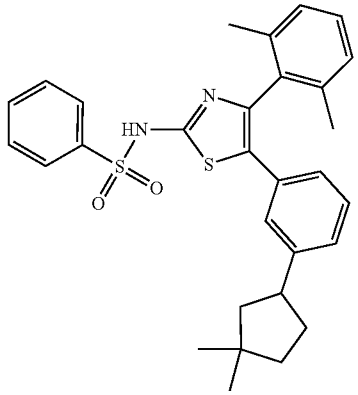 [SMILES: Cc1cccc(C)c1-c1nc(NS(=O)(=O)c2ccccc2)sc1-c1cccc(C2CCC(C)(C)C2)c1]
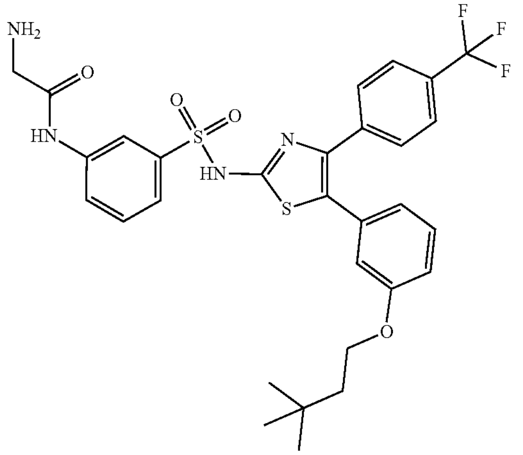 [SMILES: CC(C)(C)CCOc1cccc(-c2sc(NS(=O)(=O)c3cccc(NC(=O)CN)c3)nc2-c2ccc(C(F)(F)F)cc2)c1]
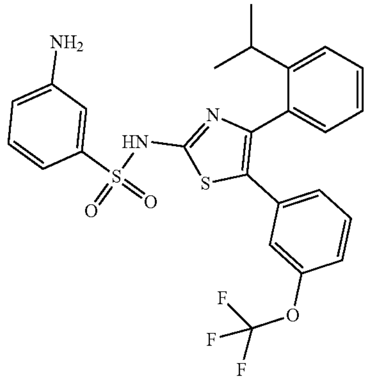 [SMILES: CC(C)c1ccccc1-c1nc(NS(=O)(=O)c2cccc(N)c2)sc1-c1cccc(OC(F)(F)F)c1]
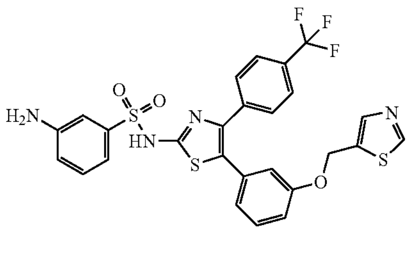 [SMILES: Nc1cccc(S(=O)(=O)Nc2nc(-c3ccc(C(F)(F)F)cc3)c(-c3cccc(OCc4cncs4)c3)s2)c1]
-continued
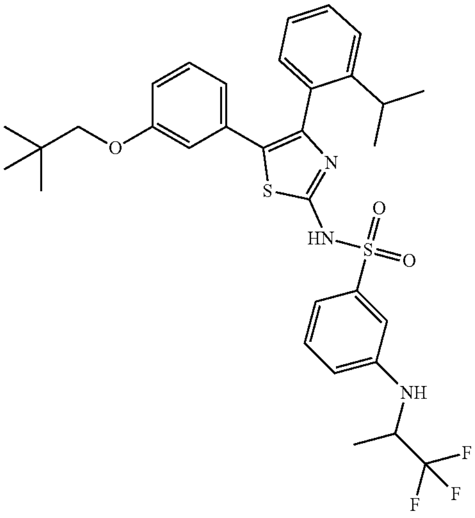 [SMILES: CC(C)c1ccccc1-c1nc(NS(=O)(=O)c2cccc(NC(C)C(F)(F)F)c2)sc1-c1cccc(OCC(C)(C)C)c1]
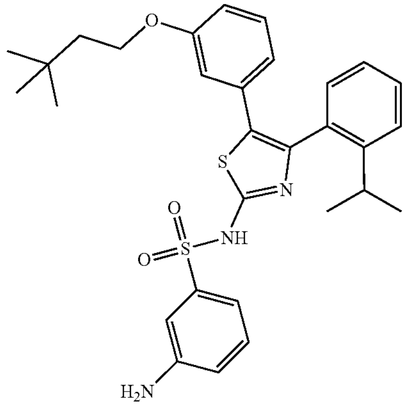 [SMILES: CC(C)c1ccccc1-c1nc(NS(=O)(=O)c2cccc(N)c2)sc1-c1cccc(OCCC(C)(C)C)c1]
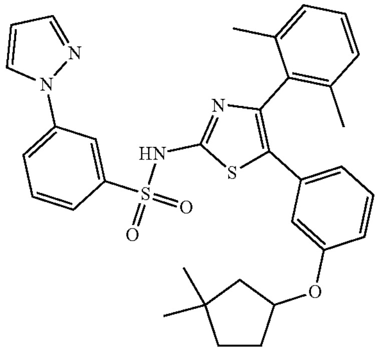 [SMILES: Cc1cccc(C)c1-c1nc(NS(=O)(=O)c2cccc(-n3cccn3)c2)sc1-c1cccc(OC2CCC(C)(C)C2)c1]
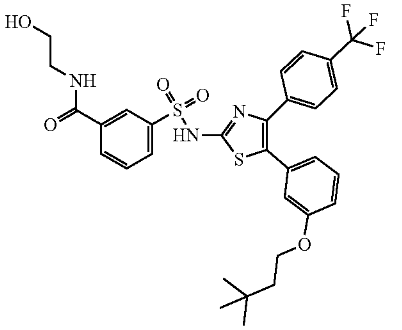 [SMILES: CC(C)(C)CCOc1cccc(-c2sc(NS(=O)(=O)c3cccc(C(=O)NCCO)c3)nc2-c2ccc(C(F)(F)F)cc2)c1]

-continued
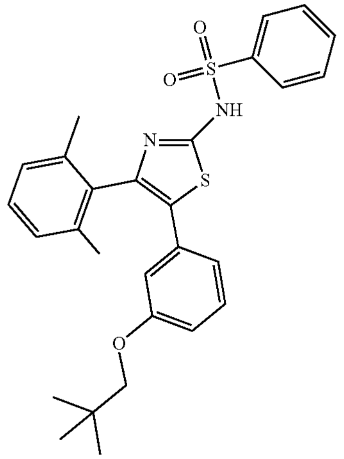 [SMILES: Cc1cccc(C)c1-c1nc(NS(=O)(=O)c2ccccc2)sc1-c1cccc(OCC(C)(C)C)c1]
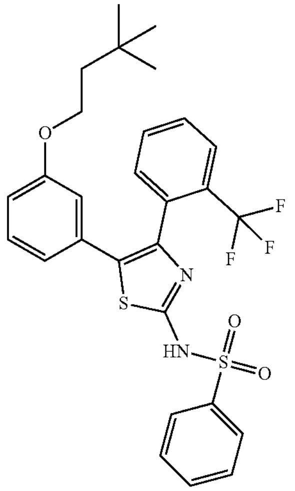 [SMILES: CC(C)(C)CCOc1cccc(-c2sc(NS(=O)(=O)c3ccccc3)nc2-c2ccccc2C(F)(F)F)c1]
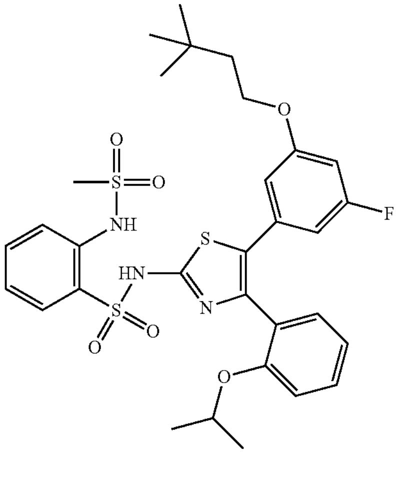 [SMILES: CC(C)Oc1ccccc1-c1nc(NS(=O)(=O)c2ccccc2NS(C)(=O)=O)sc1-c1cc(F)cc(OCCC(C)(C)C)c1]
-continued
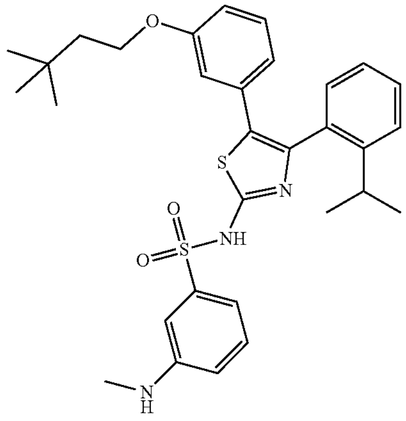 [SMILES: CNc1cccc(S(=O)(=O)Nc2nc(-c3ccccc3C(C)C)c(-c3cccc(OCCC(C)(C)C)c3)s2)c1]
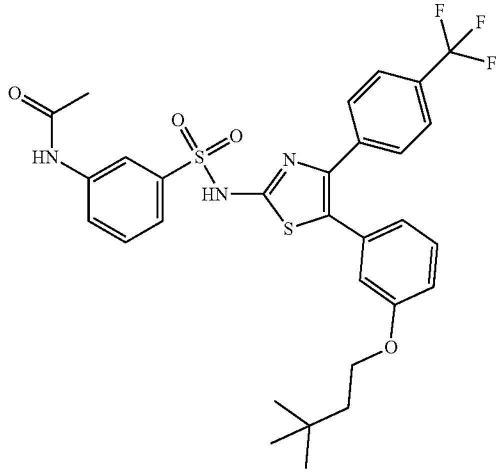 [SMILES: CC(=O)Nc1cccc(S(=O)(=O)Nc2nc(-c3ccc(C(F)(F)F)cc3)c(-c3cccc(OCCC(C)(C)C)c3)s2)c1]
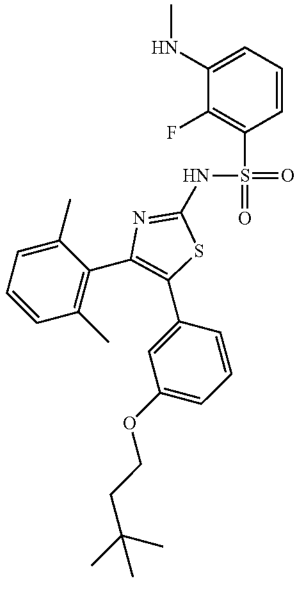 [SMILES: CNc1cccc(S(=O)(=O)Nc2nc(-c3c(C)cccc3C)c(-c3cccc(OCCC(C)(C)C)c3)s2)c1F]

-continued
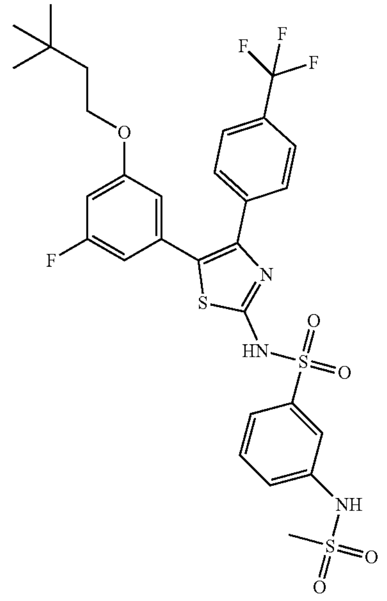 [SMILES: CC(C)(C)CCOc1cc(F)cc(-c2sc(NS(=O)(=O)c3cccc(NS(C)(=O)=O)c3)nc2-c2ccc(C(F)(F)F)cc2)c1]
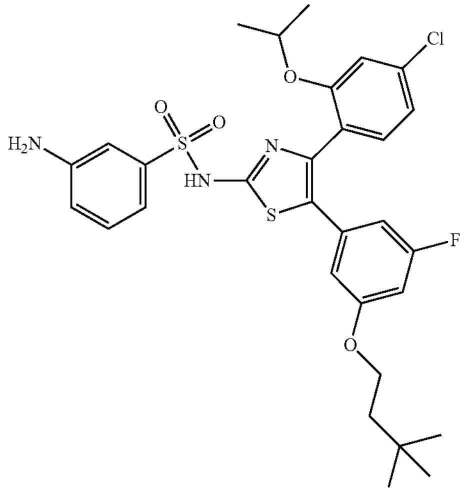 [SMILES: CC(C)Oc1cc(Cl)ccc1-c1nc(NS(=O)(=O)c2cccc(N)c2)sc1-c1cc(F)cc(OCCC(C)(C)C)c1]
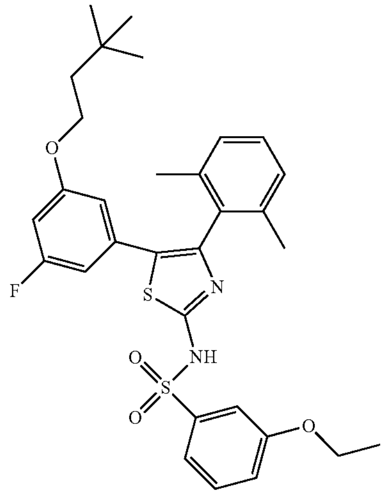 [SMILES: CCOc1cccc(S(=O)(=O)Nc2nc(-c3c(C)cccc3C)c(-c3cc(F)cc(OCCC(C)(C)C)c3)s2)c1]
-continued
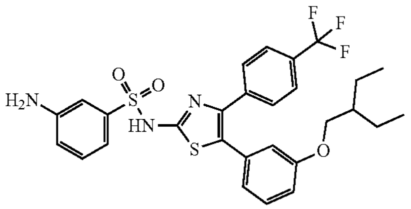 [SMILES: CCC(CC)COc1cccc(-c2sc(NS(=O)(=O)c3cccc(N)c3)nc2-c2ccc(C(F)(F)F)cc2)c1]
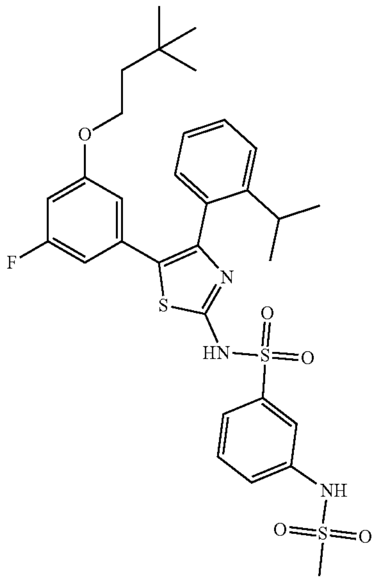 [SMILES: CC(C)c1ccccc1-c1nc(NS(=O)(=O)c2cccc(NS(C)(=O)=O)c2)sc1-c1cc(F)cc(OCCC(C)(C)C)c1]
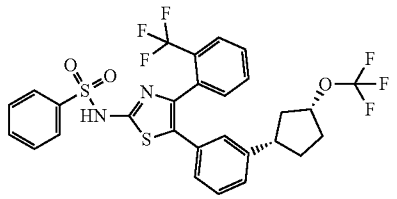 [SMILES: O=S(=O)(Nc1nc(-c2ccccc2C(F)(F)F)c(-c2cccc([C@H]3CC[C@@H](OC(F)(F)F)C3)c2)s1)c1ccccc1]
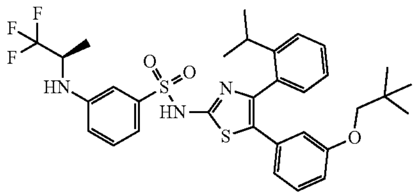 [SMILES: CC(C)c1ccccc1-c1nc(NS(=O)(=O)c2cccc(N[C@H](C)C(F)(F)F)c2)sc1-c1cccc(OCC(C)(C)C)c1]

-continued
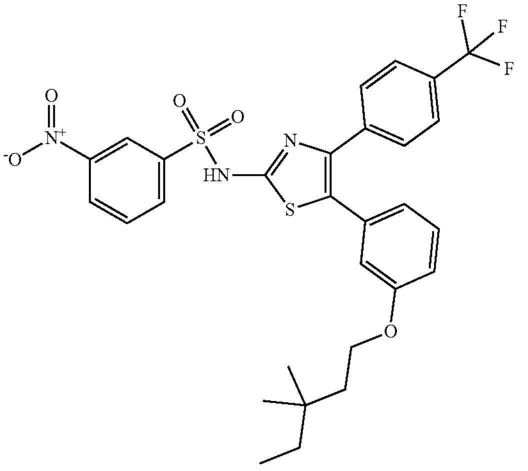
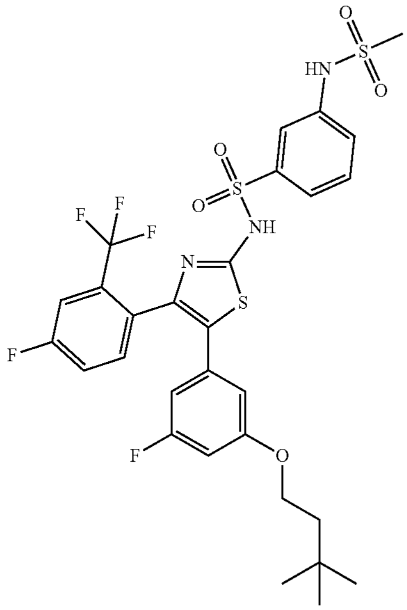 [SMILES: CC(C)(C)CCOc1cc(F)cc(-c2sc(NS(=O)(=O)c3cccc(NS(C)(=O)=O)c3)nc2-c2ccc(F)cc2C(F)(F)F)c1]
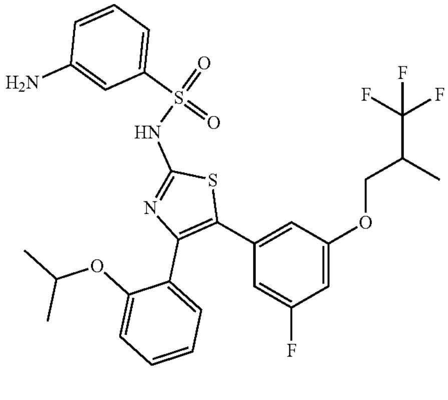 [SMILES: CC(C)Oc1ccccc1-c1nc(NS(=O)(=O)c2cccc(N)c2)sc1-c1cc(F)cc(OCC(C)C(F)(F)F)c1]
-continued
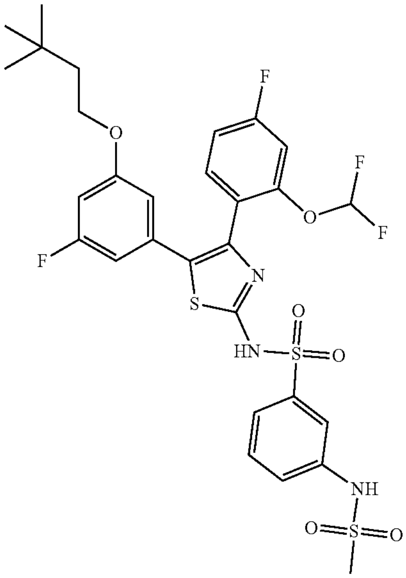 [SMILES: CC(C)(C)CCOc1cc(F)cc(-c2sc(NS(=O)(=O)c3cccc(NS(C)(=O)=O)c3)nc2-c2ccc(F)cc2OC(F)F)c1]
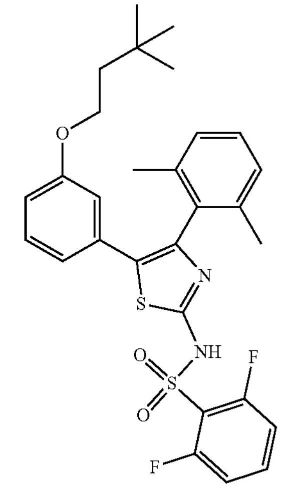 [SMILES: Cc1cccc(C)c1-c1nc(NS(=O)(=O)c2c(F)cccc2F)sc1-c1cccc(OCCC(C)(C)C)c1]
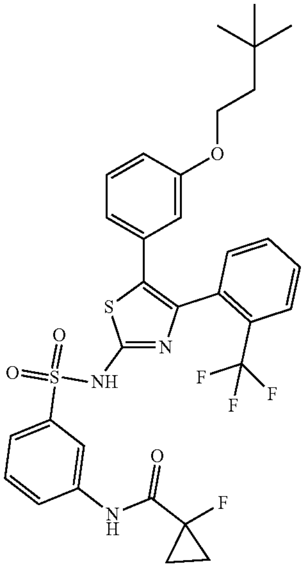 [SMILES: CC(C)(C)CCOc1cccc(-c2sc(NS(=O)(=O)c3cccc(NC(=O)C4(F)CC4)c3)nc2-c2ccccc2C(F)(F)F)c1]

-continued
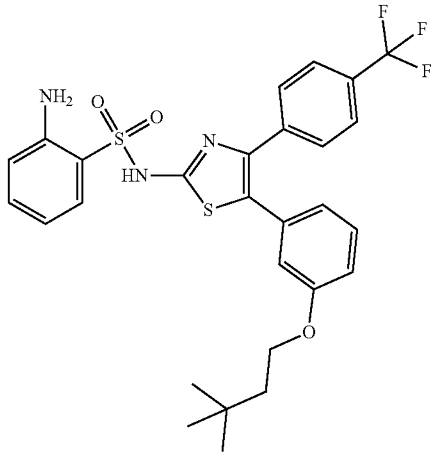 [SMILES: CC(C)(C)CCOc1cccc(-c2sc(NS(=O)(=O)c3ccccc3N)nc2-c2ccc(C(F)(F)F)cc2)c1]
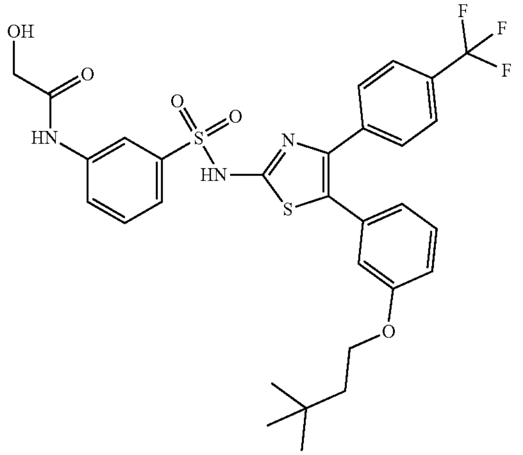 [SMILES: CC(C)(C)CCOc1cccc(-c2sc(NS(=O)(=O)c3cccc(NC(=O)CO)c3)nc2-c2ccc(C(F)(F)F)cc2)c1]
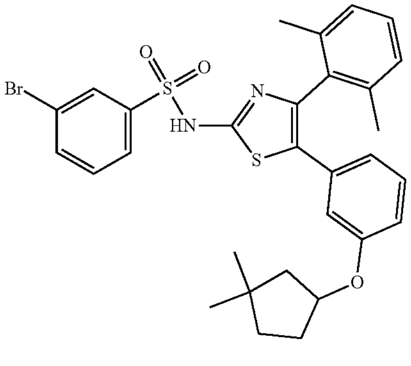 [SMILES: Cc1cccc(C)c1-c1nc(NS(=O)(=O)c2cccc(Br)c2)sc1-c1cccc(OC2CCC(C)(C)C2)c1]
-continued
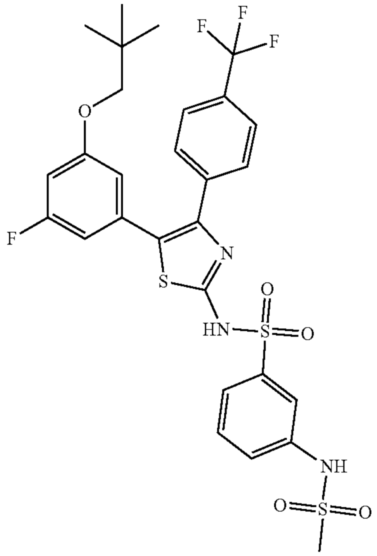 [SMILES: CC(C)(C)COc1cc(F)cc(-c2sc(NS(=O)(=O)c3cccc(NS(C)(=O)=O)c3)nc2-c2ccc(C(F)(F)F)cc2)c1]
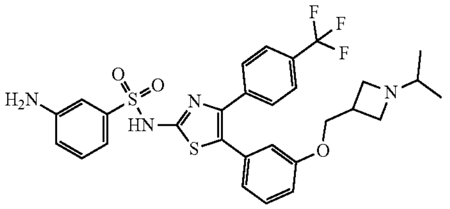 [SMILES: CC(C)N1CC(COc2cccc(-c3sc(NS(=O)(=O)c4cccc(N)c4)nc3-c3ccc(C(F)(F)F)cc3)c2)C1]
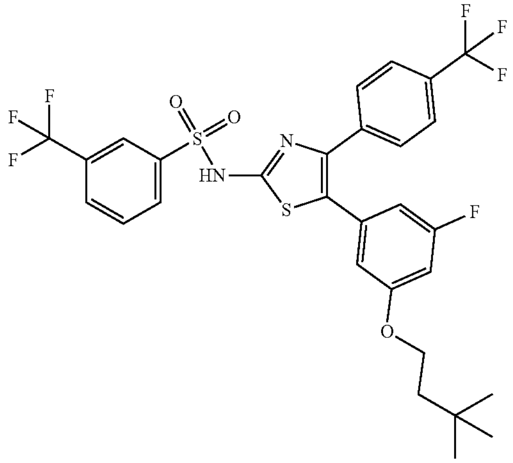 [SMILES: CC(C)(C)CCOc1cc(F)cc(-c2sc(NS(=O)(=O)c3cccc(C(F)(F)F)c3)nc2-c2ccc(C(F)(F)F)cc2)c1]
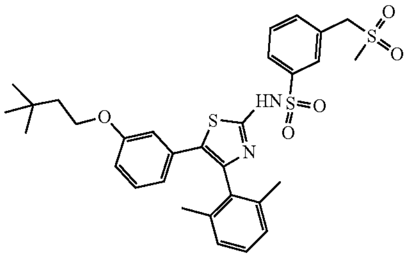 [SMILES: Cc1cccc(C)c1-c1nc(NS(=O)(=O)c2cccc(CS(C)(=O)=O)c2)sc1-c1cccc(OCCC(C)(C)C)c1]

-continued
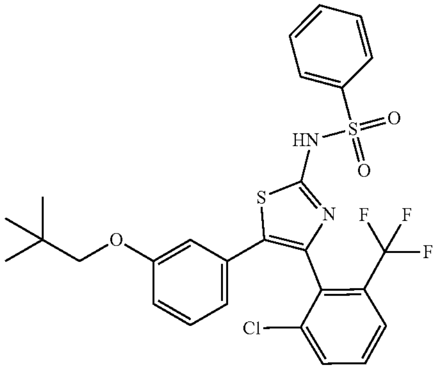 [SMILES: CC(C)(C)COc1cccc(-c2sc(NS(=O)(=O)c3ccccc3)nc2-c2c(Cl)cccc2C(F)(F)F)c1]
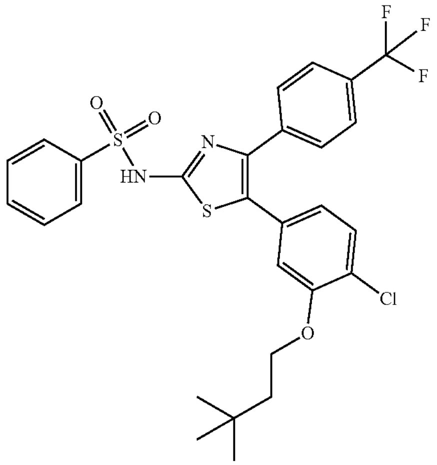 [SMILES: CC(C)(C)CCOc1cc(-c2sc(NS(=O)(=O)c3ccccc3)nc2-c2ccc(C(F)(F)F)cc2)ccc1Cl]
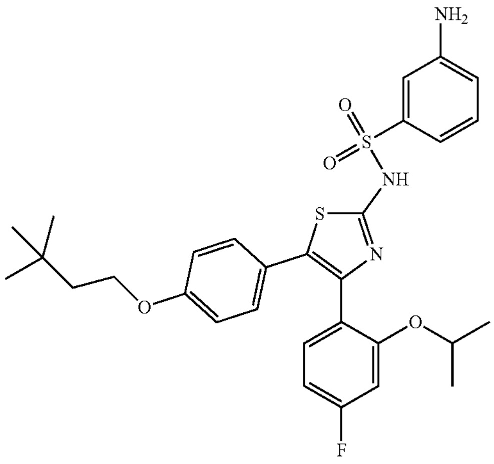 [SMILES: CC(C)Oc1cc(F)ccc1-c1nc(NS(=O)(=O)c2cccc(N)c2)sc1-c1ccc(OCCC(C)(C)C)cc1]
-continued
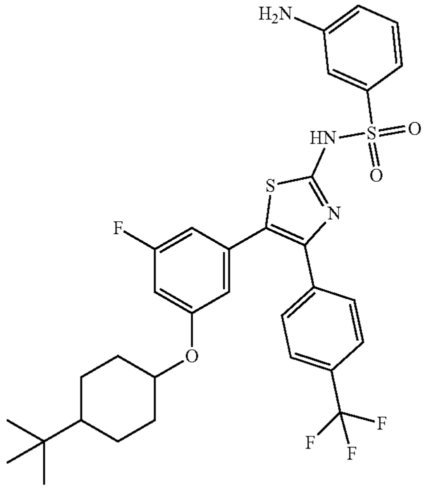 [SMILES: CC(C)(C)C1CCC(Oc2cc(F)cc(-c3sc(NS(=O)(=O)c4cccc(N)c4)nc3-c3ccc(C(F)(F)F)cc3)c2)CC1]
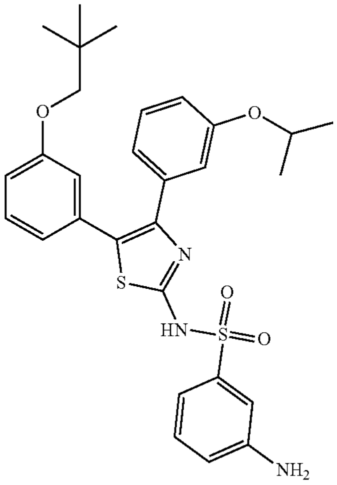 [SMILES: CC(C)Oc1cccc(-c2nc(NS(=O)(=O)c3cccc(N)c3)sc2-c2cccc(OCC(C)(C)C)c2)c1]
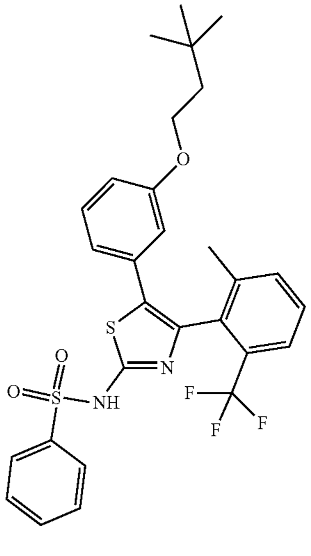 [SMILES: Cc1cccc(C(F)(F)F)c1-c1nc(NS(=O)(=O)c2ccccc2)sc1-c1cccc(OCCC(C)(C)C)c1]

-continued
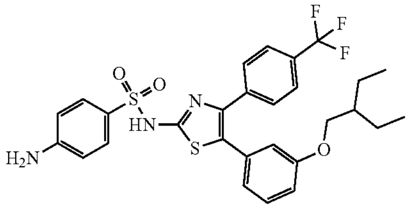 [SMILES: CCC(CC)COc1cccc(-c2sc(NS(=O)(=O)c3ccc(N)cc3)nc2-c2ccc(C(F)(F)F)cc2)c1]
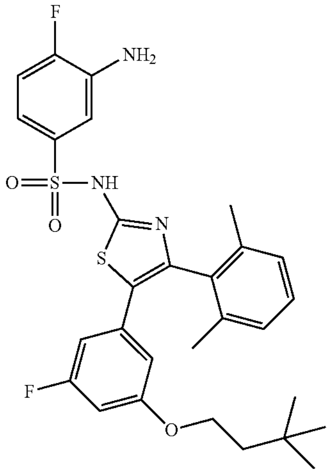 [SMILES: Cc1cccc(C)c1-c1nc(NS(=O)(=O)c2ccc(F)c(N)c2)sc1-c1cc(F)cc(OCCC(C)(C)C)c1]
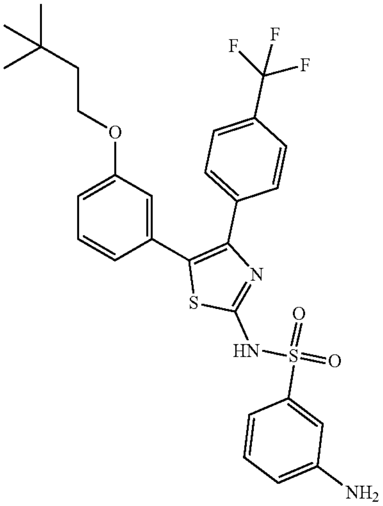 [SMILES: CC(C)(C)CCOc1cccc(-c2sc(NS(=O)(=O)c3cccc(N)c3)nc2-c2ccc(C(F)(F)F)cc2)c1]
-continued
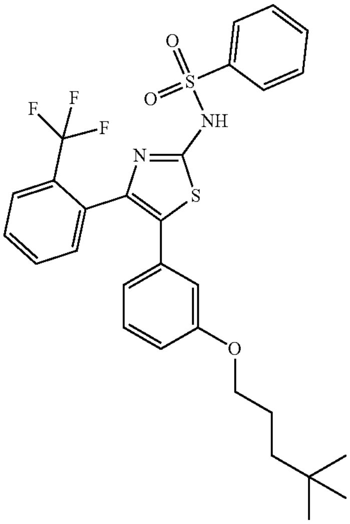 [SMILES: CC(C)(C)CCCOc1cccc(-c2sc(NS(=O)(=O)c3ccccc3)nc2-c2ccccc2C(F)(F)F)c1]
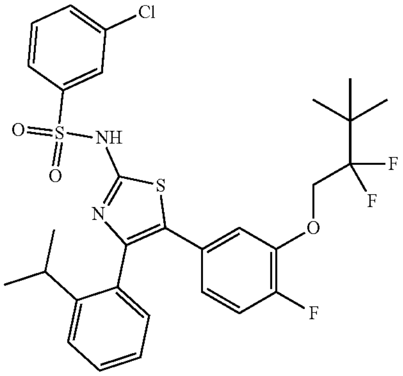 [SMILES: CC(C)c1ccccc1-c1nc(NS(=O)(=O)c2cccc(Cl)c2)sc1-c1ccc(F)c(OCC(F)(F)C(C)(C)C)c1]
and
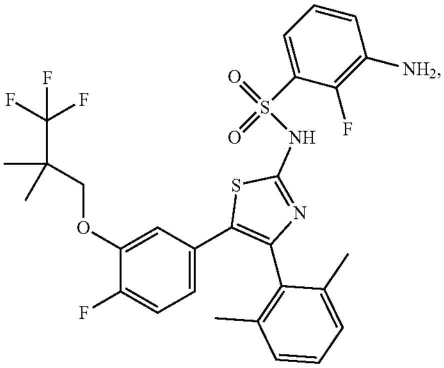 [SMILES: Cc1cccc(C)c1-c1nc(NS(=O)(=O)c2cccc(N)c2F)sc1-c1ccc(F)c(OCC(C)(C)C(F)(F)F)c1]
NH2, -continued
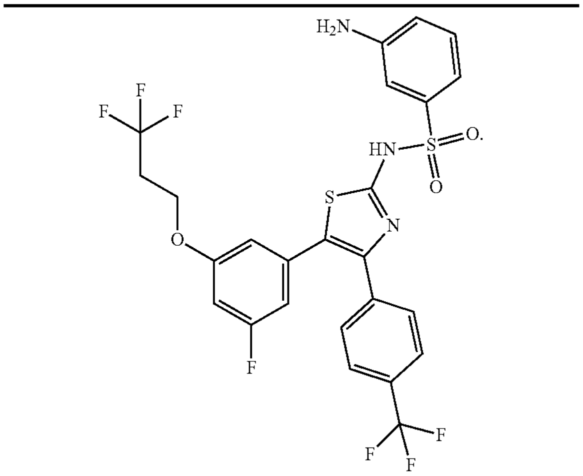
or a tautomer, or a pharmaceutically acceptable salt thereof.
37. A compound selected from the group consisting of
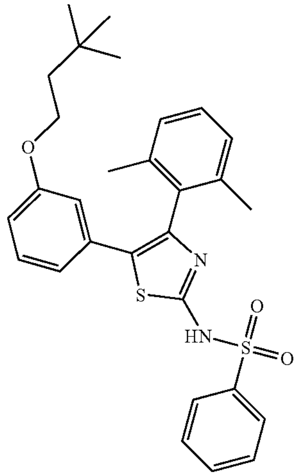 [SMILES: Cc1cccc(C)c1-c1nc(NS(=O)(=O)c2ccccc2)sc1-c1cccc(OCCC(C)(C)C)c1]
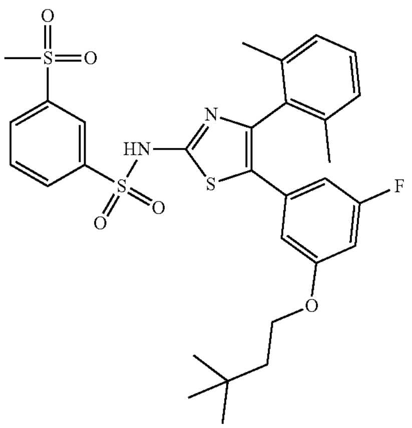 [SMILES: Cc1cccc(C)c1-c1nc(NS(=O)(=O)c2cccc(S(C)(=O)=O)c2)sc1-c1cc(F)cc(OCCC(C)(C)C)c1]

-continued
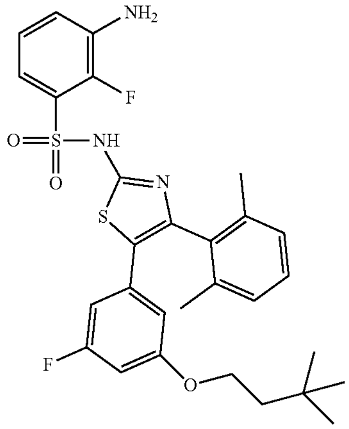 [SMILES: Cc1cccc(C)c1-c1nc(NS(=O)(=O)c2cccc(N)c2F)sc1-c1cc(F)cc(OCCC(C)(C)C)c1]
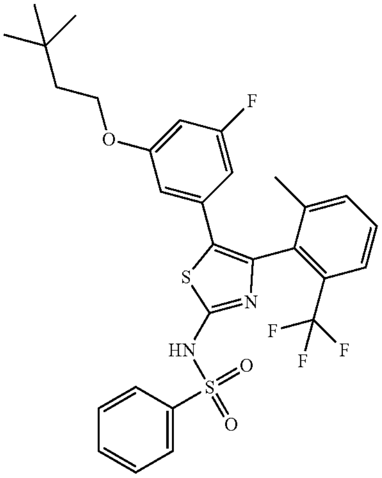 [SMILES: Cc1cccc(C(F)(F)F)c1-c1nc(NS(=O)(=O)c2ccccc2)sc1-c1cc(F)cc(OCCC(C)(C)C)c1]
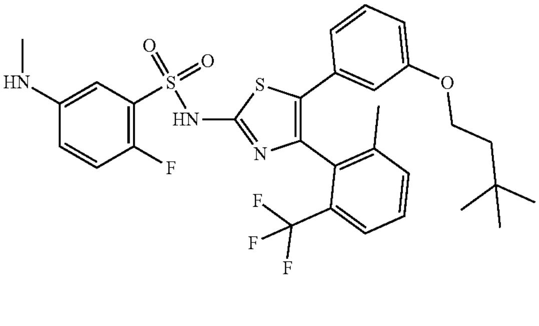 [SMILES: CNc1ccc(F)c(S(=O)(=O)Nc2nc(-c3c(C)cccc3C(F)(F)F)c(-c3cccc(OCCC(C)(C)C)c3)s2)c1]

-continued
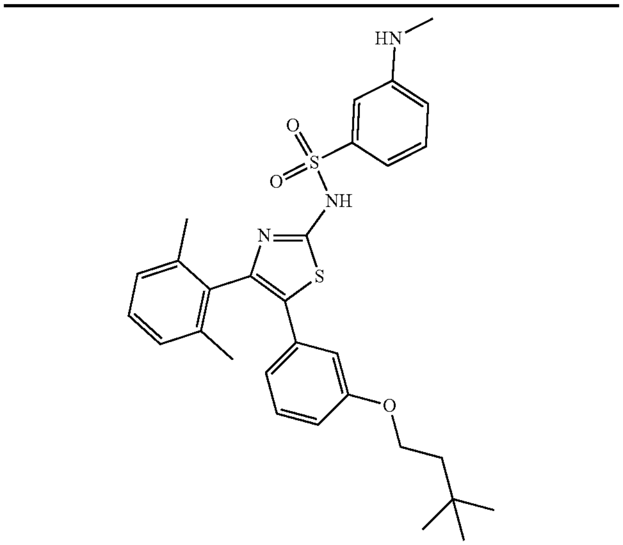
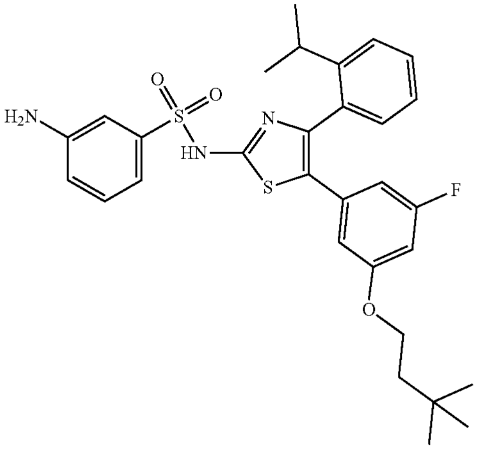 [SMILES: CC(C)c1ccccc1-c1nc(NS(=O)(=O)c2cccc(N)c2)sc1-c1cc(F)cc(OCCC(C)(C)C)c1]
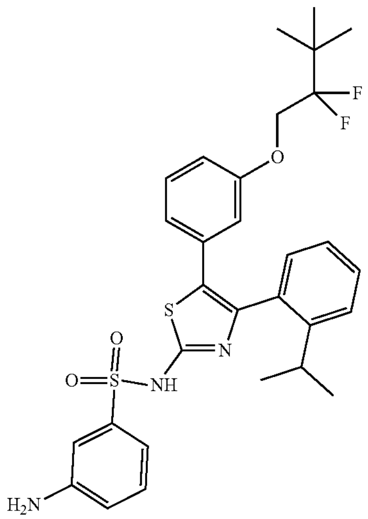 [SMILES: CC(C)c1ccccc1-c1nc(NS(=O)(=O)c2cccc(N)c2)sc1-c1cccc(OCC(F)(F)C(C)(C)C)c1]

-continued
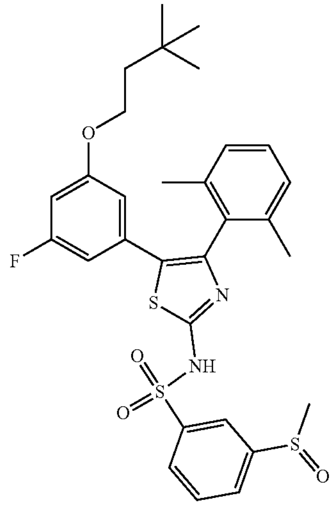 [SMILES: Cc1cccc(C)c1-c1nc(NS(=O)(=O)c2cccc(S(C)=O)c2)sc1-c1cc(F)cc(OCCC(C)(C)C)c1]
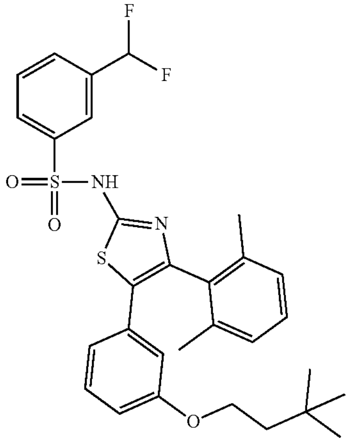 [SMILES: Cc1cccc(C)c1-c1nc(NS(=O)(=O)c2cccc(C(F)F)c2)sc1-c1cccc(OCCC(C)(C)C)c1]
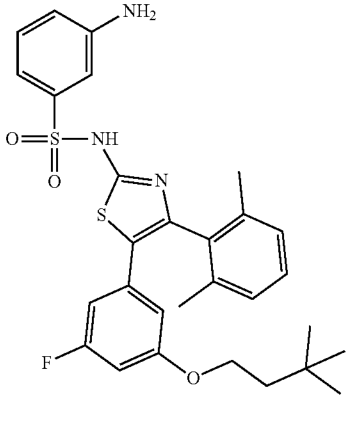 [SMILES: Cc1cccc(C)c1-c1nc(NS(=O)(=O)c2cccc(N)c2)sc1-c1cc(F)cc(OCCC(C)(C)C)c1]

-continued
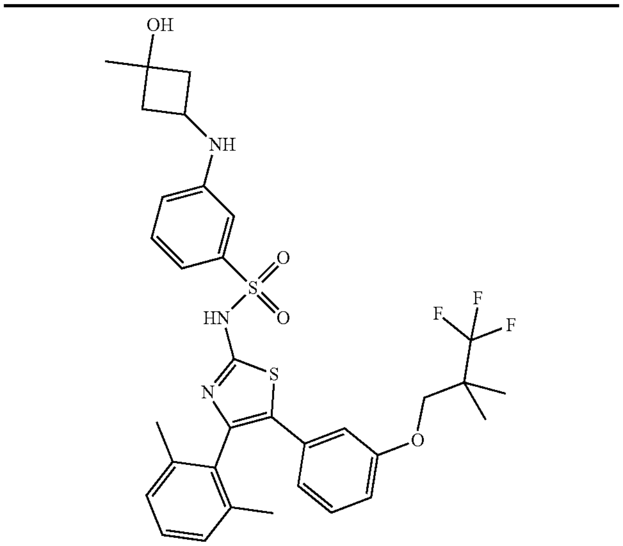
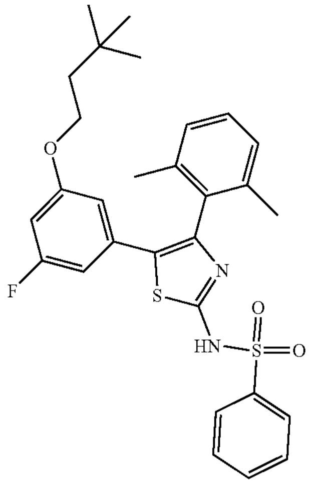 [SMILES: Cc1cccc(C)c1-c1nc(NS(=O)(=O)c2ccccc2)sc1-c1cc(F)cc(OCCC(C)(C)C)c1]
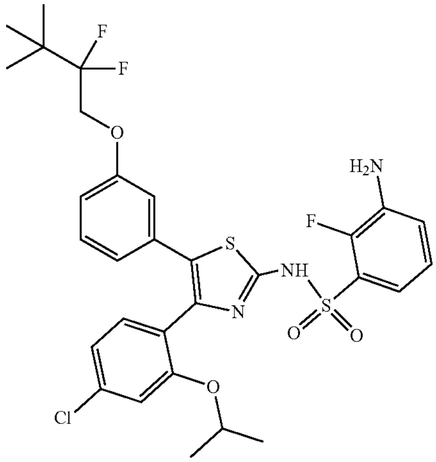 [SMILES: CC(C)Oc1cc(Cl)ccc1-c1nc(NS(=O)(=O)c2cccc(N)c2F)sc1-c1cccc(OCC(F)(F)C(C)(C)C)c1]

-continued
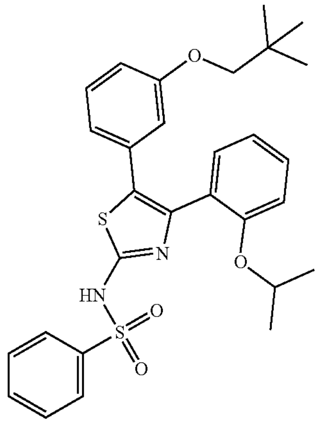 [SMILES: CC(C)Oc1ccccc1-c1nc(NS(=O)(=O)c2ccccc2)sc1-c1cccc(OCC(C)(C)C)c1]
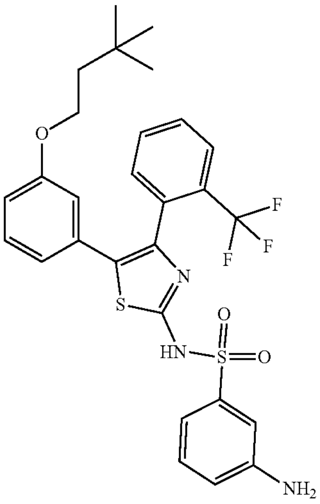 [SMILES: CC(C)(C)CCOc1cccc(-c2sc(NS(=O)(=O)c3cccc(N)c3)nc2-c2ccccc2C(F)(F)F)c1]
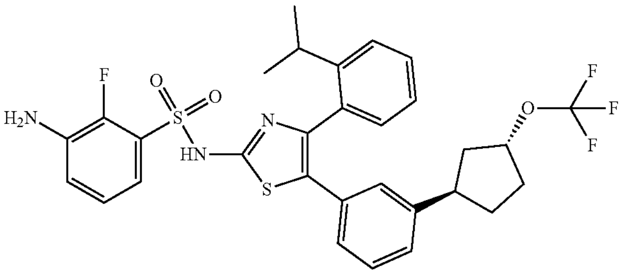 [SMILES: CC(C)c1ccccc1-c1nc(NS(=O)(=O)c2cccc(N)c2F)sc1-c1cccc([C@@H]2CC[C@@H](OC(F)(F)F)C2)c1]
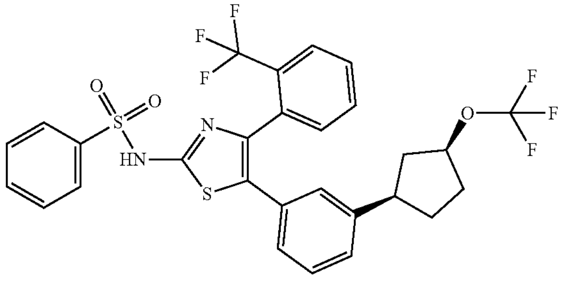 [SMILES: O=S(=O)(Nc1nc(-c2ccccc2C(F)(F)F)c(-c2cccc([C@@H]3CC[C@H](OC(F)(F)F)C3)c2)s1)c1ccccc1]

-continued
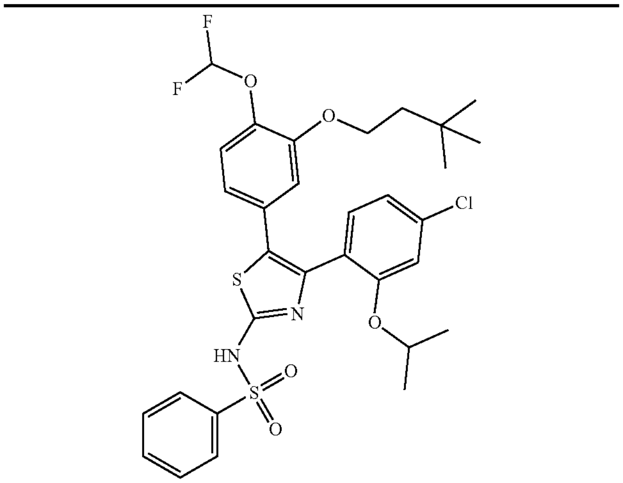
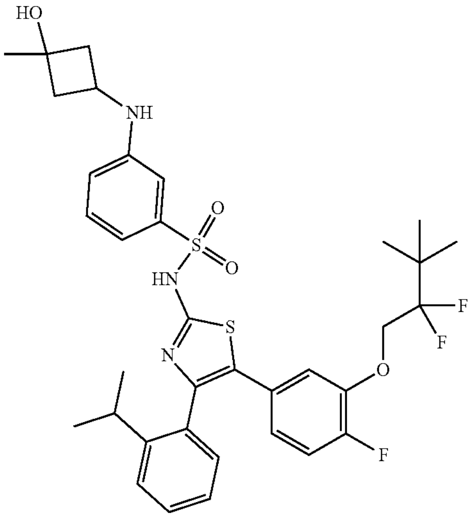 [SMILES: CC(C)c1ccccc1-c1nc(NS(=O)(=O)c2cccc(NC3CC(C)(O)C3)c2)sc1-c1ccc(F)c(OCC(F)(F)C(C)(C)C)c1]
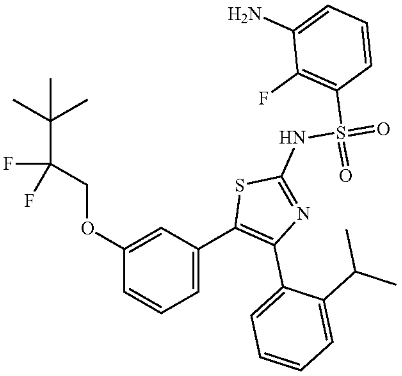 [SMILES: CC(C)c1ccccc1-c1nc(NS(=O)(=O)c2cccc(N)c2F)sc1-c1cccc(OCC(F)(F)C(C)(C)C)c1]

-continued
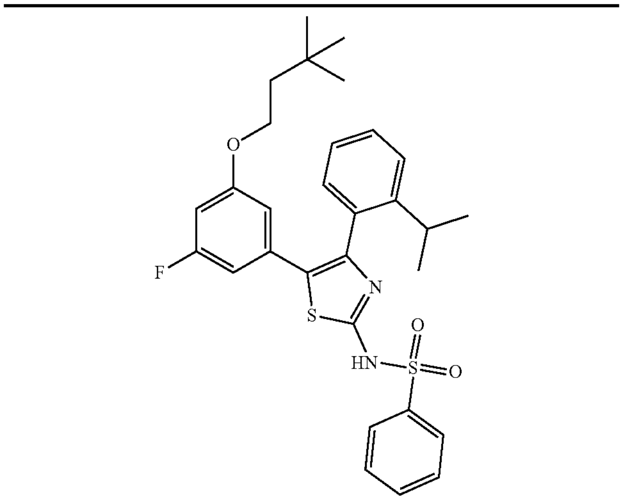
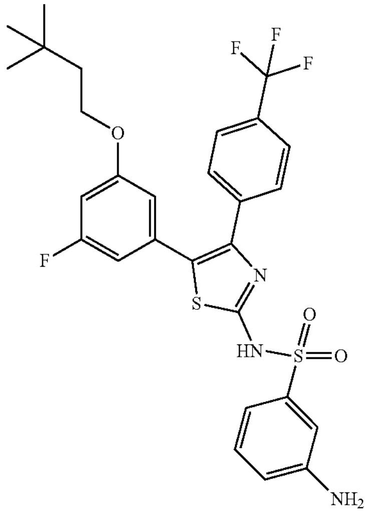 [SMILES: CC(C)(C)CCOc1cc(F)cc(-c2sc(NS(=O)(=O)c3cccc(N)c3)nc2-c2ccc(C(F)(F)F)cc2)c1]
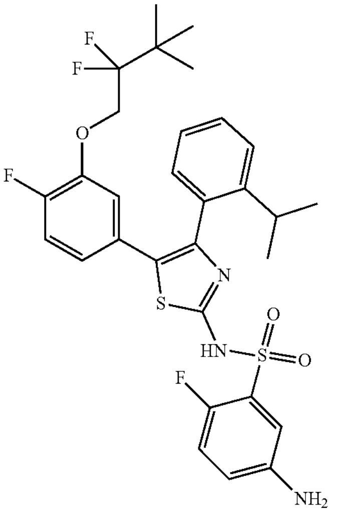 [SMILES: CC(C)c1ccccc1-c1nc(NS(=O)(=O)c2cc(N)ccc2F)sc1-c1ccc(F)c(OCC(F)(F)C(C)(C)C)c1]

-continued
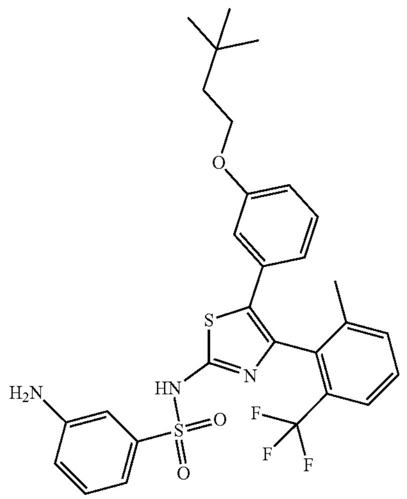 [SMILES: Cc1cccc(C(F)(F)F)c1-c1nc(NS(=O)(=O)c2cccc(N)c2)sc1-c1cccc(OCCC(C)(C)C)c1]
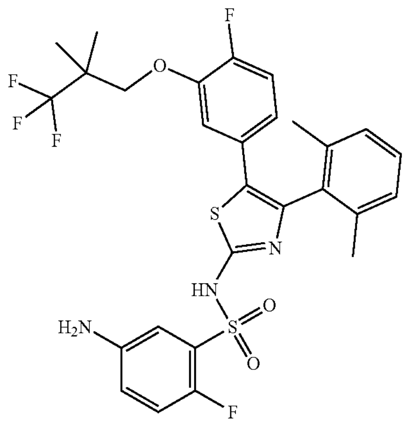 [SMILES: Cc1cccc(C)c1-c1nc(NS(=O)(=O)c2cc(N)ccc2F)sc1-c1ccc(F)c(OCC(C)(C)C(F)(F)F)c1]
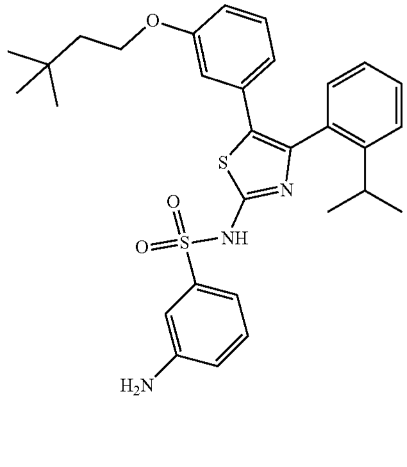 [SMILES: CC(C)c1ccccc1-c1nc(NS(=O)(=O)c2cccc(N)c2)sc1-c1cccc(OCCC(C)(C)C)c1]

-continued
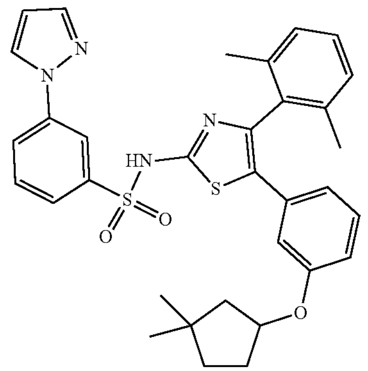 [SMILES: Cc1cccc(C)c1-c1nc(NS(=O)(=O)c2cccc(-n3cccn3)c2)sc1-c1cccc(OC2CCC(C)(C)C2)c1]
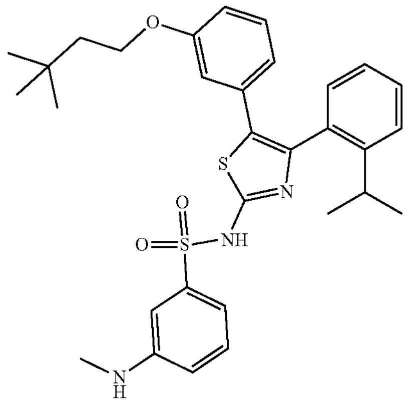 [SMILES: CNc1cccc(S(=O)(=O)Nc2nc(-c3ccccc3C(C)C)c(-c3cccc(OCCC(C)(C)C)c3)s2)c1]
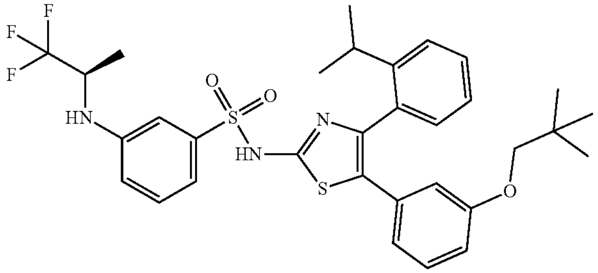 [SMILES: CC(C)c1ccccc1-c1nc(NS(=O)(=O)c2cccc(N[C@H](C)C(F)(F)F)c2)sc1-c1cccc(OCC(C)(C)C)c1]
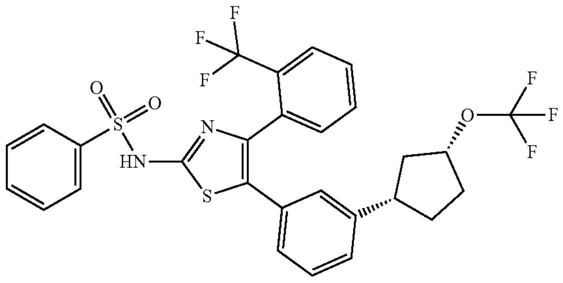 [SMILES: O=S(=O)(Nc1nc(-c2ccccc2C(F)(F)F)c(-c2cccc([C@H]3CC[C@@H](OC(F)(F)F)C3)c2)s1)c1ccccc1]

-continued
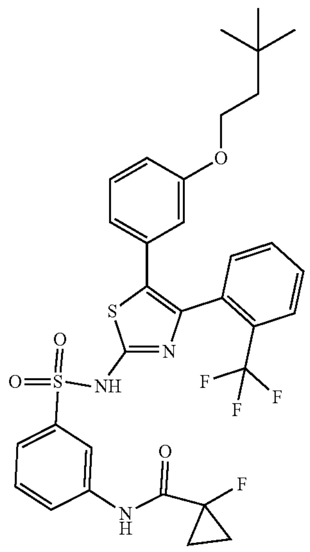 [SMILES: CC(C)(C)CCOc1cccc(-c2sc(NS(=O)(=O)c3cccc(NC(=O)C4(F)CC4)c3)nc2-c2ccccc2C(F)(F)F)c1]
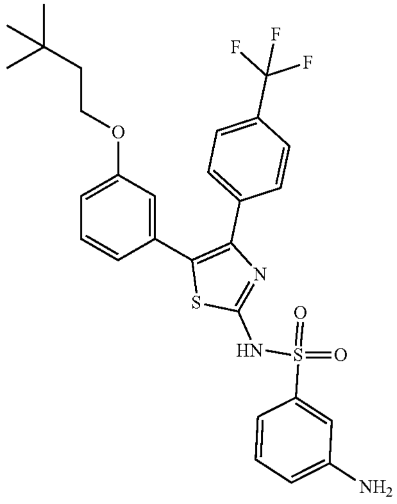 [SMILES: CC(C)(C)CCOc1cccc(-c2sc(NS(=O)(=O)c3cccc(N)c3)nc2-c2ccc(C(F)(F)F)cc2)c1]
and
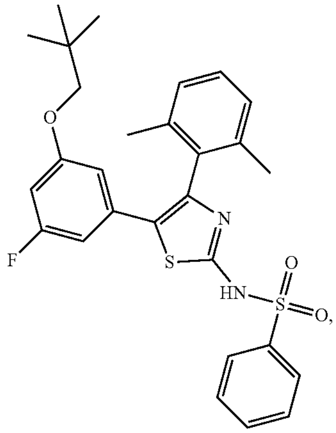 [SMILES: Cc1cccc(C)c1-c1nc(NS(=O)(=O)c2ccccc2)sc1-c1cc(F)cc(OCC(C)(C)C)c1]
, or a tautomer, or a pharmaceutically acceptable salt thereof.

38. A pharmaceutical composition comprising a compound of claim 1, and a pharmaceutically acceptable carrier or excipient.

39. The pharmaceutical composition of claim 38, further comprising one or more CFTR therapeutic agents.

40. A method of treating deficient CFTR activity in a cell, comprising contacting the cell with a compound of claim 1.

41. The method of claim 40, wherein contacting the cell occurs in a subject in need thereof, thereby treating a CFTR-mediated condition and/or disease.

42. The method of claim 41, wherein the disease or condition is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), congenital pneumonia, intestinal malabsorption, celiac disease, nasal polyposis, non-tuberculous mycobacterial infection, pancreatic steatorrhea, intestinal atresia, liver disease, hereditary emphysema, hereditary hemochromatosis, coagulation-fibrinolysis deficiencies, protein C deficiency, Type 1 hereditary angioedema, lipid processing deficiencies, familial hypercholesterolemia, Type 1 chylomicronemia, abetalipoproteinemia, lysosomal storage diseases, I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases, Alzheimer's disease, Parkinson's disease, amyotrophic lateral sclerosis, progressive supranuclear palsy, Pick's disease, several polyglutamine neurological disorders, Huntington's, spinocerebullar ataxia type I, spinal and bulbar muscular atrophy, dentatorubal pallidoluysian, myotonic dystrophy, spongiform encephalopathies, hereditary Creutzfeldt-Jakob disease, Fabry disease, Straussler-Scheinker syndrome, COPD, dry-eye disease, Sjogren's disease, Osteoporosis, Osteopenia, bone healing and bone growth, bone repair, bone regeneration, reducing bone resorption, increasing bone deposition, Gorham's Syndrome, chloride channelopathies, myotonia congenita, Bartter's syndrome type III, Dent's disease, hyperekplexia, epilepsy, hyperekplexia, lysosomal storage disease, Angelman syndrome, Primary Ciliary Dyskinesia (PCD), PCD with situs inversus, PCD without situs inversus and ciliary aplasia.

43. The method of claim 42, wherein the disease or condition is selected from cystic fibrosis, congenital bilateral absence of vas deferens (CBAVD), acute, recurrent, or chronic pancreatitis, disseminated bronchiectasis, asthma, allergic pulmonary aspergillosis, congenital pneumonia, intestinal malabsorption, celiac disease, nasal polyposis, non-tuberculous mycobacterial infection, pancreatic steatorrhea, intestinal atresia, chronic obstructive pulmonary disease (COPD), chronic rhinosinusitis, dry eye disease, protein C deficiency, abetalipoproteinemia, lysosomal storage disease, type 1 chylomicronemia, mild pulmonary disease, lipid processing deficiencies, type 1 hereditary angioedema, coagulation-fibrinolyis, hereditary hemochromatosis, CFTR-related metabolic syndrome, chronic bronchitis, constipation, pancreatic insufficiency, hereditary emphysema, and Sjogren's syndrome.

44. The method of claim 42, wherein the disease or condition is cystic fibrosis.

45. A method of treating cystic fibrosis or a symptom thereof in a subject, comprising administering to the subject a therapeutically effective amount of a compound of claim 1.

46. The method of claim 45, wherein the subject is human.

47. The method according to claim 46, wherein said subject is at risk of developing cystic fibrosis, and wherein said administering step is carried out prior to the onset of symptoms of cystic fibrosis in said subject.

48. The compound of claim 1, wherein the compound is

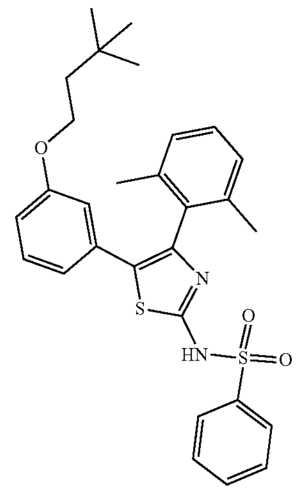 [SMILES: Cc1cccc(C)c1-c1nc(NS(=O)(=O)c2ccccc2)sc1-c1cccc(OCCC(C)(C)C)c1]

or a tautomer of a pharmaceutically acceptable salt thereof.

49. The compound of claim 48, wherein the compound is a tautomer of the compound of claim 48, represented by the following structure:

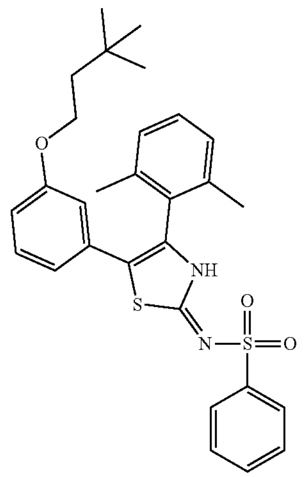 [SMILES: Cc1cccc(C)c1-c1[nH]/c(=N\S(=O)(=O)c2ccccc2)sc1-c1cccc(OCCC(C)(C)C)c1]

or a pharmaceutically acceptable salt thereof.

* * * * *